(12) United States Patent
Kuroita et al.

(10) Patent No.: US 7,803,940 B2
(45) Date of Patent: Sep. 28, 2010

(54) HETEROMONOCYCLIC COMPOUND OR A SALT THEREOF HAVING STRONG ANTIHYPERTENSIVE ACTION, INSULIN SENSITIZING ACTIVITY AND THE LIKE PRODUCTION THEREOF AND USE THEREOF FOR PROPHYLAXIS OR TREATMENT OF CARDIOVASCULAR DISEASES, METABOLIC DISEASES AND/OR CENTRAL NERVOUS SYSTEM DISEASES

(75) Inventors: Takanobu Kuroita, Osaka (JP); Hiroki Sakamoto, Osaka (JP); Hideyuki Igawa, Osaka (JP); Minoru Sasaki, Osaka (JP); Kouhei Asano, Osaka (JP); Tsuyoshi Maekawa, Osaka (JP); Koji Fuji, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/114,048

(22) Filed: May 2, 2008

(65) Prior Publication Data
US 2009/0176812 A1 Jul. 9, 2009

Related U.S. Application Data

(63) Continuation-in-part of application No. 11/943,910, filed on Nov. 21, 2007, now abandoned.

(30) Foreign Application Priority Data
Nov. 24, 2006 (JP) ............................ 2006/317839
Sep. 6, 2007 (JP) ............................ 2007/232106

(51) Int. Cl.
*C07D 401/00* (2006.01)
(52) U.S. Cl. ...................... 544/328; 548/132
(58) Field of Classification Search ................ 544/328; 548/132
See application file for complete search history.

(56) References Cited

U.S. PATENT DOCUMENTS 5,162,326 A   11/1992   Naka et al.

(Continued)

FOREIGN PATENT DOCUMENTS

EP   0 685 467 A1   12/1995

(Continued)

OTHER PUBLICATIONS

Jordan, V. C. Nature Reviews: Drug Discovery, 2, 2003, p. 205.*
Vippagunta, et al. Advanced Drug Delivery Reviews, 48, 2001, p. 18.*

(Continued)

Primary Examiner—James O Wilson
Assistant Examiner—Douglas M Willis
(74) Attorney, Agent, or Firm—Foley & Lardner LLP

(57) ABSTRACT

A compound represented by the formula (I):

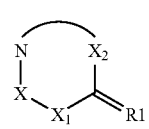

wherein R1 is an oxo group, =N—R or the like; a group represented by the formula:

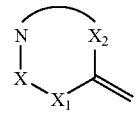

is a group represented by the formula:

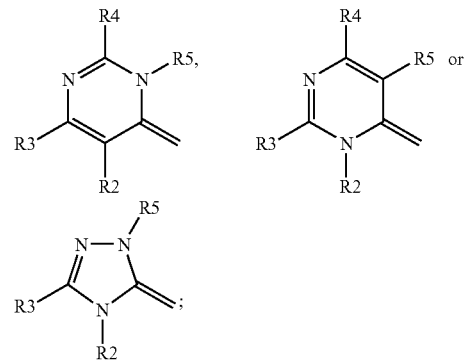

R2 is a group represented by the formula:

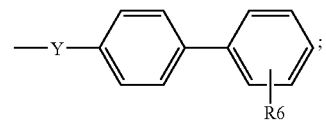

R3 and R4 are each H, or C1-C6 alkyl, C3-C6 cycloalkyl, C1-C6 alkoxy, C1-C6 alkylamino, di(C1-C6)alkylamino or C1-C6 alkylthio, each of which is optionally substituted; and R5 is H, or C1-C6 alkyl, C2-C6 alkenyl, cyclic group, each of which is optionally substituted, —CO—R8 or —O—R8', or a salt thereof. The compound of the present invention is useful as a drug for the prophylaxis or treatment of cardiovascular diseases, metabolic diseases and/or central nervous system diseases.

8 Claims, No Drawings

U.S. PATENT DOCUMENTS

| | | | |
|---|---|---|---|
| 5,166,206 | A | 11/1992 | Allen et al. |
| 5,183,899 | A | 2/1993 | Naka et al. |
| 5,243,054 | A | 9/1993 | Naka et al. |
| 5,304,565 | A | 4/1994 | Morimoto et al. |
| 5,411,980 | A | 5/1995 | Ashton et al. |
| 5,472,967 | A | 12/1995 | Hoornaert et al. |
| 5,496,835 | A | 3/1996 | Kubo et al. |
| 5,500,427 | A | 3/1996 | Kubo et al. |
| 5,565,464 | A | 10/1996 | Salimbeni et al. |
| 5,583,141 | A * | 12/1996 | Naka et al. .......... 514/303 |
| 5,877,121 | A | 3/1999 | Andree et al. |
| 2001/0020100 | A1 | 9/2001 | Manning et al. |
| 2004/0039038 | A1 | 2/2004 | Bernardon et al. |
| 2008/0207654 | A1 | 8/2008 | Kuroita et al. |

FOREIGN PATENT DOCUMENTS

| | | | |
|---|---|---|---|
| WO | WO 92/17469 | A2 | 10/1992 |
| WO | WO 94/08990 | A1 | 4/1994 |
| WO | WO 94/21629 | A1 | 9/1994 |
| WO | WO 95/16677 | A1 | 6/1995 |
| WO | WO 96/07647 | A1 | 3/1996 |
| WO | WO 02/12210 | A1 | 2/2002 |
| WO | WO 2006/074057 | A2 | 7/2006 |
| WO | WO 2006/100520 | A1 | 9/2006 |
| WO | WO 2007/003271 | A1 | 1/2007 |
| WO | WO 2008/062905 | A3 | 5/2008 |

OTHER PUBLICATIONS

Wolff, Manfred E., Ed. Burger's Medicinal Chemistry and Drug Discovery—Fifth Edition, New York: John Wiley & Sons, 1996, vol. 1, pp. 975-976.*

Benson et al., "Identification of Telmisartan as a Unique Angiotensin II Receptor Antagonist with Selective PPARy-Modulating Activity," Hypertension, May 2004, 43:993-1002.

Schupp et al., "Regulation of Peroxisome Proliferator-Activated Receptor y Activity by Losartan Metabolites," Hypertension, Mar. 2006 Part II, 47:586-589.

International Search Report and Written Opinion of Aug. 24, 2009, in corresponding PCT/JP2009/058796, 18 pages.

Ferrari et al., "Development of Tetrazole Bioisosteres in Angiotensin II Antagonists," Bioorganic & Medicinal Chemistry Letters, 1994, 4(1):45-50.

U.S. Appl. No. 12/516,099, filed Nov. 21, 2007, Kuroita et al.

Notice of Opposition filed Oct. 22, 2009, in corresponding Costa Rican Application No. 10847, 9 pages.

English translation of Notice of Opposition filed Oct. 22, 2009, in corresponding Costa Rican Application No. 10847, 10 pages.

Notice of Opposition against Ecuadorian Patent Application No. SP-09-9461, dated Mar. 4, 2010, 10 pages, with English translation, 8 pages.

Hoyer et al., "Molecular, pharmacological and functional diversity of 5-HT receptors," Pharmacology, Biochemistry and Behavior, 2002, 71:533-554.

WHO Drug Information, 2006, 20(2):61-162.

* cited by examiner

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial
<220> FEATURE:
<223> OTHER INFORMATION: primer

<400> SEQUENCE: 1
gtgggtaccg aaatgaccat ggttgacaca gag                           33

<210> SEQ ID NO 2
<211> LENGTH: 33
<212> TYPE: DNA
<213> ORGANISM: Artificial
<220> FEATURE:
<223> OTHER INFORMATION: primer

<400> SEQUENCE: 2
ggggtcgacc aggactctct gctagtacaa gtc                           33

<210> SEQ ID NO 3
<211> LENGTH: 33
<212> TYPE: DNA
```

-continued

```
<213> ORGANISM: Artificial
<220> FEATURE:
<223> OTHER INFORMATION: primer

<400> SEQUENCE: 3
ttagaattcg acatggacac caaacatttc ctg                                33

<210> SEQ ID NO 4
<211> LENGTH: 33
<212> TYPE: DNA
<213> ORGANISM: Artificial
<220> FEATURE:
<223> OTHER INFORMATION: primer

<400> SEQUENCE: 4
cccctcgagc taagtcattt ggtgcggcgc ctc                                33

<210> SEQ ID NO 5
<211> LENGTH: 36
<212> TYPE: DNA
<213> ORGANISM: Artificial
<220> FEATURE:
<223> OTHER INFORMATION: primer

<400> SEQUENCE: 5
tcgacagggg accaggacaa aggtcacgtt cgggag                             36

<210> SEQ ID NO 6
<211> LENGTH: 36
<212> TYPE: DNA
<213> ORGANISM: Artificial
<220> FEATURE:
<223> OTHER INFORMATION: primer

<400> SEQUENCE: 6
tcgactcccg aacgtgacct ttgtcctggt cccctg                             36

<210> SEQ ID NO 7
<211> LENGTH: 28
<212> TYPE: DNA
<213> ORGANISM: Artificial
<220> FEATURE:
<223> OTHER INFORMATION: primer

<400> SEQUENCE: 7
cccagatctc cccagcgtct tgtcattg                                      28

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
tcaccatggt caagctttta agcgggtc                                      28
```

HETEROMONOCYCLIC COMPOUND OR A SALT THEREOF HAVING STRONG ANTIHYPERTENSIVE ACTION, INSULIN SENSITIZING ACTIVITY AND THE LIKE PRODUCTION THEREOF AND USE THEREOF FOR PROPHYLAXIS OR TREATMENT OF CARDIOVASCULAR DISEASES, METABOLIC DISEASES AND/OR CENTRAL NERVOUS SYSTEM DISEASES

This application is a continuation-in-part of application Ser. No. 11/943,910, filed Nov. 21, 2007, which claims the benefit of Japanese patent application No. 2006-317839, filed Nov. 24, 2006, and Japanese patent application No. 2007-232106, filed Sep. 6, 2007, the contents of which are incorporated in full herein by this reference.

TECHNICAL FIELD

The present invention relates to a novel heteromonocyclic compound having superior properties as a pharmaceutical agent, a production method thereof and use thereof. More particularly, the present invention relates to a heteromonocyclic compound having a particular structure and superior pharmacological action such as strong and sustained antihypertensive action, insulin sensitizing activity and the like, and superior property such as crystallinity and stability and the like, which is useful as an agent for the prophylaxis or treatment of cardiovascular diseases such as hypertension, cardiac disease (cardiac hypertrophy, heart failure, myocardial infarction and the like), arteriosclerosis, kidney disease (diabetic nephropathy, chronic glomerulonephritis and the like), stroke and the like; metabolic diseases such as dyslipidemia, obesity, diabetes and the like; and/or central nervous system diseases such as depression, dementia, Alzheimer's disease and the like, or a salt thereof, or a prodrug thereof, a production method thereof, and use thereof and the like.

BACKGROUND OF THE INVENTION

U.S. Pat. No. 5,183,899 (JP-A-3-218371) describes a compound represented by the formula

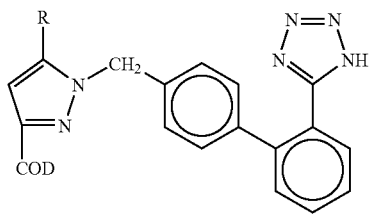

wherein R is an alkyl group and D is an alkoxy group, a hydroxyl group, a halogen atom or an amino group which may be substituted, or a salt thereof, and that the compound has an angiotensin II receptor antagonistic action and a antihypertensive action and is useful as a therapeutic agent for cardiovascular diseases such as hypertension, cardiac disease, stroke and the like.

U.S. Pat. No. 5,162,326 (JP-A-4-330072) describes a compound represented by the formula

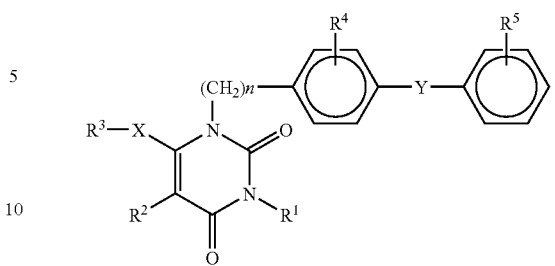

wherein $R^1$ is hydrogen or a hydrocarbon residue which may be substituted; $R^2$ is hydrogen, halogen, nitro, optionally substituted amino, formyl or a hydrocarbon residue which may be substituted; $R^3$ is a hydrocarbon residue which may be substituted; $R^4$ is hydrogen, halogen or nitro; $R^5$ is a residue capable of forming an anion or a residue convertible into an anion; X is a direct bond or a spacer having one atomic length and containing an oxygen, nitrogen or sulfur atom; Y is a direct bond or a spacer having atomic length of two or less between the phenylene group and the phenyl group; n is an integer of 1 or 2; or a salt thereof, and that the compound has an angiotensin II receptor antagonistic action and a antihypertensive action and is useful as a therapeutic agent for cardiovascular diseases such as hypertension, cardiac disease, stroke and the like.

U.S. Pat. No. 5,304,565 (JP-A-5-155862) describes a compound represented by the formula

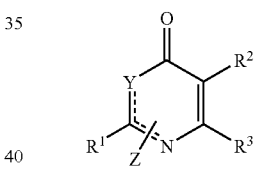

wherein $R^1$, which may be optionally bound through a hetero atom, is a hydrocarbon residue which may be substituted; $R^2$ and $R^3$ which may be same or different, are each independently hydrogen, cyano, nitro, optionally substituted lower alkyl, or a group of the formula —COD wherein D is alkoxy, hydroxy, halogen, or optionally substituted amino, or $R^2$ and $R^3$ are taken together to form a benzene ring which may be substituted; Y is N or CH; Z is bound to a ring nitrogen atom and is a group having the formula

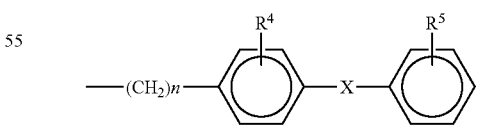

wherein $R^4$ is hydrogen, halogen or nitro, and $R^5$ is a residue capable of forming an anion or a residue convertible into an anion; X is a direct bond or a spacer having atomic length of two or less between the phenylene group and the phenyl group; n is an integer of 1 or 2; and the dotted line shows that one double bond exists; or a salt thereof, and the compound has an angiotensin II receptor antagonistic action and a antihypertensive action and is useful as a therapeutic agent for cardiovascular diseases such as hypertension, cardiac disease, stroke and the like.

U.S. Pat. No. 5,243,054 (JP-A-5-271228) describes a compound represented by the formula

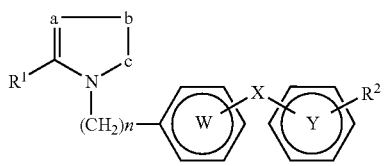

wherein $R^1$ is an optionally substituted hydrocarbon residue which is optionally bonded through a hetero atom; $R^2$ is an optionally substituted 5-7 membered heterocyclic residue having, as a group capable of constituting the ring, a carbonyl group, a thiocarbonyl group, an optionally oxidized sulfur atom or a group convertible into them; X is a direct bond or a spacer having an atomic length of two or less between the ring Y and the ring W; W and Y are independently an optionally substituted aromatic hydrocarbon residue optionally containing a hetero atom or an optionally substituted heterocyclic residue; n is an integer of 1 or 2; a and b forming the heterocyclic residue are independently one or two optionally substituted carbon or hetero atoms; c is an optionally substituted carbon or hetero atom; and, in the group of the formula

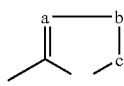

substituents on adjacent two atoms forming the ring are optionally bonded to each other to form a 5-6 membered ring together with the two atoms forming the ring, or a salt thereof, and that the compound has an angiotensin II receptor antagonistic action, a antihypertensive action and a central nervous system action and is useful as a therapeutic agent for cardiovascular diseases such as hypertension, cardiac disease, stroke, kidney diseases, arteriosclerosis and the like, or Alzheimer's disease or senile dementia.

U.S. Pat. No. 5,500,427 (JP-A-6-239859) describes a compound represented by the formula

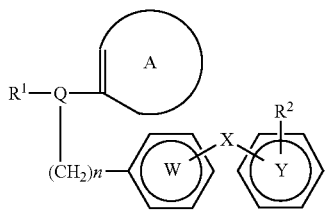

wherein $R^1$ is an optionally substituted hydrocarbon residue which is optionally bound through a hetero atom or an optionally substituted acyl group; $R^2$ is an optionally substituted 5-7 membered heterocyclic residue having, as a group capable of constituting the ring, carbonyl group, thiocarbonyl group, an optionally oxidized sulfur atom or a group convertible into them; Q is CH or N; X is a direct bond or a spacer having an atomic length of two or less between the ring Y and the ring W; rings W and Y are each an optionally substituted aromatic hydrocarbon residue optionally containing a hetero atom or an optionally substituted heterocyclic residue; n is an integer of 1 or 2; the ring A is an optionally substituted 5-8 membered cyclic group, and two of is the substituents are optionally bound to each other to form a ring, or a salt thereof, and that the compound has an angiotensin II receptor antagonistic action and a antihypertensive action, and is useful as a therapeutic agent for cardiovascular diseases such as hypertension, cardiac disease, kidney diseases (or nephropathy), stroke and the like, or an agent for improving cerebral function.

U.S. Pat. No. 5,496,835 (JP-A-7-070118) describes a compound represented by the formula

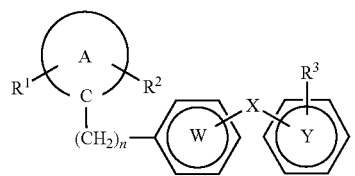

wherein the ring A is a 5-10 membered aromatic heterocyclic group optionally having, besides $R^1$ and $R^2$, further substituents; $R^1$ is an optionally substituted hydrocarbon residue which is optionally bonded through a hetero atom; $R^2$ is a group capable of liberating proton in a living body or a group convertible thereinto; $R^3$ is an 5-7 membered optionally substituted heterocyclic residue having, as a group capable of constituting the ring, carbonyl group, thiocarbonyl group, an optionally oxidized sulfur atom or a group convertible into them; X shows that the ring Y and the ring W are bonded to each other directly or through a spacer having an atomic length of two or less; the ring W and the ring Y are each an optionally substituted aromatic hydrocarbon or aromatic heterocyclic residue; and n is an integer of 1 to 3, or a salt thereof, and that compound has an angiotensin II receptor antagonistic action and a antihypertensive action and is useful as a therapeutic agent for cardiovascular diseases such as hypertension, cardiac disease, stroke and the like, or an agent for improving cerebral function.

However, there is no report that the above-mentioned compounds have an angiotensin II receptor antagonistic action and a peroxisome proliferator-activated receptor (PPAR) agonistic action.

BRIEF SUMMARY OF THE INVENTION

An object of the present invention is to provide a novel compound superior as a pharmaceutical agent for the prophylaxis or treatment of cardiovascular diseases such as hypertension and the like; metabolic diseases such as diabetes and the like; central nervous system diseases such as dementia and the like; and the like.

The present inventors have conducted intensive studies in an attempt to find a new compound having a superior pharmacological action and superior physicochemical properties so as to provide a pharmaceutical agent more useful as a prophylactic or therapeutic drug for cardiovascular diseases, metabolic diseases, central nervous system diseases, and the like. As a result, they have found that a compound represented by the following formula (I) or a salt thereof (to be referred to as "compound (I)" in the present specification) has an angiotensin II receptor antagonistic action and a peroxisome proliferator-activated receptor (PPAR) agonistic action (including a partial agonistic action) and is useful as an agent for the prophylaxis or treatment for cardiovascular diseases such as hypertension, cardiac disease (cardiac hypertrophy, cardiac failure, myocardial infarction and the like), arteriosclerosis, kidney disease (diabetic nephropathy, chronic glomerulonephritis and the like), stroke and the like; metabolic diseases such as dyslipidemia, obesity, diabetes and the like; and/or central nervous system diseases such as depression, dementia, Alzheimer's disease and the like, which resulted in the completion of the present invention.

Accordingly, the present invention relates to [1] A compound represented by the following formula (I):

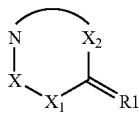
(I)

wherein
R1 is
(1) an oxo group;
(2) a thioxo group;
(3) a group represented by the formula: =N—R wherein
R is
  (i) an optionally substituted C1-C6 alkyl group;
  (ii) an optionally substituted C3-C6 cycloalkyl group;
  (iii) a group represented by the formula: —O—Ra
  wherein Ra is hydrogen, an optionally substituted C1-C6 alkyl group or an optionally substituted C3-C6 cycloalkyl group; or
  (iv) a group represented by the formula: —N(Rb)—Rc
  wherein Rb and Rc are each independently hydrogen, an optionally substituted C1-C6 alkyl group or an optionally substituted C3-C6 cycloalkyl group, or Rb and Rc are bonded to each other to form, together with the nitrogen atom bonded thereto, an optionally substituted nitrogen-containing heterocyclic group;
(4) a group represented by the formula: =N—CO—R'
  wherein R' is an optionally substituted C1-C6 alkyl group or an optionally substituted cyclic group;
(5) a group represented by the formula: =N—CO—OR'
  wherein R' is as defined above; or
(6) a group represented by the formula: =N—SO₂—R'
  wherein R' is as defined above; and
a group represented by the formula:

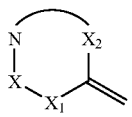
is
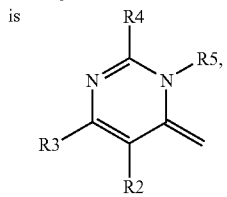, 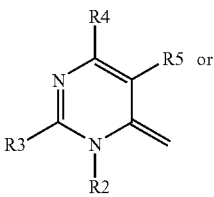

-continued
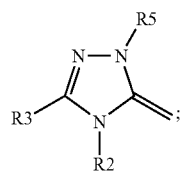;

wherein
R2 is a group represented by the formula:

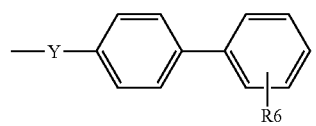

wherein R6 is a group represented by the formula:

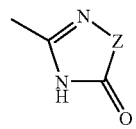

wherein Z is O or S(O)n (n is an integer of 0 to 2), and Y is an optionally substituted C1-C4 alkylene group or a group represented by the formula: —O—W—, —W—O—, —N(Rd)-W— or —W—N(Rd)-
wherein W is a bond or an optionally substituted C1-C4 alkylene group, and Rd is an optionally substituted C1-C6 alkyl group or an optionally substituted C3-C6 cycloalkyl group (the biphenyl group is optionally further substituted);

R3 and R4 are each independently
(1) hydrogen,
(2) an optionally substituted C1-C6 alkyl group,
(3) an optionally substituted C3-C6 cycloalkyl group,
(4) an optionally substituted C1-C6 alkoxy group,
(5) an optionally substituted C3-C6 cycloalkyloxy group,
(6) an optionally substituted C1-C6 alkylamino group,
(7) an optionally substituted di(C1-C6)alkylamino group or
(8) an optionally substituted C1-C6 alkylthio group; and R5 is
(1) hydrogen,
(2) an optionally substituted C1-C6 alkyl group,
(3) an optionally substituted C2-C6 alkenyl group,
(4) an optionally substituted cyclic group,
(5) a group represented by the formula: —CO—R8 wherein R8 is an optionally substituted C1-C6 alkyl group or an optionally substituted cyclic group, or
(6) a group represented by the formula: —O—R8' wherein R8' is an optionally substituted C1-C6 alkyl group or an optionally substituted cyclic group, or a salt thereof;

[2] The compound of aforementioned [1], wherein R1 is an oxo group;
[3] The compound of aforementioned [1], wherein R2 is a group represented by the formula:

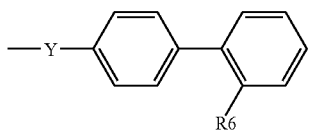

wherein R6 is a group represented by the formula:

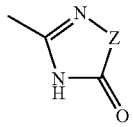

wherein Z is O or S(O)n (n is an integer of 0 to 2), and Y is a C1-C4 alkylene group, (the biphenyl group is optionally further substituted);

[4] The compound of aforementioned [3], wherein R2 is a group represented by the formula:

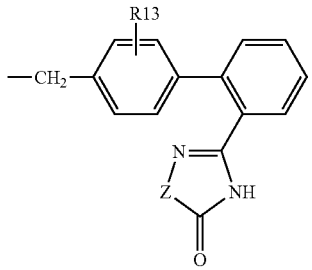

wherein R13 is
(1) hydrogen,
(2) halogen,
(3) a C1-C6 alkoxy group, or
(4) a C1-C6 alkyl group optionally having 1 to 3 substituents selected from the group consisting of halogen and a C1-C6 alkoxy group, and Z is O or S;

[5] The compound of aforementioned [1], wherein a group represented by the formula:

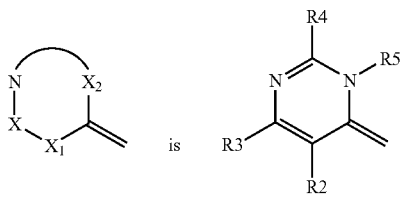

wherein R2, R3, R4 and R5 are as defined in aforementioned [1];

[6] The compound of aforementioned [5], wherein R3 is (1) a C1-C6 alkyl group optionally substituted by 1 to 3 substituents selected from the group consisting of a C1-C6 alkoxy group, halogen, a hydroxy group and a C3-C6 cycloalkyl group;
(2) a C3-C6 cycloalkyl group;
(3) a C1-C6 alkoxy group; or
(4) a C1-C6 alkylthio group;

[7] The compound of aforementioned [5], wherein R4 is (1) hydrogen;
(2) a C1-C6 alkyl group optionally substituted by 1 to 3 substituents selected from the group consisting of a C1-C6 alkoxy group, a hydroxy group, halogen, a cyclic hydrocarbon group and a heterocyclic group;
(3) a C3-C6 cycloalkyl group;
(4) a C1-C6 alkoxy group; or
(5) a di(C1-C6)alkylamino group;

[8] The compound of aforementioned [5], wherein R5 is an optionally substituted C1-C6 alkyl group or an optionally substituted cyclic group;

[9] The compound of aforementioned [8], wherein R5 is an optionally substituted C6-C14 aryl group;

[10] The compound of aforementioned [9], wherein R5 is a C6-C14 aryl group optionally substituted by 1 to 3 substituents selected from the group consisting of
(i) halogen;
(ii) a hydroxy group;
(iii) a C1-C6 alkyl group optionally substituted by 1 to 3 substituents selected from the group consisting of halogen, a hydroxy group, a C1-C6 alkoxy group and a C1-C6 alkyl-carbonyl group;
(iv) a C2-C6 alkenyl group optionally substituted by 1 to 3 substituents selected from the group consisting of halogen and a hydroxy group;
(v) a C1-C6 alkoxy group optionally substituted by 1 to 3 substituents selected from the group consisting of a C2-C6 alkynyl group, a C1-C6 alkoxy group, halogen, a cyano group, a hydroxy group, a C3-C6 cycloalkyl group, a C1-C6 alkoxy-carbonyl group and a carbamoyl group;
(vi) a C2-C6 alkenyloxy group;
(vii) a C2-C6 alkynyloxy group;
(viii) a C1-C6 alkyl-carbonylamino group;
(ix) a C1-C6 alkylthio group;
(x) a C1-C6 alkylsulfinyl group;
(xi) a C1-C6 alkylsulfonyl group;
(xii) a C1-C6 alkyl-carbonyl group;
(xiii) a C1-C6 alkyl-carbamoyl group; and
(xiv) a di(C1-C6)alkyl-carbamoyl group;

[11] 3-(4-Isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[12] 6-Butyl-2-methoxy-5-{[2'-(5-oxo-4,5-dihydro-1,2,4-oxadiazol-3-yl)biphenyl-4-yl]methyl}-3-phenylpyrimidin-4(3H)-one or a salt thereof;

[13] 6-Butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one or a salt thereof;

[14] 6-Butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one or a salt thereof;

[15] 6-Butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one or a salt thereof;

[16] 3-[4-(1-Ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[17] 3-(4-tert-Butoxyphenyl)-2-ethyl-5-{[2'-(5-oxo-4,5-dihydro-1,2,4-oxadiazol-3-yl)biphenyl-4-yl]methyl}-6-propylpyrimidin-4(3H)-one or a salt thereof;

[18] 2-Ethyl-3-[4-(2-hydroxy-1,1-dimethylethoxy)phenyl]-5-{[2'-(5-oxo-4,5-dihydro-1,2,4-oxadiazol-3-yl)biphenyl-4-yl]methyl}-6-propylpyrimidin-4(3H)-one or a salt thereof;

[19] 2-Ethyl-3-[4-(2-hydroxy-1,1-dimethylpropoxy)phenyl]-5-{[2'-(5-oxo-4,5-dihydro-1,2,4-oxadiazol-3-yl)biphenyl-4-yl]methyl}-6-propylpyrimidin-4(3H)-one or a salt thereof;

[20] A crystalline compound of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[21] A crystalline compound of hydrate of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[22] A crystalline compound of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 4.64, 5.46, 8.40, 11.10, 12.60, 13.10, 14.14, 14.36, 14.60, 15.58, 15.86, 16.24, 16.86, 17.52, 19.26, 19.72, 20.00, 20.40, 20.80, 21.12, 21.70;

[23] A crystalline compound of hydrate of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt, which has an X-ray powder diffraction analysis pattern with peaks at diffraction angle: 2θ(°) of 4.46, 6.32, 12.66, 12.84, 13.46, 13.74, 16.82, 17.08, 17.82, 17.98, 18.38, 19.70, 20.34, 21.80, 22.18, 22.80, 24.08, 25.40, 26.70;

[24] The compound of aforementioned [9], wherein R5 is a C6-C14 aryl group optionally substituted by 1 to 3 substituents selected from the group consisting of (i) a C3-C6 cycloalkyl group;

(ii) a C3-C10 cycloalkyloxy group optionally substituted by 1 to 3 substituents selected from the group consisting of halogen, an oxo group, a hydroxy group, a C1-C6 alkyl group, a C1-C6 alkoxy group optionally substituted by 1 to 3 halogens, a hydroxy-C1-C6 alkyl group and a C1-C6 alkoxy-C1-C6 alkyl group;

(iii) a C6-C14 aryloxy group;

(iv) a heterocyclyl-oxy group optionally substituted by 1 to 3 C1-C6 alkyl groups;

(v) a heterocyclyl-C1-C6 alkyloxy group; and (vi) a heterocyclic group;

[25] 3-[4-(Cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[26] 3-[4-(Cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[27] 3-[4-(Cyclopentyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[28] 2-Ethyl-5-{[2'-(5-oxo-4,5-dihydro-1,2,4-oxadiazol-3-yl)biphenyl-4-yl]methyl}-6-propyl-3-[4-(tetrahydro-2H-pyran-4-yloxy)phenyl]pyrimidin-4(3H)-one or a salt thereof;

[29] 2-Ethyl-3-(4-{[(2R)-2-hydroxycyclopentyl]oxy}phenyl)-5-{[2'-(5-oxo-4,5-dihydro-1,2,4-oxadiazol-3-yl)biphenyl-4-yl]methyl}-6-propylpyrimidin-4(3H)-one or a salt thereof;

[30] 2-Ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one or a salt thereof;

[31] 2-Ethyl-3-{4-[(cis-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one or a salt thereof;

[32] 2-Ethyl-3-{4-[(4-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one or a salt thereof;

[33] 3-(4-{[(2R,4S,6S)-2,6-Dimethyltetrahydro-2H-pyran-4-yl]oxy}phenyl)-2-ethyl-5-{[2'-(5-oxo-4,5-dihydro-1,2,4-oxadiazol-3-yl)biphenyl-4-yl]methyl}-6-propylpyrimidin-4(3H)-one or a salt thereof;

[34] 2-Ethyl-3-{4-[(3-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one or a salt thereof;

[35] A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one or a salt thereof;

[36] A crystalline compound of hydrate of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one or a salt thereof;

[37] A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 4.60, 8.38, 9.28, 9.66, 10.46, 12.26, 12.86, 13.98, 16.92, 17.32, 18.70, 18.94, 19.62, 20.18, 20.98;

[38] A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 8.50, 11.86, 12.26, 13.98, 17.14, 18.46, 19.04, 19.28, 19.62, 20.16, 20.48, 22.58, 24.60;

[39] A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 7.36, 7.66, 11.58, 12.84, 13.28, 13.64, 14.50, 15.28, 15.50, 18.38, 18.66, 19.28, 20.20, 20.70, 21.72, 22.14, 22.82;

[40] A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 8.34, 9.16, 10.64, 11.08, 11.42, 12.42, 13.18, 13.88, 14.78, 15.58, 16.28, 17.10, 17.80, 18.56, 18.94, 19.18, 20.14, 20.86, 21.56, 22.04, 22.44, 23.14, 23.66, 24.80, 26.18, 27.96, 29.16;

[41] A crystalline compound of hydrate of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt, which has an X-ray powder diffraction analysis pattern with peaks at diffraction angle: 2θ(°) of 4.32, 8.70, 9.86, 12.76, 13.10, 15.48, 18.36, 19.68, 20.62, 21.36, 21.76, 22.04, 22.44, 23.10, 24.22, 24.62, 27.94, 28.24;

[42] A crystalline compound of hydrate of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt, which has an X-ray powder diffraction analysis pattern with peaks at diffraction angle: 2θ(°) of 6.32, 6.84, 8.90, 14.36, 16.64, 17.96, 19.18, 19.94, 21.82, 22.04, 22.90, 23.62, 24.92;

[43] The compound of aforementioned [8], wherein R5 is an optionally substituted heterocyclic group;

[44] The compound of aforementioned [43], wherein R5 is a heterocyclic group optionally substituted by 1 to 3 substituents selected from the group consisting of
(i) halogen;
(ii) an oxo group;
(iii) a hydroxy group;
(iv) an amino group;
(v) a C1-C6 alkyl group optionally substituted by 1 to 3 substituents selected from the group consisting of halogen, a hydroxy group and a C1-C6 alkoxy group;
(vi) a C1-C6 alkoxy group optionally substituted by 1 to 3 substituents selected from the group consisting of halogen, a hydroxy group and a C3-C6 cycloalkyl group;
(vii) a heterocyclyl-oxy group;
(viii) a C1-C6 alkyl-carbonylamino group; and
(ix) a C1-C6 alkoxy-carbonyl group;

[45] 6-Butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one or a salt thereof;

[46] 6-Butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one or a salt thereof;

[47] 6-Butyl-3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}pyrimidin-4(3H)-one or a salt thereof;

[48] 3-(2,2-Dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[49] 3-(4-Hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[50] 6-Butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one or a salt thereof;

[51] 2-Methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one or a salt thereof;

[52] 3-(2,2-Dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[53] 3-(7-Fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[54] A crystalline compound of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[55] A crystalline compound of hydrate of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof;

[56] A crystalline compound of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 4.76, 6.10, 7.30, 7.86, 8.16, 9.18, 9.60, 10.66, 11.28, 11.94, 12.58, 13.34, 14.62, 15.10, 15.46, 16.34, 16.90, 17.76, 18.64, 19.34, 20.86, 21.58, 22.42, 24.36, 24.86;

[57] A crystalline compound of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 4.38, 7.42, 8.90, 9.68, 10.92, 11.24, 11.90, 12.56, 12.88, 13.34, 14.06, 14.92, 16.64, 17.30, 17.80, 18.70, 19.08, 19.40, 20.36, 20.90, 21.20, 21.50, 21.98, 22.40, 22.72, 22.98, 23.68;

[58] A crystalline compound of hydrate of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt, which has an X-ray powder diffraction analysis pattern with peaks at diffraction angle: 2θ(°) of 5.02, 5.36, 9.46, 10.66, 11.80, 13.42, 17.06, 17.78, 19.00, 19.18, 20.18, 20.88, 21.38, 23.26, 23.78, 25.06, 25.74, 26.06, 26.90, 27.34;

[59] The compound of aforementioned [8], wherein R5 is an optionally substituted C1-C6 alkyl group;

[60] The compound of aforementioned [59], wherein R5 is a C1-C6 alkyl group optionally substituted by 1 to 3 substituents selected from the group consisting of
(i) a hydroxy group;
(ii) a carboxy group;
(iii) a C1-C6 alkoxy-carbonyl group;
(iv) a C1-C6 alkyl-carbonyl group;
(v) a C3-C10 cycloalkyl-carbonyl group;
(vi) a C6-C14 aryl-carbonyl group optionally substituted by 1 to 3 substituents selected from the group consisting of halogen and a C1-C6 alkoxy group;
(vii) a heterocyclyl-carbonyl group;
(viii) a C1-C6 alkyl-carbamoyl group;
(ix) a C3-C6 cycloalkyl group;
(x) an adamantyl group;
(xi) a C6-C14 aryl group optionally substituted by 1 to 3 substituents selected from the group consisting of halogen; a C1-C6 alkyl group optionally substituted by 1 to 3 substituents selected from the group consisting of halogen, a hydroxy group and a C1-C6 alkoxy group; a C1-C6 alkoxy group optionally substituted by 1 to 3 substituents selected from the group consisting of halogen and a hydroxy group; a C1-C6 alkylsulfonyl group; a carboxy group; a C1-C6 alkoxy-carbonyl group; a C1-C6 alkyl-carbonyl group; and a heterocyclyl-carbonyl group;
(xii) a heterocyclic group optionally substituted by 1 to 3 substituents selected from the group consisting of halogen; a hydroxy group; a C1-C6 alkyl group optionally substituted by 1 to 3 substituents selected from the group consisting of halogen, a hydroxy group and a C1-C6 alkoxy group; a C6-C14 aryl group; a C7-C16 aralkyl group; a heterocyclic group; and a C1-C6 alkoxy group optionally substituted by 1 to 3 substituents selected from the group consisting of halogen and a hydroxy group; and
(xiii) a C1-C6 alkoxyimino group;

[61] 6-Butyl-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one;

6-butyl-3-(3,3-dimethyl-2-oxobutyl)-2-methyl-5-{[2'-(5-oxo-4,5-dihydro-1,2,4-oxadiazol-3-yl)biphenyl-4-yl]methyl}pyrimidin-4(3H)-one;

3-benzyl-6-butyl-2-methyl-5-{[2'-(5-oxo-4,5-dihydro-1,2,4-oxadiazol-3-yl)biphenyl-4-yl]methyl}pyrimidin-4(3H)-one;

6-butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one;

6-butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one;

6-butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one;

3-(1,3-benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one;

2-methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one;

6-butyl-2-methyl-5-{[2'-(5-oxo-4,5-dihydro-1,2,4-oxadiazol-3-yl)biphenyl-4-yl]methyl}-3-[(5-phenyl-1,2,4-oxadiazol-3-yl)methyl]pyrimidin-4(3H)-one; or 6-butyl-3-(2,6-difluorobenzyl)-2-methyl-5-{[2'-(5-oxo-4,5-dihydro-1,2,4-oxadiazol-3-yl)biphenyl-4-yl]methyl}pyrimidin-4(3H)-one;

or a salt thereof;

[62] The compound of aforementioned [1], wherein the group represented by the formula:

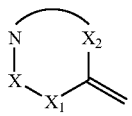

is a group represented by the formula:

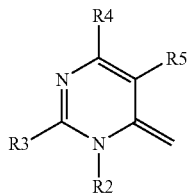

wherein R2, R3, R4 and R5 are as defined in aforementioned [1];

[63] The compound of aforementioned [62], wherein R3 is
(1) a C1-C6 alkyl group optionally substituted by 1 to 3 substituents selected from the group consisting of a C1-C6 alkoxy group, halogen, a hydroxy group and a C3-C6 cycloalkyl group;
(2) a C3-C6 cycloalkyl group;
(3) a C1-C6 alkoxy group; or
(4) a C1-C6 alkylthio group;

[64] The compound of aforementioned [62], wherein R4 is
(1) hydrogen;
(2) a C1-C6 alkyl group optionally substituted by 1 to 3 substituents selected from the group consisting of a C1-C6 alkoxy group, a hydroxy group, halogen, a cyclic hydrocarbon group and a heterocyclic group;
(3) a C3-C6 cycloalkyl group;
(4) a C1-C6 alkoxy group; or
(5) a di(C1-C6)alkylamino group;

[65] The compound of aforementioned [62], wherein R5 is an optionally substituted C1-C6 alkyl group or an optionally substituted cyclic group;

[66] 5-Benzyl-2-ethoxy-6-methyl-3-{[2'-(5-oxo-4,5-dihydro-1,2,4-oxadiazol-3-yl)biphenyl-4-yl]methyl}pyrimidin-4(3H)-one;

6-methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one;

5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one;

5-benzyl-6-methyl-3-{[2'-(5-oxo-4,5-dihydro-1,2,4-oxadiazol-3-yl)biphenyl-4-yl]methyl}-2-propylpyrimidin-4(3H)-one;

2-butyl-5-[hydroxy(phenyl)methyl]-6-methyl-3-{[2'-(5-oxo-4,5-dihydro-1,2,4-oxadiazol-3-yl)biphenyl-4-yl]methyl}pyrimidin-4(3H)-one;

5-benzoyl-2-butyl-6-methyl-3-{[2'-(5-oxo-4,5-dihydro-1,2,4-oxadiazol-3-yl)biphenyl-4-yl]methyl}pyrimidin-4(3H)-one;

6-ethyl-5-(morpholin-4-ylmethyl)-3-{[2'-(5-oxo-4,5-dihydro-1,2,4-oxadiazol-3-yl)biphenyl-4-yl]methyl}-2-propylpyrimidin-4(3H)-one;

6-ethyl-5-(1-hydroxy-2-methylpropyl)-3-{[2'-(5-oxo-4,5-dihydro-1,2,4-oxadiazol-3-yl)biphenyl-4-yl]methyl}-2-propylpyrimidin-4(3H)-one;

6-ethyl-5-(6-isopropoxypyridin-3-yl)-3-{[2'-(5-oxo-4,5-dihydro-1,2,4-oxadiazol-3-yl)biphenyl-4-yl]methyl}-2-propylpyrimidin-4(3H)-one; or 6-ethyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}-2-propylpyrimidin-4(3H)-one;

or a salt thereof;

[67] The compound of aforementioned [1], wherein the group represented by the formula:

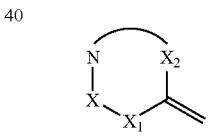

is a group represented by the formula:

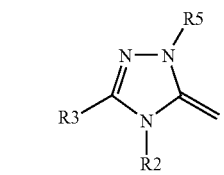

wherein R2, R3 and R5 are as defined in aforementioned [1];

[68] The compound of aforementioned [67], wherein R3 is a C1-C6 alkyl group;

[69] The compound of aforementioned [67], wherein R5 is an optionally substituted C1-C6 alkyl group or an optionally substituted cyclic group;

[70] 3-(4'-{[3-Butyl-1-(2,2-dimethylpropyl)-5-oxo-1,5-dihydro-4H-1,2,4-triazol-4-yl]methyl}biphenyl-2-yl)-1,2,4-oxadiazol-5(4H)-one;

3-(4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one;

3-(4'-{[3-butyl-5-oxo-1-(2-phenylethyl)-1,5-dihydro-4H-1,2,4-triazol-4-yl]methyl}biphenyl-2-yl)-1,2,4-oxadiazol-5(4H)-one;

3-{4'-[(3-butyl-1-sec-butyl-5-oxo-1,5-dihydro-4H-1,2,4-triazol-4-yl)methyl]biphenyl-2-yl}-1,2,4-oxadiazol-5(4H)-one;

3-{4'-[(3-butyl-5-oxo-1-phenyl-1,5-dihydro-4H-1,2,4-triazol-4-yl)methyl]biphenyl-2-yl}-1,2,4-oxadiazol-5(4H)-one;

3-(4'-{[3-butyl-5-oxo-1-(tetrahydro-2H-pyran-2-ylmethyl)-1,5-dihydro-4H-1,2,4-triazol-4-yl]methyl}biphenyl-2-yl)-1,2,4-oxadiazol-5(4H)-one;

3-[4'-({3-butyl-1-[2-(4-fluorophenyl)-2-oxoethyl]-5-oxo-1,5-dihydro-4H-1,2,4-triazol-4-yl}methyl)biphenyl-2-yl]-1,2,4-oxadiazol-5(4H)-one;

3-[4'-({3-butyl-1-[2-(4-methoxyphenyl)-2-oxoethyl]-5-oxo-1,5-dihydro-4H-1,2,4-triazol-4-yl}methyl)biphenyl-2-yl]-1,2,4-oxadiazol-5(4H)-one; or 3-(4'-{[3-butyl-1-(3,3-dimethyl-2-oxobutyl)-5-oxo-1,5-dihydro-4H-1,2,4-triazol-4-yl]methyl}biphenyl-2-yl)-1,2,4-oxadiazol-5(4H)-one;

or a salt thereof;

[71] A prodrug of the compound of aforementioned [1];

[72] A pharmaceutical agent comprising the compound of aforementioned [1] or a prodrug thereof as an active ingredient;

[73] The pharmaceutical agent of aforementioned [72], which has an angiotensin II receptor inhibitory activity and/or a peroxisome proliferator-activated receptor agonistic activity;

[74] The pharmaceutical agent of aforementioned [72], which is an agent for the prophylaxis or treatment of cardiovascular diseases, metabolic diseases and/or central nervous system diseases;

[75] The pharmaceutical agent of aforementioned [72], which is an agent for the prophylaxis or treatment of hypertension, cardiac disease, arteriosclerosis, kidney disease, stroke, dyslipidemia, obesity, diabetes, nonalcoholic steatohepatitis, dementia and/or Alzheimer's disease;

[76] A method for inhibiting an angiotensin II receptor and/or activating a peroxisome proliferator-activated receptor in a mammal, which comprises administering the compound of aforementioned [1] or a prodrug thereof to said mammal;

[77] A method for preventing or treating cardiovascular diseases, metabolic diseases and/or central nervous system diseases in a mammal, which comprises administering the compound of aforementioned [1] or a prodrug thereof to said mammal;

[78] A method for preventing or treating hypertension, cardiac disease, arteriosclerosis, kidney disease, stroke, dyslipidemia, obesity, diabetes, nonalcoholic steatohepatitis, dementia and/or Alzheimer's disease in a mammal, which comprises administering the compound of aforementioned [1] or a prodrug thereof to said mammal; and the like.

DETAILED DESCRIPTION OF THE INVENTION

The definition of each symbol used in the present specification is described in detail in the following.

In the present specification, the "halogen" is fluorine, chlorine, bromine or iodine.

In the present specification, the "C1-C6 alkyl group" is, for example, methyl, ethyl, propyl, isopropyl, butyl, isobutyl, sec-butyl, tert-butyl, pentyl, isopentyl, neopentyl, tert-pentyl, hexyl, —$CH_2CH_2C(CH_3)_3$ or the like.

In the present specification, the "C2-C6 alkenyl group" is, for example, vinyl, allyl, propenyl, isopropenyl, but-3-en-1-yl, pent-4-en-1-yl, hex-5-en-1-yl, 2-methylprop-1-en-1-yl or the like.

In the present specification, the "C2-C6 alkynyl group" is, for example, ethynyl, prop-2-yn-1-yl, but-3-yn-1-yl, pent-4-yn-1-yl, hex-5-yn-1-yl or the like.

In the present specification, the "C3-C6 cycloalkyl group" is cyclopropyl, cyclobutyl, cyclopentyl or cyclohexyl.

In the present specification, the "C6-C14 aryl group" is, for example, phenyl, naphthyl (e.g., 1-naphthyl, 2-naphthyl), anthryl, phenanthryl or the like, preferably phenyl or naphthyl, more preferably phenyl.

In the present specification, the "C7-C16 aralkyl group" is, for example, benzyl, 1-phenylethyl, 2-phenylethyl, naphthylmethyl (1-naphthylmethyl, 2-naphthylmethyl), 3-phenylpropyl, 4-phenylbutyl, 5-phenylpentyl or the like.

In the present specification, the "C1-C6 alkoxy group" is, for example, methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, —$OCH(CH_2CH_3)_2$ or the like.

In the present specification, the "optionally halogenated C1-C6 alkyl group" is the above-mentioned "C1-C6 alkyl group" optionally substituted by 1 to 5 of the above-mentioned "halogen". For example, methyl, ethyl, propyl, isopropyl, butyl, tert-butyl, isobutyl, trifluoromethyl and the like can be mentioned.

In the present specification, the "optionally halogenated C1-C6 alkoxy group" is the above-mentioned "C1-C6 alkoxy group" optionally substituted by 1 to 5 of the above-mentioned "halogen". For example, methoxy, ethoxy, propoxy, isopropoxy, butoxy, tert-butoxy, trifluoromethoxy, 2-fluoroethoxy and the like can be mentioned.

In the present specification, the "heterocyclic group" is, unless otherwise specified, for example, a 4- to 14-membered (preferably 5- to 10-membered) (monocyclic, bicyclic or tricyclic) heterocyclic group, preferably (i) a 5- to 14-membered (preferably 5- to 10-membered) aromatic heterocyclic group, (ii) a 4- to 10-membered (preferably 5- to 10-membered) non-aromatic heterocyclic group, each containing, as a ring-constituting atom besides carbon atom, 1 to 4 hetero atoms of 1 or 2 kinds selected from the group consisting of nitrogen atom, sulfur atom and oxygen atom or the like.

The "aromatic heterocyclic group" is, for example, a monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl or the like; or an aromatic fused heterocyclic group such as benzofuryl, isobenzofuryl, benzo[b]thienyl, indolyl, isoindolyl, 1H-indazolyl, benzimidazolyl, benzoxazolyl, benzo[d]isoxazolyl, benzothiazolyl, benzo[d]isothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyrazinyl, imidazo[1,2-a]pyrimidinyl, 1,2,4-triazolo[4,3-a]pyridyl, 1,2,4-triazolo[4,3-b]pyridazinyl or the like.

The "non-aromatic heterocyclic group" is, for example, a monocyclic non-aromatic heterocyclic group such as azetidinyl, oxetanyl, thietanyl, pyrrolidinyl, tetrahydrofuryl, thiolanyl, imidazolidinyl, pyrazolidinyl, oxazolidinyl, thiazolidinyl, piperidyl, tetrahydropyranyl, morpholinyl, thiomorpholinyl, piperazinyl or the like; or a non-aromatic fused heterocyclic group such as isochromanyl, dihydrobenzopyranyl, isochromenyl, chromenyl (2H-chromenyl, 4H-chromenyl), 1,2,3,4-tetrahydroisoquinolyl, 1,2,3,4-tetrahydroquinolyl, 2,3-dihydrobenzofuranyl, 1,3-benzodioxolyl or the like.

In the present specification, the "C2-C6 alkenyloxy group" is, for example, vinyloxy, allyloxy, propenyloxy, isopropenyloxy, but-3-en-1-yloxy, pent-4-en-1-yloxy, hex-5-en-1-yloxy or the like.

In the present specification, the "C2-C6 alkynyloxy group" is, for example, ethynyloxy, prop-2-yn-1-yloxy, but-3-yn-1-yloxy, pent-4-yn-1-yloxy, hex-5-yn-1-yloxy, 1-methylbut-3-yn-1-yloxy or the like.

In the present specification, the "C3-C6 cycloalkyloxy group" is cyclopropyloxy, cyclobutyloxy, cyclopentyloxy or cyclohexyloxy.

In the present specification, the "C3-C10 cycloalkyloxy group" is cyclopropyloxy, cyclobutyloxy, cyclopentyloxy, cyclohexyloxy, cycloheptyloxy, cyclooctyloxy or the like.

In the present specification, the "C6-C14 aryloxy group" is, for example, phenoxy, 1-naphthyloxy, 2-naphthyloxy or the like.

In the present specification, the "C7-C16 aralkyloxy group" is, for example, benzyloxy, phenethyloxy or the like.

In the present specification, the "heterocyclyl-oxy group" is, for example, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom. Preferable examples of the "heterocyclyl-oxy group" include tetrahydrofuranyloxy (e.g., tetrahydrofuran-3-yloxy), tetrahydropyranyloxy (e.g., tetrahydropyran-4-yloxy), piperidinyloxy (e.g., piperidin-4-yloxy) and the like.

In the present specification, the "heterocyclyl-C1-C6 alkyloxy group" is, for example, a heterocyclyl-(C1-C6)alkyloxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom. Preferable examples of the "heterocyclyl-C1-C6 alkyloxy group" include tetrahydrofuranylmethoxy (e.g., tetrahydrofuran-3-ylmethoxy), tetrahydropyranylmethoxy (e.g., tetrahydropyran-4-ylmethoxy), piperidinylmethoxy (e.g., piperidin-4-ylmethoxy) and the like.

In the present specification, the "C1-C6 alkylamino group" is, for example, an amino group monosubstituted by the above-mentioned "C1-C6 alkyl group". For example, methylamino, ethylamino, propylamino, isopropylamino, butylamino, isobutylamino, sec-butylamino, tert-butylamino, pentylamino, isopentylamino, neopentylamino, tert-pentylamino, hexylamino and the like can be mentioned.

In the present specification, the "di(C1-C6)alkylamino group" is, for example, an amino group disubstituted by the above-mentioned "C1-C6 alkyl group". For example, dimethylamino, diethylamino, N-ethyl-N-methylamino and the like can be mentioned.

In the present specification, the "C6-C14 arylamino group" is, for example, an amino group monosubstituted by the above-mentioned "C6-C14 aryl group". For example, phenylamino, 1-naphthylamino, 2-naphthylamino and the like can be mentioned.

In the present specification, the "di(C6-C14)arylamino group" is, for example, an amino group disubstituted by the above-mentioned "C6-C14 aryl group". For example, diphenylamino, dinaphthylamino and the like can be mentioned.

In the present specification, the "C7-C16 aralkylamino group" is, for example, an amino group monosubstituted by the above-mentioned "C7-C16 aralkyl group". For example, benzylamino, phenethylamino and the like can be mentioned.

In the present specification, the "di(C7-C16)aralkylamino group" is, for example, an amino group disubstituted by the above-mentioned "C7-C16 aralkyl group". For example, dibenzylamino, diphenethylamino and the like can be mentioned.

In the present specification, the "N—(C1-C6)alkyl-N—(C6-C14)arylamino group" is, for example, an amino group substituted by the above-mentioned "C1-C6 alkyl group" and the above-mentioned "C6-C14 aryl group". For example, N-methyl-N-phenylamino, N-ethyl-N-phenylamino and the like can be mentioned.

In the present specification, the "N—(C1-C6)alkyl-N—(C7-C16)aralkylamino group" is, for example, an amino group substituted by the above-mentioned "C1-C6 alkyl group" and the above-mentioned "C7-C16 aralkyl group". For example, N-methyl-N-benzylamino, N-ethyl-N-benzylamino and the like can be mentioned.

In the present specification, the "C1-C6 alkyl-carbonylamino group" is, for example, acetylamino, propanoylamino, butanoylamino, 2-methylpropanoylamino, pentanoylamino, 3-methylbutanoylamino, 2,2-dimethylpropanoylamino or the like.

In the present specification, the "C1-C6 alkylthio group" is, for example, methylthio, ethylthio, propylthio, isopropylthio, butylthio, sec-butylthio, tert-butylthio or the like.

In the present specification, the "C1-C6 alkylsulfinyl group" is, for example, methylsulfinyl, ethylsulfinyl, propylsulfinyl, isopropylsulfinyl, butylsulfinyl, sec-butylsulfinyl, tert-butylsulfinyl or the like.

In the present specification, the "C1-C6 alkylsulfonyl group" is, for example, methylsulfonyl, ethylsulfonyl, propylsulfonyl, isopropylsulfonyl, butylsulfonyl, sec-butylsulfonyl, tert-butylsulfonyl or the like.

In the present specification, the "optionally esterified carboxy group" is, for example, carboxy group, C1-C6 alkoxycarbonyl group (e.g., methoxycarbonyl, ethoxycarbonyl, propoxycarbonyl, tert-butoxycarbonyl and the like), C6-C14 aryloxy-carbonyl group (e.g., phenoxycarbonyl and the like), C7-C16 aralkyloxy-carbonyl group (e.g., benzyloxycarbonyl, phenethyloxycarbonyl and the like) or the like.

In the present specification, the "C1-C6 alkyl-carbonyl group" is, for example, acetyl, propanoyl, butanoyl, 2-methylpropanoyl, pentanoyl, 3-methylbutanoyl, 2,2-dimethylpropanoyl or the like.

In the present specification, the "C3-C10 cycloalkyl-carbonyl group" is, for example, cyclopentylcarbonyl, cyclohexylcarbonyl, adamantylcarbonyl or the like.

In the present specification, the "C6-C14 aryl-carbonyl group" is, for example, benzoyl, 1-naphthoyl, 2-naphthoyl or the like.

In the present specification, the "C7-C16 aralkyl-carbonyl group" is, for example, phenylacetyl, 3-phenylpropanoyl or the like.

In the present specification, the "C1-C6 alkoxy-carbonyl group" is, for example, methoxycarbonyl, ethoxycarbonyl, propoxycarbonyl, tert-butoxycarbonyl or the like.

In the present specification, the "C6-C14 aryloxy-carbonyl group" is, for example, phenoxycarbonyl, 1-naphthyloxycarbonyl, 2-naphthyloxycarbonyl or the like.

In the present specification, the "C7-C16 aralkyloxy-carbonyl group" is, for example, benzyloxycarbonyl, phenethyloxycarbonyl or the like.

In the present specification, the "heterocyclyl-carbonyl group" is, for example, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom. Preferable examples of the "heterocyclyl-carbonyl group" include 1-pyrrolidinylcarbonyl, piperidinocarbonyl, 1-piperazinylcarbonyl, morpholinocarbonyl, thiomorpholinocarbonyl and the like.

In the present specification, the "C1-C6 alkyl-carbamoyl group" is, for example, a carbamoyl group monosubstituted by the above-mentioned "C1-C6 alkyl group". For example, methylcarbamoyl, ethylcarbamoyl and the like can be mentioned.

In the present specification, the "di(C1-C6)alkyl-carbamoyl group" is, for example, a carbamoyl group disubstituted by the above-mentioned "C1-C6 alkyl group". For example, dimethylcarbamoyl, diethylcarbamoyl, N-ethyl-N-methylcarbamoyl and the like can be mentioned.

In the present specification, the "C6-C14 aryl-carbamoyl group" is, for example, a carbamoyl group monosubstituted by the above-mentioned "C6-C14 aryl group". For example, phenylcarbamoyl, 1-naphthylcarbamoyl, 2-naphthylcarbamoyl and the like can be mentioned.

In the present specification, the "di(C6-C14)aryl-carbamoyl group" is, for example, a carbamoyl group disubstituted by the above-mentioned "C6-C14 aryl group". For example, diphenylcarbamoyl, dinaphthylcarbamoyl and the like can be mentioned.

In the present specification, the "C1-C6 alkylsulfamoyl group" is, for example, a sulfamoyl group monosubstituted by the above-mentioned "C1-C6 alkyl group". For example, methylsulfamoyl, ethylsulfamoyl and the like can be mentioned.

In the present specification, the "di(C1-C6)alkylsulfamoyl group" is, for example, a sulfamoyl group disubstituted by the above-mentioned "C1-C6 alkyl group". For example, dimethylsulfamoyl, diethylsulfamoyl, N-ethyl-N-methylsulfamoyl and the like can be mentioned.

In the present specification, the "C6-C14 arylsulfamoyl group" is, for example, a sulfamoyl group monosubstituted by the above-mentioned "C6-C14 aryl group". For example, phenylsulfamoyl, 1-naphthylsulfamoyl, 2-naphthylsulfamoyl and the like can be mentioned.

In the present specification, the "di(C6-C14)arylsulfamoyl group" is, for example, a sulfamoyl group disubstituted by the above-mentioned "C6-C14 aryl group". For example, diphenylsulfamoyl, dinaphthylsulfamoyl and the like can be mentioned.

In the present specification, the "C1-C6 alkoxyimino group" is, for example, methoxyimino, ethoxyimino, propoxyimino, isopropoxyimino, butoxy imino, isobutoxyimino, sec-butoxy imino, tert-butoxy imino, pentyloxyimino, hexyloxyimino or the like.

In the present specification, the "hydroxy-C1-C6 alkyl group" is, for example, hydroxymethyl, 2-hydroxyethyl, 1-hydroxyethyl, 3-hydroxypropyl, 1-hydroxy-1-methylethyl or the like.

In the present specification, the "C1-C6 alkoxy-C1-C6 alkyl group" is, for example, methoxymethyl, 2-methoxyethyl, 1-methoxyethyl, ethoxymethyl, 2-ethoxyethyl or the like.

In the present specification, the "optionally substituted C1-C6 alkyl group", "optionally substituted C2-C6 alkenyl group", "optionally substituted C2-C6 alkynyl group", "optionally substituted C1-C6 alkoxy group" or "optionally substituted C1-C6 alkylthio group" is, for example, "C1-C6 alkyl group", "C2-C6 alkenyl group", "C2-C6 alkynyl group", "C1-C6 alkoxy group" or "C1-C6 alkylthio group", each optionally substituted by 1 to 5, preferably 1 to 3, substituents selected from the group consisting of (1) halogen,
(2) a hydroxy group,
(3) an amino group,
(4) a nitro group,
(5) a cyano group,
(6) an optionally halogenated C1-C6 alkoxy group,
(7) a C3-C6 cycloalkyloxy group,
(8) a C6-C14 aryloxy group,
(9) a C7-C16 aralkyloxy group,
(10) a C1-C6 alkylamino group,
(11) a di(C1-C6)alkylamino group,
(12) a C6-C14 arylamino group,
(13) a di(C6-C14)arylamino group,
(14) a C7-C16 aralkylamino group,
(15) a di(C7-C16)aralkylamino group,
(16) a N—(C1-C6)alkyl-N—(C6-C14)arylamino group,
(17) an N—(C1-C6)alkyl-N—(C7-C16)aralkylamino group,
(18) a C1-C6 alkyl-carbonylamino group,
(19) a C1-C6 alkylthio group,
(20) a C1-C6 alkylsulfinyl group,
(21) a C1-C6 alkylsulfonyl group,
(22) an optionally esterified carboxy group,
(23) a C1-C6 alkyl-carbonyl group,
(24) a C3-C10 cycloalkyl-carbonyl group,
(25) an optionally substituted C6-C14 aryl-carbonyl group,
(26) a C7-C16 aralkyl-carbonyl group,
(27) a heterocyclyl-carbonyl group,
(28) a carbamoyl group,
(29) a thiocarbamoyl group,
(30) a C1-C6 alkyl-carbamoyl group,
(31) a di(C1-C6)alkyl-carbamoyl group,
(32) a C6-C14 aryl-carbamoyl group,
(33) a di(C6-C14)aryl-carbamoyl group,
(34) a sulfamoyl group,
(35) a C1-C6 alkylsulfamoyl group,
(36) a di(C1-C6)alkylsulfamoyl group,
(37) a C6-C14 arylsulfamoyl group,
(38) a di(C6-C14)arylsulfamoyl group,
(39) an optionally substituted cyclic group,
(40) a C1-C6 alkoxyimino group,
and the like. Here, the "optionally substituted cyclic group" includes, for example, those similar to the below-mentioned "optionally substituted cyclic group" for R5.

In the present specification, the "C6-C14 aryl-carbonyl group" of the "optionally substituted C6-C14 aryl-carbonyl group" optionally has 1 to 5, preferably 1 to 3, substituents at substitutable position(s). Examples of such substituent include halogen, a hydroxy group, an optionally halogenated C1-C6 alkyl group, an optionally halogenated C1-C6 alkoxy group, an amino group, a C1-C6 alkylamino group, a di(C1-C6)alkylamino group, a C1-C6 alkylthio group, a C1-C6 alkylsulfonyl group, a carboxy group, a C1-C6 alkoxy-carbonyl group, a C1-C6 alkyl-carbonyl group and the like.

In the present specification, the "optionally substituted C1-C6 alkylamino group" is, for example, an amino group monosubstituted by the above-mentioned "optionally substituted C1-C6 alkyl group".

In the present specification, the "optionally substituted di(C1-C6)alkylamino group" is, for example, an amino group disubstituted by the above-mentioned "optionally substituted C1-C6 alkyl group".

In the aforementioned formulas, R5 is hydrogen, an optionally substituted C1-C6 alkyl group, an optionally substituted C2-C6 alkenyl group, an optionally substituted cyclic group, a group represented by the formula: —CO—R8 wherein R8 is an optionally substituted C1-C6 alkyl group or an optionally substituted cyclic group, or a group represented by the formula: —O—R8' wherein R8' is an optionally substituted C1-C6 alkyl group or an optionally substituted cyclic group.

Preferably, R5 is an optionally substituted C1-C6 alkyl group or an optionally substituted cyclic group, more preferably an optionally substituted cyclic group.

The "cyclic group" of the "optionally substituted cyclic group" for R5 is, for example, a cyclic hydrocarbon group or a heterocyclic group.

The "cyclic hydrocarbon group" is, for example, an alicyclic hydrocarbon group constituted by 3 to 14 carbon atoms, an aromatic hydrocarbon group constituted by 6 to 14 carbon atoms, or the like.

The "alicyclic hydrocarbon group" is, for example, a C3-C6 cycloalkyl group (e.g., cyclopropyl, cyclobutyl, cyclopentyl, cyclohexyl and the like), a C3-C6 cycloalkenyl group (e.g., cyclopentenyl, cyclohexenyl and the like), a C5-C14 cycloalkadienyl group (e.g., 2,4-cyclopentadienyl, 1,3-cyclohexadienyl and the like), an indanyl group, an adamantyl group or the like.

The "aromatic hydrocarbon group" is, for example, a C6-C14 aryl group (e.g., phenyl, naphthyl, anthryl, phenanthryl and the like) or the like.

The "heterocyclic group" is, for example, a 4- to 14-membered (preferably 5- to 10-membered) (monocyclic, bicyclic or tricyclic) heterocyclic group, preferably (i) a 5- to 14-membered (preferably 5- to 10-membered) aromatic heterocyclic group or (ii) a 4- to 10-membered (preferably 5- to 10-membered) non-aromatic heterocyclic group, each containing, as a ring-constituting atom besides carbon atom, 1 to 4 hetero atoms of 1 or 2 kinds selected from the group consisting of nitrogen atom, sulfur atom and oxygen atom, or the like.

The "aromatic heterocyclic group" is, for example, a monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl or the like; or an aromatic fused heterocyclic group such as benzofuryl, isobenzofuryl, benzo[b]thienyl, indolyl, isoindolyl, 1H-indazolyl, benzimidazolyl, benzoxazolyl, benzo[d]isoxazolyl, benzothiazolyl, benzo[d]isothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazinyl, imidazo[1,2-a]pyrimidinyl, 1,2,4-triazolo[4,3-a]pyridyl, 1,2,4-triazolo[4,3-b]pyridazinyl or the like.

The "non-aromatic heterocyclic group" is, for example, a monocyclic non-aromatic heterocyclic group such as oxiranyl, azetidinyl, oxetanyl, thietanyl, pyrrolidinyl, tetrahydrofuryl, thiolanyl, imidazolidinyl, pyrazolidinyl, oxazolidinyl, thiazolidinyl, piperidyl, tetrahydropyranyl, morpholinyl, thiomorpholinyl, piperazinyl or the like; or a non-aromatic fused heterocyclic group such as isochromanyl, dihydrobenzopyranyl, isochromenyl, chromenyl (2H-chromenyl, 4H-chromenyl), 1,2,3,4-tetrahydroisoquinolyl, 1,2,3,4-tetrahydroquinolyl, 2,3-dihydrobenzofuranyl, 1,3-benzodioxolyl or the like.

The "cyclic group" of the "optionally substituted cyclic group" for R5 is preferably a C3-C6 cycloalkyl group, a C3-C6 cycloalkenyl group, an indanyl group, a C6-C14 aryl group, a heterocyclic group or the like, more preferably a C6-C14 aryl group or a heterocyclic group.

The "cyclic group" of the "optionally substituted cyclic group" for R5 optionally has 1 to 5, preferably 1 to 3, substituents at substitutable position(s). Such substituent includes, for example, (1) halogen,
(2) an oxo group,
(3) a hydroxy group,
(4) an amino group,
(5) a nitro group,
(6) a cyano group,
(7) a C1-C6 alkyl group,
(8) a C2-C6 alkenyl group,
(9) a C2-C6 alkynyl group,
(10) a C3-C6 cycloalkyl group,
(11) a C6-C14 aryl group,
(12) a C7-C16 aralkyl group,
(13) a heterocyclic group,
(14) a C1-C6 alkoxy group,
(15) a C2-C6 alkenyloxy group,
(16) a C2-C6 alkynyloxy group,
(17) an optionally substituted C3-C10 cycloalkyloxy group (preferably, a C3-C10 cycloalkyloxy group optionally substituted by 1 to 3 substituents selected from the group consisting of halogen, an oxo group, a hydroxy group, a C1-C6 alkyl group, a C1-C6 alkoxy group optionally substituted by 1 to 3 halogens, a hydroxy-C1-C6 alkyl group and a C1-C6 alkoxy-C1-C6 alkyl group),
(18) a C6-C14 aryloxy group,
(19) a C7-C16 aralkyloxy group,
(20) an optionally substituted heterocyclyl-oxy group (preferably, a heterocyclyl-oxy group optionally substituted by 1 to 3 C1-C6 alkyl groups),
(21) a heterocyclyl-C1-C6 alkyloxy group,
(22) a C1-C6 alkylamino group,
(23) a di(C1-C6)alkylamino group,
(24) a C6-C14 arylamino group,
(25) a di(C6-C14)arylamino group,
(26) a C7-C16 aralkylamino group,
(27) a di(C7-C16)aralkylamino group,
(28) an N—(C1-C6)alkyl-N—(C6-C14)arylamino group,
(29) an N—(C1-C6)alkyl-N—(C7-C16)aralkylamino group,
(30) a C1-C6 alkyl-carbonylamino group,
(31) a C1-C6 alkylthio group,
(32) a C1-C6 alkylsulfinyl group,
(33) a C1-C6 alkylsulfonyl group,
(34) an optionally esterified carboxy group,
(35) a C1-C6 alkyl-carbonyl group,
(36) a C3-C6 cycloalkyl-carbonyl group,
(37) a C6-C14 aryl-carbonyl group,
(38) a C7-C16 aralkyl-carbonyl group,
(39) a heterocyclyl-carbonyl group,

(40) a carbamoyl group,
(41) a thiocarbamoyl group,
(42) a C1-C6 alkyl-carbamoyl group,
(43) a di(C1-C6)alkyl-carbamoyl group,
(44) a C6-C14 aryl-carbamoyl group,
(45) a di(C6-C14)aryl-carbamoyl group,
(46) a sulfamoyl group,
(47) a C1-C6 alkylsulfamoyl group,
(48) a di(C1-C6)alkylsulfamoyl group,
(49) a C6-C14 arylsulfamoyl group,
(50) a di(C6-C14)arylsulfamoyl group,
and the like. Here, the "C1-C6 alkyl group", "C2-C6 alkenyl group" and "C2-C6 alkynyl group" are each optionally substituted by 1 to 3 substituents selected from the group consisting of a C1-C6 alkoxy group, halogen, a cyano group, a hydroxy group, a C1-C6 alkylamino group, a di(C1-C6)alkylamino group, a C3-C6 cycloalkyl group, a C1-C6 alkyl-carbonyl group, a C1-C6 alkoxy-carbonyl group and a carbamoyl group. In addition, the "C1-C6 alkoxy group" is optionally substituted by 1 to 3 substituents selected from the group consisting of a C2-C6 alkynyl group, a C1-C6 alkoxy group, halogen, a cyano group, a hydroxy group, a C1-C6 alkylamino group, a di(C1-C6) alkylamino group, a C3-C6 cycloalkyl group, a C1-C6 alkyl-carbonyl group, a C1-C6 alkoxy-carbonyl group and a carbamoyl group.

The "optionally substituted cyclic group" for R5 is preferably a cyclic group optionally substituted by 1 to 3 substituents selected from the group consisting of
(1) a C1-C6 alkyl group,
(2) a C2-C6 alkenyl group,
(3) a C3-C6 cycloalkyl group,
(4) an oxo group,
(5) a hydroxy group,
(6) an amino group,
(7) a C1-C6 alkoxy group,
(8) a C2-C6 alkenyloxy group,
(9) a C2-C6 alkynyloxy group,
(10) an optionally substituted C3-C10 cycloalkyloxy group (preferably, a C3-C10 cycloalkyloxy group optionally substituted by 1 to 3 substituents selected from the group consisting of halogen, an oxo group, a hydroxy group, a C1-C6 alkyl group, a C1-C6 alkoxy group optionally substituted by 1 to 3 halogens, a hydroxy-C1-C6 alkyl group and a C1-C6 alkoxy-C1-C6 alkyl group),
(11) a C6-C14 aryloxy group,
(12) an optionally substituted heterocyclyl-oxy group (preferably, a heterocyclyl-oxy group optionally substituted by 1 to 3 C1-C6 alkyl groups),
(13) a heterocyclyl-C1-C6 alkyloxy group,
(14) a C1-C6 alkylamino group,
(15) a di(C1-C6)alkylamino group,
(16) a C1-C6 alkyl-carbonylamino group,
(17) a C1-C6 alkylthio group,
(18) a C1-C6 alkylsulfinyl group,
(19) a C1-C6 alkylsulfonyl group,
(20) a C1-C6 alkoxy-carbonyl group,
(21) a C1-C6 alkyl-carbonyl group,
(22) a C1-C6 alkyl-carbamoyl group,
(23) a di(C1-C6)alkyl-carbamoyl group,
(24) a heterocyclic group,
(25) halogen (wherein the "C1-C6 alkyl group" and "C2-C6 alkenyl group" are each optionally substituted by 1 to 3 substituents selected from the group consisting of a C1-C6 alkoxy group, halogen, a cyano group, a hydroxy group, a C1-C6 alkylamino group, a di(C1-C6)alkylamino group, a C3-C6 cycloalkyl group, a C1-C6 alkyl-carbonyl group, a C1-C6 alkoxy-carbonyl group and a carbamoyl group, and the "C1-C6 alkoxy group" is optionally substituted by 1 to 3 substituents selected from the group consisting of a C2-C6 alkynyl group, a C1-C6 alkoxy group, halogen, a cyano group, a hydroxy group, a C1-C6 alkylamino group, a di(C1-C6)alkylamino group, a C3-C6 cycloalkyl group, a C1-C6 alkyl-carbonyl group, a C1-C6 alkoxy-carbonyl group and a carbamoyl group) and the like.

The "optionally substituted cyclic group" for R5 is more preferably
(1) a C3-C6 cycloalkyl group (e.g., cyclopropyl and the like),
(2) a C3-C6 cycloalkenyl group (e.g., cyclohexenyl and the like),
(3) an indanyl group optionally substituted by an oxo group or a hydroxy group,
(4) a C6-C14 aryl group (e.g., phenyl, naphthyl and the like, preferably phenyl) optionally substituted by 1 to 3 substituents selected from the group consisting of
(i) halogen (e.g., F, Cl, Br and the like);
(ii) a hydroxy group;
(iii) a C1-C6 alkyl group optionally substituted by 1 to 3 substituents selected from the group consisting of halogen, a hydroxy group, a C1-C6 alkoxy group and a C1-C6 alkyl-carbonyl group (e.g., methyl, ethyl, isopropyl, isobutyl, tert-butyl, trifluoromethyl, hydroxymethyl, 1-hydroxyethyl and the like);
(iv) a C2-C6 alkenyl group (e.g., vinyl and the like) optionally substituted by 1 to 3 substituents selected from the group consisting of halogen and a hydroxy group;
(v) a C3-C6 cycloalkyl group (e.g., cyclopropyl and the like);
(vi) a C1-C6 alkoxy group (e.g., methoxy, ethoxy, propoxy, isopropoxy, isobutoxy, sec-butoxy, tert-butoxy, neopentyloxy and the like) optionally substituted by 1 to 3 substituents selected from the group consisting of a C2-C6 alkynyl group, a C1-C6 alkoxy group, halogen, a cyano group, a hydroxy group, a C3-C6 cycloalkyl group, a C1-C6 alkoxy-carbonyl group and a carbamoyl group;
(vii) a C2-C6 alkenyloxy group (e.g., vinyloxy and the like);
(viii) a C2-C6 alkynyloxy group (e.g., 1-methylbut-3-yn-1-yloxy and the like);
(ix) a C3-C10 cycloalkyloxy group (e.g., cyclopropyloxy, cyclobutyloxy, cyclopentyloxy, cyclohexyloxy, cycloheptyloxy and the like) optionally substituted by 1 to 3 substituents selected from the group consisting of halogen, an oxo group, a hydroxy group, a C1-C6 alkyl group, a C1-C6 alkoxy group optionally substituted by 1 to 3 halogens, a hydroxy-C1-C6 alkyl group and a C1-C6 alkoxy-C1-C6 alkyl group;
(x) a C6-C14 aryloxy group (e.g., phenoxy and the like);
(xi) a heterocyclyl-oxy group (preferably, a heterocyclyl-oxy group wherein the heterocyclyl moiety is 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydrofuranyloxy, tetrahydropyranyloxy, piperidinyloxy and the like) optionally substituted by 1 to 3 C1-C6 alkyl groups;
(xii) a heterocyclyl-C1-C6 alkyloxy group (preferably, a heterocyclyl-C1-C6 alkyloxy group wherein the heterocyclyl moiety is 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranylmethoxy and the like);
(xiii) a C1-C6 alkyl-carbonylamino group (e.g., acetylamino and the like);
(xiv) a C1-C6 alkylthio group (e.g., methylthio, isopropylthio and the like);
(xv) a C1-C6 alkylsulfinyl group (e.g., methylsulfinyl, isopropylsulfinyl and the like)
(xvi) a C1-C6 alkylsulfonyl group (e.g., methylsulfonyl, isopropylsulfonyl and the like);
(xvii) a C1-C6 alkyl-carbonyl group (e.g., acetyl and the like);
(xviii) a C1-C6 alkyl-carbamoyl group (e.g., methylcarbamoyl and the like);
(xix) a di(C1-C6)alkyl-carbamoyl group (e.g., dimethylcarbamoyl and the like);
(xx) a heterocyclic group (preferably, 5- or 6-membered, aromatic or non-aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like), and the like,
(5) a heterocyclic group (preferably, 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, isoxazolyl, pyrazolyl, pyridyl, dihydrobenzopyranyl, chromenyl, 2,3-dihydrobenzofuranyl, 1,3-benzodioxolyl, tetrahydropyranyl, indolyl and the like) optionally substituted by 1 to 3 substituents selected from the group consisting of
(i) halogen (e.g., F, Cl, Br and the like);
(ii) an oxo group;
(iii) a hydroxy group;
(iv) an amino group;
(v) a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like);
(vi) a C1-C6 alkoxy group optionally substituted by 1 to 3 substituents selected from the group consisting of halogen, a hydroxy group and a C3-C6 cycloalkyl group (e.g., methoxy, ethoxy, isopropoxy, neopentyloxy, trifluoromethoxy and the like);
(vii) a heterocyclyl-oxy group (preferably, a heterocyclyl-oxy group wherein the heterocyclyl moiety is 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyloxy and the like);
(viii) a C1-C6 alkyl-carbonylamino group (e.g., acetylamino and the like);
(ix) a C1-C6 alkoxy-carbonyl group (e.g., methoxycarbonyl and the like)
and the like, or the like.

The "C1-C6 alkyl group" of the "optionally substituted C1-C6 alkyl group" or "C2-C6 alkenyl group" of the "optionally substituted C2-C6 alkenyl group" for R5 optionally has 1 to 5, preferably 1 to 3, substituents at substitutable position(s). Such substituent includes, for example,
(1) halogen,
(2) a hydroxy group,
(3) an amino group,
(4) a nitro group,
(5) a cyano group,
(6) an optionally halogenated C1-C6 alkoxy group,
(7) a C3-C6 cycloalkyloxy group,
(8) a C6-C14 aryloxy group,
(9) a C7-C16 aralkyloxy group,
(10) a C1-C6 alkylamino group,
(11) a di(C1-C6)alkylamino group,
(12) a C6-C14 arylamino group,
(13) a di(C6-C14)arylamino group,
(14) a C7-C16 aralkylamino group,
(15) a di(C7-C16)aralkylamino group,
(16) an N—(C1-C6)alkyl-N—(C6-C14)arylamino group,
(17) an N—(C1-C6)alkyl-N—(C7-C16)aralkylamino group,
(18) a C1-C6 alkyl-carbonylamino group,
(19) a C1-C6 alkylthio group,
(20) a C1-C6 alkylsulfinyl group,
(21) a C1-C6 alkylsulfonyl group,
(22) an optionally esterified carboxy group,
(23) a C1-C6 alkyl-carbonyl group,
(24) a C3-C10 cycloalkyl-carbonyl group,
(25) an optionally substituted C6-C14 aryl-carbonyl group,
(26) a C7-C16 aralkyl-carbonyl group,
(27) a heterocyclyl-carbonyl group,
(28) a carbamoyl group,
(29) a thiocarbamoyl group,
(30) a C1-C6 alkyl-carbamoyl group,
(31) a di(C1-C6)alkyl-carbamoyl group,
(32) a C6-C14 aryl-carbamoyl group,
(33) a di(C6-C14)aryl-carbamoyl group,
(34) a sulfamoyl group,
(35) a C1-C6 alkylsulfamoyl group,
(36) a di(C1-C6)alkylsulfamoyl group,
(37) a C6-C14 arylsulfamoyl group,
(38) a di(C6-C14)arylsulfamoyl group,
(39) an optionally substituted cyclic group,
(40) a C1-C6 alkoxyimino group,
and the like.

The "optionally substituted C6-C14 aryl-carbonyl group" as a substituent of the above-mentioned "optionally substituted C1-C6 alkyl group" or "optionally substituted C2-C6 alkenyl group" for R5 is preferably a C6-C14 aryl-carbonyl group optionally substituted by 1 to 3 substituents selected from the group consisting of halogen and a C1-C6 alkoxy group.

Examples of the "optionally substituted cyclic group" as a substituent of the above-mentioned "optionally substituted C1-C6 alkyl group" or "optionally substituted C2-C6 alkenyl group" for R5 include those similar to the aforementioned "optionally substituted cyclic group" for R5.

The "cyclic group" of the "optionally substituted cyclic group" is preferably C3-C6 cycloalkyl group, adamantyl group, C6-C14 aryl group, a heterocyclic group or the like.

The "cyclic group" of the "optionally substituted cyclic group" optionally has 1 to 5, preferably 1 to 3, substituents at substitutable position(s). Examples of such substituent preferably include
(1) halogen,
(2) a hydroxy group,
(3) a C1-C6 alkyl group optionally substituted by 1 to 3 substituents selected from the group consisting of halogen, a hydroxy group and a C1-C6 alkoxy group,
(4) a C6-C14 aryl group,
(5) a C7-C16 aralkyl group,
(6) a heterocyclic group, (7) a C1-C6 alkoxy group optionally substituted by 1 to 3 substituents selected from the group consisting of halogen and a hydroxy group,
(8) a C1-C6 alkylsulfonyl group,
(9) a carboxy group,
(10) a C1-C6 alkoxy-carbonyl group,
(11) a C1-C6 alkyl-carbonyl group,
(12) a heterocyclyl-carbonyl group,
and the like.

The "optionally substituted C1-C6 alkyl group" for R5 is preferably a C1-C6 alkyl group optionally substituted by 1 to 3 substituents selected from the group consisting of a hydroxy group, a C1-C6 alkoxy group, a C1-C6 alkylamino group, a carboxy group, a C1-C6 alkoxy-carbonyl group, a C1-C6 alkyl-carbonyl group, a C3-C10 cycloalkyl-carbonyl group, an optionally substituted C6-C14 aryl-carbonyl group, a heterocyclyl-carbonyl group, a C1-C6 alkyl-carbamoyl group, halogen, an optionally substituted cyclic group and a C1-C6 alkoxyimino group.

The "optionally substituted C1-C6 alkyl group" for R5 is more preferably a C1-C6 alkyl group optionally substituted by 1 to 3 substituents selected from the group consisting of
(1) a hydroxy group,
(2) a C1-C6 alkoxy group,
(3) a C1-C6 alkylamino group,
(4) a carboxy group,
(5) a C1-C6 alkoxy-carbonyl group (e.g., ethoxycarbonyl and the like),
(6) a C1-C6 alkyl-carbonyl group (e.g., pivaloyl and the like),
(7) a C3-C10 cycloalkyl-carbonyl group (e.g., cyclohexylcarbonyl, adamantylcarbonyl and the like),
(8) a C6-C14 aryl-carbonyl group (e.g., benzoyl and the like) optionally substituted by 1 to 3 substituents selected from the group consisting of halogen and a C1-C6 alkoxy group,
(9) a C1-C6 alkyl-carbamoyl group (e.g., tert-butylcarbamoyl and the like),
(10) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like),
(11) a C3-C6 cycloalkyl group (e.g., cyclopropyl, cyclohexyl and the like),
(12) an adamantyl group,
(13) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxy-carbonyl group (e.g., methoxycarbonyl and the like); a C1-C6 alkyl-carbonyl group (e.g., acetyl and the like); a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like) and the like,
(14) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, thiazolyl, isoxazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like,
(15) a C1-C6 alkoxyimino group (e.g., isopropoxyimino group),
and the like.

The "optionally substituted C2-C6 alkenyl group" for R5 is preferably a C2-C6 alkenyl group (e.g., vinyl, allyl, propenyl, isopropenyl, but-3-en-1-yl, pent-4-en-1-yl, hex-5-en-1-yl, 2-methylprop-1-en-1-yl) optionally substituted by 1 to 3 substituents selected from the group consisting of a hydroxy group, a C1-C6 alkoxy group, a C1-C6 alkylamino group, a carboxy group, a C1-C6 alkoxy-carbonyl group, a C1-C6 alkyl-carbonyl group, a C3-C10 cycloalkyl-carbonyl group, an optionally substituted C6-C14 aryl-carbonyl group, a heterocyclyl-carbonyl group, a C1-C6 alkyl-carbamoyl group, halogen, an optionally substituted cyclic group and a C1-C6 alkoxyimino group.

Examples of the "optionally substituted C1-C6 alkyl group" for R8 or R8' include those similar to the aforementioned "optionally substituted C1-C6 alkyl" for R5.

Examples of the "optionally substituted cyclic group" for R8 or R8' include those similar to the aforementioned "optionally substituted cyclic group" for R5.

R8 and R8' are preferably optionally substituted cyclic groups.

The "cyclic group" of the "optionally substituted cyclic group" for R8 or R8' is preferably a C6-C14 aryl group, a heterocyclic group or the like.

The "cyclic group" of the "optionally substituted cyclic group" for R8 or R8' optionally has 1 to 5, preferably 1 to 3, substituents at substitutable position(s). Examples of such substituent include
(1) halogen,
(2) a hydroxy group,
(3) an amino group, (4) a C1-C6 alkyl group optionally substituted by 1 to 3 substituents selected from the group consisting of halogen, a hydroxy group and a C1-C6 alkoxy group,
(5) a C1-C6 alkoxy group optionally substituted by 1 to 3 substituents selected from the group consisting of halogen and a hydroxy group,
(6) a C1-C6 alkylamino group,
(7) a di(C1-C6)alkylamino group,
(8) a C1-C6 alkylthio group,
(9) a C1-C6 alkylsulfonyl group,
(10) a carboxy group,
(11) a C1-C6 alkoxy-carbonyl group,
(12) a C1-C6 alkyl-carbonyl group
and the like.

Examples of the "optionally substituted cyclic group" for R8 preferably include
(1) a C6-C14 aryl group (e.g., phenyl),
(2) a heterocyclic group (preferably a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., thienyl, thiazolyl, isoxazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 1,3-benzodioxolyl, 2,3-dihydrobenzofuranyl, preferably, morpholinyl),
and the like.

Examples of the group represented by the formula: —CO—R8 preferably include
(1) a C6-C14 aryl (e.g., phenyl)-carbonyl group,
(2) a heterocyclyl-carbonyl group (heterocyclyl moiety of the heterocyclyl-carbonyl group is preferably a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring (e.g., thienyl, thiazolyl, isoxazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 1,3-benzodioxolyl, 2,3-dihydrobenzofuranyl)),
and the like.

Examples of the "optionally substituted cyclic group" for R8' preferably include
(1) a C6-C14 aryl group (e.g., phenyl) optionally having 1 to 3 substituents selected from halogen; a C1-C6 alkyl group; and a C1-C6 alkoxy group optionally substituted by a hydroxy group,
(2) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring (e.g., thienyl, thiazolyl, isoxazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 1,3-benzodioxolyl, 2,3-dihydrobenzofuranyl)) optionally substituted by 1 to 3 C1-C6 alkyl groups, and the like.

Examples of the group represented by the formula: —O—R8' preferably include
(1) a C6-C14 aryl (e.g., phenyl)-oxy group optionally having 1 to 3 substituents selected from halogen; a C1-C6 alkyl group; and a C1-C6 alkoxy group optionally substituted by hydroxy group,
(2) a heterocyclyl-oxy group (preferably, the heterocyclyl moiety of the heterocyclyl-oxy group is a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring (e.g., thienyl, thiazolyl, isoxazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 1,3-benzodioxolyl, 2,3-dihydrobenzofuranyl)) optionally substituted by 1 to 3 C1-C6 alkyl groups, and the like.

R6 is a monocycle heterocyclic group represented by the formula

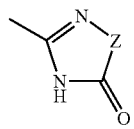

wherein Z is O or S(O)n (n is an integer of 0 to 2). Z is preferably O or S.

While the substitutable position of R6 may be any of ortho, meta and para, with preference given to ortho position.

The monocycle heterocyclic group for R6 includes the following three tautomers of a', b' and c'.

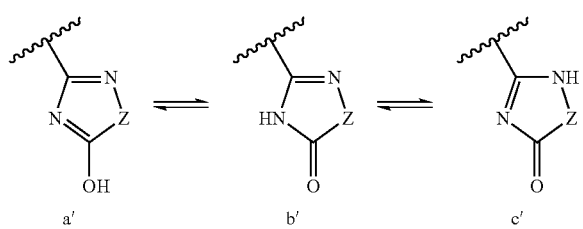

The above-mentioned heterocyclic group (R6) is optionally substituted by a group for R10, as shown below.

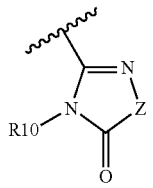

b″

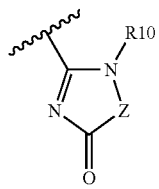

c″

As the above-mentioned group for R10, a group represented by the formula —CH(R11)-OCOR12 [wherein R11 is hydrogen, a straight chain or branched alkyl group having 1 to 6 carbon atoms (e.g., methyl, ethyl, propyl, isopropyl, butyl, isobutyl, sec-butyl, tert-butyl, pentyl, isopentyl, neopentyl and the like), a straight chain or a branched alkenyl group having 2 to 6 carbon atoms or a cycloalkyl group having 3 to 8 carbon atoms (e.g., cyclopentyl, cyclohexyl, cycloheptyl and the like), and R12 is a straight chain or a branched alkyl group having 1 to 6 carbon atoms (e.g., methyl, ethyl, propyl, isopropyl, butyl, isobutyl, sec-butyl, tert-butyl, pentyl, isopentyl, neopentyl and the like), a straight chain or a branched alkenyl group having 2 to 6 carbon atoms, a cycloalkyl group having 3 to 8 carbon atoms (e.g., cyclopentyl, cyclohexyl, cycloheptyl and the like), an alkyl group having 1 to 3 carbon atoms substituted by a cycloalkyl group having 3 to 8 carbon atoms (e.g., cyclopentyl, cyclohexyl, cycloheptyl and the like) or an optionally substituted aryl group having 6 to 14 carbon atoms such as phenyl (e.g., benzyl, p-chlorobenzyl, phenethyl, cyclopentylmethyl, cyclohexylmethyl and the like), an alkenyl group having 2 or 3 carbon atoms substituted by a cycloalkyl group having 3 to 8 carbon atoms or an optionally substituted aryl group having 6 to 14 carbon atoms such as phenyl (e.g., those having alkenyl moiety such as vinyl, propenyl, allyl, isopropenyl and the like (e.g., cinnamyl and the like)), an optionally substituted aryl group having 6 to 14 carbon atoms such as phenyl (e.g., phenyl, p-tolyl, naphthyl and the like), a straight chain or a branched alkoxy group having 1 to 6 carbon atoms (e.g., methoxy, ethoxy, propoxy, isopropoxy, butoxy, isobutoxy, sec-butoxy, tert-butoxy, pentyloxy, isopentyloxy, neopentyloxy and the like), a straight chain or a branched alkenyloxy group having 2 to 8 carbon atoms (e.g., allyloxy, isobutenyloxy and the like), a cycloalkyloxy group having 3 to 8 carbon atoms (e.g., cyclopentyloxy, cyclohexyloxy, cycloheptyloxy and the like), an alkoxy group having 1 to 3 carbon atoms substituted by a cycloalkyl group having 3 to 8 carbon atoms (e.g., cyclopentyl, cyclohexyl, cycloheptyl and the like) or an optionally substituted aryl group having 6 to 14 carbon atoms such as phenyl (e.g., those having alkoxy moiety such as methoxy, ethoxy, propoxy, isopropoxy and the like (e.g., benzyloxy, phenethyloxy, cyclopentylmethyloxy, cyclohexylmethyloxy and the like)), an alkenyloxy group having 2 or 3 carbon atoms substituted by a cycloalkyl group having 3 to 8 carbon atoms (e.g., cyclopentyl, cyclohexyl, cycloheptyl and the like) or an optionally substituted aryl group having 6 to 14 carbon atoms such as phenyl (e.g., those having alkenyloxy moiety such as vinyloxy, propenyloxy, allyloxy, isopropenyloxy and the like (e.g., cinnamyloxy and the like)), or an optionally substituted aryloxy group having 6 to 14 carbon atoms such as phenoxy (e.g., phenoxy, p-nitrophenoxy, naphthoxy and the like)]; an optionally substituted alkyl group (e.g., C1-C6 alkyl group); or an acyl group (e.g., C2-C5 alkanoyl group, optionally substituted benzoyl group and the like); and the like can be mentioned. Examples of substituent R10 include methyl, ethyl, propyl, tert-butyl, methoxymethyl, triphenylmethyl, cyanoethyl, acetyl, propionyl, pivaloyloxymethyl, 1-(cyclohexyloxycarbonyloxy)ethyl, 5-methyl-2-oxo-1,3-dioxolen-4-ylmethyl, acetoxymethyl, propionyloxymethyl, butyryloxymethyl, isobutyryloxymethyl, 1-(ethoxycarbonyloxy)ethyl, 1-(acetyloxy)ethyl, 1-(isobutyryloxy)ethyl, cyclohexylcarbonyloxymethyl, benzoyloxymethyl, cinnamyl, cyclopentylcarbonyloxymethyl and the like. Such group may be any as long as it is a substituent that is easily converted to the original heterocyclic group represented by the formula

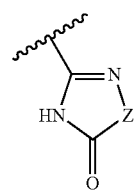

biologically, or under physiological conditions (e.g., in vivo reaction such as oxidation, reduction or hydrolysis and the like by biological enzymes and the like), or chemically (what is called a prodrug).

In addition, substituent R6 may further have substituent(s) in addition to the above-mentioned groups for R10. Examples thereof include substituents such as an optionally substituted C1-C6 alkyl group (e.g., methyl, triphenylmethyl and the like), halogen (e.g., F, Cl, Br and the like), a nitro group, a cyano group, a C1-C6 alkoxy group, an amino group, a C1-C6 alkylamino group (e.g., methylamino and the like), a di(C1-C6)alkylamino group (e.g., dimethylamino and the like) and the like.

R1 is an oxo group; a thioxo group; or a group represented by the formula: =N—R, =N—CO—R', =N—CO—OR' or =N—SO₂—R'.

R is an optionally substituted C1-C6 alkyl group; an optionally substituted C3-C6 cycloalkyl group; a group represented by the formula: —O—Ra; or a group represented by the formula: —N(Rb)—Rc.

Ra is hydrogen, an optionally substituted C1-C6 alkyl group or an optionally substituted C3-C6 cycloalkyl group.

Rb and Rc are each independently hydrogen, an optionally substituted C1-C6 alkyl group or an optionally substituted C3-C6 cycloalkyl group, or Rb and Rc are bonded to each other to form, together with the nitrogen atom bonded thereto, an optionally substituted nitrogen-containing heterocyclic group.

Examples of the "optionally substituted C1-C6 alkyl group" for R, Ra, Rb or Rc include those similar to the "optionally substituted C1-C6 alkyl group" for R5. The "optionally substituted C1-C6 alkyl group" for R, Ra, Rb or Rc is preferably a C1-C6 alkyl group.

The "C3-C6 cycloalkyl group" of the "optionally substituted C3-C6 cycloalkyl group" for R, Ra, Rb or Rc optionally has 1 to 5, preferably 1 to 3, substituent(s) at substitutable position(s). Examples of such substituent include those recited as examples of the substituent of the "optionally substituted cyclic group" for R5. The "optionally substituted C3-C6 cycloalkyl group" for R, Ra, Rb or Rc is preferably a C3-C6 cycloalkyl group.

Rb and Rc may be bonded to each other to form, together with the nitrogen atom bonded thereto, an optionally substituted nitrogen containing heterocyclic group. The "nitrogen containing heterocyclic group" is, for example, a 4 to 8-membered (preferably 5- to 7-membered, more preferably 5- or 6-membered) nonaromatic heterocyclic group which contains, as a ring-constituting atom besides carbon atom, one nitrogen atom, and may further contain a hetero atom selected from the group consisting of nitrogen atom, sulfur atom and oxygen atom. Preferable examples of the nitrogen-containing heterocyclic group include 1-azetidinyl, 1-pyrrolidinyl, 1-imidazolidinyl, 1-pyrazolidinyl, 1-piperidinyl, 1-piperazinyl, 4-morpholinyl, 4-thiomorpholinyl, 3-thiazolidinyl, 3-oxazolidinyl, 1-azepanyl, 1-azocanyl, 1,4-diazepan-1-yl, 1,4-oxazepan-4-yl, 1,4-thiazepan-4-yl and the like. The "nitrogen-containing heterocyclic group" optionally has 1 or 2 substituents at substitutable position(s). Examples of the substituent include a hydroxy group, an optionally halogenated C1-C6 alkyl group, a C6-C14 aryl group, a C7-C16 aralkyl group, a C1-C6 alkyl-carbonyl group, a C1-C6 alkoxy-carbonyl group and the like.

R' is an optionally substituted C1-C6 alkyl group or an optionally substituted cyclic group.

Examples of the "optionally substituted C1-C6 alkyl group" for R' include those similar to the "optionally substituted C1-C6 alkyl group" for R5. Preferable examples of the "optionally substituted C1-C6 alkyl group" for R' include a C1-C6 alkyl group.

Examples of the "optionally substituted cyclic group" for R' include those similar to "optionally substituted cyclic group" for R5. Preferable examples of the "optionally substituted cyclic group" for R' include a C6-C14 aryl group.

R1 is preferably an oxo group or a group represented by the formula: $=N-SO_2-R'$ (R' is preferably a C1-C6 alkyl group or a C6-C14 aryl group), more preferably an oxo group.

A group represented by the formula:

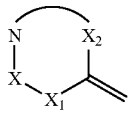

is preferably

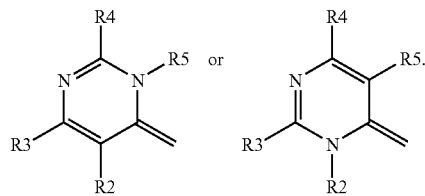

Y is an optionally substituted C1-C4 alkylene group or a group represented by the formula: $-O-W-$, $-W-O-$, $-N(Rd)-W-$ or $-W-N(Rd)-$, wherein W is a bond or an optionally substituted C1-C4 alkylene group, and Rd is an optionally substituted C1-C6 alkyl group or an optionally substituted C3-C6 cycloalkyl group.

The "C1-C4 alkylene group" for Y or W may be a straight chain or a branched chain, for example, methylene, ethylene, $-(CH_2)_3-$, $-(CH_2)_4-$, $-CH(CH_3)-$, $-C(CH_3)_2-$, $-CH(CH_3)-CH_2-$, $-CH_2-CH(CH_3)-$, $-C(CH_3)_2-CH_2-$, $-CH_2-C(CH_3)_2-$ and the like can be mentioned.

The "C1-C4 alkylene group" for Y or W optionally has 1 to 3 substituents at substitutable position(s). Examples of the substituent include halogen (e.g., F, Cl, Br and the like), an oxo group, a hydroxy group, a nitro group, a cyano group, an optionally halogenated C1-C6 alkoxy group (e.g., methoxy, ethoxy, trifluoromethoxy and the like), an amino group, a C1-C6 alkylamino group (e.g., methylamino and the like), a di(C1-C6)alkylamino group (e.g., dimethylamino and the like), a C1-C6 alkyl-carbonylamino group (e.g., acetylamino and the like)
and the like.

Examples of the "optionally substituted C1-C6 alkyl group" for Rd include those similar to the "optionally substituted C1-C6 alkyl group" for R5. The "optionally substituted C1-C6 alkyl group" for Rd is preferably a C1-C6 alkyl group.

Examples of the "optionally substituted C3-C6 cycloalkyl group" for Rd include those similar to the "optionally substituted C3-C6 cycloalkyl group" for R. Ra, Rb or Rc. The "optionally substituted C3-C6 cycloalkyl group" for Rd is preferably a C3-C6 cycloalkyl group.

Y is preferably a C1-C4 alkylene group, more preferably methylene or ethylene, and particularly preferably methylene.

In the group represented by the formula:

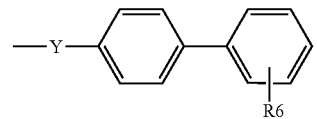

the biphenyl group may be further optionally substituted. Examples of the substituent include 1 to 3 substituents selected from the group consisting of halogen (e.g., F, Cl, Br and the like), a hydroxy group, a nitro group, a cyano group, an optionally halogenated C1-C6 alkyl group (e.g., methyl, ethyl, trifluoromethyl and the like), an optionally halogenated C1-C6 alkoxy group (e.g., methoxy, ethoxy, trifluoromethoxy and the like), an amino group, a C1-C6 alkylamino group (e.g., methylamino and the like), a di(C1-C6) alkylamino group (e.g., dimethylamino and the like), a C1-C6 alkyl-carbonylamino group (e.g., acetylamino and the like) and the like.

Preferable examples of the substituent that the biphenyl group optionally further has include 1 to 3 substituents selected from the group consisting of
(1) halogen (e.g., F, Cl, Br and the like);
(2) a C1-C6 alkoxy group (e.g., methoxy, ethoxy and the like); and
(3) a C1-C6 alkyl group optionally having 1 to 3 substituents selected from the group consisting of halogen and C1-C6 alkoxy, and the like. More preferred is halogen (e.g., F, Cl, Br and the like), and still more preferred is fluorine.

Preferable examples of R2 represented by the formula

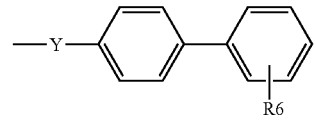

(each symbol is as defined above, and the biphenyl group may be further substituted) are, for example, a group represented by the formula

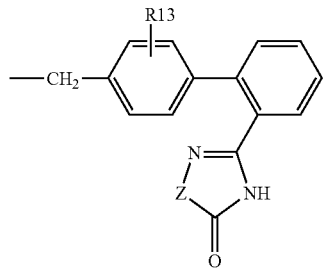

[wherein

R13 is (1) hydrogen,
(2) halogen (e.g., F, Cl, Br and the like),
(3) a C1-C6 alkoxy group (e.g., methoxy, ethoxy and the like), or
(4) a C1-C6 alkyl group optionally having 1 to 3 substituents selected from the group consisting of halogen and a C1-C6 alkoxy group, more preferably halogen (e.g., F, Cl, Br and the like), and still more preferably fluorine; and Z is O or S.], and specifically,

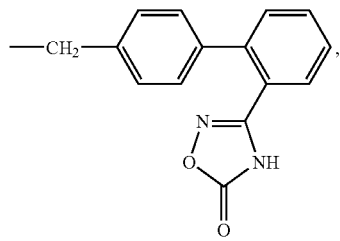

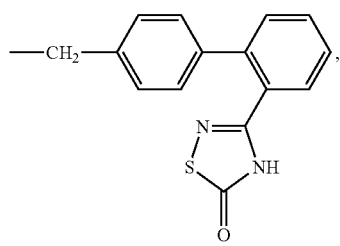

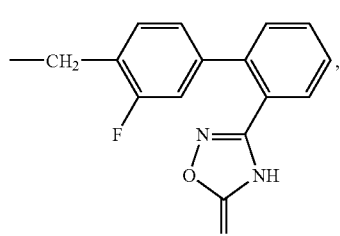

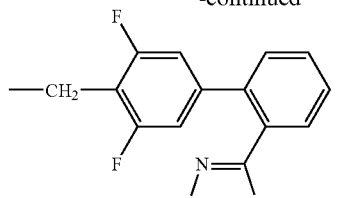

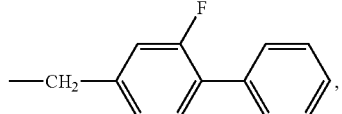

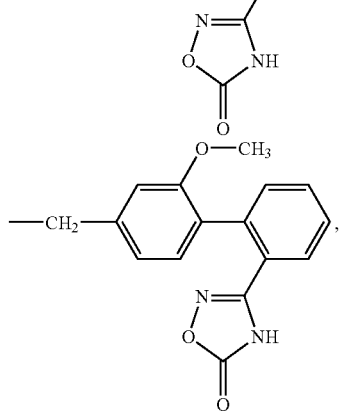

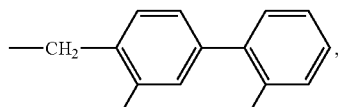

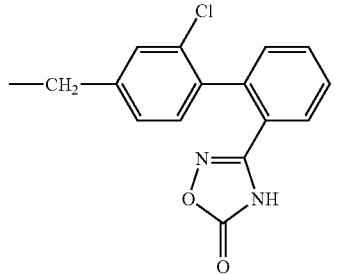

and the like are preferable.

Examples of the "optionally substituted C1-C6 alkyl group" for R3 or R4 include those similar to the "optionally substituted C1-C6 alkyl group" for R5.

As the "optionally substituted C1-C6 alkyl group" for R3 is preferably a C1-C6 alkyl group optionally substituted by 1 to 3 substituents selected from the group consisting of a C1-C6 alkoxy group, a C3-C6 cycloalkyloxy group, halogen, a hydroxy group, an oxo group and a C3-C6 cycloalkyl group, and a C1-C6 alkyl group optionally substituted by 1 to 3 substituents selected from the group consisting of a C1-C6 alkoxy group, halogen, a hydroxy group and a C3-C6 cycloalkyl group is more preferable, and a C1-C6 alkyl group is further more preferable.

The "optionally substituted C1-C6 alkyl group" for R4 is preferably a C1-C6 alkyl group optionally substituted by 1 to 3 substituents selected from the group consisting of a C1-C6 alkoxy group, a C3-C6 cycloalkyloxy group, a hydroxy group, halogen, a cyclic hydrocarbon group (preferably, a C3-C6 cycloalkyl group or a C6-C14 aryl group), a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom, for example, morpholinyl and the like) and a C1-C6 alkoxy-carbonyl group.

Examples of the "optionally substituted C3-C6 cycloalkyl group" for R3 or R4 include those similar to the "optionally substituted C3-C6 cycloalkyl group" for R, Ra, Rb or Rc. The "optionally substituted C3-C6 cycloalkyl group" for R3 or R4 is preferably a C3-C6 cycloalkyl group.

The "optionally substituted C1-C6 alkoxy group" for R3 or R4 optionally has 1 to 5, preferably 1 to 3, substituents at substitutable position(s). Examples of the substituent include those recited as the substituent of the "optionally substituted C1-C6 alkyl group" for R5. The "optionally substituted C1-C6 alkoxy group" for R3 or R4 is preferably a C1-C6 alkoxy group.

Examples of the "optionally substituted C1-C6 alkylamino group" for R3 or R4 include an amino group monosubstituted by "optionally substituted C1-C6 alkyl group" can be mentioned. Examples of the "optionally substituted C1-C6 alkyl group" include those similar to the "optionally substituted C1-C6 alkyl group" for R5. The "optionally substituted C1-C6 alkylamino group" for R3 or R4 is preferably a C1-C6 alkylamino group.

Examples of the "optionally substituted di(C1-C6)alkylamino group" for R3 or R4 include an amino group disubstituted by "optionally substituted C1-C6 alkyl group". Examples of the "optionally substituted C1-C6 alkyl group" include those similar to the "optionally substituted C1-C6 alkyl group" for R5. The "optionally substituted di(C1-C6) alkylamino group" for R3 or R4 is preferably a di(C1-C6) alkylamino group.

The "optionally substituted alkylthio group" for R3 or R4 optionally has 1 to 5, preferably 1 to 3, substituents at substitutable position(s). Examples of the substituent include those similar to the substituents of the "optionally substituted C1-C6 alkyl group" for R5. The "optionally substituted alkylthio group" for R3 or R4 is preferably a C1-C6 alkylthio group.

As R3,
a C1-C6 alkyl group optionally substituted by 1 to 3 substituents selected from the group consisting of a C1-C6 alkoxy group, a C3-C6 cycloalkyloxy group, halogen, a hydroxy group, an oxo group and a C3-C6 cycloalkyl group;
a C3-C6 cycloalkyl group;
a C1-C6 alkoxy group;
a C3-C6 cycloalkyloxy group; or
a C1-C6 alkylthio group is preferable,
a C1-C6 alkyl group optionally substituted by 1 to 3 substituents selected from the group consisting of a C1-C6 alkoxy group, halogen, a hydroxy group and a C3-C6 cycloalkyl group;
a C3-C6 cycloalkyl group;
a C1-C6 alkoxy group; or
a C1-C6 alkylthio group is more preferable, and
a C1-C6 alkyl group is further more preferable.

As R4,
hydrogen;
a C1-C6 alkyl group optionally substituted by 1 to 3 substituents selected from the group consisting of a C1-C6 alkoxy group, a C3-C6 cycloalkyloxy group, a hydroxy group, halogen, a cyclic hydrocarbon group (preferably, a C3-C6 cycloalkyl group or a C6-C14 aryl group), a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom, for example, morpholinyl and the like) and a C1-C6 alkoxy-carbonyl group;
a C3-C6 cycloalkyl group;
a C1-C6 alkoxy group;
a C3-C6 cycloalkyloxy group; or
a di(C1-C6)alkylamino group is preferable, and
a C1-C6 alkyl group is further more preferable.

In the compounds of the present invention, when R1 is an oxo group, and R5 is bonded to a nitrogen atom on the heterocycle and is hydrogen, a tautomer shown below may be present.

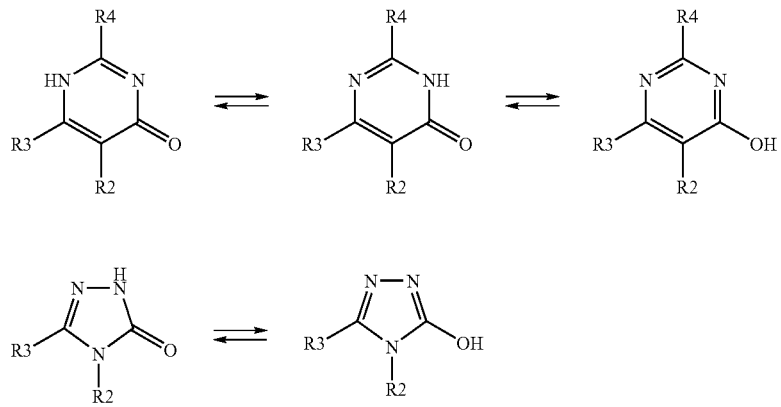

When R1 is =N—R, =N—CO—R', =N—CO—OR' or =N—SO$_2$—R', and R5 is bonded to the nitrogen atom on the heterocycle and is hydrogen, a tautomer shown below can be present.

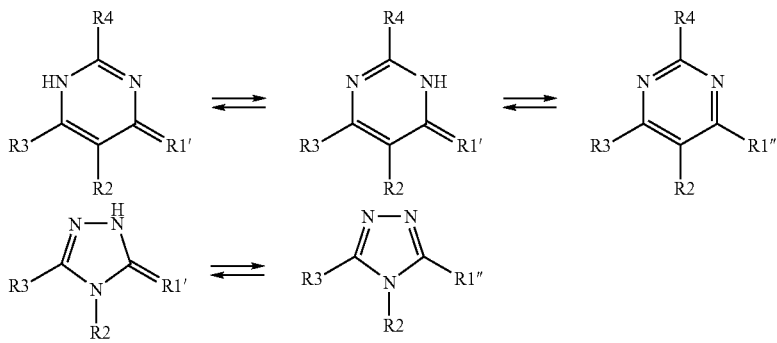

wherein R1' is =N—R, =N—CO—R', =N—CO—OR' or =N—SO₂—R', R1" is —NH—R, —NH—CO—R', —NH—CO—OR' or —NH—SO₂—R', and R and R' are as defined above.

These tautomers are also encompassed in the scope of the present invention.

Preferable embodiments of a compound represented by the formula (I) include the following compounds.

[Compound A]

A compound represented by the formula:

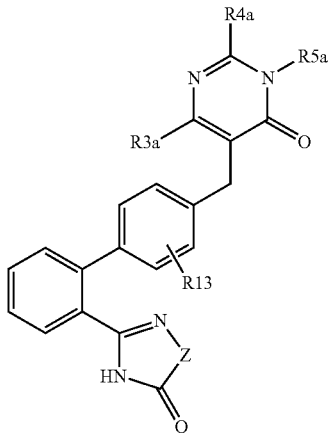

wherein R3a, R4a and R5a are as defined for R3, R4 and R5, respectively, and other symbols are as defined above, or a salt thereof.

[Compound A-I]

Compound A wherein R3a is (1) a C1-C6 alkyl group optionally substituted by 1 to 3 substituents selected from the group consisting of a C1-C6 alkoxy group, halogen, a hydroxy group and a C3-C6 cycloalkyl group;
(2) a C3-C6 cycloalkyl group;
(3) a C1-C6 alkoxy group; or
(4) a C1-C6 alkylthio group, R4a is (1) hydrogen;
(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);
(3) a C3-C6 cycloalkyl group;
(4) a C1-C6 alkoxy group; or
(5) a di(C1-C6)alkylamino group, R5a is (1) hydrogen
(2) a C1-C6 alkyl group optionally substituted by 1 to 3 substituents selected from the group consisting of
(i) a hydroxy group,
(ii) a carboxy group,
(iii) a C1-C6 alkoxy-carbonyl group (e.g., ethoxycarbonyl and the like),
(iv) a C1-C6 alkyl-carbonyl group (e.g., pivaloyl and the like),
(v) a C3-C10 cycloalkyl-carbonyl group (e.g., cyclohexylcarbonyl, adamantylcarbonyl and the like),
(vi) a C6-C14 aryl-carbonyl group (e.g., benzoyl and the like) optionally substituted by 1 to 3 substituents selected from the group consisting of halogen and a C1-C6 alkoxy group,
(vii) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like),
(viii) a C1-C6 alkyl-carbamoyl group (e.g., tert-butylcarbamoyl and the like),
(ix) a C3-C6 cycloalkyl group (e.g., cyclopropyl, cyclohexyl and the like),
(x) an adamantyl group,
(xi) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxy-carbonyl group (e.g., methoxycarbonyl and the like); a C1-C6 alkyl-carbonyl group (e.g., acetyl and the like); a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like) and the like, (xii) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, isoxazolyl, thiazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like, (xiii) a C1-C6 alkoxyimino group (e.g., isopropoxyimino and the like), and the like;

(3) an indanyl group optionally substituted by an oxo group or a hydroxy group;

(4) a C6-C14 aryl group (e.g., phenyl, naphthyl and the like, preferably phenyl) optionally substituted by 1 to 3 substituents selected from the group consisting of (i) halogen (e.g., F, Cl, Br and the like);
(ii) a hydroxy group;
(iii) a C1-C6 alkyl group optionally substituted by 1 to 3 substituents selected from the group consisting of halogen, a hydroxy group, a C1-C6 alkoxy group and a C1-C6 alkyl-carbonyl group (e.g., methyl, ethyl, isopropyl, isobutyl, tert-butyl, trifluoromethyl, hydroxymethyl, 1-hydroxyethyl and the like);
(iv) a C2-C6 alkenyl group (e.g., vinyl and the like) optionally substituted by 1 to 3 substituents selected from the group consisting of halogen and a hydroxy group;
(v) a C3-C6 cycloalkyl group (e.g., cyclopropyl and the like);
(vi) a C1-C6 alkoxy group (e.g., methoxy, ethoxy, propoxy, isopropoxy, isobutoxy, sec-butoxy, tert-butoxy, neopentyloxy and the like) optionally substituted by 1 to 3 substituents selected from the group consisting of a C2-C6 alkynyl group, a C1-C6 alkoxy group, halogen, a cyano group, a hydroxy group, a C3-C6 cycloalkyl group, a C1-C6 alkoxy-carbonyl group and a carbamoyl group;
(vii) a C2-C6 alkenyloxy group (e.g., vinyloxy and the like);
(viii) a C2-C6 alkynyloxy group (e.g., 1-methylbut-3-yn-1-yloxy and the like);
(ix) a C3-C10 cycloalkyloxy group (e.g., cyclopropyloxy, cyclobutyloxy, cyclopentyloxy, cyclohexyloxy, cycloheptyloxy and the like) optionally substituted by 1 to 3 substituents selected from the group consisting of halogen, an oxo group, a hydroxy group, a C1-C6 alkyl group, a C1-C6 alkoxy group optionally substituted by 1 to 3 halogens, a hydroxy-C1-C6 alkyl group and a C1-C6 alkoxy-C1-C6 alkyl group;
(x) a C6-C14 aryloxy group (e.g., phenoxy and the like);
(xi) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydrofuranyloxy, tetrahydropyranyloxy, piperidinyloxy and the like) optionally substituted by 1 to 3 C1-C6 alkyl groups;
(xii) a heterocyclyl-C1-C6 alkyloxy group (preferably, a heterocyclyl-C1-C6 alkyloxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranylmethoxy and the like);
(xiii) a C1-C6 alkyl-carbonylamino group (e.g., acetylamino and the like);
(xiv) a C1-C6 alkylthio group (e.g., methylthio, isopropylthio and the like);
(xv) a C1-C6 alkylsulfinyl group (e.g., methylsulfinyl, isopropylsulfinyl and the like);
(xvi) a C1-C6 alkylsulfonyl group (e.g., methylsulfonyl, isopropylsulfonyl and the like);
(xvii) a C1-C6 alkyl-carbonyl group (e.g., acetyl and the like);
(xviii) a C1-C6 alkyl-carbamoyl group (e.g., methylcarbamoyl and the like);
(xix) a di(C1-C6)alkyl-carbamoyl group (e.g., dimethylcarbamoyl and the like);
(xx) a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like)

and the like;

(5) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, pyridyl, dihydrobenzopyranyl, chromenyl, 2,3-dihydrobenzofuranyl, 1,3-benzodioxolyl, tetrahydropyranyl, indolyl and the like) optionally substituted by 1 to 3 substituents selected from the group consisting of (i) halogen (e.g., F, Cl, Br and the like);
(ii) an oxo group;
(iii) a hydroxy group;
(iv) an amino group;
(v) a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like);

(vi) a C1-C6 alkoxy group optionally substituted by 1 to 3 substituents selected from the group consisting of halogen, a hydroxy group and a C3-C6 cycloalkyl group (e.g., methoxy, ethoxy, isopropoxy, neopentyloxy, trifluoromethoxy and the like);

(vii) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyloxy and the like);

(viii) a C1-C6 alkyl-carbonylamino group (e.g., acetylamino and the like);

(ix) a C1-C6 alkoxy-carbonyl group (e.g., methoxycarbonyl and the like)

and the like;

(6) a C2-C6 alkenyl group; or (7) a heterocyclyl-oxy group (preferably, wherein the heterocyclyl moiety of the group is a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring (e.g., thienyl, thiazolyl, isoxazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 1,3-benzodioxolyl, 2,3-dihydrobenzofuranyl)) optionally substituted by 1 to 3 C1-C6 alkyl groups, R13 is (1) hydrogen;

(2) halogen (e.g., F, Cl, Br and the like);

(3) a C1-C6 alkoxy group (e.g., methoxy, ethoxy and the like); or (4) a C1-C6 alkyl group optionally having 1 to 3 substituents selected from the group consisting of halogen and a C1-C6 alkoxy group, and Z is O or S.

Preferably,

R3a is (1) a C1-C6 alkyl group optionally substituted by 1 to 3 substituents selected from the group consisting of a C1-C6 alkoxy group, halogen, a hydroxy group and a C3-C6 cycloalkyl group;

(2) a C3-C6 cycloalkyl group;

(3) a C1-C6 alkoxy group; or (4) a C1-C6 alkylthio group,

R4a is (1) hydrogen;

(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);

(3) a C3-C6 cycloalkyl group;

(4) a C1-C6 alkoxy group; or (5) a di(C1-C6)alkylamino group,

R5a is (1) a C6-C14 aryl group (e.g., phenyl, naphthyl and the like, preferably phenyl) optionally substituted by 1 to 3 substituents selected from the group consisting of (i) halogen (e.g., F, Cl, Br and the like);

(ii) a hydroxy group;

(iii) a C1-C6 alkyl group optionally substituted by 1 to 3 substituents selected from the group consisting of halogen, a hydroxy group, a C1-C6 alkoxy group and a C1-C6 alkyl-carbonyl group (e.g., methyl, ethyl, isopropyl, isobutyl, tert-butyl, trifluoromethyl, hydroxymethyl, 1-hydroxyethyl and the like);

(iv) a C2-C6 alkenyl group (e.g., vinyl and the like) optionally substituted by 1 to 3 substituents selected from the group consisting of halogen and a hydroxy group;

(v) a C3-C6 cycloalkyl group (e.g., cyclopropyl and the like);

(vi) a C1-C6 alkoxy group (e.g., methoxy, ethoxy, propoxy, isopropoxy, isobutoxy, sec-butoxy, tert-butoxy, neopentyloxy and the like) optionally substituted by 1 to 3 substituents selected from the group consisting of a C2-C6 alkynyl group, a C1-C6 alkoxy group, halogen, a cyano group, a hydroxy group, a C3-C6 cycloalkyl group, a C1-C6 alkoxy-carbonyl group and a carbamoyl group;

(vii) a C2-C6 alkenyloxy group (e.g., vinyloxy and the like);

(viii) a C2-C6 alkynyloxy group (e.g., 1-methylbut-3-yn-1-yloxy and the like);

(ix) a C3-C10 cycloalkyloxy group (e.g., cyclopropyloxy, cyclobutyloxy, cyclopentyloxy, cyclohexyloxy, cycloheptyloxy and the like) optionally substituted by 1 to 3 substituents selected from the group consisting of halogen, an oxo group, a hydroxy group, a C1-C6 alkyl group, a C1-C6 alkoxy group optionally substituted by 1 to 3 halogens, a hydroxy-C1-C6 alkyl group and a C1-C6 alkoxy-C1-C6 alkyl group;

(x) a C6-C14 aryloxy group (e.g., phenoxy and the like);

(xi) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydrofuranyloxy, tetrahydropyranyloxy, piperidinyloxy and the like) optionally substituted by 1 to 3 C1-C6 alkyl groups;

(xii) a heterocyclyl-C1-C6 alkyloxy group (preferably, a heterocyclyl-C1-C6 alkyloxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranylmethoxy and the like);

(xiii) a C1-C6 alkyl-carbonylamino group (e.g., acetylamino and the like);

(xiv) a C1-C6 alkylthio group (e.g., methylthio, isopropylthio and the like);

(xv) a C1-C6 alkylsulfinyl group (e.g., methylsulfinyl, isopropylsulfinyl and the like);

(xvi) a C1-C6 alkylsulfonyl group (e.g., methylsulfonyl, isopropylsulfonyl and the like);

(xvii) a C1-C6 alkyl-carbonyl group (e.g., acetyl and the like);

(xviii) a C1-C6 alkyl-carbamoyl group (e.g., methylcarbamoyl and the like);

(xix) a di(C1-C6)alkyl-carbamoyl group (e.g., dimethylcarbamoyl and the like);
(xx) a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like)
and the like;
(2) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, pyridyl, dihydrobenzopyranyl, chromenyl, 2,3-dihydrobenzofuranyl, 1,3-benzodioxolyl, tetrahydropyranyl, indolyl and the like) optionally substituted by 1 to 3 substituents selected from the group consisting of
(i) halogen (e.g., F, Cl, Br and the like);
(ii) an oxo group;
(iii) a hydroxy group;
(iv) an amino group;
(v) a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like);
(vi) a C1-C6 alkoxy group optionally substituted by 1 to 3 substituents selected from the group consisting of halogen, a hydroxy group and a C3-C6 cycloalkyl group (e.g., methoxy, ethoxy, isopropoxy, neopentyloxy, trifluoromethoxy and the like);
(vii) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyloxy and the like);
(viii) a C1-C6 alkyl-carbonylamino group (e.g., acetylamino and the like);
(ix) a C1-C6 alkoxy-carbonyl group (e.g., methoxycarbonyl and the like)
and the like; or
(3) a C1-C6 alkyl group optionally substituted by 1 to 3 substituents selected from the group consisting of
(i) a hydroxy group,
(ii) a carboxy group,
(iii) a C1-C6 alkoxy-carbonyl group (e.g., ethoxycarbonyl and the like),
(iv) a C1-C6 alkyl-carbonyl group (e.g., pivaloyl and the like),
(v) a C3-C10 cycloalkyl-carbonyl group (e.g., cyclohexylcarbonyl, adamantylcarbonyl and the like),
(vi) a C6-C14 aryl-carbonyl group (e.g., benzoyl and the like) optionally substituted by 1 to 3 substituents selected from the group consisting of halogen and a C1-C6 alkoxy group,
(vii) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like),
(viii) a C1-C6 alkyl-carbamoyl group (e.g., tert-butylcarbamoyl and the like),
(ix) a C3-C6 cycloalkyl group (e.g., cyclopropyl, cyclohexyl and the like),
(x) an adamantyl group,
(xi) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxy-carbonyl group (e.g., methoxycarbonyl and the like); a C1-C6 alkyl-carbonyl group (e.g., acetyl and the like); a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like) and the like,
(xii) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, isoxazolyl, thiazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like,
(xiii) a C1-C6 alkoxyimino group (e.g., isopropoxyimino and the like),
and the like, R13 is
(1) hydrogen;
(2) halogen (e.g., F, Cl, Br and the like);
(3) a C1-C6 alkoxy group (e.g., methoxy, ethoxy and the like); or
(4) a C1-C6 alkyl group optionally having 1 to 3 substituents selected from the group consisting of halogen and a C1-C6 alkoxy group, and
Z is O or S.

[Compound A-II]

Compound A wherein R3a is
(1) a C1-C6 alkyl group optionally substituted by 1 to 3 substituents selected from the group consisting of a C1-C6 alkoxy group, halogen, a hydroxy group and a C3-C6 cycloalkyl group;
(2) a C3-C6 cycloalkyl group;
(3) a C1-C6 alkoxy group; or
(4) a C1-C6 alkylthio group, R4a is
(1) hydrogen;
(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);
(3) a C3-C6 cycloalkyl group;
(4) a C1-C6 alkoxy group; or
(5) a di(C1-C6)alkylamino group, R5a is a C6-C14 aryl group (e.g., phenyl, naphthyl and the like, preferably phenyl) optionally substituted by 1 to 3 substituents selected from the group consisting of
(i) halogen (e.g., F, Cl, Br and the like);
(ii) a hydroxy group;
(iii) a C1-C6 alkyl group optionally substituted by 1 to 3 substituents selected from the group consisting of halogen, a hydroxy group, a C1-C6 alkoxy group and a C1-C6 alkyl-carbonyl group (e.g., methyl, ethyl, isopropyl, isobutyl, tert-butyl, trifluoromethyl, hydroxymethyl, 1-hydroxyethyl and the like);
(iv) a C2-C6 alkenyl group (e.g., vinyl and the like) optionally substituted by 1 to 3 substituents selected from the group consisting of halogen and a hydroxy group;
(v) a C1-C6 alkoxy group (e.g., methoxy, ethoxy, propoxy, isopropoxy, isobutoxy, sec-butoxy, tert-butoxy, neopentyloxy and the like) optionally substituted by 1 to 3 substituents selected from the group consisting of a C2-C6 alkynyl group, a C1-C6 alkoxy group, halogen, a cyano group, a hydroxy group, a C3-C6 cycloalkyl group, a C1-C6 alkoxy-carbonyl group and a carbamoyl group;
(vi) a C2-C6 alkenyloxy group (e.g., vinyloxy and the like);
(vii) a C2-C6 alkynyloxy group (e.g., 1-methylbut-3-yn-1-yloxy and the like);
(viii) a C1-C6 alkyl-carbonylamino group (e.g., acetylamino and the like);
(ix) a C1-C6 alkylthio group (e.g., methylthio, isopropylthio and the like);
(x) a C1-C6 alkylsulfinyl group (e.g., methylsulfinyl, isopropylsulfinyl and the like);
(xi) a C1-C6 alkylsulfonyl group (e.g., methylsulfonyl, isopropylsulfonyl and the like);
(xii) a C1-C6 alkyl-carbonyl group (e.g., acetyl and the like);
(xiii) a C1-C6 alkyl-carbamoyl group (e.g., methylcarbamoyl and the like);
(xiv) a di(C1-C6)alkyl-carbamoyl group (e.g., dimethylcarbamoyl and the like);
and the like, R13 is
(1) hydrogen;
(2) halogen (e.g., F, Cl, Br and the like);
(3) a C1-C6 alkoxy group (e.g., methoxy, ethoxy and the like); or
(4) a C1-C6 alkyl group optionally having 1 to 3 substituents selected from the group consisting of halogen and a C1-C6 alkoxy group, and Z is O or S.

[Compound A-IIA]
3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one (Example 88);
6-butyl-2-methoxy-5-{[2'-(5-oxo-4,5-dihydro-1,2,4-oxadiazol-3-yl)biphenyl-4-yl]methyl}-3-phenylpyrimidin-4(3H)-one (Example 108);
6-butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one (Example 202);
6-butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one (Example 217);
6-butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one (Example 222);
3-[4-(1-ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one (Example 256);
3-(4-tert-butoxyphenyl)-2-ethyl-5-{[2'-(5-oxo-4,5-dihydro-1,2,4-oxadiazol-3-yl)biphenyl-4-yl]methyl}-6-propylpyrimidin-4(3H)-one (Example 364);
2-ethyl-3-[4-(2-hydroxy-1,1-dimethylethoxy)phenyl]-5-{[2'-(5-oxo-4,5-dihydro-1,2,4-oxadiazol-3-yl)biphenyl-4-yl]methyl}-6-propylpyrimidin-4(3H)-one (Example 377); or
2-ethyl-3-[4-(2-hydroxy-1,1-dimethylpropoxy)phenyl]-5-{[2'-(5-oxo-4,5-dihydro-1,2,4-oxadiazol-3-yl)biphenyl-4-yl]methyl}-6-propylpyrimidin-4(3H)-one (Example 444);
or a salt thereof.

[Compound A-III]

Compound A wherein R3a is
(1) a C1-C6 alkyl group optionally substituted by 1 to 3 substituents selected from the group consisting of a C1-C6 alkoxy group, halogen, a hydroxy group and a C3-C6 cycloalkyl group;
(2) a C3-C6 cycloalkyl group;
(3) a C1-C6 alkoxy group; or
(4) a C1-C6 alkylthio group, R4a is
(1) hydrogen;
(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);
(3) a C3-C6 cycloalkyl group;
(4) a C1-C6 alkoxy group; or
(5) a di(C1-C6)alkylamino group, R5a is a C6-C14 aryl group (e.g., phenyl, naphthyl and the like, preferably phenyl) optionally substituted by 1 to 3 substituents selected from the group consisting of
(i) a C3-C6 cycloalkyl group (e.g., cyclopropyl and the like);
(ii) a C3-C10 cycloalkyloxy group (e.g., cyclopropyloxy, cyclobutyloxy, cyclopentyloxy, cyclohexyloxy, cycloheptyloxy and the like) optionally substituted by 1 to 3 substituents selected from the group consisting of halogen, an oxo group, a hydroxy group, a C1-C6 alkyl group, a C1-C6 alkoxy group optionally substituted by 1 to 3 halogens, a hydroxy-C1-C6 alkyl group and a C1-C6 alkoxy-C1-C6 alkyl group;
(iii) a C6-C14 aryloxy group (e.g., phenoxy and the like);
(iv) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydrofuranyloxy, tetrahydropyranyloxy, piperidinyloxy and the like) optionally substituted by 1 to 3 C1-C6 alkyl groups;
(v) a heterocyclyl-C1-C6 alkyloxy group (preferably, a heterocyclyl-C1-C6 alkyloxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranylmethoxy and the like);
(vi) a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like)
and the like, R13 is
(1) hydrogen;
(2) halogen (e.g., F, Cl, Br and the like);
(3) a C1-C6 alkoxy group (e.g., methoxy, ethoxy and the like); or
(4) a C1-C6 alkyl group optionally having 1 to 3 substituents selected from the group consisting of halogen and a C1-C6 alkoxy group, and
Z is O or S.

[Compound A-IIIA]

3-[4-(cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one (Example 255);
3-[4-(cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one (Example 265);
3-[4-(cyclopentyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one (Example 319);
2-ethyl-5-{[2'-(5-oxo-4,5-dihydro-1,2,4-oxadiazol-3-yl)biphenyl-4-yl]methyl}-6-propyl-3-[4-(tetrahydro-2H-pyran-4-yloxy)phenyl]pyrimidin-4(3H)-one (Example 378);
2-ethyl-3-(4-{[(2R)-2-hydroxycyclopentyl]oxy}phenyl)-5-{[2'-(5-oxo-4,5-dihydro-1,2,4-oxadiazol-3-yl)biphenyl-4-yl]methyl}-6-propylpyrimidin-4(3H)-one (Example 381);
2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (Example 414);
2-ethyl-3-{4-[(cis-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (Example 415);
2-ethyl-3-{4-[(4-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (Example 416);
3-(4-{[(2R,4s,6S)-2,6-dimethyltetrahydro-2H-pyran-4-yl]oxy}phenyl)-2-ethyl-5-{[2'-(5-oxo-4,5-dihydro-1,2,4-oxadiazol-3-yl)biphenyl-4-yl]methyl}-6-propylpyrimidin-4(3H)-one (Example 417); or
2-ethyl-3-{4-[(3-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (Example 422);
or a salt thereof.

[Compound A-IV]

Compound A wherein R3a is
(1) a C1-C6 alkyl group optionally substituted by 1 to 3 substituents selected from the group consisting of a C1-C6 alkoxy group, halogen, a hydroxy group and a C3-C6 cycloalkyl group;
(2) a C3-C6 cycloalkyl group;
(3) a C1-C6 alkoxy group; or
(4) a C1-C6 alkylthio group, R4a is
(1) hydrogen;
(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);
(3) a C3-C6 cycloalkyl group;
(4) a C1-C6 alkoxy group; or
(5) a di(C1-C6)alkylamino group, R5a is a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, pyridyl, dihydrobenzopyranyl, chromenyl, 2,3-dihydrobenzofuranyl, 1,3-benzodioxolyl, tetrahydropyranyl, indolyl and the like) optionally substituted by 1 to 3 substituents selected from the group consisting of
(i) halogen (e.g., F, Cl, Br and the like);
(ii) an oxo group;
(iii) a hydroxy group;
(iv) an amino group;
(v) a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like);
(vi) a C1-C6 alkoxy group optionally substituted by 1 to 3 substituents selected from the group consisting of halogen, a hydroxy group and a C3-C6 cycloalkyl group (e.g., methoxy, ethoxy, isopropoxy, neopentyloxy, trifluoromethoxy and the like);
(vii) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyloxy and the like);
(viii) a C1-C6 alkyl-carbonylamino group (e.g., acetylamino and the like);
(ix) a C1-C6 alkoxy-carbonyl group (e.g., methoxycarbonyl and the like) and the like, R13 is
(1) hydrogen;
(2) halogen (e.g., F, Cl, Br and the like);
(3) a C1-C6 alkoxy group (e.g., methoxy, ethoxy and the like); or
(4) a C1-C6 alkyl group optionally having 1 to 3 substituents selected from the group consisting of halogen and a C1-C6 alkoxy group, and Z is O or S.

[Compound A-IVA]
6-butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one (Example 112);
6-butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one (Example 118);
6-butyl-3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}pyrimidin-4(3H)-one (Example 128);
3-(2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one (Example 131);
3-(4-hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one (Example 144);
6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one (Example 234);
2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one (Example 235);
3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one (Example 239); or
3-(7-fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one (Example 275);
or a salt thereof.

[Compound A-V]

Compound A wherein R3a is
(1) a C1-C6 alkyl group optionally substituted by 1 to 3 substituents selected from the group consisting of a C1-C6 alkoxy group, halogen, a hydroxy group and a C3-C6 cycloalkyl group;
(2) a C3-C6 cycloalkyl group;
(3) a C1-C6 alkoxy group; or
(4) a C1-C6 alkylthio group, R4a is
(1) hydrogen;
(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);
(3) a C3-C6 cycloalkyl group;
(4) a C1-C6 alkoxy group; or
(5) a di(C1-C6)alkylamino group, R5a is
a C1-C6 alkyl group optionally substituted by 1 to 3 substituents selected from the group consisting of
(i) a hydroxy group,
(ii) a carboxy group,
(iii) a C1-C6 alkoxy-carbonyl group (e.g., ethoxycarbonyl and the like),
(iv) a C1-C6 alkyl-carbonyl group (e.g., pivaloyl and the like),
(v) a C3-C10 cycloalkyl-carbonyl group (e.g., cyclohexylcarbonyl, adamantylcarbonyl and the like),
(vi) a C6-C14 aryl-carbonyl group (e.g., benzoyl and the like) optionally substituted by 1 to 3 substituents selected from the group consisting of halogen and a C1-C6 alkoxy group,
(vii) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like),
(viii) a C1-C6 alkyl-carbamoyl group (e.g., tert-butylcarbamoyl and the like),
(ix) a C3-C6 cycloalkyl group (e.g., cyclopropyl, cyclohexyl and the like),
(x) an adamantyl group,
(xi) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxy-carbonyl group (e.g., methoxycarbonyl and the like); a C1-C6 alkyl-carbonyl group (e.g., acetyl and the like); a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like) and the like, (xii) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, isoxazolyl, thiazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like, (xiii) a C1-C6 alkoxyimino group (e.g., isopropoxyimino and the like), and the like, R13 is (1) hydrogen;
(2) halogen (e.g., F, Cl, Br and the like);
(3) a C1-C6 alkoxy group (e.g., methoxy, ethoxy and the like); or
(4) a C1-C6 alkyl group optionally having 1 to 3 substituents selected from the group consisting of halogen and a C1-C6 alkoxy group, and Z is O or S.

[Compound A-VA]

6-butyl-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one (Example 32);

6-butyl-3-(3,3-dimethyl-2-oxobutyl)-2-methyl-5-{[2'-(5-oxo-4,5-dihydro-1,2,4-oxadiazol-3-yl)biphenyl-4-yl]methyl}pyrimidin-4(3H)-one (Example 37);

3-benzyl-6-butyl-2-methyl-5-{[2'-(5-oxo-4,5-dihydro-1,2,4-oxadiazol-3-yl)biphenyl-4-yl]methyl}pyrimidin-4(3H)-one (Example 47);

6-butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one (Example 48);

6-butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one (Example 50);

6-butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one (Example 58);

3-(1,3-benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one (Example 64);

2-methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one (Example 81);

6-butyl-2-methyl-5-{[2'-(5-oxo-4,5-dihydro-1,2,4-oxadiazol-3-yl)biphenyl-4-yl]methyl}-3-[(5-phenyl-1,2,4-oxadiazol-3-yl)methyl]pyrimidin-4(3H)-one (Example 152); or 6-butyl-3-(2,6-difluorobenzyl)-2-methyl-5-{[2'-(5-oxo-4,5-dihydro-1,2,4-oxadiazol-3-yl)biphenyl-4-yl] methyl}pyrimidin-4(3H)-one (Example 165);

or a salt thereof.

[Compound A1]

Compound A wherein R3a is (1) a C1-C6 alkyl group optionally substituted by 1 to 3 substituents selected from the group consisting of a C1-C6 alkoxy group, a C3-C6 cycloalkyl group and halogen;
(2) a C3-C6 cycloalkyl group;
(3) a C1-C6 alkoxy group; or
(4) a C1-C6 alkylthio group, R4a is (1) hydrogen;
(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);
(3) a C3-C6 cycloalkyl group;
(4) a C1-C6 alkoxy group; or
(5) a di(C1-C6)alkylamino group, R5a is (1) hydrogen;
(2) a C1-C6 alkyl group optionally substituted by 1 to 3 substituents selected from the group consisting of
(i) a hydroxy group,
(ii) a carboxy group,
(iii) a C1-C6 alkoxy-carbonyl group (e.g., ethoxycarbonyl and the like),
(iv) a C1-C6 alkyl-carbonyl group (e.g., pivaloyl and the like),
(v) a C3-C10 cycloalkyl-carbonyl group (e.g., cyclohexylcarbonyl, adamantylcarbonyl and the like),
(vi) a C6-C14 aryl-carbonyl group (e.g., benzoyl and the like) optionally substituted by 1 to 3 substituents selected from the group consisting of halogen and a C1-C6 alkoxy group,
(vii) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like),
(viii) a C1-C6 alkyl-carbamoyl group (e.g., tert-butylcarbamoyl and the like),
(ix) a C3-C6 cycloalkyl group (e.g., cyclopropyl, cyclohexyl and the like),
(x) an adamantyl group,
(xi) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxycarbonyl group (e.g., methoxycarbonyl and the like); a C1-C6 alkyl-carbonyl group (e.g., acetyl and the like); a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like)
and the like,
(xii) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, isoxazolyl, thiazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like,
(xiii) a C1-C6 alkoxyimino group (e.g., isopropoxyimino and the like),
and the like;
(3) an indanyl group optionally substituted by an oxo group or a hydroxy group;
(4) a C6-C14 aryl group (e.g., phenyl, naphthyl and the like) optionally substituted by 1 to 3 substituents selected from the group consisting of
(i) halogen (e.g., F, Cl, Br and the like);
(ii) a hydroxy group;
(iii) a C1-C6 alkyl group optionally substituted by 1 to 3 substituents selected from the group consisting of halogen, a hydroxy group, a C1-C6 alkoxy group and a C1-C6 alkyl-carbonyl group (e.g., methyl, ethyl, isopropyl, isobutyl, tert-butyl, trifluoromethyl, hydroxymethyl, 1-hydroxyethyl and the like);
(iv) a C2-C6 alkenyl group (e.g., vinyl and the like) optionally substituted by 1 to 3 substituents selected from the group consisting of halogen and a hydroxy group;
(v) a C3-C6 cycloalkyl group (e.g., cyclopropyl and the like);
(vi) a C1-C6 alkoxy group (e.g., methoxy, ethoxy, propoxy, isopropoxy, isobutoxy, sec-butoxy, tert-butoxy, neopentyloxy and the like) optionally substituted by 1 to 3 substituents selected from the group consisting of a C2-C6 alkynyl group, a C1-C6 alkoxy group, halogen, a cyano group, a hydroxy group, a C3-C6 cycloalkyl group, a C1-C6 alkoxy-carbonyl group and a carbamoyl group;
(vii) a C2-C6 alkenyloxy group (e.g., vinyloxy and the like);
(viii) a C2-C6 alkynyloxy group (e.g., 1-methylbut-3-yn-1-yloxy and the like);
(ix) a C3-C10 cycloalkyloxy group (e.g., cyclopropyloxy, cyclobutyloxy, cyclopentyloxy, cyclohexyloxy, cycloheptyloxy and the like) optionally substituted by 1 to 3 substituents selected from the group consisting of an oxo group, a hydroxy group, a C1-C6 alkyl group, a hydroxy-C1-C6 alkyl group and a C1-C6 alkoxy-C1-C6 alkyl group;
(x) a C6-C14 aryloxy group (e.g., phenoxy and the like);
(xi) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydrofuranyloxy, tetrahydropyranyloxy, piperidinyloxy and the like) optionally substituted by 1 to 3 C1-C6 alkyl groups;
(vxii) a heterocyclyl-C1-C6 alkyloxy group (preferably, a heterocyclyl-C1-C6 alkyloxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranylmethoxy and the like);
(xiii) a C1-C6 alkyl-carbonylamino group (e.g., acetylamino and the like);
(xiv) a C1-C6 alkylthio group (e.g., methylthio, isopropylthio and the like);
(xv) a C1-C6 alkylsulfonyl group (e.g., methylsulfonyl, isopropylsulfonyl and the like);
(xvi) a C1-C6 alkyl-carbonyl group (e.g., acetyl and the like);
(xvii) a C1-C6 alkyl-carbamoyl group (e.g., methylcarbamoyl and the like);
(xviii) a di(C1-C6)alkyl-carbamoyl group (e.g., dimethylcarbamoyl and the like);
(xix) a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like)
and the like; or
(5) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, pyridyl, dihydrobenzopyranyl, chromenyl, 2,3-dihydrobenzofuranyl, 1,3-benzodioxolyl, tetrahydropyranyl, indolyl and the like) optionally substituted by 1 to 3 substituents selected from the group consisting of
(i) halogen (e.g., F, Cl, Br and the like);
(ii) an oxo group;
(iii) a hydroxy group;

(iv) an amino group;
(v) a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like);
(vi) a C1-C6 alkoxy group optionally substituted by 1 to 3 substituents selected from the group consisting of halogen, a hydroxy group and a C3-C6 cycloalkyl group (e.g., methoxy, ethoxy, isopropoxy, neopentyloxy, trifluoromethoxy and the like);
(vii) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyloxy and the like);
(viii) a C1-C6 alkyl-carbonylamino group (e.g., acetylamino and the like);
(ix) a C1-C6 alkoxy-carbonyl group (e.g., methoxycarbonyl and the like)
and the like, R13 is hydrogen, halogen or C1-C6 alkoxy group, and
Z is O or S.

[Compound A2]

Compound A wherein R3a is
(1) a C1-C6 alkyl group optionally substituted by 1 to 3 substituents selected from the group consisting of a C1-C6 alkoxy group, a C3-C6 cycloalkyl group and halogen;
(2) a C3-C6 cycloalkyl group; or
(3) a C1-C6 alkoxy group, R4a is
(1) hydrogen;
(2) a C1-C6 alkyl group optionally substituted by 1 to 3 substituents selected from the group consisting of a C1-C6 alkoxy group, a hydroxy group, halogen and a cyclic hydrocarbon group (preferably, a C3-C6 cycloalkyl group or a C6-C14 aryl group);
(3) a C3-C6 cycloalkyl group;
(4) a C1-C6 alkoxy group; or
(5) a di(C1-C6)alkylamino group, R5a is
(1) hydrogen;
(2) a C1-C6 alkyl group optionally substituted by 1 to 3 substituents selected from the group consisting of
(i) a hydroxy group,
(ii) a carboxy group,
(iii) a C1-C6 alkoxy-carbonyl group (e.g., ethoxycarbonyl and the like),
(iv) a C1-C6 alkyl-carbonyl group (e.g., pivaloyl and the like),
(v) a C3-C10 cycloalkyl-carbonyl group (e.g., cyclohexylcarbonyl, adamantylcarbonyl and the like),
(vi) a C6-C14 aryl-carbonyl group (e.g., benzoyl and the like) optionally substituted by 1 to 3 substituents selected from the group consisting of halogen and a C1-C6 alkoxy group,
(vii) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like),
(viii) a C1-C6 alkyl-carbamoyl group (e.g., tert-butylcarbamoyl and the like),
(ix) a C3-C6 cycloalkyl group (e.g., cyclopropyl, cyclohexyl and the like),
(x) an adamantyl group,
(xi) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxycarbonyl group (e.g., methoxycarbonyl and the like); a C1-C6 alkyl-carbonyl group (e.g., acetyl and the like); a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like)
and the like,
(xii) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, isoxazolyl, thiazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like,
and the like;
(3) an indanyl group optionally substituted by an oxo group or a hydroxy group;
(4) a C6-C14 aryl group (e.g., phenyl, naphthyl and the like) optionally substituted by 1 to 3 substituents selected from the group consisting of
(i) halogen (e.g., F, Cl, Br and the like);
(ii) a hydroxy group;
(iii) a C1-C6 alkyl group optionally substituted by 1 to 3 substituents selected from the group consisting of halogen and a hydroxy group (e.g., methyl, ethyl, isopropyl, isobutyl, tert-butyl, trifluoromethyl, hydroxymethyl, 1-hydroxyethyl and the like);

(iv) a C2-C6 alkenyl group (e.g., vinyl and the like) optionally substituted by 1 to 3 substituents selected from the group consisting of halogen and a hydroxy group;

(v) a C3-C6 cycloalkyl group (e.g., cyclopropyl and the like);

(vi) a C1-C6 alkoxy group (e.g., methoxy, ethoxy, propoxy, isopropoxy, isobutoxy, tert-butoxy, neopentyloxy and the like) optionally substituted by 1 to 3 substituents selected from the group consisting of a C1-C6 alkoxy group, halogen, a hydroxy group, a C3-C6 cycloalkyl group and a C1-C6 alkoxy-carbonyl group;

(vii) a C3-C6 cycloalkyloxy group (e.g., cyclopropyloxy, cyclobutyloxy and the like);

(viii) a C6-C14 aryloxy group (e.g., phenoxy and the like);

(ix) a C1-C6 alkyl-carbonylamino group (e.g., acetylamino and the like);

(x) a C1-C6 alkylthio group (e.g., methylthio, isopropylthio and the like);

(xi) a C1-C6 alkylsulfonyl group (e.g., methylsulfonyl, isopropylsulfonyl and the like);

(xii) a C1-C6 alkyl-carbonyl group (e.g., acetyl and the like);

(xiii) a C1-C6 alkyl-carbamoyl group (e.g., methylcarbamoyl and the like);

(xiv) a di(C1-C6)alkyl-carbamoyl group (e.g., dimethylcarbamoyl and the like)

and the like; or (5) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, pyridyl, dihydrobenzopyranyl, chromenyl, 2,3-dihydrobenzofuranyl, 1,3-benzodioxolyl and the like) optionally substituted by 1 to 3 substituents selected from the group consisting of (i) halogen (e.g., F, Cl, Br and the like);

(ii) an oxo group;

(iii) a hydroxy group;

(iv) an amino group;

(v) a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like);

(vi) a C1-C6 alkoxy group optionally substituted by 1 to 3 substituents selected from the group consisting of halogen and a hydroxy group (e.g., methoxy, ethoxy, trifluoromethoxy and the like);

(vii) a C1-C6 alkyl-carbonylamino group (e.g., acetylamino and the like);

(viii) a C1-C6 alkoxy-carbonyl group (e.g., methoxycarbonyl and the like)

and the like,

R13 is hydrogen or halogen, and

Z is O or S.

[Compound B]

A compound represented by the formula:

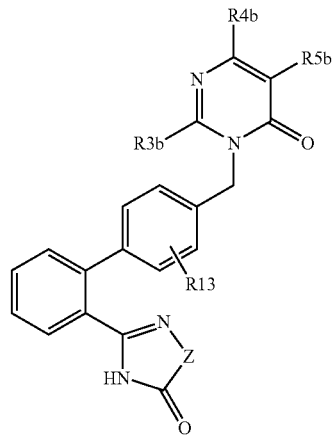

wherein R3b, R4b and R5b are as defined for R3, R4 and R5, respectively, and other symbols are as defined above, or a salt thereof.

[Compound B-I]

Compound B wherein R3b is (1) a C1-C6 alkyl group optionally substituted by 1 to 3 substituents selected from the group consisting of a C1-C6 alkoxy group, halogen, a hydroxy group and a C3-C6 cycloalkyl group;

(2) a C3-C6 cycloalkyl group;

(3) a C1-C6 alkoxy group; or (4) a C1-C6 alkylthio group,

R4b is (1) hydrogen;

(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);

(3) a C3-C6 cycloalkyl group;

(4) a C1-C6 alkoxy group; or (5) a di(C1-C6)alkylamino group,

R5b is (1) hydrogen;

(2) a C1-C6 alkyl group optionally substituted by 1 to 3 substituents selected from the group consisting of (i) a hydroxy group, (ii) a carboxy group, (iii) a C1-C6 alkoxy-carbonyl group (e.g., ethoxycarbonyl and the like), (iv) a C1-C6 alkyl-carbonyl group (e.g., pivaloyl and the like), (v) a C3-C10 cycloalkyl-carbonyl group (e.g., cyclohexylcarbonyl, adamantylcarbonyl and the like), (vi) a C6-C14 aryl-carbonyl group (e.g., benzoyl and the like) optionally substituted by 1 to 3 substituents selected from the group consisting of halogen and a C1-C6 alkoxy group, (vii) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like), (viii) a C1-C6 alkyl-carbamoyl group (e.g., tert-butylcarbamoyl and the like), (ix) a C3-C6 cycloalkyl group (e.g., cyclopropyl, cyclohexyl and the like), (x) an adamantyl group, (xi) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxy-carbonyl group (e.g., methoxycarbonyl and the like); a C1-C6 alkyl-carbonyl group (e.g., acetyl and the like); a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like) and the like, (xii) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, isoxazolyl, thiazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like, (xiii) a C1-C6 alkoxyimino group (e.g., isopropoxyimino and the like), and the like;

(3) an indanyl group optionally substituted by an oxo group or a hydroxy group;

(4) a C6-C14 aryl group (e.g., phenyl, naphthyl and the like) optionally substituted by 1 to 3 substituents selected from the group consisting of (i) halogen (e.g., F, Cl, Br and the like);

(ii) a hydroxy group;

(iii) a C1-C6 alkyl group optionally substituted by 1 to 3 substituents selected from the group consisting of halogen, a hydroxy group, a C1-C6 alkoxy group and a C1-C6 alkyl-carbonyl group (e.g., methyl, ethyl, isopropyl, isobutyl, tert-butyl, trifluoromethyl, hydroxymethyl, 1-hydroxyethyl and the like);

(iv) a C2-C6 alkenyl group (e.g., vinyl and the like) optionally substituted by 1 to 3 substituents selected from the group consisting of halogen and a hydroxy group;

(v) a C3-C6 cycloalkyl group (e.g., cyclopropyl and the like);

(vi) a C1-C6 alkoxy group (e.g., methoxy, ethoxy, propoxy, isopropoxy, isobutoxy, sec-butoxy, tert-butoxy, neopentyloxy and the like) optionally substituted by 1 to 3 substituents selected from the group consisting of a C2-C6 alkynyl group, a C1-C6 alkoxy group, halogen, a cyano group, a hydroxy group, a C3-C6 cycloalkyl group, a C1-C6 alkoxy-carbonyl group and a carbamoyl group;

(vii) a C2-C6 alkenyloxy group (e.g., vinyloxy and the like);

(viii) a C2-C6 alkynyloxy group (e.g., 1-methylbut-3-yn-1-yloxy and the like);

(ix) a C3-C10 cycloalkyloxy group (e.g., cyclopropyloxy, cyclobutyloxy, cyclopentyloxy, cyclohexyloxy, cycloheptyloxy and the like) optionally substituted by 1 to 3 substituents selected from the group consisting of halogen, an oxo group, a hydroxy group, a C1-C6 alkyl group, a C1-C6 alkoxy group optionally substituted by 1 to 3 halogens, a hydroxy-C1-C6 alkyl group and a C1-C6 alkoxy-C1-C6 alkyl group;

(x) a C6-C14 aryloxy group (e.g., phenoxy and the like);

(xi) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydrofuranyloxy, tetrahydropyranyloxy, piperidinyloxy and the like) optionally substituted by 1 to 3 C1-C6 alkyl groups;

(xii) a heterocyclyl-C1-C6 alkyloxy group (preferably, a heterocyclyl-C1-C6 alkyloxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranylmethoxy and the like);

(xiii) a C1-C6 alkyl-carbonylamino group (e.g., acetylamino and the like);

(xiv) a C1-C6 alkylthio group (e.g., methylthio, isopropylthio and the like);

(xv) a C1-C6 alkylsulfinyl group (e.g., methylsulfinyl, isopropylsulfinyl and the like);

(xvi) a C1-C6 alkylsulfonyl group (e.g., methylsulfonyl, isopropylsulfonyl and the like);

(xvii) a C1-C6 alkyl-carbonyl group (e.g., acetyl and the like);

(xviii) a C1-C6 alkyl-carbamoyl group (e.g., methylcarbamoyl and the like);

(xix) a di(C1-C6)alkyl-carbamoyl group (e.g., dimethylcarbamoyl and the like);

(xx) a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like)
and the like;
(5) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, pyridyl, dihydrobenzopyranyl, chromenyl, 2,3-dihydrobenzofuranyl, 1,3-benzodioxolyl, tetrahydropyranyl, indolyl and the like) optionally substituted by 1 to 3 substituents selected from the group consisting of
(i) halogen (e.g., F, Cl, Br and the like);
(ii) an oxo group;
(iii) a hydroxy group;
(iv) an amino group;
(v) a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like);
(vi) a C1-C6 alkoxy group optionally substituted by 1 to 3 substituents selected from the group consisting of halogen, a hydroxy group and a C3-C6 cycloalkyl group (e.g., methoxy, ethoxy, isopropoxy, neopentyloxy, trifluoromethoxy and the like);
(vii) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyloxy and the like);
(viii) a C1-C6 alkyl-carbonylamino group (e.g., acetylamino and the like);
(ix) a C1-C6 alkoxy-carbonyl group (e.g., methoxycarbonyl and the like)
and the like;
(6) a C6-C14 aryl (e.g., phenyl)-carbonyl group;
(7) a heterocyclyl-carbonyl group (the heterocyclyl moiety of the group is, preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring (e.g., thienyl, thiazolyl, isoxazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 1,3-benzodioxolyl, 2,3-dihydrobenzofuranyl));
(8) a C6-C14 aryl (e.g., phenyl)-oxy group optionally having 1 to 3 substituents selected from halogen; a C1-C6 alkyl group; a C1-C6 alkoxy group optionally substituted by a hydroxy group; or
(9) a heterocyclyl-oxy group (preferably, the heterocyclyl moiety of the group is a 5- or 6-membered heterocyclic group containing, as a ring-constituting carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring (e.g., thienyl, thiazolyl, isoxazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 1,3-benzodioxolyl, 2,3-dihydrobenzofuranyl)) optionally substituted by 1 to 3 C1-C6 alkyl groups, R13 is
(1) hydrogen;
(2) halogen (e.g., F, Cl, Br and the like);
(3) a C1-C6 alkoxy group (e.g., methoxy, ethoxy and the like); or
(4) a C1-C6 alkyl group optionally having 1 to 3 substituents selected from the group consisting of halogen and a C1-C6 alkoxy group, and
Z is O or S.

Preferably,

R3b is
(1) a C1-C6 alkyl group optionally substituted by 1 to 3 substituents selected from the group consisting of a C1-C6 alkoxy group, halogen, a hydroxy group and a C3-C6 cycloalkyl group;
(2) a C3-C6 cycloalkyl group;
(3) a C1-C6 alkoxy group; or
(4) a C1-C6 alkylthio group, R4b is
(1) hydrogen;
(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);
(3) a C3-C6 cycloalkyl group;
(4) a C1-C6 alkoxy group; or
(5) a di(C1-C6)alkylamino group, R5b is
(1) a C6-C14 aryl group (e.g., phenyl, naphthyl and the like) optionally substituted by 1 to 3 substituents selected from the group consisting of
(i) halogen (e.g., F, Cl, Br and the like);
(ii) a hydroxy group;
(iii) a C1-C6 alkyl group optionally substituted by 1 to 3 substituents selected from the group consisting of halogen, a hydroxy group, a C1-C6 alkoxy group and a C1-C6 alkyl-carbonyl group (e.g., methyl, ethyl, isopropyl, isobutyl, tert-butyl, trifluoromethyl, hydroxymethyl, 1-hydroxyethyl and the like);
(iv) a C2-C6 alkenyl group (e.g., vinyl and the like) optionally substituted by 1 to 3 substituents selected from the group consisting of halogen and a hydroxy group;
(v) a C3-C6 cycloalkyl group (e.g., cyclopropyl and the like);
(vi) a C1-C6 alkoxy group (e.g., methoxy, ethoxy, propoxy, isopropoxy, isobutoxy, sec-butoxy, tert-butoxy, neopentyloxy and the like) optionally substituted by 1 to 3 substituents selected from the group consisting of a C2-C6 alkynyl group, a C1-C6 alkoxy group, halogen, a cyano group, a hydroxy group, a C3-C6 cycloalkyl group, a C1-C6 alkoxy-carbonyl group and a carbamoyl group;

(vii) a C2-C6 alkenyloxy group (e.g., vinyloxy and the like);
(viii) a C2-C6 alkynyloxy group (e.g., 1-methylbut-3-yn-1-yloxy and the like);
(ix) a C3-C10 cycloalkyloxy group (e.g., cyclopropyloxy, cyclobutyloxy, cyclopentyloxy, cyclohexyloxy, cycloheptyloxy and the like) optionally substituted by 1 to 3 substituents selected from the group consisting of halogen, an oxo group, a hydroxy group, a C1-C6 alkyl group, a C1-C6 alkoxy group optionally substituted by 1 to 3 halogens, a hydroxy-C1-C6 alkyl group and a C1-C6 alkoxy-C1-C6 alkyl group;
(x) a C6-C14 aryloxy group (e.g., phenoxy and the like);
(xi) a heterocyclyl-oxy group optionally substituted by 1 to 3 C1-C6 alkyl groups (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydrofuranyloxy, tetrahydropyranyloxy, piperidinyloxy and the like);
(xii) a heterocyclyl-C1-C6 alkyloxy group (preferably, a heterocyclyl-C1-C6 alkyloxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranylmethoxy and the like);
(xiii) a C1-C6 alkyl-carbonylamino group (e.g., acetylamino and the like);
(xiv) a C1-C6 alkylthio group (e.g., methylthio, isopropylthio and the like);
(xv) a C1-C6 alkylsulfinyl group (e.g., methylsulfinyl, isopropylsulfinyl and the like);
(xvi) a C1-C6 alkylsulfonyl group (e.g., methylsulfonyl, isopropylsulfonyl and the like);
(xvii) a C1-C6 alkyl-carbonyl group (e.g., acetyl and the like);
(xviii) a C1-C6 alkyl-carbamoyl group (e.g., methylcarbamoyl and the like);
(xix) a di(C1-C6)alkyl-carbamoyl group (e.g., dimethylcarbamoyl and the like);
(xix) a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like)
and the like;
(2) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, pyridyl, dihydrobenzopyranyl, chromenyl, 2,3-dihydrobenzofuranyl, 1,3-benzodioxolyl, tetrahydropyranyl, indolyl and the like) optionally substituted by 1 to 3 substituents selected from the group consisting of
(i) halogen (e.g., F, Cl, Br and the like);
(ii) an oxo group;
(iii) a hydroxy group;
(iv) an amino group;
(v) a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like);
(vi) a C1-C6 alkoxy group optionally substituted by 1 to 3 substituents selected from the group consisting of halogen, a hydroxy group and a C3-C6 cycloalkyl group (e.g., methoxy, ethoxy, isopropoxy, neopentyloxy, trifluoromethoxy and the like);
(vii) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyloxy and the like);
(viii) a C1-C6 alkyl-carbonylamino group (e.g., acetylamino and the like);
(ix) a C1-C6 alkoxy-carbonyl group (e.g., methoxycarbonyl and the like)
and the like; or
(3) a C1-C6 alkyl group optionally substituted by 1 to 3 substituents selected from the group consisting of
(i) a hydroxy group,
(ii) a carboxy group,
(iii) a C1-C6 alkoxy-carbonyl group (e.g., ethoxycarbonyl and the like),
(iv) a C1-C6 alkyl-carbonyl group (e.g., pivaloyl and the like),
(v) a C3-C10 cycloalkyl-carbonyl group (e.g., cyclohexylcarbonyl, adamantylcarbonyl and the like),
(vi) a C6-C14 aryl-carbonyl group (e.g., benzoyl and the like) optionally substituted by 1 to 3 substituents selected from the group consisting of halogen and a C1-C6 alkoxy group,
(vii) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like),
(viii) a C1-C6 alkyl-carbamoyl group (e.g., tert-butylcarbamoyl and the like),
(ix) a C3-C6 cycloalkyl group (e.g., cyclopropyl, cyclohexyl and the like),
(x) an adamantyl group,
(xi) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxy-carbonyl group (e.g., methoxycarbonyl and the like); a C1-C6 alkyl-carbonyl group (e.g., acetyl and the like); a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like) and the like, (xii) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, isoxazolyl, thiazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen, a hydroxy group and a C1-C6 alkoxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like, (xiii) a C1-C6 alkoxyimino group (e.g., isopropoxyimino and the like), and the like, R13 is (1) hydrogen;

(2) halogen (e.g., F, Cl, Br and the like);

(3) a C1-C6 alkoxy group (e.g., methoxy, ethoxy and the like); or (4) a C1-C6 alkyl group optionally having 1 to 3 substituents selected from the group consisting of halogen and a C1-C6 alkoxy group, and Z is O or S.

[Compound B-IA]

5-benzyl-2-ethoxy-6-methyl-3-{[2'-(5-oxo-4,5-dihydro-1,2,4-oxadiazol-3-yl)biphenyl-4-yl]methyl}pyrimidin-4(3H)-one (Example 4);

6-methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one (Example 7);

5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one (Example 28);

5-benzyl-6-methyl-3-{[2'-(5-oxo-4,5-dihydro-1,2,4-oxadiazol-3-yl)biphenyl-4-yl]methyl}-2-propylpyrimidin-4(3H)-one (Example 287);

2-butyl-5-[hydroxy(phenyl)methyl]-6-methyl-3-{[2'-(5-oxo-4,5-dihydro-1,2,4-oxadiazol-3-yl)biphenyl-4-yl]methyl}pyrimidin-4(3H)-one (Example 452);

5-benzoyl-2-butyl-6-methyl-3-{[2'-(5-oxo-4,5-dihydro-1,2,4-oxadiazol-3-yl)biphenyl-4-yl]methyl}pyrimidin-4(3H)-one (Example 453);

6-ethyl-5-(morpholin-4-ylmethyl)-3-{[2'-(5-oxo-4,5-dihydro-1,2,4-oxadiazol-3-yl)biphenyl-4-yl]methyl}-2-propylpyrimidin-4(3H)-one (Example 455);

6-ethyl-5-(1-hydroxy-2-methylpropyl)-3-{[2'-(5-oxo-4,5-dihydro-1,2,4-oxadiazol-3-yl)biphenyl-4-yl]methyl}-2-propylpyrimidin-4(3H)-one (Example 473b);

6-ethyl-5-(6-isopropoxypyridin-3-yl)-3-{[2'-(5-oxo-4,5-dihydro-1,2,4-oxadiazol-3-yl)biphenyl-4-yl]methyl}-2-propylpyrimidin-4(3H)-one (Example 483); or 6-ethyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}-2-propylpyrimidin-4(3H)-one (Example 512);

or a salt thereof.

[Compound B1]

Compound B wherein R3b is (1) a C1-C6 alkyl group optionally substituted by 1 to 3 substituents selected from the group consisting of a C1-C6 alkoxy group, a C3-C6 cycloalkyl group and halogen;

(2) a C3-C6 cycloalkyl group;

(3) a C1-C6 alkoxy group; or (4) a C1-C6 alkylthio group,

R4b is (1) hydrogen;

(2) a C1-C6 alkyl group optionally substituted by 1 to 3 substituents selected from the group consisting of a C1-C6 alkoxy group, a hydroxy group, halogen, a cyclic hydrocarbon group (preferably, a C3-C6 cycloalkyl group or a C6-C14 aryl group) and a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like);

(3) a C3-C6 cycloalkyl group;

(4) a C1-C6 alkoxy group; or (5) a di(C1-C6)alkylamino group,

R5b is (1) hydrogen;

(2) a C1-C6 alkyl group optionally substituted by 1 to 3 substituents selected from the group consisting of (i) a hydroxy group, (ii) a carboxy group, (iii) a C1-C6 alkoxy-carbonyl group (e.g., ethoxycarbonyl and the like), (iv) a C1-C6 alkyl-carbonyl group (e.g., pivaloyl and the like), (v) a C3-C10 cycloalkyl-carbonyl group (e.g., cyclohexylcarbonyl, adamantylcarbonyl and the like), (vi) a C6-C14 aryl-carbonyl group (e.g., benzoyl and the like) optionally substituted by 1 to 3 substituents selected from the group consisting of halogen and a C1-C6 alkoxy group, (vii) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like), (viii) a C1-C6 alkyl-carbamoyl group (e.g., tert-butylcarbamoyl and the like), (ix) a C3-C6 cycloalkyl group (e.g., cyclopropyl, cyclohexyl and the like), (x) an adamantyl group, (xi) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxycarbonyl group (e.g., methoxycarbonyl and the like); a C1-C6 alkyl-carbonyl group (e.g., acetyl and the like); a heterocyclyl-carbonyl group (preferably, a heterocyclylcarbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like)
and the like, (xii) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, isoxazolyl, thiazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like, (xiii) a C1-C6 alkoxyimino group (e.g., isopropoxyimino and the like),
and the like;

(3) an indanyl group optionally substituted by an oxo group or a hydroxy group;

(4) a C6-C14 aryl group (e.g., phenyl, naphthyl and the like) optionally substituted by 1 to 3 substituents selected from the group consisting of
(i) halogen (e.g., F, Cl, Br and the like);
(ii) a hydroxy group;
(iii) a C1-C6 alkyl group optionally substituted by 1 to 3 substituents selected from the group consisting of halogen, a hydroxy group, a C1-C6 alkoxy group and a C1-C6 alkyl-carbonyl group (e.g., methyl, ethyl, isopropyl, isobutyl, tert-butyl, trifluoromethyl, hydroxymethyl, 1-hydroxyethyl and the like);
(iv) a C2-C6 alkenyl group (e.g., vinyl and the like) optionally substituted by 1 to 3 substituents selected from the group consisting of halogen and a hydroxy group;
(v) a C3-C6 cycloalkyl group (e.g., cyclopropyl and the like);
(vi) a C1-C6 alkoxy group (e.g., methoxy, ethoxy, propoxy, isopropoxy, isobutoxy, sec-butoxy, tert-butoxy, neopentyloxy and the like) optionally substituted by 1 to 3 substituents selected from the group consisting of a C2-C6 alkynyl group, a C1-C6 alkoxy group, halogen, a cyano group, a hydroxy group, a C3-C6 cycloalkyl group, a C1-C6 alkoxy-carbonyl group and a carbamoyl group;
(vii) a C2-C6 alkenyloxy group (e.g., vinyloxy and the like);
(viii) a C2-C6 alkynyloxy group (e.g., 1-methylbut-3-yn-1-yloxy and the like);
(ix) a C3-C10 cycloalkyloxy group (e.g., cyclopropyloxy, cyclobutyloxy, cyclopentyloxy, cyclohexyloxy, cycloheptyloxy and the like) optionally substituted by 1 to 3 substituents selected from the group consisting of an oxo group, a hydroxy group, a C1-C6 alkyl group, a hydroxy-C1-C6 alkyl group and a C1-C6 alkoxy-C1-C6 alkyl group;
(x) a C6-C14 aryloxy group (e.g., phenoxy and the like);
(xi) a heterocyclyl-oxy group optionally substituted by 1 to 3 C1-C6 alkyl groups (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydrofuranyloxy, tetrahydropyranyloxy, piperidinyloxy and the like);
(xii) a heterocyclyl-C1-C6 alkyloxy group (preferably, a heterocyclyl-C1-C6 alkyloxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranylmethoxy and the like);
(xiii) a C1-C6 alkyl-carbonylamino group (e.g., acetylamino and the like);
(xiv) a C1-C6 alkylthio group (e.g., methylthio, isopropylthio and the like);
(xv) a C1-C6 alkylsulfonyl group (e.g., methylsulfonyl, isopropylsulfonyl and the like);
(xvi) a C1-C6 alkyl-carbonyl group (e.g., acetyl and the like);
(xvii) a C1-C6 alkyl-carbamoyl group (e.g., methylcarbamoyl and the like);
(xviii) a di(C1-C6)alkyl-carbamoyl group (e.g., dimethylcarbamoyl and the like);
(xix) a heterocyclic group (preferably, a 5- or 6-membered, aromatic or a nonaromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., morpholinyl and the like)
and the like; or (5) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, pyridyl, dihydrobenzopyranyl, chromenyl, 2,3-dihydrobenzofuranyl, 1,3-benzodioxolyl, tetrahydropyranyl, indolyl and the like) optionally substituted by 1 to 3 substituents selected from the group consisting of
(i) halogen (e.g., F, Cl, Br and the like);
(ii) an oxo group;
(iii) a hydroxy group;

(iv) an amino group;
(v) a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like);
(vi) a C1-C6 alkoxy group optionally substituted by 1 to 3 substituents selected from the group consisting of halogen, a hydroxy group and a C3-C6 cycloalkyl group (e.g., methoxy, ethoxy, isopropoxy, neopentyloxy, trifluoromethoxy and the like);
(vii) a heterocyclyl-oxy group (preferably, a heterocyclyl-oxy group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyloxy and the like);
(viii) a C1-C6 alkyl-carbonylamino group (e.g., acetylamino and the like);
(ix) a C1-C6 alkoxy-carbonyl group (e.g., methoxycarbonyl and the like)
and the like,
R13 is hydrogen, halogen or C1-C6 alkoxy group, and
Z is O or S.

[Compound B2]

Compound B wherein R3b is
(1) a C1-C6 alkyl group optionally substituted by 1 to 3 substituents selected from the group consisting of a C1-C6 alkoxy group, a C3-C6 cycloalkyl group and halogen;
(2) a C3-C6 cycloalkyl group; or
(3) a C1-C6 alkoxy group, R4b is
(1) hydrogen;
(2) a C1-C6 alkyl group optionally substituted by 1 to 3 substituents selected from the group consisting of a C1-C6 alkoxy group, a hydroxy group, halogen and a cyclic hydrocarbon group (preferably, a C3-C6 cycloalkyl group or a C6-C14 aryl group);
(3) a C3-C6 cycloalkyl group;
(4) a C1-C6 alkoxy group; or
(5) a di(C1-C6)alkylamino group, R5b is
(1) hydrogen;
(2) a C1-C6 alkyl group optionally substituted by 1 to 3 substituents selected from the group consisting of
(i) a hydroxy group,
(ii) a carboxy group,
(iii) a C1-C6 alkoxy-carbonyl group (e.g., ethoxycarbonyl and the like),
(iv) a C1-C6 alkyl-carbonyl group (e.g., pivaloyl and the like),
(v) a C3-C10 cycloalkyl-carbonyl group (e.g., cyclohexylcarbonyl, adamantylcarbonyl and the like),
(vi) a C6-C14 aryl-carbonyl group (e.g., benzoyl and the like) optionally substituted by 1 to 3 substituents selected from the group consisting of halogen and a C1-C6 alkoxy group,
(vii) a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom, for example, morpholinocarbonyl and the like),
(viii) a C1-C6 alkyl-carbamoyl group (e.g., tert-butylcarbamoyl and the like),
(ix) a C3-C6 cycloalkyl group (e.g., cyclopropyl, cyclohexyl and the like),
(x) an adamantyl group,
(xi) a C6-C14 aryl group (e.g., phenyl, naphthyl and the like) optionally substituted by 1 to 3 substituents selected from the group consisting of halogen (e.g., F, Cl, Br and the like); a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like); a C1-C6 alkoxy group optionally substituted by 1 to 3 substituents selected from the group consisting of halogen and a hydroxy group (e.g., methoxy, ethoxy, trifluoromethoxy and the like); a C1-C6 alkylsulfonyl group (e.g., methylsulfonyl and the like); a carboxy group; a C1-C6 alkoxy-carbonyl group (e.g., methoxycarbonyl and the like); a C1-C6 alkyl-carbonyl group (e.g., acetyl and the like); a heterocyclyl-carbonyl group (preferably, a heterocyclyl-carbonyl group wherein the heterocyclyl moiety is a 5- or 6-membered, aromatic or non-aromatic heterocycle containing, as a ring-constituting atom besides carbon atom, 1 to 4 hetero atoms of 1 or 2 kinds selected from the group consisting of nitrogen atom, sulfur atom and oxygen atom) (e.g., morpholinocarbonyl and the like)
and the like,
(xii) a heterocyclic group (preferably, a 4- to 6-membered (preferably 5- or 6-membered) heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 4- to 6-membered (preferably 5- or 6-membered) heterocyclic group is condensed with benzene ring) (e.g., thienyl, isoxazolyl, thiazolyl, pyrazolyl, 1,2,4-oxadiazolyl, pyridyl, pyrimidinyl, pyrazinyl, benzo[b]thienyl, 1H-indazolyl, benzimidazolyl, benzo[d]isoxazolyl, benzothiazolyl, 1H-benzotriazolyl, quinolyl, oxetanyl, tetrahydrofuryl, morpholinyl, tetrahydropyranyl, 2,3-dihydrobenzofuranyl and the like) optionally substituted by 1 to 3 substituents selected from the group consisting of halogen (e.g., F, Cl, Br and the like); a hydroxy group; a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like); a C6-C14 aryl group (e.g., phenyl and the like); a C7-C16 aralkyl group (e.g., benzyl and the like); a heterocyclic group (preferably, a 5- or 6-membered aromatic heterocyclic group containing, as a ring-constituting atom besides carbon atom, 1 to 4 hetero atoms of 1 or 2 kinds selected from the group consisting of nitrogen atom, sulfur atom and oxygen atom) (e.g., thienyl, pyridyl and the like); a C1-C6 alkoxy group optionally substituted by 1 to 3 substituents selected from the group consisting of halogen and a hydroxy group (e.g., methoxy, ethoxy, trifluoromethoxy and the like) and the like,
and the like;
(3) an indanyl group optionally substituted by an oxo group or a hydroxy group;
(4) a C6-C14 aryl group (e.g., phenyl, naphthyl and the like) optionally substituted by 1 to 3 substituents selected from the group consisting of
(i) halogen (e.g., F, Cl, Br and the like);
(ii) a hydroxy group;
(iii) a C1-C6 alkyl group optionally substituted by 1 to 3 substituents selected from the group consisting of halogen and a hydroxy group (e.g., methyl, ethyl, isopropyl, isobutyl, tert-butyl, trifluoromethyl, hydroxymethyl, 1-hydroxyethyl and the like);

(iv) a C2-C6 alkenyl group (e.g., vinyl and the like) optionally substituted by 1 to 3 substituents selected from the group consisting of halogen and a hydroxy group;

(v) a C3-C6 cycloalkyl group (e.g., cyclopropyl and the like);

(vi) a C1-C6 alkoxy group (e.g., methoxy, ethoxy, propoxy, isopropoxy, isobutoxy, tert-butoxy, neopentyloxy and the like) optionally substituted by 1 to 3 substituents selected from the group consisting of a C1-C6 alkoxy group, halogen, a hydroxy group, a C3-C6 cycloalkyl group and a C1-C6 alkoxy-carbonyl group;

(vii) a C3-C6 cycloalkyloxy group (e.g., cyclopropyloxy, cyclobutyloxy and the like);

(viii) a C6-C14 aryloxy group (e.g., phenoxy and the like);

(ix) a C1-C6 alkyl-carbonylamino group (e.g., acetylamino and the like);

(x) a C1-C6 alkylthio group (e.g., methylthio, isopropylthio and the like);

(xi) a C1-C6 alkylsulfonyl group (e.g., methylsulfonyl, isopropylsulfonyl and the like);

(xii) a C1-C6 alkyl-carbonyl group (e.g., acetyl and the like);

(xiii) a C1-C6 alkyl-carbamoyl group (e.g., methylcarbamoyl and the like);

(xiv) a di(C1-C6)alkyl-carbamoyl group (e.g., dimethylcarbamoyl and the like), and the like; or (5) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., furyl, thienyl, pyridyl, dihydrobenzopyranyl, chromenyl, 2,3-dihydrobenzofuranyl, 1,3-benzodioxolyl and the like) optionally substituted by 1 to 3 substituents selected from the group consisting of (i) halogen (e.g., F, Cl, Br and the like);

(ii) an oxo group;

(iii) a hydroxy group;

(iv) an amino group;

(v) a C1-C6 alkyl group optionally substituted by 1 to 3 substituents selected from the group consisting of halogen and a hydroxy group (e.g., methyl, ethyl, tert-butyl, trifluoromethyl, hydroxymethyl, 1-hydroxyethyl and the like);

(vi) a C1-C6 alkoxy group optionally substituted by 1 to 3 substituents selected from the group consisting of halogen and a hydroxy group (e.g., methoxy, ethoxy, trifluoromethoxy and the like);

(vii) a C1-C6 alkyl-carbonylamino group (e.g., acetylamino and the like);

(viii) a C1-C6 alkoxy-carbonyl group (e.g., methoxycarbonyl and the like)

and the like,

R13 is hydrogen or halogen, and

Z is O or S.

[Compound C]

A compound represented by the formula:

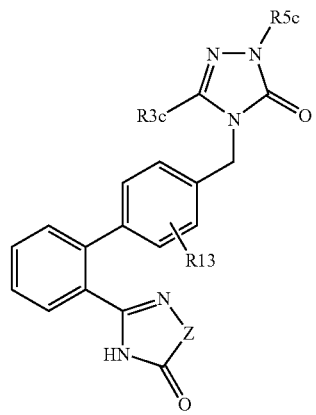

wherein R3c and R5c are as defined for R3 and R5, respectively, and other symbols are as defined above, or a salt thereof.

[Compound C—I]

Compound C wherein R3c is a C1-C6 alkyl group,

R5c is (1) a C1-C6 alkyl group optionally substituted by 1 to 3 substituents selected from the group consisting of (i) a C1-C6 alkyl-carbonyl group (e.g., pivaloyl and the like), (ii) a C6-C14 aryl-carbonyl group (e.g., benzoyl and the like) optionally substituted by 1 to 3 substituents selected from the group consisting of halogen and a C1-C6 alkoxy group, (iii) a C6-C14 aryl group (e.g., phenyl, naphthyl and the like), (iv) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyl and the like), and the like;

(2) a C6-C14 aryl group (e.g., phenyl, naphthyl and the like, preferably phenyl); or (3) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., 2,3-dihydrobenzofuranyl and the like) optionally substituted by 1 to 3 C1-C6 alkyl groups, R13 is (1) hydrogen;

(2) halogen (e.g., F, Cl, Br and the like);

(3) a C1-C6 alkoxy group (e.g., methoxy, ethoxy and the like); or (4) a C1-C6 alkyl group optionally having 1 to 3 substituents selected from the group consisting of halogen and a C1-C6 alkoxy group, and Z is O or S.

[Compound C1]

Compound C wherein R3c is a C1-C6 alkyl group,

R5c is
(1) a C1-C6 alkyl group optionally substituted by 1 to 3 substituents selected from the group consisting of
  (i) a C1-C6 alkyl-carbonyl group (e.g., pivaloyl and the like),
  (ii) a C6-C14 aryl-carbonyl group (e.g., benzoyl and the like) optionally substituted by 1 to 3 substituents selected from the group consisting of halogen and a C1-C6 alkoxy group,
  (iii) a C6-C14 aryl group (e.g., phenyl, naphthyl and the like),
  (iv) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom) (e.g., tetrahydropyranyl and the like)
and the like;
(2) a C6-C14 aryl group (e.g., phenyl, naphthyl and the like, preferably phenyl); or
(3) a heterocyclic group (preferably, a 5- or 6-membered heterocyclic group containing, as a ring-constituting atom besides carbon atom, 1 to 4 hetero atoms of 1 or 2 kinds selected from the group consisting of nitrogen atom, sulfur atom and oxygen atom, or a fused heterocyclic group wherein said 5- or 6-membered heterocyclic group is condensed with benzene ring) (e.g., 2,3-dihydrobenzofuranyl and the like) optionally substituted by 1 to 3 C1-C6 alkyl groups,
R13 is hydrogen or halogen, and
Z is O or S.

[Compound C-IA]

3-(4'-{[3-butyl-1-(2,2-dimethylpropyl)-5-oxo-1,5-dihydro-4H-1,2,4-triazol-4-yl]methyl}biphenyl-2-yl)-1,2,4-oxadiazol-5(4H)-one (Example 14);

3-(4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one (Example 136);

3-(4'-{[3-butyl-5-oxo-1-(2-phenylethyl)-1,5-dihydro-4H-1,2,4-triazol-4-yl]methyl}biphenyl-2-yl)-1,2,4-oxadiazol-5(4H)-one (Example 180);

3-{4'-[(3-butyl-1-sec-butyl-5-oxo-1,5-dihydro-4H-1,2,4-triazol-4-yl)methyl]biphenyl-2-yl}-1,2,4-oxadiazol-5(4H)-one (Example 181);

3-{4'-[(3-butyl-5-oxo-1-phenyl-1,5-dihydro-4H-1,2,4-triazol-4-yl)methyl]biphenyl-2-yl}-1,2,4-oxadiazol-5(4H)-one (Example 182);

3-(4'-{[3-butyl-5-oxo-1-(tetrahydro-2H-pyran-2-ylmethyl)-1,5-dihydro-4H-1,2,4-triazol-4-yl]methyl}biphenyl-2-yl)-1,2,4-oxadiazol-5(4H)-one (Example 183);

3-[4'-({3-butyl-1-[2-(4-fluorophenyl)-2-oxoethyl]-5-oxo-1,5-dihydro-4H-1,2,4-triazol-4-yl}methyl)biphenyl-2-yl]-1,2,4-oxadiazol-5(4H)-one (Example 200);

3-[4'-({3-butyl-1-[2-(4-methoxyphenyl)-2-oxoethyl]-5-oxo-1,5-dihydro-4H-1,2,4-triazol-4-yl}methyl)biphenyl-2-yl]-1,2,4-oxadiazol-5(4H)-one (Example 301); or 3-(4'-{[3-butyl-1-(3,3-dimethyl-2-oxobutyl)-5-oxo-1,5-dihydro-4H-1,2,4-triazol-4-yl]methyl}biphenyl-2-yl)-1,2,4-oxadiazol-5(4H)-one (Example 302);
or a salt thereof.

[Compound AA]

(1) A crystalline compound of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof.

(2) A crystalline compound of hydrate of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof.

(3) A crystalline compound of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 4.64, 5.46, 8.40, 11.10, 12.60, 13.10, 14.14, 14.36, 14.60, 15.58, 15.86, 16.24, 16.86, 17.52, 19.26, 19.72, 20.00, 20.40, 20.80, 21.12, 21.70.

(4) A crystalline compound of hydrate of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt, which has an X-ray powder diffraction analysis pattern with peaks at diffraction angle: 2θ(°) of 4.46, 6.32, 12.66, 12.84, 13.46, 13.74, 16.82, 17.08, 17.82, 17.98, 18.38, 19.70, 20.34, 21.80, 22.18, 22.80, 24.08, 25.40, 26.70.

[Compound AB]

(1) A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one or a salt thereof.

(2) A crystalline compound of hydrate of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one or a salt thereof.

(3) A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 4.60, 8.38, 9.28, 9.66, 10.46, 12.26, 12.86, 13.98, 16.92, 17.32, 18.70, 18.94, 19.62, 20.18, 20.98.

(4) A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 8.50, 11.86, 12.26, 13.98, 17.14, 18.46, 19.04, 19.28, 19.62, 20.16, 20.48, 22.58, 24.60.

(5) A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 7.36, 7.66, 11.58, 12.84, 13.28, 13.64, 14.50, 15.28, 15.50, 18.38, 18.66, 19.28, 20.20, 20.70, 21.72, 22.14, 22.82.

(6) A crystalline compound of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 8.34, 9.16, 10.64, 11.08, 11.42, 12.42, 13.18, 13.88, 14.78, 15.58, 16.28, 17.10, 17.80, 18.56, 18.94, 19.18, 20.14, 20.86, 21.56, 22.04, 22.44, 23.14, 23.66, 24.80, 26.18, 27.96, 29.16.

(7) A crystalline compound of hydrate of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt, which has an X-ray powder diffraction analysis pattern with peaks at diffraction angle: 2θ(°) of 4.32, 8.70, 9.86, 12.76, 13.10, 15.48, 18.36, 19.68, 20.62, 21.36, 21.76, 22.04, 22.44, 23.10, 24.22, 24.62, 27.94, 28.24.

(8) A crystalline compound of hydrate of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt, which has an X-ray powder diffraction analysis pattern with peaks at diffraction angle: 2θ(°) of 6.32, 6.84, 8.90, 14.36, 16.64, 17.96, 19.18, 19.94, 21.82, 22.04, 22.90, 23.62, 24.92.

[Compound AC]

(1) A crystalline compound of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof.

(2) A crystalline compound of hydrate of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof.

(3) A crystalline compound of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 4.76, 6.10, 7.30, 7.86, 8.16, 9.18, 9.60, 10.66, 11.28, 11.94, 12.58, 13.34, 14.62, 15.10, 15.46, 16.34, 16.90, 17.76, 18.64, 19.34, 20.86, 21.58, 22.42, 24.36, 24.86.

(4) A crystalline compound of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle: 2θ(°) of 4.38, 7.42, 8.90, 9.68, 10.92, 11.24, 11.90, 12.56, 12.88, 13.34, 14.06, 14.92, 16.64, 17.30, 17.80, 18.70, 19.08, 19.40, 20.36, 20.90, 21.20, 21.50, 21.98, 22.40, 22.72, 22.98, 23.68.

(5) A crystalline compound of hydrate of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt, which has an X-ray powder diffraction analysis pattern with peaks at diffraction angle: 2θ(°) of 5.02, 5.36, 9.46, 10.66, 11.80, 13.42, 17.06, 17.78, 19.00, 19.18, 20.18, 20.88, 21.38, 23.26, 23.78, 25.06, 25.74, 26.06, 26.90, 27.34.

As the salt of a compound represented by the formula (I), a pharmacologically acceptable salt and the like can be mentioned. Examples thereof include acid addition salt with an acid such as trifluoroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid and the like; salt with a metal salt such as sodium, potassium, magnesium, calcium and the like; salt with an organic base such as trimethylamine, triethylamine, pyridine, picoline, N-methylpyrrolidine, N-methylpiperidine, N-methylmorpholine and the like, and the like.

A prodrug of the compound (I) means a compound which is converted to the compound (I) with a reaction due to an enzyme, a gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug of the compound (I) may also be one which is converted into the compound (I) under a physiological condition, such as those described in IYAKUHIN no KAIHATSU (Development of Pharmaceuticals), Vol. 7, Design of Molecules, p. 163-198, 1990, Published by HIROKAWA SHOTEN.

When the compound (I) has isomers such as optical isomer, stereoisomer, positional isomer, rotational isomer and the like, and any isomers and mixture of isomers are encompassed in the compound (I). For example, when the compound (I) has an optical isomer, an optical isomer separated from a racemate is also encompassed in the compound (I). These isomers can be obtained as independent products by a synthesis means or a separation means (e.g., concentration, solvent extraction, column chromatography, recrystallization and the like), and the like known per se.

The compound (I) may be a crystal or an amorphous form. When the compound (I) is a crystal, both a single crystal and crystal mixtures are encompassed in the compound (I). Crystals can be produced by crystallization according to crystallization methods known per se.

The compound (I) may be a solvate (e.g., hydrate etc.) or a non-solvate, both of which are encompassed in the compound (I).

The compound (I) may be labeled with an isotope (e.g., $^3$H, $^{14}$C, $^{35}$S, $^{125}$I and the like) and the like.

Deuterium-converted compound wherein $^1$H has been converted to $^2$H(D) are also encompassed in the compound (I).

Since the compound of the present invention has a strong angiotensin II antagonistic activity (or inhibitory activity) (particularly, AT1 receptor antagonistic activity), the compound of the present invention is useful as an agent for the prophylaxis or treatment of a disease (or a disease whose onset is promoted) developed by the contraction or growth of blood vessels or organ disorder, which expresses via an angiotensin II receptor, or due to the presence of angiotensin II, or a factor induced by the presence of angiotensin II, in mammals (e.g., human, monkey, cat, pig, horse, bovine, mouse, rat, guinea pig, dog, rabbit etc.).

As such diseases, for example, hypertension (including blood pressure circadian rhythm abnormality), heart diseases (e.g., cardiac hypertrophy, heart failure (e.g., acute heart failure, chronic heart failure including congestive heart failure, diastolic heart failure, systolic heart failure, ventricular dysfunction), cardiomyopathy, acute coronary syndromes, angina pectoris, myocarditis, atrial fibrillation, arrhythmia, tachycardia, myocardial infarction etc.), cerebrovascular disorders (e.g., asymptomatic cerebrovascular disorder, transient cerebral ischemia, stroke, cerebrovascular dementia, hypertensive encephalopathy, cerebral infarction etc.), cerebral edema, cerebral circulatory disorder, recurrence and sequela of cerebrovascular disorders (e.g., neurotic symptom, psychic symptom, subjective symptom, disorder in daily living activities etc.), ischemic peripheral circulation disorder, peripheral arterial diseases, venous insufficiency, progression of cardiac dysfunction after myocardial infarction (post-myocardial infarction), acute or chronic kidney diseases (e.g., nephritis, glomerulonephritis including chronic glomerulonephritis, glomerulosclerosis, renal failure, thrombotic vasculopathy, diabetic nephropathy, complication of dialysis, organ dysfunction including nephropathy by radiation damage etc.), arteriosclerosis including atherosclerosis (e.g., aneurysm, coronary arteriosclerosis, cerebral arteriosclerosis, peripheral arteriosclerosis etc.), vascular hypertrophy, vascular hypertrophy, restenosis, obliteration or re-obliteration and organ disorders after intervention (e.g., percutaneous transluminal coronary angioplasty, stenting, Coronary artery bypass graft (CABG) surgery, coronary angioscopy, intravascular ultrasound, intracoronary thrombolysis etc.), polycythemia, hypertension, organ disorder and vascular hypertrophy after transplantation, rejection after transplantation, ocular diseases (e.g., glaucoma, ocular hypertension etc.), thrombosis, multiple organ disorder, endothelial dysfunction, hypertensive tinnitus, other cardiovascular diseases (e.g., deep vein thrombosis, obstructive peripheral circulatory disorder, arteriosclerosis obliterans, thromboangiitis obliterans, ischemic cerebral circulatory disorder, Raynaud's disease, Buerger's disease etc.), metabolic and/or nutritional disorders (e.g., obesity, glucose intolerance, hyperlipidemia, hypercholesterolemia, hypertriglyceridemia, hypoHDL-cholesterolemia, hyperuricacidemia, hyperkalemia, hypernatremia etc.), nerve degeneration diseases (e.g., Alzheimer's disease, Parkinson's disease, amyotrophic lateral sclerosis, AIDS encephalopathy etc.), central nervous system disorders (e.g., disorders such as cerebral hemorrhage, cerebral infarction etc., and their sequela and complication, head injury, spinal injury, cerebral edema, sensory malfunction, sensory functional disorder, autonomic nervous system disorder, autonomic nervous system malfunction, multiple sclerosis etc.), migraine headache, dementia, defects of memory, disorder of consciousness, amnesia, anxiety symptom, catatonic symptom, discomfort mental state, psychopathies (e.g., depressive psychosis, epilepsy, alcoholism etc.), inflammatory diseases (e.g., arthritis such as rheumatoid arthritis, osteoarthritis, rheumatoid myelitis, periostitis etc.; inflammation after operation and injury; remission of swelling; pharyngitis; cystitis; pneumonia; atopic dermatitis; inflammatory intestinal diseases such as Crohn's disease, ulcerative colitis etc.; meningitis; inflammatory ocular disease; inflammatory pulmonary disease such as pneumonia, pulmonary silicosis, pulmonary sarcoidosis, pulmonary tuberculosis etc.), allergic diseases (e.g., allergic rhinitis, conjunctivitis, gastrointestinal allergy, pollinosis, anaphylaxis etc.), chronic obstructive pulmonary disease, interstitial pneumonia, pneumocytis carinni pneumonia, collagen diseases (e.g., systemic lupus erythematosus, scleroderma, polyarteritis etc.), hepatic diseases (e.g., hepatitis including chronic hepatitis, hepatic cirrhosis, liver fibrosis, Nonalcoholic fatty liver disease, nonalcoholic steatohepatitis etc.), portal hypertension, digestive system disorders (e.g., gastritis, gastric ulcer, gastric cancer, gastric disorder after operation, dyspepsia, esophageal ulcer, pancreatitis, colon polyp, cholelithiasis, hemorrhoidal disease, varices ruptures of esophagus and stomach etc.), blood and/or myelopoietic diseases (e.g., erythrocytosis, vascular purpura, autoimmune hemolytic anemia, disseminated intravascular coagulation syndrome, multiple myelopathy etc.), bone diseases (e.g., fracture, refracture, osteoporosis, osteomalacia, bone Paget's disease, sclerosing myelitis, rheumatoid arthritis, osteoarthritis of the knee and joint tissue dysfunction and the like caused by diseases similar to these etc.), solid tumor, tumors (e.g., malignant melanoma, malignant lymphoma, cancer of digestive organs (e.g., stomach, intestine etc.) etc.), cancer and cachexia following cancer, metastasis cancer, endocrinopathy (e.g., Addison's disease, Cushing's syndrome, pheochromocytoma, primary aldosteronism etc.), Creutzfeldt-Jakob disease, urinary organ and/or male genital diseases (e.g., cystitis, prostatic hypertrophy, prostatic cancer, sex infectious disease etc.), female disorders (e.g., climacteric disorder, gestosis, endometriosis, hysteromyoma, ovarian disease, breast disease, sex infectious disease etc.), disease relating to environment and occupational factors (e.g., radiation hazard, hazard by ultraviolet, infrared or laser beam, altitude sickness etc.), respiratory diseases (e.g., cold syndrome, pneumonia, asthma, pulmonary hypertension, pulmonary thrombosis and pulmonary embolism etc.), infectious diseases (e.g., viral infectious diseases with cytomegalovirus, influenza virus, herpes virus etc., rickettsiosis, bacterial infectious disease etc.), toxemias (e.g., sepsis, septic shock, endotoxin shock, Gram-negative sepsis, toxic shock syndrome etc.), otorhinolaryngological diseases (e.g., Meniere's syndrome, tinnitus, dysgeusia, vertigo, disequilibrium, dysphagia etc.), skin diseases (e.g., keloid, hemangioma, psoriasis etc.), intradialytic hypotension, myasthenia gravis, systemic diseases such as chronic fatigue syndrome, apnea (e.g., sleep apnea etc.), disorders associated with apnea (e.g., hypertension etc.) and the like can be mentioned.

Since the compound of the present invention can maintain a certain antihypertensive action through day and night, the dose and frequency can be reduced as compared to the administration of a compound other than the present invention, and moreover, elevation of blood pressure before and after awakening, which is particularly problematic in patients with hypertension, can be suppressed more effectively.

In addition, long-term suppression of action of angiotensin II by the compound of the present invention results in the improvement or suppression of promotion of disorder or abnormality in the biological function and physiological action, that causes adult disorders and various diseases linked with aging and the like, which in turn leads to the primary and secondary prophylaxis of diseases or clinical conditions caused thereby or suppression of the progression thereof. As the disorder or abnormality in the biological function and physiological action, for example, disorder or abnormality in automatic controlling capability of cerebral circulation and/or renal circulation, disorder of circulation (e.g., peripheral, cerebral, microcirculation etc.), disorder of blood-brain-barrier, salt sensitivity, abnormal state of coagulation and fibrinolysis system, abnormal state of blood and blood cell components (e.g., accentuation of platelet aggregation action, malfunction of erythrocyte deformability, accentuation of leukocyte adhesiveness, rise of blood viscosity etc.), production and function accentuation of growth factor and cytokines (e.g., PDGF, VEGF, FGF, interleukin, TNF-$\alpha$, MCP-1 etc.), accentuation of production and infiltration of inflammatory cells, accentuation of production of free radical, liposteatosis accentuation, endothelial function disorder, endothelium, cell and organ dysfunction, edema, cell morphogenesis change of smooth muscle etc. (morphogenesis to proliferation type etc.), production and function accentuation of vasoactive substance and thrombosis inducers (e.g., endothelin, thromboxane $A_2$ etc.), abnormal constriction of blood vessel etc., metabolic disorder (serum lipid abnormalities, dysglycemia etc.), abnormal growth of cell etc., angiogenesis (including abnormal vasculogenesis during abnormal capillary reticular formation in adventitial coat of arteriosclerotic lesion) and the like can be mentioned. The compound of the present invention can be used as an agent for the primary and secondary prophylaxis or treatment of organ disorders associated with various diseases (e.g., cerebrovascular disorder and organ disorder associated therewith, organ disorder associated with cardiovascular disease, organ disorder associated with diabetes, organ disorder after intervention etc.). In particular, since the compound has an activity of inhibiting proteinuria, the compound of the present invention can be used as an agent for protecting kidney.

Therefore, the compound of the present invention can be advantageously used when the patients with insulin resistance, impaired glucose tolerance, diabetes or hyperinsulinemia have concurrently developed the above-mentioned diseases or clinical condition.

The compound of the present invention can be used as insulin sensitizer, agent for enhancing insulin sensitivity, retinoid related receptor function regulator, peroxisome proliferator-activated receptor ligand, retinoid X receptor ligand and the like. As used herein, the function regulator means both agonist and antagonist.

The compound of the present invention has hypoglycemic action, hypolipidemic action, insulin resistance improving action, insulin sensitizing action and peroxisome proliferator-activated receptor (hereinafter sometimes to be abbreviated as PPAR) γ (GenBank Accession No. L40904) agonist action. As used herein, PPARγ may form a heterodimer receptor with retinoid X receptor (hereinafter sometimes to be abbreviated as RXR) α (GenBank Accession No. X52773), RXRβ (GenBank Accession No. M84820) or RXRγ (GenBank Accession No. U38480). The compound of the present invention has a selective agonist action on PPARγ.

Since the compound of the present invention normalizes the intracellular insulin signal transduction mechanism, which mainly causes insulin resistance, thereby reducing insulin resistance and enhancing insulin action, and has a glucose tolerance improvement action. Therefore, the compound of the present invention or a salt thereof or a prodrug thereof (containing the compound of the present invention) can be used for mammals (e.g., human, monkey, cat, pig, horse, bovine, mouse, rat, guinea pig, dog, rabbit etc.) as an improving agent or an agent for the prophylaxis and/or treatment of the diseases in which insulin resistance is involved.

The compound of the present invention can be used, for example, as an agent for the prophylaxis or treatment of diabetes (e.g., type 1 diabetes, type 2 diabetes, gestational diabetes, obesity type diabetes); an agent for the prophylaxis or treatment of dyslipidemia (e.g., hypertriglyceridemia, hypercholesterolemia, hypoHDL-emia, postprandial hyperlipemia); an insulin sensitizer; an agent for enhancing insulin sensitivity; an agent for the prophylaxis or treatment of impaired glucose tolerance (IGT); and an agent for preventing progression from impaired glucose tolerance to diabetes.

In addition, the compound of the present invention can be used, for example, as an agent for the prophylaxis or treatment of hyperinsulinemia, metabolic syndrome, hypertension associated with insulin resistance, hypertension associated with impaired glucose tolerance, hypertension associated with diabetes (e.g., type II diabetes and the like), hypertension associated with hyperinsulinemia, insulin resistance associated with hypertension, impaired glucose tolerance associated with hypertension, diabetes associated with hypertension, and hyperinsulinemia associated with hypertension.

Moreover, the compound of the present invention can also be used for the treatment of patients with diabetes, who shows a normal high blood pressure value.

The compound of the present invention can be also used as an agent for the prophylaxis or treatment of, for example, diabetic complications [e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, skin and soft tissue infection, lower limb infection), diabetic gangrene, xerostomia, lowered sense of hearing, cerebrovascular disease, peripheral circulatory disturbance], obesity, osteoporosis, cachexia (e.g., cancer cachexia, tuberculous cachexia, diabetic cachexia, hemopathic cachexia, endocrinopathic cachexia, infectious cachexia, cachexia induced by acquired immunodeficiency syndrome), fatty liver, hepatic cirrhosis, hypertension, polycystic ovary syndrome, renal diseases (e.g., diabetic nephropathy, glomerular nephritis, glomerulosclerosis, nephrotic syndrome, hypertensive nephrosclerosis, end-stage renal disease), muscular dystrophy, myocardial infarction, angina pectoris, cerebrovascular disease (e.g., cerebral infarction, stroke), insulin resistant syndrome, syndrome X, metabolic syndrome (clinical conditions showing at least three selected from hypertriglyceridemia, hypo-HDL-cholesterolemia, hypertension, abdominal obesity and impaired glucose tolerance), hyperinsulinemia, hyperinsulinemia-induced sensory disorder, tumor (e.g., leukemia, breast cancer, prostate cancer, skin cancer), irritable bowel syndrome, acute or chronic diarrhea, inflammatory diseases (e.g., arteriosclerosis (e.g., atherosclerosis etc.), rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, pancreatitis, inflammatory colitis, ulcerative colitis), visceral obesity syndrome and the like.

The compound of the present invention can be used for the improvement of symptoms associated with peptic ulcer, acute or chronic gastritis, biliary dyskinesia, cholecystitis or the like, such as abdominal pain, nausea, vomiting, epigastric discomfort and the like.

The compound of the present invention is also used as an agent for the prophylaxis or treatment of inflammatory diseases in which TNF-α is involved. Here, the inflammatory diseases in which TNF-α is involved means inflammatory diseases developed by the presence of TNF-α, and treated by a TNF-α suppressing effect. Examples of such inflammatory diseases include diabetic complications (e.g., retinopathy, nephropathy, neuropathy, macroangiopathy etc.), rheumatoid arthritis, spondylitis deformans, osteoarthritis, lumbago, gout, postoperative or traumatic inflammation, swelling, neuralgia, pharyngolaryngitis, cystitis, hepatitis, pneumonia, gastric mucosal injury (including aspirin-induced gastric mucosal injury) and the like.

The compound of the present invention has an apoptosis inhibitory activity, and can be used as an agent for the prophylaxis or treatment of diseases mediated by promotion of apoptosis. Examples of the diseases mediated by promotion of apoptosis include viral diseases (e.g., AIDS, fulminant hepatitis etc.), neurodegenerative diseases (e.g., Alzheimer's disease, Parkinson's disease, amyotrophic lateral sclerosis, retinitis pigmentosa, cerebellar degeneration etc.), myelodysplasia (e.g., aplastic anemia etc.), ischemic diseases (e.g., myocardial infarction, stroke etc.), hepatic diseases (e.g., alcoholic hepatitis, hepatitis B, hepatitis C etc.), joint diseases (e.g., osteoarthritis etc.), atherosclerosis and the like.

The compound of the present invention can be used for reducing visceral fats, inhibiting accumulation of visceral fats, ameliorating glycometabolism, ameliorating lipid metabolism, ameliorating insulin resistance, inhibiting oxidized LDL production, ameliorating lipoprotein metabolism, ameliorating coronary artery diseases, preventing or treating cardiovascular complications, preventing or treating heart failure complications, lowering blood remnant, preventing or treating anovulation, preventing or treating hirsutism, preventing or treating hyperandrogenism, and the like.

The compound of the present invention is also used for the secondary prevention of various diseases mentioned above (e.g., cardiovascular event such as myocardial infarction etc.) and suppression of progression thereof.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can also be used as an agent for improving or the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria, or further, as an agent for treating hypertension of hypertensive patients having not less than the above-mentioned diagnostic criteria (e.g., fasting blood sugar level of 126 mg/dl). Moreover, the compound of the present invention can prevent progression of borderline type, impaired glucose tolerance, IFG (Impaired Fasting Glucose) or IFG (Impaired Fasting Glycemia) into diabetes.

The compound of the present invention is effective as a drug for the suppression or improvement of cardiac dysfunction, progression of cardiac remodeling and aggravation of conditions in, or a drug for the suppression of decreased survival rate of, cardiac patients (e.g., cardiac hypertrophy, acute heart failure, chronic heart failure including congestive heart failure, impaired vasodilation, cardiomyopathy, angina pectoris, myocarditis, atrial fibrillation, arrhythmia, tachycardia, myocardial infarction and the like) with diabetes. In addition, it is effective for the prevention of the onset of a cardiac disease (e.g., cardiac hypertrophy, acute heart failure, chronic heart failure including congestive heart failure, impaired vasodilation, cardiomyopathy, angina pectoris, myocarditis, atrial fibrillation, arrhythmia, tachycardia, myocardial infarction and the like) and a cerebrovascular disorder (e.g., asymptomatic cerebrovascular disorder, transient cerebral ischemic attack, stroke, cerebrovascular dementia, hypertensive encephalopathia, cerebral infarction and the like) in diabetic patients.

Since the compound of the present invention has an activity of inhibiting body weight gain, the compound of the present invention can be used as a body weight gain inhibitor to mammals. Target mammals may be any mammals of which body weight gain is to be avoided. The mammals may have a risk of body weight gain genetically or may be suffering from lifestyle-related diseases such as diabetes, hypertension and/or dyslipidemia etc. The body weight gain may be caused by excessive feeding or diet without nutrient balance, or may be derived from combination drug, for example, agents for enhancing insulin sensitivity having PPARγ-agonistic activity such as troglitazone, rosiglitazone, englitazone, ciglitazone, pioglitazone etc. and the like. In addition, body weight gain may be preliminary to obesity, or may be body weight gain of obesity patients. Here, obesity is defined that BMI (body mass index; body weight (kg)/[height (m)]$^2$) is at least twenty-five for Japanese (criterion by Japan Society for the Study of Obesity), or at least thirty for westerner (criterion by WHO).

The compound of the present invention is useful as an agent for the prophylaxis or treatment of metabolic syndrome. Because patients with metabolic syndrome have an extreme high incidence of cardiovascular diseases as compared to patients with single lifestyle-related diseases, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high serum triglycerides or low HDL cholesterol) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in the United States, patients with at least three of abdominal obesity, hypertriglyceridemia, hypo-HDL cholesterolemia, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can be used for treating patients of hypertension with metabolic syndrome.

Since the compound of the present invention has an anti-inflammatory action, the compound of the present invention can be used as an anti-inflammatory agent for preventing or treating inflammatory diseases. Examples of inflammatory diseases include inflammatory diseases due to various diseases such as arthritis (e.g. rheumatoid arthritis, osteoarthritis, rheumatoid myelitis, gouty arthritis, synovitis), asthma, allergic diseases, arteriosclerosis including atherosclerosis (aneurysm, coronary sclerosis, cerebral arterial sclerosis, peripheral arterial sclerosis etc.), digestive tract disease such as inflammatory intestine disease (e.g. Crohn's disease, ulcerative colitis), diabetic complication (diabetic neuropathy, diabetic vascular disorder), atopic dermatitis, chronic obstructive pulmonary disease, systemic lupus erythematosus, visceral inflammatory disease (nephritic, hepatitis), autoimmune hemolytic anemia, psoriasis, nervous degenerative disease (e.g. Alzheimer's disease, Parkinson's diseases, amyotrophic lateral sclerosis, AIDS encephalopathy), central nervous disorder (e.g. cerebrovascular disorder such as cerebral hemorrhage and cerebral infarct, head trauma, spinal damage, cerebral edema, multiple sclerosis), meningitis, angina pectoris, myocaridial infarction, congestive heart failure, vascular hypertrophy or occlusion and organ disorder after intervention (percutaneous transluminal coronary angioplasty, stenting, coronary artery bypass graft, coronary angioscopy, intravascular ultrasound, intracoronary thrombolysis etc), vascular reocclusion or restenosis after bypass operation, endothelial functional disorder, other circulatory disease (intermittent claudication, obstructive peripheral circulatory disorder, arteriosclerosis obliterans, thromboangiitis obliterans, ischemic cerebral circulatory disorder, Raynaud's disease, Buerger's disease), inflammatory ocular disease, inflammatory pulmonary disease (e.g. chronic pneumonia, silicosis, pulmonary sarcoidosis, pulmonary tuberculosis), endometritis, toxemia (e.g. sepsis, septic shock, endotoxin shock, gram negative sepsis, toxin shock syndrome), cachexia (e.g. cachexia due to infection, carcinomatous cachexia, cachexia due to acquired immunodeficiency syndrome), cancer, Addison's disease, Creutzfeldt-Jakob disease, virus infection (e.g. infection of virus such as cytomegalovirus, influenza virus, herpes virus etc.), disseminated intravascular coagulation.

In addition, since the compound of the present invention has an analgesic action, the compound of the present invention can be also used as an analgesic agent for preventing or treating pain. Examples of pain diseases include acute pain due to inflammation, pain associated with chronic inflammation, pain associated with acute inflammation, pain after operation (pain of incisional, deep pain, organ pain, chronic pain after operation etc.), muscular pain (muscular pain associated with chronic pain disease, shoulder stiffness etc.), arthralgia, toothache, gnathicarthralgia, headache (migraine, catatonic headache, headache associated with fever, headache associated hypertension), organ pain (cardiac pain, angina pain, abdominal pain, renal pain, ureterane pain, bladder pain), pain in obstetrics area (mittelschmerz, dysmenorrheal, labor pain), neuralgia (disc hernia, nerve root pain, neuralgia after herpes zoster, trigeminal neuralgia), carcinomatous pain, reflex sympathetic atrophy, complex local pain syndrome, and the like. The compound of the present invention is effective in alleviate directly and rapidly various pains such as nervous pain, carcinomatous pain and inflammatory pain, and exhibits the particularly excellent analgesic effect to patients and pathologies in which a pain sense threshold is lowered.

The compound of the present invention is particularly useful as an analgesic agent for pain associated with chronic inflammation or pain associated with hypertension, or as an agent for preventing or treating inflammatory disease or pain due to (1) arteriosclerosis including atherosclerosis, (2) vascular hypertrophy, occlusion or organ disorder after intervention, (3) reocclusion, restenosis or endothelial functional disorder after bypass operation, (4) intermittent claudication, (5) obstructive peripheral circulatory disorder, or (6) arteriosclerosis obliterans.

In one embodiment, since the compound of the present invention has an angiotensin II receptor antagonistic action (particularly an AT1 receptor antagonistic action) and a PPAR agonistic action (particularly a selective agonist action on PPARγ), the compound is useful as an agent for the prophylaxis or treatment of cardiovascular diseases such as hypertension, cardiac disease (cardiac hypertrophy, heart failure, myocardial infarction and the like), arteriosclerosis, kidney disease (diabetic nephropathy, chronic glomerulonephritis and the like), stroke and the like; metabolic diseases such as dyslipidemia, obesity, diabetes and the like; and/or central nervous system diseases such as depression, dementia, Alzheimer's disease and the like.

In further embodiment, the compound of the present invention is useful as an agent for the prophylaxis or treatment of hypertension, cardiac disease (cardiac hypertrophy, heart failure, myocardial infarction and the like), arteriosclerosis, kidney disease (diabetic nephropathy, chronic glomerulonephritis and the like), stroke, dyslipidemia, obesity, diabetes, dementia, Alzheimer's disease and the like.

The content of the compound of the present invention in a pharmaceutical composition is generally about 0.01-about 99.9 wt %, preferably about 0.1-about 50 wt %, relative to the entire preparation.

The dose of the compound of the present invention is determined in consideration of age, body weight, general health condition, sex, diet, administration time, administration method, clearance rate, combination of drugs, the level of disease for which the patient is under treatment then, and other factors.

While the dose varies depending on the target disease, condition, subject of administration, administration method and the like, for oral administration as a therapeutic agent for essential hypertension in adult, the daily dose of 0.1-600 mg is preferably administered in a single dose or in 2 or 3 portions.

In addition, since the compound of the present invention is superior in safety, it can be administered for a long period.

The compound of the present invention can be used in combination with pharmaceutical agents such as a therapeutic agent for diabetes, a therapeutic agent for diabetic complications, an anti-hyperlipidemia agent, a therapeutic agent for cardiovascular disease (e.g. heart failure, angina pectoris, and like that), an anti-arteriosclerotic agent, an anti-hypertensive agent, an anti-obesity agent, a diuretic, an antigout agent, an antithrombotic agent, an anti-inflammatory agent, a chemotherapeutic agent, an immunotherapeutic agent, a therapeutic agent for osteoporosis, an anti-dementia agent, an erectile dysfunction amelioration agent, a therapeutic agent for urinary incontinence/urinary frequency, a therapeutic agent for dysurea and the like (hereinafter to be abbreviated as a concomitant drug). These concomitant drugs may be low-molecular-weight compounds, high-molecular-weight proteins, polypeptides, antibodies, vaccines and the like. In this case, the administration mode of the compound of the present invention and the concomitant drug is not particularly restricted, and it is sufficient that the compound of the present invention and the concomitant drug are combined in administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like. The dose of the concomitant drug can be appropriately determined based on the dose clinically employed. The mixing ratio of the compound of the present invention and the concomitant drug can be appropriately selected according to the administration subject, administration route, target disease, condition, combination, and other factors. In cases where the administration subject is human, for example, the concomitant drug may be used in an amount of 0.01 to 100 parts by weight per part by weight of the compound of the present invention.

Examples of other therapeutic agents for diabetes include insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Netoglitazone (MCC-555), Rivoglitazone (CS-011), FK-614, compounds described in WO01/38325, Tesaglitazar (AZ-242), Ragaglitazar (N,N-622), Muraglitazar (BMS-298585), Edaglitazone (BM-13-1258), Metaglidasen (MBX-102), Naveglitazar (LY-519818), MX-6054, LY-510929, AMG131 (T-131) or a salt thereof, THR-0921), α-glucosidase inhibitors (e.g., voglibose, acarbose, miglitol, emiglitate), biguanides (e.g., phenformin, metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Vidagliptin (LAF237), P32/98, Sitagliptin (MK-431), P93/01, PT-100, Saxagliptin (BMS-477118), T-6666, TS-021), β3 agonists (e.g., AJ-9677), GPR40 agonists, GLP-1 receptor agonists [e.g., GLP-1, GLP-1MR agent, N,N-2211, AC-2993 (exendin-4), BIM-51077, Aib(8,35) hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095), 11β-hydroxysteroid dehydrogenase inhibitors (e.g., BVT-3498), adiponectin or agonists thereof, IKK inhibitors (e.g., AS-2868), leptin resistance improving drugs, somatostatin receptor agonists (compounds described in WO01/25228, WO03/42204, WO98/44921, WO98/45285, WO99/22735 etc.), glucokinase activators (e.g., Ro-28-1675) and the like.

Examples of the therapeutic agents for diabetic complications include aldose reductase inhibitors (e.g., tolrestat, epalrestat, zenarestat, zopolrestat, minalrestat, fidarestat, CT-112, ranirestat (AS-3201)), neurotrophic factors and enhancers thereof (e.g., NGF, NT-3, BDNF, neurotrophin production/secretion promoting agents described in WO01/14372 (e.g., 4-(4-chlorophenyl)-2-(2-methyl-1-imidazolyl)-5-[3-(2-methylphenoxy)propyl]oxazole)), PKC inhibitors (e.g., ruboxistaurin mesylate), AGE inhibitors (e.g., ALT946, pimagedine, N-phenacylthiazolium bromide (ALT766), EXO-226, Pyridorin, pyridoxamine), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitors and the like.

Examples of the anti-hyperlipidemia agents include statin compounds which are cholesterol synthesis inhibitors (e.g., cerivastatin, pravastatin, simvastatin, lovastatin, atorvastatin, fluvastatin, itavastatin or salts thereof (e.g., sodium salt etc.) etc.), squalene synthetase inhibitors (e.g. TAK-475 etc.) or fibrate compounds having a triglyceride lowering effect (e.g., bezafibrate, clofibrate, simfibrate, clinofibrate etc.), anion exchange resin (e.g., colestyramine), probucol, nicotinic acid drug (e.g., nicomol, niceritrol), phytosterol (e.g., soysterol, γ-oryzanol), EPA, DHA and the like.

Examples of the anti-arteriosclerotic agents include an acyl-Coenzyme A cholesterol acyltransferase (ACAT) inhibitor (e.g. melinamide, Avasimibe, Eflucimibe etc.) and a lipid rich plaque regressing agent (e.g. compounds described in WO 02/06264, WO 03/059900 etc.) and the like.

Examples of the anti-hypertensive agents include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, termisartan, irbesartan, tasosartan, olmesartan, olmesartan medoxomil etc.), calcium antagonists (e.g., manidipine, nifedipine, amlodipine, efonidipine, nicardipine etc.), diuretics, renin inhibitor (e.g., aliskiren etc.), aldosterone antagonists (e.g., spironolactone, eplerenone etc.), β-blocker (e.g., metoprolol, atenolol, propranolol, carvedilol, pindolol etc.), vasodilators (e.g., nitrate, soluble guanylate cyclase stimulator or activator, prostacycline etc.), angiotensin vaccine, clonidine and the like.

Examples of the therapeutic agents for the pulmonary arterial hypertension include endothelin antagonist (e.g., bosentan, sitaxsentan, etc.), phosphodiesterase 5 inhibitor (e.g., sildenafil, tadalafil, vardenafil, etc), soluble guanylate cyclase stimulator or activator (e.g., BAY58-2667, BAY63-2521, HMR-1766, etc).

Examples of the anti-obesity agents include anti-obesity agents acting on the central nervous system (e.g., dexfenfluramine, fenfluramine, phentermine, sibutramine, amfepramone, dexamphetamine, mazindol, phenylpropanolamine, clobenzorex etc.), MCH receptor antagonists (e.g., SB-568849; SNAP-7941; compounds described in WO01/82925 and WO01/87834), neuropeptide Y antagonists (e.g., CP-422935), cannabinoid receptor antagonists (e.g., SR-141716, SR-147778), ghrelin antagonists, 11β-hydroxysteroid dehydrogenase inhibitors (e.g., BVT-3498), pancreatic lipase inhibitors (e.g., orlistat etc.), β3 agonists (e.g., CL-316243, SR-58611-A, UL-TG-307, SB-226552, AJ-9677, BMS-196085, AZ40140 etc.), peptide anorexiants (e.g., leptin, CNTF (Ciliary Neurotropic Factor) etc.), cholecystokinin agonists (e.g., lintitript, FPL-15849 etc.), feeding deterrent (e.g., P-57) and the like.

Examples of the diuretics include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, eplerenone, triamterene etc.), carbonate dehydratase inhibitors (e.g., acetazolamide and the like), chlorobenzenesulfonamide preparations (e.g., chlortalidone, mefruside, indapamide etc.), azosemide, isosorbide, etacrynic acid, piretanide, bumetanide, furosemide and the like.

Examples of the antigout agents include allopurinol, probenecid, colchicine, benzbromarone, febuxostat, citrate and the like.

Examples of the antithrombotic agents include anticoagulating agent [e.g., heparin sodium, heparin potassium, warfarin potassium (warfarin), anti-thrombin drug (e.g., argatroban), activated blood coagulation factor X inhibitor (e.g., compounds described in WO 2004/048363 etc.) and the like], thrombolytic agent [e.g., tPA, urokinase], antiplatelet agent [e.g., aspirin, sulfinpyrazone (Anturan), dipyridamole (Persantin), ticlopidine (Panaldine), cilostazol (Pletal), GPIIb/IIIa antagonist (e.g., ReoPro), clopidogrel etc.], and the like.

Examples of the anti-inflammatory agents include nonsteroidal anti-inflammatory agents, such as acetaminophen, fenasetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizol, tiaramide hydrochloride, zaltoprofen, gabexate mesylate, camostat mesylate, ulinastatin, colchicine, probenecid, sulfinpyrazone, benzbromarone, allopurinol, sodium gold thiomalate, sodium hyaluronate, sodium salicylate, morphine hydrochloride, salicylic acid, atropine, scopolamine, morphine, pethidine, levorphanol, ketoprofen, naproxen, oxymorphone and their salts etc., and the like.

Examples of the chemotherapeutic agents include alkylating agents (e.g., cyclophosphamide, ifosfamide etc.), metabolic antagonists (e.g., methotrexate, 5-fluorouracil etc.), antitumor antibiotics (e.g., mitomycin, adriamycin etc.), plant-derived antitumor agent (e.g., vincristine, vindesine, Taxol etc.), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivative, Picibanil etc.), polysaccharides having immunity potentiating activity (e.g., lentinan, schizophyllan, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to IL-1, IL-2, IL-12 and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium and the like.

Examples of the anti-dementia agents include tacrine, donepezil, rivastigmine, galanthamine and the like.

Examples of the erectile dysfunction amelioration agents include apomorphine, sildenafil citrate and the like.

Examples of the therapeutic agents for urinary incontinence/urinary frequency include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentanoic acid etc.) [British Journal of Cancer, Vol. 68, pages 314-318, 1993], growth hormones, IGF-1, or antibodies to a cachexia-inducing factor such as TNF-$\alpha$, LIF, IL-6, oncostatin M and the like, can be used in combination with the compound of the present invention.

Furthermore, examples of the concomitant drug include nerve regeneration promoting drugs (e.g., Y-128, VX853, prosaptide), antidepressants (e.g., desipramine, amitriptyline, imipramine), antiepileptics (e.g., lamotrigine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin), $\alpha 2$ receptor agonists (e.g., clonidine), local analgesics (e.g., capsaicin), antianxiety drugs (e.g., benzodiazepines), dopamine agonists (e.g., apomorphine), midazolam, ketoconazole and the like.

The combination drug preferably includes a diuretic, a calcium antagonists, an aldosterone antagonist, a renin inhibitor, a statin compound, an insulin preparation, an insulin sensitizer, an $\alpha$-glucosidase inhibitor, a biguanide agent, an insulin secretagogue (preferably sulfonylurea agent) and the like. Particularly, a diuretic such as hydrochlorothiazide and the like and a calcium antagonists such as amlodipine and the like and an insulin sensitizer such as pioglitazone hydrochloride and the like are preferable.

The above-mentioned combination drug may be a combination of two or more kinds thereof combined at appropriate ratios.

When the compound of the present invention is used in combination with a drug for combined use, the amount of each drug can be reduced within a safe range in consideration of the opposite effect of these drugs. Particularly, the dose of the insulin sensitizer, insulin secretagogue and biguanide can be reduced from conventional level. As a result, the side effects possibly caused by the combination of these agents can be prevented safely. In addition, the dose of the therapeutic agent for diabetic complications, anti-hyperlipidemia agent or anti-hypertensive agent can be reduced and, as a result, the side effects possibly caused by these drugs can be effectively prevented.

Since the compound of the present invention potentiates hypoglycemic activity of other insulin sensitizers, a combined use of the compound of the present invention or a salt thereof or a prodrug thereof (particularly, the compound of the present invention) and other insulin sensitizers (preferably pioglitazone hydrochloride) markedly enhances a prophylactic and/or therapeutic effect against diseases in which insulin resistance is involved, such as type II diabetes and the like.

In the pharmaceutical agent of the present invention, the compound (I) can be administered orally or parenterally as it is or after mixing with a pharmacologically acceptable carrier.

The dosage form of a pharmaceutical agent containing compound (I) of the present invention when used for oral administration include tablet (including sugar-coated tablet, film-coated tablet, sublingual tablet, orally disintegrating tablet), pill, granule, powder, capsule (including soft capsule, microcapsule), syrup, emulsion, suspension, film (e.g., orally disintegrating film) and the like, and the dosage form thereof for parenteral administration is, for example, injection, injecting agent, instillation, suppository and the like. In addition, it is effective to make a sustained release preparation by combining with a suitable base (e.g., polymer of butyric acid, polymer of glycolic acid, copolymer of butyric acid-glycolic acid, a mixture of polymer of butyric acid and polymer of glycolic acid, polyglycerol fatty acid ester etc.).

As a method to produce the compound (I) in the above-mentioned dosage form, a known production method generally used in the pertinent field can be applied. When the above-mentioned dosage form is produced, suitable amounts of additives such as an excipients, a binder, a disintegrant, a lubricant, a sweetener, a surfactant, a suspending agent, an emulsifier and the like generally used in the pertinent field are appropriately added as necessary, and produced.

When the compound (I) is prepared into a tablet, for example, it can be produced by adding an excipient, a binder, a disintegrant, a lubricant and the like, and when a pill and a granule are to be prepared, they can be produced by adding an excipient, a binder, a disintegrant and the like. When a powder and a capsule are to be prepared, they can be produced by adding an excipient and the like, and when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, saccharose, microcrystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound (I) is produced in the above-mentioned dosage form, a suitable amount of a colorant, a preservative, an aromatic, a corrigent, a stabilizer, a thickening agent and the like typically used in the field of preparation can be added on demand.

When the compound (I) is administered parenterally, it is generally administered in the form of a liquid formulation (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg of body weight, which is preferably given by intravenous injection. As the injection, intravenous injection as well as subcutaneous injection, intracutaneous injection, intramuscular injection, instillation and the like are mentioned, and as a sustained release preparation, iontophoresis transdermal agent and the like are mentioned. Such injections are prepared by methods known per se, or by dissolving, suspending or emulsifying the compound (I) in a sterilized aqueous solution or oily liquid. As an aqueous solution for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), non-ionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like may be mixed therewith. A prepared injection is generally filled in an ampoule.

Production Methods

The production methods of the compound of the present invention are explained in the following.

In the following Production Methods, unless otherwise specified, the starting compound is easily commercially available, or can be produced by a method known per se or a method analogous thereto.

Compound (I) of the present invention can be produced, for example, by the method shown below or a method analogous thereto and the like. In the following synthetic methods, the starting compounds may be used in the form of salt and, as such salt, those exemplified as the salt of compound (I) can be used.

While the yield of compound (I) obtained by each of the following methods may vary depending on the reaction conditions used, compound (I) can be obtained easily at a high purity from the resultant products by a conventional separation and purification means (recrystallization, column chromatography and the like).

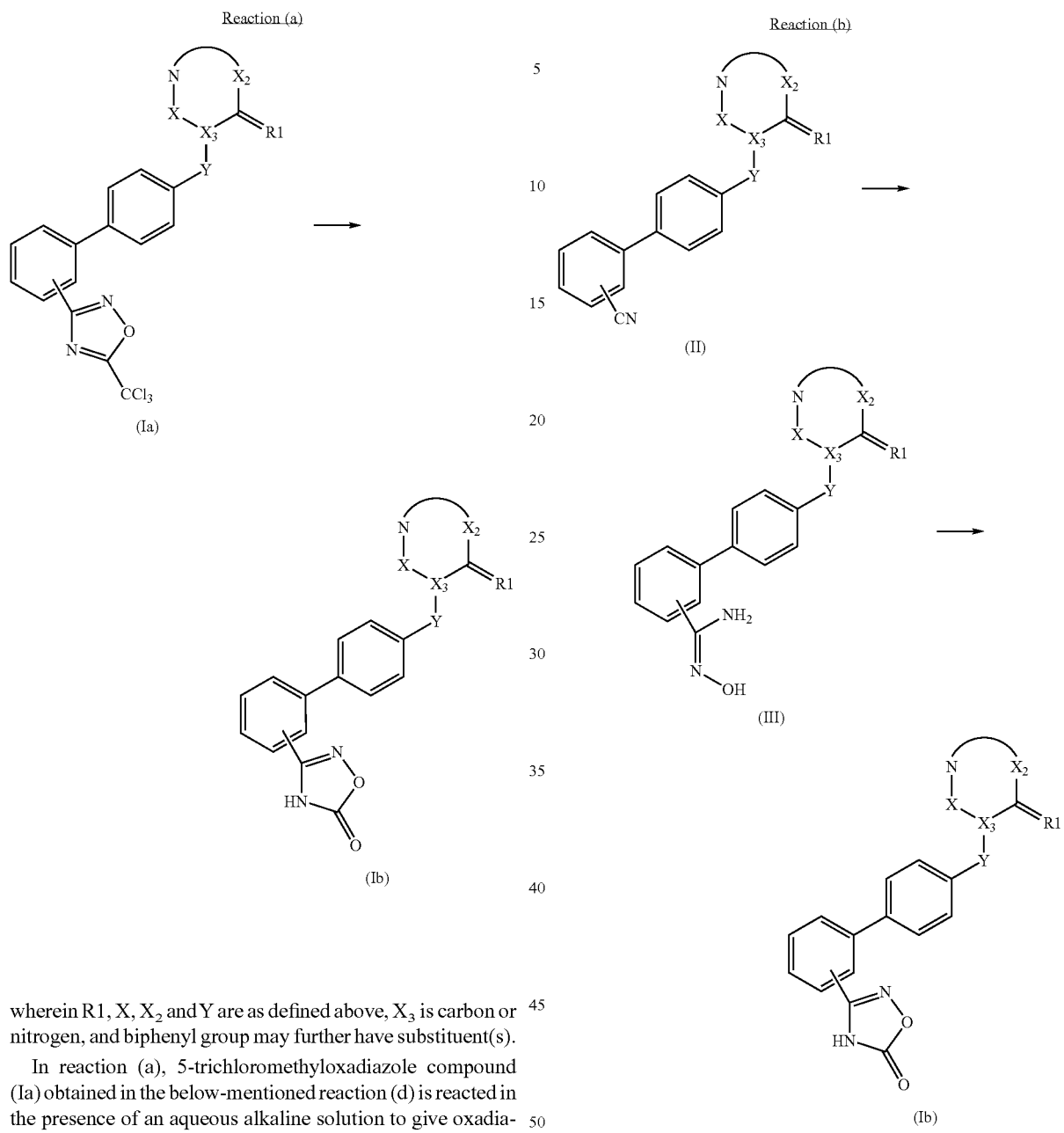

wherein R1, X, $X_2$ and Y are as defined above, $X_3$ is carbon or nitrogen, and biphenyl group may further have substituent(s).

In reaction (a), 5-trichloromethyloxadiazole compound (Ia) obtained in the below-mentioned reaction (d) is reacted in the presence of an aqueous alkaline solution to give oxadiazolone compound (Ib). Generally, the reaction is performed in an inert solvent using about 1 to 3 molar equivalents of the aqueous alkaline solution relative to compound (Ia).

Examples of the inert solvent for reaction include ethers such as 1,4-dioxane, tetrahydrofuran and the like; alcohols such as methanol, ethanol and the like; water and the like. These solvents may be used as a mixture of two or more kinds thereof at an appropriate ratio.

Examples of the alkali to be used for alkaline aqueous solution include sodium hydroxide, potassium hydroxide, lithium hydroxide, sodium carbonate, potassium carbonate and the like.

The reaction temperature is generally about −50° C. to about 150° C., preferably about 0° C. to about 60° C.

The reaction time is generally about 0.5 to about 20 hr.

wherein R1, X, $X_2$, $X_3$ and Y are as defined above, and biphenyl group may further have substituent(s).

In reaction (b), cyano compound (II) obtained in the below-mentioned reactions (d) to (g) is converted to amidoxime compound (III), which is then subjected to ring closure to give oxadiazolone compound (Ib).

The reaction to obtain compound (III) is performed in an inert organic solvent using about 1 to 20 mol of hydroxylamine per 1 mol of compound (II).

Examples of such solvent include sulfoxides such as dimethyl sulfoxide and the like; amides such as N,N-dimethylformamide, N,N-dimethylacetamide and the like; alcohols such as methanol, ethanol and the like; ethers such as 1,4- dioxane, tetrahydrofuran etc. and the like. These solvents may be used as a mixture of two or more kinds thereof at an appropriate ratio.

When an inorganic acid salt such as hydroxylamine hydrochloride, hydroxylamine sulfate and the like, or an organic acid salt such as hydroxylamine oxalate and the like is used as hydroxylamine, the reaction is performed in the presence of an equivalent amount or a small excess of a suitable base such as potassium carbonate, sodium hydrogen carbonate, sodium hydroxide, triethylamine, sodium methoxide, sodium hydride and the like.

When an inorganic acid salt or organic acid salt of hydroxylamine is used, the reaction may be performed with addition of about 5 to 20 wt % of water to an organic solvent.

The reaction temperature is generally about −50° C. to about 150° C., preferably about 25° C. to about 100° C.

The reaction time is generally about 3 to about 48 hr.

The reaction to obtain oxadiazolone compound (Ib) from amidoxime compound (III) is performed using about 1 to 2 molar equivalents of a carbonylation reagent relative to amidoxime compound (III) in a solvent that does not adversely influence the reaction in the presence of an equivalent amount or a small excess of a base.

Examples of the carbonylation reagent include N,N'-carbonyldiimidazole, triphosgene, methyl chlorocarbonate, ethyl chlorocarbonate and the like.

Examples of the base include organic amines such as triethylamine, pyridine, diisopropylethylamine, 1,8-diazabicyclo[5.4.0]undec-7-ene and the like; inorganic salts such as potassium carbonate, sodium carbonate etc. and the like.

Examples of the solvent include halogenated hydrocarbons such as dichloromethane, chloroform, carbon tetrachloride and the like; amides such as N,N-dimethylformamide, N,N-dimethylacetamide and the like; ethers such as diethyl ether, 1,4-dioxane, tetrahydrofuran etc. and the like. These solvents may be used as a mixture of two or more kinds thereof at an appropriate ratio.

The reaction temperature is generally about −50° C. to about 100° C., preferably about 0° C. to about 50° C.

The reaction time is generally about 0.1 to about 5 hr.

Reaction (c)

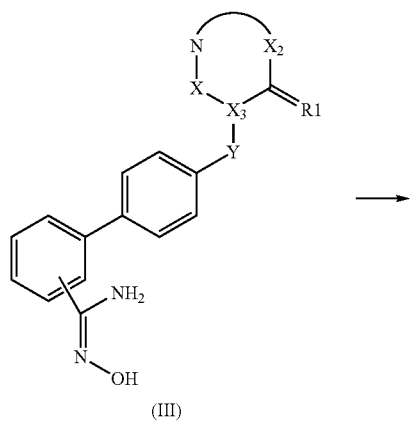

(III)

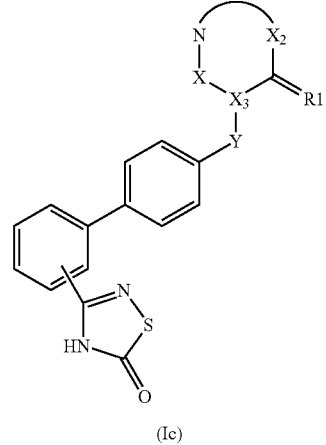

(Ic)

wherein R1, X, $X_2$, $X_3$ and Y are as defined above, and biphenyl group may further have substituent(s).

In reaction (c), amidoxime compound (III) obtained in reaction (b) is subjected to ring closure to give thiadiazolone compound (Ic).

The reaction to obtain compound (Ic) is performed using about 1 to 2 mol of 1,1'-thiocarbonyldiimidazole per 1 mol of compound (III) in the presence of Lewis acid in an organic solvent that does not adversely influence the reaction.

The Lewis acid is not particularly limited as long as the reaction proceeds and, for example, boron trifluoride diethyl ether complex, tin(II) chloride, zinc chloride, copper(I) chloride, silica gel and the like can be mentioned. The amount of the Lewis acids to be used is preferably about 1 to 3 mol per 1 mol of compound (III).

Examples of the solvent include halogenated hydrocarbons such as dichloromethane, chloroform, carbon tetrachloride and the like; amides such as N,N-dimethylformamide, N,N-dimethylacetamide and the like; dimethyl sulfoxide and the like; ethers such as diethyl ether, 1,4-dioxane, tetrahydrofuran etc. and the like. These solvents may be used as a mixture of two or more kinds thereof at an appropriate ratio.

The reaction temperature is generally about −50° C. to about 100° C., preferably about 0° C. to about 50° C.

The reaction time is generally about 0.1 to about 5 hr.

Reaction (d)

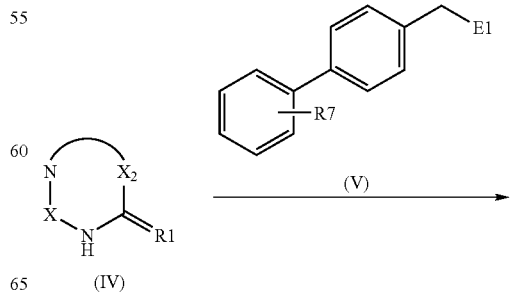

(IV)

-continued

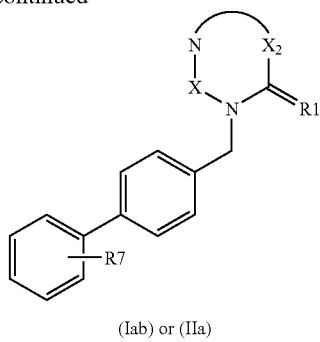

(Iab) or (IIa)

wherein R1, X and $X_2$ are as defined above, R7 is a cyano group or a 5-trichloromethyl-1,2,4-oxadiazol-3-yl group, E1 is a leaving group (e.g., halogen atom such as chlorine, bromine, iodine and the like; substituted sulfonic acid ester such as methanesulfonic acid ester, p-toluenesulfonic acid ester and the like; hydroxy group and the like), and biphenyl group may further have substituent(s).

In reaction (d), compound (IV) is reacted with compound (v) to give, from among the starting compounds (Ia) to be used in the above-mentioned reaction (a), compound (Iab) wherein $X_3$ is nitrogen or, from among the starting compounds (II) to be used in the above-mentioned reaction (b), compound (IIa) wherein $X_3$ is nitrogen. Generally, the reaction is performed using 1 to 3 mol of compound (V) per 1 mol of compound (IV) in an organic solvent that does not adversely influence the reaction.

The starting compound (V) to be used in the above-mentioned reaction (d) can be produced by a method known per se, for example, the method described in U.S. Pat. No. 5,243,054 (JP-A-5-271228) or a method analogous thereto.

In reaction (d), when E1 is halogen atom or substituted sulfonic acid ester, the reaction is performed according to a conventional method in a solvent that does not adversely influence the reaction in the presence of base.

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide etc. and the like.

The amount of the bases to be used is preferably about 1 to about 5 molar equivalents relative to compound (IV).

Examples of the solvent that does not adversely influence the reaction include aromatic hydrocarbons such as benzene, toluene, xylene and the like; nitrites such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc. and the like. These solvents may be used as a mixture of two or more kinds thereof at an appropriate ratio.

The reaction temperature is generally about −50° C. to about 150° C., preferably about −10° C. to about 100° C.

The reaction time is generally about 0.5 to about 20 hr.

In reaction (d), when E1 is a hydroxy group, this reaction is performed by a method known per se, for example, the method described in Synthesis, p. 1 (1981) and the like or a method analogous thereto. That is, this reaction is generally performed in the presence of an organic phosphorus compound and an azo reagent, in a solvent that does not adversely influence the reaction.

Examples of the organic phosphorus compound include triphenylphosphine, tri(n-butyl)phosphine and the like.

Examples of the azo reagent include diethyl azodicarboxylate, diisopropyl azodicarboxylate, 1,1'-(azodicarbonyl)dipiperidine and the like.

The amount of the organic phosphorus compound and azo reagent to be used is preferably about 1 to about 5 molar equivalents relative to compound (IV).

Examples of the solvent that does not adversely influence the reaction include ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like, and the like. These solvents may be used as a mixture of two or more kinds thereof at an appropriate ratio.

The reaction temperature is generally about −50° C. to about 150° C., preferably about −10° C. to about 100° C.

The reaction time is generally about 0.5 to about 20 hr.

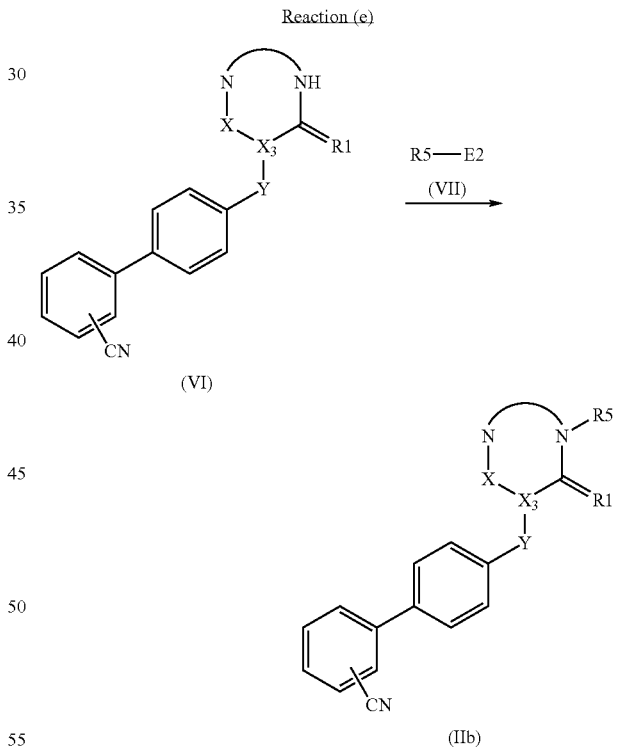

wherein R1, X, $X_3$ and R5 are as defined above, and E2 is a leaving group (e.g., a halogen atom such as chlorine, bromine, iodine and the like; a substituted sulfonic acid ester such as methanesulfonic acid ester, p-toluenesulfonic acid ester and the like; boronic acid or a boronic acid ester; a hydroxy group and the like). The biphenyl group may further have substituent(s).

In reaction (e), compound (VI) is reacted with compound (VII) to give compound (IIb), which is starting compound (II) (used in the above-mentioned reaction (b)) wherein $X_2$ is a N—R5 group. The reaction is generally performed using 1 to 4 molar equivalents of compound (VII) relative to starting compound (VI).

The starting compound (VI) to be used in the above-mentioned reaction (e) can be produced by a method known per se, for example, the method described in Journal of Medicinal Chemistry, vol. 37, p. 2371 (1994) or a method analogous thereto.

When E2 is a halogen atom, a substituted sulfonic acid ester or a hydroxy group, the above-mentioned reaction (e) can be performed by a method similar to the method shown in reaction (d).

Particularly when E2 is a halogen atom or a substituted sulfonic acid ester, and R5 is an aryl group, reaction (e) can be also promoted by a method known per se, for example, the method described in Journal of the American Chemical Society, vol. 124, p. 7421 (2002) and the like or a method analogous thereto, in the presence of a metal catalyst. Examples of the metal catalyst include palladium complexes (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), copper compounds (e.g., copper powder, copper(I) chloride, copper(I) iodide, copper(I) acetate and the like), nickel compounds (e.g., tetrakis (triphenylphosphine)nickel and the like), rhodium compounds (e.g., tris(triphenylphosphine)rhodium chloride and the like), platinum compounds and the like.

The amount of the metal catalyst to be used is about 0.000001 to 5 molar equivalents, preferably 0.0001 to 1 molar equivalent, relative to compound (VII).

The above-mentioned reaction may be performed using a base and a ligand. Examples of the base include metal alkoxides such as potassium phenoxide, sodium tert-butoxide and the like; inorganic salts such as potassium carbonate, sodium carbonate, cesium carbonate, potassium phosphate etc., and the like. Examples of the ligand include organic phosphorus compounds such as triphenylphosphine, tri-tert-butylphosphine, tricyclohexylphosphine, BINAP (2,2'-bis(diphenylphosphino)-1,1'-binaphthyl) and the like; organic amine compounds such as N,N'-dimethyl-cyclohexane-1,2-diamine, 2,2'-bipyridyl and the like, and the like.

When a metal catalyst unstable to oxygen is used, this reaction is preferably performed under an inert gas (e.g., argon, nitrogen and the like) atmosphere.

The reaction temperature is generally about −50° C. to about 150° C., preferably about −10° C. to about 100° C.

The reaction time is generally about 0.5 to about 20 hr.

In reaction (e), when E2 is a boronic acid or a boronic acid ester, this reaction is performed by a method known per se, for example, the method described in Tetrahedron Letters, vol. 39, p. 2933 (1998) and the like or a method analogous thereto, in the presence of a base and a metal catalyst, in a solvent that does not adversely influence the reaction.

Examples of the base include inorganic salts such as potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene etc. and the like. These bases may be used as a mixture of two or more kinds thereof at an appropriate ratio.

Examples of the metal catalyst include copper or salts thereof (e.g., copper(II) acetate, copper(II) chloride and the like), palladium complexes (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compounds (e.g., tetrakis(triphenylphosphine)nickel and the like), rhodium compounds (e.g., tris(triphenylphosphine)rhodium chloride and the like), platinum compounds and the like. Of these, copper or salts thereof is preferable.

Examples of the solvent that does not adversely influence the reaction include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc. and the like. These solvents may be used as a mixture of two or more kinds thereof at an appropriate ratio.

When copper or a salt thereof is used as a metal catalyst, this reaction is preferably performed under an air atmosphere or an oxygen atmosphere. When a metal catalyst unstable to oxygen is used, this reaction is preferably performed under an inert gas (e.g., argon, nitrogen and the like) atmosphere. In addition, this reaction may be performed using molecular sieves.

The amount of the metal catalyst to be used is about 0.000001 to 5 molar equivalents, preferably 0.0001 to 1 molar equivalent, relative to compound (VII).

The reaction temperature is generally about 0° C. to about 200° C., preferably 10° C. to about 100° C.

The reaction time is generally about 2 to about 96 hr.

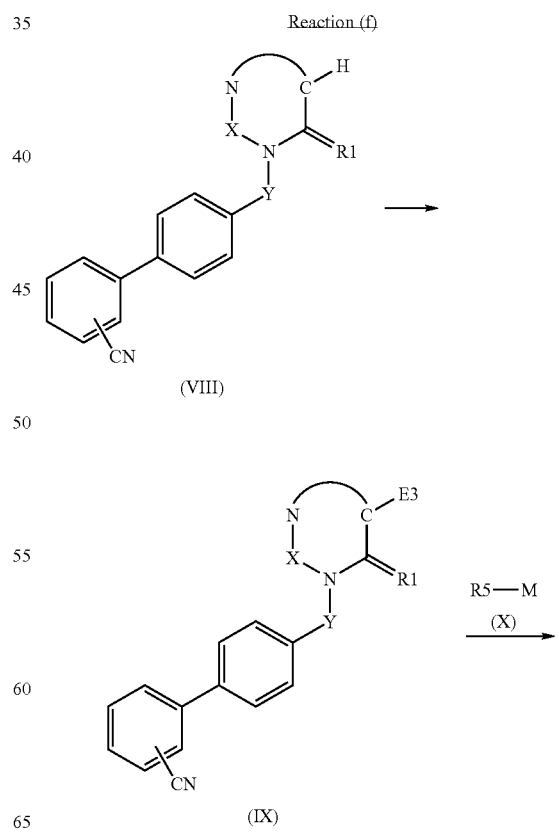

Reaction (f)

(VIII)

(IX)

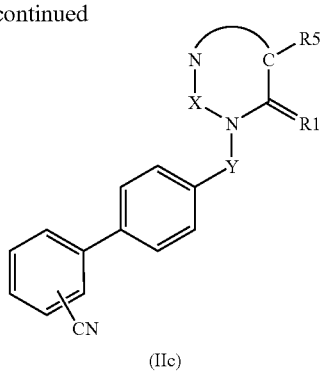

(IIc)

wherein R1, X, Y and R5 are as defined above, E3 is a leaving group (e.g., a halogen atom such as chlorine, bromine, iodine etc. and the like), and M is a metal (e.g., potassium, sodium, lithium, magnesium, copper, mercury, zinc, thallium, boron, tin and the like, they may form a complex). The biphenyl group may further have substituent(s).

In reaction (f), the leaving group E3 is introduced into compound (VIII) to give compound (IX), which is then reacted with compound (X) to give compound (IIc), which is starting compound (II) (used in the aforementioned reaction (b)) wherein $X_2$ is a C—R5 group.

The starting compound (VIII) to be used in the above-mentioned reaction (f) can be produced by the method shown in reaction (d) or a method analogous thereto.

In the above-mentioned reaction (f), the reaction to obtain compound (IX) from compound (VIII) is performed by a method known per se, for example, the method described in Journal of the Chemical Society, vol. 37, p. 3478 and the like or a method analogous thereto, using a halogenating agent (e.g., chlorine, bromine, iodine, halogenated succinimide, dihalogenated barbituric acid and the like). The amount of the halogenating agent to be used is preferably about 1 to about 5 molar equivalents relative to compound (VIII).

In the above-mentioned reaction (f), the reaction to obtain compound (IX) from compound (VIII) is performed in a solvent that does not adversely influence the reaction. Examples of the solvent include alcohols (e.g., methanol, ethanol, ethylene glycol and the like), halogenated hydrocarbons (e.g., dichloromethane, chloroform and the like), organic acids (e.g., acetic acid, formic acid and the like) and the like. These solvents may be used as a mixture of two or more kinds thereof at an appropriate ratio.

The reaction temperature is generally about −50° C. to about 150° C., preferably about −10° C. to about 100° C.

The reaction time is generally about 0.5 to about 20 hr.

Compound (X) to be used in the above-mentioned reaction (f) can be produced according to a method known per se or a method analogous thereto. The amount of compound (X) to be used is preferably about 1 to about 5 molar equivalents relative to compound (IX).

In the above-mentioned reaction (f), the reaction to obtain compound (IIc) from compound (IX) and compound (X) is performed in a solvent that does not adversely influence the reaction. Preferable examples of such solvent include alcohols (e.g., methanol, ethanol, ethylene glycol and the like), ethers (e.g., diethyl ether, tetrahydrofuran, 1,4-dioxane, 1,2-dimethoxyethane and the like), amides (e.g., N,N-dimethylformamide, N,N-dimethylacetamide, N-methylpyrrolidone and the like), aromatic hydrocarbons (e.g., toluene, xylene and the like) and the like. These solvents may be used as a mixture of two or more kinds thereof at an appropriate ratio. Furthermore, water may be mixed with the above-mentioned solvent at an appropriate ratio.

In the above-mentioned reaction (f), the reaction to obtain compound (IIc) from compound (IX) and compound (X) can be generally promoted using a metal catalyst. Examples of the metal catalyst include various metal complex having a ligand, for example, palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compounds (e.g., tetrakis(triphenylphosphine)nickel and the like), rhodium compounds (e.g., tris(triphenylphosphine)rhodium chloride and the like), platinum compounds and the like. Of these, palladium compounds are preferable. The amount of the metal catalyst to be used is about 0.000001 to 5 molar equivalents, preferably 0.0001 to 1 molar equivalent, relative to compound (IX). When a metal catalyst unstable to oxygen is used, this reaction is preferably performed under an inert gas (e.g., argon, nitrogen and the like) atmosphere.

In the above-mentioned reaction (f), the reaction to obtain compound (IIc) from compound (IX) and compound (X) may be performed using an inorganic salt. Examples of the inorganic salt include potassium carbonate, sodium carbonate, cesium carbonate, potassium phosphate, lithium chloride, sodium chloride and the like. The amount of the inorganic salt to be used is preferably about 1 to about 10 molar equivalents relative to compound (IX).

The reaction temperature is generally about −50° C. to about 150° C., preferably about −10° C. to about 100° C.

The reaction time is generally about 0.5 to about 24 hr.

Reaction (g)

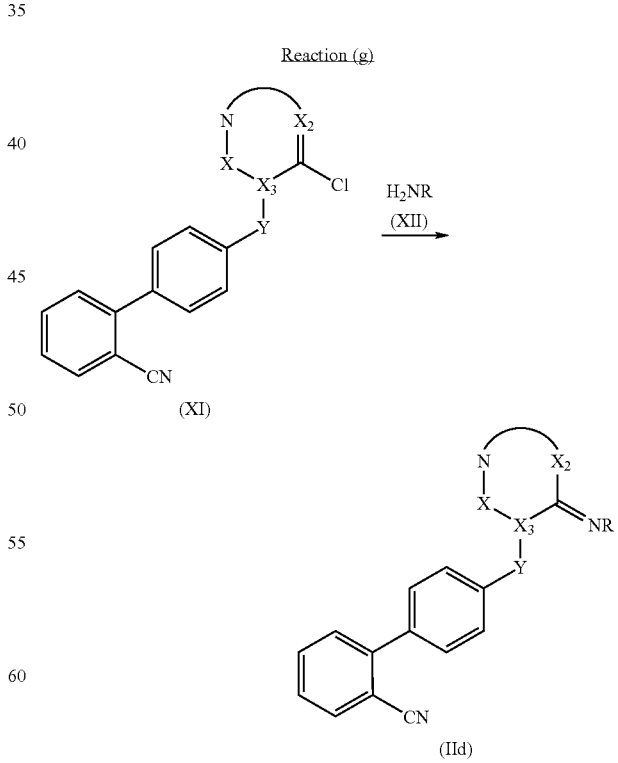

wherein X, $X_2$, $X_3$, Y and R are as defined above, and biphenyl group may further have substituent(s).

In reaction (g), compound (XI) is reacted with compound (XII) in the presence of a base to give compound (IId), which is starting compound (II) (used in the above-mentioned reaction (b)) wherein R1 is =N—R group. Generally, the amount of compound (XII) to be used is preferably about 1 to about 5 molar equivalents relative to compound (XI).

Examples of the base include alkali metal salts such as sodium hydrogen carbonate, potassium carbonate, sodium carbonate, cesium carbonate and the like; amines such as pyridine, N,N-diisopropylethylamine, N,N-dimethylaniline, 1,8-diazabicyclo[5.4.0]undec-7-ene etc. and the like. The amount of the base to be used is preferably about 1 to about 5 molar equivalents relative to compound (XI).

The starting compound (XI) to be used in the above-mentioned reaction (g) can be produced by a method known per se, for example, the method described in Journal of Medicinal Chemistry, vol. 37, p. 2371 (1994) or a method analogous thereto. Compound (XII) to be used in the above-mentioned reaction (g) can be produced according to a method known per se or a method analogous thereto.

The above-mentioned reaction (g) is performed in a solvent that does not adversely influence the reaction. Preferable examples of such solvent include ethers (e.g., tetrahydrofuran, 1,4-dioxane, 1,2-dimethoxyethane and the like), amides (e.g., N,N-dimethylformamide, N,N-dimethylacetamide, N-methylpyrrolidone and the like), aromatic hydrocarbons (e.g., toluene, xylene and the like) and the like.

The reaction temperature is generally about −50° C. to about 250° C., preferably about 50° C. to about 170° C.

The reaction time is generally about 0.5 to about 48 hr.

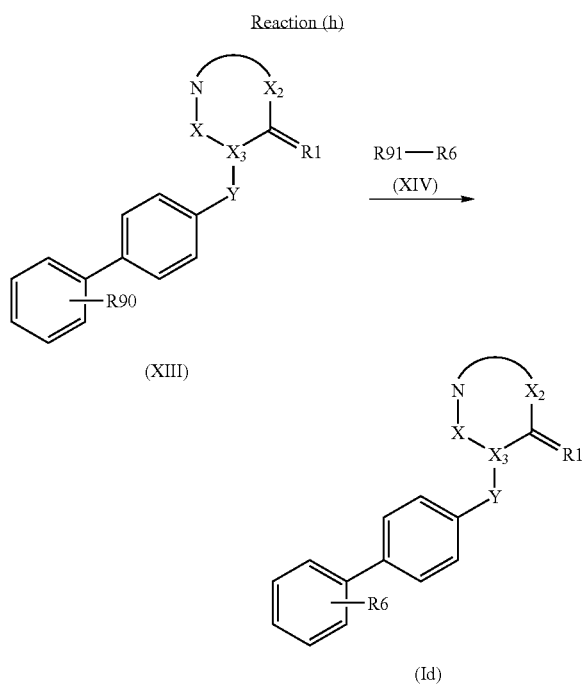

(XIII)

(Id)

wherein X, $X_2$, $X_3$, Y, R1 and R6 are as defined above, one of R90 and R91 is a leaving group (e.g., a halogen atom such as chlorine, bromine, iodine and the like; a substituted sulfonic acid ester such as trifluoromethanesulfonic acid ester, methanesulfonic acid ester, p-toluenesulfonic acid ester and the like; a hydroxy group and the like), and the other is a metal (e.g., potassium, sodium, lithium, magnesium, copper, mercury, zinc, thallium, boron, tin and the like).

In the above-mentioned reaction (h), compound (XIII) is reacted with compound (XIV) to give compound (Id).

The reaction to obtain compound (Id) is performed using 1 to 3 mol of compound (XIV) per 1 mol of compound (XIII) in an organic solvent that does not adversely influence the reaction.

Examples of the solvent include alcohols such as methanol, ethanol, ethylene glycol and the like; ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide etc. and the like. These solvents may be used as a mixture of two or more kinds thereof at an appropriate ratio. Furthermore, water may be mixed with the above-mentioned solvent at an appropriate ratio.

The starting compound (XIII) used in the above-mentioned reaction (h) can be produced by a method known per se, for example, the method described in Journal of Medicinal Chemistry, vol. 37, p. 2371 (1994) or a method analogous thereto, or the production methods shown in the aforementioned reactions (d) to (g) or methods analogous thereto.

The above-mentioned reaction (h) may be also promoted by a method known per se, for example, the method described in Journal of the American Chemical Society, vol. 124, p. 7421 (2002) and the like or a method analogous thereto, in the presence of a metal catalyst.

Examples of the metal catalyst include palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), copper compounds (e.g., copper powder, copper(I) chloride, copper(I) iodide, copper (I) acetate and the like), nickel compounds (e.g., tetrakis(triphenylphosphine)nickel and the like), rhodium compounds (e.g., tris(triphenylphosphine)rhodium chloride and the like), platinum compounds and the like.

The amount of the metal catalyst to be used is about 0.000001 to 5 molar equivalents, preferably 0.0001 to 1 molar equivalent, relative to compound (XIII).

The above-mentioned reaction may be performed using a base and a ligand.

Examples of the base include metal alkoxides such as potassium phenoxide, sodium tert-butoxide and the like; inorganic salts such as potassium carbonate, sodium carbonate, cesium carbonate, potassium phosphate etc. and the like.

The amount of the base to be used is about 0.1 to 10 molar equivalents, preferably about 1 to 3 molar equivalents, relative to compound (XIII).

Examples of the ligand include organic phosphorus compounds such as triphenylphosphine, tri-tert-butylphosphine, tricyclohexylphosphine, BINAP (2,2'-bis(diphenylphosphino)-1,1'-binaphthyl) and the like; organic amine compounds such as N,N'-dimethyl-cyclohexane-1,2-diamine, 2,2'-bipyridyl etc. and the like.

The amount of the ligand to be used is about 0.000001 to 5 molar equivalents, preferably about 0.0001 to 1 molar equivalent, relative to compound (XIII).

When a metal catalyst unstable to oxygen is used in the above-mentioned reaction, the reaction is preferably performed under an inert gas (e.g., argon, nitrogen and the like) atmosphere.

The reaction temperature is generally about −50° C. to about 150° C., preferably about −10° C. to about 120° C.

The reaction time is generally about 0.5 to about 20 hr.

Reaction (i)

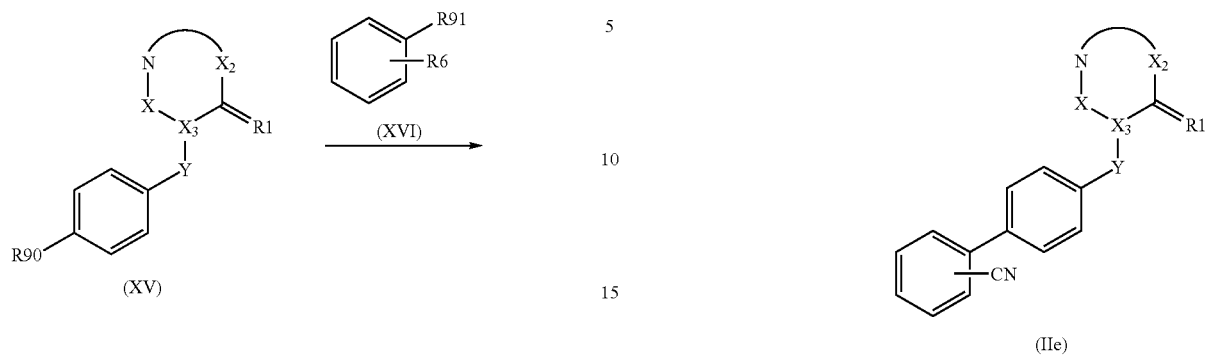

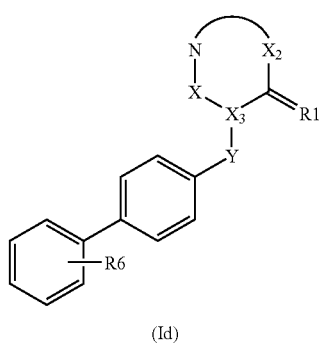

wherein X, X$_2$, X$_3$, Y, R1, R6, R90 and R91 are as defined above.

In the above-mentioned reaction (i), compound (XV) is reacted with compound (XVI) to give compound (Id).

The above-mentioned reaction (i) can be performed by a method similar to the method shown in reaction (h).

The starting compound (XV) used in the above-mentioned reaction (i) can be produced by a method known per se, for example, the method described in Journal of Medicinal Chemistry, vol. 37, p. 2371 (1994) or a method analogous thereto, or the production methods shown in the aforementioned reactions (d) to (g) or methods analogous thereto.

Reaction (j)

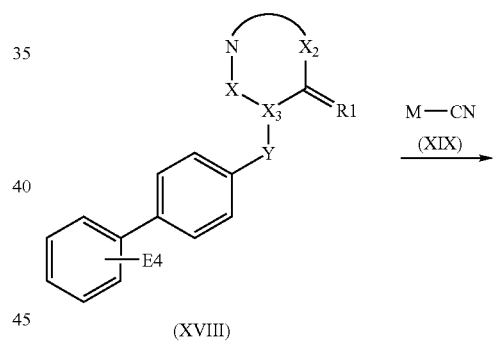

wherein X, X$_2$, X$_3$, Y, R1, R90 and R91 are as defined above.

In the above-mentioned reaction (j), compound (XV) is reacted with compound (XVII) to give compound (IIe).

The above-mentioned reaction (j) can be performed by a method similar to the method shown in reaction (h).

Reaction (k)

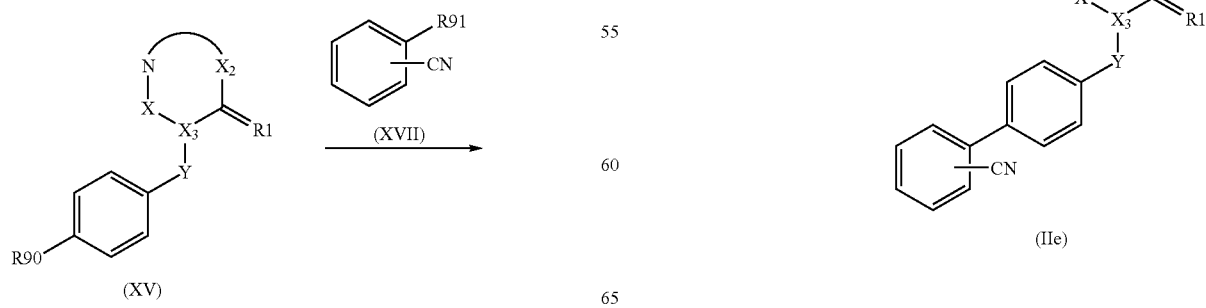

wherein X, X$_2$, X$_3$, Y and R1 are as defined above, E4 is a leaving group (e.g., a halogen atom such as chlorine, bromine, iodine etc. and the like; a substituted sulfonic acid ester such as trifluoromethanesulfonic acid ester etc. and the like), and M is a metal (e.g., potassium, sodium, lithium, magnesium, copper, mercury, zinc, thallium, boron, tin, silicon and the like).

In the above-mentioned reaction (k), compound (XVIII) is reacted with compound (XIX) to give compound (IIe). The amount of compound (XIX) to be used is preferably about 1 to about 5 molar equivalents relative to compound (XVIII).

In the above-mentioned reaction (k), the reaction to obtain compound (IIe) from compound (XVIII) is performed in a solvent that does not adversely influence the reaction.

Preferable examples of such solvent include alcohols (e.g., methanol, ethanol, ethylene glycol and the like), ethers (e.g., diethyl ether, tetrahydrofuran, 1,4-dioxane, 1,2-dimethoxyethane and the like), amides (e.g., N,N-dimethylformamide, N,N-dimethylacetamide, N-methylpyrrolidone and the like), aromatic hydrocarbons (e.g., toluene, xylene and the like) and the like. These solvents may be used as a mixture of two or more kinds thereof at an appropriate ratio. Furthermore, water may be mixed with the above-mentioned solvent at an appropriate ratio.

In the above-mentioned reaction (k), the reaction to obtain compound (IIe) from compound (XVIII) can be also promoted by a method known per se, for example, the method described in Tetrahedron Letters, vol. 40, p. 8193 (1999) and the like or a method analogous thereto, in the presence of a metal catalyst.

Examples of the metal catalyst include palladium compounds (e.g., palladium acetate, palladium chloride, tetrakis (triphenylphosphine)palladium, dichlorobis(triphenylphosphine)palladium, [1,1'-bis(diphenylphosphino)ferrocene] dichloropalladium and the like), copper compounds (e.g., copper powder, copper(I) chloride, copper(I) iodide, copper (I) acetate and the like), nickel compounds (e.g., tetrakis (triphenylphosphine)nickel and the like), rhodium compounds (e.g., tris(triphenylphosphine)rhodium chloride and the like), platinum compounds and the like.

The amount of the metal catalyst to be used is about 0.000001 to 5 molar equivalents, preferably 0.0001 to 1 molar equivalent, relative to compound (XVIII).

The above-mentioned reaction may be performed using a ligand. Examples of the ligand include organic phosphorus compounds such as triphenylphosphine, tri-tert-butylphosphine, tricyclohexylphosphine, BINAP (2,2'-bis(diphenylphosphino)-1,1'-binaphthyl) and the like; organic amine compounds such as N,N'-dimethyl-cyclohexane-1,2-diamine, 2,2'-bipyridyl etc. and the like.

The amount of the ligand to be used is about 0.000001 to 5 molar equivalents, preferably about 0.00001 to 1 molar equivalent, relative to compound (XVIII).

When a metal catalyst unstable to oxygen is used, this reaction is preferably performed under an inert gas (e.g., argon, nitrogen and the like) atmosphere.

The reaction temperature is generally about −50° C. to about 300° C., preferably about −10° C. to about 150° C.

The reaction time is generally about 0.5 to about 20 hr.

The starting compound (XVIII) used in the above-mentioned reaction (k) can be produced by a method known per se, for example, the method described in Journal of Medicinal Chemistry, vol. 37, p. 2371 (1994) or a method analogous thereto, or the production methods shown in the aforementioned reactions (d) to (g) or methods analogous thereto.

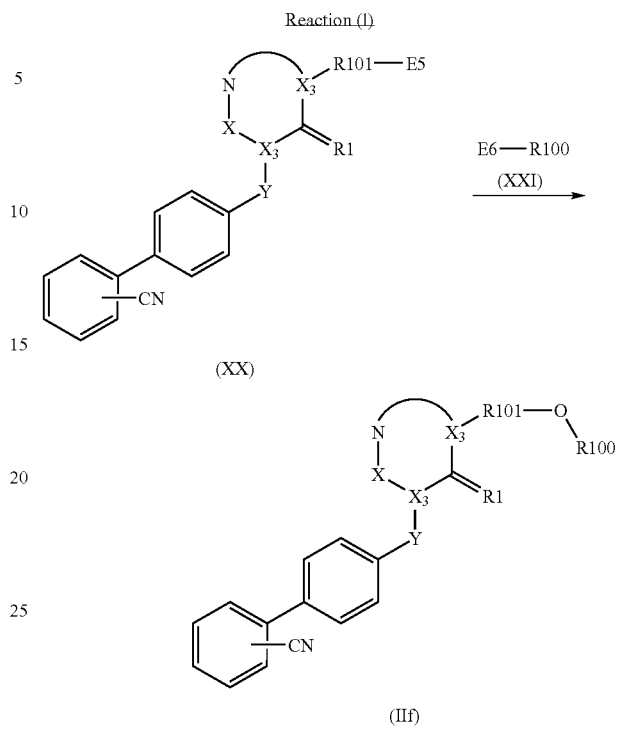

wherein X, $X_3$, Y and R1 are as defined above, R101 is a C6-C14 aryl group or a aromatic heterocyclic group, and R100 is a C1-C6 alkyl group or a C3-C10 cycloalkyl group (these groups may be optionally substituted by 1 to 3 substituents selected from a halogen, a hydroxy group and the like, respectively). E5 and E6 are both leaving groups (e.g., a halogen atom such as chlorine, bromine, iodine and the like; a substituted sulfonic acid ester such as methanesulfonic acid ester, p-toluenesulfonic acid ester and the like), and/or a hydroxy group.

In the above-mentioned reaction (l), compound (XX) is reacted with compound (XXI) to give compound (IIf).

The reaction to obtain compound (IIf) is performed using about 1 to 10 mol of compound (XXI) per 1 mol of compound (XX), in an organic solvent that does not adversely influence the reaction.

The starting compound (XX) used in the above-mentioned reaction (l) can be produced by a method known per se, for example, the method described in Journal of Medicinal Chemistry, vol. 37, p. 2371 (1994) or a method analogous thereto, or the production methods shown in the aforementioned reactions (d) to (g) or methods analogous thereto.

In the above-mentioned reaction (l), when E5 is a leaving group (e.g., a halogen atom such as chlorine, bromine, iodine and the like; a substituted sulfonic acid ester such as trifluoromethanesulfonic acid ester etc. and the like), and E6 is a hydroxy group, the reaction can be also promoted by a method known per se, for example, the method described in Journal of the American Chemical Society, vol. 127, p. 8146 (2005) and the like or a method analogous thereto, in the presence of a metal catalyst.

Examples of the metal catalyst include palladium compounds (e.g., palladium acetate, palladium chloride, tetrakis (triphenylphosphine)palladium, dichlorobis(triphenylphosphine)palladium, [1,1'-bis(diphenylphosphino)ferrocene] dichloropalladium and the like), copper compounds (e.g., copper powder, copper(I) chloride, copper(I) iodide, copper (I) acetate and the like), nickel compounds (e.g., tetrakis (triphenylphosphine)nickel and the like), rhodium compounds (e.g., tris(triphenylphosphine)rhodium chloride and the like), platinum compounds and the like.

The amount of the metal catalyst to be used is about 0.000001 to 5 molar equivalents, preferably 0.0001 to 1 molar equivalent, relative to compound (XX).

The above-mentioned reaction may be performed using a base and a ligand.

Examples of the base include metal alkoxides such as potassium phenoxide, sodium tert-butoxide and the like; inorganic salts such as potassium carbonate, sodium carbonate, cesium carbonate, potassium phosphate and the like, and the like.

The amount of the base to be used is about 0.1 to 10 molar equivalents, preferably about 1 to 3 molar equivalents, relative to compound (XX).

Examples of the ligand include organic phosphorus compounds such as triphenylphosphine, tri-tert-butylphosphine, tricyclohexylphosphine, BINAP (2,2'-bis(diphenylphosphino)-1,1'-binaphthyl) and the like; organic amine compounds such as N,N'-dimethyl-cyclohexane-1,2-diamine, 2,2'-bipyridyl and the like, and the like.

The amount of the ligand to be used is about 0.000001 to 5 molar equivalents, preferably about 0.00001 to 1 molar equivalent, relative to compound (XX).

Examples of the solvent that does not adversely influence the reaction include alcohols such as methanol, ethanol, ethylene glycol and the like; ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide etc. and the like. These solvents may be used as a mixture of two or more kinds thereof at an appropriate ratio. Furthermore, water may be mixed with the above-mentioned solvent at an appropriate ratio.

When a metal catalyst unstable to oxygen is used in the above-mentioned reaction, the reaction is preferably performed under an inert gas (e.g., argon, nitrogen and the like) atmosphere.

The reaction temperature is generally about −50° C. to about 150° C., preferably about −10° C. to about 120° C.

The reaction time is generally about 0.5 to about 20 hr.

In the above-mentioned reaction (l), when E5 and E6 are both hydroxy groups, the reaction is performed by a method known per se, for example, the method described in Organic Reactions, vol. 42, p. 335 (1992) and the like or a method analogous thereto. This reaction is performed in the presence of an organic phosphorus compound and an azo reagent.

Examples of the organic phosphorus compound include triphenylphosphine, tri(n-butyl)phosphine and the like.

Examples of the azo reagent include diethyl azodicarboxylate, diisopropyl azodicarboxylate, 1,1'-(azodicarbonyl)dipiperidine and the like.

The amount of the organic phosphorus compound and azo reagent to be used is preferably about 1 to about 5 molar equivalents relative to compound (XX), respectively.

Examples of the solvent that does not adversely influence the reaction include ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide etc. and the like. These solvents may be used as a mixture of two or more kinds thereof at an appropriate ratio.

The reaction temperature is generally about −50° C. to about 150° C., preferably about −10° C. to about 100° C.

The reaction time is generally about 0.5 to about 20 hr.

In the above-mentioned reaction (l), when E5 is a hydroxy group and E6 is a leaving group (e.g., a halogen atom such as chlorine, bromine, iodine and the like; a substituted sulfonic acid ester such as trifluoromethanesulfonic acid ester etc. and the like), this reaction is performed according to a conventional method, in a solvent that does not adversely influence the reaction, in the presence of a base.

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide etc. and the like.

The amount of the base to be used is preferably about 1 to about 5 molar equivalents relative to compound (XX).

Examples of the solvent that does not adversely influence the reaction include aromatic hydrocarbons such as benzene, toluene, xylene and the like; nitrites such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc. and the like. These solvents may be used as a mixture of two or more kinds thereof at an appropriate ratio.

The reaction temperature is generally about −50° C. to about 150° C., preferably about −10° C. to about 100° C.

The reaction time is generally about 0.5 to about 20 hr.

The starting compound (XX) used in the above-mentioned reaction (l) can be produced by a method known per se, for example, the method described in Journal of Medicinal Chemistry, vol. 37, p. 2371 (1994) or a method analogous thereto, or the production methods shown in the aforementioned reactions (d) to (g) and (j) to (k) or methods analogous thereto.

In each of the aforementioned reactions, when the starting compound has a hydroxy group, an amino group, a carboxyl group or a carbonyl group as a substituent, a protecting group generally used in the peptide chemistry and the like may be introduced into these groups. By removing the protecting group as necessary after the reaction, the object compound can be obtained.

Examples of the protecting group of hydroxy group include C1-C6 alkyl group (e.g., methyl, ethyl, propyl, isopropyl, butyl, tert-butyl), phenyl group, trityl group, C7-C10 aralkyl group (e.g., benzyl), formyl group, C1-C6 alkyl-carbonyl group (e.g., acetyl, propionyl), benzoyl group, C7-C10 aralkyl-carbonyl group (e.g., benzylcarbonyl), 2-tetrahydropyranyl group, 2-tetrahydrofuranyl group, silyl group (e.g., trimethylsilyl, triethylsilyl, dimethylphenylsilyl, tert-butyldimethylsilyl, tert-butyldiethylsilyl), C2-C6 alkenyl group (e.g., 1-allyl) and the like. These groups are optionally substituted by 1 to 3 substituents selected from halogen atom (e.g., fluorine, chlorine, bromine, iodine), C1-C6 alkyl group (e.g., methyl, ethyl, propyl), C1-C6 alkoxy group (e.g., methoxy, ethoxy, propoxy), nitro group and the like.

Examples of the amino-protecting group include formyl group, C1-C6 alkyl-carbonyl group (e.g., acetyl, propionyl), C1-C6 alkoxy-carbonyl group (e.g., methoxycarbonyl, ethoxycarbonyl, tert-butoxycarbonyl), benzoyl group, C7-C10 aralkyl-carbonyl group (e.g., benzylcarbonyl), C7-C14 aralkyloxy-carbonyl group (e.g., benzyloxycarbonyl, 9-fluorenylmethoxycarbonyl), trityl group, phthaloyl group, N,N-dimethylaminomethylene group, silyl group (e.g., trimethylsilyl, triethylsilyl, dimethylphenylsilyl, tert-butyldimethylsilyl, tert-butyldiethylsilyl), C2-C6 alkenyl group (e.g., 1-allyl) and the like. These groups are optionally substituted by 1 to 3 substituents selected from halogen atom (e.g., fluorine, chlorine, bromine, iodine), C1-C6 alkoxy group (e.g., methoxy, ethoxy, propoxy), nitro group and the like.

Examples of the protecting group of carboxyl group include C1-C6 alkyl group (e.g., methyl, ethyl, propyl, isopropyl, butyl, tert-butyl), C7-C10 aralkyl group (e.g., benzyl), phenyl group, trityl group, silyl group (e.g., trimethylsilyl, triethylsilyl, dimethylphenylsilyl, tert-butyldimethylsilyl, tert-butyldiethylsilyl, tert-butyldiphenylsilyl), C2-C6 alkenyl group (e.g., 1-allyl) and the like. These groups are optionally substituted by 1 to 3 substituents selected from halogen atom (e.g., fluorine, chlorine, bromine, iodine), C1-C6 alkoxy group (e.g., methoxy, ethoxy, propoxy), nitro group and the like.

Examples of the protecting group of carbonyl group include cyclic acetal (e.g., 1,3-dioxane), acyclic acetal (e.g., di-C1-C6 alkyl acetal) and the like.

These protecting groups can be removed according to a method known per se, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide and the like) and the like, reduction method and the like can be used.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, (+)-cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (phosphate buffer, etc.) and organic solvents (ethanol, methanol, isopropanol, acetonitrile, trifluoroacetic acid, diethylamine, etc.) solely or in admixture to separate the optical isomer.

3) Diastereomer Method

A method wherein a racemic mixture is prepared into a diastereomeric mixture by chemical reaction with an optically active reagent, which is made into a single substance by a typical separation means (a fractional recrystallization method, a chromatography method, etc.) and the like, and is subjected to a chemical treatment such as hydrolysis and the like to separate an optically active reagent moiety, whereby an optical isomer is obtained. For example, when compound (I) contains hydroxy, or primary or secondary amino in a molecule, the compound and an optically active organic acid (MTPA [α-methoxy-α-(trifluoromethyl)phenylacetic acid], (−)-menthoxyacetic acid, etc.) and the like are subjected to condensation reaction to give diastereomers in the ester form or in the amide form, respectively. When compound (I) has a carboxylic acid group, this compound and an optically active amine or an alcohol reagent are subjected to condensation reaction to give diastereomers in the amide form or in the ester form, respectively. The separated diastereomer is converted to an optical isomer of the original compound by acid hydrolysis or base hydrolysis.

EXAMPLES

The present invention is described in detail by way of the following Experimental Examples, Reference Examples, Examples and Formulation Examples, which are not to be construed as limitative.

In the following Reference Examples and Examples, the room temperature means 1° C.-30° C.

As for NMR spectra, the chemical shift was indicated by δ, and a coupling constant was indicated by Hz. The numeric value in parenthesis with regard to a mixed solvent is a volumetric mixing ratio of each solvent. Moreover, "%" in the solution represents the number of grams in 100 ml of a solution. The abbreviations used in the present specification mean the following.

s: singlet
d: doublet
t: triplet
q: quartet
dd: double doublet
dt: double triplet
m: multiplet
br: broad
J: coupling constant
$CDCl_3$: deuterated chloroform
DMSO-$d_6$: dimethyl sulfoxide-$d_6$
$^1$H NMR: proton nuclear magnetic resonance
TBS: tert-butyl(dimethyl)silyl
TBDMS: tert-butyl(dimethyl)silyl
TIPS: triisopropylsilyl As for X-ray analysis, the X-ray powder diffraction pattern of this crystal was measured using Cu—Kα ray (tube voltage: 40 KV; tube current: 50 mA) as a radiation source with scan speed of 6.000°/min.

Example 1

3-(2,2-dimethyl-2,3-dihydro-1-benzofuran-5-yl)-2-methoxy-5-{[2'-(5-oxo-4,5-dihydro-1,2,4-oxadiazol-3-yl)biphenyl-4-yl]methyl}-6-propylpyrimidin-4(3H)-one

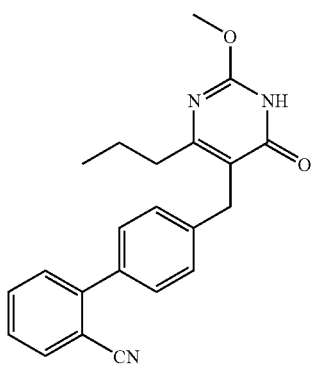

1a) 4'-[(2-methoxy-6-oxo-4-propyl-1,6-dihydropyrimidin-5-yl)methyl]biphenyl-2-carbonitrile A solution of methyl imidocarbamate sulfate (10 g), 28% sodium methoxide (26 mL) and ethyl 2-[(2'-cyanobiphenyl-4-yl)methyl]-3-oxohexanoate (15.8 g) in methanol (100 mL) was stirred overnight at room temperature. The solvent was evaporated under reduced pressure, and water and acetic acid were added. The precipitated solid was collected by filtration, washed with water and diethyl ether to give the title compound (2.62 g, 16%) as a colorless solid.

$^1$H NMR (300 MHz, DMSO-$d_6$) δ 0.86 (3H, t, J=7.2), 1.46-1.64 (2H, m), 2.46 (2H, t, J=7.2), 3.82 (2H, s), 3.86 (3H, s), 7.32 (2H, d, J=8.4), 7.47 (2H, d, J=8.4), 7.52-7.63 (2H, m), 7.72-7.82 (1H, m), 7.92 (1H, d, J=6.6), 12.21 (1H, br)

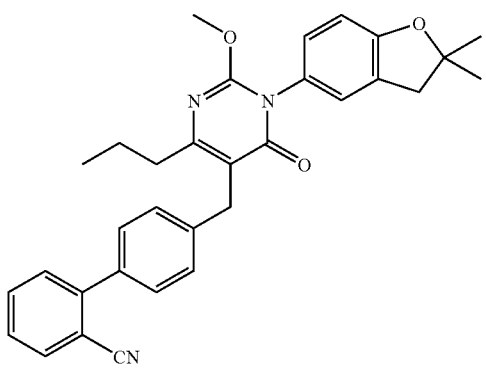

1b) 4'-{[1-(2,2-dimethyl-2,3-dihydro-1-benzofuran-5-yl)-2-methoxy-6-oxo-4-propyl-1,6-dihydropyrimidin-5-yl]methyl}biphenyl-2-carbonitrile To a suspension of 4'-[(2-methoxy-6-oxo-4-propyl-1,6-dihydropyrimidin-5-yl)methyl]biphenyl-2-carbonitrile (2.6 g), (2,2-dimethyl-2,3-dihydro-1-benzofuran-5-yl)boronic acid (2.78 g), triethylamine (5.0 mL), pyridine (2.9 mL) and molecular sieves 4A (5.2 g) in dichloromethane (50 mL) was added copper(II) acetate (2.6 g), and the mixture was stirred for 2 days. The reaction mixture was diluted with ethyl acetate, the insoluble material was filtered off through celite, and the filtrate was concentrated. The residue was purified by silica gel column chromatography to give the title compound as colorless crystals (1.85 g, 51%).

$^1$H NMR (300 MHz, DMSO-$d_6$) δ 0.92 (3H, t, J=7.2), 1.44 (6H, s), 1.55-1.70 (2H, m), 2.54 (2H, t, J=7.2), 3.04 (2H, s), 3.82 (3H, s), 3.83 (2H, s), 6.75 (1H, d, J=8.4), 6.99 (1H, d, J=8.4), 7.09 (1H, s), 7.37 (2H, d, J=8.4), 7.48 (2H, d, J=8.4), 7.52-7.62 (2H, m), 7.73-7.81 (1H, m), 7.93 (1H, d, J=7.8)

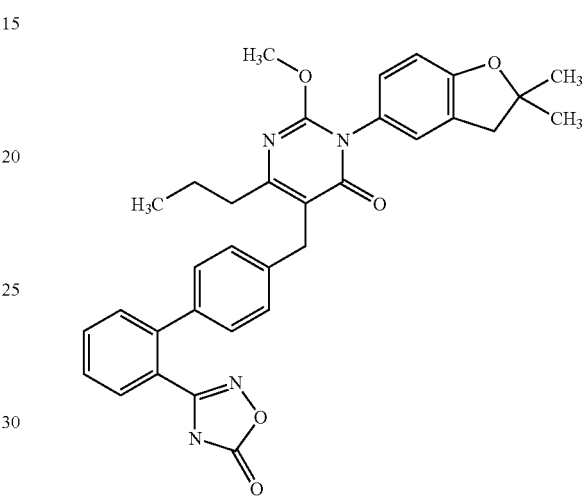

1c) 3-(2,2-dimethyl-2,3-dihydro-1-benzofuran-5-yl)-2-methoxy-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (4.33 g), sodium hydrogen carbonate (6.16 g) and dimethyl sulfoxide (20 mL) was stirred at 40° C. for 30 min, 4'-{[1-(2,2-dimethyl-2,3-dihydro-1-benzofuran-5-yl)-2-methoxy-6-oxo-4-propyl-1,6-dihydropyrimidin-5-yl]methyl}biphenyl-2-carbonitrile (1.85 g) was added, and the mixture was stirred at 90° C. for 5 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate, and the solvent was evaporated. The residue was dissolved in tetrahydrofuran (20 mL), N,N'-carbonyldiimidazole (0.48 g) and then 1,8-diazabicyclo[5.4.0]undec-7-ene (0.45 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.74 g, 66%).

$^1$H NMR (300 MHz, DMSO-$d_6$) δ 0.90 (3H, t, J=7.2), 1.44 (6H, s), 1.50-1.67 (2H, m), 2.50-2.60 (2H, m), 3.04 (2H, s), 3.81 (3H, s), 3.83 (2H, s), 6.75 (1H, d, J=8.4), 6.97 (1H, d,

J=8.4), 7.08 (1H, s), 7.17-7.32 (4H, m), 7.46-7.58 (2H, m), 7.61-7.73 (2H, m), 12.37 (1H, s)

Example 2

2-(dimethylamino)-3-(2,2-dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one

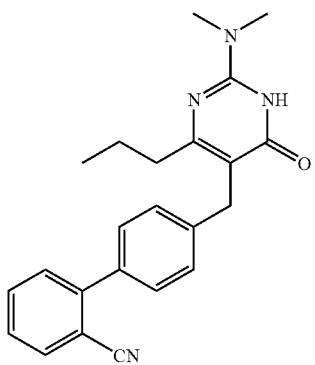

2a) 4'-{[2-(dimethylamino)-6-oxo-4-propyl-1,6-dihydropyrimidin-5-yl]methyl}biphenyl-2-carbonitrile To a solution of ethyl 2-[(2'-cyanobiphenyl-4-yl)methyl]-3-oxohexanoate (6.41 g) and N,N-dimethylguanidine sulfate (5.0 g) in ethanol (100 mL) was added 20% sodium ethoxide-ethanol solution (11 mL), and the mixture was heated under reflux for 24 hr. The reaction mixture was allowed to cool to room temperature, and the solvent was evaporated under reduced pressure. The residue was washed with water and diethyl ether to give the title compound (2.06 g, 30%) as a pale-yellow solid.

$^1$H NMR (300 MHz, DMSO-d$_6$) δ 0.85 (3H, t, J=7.5), 1.42-1.63 (2H, m), 2.37 (2H, t, J=7.5), 3.02 (6H, s), 3.78 (2H, s), 7.31 (2H, d, J=7.8), 7.46 (2H, d, J=7.8), 7.50-7.63 (2H, m), 7.70-7.82 (1H, m), 7.92 (1H, d, J=8.1), 10.94 (1H, br)

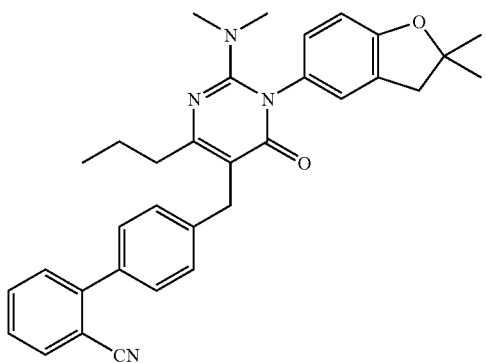

2b) 4'-{[2-(dimethylamino)-1-(2,2-dimethyl-2,3-dihydro-1-benzofuran-5-yl)-6-oxo-4-propyl-1,6-dihydropyrimidin-5-yl]methyl}biphenyl-2-carbonitrile To a suspension of 4'-{[2-(dimethylamino)-6-oxo-4-propyl-1,6-dihydropyrimidin-5-yl]methyl}biphenyl-2-carbonitrile (2.1 g), (2,2-dimethyl-2,3-dihydro-1-benzofuran-5-yl)boronic acid (2.1 g), triethylamine (3.8 mL), pyridine (2.2 mL) and molecular sieves 4A (4 g) in dichloromethane (50 mL) was added copper(II) acetate (2 g), and the mixture was stirred for 2 days. The reaction mixture was diluted with ethyl acetate, the insoluble material was filtered off through celite, and the filtrate was concentrated. The residue was purified by silica gel column chromatography to give the title compound as colorless crystals (0.31 g, 11%).

$^1$H NMR (300 MHz, CDCl$_3$) δ 0.95 (3H, t, J=7.2), 1.47 (6H, s), 1.52-1.62 (2H, m), 2.17 (2H, s), 2.61 (2H, t, J=7.2), 2.99 (6H, s), 4.04 (2H, s), 6.65 (1H, d, J=9.3), 6.78-6.87 (2H, m), 7.30-7.52 (6H, m), 7.57-7.66 (1H, m), 7.74 (1H, d, J=7.5)

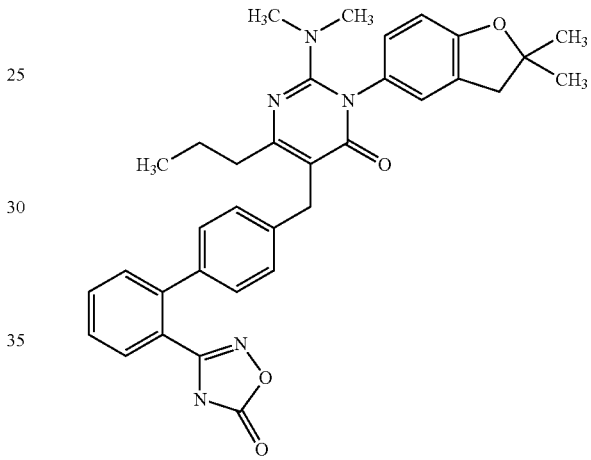

2c) 2-(dimethylamino)-3-(2,2-dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.71 g), sodium hydrogen carbonate (1.01 g) and dimethyl sulfoxide (5 mL) was stirred at 40° C. for 30 min, 4'-{[2-(dimethylamino)-1-(2,2-dimethyl-2,3-dihydro-1-benzofuran-5-yl)-6-oxo-4-propyl-1,6-dihydropyrimidin-5-yl]methyl}biphenyl-2-carbonitrile (0.31 g) was added, and the mixture was stirred at 90° C. for 16 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate, and the solvent was evaporated. The residue was dissolved in tetrahydrofuran (20 mL), N,N'-carbonyldiimidazole (0.13 g) and then 1,8-diazabicyclo[5.4.0]undec-7-ene (0.12 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.1 g, 33%).

$^1$H NMR (300 MHz, DMSO-d$_6$) δ 0.88 (3H, t, J=7.2), 1.40 (6H, s), 1.49-1.65 (2H, m), 2.50-2.58 (2H, m), 2.91 (6H, s), 2.99 (2H, s), 3.98 (2H, s), 6.66 (1H, d, J=8.7), 6.81 (1H, d, J=8.7), 6.90 (1H, s), 7.25 (4H, s), 7.47-7.59 (2H, m), 7.61-7.72 (2H, m), 12.36 (1H, br)

Example 3

5-benzyl-2-(ethylthio)-6-methyl-3-{[2'-(5-oxo-4,5-dihydro-1,2,4-oxadiazol-3-yl)biphenyl-4-yl]methyl}pyrimidin-4(3H)-one

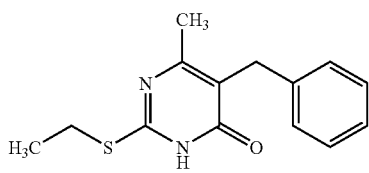

3a) 5-benzyl-2-(ethylthio)-6-methylpyrimidin-4(3H)-one

To a solution of 5-benzyl-6-methyl-2-thioxo-2,3-dihydropyrimidin-4(1H)-one (0.2 g) and potassium carbonate (0.24 g) in N,N-dimethylformamide (4 mL) was added ethyl iodide (0.035 mL), and the mixture was stirred for 4 hr. The insoluble material was filtered off. The filtrate was diluted with ethyl acetate, washed with 1 M hydrochloric acid and saturated brine, and dried over anhydrous sodium sulfate. The solvent was evaporated under reduced pressure to give the title compound (0.22 g, 97%) as a pale-yellow solid.

$^1$H NMR (300 MHz, DMSO-d$_6$) δ 1.28 (3H, t, J=7.5), 2.18 (3H, s), 3.08 (2H, q, J=7.5), 3.74 (2H, s), 7.02-7.34 (5H, m)

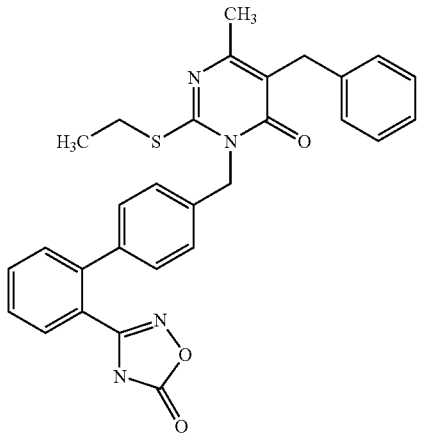

3b) 5-benzyl-2-(ethylthio)-6-methyl-3-{[2'-(5-oxo-4,5-dihydro-1,2,4-oxadiazol-3-yl)biphenyl-4-yl]methyl}pyrimidin-4(3H)-one To a solution of 5-benzyl-2-(ethylthio)-6-methylpyrimidin-4(3H)-one (0.22 g) and 3-[4'-(bromomethyl)biphenyl-2-yl]-5-(trichloromethyl)-1,2,4-oxadiazole (0.44 g) in N,N-dimethylformamide (5 mL) was added cesium carbonate (0.36 g), and the mixture was stirred for 12 hr. The reaction mixture was diluted with ethyl acetate, washed with 1 M hydrochloric acid and saturated brine and dried over anhydrous sodium sulfate. The solvent was evaporated under reduced pressure. The residue was dissolved in tetrahydrofuran-ethanol (1:1, 4 mL), 1 M sodium hydroxide (2 mL) was added and the mixture was stirred for 30 min. The reaction mixture was weakly acidified with 1 M hydrochloric acid and extracted with ethyl acetate. The organic layer was washed with saturated brine and dried over anhydrous sodium sulfate. The solvent was evaporated under reduced pressure. The residue was purified by silica gel column chromatography to give the title compound (0.025 g, 6%) as a colorless solid.

$^1$H NMR (300 MHz, CDCl$_3$) δ 1.35 (3H, t, J=7.5), 2.27 (3H, s), 3.17 (2H, q, J=7.5), 3.76 (2H, s), 5.20 (2H, s), 7.07-7.30 (9H, m), 7.37-7.47 (2H, m), 7.52-7.62 (1H, m), 7.66 (1H, d, J=7.5)

5-Benzyl-2-(ethylthio)-6-methyl-3-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

5-benzyl-2-(ethylthio)-6-methyl-3-{[2'-(5-oxo-4,5-dihydro-1,2,4-oxadiazol-3-yl)biphenyl-4-yl]methyl}pyrimidin-4(3H)-one sodium salt 5-benzyl-2-(ethylthio)-6-methyl-3-{[2'-(5-oxo-4,5-dihydro-1,2,4-oxadiazol-3-yl)biphenyl-4-yl]methyl}pyrimidin-4(3H)-one potassium salt 5-benzyl-2-(ethylthio)-6-methyl-3-{[2'-(5-oxo-4,5-dihydro-1,2,4-oxadiazol-3-yl)biphenyl-4-yl]methyl}pyrimidin-4(3H)-one 0.5 calcium salt 5-benzyl-2-(ethylthio)-6-methyl-3-{[2'-(5-oxo-4,5-dihydro-1,2,4-oxadiazol-3-yl)biphenyl-4-yl]methyl}pyrimidin-4(3H)-one hydrochloride 5-benzyl-2-(ethylthio)-6-methyl-3-{[2'-(5-oxo-4,5-dihydro-1,2,4-oxadiazol-3-yl)biphenyl-4-yl]methyl}pyrimidin-4(3H)-one hydrobromide Example 4

5-benzyl-2-ethoxy-6-methyl-3-{[2'-(5-oxo-4,5-dihydro-1,2,4-oxadiazol-3-yl)biphenyl-4-yl]methyl}pyrimidin-4(3H)-one

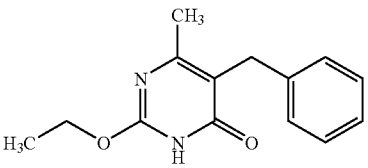

4a) 5-benzyl-2-ethoxy-6-methylpyrimidin-4(3H)-one

To a solution of ethyl imidocarbamate tetrafluoroborate (2.4 g) and ethyl 2-benzyl-3-oxobutanoate (1 g) in methanol (20 mL) was added sodium methoxide (28% methanol solution, 5.25 mL), and the mixture was stirred for 12 hr. The reaction mixture was concentrated, and the residue was dissolved in water. The solution was weakly acidified with acetic acid, extracted with ethyl acetate, washed with saturated brine and dried over anhydrous sodium sulfate. The solvent was evaporated under reduced pressure. The residue was crystallized from diisopropyl ether to give the title compound (0.27 g, 24%) as a colorless solid.

$^1$H NMR (300 MHz, DMSO-d$_6$) δ 1.28 (3H, t, J=7.2), 2.12 (3H, s), 3.70 (2H, s), 4.31 (2H, q, J=7.2), 7.03-7.33 (5H, m), 12.17 (1H, br)

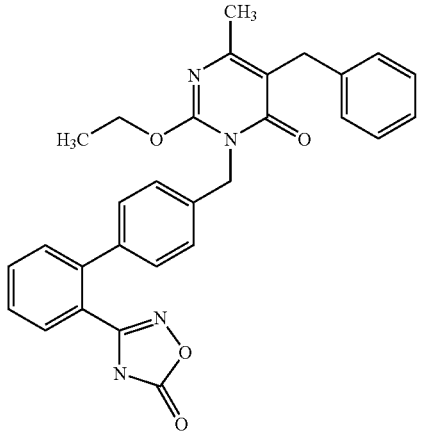

4b) 5-benzyl-2-ethoxy-6-methyl-3-{[2'-(5-oxo-4,5-dihydro-1,2,4-oxadiazol-3-yl)biphenyl-4-yl]methyl}pyrimidin-4(3H)-one To a solution of 5-benzyl-2-ethoxy-6-methylpyrimidin-4 (3H)-one (0.27 g) and 3-[4'-(bromomethyl)biphenyl-2-yl]-5-(trichloromethyl)-1,2,4-oxadiazole (0.58 g) in N,N-dimethylformamide (5 mL) was added cesium carbonate (0.44 g), and the mixture was stirred for 12 hr. The reaction mixture was diluted with ethyl acetate, washed with 1 M hydrochloric acid and saturated brine and dried over anhydrous sodium sulfate. The solvent was evaporated under reduced pressure. The residue was dissolved in tetrahydrofuran-ethanol (1:1, 4 mL), 1 M sodium hydroxide (2 mL) was added and the mixture was stirred for 30 min. The reaction mixture was weakly acidified with 1 M hydrochloric acid and extracted with ethyl acetate. The organic layer was washed with saturated brine and dried over anhydrous sodium sulfate. The solvent was evaporated under reduced pressure. The residue was purified by silica gel column chromatography to give the title compound (0.11 g, 20%) as a colorless solid.

$^1$H NMR (300 MHz, CDCl$_3$) δ 1.38 (3H, t, J=7.2), 2.20 (3H, s), 3.78 (2H, s), 4.43 (2H, q, J=7.2), 5.14 (2H, s), 7.10-7.30 (7H, m), 7.34-7.51 (4H, m), 7.55-7.64 (1H, m), 7.75 (1H, d, J=7.8)

5-Benzyl-2-ethoxy-6-methyl-3-{[2'-(5-oxo-4,5-dihydro-1,2,4-oxadiazol-3-yl)biphenyl-4-yl]methyl}pyrimidin-4 (3H)-one obtained above is subjected to a conventional method of salt formation to give the following salts.

5-benzyl-2-ethoxy-6-methyl-3-{[2'-(5-oxo-4,5-dihydro-1,2,4-oxadiazol-3-yl)biphenyl-4-yl]methyl}pyrimidin-4(3H)-one sodium salt 5-benzyl-2-ethoxy-6-methyl-3-{[2'-(5-oxo-4,5-dihydro-1,2,4-oxadiazol-3-yl)biphenyl-4-yl]methyl}pyrimidin-4(3H)-one potassium salt 5-benzyl-2-ethoxy-6-methyl-3-{[2'-(5-oxo-4,5-dihydro-1,2,4-oxadiazol-3-yl)biphenyl-4-yl]methyl}pyrimidin-4(3H)-one 0.5 calcium salt 5-benzyl-2-ethoxy-6-methyl-3-{[2'-(5-oxo-4,5-dihydro-1,2,4-oxadiazol-3-yl)biphenyl-4-yl]methyl}pyrimidin-4(3H)-one hydrochloride 5-benzyl-2-ethoxy-6-methyl-3-{[2'-(5-oxo-4,5-dihydro-1,2,4-oxadiazol-3-yl)biphenyl-4-yl]methyl}pyrimidin-4(3H)-one hydrobromide Example 5

2-butyl-5-(4-fluorophenyl)-6-methyl-3-{[2'-(5-oxo-4,5-dihydro-1,2,4-oxadiazol-3-yl)biphenyl-4-yl]methyl}pyrimidin-4(3H)-one

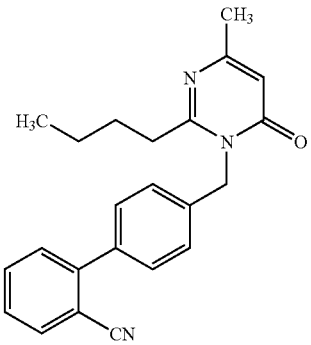

5a) 4'-[(2-butyl-4-methyl-6-oxopyrimidin-1(6H)-yl)methyl]biphenyl-2-carbonitrile To a solution of 2-butyl-6-methylpyrimidin-4(3H)-one (3.38 g) and 4'-(bromomethyl)biphenyl-2-carbonitrile (6.64 g) in acetonitrile (50 mL) was added cesium carbonate (8.61 g), and the mixture was stirred at 50° C. for 12 hr. The insoluble material was filtered off, and the filtrate was concentrated. The residue was purified by silica gel column chromatography to give the title compound (2.09 g, 29%) as a colorless viscous substance.

$^1$H NMR (300 MHz, CDCl$_3$) δ 0.90 (3H, t, J=7.2), 1.30-1.46 (2H, m), 1.61-1.74 (2H, m), 2.29 (3H, s), 2.68 (2H, t, J=6.6), 5.36 (2H, s), 6.29 (1H, s), 7.23-7.32 (2H, m), 7.40-7.57 (4H, m), 7.59-7.69 (1H, m), 7.76 (1H, d, J=7.8)

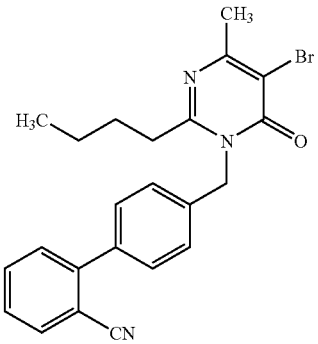

5b) 4'-[(5-bromo-2-butyl-4-methyl-6-oxopyrimidin-1(6H)-yl)methyl]biphenyl-2-carbonitrile To a solution of 4'-[(2-butyl-4-methyl-6-oxopyrimidin-1(6H)-yl)methyl]biphenyl-2-carbonitrile (1.8 g) in acetic acid (40 mL) was added bromine (0.77 mL), and the mixture was stirred at 70° C. for 2 hr. The reaction mixture was allowed to cool to room temperature. The mixture was diluted with ethyl acetate, washed with saturated aqueous sodium hydrogen carbonate and saturated brine, and dried over anhydrous sodium sulfate. The solvent was evaporated under reduced pressure and the residue was purified by silica gel column chromatography to give the title compound (1.96 g, 88%) as a colorless solid.

$^1$H NMR (300 MHz, CDCl$_3$) δ 0.91 (3H, t, J=7.5), 1.30-1.47 (2H, m), 1.60-1.75 (2H, m), 2.49 (3H, s), 2.69 (2H, t, J=7.5), 5.39 (2H, s), 7.31 (2H, d, J=8.1), 7.40-7.58 (4H, m), 7.60-7.70 (1H, m), 7.76 (1H, d, J=6.9)

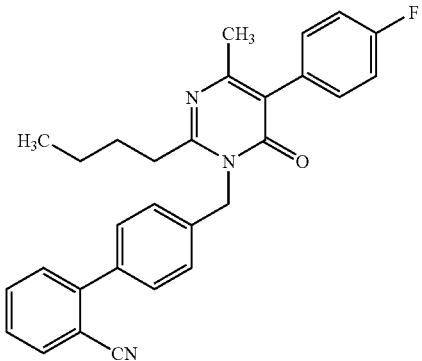

5c) 4'-{[2-butyl-5-(4-fluorophenyl)-4-methyl-6-oxopyrimidin-1(6H)-yl]methyl}biphenyl-2-carbonitrile To a solution of 4'-[(5-bromo-2-butyl-4-methyl-6-oxopyrimidin-1(6H)-yl)methyl]biphenyl-2-carbonitrile (1.0 g) and 4-fluorophenylboronic acid (0.48 g) in 1,4-dioxane (20 mL) were added 2 M aqueous cesium carbonate solution (4 mL) and [1,1'-bis(diphenylphosphino)ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (1.0 g, 97%) as a colorless solid.

$^1$H NMR (300 MHz, CDCl$_3$) δ 0.93 (3H, t, J=7.2), 1.34-1.52 (2H, m), 1.66-1.81 (2H, m), 2.22 (3H, s), 2.75 (2H, t, J=7.8), 5.38 (2H, s), 7.09-7.17 (2H, m), 7.28-7.38 (4H, m), 7.40-7.58 (4H, m), 7.59-7.69 (1H, m), 7.76 (1H, d, J=7.8)

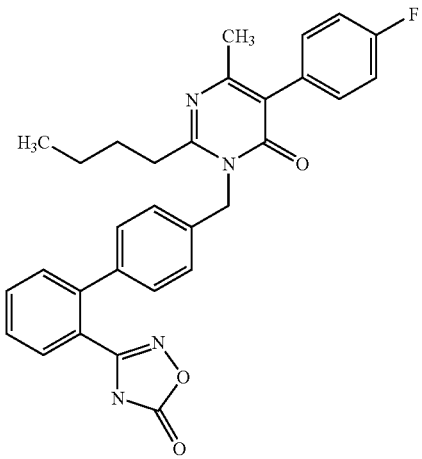

5d) 2-butyl-5-(4-fluorophenyl)-6-methyl-3-{[2'-(5-oxo-4,5-dihydro-1,2,4-oxadiazol-3-yl)biphenyl-4-yl]methyl}pyrimidin-4(3H)-one A mixture of hydroxylammonium chloride (2.62 g), sodium hydrogen carbonate (3.72 g) and dimethyl sulfoxide (10 mL) was stirred at 40° C. for 30 min, 4'-{[2-butyl-5-(4-fluorophenyl)-4-methyl-6-oxopyrimidin-1(6H)-yl]methyl}biphenyl-2-carbonitrile (1 g) was added, and the mixture was stirred at 90° C. for 16 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (20 mL), N,N'-carbonyldiimidazole (0.54 g) and then 1,8-diazabicyclo[5.4.0]undec-7-ene (0.50 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.81 g, 72%).

$^1$H NMR (300 MHz, DMSO-d$_6$) δ 0.82 (3H, t, J=7.2), 1.21-1.38 (2H, m), 1.50-1.66 (2H, m), 2.11 (3H, s), 2.69 (2H, t, J=7.5), 5.36 (2H, s), 7.18-7.42 (8H, m), 7.47-7.62 (2H, m), 7.62-7.74 (2H, m), 12.41 (1H, s)

Example 6

2-butyl-5-(2,3-dihydro-1-benzofuran-5-yl)-6-methyl-3-{[2'-(5-oxo-4,5-dihydro-1,2,4-oxadiazol-3-yl)biphenyl-4-yl]methyl}pyrimidin-4(3H)-one

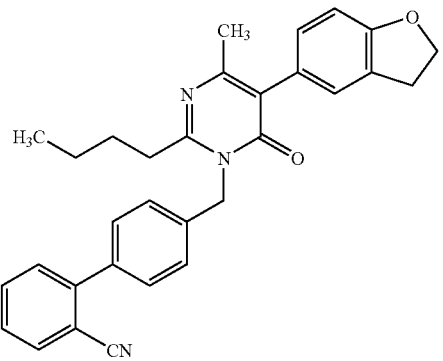

6a) 4'-{[2-butyl-5-(2,3-dihydro-1-benzofuran-5-yl)-4-methyl-6-oxopyrimidin-1(6H)-yl]methyl}biphenyl-2-carbonitrile To a solution of 4'-[(5-bromo-2-butyl-4-methyl-6-oxopyrimidin-1(6H)-yl)methyl]biphenyl-2-carbonitrile (0.96 g)

and 2,3-dihydro-1-benzofuran-5-ylboronic acid (0.54 g) in 1,4-dioxane were added 2 M aqueous cesium carbonate solution (4 mL) and [1,1'-bis(diphenylphosphino)ferrocene]dichloropalladium (0.09 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.75 g, 72%) as a colorless solid.

$^1$H NMR (300 MHz, CDCl$_3$) δ 0.93 (3H, t, J=7.2), 1.33-1.51 (2H, m), 1.65-1.81 (2H, m), 2.24 (3H, s), 2.74 (2H, t, J=7.8), 3.24 (2H, t, J=8.4), 4.59 (2H, t, J=8.4), 5.38 (2H, s), 6.83 (1H, d, J=8.1), 7.05 (1H, d, J=8.1), 7.19 (1H, s), 7.34 (2H, d, J=8.1), 7.40-7.57 (4H, m), 7.59-7.69 (1H, m), 7.76 (1H, d, J=7.8)

hydrochloric acid and then with saturated brine, and dried over anhydrous sodium sulfate. The solvent was evaporated under reduced pressure. The residue was purified by silica gel column chromatography to give the title compound as colorless crystals (0.63 g, 74%).

$^1$H NMR (300 MHz, DMSO-d$_6$) δ 0.82 (3H, t, J=7.2), 1.21-1.38 (2H, m), 1.51-1.65 (2H, m), 2.12 (3H, s), 2.68 (2H, t, J=7.2), 3.20 (2H, t, J=8.4), 4.55 (2H, t, J=8.4), 5.35 (2H, s), 6.78 (1H, d, J=8.1), 7.00 (1H, d, J=8.1), 7.16 (1H, s), 7.25 (2H, d, J=8.1), 7.32 (2H, d, J=8.1), 7.48-7.61 (2H, m), 7.64-7.74 (2H, m), 12.41 (1H, s)

Example 7

6-methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one

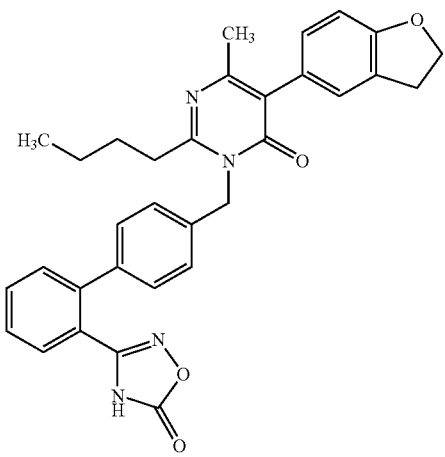

6b) 2-butyl-5-(2,3-dihydro-1-benzofuran-5-yl)-6-methyl-3-{[2'-(5-oxo-4,5-dihydro-1,2,4-oxadiazol-3-yl)biphenyl-4-yl]methyl}pyrimidin-4(3H)-one

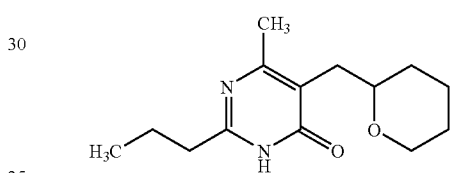

7a) 6-methyl-2-propyl-5-(tetrahydro-2H-pyran-2-ylmethyl)pyrimidin-4(3H)-one

A mixture of hydroxylammonium chloride (1.86 g), sodium hydrogen carbonate (2.65 g) and dimethyl sulfoxide (10 mL) was stirred at 40° C. for 30 min, 4'-{[2-butyl-5-(2,3-dihydro-1-benzofuran-5-yl)-4-methyl-6-oxopyrimidin-1(6H)-yl]methyl}biphenyl-2-carbonitrile (0.75 g) was added, and the mixture was stirred at 90° C. for 16 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (15 mL), N,N'-carbonyldiimidazole (0.38 g) and then 1,8-diazabicyclo[5.4.0]undec-7-ene (0.35 mL) were added, and the mixture was stirred at room temperature for 30 min. The reaction mixture was diluted with ethyl acetate, washed with 1 M To a solution of ethyl 3-oxo-2-(tetrahydro-2H-pyran-2-ylmethyl)butyrate (0.73 g) and butylamidine hydrochloride (0.78 g) in methanol (50 mL) was added sodium methoxide (25 mL, 28% methanol solution), and the mixture was stirred for 12 hr. The reaction mixture was concentrated, and the residue was dissolved in water and diethyl ether. The aqueous layer was separated, weakly acidified with 1 M hydrochloric acid, and the mixture was extracted with ethyl acetate. The extract was washed with saturated brine, and dried over anhydrous sodium sulfate to give the title compound (0.46 g, 57%) as a colorless solid.

$^1$H NMR (300 MHz, CDCl$_3$) δ 0.88 (3H, t, J=7.2), 1.08-1.80 (8H, m), 2.18 (3H, s), 2.41 (2H, t, J=7.2), 2.48-2.50 (2H, m), 3.12-3.28 (1H, m), 3.33-3.47 (1H, m), 3.79 (1H, d, J=10.8), 12.15 (1H, br)

125

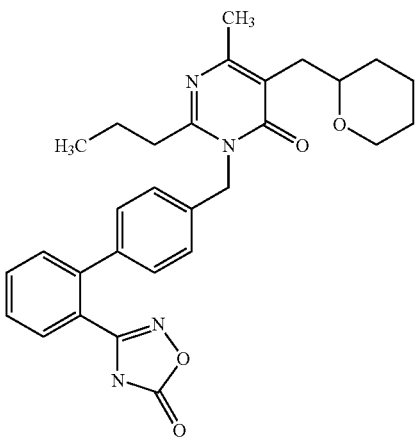

7b) 6-methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one To a solution of 6-methyl-2-propyl-5-(tetrahydro-2H-pyran-2-ylmethyl)pyrimidin-4(3H)-one (0.46 g) and 3-[4'-(bromomethyl)biphenyl-2-yl]-5-(trichloromethyl)-1,2,4-oxadiazole (0.95 g) in acetonitrile (20 mL) was added potassium carbonate (0.51 g), and the mixture was stirred for 12 hr. The reaction mixture was diluted with ethyl acetate, washed with 1 M hydrochloric acid and saturated brine and dried over anhydrous sodium sulfate. The solvent was evaporated under reduced pressure. The residue was dissolved in tetrahydrofuran-ethanol (1:1, 4 mL), 1 M sodium hydroxide (2 mL) was added and the mixture was stirred for 30 min. The reaction mixture was weakly acidified with 1 M hydrochloric acid and extracted with ethyl acetate. The organic layer was washed with saturated brine and dried over anhydrous sodium sulfate. The solvent was evaporated under reduced pressure. The residue was purified by silica gel column chromatography to give the title compound (0.15 g, 17%) as a colorless solid.
$^1$H NMR (300 MHz, DMSO-$d_6$) δ 0.85 (3H, t, J=7.2), 1.15-1.32 (1H, m), 1.32-1.49 (3H, m), 1.49-1.64 (3H, m), 1.75 (1H, m), 2.25 (3H, s), 2.54-2.66 (4H, m), 3.16-3.29 (1H, m), 3.37-3.51 (1H, m), 3.81 (1H, d, J=10.2), 5.31 (2H, s), 7.17 (2H, d, J=8.4), 7.29 (2H, d, J=8.4), 7.46-7.62 (2H, m), 7.63-7.75 (2H, m), 12.38 (1H, br)

6-Methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one obtained above is subjected to a conventional method of salt formation to give the following salts.

6-methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one sodium salt 6-methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one potassium salt 6-methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one 0.5 calcium salt 6-methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one hydrochloride 6-methyl-3-{[2'-(5-oxo-4,5-dihydro-1,2,4-oxadiazol-3-yl)biphenyl-4-yl]methyl}-2-propyl-5-(tetrahydro-2H-pyran-2-ylmethyl)pyrimidin-4(3H)-one hydrobromide

126

Example 8

2-butyl-5-cyclohex-1-en-1-yl-6-methyl-3-{[2'-(5-oxo-4,5-dihydro-1,2,4-oxadiazol-3-yl)biphenyl-4-yl]methyl}pyimidin-4(3H)-one

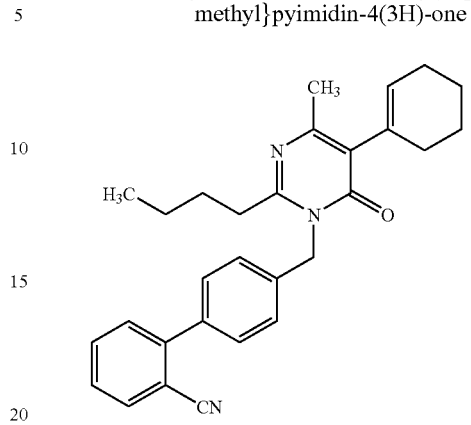

8a) 4'-[(2-butyl-5-cyclohex-1-en-1-yl-4-methyl-6-oxopyrimidin-1(6H)-yl)methyl]biphenyl-2-carbonitrile To a solution of 4'-[(5-bromo-2-butyl-4-methyl-6-oxopyrimidin-1(6H)-yl)methyl]biphenyl-2-carbonitrile (0.67 g) and 2-cyclohex-1-en-1-yl-4,4,5,5-tetramethyl-1,3,2-dioxaborolane (0.48 g) in tetrahydrofuran (40 mL) were added 2 M aqueous cesium carbonate solution (4 mL) and [1,1'-bis(diphenylphosphino)ferrocene]dichloropalladium (0.06 g), and the mixture was stirred at 70° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.58 g, 86%) as a colorless solid.
$^1$H NMR (300 MHz, CDCl$_3$) δ 0.91 (3H, t, J=7.5), 1.31-1.46 (2H, m), 1.61-1.83 (6H, m), 2.11-2.24 (4H, m), 2.28 (3H, s), 2.67 (2H, t, J=7.8), 5.33 (2H, s), 5.63 (1H, s), 7.27-7.34 (2H, m), 7.39-7.57 (4H, m), 7.58-7.69 (1H, m), 7.75 (1H, d, J=7.8)

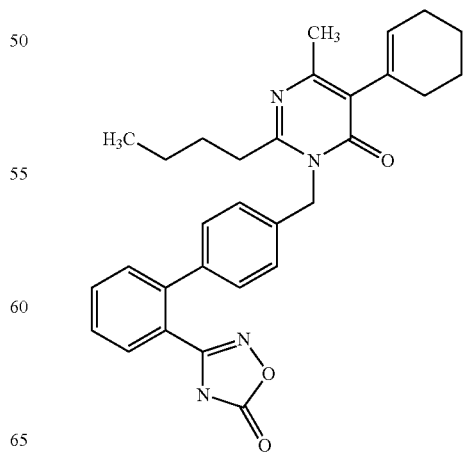

8b) 2-butyl-5-cyclohex-1-en-1-yl-6-methyl-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.78 g), sodium hydrogen carbonate (1.11 g) and dimethyl sulfoxide (10 mL) was stirred at 40° C. for 30 min, 4'-[(2-butyl-5-cyclohex-1-en-1-yl-4-methyl-6-oxopyrimidin-1(6H)-yl)methyl]biphenyl-2-carbonitrile (0.58 g) was added, and the mixture was stirred at 90° C. for 16 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (15 mL), N,N'-carbonyldiimidazole (0.33 g) and then 1,8-diazabicyclo[5.4.0]undec-7-ene (0.30 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.33 g, 49%).

$^1$H NMR (300 MHz, DMSO-$d_6$) δ 0.80 (3H, t, J=7.5), 1.18-1.35 (2H, m), 1.47-1.73 (6H, m), 2.11 (4H, br), 2.18 (3H, s), 2.62 (2H, t, J=7.5), 5.29 (2H, s), 5.53 (1H, s), 7.20 (2H, d, J=8.4), 7.30 (2H, d, J=8.4), 7.47-7.61 (2H, m), 7.63-7.74 (2H, m), 12.41 (1H, br)

Example 9

6-ethyl-5-(4-fluorophenyl)-3-{[2'-(5-oxo-4,5-dihydro-1,2,4-oxadiazol-3-yl)biphenyl-4-yl]methyl}-2-propylpyrimidin-4(3H)-one

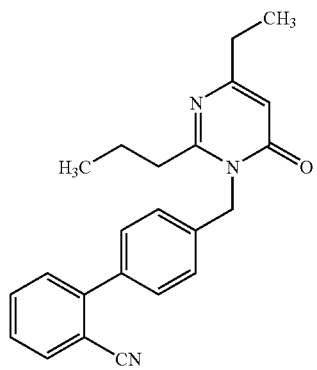

9a) 4'-[(4-ethyl-6-oxo-2-propylpyrimidin-1(6H)-yl)methyl]biphenyl-2-carbonitrile To a solution of 6-ethyl-2-propylpyrimidin-4(3H)-one (5.0 g) and 4'-(bromomethyl)biphenyl-2-carbonitrile (9.0 g) in acetonitrile (150 mL) was added potassium carbonate (8.32 g), and the mixture was stirred at 50° C. for 12 hr. The insoluble material was filtered off, the filtrate was concentrated, and the residue was purified by silica gel column chromatography to give the title compound (4.95 g, 46%) as a colorless viscous substance.

$^1$H NMR (300 MHz, CDCl$_3$) δ 0.98 (3H, t, J=7.5), 1.25 (3H, t, J=7.2), 1.67-1.83 (2H, m), 2.56 (2H, q, J=7.2), 2.66 (2H, t, J=7.5), 5.36 (2H, br), 6.29 (1H, s), 7.29 (2H, d, J=8.1), 7.40-7.59 (4H, m), 7.60-7.70 (1H, m), 7.76 (1H, d, J=7.8)

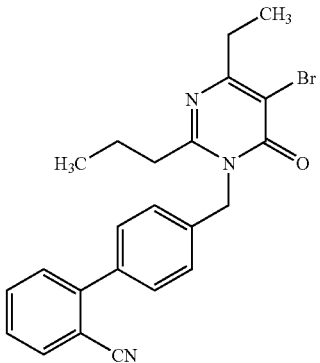

9b) 4'-[(5-bromo-4-ethyl-6-oxo-2-propylpyrimidin-1(6H)-yl)methyl]biphenyl-2-carbonitrile To a solution of 4'-[(4-ethyl-6-oxo-2-propylpyrimidin-1(6H)-yl)methyl]biphenyl-2-carbonitrile (4.95 g) and sodium acetate (1.25 g) in acetic acid (100 mL) was added bromine (0.78 mL), and the mixture was stirred for 2 hr. The reaction mixture was diluted with ethyl acetate, washed with saturated aqueous sodium hydrogen carbonate and saturated brine, and dried over anhydrous sodium sulfate. The solvent was evaporated under reduced pressure and the residue was purified by silica gel column chromatography to give the title compound (4.3 g, 71%) as a colorless solid.

$^1$H NMR (300 MHz, CDCl$_3$) δ 0.98 (3H, t, J=7.2), 1.26 (3H, t, J=7.2), 1.70-1.83 (2H, m), 2.68 (2H, t, J=7.2), 2.79 (2H, q, J=7.2), 5.39 (2H, br), 7.32 (2H, d, J=8.1), 7.42-7.55 (4H, m), 7.62-7.67 (1H, m), 7.76 (1H, d, J=7.5)

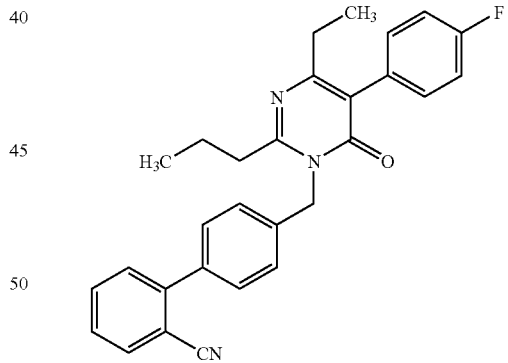

9c) 4'-{[4-ethyl-5-(4-fluorophenyl)-6-oxo-2-propylpyrimidin-1(6H)-yl]methyl}biphenyl-2-carbonitrile To a solution of 4'-[(5-bromo-4-ethyl-6-oxo-2-propylpyrimidin-1(6H)-yl)methyl]biphenyl-2-carbonitrile (1.0 g) and 4-fluorophenylboronic acid (0.48 g) in 1,4-dioxane (20 mL) were added 2 M aqueous cesium carbonate solution (4 mL) and [1,1'-bis(diphenylphosphino) ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.94 g, 91%) as a colorless solid.

$^1$H NMR (300 MHz, CDCl$_3$) δ 1.02 (3H, t, J=7.2), 1.18 (3H, t, J=7.5), 1.73-1.90 (2H, m), 2.45 (2H, q, J=7.5), 2.74 (2H, t, J=7.2), 5.37 (2H, s), 7.04-7.16 (2H, m), 7.24-7.39 (4H, m), 7.40-7.57 (4H, m), 7.60-7.69 (1H, m), 7.76 (1H, d, J=8.1)

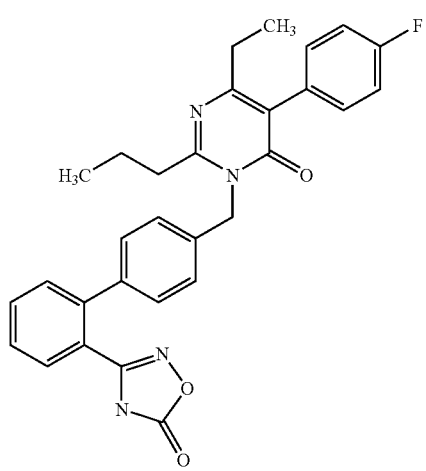

9d) 6-ethyl-5-(4-fluorophenyl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (2.46 g), sodium hydrogen carbonate (3.5 g) and dimethyl sulfoxide (10 mL) was stirred at 40° C. for 30 min, 4'-{[4-ethyl-5-(4-fluorophenyl)-6-oxo-2-propylpyrimidin-1(6H)-yl]methyl}biphenyl-2-carbonitrile (0.94 g) was added, and the mixture was stirred at 90° C. for 16 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (15 mL), N,N'-carbonyldiimidazole (0.51 g) and then 1,8-diazabicyclo[5.4.0]undec-7-ene (0.47 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.77 g, 72%).

$^1$H NMR (300 MHz, DMSO-d$_6$) δ 0.90 (3H, t, J=7.5), 1.10 (3H, t, J=7.2), 1.57-1.75 (2H, m), 2.34 (2H, q, J=7.2), 2.69 (2H, t, J=7.5), 5.35 (2H, s), 7.18-7.40 (8H, m), 7.48-7.62 (2H, m), 7.62-7.76 (2H, m), 12.40 (1H, br)

Example 10

5-(2,3-dihydro-1-benzofuran-5-yl)-6-ethyl-3-{[2'-(5-oxo-4,5-dihydro-1,2,4-oxadiazol-3-yl)biphenyl-4-yl]methyl}-2-propylpyrimidin-4(3H)-one

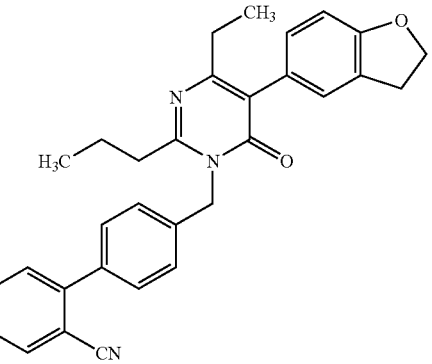

10a) 4'-{[5-(2,3-dihydro-1-benzofuran-5-yl)-4-ethyl-6-oxo-2-propylpyrimidin-1(6H)-yl]methyl}biphenyl-2-carbonitrile To a solution of 4'-[(5-bromo-4-ethyl-6-oxo-2-propylpyrimidin-1(6H)-yl)methyl]biphenyl-2-carbonitrile (1.0 g) and 2,3-dihydro-1-benzofuran-5-ylboronic acid (0.56 g) in 1,4-dioxane (20 mL) were added 2 M aqueous cesium carbonate solution (4 mL) and [1,1'-bis(diphenylphosphino)ferrocene]dichloropalladium (0.09 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.95 g, 87%) as a colorless solid.

$^1$H NMR (300 MHz, CDCl$_3$) δ 1.02 (3H, t, J=7.2), 1.18 (3H, t, J=7.2), 1.71-1.91 (2H, m), 2.49 (2H, q, J=7.2), 2.73 (2H, t, J=8.1), 3.24 (2H, t, J=8.4), 4.58 (2H, t, J=8.4), 5.37 (2H, s), 6.83 (1H, d, J=8.4), 6.98-7.06 (1H, m), 7.16 (1H, br), 7.35 (2H, d, J=8.1), 7.41-7.57 (4H, m), 7.60-7.68 (1H, m), 7.76 (1H, d, J=6.9)

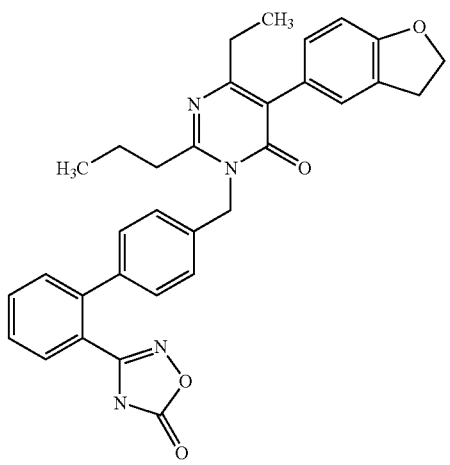

10b) 5-(2,3-dihydro-1-benzofuran-5-yl)-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (2.36 g), sodium hydrogen carbonate (3.36 g) and dimethyl sulfoxide (10 mL) was stirred at 40° C. for 30 min, 4'-{[5-(2,3-dihydro-1-benzofuran-5-yl)-4-ethyl-6-oxo-2-propylpyrimidin-1(6H)-yl]methyl}biphenyl-2-carbonitrile (0.95 g) was added, and the mixture was stirred at 90° C. for 16 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (15 mL), N,N'-carbonyldiimidazole (0.49 g) and then 1,8-diazabicyclo[5.4.0]undec-7-ene (0.46 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.69 g, 65%).

$^1$H NMR (300 MHz, DMSO-d$_6$) δ 0.89 (3H, t, J=7.5), 1.10 (3H, t, J=7.5), 1.58-1.73 (2H, m), 2.36 (2H, q, J=7.5), 2.68 (2H, t, J=7.5), 3.20 (2H, t, J=8.1), 4.55 (2H, t, J=8.1), 5.33 (2H, s), 6.79 (1H, d, J=8.1), 6.98 (1H, d, J=8.1), 7.12 (1H, s), 7.21-7.35 (4H, m), 7.46-7.61 (2H, m), 7.62-7.76 (2H, m), 12.40 (1H, s)

Example 11

5-cyclopropyl-6-ethyl-3-{[2'-(5-oxo-4,5-dihydro-1,2,4-oxadiazol-3-yl)biphenyl-4-yl]methyl}-2-propylpyrimidin-4(3H)-one

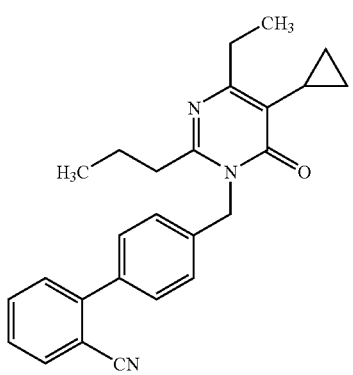

11a) 4'-[(5-cyclopropyl-4-ethyl-6-oxo-2-propylpyrimidin-1(6H)-yl)methyl]biphenyl-2-carbonitrile To a solution of 4'-[(5-bromo-4-ethyl-6-oxo-2-propylpyrimidin-1(6H)-yl)methyl]biphenyl-2-carbonitrile (1.0 g), cyclopropylboronic acid (0.26 g), potassium phosphate (1.7 g) and tricyclohexylphosphine (0.064 g) in toluene-water (20:1, 21 mL) was added palladium acetate (0.026 g), and the mixture was stirred at 100° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.79 g, 87%) as a colorless solid.

$^1$H NMR (300 MHz, CDCl$_3$) δ 0.77-0.86 (2H, m), 0.89-1.04 (5H, m), 1.26 (3H, t, J=7.2), 1.50-1.60 (1H, m), 1.65-1.82 (2H, m), 2.64 (2H, q, J=7.2), 2.79 (2H, t, J=7.2), 5.30 (2H, s), 7.27-7.37 (2H, m), 7.39-7.57 (4H, m), 7.59-7.69 (1H, m), 7.76 (1H, d, J=7.8)

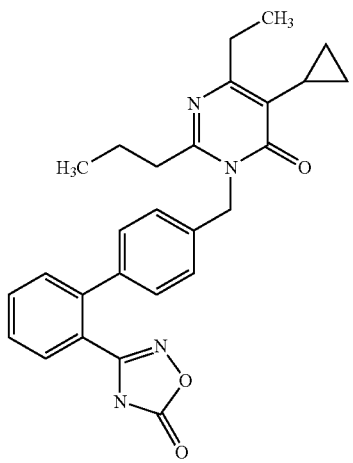

11b) 5-cyclopropyl-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (2.35 g), sodium hydrogen carbonate (3.34 g) and dimethyl sulfoxide (10 mL) was stirred at 40° C. for 30 min, 4'-[(5-cyclopropyl-4-ethyl-6-oxo-2-propylpyrimidin-1(6H)-yl)methyl]biphenyl-2-carbonitrile (0.79 g) was added, and the mixture was stirred at 90° C. for 16 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (15 mL), N,N'-carbonyldiimidazole (0.48 g) and then 1,8-diazabicyclo[5.4.0]undec-7-ene (0.45 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.38 g, 42%).

$^1$H NMR (300 MHz, DMSO-d$_6$) δ 0.77-0.91 (7H, m), 1.18 (3H, t, J=7.2), 1.51-1.66 (3H, m), 2.55 (2H, t, J=7.2), 2.69 (2H, q, J=7.5), 5.26 (2H, s), 7.17 (2H, d, J=7.8), 7.29 (2H, d, J=7.8), 7.49-7.60 (2H, m), 7.63-7.74 (2H, m), 12.39 (1H, br)

Example 12

2-butyl-3-{[3-fluoro-2'-(5-oxo-4,5-dihydro-1,2,4-oxadiazol-3-yl)biphenyl-4-yl]methyl}-5-(4-fluorophenyl)-6-methylpyrimidin-4(3H)-one

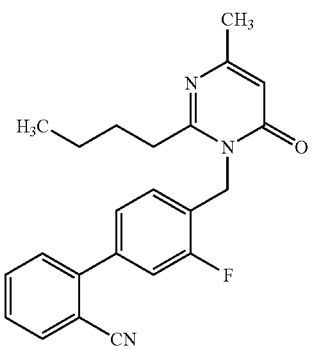

12a) 4'-[(2-butyl-4-methyl-6-oxopyrimidin-1(6H)-yl)methyl]-3'-fluorobiphenyl-2-carbonitrile To a solution of 2-butyl-6-methylpyrimidin-4(3H)-one (2.24 g) and 4'-(bromomethyl)-3'-fluorobiphenyl-2-carbonitrile (4.3 g) in acetonitrile (30 mL) was added potassium carbonate (3.72 g), and the mixture was stirred at 50° C. for 12 hr. The insoluble material was filtered off, and the filtrate was concentrated. The residue was purified by silica gel column chromatography to give the title compound (1.48 g, 29%) as a colorless viscous substance.

$^1$H NMR (300 MHz, CDCl$_3$) δ 0.91 (3H, t, J=7.2), 1.31-1.47 (2H, m), 1.63-1.76 (2H, m), 2.29 (3H, s), 2.68 (2H, t, J=7.2), 5.39 (2H, s), 6.29 (1H, s), 7.08-7.19 (1H, m), 7.24-7.35 (2H, m), 7.42-7.52 (2H, m), 7.60-7.71 (1H, m), 7.77 (1H, d, J=8.1)

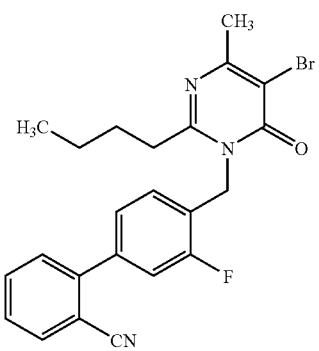

12b) 4'-[(5-bromo-2-butyl-4-methyl-6-oxopyrimidin-1(6H)-yl)methyl]-3'-fluorobiphenyl-2-carbonitrile To a solution of 4'-[(2-butyl-4-methyl-6-oxopyrimidin-1(6H)-yl)methyl]-3'-fluorobiphenyl-2-carbonitrile (1.48 g) and sodium acetate (0.36 g) in acetic acid (20 mL) was added bromine (0.22 mL), and the mixture was stirred for 2 hr. The reaction mixture was diluted with ethyl acetate, washed with saturated aqueous sodium hydrogen carbonate and saturated brine and dried over anhydrous sodium sulfate. The solvent was evaporated under reduced pressure and the residue was purified by silica gel column chromatography to give the title compound (1.07 g, 60%) as a colorless solid.

$^1$H NMR (300 MHz, CDCl$_3$) δ 0.92 (3H, t, J=7.2), 1.32-1.48 (2H, m), 1.63-1.76 (2H, m), 2.50 (3H, s), 2.69 (2H, t, J=7.2), 5.42 (2H, s), 7.15-7.36 (3H, m), 7.48 (2H, t, J=7.5), 7.60-7.71 (1H, m), 7.77 (1H, d, J=8.1)

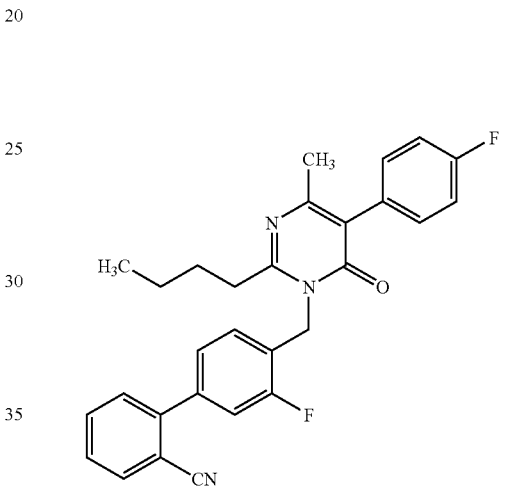

12c) 4'-{[2-butyl-5-(4-fluorophenyl)-4-methyl-6-oxopyrimidin-1(6H)-yl]methyl}-3'-fluorobiphenyl-2-carbonitrile To a solution of 4'-[(5-bromo-2-butyl-4-methyl-6-oxopyrimidin-1(6H)-yl)methyl]-3'-fluorobiphenyl-2-carbonitrile (0.5 g) and 4-fluorophenylboronic acid (0.23 g) in 1,4-dioxane (10 mL) were added 2 M aqueous cesium carbonate solution (2 mL) and [1,1'-bis(diphenylphosphino)ferrocene]dichloropalladium (0.05 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.51 g, 98%) as a colorless solid.

$^1$H NMR (300 MHz, CDCl$_3$) δ 0.94 (3H, t, J=7.2), 1.37-1.51 (2H, m), 1.67-1.81 (2H, m), 2.23 (3H, s), 2.74 (2H, t, J=7.8), 5.41 (2H, s), 7.06-7.16 (2H, m), 7.21-7.36 (5H, m), 7.43-7.53 (2H, m), 7.61-7.71 (1H, m), 7.77 (1H, d, J=6.9)

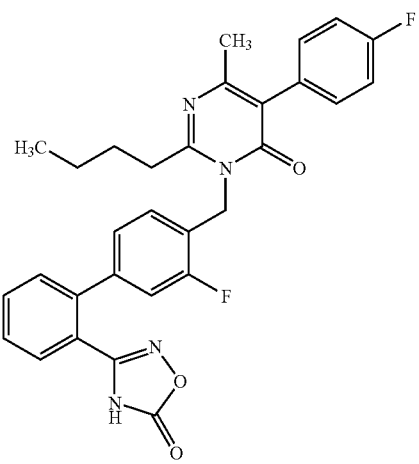

12d) 2-butyl-3-{[3-fluoro-2'-(5-oxo-4,5-dihydro-1,2,
4-oxadiazol-3-yl)biphenyl-4-yl]methyl}-5-(4-fluo-
rophenyl)-6-methylpyrimidin-4(3H)-one A mixture of hydroxylammonium chloride (1.02 g), sodium hydrogen carbonate (1.45 g) and dimethyl sulfoxide (5 mL) was stirred at 40° C. for 30 min, 4'-{[2-butyl-5-(4-fluorophenyl)-4-methyl-6-oxopyrimidin-1(6H)-yl]methyl}-3'-fluorobiphenyl-2-carbonitrile (0.51 g) was added, and the mixture was stirred at 90° C. for 16 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (15 mL), N,N'-carbonyldiimidazole (0.26 g) and then 1,8-diazabicyclo[5.4.0]undec-7-ene (0.24 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.41 g, 73%).

$^1$H NMR (300 MHz, DMSO-$d_6$) δ 0.85 (3H, t, J=7.5), 1.24-1.41 (2H, m), 1.52-1.70 (2H, m), 2.13 (3H, s), 2.71 (2H, t, J=7.5), 5.36 (2H, s), 6.96-7.14 (2H, m), 7.18-7.29 (3H, m), 7.30-7.39 (2H, m), 7.50-7.64 (2H, m), 7.65-7.75 (2H, m), 12.49 (1H, br)

Example 13

2-butyl-5-(2,3-dihydro-1-benzofuran-5-yl)-3-{[3-
fluoro-2'-(5-oxo-4,5-dihydro-1,2,4-oxadiazol-3-yl)
biphenyl-4-yl]methyl}-6-methylpyrimidin-4(3H)-
one

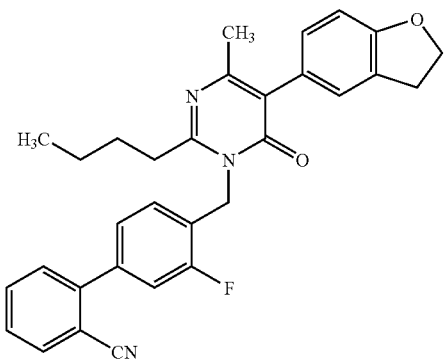

13a) 4'-{[2-butyl-5-(2,3-dihydro-1-benzofuran-5-yl)-
4-methyl-6-oxopyrimidin-1(6H)-yl]methyl}-3'-fluo-
robiphenyl-2-carbonitrile To a solution of 4'-[(5-bromo-2-butyl-4-methyl-6-oxopyrimidin-1(6H)-yl)methyl]-3'-fluorobiphenyl-2-carbonitrile (0.5 g) and 2,3-dihydro-1-benzofuran-5-ylboronic acid (0.27 g) in 1,4-dioxane (10 mL) were added 2 M aqueous cesium carbonate solution (2 mL) and [1,1'-bis(diphenylphosphino)ferrocene]dichloropalladium (0.05 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.43 g, 79%) as a colorless solid.

$^1$H NMR (300 MHz, CDCl$_3$) δ 0.94 (3H, t, J=7.2), 1.35-1.51 (2H, m), 1.66-1.82 (2H, m), 2.25 (3H, s), 2.73 (2H, t, J=8.1), 3.25 (2H, t, J=8.7), 4.59 (2H, t, J=8.7), 5.41 (2H, s), 6.83 (1H, d, J=8.1), 7.05 (1H, d, J=8.4), 7.19 (1H, s), 7.24-7.36 (3H, m), 7.43-7.53 (2H, m), 7.61-7.71 (1H, m), 7.77 (1H, d, J=7.2)

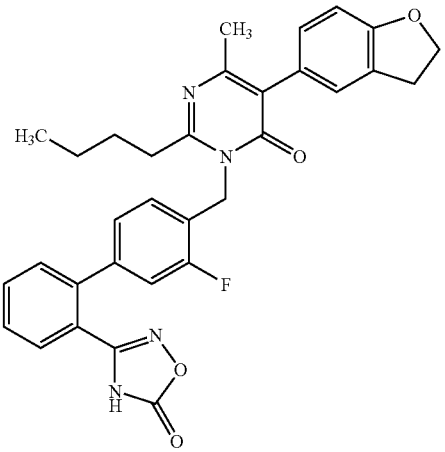

13b) 2-butyl-5-(2,3-dihydro-1-benzofuran-5-yl)-3-
{[3-fluoro-2'-(5-oxo-4,5-dihydro-1,2,4-oxadiazol-3-
yl)biphenyl-4-yl]methyl}-6-methylpyrimidin-4(3H)-
one A mixture of hydroxylammonium chloride (1.02 g), sodium hydrogen carbonate (1.45 g) and dimethyl sulfoxide (5 mL) was stirred at 40° C. for 30 min, 4'-{[2-butyl-5-(2,3-dihydro-1-benzofuran-5-yl)-4-methyl-6-oxopyrimidin-1(6H)-yl]methyl}-3'-fluorobiphenyl-2-carbonitrile (0.43 g) was added, and the mixture was stirred at 90° C. for 16 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.21 g) and then 1,8-diazabicyclo[5.4.0]undec-7-ene (0.19 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.38 g, 84%).

$^1$H NMR (300 MHz, DMSO-$d_6$) δ 0.85 (3H, t, J=7.5), 1.24-1.40 (2H, m), 1.53-1.70 (2H, m), 2.13 (3H, s), 2.70 (2H, t, J=7.5), 3.19 (2H, t, J=8.7), 4.55 (2H, t, J=8.7), 5.34 (2H, s), 6.78 (1H, d, J=8.4), 6.94-7.17 (4H, m), 7.19-7.29 (1H, m), 7.50-7.64 (2H, m), 7.65-7.75 (2H, m), 12.49 (1H, br)

Example 14

3-(4'-{[3-butyl-1-(2,2-dimethylpropyl)-5-oxo-1,5-dihydro-4H-1,2,4-triazol-4-yl]methyl}biphenyl-2-yl)-1,2,4-oxadiazol-5(4H)-one $^1$H NMR (300 MHz, CDCl$_3$) δ 0.88 (3H, t, J=7.3), 1.01 (9H, s), 1.35 (2H, dq, J=7.5, 7.3), 1.52-1.65 (2H, m), 2.39-2.46 (2H, m), 3.61 (2H, s), 4.90 (2H, s), 7.35 (2H, d, J=8.5), 7.42-7.57 (4H, m), 7.65 (1H, dt, J=7.7, 1.3), 7.77 (1H, dd, J=7.6, 0.8)

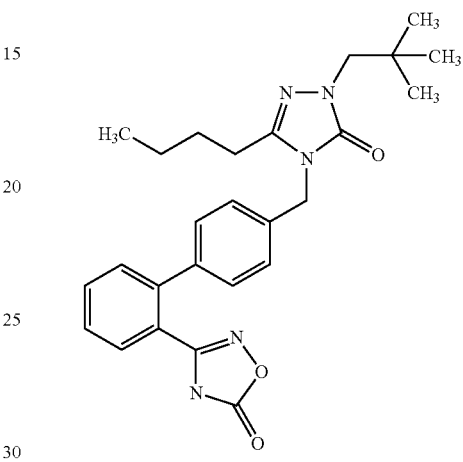

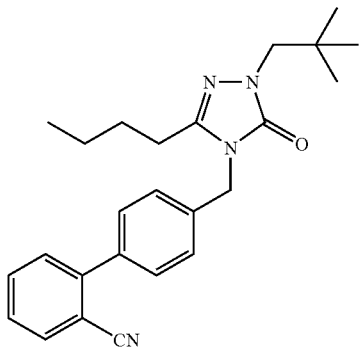

14a) 4'-{[3-butyl-1-(2,2-dimethylpropyl)-5-oxo-1,5-dihydro-4H-1,2,4-triazol-4-yl]methyl}biphenyl-2-carbonitrile A mixture of 4'-[(3-butyl-5-oxo-1,5-dihydro-4H-1,2,4-triazol-4-yl)methyl]biphenyl-2-carbonitrile (1 g), sodium hydride (0.24 g) and N,N-dimethylformamide (10 mL) was stirred at room temperature for 10 min, 1-iodo-2,2-dimethylpropane (2 mL) was added, and the mixture was stirred at 40° C. for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.6 g, 50%).

14b) 3-(4'-{[3-butyl-1-(2,2-dimethylpropyl)-5-oxo-1,5-dihydro-4H-1,2,4-triazol-4-yl]methyl}biphenyl-2-yl)-1,2,4-oxadiazol-5(4H)-one A mixture of hydroxylammonium chloride (1.24 g), sodium hydrogen carbonate (1.88 g) and dimethyl sulfoxide (15 mL) was stirred at 40° C. for 30 min, 4'-{[3-butyl-1-(2,2-dimethylpropyl)-5-oxo-1,5-dihydro-4H-1,2,4-triazol-4-yl]methyl}biphenyl-2-carbonitrile (0.6 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.29 g) and then 1,8-diazabicyclo [5.4.0]undec-7-ene (0.25 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.46 g, 72%).

$^1$H NMR (300 MHz, DMSO-$d_6$) δ 0.80 (3H, t, J=7.3), 0.93 (9H, s), 1.17-1.33 (2H, m), 1.37-1.54 (2H, m), 2.43 (2H, t, J=7.4), 3.48 (2H, s), 4.88 (2H, s), 7.20-7.36 (4H, m), 7.47-7.61 (2H, m), 7.64-7.76 (2H, m), 12.40 (1H, s)

Example 15

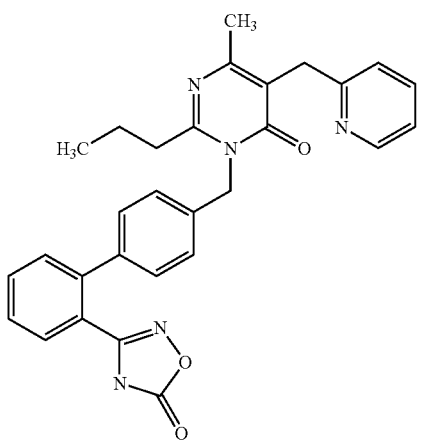

6-methyl-3-{[2'-(5-oxo-4,5-dihydro-1,2,4-oxadiazol-3-yl)biphenyl-4-yl]methyl}-2-propyl-5-(pyridin-2-ylmethyl)pyrimidin-4(3H)-one To a solution of 6-methyl-2-propyl-5-(pyridin-2-ylmethyl)pyrimidin-4(3H)-one (0.51 g) and 3-[4'-(bromomethyl)biphenyl-2-yl]-5-(trichloromethyl)-1,2,4-oxadiazole (1.0 g) in acetonitrile (20 mL) was added potassium carbonate (0.58 g), and the mixture was stirred for 12 hr. The reaction mixture was diluted with ethyl acetate, washed with 1 M hydrochloric acid and saturated brine, and dried over anhydrous sodium sulfate. The solvent was evaporated under reduced pressure. The residue was dissolved in tetrahydrofuran-ethanol (1:1, 4 mL), 1 M sodium hydroxide (2 mL) was added and the mixture was stirred for 30 min. The reaction mixture was weakly acidified with 1 M hydrochloric acid and extracted with ethyl acetate. The organic layer was washed with saturated brine and dried over anhydrous sodium sulfate. The solvent was evaporated under reduced pressure. The residue was purified by silica gel column chromatography to give the title compound (0.043 g, 4%) as a pale-yellow solid.

$^1$H NMR (300 MHz, DMSO-$d_6$) δ 0.86 (3H, t, J=7.2), 1.52-1.67 (2H, m), 2.27 (3H, s), 2.62 (2H, t, J=7.2), 4.00 (2H, s), 5.33 (2H, s), 7.15-7.27 (4H, m), 7.30 (2H, d, J=8.1), 7.49-7.61 (2H, m), 7.63-7.75 (3H, s), 8.44 (1H, d, J=3.6), 12.41 (1H, br)

Example 16

5-(3-acetylbenzyl)-6-methyl-3-{[2'-(5-oxo-4,5-dihydro-1,2,4-oxadiazol-3-yl)biphenyl-4-yl]methyl}-2-propylpyrimidin-4(3H)-one

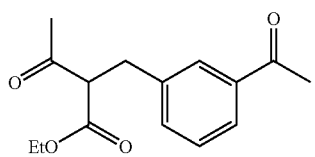

16a) ethyl 2-(3-acetylbenzyl)-3-oxobutanoate

A solution of 3-acetylbenzyl bromide (4 g) and ethyl acetoacetate sodium salt (3.42 g) in tetrahydrofuran (50 mL) was stirred for 12 hr. The insoluble material was filtered off and the filtrate was concentrated. The residue was purified by silica gel column chromatography to give the title compound (2.42 g, 49%) as a colorless viscous oil.

$^1$H NMR (300 MHz, CDCl$_3$) δ 1.21 (3H, t, J=7.2), 2.20 (3H, s), 2.59 (3H, s), 3.21 (2H, d, J=7.2), 3.80 (1H, d, J=7.2), 4.15 (2H, q, J=7.2), 7.31-7.47 (2H, m), 7.74-7.86 (2H, m)

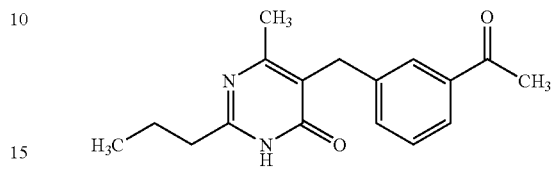

16b) 5-(3-acetylbenzyl)-6-methyl-2-propylpyrimidin-4(3H)-one

To a solution of ethyl 2-(3-acetylbenzyl)-3-oxobutanoate (2.39 g) and butanimidamide hydrochloride (1.68 g) in methanol (20 mL) was added 28% sodium methoxide-methanol solution (5.27 mL), and the mixture was stirred for 12 hr. The reaction mixture was concentrated, and the residue was dissolved in water and diethyl ether. The aqueous layer was separated, and weakly acidified with 1 M hydrochloric acid. The precipitate was collected by filtration and dried under reduced pressure to give the title compound (2.02 g, 78%) as a colorless solid.

$^1$H NMR (300 MHz, DMSO-$d_6$) δ 0.89 (3H, t, J=7.5), 1.55-1.74 (2H, m), 2.18 (3H, s), 2.45 (2H, t, J=7.5), 2.54 (3H, s), 3.83 (2H, s), 7.33-7.52 (2H, m), 7.68-7.86 (2H, m), 12.31 (1H, br)

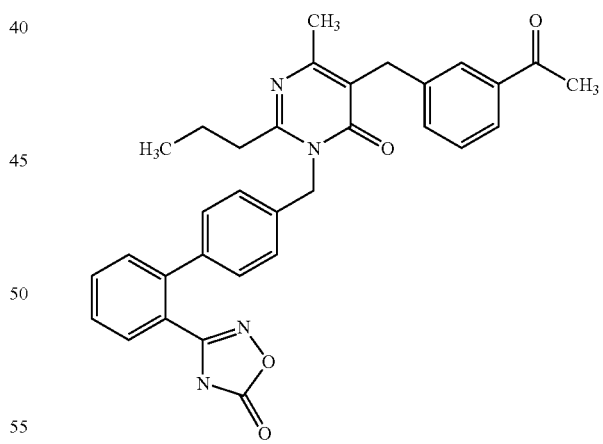

16c) 5-(3-acetylbenzyl)-6-methyl-3-{[2'-(5-oxo-4,5-dihydro-1,2,4-oxadiazol-3-yl)biphenyl-4-yl]methyl}-2-propylpyrimidin-4(3H)-one To a solution of 5-(3-acetylbenzyl)-6-methyl-2-propylpyrimidin-4(3H)-one (1 g) and 3-[4'-(bromomethyl)biphenyl-2-yl]-5-(trichloromethyl)-1,2,4-oxadiazole (1.68 g) in acetonitrile (30 mL) was added potassium carbonate (0.98 g), and the mixture was stirred for 12 hr. The reaction mixture was diluted with ethyl acetate, washed with 1 M hydrochloric acid and saturated brine, and dried over anhydrous sodium sulfate. The solvent was evaporated under reduced pressure. The residue was dissolved in tetrahydrofuran-ethanol (1:1, 8 mL), 1 M sodium hydroxide (2 mL) was added, and the mixture was stirred for 30 min. The reaction mixture was weakly acidified with 1 M hydrochloric acid, and extracted with ethyl acetate. The organic layer was washed with saturated brine and dried over anhydrous sodium sulfate. The solvent was evaporated under reduced pressure. The residue was purified by silica gel column chromatography to give the title compound (0.40 g, 21%) as a colorless solid.

$^1$H NMR (300 MHz, DMSO-$d_6$) δ 0.85 (3H, t, J=7.2), 1.51-1.66 (2H, m), 2.25 (3H, s), 2.54 (3H, s), 2.62 (2H, t, J=7.2), 3.93 (2H, s), 5.36 (2H, s), 7.20 (2H, d, J=8.4), 7.31 (2H, d, J=8.4), 7.39-7.61 (4H, m), 7.63-7.74 (2H, m), 7.75-7.83 (2H, m), 12.40 (1H, s)

Example 17

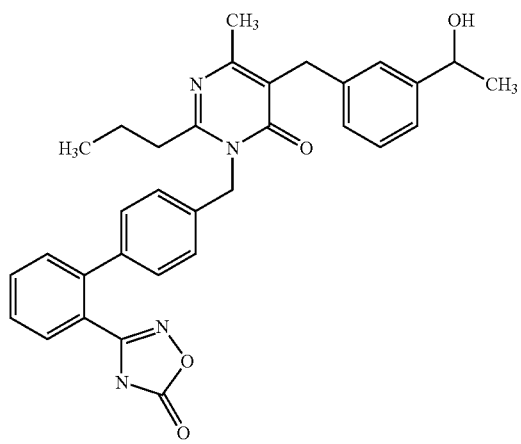

5-[3-(1-hydroxyethyl)benzyl]-6-methyl-3-{[2'-(5-oxo-4,5-dihydro-1,2,4-oxadiazol-3-yl)biphenyl-4-yl]methyl}-2-propylpyrimidin-4(3H)-one To a solution of 5-(3-acetylbenzyl)-6-methyl-3-{[2'-(5-oxo-4,5-dihydro-1,2,4-oxadiazol-3-yl)biphenyl-4-yl]methyl}-2-propylpyrimidin-4(3H)-one (0.20 g) in tetrahydrofuran-methanol (1:1, 4 mL) was added sodium borohydride (0.014 g), and the mixture was stirred for 30 min. The reaction mixture was diluted with ethyl acetate, washed with 1 M hydrochloric acid, saturated aqueous sodium hydrogen carbonate and saturated brine, and dried over anhydrous sodium sulfate. The solvent was evaporated under reduced pressure. The residue was purified by silica gel column chromatography to give the title compound (0.14 g, 69%) as a colorless solid.

$^1$H NMR (300 MHz, DMSO-$d_6$) δ 0.85 (3H, t, J=7.2), 1.27 (3H, d, J=6.6), 1.52-1.65 (2H, m), 2.23 (3H, s), 2.61 (2H, t, J=7.2), 3.85 (2H, s), 4.58-4.71 (1H, m), 5.10 (1H, d, J=4.2), 5.36 (2H, s), 7.01-7.25 (6H, m), 7.29 (2H, d, J=8.1), 7.48-7.61 (2H, m), 7.63-7.74 (2H, m), 12.40 (1H, s)

Example 18

2-butyl-6-methyl-3-{[2'-(5-oxo-4,5-dihydro-1,2,4-oxadiazol-3-yl)biphenyl-4-yl]methyl}-5-(2-thienyl)pyrimidin-4(3H)-one

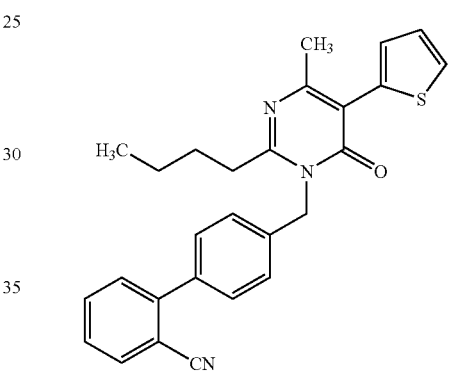

18a) 4'-{[2-butyl-4-methyl-6-oxo-5-(2-thienyl)pyrimidin-1(6H)-yl]methyl}biphenyl-2-carbonitrile To a solution of 4'-[(5-bromo-2-butyl-4-methyl-6-oxopyrimidin-1(6H)-yl)methyl]biphenyl-2-carbonitrile (0.5 g), tributyl(2-thienyl)tin (0.64 g) and lithium chloride (0.15 g) in N,N-dimethylformamide (10 mL) was added dichlorobis(triphenylphosphine)palladium (0.04 g), and the mixture was stirred for 12 hr under an argon atmosphere. The reaction mixture was allowed to cool to room temperature and diluted with ethyl acetate. A 20% aqueous potassium fluoride solution was added, and the mixture was stirred for 2 hr. The insoluble material was filtered off through celite. The organic layer of the filtrate was separated, washed with 1 M hydrochloric acid, saturated aqueous sodium hydrogen carbonate and saturated brine, and dried over anhydrous sodium sulfate. The solvent was evaporated under reduced pressure. The residue was purified by silica gel column chromatography to give the title compound (0.38 g, 75%) as a colorless viscous oil.

$^1$H NMR (300 MHz, CDCl$_3$) δ 0.93 (3H, t, J=7.2), 1.33-1.49 (2H, m), 1.67-1.79 (2H, m), 2.45 (3H, s), 2.74 (2H, t, J=8.1), 5.41 (2H, s), 7.07-7.14 (1H, m), 7.16-7.22 (1H, m), 7.34 (2H, d, J=8.1), 7.40-7.57 (5H, m), 7.60-7.59 (1H, m), 7.75 (1H, d, J=7.5)

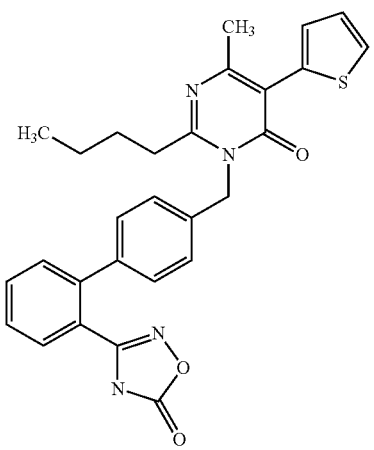

18b) 2-butyl-6-methyl-3-{[2'-(5-oxo-4,5-dihydro-1, 2,4-oxadiazol-3-yl)biphenyl-4-yl]methyl}-5-(2-thienyl)pyrimidin-4(3H)-one A mixture of hydroxylammonium chloride (0.54 g), sodium hydrogen carbonate (0.76 g) and dimethyl sulfoxide (10 mL) was stirred at 40° C. for 30 min, 4'-{[2-butyl-4-methyl-6-oxo-5-(2-thienyl)pyrimidin-1(6H)-yl]methyl}biphenyl-2-carbonitrile (0.38 g) was added, and the mixture was stirred at 90° C. for 16 hr. The mixture was allowed to cool to room temperature. Water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.21 g) and then 1,8-diazabicyclo[5.4.0]undec-7-ene (0.19 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.38 g, 78%).

$^1$H NMR (300 MHz, DMSO-d$_6$) δ 0.83 (3H, t, J=7.2), 1.22-1.38 (2H, m), 1.51-1.66 (2H, m), 2.38 (3H, s), 2.71 (2H, t, J=7.2), 5.38 (2H, s), 7.09-7.16 (1H, m), 7.20-7.28 (3H, m), 7.31 (2H, d, J=8.4), 7.48-7.74 (5H, m), 12.42 (1H, br)

Example 19

2-butyl-6-cyclopropyl-5-(2-methyl-2,3-dihydro-1-benzofuran-5-yl)-3-{[2'-(5-oxo-4,5-dihydro-1,2,4-oxadiazol-3-yl)biphenyl-4-yl]methyl}pyrimidin-4(3H)-one

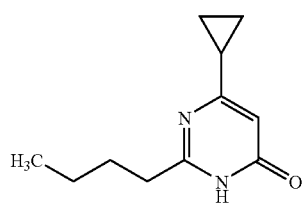

19a) 2-butyl-6-cyclopropylpyrimidin-4(3H)-one

To a solution of methyl 3-cyclopropyl-3-oxopropionate (2.39 g) and pentylamidine hydrochloride (1.68 g) in methanol (20 mL) was added 28% sodium methoxide-methanol solution (5.27 mL), and the mixture was stirred for 12 hr. The reaction mixture was concentrated, and the residue was dissolved in water and diethyl ether. The aqueous layer was separated, and weakly acidified with 1 M hydrochloric acid. The precipitate was collected by filtration and dried under reduced pressure to give the title compound (2.02 g, 78%) as a colorless solid.

$^1$H NMR (300 MHz, CDCl$_3$) δ 0.87-0.99 (5H, m), 1.01-1.10 (2H, m), 1.29-1.46 (2H, m), 1.61-1.85 (3H, m), 2.61 (2H, t, J=7.5), 6.15 (1H, s), 12.89 (1H, br)

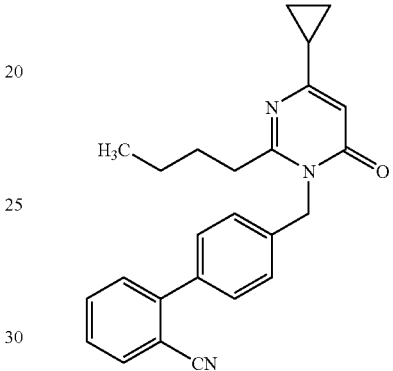

19b) 4'-[(2-butyl-4-cyclopropyl-6-oxopyrimidin-1(6H)-yl)methyl]biphenyl-2-carbonitrile To a solution of 2-butyl-6-cyclopropylpyrimidin-4(3H)-one (6 g) and 4'-(bromomethyl)biphenyl-2-carbonitrile (9.34 g) in acetonitrile (180 mL) was added potassium carbonate (8.63 g), and the mixture was stirred at 50° C. for 12 hr. The insoluble material was filtered off, and the filtrate was concentrated. The residue was purified by silica gel column chromatography to give the title compound (5.23 g, 44%) as a colorless viscous substance.

$^1$H NMR (300 MHz, CDCl$_3$) δ 0.88 (3H, t, J=7.2), 0.90-1.00 (2H, m), 1.03-1.12 (2H, m), 1.24-1.42 (2H, m), 1.57-1.70 (2H, m), 1.73-1.84 (1H, m), 2.62 (2H, t, J=7.5), 5.33 (2H, s), 6.32 (1H, s), 7.28 (2H, d, J=8.1), 7.40-7.56 (4H, m), 7.60-7.68 (1H, m), 7.76 (1H, d, J=7.8)

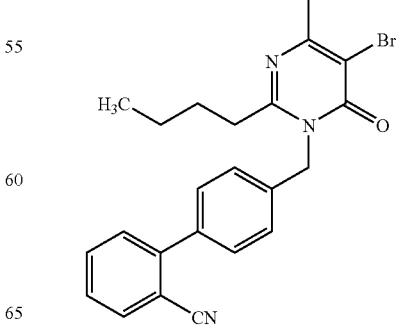

19c) 4'-[(5-bromo-2-butyl-4-cyclopropyl-6-oxopyrimidin-1(6H)-yl)methyl]biphenyl-2-carbonitrile To a solution of 4'-[(2-butyl-4-cyclopropyl-6-oxopyrimidin-1(6H)-yl)methyl]biphenyl-2-carbonitrile (5.22 g) in acetic acid (60 mL) was added bromine (1.39 mL), and the mixture was stirred at 70° C. for 2 hr. The reaction mixture was diluted with ethyl acetate, washed with 1 M aqueous sodium thiosulfate solution, saturated aqueous sodium hydrogen carbonate and saturated brine, and dried over anhydrous sodium sulfate. The solvent was evaporated under reduced pressure and the residue was purified by silica gel column chromatography to give the title compound (5.4 g, 80%) as a colorless solid.

$^1$H NMR (300 MHz, DMSO-$d_6$) δ 0.79 (3H, t, J=7.5), 1.06 (4H, d, J=6.0), 1.16-1.32 (2H, m), 1.46-1.61 (2H, m), 2.29-2.41 (1H, m), 2.66 (2H, t, J=7.5), 5.38 (2H, s), 7.30 (2H, d, J=8.4), 7.53-7.65 (4H, m), 7.74-7.84 (1H, m), 7.95 (1H, d, J=7.2)

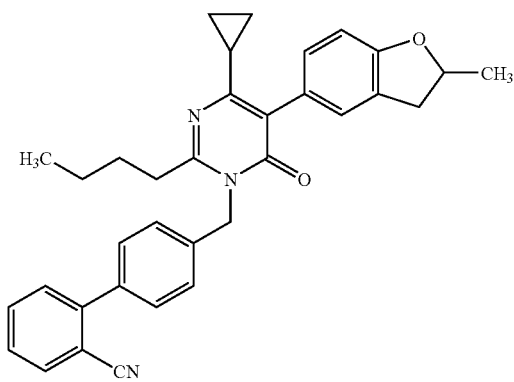

19d) 4'-{[2-butyl-4-cyclopropyl-5-(2-methyl-2,3-dihydro-1-benzofuran-5-yl)-6-oxopyrimidin-1(6H)-yl]methyl}biphenyl-2-carbonitrile To a solution of 4'-[(5-bromo-2-butyl-4-cyclopropyl-6-oxopyrimidin-1(6H)-yl)methyl]biphenyl-2-carbonitrile (0.5 g) and 2-methyl-2,3-dihydro-1-benzofuran-5-ylboronic acid (0.29 g) in 1,4-dioxane (10 mL) were added 2 M aqueous cesium carbonate solution (2 mL) and [1,1'-bis(diphenylphosphino)ferrocene]dichloropalladium (0.05 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.47 g, 84%) as a pale-yellow solid.

$^1$H NMR (300 MHz, CDCl$_3$) δ 0.78-0.87 (2H, m), 0.91 (3H, t, J=7.2), 1.10-1.19 (2H, m), 1.30-1.44 (2H, m), 1.48 (3H, d, J=6.3), 1.62-1.76 (2H, m), 1.86-1.97 (1H, m), 2.67 (2H, t, J=7.2), 2.86 (1H, dd, J=15.3, 7.8), 3.25 (1H, dd, J=15.3, 8.7), 4.87-5.01 (1H, m), 5.34 (2H, s), 6.80 (1H, d, J=8.1), 7.17 (1H, d, J=8.1), 7.25-7.78 (1H, m), 7.35 (2H, d, J=8.1), 7.40-7.55 (4H, m), 7.60-7.58 (1H, m), 7.76 (1H, d, J=8.1)

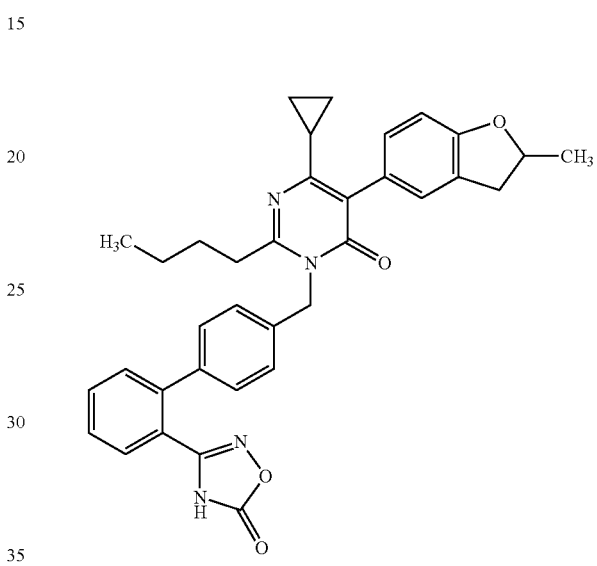

19e) 2-butyl-6-cyclopropyl-5-(2-methyl-2,3-dihydro-1-benzofuran-5-yl)-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.54 g), sodium hydrogen carbonate (0.76 g) and dimethyl sulfoxide (10 mL) was stirred at 40° C. for 30 min, 4'-{[2-butyl-4-cyclopropyl-5-(2-methyl-2,3-dihydro-1-benzofuran-5-yl)-6-oxopyrimidin-1(6H)-yl]methyl}biphenyl-2-carbonitrile (0.46 g) was added, and the mixture was stirred at 90° C. for 16 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.22 g) and then 1,8-diazabicyclo[5.4.0]undec-7-ene (0.2 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.43 g, 82%).

¹H NMR (300 MHz, DMSO-d₆) δ 0.75-0.87 (5H, m), 0.96-1.17 (2H, m), 1.18-1.34 (2H, m), 1.40 (3H, d, J=6.0), 1.48-1.62 (2H, m), 1.72-1.85 (1H, m), 2.64 (2H, t, J=7.2), 2.75-2.87 (1H, m), 3.25-3.41 (1H, m), 4.85-5.01 (1H, m), 5.31 (2H, s), 6.77 (1H, d, J=8.1), 7.06 (1H, d, J=8.1), 7.18 (1H, s), 7.24 (2H, d, J=8.4), 7.31 (2H, d, J=8.4), 7.48-7.61 (2H, m), 7.63-7.74 (2H, m), 12.41 (1H, s)

Example 20

2-butyl-6-cyclopropyl-5-(4-ethoxyphenyl)-3-{[2'-(5-oxo-4,5-dihydro-1,2,4-oxadiazol-3-yl)biphenyl-4-yl]methyl}pyrimidin-4(3H)-one

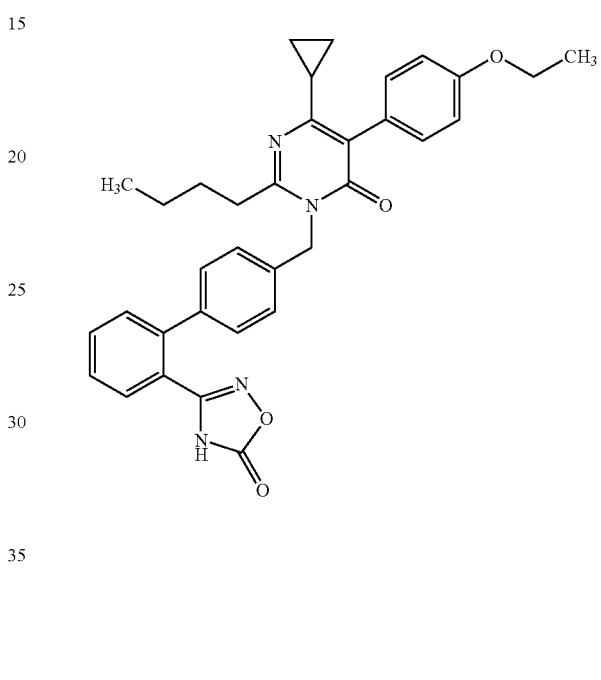

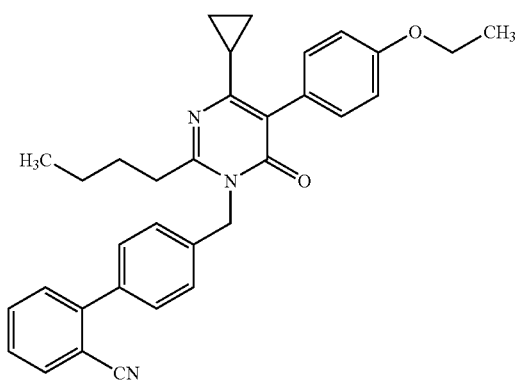

20a) 4'-{[2-butyl-4-cyclopropyl-5-(4-ethoxyphenyl)-6-oxopyrimidin-1(6H)-yl]methyl}biphenyl-2-carbonitrile To a solution of 4'-[(5-bromo-2-butyl-4-cyclopropyl-6-oxopyrimidin-1(6H)-yl)methyl]biphenyl-2-carbonitrile (0.5 g) and 4-ethoxyphenylboronic acid (0.27 g) in 1,4-dioxane (10 mL) were added 2 M aqueous cesium carbonate solution (2 mL) and [1,1'-bis(diphenylphosphino)ferrocene]dichloropalladium (0.05 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.38 g, 70%) as a colorless solid.

¹H NMR (300 MHz, CDCl₃) δ 0.76-0.87 (2H, m), 0.91 (3H, t, J=7.5), 1.10-1.20 (2H, m), 1.31-1.47 (5H, m), 1.61-1.75 (2H, m), 1.83-1.96 (1H, m), 2.67 (2H, t, J=7.5), 4.06 (2H, q, J=7.5), 5.35 (2H, s), 6.96 (2H, d, J=8.1), 7.31-7.56 (8H, m), 7.60-7.69 (1H, m), 7.76 (1H, d, J=7.5)

20b) 2-butyl-6-cyclopropyl-5-(4-ethoxyphenyl)-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.54 g), sodium hydrogen carbonate (0.76 g) and dimethyl sulfoxide (10 mL) was stirred at 40° C. for 30 min, 4'-{[2-butyl-4-cyclopropyl-5-(4-ethoxyphenyl)-6-oxopyrimidin-1(6H)-yl]methyl}biphenyl-2-carbonitrile (0.38 g) was added, and the mixture was stirred at 90° C. for 16 hr. The mixture was allowed to cool to room temperature. Water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.18 g) and then 1,8-diazabicyclo[5.4.0]undec-7-ene (0.17 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.38 g, 90%).

$^1$H NMR (300 MHz, DMSO-$d_6$) δ 0.76-1.89 (5H, m), 0.97-1.09 (2H, m), 1.19-1.39 (5H, m), 1.47-1.62 (2H, m), 1.70-1.82 (1H, m), 2.64 (2H, t, J=7.2), 4.05 (2H, q, J=7.2), 5.32 (2H, s), 6.98 (2H, d, J=8.4), 7.19-7.36 (6H, m), 7.47-7.62 (2H, m), 7.63-7.75 (2H, m), 12.41 (1H, s)

Example 21

2-butyl-6-ethyl-5-(2-methyl-2,3-dihydro-1-benzofuran-5-yl)-3-{[2'-(5-oxo-4,5-dihydro-1,2,4-oxadiazol-3-yl)biphenyl-4-yl]methyl}pyrimidin-4(3H)-one

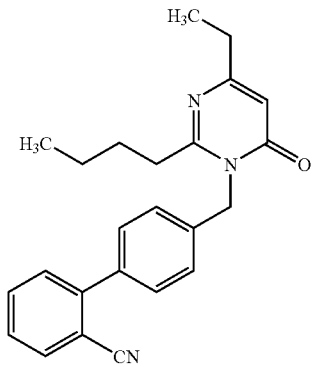

21a) 4'-[(2-butyl-4-ethyl-6-oxopyrimidin-1(6H)-yl)methyl]biphenyl-2-carbonitrile To a solution of 2-butyl-6-ethylpyrimidin-4(3H)-one (4 g) and 4'-(bromomethyl)biphenyl-2-carbonitrile (6.64 g) in acetonitrile (120 mL) was added potassium carbonate (6.1 g), and the mixture was stirred at 50° C. for 12 hr. The insoluble material was filtered off, the filtrate was concentrated, and the residue was purified by silica gel column chromatography to give the title compound (2.09 g, 25%) as a colorless solid.

$^1$H NMR (300 MHz, CDCl$_3$) δ 0.90 (3H, t, J=7.2), 1.25 (3H, t, J=7.5), 1.31-1.46 (2H, m), 1.61-1.76 (2H, m), 2.56 (2H, q, J=7.5), 2.68 (2H, t, J=7.2), 5.36 (2H, s), 6.29 (1H, s), 7.29 (2H, d, J=8.1), 7.40-7.57 (4H, m), 7.60-7.69 (1H, m), 7.76 (1H, d, J=7.8)

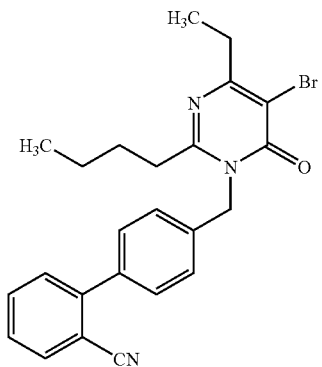

21b) 4'-[(5-bromo-2-butyl-4-ethyl-6-oxopyrimidin-1(6H)-yl)methyl]biphenyl-2-carbonitrile To a solution of 4'-[(2-butyl-4-ethyl-6-oxopyrimidin-1(6H)-yl)methyl]biphenyl-2-carbonitrile (1.67 g) in acetic acid (20 mL) was added bromine (0.46 mL), and the mixture was stirred at 70° C. for 2 hr. The reaction mixture was diluted with ethyl acetate, washed with 1 M aqueous sodium thiosulfate solution, saturated aqueous sodium hydrogen carbonate and saturated brine, and dried over anhydrous sodium sulfate. The solvent was evaporated under reduced pressure and the residue was purified by silica gel column chromatography to give the title compound (1.26 g, 62%) as a colorless solid.

$^1$H NMR (300 MHz, DMSO-$d_6$) δ 0.81 (3H, t, J=7.2), 1.19 (3H, t, J=7.5), 1.23-1.36 (2H, m), 1.52-1.67 (2H, m), 2.65-2.78 (4H, m), 5.41 (2H, s), 7.32 (2H, d, J=8.4), 7.53-7.64 (4H, m), 7.74-7.84 (1H, m), 7.95 (1H, d, J=7.5)

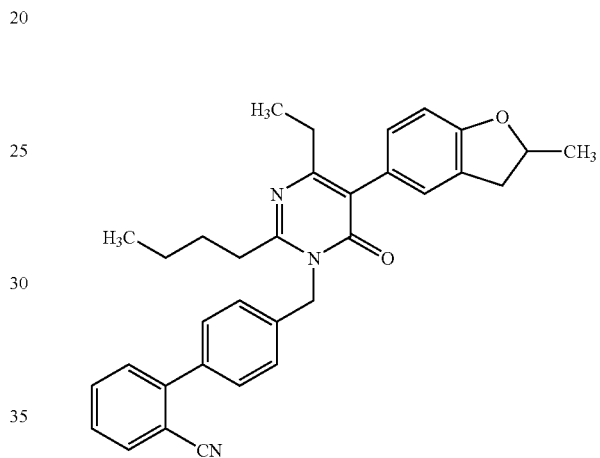

21c) 4'-{[2-butyl-4-ethyl-5-(2-methyl-2,3-dihydro-1-benzofuran-5-yl)-6-oxopyrimidin-1(6H)-yl]methyl}biphenyl-2-carbonitrile To a solution of 4'-[(5-bromo-2-butyl-4-ethyl-6-oxopyrimidin-1(6H)-yl)methyl]biphenyl-2-carbonitrile (0.5 g) and 2-methyl-2,3-dihydro-1-benzofuran-5-ylboronic acid (0.30 g) in 1,4-dioxane (10 mL) were added 2 M aqueous cesium carbonate solution (2 mL) and [1,1'-bis(diphenylphosphino)ferrocene]dichloropalladium (0.05 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.46 g, 82%) as a pale-yellow solid.

$^1$H NMR (300 MHz, CDCl$_3$) δ 0.93 (3H, t, J=7.2), 1.18 (3H, t, J=7.5), 1.35-1.52 (5H, m), 1.68-1.83 (2H, m), 2.49 (2H, q, J=7.5), 2.75 (2H, t, J=7.2), 2.86 (1H, dd, J=15.6, 8.1), 3.34 (1H, dd, J=15.6, 8.7), 4.86-5.02 (1H, m), 5.36 (2H, s), 6.79 (1H, d, J=8.4), 7.01 (1H, d, J=8.4), 7.12 (1H, s), 7.36 (2H, d, J=8.1), 7.40-7.57 (4H, m), 7.60-7.69 (1H, m), 7.76 (1H, d, J=7.8)

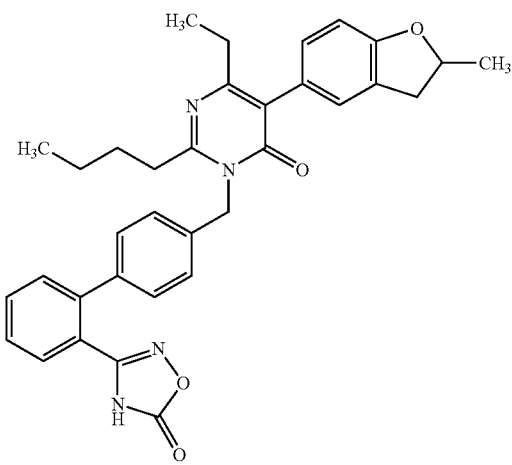

21d) 2-butyl-6-ethyl-5-(2-methyl-2,3-dihydro-1-benzofuran-5-yl)-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.54 g), sodium hydrogen carbonate (0.76 g) and dimethyl sulfoxide (10 mL) was stirred at 40° C. for 30 min, 4'-{[2-butyl-4-ethyl-5-(2-methyl-2,3-dihydro-1-benzofuran-5-yl)-6-oxopyrimidin-1(6H)-yl]methyl}biphenyl-2-carbonitrile (0.46 g) was added, and the mixture was stirred at 90° C. for 16 hr. The mixture was allowed to cool to room temperature. Water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.22 g) and then 1,8-diazabicyclo[5.4.0]undec-7-ene (0.20 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.45 g, 88%).

$^1$H NMR (300 MHz, DMSO-$d_6$) δ 0.83 (3H, t, J=7.5), 1.10 (3H, t, J=7.5), 1.38-1.45 (2H, m), 1.40 (3H, d, J=6.0), 1.53-1.68 (2H, m), 2.36 (2H, q, J=7.5), 2.69 (2H, t, J=7.5), 2.74-2.86 (1H, m), 3.26-3.40 (1H, m), 4.86-5.00 (1H, m), 5.33 (2H, s), 6.75 (1H, d, J=8.1), 6.96 (1H, d, J=8.1), 7.09 (1H, s), 7.25 (2H, d, J=8.1), 7.32 (2H, d, J=8.1), 7.48-7.62 (2H, m), 7.64-7.74 (2H, m), 12.41 (1H, s)

Example 22

2-ethoxy-6-methyl-3-{[2'-(5-oxo-4,5-dihydro-1,2,4-oxadiazol-3-yl)biphenyl-4-yl]methyl}-5-phenylpyrimidin-4(3H)-one

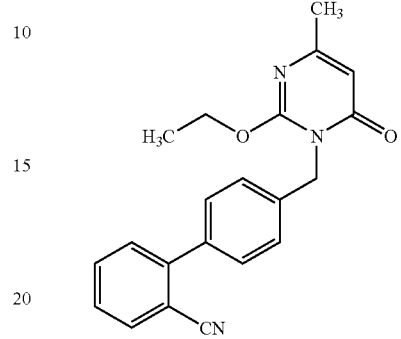

22a) 4'-[(2-ethoxy-4-methyl-6-oxopyrimidin-1(6H)-yl)methyl]biphenyl-2-carbonitrile To a solution of 2-ethoxy-6-methylpyrimidin-4(3H)-one (4.9 g) and 4'-(bromomethyl)biphenyl-2-carbonitrile (10.3 g) in acetonitrile (120 mL) was added potassium carbonate (5.24 g), and the mixture was stirred at 50° C. for 12 hr. The insoluble material was filtered off, and the filtrate was concentrated. The residue was purified by silica gel column chromatography to give the title compound (6.15 g, 56%) as a colorless solid.

$^1$H NMR (300 MHz, CDCl$_3$) δ 1.37 (3H, t, J=7.2), 2.18 (3H, s), 4.43 (2H, q, J=7.2), 5.21 (2H, s), 6.03 (1H, s), 7.39-7.56 (6H, m), 7.58-7.69 (1H, m), 7.75 (1H, d, J=7.8)

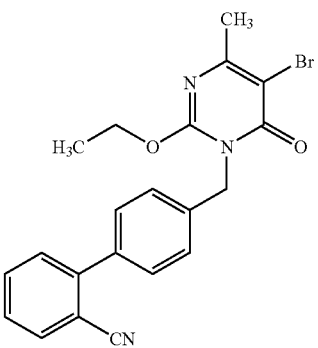

22b) 4'-[(5-bromo-2-ethoxy-4-methyl-6-oxopyrimidin-1(6H)-yl)methyl]biphenyl-2-carbonitrile To a solution of 4'-[(2-ethoxy-4-methyl-6-oxopyrimidin-1(6H)-yl)methyl]biphenyl-2-carbonitrile (6.15 g) and sodium acetate (1.46 g) in acetic acid (100 mL) was added bromine (0.91 mL), and the mixture was stirred for 2 hr. The reaction mixture was diluted with ethyl acetate, washed with 1 M aqueous sodium thiosulfate solution, saturated aqueous sodium hydrogen carbonate and saturated brine, and dried over anhydrous sodium sulfate. The solvent was evaporated under reduced pressure and the residue was purified by silica gel column chromatography to give the title compound (7.12 g, 94%) as a colorless solid.

$^1$H NMR (300 MHz, DMSO-$d_6$) δ 1.30 (3H, t, J=7.2), 2.36 (3H, s), 4.42 (2H, q, J=7.2), 5.19 (2H, s), 7.43 (2H, d, J=8.1), 7.51-7.66 (4H, m), 7.74-7.85 (1H, m), 7.95 (1H, d, J=7.8)

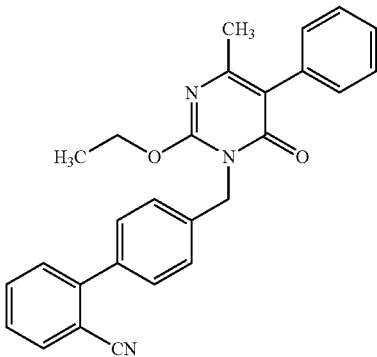

22c) 4'-[(2-ethoxy-4-methyl-6-oxo-5-phenylpyrimidin-1(6H)-yl)methyl]biphenyl-2-carbonitrile To a solution of 4'-[(5-bromo-2-ethoxy-4-methyl-6-oxopyrimidin-1(6H)-yl)methyl]biphenyl-2-carbonitrile (1 g) and phenylboronic acid (0.43 g) in 1,4-dioxane (20 mL) were added 2 M aqueous cesium carbonate solution (2 mL) and [1,1'-bis(diphenylphosphino)ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.77 g, 78%) as a pale-yellow solid.

$^1$H NMR (300 MHz, DMSO-$d_6$) δ 1.32 (3H, t, J=7.2), 2.07 (3H, s), 4.45 (2H, q, J=7.2), 5.19 (2H, s), 7.23-7.50 (7H, m), 7.53-7.65 (4H, m), 7.74-7.84 (1H, m), 7.95 (1H, d, J=7.8)

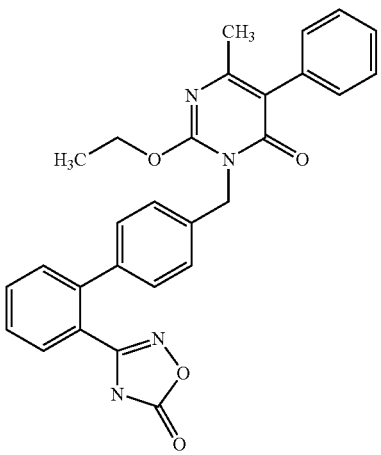

22d) 2-ethoxy-6-methyl-3-{[2'-(5-oxo-4,5-dihydro-1,2,4-oxadiazol-3-yl)biphenyl-4-yl]methyl}-5-phenylpyrimidin-4(3H)-one A mixture of hydroxylammonium chloride (1.08 g), sodium hydrogen carbonate (1.53 g) and dimethyl sulfoxide (10 mL) was stirred at 40° C. for 30 min, 4'-[(2-ethoxy-4-methyl-6-oxo-5-phenylpyrimidin-1(6H)-yl)methyl]biphenyl-2-carbonitrile (0.77 g) was added, and the mixture was stirred at 90° C. for 5 hr. The mixture was allowed to cool to room temperature. Water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.44 g) and then 1,8-diazabicyclo[5.4.0]undec-7-ene (0.41 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.21 g, 24%).

$^1$H NMR (300 MHz, DMSO-$d_6$) δ 1.29 (3H, t, J=7.5), 2.06 (3H, s), 4.42 (2H, q, J=7.5), 5.14 (2H, s), 7.21-7.48 (9H, m), 7.48-7.61 (2H, m), 7.62-7.75 (2H, m), 12.40 (1H, br)

Example 23

2-ethoxy-6-methyl-5-(2-methyl-2,3-dihydro-1-benzofuran-5-yl)-3-{[2'-(5-oxo-4,5-dihydro-1,2,4-oxadiazol-3-yl)biphenyl-4-yl]methyl}pyrimidin-4(3H)-one

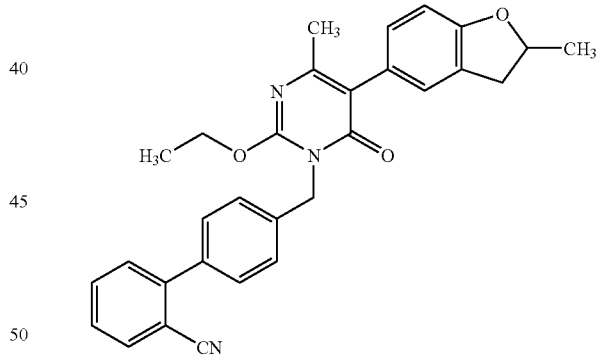

23a) 4'-{[2-ethoxy-4-methyl-5-(2-methyl-2,3-dihydro-1-benzofuran-5-yl)-6-oxopyrimidin-1(6H)-yl]methyl}biphenyl-2-carbonitrile To a solution of 4'-[(5-bromo-2-ethoxy-4-methyl-6-oxopyrimidin-1(6H)-yl)methyl]biphenyl-2-carbonitrile (1 g) and 2-methyl-2,3-dihydro-1-benzofuran-5-ylboronic acid (0.63 g) in 1,4-dioxane (20 mL) were added 2 M aqueous cesium carbonate solution (2 mL) and [1,1'-bis(diphenylphosphino)ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure and the residue was purified by silica gel column chromatography to give the title compound (0.77 g, 68%) as a pale-yellow solid.

$^1$H NMR (300 MHz, DMSO-d$_6$) δ 1.31 (3H, t, J=7.2), 1.40 (3H, d, J=6.6), 2.07 (3H, s), 2.79 (1H, dd, J=15.6, 7.8), 3.32 (1H, dd, J=15.6, 9.0), 4.43 (2H, q, J=7.2), 4.84-4.99 (1H, m), 5.17 (2H, s), 6.73 (1H, d, J=8.1), 6.95 (1H, d, J=8.1), 7.08 (1H, s), 7.45 (2H, d, J=8.4), 7.54-7.63 (4H, m), 7.74-7.84 (1H, m), 7.95 (1H, d, J=7.5)

(1H, dd, J=15.6, 9.0), 4.40 (2H, q, J=7.5), 4.81-5.03 (1H, m), 5.13 (2H, s), 6.73 (1H, d, J=8.4), 6.95 (1H, d, J=8.4), 7.07 (1H, s), 7.23-7.40 (4H, m), 7.49-7.61 (2H, m), 7.61-7.76 (2H, m), 12.40 (1H, br)

Example 24

2-butyl-5-(3,5-dimethylisoxazol-4-yl)-6-methyl-3-{[2'-(5-oxo-4,5-dihydro-1,2,4-oxadiazol-3-yl)biphenyl-4-yl]methyl}pyrimidin-4(3H)-one

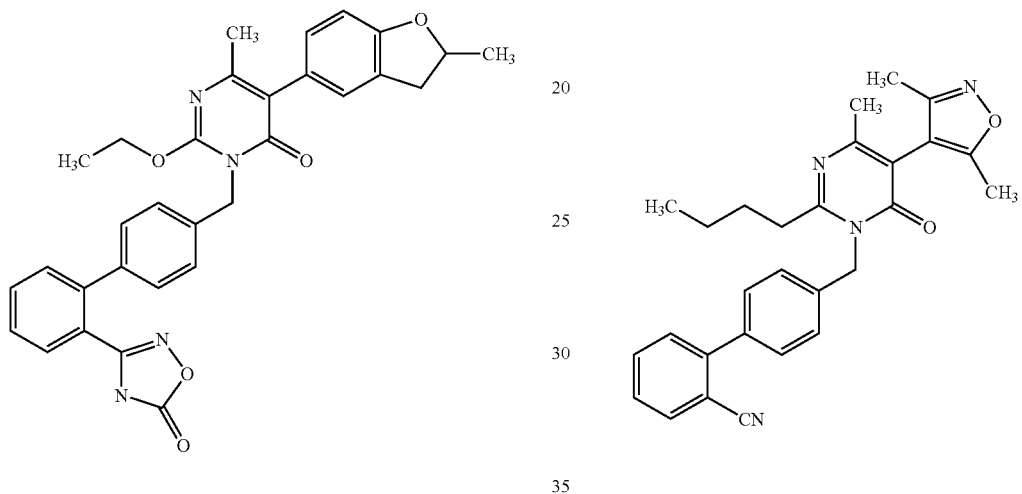

23b) 2-ethoxy-6-methyl-5-(2-methyl-2,3-dihydro-1-benzofuran-5-yl)-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.95 g), sodium hydrogen carbonate (1.35 g) and dimethyl sulfoxide (10 mL) was stirred at 40° C. for 30 min, 4'-{[2-ethoxy-4-methyl-5-(2-methyl-2,3-dihydro-1-benzofuran-5-yl)-6-oxopyrimidin-1(6H)-yl]methyl}biphenyl-2-carbonitrile (0.77 g) was added, and the mixture was stirred at 90° C. for 5 hr. The mixture was allowed to cool to room temperature. Water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.39 g) and then 1,8-diazabicyclo[5.4.0]undec-7-ene (0.36 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.58 g, 69%).

$^1$H NMR (300 MHz, DMSO-d$_6$) δ 1.28 (3H, t, J=7.5), 1.41 (3H, d, J=6.6), 2.06 (3H, s), 2.80 (1H, dd, J=15.6, 7.5), 3.33

24a) 4'-{[2-butyl-5-(3,5-dimethylisoxazol-4-yl)-4-methyl-6-oxopyrimidin-1(6H)-yl]methyl}biphenyl-2-carbonitrile To a solution of 4'-[(5-bromo-2-butyl-4-methyl-6-oxopyrimidin-1(6H)-yl)methyl]biphenyl-2-carbonitrile (1 g) and 3,5-dimethylisoxazol-4-ylboronic acid (0.48 g) in 1,4-dioxane (20 mL) were added 2 M aqueous cesium carbonate solution (4 mL) and [1,1'-bis(diphenylphosphino)ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure, and the residue was purified by silica gel column chromatography to give the title compound (0.32 g, 31%) as a pale-yellow solid.

$^1$H NMR (300 MHz, CDCl$_3$) δ 0.93 (3H, t, J=7.5), 1.33-1.50 (2H, m), 1.64-1.81 (2H, m), 2.18 (6H, s), 2.29 (3H, s), 2.74 (2H, t, J=7.5), 5.38 (2H, s), 7.28-7.35 (2H, m), 7.39-7.58 (4H, m), 7.60-7.70 (1H, m), 7.77 (1H, d, J=7.5)

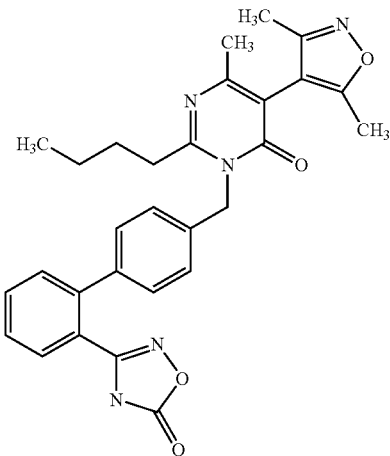

24b) 2-butyl-5-(3,5-dimethylisoxazol-4-yl)-6-methyl-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.42 g), sodium hydrogen carbonate (0.6 g) and dimethyl sulfoxide (5 mL) was stirred at 40° C. for 30 min, 4'-{[2-butyl-5-(3,5-dimethylisoxazol-4-yl)-4-methyl-6-oxopyrimidin-1(6H)-yl]methyl}biphenyl-2-carbonitrile (0.32 g) was added, and the mixture was stirred at 90° C. for 5 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.12 g) and then 1,8-diazabicyclo[5.4.0]undec-7-ene (0.11 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.12 g, 19%).

$^1$H NMR (300 MHz, DMSO-d$_6$) δ 0.83 (3H, t, J=7.8), 1.23-1.37 (2H, m), 1.53-1.65 (2H, m), 2.05 (3H, s), 2.10 (3H, s), 2.23 (3H, s), 2.70 (2H, t, J=7.5), 5.29-5.45 (2H, m), 7.22 (2H, d, J=8.4), 7.31 (2H, d, J=8.4), 7.48-7.61 (2H, m), 7.64-7.74 (2H, m), 12.41 (1H, s)

Example 25

2-butyl-5-(2,2-dimethyl-2,3-dihydro-1-benzofuran-5-yl)-6-methyl-3-{[2'-(5-oxo-4,5-dihydro-1,2,4-oxadiazol-3-yl)biphenyl-4-yl]methyl}pyrimidin-4(3H)-one

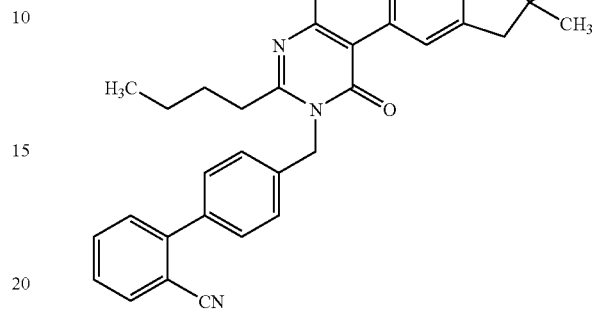

25a) 4'-{[2-butyl-5-(2,2-dimethyl-2,3-dihydro-1-benzofuran-5-yl)-4-methyl-6-oxopyrimidin-1(6H)-yl]methyl}biphenyl-2-carbonitrile To a solution of 4'-[(5-bromo-2-butyl-4-methyl-6-oxopyrimidin-1(6H)-yl)methyl]biphenyl-2-carbonitrile (0.76 g) and 2,2-dimethyl-2,3-dihydro-1-benzofuran-5-ylboronic acid (0.50 g) in 1,4-dioxane (20 mL) were added 2 M aqueous cesium carbonate solution (4 mL) and [1,1'-bis(diphenylphosphino)ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure, and the residue was purified by silica gel column chromatography to give the title compound (0.72 g, 82%) as a colorless solid.

$^1$H NMR (300 MHz, CDCl$_3$) δ 0.93 (3H, t, J=7.5), 1.35-1.50 (2H, m), 1.49 (6H, s), 1.65-1.79 (2H, m), 2.25 (3H, s), 2.76 (2H, t, J=7.5), 3.04 (2H, s), 5.38 (2H, s), 6.76 (1H, d, J=8.1), 7.04 (1H, d, J=8.1), 7.13 (1H, s), 7.35 (2H, d, J=8.1), 7.40-7.56 (4H, m), 7.60-7.68 (1H, m), 7.76 (1H, d, J=7.5)

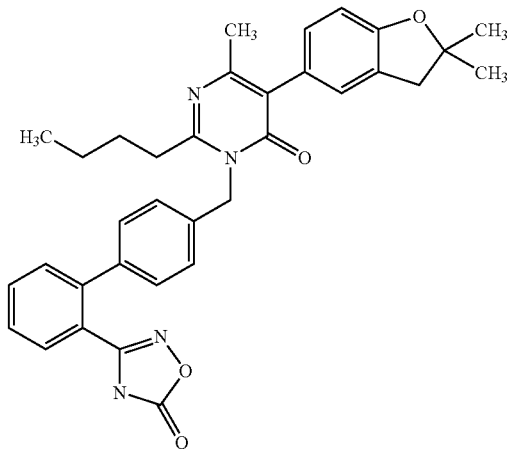

25b) 2-butyl-5-(2,2-dimethyl-2,3-dihydro-1-benzofuran-5-yl)-6-methyl-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.84 g), sodium hydrogen carbonate (1.2 g) and dimethyl sulfoxide (15 mL) was stirred at 40° C. for 30 min, 4'-{[2-butyl-5-(2,2-dimethyl-2,3-dihydro-1-benzofuran-5-yl)-4-methyl-6-oxopyrimidin-1(6H)-yl]methyl}biphenyl-2-carbonitrile (0.72 g) was added, and the mixture was stirred at 90° C. for 5 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.35 g) and then 1,8-diazabicyclo[5.4.0]undec-7-ene (0.33 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.68 g, 85%).

$^1$H NMR (300 MHz, DMSO-d$_6$) δ 0.82 (3H, t, J=7.5), 1.22-1.37 (2H, m), 1.43 (6H, s), 1.49-1.65 (2H, m), 2.13 (3H, s), 2.68 (2H, t, J=7.5), 3.30 (2H, s), 5.34 (2H, s), 6.72 (1H, d, J=8.1), 7.00 (1H, d, J=8.1), 7.12 (1H, s), 7.25 (2H, d, J=8.1), 7.32 (2H, d, J=8.1), 7.49-7.61 (2H, m), 7.64-7.74 (2H, m), 12.43 (1H, s)

Example 26

2-butyl-6-methyl-5-(1-methyl-1H-pyrazol-4-yl)-3-{[2'-(5-oxo-4,5-dihydro-1,2,4-oxadiazol-3-yl)biphenyl-4-yl]methyl}pyrimidin-4(3H)-one

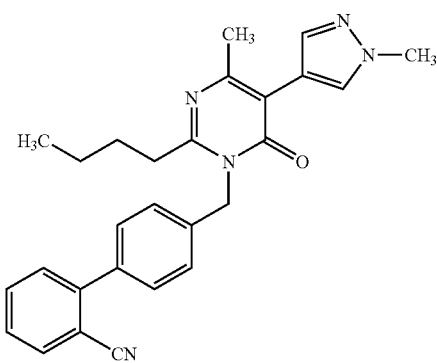

26a) 4'-{[2-butyl-4-methyl-5-(1-methyl-1H-pyrazol-4-yl)-6-oxopyrimidin-1(6H)-yl]methyl}biphenyl-2-carbonitrile To a solution of 4'-[(5-bromo-2-butyl-4-methyl-6-oxopyrimidin-1(6H)-yl)methyl]biphenyl-2-carbonitrile (1 g) and 1-methyl-4-(4,4,5,5-tetramethyl-1,3,2-dioxaborolan-2-yl)-1H-pyrazole (0.72 g) in 1,4-dioxane (20 mL) were added 2 M aqueous cesium carbonate solution (4 mL) and [1,1'-bis(diphenylphosphino)ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure, and the residue was purified by silica gel column chromatography to give the title compound (0.44 g, 43%) as a colorless solid.

$^1$H NMR (300 MHz, CDCl$_3$) δ 0.92 (3H, t, J=7.2), 1.34-1.48 (2H, m), 1.64-1.78 (2H, m), 2.49 (3H, s), 2.72 (2H, t, J=7.2), 3.94 (3H, s), 5.40 (2H, s), 7.30 (2H, d, J=8.4), 7.40-7.50 (2H, m), 7.53 (2H, d, J=8.4), 7.60-7.67 (1H, m), 7.71 (1H, s), 7.75 (1H, d, J=7.5), 7.95 (1H, s)

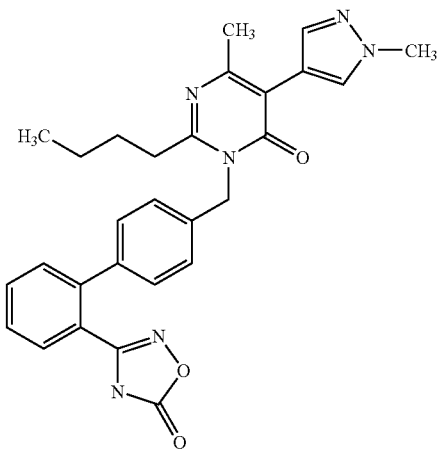

26b) 2-butyl-6-methyl-5-(1-methyl-1H-pyrazol-4-yl)-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.7 g), sodium hydrogen carbonate (1 g) and dimethyl sulfoxide (15 mL) was stirred at 40° C. for 30 min, 4'-{[2-butyl-4-methyl-5-(1-methyl-1H-pyrazol-4-yl)-6-oxopyrimidin-1(6H)-yl]methyl}biphenyl-2-carbonitrile (0.44 g) was added, and the mixture was stirred at 90° C. for 5 hr. The mixture was allowed to cool to room temperature. Water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.24 g) and then 1,8-diazabicyclo[5.4.0]undec-7-ene (0.22 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.13 g, 27%).

$^1$H NMR (300 MHz, DMSO-d$_6$) δ 0.82 (3H, t, J=7.5), 1.21-1.37 (2H, m), 1.51-1.65 (2H, m), 2.38 (3H, s), 2.67 (2H, t, J=7.5), 3.87 (3H, s), 5.37 (2H, s), 7.22 (2H, d, J=8.4), 7.30 (2H, d, J=8.4), 7.48-7.60 (2H, m), 7.63-7.73 (3H, m), 8.05 (1H, s), 12.41 (1H, br)

Example 27

2-(ethylthio)-6-methyl-3-{[2'-(5-oxo-4,5-dihydro-1,2,4-oxadiazol-3-yl)biphenyl-4-yl]methyl}-5-phenylpyrimidin-4(3H)-one

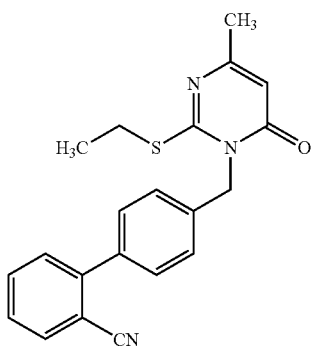

27a) 4'-{[2-(ethylthio)-4-methyl-6-oxopyrimidin-1(6H)-yl]methyl}biphenyl-2-carbonitrile To a solution of 2-ethylthio-6-methylpyrimidin-4(3H)-one (6.1 g) and 4'-(bromomethyl)biphenyl-2-carbonitrile (10.6 g) in acetonitrile (120 mL) was added potassium carbonate (5.9 g), and the mixture was stirred at 50° C. for 12 hr. The insoluble material was filtered off, and the filtrate was concentrated. The residue was purified by silica gel column chromatography to give the title compound (3.83 g, 30%) as a colorless solid.

$^{1}$H NMR (300 MHz, CDCl$_{3}$) δ 1.36 (3H, t, J=7.2), 2.24 (3H, s), 3.18 (2H, q, J=7.2), 5.31 (2H, s), 6.12 (1H, s), 7.38-7.55 (6H, m), 7.59-7.67 (1H, m), 7.75 (1H, d, J=7.8)

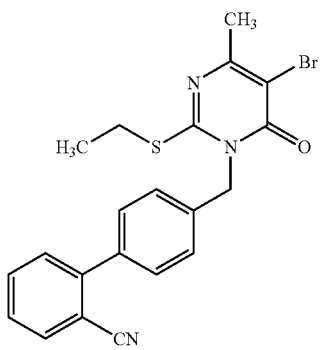

27b) 4'-{[5-bromo-2-(ethylthio)-4-methyl-6-oxopyrimidin-1(6H)-yl]methyl}biphenyl-2-carbonitrile To a solution of 4'-{[2-(ethylthio)-4-methyl-6-oxopyrimidin-1(6H)-yl]methyl}biphenyl-2-carbonitrile (3.83 g) and sodium acetate (0.87 g) in acetic acid (40 mL) was added bromine (0.54 mL), and the mixture was stirred for 2 hr. The reaction mixture was diluted with ethyl acetate, washed with 1 M aqueous sodium thiosulfate solution, saturated aqueous sodium hydrogen carbonate and saturated brine, and dried over anhydrous sodium sulfate. The solvent was evaporated under reduced pressure, and the residue was purified by silica gel column chromatography to give the title compound (4.66 g, 99%) as a colorless solid.

$^{1}$H NMR (300 MHz, CDCl$_{3}$) δ 1.38 (3H, t, J=7.2), 2.46 (3H, s), 3.20 (2H, q, J=7.2), 5.34 (2H, s), 7.40-7.53 (6H, m), 7.60-7.68 (1H, m), 7.75 (1H, d, J=7.8)

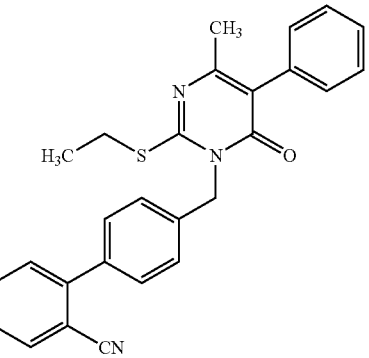

27c) 4'-{[2-(ethylthio)-4-methyl-6-oxo-5-phenylpyrimidin-1(6H)-yl]methyl}biphenyl-2-carbonitrile To a solution of 4'-{[5-bromo-2-(ethylthio)-4-methyl-6-oxopyrimidin-1(6H)-yl]methyl}biphenyl-2-carbonitrile (0.76 g) and phenylboronic acid (0.32 g) in 1,4-dioxane (10 mL) solution were added 2 M aqueous cesium carbonate solution (2 mL) and tetrakis(triphenylphosphine)palladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure, and the residue was purified by silica gel column chromatography to give the title compound (0.2 g, 26%) as a colorless solid.

$^{1}$H NMR (300 MHz, CDCl$_{3}$) δ 1.42 (3H, t, J=7.5), 2.20 (3H, s), 3.24 (2H, q, J=7.5), 5.34 (2H, s), 7.28-7.36 (3H, m), 7.36-7.59 (8H, m), 7.59-7.68 (1H, m), 7.75 (1H, d, J=8.1)

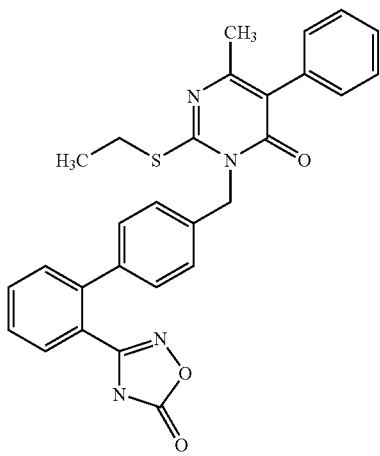

27d) 2-(ethylthio)-6-methyl-3-{[2'-(5-oxo-4,5-dihydro-1,2,4-oxadiazol-3-yl)biphenyl-4-yl]methyl}-5-phenylpyrimidin-4(3H)-one A mixture of hydroxylammonium chloride (0.27 g), sodium hydrogen carbonate (0.38 g) and dimethyl sulfoxide (5 mL) was stirred at 40° C. for 30 min, 4'-{[2-(ethylthio)-4-methyl-6-oxo-5-phenylpyrimidin-1(6H)-yl]methyl}biphenyl-2-carbonitrile (0.20 g) was added, and the mixture was stirred at 90° C. for 5 hr. The mixture was allowed to cool to room temperature, water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (5 mL), N,N'-carbonyldiimidazole (0.11 g) and then 1,8-diazabicyclo[5.4.0]undec-7-ene (0.1 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.11 g, 50%).

$^1$H NMR (300 MHz, DMSO-$d_6$) δ 1.32 (3H, t, J=7.2), 2.13 (3H, s), 3.19 (2H, q, J=7.2), 5.26 (2H, s), 7.28-7.47 (9H, m), 7.49-7.61 (2H, m), 7.63-7.75 (2H, m), 12.43 (1H, br)

Example 28

5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one

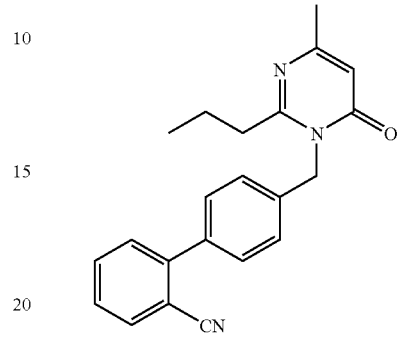

28a) 4'-[(4-methyl-6-oxo-2-propylpyrimidin-1(6H)-yl)methyl]biphenyl-2-carbonitrile To a solution of 6-methyl-2-propylpyrimidin-4(3H)-one (8 g) and 4'-(bromomethyl)biphenyl-2-carbonitrile (15.7 g) in acetonitrile (200 mL) was added potassium carbonate (14.5 g), and the mixture was stirred at 50° C. for 12 hr. The insoluble material was filtered off, and the filtrate was concentrated. The residue was purified by silica gel column chromatography to give the title compound (8.44 g, 47%) as a colorless solid.

$^1$H NMR (300 MHz, CDCl$_3$) δ 0.98 (3H, t, J=7.2), 1.66-1.81 (2H, m), 2.29 (3H, s), 2.66 (2H, t, J=7.2), 5.36 (2H, s), 6.29 (1H, s), 7.27 (2H, d, J=8.1), 7.40-7.56 (4H, m), 7.60-7.67 (1H, m), 7.75 (1H, d, J=6.9)

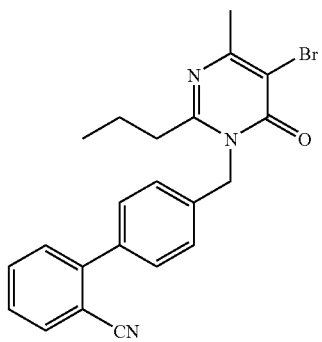

28b) 4'-[(5-bromo-4-methyl-6-oxo-2-propylpyrimidin-1(6H)-yl)methyl]biphenyl-2-carbonitrile To a solution of 4'-[(4-methyl-6-oxo-2-propylpyrimidin-1(6H)-yl)methyl]biphenyl-2-carbonitrile (8.44 g) and sodium acetate (2.22 g) in acetic acid (100 mL) was added bromine (1.39 mL), and the mixture was stirred for 2 hr. The reaction mixture was diluted with ethyl acetate, washed with 1 M aqueous sodium thiosulfate solution, saturated aqueous sodium hydrogen carbonate and saturated brine, and dried over anhydrous sodium sulfate. The solvent was evaporated under reduced pressure, and the residue was purified by silica gel column chromatography to give the title compound (6.68 g, 64%) as a colorless solid.

$^1$H NMR (300 MHz, DMSO-d$_6$) δ 0.86 (3H, t, J=7.2), 1.55-1.70 (2H, m), 2.40 (3H, s), 2.67 (2H, t, J=7.2), 5.39 (2H, s), 7.29 (2H, d, J=8.1), 7.50-7.63 (4H, m), 7.72-7.82 (1H, m), 7.92 (1H, d, J=7.5)

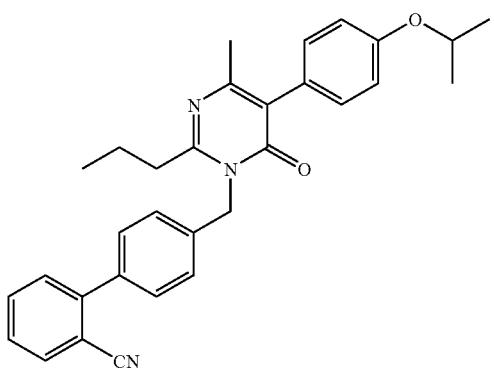

28c) 4'-{[5-(4-isopropoxyphenyl)-4-methyl-6-oxo-2-propylpyrimidin-1(6H)-yl]methyl}biphenyl-2-carbonitrile To a solution of 4'-[(5-bromo-4-methyl-6-oxo-2-propylpyrimidin-1(6H)-yl)methyl]biphenyl-2-carbonitrile (1.0 g) and 4-isopropoxyphenylboronic acid (0.64 g) in 1,4-dioxane (20 mL) were added 2 M aqueous cesium carbonate solution (4 mL) and [1,1'-bis(diphenylphosphino)ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure, and the residue was purified by silica gel column chromatography to give the title compound (1.01 g, 89%) as a colorless solid.

$^1$H NMR (300 MHz, CDCl$_3$) δ 1.02 (3H, t, J=7.2), 1.34 (6H, d, J=6.0), 1.71-1.85 (2H, m), 2.25 (3H, s), 2.72 (2H, t, J=7.2), 4.50-4.63 (1H, m), 5.38 (2H, s), 6.93 (2H, d, J=8.7), 7.23 (2H, d, J=8.7), 7.30-7.38 (2H, m), 7.39-7.57 (4H, m), 7.58-7.68 (1H, m), 7.75 (1H, d, J=7.5)

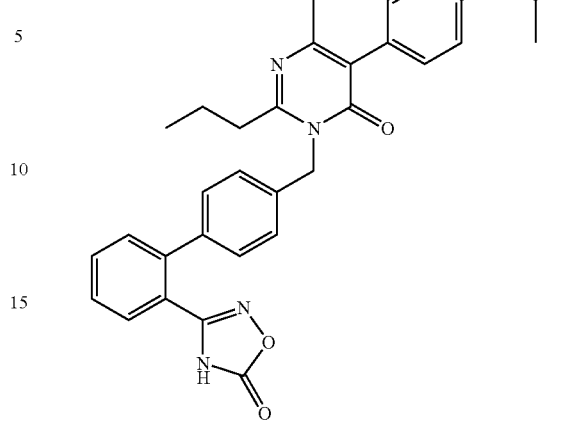

28d) 5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (2.49 g), sodium hydrogen carbonate (3.54 g) and dimethyl sulfoxide (20 mL) was stirred at 40° C. for 30 min, 4'-{[5-(4-isopropoxyphenyl)-4-methyl-6-oxo-2-propylpyrimidin-1(6H)-yl]methyl}biphenyl-2-carbonitrile (1.01 g) was added, and the mixture was stirred at 90° C. for 5 hr. The mixture was allowed to cool to room temperature. Water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (10 mL), N,N'-carbonyldiimidazole (0.51 g) and then 1,8-diazabicyclo[5.4.0]undec-7-ene (0.47 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.75 g, 66%).

$^1$H NMR (300 MHz, DMSO-d$_6$) δ 0.88 (3H, t, J=7.2), 1.29 (6H, d, J=6.3), 1.52-1.71 (2H, m), 2.13 (3H, s), 2.66 (2H, t, J=7.2), 4.55-4.73 (1H, m), 5.35 (2H, s), 6.93 (2H, d, J=8.1), 7.16-7.37 (6H, m), 7.47-7.62 (2H, m), 7.63-7.75 (2H, m), 12.40 (1H, br)

5-(4-Isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one obtained above is subjected to a conventional method of salt formation to give the following is salts.

5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one sodium salt 5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one potassium salt 5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one 0.5 calcium salt 5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one hydrochloride 5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one hydrobromide Example 29

5-(2,2-dimethyl-2,3-dihydro-1-benzofuran-5-yl)-6-methyl-3-{[2'-(5-oxo-4,5-dihydro-1,2,4-oxadiazol-3-yl)biphenyl-4-yl]methyl}-2-propylpyrimidin-4(3H)-one

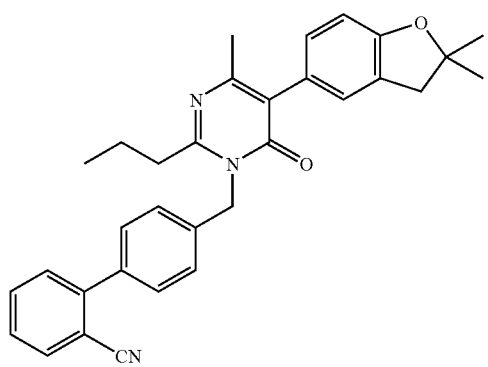

29a) 4'-{[5-(2,2-dimethyl-2,3-dihydro-1-benzofuran-5-yl)-4-methyl-6-oxo-2-propylpyrimidin-1(6H)-yl]methyl}biphenyl-2-carbonitrile To a solution of 4'-[(5-bromo-4-methyl-6-oxo-2-propylpyrimidin-1(6H)-yl)methyl]biphenyl-2-carbonitrile (1.0 g) and 2,2-dimethyl-2,3-dihydro-1-benzofuran-5-ylboronic acid (0.68 g) in 1,4-dioxane (20 mL) were added 2 M aqueous cesium carbonate solution (4 mL) and [1,1'-bis(diphenylphosphino)ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure, and the residue was purified by silica gel column chromatography to give the title compound (1.03 g, 89%) as a colorless solid.

$^1$H NMR (300 MHz, CDCl$_3$) δ 1.02 (3H, t, J=7.2), 1.49 (6H, s), 1.69-1.85 (2H, m), 2.25 (3H, s), 2.71 (2H, t, J=7.2), 3.04 (2H, s), 5.37 (2H, s), 6.76 (1H, d, J=8.4), 7.03 (1H, d, J=8.4), 7.13 (1H, s), 7.28-7.38 (2H, m), 7.39-7.57 (4H, m), 7.59-7.68 (1H, m), 7.76 (1H, d, J=7.5)

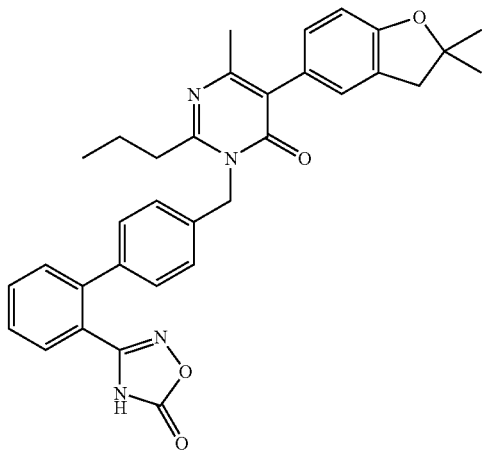

29b) 5-(2,2-dimethyl-2,3-dihydro-1-benzofuran-5-yl)-6-methyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (2.49 g), sodium hydrogen carbonate (3.54 g) and dimethyl sulfoxide (20 mL) was stirred at 40° C. for 30 min, 4'-{[5-(2,2-dimethyl-2,3-dihydro-1-benzofuran-5-yl)-4-methyl-6-oxo-2-propylpyrimidin-1(6H)-yl]methyl}biphenyl-2-carbonitrile (1.03 g) was added, and the mixture was stirred at 90° C. for 5 hr. The mixture was allowed to cool to room temperature. Water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (10 mL), N,N'-carbonyldiimidazole (0.51 g) and then 1,8-diazabicyclo[5.4.0]undec-7-ene (0.47 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.18 g, 16%).

$^1$H NMR (300 MHz, DMSO-d$_6$) δ 0.88 (3H, t, J=7.2), 1.43 (6H, s), 1.55-1.70 (2H, m), 2.13 (3H, s), 2.66 (2H, t, J=7.2), 3.02 (2H, s), 5.34 (2H, s), 6.72 (1H, d, J=7.8), 7.11 (1H, d, J=7.8), 7.12 (1H, s), 7.24 (2H, d, J=8.4), 7.31 (2H, d, J=8.4), 7.49-7.60 (2H, m), 7.63-7.73 (2H, m), 12.39 (1H, s)

Example 30

5-(2,2-dimethyl-3,4-dihydro-2H-chromen-6-yl)-6-methyl-3-{[2'-(5-oxo-4,5-dihydro-1,2,4-oxadiazol-3-yl)biphenyl-4-yl]methyl}-2-propylpyrimidin-4(3H)-one

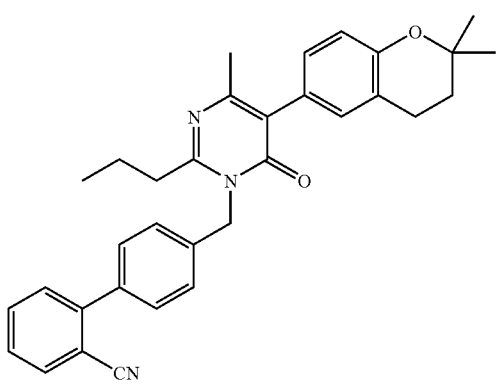

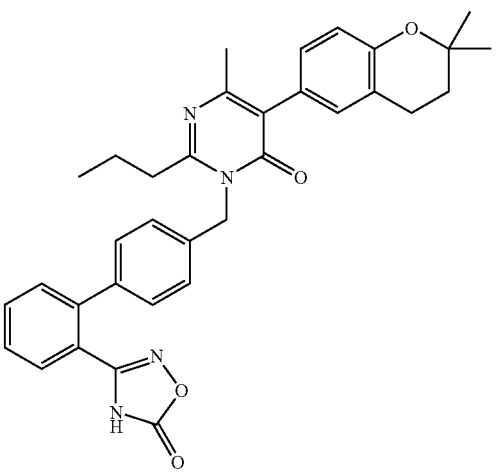

30a) 4'-{[5-(2,2-dimethyl-3,4-dihydro-2H-chromen-6-yl)-4-methyl-6-oxo-2-propylpyrimidin-1(6H)-yl]methyl}biphenyl-2-carbonitrile To a solution of 4'-[(5-bromo-4-methyl-6-oxo-2-propylpyrimidin-1(6H)-yl)methyl]biphenyl-2-carbonitrile (1.0 g) and (2,2-dimethyl-3,4-dihydro-2H-chromen-6-yl)boronic acid (0.73 g) in 1,4-dioxane (20 mL) were added 2 M aqueous cesium carbonate solution (4 mL) and [1,1'-bis(diphenylphosphino)ferrocene]dichloropalladium (0.1 g), and the mixture was stirred at 90° C. for 12 hr under an argon atmosphere. The reaction mixture was diluted with ethyl acetate, and the insoluble material was filtered off through celite. The filtrate was washed successively with 1 M hydrochloric acid, saturated aqueous sodium hydrogen carbonate and saturated brine, and dried over anhydrous sodium sulfate. The solvent was evaporated under reduced pressure, and the residue was purified by silica gel column chromatography to give the title compound (0.58 g, 49%) as a colorless solid.

$^1$H NMR (300 MHz, CDCl$_3$) δ 1.03 (3H, t, J=7.2), 1.35 (6H, s), 1.72-1.86 (4H, m), 2.25 (3H, s), 2.67-2.74 (2H, m), 2.80 (2H, t, J=6.6), 5.38 (2H, s), 6.81 (1H, d, J=8.1), 7.00-7.08 (2H, m), 7.34 (2H, d, J=8.1), 7.40-7.56 (4H, m), 7.60-7.68 (1H, m), 7.76 (1H, d, J=7.8)

30b) 5-(2,2-dimethyl-3,4-dihydro-2H-chromen-6-yl)-6-methyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (1.37 g), sodium hydrogen carbonate (1.95 g) and dimethyl sulfoxide (10 mL) was stirred at 40° C. for 30 min, 4'-{[5-(2,2-dimethyl-3,4-dihydro-2H-chromen-6-yl)-4-methyl-6-oxo-2-propylpyrimidin-1(6H)-yl]methyl}biphenyl-2-carbonitrile (0.58 g) was added, and the mixture was stirred at 90° C. for 5 hr. The mixture was allowed to cool to room temperature. Water was added to the reaction mixture, and the precipitate was collected by filtration. The obtained solid was dissolved in ethyl acetate. The solution was washed with saturated brine and dried over anhydrous sodium sulfate, and the solvent was evaporated. The residue was dissolved in tetrahydrofuran (10 mL), N,N'-carbonyldiimidazole (0.28 g) and then 1,8-diazabicyclo[5.4.0]undec-7-ene (0.26 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as colorless crystals (0.46 g, 70%).

$^1$H NMR (300 MHz, DMSO-d$_6$) δ 0.88 (3H, t, J=7.2), 1.30 (6H, s), 1.55-1.70 (2H, m), 1.78 (2H, t, J=6.6), 2.13 (3H, s), 2.60-2.70 (2H, m), 2.74 (2H, t, J=6.6), 5.34 (2H, s), 6.72 (1H, d, J=8.1), 6.95-7.05 (2H, m), 7.21-7.35 (4H, m), 7.49-7.61 (2H, m), 7.63-7.74 (2H, m), 12.40 (1H, br)

Example 31

6-butyl-3-[2-(4-methoxyphenyl)-2-oxoethyl]-2-methyl-5-{[2'-(5-oxo-4,5-dihydro-1,2,4-oxadiazol-3-yl)biphenyl-4-yl]methyl}pyrimidin-4(3H)-one

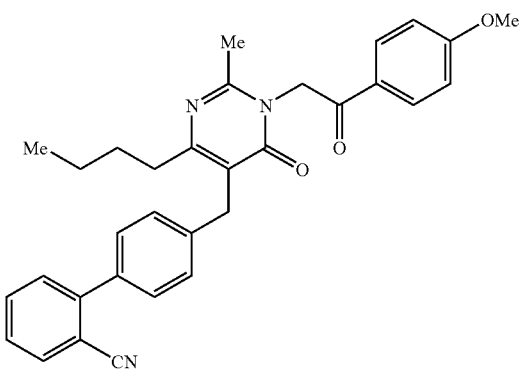

31a) 4'-({4-butyl-1-[2-(4-methoxyphenyl)-2-oxoethyl]-2-methyl-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 2-bromo-1-(4-methoxyphenyl)ethanone (0.77 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless solid (0.68 g, 48%).

$^1$H NMR (300 MHz, CDCl$_3$) δ 0.88 (3H, t, J=7.3), 1.29-1.43 (2H, m), 1.45-1.61 (2H, m), 2.45 (3H, s), 2.65-2.73 (2H, m), 3.87 (3H, s), 4.13 (2H, s), 5.62 (2H, s), 6.93-6.99 (2H, m), 7.32-7.52 (6H, m), 7.58-7.66 (1H, m), 7.75 (1H, dd, J=7.7, 0.9), 7.92-8.00 (2H, m)

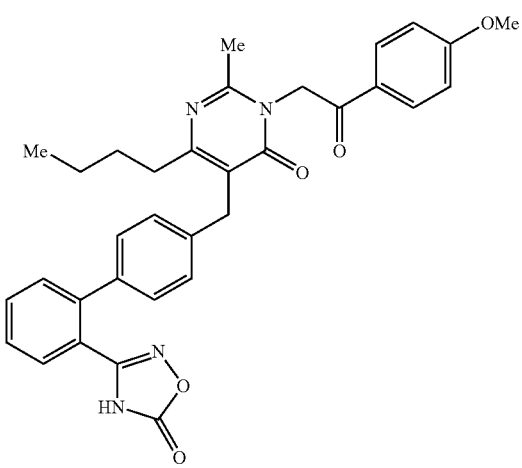

31b) 6-butyl-3-[2-(4-methoxyphenyl)-2-oxoethyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.12 g), sodium hydrogen carbonate (1.69 g) and dimethyl sulfoxide (15 mL) was stirred at 40° C. for 30 min, 4'-({4-butyl-1-[2-(4-methoxyphenyl)-2-oxoethyl]-2-methyl-6-oxo-1,6-dihydropyrimidin-5-yl}methyl)biphenyl-2-carbonitrile (0.68 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.19 g) and then 1,8-diazabicyclo[5.4.0]undec-7-ene (0.17 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as colorless crystals (0.051 g, 7%).

$^1$H NMR (300 MHz, DMSO-d$_6$) δ 0.85 (3H, t, J=7.4), 1.20-1.38 (2H, m), 1.40-1.59 (2H, m), 2.35 (3H, s), 2.51-2.57 (2H, m), 3.76-3.93 (5H, m), 5.60 (2H, s), 7.13 (2H, d, J=9.0), 7.17-7.34 (4H, m), 7.44-7.58 (2H, m), 7.59-7.72 (2H, m), 8.08 (2H, d, J=8.9), 12.41 (1H, br)

Example 32

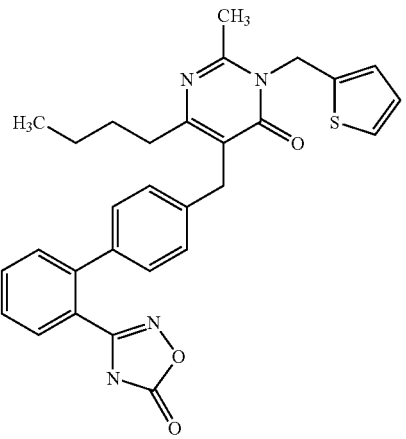

6-butyl-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 2-(bromomethyl)thiophene (5 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (1.1 g), sodium hydrogen carbonate (1.66 g) and dimethyl sulfoxide (10 mL) previously stirred at 40° C. for 30 min. The reaction mixture was stirred at 90° C. for 16 hr. The mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.26 g) and then 1,8-diazabicyclo[5.4.0]undec-7-ene (0.22 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as colorless crystals (0.41 g, 61%).

$^1$H NMR (300 MHz, DMSO-d$_6$) δ 0.81 (3H, t, J=7.3), 1.21-1.32 (2H, m), 1.35-1.47 (2H, m), 2.43-2.49 (2H, m), 2.54 (3H, s), 3.89 (2H, s), 5.38 (2H, s), 6.99 (1H, dd, J=5.1, 3.4), 7.16-7.28 (5H, m), 7.44-7.58 (3H, m), 7.62-7.72 (2H, m), 12.39 (1H, s)

6-Butyl-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one obtained above is subjected to a conventional method of salt formation to give the following salts.
6-butyl-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one sodium salt
6-butyl-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one potassium salt
6-butyl-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one 0.5 calcium salt
6-butyl-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one hydrochloride
6-butyl-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one hydrobromide Example 33

6-butyl-3-(2,2-dimethylpropyl)-2-methyl-5-{[2'-(5-oxo-4,5-dihydro-1,2,4-oxadiazol-3-yl)biphenyl-4-yl]methyl}pyrimidin-4(3H)-one

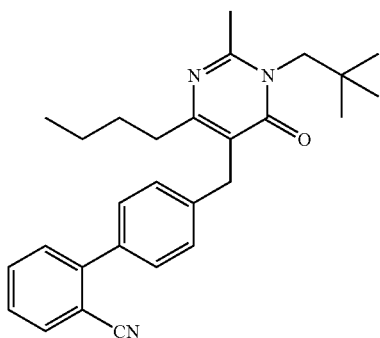

33a) 4'-{[4-butyl-1-(2,2-dimethylpropyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), cesium carbonate (1.82 g), 1-iodo-2,2-dimethylpropane (0.74 mL) and N,N-dimethylacetamide (10 mL) was stirred at 130° C. for 2 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless solid (0.36 g, 30%).

$^1$H NMR (300 MHz, CDCl$_3$) δ 0.91 (3H, t, J=7.3), 1.00 (9H, s), 1.32-1.44 (2H, m), 1.51-1.63 (2H, m), 2.51-2.62 (5H, m), 3.80-4.10 (4H, m), 7.31-7.51 (6H, m), 7.57-7.66 (1H, m), 7.74 (1H, dd, J=7.7, 0.9)

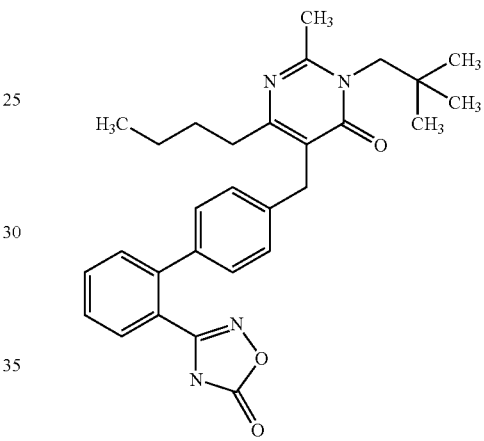

33b) 6-butyl-3-(2,2-dimethylpropyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.7 g), sodium hydrogen carbonate (1.06 g) and dimethyl sulfoxide (15 mL) was stirred at 40° C. for 30 min, 4'-{[4-butyl-1-(2,2-dimethylpropyl)-2-methyl-6-oxo-1,6-dihydropyrimidin-5-yl]methyl}biphenyl-2-carbonitrile (0.36 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.16 g) and then 1,8-diazabicyclo [5.4.0]undec-7-ene (0.14 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless solid (0.13 g, 31%).

$^1$H NMR (300 MHz, DMSO-d$_6$) δ 0.83 (3H, t, J=7.3), 0.91 (9H, s), 1.20-1.34 (2H, m), 1.38-1.52 (2H, m), 2.41-2.48 (2H, m), 3.32 (3H, s), 3.84 (2H, s), 3.95 (2H, br), 7.16-7.26 (4H, m), 7.45-7.58 (2H, m), 7.62-7.71 (2H, m), 12.37 (1H, s)

Example 34

6-butyl-3-(2-hydroxyethyl)-2-methyl-5-{[2'-(5-oxo-4,5-dihydro-1,2,4-oxadiazol-3-yl)biphenyl-4-yl]methyl}pyrimidin-4(3H)-one

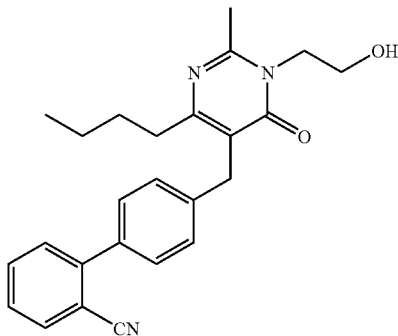

34a) 4'-{[4-butyl-1-(2-hydroxyethyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 2-bromoethanol (0.40 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless solid (0.26 g, 23%).

$^1$H NMR (300 MHz, CDCl$_3$) δ 0.90 (3H, t, J=7.3), 1.31-1.45 (2H, m), 1.53-1.62 (2H, m), 2.58 (3H, s), 2.69-2.79 (2H, m), 3.17 (1H, t, J=5.2), 3.84 (2H, d, J=3.6), 4.03 (2H, s), 4.45-4.53 (2H, m), 7.21-7.28 (2H, m), 7.39-7.51 (4H, m), 7.59-7.67 (1H, m), 7.75 (1H, dd, J=7.4, 1.0)

34b) 6-butyl-3-(2-hydroxyethyl)-2-methyl-5-{[2'-(5-oxo-4,5-dihydro-1,2,4-oxadiazol-3-yl)biphenyl-4-yl]methyl}pyrimidin-4(3H)-one A mixture of 4'-{[4-butyl-1-(2-hydroxyethyl)-2-methyl-6-oxo-1,6-dihydropyrimidin-5-yl]methyl}biphenyl-2-carbonitrile (0.26 g), tert-butyl(dimethyl)silyl trifluoromethanesulfonate (0.45 mL), 2,6-lutidine (0.25 mL) and tetrahydrofuran (10 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (10 mL), and added to a mixture of hydroxylammonium chloride (0.4 g), sodium hydrogen carbonate (0.61 g) and dimethyl sulfoxide (10 mL) previously stirred at 40° C. for 30 min. The reaction mixture was stirred at 90° C. for 16 hr. The mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.094 g) and then 1,8-diazabicyclo[5.4.0]undec-7-ene (0.08 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was dissolved in tetrahydrofuran (20 mL). Tetrabutylammonium fluoride (1.0 M tetrahydrofuran solution, 2.08 mL) was added thereto, and the mixture was stirred at room temperature for 3 hr. The reaction mixture was extracted with 1 M hydrochloric acid and ethyl acetate, and the ethyl acetate layer was washed with saturated brine and concentrated. The residue was purified by silica gel column chromatography to give the title compound as colorless crystals (0.055 g, 19%).

$^1$H NMR (300 MHz, DMSO-d$_6$) δ 0.82 (3H, t, J=7.3), 1.21-1.33 (2H, m), 1.39-1.50 (2H, m), 2.45 (3H, s), 2.57-2.66 (2H, m), 3.66-3.73 (2H, m), 3.98 (2H, s), 4.30-4.37 (2H, m), 4.79-4.89 (1H, m), 7.18-7.26 (4H, m), 7.46-7.58 (2H, m), 7.62-7.71 (2H, m), 12.36 (1H, s)

Example 35

2-methyl-5-{[2'-(5-oxo-4,5-dihydro-1,2,4-oxadiazol-3-yl)biphenyl-4-yl]methyl}-6-propyl-3-(2-thienylmethyl)pyrimidin-4(3H)-one

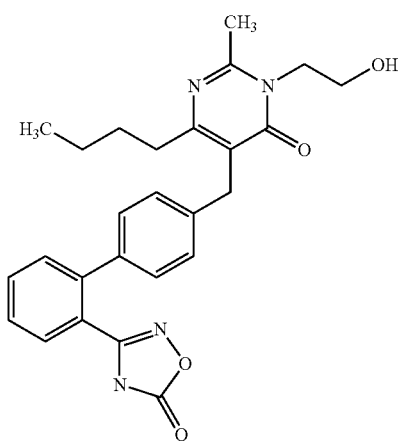

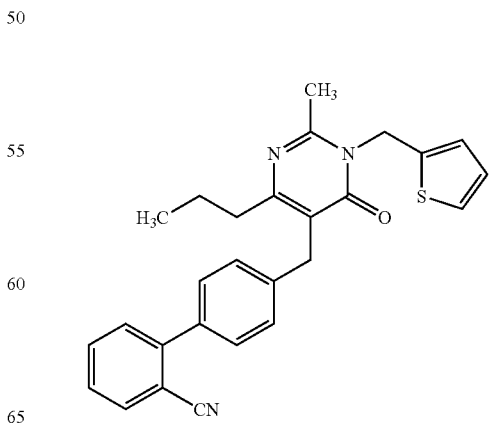

35a) 4'-{[2-methyl-6-oxo-4-propyl-1-(2-thienylmethyl)-1,6-dihydropyrimidin-5-yl]methyl}biphenyl-2-carbonitrile A mixture of 4'-[(2-methyl-6-oxo-4-propyl-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 2-(bromomethyl)thiophene (4.5 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless solid (0.74 g, 58%).

$^1$H NMR (300 MHz, CDCl$_3$) δ 0.94 (3H, t, J=7.3), 1.53-1.65 (2H, m), 2.51-2.59 (2H, m), 2.61 (3H, s), 4.00 (2H, s), 5.38 (2H, s), 6.96 (1H, dd, J=5.1, 3.6), 7.07 (1H, dd, J=3.4, 0.9), 7.23-7.28 (1H, m), 7.34-7.52 (6H, m), 7.58-7.66 (1H, m), 7.74 (1H, dd, J=7.7, 0.9)

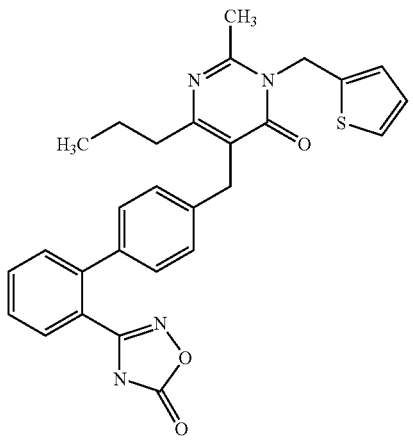

35b) 2-methyl-5-{[2'-(5-oxo-4,5-dihydro-1,2,4-oxadiazol-3-yl)biphenyl-4-yl]methyl}-6-propyl-3-(2-thienylmethyl)pyrimidin-4(3H)-one A mixture of hydroxylammonium chloride (1.41 g), sodium hydrogen carbonate (2.13 g) and dimethyl sulfoxide (15 mL) was stirred at 40° C. for 30 min, 4'-{[2-methyl-6-oxo-4-propyl-1-(2-thienylmethyl)-1,6-dihydropyrimidin-5-yl]methyl}biphenyl-2-carbonitrile (0.74 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.33 g) and then 1,8-diazabicyclo[5.4.0]undec-7-ene (0.28 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless solid (0.39 g, 46%).

$^1$H NMR (300 MHz, DMSO-d$_6$) δ 0.82 (3H, t, J=7.3), 1.40-1.53 (2H, m), 2.45 (2H, dd, J=8.6, 6.7), 2.54 (3H, s), 3.90 (2H, s), 5.38 (2H, s), 6.99 (1H, dd, J=5.1, 3.4), 7.16-7.28 (5H, m), 7.44-7.58 (3H, m), 7.63-7.72 (2H, m), 12.38 (1H, s)

Example 36

6-butyl-3-(2-hydroxy-3,3-dimethylbutyl)-2-methyl-5-{[2'-(5-oxo-4,5-dihydro-1,2,4-oxadiazol-3-yl)biphenyl-4-yl]methyl}pyrimidin-4(3H)-one

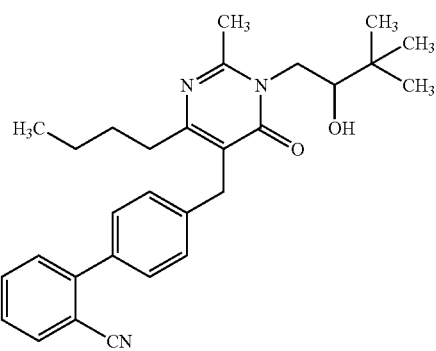

36a) 4'-{[4-butyl-1-(2-hydroxy-3,3-dimethylbutyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-bromo-3,3-dimethylbutan-2-one (0.75 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in methanol (10 mL), sodium borohydride (0.092 g) was added, and the mixture was stirred at room temperature for 3 hr. The reaction mixture was concentrated, and the residue was extracted with ethyl acetate and saturated aqueous ammonium chloride solution. The ethyl acetate layer was washed with saturated brine, and dried over anhydrous magnesium sulfate. The solvent was evaporated under reduced pressure, and the residue was purified by silica gel column chromatography to give the title compound as a colorless solid (0.21 g, 16%).

$^1$H NMR (300 MHz, CDCl$_3$) δ 0.90 (3H, t, J=7.2), 1.03 (9H, s), 1.31-1.44 (2H, m), 1.49-1.65 (2H, m), 2.53-2.63 (5H, m), 3.64 (1H, dd, J=10.3, 1.8), 3.96 (2H, s), 4.01-4.11 (1H, m), 4.17-4.28 (1H, m), 7.29-7.36 (2H, m), 7.37-7.50 (4H, m), 7.58-7.66 (1H, m), 7.74 (1H, dd, J=7.7, 1.1)

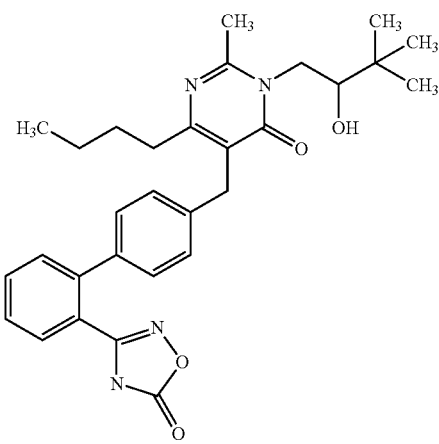

36b) 6-butyl-3-(2-hydroxy-3,3-dimethylbutyl)-2-methyl-5-{[2'-(5-oxo-4,5-dihydro-1,2,4-oxadiazol-3-yl)biphenyl-4-yl]methyl}pyrimidin-4(3H)-one A mixture of 4'-{[4-butyl-1-(2-hydroxy-3,3-dimethylbutyl)-2-methyl-6-oxo-1,6-dihydropyrimidin-5-yl]methyl}biphenyl-2-carbonitrile (0.21 g), tert-butyl(dimethyl)silyl trifluoromethanesulfonate (0.36 mL), 2,6-lutidine (0.16 mL) and tetrahydrofuran (10 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.97 g), sodium hydrogen carbonate (1.47 g) and dimethyl sulfoxide (10 mL) previously stirred at 40° C. for 30 min. The reaction mixture was stirred at 90° C. for 16 hr. The mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.14 g) and then 1,8-diazabicyclo[5.4.0]undec-7-ene (0.12 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure. The residue was dissolved in tetrahydrofuran (20 mL), tetrabutylammonium fluoride (1.0 M tetrahydrofuran solution, 3.5 mL) was added, and the mixture was stirred at room temperature for 3 hr. The reaction mixture was extracted with 1 M hydrochloric acid and ethyl acetate, and the ethyl acetate layer was washed with saturated brine, and dried over anhydrous magnesium sulfate. The solvent was evaporated under reduced pressure, and the residue was purified by silica gel column chromatography to give the title compound as colorless amorphous crystals (0.2 g, 55%).

$^1$H NMR (300 MHz, DMSO-$d_6$) δ 0.83 (3H, t, J=7.2), 0.93 (9H, s), 1.22-1.33 (2H, m), 1.38-1.50 (2H, m), 2.41-2.48 (2H, m), 2.55 (3H, s), 3.42-3.51 (1H, m), 3.63 (1H, dd, J=13.2, 10.5), 3.84 (2H, q, J=15.1), 4.24 (1H, d, J=11.9), 5.03 (1H, d, J=5.7), 7.18-7.27 (4H, m), 7.47-7.58 (2H, m), 7.61-7.72 (2H, m), 12.39 (1H, br)

Example 37

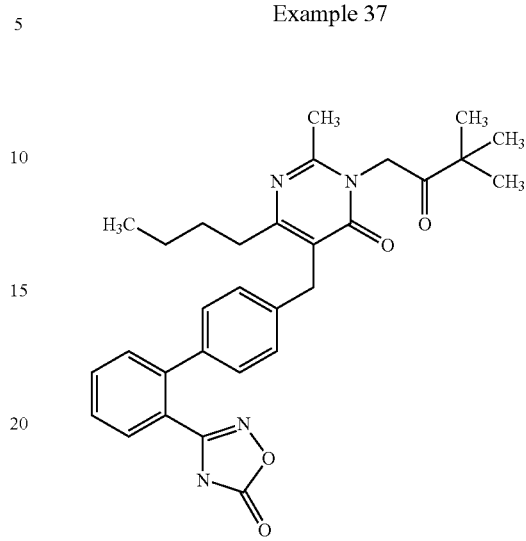

6-butyl-3-(3,3-dimethyl-2-oxobutyl)-2-methyl-5-{[2'-(5-oxo-4,5-dihydro-1,2,4-oxadiazol-3-yl)biphenyl-4-yl]methyl}pyrimidin-4(3H)-one A mixture of 4'-[(4-butyl-2-methyl-6-oxo-1,6-dihydropyrimidin-5-yl)methyl]biphenyl-2-carbonitrile (0.19 g), 1,1,1-tris(acetyloxy)-1,1-dihydro-1,2-benziodoxol-3(1H)-one (0.18 g) and methylene chloride (10 mL) was stirred at room temperature for 2 hr. A saturated aqueous sodium hydrogen carbonate solution and sodium thiosulfate were added to the reaction mixture, and the mixture was stirred at room temperature for 2 hr and extracted with chloroform. The chloroform layer was washed with saturated brine, and dried over anhydrous magnesium sulfate. The solvent was evaporated under reduced pressure. The obtained residue was purified by silica gel column chromatography to give the title compound as colorless crystals (0.13 g, 69%).

$^1$H NMR (300 MHz, DMSO-$d_6$) δ 0.83 (3H, t, J=7.3), 1.22 (9H, s), 1.25-1.34 (2H, m), 1.38-1.51 (2H, m), 2.28 (3H, s), 2.45-2.49 (2H, m), 3.83 (2H, s), 5.16 (2H, s), 7.21 (4H, s), 7.52 (2H, dd, J=16.3, 7.6), 7.62-7.72 (2H, m), 12.38 (1H, s)

6-Butyl-3-(3,3-dimethyl-2-oxobutyl)-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(3,3-dimethyl-2-oxobutyl)-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-(3,3-dimethyl-2-oxobutyl)-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-(3,3-dimethyl-2-oxobutyl)-2-methyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(3,3-dimethyl-2-oxobutyl)-2-methyl-5-{[2'-(5-oxo-4,5-dihydro-1,2,4-oxadiazol-3-yl)biphenyl-4-yl]methyl}pyrimidin-4(3H)-one hydrochloride 6-butyl-3-(3,3-dimethyl-2-oxobutyl)-2-methyl-5-{[2'-(5-oxo-4,5-dihydro-1,2,4-oxadiazol-3-yl)biphenyl-4-yl]methyl}pyrimidin-4(3H)-one hydrobromide

Example 38

3-(1-benzothien-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one

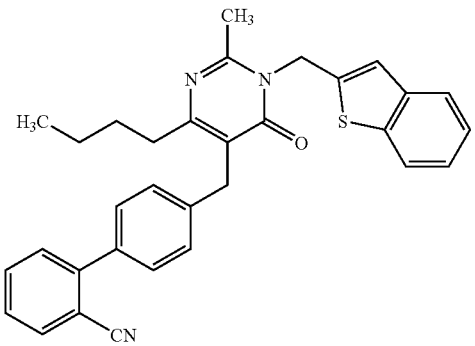

38a) 4'-{[1-(1-benzothien-2-ylmethyl)-4-butyl-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.23 g), tributylphosphine (1.52 mL), 1-benzothien-2-ylmethanol (0.56 g) and tetrahydrofuran (50 mL) was stirred at room temperature for 4 hr. The reaction mixture was diluted with ethyl acetate, washed with 1 M hydrochloric acid and then with saturated brine, and dried over anhydrous magnesium sulfate. The solvent was evaporated under reduced pressure, and the residue was purified by silica gel column chromatography to give the title compound as a colorless solid (0.55 g, 45%).

$^1$H NMR (300 MHz, CDCl$_3$) δ 0.90 (3H, t, J=7.3), 1.31-1.43 (2H, m), 1.49-1.57 (2H, m), 2.55-2.62 (2H, m), 2.64 (3H, s), 4.02 (2H, s), 5.48 (2H, s), 7.24-7.28 (2H, m), 7.30-7.34 (2H, m), 7.37-7.51 (5H, m), 7.57-7.68 (1H, m), 7.68-7.81 (3H, m)

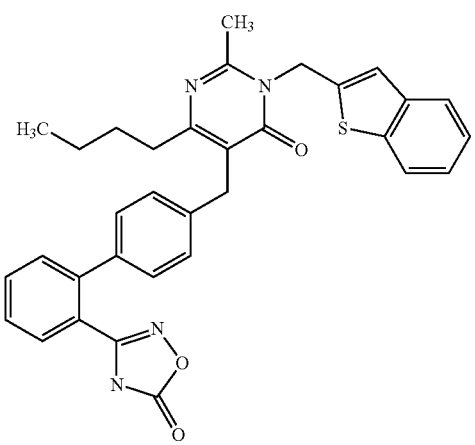

38b) 3-(1-benzothien-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.91 g), sodium hydrogen carbonate (1.38 g) and dimethyl sulfoxide (15 mL) was stirred at 40° C. for 30 min, 4'-{[1-(1-benzothien-2-ylmethyl)-4-butyl-2-methyl-6-oxo-1,6-dihydropyrimidin-5-yl]methyl}biphenyl-2-carbonitrile (0.55 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.21 g) and then 1,8-diazabicyclo[5.4.0]undec-7-ene (0.18 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as colorless crystals (0.31 g, 51%).

$^1$H NMR (300 MHz, DMSO-d$_6$) δ 0.82 (3H, t, J=7.3), 1.20-1.33 (2H, m), 1.36-1.48 (2H, m), 2.43-2.49 (2H, m), 2.57 (3H, s), 3.92 (2H, s), 5.51 (2H, s), 7.21-7.30 (4H, m), 7.30-7.39 (2H, m), 7.45-7.58 (3H, m), 7.64-7.71 (2H, m), 7.79-7.86 (1H, m), 7.89-7.96 (1H, m), 12.39 (1H, s)

Example 39

6-butyl-3-[(5-chloro-2-thienyl)methyl]-2-methyl-5-{[2'-(5-oxo-4,5-dihydro-1,2,4-oxadiazol-3-yl)biphenyl-4-yl]methyl}pyrimidin-4(3H)-one

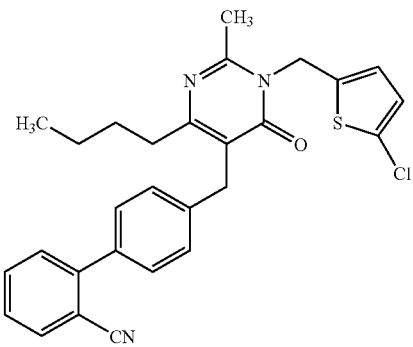

39a) 4'-({4-butyl-1-[(5-chloro-2-thienyl)methyl]-2-methyl-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 2-chloro-5-(chloromethyl)thiophene (2.39 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless solid (0.63 g, 45%).

$^1$H NMR (300 MHz, CDCl$_3$) δ 0.90 (3H, t, J=7.3), 1.37 (2H, dq, J=7.3, 7.1), 1.48-1.59 (2H, m), 2.53-2.66 (5H, m), 3.99 (2H, s), 5.24 (2H, s), 6.76 (1H, d, J=3.8), 6.85 (1H, d, J=3.8), 7.34-7.51 (6H, m), 7.55-7.67 (1H, m), 7.74 (1H, d, J=7.3)

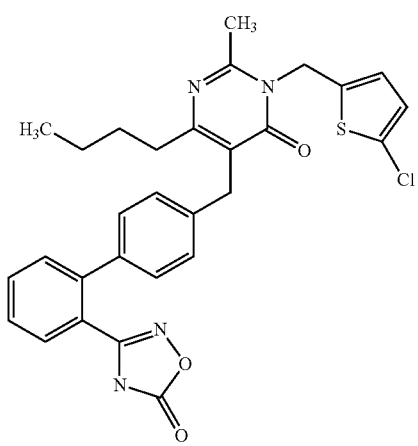

39b) 6-butyl-3-[(5-chloro-2-thienyl)methyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.1 g), sodium hydrogen carbonate (1.64 g) and dimethyl sulfoxide (15 mL) was stirred at 40° C. for 30 min, 4'-({4-butyl-1-[(5-chloro-2-thienyl)methyl]-2-methyl-6-oxo-1,6-dihydropyrimidin-5-yl}methyl)biphenyl-2-carbonitrile (0.64 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.25 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless solid (0.32 g, 45%).

$^1$H NMR (300 MHz, DMSO-d$_6$) δ 0.81 (3H, t, J=7.3), 1.20-1.32 (2H, m), 1.35-1.46 (2H, m), 2.43-2.50 (2H, m), 2.55 (3H, s), 3.89 (2H, s), 5.28 (2H, s), 7.00 (1H, d, J=3.8), 7.11 (1H, d, J=3.8), 7.19-7.28 (4H, m), 7.47-7.58 (2H, m), 7.63-7.72 (2H, m), 12.38 (1H, br)

Example 40

6-butyl-2-methyl-3-[(3-methyloxetan-3-yl)methyl]-5-{[2'-(5-oxo-4,5-dihydro-1,2,4-oxadiazol-3-yl)biphenyl-4-yl]methyl}pyrimidin-4(3H)-one

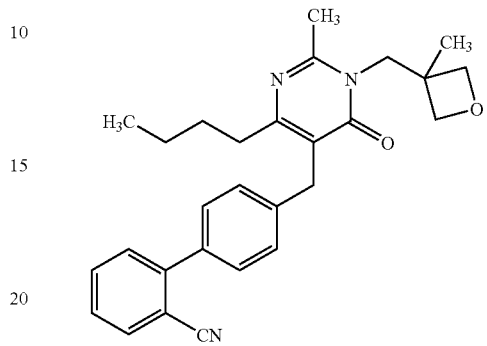

40a) 4'-({4-butyl-2-methyl-1-[(3-methyloxetan-3-yl)methyl]-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.44 g), tributylphosphine (1.78 mL), (3-methyloxetan-3-yl)methanol (0.44 g) and tetrahydrofuran (50 mL) was stirred at room temperature for 4 hr. The reaction mixture was diluted with ethyl acetate, washed with 1 M hydrochloric acid and then with saturated brine, and dried over anhydrous magnesium sulfate. The solvent was evaporated under reduced pressure, and the residue was purified by silica gel column chromatography to give the title compound as a colorless solid (0.78 g, 62%).

$^1$H NMR (300 MHz, CDCl$_3$) δ 0.91 (3H, t, J=7.2), 1.34-1.46 (2H, m), 1.55-1.69 (2H, m), 2.17 (3H, s), 2.59 (3H, s), 2.71-2.82 (2H, m), 4.02 (2H, s), 4.26-4.48 (6H, m), 7.20 (2H, d, J=8.1), 7.38-7.52 (4H, m), 7.57-7.67 (1H, m), 7.75 (1H, d, J=7.7)

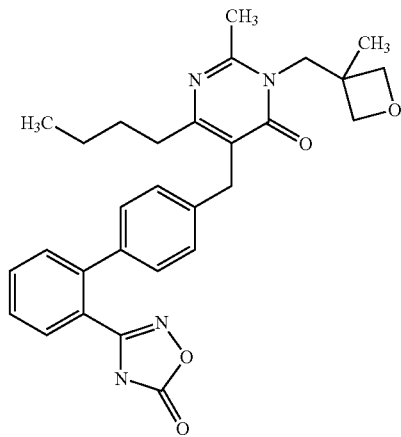

40b) 6-butyl-2-methyl-3-[(3-methyloxetan-3-yl)methyl]-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.47 g), sodium hydrogen carbonate (2.23 g) and dimethyl sulfoxide (15 mL) was stirred at 40° C. for 30 min, 4'-({4-butyl-2-methyl-1-[(3-methyloxetan-3-yl)methyl]-6-oxo-1,6-dihydropyrimidin-5-yl}methyl)biphenyl-2-carbonitrile (0.78 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.34 g) and then 1,8-diazabicyclo[5.4.0]undec-7-ene (0.29 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless powder (0.048 g, 5%).

$^1$H NMR (300 MHz, DMSO-$d_6$) δ 0.85 (3H, t, J=7.4), 1.20 (3H, s), 1.25-1.37 (2H, m), 1.44-1.57 (2H, m), 2.47 (3H, s), 2.65-2.75 (2H, m), 3.96 (2H, s), 4.20 (2H, d, J=6.0), 4.31-4.39 (4H, m), 7.13-7.24 (4H, m), 7.46 (1H, d, J=7.7), 7.54 (1H, dt, J=7.5, 1.3), 7.62-7.72 (2H, m), 12.38 (1H, br)

Example 41

6-butyl-3-[(6-fluoro-1,2-benzisoxazol-3-yl)methyl]-2-methyl-5-{[2'-(5-oxo-4,5-dihydro-1,2,4-oxadiazol-3-yl)biphenyl-4-yl]methyl}pyrimidin-4(3H)-one

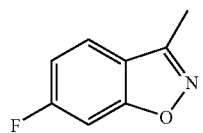

41a) 6-fluoro-3-methyl-1,2-benzisoxazole

A mixture of 1-(4-fluoro-2-hydroxyphenyl)ethanone (20 g), hydroxyammonium chloride (18.1 g), sodium acetate (16 g) and methanol (500 mL) was stirred at 60° C. for 1 hr. The reaction mixture was added to ice water, and the obtained crystallized product was collected by filtration and dissolved in tetrahydrofuran (400 mL). N,N'-carbonyldiimidazole (22.5 g) and then a solution of triethylamine (22.3 mL) in tetrahydrofuran (100 mL) were added, and the mixture was stirred at 70° C. for 1 hr. The reaction mixture was diluted with diethyl ether, washed with water and then with saturated brine, and dried over anhydrous magnesium sulfate. The solvent was evaporated under reduced pressure to give the title compound as colorless crystals (13.7 g, 70%).

$^1$H NMR (300 MHz, CDCl$_3$) δ 2.34 (3H, s), 6.52-6.74 (2H, m), 7.39 (1H, dd, J=8.8, 6.3)

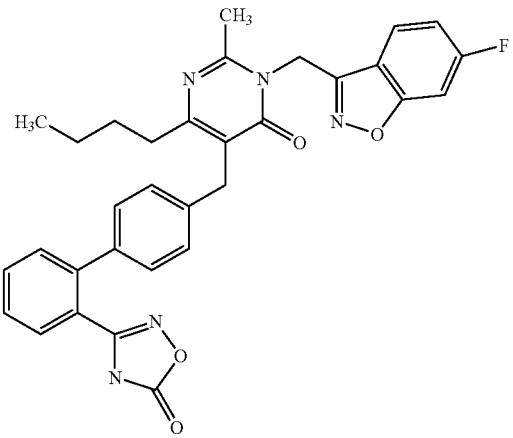

41b) 6-butyl-3-[(6-fluoro-1,2-benzisoxazol-3-yl)methyl]-2-methyl-5-{[2'-(5-oxo-4,5-dihydro-1,2,4-oxadiazol-3-yl)biphenyl-4-yl]methyl}pyrimidin-4(3H)-one To a mixture of 6-fluoro-3-methyl-1,2-benzisoxazole (2.0 g) and carbon tetrachloride (100 mL) was added a mixture of N-bromosuccinimide (2.58 g) and benzoyl peroxide (0.43 g) at 80° C., and the mixture was stirred at the same temperature for 4 hr. The reaction mixture was concentrated under reduced pressure, and the obtained residue was extracted with water and ethyl acetate. The ethyl acetate layer was washed with saturated brine, and dried over anhydrous magnesium sulfate. The solvent was evaporated under reduced pressure, and the obtained oil was added to a mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) previously stirred at room temperature for 10 min. The reaction mixture was stirred at room temperature for 16 hr. and diluted with ethyl acetate. The mixture was washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxyammonium chloride (1.03 g), sodium hydrogen carbonate (1.65 g) and dimethyl sulfoxide (10 mL) previously stirred at 40° C. for 30 min. The reaction mixture was stirred at 90° C. for 16 hr. and diluted with ethyl acetate. The mixture was washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.19 g) and then 1,8-diazabicyclo[5.4.0]undec-7-ene (0.16 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as a colorless solid (0.14 g, 25%).

$^1$H NMR (300 MHz, DMSO-$d_6$) δ 0.84 (3H, t, J=7.4), 1.22-1.38 (2H, m), 1.39-1.54 (2H, m), 2.50-2.55 (2H, m), 2.57 (3H, s), 3.88 (2H, s), 5.69 (2H, s), 7.17-7.27 (4H, m), 7.33 (1H, dt, J=9.1, 2.3), 7.46-7.59 (2H, m), 7.62-7.71 (2H, m), 7.76 (1H, dd, J=9.0, 2.3), 7.97 (1H, dd, J=8.9, 5.3), 12.39 (1H, br)

Example 42

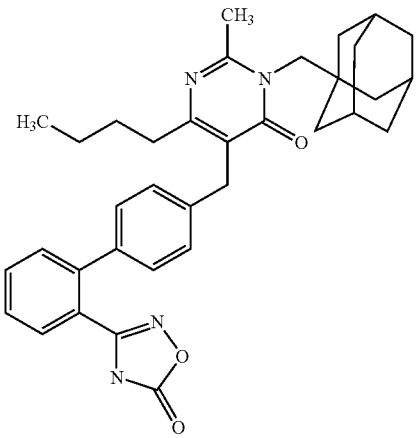

3-(1-adamantylmethyl)-6-butyl-2-methyl-5-{[2'-(5-oxo-4,5-dihydro-1,2,4-oxadiazol-3-yl)biphenyl-4-yl]methyl}pyrimidin-4(3H)-one A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-(bromomethyl)adamantane (1.9 g) was added, and the mixture was stirred at 150° C. for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (1.1 g), sodium hydrogen carbonate (1.78 g) and dimethyl sulfoxide (10 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.21 g) and then 1,8-diazabicyclo[5.4.0]undec-7-ene (0.17 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as colorless crystals (0.11 g, 19%).

$^1$H NMR (300 MHz, DMSO-$d_6$) δ 0.83 (3H, t, J=7.3), 1.22-1.34 (2H, m), 1.39-1.48 (2H, m), 1.49-1.67 (12H, m), 1.91 (3H, s), 2.44 (2H, m), 2.50 (3H, s), 3.57-4.13 (4H, m), 7.16-7.26 (4H, m), 7.44-7.57 (2H, m), 7.61-7.71 (2H, m), 12.37 (1H, br)

3-(1-Adamantylmethyl)-6-butyl-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

3-(1-adamantylmethyl)-6-butyl-2-methyl-5-{[2'-(5-oxo-4,5-dihydro-1,2,4-oxadiazol-3-yl)biphenyl-4-yl]methyl}pyrimidin-4(3H)-one sodium salt 3-(1-adamantylmethyl)-6-butyl-2-methyl-5-{[2'-(5-oxo-4,5-dihydro-1,2,4-oxadiazol-3-yl)biphenyl-4-yl]methyl}pyrimidin-4(3H)-one potassium salt 3-(1-adamantylmethyl)-6-butyl-2-methyl-5-{[2'-(5-oxo-4,5-dihydro-1,2,4-oxadiazol-3-yl)biphenyl-4-yl]methyl}pyrimidin-4(3H)-one 0.5 calcium salt 3-(1-adamantylmethyl)-6-butyl-2-methyl-5-{[2'-(5-oxo-4,5-dihydro-1,2,4-oxadiazol-3-yl)biphenyl-4-yl]methyl}pyrimidin-4(3H)-one hydrochloride 3-(1-adamantylmethyl)-6-butyl-2-methyl-5-{[2'-(5-oxo-4,5-dihydro-1,2,4-oxadiazol-3-yl)biphenyl-4-yl]methyl}pyrimidin-4(3H)-one hydrobromide

Example 43

6-butyl-2-methyl-3-(2-methyl-2-phenylpropyl)-5-{[2'-(5-oxo-4,5-dihydro-1,2,4-oxadiazol-3-yl)biphenyl-4-yl]methyl}pyrimidin-4(3H)-one

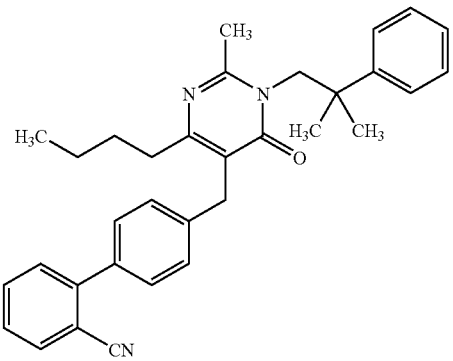

43a) 4'-{[4-butyl-2-methyl-1-(2-methyl-2-phenylpropyl)-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), cyanomethylene tri-n-butylphosphorane (1 g), 2-methyl-2-phenylpropan-1-ol (0.63 g) and toluene (30 mL) was stirred at 100° C. for 16 hr. The reaction mixture was concentrated under reduced pressure, and the residue was purified by silica gel column chromatography to give the title compound as a colorless solid (0.13 g, 10%).

¹H NMR (300 MHz, CDCl₃) δ 0.91 (3H, t, J=7.2), 1.30-1.48 (8H, m), 1.49-1.63 (2H, m), 1.70 (3H, s), 2.51-2.61 (2H, m), 3.94-4.00 (4H, m), 7.19-7.51 (11H, m), 7.56-7.66 (1H, m), 7.73 (1H, dd, J=7.7, 1.3)

Example 44

3-[2-(1-adamantyl)-2-hydroxyethyl]-6-butyl-2-methyl-5-{[2'-(5-oxo-4,5-dihydro-1,2,4-oxadiazol-3-yl)biphenyl-4-yl]methyl}pyrimidin-4(3H)-one

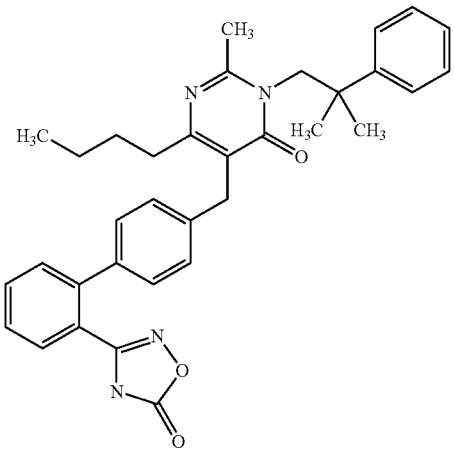

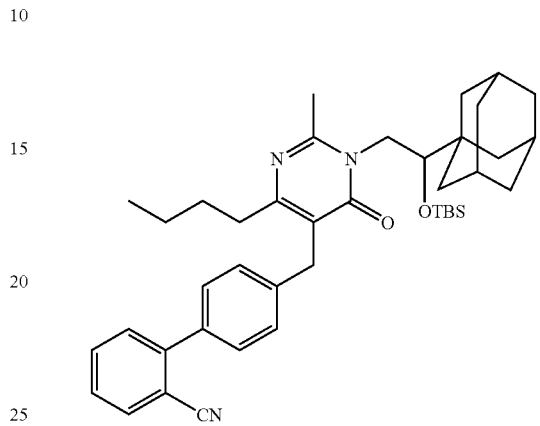

43b) 6-butyl-2-methyl-3-(2-methyl-2-phenylpropyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.27 g), sodium hydrogen carbonate (0.45 g) and dimethyl sulfoxide (10 mL) was stirred at 40° C. for 30 min, 4'-{[4-butyl-2-methyl-1-(2-methyl-2-phenylpropyl)-6-oxo-1,6-dihydropyrimidin-5-yl]methyl}biphenyl-2-carbonitrile (0.13 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.052 g) and then 1,8-diazabicyclo[5.4.0]undec-7-ene (0.044 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as colorless crystals (0.036 g, 24%).

¹H NMR (300 MHz, DMSO-d₆) δ 0.83 (3H, t, J=7.3), 1.20-1.48 (10H, m), 1.72 (3H, s), 2.38-2.48 (2H, m), 3.87 (2H, s), 4.18 (2H, s), 7.19-7.34 (8H, m), 7.46-7.57 (2H, m), 7.62-7.73 (2H, m), 12.38 (1H, br)

44a) 4'-{[1-(2-(1-adamantyl)-2-{[tert-butyl(dimethyl)silyl]oxy}ethyl)-4-butyl-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-(1-adamantyl)-2-bromoethanone (1.08 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in methanol (20 mL), sodium borohydride (0.12 g) was added, and the mixture was stirred at room temperature for 3 hr. The reaction mixture was concentrated, and the residue was extracted with ethyl acetate and saturated aqueous ammonium chloride solution. The ethyl acetate layer was washed with saturated brine, and concentrated. The obtained residue was dissolved in tetrahydrofuran (20 mL), and tert-butyl(dimethyl)silyl trifluoromethanesulfonate (0.47 mL) and 2,6-lutidine (0.24 mL) were added at 0° C. The reaction mixture was stirred at 0° C. for 3 hr, and diluted with ethyl acetate. The mixture was washed with water and then with saturated brine, and dried over anhydrous magnesium sulfate. The solvent was evaporated under reduced pressure, and the residue was purified by silica gel column chromatography to give the title compound as a colorless solid (0.56 g, 31%).

¹H NMR (300 MHz, CDCl₃) δ 0.87-0.93 (18H, m), 1.31-1.44 (2H, m), 1.47-1.82 (14H, m), 2.01 (3H, br), 2.56-2.70 (5H, m), 3.64-3.78 (1H, m), 3.81-3.91 (1H, m), 4.43 (1H, d, J=13.0), 7.33-7.50 (6H, m), 7.57-7.65 (1H, m), 7.74 (1H, d, J=7.7)

J=12.1), 4.88 (1H, d, J=5.8), 7.17-7.28 (4H, m), 7.45-7.59 (2H, m), 7.61-7.73 (2H, m), 12.38 (1H, s)

Example 45

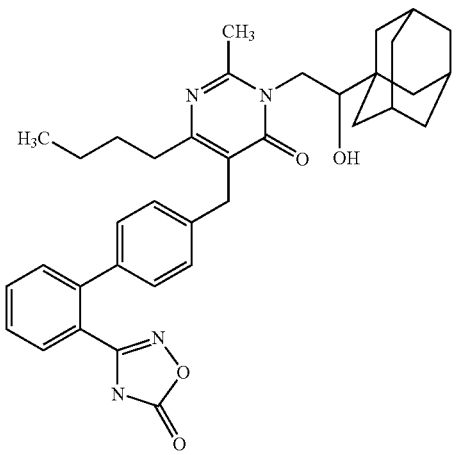

44b) 3-[2-(1-adamantyl)-2-hydroxyethyl]-6-butyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.90 g), sodium hydrogen carbonate (1.44 g) and dimethyl sulfoxide (15 mL) was stirred at 40° C. for 30 min, 4'-{[1-(2-(1-adamantyl)-2-{[tert-butyl(dimethyl)silyl]oxy}ethyl)-4-butyl-2-methyl-6-oxo-1,6-dihydropyrimidin-5-yl]methyl}biphenyl-2-carbonitrile (0.56 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.17 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure. The residue was dissolved in tetrahydrofuran (20 mL), tetrabutylammonium fluoride (1.0 M tetrahydrofuran solution, 3.9 mL) was added, and the mixture was stirred at room temperature for 3 hr. The reaction mixture was extracted with 1 M hydrochloric acid and ethyl acetate, and the ethyl acetate layer was washed with saturated brine and concentrated. The residue was purified by silica gel column chromatography to give the title compound as colorless crystals (0.11 g, 24%).

$^1$H NMR (300 MHz, DMSO-$d_6$) δ 0.83 (3H, t, J=7.4), 1.20-1.33 (2H, m), 1.36-1.48 (2H, m), 1.51-1.74 (12H, m), 1.96 (3H, s), 2.39-2.48 (2H, m), 2.52 (3H, s), 3.25-3.31 (1H, m), 3.62-3.72 (1H, m), 3.74-3.93 (2H, m), 4.24 (1H, d,

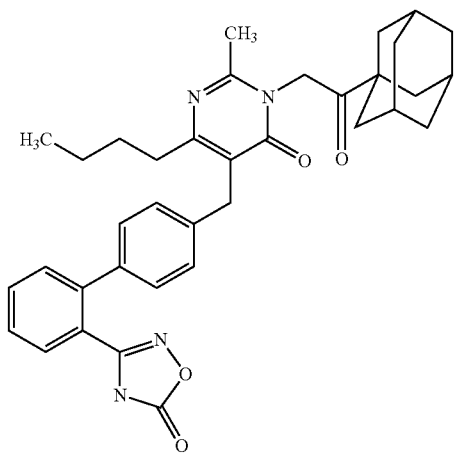

3-[2-(1-adamantyl)-2-oxoethyl]-6-butyl-2-methyl-5-{[2'-(5-oxo-4,5-dihydro-1,2,4-oxadiazol-3-yl)biphenyl-4-yl]methyl}pyrimidin-4(3H)-one A mixture of 3-[2-(1-adamantyl)-2-hydroxyethyl]-6-butyl-2-methyl-5-{[2'-(5-oxo-4,5-dihydro-1,2,4-oxadiazol-3-yl)biphenyl-4-yl]methyl}pyrimidin-4(3H)-one (0.078 g), 1,1,1-tris(acetyloxy)-1,1-dihydro-1,2-benziodoxol-3(1H)-one (0.067 g) and methylene chloride (10 mL) was stirred at room temperature for 2 hr. A saturated aqueous sodium hydrogen carbonate solution and sodium thiosulfate were added to the reaction mixture. The mixture was stirred at room temperature for 2 hr and extracted with chloroform. The chloroform layer was washed with saturated brine, and dried over anhydrous magnesium sulfate. The solvent was evaporated under reduced pressure. The obtained residue was purified by silica gel column chromatography to give the title compound as colorless crystals (0.057 g, 73%).

$^1$H NMR (300 MHz, DMSO-$d_6$) δ 0.83 (3H, t, J=7.4), 1.19-1.35 (2H, m), 1.39-1.55 (2H, m), 1.63-1.79 (6H, m), 1.82-1.96 (6H, m), 2.03 (3H, s), 2.26 (3H, s), 2.43-2.48 (2H, m), 3.83 (2H, s), 5.13 (2H, s), 7.20 (4H, s), 7.45-7.58 (2H, m), 7.60-7.73 (2H, m), 12.38 (1H, s)

Example 46

6-butyl-3-(4-fluorobenzyl)-2-methyl-5-{[2'-(5-oxo-4,5-dihydro-1,2,4-oxadiazol-3-yl)biphenyl-4-yl]methyl}pyrimidin-4(3H)-one

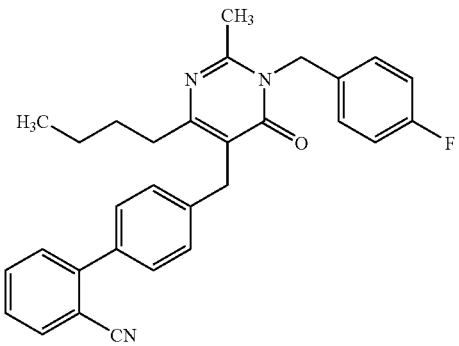

46a) 4'-{[4-butyl-1-(4-fluorobenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-(bromomethyl)-4-fluorobenzene (0.52 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.76 g, 58%).

$^1$H NMR (300 MHz, CDCl$_3$) δ 0.91 (3H, t, J=7.3), 1.31-1.46 (2H, m), 1.51-1.61 (2H, m), 2.46 (3H, s), 2.56-2.66 (2H, m), 4.00 (2H, s), 5.26 (2H, s), 6.98-7.10 (2H, m), 7.15-7.22 (2H, m), 7.33-7.52 (6H, m), 7.58-7.66 (1H, m), 7.75 (1H, d, J=8.5)

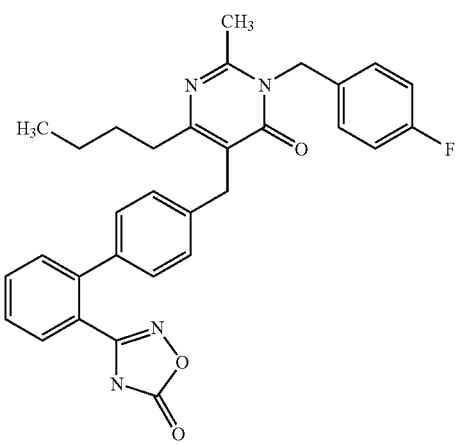

46b) 6-butyl-3-(4-fluorobenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.7 g), sodium hydrogen carbonate (2.74 g) and dimethyl sulfoxide (15 mL) was stirred at 40° C. for 30 min, 4'-{[4-butyl-1-(4-fluorobenzyl)-2-methyl-6-oxo-1,6-dihydropyrimidin-5-yl]methyl}biphenyl-2-carbonitrile (0.76 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.32 g) and then 1,8-diazabicyclo[5.4.0]undec-7-ene (0.27 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.55 g, 65%).

$^1$H NMR (300 MHz, DMSO-d$_6$) δ 0.83 (3H, t, J=7.4), 1.21-1.36 (2H, m), 1.38-1.56 (2H, m), 2.39 (3H, s), 2.43-2.51 (2H, m), 3.90 (2H, s), 5.26 (2H, s), 7.14-7.36 (8H, m), 7.44-7.59 (2H, m), 7.60-7.76 (2H, m), 12.40 (1H, s)

Example 47

3-benzyl-6-butyl-2-methyl-5-{[2'-(5-oxo-4,5-dihydro-1,2,4-oxadiazol-3-yl)biphenyl-4-yl]methyl}pyrimidin-4(3H)-one

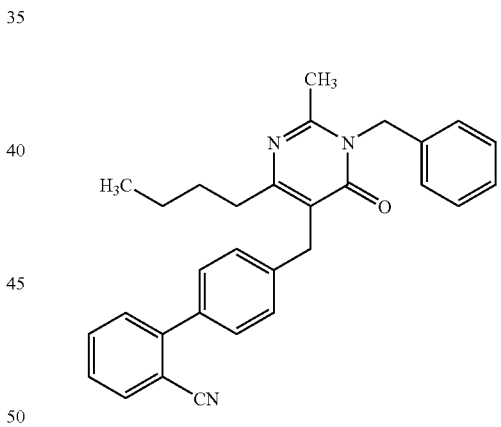

47a) 4'-[(1-benzyl-4-butyl-2-methyl-6-oxo-1,6-dihydropyrimidin-5-yl)methyl]biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, (bromomethyl)benzene (0.67 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.64 g, 51%).

¹H NMR (300 MHz, CDCl₃) δ 0.91 (3H, t, J=7.3), 1.32-1.45 (2H, m), 1.52-1.62 (2H, m), 2.45 (3H, s), 2.55-2.67 (2H, m), 4.01 (2H, s), 5.30 (2H, s), 7.16-7.23 (2H, m), 7.26-7.41 (6H, m), 7.43-7.51 (3H, m), 7.61 (1H, dd, J=7.6, 1.2), 7.74 (1H, dd, J=7.7, .9)

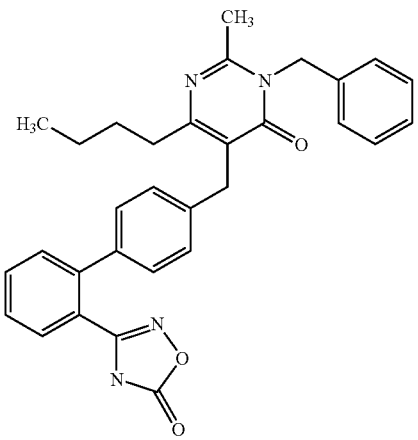

47b) 3-benzyl-6-butyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.49 g), sodium hydrogen carbonate (2.40 g) and dimethyl sulfoxide (15 mL) was stirred at 40° C. for 30 min, 4'-[(1-benzyl-4-butyl-2-methyl-6-oxo-1,6-dihydropyrimidin-5-yl)methyl]biphenyl-2-carbonitrile (0.64 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.28 g) and then 1,8-diazabicyclo[5.4.0]undec-7-ene (0.24 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.36 g, 49%).

¹H NMR (300 MHz, DMSO-d₆) δ 0.83 (3H, t, J=7.3), 1.23-1.38 (2H, m), 1.37-1.56 (2H, m), 2.38 (3H, s), 2.46-2.57 (2H, m), 3.91 (2H, s), 5.29 (2H, s), 7.13-7.42 (9H, m), 7.47-7.61 (2H, m), 7.61-7.74 (2H, m), 12.39 (1H, s)

3-Benzyl-6-butyl-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

3-benzyl-6-butyl-2-methyl-5-{[2'-(5-oxo-4,5-dihydro-1,2,4-oxadiazol-3-yl)biphenyl-4-yl]methyl}pyrimidin-4(3H)-one sodium salt 3-benzyl-6-butyl-2-methyl-5-{[2'-(5-oxo-4,5-dihydro-1,2,4-oxadiazol-3-yl)biphenyl-4-yl]methyl}pyrimidin-4(3H)-one potassium salt 3-benzyl-6-butyl-2-methyl-5-{[2'-(5-oxo-4,5-dihydro-1,2,4-oxadiazol-3-yl)biphenyl-4-yl]methyl}pyrimidin-4(3H)-one 0.5 calcium salt 3-benzyl-6-butyl-2-methyl-5-{[2'-(5-oxo-4,5-dihydro-1,2,4-oxadiazol-3-yl)biphenyl-4-yl]methyl}pyrimidin-4(3H)-one hydrochloride 3-benzyl-6-butyl-2-methyl-5-{[2'-(5-oxo-4,5-dihydro-1,2,4-oxadiazol-3-yl)biphenyl-4-yl]methyl}pyrimidin-4(3H)-one hydrobromide Example 48

6-butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one

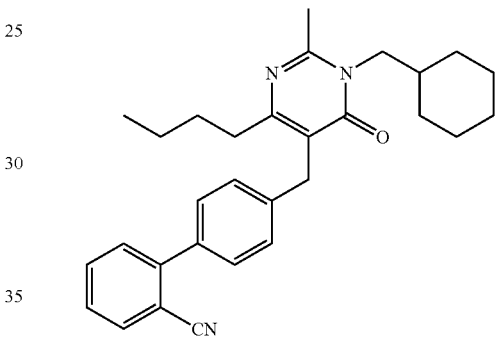

48a) 4'-{[4-butyl-1-(cyclohexylmethyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, (bromomethyl)cyclohexane (0.70 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.38 g, 30%).

¹H NMR (300 MHz, CDCl₃) δ 0.91 (3H, t, J=7.2), 0.99-1.26 (4H, m), 1.32-1.43 (2H, m), 1.50-1.78 (8H, m), 1.79-1.92 (1H, m), 2.53 (3H, s), 2.54-2.61 (2H, m), 3.86 (2H, d, J=7.0), 3.95 (2H, s), 7.31-7.49 (6H, m), 7.57-7.65 (1H, m), 7.74 (1H, dd, J=7.7, 0.9)

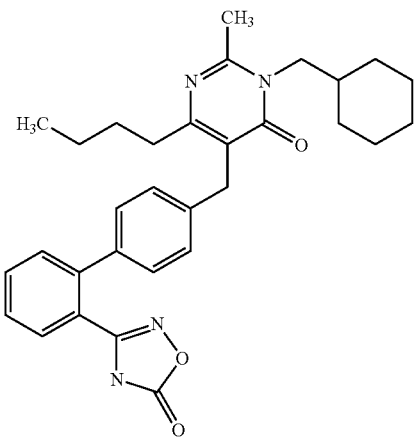

48b) 6-butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.88 g), sodium hydrogen carbonate (1.41 g) and dimethyl sulfoxide (15 mL) was stirred at 40° C. for 30 min, 4'-{[4-butyl-1-(cyclohexylmethyl)-2-methyl-6-oxo-1,6-dihydropyrimidin-5-yl]methyl}biphenyl-2-carbonitrile (0.38 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.16 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.14 g, 33%).

$^1$H NMR (300 MHz, DMSO-d$_6$) δ 0.82 (3H, t, J=7.3), 0.97-1.90 (15H, m), 2.40-2.50 (5H, m), 3.84 (4H, s), 7.03-7.27 (4H, m), 7.43-7.58 (2H, m), 7.60-7.72 (2H, m), 12.37 (1H, s)

6-Butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one dihydrochloride 6-butyl-3-(cyclohexylmethyl)-2-methyl-5-{[2'-(5-oxo-4,5-dihydro-1,2,4-oxadiazol-3-yl)biphenyl-4-yl]methyl}pyrimidin-4(3H)-one dihydrobromide Example 49

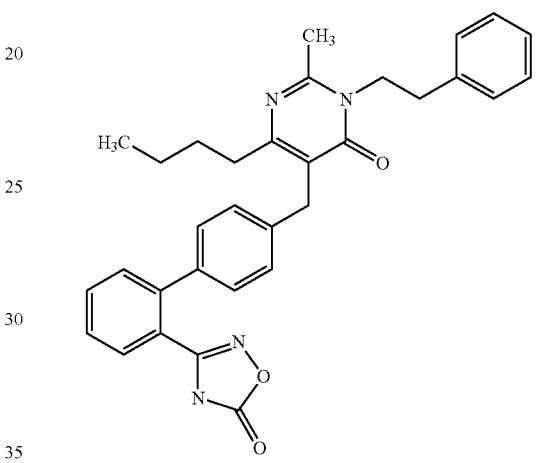

6-butyl-2-methyl-5-{[2'-(5-oxo-4,5-dihydro-1,2,4-oxadiazol-3-yl)biphenyl-4-yl]methyl}-3-(2-phenylethyl)pyrimidin-4(3H)-one A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, (2-bromoethyl)benzene (0.76 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.9 g), sodium hydrogen carbonate (1.45 g) and dimethyl sulfoxide (10 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.17 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.14 g, 31%).

$^1$H NMR (300 MHz, DMSO-$d_6$) δ 0.83 (3H, t, J=7.2), 1.17-1.33 (2H, m), 1.35-1.50 (2H, m), 2.37 (3H, s), 2.41-2.48 (2H, m), 2.94 (2H, t, J=7.5), 3.87 (2H, s), 4.14 (2H, t, J=8.1), 7.18-7.36 (9H, m), 7.47-7.57 (2H, m), 7.61-7.73 (2H, m), 12.38 (1H, br)

Example 50

6-butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one

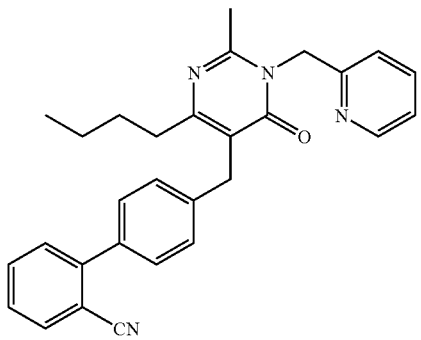

50a) 4'-{[4-butyl-2-methyl-6-oxo-1-(pyridin-2-ylmethyl)-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), potassium carbonate (0.77 g), 2-(bromomethyl)pyridine hydrobromide (1.06 g) and N,N-dimethylformamide (10 mL) was stirred at 50° C. for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.87 g, 69%).

$^1$H NMR (300 MHz, CDCl$_3$) δ 0.91 (3H, t, J=7.4), 1.30-1.44 (2H, m), 1.49-1.64 (2H, m), 2.56-2.65 (5H, m), 3.98 (2H, s), 5.38 (2H, s), 7.16-7.29 (2H, m), 7.32-7.52 (6H, m), 7.56-7.69 (2H, m), 7.74 (1H, dd, J=7.7, 0.9), 8.51-8.57 (1H, m)

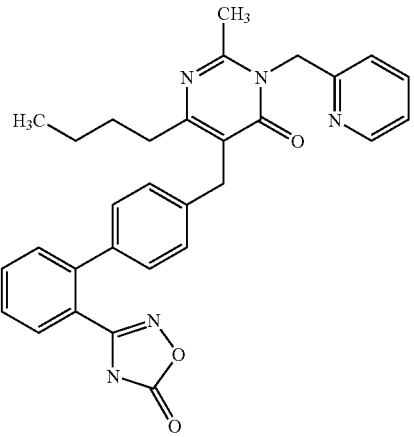

50b) 6-butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one A mixture of hydroxylammonium chloride (2.02 g), sodium hydrogen carbonate (3.24 g) and dimethyl sulfoxide (15 mL) was stirred at 40° C. for 30 min, 4'-{[4-butyl-2-methyl-6-oxo-1-(pyridin-2-ylmethyl)-1,6-dihydropyrimidin-5-yl]methyl}biphenyl-2-carbonitrile (0.87 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.24 g) and then 1,8-diazabicyclo[5.4.0]undec-7-ene (0.2 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (0.076 g, 8%).

$^1$H NMR (300 MHz, DMSO-$d_6$) δ 0.84 (3H, t, J=7.3), 1.22-1.38 (2H, m), 1.39-1.54 (2H, m), 2.42-2.52 (5H, m), 3.85 (2H, s), 5.34 (2H, s), 7.13-7.25 (4H, m), 7.25-7.40 (2H, m), 7.44-7.60 (2H, m), 7.59-7.76 (2H, m), 7.74-7.86 (1H, m), 8.42-8.55 (1H, m), 12.38 (1H, s)

6-Butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one obtained above is subjected to a conventional method of salt formation to give the following salts.

6-butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one sodium salt 6-butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one potassium salt 6-butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one 0.5 calcium salt 6-butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one hydrochloride

201

6-butyl-2-methyl-5-{[2'-(5-oxo-4,5-dihydro-1,2,4-oxadiazol-3-yl)biphenyl-4-yl]methyl}-3-(pyridin-2-ylmethyl)pyrimidin-4(3H)-one hydrobromide

Example 51

6-butyl-3-(2,2-dimethylpropyl)-2-(methoxymethyl)-5-{[2'-(5-oxo-4,5-dihydro-1,2,4-oxadiazol-3-yl)biphenyl-4-yl]methyl}pyrimidin-4(3H)-one

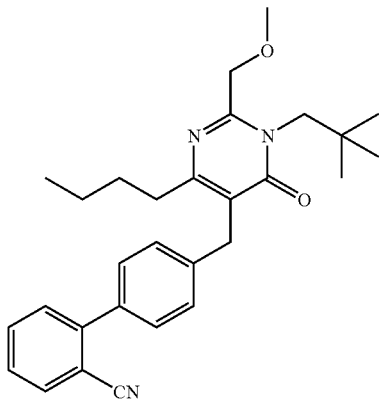

51a) 4'-{[4-butyl-1-(2,2-dimethylpropyl)-2-(methoxymethyl)-6-oxo-1,6-dihydropyrimidin-5-yl]methyl}biphenyl-2-carbonitrile A mixture of 4'-{[4-butyl-2-(methoxymethyl)-6-oxo-1,6-dihydropyrimidin-5-yl]methyl}biphenyl-2-carbonitrile (5 g), cesium carbonate (8.4 g), 1-iodo-2,2-dimethylpropane (3.4 mL) and N,N-dimethylacetamide (50 mL) was stirred at 130° C. for 2 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (1.76 g, 30%).

$^1$H NMR (300 MHz, CDCl$_3$) δ 0.91 (3H, t, J=7.4), 0.98 (9H, s), 1.30-1.45 (2H, m), 1.52-1.67 (2H, m), 2.57-2.66 (2H, m), 3.38 (3H, s), 3.97 (2H, s), 4.13 (2H, br), 4.54 (2H, br), 7.31-7.50 (6H, m), 7.57-7.65 (1H, m), 7.74 (1H, dd, J=7.7, 0.8)

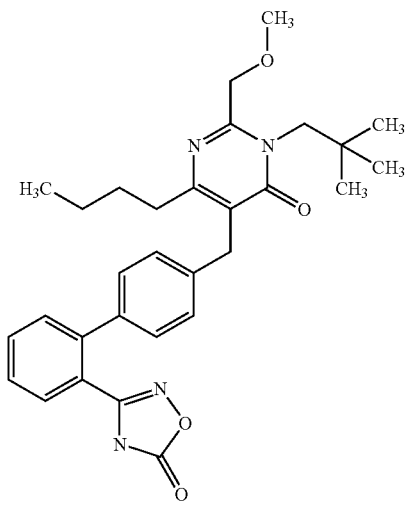

202

51b) 6-butyl-3-(2,2-dimethylpropyl)-2-(methoxymethyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (4.01 g), sodium hydrogen carbonate (6.50 g) and dimethyl sulfoxide (30 mL) was stirred at 40° C. for 30 min, 4'-{[4-butyl-1-(2,2-dimethylpropyl)-2-(methoxymethyl)-6-oxo-1,6-dihydropyrimidin-5-yl]methyl}biphenyl-2-carbonitrile (1.76 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (40 mL), N,N'-carbonyldiimidazole (0.75 g) and then 1,8-diazabicyclo[5.4.0]undec-7-ene (0.63 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.78 g, 39%).

$^1$H NMR (300 MHz, DMSO-d$_6$) δ 0.83 (3H, t, J=7.3), 0.90 (9H, s), 1.20-1.36 (2H, m), 1.41-1.55 (2H, m), 2.45-2.59 (5H, m), 3.88 (2H, s), 4.00 (2H, s), 4.47 (2H, s), 7.15-7.29 (4H, m), 7.52 (2H, dd, J=18.3, 7.5), 7.61-7.75 (2H, m), 12.37 (1H, s)

6-Butyl-3-(2,2-dimethylpropyl)-2-(methoxymethyl)-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(2,2-dimethylpropyl)-2-(methoxymethyl)-5-{[2'-(5-oxo-4,5-dihydro-1,2,4-oxadiazol-3-yl)biphenyl-4-yl]methyl}pyrimidin-4(3H)-one sodium salt 6-butyl-3-(2,2-dimethylpropyl)-2-(methoxymethyl)-5-{[2'-(5-oxo-4,5-dihydro-1,2,4-oxadiazol-3-yl)biphenyl-4-yl]methyl}pyrimidin-4(3H)-one potassium salt 6-butyl-3-(2,2-dimethylpropyl)-2-(methoxymethyl)-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(2,2-dimethylpropyl)-2-(methoxymethyl)-5-{[2'-(5-oxo-4,5-dihydro-1,2,4-oxadiazol-3-yl)biphenyl-4-yl]methyl}pyrimidin-4(3H)-one hydrochloride 6-butyl-3-(2,2-dimethylpropyl)-2-(methoxymethyl)-5-{[2'-(5-oxo-4,5-dihydro-1,2,4-oxadiazol-3-yl)biphenyl-4-yl]methyl}pyrimidin-4(3H)-one hydrobromide

Example 52

6-butyl-3-(2-hydroxy-2-phenylethyl)-2-methyl-5-{[2'-(5-oxo-4,5-dihydro-1,2,4-oxadiazol-3-yl)biphenyl-4-yl]methyl}pyrimidin-4(3H)-one

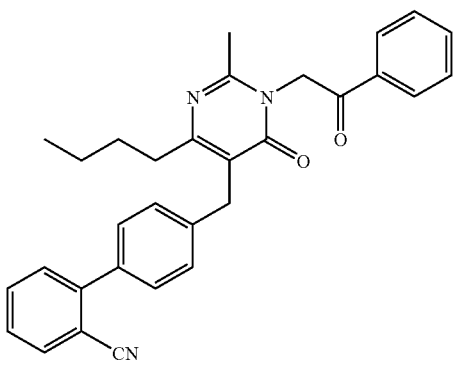

52a) 4'-{[4-butyl-2-methyl-6-oxo-1-(2-oxo-2-phenylethyl)-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.5 g), sodium hydride (0.25 g) and N,N-dimethylformamide (30 mL) was stirred at room temperature for 10 min, 2-bromo-1-phenylethanone (1.25 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.87 g, 43%).

$^1$H NMR (300 MHz, CDCl$_3$) δ 0.92 (3H, t, J=7.3), 1.31-1.49 (2H, m), 1.53-1.68 (2H, m), 2.41 (3H, s), 2.58-2.67 (2H, m), 3.97 (2H, s), 5.51 (2H, s), 7.31-7.68 (10H, m), 7.73 (1H, dd, J=7.7, 1.3), 8.00-8.08 (2H, m)

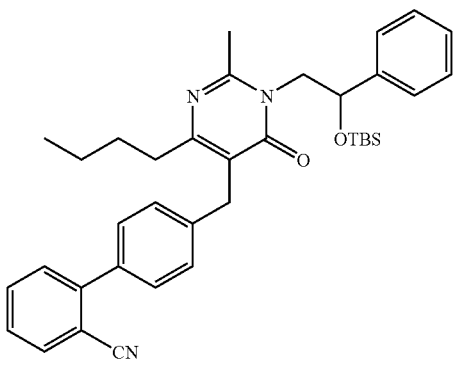

52b) 4'-{[4-butyl-1-(2-{[tert-butyl(dimethyl)silyl]oxy}-2-phenylethyl)-2-methyl-6-oxo-1,6-dihydropyrimidin-5-yl]methyl}biphenyl-2-carbonitrile A mixture of 4'-{[4-butyl-2-methyl-6-oxo-1-(2-oxo-2-phenylethyl)-1,6-dihydropyrimidin-5-yl]methyl}biphenyl-2-carbonitrile (0.87 g), sodium borohydride (0.21 g) and methanol (25 mL) was stirred at room temperature for 3 hr. The reaction mixture was concentrated. The residue was extracted with ethyl acetate and saturated aqueous ammonium chloride solution. The ethyl acetate layer was washed with saturated brine, and dried over anhydrous magnesium sulfate. The solvent was evaporated under reduced pressure. The obtained residue was dissolved in tetrahydrofuran (20 mL), and 2,6-lutidine (0.50 mL) and tert-butyl(dimethyl)silyl trifluoromethanesulfonate (0.98 mL) were added at 0° C. The reaction mixture was stirred at 0° C. for 3 hr, and diluted with ethyl acetate. The mixture was washed with water and then with saturated brine, and dried over anhydrous magnesium sulfate. The solvent was evaporated under reduced pressure and the residue was purified by silica gel column chromatography to give the title compound as a colorless solid (0.73 g, 29%).

$^1$H NMR (300 MHz, CDCl$_3$) δ −0.29-0.22 (6H, m), 0.78 (9H, s), 0.92 (3H, t, J=7.3), 1.32-1.45 (2H, m), 1.50-1.64 (2H, m), 2.51-2.75 (5H, m), 3.75 (1H, br), 3.98 (2H, dd, J=25.6, 15.1), 4.33-4.43 (1H, m), 5.22 (1H, dd, J=9.9, 2.9), 7.28-7.50 (11H, m), 7.58-7.65 (1H, m), 7.74 (1H, dd, J=7.7, 0.9)

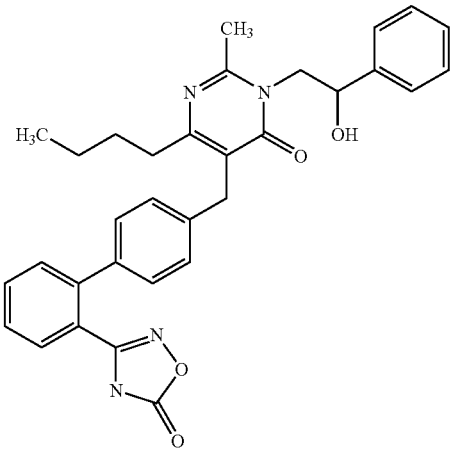

52c) 6-butyl-3-(2-hydroxy-2-phenylethyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.29 g), sodium hydrogen carbonate (2.07 g) and dimethyl sulfoxide (15 mL) was stirred at 40° C. for 30 min, 4'-{[4-butyl-1-(2-{[tert-butyl(dimethyl)silyl]oxy}-2-phenylethyl)-2-methyl-6-oxo-1,6-dihydropyrimidin-5-yl]methyl}biphenyl-2-carbonitrile (0.73 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.24 g) and then 1,8-diazabicyclo[5.4.0]undec-7-ene (0.20 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure. The residue was dissolved in tetrahydrofuran (20 mL), tetrabutylammonium fluoride (1.0 M tetrahydrofuran solution, 3.7 mL) was added, and the mixture was stirred at 70° C. for 6 hr. The reaction mixture was extracted with 1 M hydrochloric acid and ethyl acetate, and the ethyl acetate layer was washed with saturated brine and concentrated. The residue was purified by silica gel column chromatography to give the title compound as colorless crystals (0.37 g, 56%).

$^1$H NMR (300 MHz, DMSO-$d_6$) δ 0.83 (3H, t, J=7.3), 1.20-1.36 (2H, m), 1.35-1.53 (2H, m), 2.39-2.62 (5H, m), 3.78-3.99 (3H, m), 4.16 (1H, dd, J=13.7, 3.1), 4.86-5.07 (1H, m), 5.77 (1H, d, J=4.5), 7.16-7.33 (5H, m), 7.34-7.47 (4H, m), 7.46-7.59 (2H, m), 7.62-7.77 (2H, m), 12.39 (1H, s)

Example 53

6-(methoxymethyl)-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one

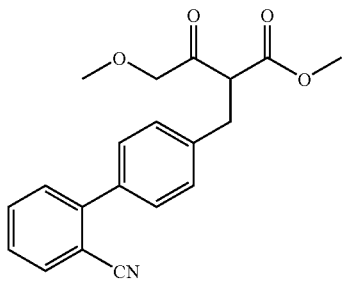

53a) methyl 2-[(2'-cyanobiphenyl-4-yl)methyl]-4-methoxy-3-oxobutanoate

A solution of methyl 4-methoxy-3-oxobutyrate (10.7 g) in tetrahydrofuran (150 mL) was added to a mixture of sodium hydride (1.91 g) and tetrahydrofuran (150 mL) at room temperature, and the mixture was stirred at room temperature for 30 min. 4'-(Bromomethyl)biphenyl-2-carbonitrile (10 g) was added to the reaction mixture, and the reaction mixture was stirred at room temperature for 3 days. The reaction mixture was concentrated. To the residue were added 5% aqueous potassium hydrogen sulfate solution and then ethyl acetate, and the mixture was extracted. The ethyl acetate layer was washed with saturated brine and concentrated. The residue was purified by silica gel column chromatography to give the title compound as a colorless oil (12.1 g, 98%).

$^1$H NMR (300 MHz, CDCl$_3$) δ 3.25 (2H, t, J=7.4), 3.34 (3H, s), 3.71 (3H, s), 3.88-4.12 (3H, m), 7.25-7.34 (2H, m), 7.39-7.51 (4H, m), 7.60-7.67 (1H, m), 7.75 (1H, d, J=7.7)

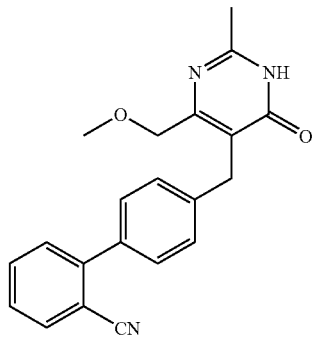

53b) 4'-{[4-(methoxymethyl)-2-methyl-6-oxo-1,6-dihydropyrimidin-5-yl]methyl}biphenyl-2-carbonitrile To a solution of acetamidine hydrochloride (3.4 g) in methanol (30 mL) was added sodium methoxide (28% methanol solution, 10.3 g) at 0° C., a solution of methyl 2-[(2'-cyanobiphenyl-4-yl)methyl]-4-methoxy-3-oxobutanoate in methanol (60 mL)-1,4-dioxane (20 mL) was added, and the mixture was stirred at room temperature for 16 hr. The reaction mixture was concentrated, and water (50 mL) and 50% aqueous acetic acid solution were added to the residue and adjusted to pH 5. The obtained crystallized product was collected by filtration and washed with water to give the title compound as colorless crystals (5.27 g, 86%).

$^1$H NMR (300 MHz, DMSO-$d_6$) δ 2.27 (3H, s), 3.27 (3H, s), 3.89 (2H, s), 4.30 (2H, s), 7.33-7.39 (2H, m), 7.45-7.51 (2H, m), 7.53-7.61 (2H, m), 7.77 (1H, dt, J=7.7, 1.0), 7.93 (1H, d, J=7.7), 12.49 (1H, s)

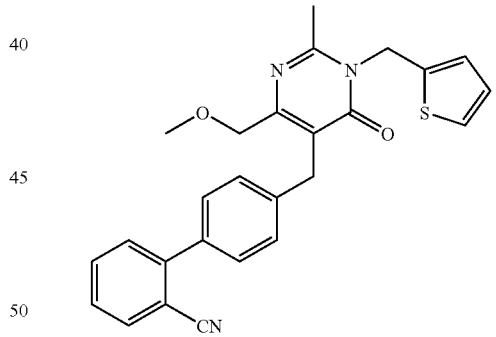

53c) 4'-{[4-(methoxymethyl)-2-methyl-6-oxo-1-(2-thienylmethyl)-1,6-dihydropyrimidin-5-yl]methyl}biphenyl-2-carbonitrile A mixture of 4'-{[4-(methoxymethyl)-2-methyl-6-oxo-1,6-dihydropyrimidin-5-yl]methyl}biphenyl-2-carbonitrile (1 g), sodium hydride (0.17 g) and N,N-dimethylformamide (10 mL) was stirred at room temperature for 10 min, 2-(bromomethyl)thiophene (4.5 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.68 g, 53%).

$^1$H NMR (300 MHz, CDCl$_3$) δ 2.66 (3H, s), 3.44 (3H, s), 4.06 (2H, s), 4.38 (2H, s), 5.39 (2H, s), 6.95 (1H, dd, J=5.1, 3.4), 7.06 (1H, dd, J=3.5, 1.0), 7.22-7.29 (1H, m), 7.37-7.43 (3H, m), 7.43-7.50 (3H, m), 7.62 (1H, dt, J=7.7, 1.4), 7.74 (1H, dd, J=7.7, 0.9)

3.4), 7.14-7.24 (3H, m), 7.26-7.32 (2H, m), 7.43-7.58 (3H, m), 7.62-7.73 (2H, m), 12.39 (1H, s)

Example 54

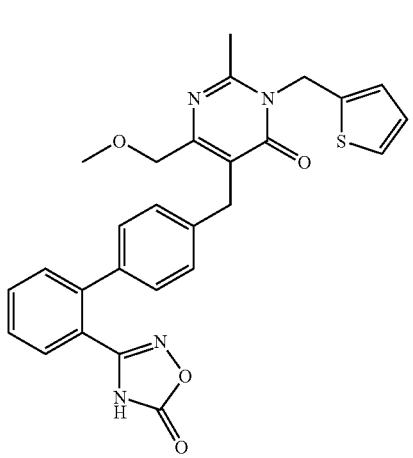

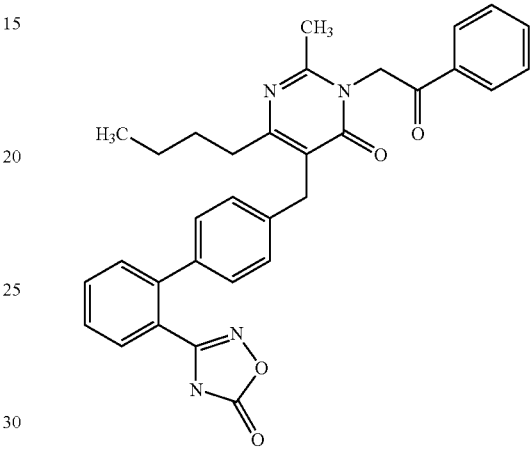

53d) 6-(methoxymethyl)-2-methyl-5-{[2'-(5-oxo-4,5-dihydro-1,2,4-oxadiazol-3-yl)biphenyl-4-yl]methyl}-3-(2-thienylmethyl)pyrimidin-4(3H)-one A mixture of hydroxylammonium chloride (1.29 g), sodium hydrogen carbonate (1.94 g) and dimethyl sulfoxide (15 mL) was stirred at 40° C. for 30 min, 4'-{[4-(methoxymethyl)-2-methyl-6-oxo-1-(2-thienylmethyl)-1,6-dihydropyrimidin-5-yl]methyl}biphenyl-2-carbonitrile (0.68 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.3 g) and then 1,8-diazabicyclo[5.4.0]undec-7-ene (0.25 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.4 g, 52%).

$^1$H NMR (300 MHz, DMSO-d$_6$) δ 2.56 (3H, s), 3.23 (3H, s), 3.93 (2H, s), 4.27 (2H, s), 5.39 (2H, s), 6.99 (1H, dd, J=5.1,

6-butyl-2-methyl-5-{[2'-(5-oxo-4,5-dihydro-1,2,4-oxadiazol-3-yl)biphenyl-4-yl]methyl}-3-(2-oxo-2-phenylethyl)pyrimidin-4(3H)-one A mixture of 6-butyl-3-(2-hydroxy-2-phenylethyl)-2-methyl-5-{[2'-(5-oxo-4,5-dihydro-1,2,4-oxadiazol-3-yl)biphenyl-4-yl]methyl}pyrimidin-4(3H)-one (0.25 g), 1,1,1-tris(acetyloxy)-1,1-dihydro-1,2-benziodoxol-3(1H)-one (0.3 g) and methylene chloride (10 mL) was stirred at room temperature for 2 hr. A saturated aqueous sodium hydrogen carbonate solution and sodium thiosulfate were added to the reaction mixture, and the mixture was stirred at room temperature for 2 hr and extracted with chloroform. The chloroform layer was washed with saturated brine, and dried over anhydrous magnesium sulfate. The solvent was evaporated under reduced pressure. The obtained residue was purified by silica gel column chromatography to give the title compound as colorless crystals (0.2 g, 78%).

$^1$H NMR (300 MHz, DMSO-d$_6$) δ 0.85 (3H, t, J=7.3), 1.22-1.39 (2H, m), 1.39-1.58 (2H, m), 2.37 (3H, s), 2.51-2.56 (2H, m), 3.85 (2H, s), 5.65 (2H, s), 7.21 (4H, s), 7.43-7.83 (7H, m), 8.02-8.15 (2H, m), 12.37 (1H, s)

Example 55

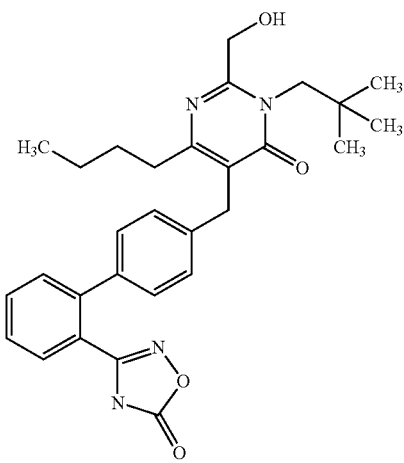

6-butyl-3-(2,2-dimethylpropyl)-2-(hydroxymethyl)-
5-{[2'-(5-oxo-4,5-dihydro-1,2,4-oxadiazol-3-yl)bi-
phenyl-4-yl]methyl}pyrimidin-4(3H)-one A mixture of 6-butyl-3-(2,2-dimethylpropyl)-2-(methoxymethyl)-5-{[2'-(5-oxo-4,5-dihydro-1,2,4-oxadiazol-3-yl)biphenyl-4-yl]methyl}pyrimidin-4(3H)-one (0.5 g), boron tribromide (1.0 M dichloromethane solution, 2.9 mL) and dichloromethane (20 mL) was stirred at room temperature for 3 hr, 0.5 M aqueous sodium hydroxide solution (10 mL) was added, and the mixture was further stirred for 1 hr. To the reaction mixture was added 1 M hydrochloric acid and adjusted to pH 5. Ethyl acetate was added, and the mixture was extracted. The ethyl acetate layer was washed with saturated brine, and dried over anhydrous magnesium sulfate. The solvent was evaporated under reduced pressure and the residue was purified by silica gel column chromatography to give the title compound as a colorless solid (0.48 g, 98%).

$^1$H NMR (300 MHz, DMSO-$d_6$) δ 0.84 (3H, t, J=7.3), 0.90 (9H, s), 1.21-1.36 (2H, m), 1.41-1.53 (2H, m), 2.50-2.57 (2H, m), 3.87 (2H, s), 4.03 (2H, s), 4.50 (2H, d, J=5.3), 5.51 (1H, t, J=5.7), 7.15-7.28 (4H, m), 7.44-7.60 (2H, m), 7.60-7.74 (2H, m), 12.37 (1H, s)

Example 56

6-butyl-3-(4-chlorobenzyl)-2-methyl-5-{[2'-(5-oxo-4,5-dihydro-1,2,4-oxadiazol-3-yl)biphenyl-4-yl]methyl}pyrimidin-4(3H)-one

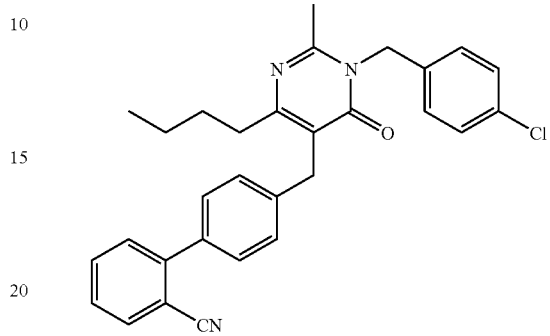

56a) 4'-{[4-butyl-1-(4-chlorobenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (15 mL) was stirred at room temperature for 10 min, 1-(bromomethyl)-4-chlorobenzene (0.69 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.84 g, 62%).

$^1$H NMR (300 MHz, CDCl$_3$) δ 0.91 (3H, t, J=7.3), 1.31-1.46 (2H, m), 1.51-1.65 (2H, m), 2.44 (3H, s), 2.56-2.65 (2H, m), 4.00 (2H, s), 5.25 (2H, s), 7.14 (2H, d, J=8.3), 7.25-7.52 (8H, m), 7.58-7.66 (1H, m), 7.75 (1H, d, J=7.3)

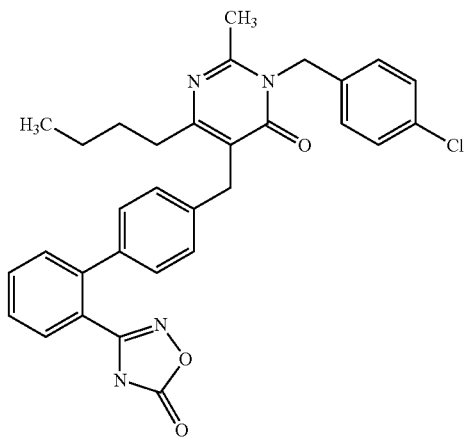

56b) 6-butyl-3-(4-chlorobenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.81 g), sodium hydrogen carbonate (2.92 g) and dimethyl sulfoxide (15 mL) was stirred at 40° C. for 30 min, 4'-{[4-butyl-1-(4-chlorobenzyl)-2-methyl-6-oxo-1,6-dihydropyrimidin-5-yl]methyl}biphenyl-2-carbonitrile (0.84 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.34 g) and then 1,8-diazabicyclo[5.4.0]undec-7-ene (0.29 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.42 g, 45%).

$^1$H NMR (300 MHz, DMSO-d$_6$) δ 0.83 (3H, t, J=7.3), 1.19-1.36 (2H, m), 1.36-1.54 (2H, m), 2.38 (3H, s), 2.43-2.49 (2H, m), 3.90 (2H, s), 5.27 (2H, s), 7.16-7.30 (6H, m), 7.37-7.47 (2H, m), 7.53 (2H, dd, J=15.6, 7.7), 7.60-7.79 (2H, m), 12.39 (1H, s)

Example 57

6-butyl-2-methyl-3-(4-methylbenzyl)-5-{[2'-(5-oxo-4,5-dihydro-1,2,4-oxadiazol-3-yl)biphenyl-4-yl]methyl}pyrimidin-4(3H)-one

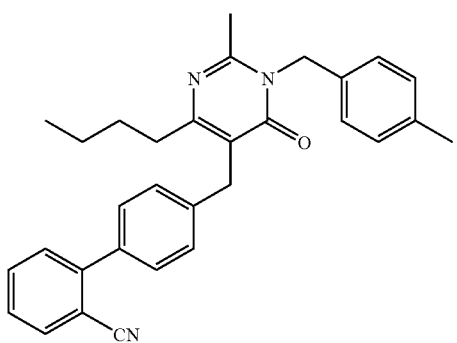

57a) 4'-{[4-butyl-2-methyl-1-(4-methylbenzyl)-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (15 mL) was stirred at room temperature for 10 min, 1-(bromomethyl)-4-methylbenzene (0.62 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.79 g, 61%).

$^1$H NMR (300 MHz, CDCl$_3$) δ 0.91 (3H, t, J=7.3), 1.30-1.46 (2H, m), 1.49-1.65 (2H, m), 2.32 (3H, s), 2.45 (3H, s), 2.55-2.64 (2H, m), 4.01 (2H, s), 5.26 (2H, s), 7.11 (4H, q, J=8.1), 7.34-7.52 (6H, m), 7.58-7.65 (1H, m), 7.75 (1H, d, J=9.0)

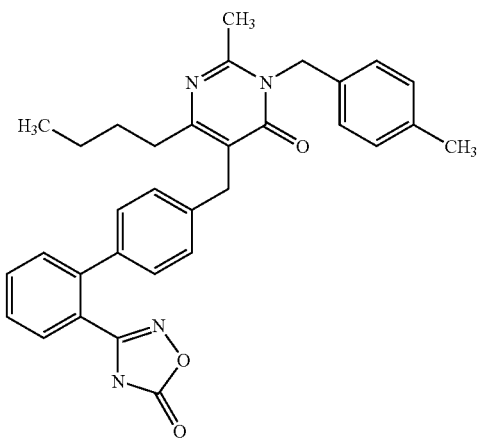

57b) 6-butyl-2-methyl-3-(4-methylbenzyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.79 g), sodium hydrogen carbonate (2.87 g) and dimethyl sulfoxide (15 mL) was stirred at 40° C. for 30 min, 4'-{[4-butyl-2-methyl-1-(4-methylbenzyl)-6-oxo-1,6-dihydropyrimidin-5-yl]methyl}biphenyl-2-carbonitrile (0.79 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.33 g) and then 1,8-diazabicyclo[5.4.0]undec-7-ene (0.28 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.53 g, 59%).

$^1$H NMR (300 MHz, DMSO-d$_6$) δ 0.83 (3H, t, J=7.3), 1.18-1.37 (2H, m), 1.36-1.53 (2H, m), 2.27 (3H, s), 2.38 (3H, s), 2.44-2.49 (2H, m), 3.90 (2H, s), 5.24 (2H, s), 7.06 (2H, d, J=8.1), 7.17 (2H, d, J=7.9), 7.20-7.29 (4H, m), 7.46-7.61 (2H, m), 7.62-7.79 (2H, m), 12.39 (1H, s)

Example 58

6-butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one

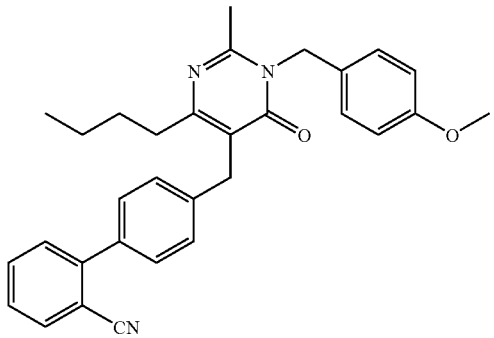

58a) 4'-{[4-butyl-1-(4-methoxybenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (15 mL) was stirred at room temperature for 10 min, 1-(chloromethyl)-4-methoxybenzene (0.46 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.83 g, 62%).

$^1$H NMR (300 MHz, CDCl$_3$) δ 0.91 (3H, t, J=7.3), 1.31-1.45 (2H, m), 1.49-1.66 (2H, m), 2.47 (3H, s), 2.54-2.64 (2H, m), 3.78 (3H, s), 4.01 (2H, s), 5.23 (2H, s), 6.88 (2H, d, J=8.7), 7.15 (2H, d, J=8.7), 7.34-7.52 (6H, m), 7.58-7.69 (1H, m), 7.72-7.79 (1H, m)

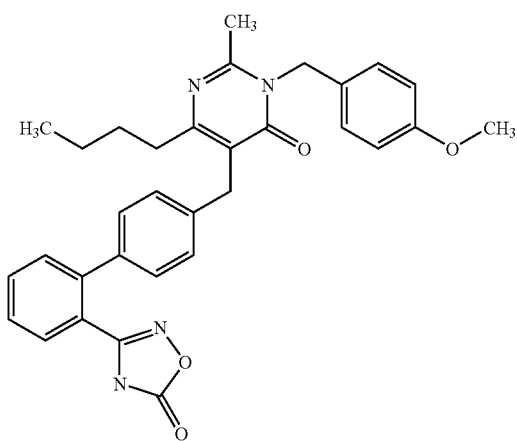

58b) 6-butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.81 g), sodium hydrogen carbonate (2.92 g) and dimethyl sulfoxide (15 mL) was stirred at 40° C. for 30 min, 4'-{[4-butyl-1-(4-methoxybenzyl)-2-methyl-6-oxo-1,6-dihydropyrimidin-5-yl]methyl}biphenyl-2-carbonitrile (0.83 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.34 g) and then 1,8-diazabicyclo[5.4.0]undec-7-ene (0.29 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.51 g, 54%).

$^1$H NMR (300 MHz, DMSO-d$_6$) δ 0.83 (3H, t, J=7.3), 1.21-1.36 (2H, m), 1.36-1.51 (2H, m), 2.39 (3H, s), 2.45-2.49 (2H, m), 3.73 (3H, s), 3.90 (2H, s), 5.21 (2H, s), 6.92 (2H, d, J=8.7), 7.14 (2H, d, J=8.7), 7.19-7.33 (4H, m), 7.47-7.61 (2H, m), 7.60-7.77 (2H, m), 12.39 (1H, s)

6-Butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one hydrochloride 6-butyl-3-(4-methoxybenzyl)-2-methyl-5-{[2'-(5-oxo-4,5-dihydro-1,2,4-oxadiazol-3-yl)biphenyl-4-yl]methyl}pyrimidin-4(3H)-one hydrobromide

Example 59

6-butyl-3-(4-tert-butylbenzyl)-2-methyl-5-{[2'-(5-oxo-4,5-dihydro-1,2,4-oxadiazol-3-yl)biphenyl-4-yl]methyl}pyrimidin-4(3H)-one

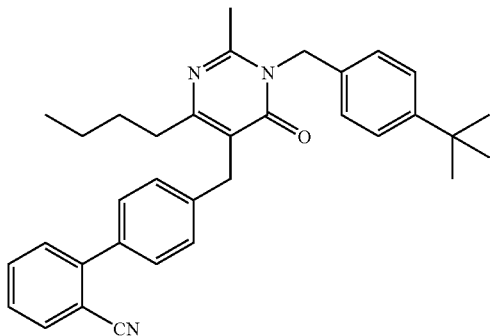

59a) 4'-{[4-butyl-1-(4-tert-butylbenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (15 mL) was stirred at room temperature for 10 min, 1-(bromomethyl)-4-tert-butylbenzene (0.62 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.86 g, 61%).

$^1$H NMR (300 MHz, CDCl$_3$) δ 0.91 (3H, t, J=7.3), 1.29 (9H, s), 1.34-1.45 (2H, m), 1.49-1.59 (2H, m), 2.47 (3H, s), 2.54-2.65 (2H, m), 4.01 (2H, s), 5.27 (2H, s), 7.13 (2H, d, J=8.3), 7.31-7.54 (8H, m), 7.55-7.67 (1H, m), 7.75 (1H, dd, J=7.7, 1.3)

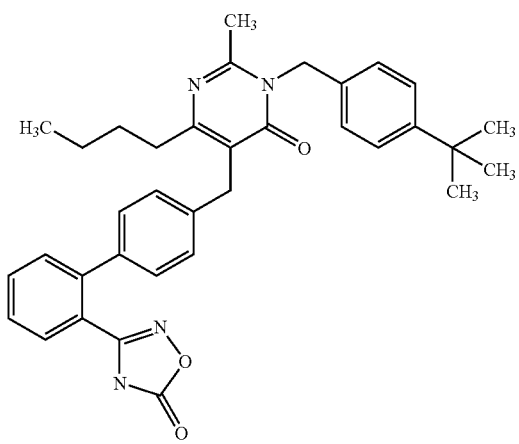

59b) 6-butyl-3-(4-tert-butylbenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.79 g), sodium hydrogen carbonate (2.87 g) and dimethyl sulfoxide (15 mL) was stirred at 40° C. for 30 min, 4'-{[4-butyl-1-(4-tert-butylbenzyl)-2-methyl-6-oxo-1,6-dihydropyrimidin-5-yl]methyl}biphenyl-2-carbonitrile (0.86 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.33 g) and then 1,8-diazabicyclo[5.4.0]undec-7-ene (0.28 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.55 g, 57%).

$^1$H NMR (300 MHz, DMSO-d$_6$) δ 0.83 (3H, t, J=7.3), 1.22-1.37 (11H, m), 1.39-1.54 (2H, m), 2.39 (3H, s), 2.45-2.49 (2H, m), 3.90 (2H, s), 5.24 (2H, s), 7.10 (2H, d, J=8.5), 7.19-7.32 (4H, m), 7.38 (2H, d, J=8.3), 7.47-7.61 (2H, m), 7.61-7.75 (2H, m), 12.39 (1H, s)

Example 60

6-butyl-2-methyl-3-[(5-methyl-1-benzothien-2-yl)methyl]-5-{[2'-(5-oxo-4,5-dihydro-1,2,4-oxadiazol-3-yl)biphenyl-4-yl]methyl}pyrimidin-4(3H)-one

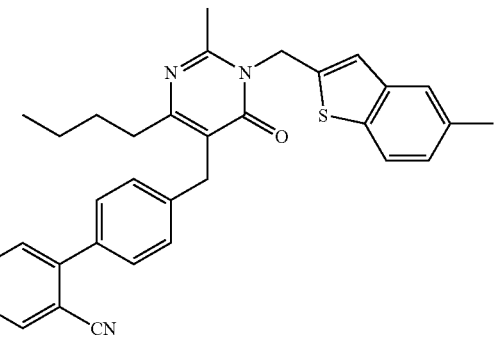

60a) 4'-({4-butyl-2-methyl-1-[(5-methyl-1-benzothien-2-yl)methyl]-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), (5-methyl-1-benzothien-2-yl)methanol (0.75 g) and tetrahydrofuran (50 mL) was stirred at room temperature for 4 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.63 g, 44%).

¹H NMR (300 MHz, CDCl₃) δ 0.90 (3H, t, J=7.4), 1.29-1.43 (2H, m), 1.48-1.60 (2H, m), 2.43 (3H, s), 2.54-2.64 (5H, m), 4.02 (2H, s), 5.45 (2H, s), 7.10-7.19 (2H, m), 7.34-7.53 (7H, m), 7.56-7.67 (2H, m), 7.74 (1H, dd, J=7.7, 0.9)

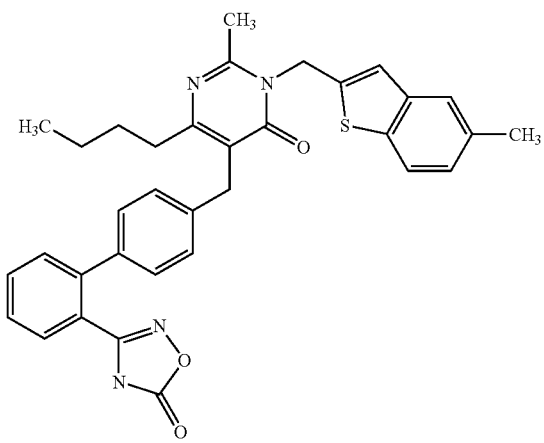

60b) 6-butyl-2-methyl-3-[(5-methyl-1-benzothien-2-yl)methyl]-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.28 g), sodium hydrogen carbonate (2.07 g) and dimethyl sulfoxide (15 mL) was stirred at 40° C. for 30 min, 4'-({4-butyl-2-methyl-1-[(5-methyl-1-benzothien-2-yl)methyl]-6-oxo-1,6-dihydropyrimidin-5-yl}methyl)biphenyl-2-carbonitrile (0.63 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.24 g) and then 1,8-diazabicyclo[5.4.0]undec-7-ene (0.2 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.25 g, 35%).

¹H NMR (300 MHz, DMSO-d₆) δ 0.81 (3H, t, J=7.2), 1.16-1.34 (2H, m), 1.35-1.53 (2H, m), 2.39 (3H, s), 2.43-2.49 (2H, m), 2.56 (3H, s), 3.91 (2H, s), 5.49 (2H, s), 7.12-7.35 (5H, m), 7.38 (1H, s), 7.44-7.74 (5H, m), 7.79 (1H, d, J=8.1), 12.38 (1H, s)

Example 61

6-butyl-3-[(2,2-dimethyl-2,3-dihydro-1-benzofuran-7-yl)methyl]-2-methyl-5-{[2'-(5-oxo-4,5-dihydro-1,2,4-oxadiazol-3-yl)biphenyl-4-yl]methyl}pyrimidin-4(3H)-one

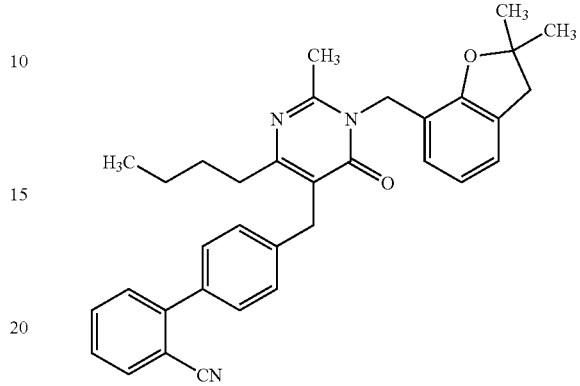

61a) 4'-({4-butyl-1-[(2,2-dimethyl-2,3-dihydro-1-benzofuran-7-yl)methyl]-2-methyl-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), (2,2-dimethyl-2,3-dihydro-1-benzofuran-7-yl)methanol (0.75 g) and tetrahydrofuran (50 mL) was stirred at room temperature for 4 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.67 g, 46%).

¹H NMR (300 MHz, CDCl₃) δ 0.90 (3H, t, J=7.3), 1.31-1.42 (2H, m), 1.44 (6H, s), 1.49-1.60 (2H, m), 2.48 (3H, s), 2.55-2.64 (2H, m), 3.01 (2H, s), 4.00 (2H, s), 5.23 (2H, s), 6.76 (1H, t, J=7.5), 6.92 (1H, d, J=7.3), 7.04 (1H, dd, J=7.2, 0.9), 7.32-7.52 (6H, m), 7.56-7.66 (1H, m), 7.74 (1H, dd, J=7.7, 0.8)

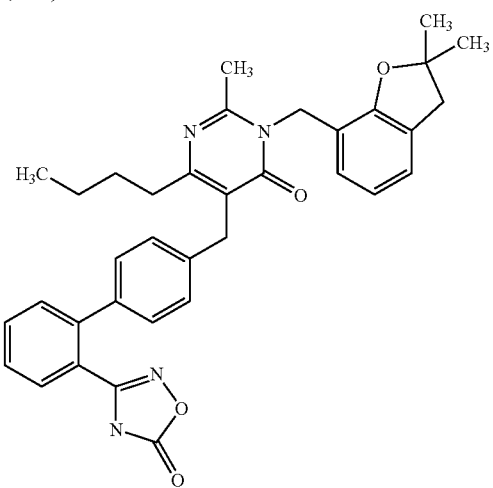

61b) 6-butyl-3-[(2,2-dimethyl-2,3-dihydro-1-benzofuran-7-yl)methyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.35 g), sodium hydrogen carbonate (2.17 g) and dimethyl sulfoxide (15 mL) was stirred at 40° C. for 30 min, 4'-({4-butyl-1-[(2,2-dimethyl-2,3-dihydro-1-benzofuran-7-yl)methyl]-2-methyl-6-oxo-1,6-dihydropyrimidin-5-yl}methyl)biphenyl-2-carbonitrile (0.67 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.25 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.16 g, 21%).

$^1$H NMR (300 MHz, DMSO-$d_6$) δ 0.83 (3H, t, J=7.2), 1.22-1.33 (2H, m), 1.36-1.51 (8H, m), 2.39 (3H, s), 2.45-2.49 (2H, m), 3.01 (2H, s), 3.88 (2H, s), 5.13 (2H, s), 6.67-6.81 (2H, m), 7.10 (1H, d, J=7.0), 7.18-7.27 (4H, m), 7.46-7.59 (2H, m), 7.61-7.72 (2H, m), 12.39 (1H, br)

Example 62

6-butyl-3-[(6-ethylpyridin-3-yl)methyl]-2-methyl-5-{[2'-(5-oxo-4,5-dihydro-1,2,4-oxadiazol-3-yl)biphenyl-4-yl]methyl}pyrimidin-4(3H)-one

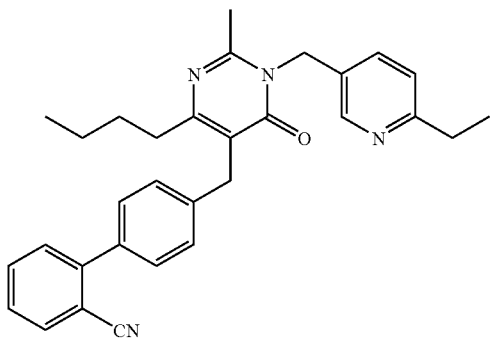

62a) 4'-({4-butyl-1-[(6-ethylpyridin-3-yl)methyl]-2-methyl-6-oxo-1,6-dihydropyrimidin-5-yl}methyl)biphenyl-2-carbonitrile A mixture of (6-ethylpyridin-3-yl)methanol hydrochloride (0.74 g) and saturated potassium carbonate (10 mL) was extracted with chloroform. The chloroform layer was dried over anhydrous magnesium sulfate, and the solvent was evaporated under reduced pressure. The residue was dissolved in tetrahydrofuran (50 mL), 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g) and tributylphosphine (1.56 mL) were added, and the mixture was stirred at room temperature for 16 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.93 g, 70%).

$^1$H NMR (300 MHz, CDCl$_3$) δ 0.93 (3H, t), 1.22-1.45 (7H, m), 2.49 (3H, s), 2.57-2.65 (2H, m), 2.75-2.89 (2H, m), 3.99 (2H, s), 5.26 (2H, s), 7.15 (1H, d, J=8.1), 7.32-7.53 (7H, m), 7.58-7.66 (1H, m), 7.74 (1H, dd, J=7.7, 0.8), 8.44 (1H, d, J=2.3)

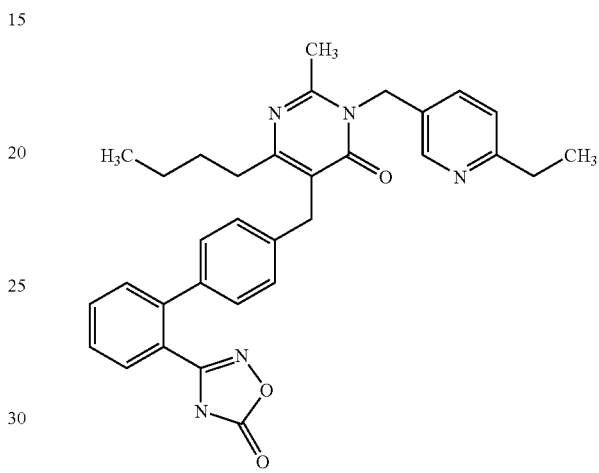

62b) 6-butyl-3-[(6-ethylpyridin-3-yl)methyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (2.04 g), sodium hydrogen carbonate (3.28 g) and dimethyl sulfoxide (15 mL) was stirred at 40° C. for 30 min, 4'-({4-butyl-1-[(6-ethylpyridin-3-yl)methyl]-2-methyl-6-oxo-1,6-dihydropyrimidin-5-yl}methyl)biphenyl-2-carbonitrile (0.93 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.38 g) and then 1,8-diazabicyclo[5.4.0]undec-7-ene (0.32 mL) were added, and the mixture was stirred at room temperature for 2 hr. Water was added to the reaction mixture, and 1 M hydrochloric acid was added and adjusted to pH 5, and the mixture was extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (0.38 g, 36%).

$^1$H NMR (300 MHz, DMSO-$d_6$) δ 0.83 (3H, t, J=7.3), 1.15-1.36 (5H, m), 1.37-1.55 (2H, m), 2.36-2.51 (5H, m), 2.72 (2H, q, J=7.5), 3.90 (2H, s), 5.26 (2H, s), 7.17-7.35 (5H, m), 7.45-7.58 (3H, m), 7.62-7.75 (2H, m), 8.40 (1H, d, J=1.9), 12.40 (1H, s)

Example 63

6-butyl-3-[(2,4-dimethyl-1,3-thiazol-5-yl)methyl]-2-methyl-5-{[2'-(5-oxo-4,5-dihydro-1,2,4-oxadiazol-3-yl)biphenyl-4-yl]methyl}pyrimidin-4(3H)-one

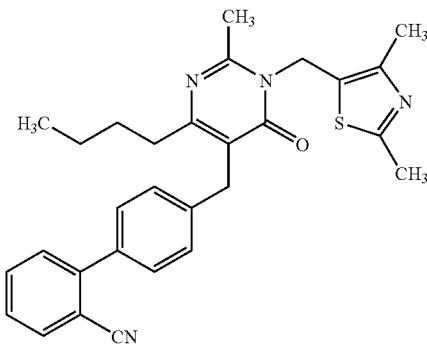

63a) 4'-({4-butyl-1-[(2,4-dimethyl-1,3-thiazol-5-yl)methyl]-2-methyl-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), (2,4-dimethyl-1,3-thiazol-5-yl)methanol (0.6 g) and tetrahydrofuran (50 mL) was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (1.33 g, 99%).

$^1$H NMR (300 MHz, CDCl$_3$) δ 0.89 (3H, t, J=7.4), 1.31-1.74 (4H, m), 2.47 (3H, s), 2.51-2.57 (5H, m), 2.59 (3H, s), 4.00 (2H, s), 5.26 (2H, s), 7.33-7.51 (6H, m), 7.58-7.66 (1H, m), 7.74 (1H, dd, J=7.7, 0.9)

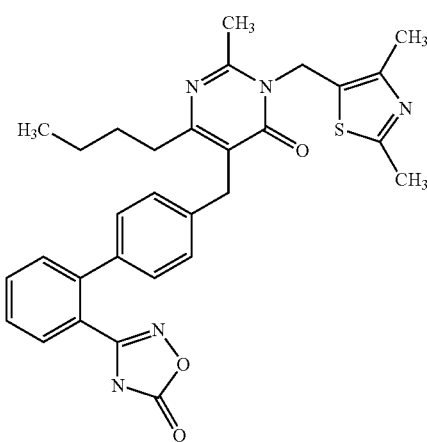

63b) 6-butyl-3-[(2,4-dimethyl-1,3-thiazol-5-yl)methyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (2.9 g), sodium hydrogen carbonate (4.7 g) and dimethyl sulfoxide (15 mL) was stirred at 40° C. for 30 min, 4'-({4-butyl-1-[(2,4-dimethyl-1,3-thiazol-5-yl)methyl]-2-methyl-6-oxo-1,6-dihydropyrimidin-5-yl}methyl)biphenyl-2-carbonitrile (1.33 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.49 g) and then 1,8-diazabicyclo[5.4.0]undec-7-ene (0.41 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.42 g, 27%).

$^1$H NMR (300 MHz, DMSO-d$_6$) δ 0.82 (3H, t, J=7.3), 1.15-1.35 (2H, m), 1.34-1.52 (2H, m), 2.39 (3H, s), 2.41-2.48 (2H, m), 2.49 (3H, s), 2.52 (3H, s), 3.89 (2H, s), 5.29 (2H, s), 7.17-7.32 (4H, m), 7.43-7.61 (2H, m), 7.61-7.80 (2H, m), 12.39 (1H, s)

Example 64

3-(1,3-benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one

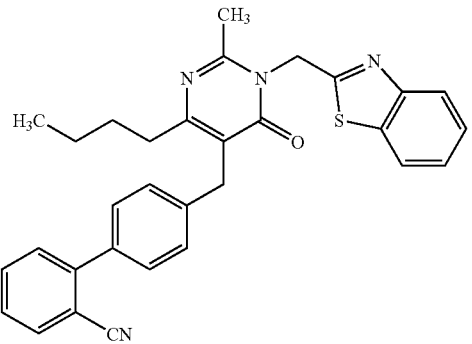

64a) 4'-{[1-(1,3-benzothiazol-2-ylmethyl)-4-butyl-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), 1,3-benzothiazol-2-ylmethanol (0.69 g) and tetrahydrofuran (50 mL) was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.63 g, 45%).

$^1$H NMR (300 MHz, CDCl$_3$) δ 0.90 (3H, t, J=7.3), 1.30-1.43 (2H, m), 1.48-1.63 (2H, m), 2.52-2.66 (2H, m), 2.70 (3H, s), 4.02 (2H, s), 5.63 (2H, s), 7.36-7.53 (8H, m), 7.57-7.66 (1H, m), 7.74 (1H, d, J=7.7), 7.87 (1H, d, J=7.3), 8.01 (1H, d, J=8.1)

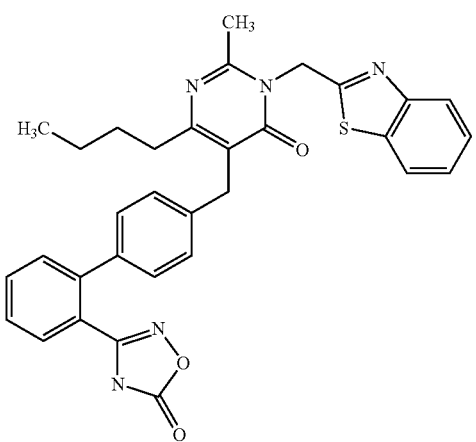

64b) 3-(1,3-benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.31 g), sodium hydrogen carbonate (2.1 g) and dimethyl sulfoxide (15 mL) was stirred at 40° C. for 30 min, 4'-{[1-(1,3-benzothiazol-2-ylmethyl)-4-butyl-2-methyl-6-oxo-1,6-dihydropyrimidin-5-yl]methyl}biphenyl-2-carbonitrile (0.63 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.24 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.2 g, 28%).

$^1$H NMR (300 MHz, DMSO-d$_6$) δ 0.83 (3H, t, J=7.3), 1.22-1.36 (2H, m), 1.38-1.52 (2H, m), 2.51-2.55 (2H, m), 2.58 (3H, s), 3.89 (2H, s), 5.66 (2H, s), 7.17-7.29 (4H, m), 7.41-7.58 (4H, m), 7.62-7.72 (2H, m), 8.02 (1H, d, J=8.7), 8.11 (1H, d, J=8.7), 12.38 (1H, s)

3-(1,3-Benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

3-(1,3-benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one sodium salt 3-(1,3-benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one potassium salt 3-(1,3-benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one 0.5 calcium salt 3-(1,3-benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one hydrochloride 3-(1,3-benzothiazol-2-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one hydrobromide Example 65

6-butyl-3-(4-fluorobenzyl)-5-{[2'-(5-oxo-4,5-dihydro-1,2,4-oxadiazol-3-yl)biphenyl-4-yl]methyl}pyrimidin-4(3H)-one

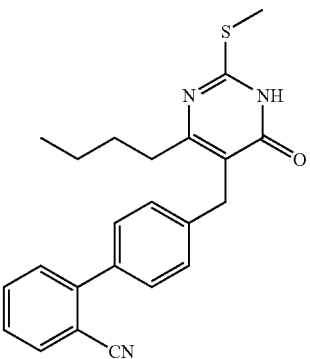

65a) 4'-{[4-butyl-2-(methylthio)-6-oxo-1,6-dihydropyrimidin-5-yl]methyl}biphenyl-2-carbonitrile A mixture of 4'-[(4-butyl-2-mercapto-6-oxo-1,6-dihydropyrimidin-5-yl)methyl]biphenyl-2-carbonitrile (2.3 g), iodomethane (0.54 mL), potassium hydroxide (0.44 g) and methanol (20 mL) was stirred at room temperature for 3 hr. The obtained crystallized product was collected by filtration and washed with water and diethyl ether to give the title compound as colorless crystals (1.98 g, 83%).

$^1$H NMR (300 MHz, CDCl$_3$) δ 0.90 (3H, t, J=7.4), 1.26-1.42 (2H, m), 1.51-1.66 (2H, m), 2.52-2.64 (5H, m), 3.95 (2H, s), 7.37-7.50 (6H, m), 7.57-7.65 (1H, m), 7.74 (1H, dd, J=7.7, 1.3), 12.56 (1H, br)

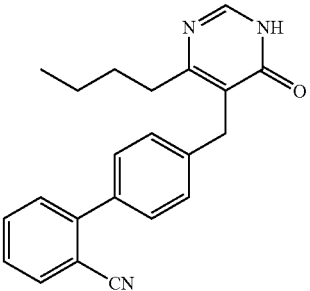

65b) 4'-[(4-butyl-6-oxo-1,6-dihydropyrimidin-5-yl)methyl]biphenyl-2-carbonitrile A mixture of 4'-{[4-butyl-2-(methylthio)-6-oxo-1,6-dihydropyrimidin-5-yl]methyl}biphenyl-2-carbonitrile (1.98 g), Raney-nickel (15 g) and 1-methoxy-2-(2-methoxyethoxy)ethane (25 mL) was stirred at 160° C. for 16 hr. The insoluble material was filtrated, and the filtrate was concentrated to give the title compound as colorless crystals (1.09 g, 63%).

$^1$H NMR (300 MHz, DMSO-$d_6$) δ 0.82 (3H, t, J=7.3), 1.19-1.35 (2H, m), 1.35-1.56 (2H, m), 2.51-2.58 (2H, m), 3.89 (2H, s), 7.34 (2H, d, J=8.3), 7.43-7.64 (4H, m), 7.71-7.82 (1H, m), 7.93 (1H, d, J=7.7), 8.06 (1H, s), 12.42 (1H, br)

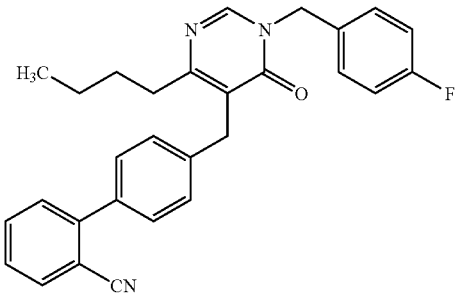

65c) 4'-{[4-butyl-1-(4-fluorobenzyl)-6-oxo-1,6-dihydropyrimidin-5-yl]methyl}biphenyl-2-carbonitrile A mixture of 4'-[(4-butyl-6-oxo-1,6-dihydropyrimidin-5-yl)methyl]biphenyl-2-carbonitrile (0.5 g), sodium hydride (0.07 g) and N,N-dimethylformamide (10 mL) was stirred at room temperature for 10 min, 1-(bromomethyl)-4-fluorobenzene (0.22 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.54 g, 82%).

$^1$H NMR (300 MHz, CDCl$_3$) δ 0.91 (3H, t, J=7.4), 1.29-1.42 (2H, m), 1.51-1.63 (2H, m), 2.57-2.68 (2H, m), 3.99 (2H, s), 5.06 (2H, s), 7.01-7.10 (2H, m), 7.30-7.50 (8H, m), 7.57-7.67 (1H, m), 7.74 (1H, dd, J=7.7, 0.9), 8.06 (1H, s)

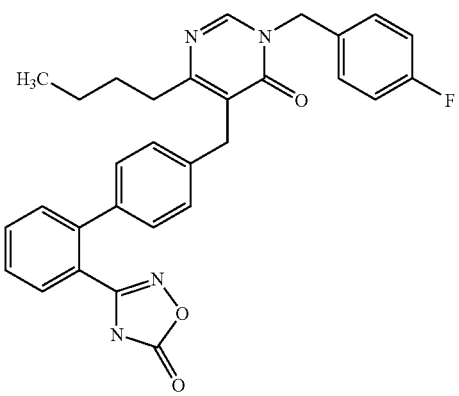

65d) 6-butyl-3-(4-fluorobenzyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.25 g), sodium hydrogen carbonate (2.02 g) and dimethyl sulfoxide (15 mL) was stirred at 40° C. for 30 min, 4'-{[4-butyl-1-(4-fluorobenzyl)-6-oxo-1,6-dihydropyrimidin-5-yl]methyl}biphenyl-2-carbonitrile (0.54 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.23 g) and then 1,8-diazabicyclo[5.4.0]undec-7-ene (0.2 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.38 g, 62%).

$^1$H NMR (300 MHz, DMSO-$d_6$) δ 0.82 (3H, t, J=7.4), 1.20-1.33 (2H, m), 1.37-1.55 (2H, m), 2.51-2.56 (2H, m), 3.87 (2H, s), 5.09 (2H, s), 7.14-7.27 (6H, m), 7.37-7.45 (2H, m), 7.46-7.59 (2H, m), 7.62-7.73 (2H, m), 8.55 (1H, s), 12.37 (1H, s)

Example 66

6-butyl-3-(3-hydroxy-2,2-dimethylpropyl)-2-methyl-5-{[2'-(5-oxo-4,5-dihydro-1,2,4-oxadiazol-3-yl)biphenyl-4-yl]methyl}pyrimidin-4(3H)-one

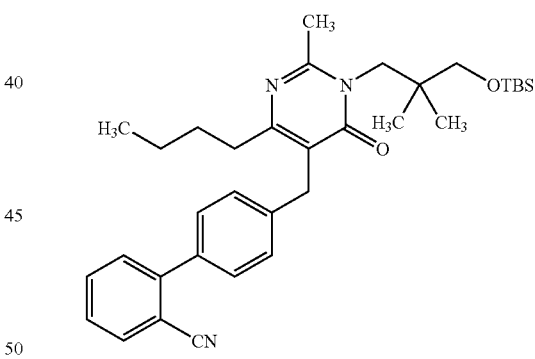

66a) 4'-{[4-butyl-1-(3-{[tert-butyl(dimethyl)silyl]oxy}-2,2-dimethylpropyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), cesium carbonate (4.1 g), (3-bromo-2,2-dimethylpropoxy)(tert-butyl)dimethylsilane (2.36 g) and N,N-dimethylacetamide (10 mL) was stirred at 130° C. for 2 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.63 g, 27%).

¹H NMR (300 MHz, CDCl₃) δ 0.03-0.11 (6H, m), 0.86-0.99 (18H, m), 1.32-1.46 (2H, m), 1.49-1.62 (2H, m), 2.50-2.65 (5H, m), 3.33 (2H, s), 3.95 (2H, s), 4.13 (2H, br), 7.31-7.40 (2H, m), 7.40-7.52 (4H, m), 7.57-7.67 (2H, m), 7.74 (2H, dd, J=7.7, 0.9)

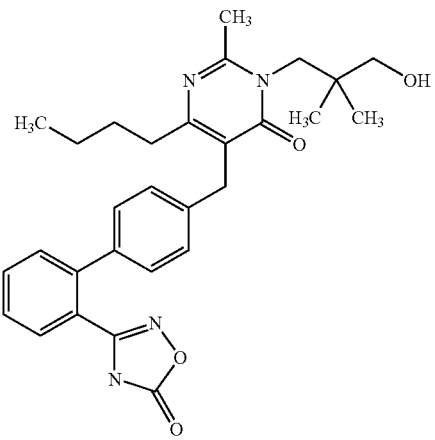

66b) 6-butyl-3-(3-hydroxy-2,2-dimethylpropyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.17 g), sodium hydrogen carbonate (1.88 g) and dimethyl sulfoxide (15 mL) was stirred at 40° C. for 30 min, 4'-{4-butyl-1-(3-{[tert-butyl(dimethyl)silyl]oxy}-2,2-dimethylpropyl)-2-methyl-6-oxo-1,6-dihydropyrimidin-5-yl]methyl}biphenyl-2-carbonitrile (0.63 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.22 g) and then 1,8-diazabicyclo[5.4.0]undec-7-ene (0.18 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure. The residue was dissolved in tetrahydrofuran (20 mL), tetrabutylammonium fluoride (1.0 M tetrahydrofuran solution, 3.7 mL) was added, and the mixture was stirred at 70° C. for 6 hr. The reaction mixture was extracted with 1 M hydrochloric acid and ethyl acetate, and the ethyl acetate layer was washed with saturated brine, and dried over anhydrous magnesium sulfate. The solvent was evaporated under reduced pressure and the residue was purified by silica gel column chromatography to give the title compound as colorless crystals (0.24 g, 48%).

¹H NMR (300 MHz, DMSO-d₆) δ 0.74-0.90 (9H, m), 1.19-1.35 (2H, m), 1.36-1.53 (2H, m), 2.41-2.48 (2H, m), 2.54 (3H, s), 3.09 (2H, d, J=4.7), 3.85 (2H, s), 3.97 (2H, s), 4.84 (1H, t, J=5.2), 7.12-7.27 (4H, m), 7.43-7.58 (2H, m), 7.61-7.74 (2H, m), 12.37 (1H, s)

Example 67

6-butyl-2-methyl-5-{[2'-(5-oxo-4,5-dihydro-1,2,4-oxadiazol-3-yl)biphenyl-4-yl]methyl}-3-(1-phenylethyl)pyrimidin-4(3H)-one

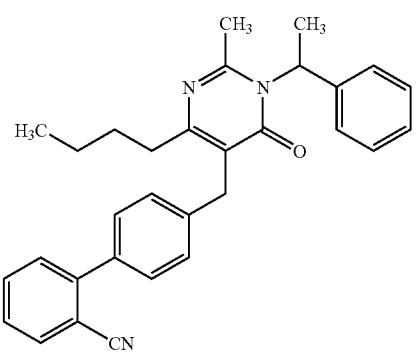

67a) 4'-{[4-butyl-2-methyl-6-oxo-1-(1-phenylethyl)-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), cesium carbonate (2.73 g), (1-bromoethyl)benzene (1.15 mL) and N,N-dimethylacetamide (10 mL) was stirred at 130° C. for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.24 g, 19%).

¹H NMR (300 MHz, CDCl₃) δ 0.91 (3H, t, J=7.3), 1.30-1.43 (2H, m), 1.48-1.63 (2H, m), 1.91 (3H, d, J=7.2), 2.27 (3H, s), 2.49-2.59 (2H, m), 3.98 (2H, s), 6.51 (1H, br), 7.16-7.51 (11H, m), 7.58-7.67 (1H, m), 7.74 (1H, dd, J=7.7, 0.9)

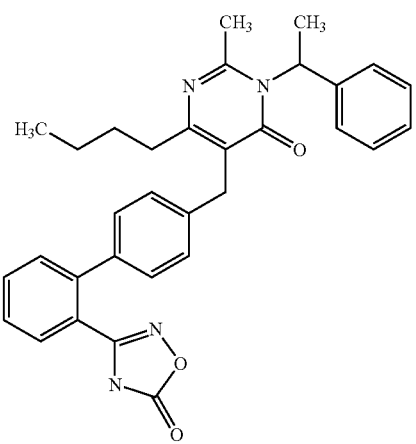

67b) 6-butyl-2-methyl-5-{[2'-(5-oxo-4,5-dihydro-1,2,4-oxadiazol-3-yl)biphenyl-4-yl]methyl}-3-(1-phenylethyl)pyrimidin-4(3H)-one A mixture of hydroxylammonium chloride (0.54 g), sodium hydrogen carbonate (0.87 g) and dimethyl sulfoxide (10 mL) was stirred at 40° C. for 30 min, 4'-{[4-butyl-2-methyl-6-oxo-1-(1-phenylethyl)-1,6-dihydropyrimidin-5-yl]methyl}biphenyl-2-carbonitrile (0.24 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.1 g) and then 1,8-diazabicyclo[5.4.0]undec-7-ene (0.09 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.07 g, 26%).

$^1$H NMR (300 MHz, DMSO-$d_6$) δ 0.83 (3H, t, J=7.3), 1.21-1.34 (2H, m), 1.36-1.50 (2H, m), 1.86 (3H, d, J=7.0), 2.33-2.47 (5H, m), 3.81 (2H, s), 6.09 (1H, br), 7.14-7.30 (7H, m), 7.32-7.39 (2H, m), 7.52 (2H, dd, J=17.6, 7.6), 7.62-7.72 (2H, m), 12.38 (1H, br)

6-Butyl-2-methyl-5-{[2'-(5-oxo-4,5-dihydro-1,2,4-oxadiazol-3-yl)biphenyl-4-yl]methyl}-3-(1-phenylethyl)pyrimidin-4(3H)-one obtained above is subjected to a conventional method of salt formation to give the following salts.

6-butyl-2-methyl-5-{[2'-(5-oxo-4,5-dihydro-1,2,4-oxadiazol-3-yl)biphenyl-4-yl]methyl}-3-(1-phenylethyl)pyrimidin-4(3H)-one sodium salt 6-butyl-2-methyl-5-{[2'-(5-oxo-4,5-dihydro-1,2,4-oxadiazol-3-yl)biphenyl-4-yl]methyl}-3-(1-phenylethyl)pyrimidin-4(3H)-one potassium salt 6-butyl-2-methyl-5-{[2'-(5-oxo-4,5-dihydro-1,2,4-oxadiazol-3-yl)biphenyl-4-yl]methyl}-3-(1-phenylethyl)pyrimidin-4(3H)-one 0.5 calcium salt 6-butyl-2-methyl-5-{[2'-(5-oxo-4,5-dihydro-1,2,4-oxadiazol-3-yl)biphenyl-4-yl]methyl}-3-(1-phenylethyl)pyrimidin-4(3H)-one hydrochloride 6-butyl-2-methyl-5-{[2'-(5-oxo-4,5-dihydro-1,2,4-oxadiazol-3-yl)biphenyl-4-yl]methyl}-3-(1-phenylethyl)pyrimidin-4(3H)-one hydrobromide

Example 68

6-butyl-3-(2-chlorobenzyl)-2-methyl-5-{[2'-(5-oxo-4,5-dihydro-1,2,4-oxadiazol-3-yl)biphenyl-4-yl]methyl}pyrimidin-4(3H)-one

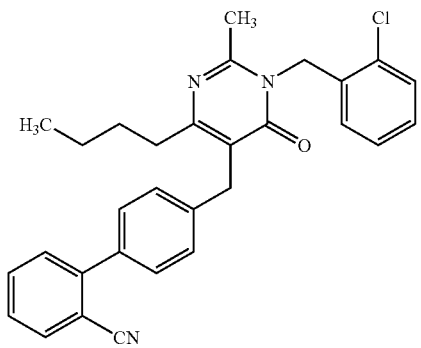

68a) 4'-{[4-butyl-1-(2-chlorobenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.13 g) and N,N-dimethylformamide (10 mL) was stirred at room temperature for 10 min, 1-(bromomethyl)-2-chlorobenzene (0.44 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.6 g, 45%).

$^1$H NMR (300 MHz, CDCl$_3$) δ 0.93 (3H, t, J=7.3), 1.31-1.48 (2H, m), 1.54-1.69 (2H, m), 2.39 (3H, s), 2.59-2.70 (2H, m), 4.01 (2H, s), 5.39 (2H, s), 6.74-6.82 (1H, m), 7.17-7.25 (2H, m), 7.36-7.51 (7H, m), 7.62 (1H, t, J=7.6), 7.74 (1H, d, J=7.7)

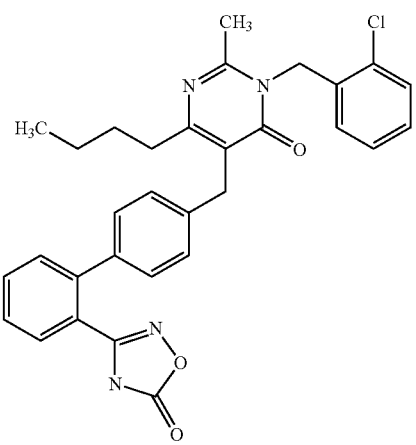

68b) 6-butyl-3-(2-chlorobenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.3 g), sodium hydrogen carbonate (2.1 g) and dimethyl sulfoxide (15 mL) was stirred at 40° C. for 30 min, 4'-{[4-butyl-1-(2-chlorobenzyl)-2-methyl-6-oxo-1,6-dihydropyrimidin-5-yl]methyl}biphenyl-2-carbonitrile (0.6 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.24 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.45 g, 67%).

¹H NMR (300 MHz, DMSO-d₆) δ 0.85 (3H, t, J=7.2), 1.24-1.35 (2H, m), 1.41-1.55 (2H, m), 2.36 (3H, s), 2.52-2.58 (2H, m), 3.89 (2H, s), 5.30 (2H, s), 6.68-6.74 (1H, m), 7.17-7.28 (4H, m), 7.30-7.38 (2H, m), 7.46-7.58 (3H, m), 7.62-7.71 (2H, m), 12.39 (1H, s)

Example 69

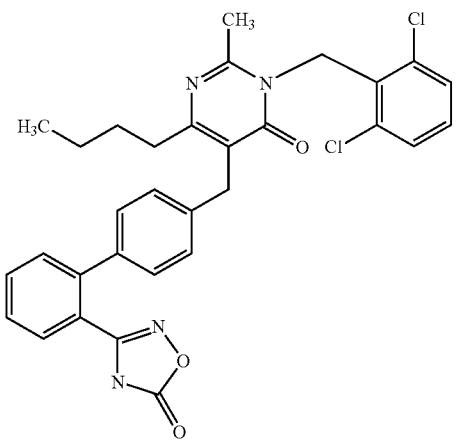

6-butyl-3-(2,6-dichlorobenzyl)-2-methyl-5-{[2'-(5-oxo-4,5-dihydro-1,2,4-oxadiazol-3-yl)biphenyl-4-yl]methyl}pyrimidin-4(3H)-one A mixture of 4'-[(4-butyl-2-methyl-6-oxo-1,6-dihydropyrimidin-5-yl)methyl]biphenyl-2-carbonitrile (1 g), sodium hydride (0.13 g) and N,N-dimethylformamide (10 mL) was stirred at room temperature for 10 min, 2-(bromomethyl)-1,3-dichlorobenzene (0.81 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.4 g), sodium hydrogen carbonate (0.65 g) and dimethyl sulfoxide (10 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.075 g) and then 1,8-diazabicyclo[5.4.0]undec-7-ene (0.064 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.047 g, 3%).

¹H NMR (300 MHz, DMSO-d₆) δ 0.82 (3H, t, J=7.4), 1.16-1.31 (2H, m), 1.36-1.51 (2H, m), 2.41-2.49 (5H, m), 3.79 (2H, s), 5.46 (2H, s), 7.10-7.20 (4H, m), 7.27-7.37 (1H, m), 7.41-7.58 (4H, m), 7.61-7.71 (2H, m), 12.39 (1H, br)

Example 70

6-butyl-2-methyl-3-(2-morpholin-4-ylethyl)-5-{[2'-(5-oxo-4,5-dihydro-1,2,4-oxadiazol-3-yl)biphenyl-4-yl]methyl}pyrimidin-4(3H)-one

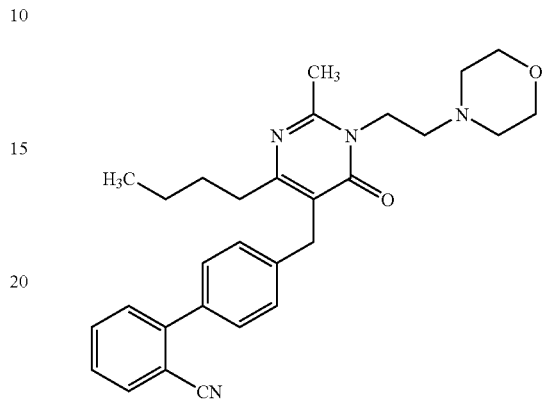

70a) 4'-{[4-butyl-2-methyl-1-(2-morpholin-4-yl-ethyl)-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), 2-morpholin-4-ylethanol (0.51 mL) and tetrahydrofuran (50 mL) was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (1.34 g, 100%).

¹H NMR (300 MHz, CDCl₃) δ 0.89 (3H, t, J=7.3), 1.31-1.49 (4H, m), 2.44-2.50 (4H, m), 2.57 (3H, s), 2.65-2.75 (4H, m), 3.59-3.69 (4H, m), 4.01 (2H, s), 4.50 (2H, t, J=5.7), 7.22-7.29 (2H, m), 7.38-7.50 (4H, m), 7.59-7.67 (1H, m), 7.75 (1H, d, J=7.7)

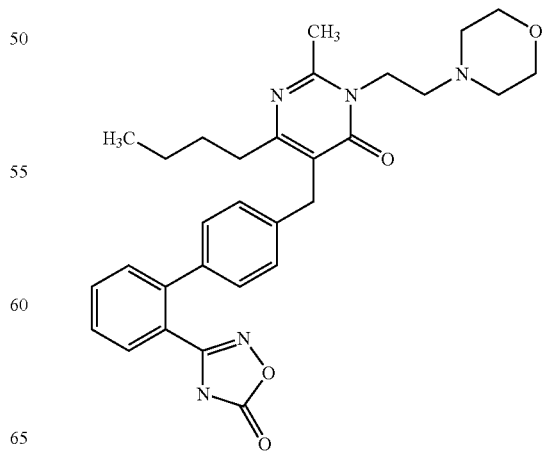

70b) 6-butyl-2-methyl-3-(2-morpholin-4-ylethyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (2.9 g), sodium hydrogen carbonate (4.77 g) and dimethyl sulfoxide (30 mL) was stirred at 40° C. for 30 min, 4'-{[4-butyl-2-methyl-1-(2-morpholin-4-ylethyl)-6-oxo-1,6-dihydropyrimidin-5-yl]methyl}biphenyl-2-carbonitrile (1.34 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.55 g) and then 1,8-diazabicyclo[5.4.0]undec-7-ene (0.47 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as a colorless solid (0.58 g, 39%).

$^1$H NMR (300 MHz, DMSO-$d_6$) δ 0.83 (3H, t, J=7.4), 1.19-1.37 (2H, m), 1.41-1.54 (2H, m), 2.37-2.48 (7H, m), 2.58-2.71 (4H, m), 3.44-3.53 (4H, m), 3.95 (2H, s), 4.45 (2H, t, J=5.6), 7.18-7.26 (4H, m), 7.44-7.61 (2H, m), 7.58-7.74 (2H, m)

Example 71

6-butyl-3-[(6-methoxypyridin-3-yl)methyl]-2-methyl-5-{[2'-(5-oxo-4,5-dihydro-1,2,4-oxadiazol-3-yl)biphenyl-4-yl]methyl}pyrimidin-4(3H)-one

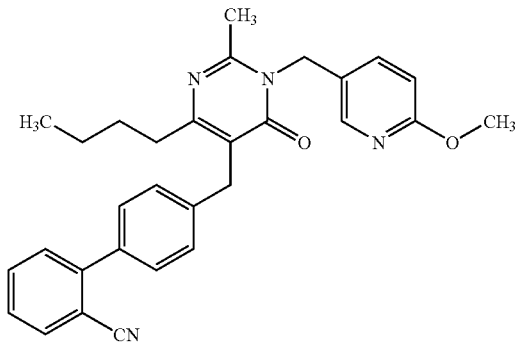

71a) 4'-({4-butyl-1-[(6-methoxypyridin-3-yl)methyl]-2-methyl-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), (6-methoxypyridin-3-yl)methanol (0.58 g) and tetrahydrofuran (50 mL) was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (1.09 g, 81%).

$^1$H NMR (300 MHz, CDCl$_3$) δ 0.90 (3H, t, J=7.2), 1.31-1.44 (2H, m), 1.49-1.63 (2H, m), 2.50 (3H, s), 2.55-2.65 (2H, m), 3.91 (3H, s), 3.99 (2H, s), 5.19 (2H, s), 6.68-6.78 (1H, m), 7.32-7.65 (8H, m), 7.74 (1H, d, J=7.7), 8.08 (1H, s)

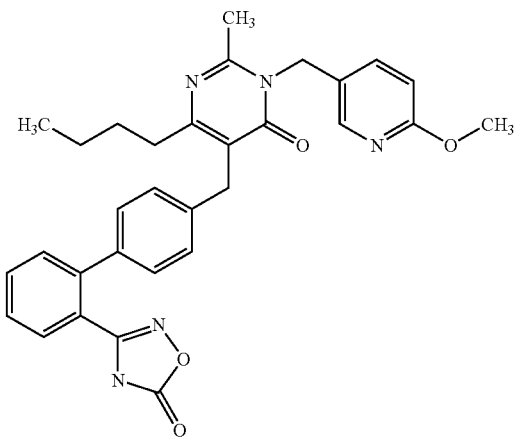

71b) 6-butyl-3-[(6-methoxypyridin-3-yl)methyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (2.37 g), sodium hydrogen carbonate (3.83 g) and dimethyl sulfoxide (15 mL) was stirred at 40° C. for 30 min, 4'-({4-butyl-1-[(6-methoxypyridin-3-yl)methyl]-2-methyl-6-oxo-1,6-dihydropyrimidin-5-yl}methyl)biphenyl-2-carbonitrile (1.09 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.44 g) and then 1,8-diazabicyclo[5.4.0]undec-7-ene (0.38 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as a colorless solid (0.38 g, 32%).

$^1$H NMR (300 MHz, DMSO-$d_6$) δ 0.82 (3H, t, J=7.3), 1.19-1.33 (2H, m), 1.36-1.52 (2H, m), 2.42-2.47 (5H, m), 3.83 (3H, s), 3.89 (2H, s), 5.21 (2H, s), 6.82 (1H, d, J=8.7), 7.17-7.30 (4H, m), 7.47-7.59 (3H, m), 7.62-7.74 (2H, m), 8.12 (1H, s), 12.39 (1H, s)

6-Butyl-3-[(6-methoxypyridin-3-yl)methyl]-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-[(6-methoxypyridin-3-yl)methyl]-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-[(6-methoxypyridin-3-yl)methyl]-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-[(6-methoxypyridin-3-yl)methyl]-2-methyl-5-
{[2'-(5-oxo-4,5-dihydro-1,2,4-oxadiazol-3-yl)biphenyl-4-
yl]methyl}pyrimidin-4(3H)-one 0.5 calcium salt 6-butyl-3-[(6-methoxypyridin-3-yl)methyl]-2-methyl-5-
{[2'-(5-oxo-4,5-dihydro-1,2,4-oxadiazol-3-yl)biphenyl-4-
yl]methyl}pyrimidin-4(3H)-one hydrochloride 6-butyl-3-[(6-methoxypyridin-3-yl)methyl]-2-methyl-5-
{[2'-(5-oxo-4,5-dihydro-1,2,4-oxadiazol-3-yl)biphenyl-4-
yl]methyl}pyrimidin-4(3H)-one hydrobromide

Example 72

6-butyl-3-[(5-chloro-1-benzothien-3-yl)methyl]-2-
methyl-5-{[2'-(5-oxo-4,5-dihydro-1,2,4-oxadiazol-3-
yl)biphenyl-4-yl]methyl}pyrimidin-4(3H)-one

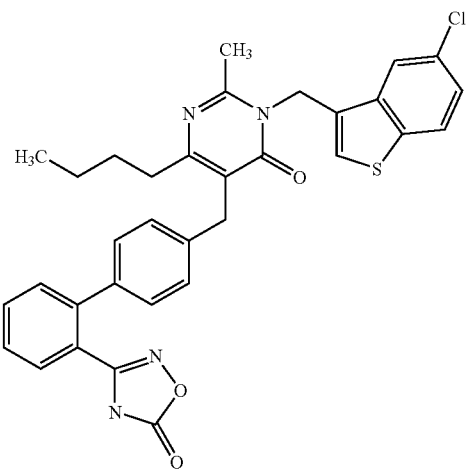

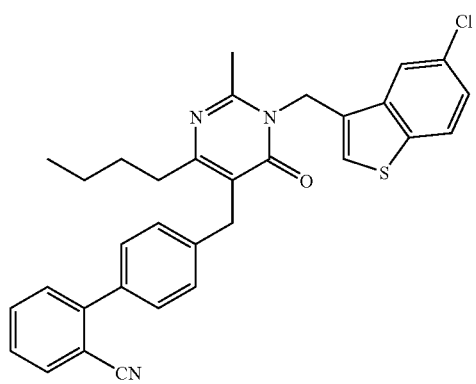

72a) 4'-({4-butyl-1-[(5-chloro-1-benzothien-3-yl)
methyl]-2-methyl-6-oxo-1,6-dihydropyrimidin-5-
yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), (5-chloro-1-benzothien-3-yl)methanol (0.83 g) and tetrahydrofuran (50 mL) was stirred at room temperature for 4 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.82 g, 55%).

$^1$H NMR (300 MHz, CDCl$_3$) δ 0.93 (3H, t, J=7.4), 1.32-1.47 (2H, m), 1.52-1.67 (2H, m), 2.48 (3H, s), 2.60-2.68 (2H, m), 4.02 (2H, s), 5.45 (2H, s), 7.05 (1H, s), 7.32-7.51 (7H, m), 7.59-7.67 (1H, m), 7.72-7.84 (3H, m)

72b) 6-butyl-3-[(5-chloro-1-benzothien-3-yl)methyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.62 g), sodium hydrogen carbonate (2.6 g) and dimethyl sulfoxide (15 mL) was stirred at 40° C. for 30 min, 4'-({4-butyl-1-[(5-chloro-1-benzothien-3-yl)methyl]-2-methyl-6-oxo-1,6-dihydropyrimidin-5-yl}methyl)biphenyl-2-carbonitrile (0.82 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.30 g) and then 1,8-diazabicyclo[5.4.0]undec-7-ene (0.26 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.58 g, 62%).

$^1$H NMR (300 MHz, DMSO-d$_6$) δ 0.83 (3H, t, J=7.3), 1.22-1.35 (2H, m), 1.41-1.52 (2H, m), 2.41-2.51 (5H, m), 3.92 (2H, s), 5.50 (2H, s), 7.25 (4H, q, J=8.2), 7.42-7.60 (4H, m), 7.63-7.74 (2H, m), 8.03-8.15 (2H, m), 12.38 (1H, br)

Example 73

6-butyl-2-methyl-5-{[2'-(5-oxo-4,5-dihydro-1,2,4-
oxadiazol-3-yl)biphenyl-4-yl]methyl}-3-[(2-phenyl-
1,3-thiazol-5-yl)methyl]pyrimidin-4(3H)-one

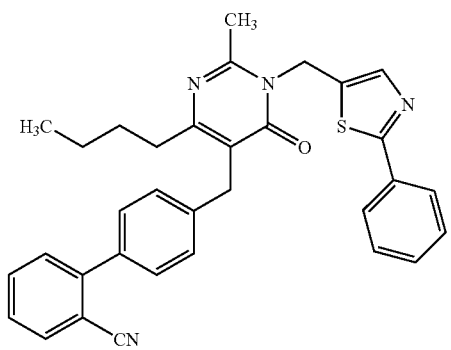

73a) 4'-({4-butyl-2-methyl-6-oxo-1-[(2-phenyl-1,3-thiazol-5-yl)methyl]-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), (2-phenyl-1,3-thiazol-5-yl)methanol (0.8 g) and tetrahydrofuran (50 mL) was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.93 g, 63%).

$^1$H NMR (300 MHz, CDCl$_3$) δ 0.90 (3H, t, J=7.3), 1.29-1.46 (2H, m), 1.50-1.62 (2H, m), 2.55-2.63 (2H, m), 2.82 (3H, s), 3.97 (2H, s), 5.37 (2H, s), 7.24-7.50 (10H, m), 7.57-7.65 (1H, m), 7.74 (1H, dd, J=7.7, 0.9), 7.88-7.96 (2H, m)

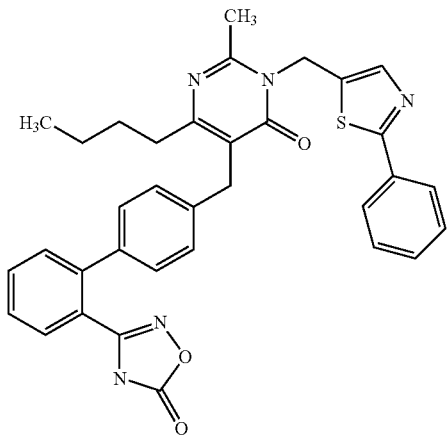

73b) 6-butyl-2-methyl-5-{[2'-(5-oxo-4,5-dihydro-1,2,4-oxadiazol-3-yl)biphenyl-4-yl]methyl}-3-[(2-phenyl-1,3-thiazol-5-yl)methyl]pyrimidin-4(3H)-one A mixture of hydroxylammonium chloride (1.83 g), sodium hydrogen carbonate (2.94 g) and dimethyl sulfoxide (15 mL) was stirred at 40° C. for 30 min, 4'-({4-butyl-2-methyl-6-oxo-1-[(2-phenyl-1,3-thiazol-5-yl)methyl]-1,6-dihydropyrimidin-5-yl}methyl)biphenyl-2-carbonitrile (0.93 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.34 g) and then 1,8-diazabicyclo[5.4.0]undec-7-ene (0.29 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (0.6 g, 58%).

$^1$H NMR (300 MHz, DMSO-d$_6$) δ 0.83 (3H, t, J=7.3), 1.20-1.35 (2H, m), 1.38-1.53 (2H, m), 2.44-2.49 (2H, m), 2.66 (3H, s), 3.86 (2H, s), 5.35 (2H, s), 7.14-7.25 (4H, m), 7.42-7.61 (6H, m), 7.59-7.69 (2H, m), 7.84-7.91 (2H, m), 12.36 (1H, s)

Example 74

6-butyl-3-[(1,5-dimethyl-1H-pyrazol-3-yl)methyl]-2-methyl-5-{[2'-(5-oxo-4,5-dihydro-1,2,4-oxadiazol-3-yl)biphenyl-4-yl]methyl}pyrimidin-4(3H)-one

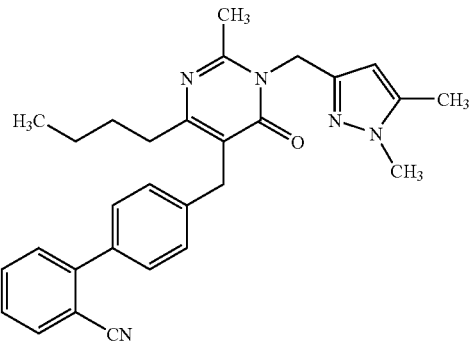

74a) 4'-({4-butyl-1-[(1,5-dimethyl-1H-pyrazol-3-yl)methyl]-2-methyl-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), (1,5-dimethyl-1H-pyrazol-3-yl)methanol (0.53 g) and tetrahydrofuran (50 mL) was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.80 g, 61%).

$^1$H NMR (300 MHz, CDCl$_3$) δ 0.87-0.95 (3H, m), 1.33-1.48 (4H, m), 2.19 (3H, s), 2.54 (3H, s), 2.56-2.66 (2H, m), 3.82 (3H, s), 3.97 (2H, s), 5.22 (2H, s), 5.74 (1H, s), 7.30-7.50 (6H, m), 7.56-7.66 (1H, m), 7.74 (1H, d, J=7.7)

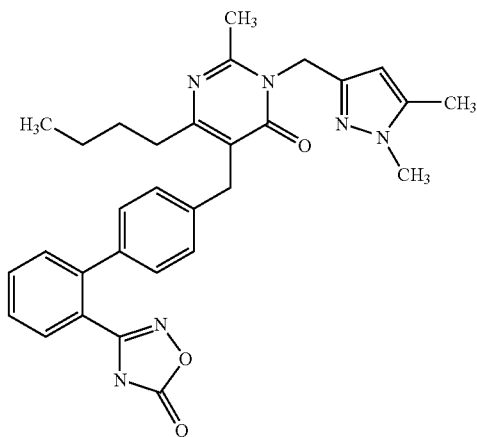

74b) 6-butyl-3-[(1,5-dimethyl-1H-pyrazol-3-yl)methyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.79 g), sodium hydrogen carbonate (2.89 g) and dimethyl sulfoxide (15 mL) was stirred at 40° C. for 30 min, 4'-({4-butyl-1-[(1,5-dimethyl-1H-pyrazol-3-yl)methyl]-2-methyl-6-oxo-1,6-dihydropyrimidin-5-yl}methyl)biphenyl-2-carbonitrile (0.8 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.34 g) and then 1,8-diazabicyclo[5.4.0]undec-7-ene (0.28 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as a colorless solid (0.25 g, 27%).

$^1$H NMR (300 MHz, DMSO-$d_6$) δ 0.83 (3H, t, J=7.2), 1.22-1.49 (4H, m), 2.05 (3H, s), 2.42-2.48 (5H, m), 3.77 (3H, s), 3.87 (2H, s), 5.23 (2H, s), 5.61 (1H, s), 7.19-7.25 (4H, m), 7.52 (2H, dd, J=17.8, 7.2), 7.62-7.73 (2H, m), 12.43 (1H, br)

Example 75

6-butyl-2-methyl-3-[(1-methyl-1H-benzimidazol-2-yl)methyl]-5-{[2'-(5-oxo-4,5-dihydro-1,2,4-oxadiazol-3-yl)biphenyl-4-yl]methyl}pyrimidin-4(3H)-one

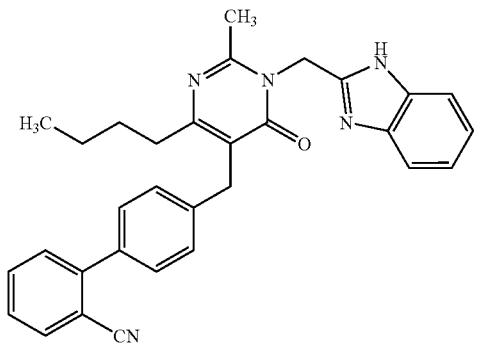

75a) 4'-{[1-(1H-benzimidazol-2-ylmethyl)-4-butyl-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), cesium carbonate (1.82 g), tert-butyl 2-(chloromethyl)-1H-benzimidazole-1-carboxylate (1.12 g), potassium iodide (0.046 g) and N,N-dimethylacetamide (10 mL) was stirred at 130° C. for 3 days. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as colorless crystals (0.24 g, 18%).

$^1$H NMR (300 MHz, CDCl$_3$) δ 0.88 (3H, t, J=7.3), 1.26-1.41 (2H, m), 1.47-1.61 (2H, m), 2.52-2.64 (2H, m), 2.83 (3H, s), 4.02 (2H, s), 5.40 (2H, s), 7.20-7.30 (3H, m), 7.34 (1H, d, J=8.3), 7.38-7.52 (5H, m), 7.57-7.68 (1H, m), 7.71-7.80 (2H, m)

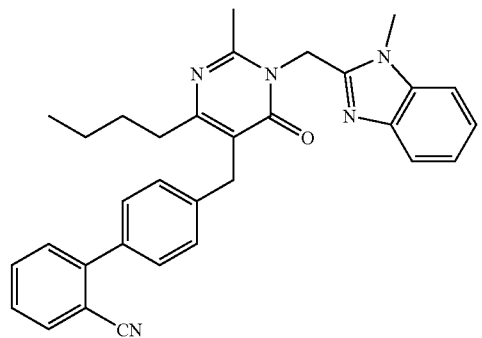

75b) 4'-({4-butyl-2-methyl-1-[(1-methyl-1H-benzimidazol-2-yl)methyl]-6-oxo-1,6-dihydropyrimidin-5-yl}methyl)biphenyl-2-carbonitrile A mixture of 4'-{[1-(1H-benzimidazol-2-ylmethyl)-4-butyl-2-methyl-6-oxo-1,6-dihydropyrimidin-5-yl]methyl}biphenyl-2-carbonitrile (0.24 g), iodomethane (0.036 mL), potassium carbonate (0.14 g) and N,N-dimethylformamide (5 mL) was stirred at room temperature for 3 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.25 g, 100%).

$^1$H NMR (300 MHz, CDCl$_3$) δ 0.90 (3H, t, J=7.3), 1.31-1.44 (2H, m), 1.51-1.65 (2H, m), 2.54-2.65 (2H, m), 2.85 (3H, s), 3.87 (3H, s), 3.95 (2H, s), 5.51 (2H, s), 7.20-7.49 (9H, m), 7.57-7.66 (1H, m), 7.68-7.76 (2H, m)

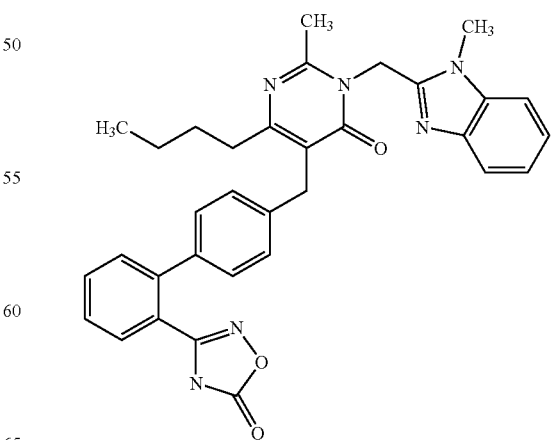

75c) 6-butyl-2-methyl-3-[(1-methyl-1H-benzimidazol-2-yl)methyl]-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.51 g), sodium hydrogen carbonate (0.82 g) and dimethyl sulfoxide (10 mL) was stirred at 40° C. for 30 min, 4'-({4-butyl-2-methyl-1-[(1-methyl-1H-benzimidazol-2-yl)methyl]-6-oxo-1,6-dihydropyrimidin-5-yl}methyl)biphenyl-2-carbonitrile (0.25 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.096 g) and then 1,8-diazabicyclo[5.4.0]undec-7-ene (0.08 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (0.18 g, 65%).

$^1$H NMR (300 MHz, DMSO-$d_6$) δ 0.86 (3H, t, J=7.2), 1.25-1.39 (2H, m), 1.41-1.56 (2H, m), 2.52-2.56 (2H, m), 2.59 (3H, s), 3.84 (2H, s), 3.90 (3H, s), 5.51 (2H, s), 7.12-7.29 (6H, m), 7.43-7.59 (4H, m), 7.61-7.71 (2H, m), 12.37 (1H, br)

Example 76

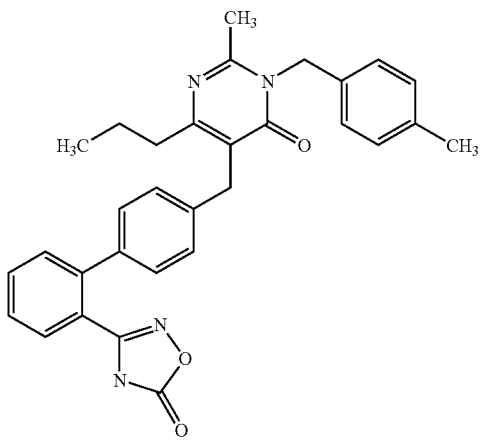

2-methyl-3-(4-methylbenzyl)-5-{[2'-(5-oxo-4,5-dihydro-1,2,4-oxadiazol-3-yl)biphenyl-4-yl]methyl}-6-propylpyrimidin-4(3H)-one A mixture of 4'-[(2-methyl-6-oxo-4-propyl-1,6-dihydropyrimidin-5-yl)methyl]biphenyl-2-carbonitrile (4 g), sodium hydride (0.7 g) and N,N-dimethylformamide (40 mL) was stirred at room temperature for 10 min, 1-(bromomethyl)-4-methylbenzene (2.57 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (15 mL), and added to a mixture of hydroxylammonium chloride (7.78 g), sodium hydrogen carbonate (12.5 g) and dimethyl sulfoxide (30 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (40 mL), N,N'-carbonyldiimidazole (1.45 g) and then 1,8-diazabicyclo[5.4.0]undec-7-ene (0.23 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (2.42 g, 64%).

$^1$H NMR (300 MHz, DMSO-$d_6$) δ 0.84 (3H, t, J=7.4), 1.41-1.60 (2H, m), 2.27 (3H, s), 2.38 (3H, s), 2.44-2.48 (2H, m), 3.91 (2H, s), 5.24 (2H, s), 7.06 (2H, d, J=8.1), 7.17 (2H, d, J=7.9), 7.20-7.30 (4H, m), 7.53 (2H, dd, J=13.4, 7.2), 7.59-7.75 (2H, m), 12.38 (1H, s)

Example 77

6-butyl-2-methyl-3-[(5-methylpyridin-2-yl)methyl]-5-{[2'-(5-oxo-4,5-dihydro-1,2,4-oxadiazol-3-yl)biphenyl-4-yl]methyl}pyrimidin-4(3H)-one

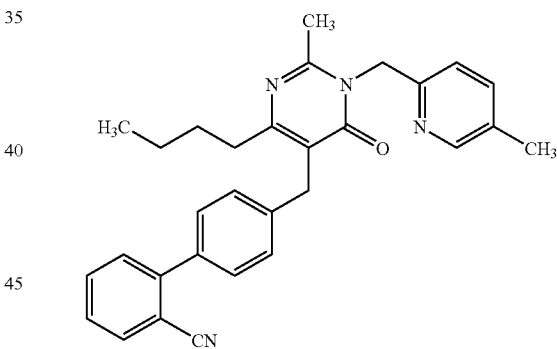

77a) 4'-({4-butyl-2-methyl-1-[(5-methylpyridin-2-yl)methyl]-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), (5-methylpyridin-2-yl)methanol (0.5 g) and tetrahydrofuran (50 mL) was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as colorless crystals (0.59 g, 47%).

$^1$H NMR (300 MHz, CDCl$_3$) δ 0.90 (3H, t, J=7.4), 1.29-1.46 (2H, m), 1.49-1.64 (2H, m), 2.31 (3H, s), 2.55-2.68 (5H, m), 3.98 (2H, s), 5.33 (2H, s), 7.16 (1H, d, J=8.0), 7.33-7.53 (7H, m), 7.57-7.67 (1H, m), 7.74 (1H, d, J=8.0), 8.35 (1H, d, J=1.9)

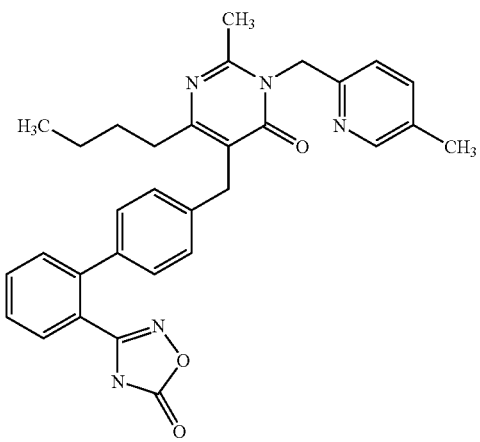

77b) 6-butyl-2-methyl-3-[(5-methylpyridin-2-yl)methyl]-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.3 g), sodium hydrogen carbonate (2.2 g) and dimethyl sulfoxide (10 mL) was stirred at 40° C. for 30 min, 4'-({4-butyl-2-methyl-1-[(5-methylpyridin-2-yl)methyl]-6-oxo-1,6-dihydropyrimidin-5-yl}methyl)biphenyl-2-carbonitrile (0.59 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.25 g) and then 1,8-diazabicyclo[5.4.0]undec-7-ene (0.21 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (0.42 g, 63%).

$^1$H NMR (300 MHz, DMSO-$d_6$) δ 0.84 (3H, t, J=7.3), 1.23-1.37 (2H, m), 1.39-1.53 (2H, m), 2.27 (3H, s), 2.44-2.51 (5H, m), 3.84 (2H, s), 5.29 (2H, s), 7.15-7.26 (5H, m), 7.45-7.74 (5H, m), 8.32 (1H, d, J=0.8), 12.38 (1H, s)

Example 78

6-butyl-2-methyl-5-{[2'-(5-oxo-4,5-dihydro-1,2,4-oxadiazol-3-yl)biphenyl-4-yl]methyl}-3-(pyrazin-2-ylmethyl)pyrimidin-4(3H)-one

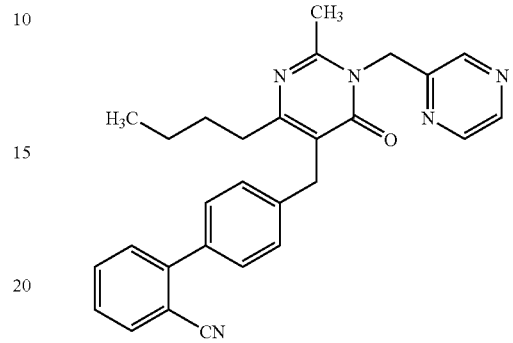

78a) 4'-{[4-butyl-2-methyl-6-oxo-1-(pyrazin-2-ylmethyl)-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.56 mL), pyrazin-2-ylmethanol (0.46 g) and tetrahydrofuran (50 mL) was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.87 g, 69%).

$^1$H NMR (300 MHz, CDCl$_3$) δ 0.87-0.98 (3H, m), 1.35-1.50 (4H, m), 2.55-2.68 (5H, m), 3.96 (2H, s), 5.37 (2H, s), 7.29-7.53 (6H, m), 7.56-7.65 (1H, m), 7.74 (1H, d, J=7.6), 8.53 (2H, s), 8.71 (1H, s)

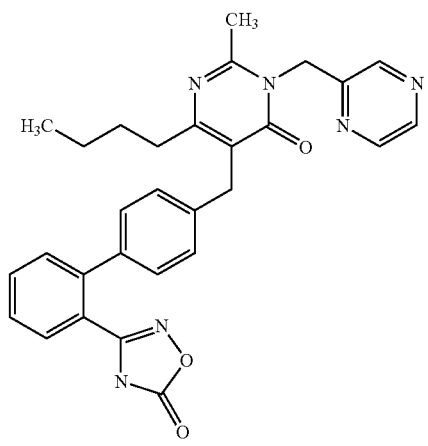

78b) 6-butyl-2-methyl-5-{[2'-(5-oxo-4,5-dihydro-1,2,4-oxadiazol-3-yl)biphenyl-4-yl]methyl}-3-(pyrazin-2-ylmethyl)pyrimidin-4(3H)-one A mixture of hydroxylammonium chloride (2.1 g), sodium hydrogen carbonate (3.2 g) and dimethyl sulfoxide (15 mL) was stirred at 40° C. for 30 min, 4'-{[4-butyl-2-methyl-6-oxo-1-(pyrazin-2-ylmethyl)-1,6-dihydropyrimidin-5-yl]methyl}biphenyl-2-carbonitrile (0.87 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.38 g) and then 1,8-diazabicyclo[5.4.0]undec-7-ene (0.32 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as a colorless solid (0.4 g, 38%).

$^1$H NMR (300 MHz, DMSO-$d_6$) δ 0.84 (3H, t, J=7.0), 1.22-1.36 (2H, m), 1.38-1.53 (2H, m), 2.42-2.58 (5H, m), 3.83 (2H, s), 5.40 (2H, s), 7.17-7.23 (4H, m), 7.43-7.59 (2H, m), 7.61-7.71 (2H, m), 8.56 (2H, s), 8.76 (1H, s), 12.02 (1H, br)

Example 79

2-methyl-5-{[2'-(5-oxo-4,5-dihydro-1,2,4-oxadiazol-3-yl)biphenyl-4-yl]methyl}-6-propyl-3-(pyridin-2-ylmethyl)pyrimidin-4(3H)-one

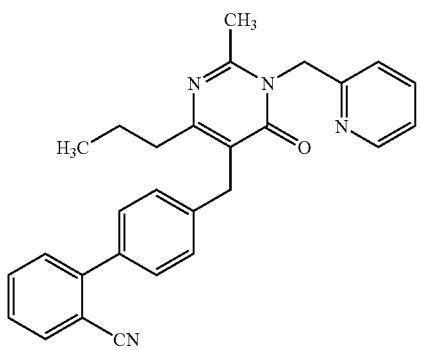

79a) 4'-{[2-methyl-6-oxo-4-propyl-1-(pyridin-2-ylmethyl)-1,6-dihydropyrimidin-5-yl]methyl}biphenyl-2-carbonitrile A mixture of 4'-[(2-methyl-6-oxo-4-propyl-1,6-dihydropyrimidin-5-yl)methyl]biphenyl-2-carbonitrile (7 g), 1,1'-(azodicarbonyl)dipiperidine (9.9 g), tributylphosphine (12.2 mL), pyridin-2-ylmethanol (2.8 mL) and tetrahydrofuran (350 mL) was stirred at room temperature for 4 hr. The reaction mixture was concentrated, and the residue was diluted with ethyl acetate, washed with water and then with saturated brine, and dried over anhydrous magnesium sulfate. The solvent was evaporated under reduced pressure and the residue was purified by silica gel column chromatography to give the title compound as colorless crystals (2.6 g, 31%).

$^1$H NMR (300 MHz, CDCl$_3$) δ 0.96 (3H, t, J=7.3), 1.56-1.72 (2H, m), 2.54-2.64 (5H, m), 3.99 (2H, s), 5.38 (2H, s), 7.12-7.27 (2H, m), 7.32-7.52 (6H, m), 7.56-7.71 (2H, m), 7.74 (1H, dd, J=7.7, 1.3), 8.54 (1H, dd, J=4.0, 0.9)

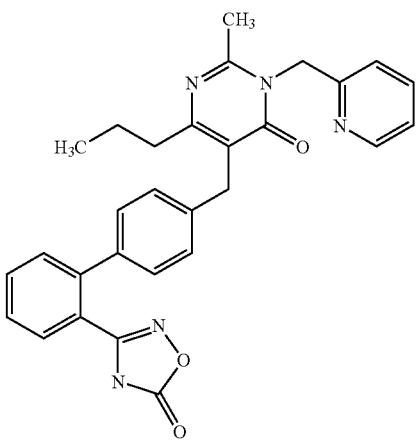

79b) 2-methyl-5-{[2'-(5-oxo-4,5-dihydro-1,2,4-oxadiazol-3-yl)biphenyl-4-yl]methyl}-6-propyl-3-(pyridin-2-ylmethyl)pyrimidin-4(3H)-one A mixture of hydroxylammonium chloride (6.23 g), sodium hydrogen carbonate (10.1 g) and dimethyl sulfoxide (30 mL) was stirred at 40° C. for 30 min, 4'-{[2-methyl-6-oxo-4-propyl-1-(pyridin-2-ylmethyl)-1,6-dihydropyrimidin-5-yl]methyl}biphenyl-2-carbonitrile (2.6 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (40 mL), N,N'-carbonyldiimidazole (1.16 g) and then 1,8-diazabicyclo[5.4.0]undec-7-ene (0.99 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (2.07 g, 70%).

$^1$H NMR (300 MHz, DMSO-$d_6$) δ 0.86 (3H, t, J=7.3), 1.42-1.60 (2H, m), 2.43-2.49 (5H, m), 3.85 (2H, s), 5.34 (2H, s), 7.16-7.25 (4H, m), 7.27-7.38 (2H, m), 7.46-7.57 (2H, m), 7.62-7.73 (2H, m), 7.76-7.85 (1H, m), 8.46-8.51 (1H, m), 12.37 (1H, s)

Example 80

6-butyl-3-(3-fluorobenzyl)-2-methyl-5-{[2'-(5-oxo-4,5-dihydro-1,2,4-oxadiazol-3-yl)biphenyl-4-yl]methyl}pyrimidin-4(3H)-one

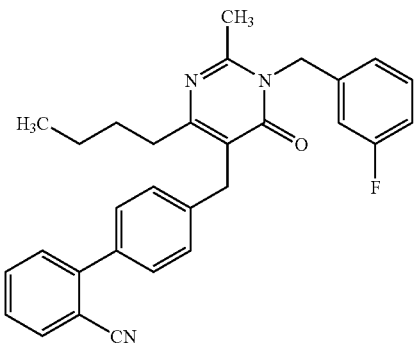

80a) 4'-{[4-butyl-1-(3-fluorobenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-(bromomethyl)-3-fluorobenzene (0.41 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.82 g, 63%).

$^1$H NMR (300 MHz, CDCl$_3$) δ 0.91 (3H, t, J=7.2), 1.30-1.46 (2H, m), 1.52-1.66 (2H, m), 2.44 (3H, s), 2.54-2.67 (2H, m), 4.01 (2H, s), 5.28 (2H, s), 6.85-7.02 (3H, m), 7.24-7.51 (7H, m), 7.62 (1H, t, J=7.8), 7.74 (1H, d, J=8.0)

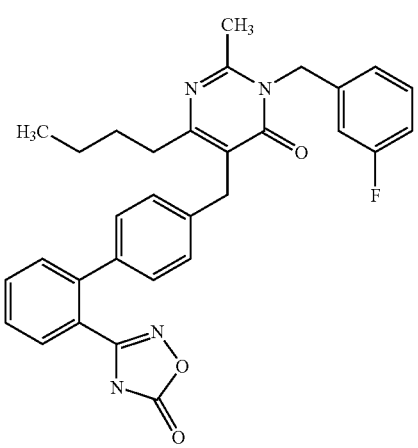

80b) 6-butyl-3-(3-fluorobenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.83 g), sodium hydrogen carbonate (2.96 g) and dimethyl sulfoxide (15 mL) was stirred at 40° C. for 30 min, 4'-{[4-butyl-1-(3-fluorobenzyl)-2-methyl-6-oxo-1,6-dihydropyrimidin-5-yl]methyl}biphenyl-2-carbonitrile (0.86 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.34 g) and then 1,8-diazabicyclo[5.4.0]undec-7-ene (0.29 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.64 g, 69%).

$^1$H NMR (300 MHz, DMSO-d$_6$) δ 0.83 (3H, t, J=7.3), 1.22-1.35 (2H, m), 1.38-1.53 (2H, m), 2.39 (3H, s), 2.46-2.53 (2H, m), 3.91 (2H, s), 5.29 (2H, s), 6.94-7.07 (2H, m), 7.08-7.18 (1H, m), 7.19-7.29 (4H, m), 7.36-7.46 (1H, m), 7.46-7.58 (2H, m), 7.62-7.72 (2H, m), 12.39 (1H, s)

Example 81

2-methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one

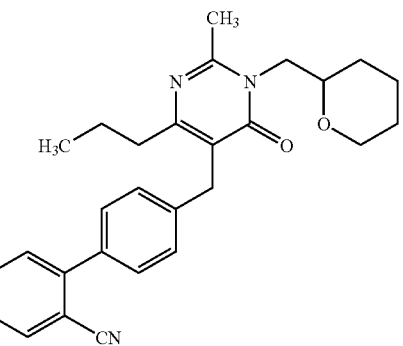

81a) 4'-{[2-methyl-6-oxo-4-propyl-1-(tetrahydro-2H-pyran-2-ylmethyl)-1,6-dihydropyrimidin-5-yl]methyl}biphenyl-2-carbonitrile A mixture of 4'-[(2-methyl-6-oxo-4-propyl-1,6-dihydropyrimidin-5-yl)methyl]biphenyl-2-carbonitrile (1 g), 2-(bromomethyl)tetrahydro-2H-pyran (0.45 mL), potassium carbonate (0.60 g) and N,N-dimethylformamide (10 mL) was stirred at 90° C. for 3 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.64 g, 48%).

¹H NMR (300 MHz, CDCl₃) δ 0.96 (3H, t, J=7.4), 1.27-1.37 (1H, m), 1.43-1.68 (5H, m), 1.69-1.79 (1H, m), 1.80-1.90 (1H, m), 2.53-2.64 (5H, m), 3.24-3.36 (1H, m), 3.62-3.75 (2H, m), 3.86-4.04 (3H, m), 4.19-4.31 (1H, m), 7.32-7.51 (6H, m), 7.57-7.65 (1H, m), 7.74 (1H, d, J=7.6)

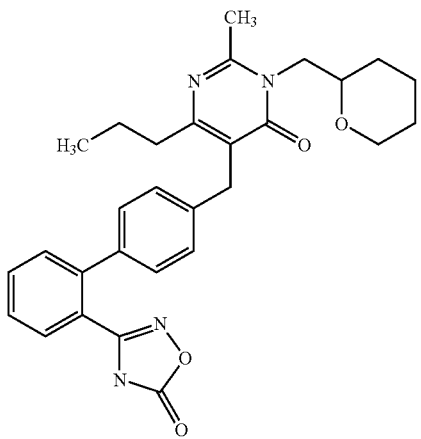

81b) 2-methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one A mixture of hydroxylammonium chloride (1.47 g), sodium hydrogen carbonate (2.37 g) and dimethyl sulfoxide (15 mL) was stirred at 40° C. for 30 min, 4'-{[2-methyl-6-oxo-4-propyl-1-(tetrahydro-2H-pyran-2-ylmethyl)-1,6-dihydropyrimidin-5-yl]methyl}biphenyl-2-carbonitrile (0.64 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.27 g) and then 1,8-diazabicyclo[5.4.0]undec-7-ene (0.23 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.48 g, 68%).

¹H NMR (300 MHz, DMSO-d₆) δ 0.84 (3H, t, J=7.3), 1.22-1.35 (1H, m), 1.37-1.55 (5H, m), 1.63 (1H, d, J=13.9), 1.78 (1H, br), 2.40-2.55 (5H, m), 3.17-3.28 (1H, m), 3.56 (1H, t, J=8.3), 3.74-3.92 (4H, m), 4.04-4.15 (1H, m), 7.16-7.28 (4H, m), 7.44-7.57 (2H, m), 7.61-7.73 (2H, m), 12.36 (1H, s)

2-Methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one obtained above is subjected to a conventional method of salt formation to give the following salts.

2-methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one sodium salt 2-methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one potassium salt 2-methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one 0.5 calcium salt 2-methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one hydrochloride 2-methyl-5-{[2'-(5-oxo-4,5-dihydro-1,2,4-oxadiazol-3-yl)biphenyl-4-yl]methyl}-6-propyl-3-(tetrahydro-2H-pyran-2-ylmethyl)pyrimidin-4(3H)-one hydrobromide Example 82

6-butyl-2-methyl-5-{[2'-(5-oxo-4,5-dihydro-1,2,4-oxadiazol-3-yl)biphenyl-4-yl]methyl}-3-(1,3-thiazol-2-ylmethyl)pyrimidin-4(3H)-one

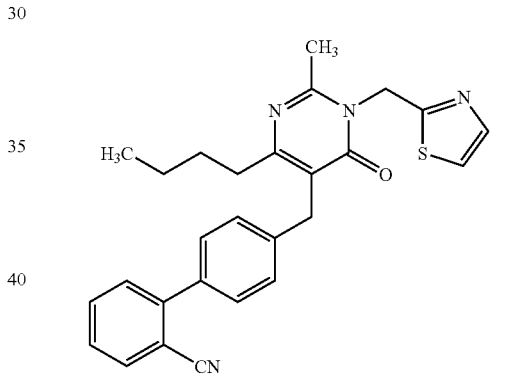

82a) 4'-{[4-butyl-2-methyl-6-oxo-1-(1,3-thiazol-2-ylmethyl)-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), 1,1'-(azodicarbonyl)dipiperidine (1.41 g), tributylphosphine (1.74 mL), 1,3-thiazol-2-ylmethanol (0.48 g) and tetrahydrofuran (50 mL) was stirred at room temperature for 4 hr. The reaction mixture was concentrated. The residue was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.96 g, 75%).

¹H NMR (300 MHz, CDCl₃) δ 0.89 (3H, t, J=7.2), 1.32-1.48 (4H, m), 2.53-2.63 (2H, m), 2.70 (3H, s), 3.99 (2H, s), 5.52 (2H, s), 7.31-7.50 (7H, m), 7.57-7.67 (1H, m), 7.70-7.78 (2H, m)

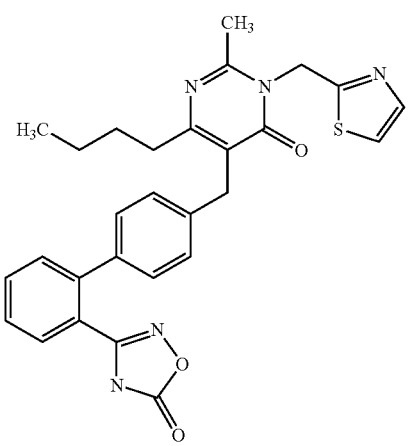

82b) 6-butyl-2-methyl-5-{[2'-(5-oxo-4,5-dihydro-1,2,4-oxadiazol-3-yl)biphenyl-4-yl]methyl}-3-(1,3-thiazol-2-ylmethyl)pyrimidin-4(3H)-one A mixture of hydroxylammonium chloride (2.2 g), sodium hydrogen carbonate (3.5 g) and dimethyl sulfoxide (15 mL) was stirred at 40° C. for 30 min, 4'-{[4-butyl-2-methyl-6-oxo-1-(1,3-thiazol-2-ylmethyl)-1,6-dihydropyrimidin-5-yl]methyl}biphenyl-2-carbonitrile (0.96 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.41 g) and then 1,8-diazabicyclo[5.4.0]undec-7-ene (0.35 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (0.47 g, 44%).

$^1$H NMR (300 MHz, DMSO-$d_6$) δ 0.82 (3H, t, J=7.2), 1.21-1.35 (2H, m), 1.36-1.51 (2H, m), 2.43-2.49 (2H, m), 2.58 (3H, s), 3.87 (2H, s), 5.52 (2H, s), 7.16-7.28 (4H, m), 7.46-7.58 (2H, m), 7.61-7.73 (3H, m), 7.77 (1H, d, J=3.2), 12.38 (1H, s)

Example 83

2-methyl-3-[4-(methylsulfonyl)benzyl]-5-{[2'-(5-oxo-4,5-dihydro-1,2,4-oxadiazol-3-yl)biphenyl-4-yl]methyl}-6-propylpyrimidin-4(3H)-one A mixture of 4'-[(2-methyl-6-oxo-4-propyl-1,6-dihydropyrimidin-5-yl)methyl]biphenyl-2-carbonitrile (1 g), sodium hydride (0.48 g) and N,N-dimethylformamide (10 mL) was stirred at room temperature for 10 min, 1-(bromomethyl)-4-(methylsulfonyl)benzene (0.87 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.51 g), sodium hydrogen carbonate (0.82 g) and dimethyl sulfoxide (10 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.096 g) and then 1,8-diazabicyclo[5.4.0]undec-7-ene (0.081 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.19 g, 11%).

$^1$H NMR (300 MHz, DMSO-$d_6$) δ 0.85 (3H, t, J=7.3), 1.46-1.61 (2H, m), 2.48 (3H, s), 2.59-2.69 (2H, m), 3.19 (3H, s), 4.03 (2H, s), 5.52 (2H, s), 7.13-7.26 (4H, m), 7.46-7.60 (4H, m), 7.62-7.72 (2H, m), 7.88 (2H, d, J=8.5), 12.38 (1H, s)

Example 84 methyl 2-[(2-methyl-6-oxo-5-{[2'-(5-oxo-4,5-dihydro-1,2,4-oxadiazol-3-yl)biphenyl-4-yl]methyl}-4-propylpyrimidin-1(6H)-yl)methyl]benzoate

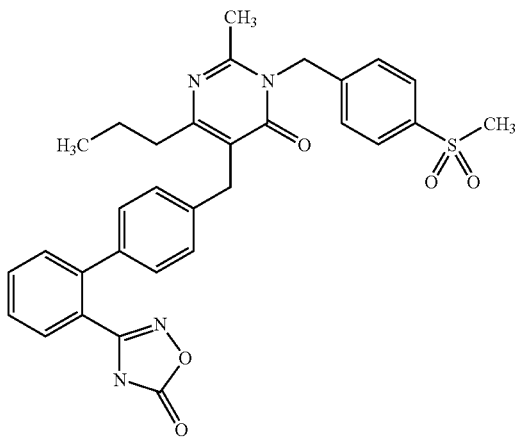

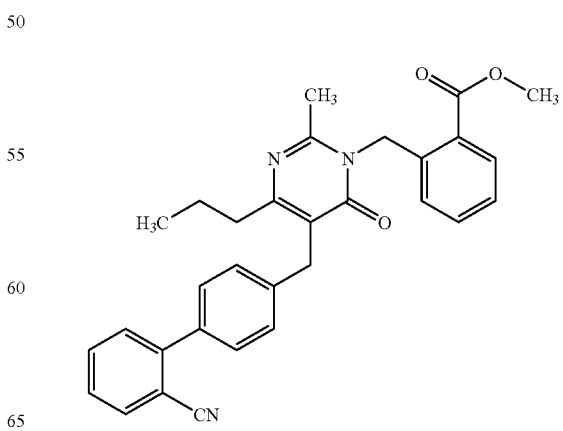

84a) methyl 2-({5-[(2'-cyanobiphenyl-4-yl)methyl]-2-methyl-6-oxo-4-propylpyrimidin-1(6H)-yl}methyl)benzoate A mixture of 4'-[(2-methyl-6-oxo-4-propyl-1,6-dihydropyrimidin-5-yl)methyl]biphenyl-2-carbonitrile (2 g), sodium hydride (0.28 g) and N,N-dimethylformamide (20 mL) was stirred at room temperature for 10 min, methyl 2-(bromomethyl)benzoate (1.6 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (1.15 g, 40%).

$^1$H NMR (300 MHz, CDCl$_3$) δ 0.99 (3H, t, J=7.3), 1.60-1.77 (2H, m), 2.39 (3H, s), 2.58-2.68 (2H, m), 3.93 (3H, s), 4.01 (2H, s), 5.76 (2H, s), 6.78 (1H, d, J=7.7), 7.30-7.51 (8H, m), 7.57-7.67 (1H, m), 7.74 (1H, dd, J=7.7, 0.9), 8.07 (1H, dd, J=7.8, 1.4)

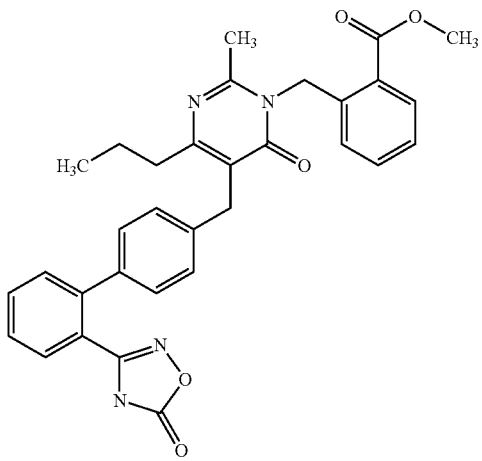

84b) methyl 2-[(2-methyl-6-oxo-5-{[2'-(5-oxo-4,5-dihydro-1,2,4-oxadiazol-3-yl)biphenyl-4-yl]methyl}-4-propylpyrimidin-1(6H)-yl)methyl]benzoate A mixture of hydroxylammonium chloride (2.44 g), sodium hydrogen carbonate (3.93 g) and dimethyl sulfoxide (30 mL) was stirred at 40° C. for 30 min, methyl 2-({5-[(2'-cyanobiphenyl-4-yl)methyl]-2-methyl-6-oxo-4-propylpyrimidin-1(6H)-yl}methyl)benzoate (1.15 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (40 mL), N,N'-carbonyldiimidazole (0.45 g) and then 1,8-diazabicyclo[5.4.0]undec-7-ene (0.39 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.48 g, 37%).

$^1$H NMR (300 MHz, DMSO-d$_6$) δ 0.87 (3H, t, J=7.4), 1.46-1.61 (2H, m), 2.32 (3H, s), 2.51-2.56 (2H, m), 3.90 (5H, s), 5.59 (2H, s), 6.70 (1H, d, J=7.3), 7.19-7.28 (4H, m), 7.39-7.72 (6H, m), 8.00 (1H, dd, J=7.7, 1.3), 12.38 (1H, s)

Example 85

6-butyl-2-(hydroxymethyl)-5-{[2'-(5-oxo-4,5-dihydro-1,2,4-oxadiazol-3-yl)biphenyl-4-yl]methyl}-3-(pyridin-2-ylmethyl)pyrimidin-4(3H)-one

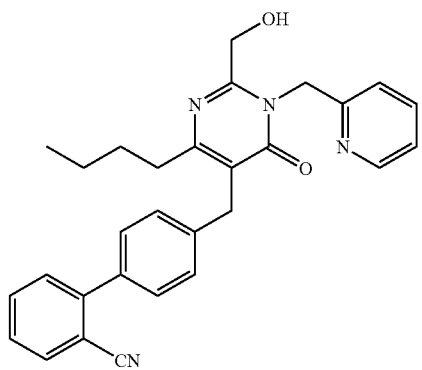

85a) 4'-{[4-butyl-2-(hydroxymethyl)-6-oxo-1-(pyridin-2-ylmethyl)-1,6-dihydropyrimidin-5-yl]methyl}biphenyl-2-carbonitrile A mixture of 4'-{[4-butyl-2-(hydroxymethyl)-6-oxo-1,6-dihydropyrimidin-5-yl]methyl}biphenyl-2-carbonitrile (1 g), cesium carbonate (2.1 g), 2-(bromomethyl)pyridine hydrobromide (0.81 g) and N,N-dimethylformamide (10 mL) was stirred at 50° C. for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.62 g, 50%).

$^1$H NMR (300 MHz, CDCl$_3$) δ 0.91 (3H, t, J=7.3), 1.30-1.45 (2H, m), 1.55-1.67 (2H, m), 2.61-2.71 (2H, m), 3.98 (2H, s), 4.75 (2H, s), 5.09 (1H, br.), 5.21 (2H, s), 7.18-7.25 (1H, m), 7.30-7.35 (2H, m), 7.37-7.50 (5H, m), 7.57-7.78 (3H, m), 8.49-8.53 (1H, m)

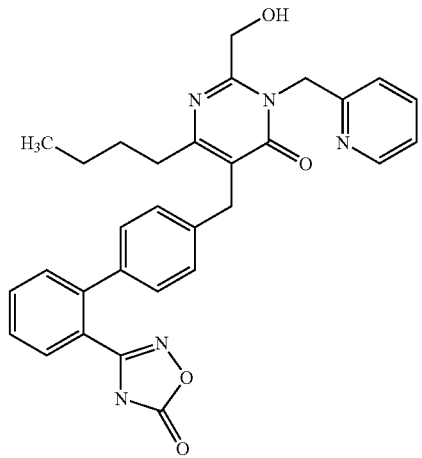

85b) 6-butyl-2-(hydroxymethyl)-5-{[2'-(5-oxo-4,5-dihydro-1,2,4-oxadiazol-3-yl)biphenyl-4-yl]methyl}-3-(pyridin-2-ylmethyl)pyrimidin-4(3H)-one A mixture of hydroxylammonium chloride (1.39 g), sodium hydrogen carbonate (2.2 g) and dimethyl sulfoxide (15 mL) was stirred at 40° C. for 30 min, 4'-{[4-butyl-2-(hydroxymethyl)-6-oxo-1-(pyridin-2-ylmethyl)-1,6-dihydropyrimidin-5-yl]methyl}biphenyl-2-carbonitrile (0.62 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.26 g) and then 1,8-diazabicyclo[5.4.0]undec-7-ene (0.22 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (0.18 g, 26%).

$^1$H NMR (300 MHz, DMSO-$d_6$) δ 0.85 (3H, t, J=7.3), 1.21-1.39 (2H, m), 1.41-1.59 (2H, m), 2.51-2.61 (2H, m), 3.86 (2H, s), 4.48 (2H, d, J=5.7), 5.41 (2H, s), 5.63 (1H, t, J=5.7), 7.21 (4H, s), 7.24-7.41 (2H, m), 7.52 (2H, dd, J=18.2, 7.6), 7.64 (2H, d, J=7.0), 7.74-7.85 (1H, m), 8.46 (1H, s), 12.38 (1H, s)

Example 86

3-[(4-hydroxytetrahydro-2H-pyran-4-yl)methyl]-2-methyl-5-{[2'-(5-oxo-4,5-dihydro-1,2,4-oxadiazol-3-yl)biphenyl-4-yl]methyl}-6-propylpyrimidin-4(3H)-one

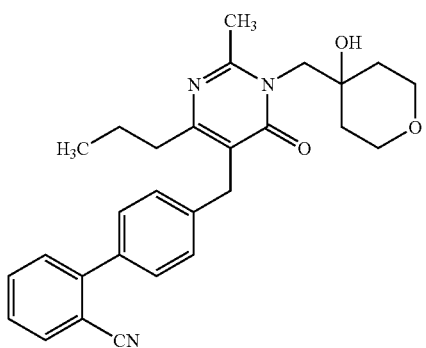

86a) 4'-({1-[(4-hydroxytetrahydro-2H-pyran-4-yl)methyl]-2-methyl-6-oxo-4-propyl-1,6-dihydropyrimidin-5-yl}methyl)biphenyl-2-carbonitrile To a mixture of tetrahydro-4H-pyran-4-one (0.73 g), diiodomethane (0.7 mL) and tetrahydrofuran (20 mL) was added methyllithium (2.1 M diethyl ether solution, 6.95 mL) at 0° C. The reaction mixture was stirred at room temperature for 4 hr, and extracted with saturated aqueous ammonium chloride solution and diethyl ether. The diethyl ether layer was washed with saturated brine and dried over anhydrous magnesium sulfate. The solvent was evaporated under reduced pressure. The obtained oil was dissolved in N,N-dimethylformamide (15 mL), 4'-[(2-methyl-6-oxo-4-propyl-1,6-dihydropyrimidin-5-yl)methyl]biphenyl-2-carbonitrile (1 g) and potassium carbonate (0.8 g) were added, and the mixture was stirred at 90° C. for 24 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.7 g, 53%).

$^1$H NMR (300 MHz, CDCl$_3$) δ 0.95 (3H, t, J=7.4), 1.48-1.81 (6H, m), 2.55-2.63 (5H, m), 3.80 (4H, d, J=7.7), 3.97 (2H, s), 4.16 (2H, s), 4.71 (1H, s), 7.25-7.50 (5H, m), 7.62 (1H, t, J=7.6), 7.74 (1H, d, J=7.5), 8.02 (1H, s)

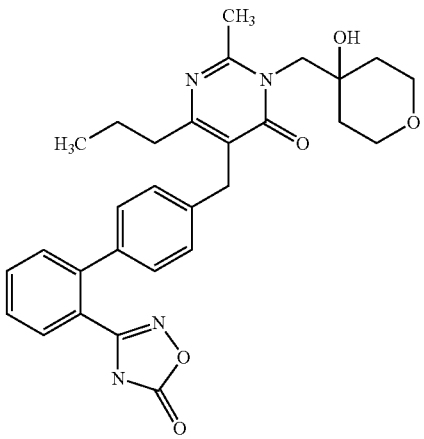

86b) 3-[(4-hydroxytetrahydro-2H-pyran-4-yl)methyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.6 g), sodium hydrogen carbonate (2.57 g) and dimethyl sulfoxide (15 mL) was stirred at 40° C. for 30 min, 4'-({1-[(4-hydroxytetrahydro-2H-pyran-4-yl)methyl]-2-methyl-6-oxo-4-propyl-1,6-dihydropyrimidin-5-yl}methyl)biphenyl-2-carbonitrile (0.7 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.26 g) and then 1,8-diazabicyclo[5.4.0]undec-7-ene (0.22 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.14 g, 18%).

$^1$H NMR (300 MHz, DMSO-$d_6$) δ 0.85 (3H, t, J=7.2), 1.13-1.73 (6H, m), 2.43 (2H, t, J=7.6), 2.61 (3H, s), 3.49-3.67

(4H, m), 3.85 (2H, s), 3.97-4.11 (2H, m), 4.96 (1H, s), 7.14-7.29 (4H, m), 7.52 (2H, dd, J=18.1, 7.5), 7.60-7.72 (2H, m), 12.37 (1H, s)

Example 87

2-methyl-3-[(1-methyl-1H-indazol-3-yl)methyl]-5-{[2'-(5-oxo-4,5-dihydro-1,2,4-oxadiazol-3-yl)biphenyl-4-yl]methyl}-6-propylpyrimidin-4(3H)-one

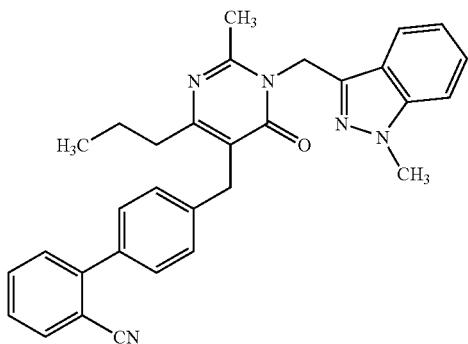

87a) 4'-({2-methyl-1-[(1-methyl-1H-indazol-3-yl)methyl]-6-oxo-4-propyl-1,6-dihydropyrimidin-5-yl}methyl)biphenyl-2-carbonitrile A mixture of 4'-[(2-methyl-6-oxo-4-propyl-1,6-dihydropyrimidin-5-yl)methyl]biphenyl-2-carbonitrile (1 g), 1,1'-(azodicarbonyl)dipiperidine (1.47 g), tributylphosphine (1.81 mL), (1-methyl-1H-indazol-3-yl)methanol (0.51 g) and tetrahydrofuran (50 mL) was stirred at room temperature for 4 hr. The reaction mixture was concentrated. The residue was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.67 g, 47%).

$^1$H NMR (300 MHz, CDCl$_3$) δ 0.93 (3H, t, J=7.4), 1.52-1.65 (2H, m), 2.48-2.58 (2H, m), 2.72 (3H, s), 4.03 (5H, s), 5.64 (2H, s), 7.01-7.12 (1H, m), 7.30-7.53 (8H, m), 7.58-7.67 (1H, m), 7.75 (1H, d, J=8.0), 7.86 (1H, d, J=8.0)

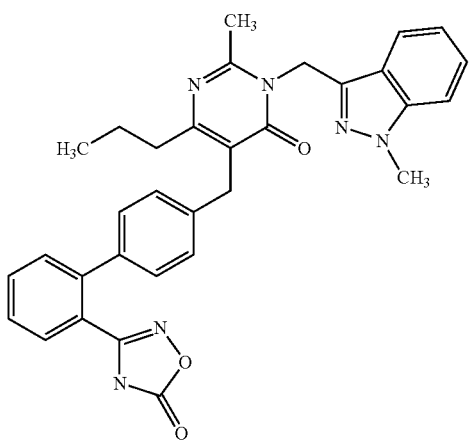

87b) 2-methyl-3-[(1-methyl-1H-indazol-3-yl)methyl]-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.43 g), sodium hydrogen carbonate (2.3 g) and dimethyl sulfoxide (15 mL) was stirred at 40° C. for 30 min, 4'-({2-methyl-1-[(1-methyl-1H-indazol-3-yl)methyl]-6-oxo-4-propyl-1,6-dihydropyrimidin-5-yl}methyl)biphenyl-2-carbonitrile (0.67 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.27 g) and then 1,8-diazabicyclo[5.4.0]undec-7-ene (0.23 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as a colorless solid (0.38 g, 51%).

$^1$H NMR (300 MHz, DMSO-d$_6$) δ 0.83 (3H, t, J=7.4), 1.40-1.56 (2H, m), 2.40-2.48 (2H, m), 2.62 (3H, s), 3.89 (2H, s), 4.00 (3H, s), 5.58 (2H, s), 7.10 (1H, t, J=7.4), 7.22 (4H, q, J=8.2), 7.40 (1H, t, J=8.0), 7.47-7.72 (5H, m), 7.79 (1H, d, J=8.3), 11.96 (1H, br)

Example 88

3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

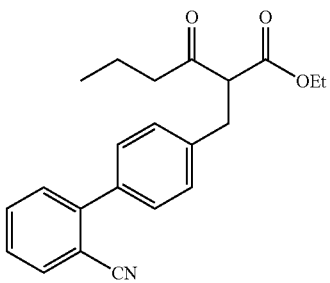

88a) ethyl 2-[(2'-cyanobiphenyl-4-yl)methyl]-3-oxohexanoate

To a suspension of sodium hydride (60% in oil, 19.1 g) in tetrahydrofuran (500 ml) was added a solution of ethyl 3-oxohexanoate (116 g) in tetrahydrofuran (500 ml) dropwise at room temperature. After being stirred at room temperature for 30 min, 4'-(bromomethyl)-biphenyl-2-carbonitrile (100 g) was added to the mixture and the mixture was stirred at room temperature for 15 hr. Ethyl acetate and saturated aqueous ammonium chloride solution were added to the mixture. The layers were separated and the aqueous layer was extracted with ethyl acetate. The combined organic layers were successively washed with water and saturated brine, dried over anhydrous magnesium sulfate and concentrated under reduced pressure. The residue was purified by silica gel column chromatography to give the title compound as a pale yellow oil (129 g, 100%).

$^1$H NMR (300 MHz, CDCl$_3$) δ 0.86 (t, J=7.4 Hz, 3 H), 1.22 (t, J=7.2 Hz, 3H), 1.48-1.66 (m, 2 H), 2.30-2.44 (m, 1 H), 3.13-3.30 (m, 2 H), 3.83 (t, J=7.5 Hz, 1H), 4.17 (q, J=7.2 Hz, 2 H), 7.28-7.79 (m, 8 H)

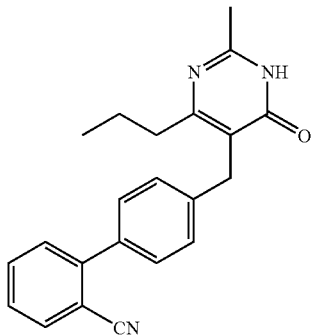

88b) 4'-[(2-methyl-6-oxo-4-propyl-1,6-dihydropyrimidin-5-yl)methyl]biphenyl-2-carbonitrile To a suspension of acetamidine hydrochloride (70 g) in methanol (500 ml) was added sodium methoxide (28% in methanol, 214 g) dropwise, followed by addition of a solution of ethyl 2-[(2'-cyanobiphenyl-4-yl)methyl]-3-oxohexanoate (129 g) in methanol (500 ml) at room temperature. After being stirred at room temperature for 15 hr, ethyl acetate and saturated aqueous ammonium chloride solution were added. The layers were separated and the aqueous layer was extracted with ethyl acetate. The combined organic layers were successively washed with water and saturated brine, dried over anhydrous magnesium sulfate and concentrated under reduced pressure. The resulting solid was collected and washed with diisopropyl ether to give the title compound as a white solid (104 g, 82%).

$^1$H NMR (300 MHz, DMSO-d$_6$) δ 0.95 (t, J=7.3 Hz, 3 H), 1.46-1.81 (m, 2 H), 2.40 (s, 3 H), 2.51-2.72 (m, 2 H), 3.97 (s, 2H), 7.33-7.79 (m, 8 H), 13.02 (s, 1 H)

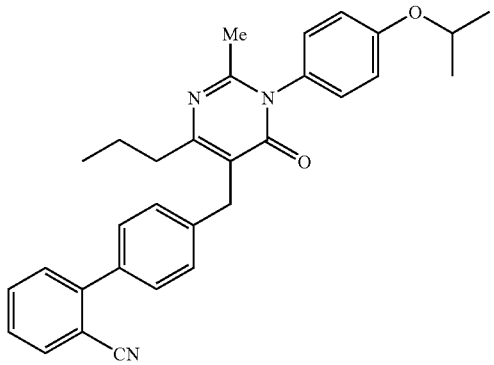

88c) 4'-{[1-(4-isopropoxyphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (2.0 g), (4-isopropoxyphenyl)boronic acid (2.0 g), triethylamine (4.0 mL), pyridine (2.0 mL) and molecular sieves 4 A (4.0 g) in methylene chloride (30 mL) was added copper(II) acetate (2.0 g), and the mixture was stirred at room temperature for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.88 g, 68%).

$^1$H NMR (300 MHz, CDCl$_3$) δ 1.01 (t, J=7.4, 3 H), 1.36 (d, J=6.1, 6 H), 1.54-1.82 (m, 2 H), 2.18 (s, 3 H), 2.47-2.79 (m, 2 H), 3.97 (s, 2 H), 4.41-4.81 (m, 1 H), 6.72-7.81 (m, 12H)

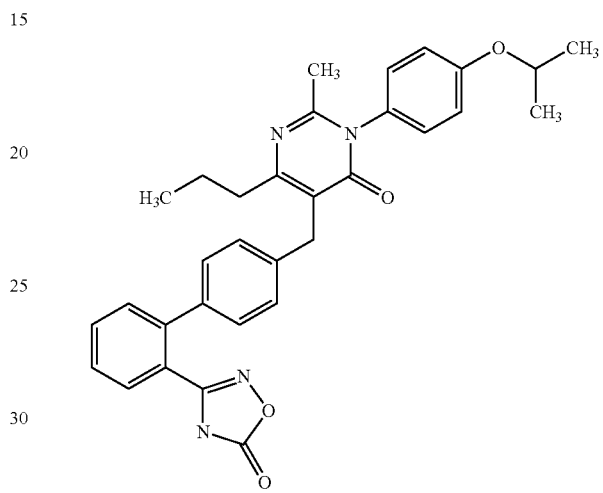

88d) 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (3.5 g), sodium hydrogen carbonate (5.0 g) and dimethyl sulfoxide (25 mL) was stirred at 40° C. for 30 min, 4'-{[1-(4-isopropoxyphenyl)-2-methyl-6-oxo-4-propyl-1,6-dihydropyrimidin-5-yl]methyl}biphenyl-2-carbonitrile (1.88 g) was added, and the mixture was stirred at 90° C. for 15 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (25 mL), N,N'-carbonyldiimidazole (0.97 g) and then 1,8-diazabicyclo[5.4.0]undec-7-ene (0.90 mL) were added, and the mixture was stirred at room temperature for 2 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (1.54 g, 73%).

$^1$H NMR (300 MHz, DMSO-d$_6$) δ 0.89 (t, J=7.2, 3 H), 1.30 (d, J=6.1, 6 H), 1.42-1.66 (m, 2H), 2.07 (s, 3 H), 2.45-2.56 (m, 2H), 3.86 (s, 2 H), 4.55-4.78 (m, 1 H), 6.98-7.73 (m, 12 H), 12.39 (s, 1 H)

88e) Crystalline 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one To a suspension of hydroxylammonium chloride (186 g) in dimethyl sulfoxide (1340 mL) was added sodium hydrogen carbonate (280 g) at 50° C. and stirred for 30 min, and then 4'-{[1-(4-isopropoxyphenyl)-2-methyl-6-oxo-4-propyl-1,6-dihydropyrimidin-5-yl]methyl}biphenyl-2-carbonitrile (160 g) was added to the mixture. After being stirred at 90° C. for 18 hr, the mixture was allowed to cool to room temperature and the mixture was poured into iced water. The mixture was stirred for 30 min and the precipitate was collected. The solid was washed with water and dried in vacuo at 80° C. The solid was dissolved in tetrahydrofuran (1300 mL), N,N'-carbonyldiimidazole (65 g) and then 1,8-diazabicyclo[5.4.0]undec-7-ene (60 mL) were added, and the mixture was stirred at room temperature for 2 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (152 g, 85%).

Powder X-ray diffraction (Cu—Kα radiation, diffraction angle: 2θ(°)): 4.64, 5.46, 8.40, 11.10, 12.60, 13.10, 14.14, 14.36, 14.60, 15.58, 15.86, 16.24, 16.86, 17.52, 19.26, 19.72, 20.00, 20.40, 20.80, 21.12, 21.70.

Anal calcd for $C_{32}H_{32}N_4O_4$: C, 71.62; H, 6.02; N, 10.44. Found C, 71.63; H, 6.03; N, 10.37.

Example 89

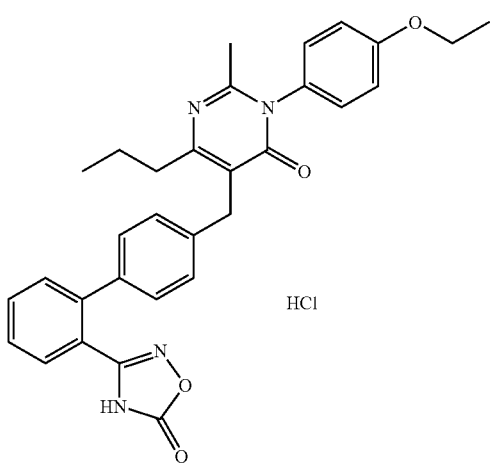

3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-(4-Isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one (0.50 g) was dissolved in ethyl acetate (3 mL), and 4 M hydrochloric acid-ethyl acetate solution (0.28 mL) was added. Diisopropyl ether was further added and the precipitated solid was collected by filtration to give the title compound (0.40 g, 75%) as a colorless solid.

$^1$H NMR (300 MHz, DMSO-$d_6$) δ 0.93 (3H, t, J=7.2), 1.30 (6H, d, J=6.0), 1.49-1.65 (2H, m), 2.27 (3H, s), 2.65 (2 H, t, J=7.7), 3.91 (2 H, s), 4.63-4.74 (1 H, m), 7.04-7.11 (2H, m), 7.20-7.37 (6 H, m), 7.48-7.59 (2 H, m), 7.63-7.73 (2 H, m), 12.43 (1 H, s)

Example 90

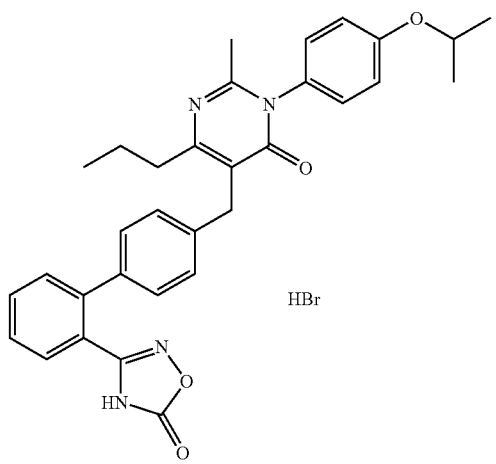

3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one hydrobromide 3-(4-Isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one (0.50 g) was dissolved in ethyl acetate (10 mL), and 10% hydrogen bromide-ethanol solution (0.75 mL) was added. After allowing to stand overnight at room temperature, the precipitated solid was collected by filtration to give the title compound (0.41 g, 71%) as a colorless solid.

$^1$H NMR (300 MHz, DMSO-$d_6$) δ 0.93 (3 H, t, J=7.1), 1.30 (6 H, d, J=6.0), 1.47-1.62 (2 H, m), 2.22 (3 H, s), 2.62 (2H, t, J=7.5), 3.91 (2H, s), 4.59-4.75 (1 H, m), 7.07 (2 H, d, J=9.0), 7.20-7.36 (6 H, m), 7.46-7.60 (2 H, m), 7.62-7.74 (2 H, m), 12.41 (1 H, s)

Example 91

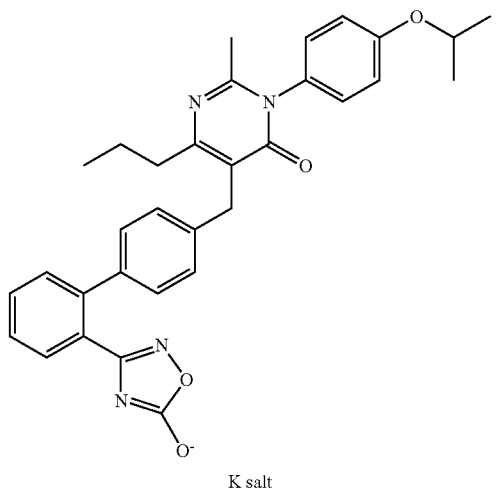

K salt

91a) 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt To a solution of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one (1.42 g) in ethanol (10.0 mL) was added 8 M aqueous potassium hydroxide solution (0.33 mL), and the mixture was stirred at room temperature for 1 hr. The reaction mixture was concentrated under reduced pressure, and the residue was triturated with diisopropyl ether to give the title compound (1.45 g, 95%) as a colorless solid.

$^1$H NMR (300 MHz, DMSO-$d_6$) δ 0.93 (t, J=7.4, 3 H), 1.30 (d, J=6.1, 6H), 1.51-1.66 (m, 2 H), 2.05 (s, 3 H), 2.51-2.57 (m, 2 H), 3.81 (s, 2 H), 4.59-4.75 (m, 1 H), 6.97-7.49 (m, 12 H)

91 b) Crystalline 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt hydrate.

To a suspension of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one (200 g), ethanol (200 mL), and diisopropyl ether (400 mL) was added potassium 2-ethyl hexanoate and the mixture was stirred at 60° C. for 1 hr. To the mixture was added diisopropyl ether (1000 mL) dropwise. The mixture was stirred at reflux temperature for 24 hr, followed by being cooled to room temperature. The obtained precipitate was collected, washed with diisopropyl ether, and dried under reduced pressure at 60° C. for 1 hr to give the title compound (120 g, 56%) as colorless crystals.

$^1$H NMR (300 MHz, DMSO-$d_6$) δ 0.93 (t, J=7.4, 3 H), 1.30 (d, J=6.1, 6 H), 1.46-1.69 (m, 2 H), 2.06 (s, 3 H), 2.47-2.61 (m, 2 H), 3.81 (s, 2 H), 4.53-4.78 (m, 1 H), 6.90-7.60 (m, 12 H)

Powder X-ray diffraction (Cu—Kα radiation, diffraction angle: 2θ(°)): 4.46, 6.32, 12.66, 12.84, 13.46, 13.74, 16.82, 17.08, 17.82, 17.98, 18.38, 19.70, 20.34, 21.80, 22.18, 22.80, 24.08, 25.40, 26.70.

Anal calcd for $C_{32}H_{31}N_4O_4K+0.5H_2O$: C, 65.84; H, 5.53; N, 9.60.

Found C, 65.67; H, 5.54; N, 9.45.

Example 92

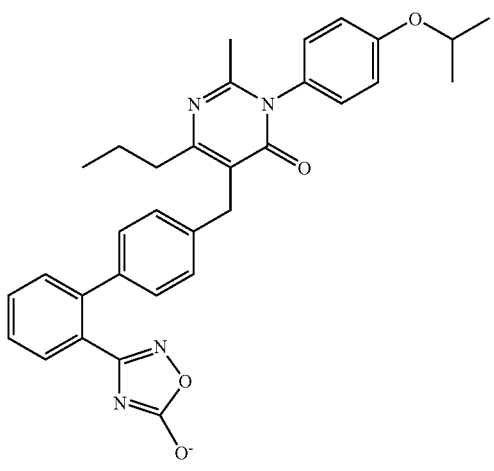

Na salt

3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one sodium salt To a solution of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one (1.07 g) in ethanol (1.0 mL) was added 8 M aqueous sodium hydroxide solution (0.25 mL), and the mixture was stirred at room temperature for 1 hr. The reaction mixture was concentrated under reduced pressure, and the residue was triturated with diisopropyl ether to give the title compound (1.13 g, 100%) as a colorless solid.

$^1$H NMR (300 MHz, DMSO-$d_6$) δ 0.93 (t, J=7.4, 3 H), 1.29 (s, 3H), 1.31 (s, 3 H), 1.49-1.68 (m, 2 H), 2.05 (s, 3 H), 2.51-2.57 (m, 2 H), 3.81 (s, 2 H), 4.58-4.74 (m, 1 H), 6.95-7.52 (m, 12 H)

Example 93

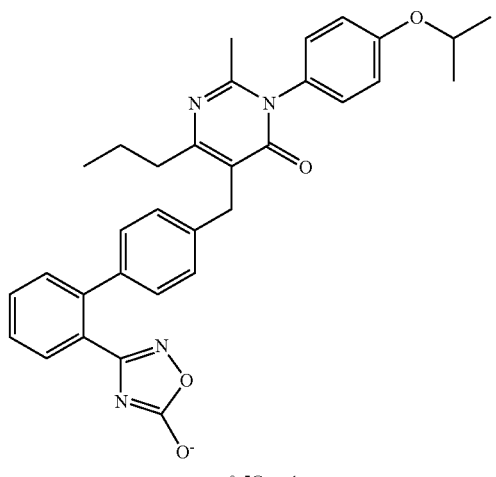

0.5Ca salt

3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt To a solution of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one sodium salt (0.56 g) in water (2.0 mL) was added calcium chloride (0.056 g), and the mixture was stirred at room temperature for 1 hr. The resulting solid was collected by filtration to give the title compound (0.40 g, 71%) as a colorless solid.

$^1$H NMR (300 MHz, DMSO-$d_6$) δ 0.92 (t, J=7.2, 3H), 1.29 (s, 3H), 1.31 (s, 3 H), 1.47-1.68 (m, 2 H), 2.06 (s, 3 H), 2.51-2.61 (m, 2H), 3.82 (s, 2 H), 4.60-4.75 (m, 1 H), 6.96-7.56 (m, 12 H)

Example 94

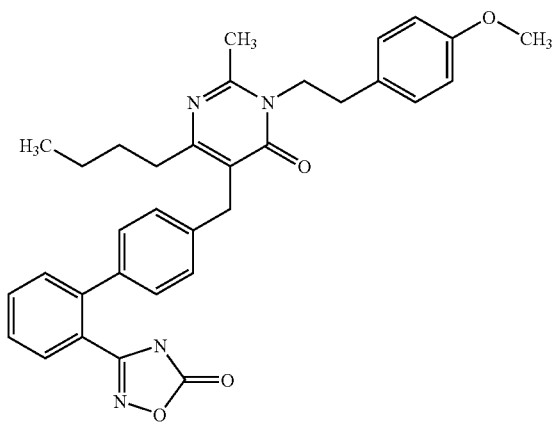

6-butyl-3-[2-(4-methoxyphenyl)ethyl]-2-methyl-5-{[2'-(5-oxo-4,5-dihydro-1,2,4-oxadiazol-3-yl)biphenyl-4-yl]methyl}pyrimidin-4(3H)-one A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-(2-bromoethyl)-4-methoxybenzene (0.95 g) was added, and the mixture was stirred at 150° C. for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.41 g), sodium hydrogen carbonate (0.59 g) and dimethyl sulfoxide (20 mL) previously stirred at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.11 g) and then 1,8-diazabicyclo[5.4.0]undec-7-ene (0.1 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.24 g, 17%).

$^1$H NMR (300 MHz, DMSO-$d_6$) δ 0.82 (3 H, t, J=7.3), 1.25 (2 H, tt, J=14.5, 7.2), 1.36-1.47 (2 H, m), 2.37 (3 H, s), 2.82-2.92 (2 H, m), 3.27-3.45 (2 H, m), 3.67-3.75 (3H, m), 3.88 (2 H, s), 4.04-4.14 (2 H, m), 6.84-6.89 (2 H, m), 7.11-7.17 (2 H, m), 7.20-7.26 (4 H, m), 7.48-7.57 (2 H, m), 7.63-7.71 (2 H, m), 11.72-12.92 (1 H, br).

6-Butyl-3-[2-(4-methoxyphenyl)ethyl]-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-[2-(4-methoxyphenyl)ethyl]-2-methyl-5-{[2'-(5-oxo-4,5-dihydro-1,2,4-oxadiazol-3-yl)biphenyl-4-yl]methyl}pyrimidin-4(3H)-one sodium salt
6-butyl-3-[2-(4-methoxyphenyl)ethyl]-2-methyl-5-{[2'-(5-oxo-4,5-dihydro-1,2,4-oxadiazol-3-yl)biphenyl-4-yl]methyl}pyrimidin-4(3H)-one potassium salt
6-butyl-3-[2-(4-methoxyphenyl)ethyl]-2-methyl-5-{[2'-(5-oxo-4,5-dihydro-1,2,4-oxadiazol-3-yl)biphenyl-4-yl]methyl}pyrimidin-4(3H)-one 0.5 calcium salt
6-butyl-3-[2-(4-methoxyphenyl)ethyl]-2-methyl-5-{[2'-(5-oxo-4,5-dihydro-1,2,4-oxadiazol-3-yl)biphenyl-4-yl]methyl}pyrimidin-4(3H)-one hydrochloride
6-butyl-3-[2-(4-methoxyphenyl)ethyl]-2-methyl-5-{[2'-(5-oxo-4,5-dihydro-1,2,4-oxadiazol-3-yl)biphenyl-4-yl]methyl}pyrimidin-4(3H)-one hydrobromide

Example 95

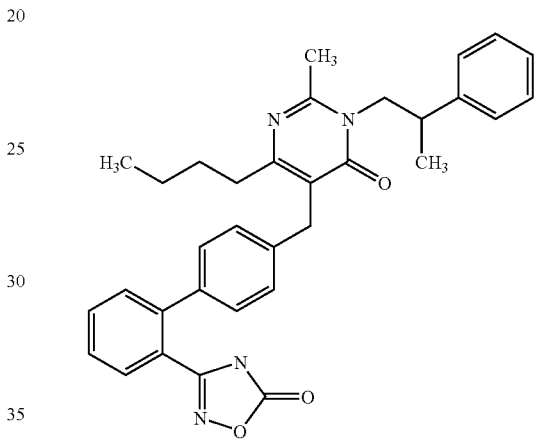

6-butyl-2-methyl-5-{[2'-(5-oxo-4,5-dihydro-1,2,4-oxadiazol-3-yl)biphenyl-4-yl]methyl}-3-(2-phenylpropyl)pyrimidin-4(3H)-one A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, (2-bromo-1-methylethyl)benzene (1.1 g) was added, and the mixture was stirred at 150° C. for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.28 g), sodium hydrogen carbonate (0.40 g) and dimethyl sulfoxide (20 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.078 g) and then 1,8-diazabicyclo[5.4.0]undec-7-ene (0.066 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.12 g, 9%).

$^1$H NMR (300 MHz, DMSO-d$_6$) δ 0.82 (3H, t, J=7.2), 1.20-1.30 (5 H, m), 1.33-1.45 (2 H, m), 2.16 (3 H, s), 2.36-2.48 (2H, m), 3.83-3.91 (4 H, m), 4.22 (1 H, dd, J=13.5, 6.9), 7.16-7.30 (9 H, m), 7.46-7.58 (2 H, m), 7.62-7.72 (2 H, m), 11.98-12.74 (1 H, m)

Example 96

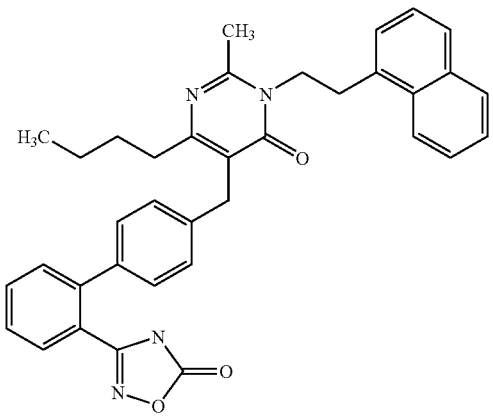

6-butyl-2-methyl-3-[2-(1-naphthyl)ethyl]-5-{[2'-(5-oxo-4,5-dihydro-1,2,4-oxadiazol-3-yl)biphenyl-4-yl]methyl}pyrimidin-4(3H)-one A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-(2-bromoethyl)naphthalene (1.0 g) was added, and the mixture was stirred at 150° C. for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.64 g), sodium hydrogen carbonate (0.92 g) and dimethyl sulfoxide (20 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.18 g) and then 1,8-diazabicyclo[5.4.0]undec-7-ene (0.15 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.33 g, 22%).

$^1$H NMR (300 MHz, DMSO-d$_6$) δ 0.79-0.86 (3H, m), 1.17-1.31 (2 H, m), 1.35-1.46 (2 H, m), 2.34 (3 H, s), 2.40-2.48 (2H, m), 3.38-3.50 (2 H, m), 3.88-3.95 (2 H, m), 4.18-4.29 (2 H, m), 7.21-7.30 (4 H, m), 7.42-7.46 (2 H, m), 7.48-7.58 (4 H, m), 7.63-7.71 (2 H, m), 7.82-7.96 (2 H, m), 8.27-8.33 (1 H, m), 12.39 (1 H, d, J=2.8)

Example 97

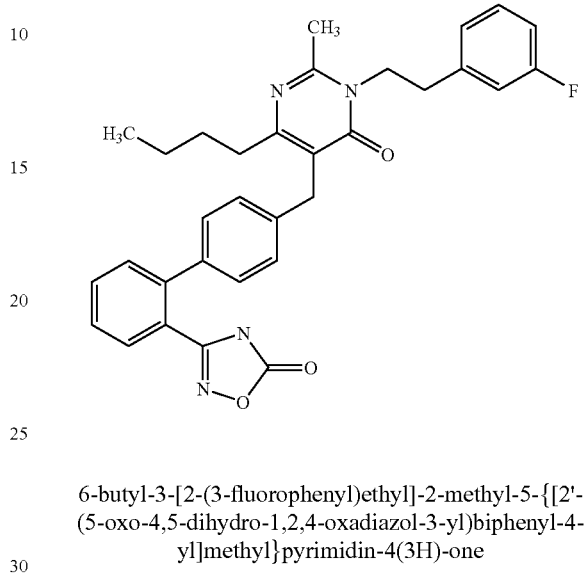

6-butyl-3-[2-(3-fluorophenyl)ethyl]-2-methyl-5-{[2'-(5-oxo-4,5-dihydro-1,2,4-oxadiazol-3-yl)biphenyl-4-yl]methyl}pyrimidin-4(3H)-one A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-(2-bromoethyl)-3-fluorobenzene (0.9 g) was added, and the mixture was stirred at 150° C. for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.64 g), sodium hydrogen carbonate (0.92 g) and dimethyl sulfoxide (20 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.18 g) and then 1,8-diazabicyclo[5.4.0]undec-7-ene (0.15 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.14 g, 10%).

$^1$H NMR (300 MHz, DMSO-d$_6$) δ 0.82 (3 H, t, J=7.3), 1.20-1.32 (2 H, m), 1.36-1.48 (2 H, m), 2.41 (3 H, s), 2.91-3.04 (2H, m), 3.26-3.42 (2 H, m), 3.87 (2 H, s), 4.10-4.22 (2

H, m), 7.03-7.14 (3 H, m), 7.20-7.27 (4 H, m), 7.29-7.40 (1H, m), 7.47-7.58 (2 H, m), 7.62-7.72 (2 H, m), 11.86-12.78 (1 H, m)

Example 98

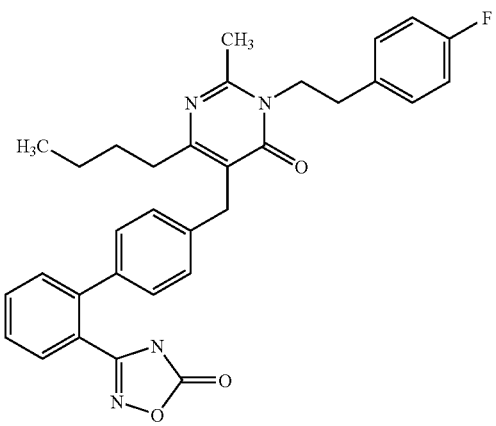

6-butyl-3-[2-(4-fluorophenyl)ethyl]-2-methyl-5-{[2'-(5-oxo-4,5-dihydro-1,2,4-oxadiazol-3-yl)biphenyl-4-yl]methyl}pyrimidin-4(3H)-one A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-(2-bromoethyl)-4-fluorobenzene (0.9 g) was added, and the mixture was stirred at 150° C. for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.9 g), sodium hydrogen carbonate (1.3 g) and dimethyl sulfoxide (20 mL) previously stirred at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.25 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.29 g, 16%).

$^1$H NMR (300 MHz, DMSO-$d_6$) δ 0.82 (3 H, t, J=7.3), 1.12-1.31 (2 H, m), 1.36-1.47 (2 H, m), 2.41 (3 H, s), 2.90-3.00 (2H, m), 3.34 (2 H, s), 3.87 (2 H, s), 4.07-4.17 (2 H, m), 7.09-7.17 (2 H, m), 7.22 (4 H, s), 7.24-7.30 (2 H, m), 7.47-7.58 (2 H, m), 7.63-7.71 (2 H, m), 12.17-12.63 (1 H, m)

Example 99

3-(2,3-dihydro-1-benzofuran-5-yl)-6-(ethoxymethyl)-2-methyl-5-{[2'-(5-oxo-4,5-dihydro-1,2,4-oxadiazol-3-yl)biphenyl-4-yl]methyl}pyrimidin-4(3H)-one

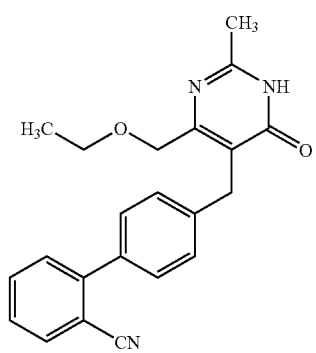

99a) 4'-{[4-(ethoxymethyl)-2-methyl-6-oxo-1,6-dihydropyrimidin-5-yl]methyl}biphenyl-2-carbonitrile A mixture of ethyl 4-ethoxy-3-oxobutanoate (15.0 g) and tetrahydrofuran (150 mL) was ice-cooled to 0° C., sodium hydride (2.58 g) was gradually added, and the mixture was stirred in situ for 30 min. To the mixture was added 4'-(bromomethyl)biphenyl-2-carbonitrile (11.7 g), and the mixture was stirred for 30 min. Thereafter, the temperature of the mixture was gradually raised to room temperature, and the mixture was stirred for 4 hr. The solvent of the reaction mixture was evaporated under reduced pressure, and the residue was diluted with ethyl acetate. The diluted solution was washed with water and saturated brine, and dried over anhydrous magnesium sulfate. The solvent was evaporated under reduced pressure. To an ice-cooled mixture of acetamidine hydrochloride (6.3 g) and methanol (50 mL) was added dropwise 28% sodium methoxide-methanol solution (19.3 mL), and a mixture of the aforementioned residue (12.2 g), 1,4-dioxane (20 mL) and methanol (30 mL) was added dropwise. The mixture was stirred at room temperature for 12 hr. The solvent of the reaction mixture was evaporated under reduced pressure. The residue was diluted with ethyl acetate, washed with 0.1 M aqueous hydrochloric acid solution, water and saturated brine, and dried over anhydrous magnesium sulfate. The solvent was evaporated under reduced pressure to give crude crystals. The crude crystals were washed with diisopropyl ether to give the title compound as colorless crystals (8.3 g, 70%).

$^1$H NMR (300 MHz, CDCl$_3$) δ 1.23 (3 H, t, J=7.0), 2.43 (3 H, s), 3.59 (2 H, q, J=7.0), 4.04 (2 H, s), 4.45 (2 H, s), 7.38-7.48 (6 H, m), 7.62 (1 H, td, J=7.7, 1.4), 7.74 (1 H, dd, J=7.7, 0.9), 12.94 (1 H, s)

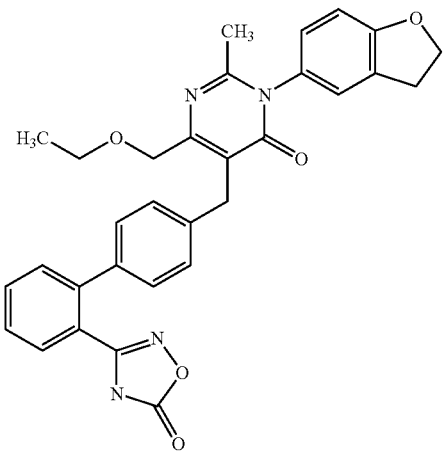

99b) 3-(2,3-dihydro-1-benzofuran-5-yl)-6-(ethoxymethyl)-2-methyl-5-{[2'-(5-oxo-4,5-dihydro-1,2,4-oxadiazol-3-yl)biphenyl-4-yl]methyl}pyrimidin-4(3H)-one A mixture of 4'-{[4-(ethoxymethyl)-2-methyl-6-oxo-1,6-dihydropyrimidin-5-yl]methyl}biphenyl-2-carbonitrile (5.0 g), (2,3-dihydro-1-benzofuran-5-yl)boronic acid (5.0 g), copper(II) acetate (5.0 g), pyridine (5.0 mL), triethylamine (10 mL), molecular sieves 4 A (10 g) and dichloromethane (100 mL) was stirred for 2 days. The reaction mixture was diluted with ethyl acetate, and the insoluble material was filtered off. The filtrate was concentrated under reduced pressure, and the residue was purified by silica gel column chromatography. The obtained residue was dissolved in dimethyl sulfoxide (10 mL), and added to a mixture of hydroxylammonium chloride (7.3 g), sodium hydrogen carbonate (10.5 g) and dimethyl sulfoxide (42.5 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (50 mL), N,N'-carbonyldiimidazole (1.9 g) and then 1,8-diazabicyclo[5.4.0]undec-7-ene (1.7 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (3.5 g, 62%).

$^1$H NMR (300 MHz, DMSO-$d_6$) δ 1.09 (3 H, t, J=7.1), 2.09 (3 H, s), 3.23 (2 H, t, J=8.8), 3.51 (2 H, q, J=7.0), 3.90 (2 H, s), 4.36 (2 H, s), 4.61 (2 H, t, J=8.8), 6.87 (1 H, d, J=8.5), 7.05 (1 H, dd, J=8.3, 2.3), 7.21 (3 H, d, J=8.3), 7.28-7.32 (2 H, m), 7.48-7.57 (2 H, m), 7.63-7.71 (2 H, m), 12.39 (1 H, s)

Example 100

6-(cyclopropylmethyl)-3-(2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one

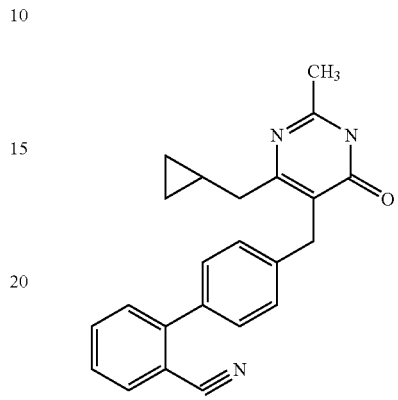

100a) 4'-{[4-(cyclopropylmethyl)-2-methyl-6-oxo-1,6-dihydropyrimidin-5-yl]methyl}biphenyl-2-carbonitrile A mixture of ethyl 4-cyclopropyl-3-oxobutanoate (15.0 g) and tetrahydrofuran (150 mL) was ice-cooled to 0° C., sodium hydride (2.6 g) was gradually added, and the mixture was stirred in situ for 30 min. To the mixture was added 4'-(bromomethyl)biphenyl-2-carbonitrile (12.0 g), and the mixture was stirred for 30 min. Thereafter, the temperature of the mixture was gradually raised to room temperature, and the mixture was stirred for 4 hr. The solvent of the reaction mixture was evaporated under reduced pressure, and the residue was diluted with ethyl acetate. The diluted solution was washed with water and saturated brine, and dried over anhydrous magnesium sulfate. The solvent was evaporated under reduced pressure. To an ice-cooled mixture of acetamidine hydrochloride (6.4 g) and methanol (50 mL) was added dropwise 28% sodium methoxide-methanol solution (20 mL), and a mixture of the aforementioned residue (12.0 g), 1,4-dioxane (20 mL) and methanol (30 mL) was added dropwise. The mixture was stirred at room temperature for 12 hr. The solvent of the reaction mixture was evaporated under reduced pressure. The residue was diluted with ethyl acetate, washed with 0.1 M aqueous hydrochloric acid solution, water and saturated brine, and dried over anhydrous magnesium sulfate. The solvent was evaporated under reduced pressure to give crude crystals. The crude crystals were washed with diisopropyl ether to give the title compound as colorless crystals (8.3 g, 69%).

$^1$H NMR (300 MHz, DMSO-$d_6$) δ 0.08 (2 H, q, J=4.8), 0.34 (2 H, ddd, J=8.0, 5.8, 4.0), 0.93-1.06 (1 H, m), 2.27 (3 H, s), 2.42 (2 H, d, J=6.4), 3.84 (2 H, s), 7.31 (2 H, d, J=8.0), 7.46 (2 H, d, J=8.3), 7.52-7.60 (2 H, m), 7.73-7.80 (1 H, m), 7.92 (1 H, d, J=8.0), 12.19 (1 H, s)

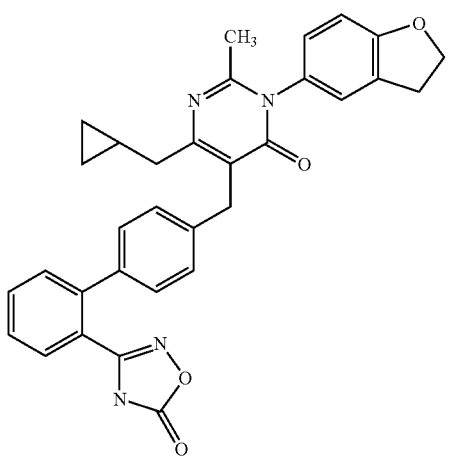
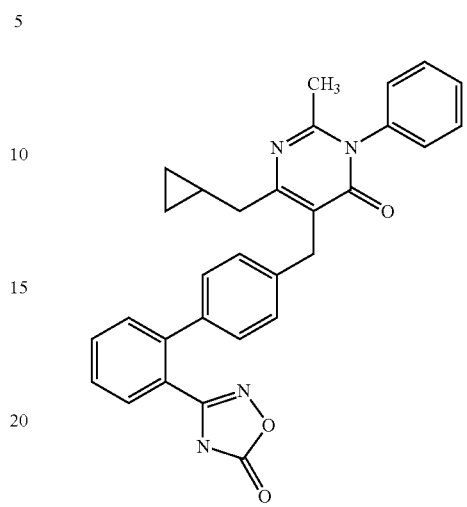

Example 101

100b) 6-(cyclopropylmethyl)-3-(2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one A mixture of 4'-{[4-(cyclopropylmethyl)-2-methyl-6-oxo-1,6-dihydropyrimidin-5-yl]methyl}biphenyl-2-carbonitrile (1.0 g), (2,3-dihydro-1-benzofuran-5-yl)boronic acid (1.0 g), copper(II) acetate (1.0 g), pyridine (1.0 mL), triethylamine (1.0 mL), molecular sieves 4 A (2.0 g) and dichloromethane (15 mL) was stirred for 6 days. The reaction mixture was diluted with ethyl acetate, and the insoluble material was filtered off. The filtrate was concentrated under reduced pressure, and the residue was purified by silica gel column chromatography. The obtained residue was dissolved in dimethyl sulfoxide (2.5 mL), and added to a mixture of hydroxylammonium chloride (1.8 g), sodium hydrogen carbonate (2.5 g) and dimethyl sulfoxide (10 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (50 mL), N,N'-carbonyldiimidazole (0.44 g) and then 1,8-diazabicyclo[5.4.0]undec-7-ene (0.41 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.61 g, 46%).

$^1$H NMR (300 MHz, DMSO-$d_6$) δ 0.06-0.20 (2 H, m), 0.38 (2H, ddd, J=8.0, 5.8, 4.1), 0.97-1.07 (2H, m), 2.07-2.14 (3H, m), 2.45 (1 H, d, J=6.8), 3.23 (2 H, s), 3.84 (2 H, s), 4.61 (2 H, t, J=8.8), 6.87 (1 H, d, J=8.3), 7.07 (1 H, dd, J=8.5, 2.3), 7.19-7.27 (5 H, m), 7.48-7.57 (2 H, m), 7.62-7.72 (2 H, m), 12.40 (1 H, s)

6-(cyclopropylmethyl)-2-methyl-5-{[2'-(5-oxo-4,5-dihydro-1,2,4-oxadiazol-3-yl)biphenyl-4-yl]methyl}-3-phenylpyrimidin-4(3H)-one A mixture of 4'-{[4-(cyclopropylmethyl)-2-methyl-6-oxo-1,6-dihydropyrimidin-5-yl]methyl}biphenyl-2-carbonitrile (1.0 g), phenylboronic acid (1.0 g), copper(II) acetate (1.0 g), pyridine (1.0 mL), triethylamine (1.0 mL), molecular sieves 4 A (2.0 g) and dichloromethane (15 mL) was stirred for 6 days. The reaction mixture was diluted with ethyl acetate, and the insoluble material was filtered off. The filtrate was concentrated under reduced pressure, and the residue was purified by silica gel column chromatography. The obtained residue was dissolved in dimethyl sulfoxide (2.5 mL), and added to a mixture of hydroxylammonium chloride (1.8 g), sodium hydrogen carbonate (2.5 g) and dimethyl sulfoxide (10 mL) previously stirred at 40° C. for 30 min. The reaction mixture was stirred at 90° C. for 16 hr, and diluted with ethyl acetate. The mixture was washed with water and then with saturated brine, and dried over anhydrous magnesium sulfate. The solvent was evaporated under reduced pressure. The residue was dissolved in tetrahydrofuran (50 mL), N,N'-carbonyldiimidazole (0.44 g) and then 1,8-diazabicyclo[5.4.0]undec-7-ene (0.41 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.91 g, 74%).

$^1$H NMR (300 MHz, DMSO-$d_6$) δ 0.10-0.17 (2 H, m), 0.39 (2H, ddd, J=8.0, 5.7, 4.1), 1.03 (1 H, s), 2.07 (3 H, s), 2.46 (1H, s), 3.34 (1 H, s), 3.86 (2 H, s), 7.24 (4 H, q, J=8.3), 7.37-7.43 (2 H, m), 7.50 (2 H, d, J=7.0), 7.55 (3 H, td, J=7.4, 1.6), 7.63-7.72 (2 H, m), 12.40 (1 H, s)

Example 102

3-benzyl-6-butyl-2-(methoxymethyl)-5-{[2'-(5-oxo-4,5-dihydro-1,2,4-oxadiazol-3-yl)biphenyl-4-yl]methyl}pyrimidin-4(3H)-one

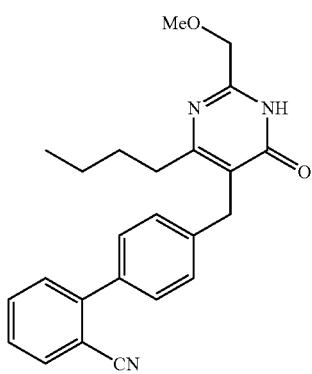

102a) 4'-{[4-butyl-2-(methoxymethyl)-6-oxo-1,6-dihydropyrimidin-5-yl]methyl}biphenyl-2-carbonitrile A solution of 2-methoxyethanimidamide hydrochloride (10 g), 28% sodium methoxide (24 mL) and methyl 2-[(2'-cyanobiphenyl-4-yl)methyl]-3-oxoheptanoate (15 g) in methanol (150 mL) and 1,4-dioxane (50 mL) was stirred overnight. The solvent was evaporated under reduced pressure, and water and acetic acid were added. The precipitated solid was collected by filtration, and washed with water and diethyl ether to give the title compound (11 g, 71%) as a pale-yellow solid.

$^1$H NMR (300 MHz, DMSO-d$_6$) δ 0.82 (3 H, t, J=7.2), 1.19-1.34 (2 H, m), 1.37-1.51 (2 H, m), 2.47-2.57 (2 H, m), 3.33 (3H, s), 3.88 (2 H, s), 4.23 (2 H, s), 7.33 (2 H, d, J=8.2), 7.44-7.62 (4 H, m), 7.73-7.81 (1 H, m), 7.90-7.95 (1 H, m), 12.38 (1 H, s)

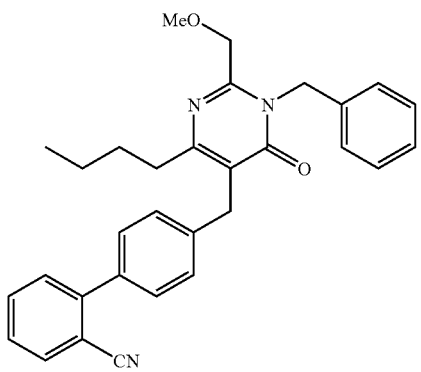

102b) 4'-{[1-benzyl-4-butyl-2-(methoxymethyl)-6-oxo-1,6-dihydropyrimidin-5-yl]methyl}biphenyl-2-carbonitrile A solution of 4'-{[4-butyl-2-(methoxymethyl)-6-oxo-1,6-dihydropyrimidin-5-yl]methyl}biphenyl-2-carbonitrile (4.5 g), benzyl bromide (1.5 mL) and cesium carbonate (4.2 g) in N,N-dimethylacetamide (45 mL) was stirred overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (1.8 g, 32%) as a colorless liquid.

$^1$H NMR (300 MHz, CDCl$_3$) δ 0.89 (3 H, t, J=7.3), 1.29-1.44 (2 H, m), 1.53-1.67 (2 H, m), 2.73-2.82 (2 H, m), 3.54 (3H, s), 4.06 (2 H, s), 4.57 (2 H, s), 5.45 (2 H, s), 7.21 (2 H, d, J=8.1), 7.24-7.36 (5 H, m), 7.37-7.51 (4 H, m), 7.58-7.67 (1 H, m), 7.75 (1 H, dd, J=7.7, 1.3)

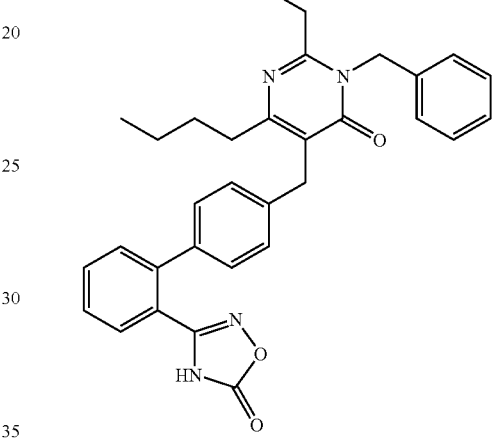

102c) 3-benzyl-6-butyl-2-(methoxymethyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (2.6 g), sodium hydrogen carbonate (3.8 g) and dimethyl sulfoxide (18 mL) was stirred at 50° C. for 30 min, 4'-{[1-benzyl-4-butyl-2-(methoxymethyl)-6-oxo-1,6-dihydropyrimidin-5-yl]methyl}biphenyl-2-carbonitrile (1.8 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (18 mL), N,N'-carbonyldiimidazole (0.92 g) and then 1,8-diazabicyclo[5.4.0]undec-7-ene (0.85 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (1.4 g, 69%) as a solid.

$^1$H NMR (300 MHz, DMSO-d$_6$) δ 0.83 (3H, t, J=7.2), 1.20-1.37 (2 H, m), 1.42-1.56 (2 H, m), 2.65-2.74 (2 H, m), 3.38 (3H, s), 4.02 (2 H, s), 4.44 (2 H, s), 5.44 (2 H, s), 7.12-7.73 (13 H, m), 12.4 (1 H, s)

Example 103

3-benzyl-6-butyl-2-(fluoromethyl)-5-{[2'-(5-oxo-4,5-dihydro-1,2,4-oxadiazol-3-yl)biphenyl-4-yl]methyl}pyrimidin-4(3H)-one

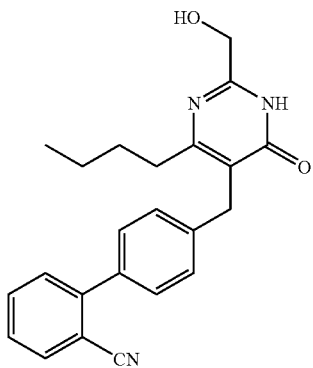

103a) 4'-{[4-butyl-2-(hydroxymethyl)-6-oxo-1,6-dihydropyrimidin-5-yl]methyl}biphenyl-2-carbonitrile 4'-{[4-Butyl-2-(methoxymethyl)-6-oxo-1,6-dihydropyrimidin-5-yl]methyl}biphenyl-2-carbonitrile (2.0 g) was dissolved in dichloromethane (20 mL), and 1.0 M boron tribromide dichloromethane solution (1.0 M, 16 mL) was added at 0° C. After stirring at room temperature for 3 hr, water was added, and the mixture was extracted with ethyl acetate. The organic layer was washed with saturated brine, and dried over anhydrous magnesium sulfate. The solvent was evaporated under reduced pressure. The residue was crystallized from ethyl acetate and diethyl ether to give the title compound (1.7 g, 86%) as a colorless solid.

$^1$H NMR (300 MHz, CDCl$_3$) δ 0.89 (3H, t, J=7.2), 1.28-1.43 (2 H, m), 1.49-1.63 (2 H, m), 2.57-2.68 (2 H, m), 3.74 (1H, s), 3.96 (2 H, s), 4.56 (2 H, s), 7.30-7.51 (6 H, m), 7.57-7.67 (1 H, m), 7.74 (1 H, dd, J=7.7, 0.94), 11.95 (1 H, s)

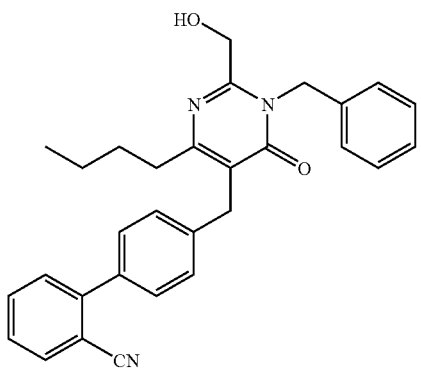

103b) 4'-{[1-benzyl-4-butyl-2-(hydroxymethyl)-6-oxo-1,6-dihydropyrimidin-5-yl]methyl}biphenyl-2-carbonitrile A solution of 4'-{[4-butyl-2-(hydroxymethyl)-6-oxo-1,6-dihydropyrimidin-5-yl]methyl}biphenyl-2-carbonitrile (1.4 g), benzyl bromide (0.49 mL) and cesium carbonate (1.3 g) in N,N-dimethylacetamide (14 mL) was stirred for 2 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.86 g, 49%) as a colorless liquid.

$^1$H NMR (300 MHz, CDCl$_3$) δ 0.92 (3H, t, J=7.2), 1.31-1.46 (2 H, m), 1.56-1.70 (2 H, m), 2.62-2.73 (2 H, m), 4.04 (2H, s), 4.32 (1 H, t, J=4.2), 4.48 (2 H, d, J=3.9), 5.15 (2H, s), 7.16-7.22 (2 H, m), 7.27-7.52 (9 H, m), 7.58-7.67 (1 H, m), 7.75 (1 H, dd, J=7.7, 0.94)

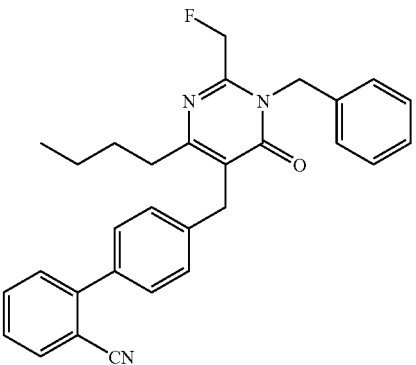

103c) 4'-{[1-benzyl-4-butyl-2-(fluoromethyl)-6-oxo-1,6-dihydropyrimidin-5-yl]methyl}biphenyl-2-carbonitrile 4'-{[1-Benzyl-4-butyl-2-(hydroxymethyl)-6-oxo-1,6-dihydropyrimidin-5-yl]methyl}biphenyl-2-carbonitrile (0.86 g) was dissolved in dichloromethane (20 mL), and bis(2-methoxyethyl)aminosulfur trifluoride (0.34 mL) was added −78° C. The mixture was stirred at 0° C. for 3 hr, a saturated aqueous sodium hydrogen carbonate solution was added, and the mixture was extracted with ethyl acetate. The organic layer was washed with saturated brine, and dried over anhydrous magnesium sulfate. The solvent was evaporated under reduced pressure and the residue was purified by silica gel column chromatography to give the title compound (0.35 g, 41%) as a colorless liquid.

$^1$H NMR (300 MHz, CDCl$_3$) δ 0.92 (3H, t, J=7.2), 1.31-1.46 (2 H, m), 1.53-1.66 (2 H, m), 2.61-2.69 (2 H, m), 4.04 (2H, s), 5.13 (1 H, s), 5.29 (1 H, s), 5.42 (2 H, s), 7.17-7.23 (2 H, m), 7.27-7.52 (9 H, m), 7.58-7.67 (1 H, m), 7.75 (1 H, dd, J=7.7, 0.94)

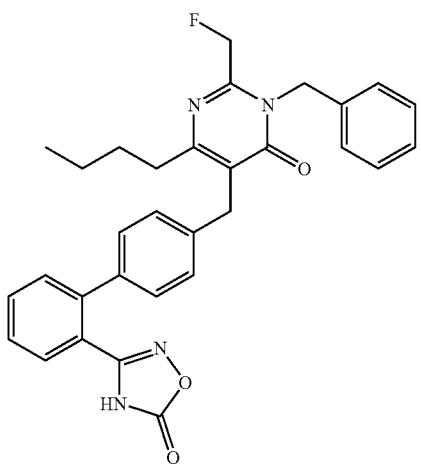

103d) 3-benzyl-6-butyl-2-(fluoromethyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.52 g), sodium hydrogen carbonate (0.76 g) and dimethyl sulfoxide (3.5 mL) was stirred at 50° C. for 30 min, 4'-{[1-benzyl-4-butyl-2-(fluoromethyl)-6-oxo-1,6-dihydropyrimidin-5-yl]methyl}biphenyl-2-carbonitrile (0.35 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (3.5 mL), N,N'-carbonyldiimidazole (0.18 g) and then 1,8-diazabicyclo[5.4.0]undec-7-ene (0.17 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.17 g, 42%) as a solid.

$^1$H NMR (300 MHz, CDCl$_3$) δ 0.94 (3H, t, J=7.2), 1.33-1.48 (2 H, m), 1.51-1.80 (2 H, m), 2.63-2.73 (2 H, m), 3.98 (2H, s), 5.12 (1 H, s), 5.28 (1 H, s), 5.34 (2 H, s), 7.12-7.18 (2 H, m), 7.23-7.51 (9 H, m), 7.55-7.63 (1 H, m), 7.82 (1 H, dd, J=7.7, 1.3)

3-Benzyl-6-butyl-2-(fluoromethyl)-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

3-benzyl-6-butyl-2-(fluoromethyl)-5-{[2'-(5-oxo-4,5-dihydro-1,2,4-oxadiazol-3-yl)biphenyl-4-yl]methyl}pyrimidin-4(3H)-one sodium salt 3-benzyl-6-butyl-2-(fluoromethyl)-5-{[2'-(5-oxo-4,5-dihydro-1,2,4-oxadiazol-3-yl)biphenyl-4-yl]methyl}pyrimidin-4(3H)-one potassium salt 3-benzyl-6-butyl-2-(fluoromethyl)-5-{[2'-(5-oxo-4,5-dihydro-1,2,4-oxadiazol-3-yl)biphenyl-4-yl]methyl}pyrimidin-4(3H)-one 0.5 calcium salt 3-benzyl-6-butyl-2-(fluoromethyl)-5-{[2'-(5-oxo-4,5-dihydro-1,2,4-oxadiazol-3-yl)biphenyl-4-yl]methyl}pyrimidin-4(3H)-one hydrochloride 3-benzyl-6-butyl-2-(fluoromethyl)-5-{[2'-(5-oxo-4,5-dihydro-1,2,4-oxadiazol-3-yl)biphenyl-4-yl]methyl}pyrimidin-4(3H)-one hydrobromide

Example 104

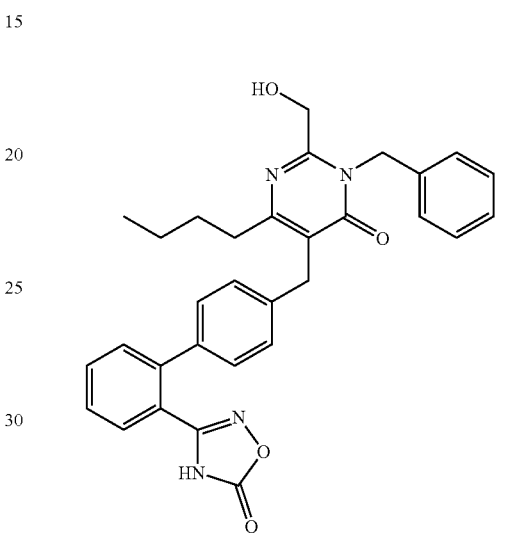

3-benzyl-6-butyl-2-(hydroxymethyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.75 g), sodium hydrogen carbonate (1.1 g) and dimethyl sulfoxide (5 mL) was stirred at 50° C. for 30 min, 4'-{[1-benzyl-4-butyl-2-(hydroxymethyl)-6-oxo-1,6-dihydropyrimidin-5-yl]methyl}biphenyl-2-carbonitrile (0.50 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL), N,N'-carbonyldiimidazole (0.18 g) and then 1,8-diazabicyclo[5.4.0]undec-7-ene (0.32 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.20 g, 35%) as a solid.

$^1$H NMR (300 MHz, DMSO-d$_6$) δ 0.84 (3H, t, J=7.2), 1.22-1.38 (2 H, m), 1.42-1.55 (2 H, m), 2.52-2.60 (2 H, m), 3.91 (2H, s), 4.37 (2 H, d, J=5.7), 5.35 (2 H, s), 5.60 (1 H, t, J=5.7), 7.12-7.40 (9H, m), 7.53 (2 H, dd, J=15.7, 7.7), 7.62-7.73 (2 H, m), 12.37 (1 H, s)

Example 105

3-benzyl-6-butyl-2-ethyl-5-{[2'-(5-oxo-4,5-dihydro-1,2,4-oxadiazol-3-yl)biphenyl-4-yl]methyl}pyrimidin-4(3H)-one

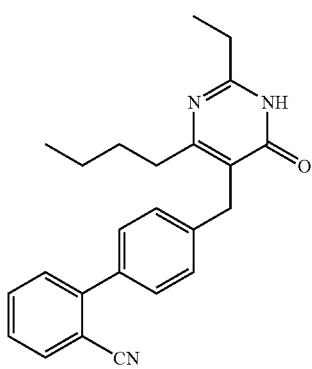

105a) 4'-[(4-butyl-2-ethyl-6-oxo-1,6-dihydropyrimidin-5-yl)methyl]biphenyl-2-carbonitrile A solution of propanimidamide hydrochloride (3.9 g), 28% sodium methoxide (11 mL) and methyl 2-[(2'-cyanobiphenyl-4-yl)methyl]-3-oxoheptanoate (6.5 g) in methanol (65 mL) was stirred overnight. The solvent was evaporated under reduced pressure, and water and acetic acid were added. The precipitated solid was collected by filtration, and washed with water and diethyl ether to give the title compound (5.5 g, 83%) as a pale-yellow solid.

$^1$H NMR (300 MHz, DMSO-$d_6$) δ 0.82 (3H, t, J=7.5), 1.17 (3H, t, J=7.5), 1.21-1.34 (2 H, m), 1.37-1.51 (2 H, m), 2.45-2.57 (4 H, m), 3.86 (2 H, s), 7.33 (2 H, d, J=8.2), 7.48 (2 H, d, J=8.2), 7.52-7.62 (2H, m), 7.74-7.81 (1 H, m), 7.89-7.96 (1 H, m), 12.30 (1 H, s)

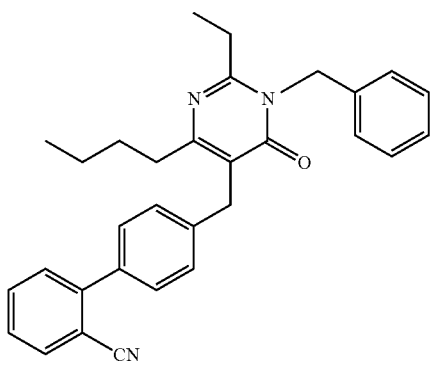

105b) 4'-[(1-benzyl-4-butyl-2-ethyl-6-oxo-1,6-dihydropyrimidin-5-yl)methyl]biphenyl-2-carbonitrile A solution of 4'-[(4-butyl-2-ethyl-6-oxo-1,6-dihydropyrimidin-5-yl)methyl]biphenyl-2-carbonitrile (1.5 g), benzyl bromide (0.58 mL) and cesium carbonate (1.6 g) in N,N-dimethylacetamide (15 mL) was stirred overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (1.0 g, 59%) as a colorless liquid.

$^1$H NMR (300 MHz, CDCl$_3$) δ 0.92 (3H, t, J=7.25), 1.23 (3H, t, J=7.3), 1.31-1.46 (2 H, m), 1.55-1.68 (2 H, m), 2.59-2.72 (4 H, m), 4.01 (2 H, s), 5.32 (2 H, s), 7.16 (2 H, d, J=6.9), 7.22-7.51 (9 H, m), 7.57-7.66 (1 H, m), 7.74 (1 H, dd, J=7.7, 1.3)

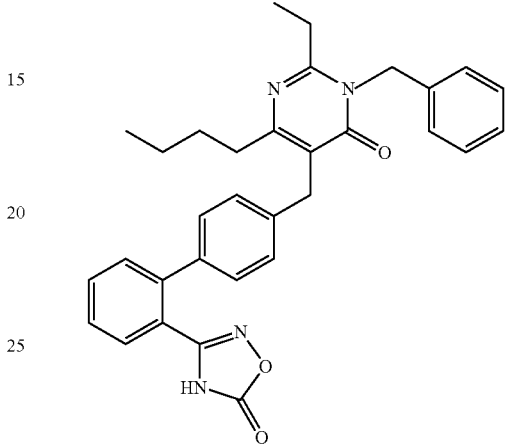

105c) 3-benzyl-6-butyl-2-ethyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.0 g), sodium hydrogen carbonate (1.7 g) and dimethyl sulfoxide (10 mL) was stirred at 50° C. for 30 min, 4'-[(1-benzyl-4-butyl-2-ethyl-6-oxo-1,6-dihydropyrimidin-5-yl)methyl]biphenyl-2-carbonitrile (1.0 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.58 g) and then 1,8-diazabicyclo[5.4.0]undec-7-ene (0.53 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.80 g, 65%) as a solid.

$^1$H NMR (300 MHz, DMSO-$d_6$) δ 0.84 (3 H, t, J=7.2), 1.09 (3 H, t, J=7.2), 1.21-1.37 (2 H, m), 1.45-1.57 (2 H, m), 2.48-2.58 (2 H, m), 2.67 (2 H, q, J=7.1), 3.92 (2 H, s), 5.31 (2 H, s), 7.14 (2 H, d, J=6.9), 7.20-7.40 (7 H, m), 7.48-7.59 (2 H, m), 7.62-7.73 (2 H, m), 12.39 (1 H, s)

3-Benzyl-6-butyl-2-ethyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

3-benzyl-6-butyl-2-ethyl-5-{[2'-(5-oxo-4,5-dihydro-1,2,4-oxadiazol-3-yl)biphenyl-4-yl]methyl}pyrimidin-4(3H)-one sodium salt 3-benzyl-6-butyl-2-ethyl-5-{[2'-(5-oxo-4,5-dihydro-1,2,4-oxadiazol-3-yl)biphenyl-4-yl]methyl}pyrimidin-4(3H)-one potassium salt 3-benzyl-6-butyl-2-ethyl-5-{[2'-(5-oxo-4,5-dihydro-1,2,4-oxadiazol-3-yl)biphenyl-4-yl]methyl}pyrimidin-4(3H)-one 0.5 calcium salt 3-benzyl-6-butyl-2-ethyl-5-{[2'-(5-oxo-4,5-dihydro-1,2,4-oxadiazol-3-yl)biphenyl-4-yl]methyl}pyrimidin-4(3H)-one hydrochloride 3-benzyl-6-butyl-2-ethyl-5-{[2'-(5-oxo-4,5-dihydro-1,2,4-oxadiazol-3-yl)biphenyl-4-yl]methyl}pyrimidin-4(3H)-one hydrobromide

Example 106

6-butyl-2-ethyl-5-{[2'-(5-oxo-4,5-dihydro-1,2,4-oxadiazol-3-yl)biphenyl-4-yl]methyl}-3-phenylpyrimidin-4(3H)-one

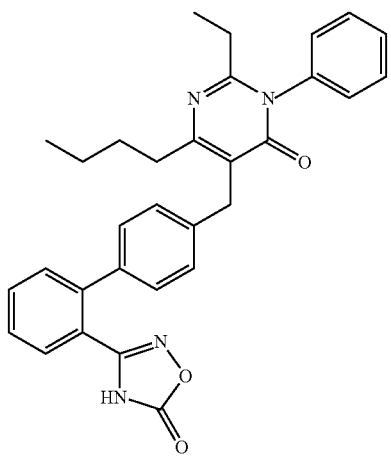

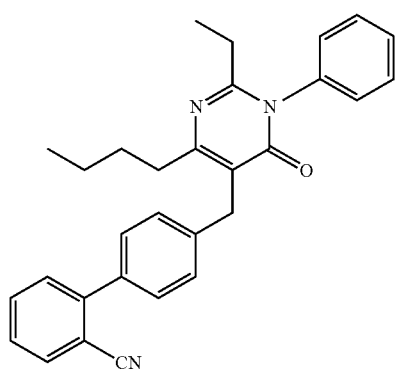

106a) 4'-[(4-butyl-2-ethyl-6-oxo-1-phenyl-1,6-dihydropyrimidin-5-yl)methyl]biphenyl-2-carbonitrile A mixture of 4'-[(4-butyl-2-ethyl-6-oxo-1,6-dihydropyrimidin-5-yl)methyl]biphenyl-2-carbonitrile (1.5 g), phenylboronic acid (0.99 g), copper(II) acetate (1.5 g), pyridine (1.6 mL), triethylamine (2.8 mL), molecular sieves 4A (1.5 g) and dichloromethane (30 mL) was stirred for 6 days. The reaction mixture was diluted with ethyl acetate, and the insoluble material was filtered off. The filtrate was concentrated under reduced pressure, and the residue was purified by silica gel column chromatography to give the title compound (1.0 g, 55%) as a colorless liquid.

$^1$H NMR (300 MHz, CDCl$_3$) δ 0.95 (3 H, t, J=7.2), 1.15 (3 H, t, J=7.4), 1.35-1.51 (2 H, m), 1.57-1.73 (2 H, m), 2.36 (2 H, q, J=7.4), 2.69 (2 H, q, J=7.2), 3.97 (2 H, s), 7.19-7.28 (2 H, m), 7.36-7.57 (9 H, m), 7.57-7.65 (1 H, m), 7.74 (1 H, dd, J=7.7, 1.1)

106b) 6-butyl-2-ethyl-5-{[2'-(5-oxo-4,5-dihydro-1,2,4-oxadiazol-3-yl)biphenyl-4-yl]methyl}-3-phenylpyrimidin-4(3H)-one A mixture of hydroxylammonium chloride (1.6 g), sodium hydrogen carbonate (2.3 g) and dimethyl sulfoxide (10 mL) was stirred at 50° C. for 30 min, 4'-[(4-butyl-2-ethyl-6-oxo-1-phenyl-1,6-dihydropyrimidin-5-yl)methyl]biphenyl-2-carbonitrile (1.0 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.54 g) and then 1,8-diazabicyclo[5.4.0]undec-7-ene (0.50 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.68 g, 60%) as a solid.

$^1$H NMR (300 MHz, DMSO-d$_6$) δ 0.86 (3 H, t, J=7.2), 1.05 (3 H, t, J=7.2), 1.26-1.41 (2 H, m), 1.46-1.60 (2 H, m), 2.26 (2 H, q, J=7.2), 2.56 (2 H, m), 3.87 (2 H, s), 7.19-7.32 (4 H, m), 7.34-7.40 (2 H, m), 7.45-7.58 (5 H, m), 7.62-7.73 (2 H, m), 12.39 (1 H, s)

Example 107

3-benzyl-6-butyl-2-methoxy-5-{[2'-(5-oxo-4,5-dihydro-1,2,4-oxadiazol-3-yl)biphenyl-4-yl]methyl}pyrimidin-4(3H)-one

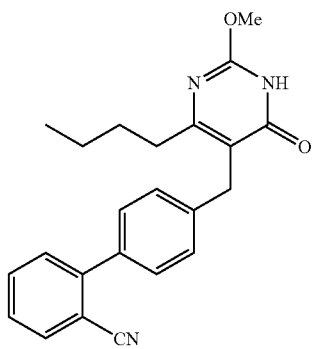

107a) 4'-[(4-butyl-2-methoxy-6-oxo-1,6-dihydropyrimidin-5-yl)methyl]biphenyl-2-carbonitrile A solution of methyl imidocarbamate sulfate (10 g), 28% sodium methoxide (29 mL) and methyl 2-[(2'-cyanobiphenyl-4-yl)methyl]-3-oxoheptanoate (9.8 g) in methanol (100 mL) was stirred at 70° C. overnight. The solvent was evaporated under reduced pressure, and water and acetic acid were added. The precipitated solid was collected by filtration, and washed with water and diethyl ether to give the title compound (3.9 g, 37%) as a pale-yellow solid.

$^1$H NMR (300 MHz, DMSO-$d_6$) δ 0.82 (3 H, t, J=7.2), 1.20-1.34 (2 H, m), 1.40-1.54 (2 H, m), 2.43-2.53 (2 H, m), 3.82 (2 H, s), 3.86 (3 H, s), 7.28-7.65 (6 H, m), 7.73-7.82 (1 H, m), 7.90-7.96 (1 H, m), 12.26 ( H, s)

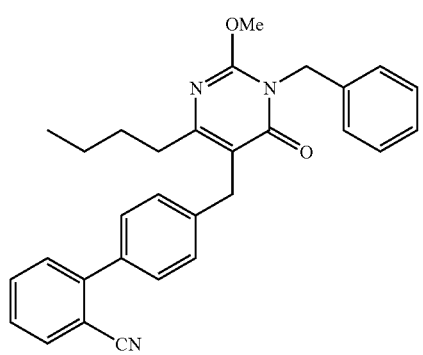

107b) 4'-[(1-benzyl-4-butyl-2-methoxy-6-oxo-1,6-dihydropyrimidin-5-yl)methyl]biphenyl-2-carbonitrile A solution of 4'-[(4-butyl-2-methoxy-6-oxo-1,6-dihydropyrimidin-5-yl)methyl]biphenyl-2-carbonitrile (1.5 g), benzyl bromide (0.53 mL) and cesium carbonate (1.4 g) in N,N-dimethylformamide (15 mL) was stirred overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.93 g, 50%) as a colorless liquid.

$^1$H NMR (300 MHz, CDCl$_3$) δ 0.90 (3 H, t, J=7.2), 1.27-1.41 (2 H, m), 1.51-1.65 (2 H, m), 2.49-2.58 (2 H, m), 3.94 (2 H, s), 3.97 (3 H, s), 5.18 (2 H, s), 7.22-7.52 (11 H , m), 7.57-7.65 (1 H, m), 7.74 (1 H, dd, J=7.7, 1.3)

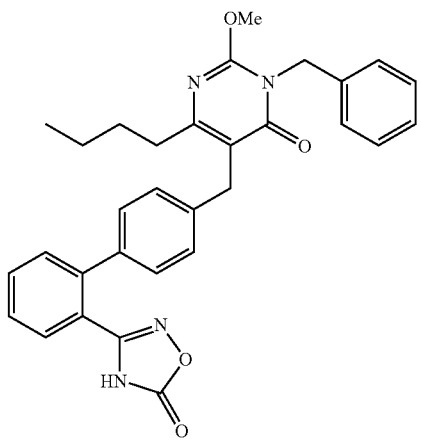

107c) 3-benzyl-6-butyl-2-methoxy-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.4 g), sodium hydrogen carbonate (2.0 g) and dimethyl sulfoxide (10 mL) was stirred at 50° C. for 30 min, 4'-[(1-benzyl-4-butyl-2-methoxy-6-oxo-1,6-dihydropyrimidin-5-yl)methyl]biphenyl-2-carbonitrile (0.93 g) was added, and the mixture was stirred at 90° C. for 2 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.32 g) and then 1,8-diazabicyclo[5.4.0]undec-7-ene (0.30 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.18 g, 17%) as a solid.

$^1$H NMR (300 MHz, DMSO-$d_6$) δ 0.83 (3 H, t, J=7.3), 1.20-1.36 (2 H, m), 1.42-1.56 (2 H, m), 2.44-2.54 (2 H, m), 3.85 (2 H, s), 3.91 (3 H, s), 5.11 (2 H, s), 7.17-7.39 (9 H, m), 7.46-7.58 (2 H, m), 7.62-7.73 (2 H, m), 12.38 (1 H, s)

3-Benzyl-6-butyl-2-methoxy-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

3-benzyl-6-butyl-2-methoxy-5-{[2'-(5-oxo-4,5-dihydro-1,2,4-oxadiazol-3-yl)biphenyl-4-yl]methyl}pyrimidin-4(3H)-one sodium salt 3-benzyl-6-butyl-2-methoxy-5-{[2'-(5-oxo-4,5-dihydro-1,2,4-oxadiazol-3-yl)biphenyl-4-yl]methyl}pyrimidin-4(3H)-one potassium salt 3-benzyl-6-butyl-2-methoxy-5-{[2'-(5-oxo-4,5-dihydro-1,2,4-oxadiazol-3-yl)biphenyl-4-yl]methyl}pyrimidin-4(3H)-one 0.5 calcium salt 3-benzyl-6-butyl-2-methoxy-5-{[2'-(5-oxo-4,5-dihydro-1,2,4-oxadiazol-3-yl)biphenyl-4-yl]methyl}pyrimidin-4(3H)-one hydrochloride 3-benzyl-6-butyl-2-methoxy-5-{[2'-(5-oxo-4,5-dihydro-1,2,4-oxadiazol-3-yl)biphenyl-4-yl]methyl}pyrimidin-4(3H)-one hydrobromide

Example 108

6-butyl-2-methoxy-5-{[2'-(5-oxo-4,5-dihydro-1,2,4-oxadiazol-3-yl)biphenyl-4-yl]methyl}-3-phenylpyrimidin-4(3H)-one

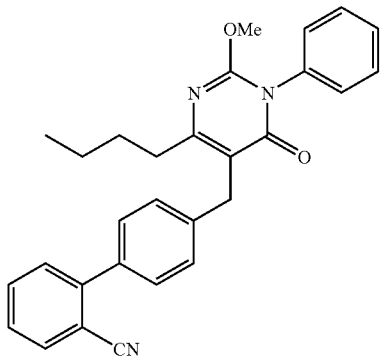

108a) 4'-[(4-butyl-2-methoxy-6-oxo-1-phenyl-1,6-dihydropyrimidin-5-yl)methyl]biphenyl-2-carbonitrile A mixture of 4'-[(4-butyl-2-methoxy-6-oxo-1,6-dihydropyrimidin-5-yl)methyl]biphenyl-2-carbonitrile (2.0 g), phenylboronic acid (1.3 g), copper(II) acetate (2.0 g), pyridine (2.2 mL), triethylamine (3.7 mL), molecular sieves 4 A (2.0 g) and dichloromethane (54 mL) was stirred overnight. The reaction mixture was diluted with ethyl acetate, and the insoluble material was filtered off. The filtrate was concentrated under reduced pressure, and the residue was purified by silica gel column chromatography to give the title compound (1.6 g, 65%) as a colorless liquid.

$^1$H NMR (300 MHz, CDCl$_3$) δ 0.95 (3 H, t, J=7.3), 1.35-1.49 (2 H, m), 1.60-1.72 (2 H, m), 2.64 (2 H, q, J=7.3), 3.88 (3 H, s), 3.94 (2 H, s), 7.20-7.25 (2 H, m), 7.36-7.52 (9 H, m), 7.57-7.65 (1 H, m), 7.74 (1 H, dd, J=7.7, 1.1)

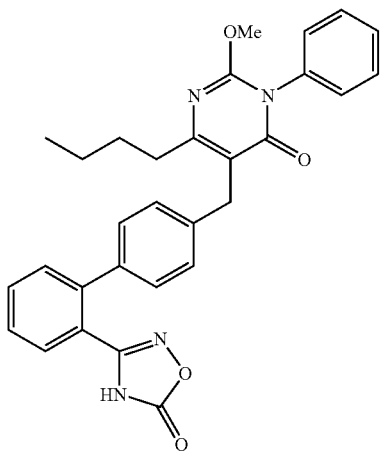

108b) 6-butyl-2-methoxy-5-{[2'-(5-oxo-4,5-dihydro-1,2,4-oxadiazol-3-yl)biphenyl-4-yl]methyl}-3-phenylpyrimidin-4(3H)-one A mixture of hydroxylammonium chloride (2.4 g), sodium hydrogen carbonate (3.5 g) and dimethyl sulfoxide (16 mL) was stirred at 50° C. for 30 min, 4'-[(4-butyl-2-methoxy-6-oxo-1-phenyl-1,6-dihydropyrimidin-5-yl)methyl]biphenyl-2-carbonitrile (1.6 g) was added, and the mixture was stirred at 90° C. for 2 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (16 mL), N,N'-carbonyldiimidazole (0.57 g) and then 1,8-diazabicyclo[5.4.0]undec-7-ene (0.52 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.40 g, 22%) as a solid.

$^1$H NMR (300 MHz, DMSO-d$_6$) δ 0.86 (3 H, t, J=7.3), 1.26-1.40 (2 H, m), 1.47-1.61 (2 H, m), 2.48-2.56 (2 H, m), 3.81 (3 H, s), 3.84 (2 H, s), 7.19-7.35 (6 H, m), 7.40-7.58 (5 H, m), 7.63-7.72 (2 H, m), 12.39 (1 H, s)

6-Butyl-2-methoxy-5-{[2'-(5-oxo-4,5-dihydro-1,2,4-oxadiazol-3-yl)biphenyl-4-yl]methyl}-3-phenylpyrimidin-4(3H)-one obtained above is subjected to a conventional method of salt formation to give the following salts.

6-butyl-2-methoxy-5-{[2'-(5-oxo-4,5-dihydro-1,2,4-oxadiazol-3-yl)biphenyl-4-yl]methyl}-3-phenylpyrimidin-4(3H)-one sodium salt 6-butyl-2-methoxy-5-{[2'-(5-oxo-4,5-dihydro-1,2,4-oxadiazol-3-yl)biphenyl-4-yl]methyl}-3-phenylpyrimidin-4(3H)-one potassium salt 6-butyl-2-methoxy-5-{[2'-(5-oxo-4,5-dihydro-1,2,4-oxadiazol-3-yl)biphenyl-4-yl]methyl}-3-phenylpyrimidin-4(3H)-one 0.5 calcium salt 6-butyl-2-methoxy-5-{[2'-(5-oxo-4,5-dihydro-1,2,4-oxadiazol-3-yl)biphenyl-4-yl]methyl}-3-phenylpyrimidin-4(3H)-one hydrochloride 6-butyl-2-methoxy-5-{[2'-(5-oxo-4,5-dihydro-1,2,4-oxadiazol-3-yl)biphenyl-4-yl]methyl}-3-phenylpyrimidin-4(3H)-one hydrobromide

Example 109

6-butyl-3-(2,3-dihydro-1-benzofuran-5-yl)-2-ethyl-5-{[2'-(5-oxo-4,5-dihydro-1,2,4-oxadiazol-3-yl)biphenyl-4-yl]methyl}pyrimidin-4(3H)-one

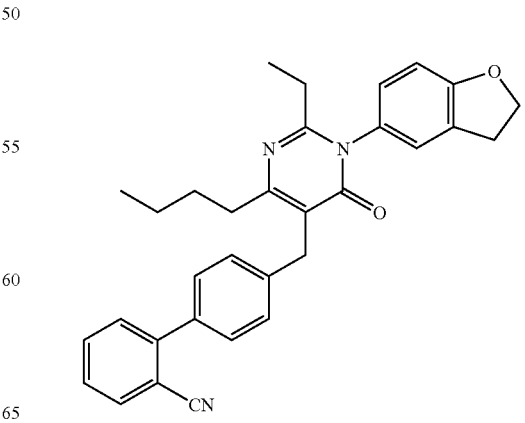

109a) 4'-{[4-butyl-1-(2,3-dihydro-1-benzofuran-5-yl)-2-ethyl-6-oxo-1,6-dihydropyrimidin-5-yl]methyl}biphenyl-2-carbonitrile A mixture of 4'-[(4-butyl-2-ethyl-6-oxo-1,6-dihydropyrimidin-5-yl)methyl]biphenyl-2-carbonitrile (5.0 g), 2,3-dihydro-1-benzofuran-5-ylboronic acid (4.4 g), copper(II) acetate (4.9 g), pyridine (5.4 mL), triethylamine (9.4 mL), molecular sieves 4 A (10 g) and dichloromethane (200 mL) was stirred for 2 days. The reaction mixture was diluted with ethyl acetate, and the insoluble material was filtered off. The filtrate was concentrated under reduced pressure, and the residue was purified by silica gel column chromatography to give the title compound (5.4 g, 82%) as a pale-yellow liquid.

$^1$H NMR (300 MHz, CDCl$_3$) δ 0.95 (3 H, t, J=7.2), 1.15 (3 H, t, J=7.2), 1.34-1.50 (2 H, m), 1.59-1.72 (2 H, m), 2.41 (2 H, q, J=7.4), 2.63-2.73 (2 H, m), 3.21-3.31 (2 H, m), 3.90-4.03 (2 H, m), 4.64 (2 H, t, J=9.0), 6.83-6.97 (2 H, m), 7.02 (1 H, d, J=1.5), 7.37-7.52 (6 H, m), 7.57-7.66 (1 H, m), 7.74 (1 H, dd, J=7.7, 0.94)

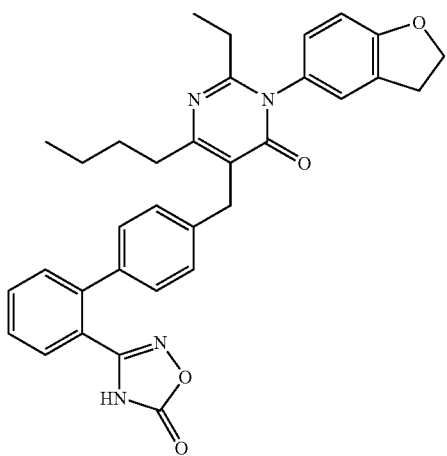

109b) 6-butyl-3-(2,3-dihydro-1-benzofuran-5-yl)-2-ethyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (9.4 g), sodium hydrogen carbonate (13.6 g) and dimethyl sulfoxide (60 mL) was stirred at 50° C. for 30 min, 4'-{[4-butyl-1-(2,3-dihydro-1-benzofuran-5-yl)-2-ethyl-6-oxo-1,6-dihydropyrimidin-5-yl]methyl}biphenyl-2-carbonitrile (5.4 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (60 mL), N,N'-carbonyldiimidazole (3.3 g) and then 1,8-diazabicyclo[5.4.0]undec-7-ene (3.0 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography and recrystallized from dichloromethane and diisopropyl ether to give the title compound (4.5 g, 75%) as a colorless solid.

$^1$H NMR (300 MHz, DMSO-d$_6$) δ 0.86 (3 H, t, J=7.3), 1.05 (3 H, t, J=7.3), 1.25-1.40 (2 H, m), 1.46-1.59 (2 H, m), 2.31 (2 H, q, J=7.3), 2.47-2.59 (2 H, m), 3.23 (2 H, t, J=8.7), 3.86 (2 H, s), 4.61 (2 H, t, J=8.7), 6.86 (1 H, d, J=8.4), 7.04 (1 H, dd, J=8.4, 2.2), 7.18-7.31 (5 H, m), 7.47-7.58 (2 H, m), 7.62-7.73 (2 H, m), 12.39 (1 H, s)

Example 110

6-butyl-2-ethyl-3-(2-hydroxy-3,3-dimethylbutyl)-5-{[2'-(5-oxo-4,5-dihydro-1,2,4-oxadiazol-3-yl)biphenyl-4-yl]methyl}pyrimidin-4(3H)-one

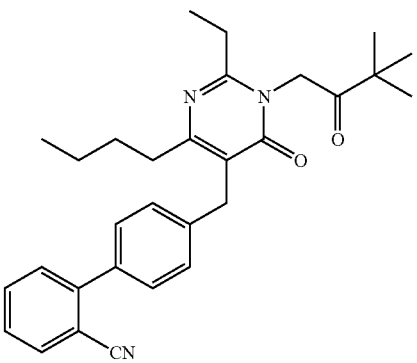

110a) 4'-{[4-butyl-1-(3,3-dimethyl-2-oxobutyl)-2-ethyl-6-oxo-1,6-dihydropyrimidin-5-yl]methyl}biphenyl-2-carbonitrile A solution of 4'-[(4-butyl-2-ethyl-6-oxo-1,6-dihydropyrimidin-5-yl)methyl]biphenyl-2-carbonitrile (20 g), 1-bromo-3,3-dimethylbutan-2-one (8.7 mL) and cesium carbonate (21 g) in N,N-dimethylformamide (200 mL) was stirred for 2 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (3.8 g, 15%) as a colorless liquid.

$^1$H NMR (300 MHz, CDCl$_3$) δ 0.90 (3 H, t, J=7.3), 1.22-1.43 (14 H, m), 1.53-1.66 (2 H, m), 2.49 (2 H, q, J=7.3), 2.56-2.63 (2 H, m), 3.95 (2 H, s), 5.06 (2 H, s), 7.29-7.50 (6H, m), 7.57-7.65 (1 H, m), 7.73 (1 H, dd, J=7.7, 0.94)

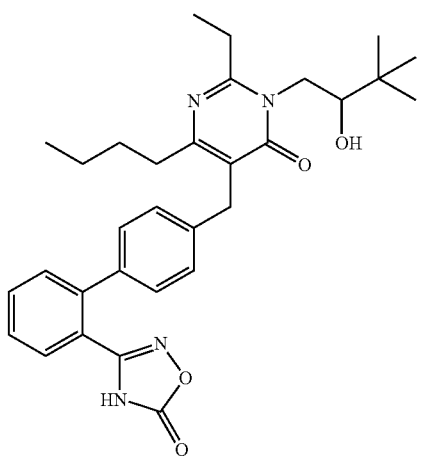

110b) 6-butyl-2-ethyl-3-(2-hydroxy-3,3-dimethylbutyl)-5-{[2'-(5-oxo-4,5-dihydro-1,2,4-oxadiazol-3-yl)biphenyl-4-yl]methyl}pyrimidin-4(3H)-one 4'-{[4-Butyl-1-(3,3-dimethyl-2-oxobutyl)-2-ethyl-6-oxo-1,6-dihydropyrimidin-5-yl]methyl}biphenyl-2-carbonitrile (3.8 g) was dissolved in methanol (40 mL) and tetrahydrofuran (40 mL), and sodium borohydride (0.92 g) was added at 0° C. After stirring for 2 hr, water was added, and the mixture was extracted with ethyl acetate. The organic layer was washed with saturated brine, and dried over anhydrous magnesium sulfate. The solvent was evaporated under reduced pressure. The residue was dissolved in dimethyl sulfoxide (40 mL), hydroxylammonium chloride (5.6 g) and sodium hydrogen carbonate (8.2 g) were added, and the mixture was stirred at 90° C. overnight. The reaction mixture was diluted with ethyl acetate, washed with water and then with saturated brine, and dried over anhydrous magnesium sulfate. The solvent was evaporated under reduced pressure. The residue was dissolved in tetrahydrofuran (40 mL), N,N'-carbonyldiimidazole (1.3 g) and then 1,8-diazabicyclo[5.4.0]undec-7-ene (1.2 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (3.5 g, 81%) as a solid.

$^1$H NMR (300 MHz, CDCl$_3$) δ 0.92-0.99 (12 H , m), 1.32 (3 H, t, J=7.3), 1.36-1.51 (2 H, m), 1.64-1.77 (2 H, m), 2.67-2.86 (4 H, m), 3.79-3.89 (3 H, m), 4.30 (1 H, dd, J=13.9, 10.7), 7.20-7.31 (5 H, m), 7.43-7.50 (2 H, m), 7.57-7.64 (1 H, m), 7.78-7.83 (1 H, m)

Example 111

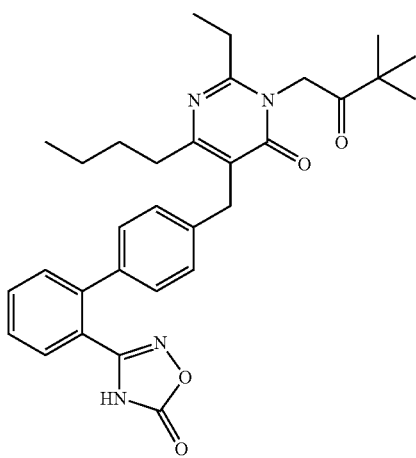

6-butyl-3-(3,3-dimethyl-2-oxobutyl)-2-ethyl-5-{[2'-(5-oxo-4,5-dihydro-1,2,4-oxadiazol-3-yl)biphenyl-4-yl]methyl}pyrimidin-4(3H)-one 6-Butyl-2-ethyl-3-(2-hydroxy-3,3-dimethylbutyl)-5-{[2'-(5-oxo-4,5-dihydro-1,2,4-oxadiazol-3-yl)biphenyl-4-yl]methyl}pyrimidin-4(3H)-one (2.9 g) was dissolved in dichloromethane (60 mL), 1,1,1-tris(acetyloxy)-1,1-dihydro-1,2-benziodoxol-3(1H)-one (2.8 g) was added, and the mixture was stirred for 1 hr. A saturated aqueous sodium hydrogen carbonate solution and sodium thiosulfate 5 hydrate were added, and the mixture was further stirred for 1 hr. The reaction mixture was extracted with ethyl acetate, washed with saturated brine, and dried over anhydrous magnesium sulfate. The solvent was evaporated under reduced pressure and the residue was purified by silica gel column chromatography to give the title compound (2.9 g, 100%) as a solid.

$^1$H NMR (300 MHz, DMSO-d$_6$) δ 0.86 (3 H, t, J=7.1), 1.14 (3 H, t, J=7.1), 1.21 (9 H, s), 1.23-1.39 (2 H, m), 1.47-1.60 (2 H, m), 2.47-2.59 (4 H, m), 3.79 (2 H, s), 5.14 (2 H, s), 7.05-7.09 (2 H, m), 7.16-7.22 (2 H, m), 7.25-7.48 (4 H, m)

Example 112

6-butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one

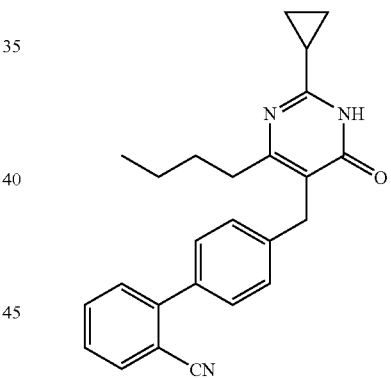

112a) 4'-[(4-butyl-2-cyclopropyl-6-oxo-1,6-dihydropyrimidin-5-yl)methyl]biphenyl-2-carbonitrile A solution of cyclopropanecarboxylmidamide hydrochloride (7.7 g), 28% sodium methoxide (17 mL) and methyl 2-[(2'-cyanobiphenyl-4-yl)methyl]-3-oxoheptanoate (10 g) in methanol (100 mL) was stirred overnight. The solvent was evaporated under reduced pressure, and water and 1 M hydrochloric acid were added. The precipitated solid was collected by filtration, and washed with water and diethyl ether to give the title compound (8.0 g, 73%) as a colorless solid.

$^1$H NMR (300 MHz, DMSO-d$_6$) δ 0.80 (3 H, t, J=7.3), 0.98 (4 H, d, J=6.0), 1.15-1.30 (2 H, m), 1.34-1.45 (2 H, m), 1.82-1.93 (1 H, m), 2.42 (2 H, t, J=7.3), 3.83 (2 H, s), 7.32 (2 H, d, J=7.9), 7.47 (2 H, d, J=7.9), 7.52-7.61 (2 H, m), 7.77 (1 H, t, J=7.5), 7.92 (1 H, d, J=7.5), 12.52 (1 H, s)

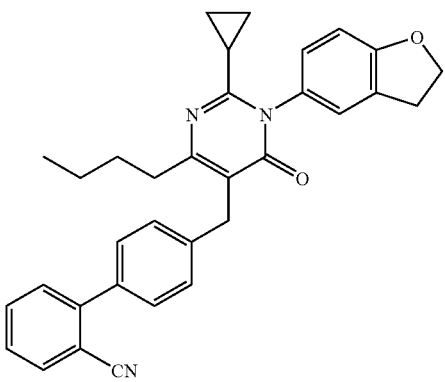

112b) 4'-{[4-butyl-2-cyclopropyl-1-(2,3-dihydro-1-benzofuran-5-yl)-6-oxo-1,6-dihydropyrimidin-5-yl]methyl}biphenyl-2-carbonitrile A mixture of 4'-[(4-butyl-2-cyclopropyl-6-oxo-1,6-dihydropyrimidin-5-yl)methyl]biphenyl-2-carbonitrile (0.58 g), 2,3-dihydro-1-benzofuran-5-ylboronic acid (0.49 g), copper (II) acetate (0.55 g), pyridine (0.61 mL), triethylamine (1.1 mL), molecular sieves 4 A (1.2 g) and dichloromethane (12 mL) was stirred for 2 days. The reaction mixture was diluted with ethyl acetate, and the insoluble material was filtered off. The filtrate was concentrated under reduced pressure, and the residue was purified by silica gel column chromatography to give the title compound (0.75 g, 100%) as a pale-yellow liquid.

$^1$H NMR (300 MHz, CDCl$_3$) δ 0.83 (2 H, dd, J=7.7, 3.9), 0.93 (3H, t, J=7.1), 1.15-1.21 (2 H, m), 1.30-1.65 (5 H, m), 2.57-2.64 (2 H, m), 3.20-3.34 (2 H, m), 3.88-4.00 (2 H, m), 4.64 (2 H, t, J=8.7), 6.86-6.90 (1 H, m), 6.99-7.04 (1 H, m), 7.11 (1 H, d, J=1.89), 7.36-7.50 (6 H, m), 7.57-7.65 (1 H, m), 7.73 (1 H, d, J=7.5)

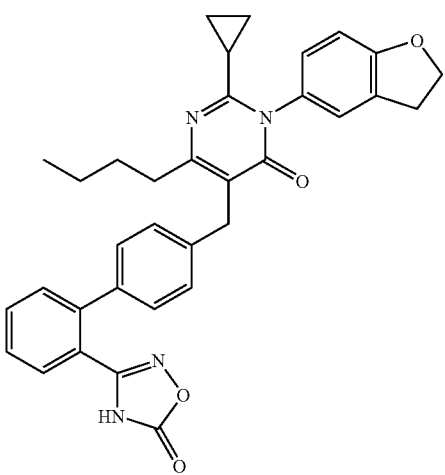

112c) 6-butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.0 g), sodium hydrogen carbonate (1.5 g) and dimethyl sulfoxide (12 mL) was stirred at 50° C. for 30 min, 4'-{[4-butyl-2-cyclopropyl-1-(2,3-dihydro-1-benzofuran-5-yl)-6-oxo-1,6-dihydropyrimidin-5-yl]methyl}biphenyl-2-carbonitrile (0.75 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (12 mL), N,N'-carbonyldiimidazole (0.37 g) and then 1,8-diazabicyclo[5.4.0]undec-7-ene (0.34 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography and recrystallized from dichloromethane and diisopropyl ether to give the title compound (0.70 g, 83%) as a colorless solid.

$^1$H NMR (300 MHz, DMSO-d$_6$) δ 0.80-0.87 (5 H, m), 0.95-1.13 (2 H, m), 1.21-1.52 (5 H, m), 2.43-2.53 (2 H, m), 3.24 (2 H, m), 3.84 (2 H, s), 4.57-4.66 (2 H, m), 6.89 (1 H, d, J=8.4), 7.07 (1 H, dd, J=8.4, 2.2), 7.18-7.29 (5 H, m), 7.47-7.58 (2 H, m), 7.61-7.72 (2 H, m), 12.38 (1 H, s)

6-Butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one sodium salt 6-butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one potassium salt 6-butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one 0.5 calcium salt 6-butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one hydrochloride 6-butyl-2-cyclopropyl-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one hydrobromide Example 113

6-butyl-3-(2,3-dihydro-1-benzofuran-5-yl)-2-ethyl-5-{[3-fluoro-2'-(5-oxo-4,5-dihydro-1,2,4-oxadiazol-3-yl)biphenyl-4-yl]methyl}pyrimidin-4(3H)-one

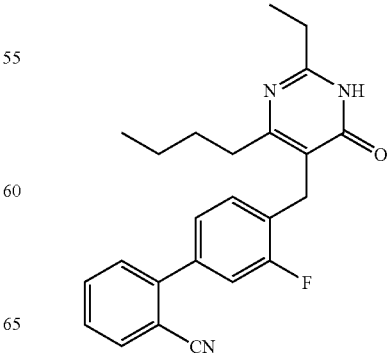

113a) 4'-[(4-butyl-2-ethyl-6-oxo-1,6-dihydropyrimidin-5-yl)methyl]-3'-fluorobiphenyl-2-carbonitrile A solution of propanimidamide hydrochloride (7.5 g), 28% sodium methoxide (23 mL) and methyl 2-[(2'-cyano-3-fluorobiphenyl-4-yl)methyl]-3-oxoheptanoate (8.4 g) in methanol (84 mL) was stirred overnight. The solvent was evaporated under reduced pressure, and water and 1 M hydrochloric acid were added. The precipitated solid was collected by filtration, and washed with water and diethyl ether to give the title compound (4.7 g, 53%) as a pale-yellow solid.

$^1$H NMR (300 MHz, DMSO-$d_6$) δ 0.82 (3 H, t, J=7.3), 1.13-1.34 (5 H, m), 1.39-1.52 (2 H, m), 2.43-2.59 (4 H, m), 3.84 (2 H, s), 7.21 (1 H, t, J=7.9), 7.28-7.34 (1 H, m), 7.42 (1 H, dd, J=10.9, 1.8), 7.55-7.65 (2 H, m), 7.74-7.83 (1 H, m), 7.91-7.98 (1 H, m), 12.33 (1 H, s)

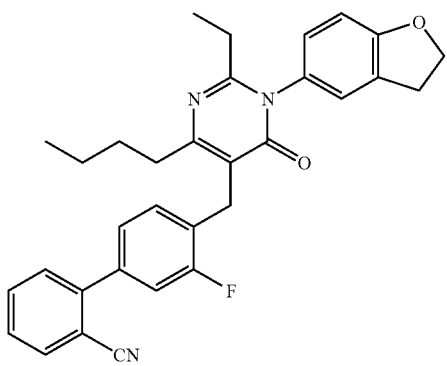

113b) 4'-{[4-butyl-1-(2,3-dihydro-1-benzofuran-5-yl)-2-ethyl-6-oxo-1,6-dihydropyrimidin-5-yl]methyl}-3'-fluorobiphenyl-2-carbonitrile A mixture of 4'-[(4-butyl-2-ethyl-6-oxo-1,6-dihydropyrimidin-5-yl)methyl]-3'-fluorobiphenyl-2-carbonitrile (0.58 g), 2,3-dihydro-1-benzofuran-5-ylboronic acid (0.49 g), copper(II) acetate (0.55 g), pyridine (0.61 mL), triethylamine (1.1 mL), molecular sieves 4 A (1.2 g) and dichloromethane (12 mL) was stirred for 2 days. The reaction mixture was diluted with ethyl acetate, and the insoluble material was filtered off. The filtrate was concentrated under reduced pressure, and the residue was purified by silica gel column chromatography to give the title compound (0.60 g, 79%) as a pale-yellow liquid.

$^1$H NMR (300 MHz, CDCl$_3$) δ 0.94 (3 H, t, J=7.3), 1.16 (3 H, t, J=7.3), 1.33-1.50 (2 H, m), 1.57-1.72 (2 H, m), 2.42 (2 H, q, J=7.3), 2.63-2.72 (2 H, m), 3.16-3.36 (2 H, m), 3.98 (2 H, s), 4.64 (2 H, t, J=9.2), 6.84-6.97 (2 H, m), 7.03 (1 H, d, J=1.7), 7.18-7.25 (2 H, m), 7.40-7.49 (3 H, m), 7.58-7.67 (1 H, m), 7.75 (1 H, dd, J=7.8, 0.85)

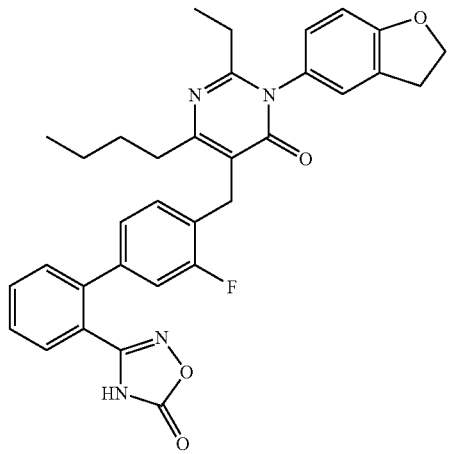

113c) 6-butyl-3-(2,3-dihydro-1-benzofuran-5-yl)-2-ethyl-5-{[3-fluoro-2'-(5-oxo-4,5-dihydro-1,2,4-oxadiazol-3-yl)biphenyl-4-yl]methyl}pyrimidin-4(3H)-one A mixture of hydroxylammonium chloride (1.0 g), sodium hydrogen carbonate (1.5 g) and dimethyl sulfoxide (6 mL) was stirred at 50° C. for 30 min, 4'-{[4-butyl-1-(2,3-dihydro-1-benzofuran-5-yl)-2-ethyl-6-oxo-1,6-dihydropyrimidin-5-yl]methyl}-3'-fluorobiphenyl-2-carbonitrile (0.60 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (6 mL), N,N'-carbonyldiimidazole (0.37 g) and then 1,8-diazabicyclo[5.4.0]undec-7-ene (0.34 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography and recrystallized from dichloromethane and diisopropyl ether to give the title compound (0.62 g, 92%) as a colorless solid.

$^1$H NMR (300 MHz, DMSO-$d_6$) δ 0.86 (3 H, t, J=7.3), 1.06 (3 H, t, J=7.3), 1.22-1.39 (2 H, m), 1.47-1.60 (2 H, m), 2.32 (2 H, q, J=7.3), 2.47-2.57 (2 H, m), 3.22 (2 H, t, J=8.7), 3.85 (2 H, s), 4.60 (2 H, t, J=8.7), 6.86 (1 H, d, J=8.2), 6.98-7.07 (2 H, m), 7.11-7.21 (3 H, m), 7.50-7.62 (2 H, m), 7.64-7.74 (2 H, m), 12.46 (1 H, s)

Example 114

6-butyl-3-(2,3-dihydro-1-benzofuran-5-yl)-5-{[2'-(5-oxo-4,5-dihydro-1,2,4-oxadiazol-3-yl)biphenyl-4-yl]methyl}-2-propylpyrimidin-4(3H)-one

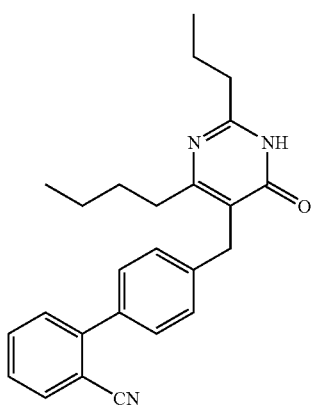

114a) 4'-[(4-butyl-6-oxo-2-propyl-1,6-dihydropyrimidin-5-yl)methyl]biphenyl-2-carbonitrile A solution of butanimidamide hydrochloride (3.5 g), 28% sodium methoxide (8.7 mL) and methyl 2-[(2'-cyanobiphenyl-4-yl)methyl]-3-oxoheptanoate (5.0 g) in methanol (50 mL) was stirred overnight. The solvent was evaporated under reduced pressure, and water and 1 M hydrochloric acid were added. The precipitated solid was collected by filtration, and washed with water and diethyl ether to give the title compound (4.5 g, 82%) as a pale-yellow solid.

$^1$H NMR (300 MHz, DMSO-$d_6$) δ 0.81 (3 H, t, J=7.3), 0.90 (3 H, t, J=7.3), 1.19-1.33 (2 H, m), 1.38-1.51 (2 H, m), 1.60-1.74 (2 H, m), 2.43-2.55 (4 H, m), 3.86 (2 H, s), 7.33 (2 H, d, J=8.3), 7.48 (2 H, d, J=8.3), 7.52-7.62 (2 H, m), 7.72-7.81 (1 H, m), 7.92 (1 H, d, J=7.9), 12.30 (1 H, s)

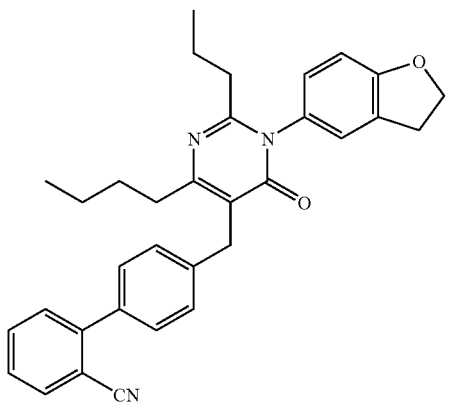

114b) 4'-{[4-butyl-1-(2,3-dihydro-1-benzofuran-5-yl)-6-oxo-2-propyl-1,6-dihydropyrimidin-5-yl]methyl}biphenyl-2-carbonitrile A mixture of 4'-[(4-butyl-6-oxo-2-propyl-1,6-dihydropyrimidin-5-yl)methyl]biphenyl-2-carbonitrile (0.58 g), 2,3-dihydro-1-benzofuran-5-ylboronic acid (0.49 g), copper(II) acetate (0.55 g), pyridine (0.61 mL), triethylamine (1.1 mL), molecular sieves 4 A (1.2 g) and dichloromethane (12 mL) was stirred for 2 days. The reaction mixture was diluted with ethyl acetate, and the insoluble material was filtered off. The filtrate was concentrated under reduced pressure, and the residue was purified by silica gel column chromatography to give the title compound (0.59 g, 79%) as a pale-yellow liquid.

$^1$H NMR (300 MHz, CDCl$_3$) δ 0.87 (3 H, t, J=7.4), 0.94 (3 H, t, J=7.2), 1.34-1.49 (2 H, m), 1.56-1.74 (4 H, m), 2.31-2.39 (2 H, m), 2.64-2.72 (2 H, m), 3.27 (2 H, t, J=8.7), 3.89-4.03 (2 H, m), 4.57-4.72 (2 H, m), 6.84-6.96 (2 H, m), 7.02 (1 H, d, J=1.1), 7.36-7.51 (6 H, m), 7.57-7.65 (1 H, m), 7.74 (1 H, dd, J=7.7, 1.3)

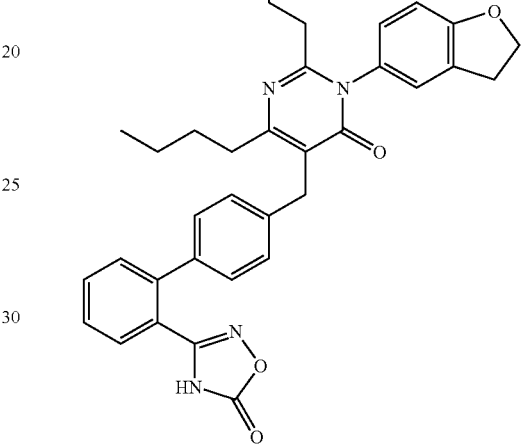

114c) 6-butyl-3-(2,3-dihydro-1-benzofuran-5-yl)-5-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (1.0 g), sodium hydrogen carbonate (1.5 g) and dimethyl sulfoxide (6 mL) was stirred at 50° C. for 30 min, 4'-{[4-butyl-1-(2,3-dihydro-1-benzofuran-5-yl)-6-oxo-2-propyl-1,6-dihydropyrimidin-5-yl]methyl}biphenyl-2-carbonitrile (0.59 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (6 mL), N,N'-carbonyldiimidazole (0.37 g) and then 1,8-diazabicyclo[5.4.0]undec-7-ene (0.34 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography and recrystallized from dichloromethane and diisopropyl ether to give the title compound (0.61 g, 92%) as a colorless solid.

$^1$H NMR (300 MHz, DMSO-$d_6$) δ 0.81 (3 H, t, J=7.3), 0.86 (3 H, t, J=7.3), 1.22-1.39 (2 H, m), 1.46-1.66 (2 H, m), 2.27 (2 H, t, J=7.4), 2.47-2.59 (4 H, m), 3.23 (2 H, t, J=8.6), 3.86 (2 H, s), 4.61 (2 H, t, J=8.6), 6.87 (1 H, d, J=8.2), 7.03 (1 H, dd, J=8.2, 2.2), 7.16-7.30 (5 H, m), 7.46-7.59 (2 H, m), 7.62-7.72 (2 H, m), 12.39 (1 H, s)

Example 115

6-butyl-2-(cyclopropylmethyl)-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one

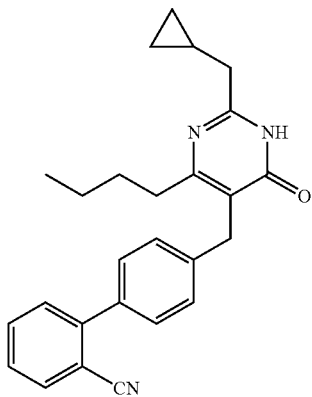

115a) 4'-{[4-butyl-2-(cyclopropylmethyl)-6-oxo-1,6-dihydropyrimidin-5-yl]methyl}biphenyl-2-carbonitrile A solution of 2-cyclopropylethanimidamide hydrochloride (3.9 g), 28% sodium methoxide (8.7 mL) and methyl 2-[(2'-cyanobiphenyl-4-yl)methyl]-3-oxoheptanoate (5.0 g) in methanol (50 mL) was stirred overnight. The solvent was evaporated under reduced pressure, and water and 1 M hydrochloric acid were added. The precipitated solid was collected by filtration, and washed with water and diethyl ether to give the title compound (4.3 g, 76%) as a pale-yellow solid.

$^1$H NMR (300 MHz, DMSO-d$_6$) δ 0.24 (2 H, q, J=4.8), 0.42-0.49 (2 H, m), 0.82 (3 H, t, J=7.3), 1.02-1.18 (1 H, m), 1.20-1.34 (2 H, m), 1.40-1.52 (2 H, m), 2.39 (2 H, d, J=7.1), 2.46-2.55 (2 H, m), 3.87 (2 H, s), 7.34 (2 H, d, J=8.3), 7.45-7.51 (2 H, m), 7.52-7.62 (2 H, m), 7.73-7.81 (1 H, m), 7.92 (1 H, d, J=6.8), 12.30 (1 H, s)

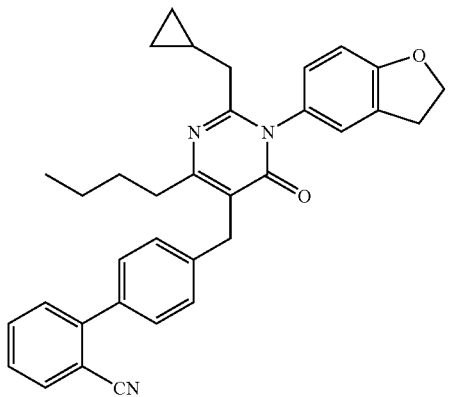

115b) 4'-{[4-butyl-2-(cyclopropylmethyl)-1-(2,3-dihydro-1-benzofuran-5-yl)-6-oxo-1,6-dihydropyrimidin-5-yl]methyl}biphenyl-2-carbonitrile A mixture of 4'-{[4-butyl-2-(cyclopropylmethyl)-6-oxo-1,6-dihydropyrimidin-5-yl]methyl}biphenyl-2-carbonitrile (0.58 g), 2,3-dihydro-1-benzofuran-5-ylboronic acid (0.49 g), copper(II) acetate (0.55 g), pyridine (0.61 mL), triethylamine (1.1 mL), molecular sieves 4 A (1.2 g) and dichloromethane (12 mL) was stirred for 2 days. The reaction mixture was diluted with ethyl acetate, and the insoluble material was filtered off. The filtrate was concentrated under reduced pressure, and the residue was purified by silica gel column chromatography to give the title compound (0.59 g, 76%) as a pale-yellow liquid.

$^1$H NMR (300 MHz, CDCl$_3$) δ 0.09 (2 H, q, J=4.8), 0.42-0.52 (2 H, m), 0.88-1.04 (4 H, m), 1.35-1.51 (2 H, m), 1.60-1.73 (2 H, m), 2.34 (2 H, d, J=6.5), 2.65-2.74 (2 H, m), 3.21-3.31 (2 H, m), 3.96 (2 H, d, J=2.6), 4.59-4.70 (2 H, m), 6.83-6.98 (2 H, m), 7.03 (1 H, s), 7.36-7.51 (6 H, m), 7.57-7.66 (1 H, m), 7.74 (1 H, d, J=7.7)

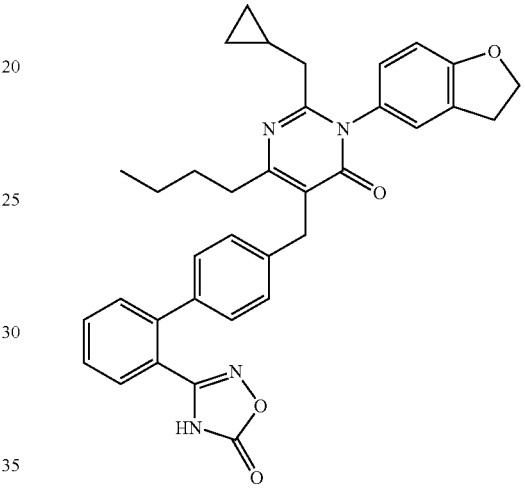

115c) 6-butyl-2-(cyclopropylmethyl)-3-(2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.0 g), sodium hydrogen carbonate (1.5 g) and dimethyl sulfoxide (6 mL) was stirred at 50° C. for 30 min, 4'-{[4-butyl-2-(cyclopropylmethyl)-1-(2,3-dihydro-1-benzofuran-5-yl)-6-oxo-1,6-dihydropyrimidin-5-yl]methyl}biphenyl-2-carbonitrile (0.59 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (6 mL), N,N'-carbonyldiimidazole (0.37 g) and then 1,8-diazabicyclo[5.4.0]undec-7-ene (0.34 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography and recrystallized from dichloromethane and diisopropyl ether to give the title compound (0.54 g, 82%) as a colorless solid.

$^1$H NMR (300 MHz, DMSO-d$_6$) δ 0.00-0.08 (2 H, m), 0.36-0.44 (2 H, m), 0.86 (3 H, t, J=7.25), 0.87-1.00 (1 H, m), 1.26-1.40 (2 H, m), 1.47-1.61 (2 H, m), 2.25 (2 H, d, J=6.5), 2.52-2.59 (2 H, m), 3.23 (2 H, t, J=8.6), 3.86 (2 H, s), 4.61 (2 H, t, J=8.6), 6.86 (1 H, d), 7.03 (1 H, dd, J=8.2, 2.2), 7.17-7.32 (5 H, m), 7.47-7.59 (2 H, m), 7.62-7.73 (2 H, m), 12.39 (1 H, s)

Example 116

6-butyl-3-(2,3-dihydro-1-benzofuran-5-yl)-2-(2-methoxyethyl)-5-{[2'-(5-oxo-4,5-dihydro-1,2,4-oxadiazol-3-yl)biphenyl-4-yl]methyl}pyrimidin-4(3H)-one

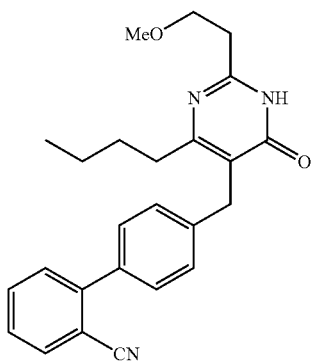

116a) 1'-{[4-butyl-2-(2-methoxyethyl)-6-oxo-1,6-dihydropyrimidin-5-yl]methyl}biphenyl-2-carbonitrile A solution of 3-methoxypropanimidamide hydrochloride (4.0 g), 28% sodium methoxide (8.7 mL) and methyl 2-[(2'-cyanobiphenyl-4-yl)methyl]-3-oxoheptanoate (5.0 g) in methanol (50 mL) was stirred overnight. The solvent was evaporated under reduced pressure, and water and 1 M hydrochloric acid were added. The precipitated solid was collected by filtration, and washed with water and diethyl ether to give the title compound (2.5 g, 44%) as a pale-yellow solid.

$^1$H NMR (300 MHz, DMSO-$d_6$) δ 0.82 (3 H, t, J=7.1), 1.18-1.34 (2 H, m), 1.37-1.52 (2 H, m), 2.46-2.54 (2 H, m), 2.75 (2 H, t, J=6.6), 3.23 (3 H, s), 3.68 (2 H, t, J=6.4), 3.86 (2 H, s), 7.33 (2 H, d, J=7.9), 7.48 (2 H, d, J=7.9), 7.51-7.61 (2 H, m), 7.77 (1 H, t, J=7.5), 7.92 (1 H, d, J=7.9), 12.34 (1 H, s)

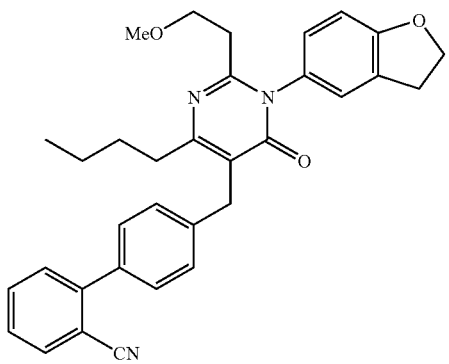

116b) 4'-{[4-butyl-1-(2,3-dihydro-1-benzofuran-5-yl)-2-(2-methoxyethyl)-6-oxo-1,6-dihydropyrimidin-5-yl]methyl}biphenyl-2-carbonitrile A mixture of 4'-{[4-butyl-2-(2-methoxyethyl)-6-oxo-1,6-dihydropyrimidin-5-yl]methyl}biphenyl-2-carbonitrile (2.5 g), 2,3-dihydro-1-benzofuran-5-ylboronic acid (2.0 g), copper(II) acetate (2.3 g), pyridine (2.5 mL), triethylamine (4.3 mL), molecular sieves 4 A (5.0 g) and dichloromethane (50 mL) was stirred for 2 days. The reaction mixture was diluted with ethyl acetate, and the insoluble material was filtered off. The filtrate was concentrated under reduced pressure, and the residue was purified by silica gel column chromatography to give the title compound (2.3 g, 72%) as a pale-yellow liquid.

$^1$H NMR (300 MHz, DMSO-$d_6$) δ 0.86 (3 H, t, J=7.3), 1.25-1.39 (2 H, m), 1.47-1.60 (2 H, m), 2.56 (4 H, q, J=7.0), 3.16 (3 H, s), 3.23 (2 H, t, J=8.7), 3.61 (2 H, t, J=6.8), 3.90 (2 H, s), 4.61 (2 H, t, J=8.9), 6.88 (1 H, d, J=8.3), 7.04 (1 H, dd, J=8.3, 2.2), 7.20 (1 H, d, J=1.89), 7.34-7.40 (2 H, m), 7.45-7.62 (5 H, m), 7.93 (1 H, d, J=7.9)

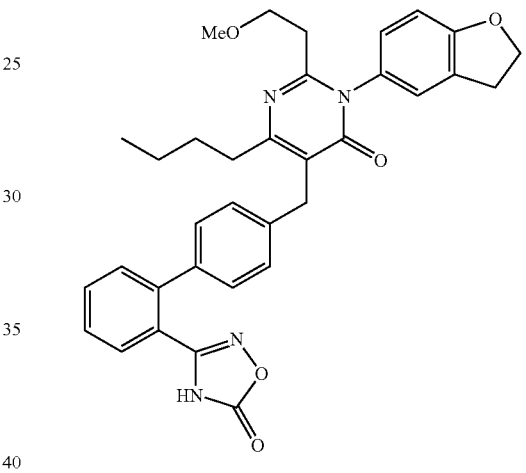

116c) 6-butyl-3-(2,3-dihydro-1-benzofuran-5-yl)-2-(2-methoxyethyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (3.1 g), sodium hydrogen carbonate (4.5 g) and dimethyl sulfoxide (24 mL) was stirred at 50° C. for 30 min, 4'-{[4-butyl-1-(2,3-dihydro-1-benzofuran-5-yl)-2-(2-methoxyethyl)-6-oxo-1,6-dihydropyrimidin-5-yl]methyl}biphenyl-2-carbonitrile (2.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (24 mL), N,N'-carbonyldiimidazole (1.1 g) and then 1,8-diazabicyclo[5.4.0]undec-7-ene (1.0 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (2.0 g, 55%) as a colorless solid.

$^1$H NMR (300 MHz, DMSO-d$_6$) δ 0.86 (3 H, t, J=7.2), 1.24-1.41 (2 H, m), 1.44-1.59 (2 H, m), 2.44-2.60 (4 H, m), 3.16 (3 H, s), 3.23 (2 H, t, J=8.5), 3.61 (2 H, t, J=6.8), 3.86 (2 H, s), 4.61 (2 H, t, J=8.7), 6.88 (1 H, d, J=8.2), 7.04 (1H, d, J=8.2), 7.16-7.31 (5 H, m), 7.47-7.59 (2 H, m), 7.63-7.73 (2 H, m), 12.40 (1 H, s)

Example 117

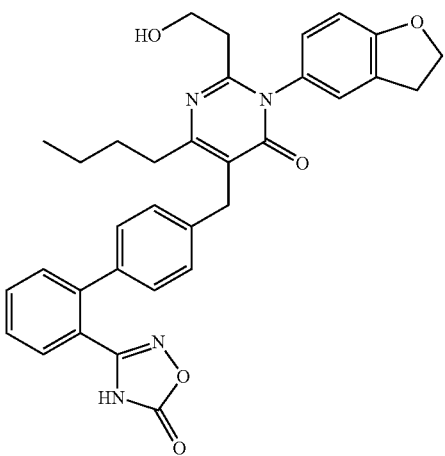

6-butyl-3-(2,3-dihydro-1-benzofuran-5-yl)-2-(2-hydroxyethyl)-5-{[2'-(5-oxo-4,5-dihydro-1,2,4-oxadiazol-3-yl)biphenyl-4-yl]methyl}pyrimidin-4(3H)-one A mixture of 6-butyl-3-(2,3-dihydro-1-benzofuran-5-yl)-2-(2-methoxyethyl)-5-{[2'-(5-oxo-4,5-dihydro-1,2,4-oxadiazol-3-yl)biphenyl-4-yl]methyl}pyrimidin-4(3H)-one (1.0 g), 2-butanone (10 mL), water (6 mL) and concentrated hydrochloric acid (2 mL) was stirred at 100° C. for 1 hr. The reaction solution was cooled to room temperature, and the solvent was removed under reduced pressure. Water was added to the residue, and the mixture was extracted with ethyl acetate. The organic layer was washed with saturated brine, and dried over anhydrous magnesium sulfate. The solvent was evaporated under reduced pressure and the residue was purified by silica gel column chromatography to give the title compound (0.57 g, 59%) as a solid.

$^1$H NMR (300 MHz, DMSO-d$_6$) δ 0.86 (3 H, t, J=7.2), 1.25-1.40 (2 H, m), 1.44-1.58 (2 H, m), 2.44-2.59 (4 H, m), 3.23 (2 H, t, J=8.6), 3.67 (2 H, q, J=6.4), 3.86 (2 H, s), 4.53-4.67 (3 H, m), 6.88 (1 H, d, J=8.4), 7.00-7.08 (1 H, m), 7.17-7.31 (5 H, m), 7.40-7.60 (2 H, m), 7.62-7.73 (2 H, m), 12.40 (1 H, s)

Example 118

6-butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one

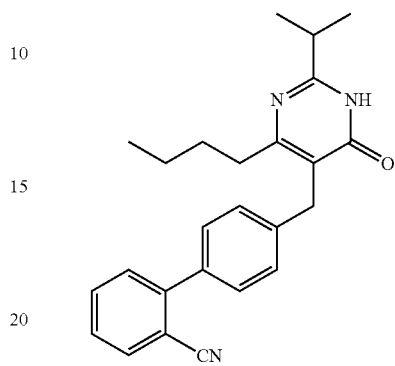

118a) 4'-[(4-butyl-2-isopropyl-6-oxo-1,6-dihydropyrimidin-5-yl)methyl]biphenyl-2-carbonitrile A solution of 2-methylpropanimidamide hydrochloride (10 g), 28% sodium methoxide (25 mL) and methyl 2-[(2'-cyanobiphenyl-4-yl)methyl]-3-oxoheptanoate (14 g) in methanol (140 mL) and 1,4-dioxane (70 mL) was stirred overnight. The solvent was evaporated under reduced pressure, and water and 1 M hydrochloric acid were added. The precipitated solid was collected by filtration, and washed with water and diethyl ether to give the title compound (9.7 g, 62%) as a pale-yellow solid.

$^1$H NMR (300 MHz, DMSO-d$_6$) δ 0.82 (3 H, t, J=7.3), 1.19 (6 H, d, J=6.8), 1.21-1.35 (2 H, m), 1.40-1.53 (2 H, m), 2.46-2.56 (2 H, m), 2.72-2.86 (1 H, m), 3.86 (2 H, s), 7.34 (2 H, d, J=7.9), 7.48 (2 H, d, J=7.9), 7.52-7.61 (2 H, m), 7.73-7.81 (1 H, m), 7.92 (1 H, d, J=7.5), 12.25 (1 H, s)

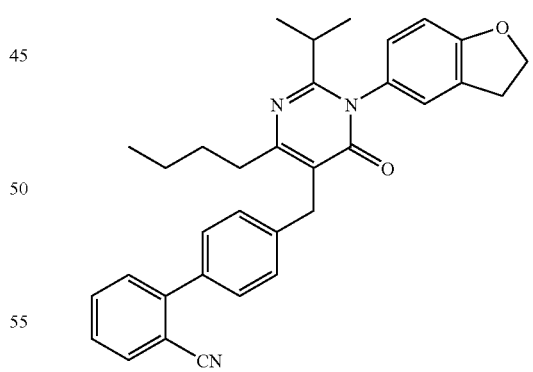

118b) 4'-{[4-butyl-1-(2,3-dihydro-1-benzofuran-5-yl)-2-isopropyl-6-oxo-1,6-dihydropyrimidin-5-yl]methyl}biphenyl-2-carbonitrile A mixture of 4'-[(4-butyl-2-isopropyl-6-oxo-1,6-dihydropyrimidin-5-yl)methyl]biphenyl-2-carbonitrile (1.0 g), 2,3-dihydro-1-benzofuran-5-ylboronic acid (0.85 g), copper(II) acetate (0.94 g), pyridine (1.1 mL), triethylamine (1.8 mL), molecular sieves 4 A (2.0 g) and dichloromethane (12 mL) was stirred for 2 days. The reaction mixture was diluted with ethyl acetate, and the insoluble material was filtered off. The filtrate was concentrated under reduced pressure, and the residue was purified by silica gel column chromatography to give the title compound (1.1 g, 79%) as a pale-yellow liquid.

$^1$H NMR (300 MHz, CDCl$_3$) δ 0.95 (3 H, t, J=7.3), 1.15 (6 H, d, J=6.7), 1.34-1.49 (2 H, m), 1.60-1.74 (2 H, m), 2.62-2.76 (3 H, m), 3.22-3.31 (2 H, m), 3.95 (2 H, d, J=2.8), 4.64 (2 H, t, J=8.9), 6.90 (2 H, q, J=8.5), 7.02 (1 H, s), 7.36-7.52 (6 H, m), 7.62 (1 H, t, J=7.7), 7.74 (1 H, d, J=7.7)

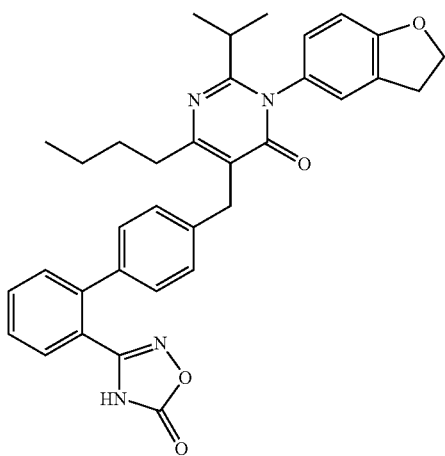

118c) 6-butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.8 g), sodium hydrogen carbonate (2.6 g) and dimethyl sulfoxide (10 mL) was stirred at 50° C. for 30 min, 4'-{[4-butyl-1-(2,3-dihydro-1-benzofuran-5-yl)-2-isopropyl-6-oxo-1,6-dihydropyrimidin-5-yl]methyl}biphenyl-2-carbonitrile (1.1 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.63 g) and then 1,8-diazabicyclo [5.4.0]undec-7-ene (0.58 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.88 g, 60%) as a colorless solid.

$^1$H NMR (300 MHz, CDCl$_3$) δ 0.94 (3 H, t, J=7.3), 1.15 (6 H, d, J=6.7), 1.32-1.48 (2 H, m), 1.56-1.72 (2 H, m), 2.59-2.76 (3 H, m), 3.27 (2 H, t, J=8.2), 3.93 (2 H, d, J=1.5), 4.64 (2 H, t, J=9.3), 6.83-6.95 (2 H, m), 7.01 (1 H, d, J=1.3), 7.30-7.40 (6 H, m), 7.41-7.48 (1 H, m), 7.53-7.59 (1 H, m)

6-Butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one sodium salt 6-butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one potassium salt 6-butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one hydrochloride 6-butyl-3-(2,3-dihydro-1-benzofuran-5-yl)-2-isopropyl-5-{[2'-(5-oxo-4,5-dihydro-1,2,4-oxadiazol-3-yl)biphenyl-4-yl]methyl}pyrimidin-4(3H)-one hydrobromide Example 119

6-butyl-2-cyclopropyl-3-(4-ethoxyphenyl)-5-{[2'-(5-oxo-4,5-dihydro-1,2,4-oxadiazol-3-yl)biphenyl-4-yl]methyl}pyrimidin-4(3H)-one

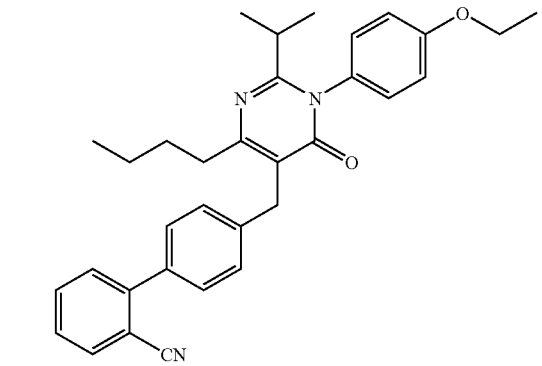

119a) 4'-{[4-butyl-2-cyclopropyl-1-(4-ethoxyphenyl)-6-oxo-1,6-dihydropyrimidin-5-yl]methyl}biphenyl-2-carbonitrile A mixture of 4'-[(4-butyl-2-cyclopropyl-6-oxo-1,6-dihydropyrimidin-5-yl)methyl]biphenyl-2-carbonitrile (1.0 g), (4-ethoxyphenyl)boronic acid (0.87 g), copper(II) acetate (0.95 g), pyridine (1.1 mL), triethylamine (1.8 mL), molecular sieves 4 A (2.0 g) and dichloromethane (20 mL) was stirred for 2 days. The reaction mixture was diluted with ethyl acetate, and the insoluble material was filtered off. The filtrate was concentrated under reduced pressure, the residue was purified by silica gel column chromatography to give the title compound (1.1 g, 84%) as a pale-yellow liquid.

$^1$H NMR (300 MHz, CDCl$_3$) δ 0.77-0.86 (2 H, m), 0.93 (3 H, t, J=7.2), 1.13-1.22 (2 H, m), 1.30-1.66 (8 H, m), 2.56-2.64 (2 H, m), 3.94 (2 H, s), 4.07 (2 H, q, J=6.9), 7.01 (2 H, d, J=8.8), 7.20 (2 H, d, J=8.6), 7.36-7.51 (6 H, m), 7.57-7.66 (1 H, m), 7.74 (1 H, dd, J=7.7, 1.1)

119b) 6-butyl-2-cyclopropyl-3-(4-ethoxyphenyl)-5-{[2'-(5-oxo-4,5-dihydro-1,2,4-oxadiazol-3-yl)biphenyl-4-yl]methyl}pyrimidin-4(3H)-one

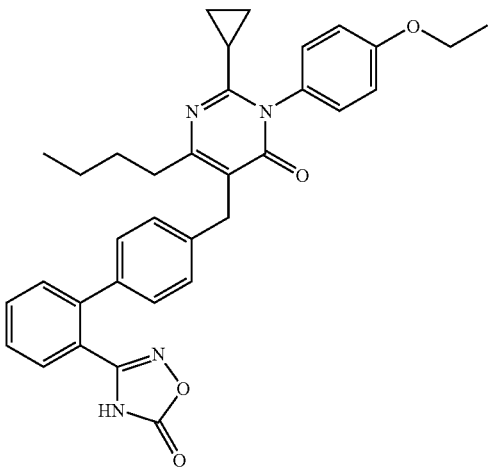

A mixture of hydroxylammonium chloride (1.8 g), sodium hydrogen carbonate (2.6 g) and dimethyl sulfoxide (10 mL) was stirred at 50° C. for 30 min, 4'-{[4-butyl-2-cyclopropyl-1-(4-ethoxyphenyl)-6-oxo-1,6-dihydropyrimidin-5-yl]methyl}biphenyl-2-carbonitrile (0.75 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.63 g) and then 1,8-diazabicyclo[5.4.0]undec-7-ene (0.59 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure. The residue was purified by silica gel column chromatography, and recrystallized from dichloromethane and diisopropyl ether to give the title compound (1.3 g, 97%) as a colorless solid.

$^1$H NMR (300 MHz, DMSO-$d_6$) δ 0.77-0.88 (5 H, m), 0.99-1.06 (2 H, m), 1.21-1.53 (8 H, m), 2.43-2.53 (2 H, m), 3.84 (2 H, s), 4.08 (2 H, q, J=6.9), 7.07 (2 H, d, J=8.8), 7.18-7.32 (6 H, m), 7.30-7.60 (2 H, m), 7.62-7.73 (2 H, m), 12.39 (1 H, s)

Example 120

6-butyl-2-cyclopropyl-5-{[2'-(5-oxo-4,5-dihydro-1,2,4-oxadiazol-3-yl)biphenyl-4-yl]methyl}-3-phenylpyrimidin-4(3H)-one

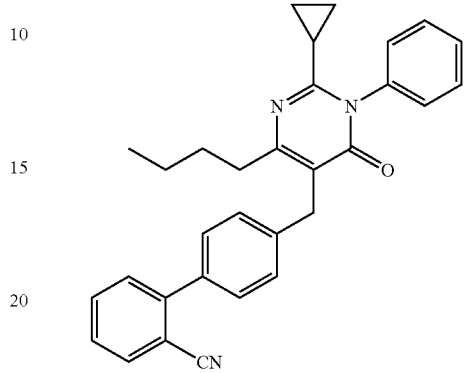

120a) 4'-[(4-butyl-2-cyclopropyl-6-oxo-1-phenyl-1,6-dihydropyrimidin-5-yl)methyl]biphenyl-2-carbonitrile A mixture of 4'-[(4-butyl-2-cyclopropyl-6-oxo-1,6-dihydropyrimidin-5-yl)methyl]biphenyl-2-carbonitrile (1.0 g), phenylboronic acid (0.64 g), copper(II) acetate (0.95 g), pyridine (1.1 mL), triethylamine (1.8 mL), molecular sieves 4A (2.0 g) and dichloromethane (20 mL) was stirred for 2 days. The reaction mixture was diluted with ethyl acetate, and the insoluble material was filtered off. The filtrate was concentrated under reduced pressure, and the residue was purified by silica gel column chromatography to give the title compound (0.80 g, 59%) as a pale-yellow liquid.

$^1$H NMR (300 MHz, CDCl$_3$) δ 0.76-0.86 (2 H, m), 0.93 (3 H, t, J=7.2), 1.13-1.25 (2 H, m), 1.26-1.46 (3 H, m), 1.53-1.67 (2 H, m), 2.57-2.66 (2 H, m), 3.95 (2 H, s), 7.29-7.35 (2 H, m), 7.36-7.57 (9 H, m), 7.57-7.66 (1 H, m), 7.74 (1 H, dd, J=7.7, 1.3)

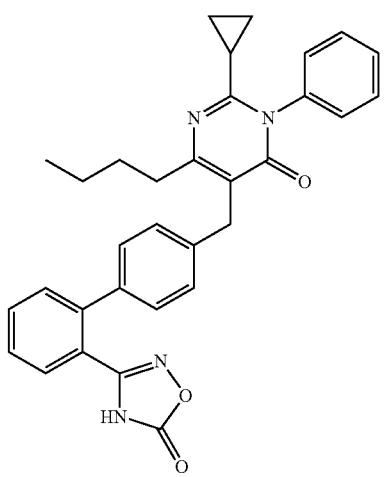

120b) 6-butyl-2-cyclopropyl-5-{[2'-(5-oxo-4,5-dihydro-1,2,4-oxadiazol-3-yl)biphenyl-4-yl]methyl}-3-phenylpyrimidin-4(3H)-one A mixture of hydroxylammonium chloride (1.1 g), sodium hydrogen carbonate (1.6 g) and dimethyl sulfoxide (8 mL) was stirred at 50° C. for 30 min, 4'-[(4-butyl-2-cyclopropyl-6-oxo-1-phenyl-1,6-dihydropyrimidin-5-yl)methyl]biphenyl-2-carbonitrile (0.80 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (8 mL), N,N'-carbonyldiimidazole (0.37 g) and then 1,8-diazabicyclo[5.4.0]undec-7-ene (0.33 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography and recrystallized from dichloromethane and diisopropyl ether to give the title compound (0.62 g, 78%) as a colorless solid.

$^1$H NMR (300 MHz, DMSO-$d_6$) δ 0.77-0.88 (5 H, m), 1.00-1.08 (2 H, m), 1.22-1.37 (3 H, m), 1.40-1.54 (2 H, m), 2.44-2.54 (2 H, m), 3.85 (2 H, s), 7.19-7.31 (4 H, m), 7.38-7.44 (2 H, m), 7.46-7.62 (5 H, m), 7.62-7.73 (2 H, m), 12.39 (1 H, s)

Example 121

3-(2,3-dihydro-1-benzofuran-5-yl)-2-ethyl-5-{[2'-(5-oxo-4,5-dihydro-1,2,4-oxadiazol-3-yl)biphenyl-4-yl]methyl}-6-propylpyrimidin-4(3H)-one

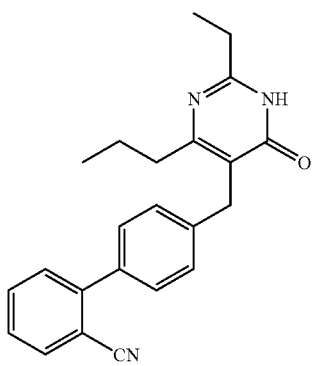

121a) 4'-[(2-ethyl-6-oxo-4-propyl-1,6-dihydropyrimidin-5-yl)methyl]biphenyl-2-carbonitrile A solution of propanimidamide hydrochloride (20 g), 28% sodium methoxide (56 mL) and methyl 2-[(2'-cyanobiphenyl-4-yl)methyl]-3-oxohexanoate (34 g) in methanol (350 mL) was stirred overnight. The solvent was evaporated under reduced pressure, and water and 1 M hydrochloric acid were added. The precipitated solid was collected by filtration, and washed with water and diethyl ether to give the title compound (27 g, 82%) as a pale-yellow solid.

$^1$H NMR (300 MHz, DMSO-$d_6$) δ 0.85 (3 H, t, J=7.1), 1.17 (3 H, t, J=7.3), 1.43-1.62 (2 H, m), 2.43-2.58 (4 H, m), 3.86 (2 H, s), 7.34 (2 H, d, J=7.9), 7.48 (2 H, d, J=7.9), 7.51-7.63 (2 H, m), 7.77 (1 H, t, J=7.6), 7.93 (1 H, d, J=7.6), 12.31 (1 H, s)

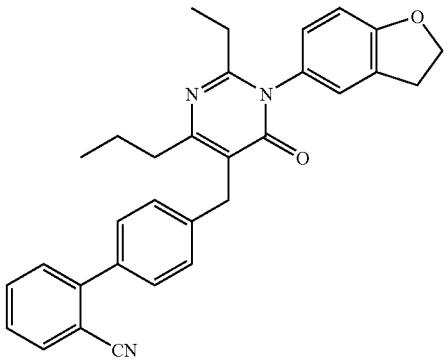

121b) 4'-{[1-(2,3-dihydro-1-benzofuran-5-yl)-2-ethyl-6-oxo-4-propyl-1,6-dihydropyrimidin-5-yl]methyl}biphenyl-2-carbonitrile A mixture of 4'-[(2-ethyl-6-oxo-4-propyl-1,6-dihydropyrimidin-5-yl)methyl]biphenyl-2-carbonitrile (3.0 g), 2,3-dihydro-1-benzofuran-5-ylboronic acid (2.8 g), copper(II) acetate (3.1 g), pyridine (3.1 mL), triethylamine (3.4 mL), molecular sieves 4 A (6.0 g) and dichloromethane (60 mL) was stirred for 2 days. The reaction mixture was diluted with ethyl acetate, and the insoluble material was filtered off. The filtrate was concentrated under reduced pressure, and the residue was purified by silica gel column chromatography to give the title compound (4.0 g, 100%) as a pale-yellow liquid.

$^1$H NMR (300 MHz, CDCl$_3$) δ 1.01 (3 H, t, J=7.3), 1.16 (3 H, t, J=7.3), 1.64-1.80 (2 H, m), 2.33-2.48 (2 H, m), 2.62-2.73 (2 H, m), 3.12-3.34 (2 H, m), 3.96 (2 H, d, J=2.6), 4.50-4.72 (2 H, m), 6.65-7.55 (9 H, m), 7.58-7.67 (1 H, m), 7.74 (1 H, d, J=7.7)

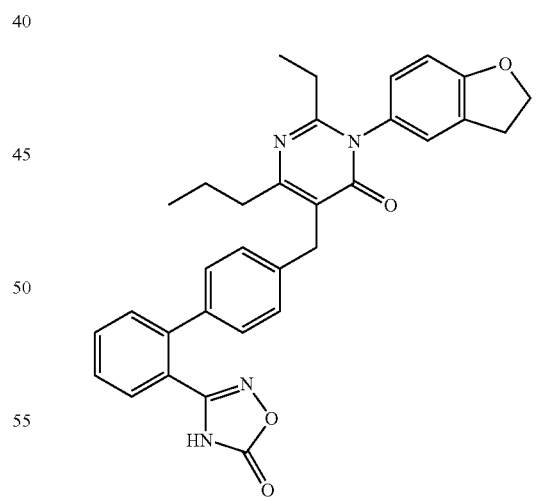

121c) 3-(2,3-dihydro-1-benzofuran-5-yl)-2-ethyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (5.8 g), sodium hydrogen carbonate (8.5 g) and dimethyl sulfoxide (30 mL) was stirred at 50° C. for 30 min, 4'-{[1-(2,3-dihydro-1-benzofuran-5-yl)-2-ethyl-6-oxo-4-propyl-1,6-dihydropyrimidin-5-yl]methyl}biphenyl-2-carbonitrile (4.0 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (2.0 g) and then 1,8-diazabicyclo[5.4.0]undec-7-ene (1.9 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (2.2 g, 48%) as a colorless solid.

$^1$H NMR (300 MHz, DMSO-$d_6$) δ 0.90 (3 H, t, J=7.25), 1.05 (3 H, t, J=7.2), 1.50-1.68 (2 H, m), 2.31 (2 H, q, J=7.2), 2.46-2.64 (2 H, m), 3.23 (2 H, t, J=8.4), 3.87 (2 H, s), 4.61 (2 H, t, J=8.6), 6.86 (1 H, d, J=8.4), 7.04 (1 H, d, J=8.4), 7.18-7.32 (5 H, m), 7.47-7.59 (2 H, m), 7.62-7.74 (2 H, m), 12.38 (1 H, s)

Example 122

2-ethyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one sure, and the residue was purified by silica gel column chromatography to give the title compound (4.1 g, 100%) as a pale-yellow liquid.

$^1$H NMR (300 MHz, CDCl$_3$) δ 1.01 (3 H, t, J=7.3), 1.11-1.20 (3 H, m), 1.45-1.55 (3 H, m), 1.64-1.80 (2 H, m), 2.35-2.48 (2 H, m), 2.63-2.73 (2 H, m), 2.78-2.95 (1 H, m), 3.29-3.42 (1 H, m), 3.97 (2 H, s), 4.93-5.10 (1 H, m), 6.79-7.03 (3 H, m), 7.36-7.53 (6 H, m), 7.57-7.66 (1 H, m), 7.74 (1 H, d, J=7.7)

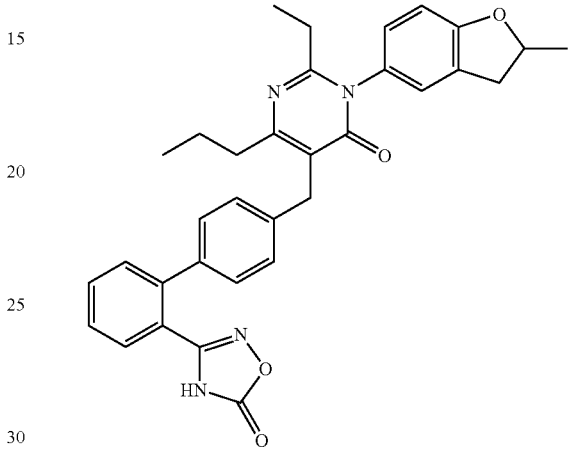

122b) 2-ethyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (5.8 g), sodium hydrogen carbonate (8.5 g) and dimethyl sulfoxide (30 mL) was stirred at 50° C. for 30 min, 4'-{[2-ethyl-1-(2-methyl-2,3-dihydro-1-benzofuran-5-yl)-6-oxo-4-propyl-1,6-dihydropyrimidin-5-yl]methyl}biphenyl-2-carbonitrile (4.1 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (2.0 g) and then 1,8-diazabicyclo[5.4.0]undec-7-ene (1.9 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (2.3 g, 49%) as a colorless solid.

$^1$H NMR (300 MHz, DMSO-$d_6$) δ 0.90 (3 H, t, J=7.3), 1.02-1.13 (3 H, m), 1.39-1.47 (3 H, m), 1.50-1.65 (2 H, m), 2.25-2.37 (2 H, m), 2.46-2.59 (2 H, m), 2.77-2.91 (1 H, m), 3.30-3.43 (1 H, m), 3.86 (2 H, s), 4.92-5.08 (1 H, m), 6.83 (1 H, d, J=8.2), 7.03 (1 H, dd, J=8.2, 1.8), 7.13-7.33 (5 H, m), 7.46-7.59 (2 H, m), 7.62-7.73 (2 H, m), 12.38 (1 H, s)

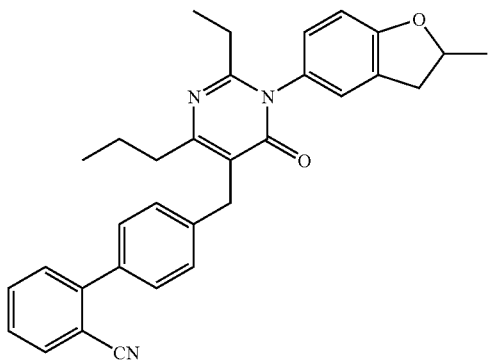

122a) 4'-{[2-ethyl-1-(2-methyl-2,3-dihydro-1-benzofuran-5-yl)-6-oxo-4-propyl-1,6-dihydropyrimidin-5-yl]methyl}biphenyl-2-carbonitrile A mixture of 4'-[(2-ethyl-6-oxo-4-propyl-1,6-dihydropyrimidin-5-yl)methyl]biphenyl-2-carbonitrile (3.0 g), (2-methyl-2,3-dihydro-1-benzofuran-5-yl)boronic acid (3.0 g), copper(II) acetate (3.1 g), pyridine (3.1 mL), triethylamine (3.4 mL), molecular sieves 4 A (6.0 g) and dichloromethane (60 mL) was stirred for 2 days. The reaction mixture was diluted with ethyl acetate, and the insoluble material was filtered off. The filtrate was concentrated under reduced pressure.

Example 123

2-ethyl-3-(4-methoxyphenyl)-5-{[2'-(5-oxo-4,5-di-hydro-1,2,4-oxadiazol-3-yl)biphenyl-4-yl]methyl}-6-propylpyrimidin-4(3H)-one

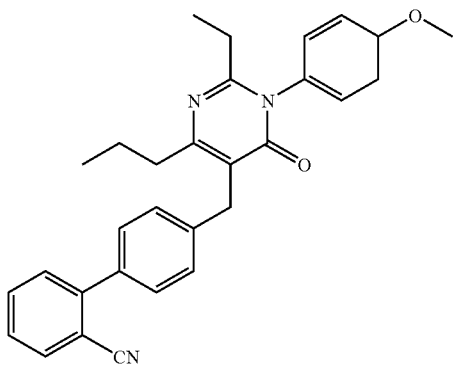

123a) 4'-{[2-ethyl-1-(4-methoxyphenyl)-6-oxo-4-propyl-1,6-dihydropyrimidin-5-yl]methyl}biphenyl-2-carbonitrile A mixture of 4'-[(2-ethyl-6-oxo-4-propyl-1,6-dihydropyrimidin-5-yl)methyl]biphenyl-2-carbonitrile (3.0 g), 4-methoxyphenylboronic acid (2.5 g), copper(II) acetate (3.1 g), pyridine (3.1 mL), triethylamine (3.4 mL), molecular sieves 4 A (6.0 g) and dichloromethane (60 mL) was stirred for 2 days. The reaction mixture was diluted with ethyl acetate, and the insoluble material was filtered off. The filtrate was concentrated under reduced pressure, and the residue was purified by silica gel column chromatography to give the title compound (4.0 g, 100%) as a pale-yellow liquid.

$^1$H NMR (300 MHz, CDCl$_3$) δ 1.01 (3 H, t, J=7.3), 1.14 (3 H, t, J=7.3), 1.64-1.79 (2 H, m), 2.38 (2 H, q, J=7.3), 2.63-2.72 (2 H, m), 3.85 (3 H, s), 3.97 (2 H, s), 6.98-7.07 (2 H, m), 7.10-7.18 (2 H, m), 7.37-7.52 (6 H, m), 7.58-7.66 (1H, m), 7.74 (1 H, dd, J=7.7, 1.3)

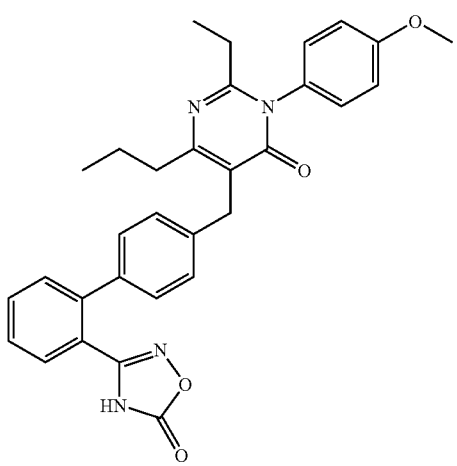

123b) 2-ethyl-3-(4-methoxyphenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (5.8 g), sodium hydrogen carbonate (8.5 g) and dimethyl sulfoxide (30 mL) was stirred at 50° C. for 30 min, 4'-{[2-ethyl-1-(4-methoxyphenyl)-6-oxo-4-propyl-1,6-dihydropyrimidin-5-yl]methyl}biphenyl-2-carbonitrile (4.0 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (2.0 g) and then 1,8-diazabicyclo[5.4.0]undec-7-ene (1.9 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (2.2 g, 51%) as a colorless solid.

$^1$H NMR (300 MHz, DMSO-d$_6$) δ 0.90 (3 H, t, J=7.2), 1.05 (3 H, t, J=7.3), 1.50-1.66 (2 H, m), 2.28 (2 H, q, J=7.3), 2.44-2.61 (2 H, m), 3.82 (3 H, s), 3.87 (2 H, s), 7.00-7.14 (2 H, m), 7.18-7.34 (6 H, m), 7.47-7.60 (2 H, m), 7.62-7.73 (2 H, m), 12.38 (1 H, s)

Example 124

2-ethyl-5-{[2'-(5-oxo-4,5-dihydro-1,2,4-oxadiazol-3-yl)biphenyl-4-yl]methyl}-3-phenyl-6-propylpyrimidin-4(3H)-one

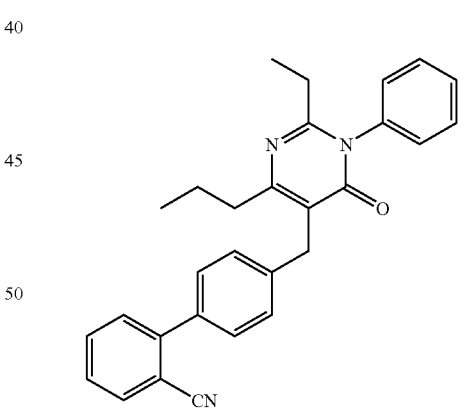

124a) 4'-[(2-ethyl-6-oxo-1-phenyl-4-propyl-1,6-dihydropyrimidin-5-yl)methyl]biphenyl-2-carbonitrile A mixture of 4'-[(2-ethyl-6-oxo-4-propyl-1,6-dihydropyrimidin-5-yl)methyl]biphenyl-2-carbonitrile (3.0 g), phenylboronic acid (2.1 g), copper(II) acetate (3.1 g), pyridine (3.1 mL), triethylamine (3.4 mL), molecular sieves 4 A (6.0 g) and dichloromethane (60 mL) was stirred for 2 days. The reaction mixture was diluted with ethyl acetate, and the insoluble material was filtered off. The filtrate was concentrated under reduced pressure, and the residue was purified by silica gel column chromatography to give the title compound (3.6 g, 100%) as a pale-yellow liquid.

$^1$H NMR (300 MHz, CDCl$_3$) δ 1.01 (3 H, t, J=7.3), 1.15 (3 H, t, J=7.3), 1.65-1.82 (2 H, m), 2.36 (2 H, q, J=7.3), 2.63-2.75 (2 H, m), 3.97 (2 H, s), 7.19-7.32 (4 H, m), 7.37-7.67 (8 H, m), 7.74 (1 H, dd, J=7.7, 0.94)

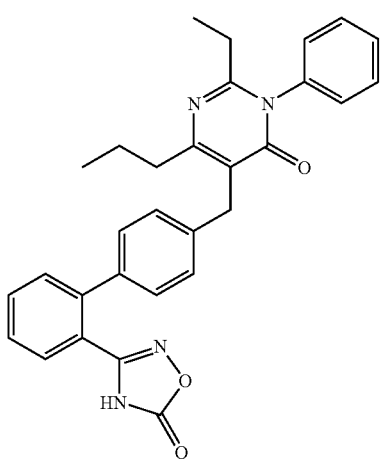

124b) 2-ethyl-5-{[2'-(5-oxo-4,5-dihydro-1,2,4-oxa-diazol-3-yl)biphenyl-4-yl]methyl}-3-phenyl-6-propylpyrimidin-4(3H)-one A mixture of hydroxylammonium chloride (5.8 g), sodium hydrogen carbonate (8.5 g) and dimethyl sulfoxide (30 mL) was stirred at 50° C. for 30 min, 4'-[(2-ethyl-6-oxo-1-phenyl-4-propyl-1,6-dihydropyrimidin-5-yl)methyl]biphenyl-2-carbonitrile (3.6 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (2.0 g) and then 1,8-diazabicyclo[5.4.0]undec-7-ene (1.9 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (1.7 g, 40%) as a colorless solid.

$^1$H NMR (300 MHz, DMSO-d$_6$) δ 0.91 (3 H, t, J=7.3), 1.04 (3 H, t, J=7.3), 1.51-1.66 (2 H, m), 2.26 (2 H, q, J=7.3), 2.47-2.60 (2 H, m), 3.88 (2 H, s), 7.19-7.41 (6 H, m), 7.45-7.59 (5 H, m), 7.63-7.73 (2 H, m), 12.40 (1 H, s)

Example 125

2-ethyl-3-(4-ethoxyphenyl)-5-{[2'-(5-oxo-4,5-dihydro-1,2,4-oxadiazol-3-yl)biphenyl-4-yl]methyl}-6-propylpyrimidin-4(3H)-one

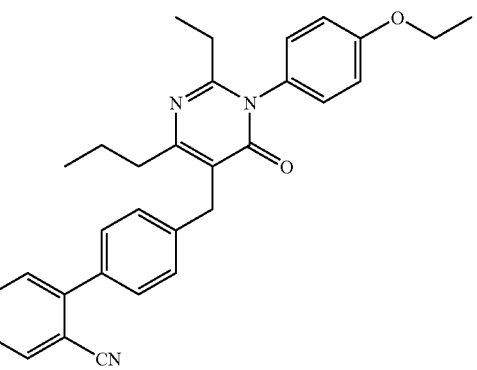

125a) 4'-{[2-ethyl-1-(4-ethoxyphenyl)-6-oxo-4-propyl-1,6-dihydropyrimidin-5-yl]methyl}biphenyl-2-carbonitrile A mixture of 4'-[(2-ethyl-6-oxo-4-propyl-1,6-dihydropyrimidin-5-yl)methyl]biphenyl-2-carbonitrile (3.0 g), 4-ethoxyphenylboronic acid (2.8 g), copper(II) acetate (3.1 g), pyridine (3.1 mL), triethylamine (3.4 mL), molecular sieves 4 A (6.0 g) and dichloromethane (60 mL) was stirred for 2 days. The reaction mixture was diluted with ethyl acetate, and the insoluble material was filtered off. The filtrate was concentrated under reduced pressure, and the residue was purified by silica gel column chromatography to give the title compound (4.0 g, 100%) as a pale-yellow liquid.

$^1$H NMR (300 MHz, CDCl$_3$) δ 1.01 (3 H, t, J=7.3), 1.14 (3 H, t, J=7.4), 1.44 (3 H, t, J=6.9), 1.64-1.80 (2 H, m), 2.38 (2 H, q, J=7.3), 2.62-2.72 (2 H, m), 3.97 (2 H, s), 4.07 (2 H, q, J=6.9), 6.95-7.04 (2 H, m), 7.08-7.16 (2 H, m), 7.36-7.51 (6 H, m), 7.57-7.66 (1 H, m), 7.74 (1 H, dd, J=7.7, 0.94)

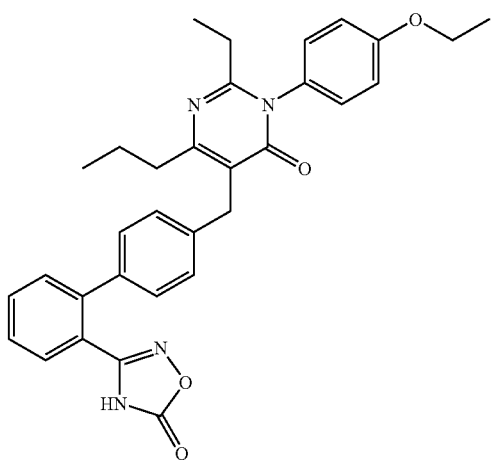

125b) 2-ethyl-3-(4-ethoxyphenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (5.8 g), sodium hydrogen carbonate (8.5 g) and dimethyl sulfoxide (30 mL) was stirred at 50° C. for 30 min, 4'-{[2-ethyl-1-(4-ethoxyphenyl)-6-oxo-4-propyl-1,6-dihydropyrimidin-5-yl]methyl}biphenyl-2-carbonitrile (4.0 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (2.0 g) and then 1,8-diazabicyclo[5.4.0]undec-7-ene (1.9 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (2.1 g, 46%) as a colorless solid.

$^1$H NMR (300 MHz, DMSO-$d_6$) δ 0.90 (3 H, t, J=7.3), 1.04 (3 H, t, J=7.3), 1.36 (3 H, t, J=6.9), 1.49-1.65 (2 H, m), 2.28 (2 H, q, J=7.3), 2.46-2.58 (2 H, m), 3.87 (2 H, s), 4.08 (2 H, q, J=6.9), 6.99-7.09 (2 H, m), 7.18-7.32 (6 H, m), 7.48-7.58 (2 H, m), 7.61-7.74 (2 H, m), 12.40 (1 H, s)

Example 126

6-butyl-2-ethyl-3-(4-methoxyphenyl)-5-{[2'-(5-oxo-4,5-dihydro-1,2,4-oxadiazol-3-yl)biphenyl-4-yl]methyl}pyrimidin-4(3H)-one

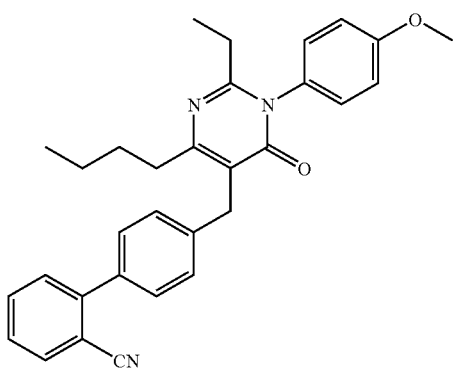

126a) 4'-{[4-butyl-2-ethyl-1-(4-methoxyphenyl)-6-oxo-1,6-dihydropyrimidin-5-yl]methyl}biphenyl-2-carbonitrile A mixture of 4'-[(4-butyl-2-ethyl-6-oxo-1,6-dihydropyrimidin-5-yl)methyl]biphenyl-2-carbonitrile (2.0 g), 4-methoxyphenylboronic acid (1.6 g), copper(II) acetate (2.0 g), pyridine (2.2 mL), triethylamine (3.8 mL), molecular sieves 4 A (4.0 g) and dichloromethane (40 mL) was stirred for 6 days. The reaction mixture was diluted with ethyl acetate, and the insoluble material was filtered off. The filtrate was concentrated under reduced pressure, and the residue was purified by silica gel column chromatography to give the title compound (2.6 g, 100%) as a colorless liquid.

$^1$H NMR (300 MHz, CDCl$_3$) δ 0.95 (3 H, t, J=7.2), 1.15 (3 H, t, J=7.4), 1.34-1.53 (2 H, m), 1.56-1.72 (2 H, m), 2.38 (2 H, q, J=7.4), 2.64-2.73 (2 H, m), 3.85 (3 H, s), 3.96 (2 H, s), 6.98-7.18 (4 H, m), 7.36-7.51 (6 H, m), 7.57-7.67 (1 H, m), 7.74 (1 H, dd, J=7.7, 1.3)

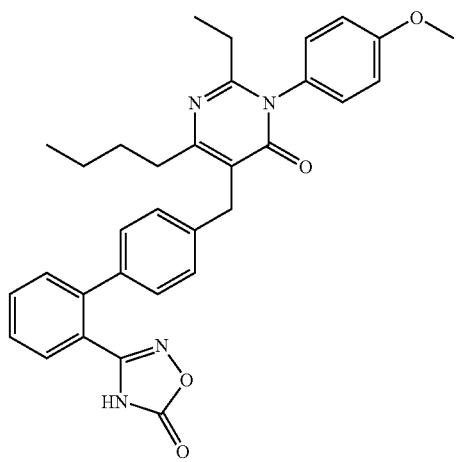

126b) 6-butyl-2-ethyl-3-(4-methoxyphenyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (3.8 g), sodium hydrogen carbonate (5.4 g) and dimethyl sulfoxide (26 mL) was stirred at 50° C. for 30 min, 4'-{[4-butyl-2-ethyl-1-(4-methoxyphenyl)-6-oxo-1,6-dihydropyrimidin-5-yl]methyl}biphenyl-2-carbonitrile (2.6 g) was added, and the mixture was stirred at 90° C. overnight. The reaction mixture was diluted with ethyl acetate, washed with water and then with saturated brine, and dried over anhydrous magnesium sulfate. The solvent was evaporated under reduced pressure. The residue was dissolved in tetrahydrofuran (26 mL), N,N'-carbonyldiimidazole (1.3 g) and then 1,8-diazabicyclo[5.4.0]undec-7-ene (1.2 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (2.0 g, 70%) as a solid.

$^1$H NMR (300 MHz, DMSO-$d_6$) δ 0.86 (3 H, t, J=7.2), 1.04 (3 H, t, J=7.3), 1.26-1.40 (2 H, m), 1.45-1.59 (2 H, m), 2.28 (2 H, q, J=7.3), 2.47-2.60 (2 H, m), 3.82 (3 H, s), 3.86 (2 H, s), 7.03-7.10 (2 H, m), 7.19-7.32 (6 H, m), 7.47-7.59 (2 H, m), 7.62-7.73 (2 H, m), 12.41 (1 H, s)

Example 127

3-(2,2-dimethyl-2,3-dihydro-1-benzofuran-5-yl)-2-ethyl-5-{[2'-(5-oxo-4,5-dihydro-1,2,4-oxadiazol-3-yl)biphenyl-4-yl]methyl}-6-propylpyrimidin-4(3H)-one

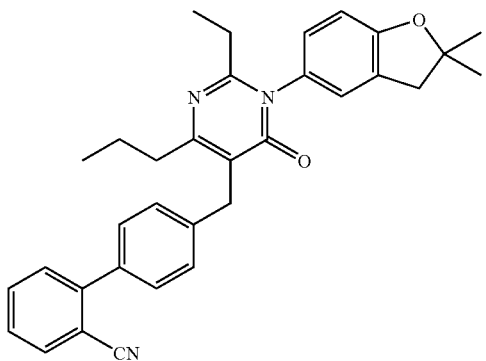

127a) 4'-{[1-(2,2-dimethyl-2,3-dihydro-1-benzofuran-5-yl)-2-ethyl-6-oxo-4-propyl-1,6-dihydropyrimidin-5-yl]methyl}biphenyl-2-carbonitrile A mixture of 4'-[(2-ethyl-6-oxo-4-propyl-1,6-dihydropyrimidin-5-yl)methyl]biphenyl-2-carbonitrile (0.50 g), (2,2-dimethyl-2,3-dihydro-1-benzofuran-5-yl)boronic acid (0.52 g), copper(II) acetate (0.49 g), pyridine (0.55 mL), triethylamine (0.94 mL), molecular sieves 4 A (1.0 g) and dichloromethane (5 mL) was stirred for 2 days. The reaction mixture was diluted with ethyl acetate, and the insoluble material was filtered off. The filtrate was concentrated under reduced pressure, and the residue was purified by silica gel column chromatography to give the title compound (0.54 g, 80%) as a pale-yellow liquid.

$^1$H NMR (300 MHz, CDCl$_3$) δ 1.01 (3 H, t, J=7.3), 1.16 (3 H, t, J=7.3), 1.48 (3 H, s), 1.52 (3 H, s), 1.64-1.80 (2 H, m), 2.41 (2 H, q, J=7.3), 2.63-2.71 (2 H, m), 3.06 (2 H, s), 3.96 (2 H, s), 6.77-7.01 (3 H, m), 7.37-7.52 (6 H, m), 7.62 (1 H, t, J=7.7), 7.74 (1 H, d, J=7.7)

127b) 3-(2,2-dimethyl-2,3-dihydro-1-benzofuran-5-yl)-2-ethyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.75 g), sodium hydrogen carbonate (1.1 g) and dimethyl sulfoxide (6 mL) was stirred at 50° C. for 30 min, 4'-{[1-(2,2-dimethyl-2,3-dihydro-1-benzofuran-5-yl)-2-ethyl-6-oxo-4-propyl-1,6-dihydropyrimidin-5-yl]methyl}biphenyl-2-carbonitrile (0.54 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (6 mL), N,N'-carbonyldiimidazole (0.26 g) and then 1,8-diazabicyclo[5.4.0]undec-7-ene (0.24 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.40 g, 66%) as a colorless solid.

$^1$H NMR (300 MHz, DMSO-d$_6$) δ 0.90 (3 H, t, J=7.3), 1.01-1.13 (3 H, m), 1.44 (3 H, s), 1.46 (3 H, s), 1.50-1.65 (2 H, m), 2.31 (2 H, q, J=7.3), 2.47-2.57 (2 H, m), 3.05 (2 H, s), 3.86 (2 H, s), 6.80 (1 H, d, J=8.4), 7.02 (1 H, dd, J=8.4, 2.3), 7.14 (1 H, d, J=2.0), 7.18-7.32 (4 H, m), 7.46-7.59 (2 H, m), 7.63-7.72 (2 H, m), 12.38 (1 H, s)

Example 128

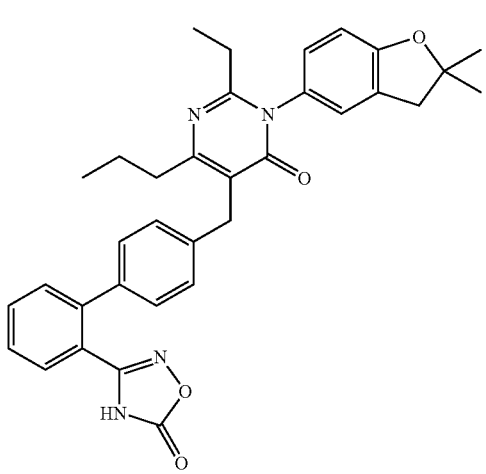

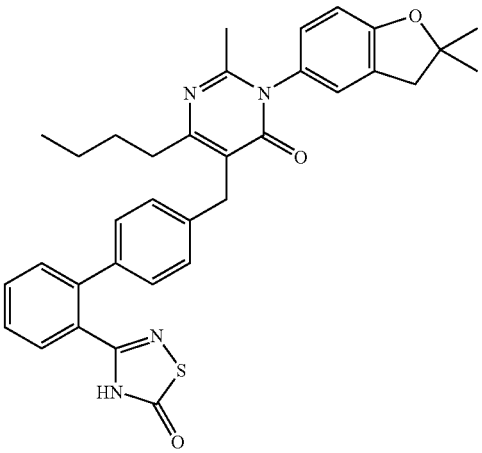

6-butyl-3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}pyrimidin-4(3H)-one A mixture of hydroxylammonium chloride (0.75 g), sodium hydrogen carbonate (1.1 g) and dimethyl sulfoxide (5 mL) was stirred at 50° C. for 30 min, 4'-{[4-butyl-1-(2,2-dimethyl-2,3-dihydro-1-benzofuran-5-yl)-2-methyl-6-oxo-1,6-dihydropyrimidin-5-yl]methyl}biphenyl-2-carbonitrile (0.50 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), thiocarbonyldiimidazole (0.21 g) was added, and the mixture was stirred at room temperature for 1 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), boron trifluoride-diethyl ether complex (0.71 mL) was added at 0° C., and the mixture was stirred for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.086 g, 32%) as a colorless solid.

$^1$H NMR (300 MHz, DMSO-$d_6$) δ 0.81-0.89 (3 H, m), 1.22-1.38 (2 H, m), 1.39-1.54 (8 H , m), 2.08 (3 H, s), 2.45-2.54 (2 H, m), 3.05 (2 H, s), 3.84 (2 H, s), 6.80 (1 H, d, J=8.4), 7.04 (1 H, dd, J=8.4, 2.2), 7.12-7.27 (5 H, m), 7.44-7.53 (2 H, m), 7.56-7.66 (2 H, m), 12.86 (1 H, s)

6-Butyl-3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}pyrimidin-4(3H)-one obtained above is subjected to a conventional method of salt formation to give the following salts.

6-butyl-3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}pyrimidin-4(3H)-one sodium salt 6-butyl-3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}pyrimidin-4(3H)-one potassium salt 6-butyl-3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}pyrimidin-4(3H)-one 0.5 calcium salt 6-butyl-3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}pyrimidin-4(3H)-one hydrochloride 6-butyl-3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}pyrimidin-4(3H)-one hydrobromide Example 129

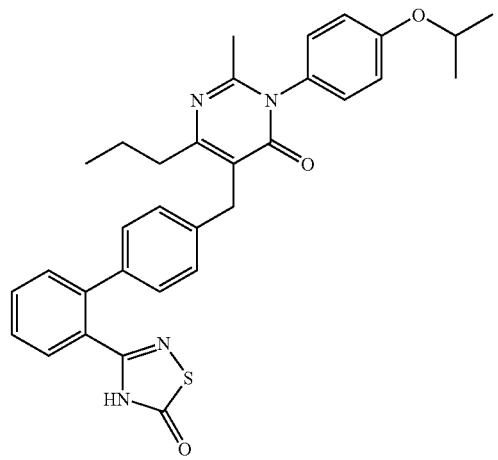

3-(4-isopropoxyphenyl)-2-methyl-5-{[2'-(5-oxo-4,5-dihydro-1,2,4-thiadiazol-3-yl)biphenyl-4-yl]methyl}-6-propylpyrimidin-4(3H)-one A mixture of hydroxylammonium chloride (1.50 g), sodium hydrogen carbonate (2.2 g) and dimethyl sulfoxide (10 mL) was stirred at 50° C. for 30 min, 4'-{[1-(4-isopropoxyphenyl)-2-methyl-6-oxo-4-propyl-1,6-dihydropyrimidin-5-yl]methyl}biphenyl-2-carbonitrile (1.0 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), thiocarbonyldiimidazole (0.43 g) was added, and the mixture was stirred at room temperature for 1 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), boron trifluoride-diethyl ether complex (1.2 mL) was added at 0° C., and the mixture was stirred for 1 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.30 g, 27%) as a colorless solid.

$^1$H NMR (300 MHz, DMSO-$d_6$) δ 0.89 (3 H, t, J=7.3), 1.30 (6 H, d, J=6.0), 1.45-1.63 (2 H, m), 2.06 (3 H, s), 2.44-2.54 (2 H, m), 3.85 (2 H, s), 4.60-4.74 (1 H, m), 6.98-7.06 (2 H, m), 7.11-7.19 (2 H, m), 7.20-7.28 (4 H, m), 7.44-7.53 (2 H, m), 7.55-7.67 (2 H, m), 12.85 (1 H, s)

Example 130

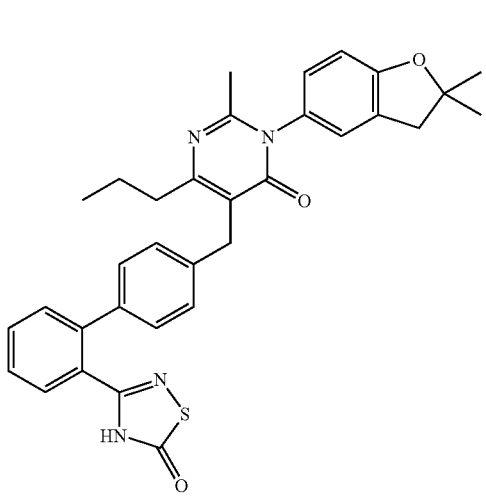

3-(2,2-dimethyl-2,3-dihydro-1-benzofuran-5-yl)-2-methyl-5-{[2'-(5-oxo-4,5-dihydro-1,2,4-thiadiazol-3-yl)biphenyl-4-yl]methyl}-6-propylpyrimidin-4(3H)-one A mixture of hydroxylammonium chloride (1.50 g), sodium hydrogen carbonate (2.2 g) and dimethyl sulfoxide (10 mL) was stirred at 50° C. for 30 min, 4'-{[1-(2,2-dimethyl-2,3-dihydro-1-benzofuran-5-yl)-2-methyl-6-oxo-4-propyl-1,6-dihydropyrimidin-5-yl]methyl}biphenyl-2-carbonitrile (1.0 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), thiocarbonyldiimidazole (0.43 g) was added, and the mixture was stirred at room temperature for 1 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), boron trifluoride-diethyl ether complex (1.2 mL) was added at 0° C., and the mixture was stirred for 1 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.31 g, 28%) as a colorless solid.

$^1$H NMR (300 MHz, DMSO-$d_6$) δ 0.88 (3 H, t, J=7.2), 1.41-1.61 (8 H , m), 2.08 (3 H, s), 2.45-2.53 (4 H, m), 3.84 (2 H, s), 6.80 (1 H, d, J=8.3), 7.04 (1 H, dd, J=8.3, 2.3), 7.11-7.19 (3 H, m), 7.21-7.27 (2 H, m), 7.44-7.53 (2 H, m), 7.56-7.66 (2 H, m), 12.85 (1 H, s)

Example 131

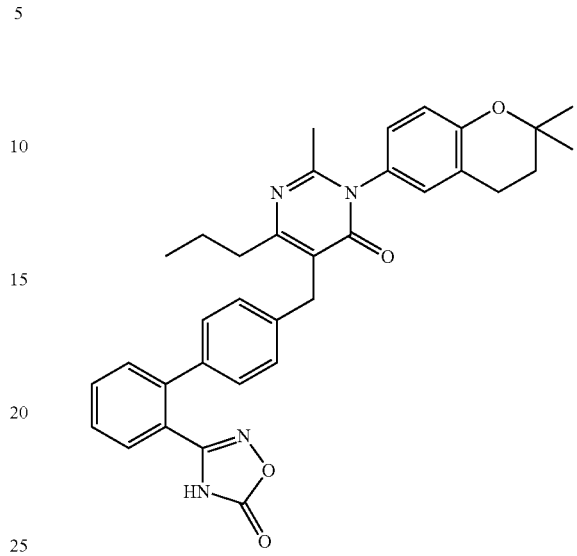

3-(2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one A mixture of 4'-[(2-methyl-6-oxo-4-propyl-1,6-dihydropyrimidin-5-yl)methyl]biphenyl-2-carbonitrile (0.50 g), (2,2-dimethyl-3,4-dihydro-2H-chromen-6-yl)boronic acid (0.30 g), copper(II) acetate (0.27 g), pyridine (0.59 mL), triethylamine (1.0 mL), molecular sieves 4 A (1.0 g) and dichloromethane (5 mL) was stirred for 3 days. The reaction mixture was diluted with ethyl acetate, and the insoluble material was filtered off. The filtrate was concentrated under reduced pressure, and the residue was purified by silica gel column chromatography. The resulting crudely purified product was added to a mixture of hydroxylammonium chloride (0.97 g), sodium hydrogen carbonate (1.4 g) and dimethyl sulfoxide (7 mL), and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (7 mL), N,N'-carbonyldiimidazole (0.34 g) and then 1,8-diazabicyclo[5.4.0]undec-7-ene (0.31 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.66 g, 80%) as a colorless solid.

$^1$H NMR (300 MHz, DMSO-$d_6$) δ 0.88 (3 H, t, J=7.1), 1.30 (3 H, s), 1.32 (3 H, s), 1.46-1.62 (2 H, m), 1.79 (2 H, t, J=6.6), 2.07 (3 H, s), 2.45-2.55 (2 H, m), 2.76 (2 H, t, J=6.4), 3.85 (2 H, s), 6.81 (1 H, d, J=8.7), 6.98-7.09 (2 H, m), 7.18-7.30 (4 H, m), 7.48-7.58 (2 H, m), 7.62-7.73 (2 H, m), 12.36 (1 H, s)

3-(2,2-Dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-(2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-(2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-(2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-(2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-(2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 132

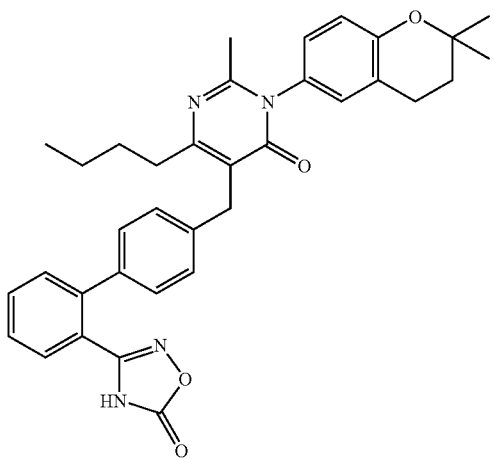

6-butyl-3-(2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}pyrimidin-4(3H)-one A mixture of 4'-[(4-butyl-2-methyl-6-oxo-1,6-dihydropyrimidin-5-yl)methyl]biphenyl-2-carbonitrile (0.50 g), (2,2-dimethyl-3,4-dihydro-2H-chromen-6-yl)boronic acid (0.30 g), copper(II) acetate (0.27 g), pyridine (0.59 mL), triethylamine (1.0 mL), molecular sieves 4 A (1.0 g) and dichloromethane (5 mL) was stirred for 3 days. The reaction mixture was diluted with ethyl acetate, and the insoluble material was filtered off. The filtrate was concentrated under reduced pressure, and the residue was purified by silica gel column chromatography. The resulting crudely purified product was added to a mixture of hydroxylammonium chloride (0.97 g), sodium hydrogen carbonate (1.4 g) and dimethyl sulfoxide (7 mL), and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (7 mL), N,N'-carbonyldiimidazole (0.34 g) and then 1,8-diazabicyclo[5.4.0]undec-7-ene (0.31 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.64 g, 80%) as a colorless solid.

$^1$H NMR (300 MHz, DMSO-$d_6$) δ 0.81-0.89 (3 H, m), 1.23-1.38 (8 H, m), 1.41-1.55 (2 H, m), 1.79 (2 H, t, J=6.5), 2.07 (3 H, s), 2.45-2.57 (2 H, m), 2.76 (2 H, t, J=6.5), 3.85 (2 H, s), 6.81 (1 H, d, J=8.6), 6.98-7.10 (2 H, m), 7.18-7.31 (4 H, m), 7.47-7.58 (2 H, m), 7.62-7.72 (2 H, m), 12.39 (1 H, s)

Example 133

6-propyl-3-[4-(2-fluoroethoxy)phenyl]-2-methyl-5-{[2'-(5-oxo-4,5-dihydro-1,2,4-oxadiazol-3-yl)biphenyl-4-yl]methyl}pyrimidin-4(3H)-one

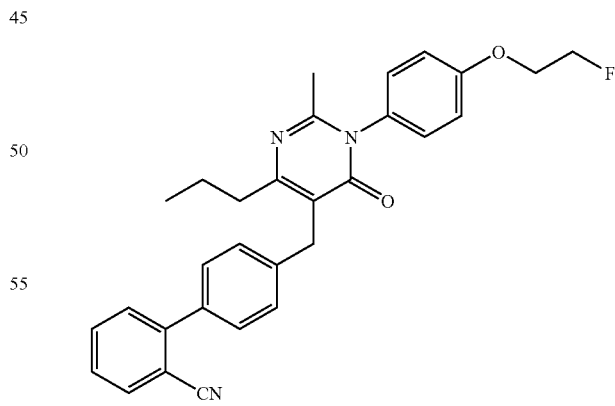

133a) 4'-({1-[4-(2-fluoroethoxy)phenyl]-2-methyl-6-oxo-4-propyl-1,6-dihydropyrimidin-5-yl}methyl)biphenyl-2-carbonitrile A solution of 4'-{[1-(4-hydroxyphenyl)-2-methyl-6-oxo-4-propyl-1,6-dihydropyrimidin-5-yl]methyl}biphenyl-2- carbonitrile (1.0 g), potassium carbonate (0.48 g) and 1-bromo-2-fluoroethane (0.25 mL) in N,N-dimethylformamide (10 mL) was stirred at 100° C. overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (1.1 g, 100%) as a pale-yellow liquid.

¹H NMR (300 MHz, CDCl₃) δ 1.01 (3 H, t, J=7.3), 1.59-1.77 (2 H, m), 2.17 (3 H, s), 2.61-2.70 (2 H, m), 3.97 (2 H, s), 4.18-4.23 (1 H, m), 4.27-4.33 (1 H, m), 4.67-4.72 (1 H, m), 4.82-4.88 (1 H, m), 7.02-7.09 (2 H, m), 7.12-7.19 (2 H, m), 7.37-7.51 (6 H, m), 7.58-7.65 (1 H, m), 7.74 (1 H, d, J=7.5)

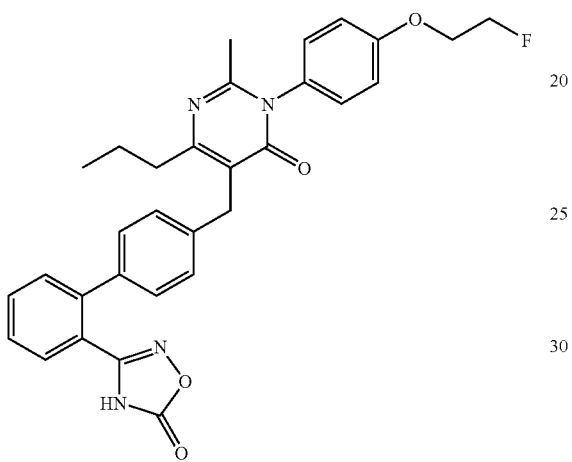

133b) 6-propyl-3-[4-(2-fluoroethoxy)phenyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.6 g), sodium hydrogen carbonate (2.3 g) and dimethyl sulfoxide (11 mL) was stirred at 50° C. for 30 min, 4'-({1-[4-(2-fluoroethoxy)phenyl]-2-methyl-6-oxo-4-propyl-1,6-dihydropyrimidin-5-yl}methyl)biphenyl-2-carbonitrile (1.1 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (11 mL), N,N'-carbonyldiimidazole (0.56 g) and then 1,8-diazabicyclo[5.4.0]undec-7-ene (0.51 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (1.1 g, 88%) as a colorless solid.

¹H NMR (300 MHz, DMSO-d₆) δ 0.89 (3 H, t, J=7.3), 1.47-1.62 (2 H, m), 2.07 (3 H, s), 2.43-2.59 (2 H, m), 3.87 (2 H, s), 4.22-4.29 (1 H, m), 4.33-4.38 (1 H, m), 4.69 (1 H, dd, J=4.6, 2.9), 4.83-4.88 (1 H, m), 7.05-7.14 (2 H, m), 7.18-7.34 (6 H, m), 7.46-7.60 (2 H, m), 7.62-7.73 (2 H, m), 12.38 (1 H, s)

Example 134

3-(2,2-dimethyl-3,4-dihydro-2H-chromen-6-yl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one

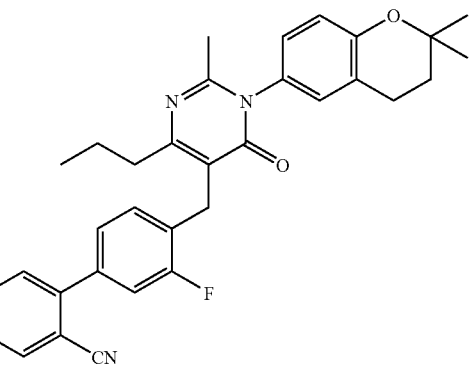

134a) 4'-{[1-(2,2-dimethyl-3,4-dihydro-2H-chromen-6-yl)-2-methyl-6-oxo-4-propyl-1,6-dihydropyrimidin-5-yl]methyl}-3'-fluorobiphenyl-2-carbonitrile A mixture of 3'-fluoro-4'-[(2-methyl-6-oxo-4-propyl-1,6-dihydropyrimidin-5-yl)methyl]biphenyl-2-carbonitrile (0.72 g), (2,2-dimethyl-3,4-dihydro-2H-chromen-6-yl)boronic acid (0.82 g), copper(II) acetate (0.73 g), pyridine (0.81 mL), triethylamine (1.4 mL), molecular sieves 4 A (1.5 g) and dichloromethane (10 mL) was stirred for 16 hr. The reaction mixture was diluted with ethyl acetate, and the insoluble material was filtered off. The filtrate was concentrated under reduced pressure, and the residue was purified by silica gel column chromatography to give the title compound (0.73 g, 70%) as a pale-yellow liquid.

¹H NMR (300 MHz, CDCl₃) δ 1.00 (3 H, t, J=7.3), 1.33 (3 H, s), 1.37 (3 H, s), 1.60-1.75 (2 H, m), 1.82 (2 H, t, J=6.8), 2.19 (3 H, s), 2.56-2.68 (2 H, m), 2.68-2.92 (2 H, m), 3.98 (2 H, s), 6.83-6.94 (3 H, m), 7.17-7.28 (2 H, m), 7.37-7.50 (3 H, m), 7.58-7.67 (1 H, m), 7.74 (1 H, d, J=7.9)

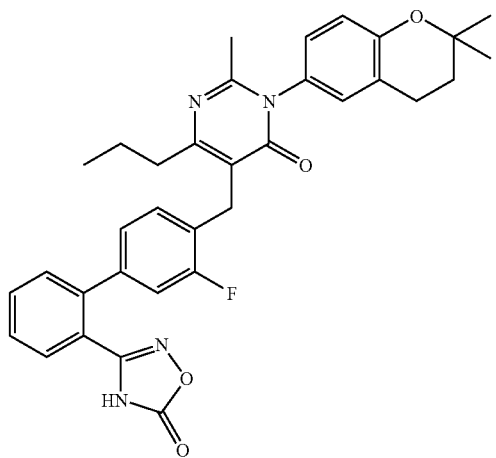

134b) 3-(2,2-dimethyl-3,4-dihydro-2H-chromen-6-yl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one A mixture of hydroxylammonium chloride (0.91 g), sodium hydrogen carbonate (1.4 g) and dimethyl sulfoxide (7 mL) was stirred at 50° C. for 30 min, 4'-{[1-(2,2-dimethyl-3,4-dihydro-2H-chromen-6-yl)-2-methyl-6-oxo-4-propyl-1,6-dihydropyrimidin-5-yl]methyl}-3'-fluorobiphenyl-2-carbonitrile (0.73 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (7 mL), N,N'-carbonyldiimidazole (0.34 g) and then 1,8-diazabicyclo[5.4.0]undec-7-ene (0.31 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.42 g, 52%) as a colorless solid.

$^1$H NMR (300 MHz, DMSO-$d_6$) δ 0.88 (3 H, t, J=7.3), 1.30 (3 H, s), 1.32 (3 H, s), 1.48-1.63 (2 H, m), 1.79 (2 H, t, J=6.5), 2.08 (3 H, s), 2.44-2.54 (2 H, m), 2.75 (2 H, t, J=6.5), 3.85 (2 H, s), 6.80 (1 H, d, J=8.4), 6.97-7.22 (5 H, m), 7.51-7.62 (2 H, m), 7.64-7.74 (2 H, m), 12.45 (1 H, s)

Example 135

3-(2,2-dimethyl-2,3-dihydro-1-benzofuran-5-yl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one

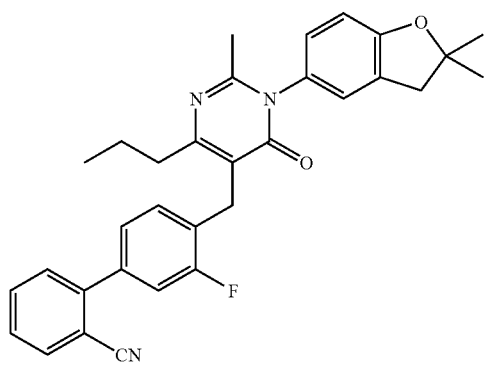

135a) 4'-{[1-(2,2-dimethyl-2,3-dihydro-1-benzofuran-5-yl)-2-methyl-6-oxo-4-propyl-1,6-dihydropyrimidin-5-yl]methyl}-3'-fluorobiphenyl-2-carbonitrile A mixture of 3'-fluoro-4'-[(2-methyl-6-oxo-4-propyl-1,6-dihydropyrimidin-5-yl)methyl]biphenyl-2-carbonitrile (0.72 g), (2,2-dimethyl-2,3-dihydro-1-benzofuran-5-yl)boronic acid (0.77 g), copper(II) acetate (0.73 g), pyridine (0.81 mL), triethylamine (1.4 mL), molecular sieves 4 A (1.5 g) and dichloromethane (10 mL) was stirred for 16 hr. The reaction mixture was diluted with ethyl acetate, and the insoluble material was filtered off. The filtrate was concentrated under reduced pressure, and the residue was purified by silica gel column chromatography to give the title compound (0.71 g, 70%) as a pale-yellow liquid.

$^1$H NMR (300 MHz, CDCl$_3$) δ 1.00 (3 H, t, J=7.38), 1.48 (3 H, s), 1.52 (3 H, s), 1.60-1.76 (2 H, m), 2.21 (3 H, s), 2.59-2.69 (2 H, m), 3.05 (2 H, s), 3.98 (2 H, s), 6.76-6.84 (1 H, m), 6.88-6.99 (2 H, m), 7.22 (2 H, d, J=9.0), 7.38-7.50 (3 H, m), 7.63 (1 H, t, J=7.0), 7.75 (1 H, d, J=7.9)

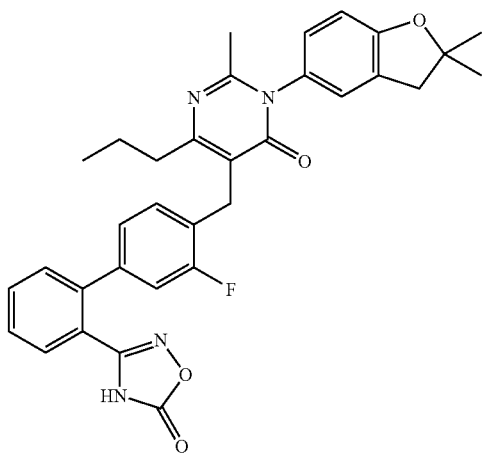

135b) 3-(2,2-dimethyl-2,3-dihydro-1-benzofuran-5-yl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one A mixture of hydroxylammonium chloride (0.91 g), sodium hydrogen carbonate (1.4 g) and dimethyl sulfoxide (7 mL) was stirred at 50° C. for 30 min, 4'-{[1-(2,2-dimethyl-2,3-dihydro-1-benzofuran-5-yl)-2-methyl-6-oxo-4-propyl-1,6-dihydropyrimidin-5-yl]methyl}-3'-fluorobiphenyl-2-carbonitrile (0.71 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (7 mL), N,N'-carbonyldiimidazole (0.34 g) and then 1,8-diazabicyclo[5.4.0]undec-7-ene (0.31 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.55 g, 70%) as a colorless solid.

$^1$H NMR (300 MHz, DMSO-$d_6$) δ 0.89 (3 H, t, J=7.3), 1.43 (3 H, s), 1.45 (3 H, s), 1.49-1.64 (2 H, m), 2.09 (3 H, s), 2.40-2.56 (2 H, m), 3.05 (2 H, s), 3.85 (2 H, s), 6.80 (1 H, d, J=8.2), 6.98-7.07 (2 H, m), 7.10-7.23 (3 H, m), 7.51-7.62 (2 H, m), 7.65-7.74 (2 H, m), 12.45 (1 H, s)

Example 136

3-(4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one

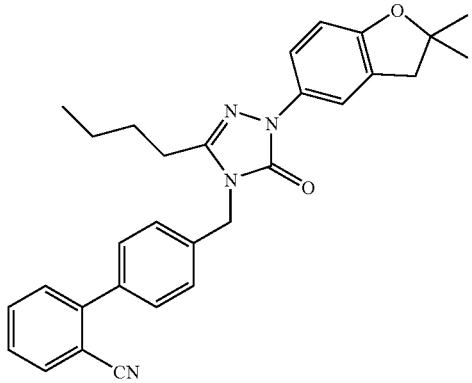

136a) 4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-carbonitrile A mixture of 4'-[(3-butyl-5-oxo-1,5-dihydro-4H-1,2,4-triazol-4-yl)methyl]biphenyl-2-carbonitrile (1.0 g), (2,2-dimethyl-2,3-dihydro-1-benzofuran-5-yl)boronic acid (1.2 g), copper(II) acetate (1.1 g), pyridine (1.2 mL), triethylamine (2.1 mL), molecular sieves 4 Å (2.0 g) and dichloromethane (10 mL) was stirred for 3 days. The reaction mixture was diluted with ethyl acetate, and the insoluble material was filtered off. The filtrate was concentrated under reduced pressure, and the residue was purified by silica gel column chromatography to give the title compound (1.4 g, 100%) as a pale-yellow liquid.

$^1$H NMR (300 MHz, CDCl$_3$) δ 0.91 (3 H, t, J=7.3), 1.33-1.47 (2 H, m), 1.48 (6 H, s), 1.60-1.73 (2 H, m), 2.47-2.55 (2 H, m), 3.04 (2 H, s), 4.95 (2 H, s), 6.76 (1 H, d, J=8.6), 7.39-7.52 (4 H, m), 7.52-7.58 (2 H, m), 7.60-7.69 (2 H, m), 7.71-7.80 (2 H, m)

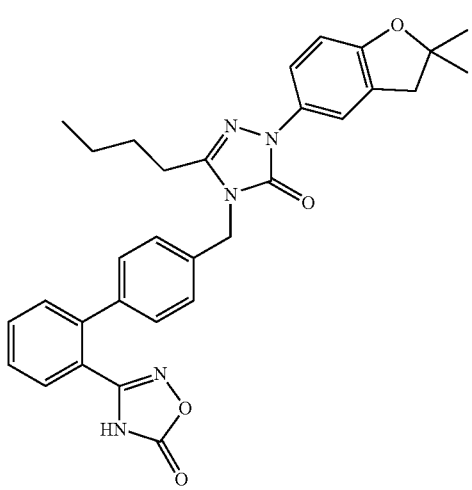

136b) 3-(4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one A mixture of hydroxylammonium chloride (2.1 g), sodium hydrogen carbonate (3.0 g) and dimethyl sulfoxide (10 mL) was stirred at 50° C. for 30 min, 4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-carbonitrile (1.4 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.73 g) and then 1,8-diazabicyclo[5.4.0]undec-7-ene (0.67 mL) were added, and the mixture was stirred at room temperature for 1 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.59 g, 38%) as a colorless solid.

$^1$H NMR (300 MHz, DMSO-d$_6$) δ 0.83 (3 H, t, J=7.1), 1.24-1.39 (2 H, m), 1.42 (6 H, s), 1.46-1.59 (2 H, m), 2.47-2.57 (2 H, m), 3.05 (2 H, s), 4.95 (2 H, s), 6.76 (1 H, d, J=8.7), 7.29-7.37 (4 H, m), 7.49-7.61 (3 H, m), 7.65-7.74 (3 H, m), 12.40 (1 H, s)

3-(4'-{[3-Butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one obtained above is subjected to a conventional method of salt formation to give the following salts.

3-(4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one sodium salt 3-(4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one potassium salt 3-(4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one 0.5 calcium salt 3-(4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one hydrochloride 3-(4'-{[3-butyl-1-(2,2-dimethyl-2,3-dihydro-1-benzofuran-5-yl)-5-oxo-1,5-dihydro-4H-1,2,4-triazol-4-yl]methyl}biphenyl-2-yl)-1,2,4-oxadiazol-5(4H)-one hydrobromide

Example 137

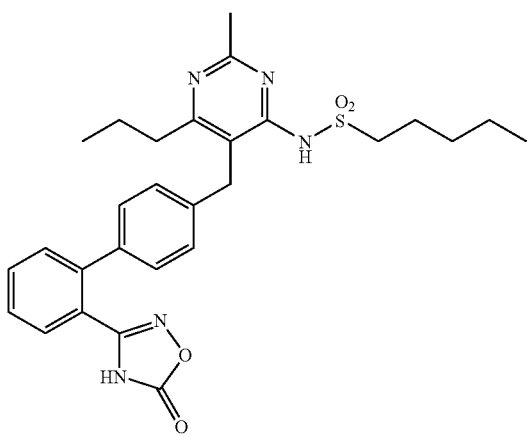

N-(2-methyl-5-{[2'-(5-oxo-4,5-dihydro-1,2,4-oxadiazol-3-yl)biphenyl-4-yl]methyl}-6-propylpyrimidin-4-yl)pentane-1-sulfonamide A solution of 4'-[(4-chloro-2-methyl-6-propylpyrimidin-5-yl)methyl]biphenyl-2-carbonitrile (0.72 g), pentane-1-sulfonamide (0.61 g) and potassium carbonate (0.55 g) in N,N-dimethylacetamide (10 mL) was stirred at 150° C. overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure. A mixture of the residue, hydroxylammonium chloride (1.4 g), sodium hydrogen carbonate (2.0 g) and dimethyl sulfoxide (10 mL) was stirred at 90° C. overnight. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.49 g) and then 1,8-diazabicyclo[5.4.0]undec-7-ene (0.45 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.40 g, 38%) as a white solid.

$^1$H NMR (300 MHz, DMSO-$d_6$) δ 0.76-0.90 (6 H, m), 1.13-1.67 (8 H, m), 2.40 (3 H, s), 2.47-2.59 (2 H, m), 3.13 (2 H, br s), 3.92 (2 H, s), 7.17-7.34 (4 H, m), 7.46-7.59 (2 H, m), 7.62-7.73 (2 H, m), 12.39 (1 H, s), 12.64 (1 H, s)

Example 138

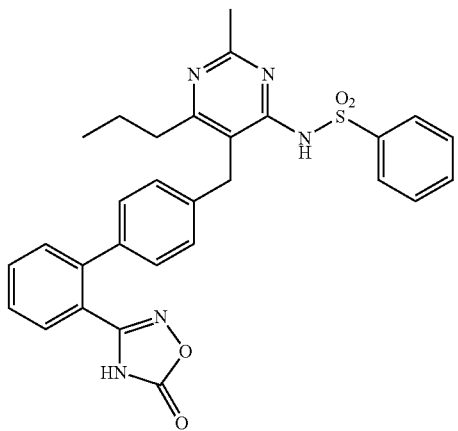

N-(2-methyl-5-{[2'-(5-oxo-4,5-dihydro-1,2,4-oxadiazol-3-yl)biphenyl-4-yl]methyl}-6-propylpyrimidin-4-yl)benzenesulfonamide A solution of 4'-[(4-chloro-2-methyl-6-propylpyrimidin-5-yl)methyl]biphenyl-2-carbonitrile (0.72 g), benzenesulfonamide (0.63 g) and potassium carbonate (0.55 g) in N,N-dimethylacetamide (10 mL) was stirred at 150° C. overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure. A mixture of the residue, hydroxylammonium chloride (1.4 g), sodium hydrogen carbonate (2.0 g) and dimethyl sulfoxide (10 mL) was stirred at 90° C. overnight. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.49 g) and then 1,8-diazabicyclo[5.4.0]undec-7-ene (0.45 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.87 g, 80%) as a white solid.

$^1$H NMR (300 MHz, DMSO-$d_6$) δ 0.83 (3 H, t, J=7.2), 1.29-1.45 (2 H, m), 2.28 (3 H, s), 2.47-2.56 (2 H, m), 3.92 (2 H, s), 7.16-7.32 (4 H, m), 7.39-7.60 (5 H, m), 7.62-7.73 (2 H, m), 7.79-7.87 (2 H, m), 12.25-12.96 (2 H, m)

Example 139

3-[4-(1-hydroxy-1-methylethyl)phenyl]-2-methyl-5-{[2'-(5-oxo-4,5-dihydro-1,2,4-oxadiazol-3-yl)biphenyl-4-yl]methyl}-6-propylpyrimidin-4(3H)-one

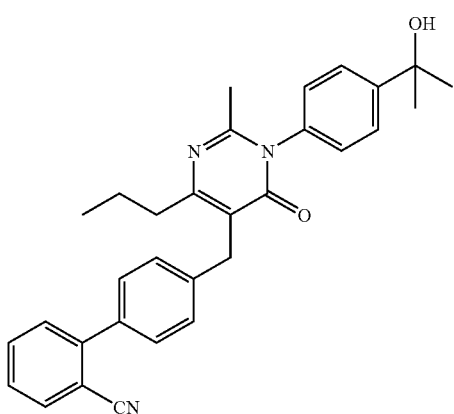

139a) 4'-({1-[4-(1-hydroxy-1-methylethyl)phenyl]-2-methyl-6-oxo-4-propyl-1,6-dihydropyrimidin-5-yl}methyl)biphenyl-2-carbonitrile 4'-{[1-(4-Acetylphenyl)-2-methyl-6-oxo-4-propyl-1,6-dihydropyrimidin-5-yl]methyl}biphenyl-2-carbonitrile (1.2 g) was dissolved in tetrahydrofuran (12 mL), methylmagnesium bromide (1.0 M tetrahydrofuran solution, 6.4 mL) was added at −78° C., and the mixture was stirred for 1 hr. A 5% aqueous potassium hydrogen sulfate solution was added to the reaction mixture, and the mixture was extracted with ethyl acetate. The organic layer was washed with saturated brine, and dried over anhydrous magnesium sulfate. The solvent was evaporated under reduced pressure and the residue was purified by silica gel column chromatography to give the title compound (0.45 g, 35%) as a pale-yellow liquid.

$^1$H NMR (300 MHz, CDCl$_3$) δ 1.01 (3 H, t, J=7.3), 1.59 (6 H, s), 1.63-1.77 (2 H, m), 2.17 (3 H, s), 2.62-2.70 (2 H, m), 3.97 (2 H, s), 7.20 (2 H, d, J=8.3), 7.37-7.51 (6 H, m), 7.57-7.68 (3 H, m), 7.74 (1 H, d, J=7.9)

139b) 3-[4-(1-hydroxy-1-methylethyl)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.65 g), sodium hydrogen carbonate (0.95 g) and dimethyl sulfoxide (5 mL) was stirred at 50° C. for 30 min, 4'-({1-[4-(1-hydroxy-1-methylethyl)phenyl]-2-methyl-6-oxo-4-propyl-1,6-dihydropyrimidin-5-yl}methyl)biphenyl-2-carbonitrile (0.45 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL), N,N'-carbonyldiimidazole (0.15 g) and then 1,8-diazabicyclo[5.4.0]undec-7-ene (0.14 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.27 g, 54%) as a colorless solid.

$^1$H NMR (300 MHz, DMSO-d$_6$) δ 0.89 (3 H, t, J=7.1), 1.43-1.62 (8 H, m), 2.05 (3 H, s), 2.46-2.57 (2 H, m), 3.86 (2 H, s), 5.13 (1 H, s), 7.18-7.31 (6 H, m), 7.47-7.73 (6 H, m), 12.36 (1 H, s)

Example 140

3-(4-fluorophenyl)-2-methyl-5-{[2'-(5-oxo-4,5-dihydro-1,2,4-oxadiazol-3-yl)biphenyl-4-yl]methyl}-6-propylpyrimidin-4(3H)-one

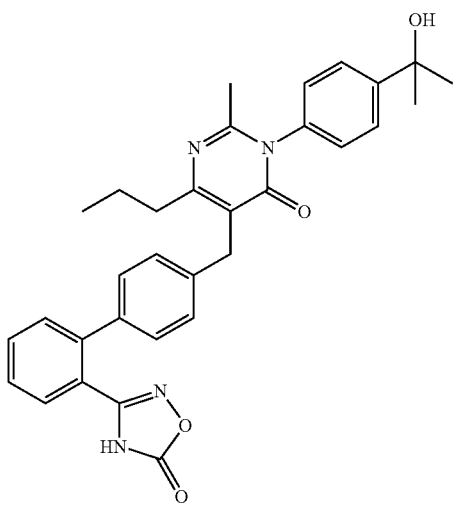

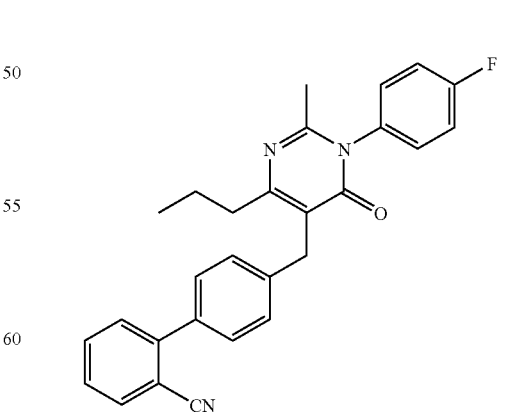

140a) 4'-{[1-(4-fluorophenyl)-2-methyl-6-oxo-4-propyl-1,6-dihydropyrimidin-5-yl]methyl}biphenyl-2-carbonitrile A mixture of 4'-[(2-methyl-6-oxo-4-propyl-1,6-dihydropyrimidin-5-yl)methyl]biphenyl-2-carbonitrile (1.0 g), 4-fluorophenylboronic acid (0.82 g), copper(II) acetate (1.1 g), pyridine (1.2 mL), triethylamine (2.0 mL), molecular sieves 4 A (2.0 g) and dichloromethane (10 mL) was stirred for 4 days. The reaction mixture was diluted with ethyl acetate, and the insoluble material was filtered off. The filtrate was concentrated under reduced pressure, and the residue was purified by silica gel column chromatography to give the title compound (0.47 g, 37%) as a colorless liquid.

$^1$H NMR (300 MHz, CDCl$_3$) δ 1.01 (3 H, t, J=7.3), 1.62-1.77 (2 H, m), 2.17 (3 H, s), 2.61-2.70 (2 H, m), 3.96 (2 H, s), 7.18-7.27 (4 H, m), 7.36-7.51 (6 H, m), 7.58-7.66 (1 H, m), 7.74 (1 H, d, J=7.5)

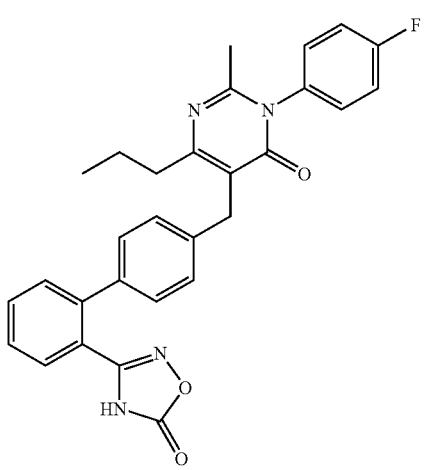

140b) 3-(4-fluorophenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.74 g), sodium hydrogen carbonate (1.1 g) and dimethyl sulfoxide (5 mL) was stirred at 50° C. for 30 min, 4'-{[1-(4-fluorophenyl)-2-methyl-6-oxo-4-propyl-1,6-dihydropyrimidin-5-yl]methyl}biphenyl-2-carbonitrile (0.47 g) was added, and the mixture was stirred at 90° C. overnight. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL), N,N'-carbonyldiimidazole (0.26 g) and then 1,8-diazabicyclo[5.4.0]undec-7-ene (0.24 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.49 g, 91%) as a colorless solid.

$^1$H NMR (300 MHz, DMSO-d$_6$) δ 0.89 (3 H, t, J=7.3), 1.47-1.63 (2 H, m), 2.06 (3 H, s), 2.46-2.56 (2 H, m), 3.87 (2 H, s), 7.18-7.32 (4 H, m), 7.32-7.43 (2 H, m), 7.42-7.59 (4 H, m), 7.62-7.72 (2 H, m), 12.37 (1 H, s)

Example 141

5-{[3-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one

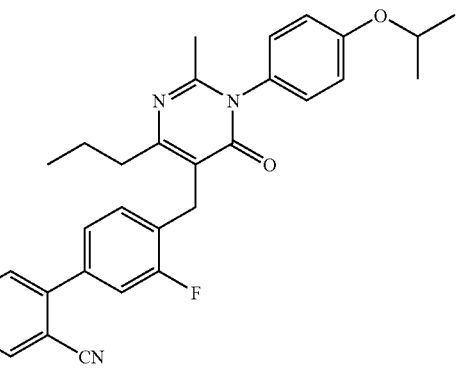

141a) 3'-fluoro-4'-{[1-(4-isopropoxyphenyl)-2-methyl-6-oxo-4-propyl-1,6-dihydropyrimidin-5-yl]methyl}biphenyl-2-carbonitrile A mixture of 3'-fluoro-4'-[(2-methyl-6-oxo-4-propyl-1,6-dihydropyrimidin-5-yl)methyl]biphenyl-2-carbonitrile (1.0 g), 4-isopropoxyphenylboronic acid (1.1 g), copper(II) acetate (1.1 g), pyridine (1.2 mL), triethylamine (2.0 mL), molecular sieves 4 A (2.0 g) and dichloromethane (10 mL) was stirred for 4 days. The reaction mixture was diluted with ethyl acetate, and the insoluble material was filtered off. The filtrate was concentrated under reduced pressure, and the residue was purified by silica gel column chromatography to give the title compound (0.56 g, 42%) as a colorless liquid.

$^1$H NMR (300 MHz, CDCl$_3$) δ 1.00 (3 H, t, J=7.3), 1.36 (6 H, d, J=6.0), 1.59-1.75 (2 H, m), 2.19 (3 H, s), 2.60-2.69 (2 H, m), 3.98 (2 H, s), 4.50-4.64 (1 H, m), 6.95-7.02 (2 H, m), 7.08-7.14 (2 H, m), 7.18-7.25 (2 H, m), 7.39-7.49 (3 H, m), 7.59-7.67 (1 H, m), 7.75 (1 H, dd, J=7.6, 0.85)

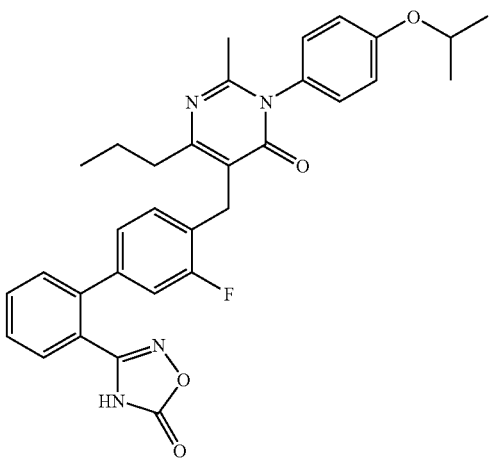

141b) 5-{[3-fluoro-2'-(5-oxo-4,5-dihydro-1,2,4-oxa-diazol-3-yl)biphenyl-4-yl]methyl}-3-(4-isopropoxyphenyl)-2-methyl-6-propylpyrimidin-4(3H)-one A mixture of hydroxylammonium chloride (0.85 g), sodium hydrogen carbonate (1.2 g) and dimethyl sulfoxide (6 mL) was stirred at 50° C. for 30 min, 3'-fluoro-4'-{[1-(4-isopropoxyphenyl)-2-methyl-6-oxo-4-propyl-1,6-dihydropyrimidin-5-yl]methyl}biphenyl-2-carbonitrile (0.56 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (6 mL), N,N'-carbonyldiimidazole (0.30 g) and then 1,8-diazabicyclo[5.4.0]undec-7-ene (0.27 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.51 g, 70%) as a colorless solid.

$^1$H NMR (300 MHz, DMSO-$d_6$) δ 0.89 (3 H, t, J=7.3), 1.29 (6 H, d, J=6.0), 1.47-1.63 (2 H, m), 2.08 (3 H, s), 2.43-2.54 (2 H, m), 3.85 (2 H, s), 4.60-4.74 (1 H, m), 6.97-7.06 (3H, m), 7.09-7.28 (4 H, m), 7.30-7.60 (2 H, m), 7.64-7.74 (2 H, m), 12.43 (1 H, s)

5-{[3-Fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one obtained above is subjected to a conventional method of salt formation to give the following salts.

5-{[3-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one sodium salt 5-{[3-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one potassium salt 5-{[3-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one 0.5 calcium salt 5-{[3-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one hydrochloride 5-{[3-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one hydrobromide Example 142

3-(2,2-dimethyl-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one

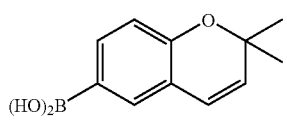

142a) (2,2-dimethyl-2H-chromen-6-yl)boronic acid

To a solution of 6-bromo-2,2-dimethyl-2H-chromene (18 g) in tetrahydrofuran (150 mL) was added butyllithium (53 mL, 1.6 M hexane solution) at −78° C. under an argon atmosphere, and the mixture was stirred for 30 min. Triisopropyl borate (21 mL) was added, and the mixture was stirred for 3 hr while allowing to warm to room temperature. 1 M hydrochloric acid (150 mL) was added to the reaction mixture, and the mixture was stirred for 2 hr and extracted with ethyl acetate. The organic layer was washed with saturated brine and dried over anhydrous magnesium sulfate, and the solvent was evaporated. The residue was purified by silica gel column chromatography to give the title compound (13 g, 82%) as colorless crystals.

$^1$H NMR (300 MHz, DMSO-$d_6$) δ 1.37 (3 H, s), 1.37 (3 H, s), 5.67-5.75 (1 H, m), 6.33-6.52 (1 H, m), 6.64-6.75 (1 H, m), 7.43-7.65 (2 H, m)

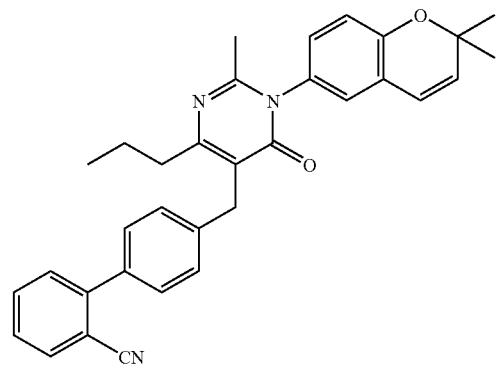

142b) 4'-{[1-(2,2-dimethyl-2H-chromen-6-yl)-2-methyl-6-oxo-4-propyl-1,6-dihydropyrimidin-5-yl]methyl}biphenyl-2-carbonitrile A mixture of 4'-[(2-methyl-6-oxo-4-propyl-1,6-dihydropyrimidin-5-yl)methyl]biphenyl-2-carbonitrile (21 g), (2,2-dimethyl-2H-chromen-6-yl)boronic acid (12 g), copper(II) acetate (11 g), pyridine (24 mL), triethylamine (42 mL), molecular sieves 4 Å (40 g) and dichloromethane (200 mL) was stirred for 4 days. The reaction mixture was diluted with ethyl acetate, and the insoluble material was filtered off. The filtrate was concentrated under reduced pressure, and the residue was purified by silica gel column chromatography to give the title compound (15 g, 51%) as a colorless solid.

$^1$H NMR (300 MHz, CDCl$_3$) δ 1.00 (3 H, t, J=7.3), 1.43 (3 H, s), 1.48 (3 H, s), 1.61-1.75 (2 H, m), 2.20 (3 H, s), 2.59-2.69 (2 H, m), 3.96 (2 H, s), 5.65 (1 H, d, J=9.8), 6.28 (1 H, d, J=9.8), 6.80-6.97 (3 H, m), 7.36-7.51 (6 H, m), 7.60 (1 H, d, J=7.5), 7.74 (1 H, d, J=7.9)

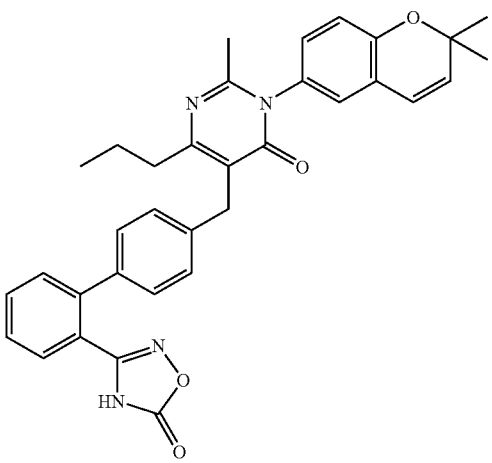

142c) 3-(2,2-dimethyl-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.70 g), sodium hydrogen carbonate (1.0 g) and dimethyl sulfoxide (5 mL) was stirred at 50° C. for 30 min, 4'-{[1-(2,2-dimethyl-2H-chromen-6-yl)-2-methyl-6-oxo-4-propyl-1,6-dihydro-pyrimidin-5-yl]methyl}biphenyl-2-carbonitrile (0.56 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL), N,N'-carbonyldiimidazole (0.24 g) and then 1,8-diazabicyclo[5.4.0]undec-7-ene (0.22 mL) were added, and the mixture was stirred at room temperature for 30 min. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound (0.42 g, 74%) as a colorless solid.

$^1$H NMR (300 MHz, DMSO-d$_6$) δ 0.88 (3 H, t, J=7.3), 1.41 (3 H, s), 1.42 (3 H, s), 1.46-1.62 (2 H, m), 2.09 (3 H, s), 2.48-2.54 (2 H, m), 3.86 (2 H, s), 5.83 (1 H, d, J=9.9), 6.41 (1 H, d, J=9.9), 6.85 (1 H, d, J=9.4), 7.06-7.12 (2 H, m), 7.18-7.30 (4 H, m), 7.48-7.58 (2 H, m), 7.62-7.72 (2 H, m), 12.38 (1 H, s)

3-(2,2-Dimethyl-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-(2,2-dimethyl-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-(2,2-dimethyl-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-(2,2-dimethyl-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-(2,2-dimethyl-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-(2,2-dimethyl-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 143

3-(4-methoxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one

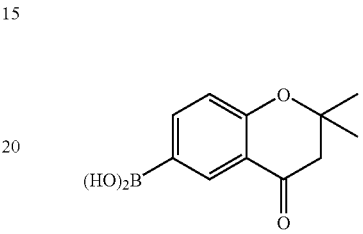

143a) (2,2-dimethyl-4-oxo-3,4-dihydro-2H-chromen-6-yl)boronic acid

A solution of 6-bromo-2,2-dimethyl-2,3-dihydro-4H-chromen-4-one (21 g), pinacol diborane (25 g), palladium acetate (0.92 g) and potassium acetate (2.4 g) in N,N-dimethylformamide (250 mL) was stirred at 90° C. for 2 hr under an argon atmosphere. Water was added to the reaction mixture, and the mixture was extracted with diethyl ether. The organic layer was washed with saturated brine, and dried over anhydrous magnesium sulfate. The solvent was evaporated under reduced pressure. The residue was dissolved in tetrahydrofuran (80 mL), and 0.5 M hydrochloric acid (40 mL) and sodium periodate (7.0 g) were added at 0° C. The reaction mixture was stirred at room temperature for 2 hr and extracted with ethyl acetate. The organic layer was washed with saturated brine, and dried over anhydrous magnesium sulfate. The solvent was evaporated under reduced pressure. The residue was crystallized from ethyl acetate and hexane to give the title compound (15 g, 84%) as a colorless solid.

$^1$H NMR (300 MHz, DMSO-d$_6$) δ 1.39 (6 H, s), 2.79 (2 H, s), 6.93 (1 H, d, J=8.3), 7.93 (1 H, dd, J=8.3, 1.7), 8.06 (2 H, s), 8.24 (1 H, d, J=1.7)

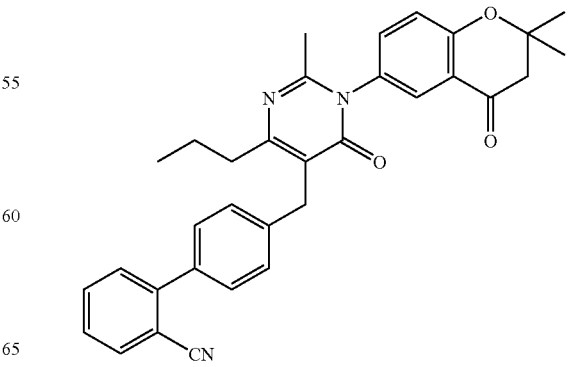

143b) 4'-{[1-(2,2-dimethyl-4-oxo-3,4-dihydro-2H-chromen-6-yl)-2-methyl-6-oxo-4-propyl-1,6-dihydropyrimidin-5-yl]methyl}biphenyl-2-carbonitrile A mixture of 4'-[(2-methyl-6-oxo-4-propyl-1,6-dihydropyrimidin-5-yl)methyl]biphenyl-2-carbonitrile (10 g), (2,2-dimethyl-4-oxo-3,4-dihydro-2H-chromen-6-yl)boronic acid (6.6 g), copper(II) acetate (5.5 g), pyridine (12 mL), triethylamine (21 mL), molecular sieves 4 A (20 g) and dichloromethane (100 mL) was stirred for 3 days. The reaction mixture was diluted with ethyl acetate, and the insoluble material was filtered off. The filtrate was concentrated under reduced pressure, and the residue was purified by silica gel column chromatography to give the title compound (7.0 g, 45%) as a colorless solid.

$^1$H NMR (300 MHz, CDCl$_3$) δ 1.00 (3 H, t, J=7.3), 1.49 (3 H, s), 1.50 (3 H, s), 1.62-1.76 (2 H, m), 2.18 (3 H, s), 2.65 (2 H, dd, J=9.0, 6.4), 2.75 (2 H, s), 3.96 (2 H, s), 7.08 (1 H, d, J=9.0), 7.30-7.51 (7 H, m), 7.58-7.65 (1 H, m), 7.69-7.76 (2 H, m)

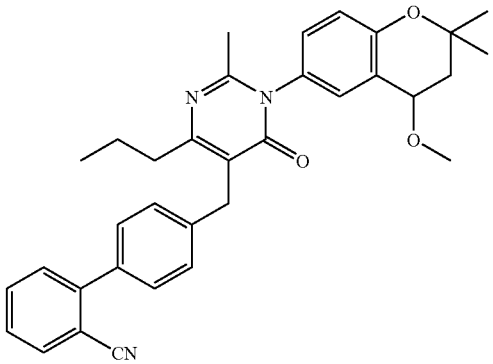

143c) 4'-{[1-(4-hydroxy-2,2-dimethyl-3,4-dihydro-2H-chromen-6-yl)-2-methyl-6-oxo-4-propyl-1,6-dihydropyrimidin-5-yl]methyl}biphenyl-2-carbonitrile 4'-{[1-(2,2-Dimethyl-4-oxo-3,4-dihydro-2H-chromen-6-yl)-2-methyl-6-oxo-4-propyl-1,6-dihydropyrimidin-5-yl]methyl}biphenyl-2-carbonitrile (7.0 g) was dissolved in methanol (35 mL) and tetrahydrofuran (35 mL), and sodium borohydride (0.61 g) was added at 0° C. After stirring for 30 min, 5% aqueous potassium hydrogen sulfate solution was added to the reaction mixture, and the mixture was extracted with ethyl acetate. The organic layer was washed with saturated brine, and dried over anhydrous magnesium sulfate. The solvent was evaporated under reduced pressure and the residue was purified by silica gel column chromatography to give the title compound (7.0 g, 100%) as a colorless solid.

$^1$H NMR (300 MHz, CDCl$_3$) δ 0.95-1.05 (3 H, m), 1.44 (3 H, s), 1.61-1.74 (2 H, m), 1.76 (3 H, s), 1.78-1.91 (1 H, m), 2.09-2.23 (4 H, m), 2.57-2.69 (2 H, m), 3.88-4.01 (2 H, m), 4.74-4.88 (1 H, m), 6.84-6.90 (1 H, m), 6.92-7.03 (1 H, m), 7.24-7.51 (7 H, m), 7.61 (1 H, t, J=7.5), 7.73 (1 H, d, J=7.5)

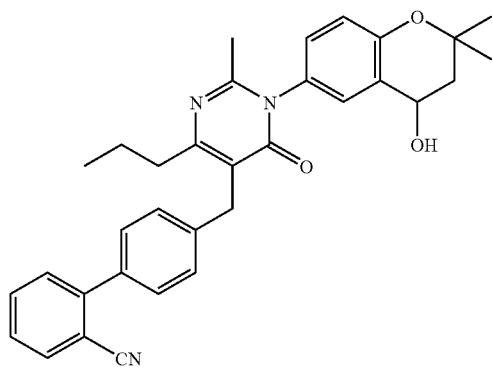

143d) 4'-{[1-(4-methoxy-2,2-dimethyl-3,4-dihydro-2H-chromen-6-yl)-2-methyl-6-oxo-4-propyl-1,6-dihydropyrimidin-5-yl]methyl}biphenyl-2-carbonitrile To a solution of 4'-{[1-(4-hydroxy-2,2-dimethyl-3,4-dihydro-2H-chromen-6-yl)-2-methyl-6-oxo-4-propyl-1,6-dihydropyrimidin-5-yl]methyl}biphenyl-2-carbonitrile (0.52 g) in N,N-dimethylformamide (5 mL) were added sodium hydride (0.080 g) and iodomethane (0.13 mL), and the mixture was stirred for 1 hr. A 5% aqueous potassium hydrogen sulfate solution was added to the reaction mixture, and the mixture was extracted with ethyl acetate. The organic layer was washed with saturated brine, and dried over anhydrous magnesium sulfate. The solvent was evaporated under reduced pressure and the residue was purified by silica gel column chromatography to give the title compound (0.41 g, 77%) as a colorless solid.

$^1$H NMR (300 MHz, CDCl$_3$) δ 1.00 (3 H, t, J=7.1), 1.29-1.50 (6 H, m), 1.68 (2 H, d, J=7.5), 1.83-2.22 (5 H, m), 2.58-2.69 (2 H, m), 3.44 (3 H, s), 3.89-4.04 (2 H, m), 4.40-4.50 (1 H, m), 6.86-6.92 (1 H, m), 6.96-7.04 (1 H, m), 7.22-7.30 (1 H, m), 7.36-7.51 (6 H, m), 7.61 (1 H, t, J=7.5), 7.74 (1 H, d, J=7.5)

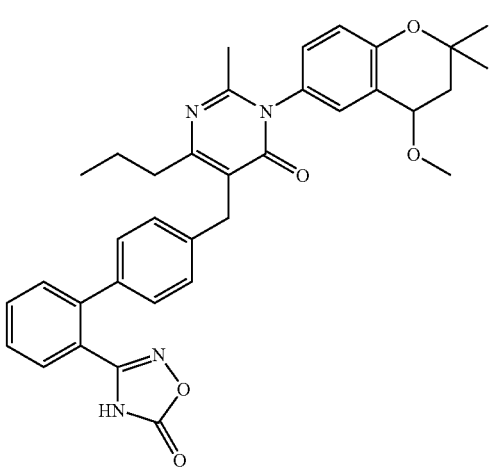

143e) 3-(4-methoxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.53 g), sodium hydrogen carbonate (0.77 g) and dimethyl sulfoxide (4 mL) was stirred at 50° C. for 30 min, 4'-{1-(4-methoxy-2,2-dimethyl-3,4-dihydro-2H-chromen-6-yl)-2-methyl-6-oxo-4-propyl-1,6-dihydropyrimidin-5-yl]methyl}biphenyl-2-carbonitrile (0.41 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (4 mL), N,N'-carbonyldiimidazole (0.19 g) and then 1,8-diazabicyclo[5.4.0]undec-7-ene (0.17 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.35 g, 77%) as a solid.

$^1$H NMR (300 MHz, DMSO-$d_6$) δ 0.88 (3 H, t, J=7.4), 1.32 (3 H, d, J=3.0), 1.40 (3 H, d, J=3.0), 1.47-1.63 (2 H, m), 1.80-1.95 (1 H, m), 2.07 (3 H, d, J=4.7), 2.12-2.26 (1 H, m), 2.46-2.56 (2 H, m), 3.39 (3 H, d, J=3.7), 3.86 (2 H, s), 4.38-4.50 (1 H, m), 6.86 (1 H, dd, J=8.6, 3.0), 7.09-7.18 (1 H, m), 7.18-7.32 (5 H, m), 7.48-7.58 (2 H, m), 7.61-7.73 (2 H, m), 12.38 (1 H, s)

Example 144

3-(4-hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one

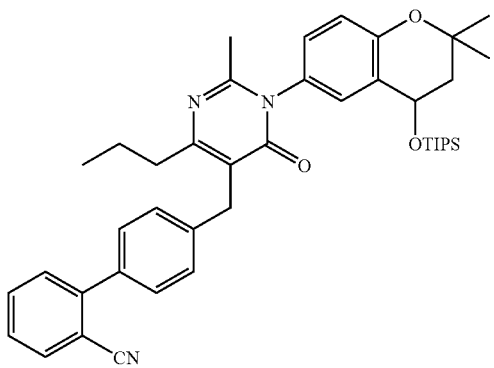

144a) 4'-[(1-{2,2-dimethyl-4-[(triisopropylsilyl)oxy]-3,4-dihydro-2H-chromen-6-yl}-2-methyl-6-oxo-4-propyl-1,6-dihydropyrimidin-5-yl)methyl]biphenyl-2-carbonitrile To a solution of 4'-{[1-(4-hydroxy-2,2-dimethyl-3,4-dihydro-2H-chromen-6-yl)-2-methyl-6-oxo-4-propyl-1,6-dihydropyrimidin-5-yl]methyl}biphenyl-2-carbonitrile (3.1 g) and 2,6-lutidine (2.1 mL) in dichloromethane (30 mL) was added triisopropylsilyl trifluoromethanesulfonate (3.2 mL), and the mixture was stirred for 1 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (4.1 g, 100%) as a solid.

$^1$H NMR (300 MHz, CDCl$_3$) δ 0.96-1.49 (30 H, m), 1.60-1.80 (2 H, m), 1.88-2.00 (1 H, m), 2.07-2.16 (1 H, m), 2.16-2.21 (3 H, m), 2.55-2.75 (2 H, m), 3.85-4.08 (2 H, m), 5.05 (1 H, s), 6.84-6.92 (1 H, m), 6.95-7.02 (1 H, m), 7.23 (1 H, d, J=2.2), 7.36-7.51 (6 H, m), 7.57-7.65 (1 H, m), 7.74 (1 H, dd, J=7.8, 1.04)

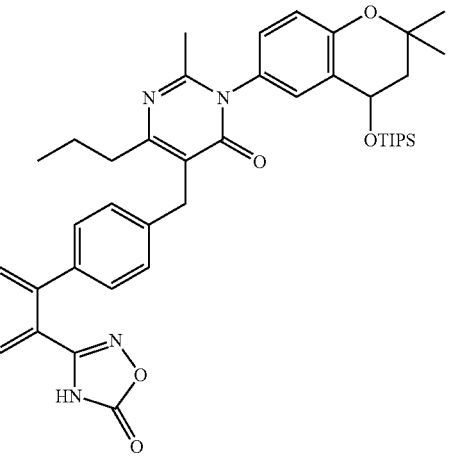

144b) 3-{2,2-dimethyl-4-[(triisopropylsilyl)oxy]-3,4-dihydro-2H-chromen-6-yl}-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (4.2 g), sodium hydrogen carbonate (6.1 g) and dimethyl sulfoxide (40 mL) was stirred at 50° C. for 30 min, 4'-[(1-{2,2-dimethyl-4-[(triisopropylsilyl)oxy]-3,4-dihydro-2H-chromen-6-yl}-2-methyl-6-oxo-4-propyl-1,6-dihydropyrimidin-5-yl)methyl]biphenyl-2-carbonitrile (4.1 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (40 mL), N,N'-carbonyldiimidazole (1.5 g) and then 1,8-diazabicyclo[5.4.0]undec-7-ene (1.3 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (4.4 g, 100%) as a solid.

$^1$H NMR (300 MHz, CDCl$_3$) δ 0.98-1.51 (30 H, m), 1.65-1.85 (2 H, m), 1.85-1.99 (1 H, m), 2.05-2.15 (1 H, m), 2.17 (3 H, s), 2.57-2.78 (2 H, m), 3.78-4.04 (2 H, m), 4.94-5.08 (1 H, m), 6.81-6.98 (2 H, m), 7.16-7.25 (3 H, m), 7.28-7.36 (2 H, m), 7.37-7.51 (2 H, m), 7.53-7.63 (1 H, m), 7.80 (1 H, d, J=7.7)

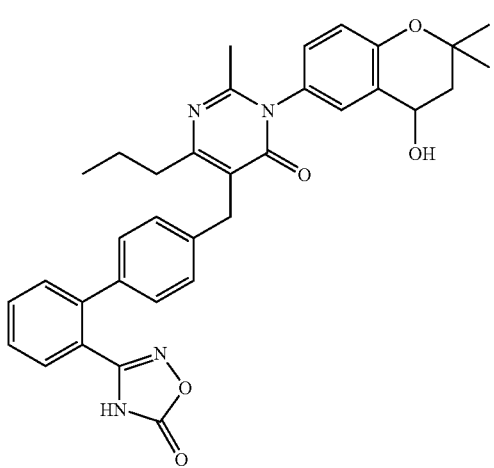

144c) 3-(4-hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one To a solution of 3-{2,2-dimethyl-4-[(triisopropylsilyl)oxy]-3,4-dihydro-2H-chromen-6-yl}-2-methyl-5-{[2'-(5-oxo-4,5-dihydro-1,2,4-oxadiazol-3-yl)biphenyl-4-yl]methyl}-6-propylpyrimidin-4(3H)-one (4.0 g) in tetrahydrofuran (20 mL) was added tetrabutylammonium fluoride (1.0 M tetrahydrofuran solution, 8.2 mL), and the mixture was stirred for 2 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (3.0 g, 95%) as a solid.

$^1$H NMR (300 MHz, DMSO-d$_6$) δ 0.88 (3 H, t, J=7.3), 1.28 (3 H, s), 1.40 (3 H, s), 1.47-1.64 (2 H, m), 1.67-1.82 (1 H, m), 2.05-2.17 (4 H, m), 2.45-2.55 (2 H, m), 3.87 (2 H, s), 4.65-4.77 (1 H, m), 5.44 (1 H, dd, J=6.0, 1.3), 6.82 (1 H, d, J=8.6), 7.05-7.14 (1 H, m), 7.18-7.34 (5 H, m), 7.48-7.59 (2 H, m), 7.62-7.73 (2 H, m), 12.38 (1 H, s)

3-(4-Hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-(4-hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-(4-hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-(4-hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-(4-hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-(4-hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 145

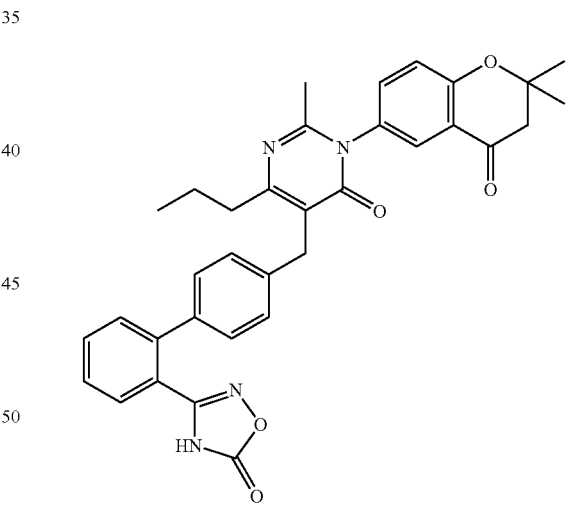

3-(2,2-dimethyl-4-oxo-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one A solution of 3-(4-hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4

(3H)-one (0.40 g) and 1,1,1-tris(acetyloxy)-1,1-dihydro-1,2-benziodoxol-3(1H)-one (0.44 g) in dichloromethane (4 mL) was stirred for 1 hr. The reaction mixture was diluted with ethyl acetate, washed with saturated aqueous sodium hydrogen carbonate solution and then with saturated brine, and dried over anhydrous magnesium sulfate. The solvent was evaporated under reduced pressure and the residue was purified by silica gel column chromatography to give the title compound (0.34 g, 86%) as a colorless solid.

$^1$H NMR (300 MHz, DMSO-$d_6$) δ 0.89 (3 H, t, J=7.4), 1.43 (3 H, s), 1.45 (3 H, s), 1.47-1.63 (2 H, m), 2.07 (3 H, s), 2.46-2.55 (2 H, m), 2.87 (2 H, s), 3.86 (2 H, s), 7.14 (1 H, d, J=8.7), 7.18-7.31 (4 H, m), 7.48-7.60 (3 H, m), 7.62-7.73 (3 H, m), 12.38 (1 H, s)

3-(2,2-Dimethyl-4-oxo-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-(2,2-dimethyl-4-oxo-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-(2,2-dimethyl-4-oxo-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-(2,2-dimethyl-4-oxo-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-(2,2-dimethyl-4-oxo-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-(2,2-dimethyl-4-oxo-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 146

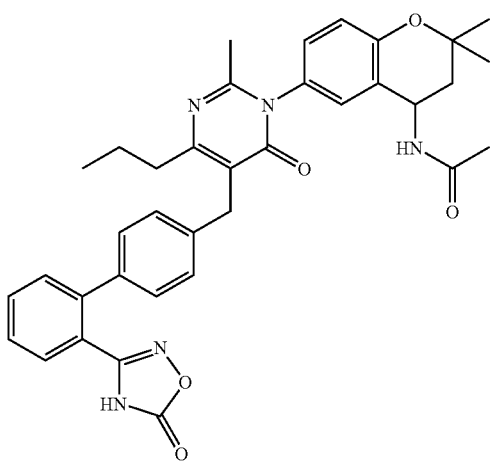

N-{2,2-dimethyl-6-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]-3,4-dihydro-2H-chromen-4-yl}acetamide 3-(4-Hydroxy-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one (1.0 g) was dissolved in acetonitrile (10 mL), and concentrated hydrochloric acid (1.0 mL) was added dropwise at 0° C. The reaction mixture was stirred at room temperature for 30 min. The reaction mixture was diluted with ethyl acetate, washed with saturated aqueous sodium hydrogen carbonate solution and then with saturated brine, and dried over anhydrous magnesium sulfate. The solvent was evaporated under reduced pressure and the residue was purified by silica gel column chromatography to give the title compound (0.82 g, 76%) as a colorless solid.

$^1$H NMR (300 MHz, DMSO-$d_6$) δ 0.84-0.94 (3 H, m), 1.29 (3 H, s), 1.41 (3 H, s), 1.46-1.62 (2 H, m), 1.66-1.79 (1 H, m), 1.89 (3 H, d, J=7.5), 1.97-2.11 (4 H, m), 2.44-2.55 (2 H, m), 3.85 (2 H, s), 5.02-5.19 (1 H, m), 6.85 (1 H, dd, J=8.4, 1.70), 7.05-7.14 (2 H, m), 7.18-7.31 (4 H, m), 7.47-7.58 (2 H, m), 7.61-7.73 (2 H, m), 8.15-8.40 (1 H, m), 12.38 (1 H, s)

Example 147

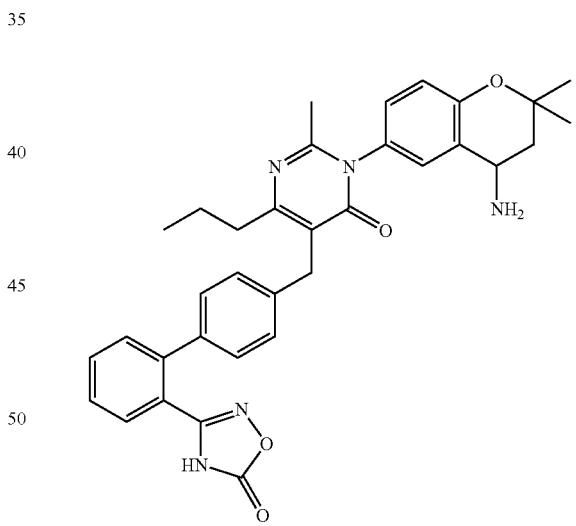

3-(4-amino-2,2-dimethyl-3,4-dihydro-2H-chromen-6-yl)-2-methyl-5-{[2'-(5-oxo-4,5-dihydro-1,2,4-oxadiazol-3-yl)biphenyl-4-yl]methyl}-6-propylpyrimidin-4(3H)-one N-{2,2-Dimethyl-6-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]-3,4-dihydro-2H-chromen-4-yl}acetamide (0.30 g) was dissolved in 6 M hydrochloric acid (1 mL) and 1,4-dioxane (2 mL), and the mixture was stirred at 90° C. for 2 days. The reaction mixture was diluted with ethyl acetate, washed with saturated aqueous sodium hydrogen carbonate solution and then with saturated brine, and dried over anhydrous magnesium sulfate. The solvent was evaporated under reduced pressure and the residue was purified by silica gel column chromatography to give the title compound (0.25 g, 90%) as a colorless solid.

$^1$H NMR (300 MHz, DMSO-$d_6$) δ 0.89-0.97 (3 H, m), 1.26 (3 H, d, J=6.0), 1.44 (3 H, s), 1.52-1.84 (3 H, m), 2.06-2.11 (3 H, m), 2.14-2.25 (1 H, m), 2.47-2.63 (2 H, m), 3.74-3.91 (2 H, m), 4.34-4.44 (1 H, m), 6.90 (1 H, dd, J=8.6, 1.3), 7.15-7.26 (5 H, m), 7.32-7.44 (3 H, m), 7.44-7.54 (3 H, m)

Example 148

6-ethyl-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one

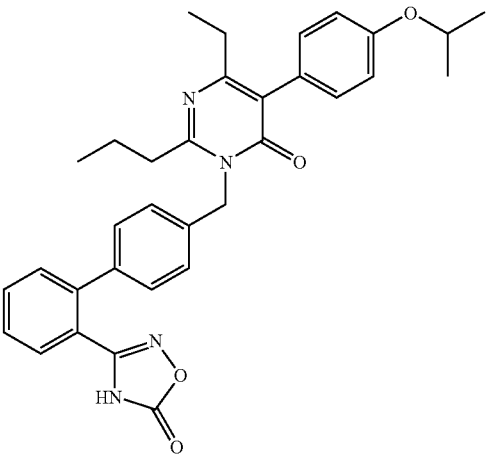

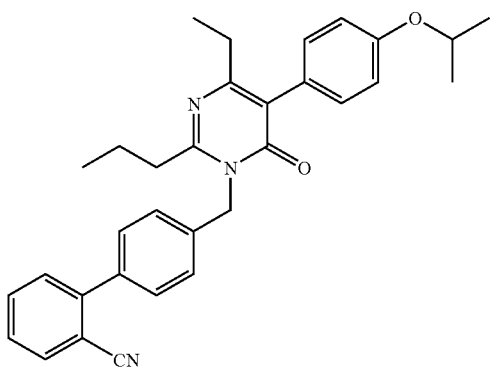

148a) 4'-{[4-ethyl-5-(4-isopropoxyphenyl)-6-oxo-2-propylpyrimidin-1(6H)-yl]methyl}biphenyl-2-carbonitrile 4'-[(5-Bromo-4-ethyl-6-oxo-2-propylpyrimidin-1(6H)-yl)methyl]biphenyl-2-carbonitrile (0.50 g), 4-isopropoxyphenylboronic acid (0.31 g) and [1,1'-bis(diphenylphosphino)ferrocene]dichloropalladium (0.050 g) were dissolved in 2 M aqueous cesium carbonate solution (2 mL) and 1,4-dioxane (10 mL), and the mixture was stirred at 90° C. overnight under an argon atmosphere. The reaction mixture was diluted with ethyl acetate, and the insoluble material was filtered off through celite. The filtrate was washed with saturated brine, and dried over anhydrous magnesium sulfate. The solvent was evaporated under reduced pressure and the residue was purified by silica gel column chromatography to give the title compound (0.50 g, 89%) as a colorless solid.

$^1$H NMR (300 MHz, CDCl$_3$) δ 1.02 (3 H, t, J=7.4), 1.18 (3 H, t, J=7.4), 1.35 (3 H, d, J=6.0), 1.36 (3 H, s), 1.74-1.89 (2 H, m), 2.49 (2 H, q, J=7.4), 2.68-2.77 (2 H, m), 4.50-4.64 (1 H, m), 5.37 (2 H, s), 6.93 (2 H, d, J=8.67), 7.22 (2 H, d, J=8.8), 7.36 (2 H, d, J=8.4), 7.41-7.56 (4 H, m), 7.60-7.68 (1 H, m), 7.76 (1 H, dd, J=7.7, 0.94)

148b) 6-ethyl-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.71 g), sodium hydrogen carbonate (1.0 g) and dimethyl sulfoxide (5 mL) was stirred at 50° C. for 30 min, 4'-{[4-ethyl-5-(4-isopropoxyphenyl)-6-oxo-2-propylpyrimidin-1(6H)-yl]methyl}biphenyl-2-carbonitrile (0.50 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL), N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.44 g, 79%) as a colorless solid.

$^1$H NMR (300 MHz, DMSO-$d_6$) δ 0.89 (3 H, t, J=7.3), 1.10 (3 H, t, J=7.4), 1.29 (3 H, d, J=6.0), 1.58-1.73 (2 H, m), 2.37 (2 H, q, J=7.4), 2.68 (2 H, t, J=7.4), 4.57-4.70 (1 H, m), 5.34 (2 H, s), 6.90-6.97 (2 H, m), 7.14-7.21 (2 H, m), 7.23-7.35 (4 H, m), 7.49-7.61 (2 H, m), 7.63-7.74 (2 H, m), 12.39 (1 H, s)

Example 149

2-butyl-5-(4-isopropoxyphenyl)-6-methyl-3-{[2'-(5-oxo-4,5-dihydro-1,2,4-oxadiazol-3-yl)biphenyl-4-yl]methyl}pyrimidin4(3H)-one

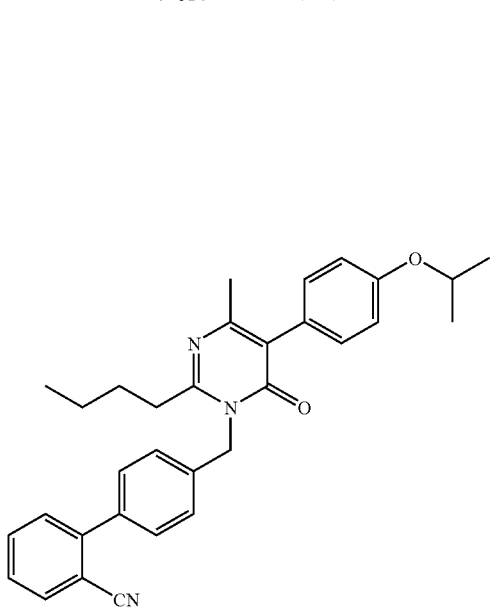

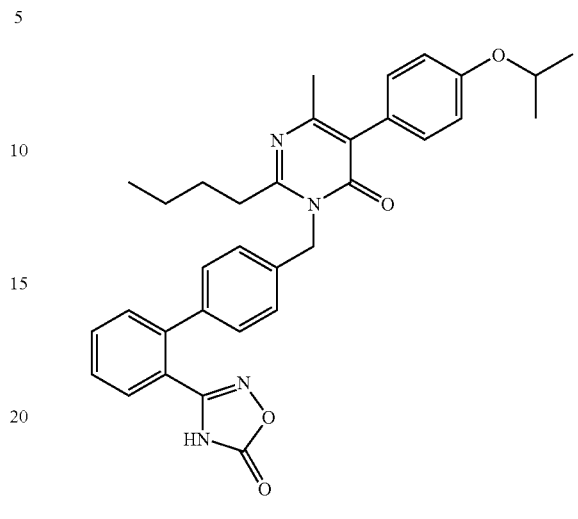

149a) 4-{[2-butyl-5-(4-isopropoxyphenyl)-4-methyl-6-oxopyrimidin-1(6H)-yl]methyl}biphenyl-2-carbonitrile 4'-[(5-Bromo-2-butyl-4-methyl-6-oxopyrimidin-1(6H)-yl)methyl]biphenyl-2-carbonitrile (0.50 g), 4-isopropoxyphenylboronic acid (0.31 g) and [1,1'-bis(diphenylphosphino)ferrocene]dichloropalladium (0.050 g) were dissolved in 2 M aqueous cesium carbonate solution (2 mL) and 1,4-dioxane (10 mL), and the mixture was stirred at 90° C. overnight under an argon atmosphere. The reaction mixture was diluted with ethyl acetate, and the insoluble material was filtered off through celite. The filtrate was washed with saturated brine, and dried over anhydrous magnesium sulfate. The solvent was evaporated under reduced pressure and the residue was purified by silica gel column chromatography to give the title compound (0.56 g, 99%) as a colorless solid.

$^1$H NMR (300 MHz, CDCl$_3$) δ 0.93 (3 H, t, J=7.3), 1.32-1.49 (2 H, m), 1.35 (3 H, d, J=6.0), 1.66-1.79 (2 H, m), 2.24 (3 H, s), 2.69-2.78 (2 H, m), 4.50-4.65 (1 H, m), 5.38 (2 H, s), 6.89-6.97 (2 H, m), 7.21-7.29 (2 H, m), 7.35 (2 H, d, J=8.4), 7.40-7.56 (4 H, m), 7.60-7.68 (1 H, m), 7.76 (1 H, dd, J=7.8, 0.85)

149b) 2-butyl-5-(4-isopropoxyphenyl)-6-methyl-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.79 g), sodium hydrogen carbonate (1.2 g) and dimethyl sulfoxide (5 mL) was stirred at 50° C. for 30 min, 4'-{[2-butyl-5-(4-isopropoxyphenyl)-4-methyl-6-oxopyrimidin-1(6H)-yl]methyl}biphenyl-2-carbonitrile (0.56 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL), N,N'-carbonyldiimidazole (0.28 g) and then 1,8-diazabicyclo[5.4.0]undec-7-ene (0.26 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.49 g, 78%) as a colorless solid.

$^1$H NMR (300 MHz, DMSO-d$_6$) δ 0.82 (3 H, t, J=7.5), 1.21-1.38 (8 H , m), 1.51-1.65 (2 H, m), 2.13 (3 H, s), 2.63-2.73 (2 H, m), 4.56-4.72 (1 H, m), 5.35 (2 H, s), 6.89-6.97 (2 H, m), 7.16-7.36 (6 H, m), 7.48-7.61 (2 H, m), 7.63-7.74 (2 H, m), 12.40 (1 H, s)

Example 150

2-ethoxy-5-(4-isopropoxyphenyl)-6-methyl-3-{[2'-(5-oxo-4,5-dihydro-1,2,4-oxadiazol-3-yl)biphenyl-4-yl]methyl}pyrimidin-4(3H)-one

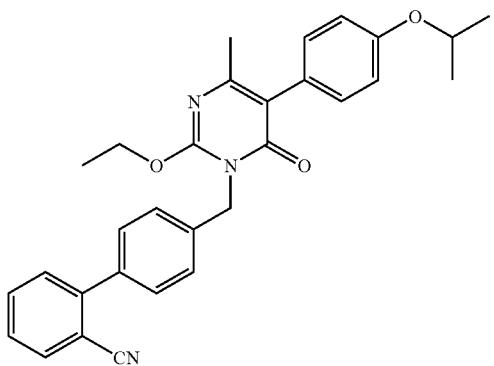

150a) 4'-{[2-ethoxy-5-(4-isopropoxyphenyl)-4-methyl-6-oxopyrimidin-1(6H)-yl]methyl}biphenyl-2-carbonitrile 4'-[(5-Bromo-2-ethoxy-4-methyl-6-oxopyrimidin-1(6H)-yl)methyl]biphenyl-2-carbonitrile (0.50 g), 4-isopropoxyphenylboronic acid (0.32 g) and [1,1'-bis(diphenylphosphino)ferrocene]dichloropalladium (0.050 g) were dissolved in 2 M aqueous cesium carbonate solution (2 mL) and 1,4-dioxane (10 mL), and the mixture was stirred at 90° C. overnight under an argon atmosphere. The reaction mixture was diluted with ethyl acetate, and the insoluble material was filtered off through celite. The filtrate was washed with saturated brine, and dried over anhydrous magnesium sulfate. The solvent was evaporated under reduced pressure and the residue was purified by silica gel column chromatography to give the title compound (0.53 g, 94%) as a colorless solid.

$^1$H NMR (300 MHz, CDCl$_3$) δ 1.35 (3 H, d, J=6.0), 1.42 (3 H, t, J=7.0), 2.13 (3 H, s), 4.43-4.62 (3 H, m), 5.25 (2 H, s), 6.87-6.96 (2 H, m), 7.16-7.23 (2 H, m), 7.39-7.52 (4 H, m), 7.54-7.67 (3 H, m), 7.75 (1 H, dd, J=7.7, 0.94)

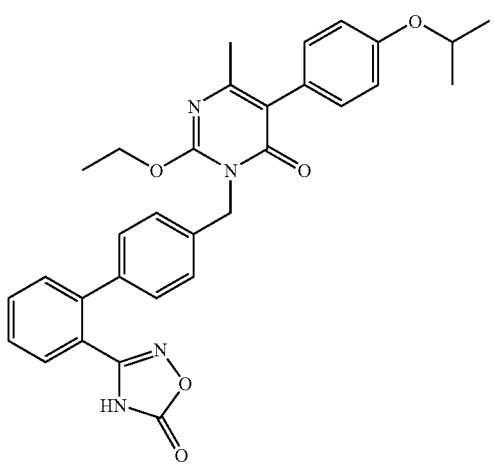

150b) 2-ethoxy-5-(4-isopropoxyphenyl)-6-methyl-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.77 g), sodium hydrogen carbonate (1.1 g) and dimethyl sulfoxide (5 mL) was stirred at 50° C. for 30 min, 4'-{[2-ethoxy-5-(4-isopropoxyphenyl)-4-methyl-6-oxopyrimidin-1(6H)-yl]methyl}biphenyl-2-carbonitrile (0.53 g) was added, and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL), N,N'-carbonyldiimidazole (0.27 g) and then 1,8-diazabicyclo[5.4.0]undec-7-ene (0.25 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.39 g, 66%) as a colorless solid.

$^1$H NMR (300 MHz, DMSO-d$_6$) δ 1.24-1.32 (9 H, m), 2.07 (3 H, s), 4.40 (2 H, q, J=7.2), 4.56-4.71 (1 H, m), 5.13 (2 H, s), 6.92 (2 H, d, J=8.8), 7.16 (2 H, d, J=8.8), 7.26-7.39 (4H, m), 7.49-7.60 (2 H, m), 7.64-7.73 (2 H, m), 12.39 (1 H, s)

Example 151

6-butyl-3-[(3,5-dimethylisoxazol-4-yl)methyl]-2-methyl-5-{[2'-(5-oxo-4,5-dihydro-1,2,4-oxadiazol-3-yl)biphenyl-4-yl]methyl}pyrimidin-4(3H)-one

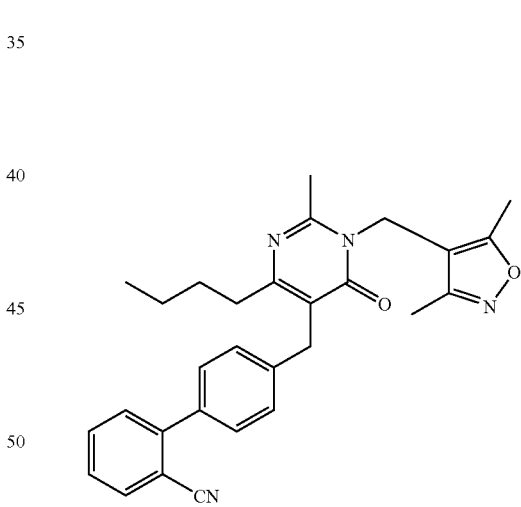

151a) 4'-({4-butyl-1-[(3,5-dimethylisoxazol-4-yl)methyl]-2-methyl-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1.02 g), potassium carbonate (1.28 g), 4-(chloromethyl)-3,5-dimethylisoxazole (0.45 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless viscous substance (0.43 g, 33%).

$^1$H NMR (300 MHz, CDCl$_3$) δ 0.92 (t, J=7.4, 3 H ), 1.31-1.44 (m, 2 H ), 1.53-1.64 (m, 2 H ), 2.10 (s, 3 H ), 2.21 (s, 3 H ), 2.43 (s, 3 H ), 2.58-2.67 (m, 2 H ), 3.98 (s, 2 H ), 5.06 (s, 2 H), 7.33-7.37 (m, 2 H ), 7.38-7.50 (m, 4 H ), 7.62 (td, J=7.7, 1.2, 1 H ), 7.74 (dd, J=7.7, 1.3, 1 H )

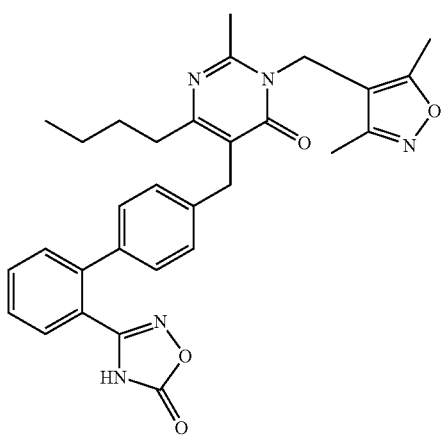

151b) 6-butyl-3-[(3,5-dimethylisoxazol-4-yl)methyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.57 g), sodium hydrogen carbonate (0.78 g) and dimethyl sulfoxide (6 mL) was stirred at 40° C. for 30 min, 4'-({4-butyl-1-[(3,5-dimethylisoxazol-4-yl)methyl]-2-methyl-6-oxo-1,6-dihydropyrimidin-5-yl}methyl)biphenyl-2-carbonitrile (0.43 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.20 g) and then 1,8-diazabicyclo[5.4.0]undec-7-ene (0.20 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.26 g, 55%).

$^1$H NMR (300 MHz, DMSO-d$_6$) δ 0.83 (t, J=7.3, 3 H ), 1.04 (d, J=6.0, 3 H ), 1.22-1.34 (m, 2 H ), 1.40-1.52 (m, 2 H ), 2.17 (s, 3 H ), 2.42 (s, 3 H ), 2.48-2.52 (m, 2 H ), 3.88 (s, 2 H ), 5.08 (s, 2 H ), 7.18-7.26 (m, 4 H ), 7.47-7.53 (m, 1 H ), 7.56 (dd, J=7.4, 1.13, 1 H ), 7.63-7.72 (m, 2 H ), 12.39 (s, 1 H )

Example 152

6-butyl-2-methyl-5-{[2'-(5-oxo-4,5-dihydro-1,2,4-oxadiazol-3-yl)biphenyl-4-yl]methyl}-3-[(5-phenyl-1,2,4-oxadiazol-3-yl)methyl]pyrimidin-4(3H)-one

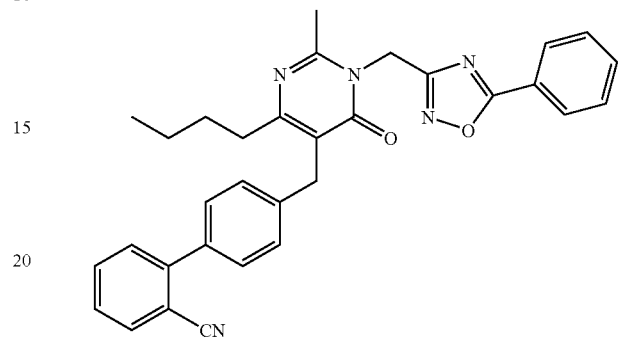

152a) 4'-({4-butyl-2-methyl-6-oxo-1-[(5-phenyl-1,2,4-oxadiazol-3-yl)methyl]-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1.24 g), potassium carbonate (0.94 g), 3-(chloromethyl)-5-phenyl-1,2,4-oxadiazole (0.68 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless viscous substance (0.79 g, 45%).

$^1$H NMR (300 MHz, CDCl$_3$) δ 0.90 (t, J=7.4, 3 H ), 1.31-1.44 (m, 2 H ), 1.52-1.65 (m, 2 H ), 2.57-2.64 (m, 5 H ), 4.00 (s, 2 H ), 5.45 (s, 2 H ), 7.31-7.49 (m, 8 H ), 7.50-7.59 (m, 2 H), 7.68 (dd, J=7.7, 0.9, 1 H ), 8.02-8.07 (m, 2 H )

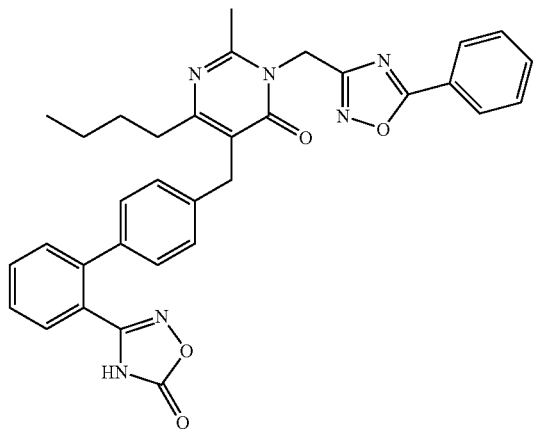

152b) 6-butyl-2-methyl-5-{[2'-(5-oxo-4,5-dihydro-1, 2,4-oxadiazol-3-yl)biphenyl-4-yl]methyl}-3-[(5-phenyl-1,2,4-oxadiazol-3-yl)methyl]pyrimidin-4 (3H)-one A mixture of hydroxylammonium chloride (0.54 g), sodium hydrogen carbonate (0.76 g) and dimethyl sulfoxide (6 mL) was stirred at 40° C. for 30 min, 4'-({4-butyl-2-methyl-6-oxo-1-[(5-phenyl-1,2,4-oxadiazol-3-yl)methyl]-1, 6-dihydropyrimidin-5-yl}methyl)biphenyl-2-carbonitrile (0.79 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.37 g) and then 1,8-diazabicyclo[5.4.0]undec-7-ene (0.34 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.61 g, 69%).

$^1$H NMR (300 MHz, DMSO-d$_6$) δ 0.84 (t, J=7.3, 3 H ), 1.24-1.38 (m, 2 H ), 1.40-1.53 (m, 2 H ), 2.46-2.55 (m, 2 H ), 2.57 (s, 3 H ), 3.87 (s, 2 H ), 5.47 (s, 2 H ), 7.17-7.26 (m, 4 H ), 7.46-7.57 (m, 2 H ), 7.58-7.78 (m, 5 H ), 8.09 (d, J=7.4, 2 H ), 12.38 (s, 1 H )

6-Butyl-2-methyl-5-{[2'-(5-oxo-4,5-dihydro-1,2,4-oxadiazol-3-yl)biphenyl-4-yl]methyl}-3-[(5-phenyl-1,2,4-oxadiazol-3-yl)methyl]pyrimidin-4(3H)-one obtained above is subjected to a conventional method of salt formation to give the following salts.

6-butyl-2-methyl-5-{[2'-(5-oxo-4,5-dihydro-1,2,4-oxadiazol-3-yl)biphenyl-4-yl]methyl}-3-[(5-phenyl-1,2,4-oxadiazol-3-yl)methyl]pyrimidin-4(3H)-one sodium salt 6-butyl-2-methyl-5-{[2'-(5-oxo-4,5-dihydro-1,2,4-oxadiazol-3-yl)biphenyl-4-yl]methyl}-3-[(5-phenyl-1,2,4-oxadiazol-3-yl)methyl]pyrimidin-4(3H)-one potassium salt 6-butyl-2-methyl-5-{[2'-(5-oxo-4,5-dihydro-1,2,4-oxadiazol-3-yl)biphenyl-4-yl]methyl}-3-[(5-phenyl-1,2,4-oxadiazol-3-yl)methyl]pyrimidin-4(3H)-one 0.5 calcium salt 6-butyl-2-methyl-5-{[2'-(5-oxo-4,5-dihydro-1,2,4-oxadiazol-3-yl)biphenyl-4-yl]methyl}-3-[(5-phenyl-1,2,4-oxadiazol-3-yl)methyl]pyrimidin-4(3H)-one hydrochloride 6-butyl-2-methyl-5-{[2'-(5-oxo-4,5-dihydro-1,2,4-oxadiazol-3-yl)biphenyl-4-yl]methyl}-3-[(5-phenyl-1,2,4-oxadiazol-3-yl)methyl]pyrimidin-4(3H)-one hydrobromide Example 153

6-butyl-3-(2-fluorobenzyl)-2-methyl-5-{[2'-(5-oxo-4, 5-dihydro-1,2,4-oxadiazol-3-yl)biphenyl-4-yl] methyl}pyrimidin-4(3H)-one

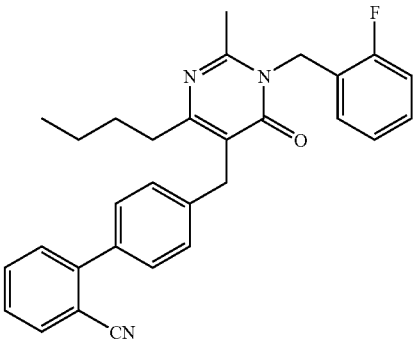

153a) 4'-{[4-butyl-1-(2-fluorobenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.23 g), potassium carbonate (0.96 g), 1-(bromomethyl)-2-fluorobenzene (0.66 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a pale-yellow viscous substance (0.93 g, 59%).

$^1$H NMR (300 MHz, CDCl$_3$) δ 0.90 (t, J=7.4, 3 H ), 1.30-1.45 (m, 2 H ), 1.53-1.66 (m, 2 H ), 2.42 (s, 3 H ), 2.58-2.65 (m, 2 H ), 4.03 (s, 2 H ), 5.34 (s, 2 H ), 6.99-7.10 (m, 3 H ), 7.16-7.26 (m, 1 H ), 7.33 (td, J=7.5, 0.9, 1 H ), 7.38-7.50 (m, 5 H ), 7.54 (td, J=7.7, 1.1, 1 H ), 7.67 (d, J=7.7, 1 H )

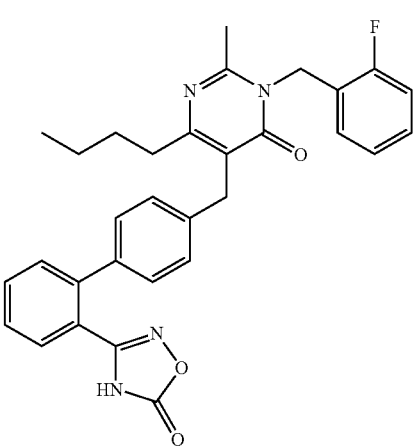

153b) 6-butyl-3-(2-fluorobenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.23 g), sodium hydrogen carbonate (1.75 g) and dimethyl sulfoxide (12 mL) was stirred at 40° C. for 30 min, 4'-{[4-butyl-1-(2-fluorobenzyl)-2-methyl-6-oxo-1,6-dihydropyrimidin-5-yl]methyl}biphenyl-2-carbonitrile (0.93 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (40 mL), N,N'-carbonyldiimidazole (0.50 g) and then 1,8-diazabicyclo[5.4.0]undec-7-ene (0.45 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.82 g, 78%).

$^1$H NMR (300 MHz, CDCl$_3$) δ 0.93 (t, J=7.4, 3 H ), 1.34-1.47 (m, 2 H ), 1.54-1.69 (m, 2 H ), 2.40 (s, 3 H ), 2.55-2.65 (m, 2 H ), 3.93 (s, 2 H ), 5.24 (s, 2 H ), 6.90-6.99 (m, 1 H), 7.02-7.14 (m, 2 H ), 7.18-7.32 (m, 5 H ), 7.38-7.48 (m, 2 H ), 7.57 (td, J=7.6, 1.1, 1 H ), 7.77 (d, J=7.6, 1 H ), 12.39 (s, 1 H )

Example 154

3-[(4-benzylmorpholin-2-yl)methyl]-6-butyl-2-methyl-5-{[2'-(5-oxo-4,5-dihydro-1,2,4-oxadiazol-3-yl)biphenyl-4-yl]methyl}pyrimidin-4(3H)-one

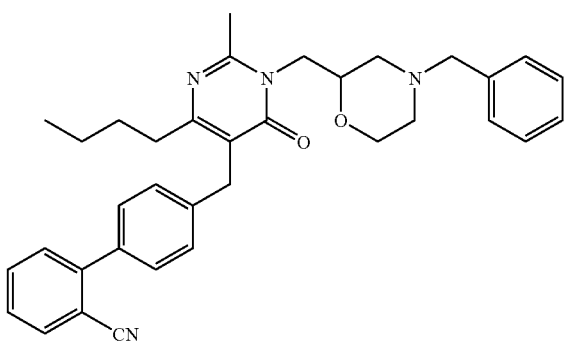

154a) 4'-({1-[(4-benzylmorpholin-2-yl)methyl]-4-butyl-2-methyl-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1.25 g), potassium carbonate (0.96 g), 4-benzyl-2-(chloromethyl)morpholine (0.87 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless viscous substance (0.62 g, 34%).

$^1$H NMR (300 MHz, CDCl$_3$) δ 0.76 (t, J=7.2, 3 H ), 1.15-1.28 (m, 2 H ), 1.36-1.49 (m, 2 H ), 1.74-1.82 (m, 1 H ), 1.90-2.01 (m, 1 H ), 2.39-2.47 (m, 6 H ), 2.76 (d, J=10.6, 1 H ), 3.26-3.43 (m, 3 H ), 3.55-3.66 (m, 2 H ), 3.73-3.89 (m, 3 H), 4.04-4.11 (m, 1 H ), 7.02-7.16 (m, 5 H ), 7.17-7.33 (m, 6 H ), 7.39 (td, J=7.7, 1.3, 1 H ), 7.52 (dd, J=7.6, 1.1, 1H)

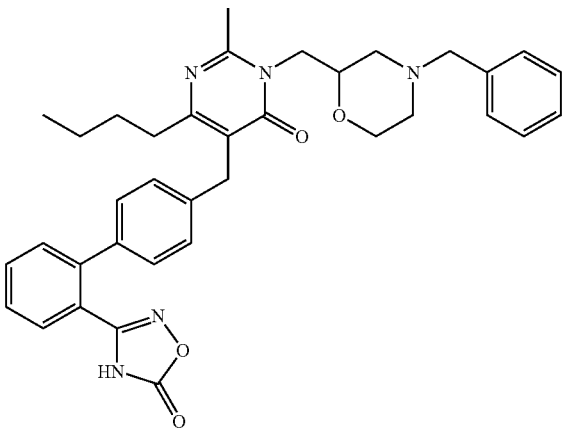

154b) 3-[(4-benzylmorpholin-2-yl)methyl]-6-butyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.23 g), sodium hydrogen carbonate (0.76 g) and dimethyl sulfoxide (7 mL) was stirred at 40° C. for 30 min, 4'-({1-[(4-benzylmorpholin-2-yl)methyl]-4-butyl-2-methyl-6-oxo-1,6-dihydropyrimidin-5-yl}methyl)biphenyl-2-carbonitrile (0.62 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (0.30 g) and then 1,8-diazabicyclo[5.4.0]undec-7-ene (0.25 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.11 g, 15%).

$^1$H NMR (300 MHz, DMSO-d$_6$) δ 0.82 (t, J=7.2, 3 H ), 1.19-1.34 (m, 2 H ), 1.35-1.50 (m, 2 H ), 1.88-2.00 (m, 1 H ), 2.06-2.19 (m, 1 H ), 2.41-2.49 (m, 2 H ), 2.63 (d, J=11, 1 H ), 2.79 (d, J=11, 1 H ), 3.32 (s, 2 H ), 3.43 (t, J=11, 2 H ), 3.53 (s, 2 H ), 3.69-3.95 (m, 5 H ), 4.03-4.12 (m, 1 H ), 7.16-7.38 (m, 9H), 7.45-7.58 (m, 2 H ), 7.62-7.72 (m, 2 H ), 12.30 (s, 1 H )

Example 155

6-butyl-2-methyl-3-[4-(morpholin-4-ylcarbonyl)benzyl]-5-{[2'-(5-oxo-4,5-dihydro-1,2,4-oxadiazol-3-yl)biphenyl-4-yl]methyl}pyrimidin-4(3H)-one

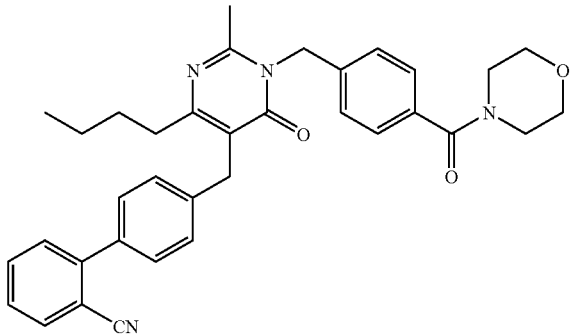

155a) 4'-({4-butyl-2-methyl-1-[4-(morpholin-4-ylcarbonyl)benzyl]-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 4-[4-(chloromethyl)benzoyl]morpholine (0.87 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (1.16 g, 61%).

$^1$H NMR (300 MHz, CDCl$_3$) δ 0.91 (t, J=7.2, 3 H), 1.30-1.45 (m, 2 H), 1.52-1.67 (m, 2 H), 2.43 (s, 3 H), 2.57-2.65 (m, 2 H), 2.83 (s, 1 H), 2.89 (s, 1 H), 3.29-3.86 (m, 6 H), 4.02 (s, 2 H), 5.32 (s, 2 H), 7.23 (d, J=8.0, 2 H), 7.38 (t, J=6.8, 5 H), 7.45-7.51 (m, 3 H), 7.60 (t, J=7.6, 1 H), 7.71 (d, J=8.0, 1 H)

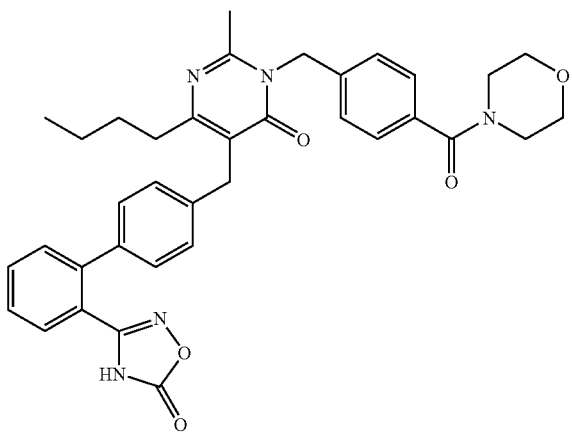

155b) 6-butyl-2-methyl-3-[4-(morpholin-4-ylcarbonyl)benzyl]-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.33 g), sodium hydrogen carbonate (1.83 g) and dimethyl sulfoxide (15 mL) was stirred at 40° C. for 30 min, 4'-({4-butyl-2-methyl-1-[4-(morpholin-4-ylcarbonyl)benzyl]-6-oxo-1,6-dihydropyrimidin-5-yl}methyl)biphenyl-2-carbonitrile (1.16 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (0.46 g) and then 1,8-diazabicyclo[5.4.0]undec-7-ene (0.45 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (1.01 g, 78%).

$^1$H NMR (300 MHz, DMSO-d$_6$) δ 0.83 (t, J=7.2, 3 H), 1.22-1.36 (m, 2 H), 1.39-1.53 (m, 2 H), 2.40 (s, 3 H), 2.47-2.55 (m, 2 H), 3.32 (s, 3 H), 3.49-3.68 (m, 5 H), 3.90 (s, 2 H), 5.32 (s, 2 H), 7.18-7.28 (m, 6 H), 7.41 (d, J=8.0, 2 H), 7.53 (dd, J=16.1, 7.8, 2 H), 7.62-7.72 (m, 2 H), 12.39 (s, 1 H)

Example 156

3-(1H-1,2,3-benzotriazol-1-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one

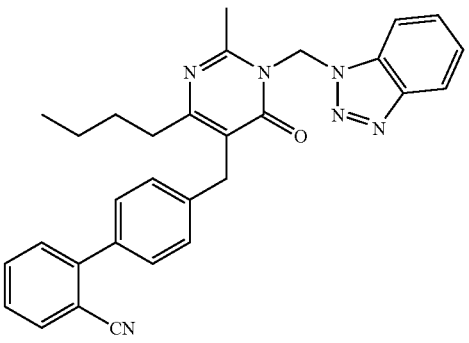

156a) 4'-{[1-(1H-1,2,3-benzotriazol-1-ylmethyl)-4-butyl-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 1-(chloromethyl)-1H-1,2,3-benzotriazole (0.62 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.55 g, 33%).

¹H NMR (300 MHz, CDCl₃) δ 0.87 (t, J=7.4, 3 H ), 1.28-1.41 (m, 2 H ), 1.47-1.60 (m, 2 H ), 2.52-2.60 (m, 2 H ), 2.96 (s, 3 H ), 3.98 (s, 2 H ), 6.86 (s, 2 H ), 7.30-7.40 (m, 4 H ), 7.42-7.54 (m, 4 H ), 7.61 (t, J=7.6, 1 H ), 7.73 (d, J=7.6, 1 H), 8.02 (d, J=8.3, 1 H ), 8.10 (d, J=8.3, 1 H )

Example 157

6-butyl-2-methyl-5-{[2'-(5-oxo-4,5-dihydro-1,2,4-oxadiazol-3-yl)biphenyl-4-yl]methyl}-3-{[5-(3-thienyl)-1,2,4-oxadiazol-3-yl]methyl}pyrimidin-4(3H)-one

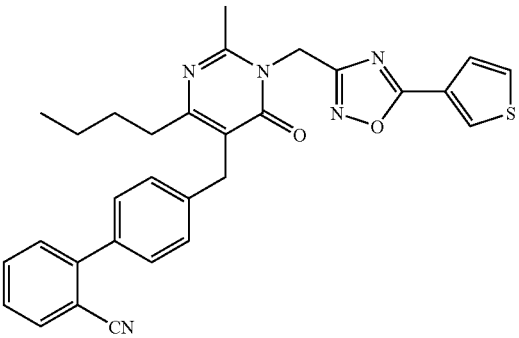

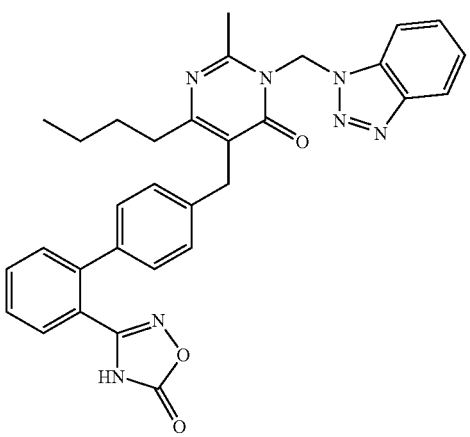

156b) 3-(1H-1,2,3-benzotriazol-1-ylmethyl)-6-butyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.73 g), sodium hydrogen carbonate (1.02 g) and dimethyl sulfoxide (6 mL) was stirred at 40° C. for 30 min, 4'-{[1-(1H-1,2,3-benzotriazol-1-ylmethyl)-4-butyl-2-methyl-6-oxo-1,6-dihydropyrimidin-5-yl]methyl}biphenyl-2-carbonitrile (0.55 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.23 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.35 g, 56%).

¹H NMR (300 MHz, DMSO-d₆) δ 0.81 (t, J=7.2, 3 H ), 1.18-1.34 (m, 2 H ), 1.34-1.49 (m, 2 H ), 2.48-2.51 (m, 2 H ), 2.86 (s, 3 H ), 3.84 (s, 2 H ), 6.90 (s, 2 H ), 7.16-7.24 (m, 4 H ), 7.40-7.52 (m, 2 H ), 7.53-7.72 (m, 4 H ), 8.05-8.13 (m, 2 H ), 12.38 (s, 1 H )

157a) 4'-[(4-butyl-2-methyl-6-oxo-1-{[5-(3-thienyl)-1,2,4-oxadiazol-3-yl]methyl}-1,6-dihydropyrimidin-5-yl)methyl]biphenyl-2-carbonitrile A mixture of 4'-[(4-butyl-2-methyl-6-oxo-1,6-dihydropyrimidin-5-yl)methyl]biphenyl-2-carbonitrile (1.23 g), potassium carbonate (0.94 g), 3-(chloromethyl)-5-(3-thienyl)-1,2,4-oxadiazole (0.75 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.79 g, 44%).

¹H NMR (300 MHz, CDCl₃) δ 0.90 (t, J=7.3, 3 H ), 1.30-1.45 (m, 2 H ), 1.51-1.64 (m, 2 H ), 2.56-2.62 (m, 5 H ), 4.00 (s, 2 H ), 5.43 (s, 2 H ), 7.32-7.48 (m, 7 H ), 7.53-7.61 (m, 2 H), 7.69 (d, J=7.7, 1 H ), 8.15-8.18 (m, 1 H )

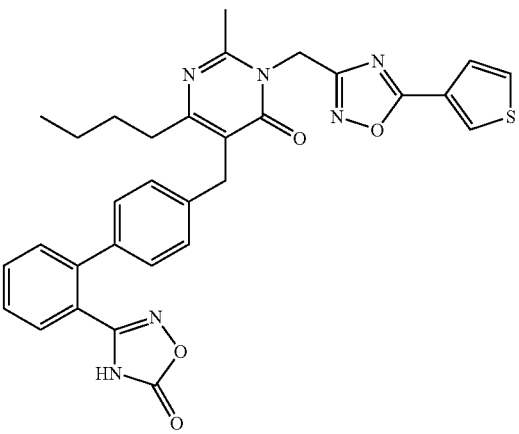

157b) 6-butyl-2-methyl-5-{[2'-(5-oxo-4,5-dihydro-1,2,4-oxadiazol-3-yl)biphenyl-4-yl]methyl}-3-{[5-(3-thienyl)-1,2,4-oxadiazol-3-yl]methyl}pyrimidin-4(3H)-one A mixture of hydroxylammonium chloride (0.89 g), sodium hydrogen carbonate (1.27 g) and dimethyl sulfoxide (10 mL) was stirred at 40° C. for 30 min, 4'-[(4-butyl-2-methyl-6-oxo-1-{[5-(3-thienyl)-1,2,4-oxadiazol-3-yl]methyl}-1,6-dihydropyrimidin-5-yl)methyl]biphenyl-2-carbonitrile (0.79 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.32 g) and then 1,8-diazabicyclo[5.4.0]undec-7-ene (0.29 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.22 g, 25%).

$^1$H NMR (300 MHz, DMSO-$d_6$) δ 0.84 (t, J=7.3, 3 H), 1.22-1.36 (m, 2 H), 1.39-1.53 (m, 2 H), 2.55 (s, 3 H), 3.32 (s, 2 H), 3.86 (s, 2 H), 5.44 (s, 2 H), 7.17-7.25 (m, 4 H), 7.45-7.52 (m, 1 H), 7.52-7.58 (m, 1 H), 7.61-7.71 (m, 3 H), 7.84 (dd, J=5.1, 3.0, 1 H), 8.60 (dd, J=2.9, 1.2, 1 H), 12.37 (s, 1 H)

Example 158

6-butyl-2-methyl-5-{[2'-(5-oxo-4,5-dihydro-1,2,4-oxadiazol-3-yl)biphenyl-4-yl]methyl}-3-(quinolin-2-ylmethyl)pyrimidin-4(3H)-one

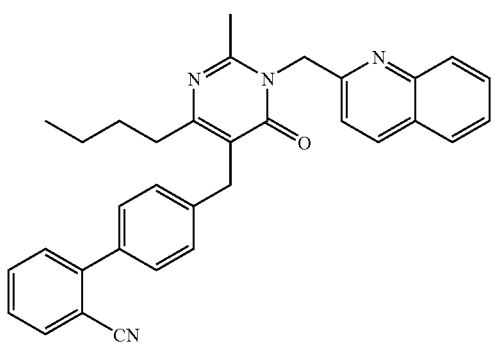

158a) 4'-{[4-butyl-2-methyl-6-oxo-1-(quinolin-2-ylmethyl)-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 2-(chloromethyl)quinolinehydrochloride (0.73 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a pale-yellow solid (0.49 g, 26%).

$^1$H NMR (300 MHz, CDCl$_3$) δ 0.92 (t, J=7.3, 3 H), 1.32-1.46 (m, 2 H), 1.53-1.66 (m, 2 H), 2.58-2.65 (m, 5 H), 4.01 (s, 2 H), 5.57 (s, 2 H), 7.35-7.41 (m, 4 H), 7.42-7.56 (m, 4 H), 7.61 (td, J=7.7, 1.2, 1 H), 7.67-7.76 (m, 2 H), 7.79 (d, J=8.1, 1 H), 8.01 (d, J=8.5, 1 H), 8.14 (d, J=8.5, 1 H)

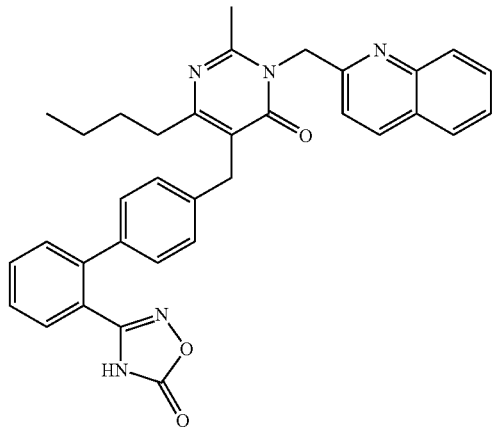

158b) 6-butyl-2-methyl-5-{[2'-(5-oxo-4,5-dihydro-1,2,4-oxadiazol-3-yl)biphenyl-4-yl]methyl}-3-(quinolin-2-ylmethyl)pyrimidin-4(3H)-one A mixture of hydroxylammonium chloride (0.51 g), sodium hydrogen carbonate (0.75 g) and dimethyl sulfoxide (6 mL) was stirred at 40° C. for 30 min, 4'-{[4-butyl-2-methyl-6-oxo-1-(quinolin-2-ylmethyl)-1,6-dihydropyrimidin-5-yl]methyl}biphenyl-2-carbonitrile (0.49 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (8 mL), N,N'-carbonyldiimidazole (0.12 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.20 g, 38%).

$^1$H NMR (300 MHz, DMSO-$d_6$) δ 0.85 (t, J=7.4, 3 H), 1.23-1.37 (m, 2 H), 1.42-1.57 (m, 2 H), 2.42-2.57 (m, 2 H), 3.33 (s, 3 H), 3.88 (s, 2 H), 5.54 (s, 2 H), 7.17-7.28 (m, 4 H), 7.46-7.53 (m, 2 H), 7.53-7.78 (m, 5 H), 7.85 (d, J=7.4, 1 H), 7.97 (d, J=7.4, 1 H), 8.38 (d, J=8.5, 1 H), 12.37 (s, 1 H)

Example 159

6-butyl-2-methyl-5-{[2'-(5-oxo-4,5-dihydro-1,2,4-oxadiazol-3-yl)biphenyl-4-yl]methyl}-3-(1,3-thiazol-4-ylmethyl)pyrimidin-4(3H)-one

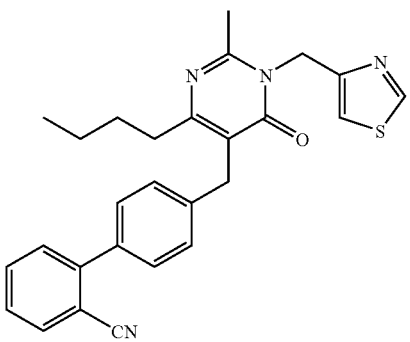

159a) 4'-{[4-butyl-2-methyl-6-oxo-1-(1,3-thiazol-4-ylmethyl)-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 4-(chloromethyl)-1,3-thiazole hydrochloride (0.58 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (1.01 g, 66%).

$^1$H NMR (300 MHz, CDCl$_3$) δ 0.88 (t, J=7.2, 3 H), 1.28-1.42 (m, 2 H), 1.49-1.62 (m, 2 H), 2.54-2.62 (m, 2 H), 2.71 (s, 3 H), 3.98 (s, 2 H), 5.38 (s, 2 H), 7.31-7.49 (m, 7 H), 7.56 (td, J=7.6, 1.1, 1 H), 7.68 (d, J=8.0, 1 H), 8.69-8.75 (m, 1 H)

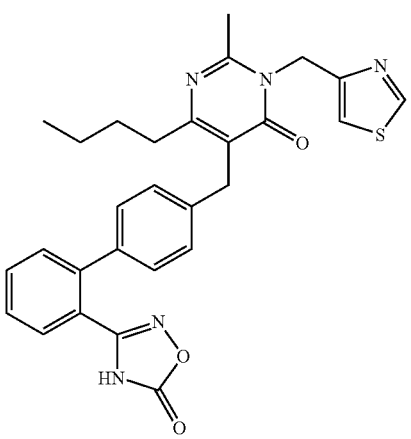

159b) 6-butyl-2-methyl-5-{[2'-(5-oxo-4,5-dihydro-1,2,4-oxadiazol-3-yl)biphenyl-4-yl]methyl}-3-(1,3-thiazol-4-ylmethyl)pyrimidin-4(3H)-one A mixture of hydroxylammonium chloride (1.32 g), sodium hydrogen carbonate (1.87 g) and dimethyl sulfoxide (15 mL) was stirred at 40° C. for 30 min, 4'-{[4-butyl-2-methyl-6-oxo-1-(1,3-thiazol-4-ylmethyl)-1,6-dihydropyrimidin-5-yl]methyl}biphenyl-2-carbonitrile (1.01 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.36 g) and then 1,8-diazabicyclo[5.4.0]undec-7-ene (0.33 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.34 g, 30%).

$^1$H NMR (300 MHz, DMSO-d$_6$) δ 0.78 (t, J=7.3, 3 H), 1.20-1.32 (m, 2 H), 1.36-1.49 (m, 2 H), 2.42-2.48 (m, 2 H), 2.57 (s, 3 H), 3.82 (s, 2 H), 5.32 (s, 2 H), 7.19 (d, J=8.3, 2 H), 7.38-7.52 (m, 4 H), 7.54-7.60 (m, 1 H), 7.79-7.82 (m, 1 H), 8.46-8.48 (m, 1 H), 9.04 (d, J=1.9, 1 H), 12.35 (s, 1 H)

Example 160

6-butyl-2-methyl-5-{[2'-(5-oxo-4,5-dihydro-1,2,4-oxadiazol-3-yl)biphenyl-4-yl]methyl}-3-(tetrahydro-2H-pyran-2-ylmethyl)pyrimidin-4(3H)-one

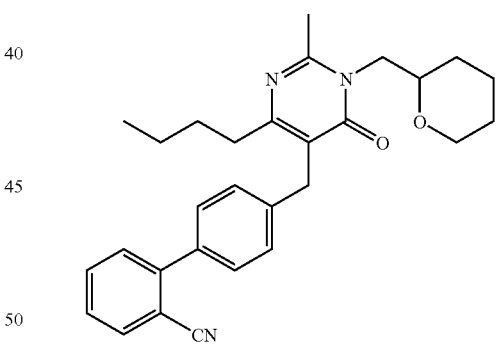

160a) 4'-{[4-butyl-2-methyl-6-oxo-1-(tetrahydro-2H-pyran-2-ylmethyl)-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 2-(bromomethyl)tetrahydro-2H-pyran (0.61 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless viscous substance (0.71 g, 46%).

¹H NMR (300 MHz, CDCl₃) δ 0.78 (t, J=7.3, 3 H), 1.18-1.31 (m, 3 H), 1.30-1.52 (m, 5 H), 1.62 (m, 1 H), 1.71 (s, 1 H), 2.43-2.52 (m, 5 H), 3.11-3.23 (m, 1 H), 3.52-3.65 (m, 2H), 3.73-3.93 (m, 3 H), 4.08-4.19 (m, 1 H), 7.21-7.29 (m, 3 H), 7.30-7.38 (m, 3 H), 7.45 (td, J=7.7, 1.2, 1 H), 7.58 (dd, J=7.7, 0.9, 1 H)

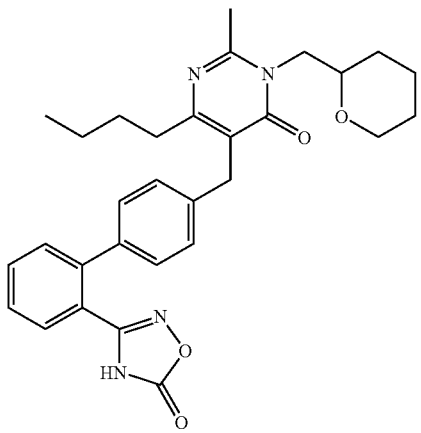

160b) 6-butyl-2-methyl-5-{[2'-(5-oxo-4,5-dihydro-1,2,4-oxadiazol-3-yl)biphenyl-4-yl]methyl}-3-(tetrahydro-2H-pyran-2-ylmethyl)pyrimidin-4(3H)-one A mixture of hydroxylammonium chloride (0.92 g), sodium hydrogen carbonate (1.31 g) and dimethyl sulfoxide (10 mL) was stirred at 40° C. for 30 min, 4'-{[4-butyl-2-methyl-6-oxo-1-(tetrahydro-2H-pyran-2-ylmethyl)-1,6-dihydropyrimidin-5-yl]methyl}biphenyl-2-carbonitrile (0.71 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.34 g) and then 1,8-diazabicyclo[5.4.0]undec-7-ene (0.31 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.26 g, 33%).

¹H NMR (300 MHz, DMSO-d₆) δ 0.83 (t, J=7.3, 3 H), 1.21-1.35 (m, 3 H), 1.36-1.51 (m, 5 H), 1.63 (d, J=12.1, 1 H), 1.78 (br s., 1 H), 2.45 (d, J=7.9, 1 H), 2.53 (s, 3 H), 3.17-3.29 (m, 1 H), 3.51-3.66 (m, 2 H), 3.76-3.94 (m, 4 H), 4.09 (dd, J=14.0, 2.4, 1 H), 7.17-7.27 (m, 4 H), 7.47-7.53 (m, 1 H), 7.55 (dd, J=7.4, 1.1, 1 H), 7.62-7.72 (m, 2H), 12.38 (s, 1 H)

6-Butyl-2-methyl-5-{[2'-(5-oxo-4,5-dihydro-1,2,4-oxadiazol-3-yl)biphenyl-4-yl]methyl}-3-(tetrahydro-2H-pyran-2-ylmethyl)pyrimidin-4(3H)-one obtained above is subjected to a conventional method of salt formation to give the following salts.

6-butyl-2-methyl-5-{[2'-(5-oxo-4,5-dihydro-1,2,4-oxadiazol-3-yl)biphenyl-4-yl]methyl}-3-(tetrahydro-2H-pyran-2-ylmethyl)pyrimidin-4(3H)-one sodium salt 6-butyl-2-methyl-5-{[2'-(5-oxo-4,5-dihydro-1,2,4-oxadiazol-3-yl)biphenyl-4-yl]methyl}-3-(tetrahydro-2H-pyran-2-ylmethyl)pyrimidin-4(3H)-one potassium salt 6-butyl-2-methyl-5-{[2'-(5-oxo-4,5-dihydro-1,2,4-oxadiazol-3-yl)biphenyl-4-yl]methyl}-3-(tetrahydro-2H-pyran-2-ylmethyl)pyrimidin-4(3H)-one 0.5 calcium salt 6-butyl-2-methyl-5-{[2'-(5-oxo-4,5-dihydro-1,2,4-oxadiazol-3-yl)biphenyl-4-yl]methyl}-3-(tetrahydro-2H-pyran-2-ylmethyl)pyrimidin-4(3H)-one hydrochloride 6-butyl-2-methyl-5-{[2'-(5-oxo-4,5-dihydro-1,2,4-oxadiazol-3-yl)biphenyl-4-yl]methyl}-3-(tetrahydro-2H-pyran-2-ylmethyl)pyrimidin-4(3H)-one hydrobromide Example 161

6-butyl-3-(2,5-difluorobenzyl)-2-methyl-5-{[2'-(5-oxo-4,5-dihydro-1,2,4-oxadiazol-3-yl)biphenyl-4-yl]methyl}pyrimidin-4(3H)-one

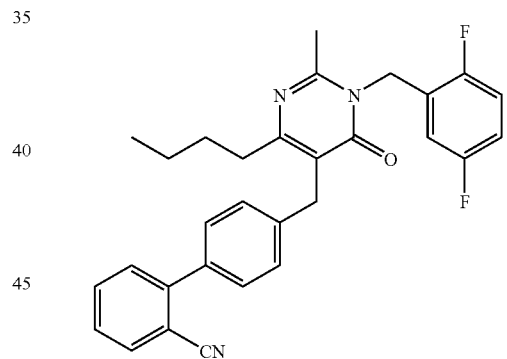

161a) 4'-{[4-butyl-1-(2,5-difluorobenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 2-(bromomethyl)-1,4-difluorobenzene (1.06 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a pale-yellow viscous substance (0.88 g, 54%).

¹H NMR (300 MHz, CDCl₃) δ 0.91 (t, J=7.4, 3 H), 1.30-1.45 (m, 2 H), 1.54-1.66 (m, 2 H), 2.44 (s, 3 H), 2.58-2.67 (m, 2 H), 4.03 (s, 2 H), 5.31 (s, 2 H), 6.76-6.84 (m, 1 H), 6.86-6.96 (m, 1 H), 6.97-7.06 (m, 1 H), 7.31-7.51 (m, 6 H), 7.53-7.59 (m, 1 H), 7.69 (dd, J=7.8, 1.0, 1 H)

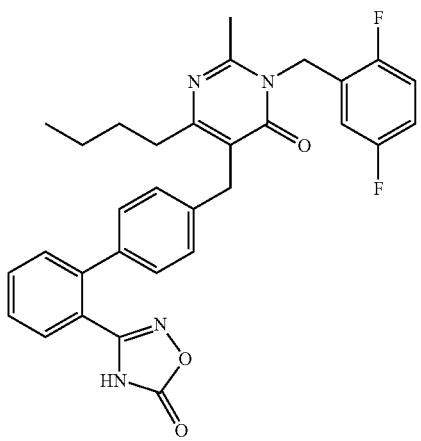

161b) 6-butyl-3-(2,5-difluorobenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.08 g), sodium hydrogen carbonate (1.53 g) and dimethyl sulfoxide (12 mL) was stirred at 40° C. for 30 min, 4'-{[4-butyl-1-(2,5-difluorobenzyl)-2-methyl-6-oxo-1,6-dihydropyrimidin-5-yl]methyl}biphenyl-2-carbonitrile (0.88 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.38 g) and then 1,8-diazabicyclo[5.4.0]undec-7-ene (0.35 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.67 g, 68%).

¹H NMR (300 MHz, DMSO-d₆) δ 0.83 (t, J=7.4, 3 H), 1.24-1.35 (m, 2 H), 1.41-1.52 (m, 2 H), 2.43 (s, 3 H), 2.48-2.53 (m, 1 H), 3.88 (s, 2 H), 5.27 (s, 2 H), 6.77-6.84 (m, 1 H), 7.16-7.26 (m, 5 H), 7.28-7.37 (m, 1 H), 7.47-7.53 (m, 1 H), 7.56 (dd, J=7.6, 1.1, 2 H), 7.63-7.72 (m, 2 H), 12.38 (s, 1 H)

Example 162

6-butyl-3-(3,3-dimethyl-2-oxobutyl)-5-{[3-fluoro-2'-(5-oxo-4,5-dihydro-1,2,4-oxadiazol-3-yl)biphenyl-4-yl]methyl}-2-methylpyrimidin-4(3H)-one

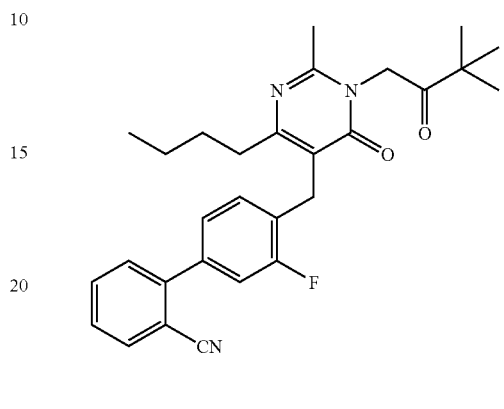

162a) 4'-{[4-butyl-1-(3,3-dimethyl-2-oxobutyl)-2-methyl-6-oxo-1,6-dihydropyrimidin-5-yl]methyl}-3'-fluorobiphenyl-2-carbonitrile A mixture of 4'-[(4-butyl-2-methyl-6-oxo-1,6-dihydropyrimidin-5-yl)methyl]-3'-fluorobiphenyl-2-carbonitrile (1.22 g), cesium carbonate (1.73 g), 1-bromo-3,3-dimethylbutan-2-one (0.71 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.86 g, 34%).

¹H NMR (300 MHz, CDCl₃) δ 0.89 (t, J=7.3, 3 H), 1.27-1.42 (m, 2 H), 1.29 (s, 9 H), 1.50-1.62 (m, 2 H), 2.34 (s, 3 H), 2.52-2.60 (m, 2 H), 3.96 (s, 2 H), 5.08 (s, 2 H), 7.19-7.28 (m, 3 H), 7.39-7.47 (m, 2 H), 7.57-7.65 (m, 1 H), 7.72 (d, J=7.3, 1 H)

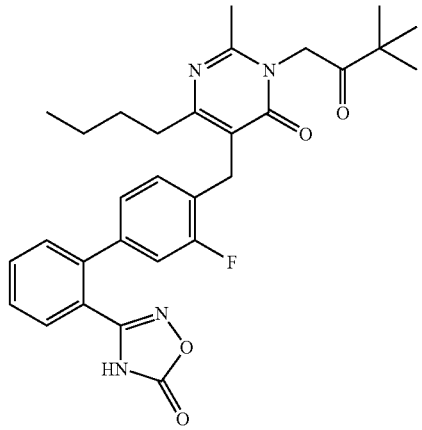

162b) 6-butyl-3-(3,3-dimethyl-2-oxobutyl)-5-{[3-fluoro-2'-(5-oxo-4,5-dihydro-1,2,4-oxadiazol-3-yl)biphenyl-4-yl]methyl}-2-methylpyrimidin-4(3H)-one 4'-{[4-Butyl-1-(3,3-dimethyl-2-oxobutyl)-2-methyl-6-oxo-1,6-dihydropyrimidin-5-yl]methyl}-3'-fluorobiphenyl-2-carbonitrile (3.82 g) and methanol (100 mL) were ice-cooled, sodium borohydride (0.92 g) was gradually added, and the mixture was stirred for 30 min. Thereafter, the temperature of the mixture was gradually raised to room temperature, and the mixture was stirred for 2 hr. The reaction mixture was diluted with ethyl acetate, washed with water and then with saturated brine, and dried over anhydrous magnesium sulfate. The solvent was evaporated under reduced pressure. A mixture of hydroxylammonium chloride (1.08 g), sodium hydrogen carbonate (1.53 g) and dimethyl sulfoxide (50 mL) was stirred at 40° C. for 30 min, the residue (4.44 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (100 mL), N,N'-carbonyldiimidazole (2.26 g) and then 1,8-diazabicyclo[5.4.0]undec-7-ene (2.05 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure. The residue was dissolved in methylene chloride (80 mL), 1,1,1-tris(acetyloxy)-1,1-dihydro-1,2-benziodoxol-3(1H)-one (1.78 g) was added, and the mixture was stirred at room temperature for 2 hr. A saturated aqueous sodium hydrogen carbonate and sodium thiosulfate pentahydrate were added to the reaction mixture, and the mixture was stirred at room temperature for 2 hr. The reaction mixture was diluted with chloroform, washed with water and then with saturated brine, and dried over anhydrous magnesium sulfate. The solvent was evaporated under reduced pressure and the residue was purified by silica gel column chromatography to give the title compound as colorless crystals (1.80 g, 18%).

$^1$H NMR (300 MHz, CDCl$_3$) δ 0.92 (t, J=7.3, 3 H), 1.27 (s, 9 H), 1.32-1.46 (m, 2 H), 1.54-1.67 (m, 2 H), 2.33 (s, 3 H), 2.56-2.64 (m, 2 H), 3.88 (s, 2 H), 5.01 (s, 2 H), 6.93-7.15 (m, 3 H), 7.40 (dd, J=7.7, 1.1, 1 H), 7.49 (td, J=7.6, 1.3, 1 H), 7.60 (td, J=7.6, 1.4, 1 H), 7.80 (dd, J=7.7, 1.3, 1 H), 12.39 (s, 1 H)

Example 163

6-butyl-2-methyl-3-[(2-methyl-1,3-thiazol-4-yl)methyl]-5-{[2'-(5-oxo-4,5-dihydro-1,2,4-oxadiazol-3-yl)biphenyl-4-yl]methyl}pyrimidin-4(3H)-one

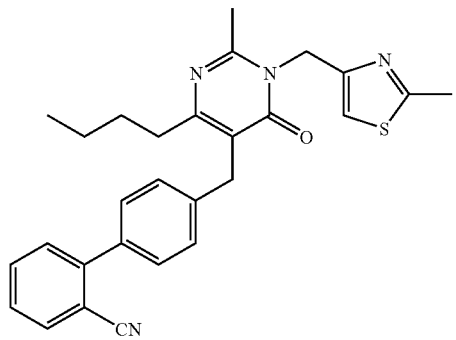

163a) 4'-({4-butyl-2-methyl-1-[(2-methyl-1,3-thiazol-4-yl)methyl]-6-oxo-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 4-(chloromethyl)-2-methyl-1,3-thiazole hydrochloride (0.63 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a pale-yellow solid (0.94 g, 55%).

$^1$H NMR (300 MHz, CDCl$_3$) δ 0.80 (t, J=7.2, 3 H), 1.20-1.33 (m, 2 H), 1.40-1.54 (m, 2 H), 2.46-2.52 (m, 2 H), 2.54 (s, 3 H), 2.61 (s, 3 H), 3.89 (s, 2 H), 5.20 (s, 2 H), 7.00 (s, 1H), 7.23-7.32 (m, 3 H), 7.32-7.41 (m, 3 H), 7.47 (t, J=7.7, 1 H), 7.60 (d, J=7.7, 1 H)

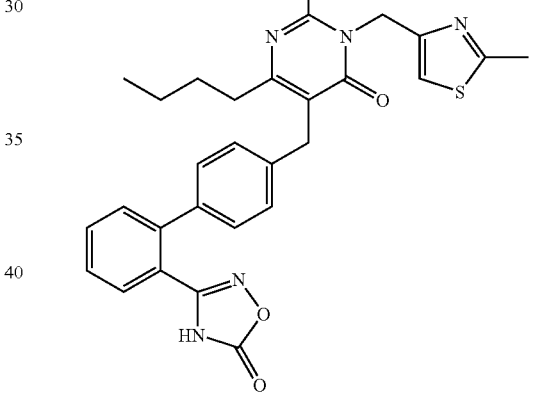

163b) 6-butyl-2-methyl-3-[(2-methyl-1,3-thiazol-4-yl)methyl]-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.19 g), sodium hydrogen carbonate (1.69 g) and dimethyl sulfoxide (15 mL) was stirred at 40° C. for 30 min, 4'-({4-butyl-2-methyl-1-[(2-methyl-1,3-thiazol-4-yl)methyl]-6-oxo-1,6-dihydropyrimidin-5-yl}methyl)biphenyl-2-carbonitrile (0.94 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (25 mL), N,N'-carbonyldiimidazole (0.47 g) and then 1,8-diazabicyclo[5.4.0]undec-7-ene (0.43 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.93 g, 87%).

$^1$H NMR (300 MHz, DMSO-$d_6$) δ 0.83 (t, J=7.2, 3 H), 1.20-1.35 (m, 2 H), 1.36-1.52 (m, 2 H), 2.43-2.49 (m, 2 H), 2.58 (s, 3 H), 2.62 (s, 3 H), 3.85 (s, 2 H), 5.23 (s, 2 H), 7.16-7.26 (m, 4 H), 7.28 (s, 1 H), 7.49 (d, J=8.0, 1 H), 7.55 (d, J=7.6, 1 H), 7.62-7.72 (m, 2 H), 12.38 (s, 1 H)

Example 164

6-butyl-2-methyl-5-{[2'-(5-oxo-4,5-dihydro-1,2,4-oxadiazol-3-yl)biphenyl-4-yl]methyl}-3-(tetrahydrofuran-2-ylmethyl)pyrimidin-4(3H)-one

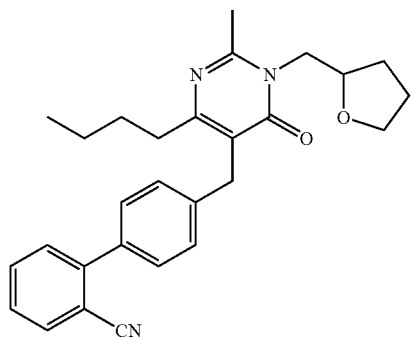

164a) 4'-{[4-butyl-2-methyl-6-oxo-1-(tetrahydrofuran-2-ylmethyl)-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 2-(bromomethyl)tetrahydrofuran (0.56 g) and N,N-dimethylformamide (20 mL) was stirred at 90° C. for 2 hr. The reaction mixture was diluted with ethyl acetate, washed with water and then with saturated brine, and dried over anhydrous magnesium sulfate. e solvent was evaporated under reduced pressure and the residue was purified by silica gel column chromatography to give the title compound as a colorless viscous substance (0.94 g, 55%).

$^1$H NMR (300 MHz, CDCl$_3$) δ 0.74 (t, J=7.4, 3 H), 1.14-1.28 (m, 2 H), 1.35-1.51 (m, 3 H), 1.61-1.80 (m, 2 H), 1.87-1.99 (m, 1 H), 2.39-2.46 (m, 2 H), 2.45 (s, 3 H), 3.50-3.76 (m, 3 H), 3.80-3.97 (m, 2 H), 4.04-4.16 (m, 1 H), 4.19-4.26 (m, 1 H), 7.16-7.25 (m, 3 H), 7.26-7.33 (m, 3H), 7.40 (t, J=7.6, 1 H), 7.53 (d, J=8.0, 1 H)

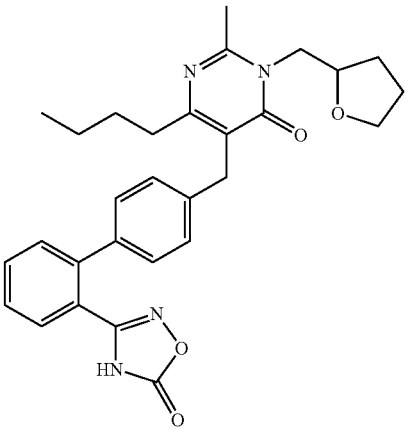

164b) 6-butyl-2-methyl-5-{[2'-(5-oxo-4,5-dihydro-1,2,4-oxadiazol-3-yl)biphenyl-4-yl]methyl}-3-(tetrahydrofuran-2-ylmethyl)pyrimidin-4(3H)-one A mixture of hydroxylammonium chloride (0.82 g), sodium hydrogen carbonate (1.16 g) and dimethyl sulfoxide (10 mL) was stirred at 40° C. for 30 min, 4'-{[4-butyl-2-methyl-6-oxo-1-(tetrahydrofuran-2-ylmethyl)-1,6-dihydropyrimidin-5-yl]methyl}biphenyl-2-carbonitrile (0.61 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL), N,N'-carbonyldiimidazole (0.32 g) and then 1,8-diazabicyclo[5.4.0]undec-7-ene (0.30 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.61 g, 89%).

$^1$H NMR (300 MHz, DMSO-$d_6$) δ 0.83 (t, J=7.2, 3 H), 1.20-1.35 (m, 2 H), 1.37-1.50 (m, 2 H), 1.52-1.66 (m, 1 H), 1.74-1.92 (m, 2 H), 1.92-2.06 (m, 1 H), 2.43-2.54 (m, 5 H), 3.58-3.67 (m, 1 H), 3.73-3.91 (m, 4 H), 4.04-4.25 (m, 2 H), 7.16-7.28 (m, 4 H), 7.47-7.58 (m, 2 H), 7.60-7.73 (m, 2 H), 12.37 (s, 1 H)

Example 165

6-butyl-3-(2,6-difluorobenzyl)-2-methyl-5-{[2'-(5-oxo-4,5-dihydro-1,2,4-oxadiazol-3-yl)biphenyl-4-yl]methyl}pyrimidin-4(3H)-one

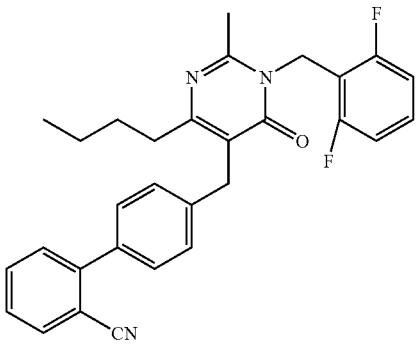

165a) 4'-{[4-butyl-1-(2,6-difluorobenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 2-(bromomethyl)-1,3-difluorobenzene (0.56 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a pale-yellow solid (0.40 g, 55%).

$^1$H NMR (300 MHz, CDCl$_3$) δ 0.89 (t, J=7.3, 3 H), 1.28-1.41 (m, 2 H), 1.49-1.62 (m, 2 H), 2.51 (s, 3 H), 2.52-2.59 (m, 2 H), 3.98 (s, 2 H), 5.38 (s, 2 H), 6.82-6.93 (m, 2 H), 7.17-7.28 (m, 1 H), 7.31-7.40 (m, 3 H), 7.45 (d, J=8.3, 3 H), 7.58 (td, J=7.7, 1.3, 1 H), 7.70 (dd, J=7.7, 1.1, 1 H)

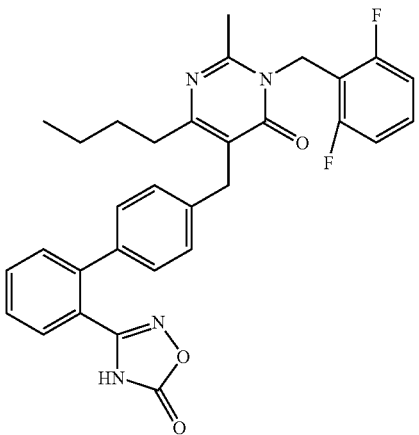

165b) 6-butyl-3-(2,6-difluorobenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.49 g), sodium hydrogen carbonate (0.70 g) and dimethyl sulfoxide (8 mL) was stirred at 40° C. for 30 min, 4'-{[4-butyl-1-(2,6-difluorobenzyl)-2-methyl-6-oxo-1,6-dihydropyrimidin-5-yl]methyl}biphenyl-2-carbonitrile (0.40 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.17 g) and then 1,8-diazabicyclo[5.4.0]undec-7-ene (0.16 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.34 g, 75%).

$^1$H NMR (300 MHz, DMSO-d$_6$) δ 0.82 (t, J=7.2, 3 H), 1.20-1.32 (m, 2 H), 1.37-1.48 (m, 2 H), 2.42-2.51 (m, 2 H), 2.50 (s, 3 H), 3.81 (s, 2 H), 5.30 (s, 2 H), 7.05-7.12 (m, 2 H), 7.17-7.21 (m, 4 H), 7.35-7.43 (m, 1 H), 7.47-7.57 (m, 2 H), 7.61-7.72 (m, 2 H), 12.38 (s, 1 H)

6-Butyl-3-(2,6-difluorobenzyl)-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(2,6-difluorobenzyl)-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-(2,6-difluorobenzyl)-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-(2,6-difluorobenzyl)-2-methyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(2,6-difluorobenzyl)-2-methyl-5-{[2'-(5-oxo-4,5-dihydro-1,2,4-oxadiazol-3-yl)biphenyl-4-yl]methyl}pyrimidin-4(3H)-one hydrochloride 6-butyl-3-(2,6-difluorobenzyl)-2-methyl-5-{[2'-(5-oxo-4,5-dihydro-1,2,4-oxadiazol-3-yl)biphenyl-4-yl]methyl}pyrimidin-4(3H)-one hydrobromide

Example 166

6-butyl-3-(2,4-difluorobenzyl)-2-methyl-5-{[2'-(5-oxo-4,5-dihydro-1,2,4-oxadiazol-3-yl)biphenyl-4-yl]methyl}pyrimidin-4(3H)-one

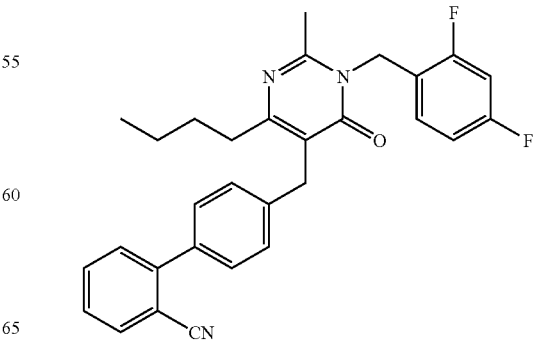

166a) 4'-{[4-butyl-1-(2,4-difluorobenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 1-(bromomethyl)-2,4-difluorobenzene (0.70 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a pale-yellow solid (0.82 g, 50%).

$^1$H NMR (300 MHz, CDCl$_3$) δ 0.91 (t, J=7.4, 3 H), 1.31-1.45 (m, 2 H), 1.53-1.64 (m, 2 H), 2.46 (s, 3 H), 2.58-2.65 (m, 2 H), 4.01 (s, 2 H), 5.29 (s, 2 H), 6.79-6.89 (m, 2 H), 7.07-7.16 (m, 1 H), 7.35-7.42 (m, 3 H), 7.45-7.50 (m, 3 H), 7.59 (td, J=7.6, 1.1, 1 H), 7.70-7.74 (m, 1 H)

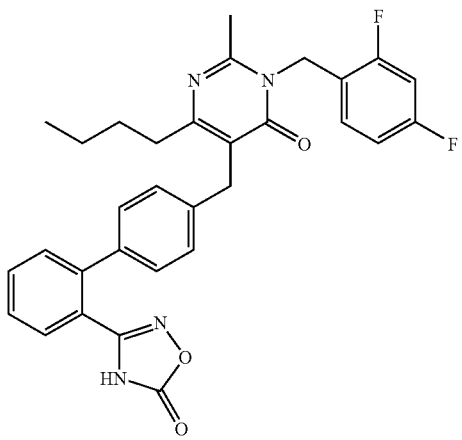

166b) 6-butyl-3-(2,4-difluorobenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.00 g), sodium hydrogen carbonate (1.43 g) and dimethyl sulfoxide (12 mL) was stirred at 40° C. for 30 min, 4'-{[4-butyl-1-(2,4-difluorobenzyl)-2-methyl-6-oxo-1,6-dihydropyrimidin-5-yl]methyl}biphenyl-2-carbonitrile (0.82 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (25 mL), N,N'-carbonyldiimidazole (0.41 g) and then 1,8-diazabicyclo[5.4.0]undec-7-ene (0.38 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.85 g, 93%).

$^1$H NMR (300 MHz, DMSO-d$_6$) δ 0.83 (t, J=7.4, 3 H), 1.21-1.36 (m, 2 H), 1.38-1.51 (m, 2 H), 2.42 (s, 3 H), 3.27-3.42 (m, 2 H), 3.88 (s, 2 H), 5.25 (s, 2 H), 6.98-7.12 (m, 2 H), 7.19-7.26 (m, 3 H), 7.31 (td, J=10.0, 2.3, 2 H), 7.50 (d, J=8.0, 1 H), 7.56 (d, J=7.6, 1 H), 7.62-7.72 (m, 2 H), 12.39 (s, 1 H)

Example 167

6-butyl-3-(2,3-difluorobenzyl)-2-methyl-5-{[2'-(5-oxo-4,5-dihydro-1,2,4-oxadiazol-3-yl)biphenyl-4-yl]methyl}pyrimidin-4(3H)-one

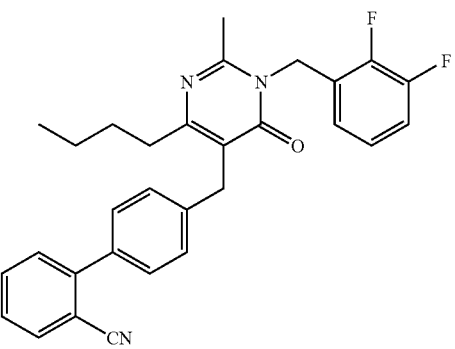

167a) 4'-{[4-butyl-1-(2,3-difluorobenzyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 1-(bromomethyl)-2,3-difluorobenzene (0.70 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.76 g, 46%).

$^1$H NMR (300 MHz, CDCl$_3$) δ 0.91 (t, J=7.4, 3 H), 1.31-1.45 (m, 2 H), 1.54-1.67 (m, 2 H), 2.45 (s, 3 H), 2.58-2.65 (m, 2 H), 4.02 (s, 2 H), 5.36 (s, 2 H), 6.78-6.85 (m, 1 H), 6.98-7.12 (m, 2 H), 7.32-7.42 (m, 3 H), 7.42-7.51 (m, 3 H), 7.57 (td, J=7.7, 1.3, 1 H), 7.67-7.71 (m, 1 H)

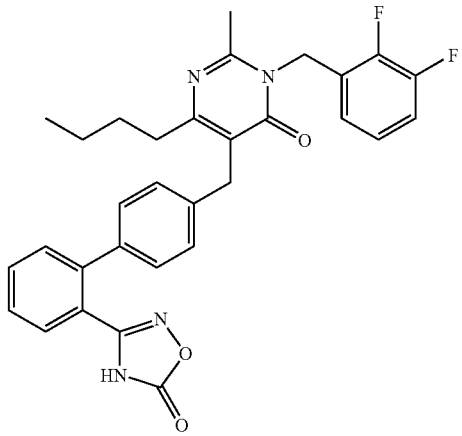

167b) 6-butyl-3-(2,3-difluorobenzyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.93 g), sodium hydrogen carbonate (1.33 g) and dimethyl sulfoxide (12 mL) was stirred at 40° C. for 30 min, 4'-{[4-butyl-1-(2,3-difluorobenzyl)-2-methyl-6-oxo-1,6-dihydropyrimidin-5-yl]methyl}biphenyl-2-carbonitrile (0.76 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.32 g) and then 1,8-diazabicyclo[5.4.0]undec-7-ene (0.30 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.72 g, 84%).

$^1$H NMR (300 MHz, DMSO-$d_6$) δ 0.84 (t, J=7.1, 3 H), 1.23-1.37 (m, 2 H), 1.38-1.53 (m, 2 H), 2.43 (s, 3 H), 2.48-2.51 (m, 2 H), 3.88 (s, 2 H), 5.33 (s, 2 H), 6.73-6.80 (m, 1 H), 7.14-7.27 (m, 5 H), 7.32-7.44 (m, 1 H), 7.47-7.53 (m, 1 H), 7.56 (dd, J=7.5, 1.1, 1 H), 7.63-7.72 (m, 2 H), 12.39 (s, 1 H)

Example 168

6-butyl-2-methyl-5-{[2'-(5-oxo-4,5-dihydro-1,2,4-oxadiazol-3-yl)biphenyl-4-yl]methyl}-3-[(2-phenyl-1,3-thiazol-4-yl)methyl]pyrimidin-4(3H)-one

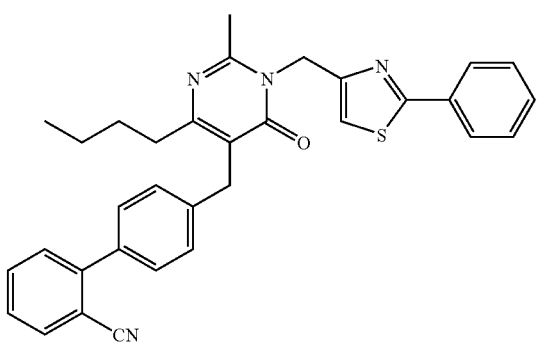

168a) 4'-({4-butyl-2-methyl-6-oxo-1-[(2-phenyl-1,3-thiazol-4-yl)methyl]-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 4-(chloromethyl)-2-phenyl-1,3-thiazole (0.71 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (1.20 g, 66%).

$^1$H NMR (300 MHz, CDCl$_3$) δ 0.89 (t, J=7.2, 3 H), 1.28-1.41 (m, 2 H), 1.51-1.63 (m, 2 H), 2.55-2.61 (m, 2 H), 2.80 (s, 3 H), 3.99 (s, 2 H), 5.34 (s, 2 H), 7.26-7.42 (m, 8 H), 7.43-7.53 (m, 3 H), 7.63-7.67 (m, 1 H), 7.85-7.89 (m, 2 H)

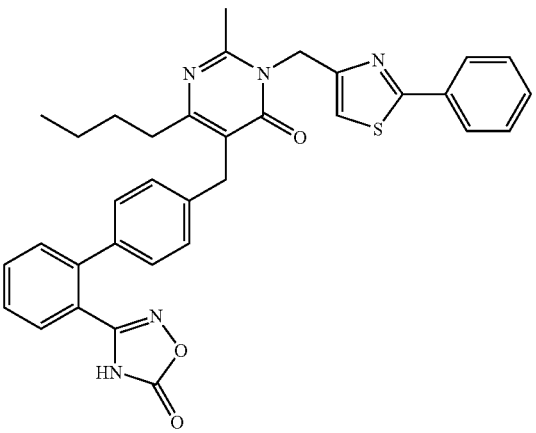

168b) 6-butyl-2-methyl-5-{[2'-(5-oxo-4,5-dihydro-1,2,4-oxadiazol-3-yl)biphenyl-4-yl]methyl}-3-[(2-phenyl-1,3-thiazol-4-yl)methyl]pyrimidin-4(3H)-one A mixture of hydroxylammonium chloride (1.34 g), sodium hydrogen carbonate (1.90 g) and dimethyl sulfoxide (18 mL) was stirred at 40° C. for 30 min, 4'-({4-butyl-2-methyl-6-oxo-1-[(2-phenyl-1,3-thiazol-4-yl)methyl]-1,6-dihydropyrimidin-5-yl}methyl)biphenyl-2-carbonitrile (1.20 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (0.42 g) and then 1,8-diazabicyclo[5.4.0]undec-7-ene (0.38 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.80 g, 60%).

$^1$H NMR (300 MHz, CDCl$_3$) δ 0.92 (t, J=7.2, 3 H), 1.33-1.46 (m, 2 H), 1.50-1.68 (m, 2 H), 2.56-2.66 (m, 2 H), 2.81 (s, 3 H), 3.90 (s, 2 H), 5.29 (s, 2 H), 7.19-7.32 (m, 5 H), 7.37-7.50 (m, 5 H), 7.59 (td, J=7.6, 1.5, 1 H), 7.82 (dd, J=8.0, 1.1, 1 H), 7.87-7.94 (m, 2 H), 12.38 (s, 1 H)

Example 169

6-butyl-2-methyl-5-{[2'-(5-oxo-4,5-dihydro-1,2,4-oxadiazol-3-yl)biphenyl-4-yl]methyl}-3-[(2-pyridin-2-yl-1,3-thiazol-4-yl)methyl]pyrimidin-4(3H)-one

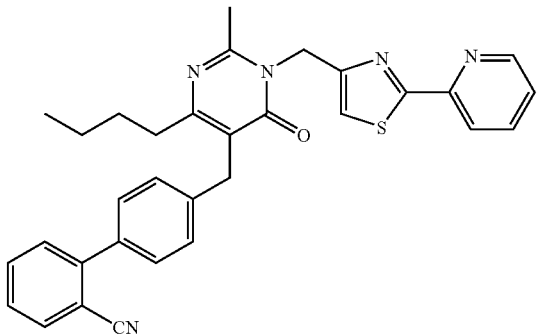

169a) 4'-({4-butyl-2-methyl-6-oxo-1-[(2-pyridin-2-yl-1,3-thiazol-4-yl)methyl]-1,6-dihydropyrimidin-5-yl}methyl)biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 2-[4-(chloromethyl)-1,3-thiazol-2-yl]pyridine (0.72 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a pale-yellow solid (0.80 g, 44%).

$^1$H NMR (300 MHz, CDCl$_3$) δ 0.89 (t, J=7.2, 3 H), 1.28-1.43 (m, 2 H), 1.52-1.63 (m, 2 H), 2.56-2.63 (m, 2 H), 2.81 (s, 3 H), 4.01 (s, 2 H), 5.39 (s, 2 H), 7.19-7.25 (m, 1 H), 7.32 (t, J=7.6, 1 H), 7.38-7.56 (m, 7 H), 7.64-7.74 (m, 2 H), 8.08 (d, J=8.0, 1 H), 8.52 (d, J=4.2, 1 H)

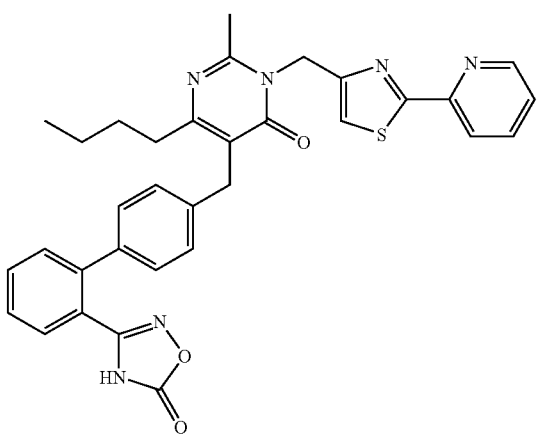

169b) 6-butyl-2-methyl-5-{[2'-(5-oxo-4,5-dihydro-1,2,4-oxadiazol-3-yl)biphenyl-4-yl]methyl}-3-[(2-pyridin-2-yl-1,3-thiazol-4-yl)methyl]pyrimidin-4(3H)-one A mixture of hydroxylammonium chloride (0.89 g), sodium hydrogen carbonate (1.26 g) and dimethyl sulfoxide (18 mL) was stirred at 40° C. for 30 min, 4'-({4-butyl-2-methyl-6-oxo-1-[(2-pyridin-2-yl-1,3-thiazol-4-yl)methyl]-1,6-dihydropyrimidin-5-yl}methyl)biphenyl-2-carbonitrile (0.80 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (0.30 g) and then 1,8-diazabicyclo[5.4.0]undec-7-ene (0.28 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.44 g, 49%).

$^1$H NMR (300 MHz, DMSO-d$_6$) δ 0.83 (t, J=7.2, 3 H), 1.21-1.35 (m, 2 H), 1.38-1.52 (m, 2 H), 2.44-2.53 (m, 2 H), 2.67 (s, 3 H), 3.87 (s, 2 H), 5.36 (s, 2 H), 7.17-7.28 (m, 4 H), 7.44-7.59 (m, 3 H), 7.62-7.71 (m, 3 H), 7.95 (td, J=7.8, 1.9, 1 H), 8.01-8.06 (m, 1 H), 8.62 (d, J=4.2, 1 H), 12.38 (s, 1 H)

Example 170

6-butyl-3-(2,3-dihydro-1-benzofuran-2-ylmethyl)-2-methyl-5-{[2'-(5-oxo-4,5-dihydro-1,2,4-oxadiazol-3-yl)biphenyl-4-yl]methyl}pyrimidin-4(3H)-one

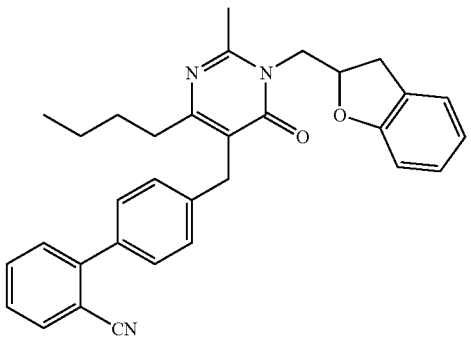

170a) 4'-{[4-butyl-1-(2,3-dihydro-1-benzofuran-2-ylmethyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), 2,3-dihydro-1-benzofuran-2-ylmethanol (1.02 g), tributylphosphine (2.1 mL), 1,1'-[(E)-diazene-1,2-diyldicarbonyl]dipiperidine (1.72 g) and tetrahydrofuran (60 mL) was stirred at room temperature for 4 hr. The reaction mixture was diluted with ethyl acetate, and the insoluble solid was filtered off. The solvent of the filtrate was evaporated under reduced pressure.

The residue was purified by silica gel column chromatography to give the title compound as a colorless viscous substance (0.86 g, 52%).

¹H NMR (300 MHz, CDCl₃) δ 0.89 (t, J=7.3, 3 H), 1.28-1.43 (m, 2 H), 1.52-1.65 (m, 2 H), 2.57 (s, 3 H), 2.68-2.76 (m, 2 H), 2.93 (dd, J=16, 6.7, 1 H), 3.20 (dd, J=15.7, 9.7, 1H), 3.79-3.94 (m, 2 H), 4.54 (s, 2 H), 4.98-5.09 (m, 1 H), 6.71-6.82 (m, 2 H), 7.00-7.11 (m, 2 H), 7.17 (d, J=7.9, 2 H), 7.32 (t, J=7.7, 1H), 7.38-7.45 (m, 3 H), 7.54 (t, J=7.6, 1 H), 7.66 (d, J=7.6, 1 H)

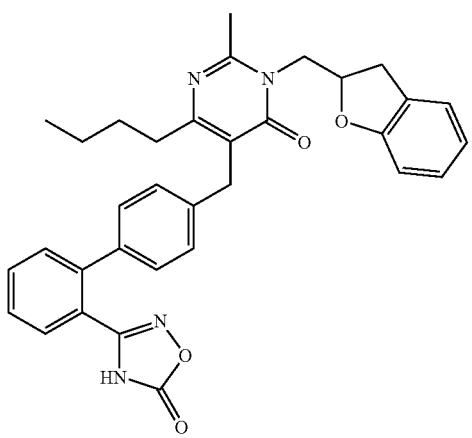

170b) 6-butyl-3-(2,3-dihydro-1-benzofuran-2-ylmethyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.04 g), sodium hydrogen carbonate (1.49 g) and dimethyl sulfoxide (15 mL) was stirred at 40° C. for 30 min, 4'-{[4-butyl-1-(2,3-dihydro-1-benzofuran-2-ylmethyl)-2-methyl-6-oxo-1,6-dihydropyrimidin-5-yl]methyl}biphenyl-2-carbonitrile (0.86 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.05 g) and then 1,8-diazabicyclo[5.4.0]undec-7-ene (0.05 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.07 g, 7%).

¹H NMR (300 MHz, DMSO-d₆) δ 0.84 (t, J=7.2, 3 H), 1.23-1.36 (m, 2 H), 1.37-1.51 (m, 2 H), 2.44-2.55 (m, 4 H), 2.99-3.08 (m, 1 H), 3.34-3.46 (m, 1 H), 3.54-3.65 (m, 1 H), 3.82-3.95 (m, 2 H), 4.10 (dd, J=14.4, 9.5, 1 H), 4.27-4.35 (m, 1 H), 5.05-5.15 (m, 1 H), 6.79 (d, J=8.0, 1 H), 6.87 (t, J=7.0, 1 H), 7.09-7.16 (m, 2 H), 7.20-7.28 (m, 5 H), 7.48-7.58 (m, 2 H), 7.63-7.72 (m, 2 H), 12.40 (s, 1 H)

Example 171

6-butyl-3-[3-(1-hydroxyethyl)benzyl]-2-methyl-5-{[2'-(5-oxo-4,5-dihydro-1,2,4-oxadiazol-3-yl)biphenyl-4-yl]methyl}pyrimidin-4(3H)-one

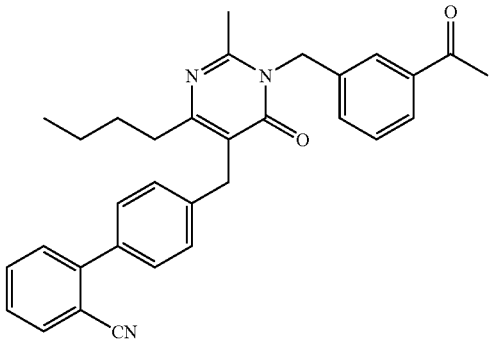

171a) 4'-{[1-(3-acetylbenzyl)-4-butyl-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1.22 g), potassium carbonate (0.94 g), 1-[3-(bromomethyl)phenyl]ethanone (0.73 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless viscous substance (1.02 g, 61%).

¹H NMR (300 MHz, CDCl₃) δ 0.90 (t, J=7.2, 3 H), 1.30-1.44 (m, 2 H), 1.52-1.65 (m, 2 H), 2.44 (s, 3 H), 2.51 (s, 3 H), 2.57-2.65 (m, 2 H), 4.04 (s, 2 H), 5.35 (s, 2 H), 7.33-7.53 (m, 8 H), 7.58 (t, J=7.6, 1 H), 7.69 (d, J=7.6, 1 H), 7.80-7.88 (m, 2 H)

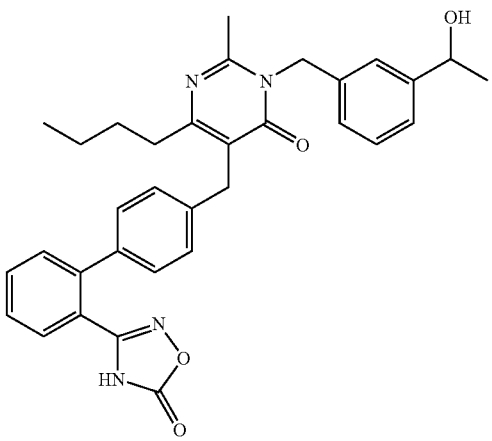

171b) 6-butyl-3-[3-(1-hydroxyethyl)benzyl]-2-methyl-5-{[2'-(5-oxo-4,5-dihydro-1,2,4-oxadiazol-3-yl)biphenyl-4-yl]methyl}pyrimidin-4(3H)-one 4'-{[1-(3-acetylbenzyl)-4-butyl-2-methyl-6-oxo-1,6-dihydropyrimidin-5-yl]methyl}biphenyl-2-carbonitrile (1.02 g) and methanol (30 mL) were ice-cooled, sodium borohydride (0.24 g) was gradually added, and the mixture was stirred for 30 min. Thereafter, the temperature of the mixture was gradually raised to room temperature, and the mixture was stirred for 2 hr. The reaction mixture was diluted with ethyl acetate, washed with water and then with saturated brine, and dried over anhydrous magnesium sulfate. The solvent was evaporated under reduced pressure. A mixture of hydroxylammonium chloride (1.17 g), sodium hydrogen carbonate (1.66 g) and dimethyl sulfoxide (18 mL) was stirred at 40° C. for 30 min, the residue obtained above (0.97 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.35 g) and then 1,8-diazabicyclo[5.4.0]undec-7-ene (0.32 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.60 g, 53%).

$^1$H NMR (300 MHz, DMSO-$d_6$) δ 0.83 (t, J=7.3, 3 H), 1.19-1.34 (m, 3 H), 1.39-1.51 (m, 2 H), 1.62 (d, J=6.6, 1 H), 2.39 (s, 3 H), 2.44-2.55 (m, 4 H), 3.38 (q, J=7.0, 1 H), 3.88-3.93 (m, 2 H), 5.27-5.33 (m, 2 H), 7.12 (d, J=7.2, 1 H), 7.17-7.30 (m, 5 H), 7.34-7.45 (m, 2 H), 7.46-7.59 (m, 2H), 7.63-7.73 (m, 2 H), 12.41 (s, 1 H)

Example 172

6-ethyl-2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one

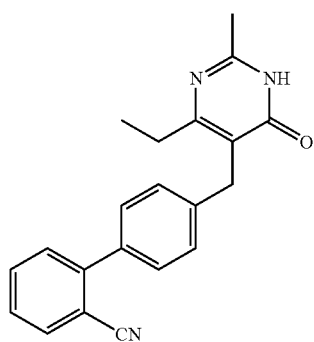

172a) 4'-[(4-ethyl-2-methyl-6-oxo-1,6-dihydropyrimidin-5-yl)methyl]biphenyl-2-carbonitrile A mixture of methyl 3-oxopentanoate (5.73 g) and tetrahydrofuran (120 mL) was ice-cooled to 0° C., 60% sodium hydride (1.32 g) was gradually added, and the mixture was stirred in situ for 30 min. To the mixture was added 4'-(bromomethyl)biphenyl-2-carbonitrile (5.99 g), and the mixture was stirred for 30 min. Thereafter, the temperature of the mixture was gradually raised to room temperature, and the mixture was stirred for 4 hr. The solvent of the reaction mixture was evaporated under reduced pressure, and the residue was diluted with ethyl acetate. The diluted solution was washed with water and saturated brine, and dried over anhydrous magnesium sulfate. The solvent was evaporated under reduced pressure. To an ice-cooled mixture of acetamidine hydrochloride (4.16 g) and methanol (36 mL) was added dropwise 28% sodium methoxide-methanol solution (17.8 mL), and a mixture of the aforementioned residue, 1,4-dioxane (24 mL) and methanol (36 mL) was added dropwise. The mixture was stirred at room temperature for 12 hr. The solvent was evaporated under reduced pressure. The residue was diluted with ethyl acetate, and the diluted solution was washed with 0.1 M aqueous hydrochloric acid solution, water and saturated brine, and dried over anhydrous magnesium sulfate. The solvent was evaporated under reduced pressure to give crude crystals. The crude crystals were washed with diisopropyl ether to give the title compound as a colorless solid (4.66 g, 64%).

$^1$H NMR (300 MHz, DMSO-$d_6$) δ 1.04 (t, J=7.4, 3 H), 2.26 (s, 3H), 2.46-2.55 (m, 2 H), 3.86 (s, 2 H), 7.33 (d, J=8.3, 2 H), 7.48 (d, J=8.3, 2 H), 7.52-7.64 (m, 2 H), 7.73-7.81 (m, 1 H), 7.93 (d, J=7.5, 1 H), 12.35 (s, 1 H)

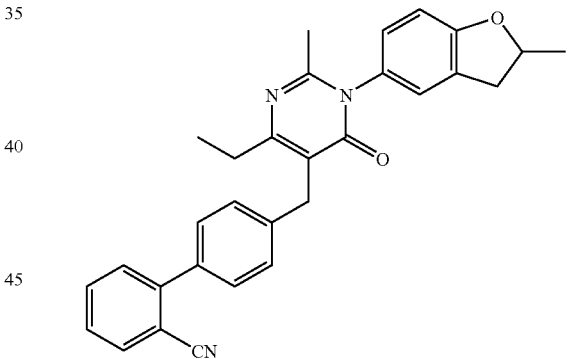

172b) 4'-{[4-ethyl-2-methyl-1-(2-methyl-2,3-dihydro-1-benzofuran-5-yl)-6-oxo-1,6-dihydropyrimidin-5-yl]methyl}biphenyl-2-carbonitrile A mixture of 4'-[(4-ethyl-2-methyl-6-oxo-1,6-dihydropyrimidin-5-yl)methyl]biphenyl-2-carbonitrile (0.99 g), (2-methyl-2,3-dihydro-1-benzofuran-5-yl)boronic acid (0.98 g), molecular sieves 4 A (0.49 g), triethylamine (2.1 mL), pyridine (1.0 mL), copper(II) acetate (1.09 g) and methylene chloride (20 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as colorless crystals (1.08 g, 78%).

$^1$H NMR (300 MHz, CDCl$_3$) δ 1.23 (t, J=7.5, 3 H), 1.50 (dd, J=10.7, 6.2, 3 H), 2.20 (d, J=4.7, 3 H), 2.70 (q, J=7.4, 2H), 2.81-2.96 (m, 1 H), 3.30-3.42 (m, 1 H), 3.97 (s, 2 H), 4.93-5.09 (m, 1 H), 6.82-6.86 (m, 1 H), 6.90-6.97 (m, 1 H), 6.99 (d, J=1.1, 1 H), 7.37-7.51 (m, 6 H), 7.58-7.66 (m, 1 H), 7.74 (dd, J=7.7, 0.8, 1 H)

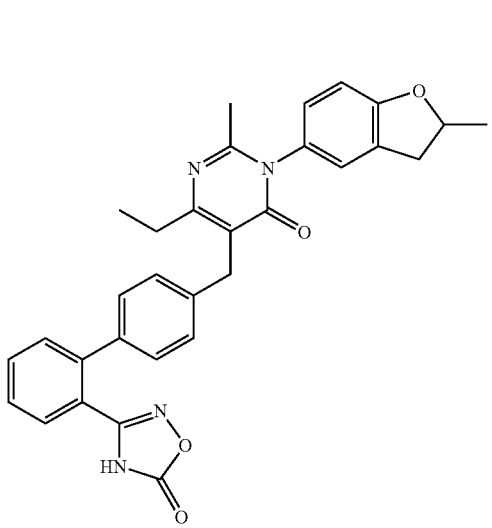

172c) 6-ethyl-2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.38 g), sodium hydrogen carbonate (1.97 g) and dimethyl sulfoxide (10 mL) was stirred at 40° C. for 30 min, 4'-{[4-ethyl-2-methyl-1-(2-methyl-2,3-dihydro-1-benzofuran-5-yl)-6-oxo-1,6-dihydropyrimidin-5-yl]methyl}biphenyl-2-carbonitrile (1.08 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (40 mL), N,N'-carbonyldiimidazole (0.65 g) and then 1,8-diazabicyclo[5.4.0]undec-7-ene (0.60 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.82 g, 67%).

$^1$H NMR (300 MHz, DMSO-d$_6$) δ 1.07 (t, J=6.6, 3 H), 1.42 (dd, J=6.1, 2.7, 3 H), 2.09 (d, J=3.0, 3 H), 2.48-2.52 (m, 2 H), 2.77-2.89 (m, 1 H), 3.19-3.53 (m, 1 H), 3.86 (s, 2 H), 4.91-5.05 (m, 1 H), 6.83 (d, J=8.3, 1 H), 7.05 (dd, J=8.3, 1.7, 1 H), 7.16 (d, J=1.9, 1 H), 7.19-7.31 (m, 4 H), 7.49-7.58 (m, 2 H), 7.63-7.72 (m, 2 H), 12.37 (s, 1 H)

Example 173

6-ethyl-2-methyl-5-{[2'-(5-oxo-4,5-dihydro-1,2,4-oxadiazol-3-yl)biphenyl-4-yl]methyl}-3-phenylpyrimidin-4(3H)-one

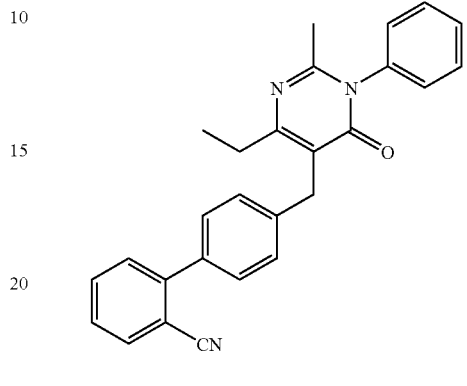

173a) 4'-[(4-ethyl-2-methyl-6-oxo-1-phenyl-1,6-dihydropyrimidin-5-yl)methyl]biphenyl-2-carbonitrile A mixture of 4'-[(4-ethyl-2-methyl-6-oxo-1,6-dihydropyrimidin-5-yl)methyl]biphenyl-2-carbonitrile (0.99 g), phenylboronic acid (0.73 g), molecular sieves 4 A (0.49 g), triethylamine (2.1 mL), pyridine (1.0 mL), copper(II) acetate (1.09 g) and methylene chloride (20 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless solid (0.42 g, 34%).

$^1$H NMR (300 MHz, CDCl$_3$) δ 1.24 (t, J=7.6, 3 H), 2.17 (s, 3 H), 2.71 (q, J=7.6, 2 H), 3.98 (s, 2 H), 7.21-7.28 (m, 3 H), 7.38-7.42 (m, 1 H), 7.42-7.46 (m, 3 H), 7.46-7.57 (m, 4 H), 7.62 (td, J=7.7, 1.4, 1 H), 7.74 (dd, J=7.7, 0.9, 1 H)

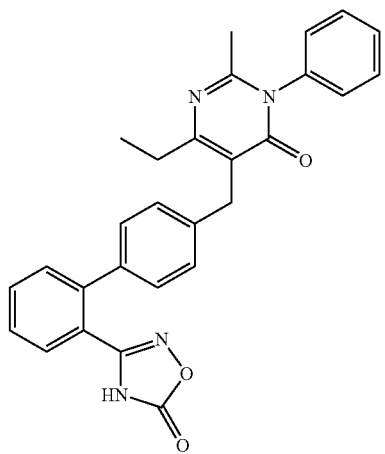

173b) 6-ethyl-2-methyl-5-{[2'-(5-oxo-4,5-dihydro-1,2,4-oxadiazol-3-yl)biphenyl-4-yl]methyl}-3-phenylpyrimidin-4(3H)-one A mixture of hydroxylammonium chloride (0.61 g), sodium hydrogen carbonate (0.87 g) and dimethyl sulfoxide (10 mL) was stirred at 40° C. for 30 min, 4'-[(4-ethyl-2-methyl-6-oxo-1-phenyl-1,6-dihydropyrimidin-5-yl)methyl]biphenyl-2-carbonitrile (0.42 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.16 g) and then 1,8-diazabicyclo[5.4.0]undec-7-ene (0.15 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.30 g, 62%).

$^1$H NMR (300 MHz, DMSO-$d_6$) δ 1.08 (t, J=7.5, 3 H), 2.49-2.53 (m, 2 H), 3.35 (s, 3 H), 3.87 (s, 2 H), 7.18-7.32 (m, 4 H), 7.36-7.43 (m, 2 H), 7.48-7.59 (m, 5 H), 7.62-7.72 (m, 2 H), 12.40 (s, 1 H)

Example 174

6-cyclopropyl-2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one

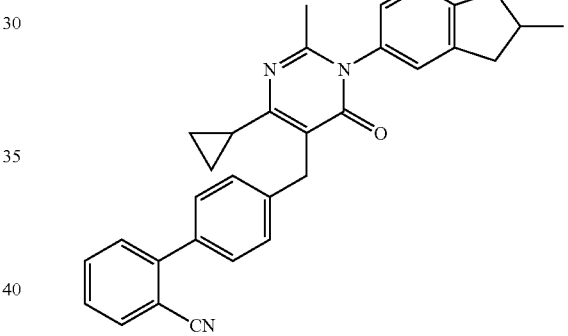

174a) 4'-[(4-cyclopropyl-2-methyl-6-oxo-1,6-dihydropyrimidin-5-yl)methyl]biphenyl-2-carbonitrile

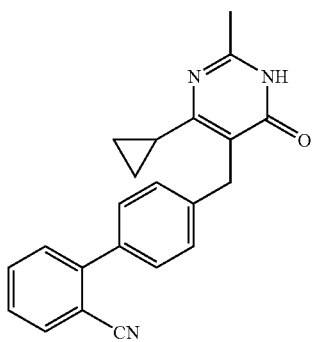

A mixture of methyl 3-cyclopropyl-3-oxopropanoate (5.99 g) and tetrahydrofuran (120 mL) was ice-cooled at 0° C., 60% sodium hydride (1.32 g) was gradually added, and the mixture was stirred in situ for 30 min. To a mixture was added 4'-(bromomethyl)biphenyl-2-carbonitrile (5.99 g), and the mixture was stirred for 30 min. Then, the temperature of the mixture was gradually raised to room temperature, and the mixture was stirred for 4 hr. The solvent was evaporated under reduced pressure, and the residue was diluted with ethyl acetate. The diluted solution was washed with water and saturated brine, and dried over anhydrous magnesium sulfate. The solvent was evaporated under reduced pressure. To an ice-cooled mixture of acetamidine hydrochloride (4.16 g) and methanol (36 mL) was added dropwise 28% sodium methoxide-methanol solution (17.8 mL), and a mixture of the aforementioned residue, 1,4-dioxane (24 mL) and methanol (36 mL) was added dropwise. The mixture was stirred at room temperature for 12 hr. The solvent of the reaction mixture was evaporated under reduced pressure, and the residue was diluted with ethyl acetate, and the diluted solution was washed with 0.1 M aqueous hydrochloric acid solution, water and saturated brine, and dried over anhydrous magnesium sulfate. The solvent was evaporated under reduced pressure to give crude crystals. The crude crystals were washed with diisopropyl ether to give the title compound as a colorless solid (3.10 g, 41%).

$^1$H NMR (300 MHz, DMSO-$d_6$) δ 0.83-0.92 (m, 2 H), 0.93-1.00 (m, 2 H), 2.10-2.18 (m, 1 H), 2.19 (s, 3 H), 3.98 (s, 2 H), 7.37-7.43 (m, 2 H), 7.46-7.65 (m, 4 H), 7.74-7.82 (m, 1 H), 7.93 (d, J=7.72, 1 H), 12.24 (s, 1 H)

174b) 4'-{[4-cyclopropyl-2-methyl-1-(2-methyl-2,3-dihydro-1-benzofuran-5-yl)-6-oxo-1,6-dihydropyrimidin-5-yl]methyl}biphenyl-2-carbonitrile A mixture of 4'-[(4-cyclopropyl-2-methyl-6-oxo-1,6-dihydropyrimidin-5-yl)methyl]biphenyl-2-carbonitrile (1.02 g), (2-methyl-2,3-dihydro-1-benzofuran-5-yl)boronic acid (0.73 g), molecular sieves 4 A (0.51 g), triethylamine (2.1 mL), pyridine (1.0 mL), copper(II) acetate (1.09 g) and methylene chloride (20 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless solid (0.81 g, 57%).

$^1$H NMR (300 MHz, CDCl$_3$) δ 0.93-1.01 (m, 2 H), 1.16-1.22 (m, 2 H), 1.48 (dd, J=10.7, 6.2, 3 H), 2.09-2.20 (m, 4 H), 2.79-2.91 (m, 1 H), 3.27-3.40 (m, 1 H), 4.09 (s, 2 H), 4.91-5.06 (m, 1 H), 6.79-6.83 (m, 1 H), 6.86-6.91 (m, 1 H), 6.95 (s,

1 H), 7.39 (td, J=7.6, 1.1, 1 H), 7.43-7.51 (m, 5 H), 7.61 (td, J=7.7, 1.3, 1 H), 7.73 (dd, J=7.8, 1.0, 1 H)

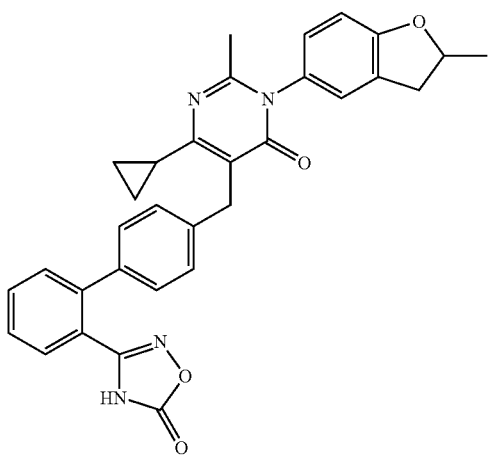

174c) 6-cyclopropyl-2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.02 g), sodium hydrogen carbonate (1.19 g) and dimethyl sulfoxide (15 mL) was stirred at 40° C. for 30 min, 4'-{[4-cyclopropyl-2-methyl-1-(2-methyl-2,3-dihydro-1-benzofuran-5-yl)-6-oxo-1,6-dihydropyrimidin-5-yl]methyl}biphenyl-2-carbonitrile (0.81 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.18 g) and then 1,8-diazabicyclo[5.4.0]undec-7-ene (0.16 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.32 g, 35%).

$^1$H NMR (300 MHz, DMSO-$d_6$) δ 0.85-0.94 (m, 2 H), 1.41 (dd, J=6.3, 1.7, 3 H), 2.02 (d, J=3.0, 3 H), 2.10-2.21 (m, 1 H), 2.48-2.53 (m, 2 H), 2.75-2.88 (m, 1 H), 3.27-3.42 (m, 1 H), 3.98 (s, 2 H), 4.91-5.06 (m, 1 H), 6.82 (d, J=8.3, 1 H), 6.98-7.04 (m, 1 H), 7.13 (d, J=1.9, 1 H), 7.20-7.26 (m, 2 H), 7.30-7.36 (m, 2 H), 7.49-7.58 (m, 2 H), 7.63-7.73 (m, 2 H), 12.41 (s, 1 H)

Example 175

6-cyclopropyl-2-methyl-5-{[2'-(5-oxo-4,5-dihydro-1,2,4-oxadiazol-3-yl)biphenyl-4-yl]methyl}-3-phenylpyrimidin-4(3H)-one

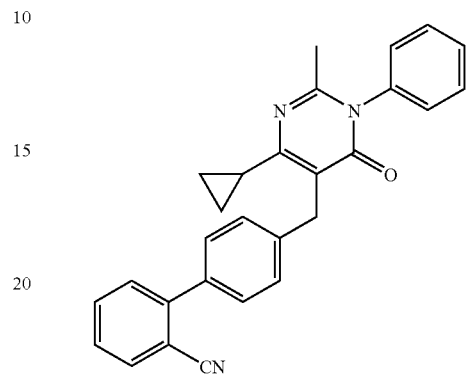

175a) 4'-[(4-cyclopropyl-2-methyl-6-oxo-1-phenyl-1,6-dihydropyrimidin-5-yl)methyl]biphenyl-2-carbonitrile A mixture of 4'-[(4-cyclopropyl-2-methyl-6-oxo-1,6-dihydropyrimidin-5-yl)methyl]biphenyl-2-carbonitrile (1.02 g), phenylboronic acid (0.73 g), molecular sieves 4 A (0.51 g), triethylamine (2.1 mL), pyridine (1.0 mL), copper(II) acetate (1.09 g) and methylene chloride (20 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless solid (0.44 g, 35%).

$^1$H NMR (300 MHz, CDCl$_3$) δ 0.94-1.02 (m, 2 H), 1.17-1.22 (m, 2 H), 2.08 (s, 3 H), 2.11-2.21 (m, 1 H), 4.10 (s, 2 H), 7.18-7.23 (m, 2 H), 7.40 (td, J=7.6, 1.2, 1 H), 7.43-7.55 (m, 8 H), 7.61 (td, J=7.7, 1.4, 1 H), 7.74 (dd, J=7.8, 1.0, 1 H)

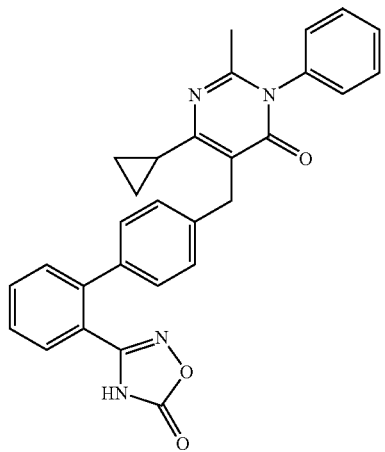

175b) 6-cyclopropyl-2-methyl-5-{[2'-(5-oxo-4,5-dihydro-1,2,4-oxadiazol-3-yl)biphenyl-4-yl]methyl}-3-phenylpyrimidin-4(3H)-one A mixture of hydroxylammonium chloride (0.62 g), sodium hydrogen carbonate (0.89 g) and dimethyl sulfoxide (10 mL) was stirred at 40° C. for 30 min, 4'-[(4-cyclopropyl-2-methyl-6-oxo-1-phenyl-1,6-dihydropyrimidin-5-yl)methyl]biphenyl-2-carbonitrile (0.44 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.19 g) and then 1,8-diazabicyclo[5.4.0]undec-7-ene (0.17 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.29 g, 57%).

$^1$H NMR (300 MHz, DMSO-d$_6$) δ 0.87-0.95 (m, 2 H), 1.99 (s, 3 H), 2.12-2.24 (m, 1 H), 2.47-2.53 (m, 2 H), 3.99 (s, 2 H), 7.21-7.26 (m, 2 H), 7.31-7.38 (m, 4 H), 7.47-7.58 (m, 5 H), 7.63-7.73 (m, 2 H), 12.41 (s, 1 H)

Example 176

6-ethyl-3-(4-isopropoxyphenyl)-2-methyl-5-{[2'-(5-oxo-4,5-dihydro-1,2,4-oxadiazol-3-yl)biphenyl-4-yl]methyl}pyrimidin-4(3H)-one

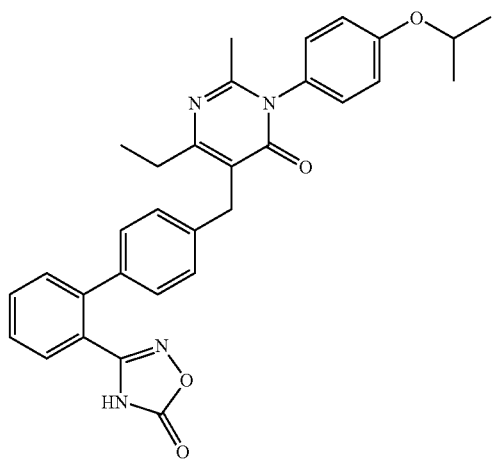

176a) 4'-{[4-ethyl-1-(4-isopropoxyphenyl)-2-methyl-6-oxo-1,6-dihydropyrimidin-5-yl]methyl}biphenyl-2-carbonitrile A mixture of 4'-[(4-ethyl-2-methyl-6-oxo-1,6-dihydropyrimidin-5-yl)methyl]biphenyl-2-carbonitrile (0.99 g), (4-isopropoxyphenyl)boronic acid (1.08 g), molecular sieves 4 A (0.49 g), triethylamine (2.1 mL), pyridine (1.0 mL), copper (II) acetate (1.09 g) and methylene chloride (20 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless solid (0.68 g, 49%).

$^1$H NMR (300 MHz, CDCl$_3$) δ 1.14 (t, J=7.5, 3 H), 2.69 (d, J=6.0 Hz, 6 H), 2.14 (s, 3 H), 2.58 (d, J=7.5, 2 H), 3.92 (s, 2 H), 4.66-4.78 (m, 1 H), 7.08-7.14 (m, 2 H), 7.25-7.38 (m, 6 H), 7.49-7.53 (m, 1 H), 7.62 (dd, J=7.5, 1.3, 1 H), 7.68-7.77 (m, 2 H)

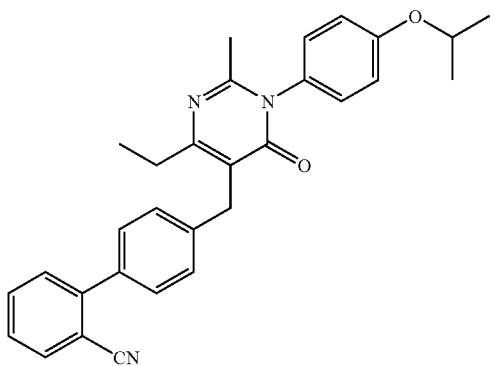

176b) 6-ethyl-3-(4-isopropoxyphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.86 g), sodium hydrogen carbonate (1.23 g) and dimethyl sulfoxide (15 mL) was stirred at 40° C. for 30 min, 4'-{[4-ethyl-1-(4-isopropoxyphenyl)-2-methyl-6-oxo-1,6-dihydropyrimidin-5-yl]methyl}biphenyl-2-carbonitrile (0.68 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.26 g) and then 1,8-diazabicyclo[5.4.0]undec-7-ene (0.24 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.62 g, 81%).

$^1$H NMR (300 MHz, DMSO-d$_6$) δ 1.07 (t, J=7.5, 3 H), 1.30 (d, J=6.0 Hz, 6 H), 2.07 (s, 3 H), 2.54 (d, J=7.5, 2 H), 3.87 (s, 2 H), 4.61-4.73 (m, 1 H), 7.01-7.06 (m, 2 H), 7.20-7.31 (m, 6 H), 7.49-7.53 (m, 1 H), 7.56 (dd, J=7.5, 1.3, 1 H), 7.63-7.71 (m, 2 H), 12.37 (s, 1 H)

Example 177

6-cyclopropyl-3-(4-isopropoxyphenyl)-2-methyl-5-{[2'-(5-oxo-4,5-dihydro-1,2,4-oxadiazol-3-yl)biphenyl-4-yl]methyl}pyrimidin-4(3H)-one

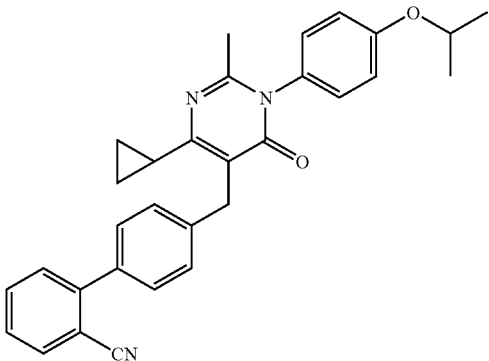

177a) 4'-{[4-cyclopropyl-1-(4-isopropoxyphenyl)-2-methyl-6-oxo-1,6-dihydropyrimidin-5-yl]methyl}biphenyl-2-carbonitrile A mixture of 4'-[(4-cyclopropyl-2-methyl-6-oxo-1,6-dihydropyrimidin-5-yl)methyl]biphenyl-2-carbonitrile (1.02 g), (4-isopropoxyphenyl)boronic acid (1.08 g), molecular sieves 4 A (0.51 g), triethylamine (2.1 mL), pyridine (1.0 mL), copper(II) acetate (1.09 g) and methylene chloride (20 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless solid (0.39 g, 27%).

$^1$H NMR (300 MHz, CDCl$_3$) δ 0.88-0.98 (m, 2 H), 1.02-1.13 (m, 2 H), 1.73 (d, J=6.0, 6 H), 2.12-2.25 (m, 1 H), 2.49-2.59 (m, 3 H), 4.02 (s, 2 H), 4.67-4.81 (m, 1 H), 7.01-7.08 (m, 2 H), 7.28-7.38 (m, 4 H), 7.39-7.44 (m, 2 H), 7.49-7.55 (m, 2 H), 7.66-7.72 (m, 2 H)

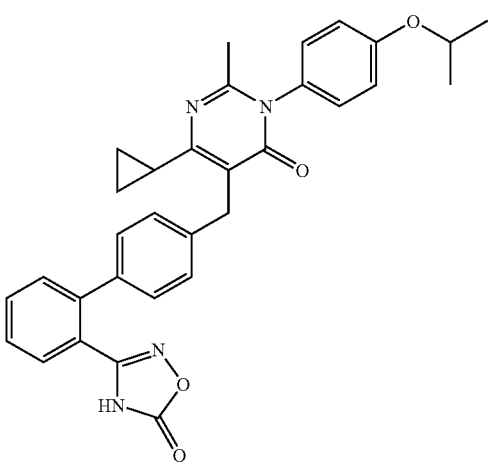

177b) 6-cyclopropyl-3-(4-isopropoxyphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.48 g), sodium hydrogen carbonate (0.69 g) and dimethyl sulfoxide (10 mL) was stirred at 40° C. for 30 min, 4'-{[4-cyclopropyl-1-(4-isopropoxyphenyl)-2-methyl-6-oxo-1,6-dihydropyrimidin-5-yl]methyl}biphenyl-2-carbonitrile (0.39 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.13 g) and then 1,8-diazabicyclo[5.4.0]undec-7-ene (0.12 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.28 g, 64%).

$^1$H NMR (300 MHz, DMSO-d$_6$) δ 0.85-0.94 (m, 2 H), 0.99-1.05 (m, 2 H), 1.29 (d, J=6.0, 6 H), 2.11-2.22 (m, 1 H), 2.45-2.53 (m, 3 H), 3.98 (s, 2 H), 4.61-4.72 (m, 1 H), 6.98-7.05 (m, 2 H), 7.18-7.26 (m, 4 H), 7.29-7.36 (m, 2 H), 7.49-7.58 (m, 2 H), 7.63-7.72 (m, 2 H), 12.40 (s, 1 H)

Example 178

3-(2,2-dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one

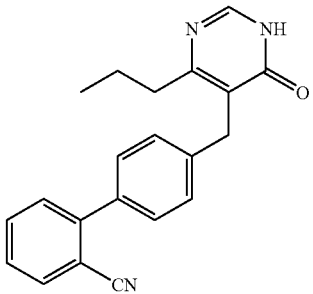

178a) 4'-[(6-oxo-4-propyl-1,6-dihydropyrimidin-5-yl)methyl]biphenyl-2-carbonitrile To an ice-cooled mixture of formamidine hydrochloride (3.73 g) and methanol (25 mL) was added dropwise 28% sodium methoxide-methanol solution (13.7 mL), and a mixture of methyl 2-[(2'-cyanobiphenyl-4-yl)methyl]-3-oxohexanoate (5.90 g), 1,4-dioxane (18 mL) and methanol (25 mL) was added dropwise. The mixture was stirred at room temperature for 12 hr. The solvent of the reaction mixture was evaporated under reduced pressure. The residue was diluted with ethyl acetate, and the diluted solution was washed with 0.1 M aqueous hydrochloric acid solution, water and saturated brine, and dried over anhydrous magnesium sulfate. The solvent was evaporated under reduced pressure to give crude crystals. The crude crystals were washed with diisopropyl ether to give the title compound as a colorless solid (3.40 g, 61%).

$^1$H NMR (300 MHz, CDCl$_3$) δ 0.94 (t, J=7.2, 3 H), 1.58-1.72 (m, 2 H), 2.57-2.67 (m, 2 H), 4.01 (s, 2 H), 7.32-7.37 (m, 2 H), 7.38-7.44 (m, 1 H), 7.45-7.51 (m, 3 H), 7.62 (td, J=7.6, 1.1, 1 H), 7.74 (dd, J=7.2, 0.8, 1 H), 8.07 (s, 1 H), 12.77-13.31 (m, 1 H)

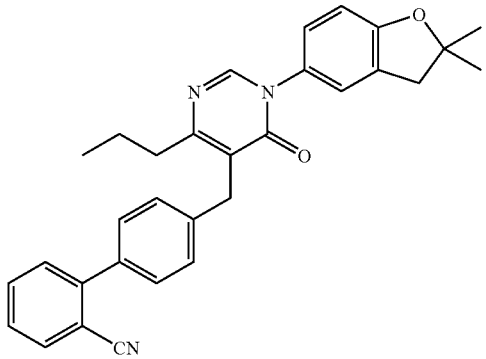

178b) 4'-{[1-(2,2-dimethyl-2,3-dihydro-1-benzofuran-5-yl)-6-oxo-4-propyl-1,6-dihydropyrimidin-5-yl]methyl}biphenyl-2-carbonitrile A mixture of 4'-[(6-oxo-4-propyl-1,6-dihydropyrimidin-5-yl)methyl]biphenyl-2-carbonitrile (1.02 g), (2,2-dimethyl-2,3-dihydro-1-benzofuran-5-yl)boronic acid (0.78 g), molecular sieves 4 A (1.98 g), triethylamine (1.7 mL), pyridine (1.0 mL), copper(II) acetate (0.65 g) and methylene chloride (15 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless solid (0.76 g, 54%).

$^1$H NMR (300 MHz, CDCl$_3$) δ 1.01 (t, J=7.4, 3 H), 1.49 (s, 6 H), 1.64-1.78 (m, 2 H), 2.65-2.74 (m, 2 H), 3.06 (s, 2 H), 4.02 (s, 2 H), 6.80 (d, J=8.3, 1 H), 7.06 (dd, J=8.5, 2.5, 1 H), 7.15-7.19 (m, 1 H), 7.37-7.51 (m, 6 H), 7.61 (td, J=7.7, 1.3, 1 H), 7.74 (dd, J=8.0, 1.1, 1 H), 8.08 (s, 1 H)

178c) 3-(2,2-dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.95 g), sodium hydrogen carbonate (1.35 g) and dimethyl sulfoxide (20 mL) was stirred at 40° C. for 30 min, 4'-{[1-(2,2-dimethyl-2,3-dihydro-1-benzofuran-5-yl)-6-oxo-4-propyl-1,6-dihydropyrimidin-5-yl]methyl}biphenyl-2-carbonitrile (0.76 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.29 g) and then 1,8-diazabicyclo[5.4.0]undec-7-ene (0.27 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.46 g, 53%).

$^1$H NMR (300 MHz, DMSO-d$_6$) δ 0.88 (t, J=7.4, 3 H), 1.44 (s, 6 H), 1.49-1.67 (m, 2 H), 2.52-2.59 (m, 2 H), 3.06 (s, 2 H), 3.92 (s, 2 H), 6.81 (d, J=8.5, 1 H), 7.14-7.32 (m, 6 H), 7.48-7.58 (m, 2 H), 7.63-7.72 (m, 2 H), 8.28 (s, 1 H), 12.38 (s, 1 H)

3-(2,2-Dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-(2,2-dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one sodium salt 3-(2,2-dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one potassium salt 3-(2,2-dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one 0.5 calcium salt 3-(2,2-dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one hydrochloride 3-(2,2-dimethyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one hydrobromide

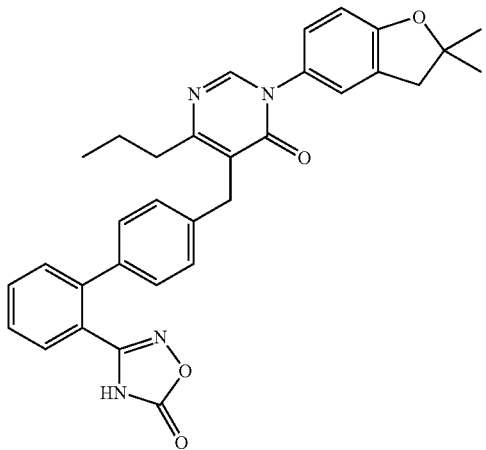

Example 179

3-(4-isopropoxyphenyl)-5-{[2'-(5-oxo-4,5-dihydro-1,2,4-oxadiazol-3-yl)biphenyl-4-yl]methyl}-6-propylpyrimidin-4(3H)-one

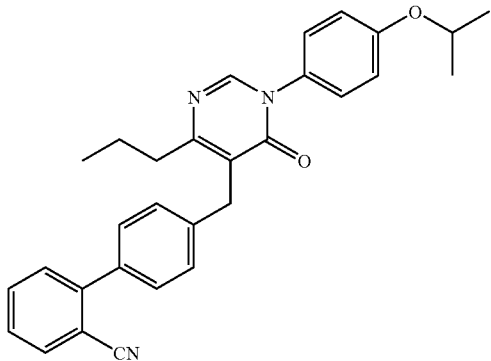

179a) 4'-{[1-(4-isopropoxyphenyl)-6-oxo-4-propyl-1,6-dihydropyrimidin-5-yl]methyl}biphenyl-2-carbonitrile A mixture of 4'-[(6-oxo-4-propyl-1,6-dihydropyrimidin-5-yl)methyl]biphenyl-2-carbonitrile (1.02 g), (4-isopropoxyphenyl)boronic acid (0.65 g), molecular sieves 4 A (1.98 g), triethylamine (1.7 mL), pyridine (1.0 mL), copper(II) acetate (0.65 g) and methylene chloride (15 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless solid (0.62 g, 44%).

$^1$H NMR (300 MHz, CDCl$_3$) δ 1.01 (t, J=7.2, 3 H), 1.35 (d, J=6.0, 6 H), 1.64-1.78 (m, 2 H), 2.66-2.73 (m, 2 H), 4.02 (s, 2 H), 4.51-4.65 (m, 1 H), 6.94-7.00 (m, 2 H), 7.25-7.31 (m, 2 H), 7.37-7.50 (m, 6 H), 7.61 (td, J=7.7, 1.3, 1 H), 7.73 (dd, J=7.8, 1.0, 1 H), 8.08 (s, 1 H)

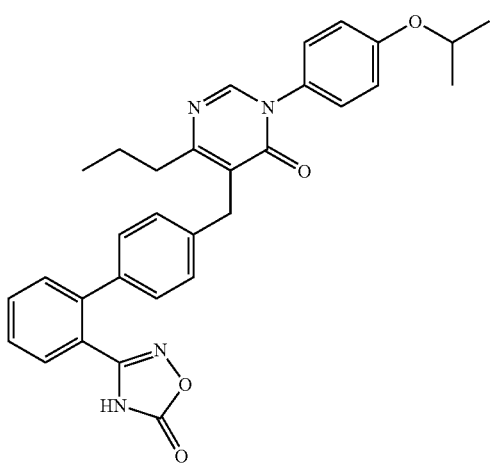

179b) 3-(4-isopropoxyphenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.79 g), sodium hydrogen carbonate (1.12 g) and dimethyl sulfoxide (20 mL) was stirred at 40° C. for 30 min, 4'-{[1-(4-isopropoxyphenyl)-6-oxo-4-propyl-1,6-dihydropyrimidin-5-yl]methyl}biphenyl-2-carbonitrile (0.62 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.30 g) and then 1,8-diazabicyclo[5.4.0]undec-7-ene (0.28 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.58 g, 83%).

$^1$H NMR (300 MHz, DMSO-d$_6$) δ 0.88 (t, J=7.4, 3 H), 1.29 (d, J=6.0 Hz, 6 H), 1.49-1.64 (m, 2 H), 2.48-2.52 (m, 1 H), 2.52-2.61 (m, 2 H), 3.92 (s, 2 H), 7.00-7.08 (m, 2 H), 7.21-7.25 (m, 2 H), 7.28-7.33 (m, 2 H), 7.34-7.41 (m, 2 H), 7.47-7.58 (m, 2 H), 7.63-7.72 (m, 2 H), 8.30 (s, 1 H), 12.38 (s, 1 H)

Example 180

3-(4'-{[3-butyl-5-oxo-1-(2-phenylethyl)-1,5-dihydro-4H-1,2,4-triazol-4-yl]methyl}biphenyl-2-yl)-1,2,4-oxadiazol-5(4H)-one

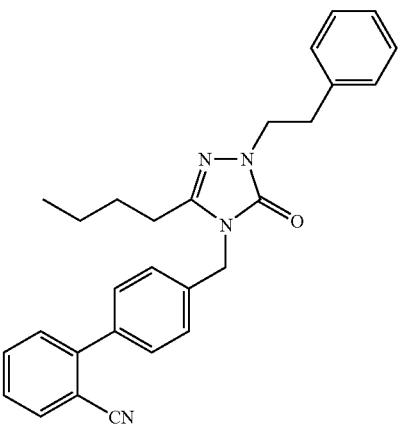

180a) 4'-{[3-butyl-5-oxo-1-(2-phenylethyl)-1,5-dihydro-4H-1,2,4-triazol-4-yl]methyl}biphenyl-2-carbonitrile To a mixture of 4'-[(3-butyl-5-oxo-1,5-dihydro-4H-1,2,4-triazol-4-yl)methyl]biphenyl-2-carbonitrile (1.00 g) and N,N-dimethylformamide (15 mL) was added 60% sodium hydride (0.60 g), and the mixture was stirred at room temperature for 30 min. To the mixture was added (2-bromoethyl)benzene (2.22 g), and the mixture was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.72 g, 55%).

¹H NMR (300 MHz, CDCl₃) δ 0.92 (t, J=7.4, 3 H), 1.28-1.44 (m, 2 H), 1.56-1.62 (m, 2 H), 2.41-2.48 (m, 2 H), 3.10 (t, J=7.4, 2 H), 4.04 (m, 2 H), 4.72 (s, 2 H), 7.17 (d, J=8.3, 2 H), 7.20-7.28 (m, 2 H), 7.29-7.41 (m, 5 H), 7.44 (dd, J=7.5, 1.13, 1 H), 7.47-7.58 (m, 1 H), 7.66-7.73 (m, 1 H), 7.81 (dd, J=7.6, 1.2, 1 H)

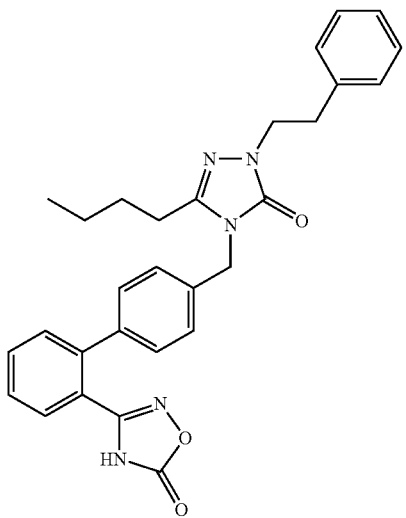

180b) 3-(4'-{[3-butyl-5-oxo-1-(2-phenylethyl)-1,5-dihydro-4H-1,2,4-triazol-4-yl]methyl}biphenyl-2-yl)-1,2,4-oxadiazol-5(4H)-one A mixture of hydroxylammonium chloride (0.97 g), sodium hydrogen carbonate (1.38 g) and dimethyl sulfoxide (10 mL) was stirred at 40° C. for 30 min, 4'-{[3-butyl-5-oxo-1-(2-phenylethyl)-1,5-dihydro-4H-1,2,4-triazol-4-yl]methyl}biphenyl-2-carbonitrile (0.72 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.27 g) and then 1,8-diazabicyclo[5.4.0]undec-7-ene (0.25 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.45 g, 55%).

¹H NMR (300 MHz, CDCl₃) δ 0.88 (t, J=7.4, 3 H), 1.24-1.40 (m, 2 H), 1.49-1.62 (m, 2 H), 2.35-2.43 (m, 2 H), 3.02 (t, J=7.4, 2 H), 3.91-3.99 (m, 2 H), 4.72 (s, 2 H), 7.10 (d, J=8.3, 2 H), 7.14-7.18 (m, 2 H), 7.19-7.32 (m, 5 H), 7.41 (dd, J=7.5, 1.1, 1 H), 7.49 (td, J=7.6, 1.2, 1 H), 7.61 (td, J=7.6, 1.3, 1 H), 7.77 (dd, J=7.6, 1.2, 1 H), 12.40 (s, 1 H)

Example 181

3-{4'-[(3-butyl-1-sec-butyl-5-oxo-1,5-dihydro-4H-1,2,4-triazol-4-yl)methyl]biphenyl-2-yl}-1,2,4-oxadiazol-5(4H)-one

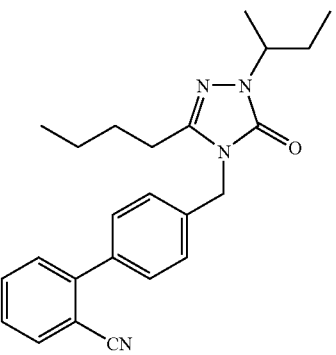

181a) 4'-[(3-butyl-1-sec-butyl-5-oxo-1,5-dihydro-4H-1,2,4-triazol-4-yl)methyl]biphenyl-2-carbonitrile To a mixture of 4'-[(3-butyl-5-oxo-1,5-dihydro-4H-1,2,4-triazol-4-yl)methyl]biphenyl-2-carbonitrile (1.00 g) and N,N-dimethylformamide (15 mL) was added 60% sodium hydride (0.60 g), and the mixture was stirred at room temperature for 30 min.

To the mixture was added 2-bromobutane (1.64 g), and the mixture was stirred at room temperature for 5 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.61 g, 53%).

¹H NMR (300 MHz, CDCl₃) δ 0.90 (t, J=7.4, 3 H), 1.07 (t, J=7.3, 3 H), 1.36 (d, J=6.8, 3 H), 1.33-1.45 (m, 2 H), 1.54-1.67 (m, 2 H), 1.70-1.81 (m, 2 H), 2.41-2.55 (m, 2 H), 3.99-4.20 (m, 1 H), 4.81 (s, 2 H), 7.23-7.34 (m, 2 H), 7.35-7.41 (m, 2 H), 7.50 (dd, J=7.7, 0.94, 1 H), 7.54 (dt, J=7.6, 1.32, 1 H), 7.70 (dt, J=7.6, 1.4, 1 H), 7.91 (dd, J=7.7, 1.1, 1 H)

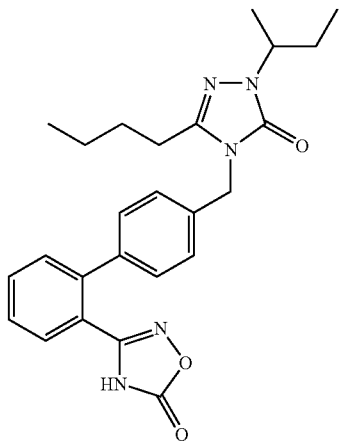

181b) 3-{4'-[(3-butyl-1-sec-butyl-5-oxo-1,5-dihydro-4H-1,2,4-triazol-4-yl)methyl]biphenyl-2-yl}-1,2,4-oxadiazol-5(4H)-one A mixture of hydroxylammonium chloride (0.93 g), sodium hydrogen carbonate (1.33 g) and dimethyl sulfoxide (10 mL) was stirred at 40° C. for 30 min, 4'-[(3-butyl-1-sec-butyl-5-oxo-1,5-dihydro-4H-1,2,4-triazol-4-yl)methyl]biphenyl-2-carbonitrile (0.61 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), N,N'-carbonyldiimidazole (0.10 g) and then 1,8-diazabicyclo[5.4.0]undec-7-ene (0.09 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.14 g, 20%).

$^1$H NMR (300 MHz, CDCl$_3$) δ 0.77 (t, J=7.4, 3 H), 0.87 (t, J=7.3, 3 H), 1.27 (d, J=6.8, 3 H), 1.30-1.39 (m, 2 H), 1.48-1.65 (m, 2 H), 1.67-1.81 (m, 2 H), 2.37-2.45 (m, 2 H), 3.96-4.10 (m, 1 H), 4.75 (s, 2 H), 7.17-7.21 (m, 2 H), 7.30-7.34 (m, 2 H), 7.42 (dd, J=7.7, 0.9, 1 H), 7.49 (td, J=7.6, 1.3, 1 H), 7.61 (td, J=7.6, 1.4, 1 H), 7.74 (dd, J=7.7, 1.1, 1 H), 12.38 (s, 1 H)

Example 182

3-{4'-[(3-butyl-5-oxo-1-phenyl-1,5-dihydro-4H-1,2,4-triazol-4-yl)methyl]biphenyl-2-yl}-1,2,4-oxadiazol-5(4H)-one

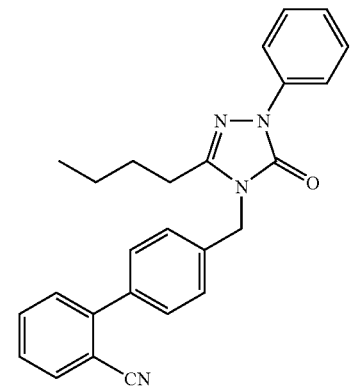

182a) 4'-[(3-butyl-5-oxo-1-phenyl-1,5-dihydro-4H-1,2,4-triazol-4-yl)methyl]biphenyl-2-carbonitrile A mixture of 4'-[(3-butyl-5-oxo-1,5-dihydro-4H-1,2,4-triazol-4-yl)methyl]biphenyl-2-carbonitrile (1.80 g), phenylboronic acid (1.98 g), molecular sieves 4 A (0.90 g), triethylamine (3.8 mL), pyridine (1.8 mL), copper(II) acetate (1.97 g) and methylene chloride (120 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless solid (1.26 g, 57%).

$^1$H NMR (300 MHz, CDCl$_3$) δ 0.91 (t, J=7.5, 3 H), 1.31-1.47 (m, 2 H), 1.59-1.75 (m, 2 H), 2.53-2.60 (m, 2 H), 5.07 (s, 2 H), 7.33 (t, J=7.4, 1 H), 7.42 (s, 4 H), 7.43-7.51 (m, 3 H), 7.56 (d, J=6.8, 1 H), 7.66-7.71 (m, 2 H), 7.96 (d, J=7.7, 2 H)

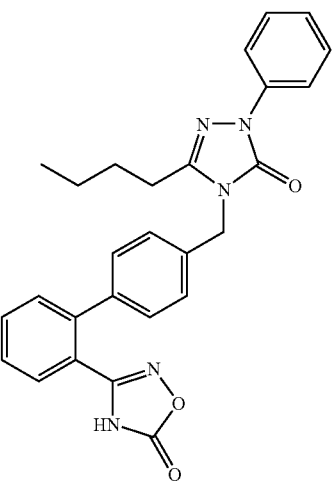

182b) 3-{4'-[(3-butyl-5-oxo-1-phenyl-1,5-dihydro-4H-1,2,4-triazol-4-yl)methyl]biphenyl-2-yl}-1,2,4-oxadiazol-5(4H)-one A mixture of hydroxylammonium chloride (3.20 g), sodium hydrogen carbonate (4.55 g) and dimethyl sulfoxide (20 mL) was stirred at 40° C. for 30 min, 4'-[(3-butyl-5-oxo-1-phenyl-1,5-dihydro-4H-1,2,4-triazol-4-yl)methyl]biphenyl-2-carbonitrile (1.26 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (30 mL), N,N'-carbonyldiimidazole (0.58 g) and then 1,8-diazabicyclo[5.4.0]undec-7-ene (0.54 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.85 g, 34%).

$^1$H NMR (300 MHz, DMSO-d$_6$) δ 0.84 (t, J=7.4, 3 H), 1.26-1.41 (m, 2 H), 1.49-1.62 (m, 2 H), 2.53-2.60 (m, 2 H), 4.97 (s, 2 H), 7.22 (t, J=7.4, 1 H), 7.33 (s, 4 H), 7.43-7.51 (m, 3 H), 7.54 (d, J=6.8, 1 H), 7.62-7.68 (m, 2 H), 7.94 (d, J=7.7, 2 H), 12.39 (s, 1 H)

Example 183

3-(4'-{[3-butyl-5-oxo-1-(tetrahydro-2H-pyran-2-ylmethyl)-1,5-dihydro-4H-1,2,4-triazol-4-yl]methyl}biphenyl-2-yl)-1,2,4-oxadiazol-5(4H)-one

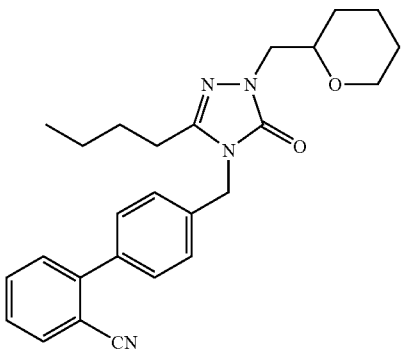

183a) 4'-{[3-butyl-5-oxo-1-(tetrahydro-2H-pyran-2-ylmethyl)-1,5-dihydro-4H-1,2,4-triazol-4-yl]methyl}biphenyl-2-carbonitrile A mixture of 4'-[(3-butyl-5-oxo-1,5-dihydro-4H-1,2,4-triazol-4-yl)methyl]biphenyl-2-carbonitrile (1.13 g), potassium carbonate (0.94 g), 2-(bromomethyl)tetrahydro-2H-pyran (0.90 g) and N,N-dimethylformamide (20 mL) was stirred at 90° C. for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.55 g, 38%).

$^1$H NMR (300 MHz, CDCl$_3$) δ 0.87 (t, J=7.4, 3 H), 1.20-1.40 (m, 4 H), 1.46-1.68 (m, 5 H), 1.85 (dd, J=6.8, 3.0, 1 H), 2.40-2.47 (m, 2 H), 3.40 (td, J=11.3, 2.1, 1 H), 3.70-3.79 (m, 2 H), 3.89-4.03 (m, 2 H), 4.90 (s, 2 H), 7.35-7.41 (m, 2 H), 7.41-7.58 (m, 4 H), 7.65 (td, J=7.7, 1.3, 1 H), 7.75 (dd, J=7.8, 1.0, 1 H)

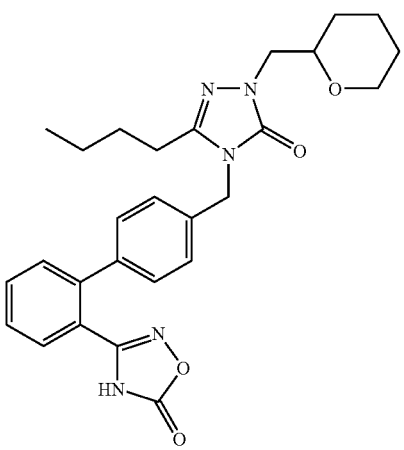

183b) 3-(4'-{[3-butyl-5-oxo-1-(tetrahydro-2H-pyran-2-ylmethyl)-1,5-dihydro-4H-1,2,4-triazol-4-yl]methyl}biphenyl-2-yl)-1,2,4-oxadiazol-5(4H)-one A mixture of hydroxylammonium chloride (0.76 g), sodium hydrogen carbonate (1.08 g) and dimethyl sulfoxide (10 mL) was stirred at 40° C. for 30 min, 4'-{[3-butyl-5-oxo-1-(tetrahydro-2H-pyran-2-ylmethyl)-1,5-dihydro-4H-1,2,4-triazol-4-yl]methyl}biphenyl-2-carbonitrile (0.55 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.31 g) and then 1,8-diazabicyclo[5.4.0]undec-7-ene (0.29 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.33 g, 53%).

$^1$H NMR (300 MHz, DMSO-d$_6$) δ 0.80 (t, J=7.3, 3 H), 1.15-1.34 (m, 3 H), 1.36-1.50 (m, 4 H), 1.52-1.61 (m, 1 H), 1.72-1.81 (m, 1 H), 2.39-2.46 (m, 2 H), 3.22-3.34 (m, 2 H), 3.52-3.65 (m, 2 H), 3.70-3.87 (m, 2 H), 4.86 (s, 2 H), 7.17-7.34 (m, 4 H), 7.50-7.55 (m, 1 H), 7.58 (dd, J=7.4, 1.2, 1 H), 7.62-7.74 (m, 2 H), 12.41 (s, 1 H)

Example 184

5-{[3-fluoro-2'-(5-oxo-4,5-dihydro-1,2,4-oxadiazol-3-yl)biphenyl-4-yl]methyl}-3-(2-hydroxy-3,3-dimethylbutyl)-2-methyl-6-propylpyrimidin-4(3H)-one

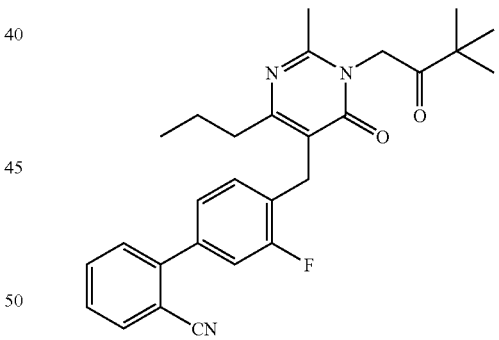

184a) 4'-{[1-(3,3-dimethyl-2-oxobutyl)-2-methyl-6-oxo-4-propyl-1,6-dihydropyrimidin-5-yl]methyl}-3'-fluorobiphenyl-2-carbonitrile A mixture of 3'-fluoro-4'-[(2-methyl-6-oxo-4-propyl-1,6-dihydropyrimidin-5-yl)methyl]biphenyl-2-carbonitrile (2.04 g), 1-bromo-3,3-dimethylbutan-2-one (1.53 g), potassium carbonate (1.59 g) and N,N-dimethylformamide (30 mL) was stirred at room temperature for 4 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.67 g, 26%).

¹H NMR (300 MHz, CDCl₃) δ 0.93 (t, J=7.4, 3 H), 1.28 (s, 9 H), 1.56-1.70 (m, 2 H), 2.33 (s, 3 H), 2.50-2.57 (m, 2 H), 3.96 (s, 2 H), 5.09 (s, 2 H), 7.19-7.27 (m, 3 H), 7.37-7.47 (m, 2 H), 7.60 (t, J=7.6, 1 H), 7.71 (d, J=7.6, 1 H)

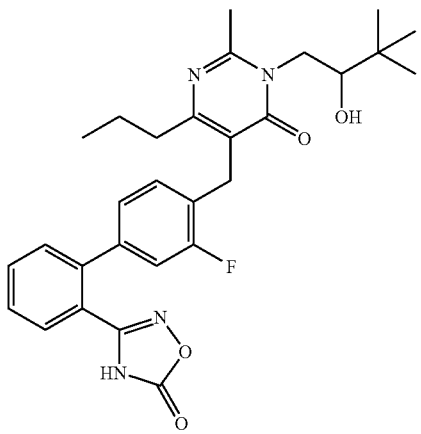

184b) 5-{[3-fluoro-2'-(5-oxo-4,5-dihydro-1,2,4-oxa-diazol-3-yl)biphenyl-4-yl]methyl}-3-(2-hydroxy-3,3-dimethylbutyl)-2-methyl-6-propylpyrimidin-4(3H)-one A mixture of 4'-{[1-(3,3-dimethyl-2-oxobutyl)-2-methyl-6-oxo-4-propyl-1,6-dihydropyrimidin-5-yl]methyl}-3'-fluorobiphenyl-2-carbonitrile (0.67 g), sodium borohydride (0.17 g) and methanol was stirred at room temperature for 12 hr. The reaction mixture was diluted with ethyl acetate, washed with water and then with saturated brine, and dried over anhydrous magnesium sulfate. The solvent was evaporated under reduced pressure. A mixture of hydroxylammonium chloride (0.76 g), sodium hydrogen carbonate (1.08 g) and dimethyl sulfoxide (10 mL) was stirred at 40° C. for 30 min, the concentrate was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (15 mL), N,N'-carbonyldiimidazole (0.31 g) and then 1,8-diazabicyclo[5.4.0]undec-7-ene (0.29 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.51 g, 67%).

¹H NMR (300 MHz, DMSO-d₆) δ 0.84 (t, J=7.2, 3 H), 0.93 (s, 9 H), 1.43-1.57 (m, 2 H), 2.38-2.45 (m, 2 H), 2.56 (s, 3 H), 3.41-3.50 (m, 1 H), 3.64 (dd, J=13.1, 10.4, 1 H), 3.76-3.91 (m, 2 H), 4.23 (d, J=12.1, 2 H), 5.02 (d, J=5.7, 1 H), 6.99 (dd, J=8.0, 1.14, 1 H), 7.06-7.17 (m, 2 H), 7.53 (d, J=8.0, 1 H), 7.59 (d, J=7.2, 1 H), 7.65-7.73 (m, 2 H), 12.44 (s, 1 H)

Example 185

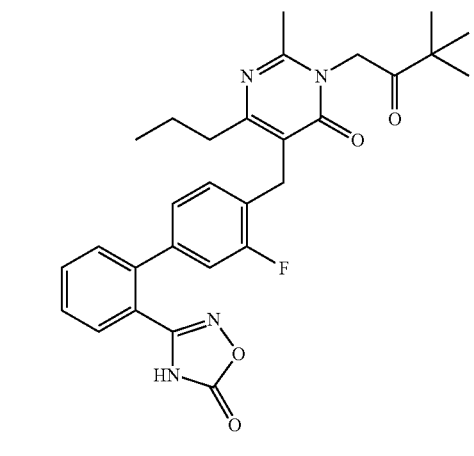

3-(3,3-dimethyl-2-oxobutyl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one A mixture of 5-{[3-fluoro-2'-(5-oxo-4,5-dihydro-1,2,4-oxadiazol-3-yl)biphenyl-4-yl]methyl}-3-(2-hydroxy-3,3-dimethylbutyl)-2-methyl-6-propylpyrimidin-4(3H)-one (0.28 g), 1,1,1-tris(acetyloxy)-1,1-dihydro-1,2-benziodoxol-3(1H)-one (0.34 g) and methylene chloride (15 mL) was stirred at room temperature for 2 hr. Saturated aqueous sodium hydrogen carbonate and sodium thiosulfate pentahydrate were added to the reaction mixture, and the mixture was stirred at room temperature for 2 hr. The reaction mixture was diluted with chloroform, washed with water and then with saturated brine, and dried over anhydrous magnesium sulfate. The solvent was evaporated under reduced pressure and the residue was purified by silica gel column chromatography to give the title compound as colorless crystals (0.15 g, 53%).

¹H NMR (300 MHz, DMSO-d₆) δ 0.85 (t, J=7.4, 3 H), 1.21 (s, 9 H), 1.46-1.59 (m, 2 H), 2.29 (s, 3 H), 2.42-2.49 (m, 2 H), 3.83 (s, 2 H), 5.16 (s, 2 H), 6.98-7.09 (m, 2 H), 7.13 (dd, J=11.0, 1.5, 1 H), 7.51-7.61 (m, 2 H), 7.65-7.73 (m, 2 H), 12.44 (s, 1 H)

Example 186

6-butyl-2-methyl-5-{[2'-(5-oxo-4,5-dihydro-1,2,4-oxadiazol-3-yl)biphenyl-4-yl]methyl}-3-phenylpyrimidin-4(3H)-one

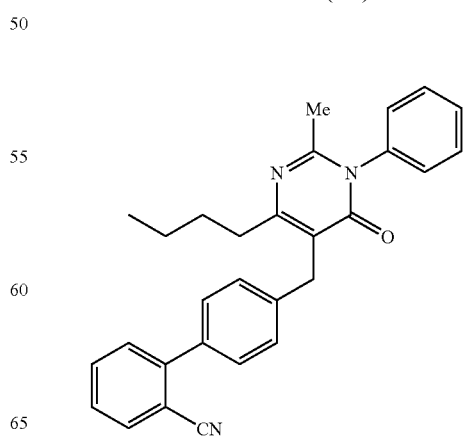

186a) 4'-[(4-butyl-2-methyl-6-oxo-1-phenyl-1,6-dihydropyrimidin-5-yl)methyl]biphenyl-2-carbonitrile To a suspension of 4'-[(4-butyl-2-methyl-6-oxo-1,6-dihydropyrimidin-5-yl)methyl]biphenyl-2-carbonitrile (1.0 g), phenylboronic acid (1.02 g), triethylamine (1.95 mL), pyridine (1.13 mL) and molecular sieves 4 A (1.0 g) in methylene chloride (15 mL) was added copper(II) acetate (1.02 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.28 g, 23%).

$^1$H NMR (300 MHz, CDCl$_3$) δ 0.95 (t, J=7.3, 3 H), 1.33-1.71 (m, 4 H), 2.16 (s, 3 H), 2.57-2.75 (m, 2 H), 3.97 (s, 2 H), 7.19-7.81 (m, 13 H)

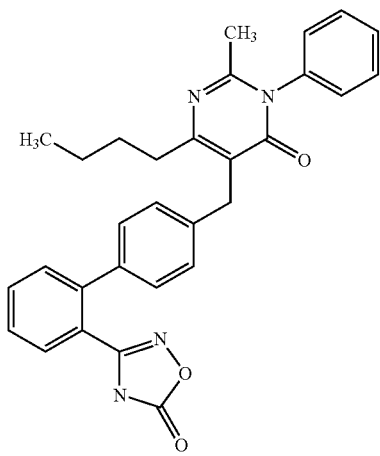

186b) 6-butyl-2-methyl-5-{[2'-(5-oxo-4,5-dihydro-1,2,4-oxadiazol-3-yl)biphenyl-4-yl]methyl}-3-phenylpyrimidin-4(3H)-one A mixture of hydroxylammonium chloride (0.36 g), sodium hydrogen carbonate (0.55 g) and dimethyl sulfoxide (5 mL) was stirred at 40° C. for 30 min, 4'-[(4-butyl-2-methyl-6-oxo-1-phenyl-1,6-dihydropyrimidin-5-yl)methyl]biphenyl-2-carbonitrile (0.28 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (5 mL), N,N'-carbonyldiimidazole (0.11 g) and then 1,8-diazabicyclo[5.4.0]undec-7-ene (0.104 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.13 g, 41%).

$^1$H NMR (300 MHz, CDCl$_3$) δ 0.97 (t, J=7.3, 3 H), 1.35-1.79 (m, 4 H), 2.11 (s, 3 H), 2.62-2.76 (m, 2 H), 3.87 (s, 2 H), 7.11-7.76 (m, 14 H)

Example 187

6-butyl-2-methyl-3-(4-methylphenyl)-5-{[2'-(5-oxo-4,5-dihydro-1,2,4-oxadiazol-3-yl)biphenyl-4-yl]methyl}pyrimidin-4(3H)-one

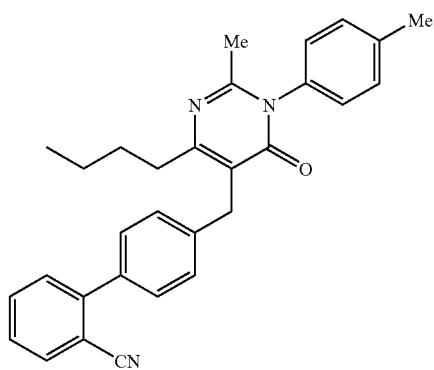

187a) 4'-{[4-butyl-2-methyl-1-(4-methylphenyl)-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 4-methylphenylboronic acid (1.0 g), triethylamine (2.0 mL), pyridine (1.0 mL) and molecular sieves 4 A (1.0 g) in tetrahydrofuran (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.98 g, 78%).

$^1$H NMR (300 MHz, CDCl$_3$) δ 0.94 (t, J=7.3, 3 H), 1.31-1.77 (m, 4 H), 2.17 (s, 3 H), 2.41 (s, 3 H), 2.56-2.76 (m, 2 H), 3.97 (s, 2 H), 7.02-7.81 (m, 12 H)

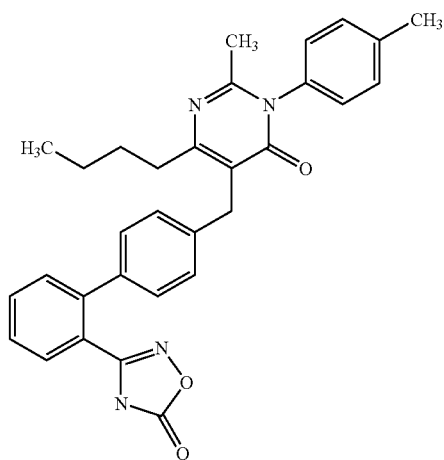

187b) 6-butyl-2-methyl-3-(4-methylphenyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.2 g), sodium hydrogen carbonate (1.8 g) and dimethyl sulfoxide (10 mL) was stirred at 40° C. for 30 min, 4'-{[4-butyl-2-methyl-1-(4-methylphenyl)-6-oxo-1,6-dihydropyrimidin-5-yl]methyl}biphenyl-2-carbonitrile (0.98 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.45 g) and then 1,8-diazabicyclo[5.4.0]undec-7-ene (0.42 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.77 g, 70%).

$^1$H NMR (300 MHz, CDCl$_3$) δ 0.97 (t, J=7.3, 3 H), 1.32-1.84 (m, 4 H), 2.13 (s, 3 H), 2.39 (s, 3 H), 2.62-2.79 (m, 2 H), 3.89 (s, 2 H), 6.85-7.94 (m, 13 H)

Example 188

6-butyl-2-methyl-3-(3-methylphenyl)-5-{[2'-(5-oxo-4,5-dihydro-1,2,4-oxadiazol-3-yl)biphenyl-4-yl]methyl}pyrimidin-4(3H)-one

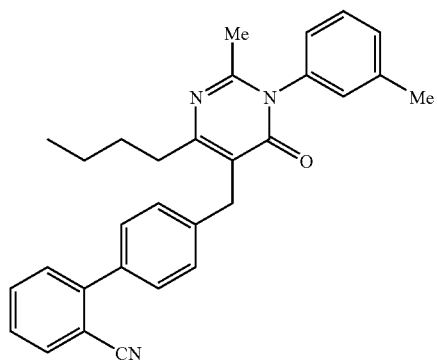

188a) 4'-{[4-butyl-2-methyl-1-(3-methylphenyl)-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 3-methylphenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.29 g, 99%).

$^1$H NMR (300 MHz, CDCl$_3$) δ 0.94 (t, J=7.3, 3 H), 1.33-1.72 (m, 4 H), 2.17 (s, 3 H), 2.40 (s, 3 H), 2.61-2.74 (m, 2 H), 3.97 (s, 2 H), 6.98-7.78 (m, 12 H)

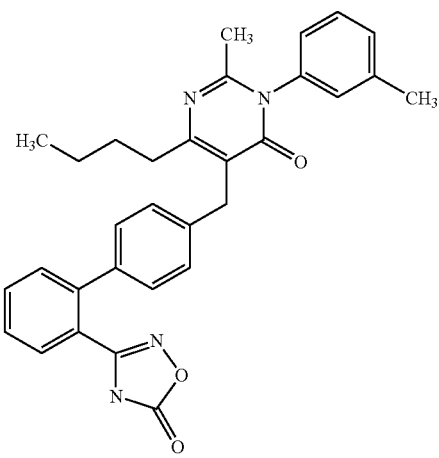

188b) 6-butyl-2-methyl-3-(3-methylphenyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.6 g), sodium hydrogen carbonate (2.4 g) and dimethyl sulfoxide (15 mL) was stirred at 40° C. for 30 min, 4'-{[4-butyl-2-methyl-1-(3-methylphenyl)-6-oxo-1,6-dihydropyrimidin-5-yl]methyl}biphenyl-2-carbonitrile (1.29 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.52 g) and then 1,8-diazabicyclo[5.4.0]undec-7-ene (0.48 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.88 g, 60%).

$^1$H NMR (300 MHz, CDCl$_3$) δ 0.96 (t, J=7.3, 3 H), 1.36-1.82 (m, 4 H), 2.10 (s, 3 H), 2.34 (s, 3 H), 2.58-2.75 (m, 2 H), 3.86 (s, 2 H), 6.82-7.88 (m, 12 H), 8.49-9.32 (m, 1 H)

Example 189

6-butyl-3-(3-isopropylphenyl)-2-methyl-5-{[2'-(5-oxo-4,5-dihydro-1,2,4-oxadiazol-3-yl)biphenyl-4-yl]methyl}pyrimidin-4(3H)-one

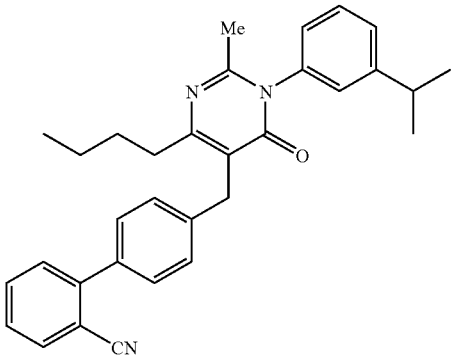

189a) 4'-{[4-butyl-1-(3-isopropylphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 3-isopropylphenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.04 g, 78%).

$^1$H NMR (300 MHz, CDCl$_3$) δ 0.94 (t, J=7.3, 3 H), 1.27 (dd, J=6.9, 1.6, 6 H), 1.34-1.70 (m, 4 H), 2.15 (s, 3 H), 2.57-2.74 (m, 2 H), 2.87-3.06 (m, 1 H), 3.91-4.05 (m, 2 H), 7.00-7.79 (m, 12 H)

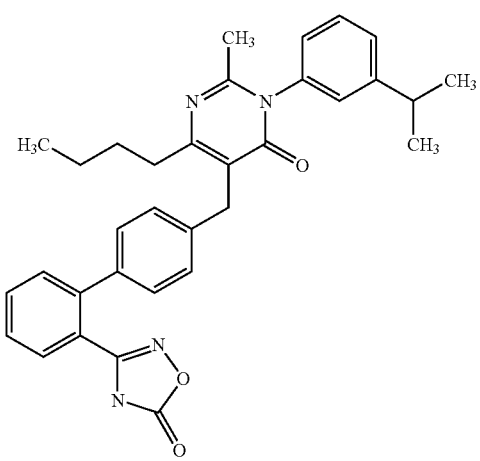

189b) 6-butyl-3-(3-isopropylphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.2 g), sodium hydrogen carbonate (1.8 g) and dimethyl sulfoxide (10 mL) was stirred at 40° C. for 30 min, 4'-{[4-butyl-1-(3-isopropylphenyl)-2-methyl-6-oxo-1,6-dihydropyrimidin-5-yl]methyl}biphenyl-2-carbonitrile (1.04 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.41 g) and then 1,8-diazabicyclo[5.4.0]undec-7-ene (0.37 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.66 g, 57%).

$^1$H NMR (300 MHz, CDCl$_3$) δ 0.96 (t, J=7.3, 3 H), 1.22 (d, J=4.1, 3 H), 1.24 (d, J=4.1, 3 H), 1.36-1.75 (m, 4 H), 2.11 (s, 3 H), 2.63-2.72 (m, 2 H), 2.84-3.02 (m, 1 H), 3.80-3.94 (m, 2 H), 6.90-7.75 (m, 12 H), 9.09 (s, 1 H)

Example 190

6-butyl-3-(3-chlorophenyl)-2-methyl-5-{[2'-(5-oxo-4,5-dihydro-1,2,4-oxadiazol-3-yl)biphenyl-4-yl]methyl}pyrimidin-4(3H)-one

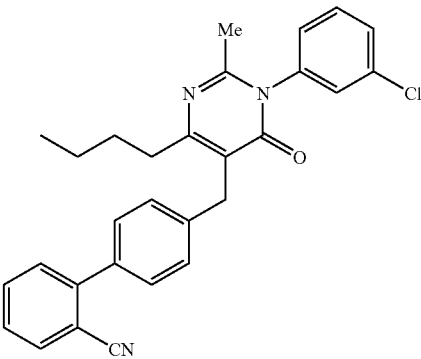

190a) 4'-{[4-butyl-1-(3-chlorophenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 3-chlorophenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow viscous substance (0.96 g, 73%).

$^1$H NMR (300 MHz, CDCl$_3$) δ 0.95 (t, J=7.3, 3 H), 1.35-1.70 (m, 4 H), 2.18 (s, 3 H), 2.61-2.73 (m, 2 H), 3.96 (s, 2 H), 7.10-7.78 (m, 12 H)

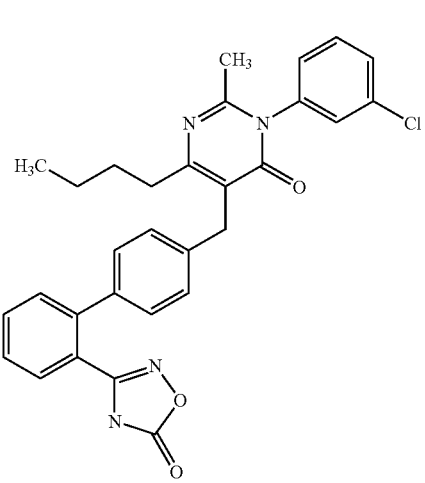

190b) 6-butyl-3-(3-chlorophenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.2 g), sodium hydrogen carbonate (1.8 g) and dimethyl sulfoxide (10 mL) was stirred at 40° C. for 30 min, 4'-{[4-butyl-1-(3-chlorophenyl)-2-methyl-6-oxo-1,6-dihydropyrimidin-5-yl]methyl}biphenyl-2-carbonitrile (0.96 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.41 g) and then 1,8-diazabicyclo[5.4.0]undec-7-ene (0.37 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.65 g, 60%).

$^1$H NMR (300 MHz, CDCl$_3$) δ 0.96 (t, J=7.3, 3 H), 1.33-1.80 (m, 4 H), 2.13 (s, 3 H), 2.60-2.84 (m, 2 H), 3.76-3.99 (m, 2 H), 6.95-7.84 (m, 12 H), 8.90 (s, 1 H)

Example 191

6-butyl-3-(3-methoxyphenyl)-2-methyl-5-{[2'-(5-oxo-4,5-dihydro-1,2,4-oxadiazol-3-yl)biphenyl-4-yl]methyl}pyrimidin-4(3H)-one

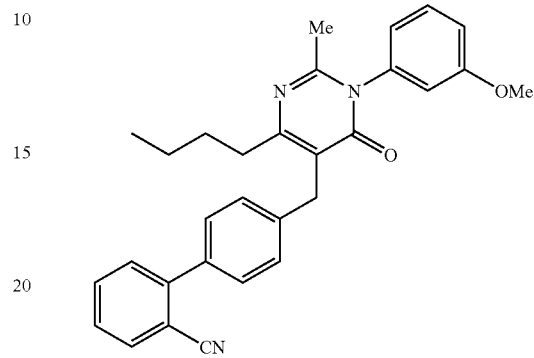

191a) 4'-{[4-butyl-1-(3-methoxyphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 3-methoxyphenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.43 g, 33%).

$^1$H NMR (300 MHz, CDCl$_3$) δ 0.95 (t, J=7.3, 3 H), 1.31-1.75 (m, 4 H), 2.19 (s, 3 H), 2.56-2.78 (m, 2 H), 3.83 (s, 3 H), 3.97 (s, 2 H), 6.70-7.84 (m, 12 H)

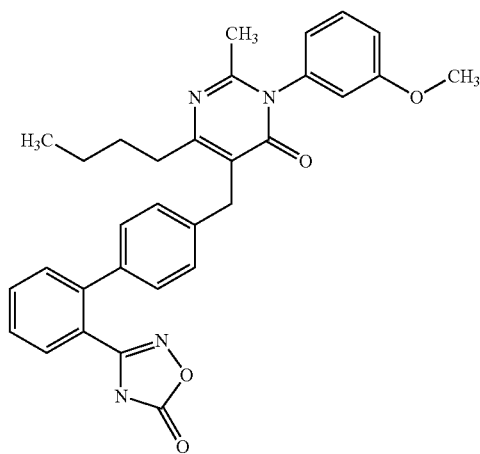

191b) 6-butyl-3-(3-methoxyphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.52 g), sodium hydrogen carbonate (0.77 g) and dimethyl sulfoxide (5 mL) was stirred at 40° C. for 30 min, 4'-{[4-butyl-1-(3-methoxyphenyl)-2-methyl-6-oxo-1,6-dihydropyrimidin-5-yl]methyl}biphenyl-2-carbonitrile (0.43 g) was added, and the mixture was stirred at 90° C. for 18 hr. The reaction mixture was allowed to cool to room temperature, ethyl acetate and water were added, and the aqueous layer was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.19 g) and then 1,8-diazabicyclo[5.4.0]undec-7-ene (0.18 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.23 g, 47%).

$^1$H NMR (300 MHz, CDCl$_3$) δ 0.96 (t, J=7.3, 3 H), 1.33-1.77 (m, 4 H), 2.13 (s, 3 H), 2.58-2.75 (m, 2 H), 3.77 (s, 3 H), 3.87 (s, 2 H), 6.63-7.74 (m, 12 H), 8.71 (s, 1 H)

Example 192

6-butyl-3-(2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one

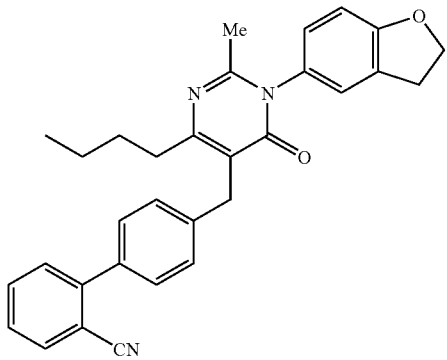

192a) 4'-{[4-butyl-1-(2,3-dihydro-1-benzofuran-5-yl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 2,3-dihydro-1-benzofuran-5-ylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.20 g, 90%).

$^1$H NMR (300 MHz, CDCl$_3$) δ 0.94 (t, J=7.3, 3 H), 1.33-1.71 (m, 4 H), 2.20 (s, 3 H), 2.56-2.75 (m, 2 H), 3.15-3.36 (m, 2 H), 3.86-4.04 (m, 2 H), 4.54-4.75 (m, 2 H), 6.83-7.79 (m, 11 H)

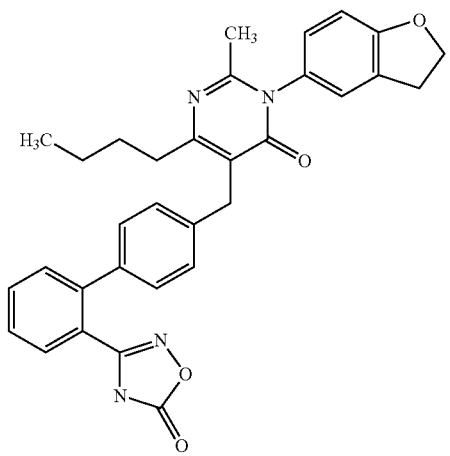

192b) 6-butyl-3-(2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.4 g), sodium hydrogen carbonate (2.1 g) and dimethyl sulfoxide (10 mL) was stirred at 40° C. for 30 min, 4'-{[4-butyl-1-(2,3-dihydro-1-benzofuran-5-yl)-2-methyl-6-oxo-1,6-dihydropyrimidin-5-yl]methyl}biphenyl-2-carbonitrile (1.20 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.56 g) and then 1,8-diazabicyclo[5.4.0]undec-7-ene (0.47 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.74 g, 55%).

$^1$H NMR (300 MHz, CDCl$_3$) δ 0.95 (t, J=7.3, 3 H), 1.33-1.72 (m, 4 H), 2.10 (s, 3 H), 2.53-2.74 (m, 2 H), 3.18 (t, J=8.8, 2 H), 3.74-3.92 (m, 2 H), 4.62 (t, J=8.8, 2 H), 6.62-7.73 (m, 11 H), 9.18 (s, 1 H)

Example 193

6-butyl-2-methyl-3-(2-methylphenyl)-5-{[2'-(5-oxo-4,5-dihydro-1,2,4-oxadiazol-3-yl)biphenyl-4-yl]methyl}pyrimidin-4(3H)-one

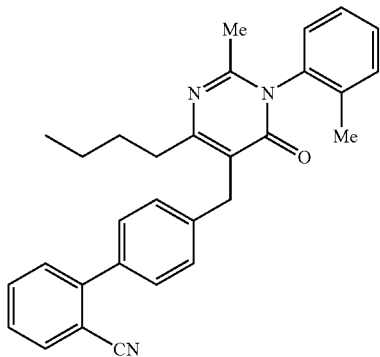

193a) 4'-{[4-butyl-2-methyl-1-(2-methylphenyl)-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 2-methylphenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.12 g, 10%).

$^1$H NMR (300 MHz, CDCl$_3$) δ 0.95 (t, J=7.3, 3 H), 1.31-1.78 (m, 4 H), 2.09 (s, 3 H), 2.10 (s, 3 H), 2.62-2.72 (m, 2 H), 3.99 (s, 2 H), 7.07-7.80 (m, 12 H)

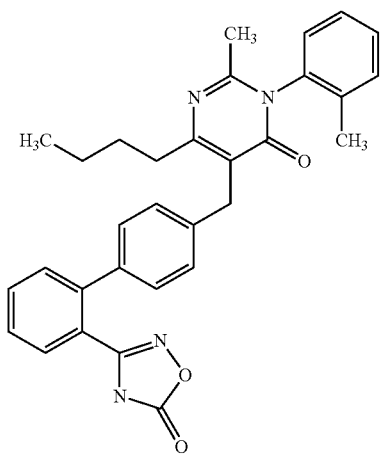

193b) 6-butyl-2-methyl-3-(2-methylphenyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.30 g), sodium hydrogen carbonate (0.45 g) and dimethyl sulfoxide (3 mL) was stirred at 40° C. for 30 min, 4'-{[4-butyl-2-methyl-1-(2-methylphenyl)-6-oxo-1,6-dihydropyrimidin-5-yl]methyl}biphenyl-2-carbonitrile (0.24 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (4 mL), N,N'-carbonyldiimidazole (0.086 g) and then 1,8-diazabicyclo[5.4.0]undec-7-ene (0.079 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.11 g, 42%).

$^1$H NMR (300 MHz, CDCl$_3$) δ 0.96 (t, J=7.3, 3 H), 1.30-1.77 (m, 4 H), 1.95 (s, 3 H), 2.03 (s, 3 H), 2.59-2.70 (m, 2 H), 3.81-3.96 (m, 2 H), 6.96-7.74 (m, 12 H), 8.74 (s, 1 H)

Example 194

6-butyl-3-(3,5-dichlorophenyl)-2-methyl-5-{[2'-(5-oxo-4,5-dihydro-1,2,4-oxadiazol-3-yl)biphenyl-4-yl]methyl}pyrimidin-4(3H)-one

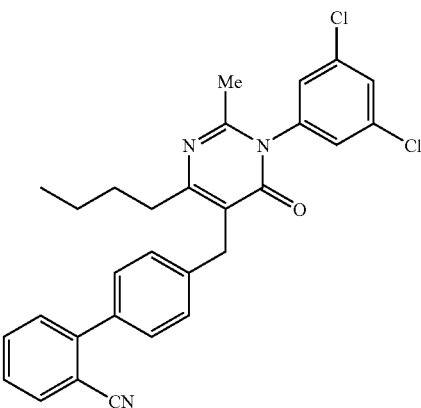

194a) 4'-{[4-butyl-1-(3,5-dichlorophenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), (3,5-dichlorophenyl)boronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow viscous substance (0.49 g, 35%).

$^1$H NMR (300 MHz, CDCl$_3$) δ 0.94 (t, J=7.3, 3 H), 1.31-1.70 (m, 4 H), 2.20 (s, 3 H), 2.61-2.73 (m, 2 H), 3.95 (s, 2 H), 7.17-7.79 (m, 11 H)

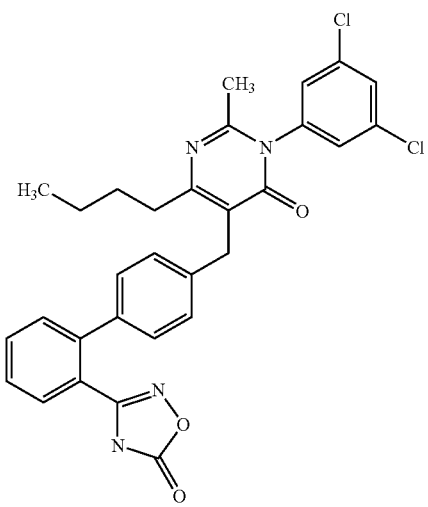

194b) 6-butyl-3-(3,5-dichlorophenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.54 g), sodium hydrogen carbonate (0.82 g) and dimethyl sulfoxide (5 mL) was stirred at 40° C. for 30 min, 4'-{[4-butyl-1-(3,5-dichlorophenyl)-2-methyl-6-oxo-1,6-dihydropyrimidin-5-yl]methyl}biphenyl-2-carbonitrile (0.49 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (1 mL), N,N'-carbonyldiimidazole (0.018 g) and then 1,8-diazabicyclo[5.4.0]undec-7-ene (0.016 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.029 g, 5%).

$^1$H NMR (300 MHz, CDCl$_3$) δ 0.96 (t, J=7.3, 3 H), 1.35-1.75 (m, 4 H), 2.16 (s, 3 H), 2.63-2.76 (m, 2 H), 3.88 (s, 2 H), 7.08-7.83 (m, 12 H)

Example 195

6-butyl-3-(4-chlorophenyl)-2-methyl-5-{[2'-(5-oxo-4,5-dihydro-1,2,4-oxadiazol-3-yl)biphenyl-4-yl]methyl}pyrimidin-4(3H)-one

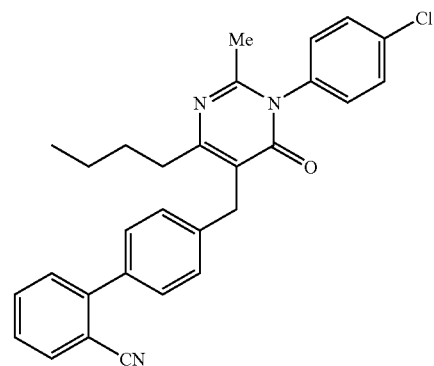

195a) 4'-{[4-butyl-1-(4-chlorophenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 4-chlorophenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow viscous substance (0.68 g, 52%).

$^1$H NMR (300 MHz, CDCl$_3$) δ 0.95 (t, J=7.3, 3 H), 1.30-1.75 (m, 4 H), 2.17 (s, 3 H), 2.52-2.78 (m, 2 H), 3.96 (s, 2 H), 7.03-7.91 (m, 12 H)

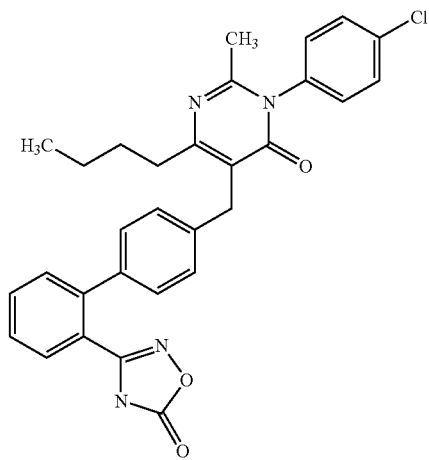

195b) 6-butyl-3-(4-chlorophenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.81 g), sodium hydrogen carbonate (1.23 g) and dimethyl sulfoxide (7 mL) was stirred at 40° C. for 30 min, 4'-{[4-butyl-1-(4-chlorophenyl)-2-methyl-6-oxo-1,6-dihydropyrimidin-5-yl]methyl}biphenyl-2-carbonitrile (0.68 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.28 g) and then 1,8-diazabicyclo[5.4.0]undec-7-ene (0.26 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.42 g, 55%).

$^1$H NMR (300 MHz, CDCl$_3$) δ 0.96 (t, J=7.3, 3 H), 1.33-1.77 (m, 4 H), 2.11 (s, 3 H), 2.56-2.76 (m, 2 H), 3.85 (s, 2 H), 6.87-7.91 (m, 12 H), 8.69 (s, 1 H)

Example 196

6-butyl-2-methyl-3-(2-naphthyl)-5-{[2'-(5-oxo-4,5-dihydro-1,2,4-oxadiazol-3-yl)biphenyl-4-yl]methyl}pyrimidin-4(3H)-one

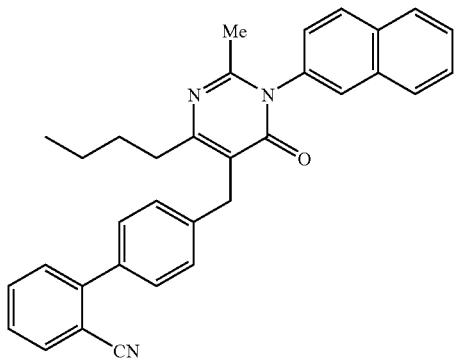

196a) 4'-{[4-butyl-2-methyl-1-(2-naphthyl)-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 2-naphthylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.13 g, 83%).

$^1$H NMR (300 MHz, CDCl$_3$) δ 0.96 (t, J=7.3, 3 H), 1.34-1.73 (m, 4 H), 2.20 (s, 3 H), 2.61-2.82 (m, 2 H), 3.90-4.09 (m, 2 H), 7.29-8.07 (m, 15 H)

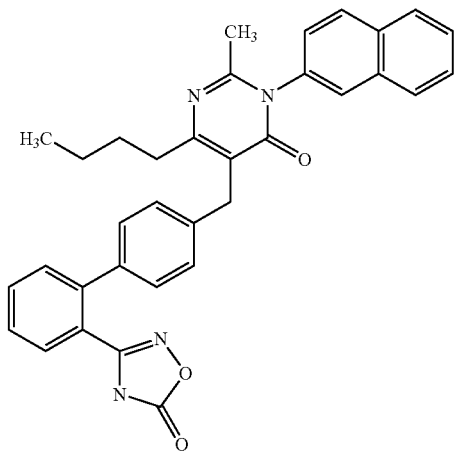

196b) 6-butyl-2-methyl-3-(2-naphthyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.30 g), sodium hydrogen carbonate (1.97 g) and dimethyl sulfoxide (10 mL) was stirred at 40° C. for 30 min, 4'-{[4-butyl-2-methyl-1-(2-naphthyl)-6-oxo-1,6-dihydropyrimidin-5-yl]methyl}biphenyl-2-carbonitrile (1.13 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.46 g) and then 1,8-diazabicyclo[5.4.0]undec-7-ene (0.42 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.89 g, 70%).

$^1$H NMR (300 MHz, DMSO-d$_6$) δ 0.84-0.90 (m, 3 H), 1.25-1.60 (m, 4 H), 2.10 (s, 3 H), 2.53-2.61 (m, 2 H), 3.90 (s, 2 H), 7.17-8.14 (m, 15 H), 12.40 (s, 1 H)

Example 197

6-butyl-3-[3-(2-hydroxyethoxy)phenyl]-2-methyl-5-{[2'-(5-oxo-4,5-dihydro-1,2,4-oxadiazol-3-yl)biphenyl-4-yl]methyl}pyrimidin-4(3H)-one

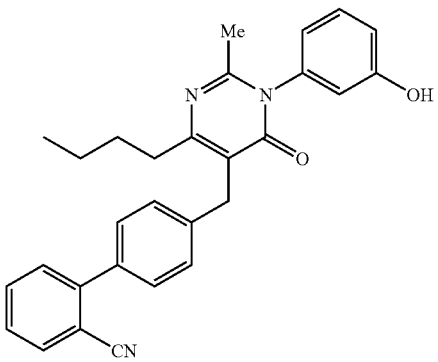

197a) 4'-{[4-butyl-1-(3-hydroxyphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (5.0 g), (3-{[tert-butyl(dimethyl)silyl]oxy}phenyl)boronic acid (9.0 g), triethylamine (10.0 mL), pyridine (5.0 mL) and molecular sieves 4 A (10.0 g) in methylene chloride (100 mL) was added copper(II) acetate (5.0 g), and the mixture was stirred for 2 days. The reaction mixture was diluted with ethyl acetate. The insoluble material was filtered off through celite, and the filtrate was concentrated. The residue was dissolved in tetrahydrofuran (20 mL), tetrabutylammonium fluoride (1.7 g) was added, and the mixture was stirred for 15 hr. Ethyl acetate and water were added to the reaction mixture, and the mixture was extracted with ethyl acetate. The organic layer was washed with saturated brine and dried over anhydrous magnesium sulfate, and the solvent was evaporated. The residue was purified by silica gel column chromatography to give the title compound as a pale-yellow viscous substance (1.71 g, 21%).

$^1$H NMR (300 MHz, CDCl$_3$) δ 0.93 (t, J=7.3, 3 H), 1.30-1.71 (m, 4 H), 2.16 (s, 3 H), 2.50-2.74 (m, 2 H), 4.02 (q, J=15.0, 2 H), 6.37-8.08 (m, 13 H)

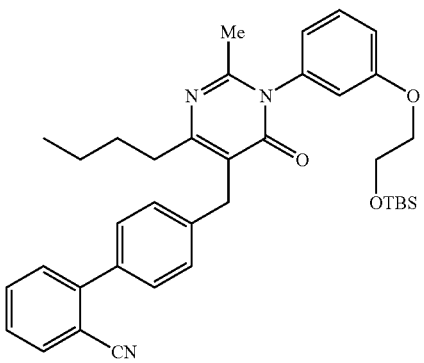

197b) 4'-({4-butyl-1-[3-(2-{[tert-butyl(dimethyl)silyl]oxy}ethoxy)phenyl]-2-methyl-6-oxo-1,6-dihydropyrimidin-5-yl}methyl)biphenyl-2-carbonitrile To a solution of 4'-{[4-butyl-1-(3-hydroxyphenyl)-2-methyl-6-oxo-1,6-dihydropyrimidin-5-yl]methyl}biphenyl-2-carbonitrile (1.0 g) and (2-bromoethoxy)(tert-butyl)dimethylsilane (0.95 mL) in N,N-dimethylformamide (10 mL) was added cesium carbonate (1.45 g), and the mixture was stirred at 60° C. for 15 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was purified by silica gel column chromatography to give the title compound as a pale-yellow viscous substance (1.13 g, 83%).

$^1$H NMR (300 MHz, CDCl$_3$) δ 0.10 (s, 6 H), 0.90 (s, 9 H), 0.95 (t, J=7.3, 3 H), 1.33-1.72 (m, 4 H), 2.19 (s, 3 H), 2.61-2.71 (m, 2 H), 3.92-4.17 (m, 6 H), 6.70-7.79 (m, 12 H)

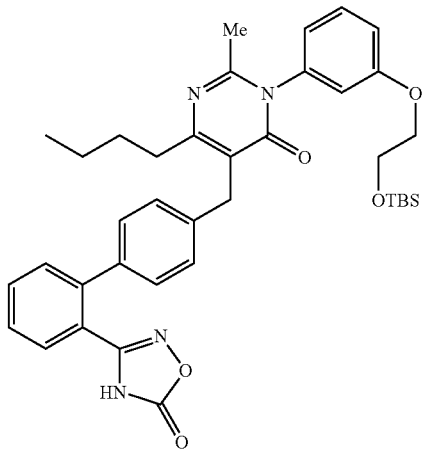

197c) 6-butyl-3-[3-(2-{[tert-butyl(dimethyl)silyl]oxy}ethoxy)phenyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.03 g), sodium hydrogen carbonate (1.55 g) and dimethyl sulfoxide (10 mL) was stirred at 40° C. for 30 min, 4'-({4-butyl-1-[3-(2-{[tert-butyl(dimethyl)silyl]oxy}ethoxy)phenyl]-2-methyl-6-oxo-1,6-dihydropyrimidin-5-yl}methyl)biphenyl-2-carbonitrile (1.13 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.45 g) and then 1,8-diazabicyclo[5.4.0]undec-7-ene (0.42 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a pale-yellow viscous substance (0.95 g, 77%).

431

$^1$H NMR (300 MHz, CDCl$_3$) δ 0.09 (s, 6 H), 0.90 (s, 9 H), 0.96 (t, J=7.2, 3 H), 1.36-1.74 (m, 4 H), 2.14 (s, 3 H), 2.62-2.72 (m, 2 H), 3.83-4.04 (m, 6 H), 6.64-7.78 (m, 12 H), 8.65 (s, 1 H)

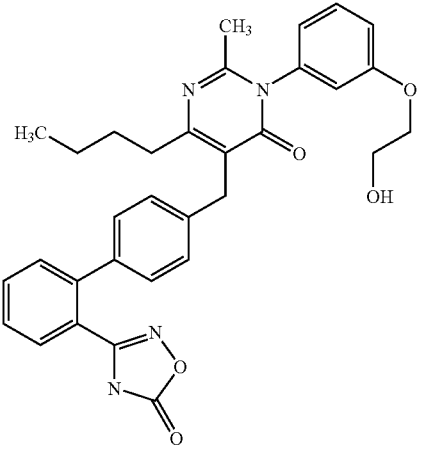

197d) 6-butyl-3-[3-(2-hydroxyethoxy)phenyl]-2-methyl-5-{[2'-(5-oxo-4,5-dihydro-1,2,4-oxadiazol-3-yl)biphenyl-4-yl]methyl}pyrimidin-4(3H)-one To a solution of 6-butyl-3-[3-(2-{[tert-butyl(dimethyl)silyl]oxy}ethoxy)phenyl]-2-methyl-5-{[2'-(5-oxo-4,5-dihydro-1,2,4-oxadiazol-3-yl)biphenyl-4-yl]methyl}pyrimidin-4(3H)-one (0.95 g) in tetrahydrofuran (7 mL) was added tetrabutylammonium fluoride (0.56 g), and the mixture was stirred at 50° C. for 12 hr. The reaction mixture was allowed to cool to room temperature, ethyl acetate and water were added, and the aqueous layer was extracted with ethyl acetate. The organic layer was washed with saturated brine and dried over anhydrous magnesium sulfate, and the solvent was evaporated. The residue was purified by silica gel column chromatography to give the title compound as a colorless solid (0.55 g, 70%).

$^1$H NMR (300 MHz, CDCl$_3$) δ 0.97 (t, J=7.4, 3 H), 1.35-1.80 (m, 4 H), 2.15 (s, 3 H), 2.45-2.82 (m, 3 H), 3.73-4.07 (m, 6 H), 6.57-7.84 (m, 12 H), 9.10 (s, 1 H)

Example 198

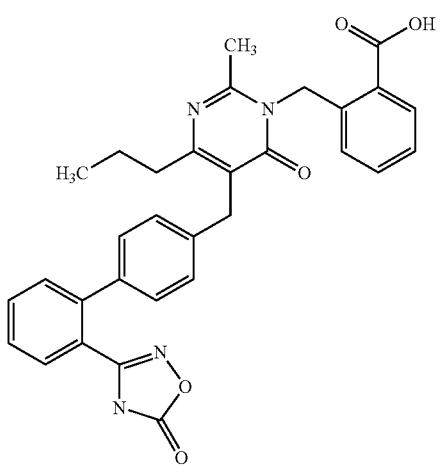

2-{[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]methyl}benzoic acid A mixture of methyl 2-{[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]methyl}benzoate (0.28 g), 2 N aqueous sodium hydroxide solution (5 mL) and methanol (5 mL) was stirred at 50° C. for 3 hr. The reaction mixture was adjusted to pH 4 with water (20 mL) and 1 M hydrochloric acid, and the obtained crystallized product was collected by filtration to give the title compound as colorless crystals (0.22 g, 80%).

$^1$H NMR (300 MHz, DMSO-d$_6$) δ 0.88 (3H, t, J=7.3), 1.44-1.63 (2H, m), 2.33 (3H, s), 2.49-2.56 (2H, m), 3.89 (2H, s), 5.61 (2H, s), 6.66 (1H, d, J=7.7), 7.22 (4H, s), 7.36-7.56 (4H, m), 7.63 (2H, dd, J=7.3, 2.8), 7.99 (1H, d, J=7.5), 12.88 (2H, br)

Example 199

6-butyl-3-[3-(1-hydroxyethyl)phenyl]-2-methyl-5-{[2'-(5-oxo-4,5-dihydro-1,2,4-oxadiazol-3-yl)biphenyl-4-yl]methyl}pyrimidin-4(3H)-one

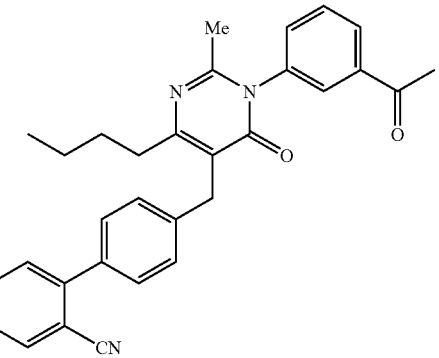

199a) 4'-{[1-(3-acetylphenyl)-4-butyl-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (5.0 g), (3-acetylphenyl)boronic acid (5.0 g), triethylamine (10.0 mL), pyridine (5.0 mL) and molecular sieves 4 A (10.0 g) in methylene chloride (100 mL) was added copper(II) acetate (5.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (2.20 g, 33%).

¹H NMR (300 MHz, CDCl₃) δ 0.95 (t, J=7.3, 3 H), 1.35-1.74 (m, 4 H), 2.17 (s, 3 H), 2.63 (s, 3 H), 2.64-2.73 (m, 2 H), 3.97 (s, 2 H), 7.29-8.12 (m, 12 H)

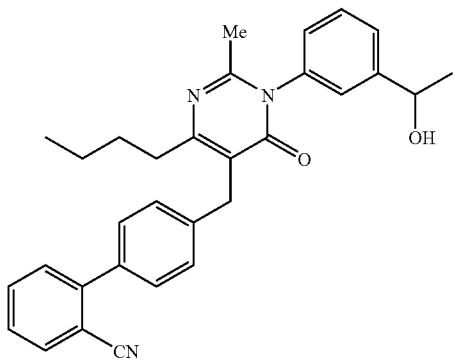

199b) 4'-({4-butyl-1-[3-(1-hydroxyethyl)phenyl]-2-methyl-6-oxo-1,6-dihydropyrimidin-5-yl}methyl)biphenyl-2-carbonitrile To a solution of 4'-{[1-(3-acetylphenyl)-4-butyl-2-methyl-6-oxo-1,6-dihydropyrimidin-5-yl]methyl}biphenyl-2-carbonitrile (2.20 g) in ethanol (20 mL) was added sodium tetrahydroboron (0.18 g), and the mixture was stirred for 3 hr. Ethyl acetate and water were added to the reaction mixture, and the mixture was extracted with ethyl acetate. The organic layer was washed with saturated brine and dried over anhydrous magnesium sulfate, and the solvent was evaporated. The residue was purified by silica gel column chromatography to give the title compound as a pale-yellow viscous substance (1.86 g, 84%).

¹H NMR (300 MHz, CDCl₃) δ 0.95 (t, J=7.3, 3 H), 1.33-1.72 (m, 7 H), 2.06-2.22 (m, 4 H), 2.60-2.74 (m, 2 H), 3.97 (s, 2 H), 4.84-5.02 (m, 1 H), 7.08-7.78 (m, 12 H)

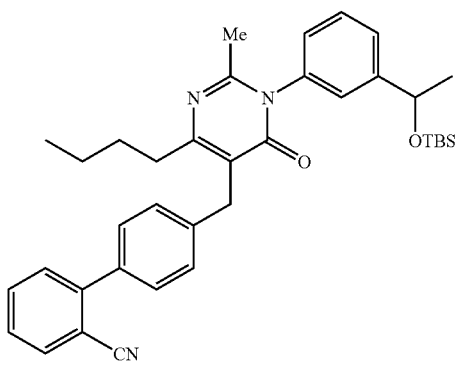

199c) 4'-({4-butyl-1-[3-(1-{[tert-butyl(dimethyl)silyl]oxy}ethyl)phenyl]-2-methyl-6-oxo-1,6-dihydropyrimidin-5-yl}methyl)biphenyl-2-carbonitrile To a solution of 4'-({4-butyl-1-[3-(1-hydroxyethyl)phenyl]-2-methyl-6-oxo-1,6-dihydropyrimidin-5-yl}methyl)biphenyl-2-carbonitrile (1.86 g), triethylamine (1.1 mL) and 4-dimethylaminopyridine (0.15 g) in N,N-dimethylformamide (20 mL) was added tert-butyl(chloro)dimethylsilane (0.88 g), and the mixture was stirred for 15 hr. Ethyl acetate and water were added to the reaction mixture, and the mixture was extracted with ethyl acetate. The organic layer was washed with saturated brine and dried over anhydrous magnesium sulfate, and the solvent was evaporated. The residue was purified by silica gel column chromatography to give the title compound as a pale-yellow viscous substance (1.98 g, 86%).

¹H NMR (300 MHz, CDCl₃) δ −0.02 (d, J=7.9, 3 H), 0.06 (d, J=9.4, 3 H), 0.89 (d, J=5.3, 9 H), 0.95 (t, J=7.3, 3 H), 1.35-1.71 (m, 7 H), 2.14 (d, J=3.2, 3 H), 2.60-2.72 (m, 2 H), 3.89-4.06 (m, 2 H), 4.80-5.00 (m, 1 H), 7.01-7.83 (m, 12 H)

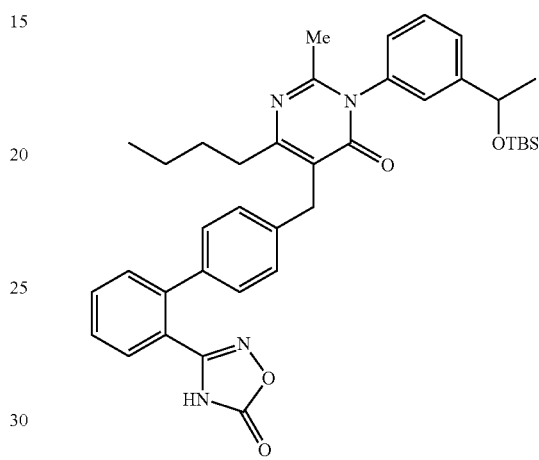

199d) 6-butyl-3-[3-(1-{[tert-butyl(dimethyl)silyl]oxy}ethyl)phenyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.86 g), sodium hydrogen carbonate (2.81 g) and dimethyl sulfoxide (15 mL) was stirred at 40° C. for 30 min, 4'-({4-butyl-1-[3-(1-{[tert-butyl(dimethyl)silyl]oxy}ethyl)phenyl]-2-methyl-6-oxo-1,6-dihydropyrimidin-5-yl}methyl)biphenyl-2-carbonitrile (1.98 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.82 g) and then 1,8-diazabicyclo[5.4.0]undec-7-ene (0.77 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a pale-yellow viscous substance (1.70 g, 78%).

¹H NMR (300 MHz, CDCl₃) δ −0.04 (d, J=9.1, 3 H), 0.05 (d, J=9.1, 3 H), 0.88 (d, J=4.5, 9 H), 0.96 (t, J=7.2, 3 H), 1.35-1.75 (m, 7 H), 2.10 (s, 3 H), 2.61-2.73 (m, 2 H), 3.80-3.97 (m, 2 H), 4.79-4.97 (m, 1 H), 6.93-7.77 (m, 12 H), 8.71 (s, 1 H)

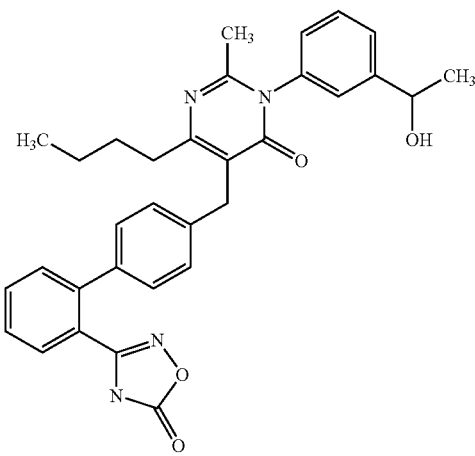

199e) 6-butyl-3-[3-(1-hydroxyethyl)phenyl]-2-methyl-5-{[2'-(5-oxo-4,5-dihydro-1,2,4-oxadiazol-3-yl)biphenyl-4-yl]methyl}pyrimidin-4(3H)-one To a solution of 6-butyl-3-[3-(1-{[tert-butyl(dimethyl)silyl]oxy}ethyl)phenyl]-2-methyl-5-{[2'-(5-oxo-4,5-dihydro-1,2,4-oxadiazol-3-yl)biphenyl-4-yl]methyl}pyrimidin-4(3H)-one (1.70 g) in tetrahydrofuran (10 mL) was added tetrabutylammonium fluoride (1.0 g), and the mixture was stirred at 50° C. for 12 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was purified by silica gel column chromatography to give the title compound as a colorless solid (0.88 g, 63%).
$^1$H NMR (300 MHz, CDCl$_3$) δ 0.98 (t, J=7.4, 3 H), 1.38-1.80 (m, 7 H), 2.13 (d, J=10.6, 3 H), 2.67-2.78 (m, 2 H), 2.99-3.48 (m, 1 H), 3.75-3.95 (m, 2 H), 4.76-4.90 (m, 1 H), 6.92-7.78 (m, 12 H), 9.32 (s, 1 H)

Example 200

3-[4'-({3-butyl-1-[2-(4-fluorophenyl)-2-oxoethyl]-5-oxo-1,5-dihydro-4H-1,2,4-triazol-4-yl}methyl)biphenyl-2-yl]-1,2,4-oxadiazol-5(4H)-one

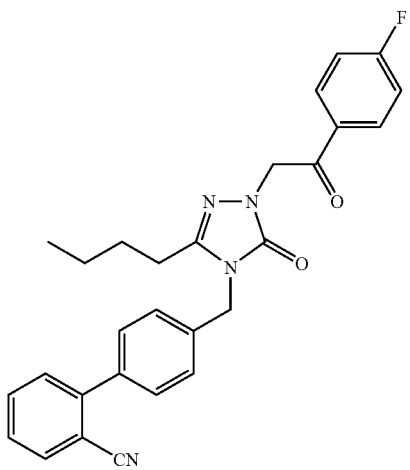

200a) 4'-({3-butyl-1-[2-(4-fluorophenyl)-2-oxoethyl]-5-oxo-1,5-dihydro-4H-1,2,4-triazol-4-yl}methyl)biphenyl-2-carbonitrile A mixture of 4'-[(3-butyl-5-oxo-1,5-dihydro-4H-1,2,4-triazol-4-yl)methyl]biphenyl-2-carbonitrile (0.7 g), potassium tert-butoxide (1.0 M tetrahydrofuran solution, 1.75 mL) and N,N-dimethylformamide (10 mL) was stirred at room temperature for 10 min, 2-bromo-1-(4-fluorophenyl)ethanone (0.35 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.6 g, 88%).
$^1$H NMR (300 MHz, CDCl$_3$) δ 0.87 (3H, t, J=7.3), 1.28-1.41 (2H, m), 1.53-1.67 (2H, m), 2.40-2.50 (2H, m), 4.95 (2H, s), 5.24 (2H, s), 7.13-7.22 (2H, m), 7.39 (2H, d, J=8.1), 7.43-7.52 (2H, m), 7.57 (2H, d, J=8.1), 7.65 (1H, dd, J=7.6, 1.2), 7.74-7.80 (1H, m), 7.97-8.08 (2H, m)

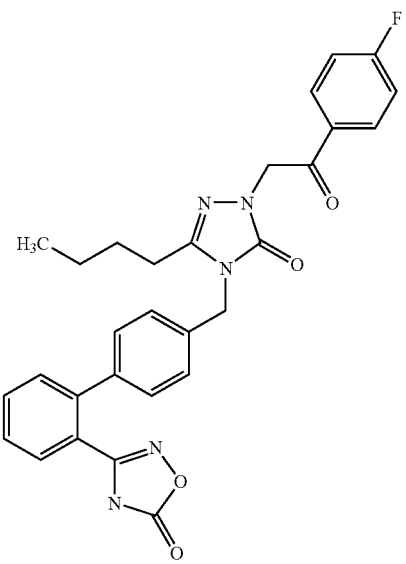

200b) 3-[4'-({3-butyl-1-[2-(4-fluorophenyl)-2-oxoethyl]-5-oxo-1,5-dihydro-4H-1,2,4-triazol-4-yl}methyl)biphenyl-2-yl]-1,2,4-oxadiazol-5(4H)-one A mixture of hydroxylammonium chloride (1.07 g), sodium hydrogen carbonate (1.61 g) and dimethyl sulfoxide (15 mL) was stirred at 40° C. for 30 min, 4'-({3-butyl-1-[2-(4-fluorophenyl)-2-oxoethyl]-5-oxo-1,5-dihydro-4H-1,2,4-triazol-4-yl}methyl)biphenyl-2-carbonitrile (0.6 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (20 mL), N,N'-carbonyldiimidazole (0.24 g) and then 1,8-diazabicyclo[5.4.0]undec-7-ene (0.2 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.2 g, 29%).

$^1$H NMR (300 MHz, DMSO-$d_6$) δ 0.79 (3H, t, J=7.3), 1.21-1.33 (2H, m), 1.36-1.55 (2H, m), 2.41-2.49 (2H, m), 4.93 (2H, s), 5.37 (2H, s), 7.27-7.37 (4H, m), 7.41 (2H, t, J=8.8), 7.51-7.64 (2H, m), 7.64-7.77 (2H, m), 8.12 (2H, dd, J=8.6, 5.6), 12.42 (1H, s)

Example 201

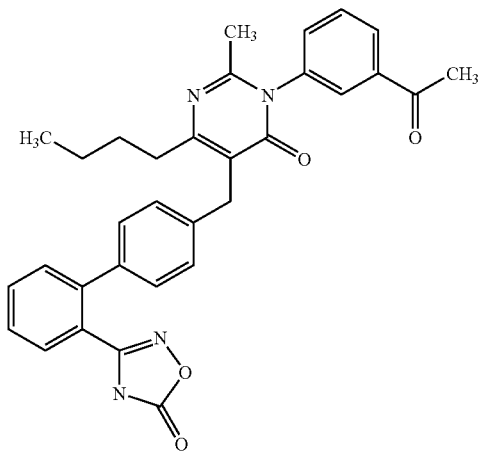

3-(3-acetylphenyl)-6-butyl-2-methyl-5-{[2'-(5-oxo-4,5-dihydro-1,2,4-oxadiazol-3-yl)biphenyl-4-yl]methyl}pyrimidin-4(3H)-one To a solution of 6-butyl-3-[3-(1-hydroxyethyl)phenyl]-2-methyl-5-{[2'-(5-oxo-4,5-dihydro-1,2,4-oxadiazol-3-yl)biphenyl-4-yl]methyl}pyrimidin-4(3H)-one (0.3 g) in acetonitrile (3 mL) was added 1,1,1-tris(acetyloxy)-1,1-dihydro-1,2-benziodoxol-3(1H)-one (0.36 g), and the mixture was stirred for 2 hr. To the reaction mixture were added ethyl acetate, water and sodium thiosulfate, and the mixture was extracted with ethyl acetate. The organic layer was washed with saturated brine and dried over anhydrous magnesium sulfate, and the solvent was evaporated. The residue was purified by silica gel column chromatography to give the title compound as a colorless solid (0.21 g, 71%).

$^1$H NMR (300 MHz, CDCl$_3$) δ 0.97 (t, J=7.4, 3 H), 1.36-1.78 (m, 4 H), 2.13 (s, 3 H), 2.60 (s, 3 H), 2.66-2.77 (m, 2 H), 3.90 (s, 2 H), 7.13-8.08 (m, 12 H), 8.30 (s, 1 H)

Example 202

6-butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one

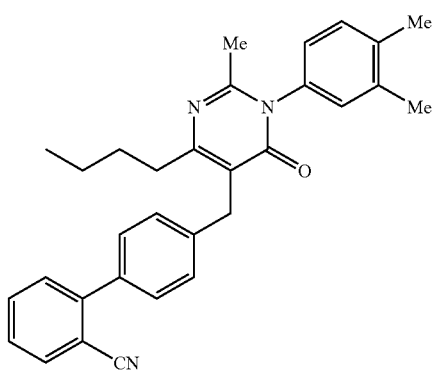

202a) 4'-{[4-butyl-1-(3,4-dimethylphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 3,4-dimethylphenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.27 g, 98%).

$^1$H NMR (300 MHz, CDCl$_3$) δ 0.94 (t, J=7.2, 3 H), 1.34-1.68 (m, 4 H), 2.17 (s, 3 H), 2.30 (d, J=2.7, 6 H), 2.59-2.71 (m, 2 H), 3.96 (s, 2 H), 6.82-7.83 (m, 11 H)

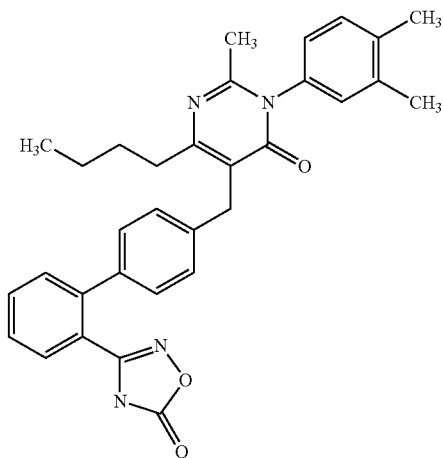

202b) 6-butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.50 g), sodium hydrogen carbonate (2.50 g) and dimethyl sulfoxide (10 mL) was stirred at 40° C. for 30 min, 4'-{[4-butyl-1-(3,4-dimethylphenyl)-2-methyl-6-oxo-1,6-dihydropyrimidin-5-yl]methyl}biphenyl-2-carbonitrile (1.27 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.65 g) and then 1,8-diazabicyclo[5.4.0]undec-7-ene (0.6 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (1.01 g, 71%).

$^1$H NMR (300 MHz, CDCl$_3$) δ 0.95 (t, J=7.2, 3 H), 1.29-1.76 (m, 4 H), 2.07 (s, 3 H), 2.22 (s, 3 H), 2.28 (s, 3 H), 2.55-2.69 (m, 2 H), 3.83 (s, 2 H), 6.68-7.66 (m, 11 H), 9.25 (s, 1 H)

6-Butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one hydrochloride 6-butyl-3-(3,4-dimethylphenyl)-2-methyl-5-{[2'-(5-oxo-4,5-dihydro-1,2,4-oxadiazol-3-yl)biphenyl-4-yl]methyl}pyrimidin-4(3H)-one hydrobromide

Example 203

6-butyl-5-{[3-fluoro-2'-(5-oxo-4,5-dihydro-1,2,4-oxadiazol-3-yl)biphenyl-4-yl]methyl}-2-methyl-3-phenylpyrimidin-4(3H)-one

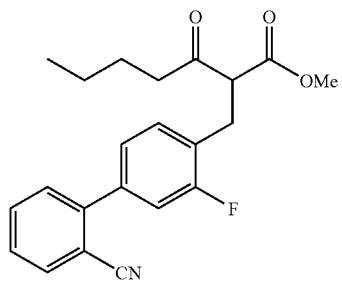

203a) methyl 2-[(2'-cyano-3-fluorobiphenyl-4-yl)methyl]-3-oxoheptanoate

To a solution of methyl 3-oxoheptanoate (10.9 g) in tetrahydrofuran (100 mL) was added 60% sodium hydride (2.07 g), and the mixture was stirred for 1 hr. A solution of 4'-(bromomethyl)-3'-fluorobiphenyl-2-carbonitrile (10.0 g) in tetrahydrofuran (50 mL) was added, and the mixture was stirred for 15 hr. Ammonium chloride and water were added to the reaction mixture, and the mixture was extracted with ethyl acetate. The organic layer was washed with saturated brine and dried over anhydrous magnesium sulfate, and the solvent was evaporated. The residue was purified by silica gel column chromatography to give the title compound as a pale-yellow viscous substance (13.0 g, 100%).

$^1$H NMR (300 MHz, CDCl$_3$) δ 0.77-0.96 (m, 3 H), 1.15-1.38 (m, 2 H), 1.43-1.64 (m, 2 H), 2.33-2.73 (m, 2 H), 3.24 (d, J=7.3, 2 H), 3.71 (s, 3 H), 3.93 (t, J=7.4 Hz, 1 H), 7.11-7.93 (m, 7 H)

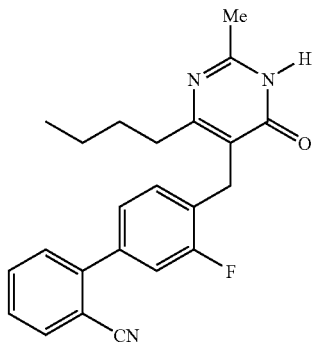

203b) 4'-[(4-butyl-2-methyl-6-oxo-1,6-dihydropyrimidin-5-yl)methyl]-3'-fluorobiphenyl-2-carbonitrile To a suspension of acetamidine hydrochloride (6.7 g) in methanol (50 mL) were added sodium methoxide (28% methanol solution, 20.5 mL) and then methyl 2-[(2'-cyano-3-fluorobiphenyl-4-yl)methyl]-3-oxoheptanoate (13.0 g), and the mixture was stirred for 15 hr. Water was added to the reaction mixture, and the mixture was extracted with ethyl acetate. The organic layer was washed with saturated brine and dried over anhydrous magnesium sulfate, and the solvent was evaporated. The residue was triturated with diisopropyl ether to give the title compound (9.15 g, 69%) as pale-yellow crystals.

$^1$H NMR (300 MHz, CDCl$_3$) δ 0.89 (t, J=7.2, 3 H), 1.25-1.63 (m, 4 H), 2.42 (s, 3 H), 2.52-2.68 (m, 2 H), 3.98 (s, 2 H), 7.11-7.82 (m, 7 H), 13.28 (s, 1 H)

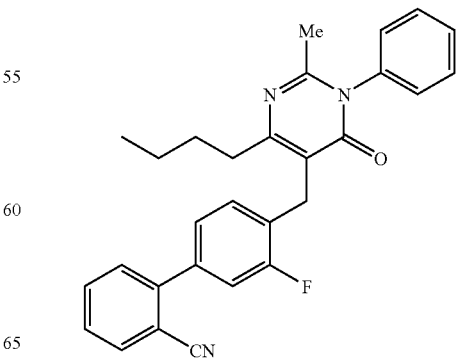

203c) 4'-[(4-butyl-2-methyl-6-oxo-1-phenyl-1,6-dihydropyrimidin-5-yl)methyl]-3'-fluorobiphenyl-2-carbonitrile To a suspension of 4'-[(4-butyl-2-methyl-6-oxo-1,6-dihydropyrimidin-5-yl)methyl]-3'-fluorobiphenyl-2-carbonitrile (1.0 g), phenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.28 g, 100%).

$^1$H NMR (300 MHz, CDCl$_3$) δ 0.94 (t, 3 H), 1.32-1.71 (m, 4 H), 2.17 (s, 3 H), 2.58-2.75 (m, 2 H), 3.99 (s, 2 H), 7.16-7.78 (m, 12 H)

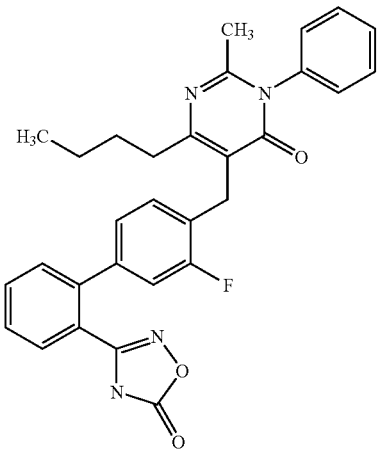

203d) 6-butyl-5-{[3-fluoro-2'-(5-oxo-4,5-dihydro-1,2,4-oxadiazol-3-yl)biphenyl-4-yl]methyl}-2-methyl-3-phenylpyrimidin-4(3H)-one A mixture of hydroxylammonium chloride (1.50 g), sodium hydrogen carbonate (2.50 g) and dimethyl sulfoxide (10 mL) was stirred at 40° C. for 30 min, 4'-[(4-butyl-2-methyl-6-oxo-1-phenyl-1,6-dihydropyrimidin-5-yl)methyl]-3'-fluorobiphenyl-2-carbonitrile (1.28 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.65 g) and then 1,8-diazabicyclo[5.4.0]undec-7-ene (0.6 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.84 g, 62%).

$^1$H NMR (300 MHz, CDCl$_3$) δ 0.95 (t, J=7.2, 3 H), 1.31-1.74 (m, 4 H), 2.10 (s, 3 H), 2.56-2.82 (m, 2 H), 3.87 (s, 2 H), 6.77-7.70 (m, 12 H), 9.37 (s, 1 H)

Example 204

6-butyl-5-{[3,5-difluoro-2'-(5-oxo-4,5-dihydro-1,2,4-oxadiazol-3-yl)biphenyl-4-yl]methyl}-2-methyl-3-phenylpyrimidin-4(3H)-one

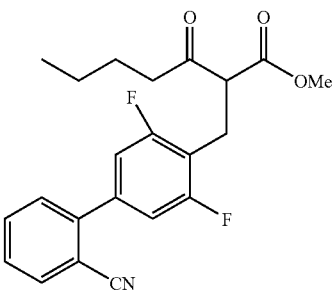

204a) methyl 2-[(2'-cyano-3,5-difluorobiphenyl-4-yl)methyl]-3-oxoheptanoate

To a solution of methyl 3-oxoheptanoate (6.82 g) in tetrahydrofuran (75 mL) was added 60% sodium hydride (1.29 g), and the mixture was stirred for 1 hr. A solution of 4'-(bromomethyl)-3',5'-difluorobiphenyl-2-carbonitrile (6.65 g) in tetrahydrofuran (25 mL), and the mixture was stirred for 15 hr. Ammonium chloride and water were added to the reaction mixture, and the mixture was extracted with ethyl acetate. The organic layer was washed with saturated brine and dried over anhydrous magnesium sulfate, and the solvent was evaporated. The residue was purified by silica gel column chromatography to give the title compound as a pale-yellow viscous substance (7.93 g, 100%).

$^1$H NMR (300 MHz, CDCl$_3$) δ 0.88 (t, J=7.3, 3 H), 1.20-1.37 (m, 2 H), 1.48-1.63 (m, 2 H), 2.38-2.72 (m, 2 H), 3.18-3.36 (m, 2 H), 3.72 (s, 3 H), 3.91 (t, J=7.6, 1 H), 6.97-7.89 (m, 6 H)

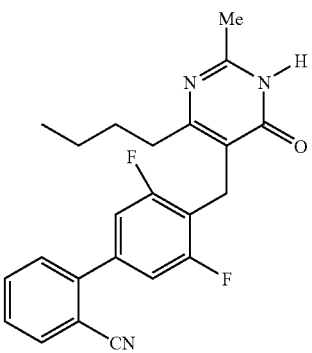

204b) 4'-[(4-butyl-2-methyl-6-oxo-1,6-dihydropyrimidin-5-yl)methyl]-3',5'-difluorobiphenyl-2-carbonitrile To a suspension of acetamidine hydrochloride (3.9 g) in methanol (30 mL) were added sodium methoxide (28% methanol solution, 12 mL) and then methyl 2-[(2'-cyano-3,5-difluorobiphenyl-4-yl)methyl]-3-oxoheptanoate (7.93 g), and the mixture was stirred for 15 hr. Water was added to the reaction mixture, and the aqueous layer was extracted with ethyl acetate. The organic layer was washed with saturated brine and dried over anhydrous magnesium sulfate, and the solvent was evaporated. The residue was triturated with diisopropyl ether to give the title compound (5.11 g, 63%) as pale-yellow crystals.

$^1$H NMR (300 MHz, CDCl$_3$) δ 0.90 (t, J=7.4, 3 H), 1.27-1.60 (m, 4 H), 2.38 (s, 3 H), 2.59-2.71 (m, 2 H), 3.95 (s, 2 H), 6.96-7.81 (m, 6 H), 13.23 (s, 1 H)

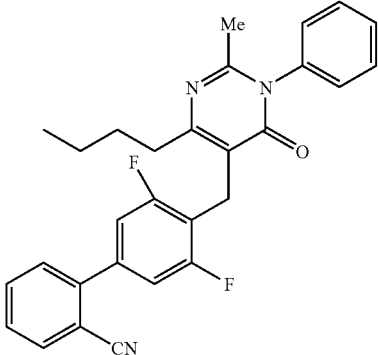

204c) 4'-[(4-butyl-2-methyl-6-oxo-1-phenyl-1,6-dihydropyrimidin-5-yl)methyl]-3',5'-difluorobiphenyl-2-carbonitrile To a suspension of 4'-[(4-butyl-2-methyl-6-oxo-1-phenyl-1,6-dihydropyrimidin-5-yl)methyl]-3',5'-difluorobiphenyl-2-carbonitrile (1.0 g), phenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.21 g, 100%).

$^1$H NMR (300 MHz, CDCl$_3$) δ 0.79-1.05 (m, 3 H), 1.33-1.66 (m, 4 H), 2.14 (s, 3 H), 2.63-2.73 (m, 2 H), 4.00 (s, 2 H), 6.95-7.86 (m, 11 H)

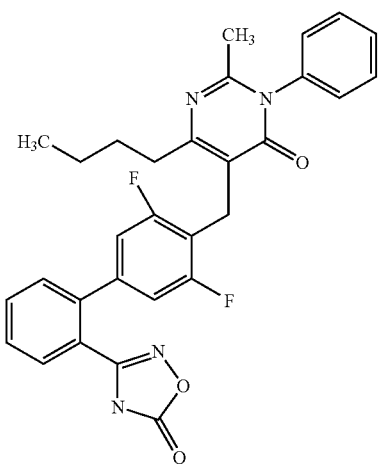

204d) 6-butyl-5-{[3,5-difluoro-2'-(5-oxo-4,5-dihydro-1,2,4-oxadiazol-3-yl)biphenyl-4-yl]methyl}-2-methyl-3-phenylpyrimidin-4(3H)-one A mixture of hydroxylammonium chloride (1.50 g), sodium hydrogen carbonate (2.50 g) and dimethyl sulfoxide (10 mL) was stirred at 40° C. for 30 min, 4'-[(4-butyl-2-methyl-6-oxo-1-phenyl-1,6-dihydropyrimidin-5-yl)methyl]-3',5'-difluorobiphenyl-2-carbonitrile (1.21 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.65 g) and then 1,8-diazabicyclo[5.4.0]undec-7-ene (0.6 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.63 g, 47%).

$^1$H NMR (300 MHz, CDCl$_3$) δ 0.96 (t, J=7.2, 3 H), 1.36-1.74 (m, 4 H), 2.13 (s, 3 H), 2.68-2.82 (m, 2 H), 3.91 (s, 2 H), 6.66-7.66 (m, 11 H), 9.99 (s, 1 H)

6-Butyl-5-{[3,5-difluoro-2'-(5-oxo-4,5-dihydro-1,2,4-oxadiazol-3-yl)biphenyl-4-yl]methyl}-2-methyl-3-phenylpyrimidin-4(3H)-one obtained above is subjected to a conventional method of salt formation to give the following salts.

6-butyl-5-{[3,5-difluoro-2'-(5-oxo-4,5-dihydro-1,2,4-oxadiazol-3-yl)biphenyl-4-yl]methyl}-2-methyl-3-phenylpyrimidin-4(3H)-one sodium salt 6-butyl-5-{[3,5-difluoro-2'-(5-oxo-4,5-dihydro-1,2,4-oxadiazol-3-yl)biphenyl-4-yl]methyl}-2-methyl-3-phenylpyrimidin-4(3H)-one potassium salt 6-butyl-5-{[3,5-difluoro-2'-(5-oxo-4,5-dihydro-1,2,4-oxadiazol-3-yl)biphenyl-4-yl]methyl}-2-methyl-3-phenylpyrimidin-4(3H)-one 0.5 calcium salt 6-butyl-5-{[3,5-difluoro-2'-(5-oxo-4,5-dihydro-1,2,4-oxadiazol-3-yl)biphenyl-4-yl]methyl}-2-methyl-3-phenylpyrimidin-4(3H)-one hydrochloride 6-butyl-5-{[3,5-difluoro-2'-(5-oxo-4,5-dihydro-1,2,4-oxadiazol-3-yl)biphenyl-4-yl]methyl}-2-methyl-3-phenylpyrimidin-4(3H)-one hydrobromide Example 205

6-butyl-2-methyl-5-{[2'-(5-oxo-4,5-dihydro-1,2,4-oxadiazol-3-yl)biphenyl-4-yl]methyl}-3-(3-thienyl)pyrimidin-4(3H)-one

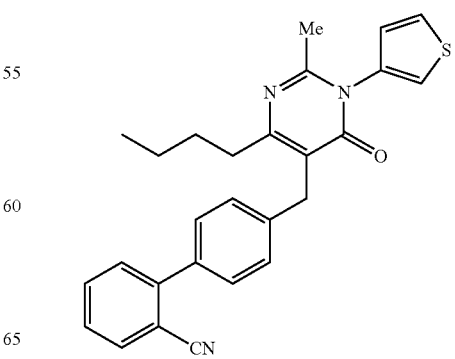

205a) 4'-{[4-butyl-2-methyl-6-oxo-1-(3-thienyl)-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 3-thienylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.53 g, 43%).

$^1$H NMR (300 MHz, CDCl$_3$) δ 0.91-0.97 (m, 3 H), 1.33-1.69 (m, 4 H), 2.23 (s, 3 H), 2.59-2.72 (m, 2 H), 3.96 (s, 2 H), 6.96-7.03 (m, 1 H), 7.28-7.31 (m, 1 H), 7.36-7.78 (m, 9 H)

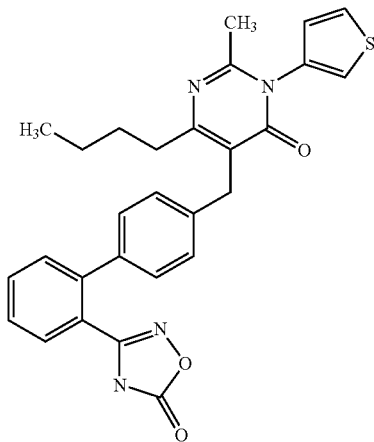

205b) 6-butyl-2-methyl-5-{[2'-(5-oxo-4,5-dihydro-1,2,4-oxadiazol-3-yl)biphenyl-4-yl]methyl}-3-(3-thienyl)pyrimidin-4(3H)-one A mixture of hydroxylammonium chloride (0.67 g), sodium hydrogen carbonate (1.02 g) and dimethyl sulfoxide (6 mL) was stirred at 40° C. for 30 min, 4'-{[4-butyl-2-methyl-6-oxo-1-(3-thienyl)-1,6-dihydropyrimidin-5-yl]methyl}biphenyl-2-carbonitrile (0.53 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.19 g) and then 1,8-diazabicyclo[5.4.0]undec-7-ene (0.18 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.33 g, 55%).

$^1$H NMR (300 MHz, CDCl$_3$) δ 0.96 (t, J=7.4, 3 H), 1.34-1.77 (m, 4 H), 2.17 (s, 3 H), 2.62-2.73 (m, 2 H), 3.86 (s, 2 H), 6.78-7.78 (m, 11 H), 8.81 (s, 1 H)

Example 206

6-butyl-3-(3-furyl)-2-methyl-5-{[2'-(5-oxo-4,5-dihydro-1,2,4-oxadiazol-3-yl)biphenyl-4-yl]methyl}pyrimidin-4(3H)-one

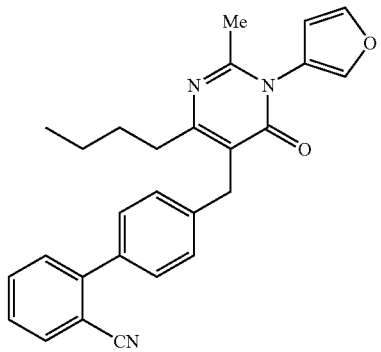

206a) 4'-{[4-butyl-1-(3-furyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 3-furylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.13 g, 11%).

$^1$H NMR (300 MHz, CDCl$_3$) δ 0.94 (t, J=7.2, 3 H), 1.28-1.76 (m, 4 H), 2.32 (s, 3 H), 2.49-2.77 (m, 2 H), 3.95 (s, 2 H), 6.46 (s, 1 H), 7.31-7.82 (m, 10 H)

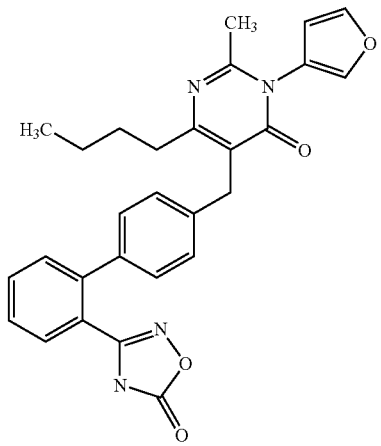

206b) 6-butyl-3-(3-furyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.31 g), sodium hydrogen carbonate (0.50 g) and dimethyl sulfoxide (3 mL) was stirred at 40° C. for 30 min, 4'-{[4-butyl-1-(3-furyl)-2-methyl-6-oxo-1,6-dihydropyrimidin-5-yl]methyl}biphenyl-2-carbonitrile (0.13 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (5 mL), N,N'-carbonyldiimidazole (0.073 g) and then 1,8-diazabicyclo[5.4.0]undec-7-ene (0.067 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.067 g, 46%).

$^1$H NMR (300 MHz, CDCl$_3$) δ 0.97 (t, J=7.4, 3 H), 1.34-1.80 (m, 4 H), 2.29 (s, 3 H), 2.64-2.74 (m, 2 H), 3.89 (s, 2 H), 6.41 (d, J=1.1, 1 H), 7.13-7.86 (m, 10 H), 8.18 (s, 1 H)

6-Butyl-3-(3-furyl)-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(3-furyl)-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-(3-furyl)-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-(3-furyl)-2-methyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(3-furyl)-2-methyl-5-{[2'-(5-oxo-4,5-dihydro-1,2,4-oxadiazol-3-yl)biphenyl-4-yl]methyl}pyrimidin-4(3H)-one hydrochloride 6-butyl-3-(3-furyl)-2-methyl-5-{[2'-(5-oxo-4,5-dihydro-1,2,4-oxadiazol-3-yl)biphenyl-4-yl]methyl}pyrimidin-4(3H)-one hydrobromide

Example 207

6-butyl-3-(4-fluoro-3-methylphenyl)-2-methyl-5-{[2'-(5-oxo-4,5-dihydro-1,2,4-oxadiazol-3-yl)biphenyl-4-yl]methyl}pyrimidin-4(3H)-one

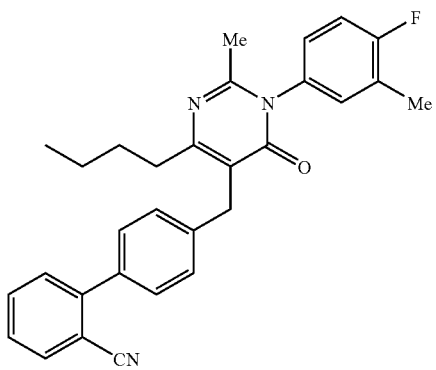

207a) 4'-{[4-butyl-1-(4-fluoro-3-methylphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), (4-fluoro-3-methylphenyl)boronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.11 g, 85%).

$^1$H NMR (300 MHz, CDCl$_3$) δ 0.94 (t, J=7.2, 3 H), 1.33-1.73 (m, 4 H), 2.17 (s, 3 H), 2.32 (d, J=1.9, 3 H), 2.55-2.78 (m, 2 H), 3.96 (s, 2 H), 6.97-7.79 (m, 11 H)

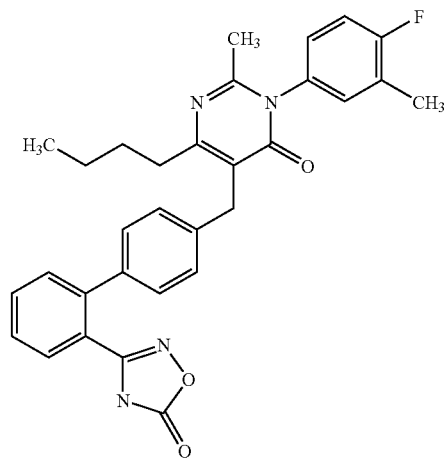

207b) 6-butyl-3-(4-fluoro-3-methylphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.5 g), sodium hydrogen carbonate (2.3 g) and dimethyl sulfoxide (10 mL) was stirred at 40° C. for 30 min, 4'-{[4-butyl-1-(4-fluoro-3-methylphenyl)-2-methyl-6-oxo-1,6-dihydropyrimidin-5-yl]methyl}biphenyl-2-carbonitrile (1.11 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.58 g) and then 1,8-diazabicyclo[5.4.0]undec-7-ene (0.53 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.85 g, 68%).

¹H NMR (300 MHz, CDCl₃) δ 0.96 (t, J=7.2, 3 H), 1.34-1.76 (m, 4 H), 2.12 (s, 3 H), 2.26 (s, 3 H), 2.59-2.76 (m, 2 H), 3.86 (s, 2 H), 6.83-7.80 (m, 11 H), 8.65 (s, 1 H)

Example 208

6-butyl-3-(4-methoxy-3-methylphenyl)-2-methyl-5-{[2'-(5-oxo-4,5-dihydro-1,2,4-oxadiazol-3-yl)biphenyl-4-yl]methyl}pyrimidin-4(3H)-one

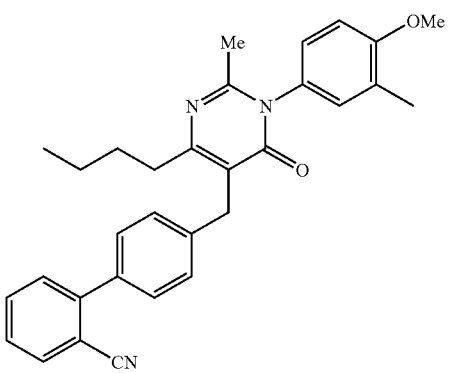

208a) 4'-{[4-butyl-1-(4-methoxy-3-methylphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), (4-methoxy-3-methylphenyl)boronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.31 g, 98%).

¹H NMR (300 MHz, CDCl₃) δ 0.91-0.97 (m, 3 H), 1.32-1.74 (m, 4 H), 2.18 (s, 3 H), 2.24 (s, 3 H), 2.59-2.72 (m, 2 H), 3.86 (s, 3 H), 3.96 (s, 2 H), 6.85-7.80 (m, 11 H)

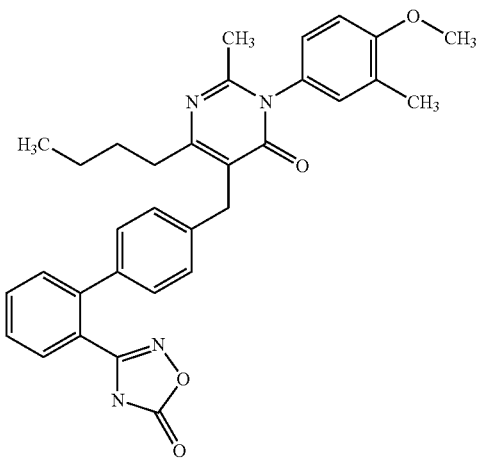

208b) 6-butyl-3-(4-methoxy-3-methylphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.5 g), sodium hydrogen carbonate (2.3 g) and dimethyl sulfoxide (10 mL) was stirred at 40° C. for 30 min, 4'-{[4-butyl-1-(4-methoxy-3-methylphenyl)-2-methyl-6-oxo-1,6-dihydropyrimidin-5-yl]methyl}biphenyl-2-carbonitrile (1.31 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.67 g) and then 1,8-diazabicyclo[5.4.0]undec-7-ene (0.61 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.96 g, 65%).

¹H NMR (300 MHz, CDCl₃) δ 0.96 (t, J=7.2, 3 H), 1.31-1.79 (m, 4 H), 2.12 (s, 3 H), 2.18 (s, 3 H), 2.56-2.74 (m, 2 H), 3.85 (s, 3 H), 3.86 (br s., 2 H), 6.79-7.78 (m, 11 H), 8.66 (s, 1 H)

Example 209

6-butyl-3-(3,4-dimethoxyphenyl)-2-methyl-5-{[2'-(5-oxo-4,5-dihydro-1,2,4-oxadiazol-3-yl)biphenyl-4-yl]methyl}pyrimidin-4(3H)-one

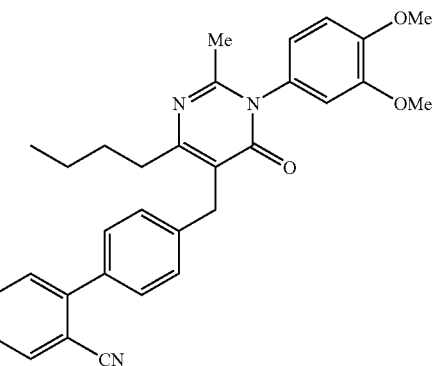

209a) 4'-{[4-butyl-1-(3,4-dimethoxyphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), (3,4-dimethoxyphenyl)boronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.28 g, 92%).

¹H NMR (300 MHz, CDCl₃) δ 0.95 (t, J=7.4, 3 H), 1.34-1.70 (m, 4 H), 2.20 (s, 3 H), 2.59-2.73 (m, 2 H), 3.88 (s, 3 H), 3.92 (s, 3 H), 3.97 (s, 2 H), 6.69-7.78 (m, 11 H)

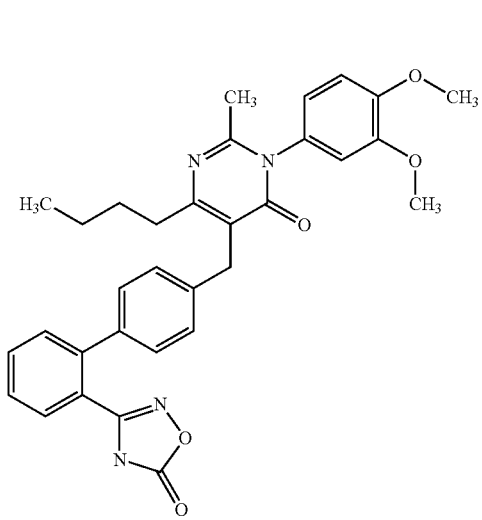

209b) 6-butyl-3-(3,4-dimethoxyphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.5 g), sodium hydrogen carbonate (2.3 g) and dimethyl sulfoxide (10 mL) was stirred at 40° C. for 30 min, 4'-{4-butyl-1-(3,4-dimethoxyphenyl)-2-methyl-6-oxo-1,6-dihydropyrimidin-5-yl]methyl}biphenyl-2-carbonitrile (1.28 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.63 g) and then 1,8-diazabicyclo[5.4.0]undec-7-ene (0.58 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.84 g, 59%).

¹H NMR (300 MHz, CDCl₃) δ 0.96 (t, J=7.4, 3 H), 1.37-1.75 (m, 4 H), 2.14 (s, 3 H), 2.60-2.73 (m, 2 H), 3.78 (s, 3 H), 3.87 (s, 2 H), 3.90 (s, 3 H), 6.50-7.76 (m, 11 H), 8.80 (s, 1 H)

Example 210

6-butyl-3-(3-ethylphenyl)-2-methyl-5-{[2'-(5-oxo-4,5-dihydro-1,2,4-oxadiazol-3-yl)biphenyl-4-yl]methyl}pyrimidin-4(3H)-one

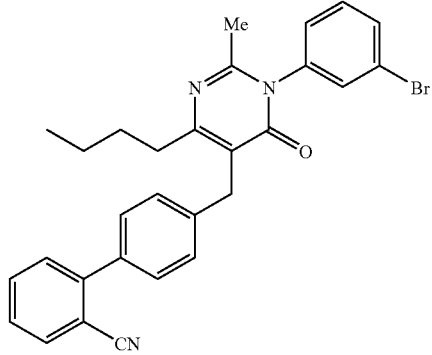

21a) 4'-{[1-(3-bromophenyl)-4-butyl-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 3-bromophenylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.00 g, 70%).

¹H NMR (300 MHz, CDCl₃) δ 0.94 (t, J=7.2, 3 H), 1.31-1.71 (m, 4 H), 2.18 (s, 3 H), 2.59-2.74 (m, 2 H), 3.96 (s, 2 H), 7.08-7.87 (m, 12 H)

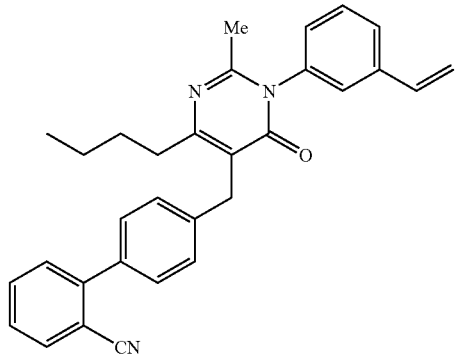

21b) 4'-{[4-butyl-2-methyl-6-oxo-1-(3-vinylphenyl)-1,6-dihydropyrimidin-5-yl]methyl}biphenyl-2-carbonitrile A suspension of 4'-{[1-(3-bromophenyl)-4-butyl-2-methyl-6-oxo-1,6-dihydropyrimidin-5-yl]methyl}biphenyl-2-carbonitrile (1.0 g), vinyltributyltin (0.86 mL), dichlorobis (triphenylphosphine)palladium(II) and lithium chloride (0.25 g) in N,N-dimethylformamide (10 mL) was stirred at 90° C. for 3 hr under an argon atmosphere. The mixture was allowed to cool to room temperature, 20% aqueous potassium fluoride solution was added, and the mixture was stirred for 12 hr. The reaction mixture was diluted with ethyl acetate, and the insoluble material was filtered off through celite. The filtrate was washed with water and then with saturated brine, and dried over anhydrous magnesium sulfate. The solvent was evaporated under reduced pressure and the residue was purified by silica gel column chromatography to give the title compound as a pale-yellow viscous substance (0.45 g, 50%).

$^1$H NMR (300 MHz, CDCl$_3$) δ 0.95 (t, J=7.4, 3 H), 1.34-1.72 (m, 4 H), 2.18 (s, 3 H), 2.58-2.76 (m, 2 H), 3.97 (s, 2 H), 5.33 (d, J=11.0, 1 H), 5.78 (d, J=17.4, 1 H), 6.72 (dd, J=17.4, 11.0, 1 H), 7.06-7.17 (m, 1 H), 7.34-7.84 (m, 11 H)

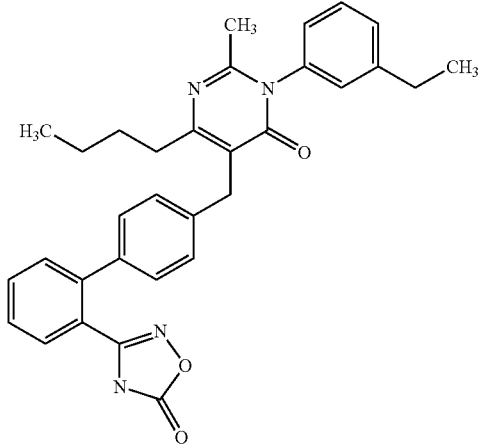

210c) 6-butyl-3-(3-ethylphenyl)-2-methyl-5-{[2'-(5-oxo-4,5-dihydro-1,2,4-oxadiazol-3-yl)biphenyl-4-yl]methyl}pyrimidin-4(3H)-one To a solution of 4'-{[4-butyl-2-methyl-6-oxo-1-(3-vinylphenyl)-1,6-dihydropyrimidin-5-yl]methyl}biphenyl-2-carbonitrile (0.25 g) in ethanol (4 mL) was added 10% palladium-carbon (50% wet, 0.015 g), and the mixture was stirred for 8 hr under hydrogen atmosphere. The reaction mixture was diluted with ethyl acetate. The insoluble material was filtered off through celite, and the solvent was evaporated under reduced pressure. The residue was added to a mixture of hydroxylammonium chloride (0.57 g), sodium hydrogen carbonate (0.92 g) and dimethyl sulfoxide (5 mL) stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (5 mL), N,N'-carbonyldiimidazole (0.10 g) and then 1,8-diazabicyclo[5.4.0]undec-7-ene (0.096 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.14 g, 48%).

$^1$H NMR (300 MHz, CDCl$_3$) δ 0.96 (t, J=7.4, 3 H), 1.22 (t, J=7.6, 3 H), 1.37-1.76 (m, 4 H), 2.11 (s, 3 H), 2.58-2.75 (m, 4 H), 3.88 (s, 2 H), 6.87-7.79 (m, 12 H), 8.58 (s, 1 H)

Example 211

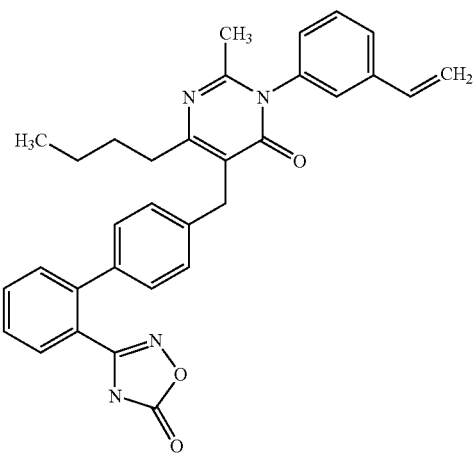

6-butyl-2-methyl-5-{[2'-(5-oxo-4,5-dihydro-1,2,4-oxadiazol-3-yl)biphenyl-4-yl]methyl}-3-(3-vinylphenyl)pyrimidin-4(3H)-one A mixture of hydroxylammonium chloride (0.44 g), sodium hydrogen carbonate (0.71 g) and dimethyl sulfoxide (4 mL) was stirred at 40° C. for 30 min, 4'-{[4-butyl-2-methyl-6-oxo-1-(3-vinylphenyl)-1,6-dihydropyrimidin-5-yl]methyl}biphenyl-2-carbonitrile (0.19 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (5 mL), N,N'-carbonyldiimidazole (0.06 g) and then 1,8-diazabicyclo[5.4.0]undec-7-ene (0.056 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.088 g, 40%).

$^1$H NMR (300 MHz, CDCl$_3$) δ 0.96 (t, J=7.2, 3 H), 1.33-1.76 (m, 4 H), 2.11 (s, 3 H), 2.58-2.77 (m, 2 H), 3.86 (s, 2 H), 5.32 (d, J=11.0, 1 H), 5.76 (d, J=17.4, 1 H), 6.67 (dd, J=17.4, 11.0, 1 H), 6.95-7.76 (m, 12 H), 8.87 (s, 1 H)

Example 212

6-butyl-3-[3-(2-methoxyethoxy)phenyl]-2-methyl-5-{[2'-(5-oxo-4,5-dihydro-1,2,4-oxadiazol-3-yl)biphenyl-4-yl]methyl}pyrimidin-4(3H)-one

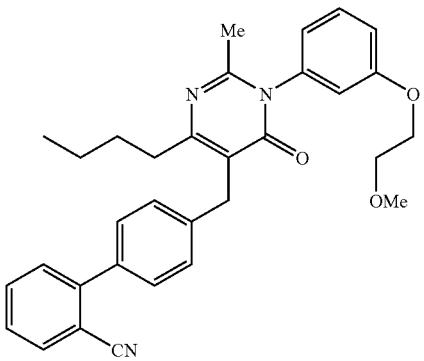

212a) 4'-({4-butyl-1-[3-(2-methoxyethoxy)phenyl]-2-methyl-6-oxo-1,6-dihydropyrimidin-5-yl}methyl)biphenyl-2-carbonitrile To a solution of 4'-{[4-butyl-1-(3-hydroxyphenyl)-2-methyl-6-oxo-1,6-dihydropyrimidin-5-yl]methyl}biphenyl-2-carbonitrile (0.69 g) and 1-bromo-2-methoxyethane (0.43 mL) in N,N-dimethylformamide (7 mL) was added cesium carbonate (0.99 g), and the mixture was stirred at 70° C. for 5 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was purified by silica gel column chromatography to give the title compound as a pale-yellow viscous substance (0.69 g, 90%).

$^1$H NMR (300 MHz, CDCl$_3$) δ 0.95 (t, J=7.2, 3 H), 1.33-1.70 (m, 4 H), 2.18 (s, 3 H), 2.61-2.71 (m, 2 H), 3.44 (s, 3 H), 3.75 (t, J=4.5, 2 H), 3.97 (s, 2 H), 4.03-4.23 (m, 2 H), 6.74-7.79 (m, 12 H)

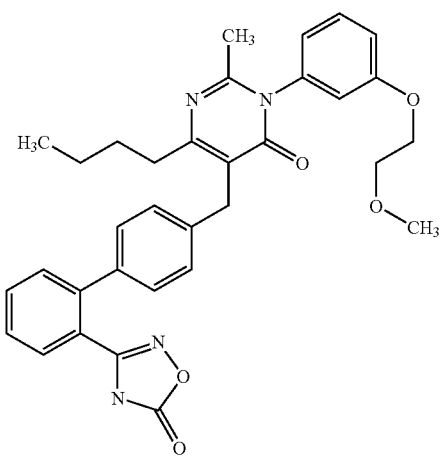

212b) 6-butyl-3-[3-(2-methoxyethoxy)phenyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.95 g), sodium hydrogen carbonate (1.40 g) and dimethyl sulfoxide (7 mL) was stirred at 40° C. for 30 min, 4'-({4-butyl-1-[3-(2-methoxyethoxy)phenyl]-2-methyl-6-oxo-1,6-dihydropyrimidin-5-yl}methyl)biphenyl-2-carbonitrile (0.69 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.33 g) and then 1,8-diazabicyclo[5.4.0]undec-7-ene (0.30 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.34 g, 44%).

$^1$H NMR (300 MHz, CDCl$_3$) δ 0.97 (t, J=7.4, 3 H), 1.34-1.78 (m, 4 H), 2.15 (s, 3 H), 2.62-2.77 (m, 2 H), 3.43 (s, 3 H), 3.73 (t, J=4.7, 2 H), 3.88 (s, 2 H), 4.00-4.18 (m, 2 H), 6.65-7.83 (m, 12 H), 8.51 (s, 1 H)

Example 213

2-methyl-5-{[2'-(5-oxo-4,5-dihydro-1,2,4-oxadiazol-3-yl)biphenyl-4-yl]methyl}-3-phenyl-6-propylpyrimidin-4(3H)-one

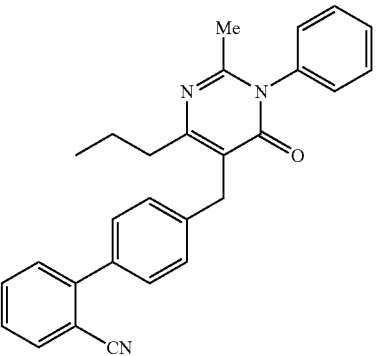

213a) 4'-[(2-methyl-6-oxo-1-phenyl-4-propyl-1,6-dihydropyrimidin-5-yl)methyl]biphenyl-2-carbonitrile To a suspension of 4'-[(2-methyl-6-oxo-4-propyl-1,6-dihydropyrimidin-5-yl)methyl]biphenyl-2-carbonitrile (1.0 g), phenylboronic acid (1.00 g), triethylamine (1.95 mL), pyridine (1.13 mL) and molecular sieves 4 A (1.0 g) in methylene chloride (15 mL) was added copper(II) acetate (1.02 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.83 g, 68%).

$^1$H NMR (300 MHz, CDCl$_3$) δ 0.98-1.04 (m, 3 H), 1.58-1.80 (, 2 H), 2.16 (s, 3 H), 2.56-2.73 (m, 2 H), 3.98 (s, 2 H), 7.16-7.79 (m, 13 H)

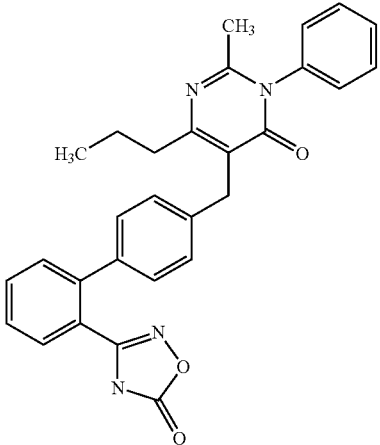

213b) 2-methyl-5-{[2'-(5-oxo-4,5-dihydro-1,2,4-oxadiazol-3-yl)biphenyl-4-yl]methyl}-3-phenyl-6-propylpyrimidin-4(3H)-one A mixture of hydroxylammonium chloride (1.40 g), sodium hydrogen carbonate (2.00 g) and dimethyl sulfoxide (10 mL) was stirred at 40° C. for 30 min, 4'-[(2-methyl-6-oxo-1-phenyl-4-propyl-1,6-dihydropyrimidin-5-yl)methyl]biphenyl-2-carbonitrile (0.83 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.48 g) and then 1,8-diazabicyclo[5.4.0]undec-7-ene (0.44 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.57 g, 41%).

$^1$H NMR (300 MHz, CDCl$_3$) δ 1.02 (t, J=7.4, 3 H), 1.55-1.87 (m, 2 H), 2.09 (s, 3 H), 2.51-2.73 (m, 2 H), 3.86 (s, 2 H), 6.87-7.82 (m, 13 H), 8.97 (s, 1 H)

Example 214

6-butyl-3-(2,3-dihydro-1-benzofuran-5-yl)-5-{[3-fluoro-2'-(5-oxo-4,5-dihydro-1,2,4-oxadiazol-3-yl)biphenyl-4-yl]methyl}-2-methylpyrimidin-4(3H)-one

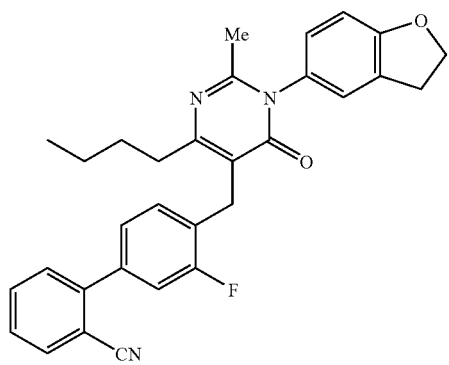

214a) 4'-{[4-butyl-1-(2,3-dihydro-1-benzofuran-5-yl)-2-methyl-6-oxo-1,6-dihydropyrimidin-5-yl]methyl}-3'-fluorobiphenyl-2-carbonitrile To a suspension of 4'-[(4-butyl-2-methyl-6-oxo-1,6-dihydropyrimidin-5-yl)methyl]-3'-fluorobiphenyl-2-carbonitrile (1.0 g), 2,3-dihydro-1-benzofuran-5-ylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.40 g, 100%).

$^1$H NMR (300 MHz, CDCl$_3$) δ 0.94 (t, J=7.4, 3 H), 1.31-1.72 (m, 4 H), 2.20 (s, 3 H), 2.48-2.81 (m, 2 H), 3.08-3.47 (m, 2 H), 3.98 (s, 2 H), 4.64 (t, J=9.1, 2 H), 6.68-7.96 (m, 10 H)

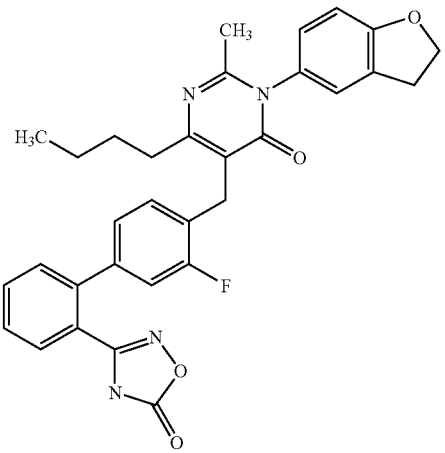

214b) 6-butyl-3-(2,3-dihydro-1-benzofuran-5-yl)-5-{[3-fluoro-2'-(5-oxo-4,5-dihydro-1,2,4-oxadiazol-3-yl)biphenyl-4-yl]methyl}-2-methylpyrimidin-4(3H)-one A mixture of hydroxylammonium chloride (1.85 g), sodium hydrogen carbonate (2.68 g) and dimethyl sulfoxide (10 mL) was stirred at 40° C. for 30 min, 4'-{[4-butyl-1-(2,3-dihydro-1-benzofuran-5-yl)-2-methyl-6-oxo-1,6-dihydropyrimidin-5-yl]methyl}-3'-fluorobiphenyl-2-carbonitrile (1.40 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (15 mL), N,N'-carbonyldiimidazole (0.56 g) and then 1,8-diazabicyclo[5.4.0]undec-7-ene (0.52 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.89 g, 60%).

$^1$H NMR (300 MHz, DMSO-d$_6$) δ 0.85 (t, J=7.2, 3 H), 1.22-1.60 (m, 4 H), 2.09 (s, 3 H), 2.44-2.55 (m, 2 H), 3.22 (t, J=8.7, 2 H), 3.84 (s, 2 H), 4.60 (t, J=8.5, 2 H), 6.81-7.76 (m, 10 H), 12.46 (s, 1 H)

Example 215

6-butyl-5-{[3-fluoro-2'-(5-oxo-4,5-dihydro-1,2,4-oxadiazol-3-yl)biphenyl-4-yl]methyl}-2-methyl-3-(3-methylphenyl)pyrimidin-4(3H)-one

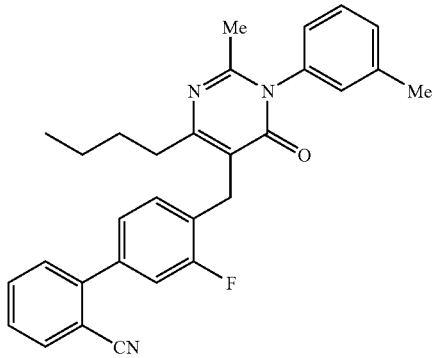

215a) 4'-{[4-butyl-2-methyl-1-(3-methylphenyl)-6-oxo-1,6-dihydropyrimidin-5-yl]methyl}-3'-fluorobiphenyl-2-carbonitrile To a suspension of 4'-[(4-butyl-2-methyl-6-oxo-1,6-dihydropyrimidin-5-yl)methyl]-3'-fluorobiphenyl-2-carbonitrile (1.0 g), (3-methylphenyl)boronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.35 g, 100%).

$^1$H NMR (300 MHz, CDCl$_3$) δ 0.94 (t, J=7.4, 3 H), 1.30-1.73 (m, 4 H), 2.17 (s, 3 H), 2.40 (s, 3 H), 2.53-2.77 (m, 2 H), 3.98 (s, 2 H), 6.54-8.02 (m, 11 H)

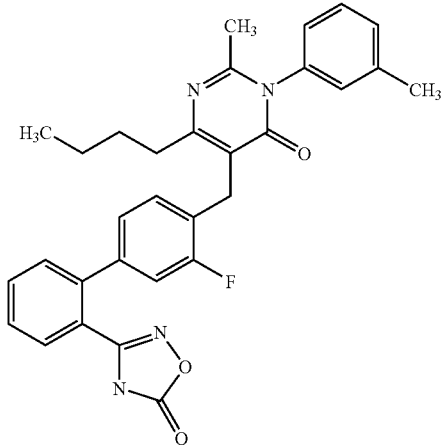

215b) 6-butyl-5-{[3-fluoro-2'-(5-oxo-4,5-dihydro-1,2,4-oxadiazol-3-yl)biphenyl-4-yl]methyl}-2-methyl-3-(3-methylphenyl)pyrimidin-4(3H)-one A mixture of hydroxylammonium chloride (1.85 g), sodium hydrogen carbonate (2.68 g) and dimethyl sulfoxide (10 mL) was stirred at 40° C. for 30 min, 4'-{[4-butyl-2-methyl-1-(3-methylphenyl)-6-oxo-1,6-dihydropyrimidin-5-yl]methyl}-3'-fluorobiphenyl-2-carbonitrile (1.35 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (15 mL), N,N'-carbonyldiimidazole (0.56 g) and then 1,8-diazabicyclo[5.4.0]undec-7-ene (0.52 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.94 g, 68%).

$^1$H NMR (300 MHz, DMSO-d$_6$) δ 0.83-0.88 (m, 3 H), 1.22-1.60 (m, 4 H), 2.07 (s, 3 H), 2.36 (s, 3 H), 2.48-2.58 (m, 2 H), 3.86 (s, 2 H), 6.95-7.75 (m, 11 H), 12.46 (s, 1 H)

Example 216

6-butyl-5-{[3-fluoro-2'-(5-oxo-4,5-dihydro-1,2,4-oxadiazol-3-yl)biphenyl-4-yl]methyl}-3-[3-(1-hydroxyethyl)phenyl]-2-methylpyrimidin-4(3H)-one

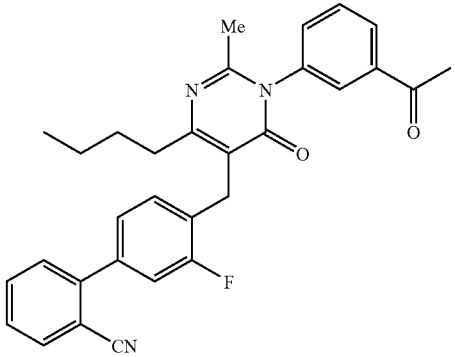

216a) 4'-{[1-(3-acetylphenyl)-4-butyl-2-methyl-6-oxo-1,6-dihydropyrimidin-5-yl]methyl}-3'-fluorobiphenyl-2-carbonitrile To a suspension of 4'-[(4-butyl-2-methyl-6-oxo-1,6-dihydropyrimidin-5-yl)methyl]-3'-fluorobiphenyl-2-carbonitrile (2.0 g), (3-acetylphenyl)boronic acid (2.0 g), triethylamine (4.0 mL), pyridine (2.0 mL) and molecular sieves 4 A (4.0 g) in methylene chloride (40 mL) was added copper(II) acetate (2.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.99 g, 76%).

$^1$H NMR (300 MHz, CDCl$_3$) δ 0.95 (t, J=7.4, 3 H), 1.32-1.72 (m, 4 H), 2.17 (s, 3 H), 2.63 (s, 3 H), 2.65-2.73 (m, 2 H), 3.99 (s, 2 H), 7.12-8.13 (m, 11 H)

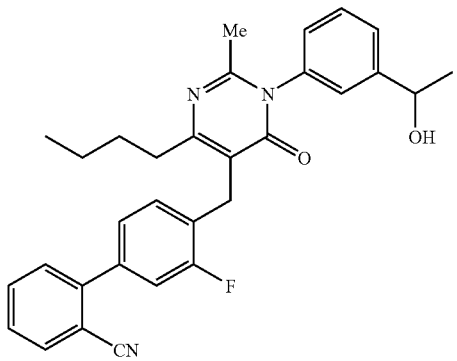

216b) 4'-({4-butyl-1-[3-(1-hydroxyethyl)phenyl]-2-methyl-6-oxo-1,6-dihydropyrimidin-5-yl}methyl)-3'-fluorobiphenyl-2-carbonitrile To a solution of 4'-{[1-(3-acetylphenyl)-4-butyl-2-methyl-6-oxo-1,6-dihydropyrimidin-5-yl]methyl}-3'-fluorobiphenyl-2-carbonitrile (1.17 g) in ethanol (10 mL) was added sodium tetrahydroboron (0.11 g), and the mixture was stirred for 3 hr. Ethyl acetate and water were added to the reaction mixture, and the mixture was extracted with ethyl acetate. The organic layer was washed with saturated brine and dried over anhydrous magnesium sulfate, and the solvent was evaporated. The residue was purified by silica gel column chromatography to give the title compound as a pale-yellow viscous substance (0.97 g, 82%).

$^1$H NMR (300 MHz, CDCl$_3$) δ 0.91-0.97 (m, 3 H), 1.34-1.70 (m, 7 H), 2.09-2.27 (m, 4 H), 2.58-2.71 (m, 2 H), 3.98 (s, 2 H), 4.86-5.01 (m, 1 H), 7.05-7.81 (m, 11 H)

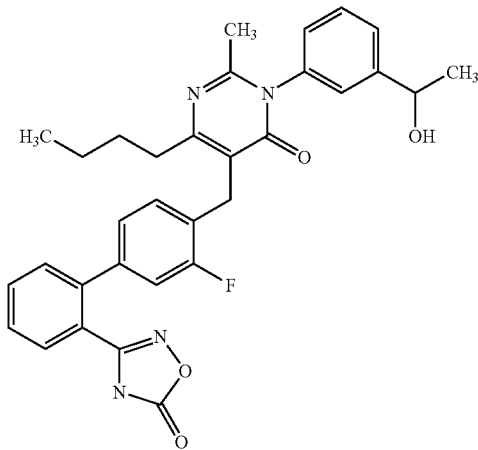

216c) 6-butyl-5-{[3-fluoro-2'-(5-oxo-4,5-dihydro-1,2,4-oxadiazol-3-yl)biphenyl-4-yl]methyl}-3-[3-(1-hydroxyethyl)phenyl]-2-methylpyrimidin-4(3H)-one A mixture of hydroxylammonium chloride (1.36 g), sodium hydrogen carbonate (1.97 g) and dimethyl sulfoxide (10 mL) was stirred at 40° C. for 30 min, 4'-({4-butyl-1-[3-(1-hydroxyethyl)phenyl]-2-methyl-6-oxo-1,6-dihydropyrimidin-5-yl}methyl)-3'-fluorobiphenyl-2-carbonitrile (0.97 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.35 g) and then 1,8-diazabicyclo[5.4.0]undec-7-ene (0.32 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.89 g, 60%).

$^1$H NMR (300 MHz, CDCl$_3$) δ 0.97 (t, J=7.3, 3 H), 1.31-1.80 (m, 8 H), 2.13 (d, J=10.0, 3 H), 2.42-2.92 (m, 2 H), 3.85 (s, 2 H), 4.72-4.91 (m, 1 H), 6.75-7.73 (m, 12 H)

Example 217

6-butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one

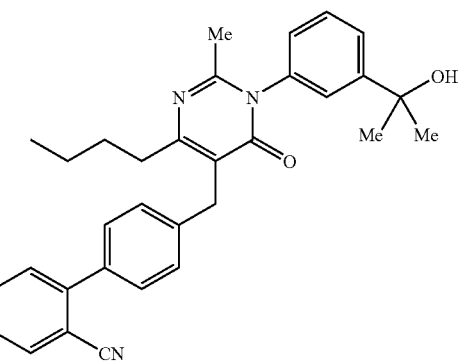

217a) 4'-({4-butyl-1-[3-(1-hydroxy-1-methylethyl)phenyl]-2-methyl-6-oxo-1,6-dihydropyrimidin-5-yl}methyl)biphenyl-2-carbonitrile To a solution of 4'-{[1-(3-acetylphenyl)-4-butyl-2-methyl-6-oxo-1,6-dihydropyrimidin-5-yl]methyl}biphenyl-2-carbonitrile (1.0 g) in tetrahydrofuran (10 mL) was added methylmagnesium bromide (1.0 M tetrahydrofuran solution, 2.5 mL) at −78° C. under an argon atmosphere, and the mixture was stirred for 12 hr while allowing to warm to room temperature. Ethyl acetate and water were added to the reaction mixture, and the mixture was extracted with ethyl acetate. The organic layer was washed with saturated brine and dried over anhydrous magnesium sulfate, and the solvent was evaporated. The residue was purified by silica gel column chromatography to give the title compound as a pale-yellow viscous substance (0.54 g, 52%).

$^1$H NMR (300 MHz, CDCl$_3$) δ 0.95 (t, J=7.4, 3 H), 1.33-1.75 (m, 10 H), 2.07-2.21 (m, 4 H), 2.56-2.77 (m, 2 H), 3.88-4.06 (m, 2 H), 7.05-7.78 (m, 12 H)

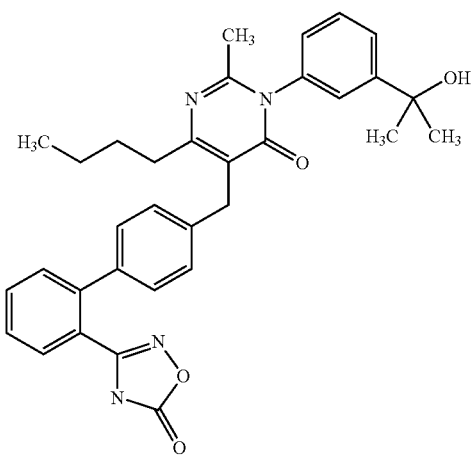

217b) 6-butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.6 g), sodium hydrogen carbonate (0.92 g) and dimethyl sulfoxide (5 mL) was stirred at 40° C. for 30 min, 4'-({4-butyl-1-[3-(1-hydroxy-1-methylethyl)phenyl]-2-methyl-6-oxo-1,6-dihydropyrimidin-5-yl}methyl)biphenyl-2-carbonitrile (0.54 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.19 g) and then 1,8-diazabicyclo[5.4.0]undec-7-ene (0.18 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.33 g, 54%).

$^1$H NMR (300 MHz, CDCl$_3$) δ 0.97 (t, J=7.3, 3 H), 1.36-1.82 (m, 10 H), 2.13 (s, 3 H), 2.58-2.84 (m, 2 H), 3.29 (s, 1 H), 3.74-3.96 (m, 2 H), 6.87-7.77 (m, 12 H), 9.48 (s, 1 H)

6-Butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one hydrochloride 6-butyl-3-[3-(1-hydroxy-1-methylethyl)phenyl]-2-methyl-5-{[2'-(5-oxo-4,5-dihydro-1,2,4-oxadiazol-3-yl)biphenyl-4-yl]methyl}pyrimidin-4(3H)-one hydrobromide Example 218

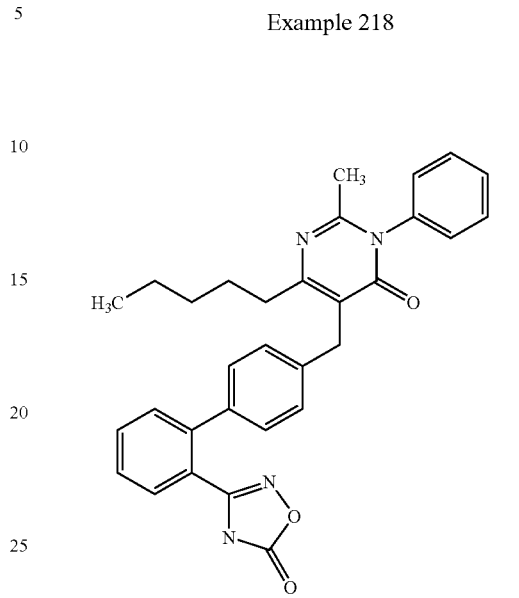

2-methyl-5-{[2'-(5-oxo-4,5-dihydro-1,2,4-oxadiazol-3-yl)biphenyl-4-yl]methyl}-6-pentyl-3-phenylpyrimidin-4(3H)-one To a suspension of 4'-[(2-methyl-6-oxo-4-pentyl-1,6-dihydropyrimidin-5-yl)methyl]biphenyl-2-carbonitrile (1.0 g), phenylboronic acid (1.00 g), triethylamine (2.0 mL), pyridine (1.0 mL) and molecular sieves 4 A (2.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was added to a mixture of hydroxylammonium chloride (1.87 g), sodium hydrogen carbonate (2.71 g) and dimethyl sulfoxide (14 mL) previously stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (15 mL), N,N'-carbonyldiimidazole (0.57 g) and then 1,8-diazabicyclo[5.4.0]undec-7-ene (0.52 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.67 g, 49%).

$^1$H NMR (300 MHz, CDCl$_3$) δ 0.88-0.95 (m, 3 H), 1.31-1.84 (m, 6 H), 2.11 (s, 3 H), 2.56-2.76 (m, 2 H), 3.87 (s, 2 H), 7.04-7.83 (m, 13 H), 8.77 (s, 1 H)

Example 219

6-butyl-2-methyl-5-{[2'-(5-oxo-4,5-dihydro-1,2,4-oxadiazol-3-yl)biphenyl-4-yl]methyl}-3-pyridin-3-ylpyrimidin-4(3H)-one

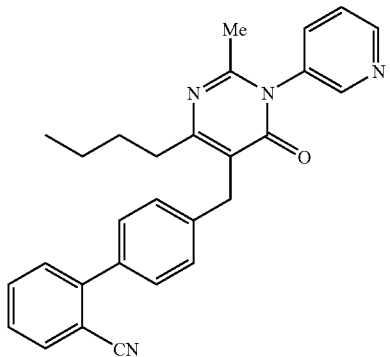

219a) 4'-[(4-butyl-2-methyl-6-oxo-1-pyridin-3-yl-1,6-dihydropyrimidin-5-yl)methyl]biphenyl-2-carbonitrile To a suspension of 4'-[(4-butyl-2-methyl-6-oxo-1,6-dihydropyrimidin-5-yl)methyl]biphenyl-2-carbonitrile (1.0 g), pyridin-3-ylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow viscous substance (0.45 g, 37%).

$^1$H NMR (300 MHz, CDCl$_3$) δ 0.95 (t, J=7.4, 3 H), 1.34-1.73 (m, 4 H), 2.17 (s, 3 H), 2.51-2.80 (m, 2 H), 3.88-4.03 (m, 2 H), 7.33-7.80 (m, 10 H), 8.54 (d, J=2.3, 1 H), 8.73 (dd, J=4.9, 1.5, 1 H)

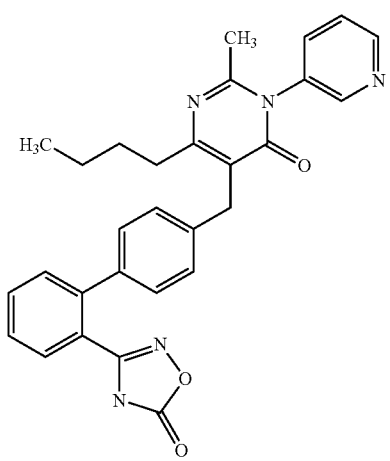

219b) 6-butyl-2-methyl-5-{[2'-(5-oxo-4,5-dihydro-1,2,4-oxadiazol-3-yl)biphenyl-4-yl]methyl}-3-pyridin-3-ylpyrimidin-4(3H)-one A mixture of hydroxylammonium chloride (0.70 g), sodium hydrogen carbonate (1.0 g) and dimethyl sulfoxide (5 mL) was stirred at 40° C. for 30 min, 4'-[(4-butyl-2-methyl-6-oxo-1-pyridin-3-yl-1,6-dihydropyrimidin-5-yl)methyl]biphenyl-2-carbonitrile (0.45 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (5 mL), N,N'-carbonyldiimidazole (0.22 g) and then 1,8-diazabicyclo[5.4.0]undec-7-ene (0.20 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.17 g, 34%).

$^1$H NMR (300 MHz, CDCl$_3$) δ 0.97 (t, J=7.2, 3 H), 1.31-1.81 (m, 4 H), 2.13 (s, 3 H), 2.58-2.80 (m, 2 H), 3.89 (s, 2 H), 7.08-7.86 (m, 11 H), 8.32-8.46 (m, 1 H), 8.54-8.72 (m, 1 H)

Example 220

3-(2,3-dihydro-1-benzofuran-5-yl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one

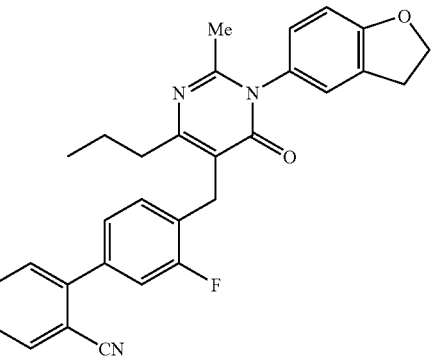

220a) 4'-{[1-(2,3-dihydro-1-benzofuran-5-yl)-2-methyl-6-oxo-4-propyl-1,6-dihydropyrimidin-5-yl]methyl}-3'-fluorobiphenyl-2-carbonitrile To a suspension of 3'-fluoro-4'-[(2-methyl-6-oxo-4-propyl-1,6-dihydropyrimidin-5-yl)methyl]biphenyl-2-carbonitrile (5.0 g), 2,3-dihydro-1-benzofuran-5-ylboronic acid (5.0 g), triethylamine (10.0 mL), pyridine (5.0 mL) and molecular sieves 4 A (10.0 g) in methylene chloride (100 mL) was added copper(II) acetate (5.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (5.41 g, 82%).

¹H NMR (300 MHz, CDCl₃) δ 1.00 (t, J=7.4, 3 H), 1.55-1.80 (m, 2 H), 2.20 (s, 3 H), 2.56-2.72 (m, 2 H), 3.14-3.35 (m, 2 H), 3.98 (s, 2 H), 4.64 (t, J=9.1, 2 H), 6.74-7.85 (m, 10 H)

Example 221

6-butyl-3-(3-cyclopropylphenyl)-2-methyl-5-{[2'-(5-oxo-4,5-dihydro-1,2,4-oxadiazol-3-yl)biphenyl-4-yl]methyl}pyrimidin-4(3H)-one

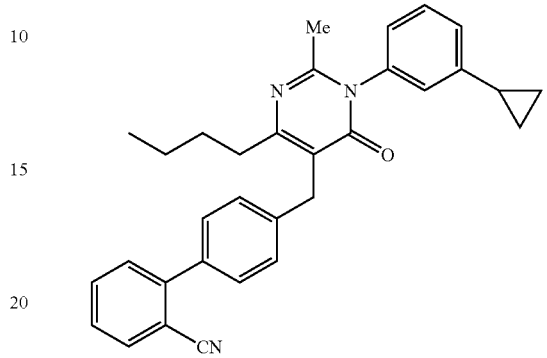

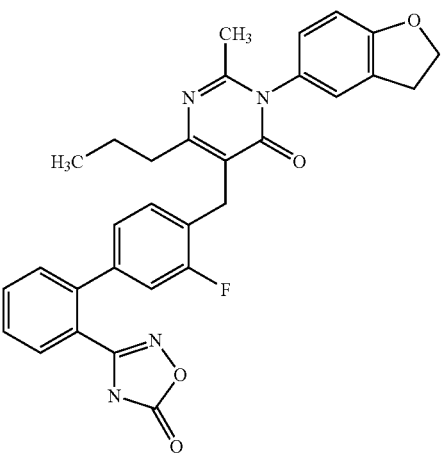

220b) 3-(2,3-dihydro-1-benzofuran-5-yl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one A mixture of hydroxylammonium chloride (7.80 g), sodium hydrogen carbonate (11.4 g) and dimethyl sulfoxide (55 mL) was stirred at 40° C. for 30 min, 4'-{[1-(2,3-dihydro-1-benzofuran-5-yl)-2-methyl-6-oxo-4-propyl-1,6-dihydropyrimidin-5-yl]methyl}-3'-fluorobiphenyl-2-carbonitrile (5.41 g) was added, and the mixture was stirred at 90° C. for 18 hr. The reaction mixture was allowed to cool to room temperature, ethyl acetate and water were added, and the aqueous layer was extracted with ethyl acetate. The organic layer was washed with saturated brine and dried over anhydrous magnesium sulfate, and the solvent was evaporated. The residue was dissolved in tetrahydrofuran (55 mL), N,N'-carbonyldiimidazole (2.74 g) and then 1,8-diazabicyclo[5.4.0]undec-7-ene (2.57 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (2.94 g, 48%).

¹H NMR (300 MHz, DMSO-d₆) δ 0.89 (t, J=7.4, 3 H), 1.45-1.66 (m, 2 H), 2.09 (s, 3 H), 2.39-2.50 (m, 2 H), 3.22 (t, J=8.7, 2 H), 3.85 (s, 2 H), 4.60 (t, J=8.9, 2 H), 6.81-7.75 (m, 10 H), 12.45 (s, 1 H)

221a) 4'-{[4-butyl-1-(3-cyclopropylphenyl)-2-methyl-6-oxo-1,6-dihydropyrimidin-5-yl]methyl}biphenyl-2-carbonitrile A suspension of 4'-{[1-(3-bromophenyl)-4-butyl-2-methyl-6-oxo-1,6-dihydropyrimidin-5-yl]methyl}biphenyl-2-carbonitrile (1.0 g), cyclopropylboronic acid (0.34 g), palladium acetate (0.04 g), tricyclohexylphosphine (0.11 g) and potassium phosphate (1.45 g) in toluene-water (95:5, 10 mL) was stirred at 100° C. for 12 hr under an argon atmosphere. The reaction mixture was diluted with ethyl acetate. The insoluble material was filtered off through celite, and the filtrate was washed with saturated brine and dried over anhydrous magnesium sulfate, and the solvent was evaporated. The residue was purified by silica gel column chromatography to give the title compound as a pale-yellow viscous substance (0.95 g, 100%).

¹H NMR (300 MHz, CDCl₃) δ 0.61-0.83 (m, 2 H), 0.96-1.06 (m, 2 H), 1.26 (t, J=7.2, 3 H), 1.35-1.50 (m, 2 H), 1.56-1.69 (m, 2 H), 1.86-1.99 (m, 1 H), 2.16 (s, 3 H), 2.59-2.73 (m, 2 H), 3.97 (s, 2 H), 6.83-7.83 (m, 12 H)

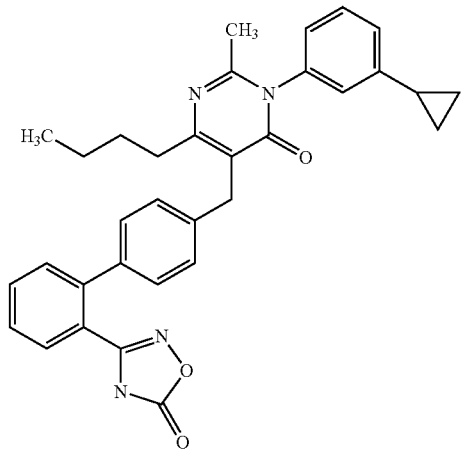

221b) 6-butyl-3-(3-cyclopropylphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.10 g), sodium hydrogen carbonate (1.64 g) and dimethyl sulfoxide (10 mL) was stirred at 40° C. for 30 min, 4'-{[4-butyl-1-(3-cyclopropylphenyl)-2-methyl-6-oxo-1,6-dihydropyrimidin-5-yl]methyl}biphenyl-2-carbonitrile (0.95 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.45 g) and then 1,8-diazabicyclo[5.4.0]undec-7-ene (0.44 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.49 g, 47%).

$^1$H NMR (300 MHz, CDCl$_3$) δ 0.45-1.04 (m, 7 H), 1.31-1.77 (m, 4 H), 1.79-1.98 (m, 1 H), 2.12 (s, 3 H), 2.55-2.77 (m, 2 H), 3.88 (s, 2 H), 6.76-7.81 (m, 12 H), 8.72 (s, 1 H)

Example 222

6-butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one

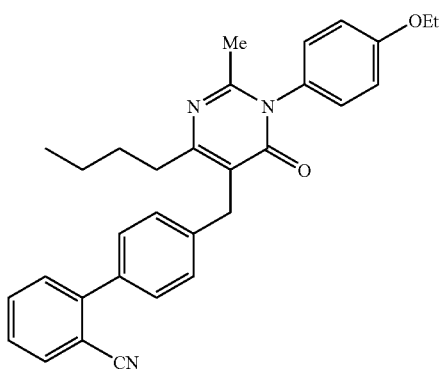

222a) 4'-{[4-butyl-1-(4-ethoxyphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), (4-ethoxyphenyl)boronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.25 g, 93%).

$^1$H NMR (300 MHz, CDCl$_3$) δ 0.94 (t, J=7.3, 3 H), 1.35-1.49 (m, 5 H), 1.55-1.71 (m, 2 H), 2.17 (s, 3 H), 2.62-2.70 (m, 2 H), 3.96 (s, 2 H), 4.07 (q, J=7.0, 2 H), 6.96-7.16 (m, 4 H), 7.36-7.79 (m, 8 H)

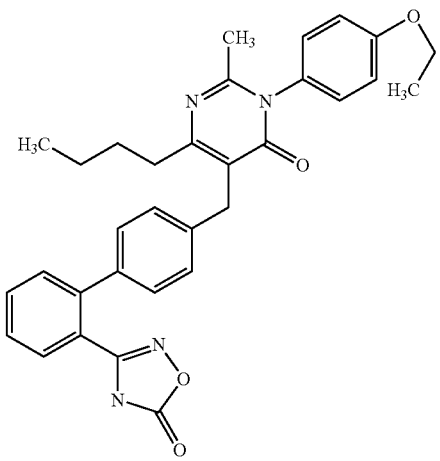

222b) 6-butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.82 g), sodium hydrogen carbonate (2.64 g) and dimethyl sulfoxide (13 mL) was stirred at 40° C. for 30 min, 4'-{[4-butyl-1-(4-ethoxyphenyl)-2-methyl-6-oxo-1,6-dihydropyrimidin-5-yl]methyl}biphenyl-2-carbonitrile (1.25 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (13 mL), N,N'-carbonyldiimidazole (0.54 g) and then 1,8-diazabicyclo[5.4.0]undec-7-ene (0.51 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (1.03 g, 73%).

$^1$H NMR (300 MHz, CDCl$_3$) δ 0.96 (t, J=7.3, 3 H), 1.36-1.73 (m, 7 H), 2.10 (s, 3 H), 2.60-2.71 (m, 2 H), 3.84 (s, 2 H), 4.04 (q, J=7.0, 2 H), 6.84-7.73 (m, 12 H), 9.10 (s, 1 H)

6-Butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one hydrochloride 6-butyl-3-(4-ethoxyphenyl)-2-methyl-5-{[2'-(5-oxo-4,5-dihydro-1,2,4-oxadiazol-3-yl)biphenyl-4-yl]methyl}pyrimidin-4(3H)-one hydrobromide Example 223

6-butyl-3-(3-fluorophenyl)-2-methyl-5-{[2'-(5-oxo-4,5-dihydro-1,2,4-oxadiazol-3-yl)biphenyl-4-yl]methyl}pyrimidin-4(3H)-one

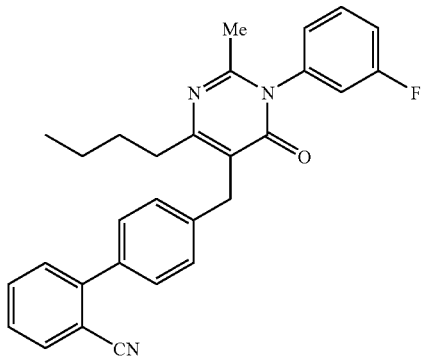

223a) 4'-{[4-butyl-1-(3-fluorophenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), (3-fluorophenyl)boronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.16 g, 92%).

$^1$H NMR (300 MHz, CDCl$_3$) δ 0.95 (t, J=7.3, 3 H), 1.32-1.72 (m, 4 H), 2.18 (s, 3 H), 2.60-2.74 (m, 2 H), 3.96 (s, 2 H), 6.96-7.24 (m, 3 H), 7.36-7.80 (m, 9 H)

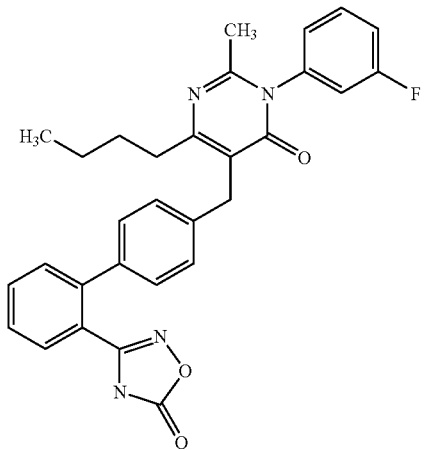

223b) 6-butyl-3-(3-fluorophenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.79 g), sodium hydrogen carbonate (2.60 g) and dimethyl sulfoxide (13 mL) was stirred at 40° C. for 30 min, 4'-{[4-butyl-1-(3-fluorophenyl)-2-methyl-6-oxo-1,6-dihydropyrimidin-5-yl]methyl}biphenyl-2-carbonitrile (1.16 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (13 mL), N,N'-carbonyldiimidazole (0.54 g) and then 1,8-diazabicyclo[5.4.0]undec-7-ene (0.51 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.87 g, 66%).

$^1$H NMR (300 MHz, CDCl$_3$) δ 0.96 (t, J=7.3, 3 H), 1.36-1.74 (m, 4 H), 2.11 (s, 3 H), 2.64-2.73 (m, 2 H), 3.79-3.91 (m, 2 H), 6.82-7.70 (m, 12 H), 8.92 (s, 1 H)

Example 224

3-(1,3-benzodioxol-5-yl)-6-butyl-2-methyl-5-{[2'-(5-oxo-4,5-dihydro-1,2,4-oxadiazol-3-yl)biphenyl-4-yl]methyl}pyrimidin-4(3H)-one

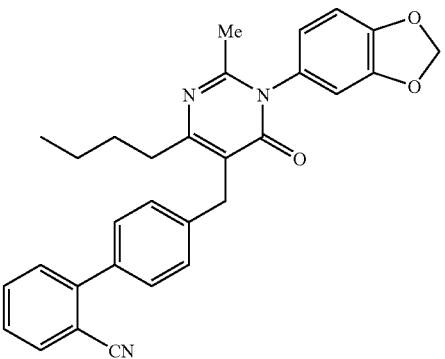

224a) 4'-{[1-(1,3-benzodioxol-5-yl)-4-butyl-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), 1,3-benzodioxol-5-ylboronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred at room temperature for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.99 g, 74%).

¹H NMR (300 MHz, CDCl₃) δ 0.94 (t, J=7.2, 3 H), 1.30-1.74 (m, 4 H), 2.21 (s, 3 H), 2.53-2.76 (m, 2 H), 3.96 (s, 2 H), 5.87-6.19 (m, 2 H), 6.55-7.02 (m, 3 H), 7.34-7.80 (m, 8 H)

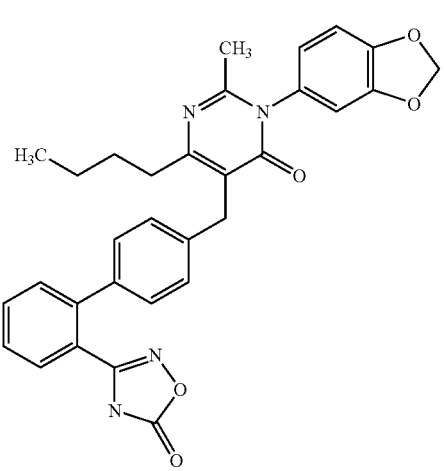

224b) 3-(1,3-benzodioxol-5-yl)-6-butyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.45 g), sodium hydrogen carbonate (2.10 g) and dimethyl sulfoxide (10 mL) was stirred at 40° C. for 30 min, 4'-{[1-(1,3-benzodioxol-5-yl)-4-butyl-2-methyl-6-oxo-1,6-dihydropyrimidin-5-yl]methyl}biphenyl-2-carbonitrile (0.99 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.49 g) and then 1,8-diazabicyclo[5.4.0]undec-7-ene (0.46 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.86 g, 77%).

¹H NMR (300 MHz, CDCl₃) δ 0.92-1.01 (m, 3 H), 1.36-1.76 (m, 4 H), 2.18 (s, 3 H), 2.58-2.78 (m, 2 H), 3.87 (s, 2 H), 6.03 (dd, J=10.4, 1.3, 2 H), 6.47-7.87 (m, 11 H), 8.57 (s, 1 H)

Example 225

N-{3-[4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]phenyl}acetamide

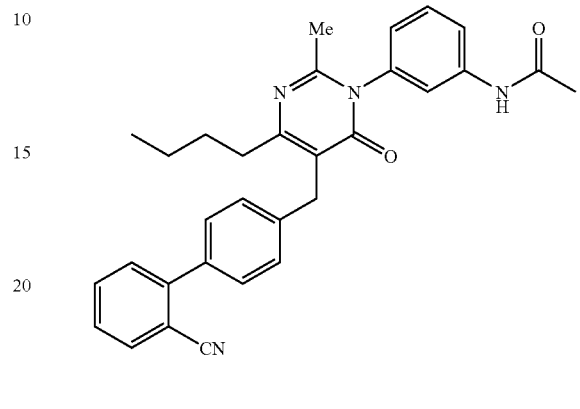

225a) N-{3-[4-butyl-5-[(2'-cyanobiphenyl-4-yl)methyl]-2-methyl-6-oxopyrimidin-1(6H)-yl]phenyl}acetamide To a suspension of 4'-[(4-butyl-2-methyl-6-oxo-1,6-dihydropyrimidin-5-yl)methyl]biphenyl-2-carbonitrile (1.0 g), [3-(acetylamino)phenyl]boronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred at room temperature for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.38 g, 28%).

¹H NMR (300 MHz, CDCl₃) δ 0.72-1.08 (m, 3 H), 1.34-1.71 (m, 4 H), 1.84 (s, 3 H), 2.19 (s, 3 H), 2.58-2.75 (m, 2 H), 3.91-4.09 (m, 2 H), 6.71-7.81 (m, 12 H), 8.66 (s, 1 H)

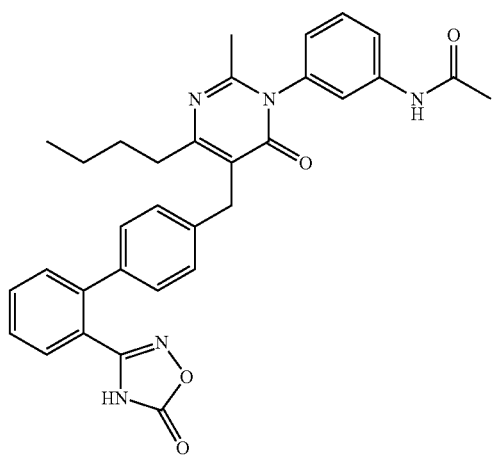

225b) N-{3-[4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]phenyl}acetamide A mixture of hydroxylammonium chloride (0.54 g), sodium hydrogen carbonate (0.78 g) and dimethyl sulfoxide (4 mL) was stirred at 40° C. for 30 min, N-{3-[4-butyl-5-[(2'-cyanobiphenyl-4-yl)methyl]-2-methyl-6-oxopyrimidin-1(6H)-yl]phenyl}acetamide (0.38 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (4 mL), N,N'-carbonyldiimidazole (0.20 g) and then 1,8-diazabicyclo[5.4.0]undec-7-ene (0.18 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.26 g, 62%).

$^1$H NMR (300 MHz, DMSO-$d_6$) δ 0.80-0.89 (m, 3 H), 1.22-1.58 (m, 4 H), 2.06 (s, 3 H), 2.07 (s, 3 H), 2.50-2.58 (m, 2 H), 3.87 (s, 2 H), 6.96-7.74 (m, 12 H), 10.16 (s, 1 H), 12.40 (s, 1 H)

Example 226

6-butyl-2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one

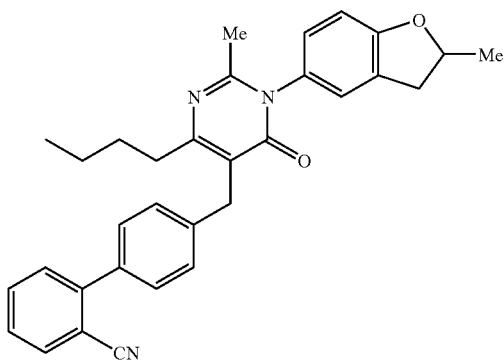

226a) 4'-{[4-butyl-2-methyl-1-(2-methyl-2,3-dihydro-1-benzofuran-5-yl)-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), (2-methyl-2,3-dihydro-1-benzofuran-5-yl)boronic acid (1.0 g), triethylamine (2.0 mL), pyridine (1.0 mL) and molecular sieves 4 A (1.0 g) in methylene chloride (15 mL) was added copper(II) acetate (1.0 g), and the mixture was stirred at room temperature for 2 days. The reaction mixture was diluted with ethyl acetate. The insoluble material was filtered off through celite, and the filtrate was concentrated. The residue was purified by silica gel column chromatography to give the title compound as a pale-yellow viscous substance (1.42 g, 100%).

$^1$H NMR (300 MHz, CDCl$_3$) δ 0.94 (t, J=7.2, 3 H), 1.31-1.82 (m, 7 H), 2.20 (d, J=4.9, 3 H), 2.59-2.70 (m, 2 H), 2.78-2.95 (m, 1 H), 3.26-3.44 (m, 1 H), 3.96 (s, 2 H), 4.88-5.09 (m, 1 H), 6.75-7.79 (m, 11 H)

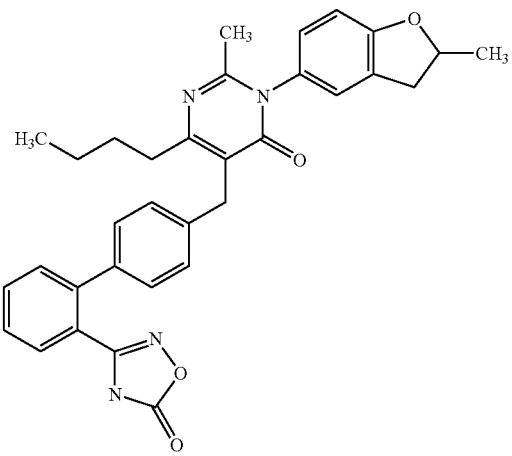

226b) 6-butyl-2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.95 g), sodium hydrogen carbonate (2.82 g) and dimethyl sulfoxide (14 mL) was stirred at 40° C. for 30 min, 4'-{[4-butyl-2-methyl-1-(2-methyl-2,3-dihydro-1-benzofuran-5-yl)-6-oxo-1,6-dihydropyrimidin-5-yl]methyl}biphenyl-2-carbonitrile (1.42 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (14 mL), N,N'-carbonyldiimidazole (0.68 g) and then 1,8-diazabicyclo[5.4.0]undec-7-ene (0.63 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (1.11 g, 73%).

$^1$H NMR (300 MHz, DMSO-$d_6$) δ 0.74-0.94 (m, 3 H), 1.21-1.57 (m, 7 H), 2.08 (d, J=3.4, 3 H), 2.48-2.56 (m, 2 H), 2.74-2.93 (m, 1 H), 3.31-3.44 (m, 1 H), 3.85 (s, 2 H), 4.89-5.10 (m, 1 H), 6.73-7.79 (m, 11 H), 12.40 (s, 1 H)

Example 227

6-butyl-5-{[3-fluoro-2'-(5-oxo-4,5-dihydro-1,2,4-oxadiazol-3-yl)biphenyl-4-yl]methyl}-2-methyl-3-(2-methyl-2,3-dihydro-1-benzofuran-5-yl)pyrimidin-4(3H)-one

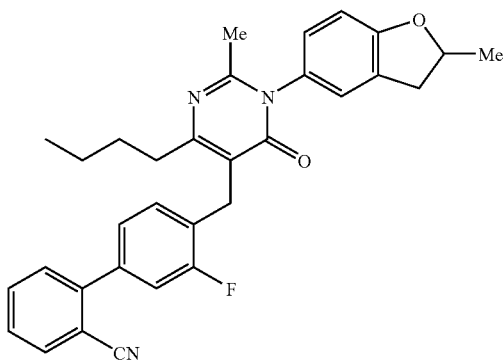

227a) 4'-{[4-butyl-2-methyl-1-(2-methyl-2,3-dihydro-1-benzofuran-5-yl)-6-oxo-1,6-dihydropyrimidin-5-yl]methyl}-3'-fluorobiphenyl-2-carbonitrile To a suspension of 4'-[(4-butyl-2-methyl-6-oxo-1,6-dihydropyrimidin-5-yl)methyl]-3'-fluorobiphenyl-2-carbonitrile (0.5 g), (2-methyl-2,3-dihydro-1-benzofuran-5-yl)boronic acid (1.0 g), triethylamine (2.0 mL), pyridine (1.0 mL) and molecular sieves 4 A (2.0 g) in methylene chloride (15 mL) was added copper(II) acetate (1.0 g), and the mixture was stirred at room temperature for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.63 g, 93%).

$^1$H NMR (300 MHz, CDCl$_3$) δ 0.94 (t, J=7.2, 3 H), 1.31-1.74 (m, 7 H), 2.20 (d, J=4.5, 3 H), 2.56-2.72 (m, 2 H), 2.74-3.01 (m, 1 H), 3.14-3.58 (m, 1 H), 3.97 (s, 2 H), 4.50-5.42 (m, 1 H), 6.55-7.89 (m, 10 H)

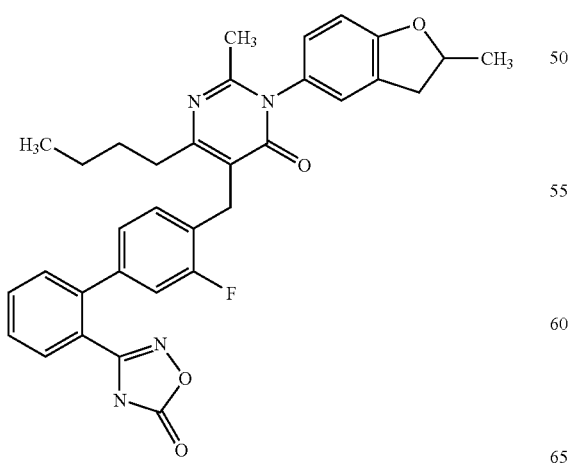

227b) 6-butyl-5-{[3-fluoro-2'-(5-oxo-4,5-dihydro-1,2,4-oxadiazol-3-yl)biphenyl-4-yl]methyl}-2-methyl-3-(2-methyl-2,3-dihydro-1-benzofuran-5-yl)pyrimidin-4(3H)-one A mixture of hydroxylammonium chloride (0.86 g), sodium hydrogen carbonate (1.25 g) and dimethyl sulfoxide (6 mL) was stirred at 40° C. for 30 min, 4'-{[4-butyl-2-methyl-1-(2-methyl-2,3-dihydro-1-benzofuran-5-yl)-6-oxo-1,6-dihydropyrimidin-5-yl]methyl}-3'-fluorobiphenyl-2-carbonitrile (0.63 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (14 mL), N,N'-carbonyldiimidazole (0.30 g) and then 1,8-diazabicyclo[5.4.0]undec-7-ene (0.28 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.42 g, 59%).

$^1$H NMR (300 MHz, DMSO-d$_6$) δ 0.85 (t, J=7.4, 3 H), 1.22-1.58 (m, 7 H), 2.09 (d, J=3.4, 3 H), 2.44-2.54 (m, 2 H), 2.73-2.89 (m, 1 H), 3.28-3.42 (m, 1 H), 3.84 (s, 2 H), 4.76-5.14 (m, 1 H), 6.67-7.87 (m, 10 H), 12.47 (s, 1 H)

Example 228

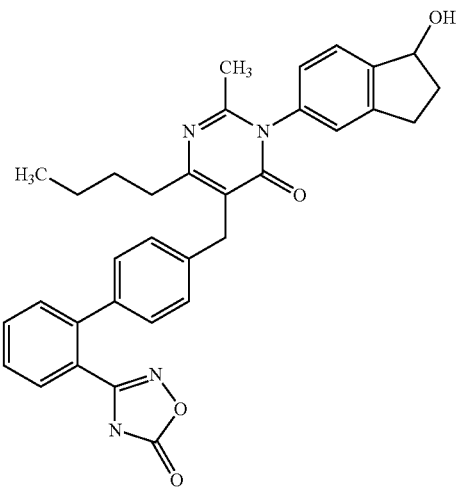

6-butyl-3-(1-hydroxy-2,3-dihydro-1H-inden-5-yl)-2-methyl-5-{[2'-(5-oxo-4,5-dihydro-1,2,4-oxadiazol-3-yl)biphenyl-4-yl]methyl}pyrimidin-4(3H)-one To a suspension of 4'-[(4-butyl-2-methyl-6-oxo-1,6-dihydropyrimidin-5-yl)methyl]biphenyl-2-carbonitrile (3.0 g), (1-oxo-2,3-dihydro-1H-inden-5-yl)boronic acid (2.87 g), triethylamine (6.0 mL), pyridine (3.0 mL) and molecular sieves 4 A (6.0 g) in tetrahydrofuran (50 mL) was added copper(II) acetate (3.0 g), and the mixture was stirred for 2 days. The reaction mixture was diluted with ethyl acetate and the insoluble material was filtered off through celite. The filtrate was concentrated and the residue was crudely purified by silica gel column chromatography. To a solution of the crudely purified product in ethanol (8 mL) was added sodium tetrahydroboron (0.083 g), and the mixture was stirred for 3 hr. Ethyl acetate and water were added to the reaction mixture, and the mixture was extracted with ethyl acetate. The organic layer was washed with saturated brine and dried over anhydrous magnesium sulfate, and the solvent was evaporated. The residue was added to a mixture of hydroxylammonium chloride (0.83 g), sodium hydrogen carbonate (1.2 g) and dimethyl sulfoxide (6 mL) previously stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.21 g) and then 1,8-diazabicyclo[5.4.0]undec-7-ene (0.20 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.12 g, 18%).

$^1$H NMR (300 MHz, DMSO-$d_6$) δ 0.85 (t, J=7.2, 3 H), 1.21-1.59 (m, 4 H), 1.73-1.93 (m, 1 H), 2.06 (d, J=6.1, 3 H), 2.29-3.06 (m, 5 H), 3.86 (s, 2 H), 5.10 (q, J=6.1, 1 H), 5.38 (dd, J=5.9, 4.0, 1 H), 7.08-7.78 (m, 11 H), 12.39 (s, 1 H)

Example 229

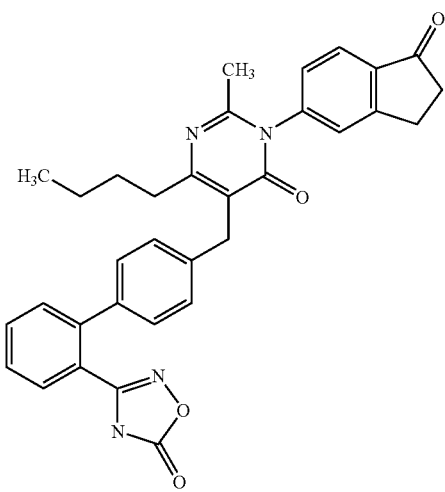

6-butyl-2-methyl-3-(1-oxo-2,3-dihydro-1H-inden-5-yl)-5-{[2'-(5-oxo-4,5-dihydro-1,2,4-oxadiazol-3-yl)biphenyl-4-yl]methyl}pyrimidin-4(3H)-one To a solution of 6-butyl-3-(1-hydroxy-2,3-dihydro-1H-inden-5-yl)-2-methyl-5-{[2'-(5-oxo-4,5-dihydro-1,2,4-oxadiazol-3-yl)biphenyl-4-yl]methyl}pyrimidin-4(3H)-one (0.055 g) in acetonitrile (2 mL) was added 1,1,1-tris(acetyloxy)-1,1-dihydro-1,2-benziodoxol-3(1H)-one (0.085 g), and the mixture was stirred for 2 hr. Ethyl acetate, water and sodium thiosulfate were added to the reaction mixture, and the mixture was extracted with ethyl acetate. The organic layer was washed with saturated brine and dried over anhydrous magnesium sulfate, and the solvent was evaporated. The residue was purified by silica gel column chromatography to give the title compound as a colorless solid (0.027 g, 49%).

$^1$H NMR (300 MHz, CDCl$_3$) δ 0.97 (t, J=7.2, 3 H), 1.35-1.78 (m, 4 H), 2.15 (s, 3 H), 2.63-2.83 (m, 4 H), 3.12-3.24 (m, 2 H), 3.91 (s, 2 H), 7.10-7.93 (m, 11 H)

Example 230

6-butyl-3-(4-methoxyphenyl)-2-methyl-5-{[2'-(5-oxo-4,5-dihydro-1,2,4-oxadiazol-3-yl)biphenyl-4-yl]methyl}pyrimidin-4(3H)-one

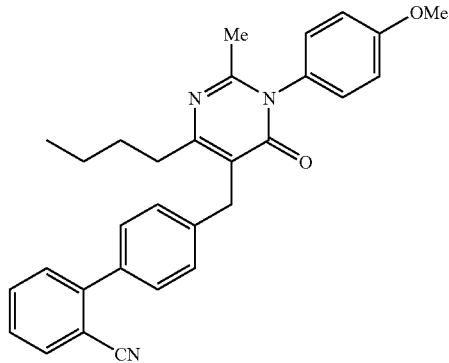

230a) 4'-{[4-butyl-1-(4-methoxyphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (3.0 g), (4-methoxyphenyl)boronic acid (3.0 g), triethylamine (6.0 mL), pyridine (3.0 mL) and molecular sieves 4 A (6.0 g) in methylene chloride (50 mL) was added copper(II) acetate (3.0 g), and the mixture was stirred at room temperature for 2 days. The reaction mixture was diluted with ethyl acetate. The insoluble material was filtered off through celite, and the filtrate was concentrated. The residue was purified by silica gel column chromatography to give the title compound as a pale-yellow viscous substance (3.03 g, 78%).

$^1$H NMR (300 MHz, CDCl$_3$) δ 0.94 (t, J=7.4, 3 H), 1.31-1.85 (m, 4 H), 2.18 (s, 3 H), 2.51-2.83 (m, 2 H), 3.85 (s, 3 H), 3.96 (s, 2 H), 6.83-7.82 (m, 12 H)

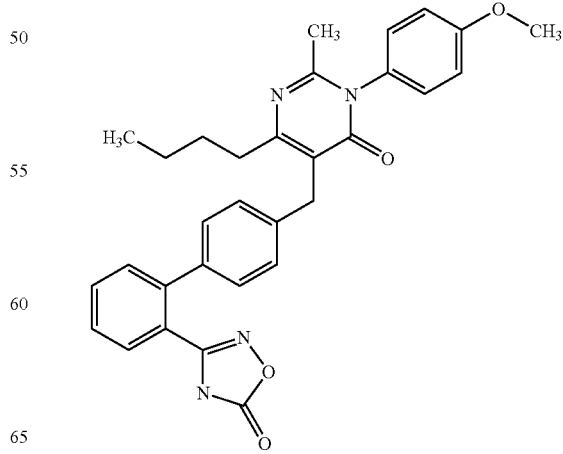

230b) 6-butyl-3-(4-methoxyphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.50 g), sodium hydrogen carbonate (2.18 g) and dimethyl sulfoxide (10 mL) was stirred at 40° C. for 30 min, 4'-{[4-butyl-1-(4-methoxyphenyl)-2-methyl-6-oxo-1,6-dihydropyrimidin-5-yl]methyl}biphenyl-2-carbonitrile (1.0 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.46 g) and then 1,8-diazabicyclo[5.4.0]undec-7-ene (0.42 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.88 g, 78%).

$^1$H NMR (300 MHz, CDCl$_3$) δ 0.96 (t, J=7.2, 3 H), 1.28-1.77 (m, 4 H), 2.10 (s, 3 H), 2.40-2.77 (m, 2 H), 3.83 (s, 2 H), 3.86 (s, 3 H), 6.85-7.83 (m, 12 H), 8.48 (s, 1 H)

Example 231

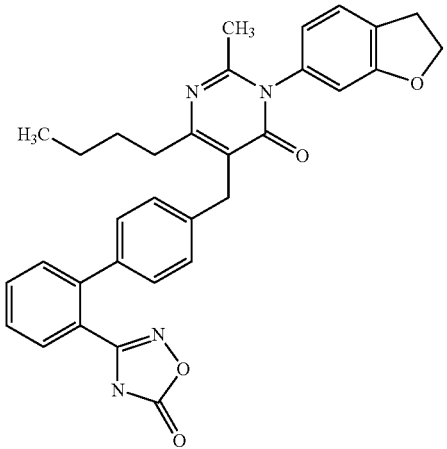

6-butyl-3-(2,3-dihydro-1-benzofuran-6-yl)-2-methyl-5-{[2'-(5-oxo-4,5-dihydro-1,2,4-oxadiazol-3-yl)biphenyl-4-yl]methyl}pyrimidin-4(3H)-one To a suspension of 4'-[(4-butyl-2-methyl-6-oxo-1,6-dihydropyrimidin-5-yl)methyl]biphenyl-2-carbonitrile (1.0 g), 2,3-dihydro-1-benzofuran-6-ylboronic acid (1.0 g), triethylamine (2.0 mL), pyridine (1.0 mL) and molecular sieves 4 A (2.0 g) in methylene chloride (15 mL) was added copper(II) acetate (1.0 g), and the mixture was stirred at room temperature for 2 days. The reaction mixture was diluted with ethyl acetate. The insoluble material was filtered off through celite, and the filtrate was concentrated. The residue was crudely purified by silica gel column chromatography. The crudely purified product was added to a mixture of hydroxylammonium chloride (1.95 g), sodium hydrogen carbonate (2.82 g) and dimethyl sulfoxide (14 mL) previously stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.59 g) and then 1,8-diazabicyclo[5.4.0]undec-7-ene (0.54 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (1.24 g, 83%).

$^1$H NMR (300 MHz, DMSO-d$_6$) δ 0.85 (t, J=7.4, 3 H), 1.20-1.53 (m, 4 H), 2.09 (s, 3 H), 2.46-2.57 (m, 2 H), 3.24 (t, J=8.8, 2 H), 3.86 (s, 2 H), 4.61 (t, J=8.8, 2 H), 6.70-7.74 (m, 11 H), 12.41 (s, 1 H)

Example 232

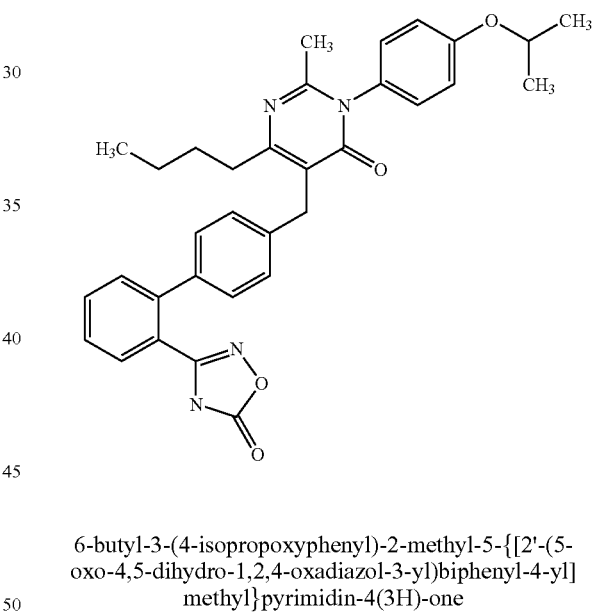

6-butyl-3-(4-isopropoxyphenyl)-2-methyl-5-{[2'-(5-oxo-4,5-dihydro-1,2,4-oxadiazol-3-yl)biphenyl-4-yl]methyl}pyrimidin-4(3H)-one To a suspension of 4'-[(4-butyl-2-methyl-6-oxo-1,6-dihydropyrimidin-5-yl)methyl]biphenyl-2-carbonitrile (1.0 g), (4-isopropoxyphenyl)boronic acid (1.0 g), triethylamine (2.0 mL), pyridine (1.0 mL) and molecular sieves 4 A (2.0 g) in tetrahydrofuran (15 mL) was added copper(II) acetate (1.0 g), and the mixture was stirred at room temperature for 2 days. The reaction mixture was diluted with ethyl acetate. The insoluble material was filtered off through celite, and the filtrate was concentrated. The residue was roughly purified by silica gel column chromatography. The crudely purified product was added to a mixture of hydroxylammonium chloride (1.95 g), sodium hydrogen carbonate (2.82 g) and dimethyl sulfoxide (14 mL) previously stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.59 g) and then 1,8-diazabicyclo[5.4.0]undec-7-ene (0.54 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (1.16 g, 75%).

$^1$H NMR (300 MHz, DMSO-$d_6$) δ 0.85 (t, J=7.4, 3 H), 1.15-1.67 (m, 10 H), 2.06 (s, 3 H), 2.50-2.56 (m, 2 H), 3.86 (s, 2 H), 4.58-4.78 (m, 1 H), 6.94-7.75 (m, 12 H), 12.41 (s, 1 H)

Example 233

6-butyl-3-(3-fluoro-4-methoxyphenyl)-2-methyl-5-{[2'-(5-oxo-4,5-dihydro-1,2,4-oxadiazol-3-yl)biphenyl-4-yl]methyl}pyrimidin-4(3H)-one

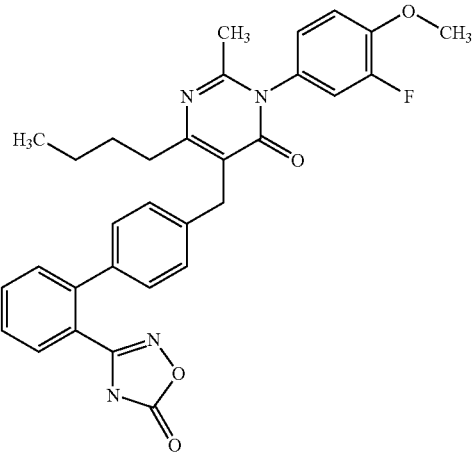

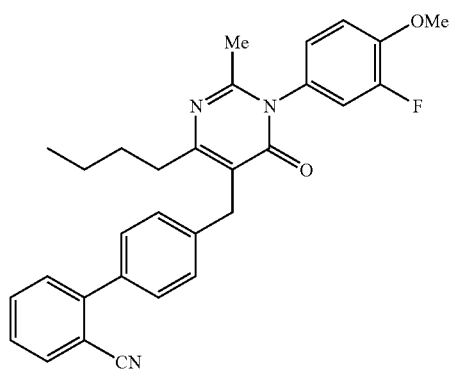

233a) 4'-{[4-butyl-1-(3-fluoro-4-methoxyphenyl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (3.0 g), (3-fluoro-4-methoxyphenyl)boronic acid (3.0 g), triethylamine (6.0 mL), pyridine (3.0 mL) and molecular sieves 4 A (6.0 g) in methylene chloride (50 mL) was added copper(II) acetate (3.0 g), and the mixture was stirred at room temperature for 2 days. The reaction mixture was diluted with ethyl acetate. The insoluble material was filtered off through celite, and the filtrate was concentrated. The residue was purified by silica gel column chromatography to give the title compound as a pale-yellow viscous substance (2.62 g, 65%).

$^1$H NMR (300 MHz, CDCl$_3$) δ 0.72-1.04 (m, 3 H), 1.28-1.78 (m, 4 H), 2.19 (s, 3 H), 2.48-2.76 (m, 2 H), 3.94 (s, 3 H), 3.96 (s, 2 H), 6.91-7.82 (m, 11 H)

233b) 6-butyl-3-(3-fluoro-4-methoxyphenyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.46 g), sodium hydrogen carbonate (2.10 g) and dimethyl sulfoxide (10 mL) was stirred at 40° C. for 30 min, 4'-{[4-butyl-1-(3-fluoro-4-methoxyphenyl)-2-methyl-6-oxo-1,6-dihydropyrimidin-5-yl]methyl}biphenyl-2-carbonitrile (1.0 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (10 mL), N,N'-carbonyldiimidazole (0.44 g) and then 1,8-diazabicyclo[5.4.0]undec-7-ene (0.40 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.78 g, 69%).

$^1$H NMR (300 MHz, DMSO-$d_6$) δ 0.85 (t, J=7.4, 3 H), 1.19-1.64 (m, 4 H), 2.08 (s, 3 H), 2.41-2.58 (m, 2 H), 3.86 (s, 2 H), 3.90 (s, 3 H), 7.14-7.75 (m, 11 H), 12.41 (s, 1 H)

Example 234

6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one

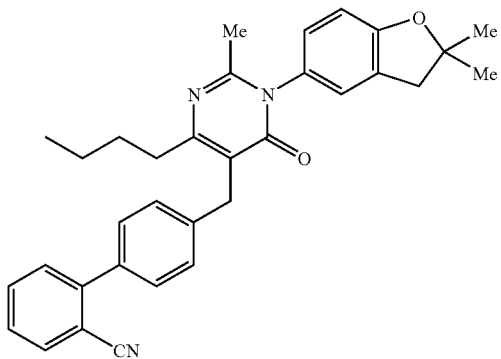

234a) 4'-{[4-butyl-1-(2,2-dimethyl-2,3-dihydro-1-benzofuran-5-yl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (1.0 g), (2,2-dimethyl-2,3-dihydro-1-benzofuran-5-yl)boronic acid (0.43 g), triethylamine (2.0 mL), pyridine (1.0 mL) and molecular sieves 4 A (2.0 g) in methylene chloride (15 mL) was added copper(II) acetate (1.0 g), and the mixture was stirred at room temperature for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.68 g, 60%).

$^1$H NMR (300 MHz, CDCl$_3$) δ 0.94 (t, J=7.4, 3 H), 1.35-1.46 (m, 2 H), 1.48 (s, 3 H), 1.52 (s, 3 H), 1.55-1.71 (m, 2 H), 2.20 (s, 3 H), 2.61-2.71 (m, 2 H), 3.06 (s, 2 H), 3.96 (s, 2 H), 6.76-7.03 (m, 3 H), 7.33-7.83 (m, 8 H)

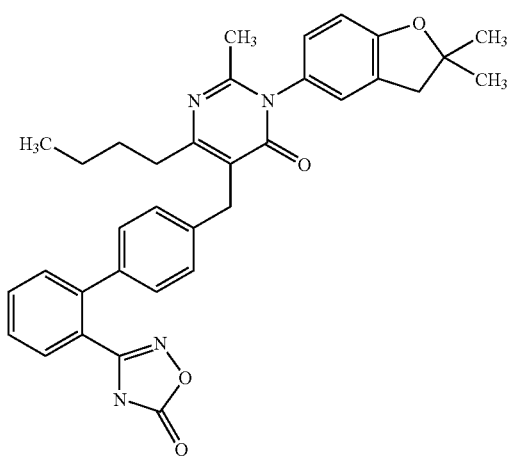

234b) 6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.1 g), sodium hydrogen carbonate (1.69 g) and dimethyl sulfoxide (7 mL) was stirred at 40° C. for 30 min, 4'-{[4-butyl-1-(2,2-dimethyl-2,3-dihydro-1-benzofuran-5-yl)-2-methyl-6-oxo-1,6-dihydropyrimidin-5-yl]methyl}biphenyl-2-carbonitrile (0.68 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (7 mL), N,N'-carbonyldiimidazole (0.33 g) and then 1,8-diazabicyclo[5.4.0]undec-7-ene (0.30 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.46 g, 61%).

$^1$H NMR (300 MHz, DMSO-d$_6$) δ 0.85 (t, J=7.2, 3 H), 1.14-1.63 (m, 10 H), 2.08 (s, 3 H), 2.49-2.61 (m, 2 H), 3.05 (s, 2 H), 3.85 (s, 2 H), 6.68-7.79 (m, 11 H), 12.40 (s, 1 H)

6-Butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one sodium salt 6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one potassium salt 6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one 0.5 calcium salt 6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one hydrochloride 6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one hydrobromide

Example 235

2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one

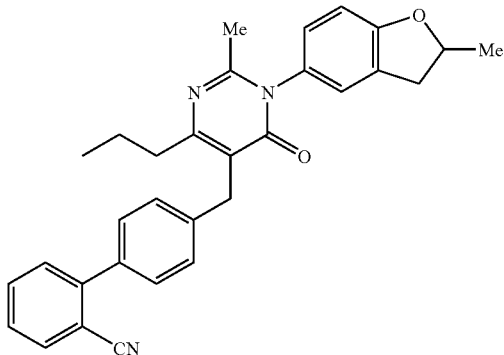

235a) 4'-{[2-methyl-1-(2-methyl-2,3-dihydro-1-benzofuran-5-yl)-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (2-methyl-2,3-dihydro-1-benzofuran-5-yl)boronic acid (0.5 g), triethylamine (2.0 mL), pyridine (1.0 mL) and molecular sieves 4 A (2.0 g) in tetrahydrofuran (15 mL) was added copper(II) acetate (1.0 g), and the mixture was stirred at room temperature for 2 days. The reaction mixture was diluted with ethyl acetate. The insoluble material was filtered off through celite, and the filtrate was concentrated. The residue was purified by silica gel column chromatography to give the title compound as a pale-yellow viscous substance (0.68 g, 49%).

$^1$H NMR (300 MHz, CDCl$_3$) δ 1.01 (t, J=7.4, 3 H), 1.43-1.78 (m, 5 H), 2.20 (d, J=4.9, 3 H), 2.58-2.70 (m, 2 H), 2.79-2.94 (m, 1 H), 3.25-3.43 (m, 1 H), 3.97 (s, 2 H), 4.89-5.10 (m, 1 H), 6.79-7.79 (m, 11 H)

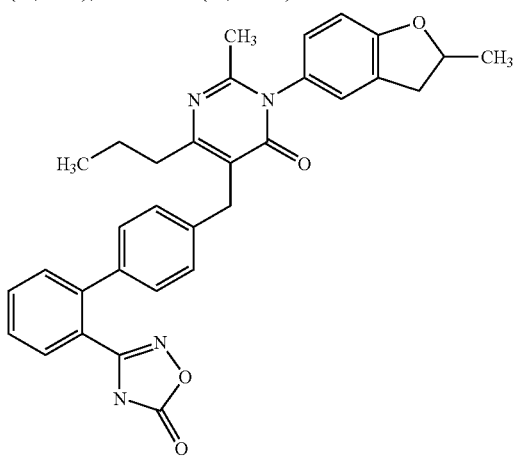

235b) 2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.20 g), sodium hydrogen carbonate (1.8 g) and dimethyl sulfoxide (7 mL) was stirred at 40° C. for 30 min, 4'-{[2-methyl-1-(2-methyl-2,3-dihydro-1-benzofuran-5-yl)-6-oxo-4-propyl-1,6-dihydropyrimidin-5-yl]methyl}biphenyl-2-carbonitrile (1.0 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate, and the solvent was evaporated. The residue was dissolved in tetrahydrofuran (7 mL), N,N'-carbonyldiimidazole (0.35 g) and then 1,8-diazabicyclo[5.4.0]undec-7-ene (0.32 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.37 g, 48%).

$^1$H NMR (300 MHz, DMSO-d$_6$) δ 0.88 (t, J=7.2, 3 H), 1.36-1.64 (m, 5 H), 2.08 (d, J=3.0, 3 H), 2.45-2.55 (m, 2 H), 2.74-2.90 (m, 1 H), 3.30-3.42 (m, 1 H), 3.86 (s, 2 H), 4.89-5.09 (m, 1 H), 6.76-7.73 (m, 11 H), 12.39 (s, 1 H)

2-Methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one sodium salt 2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one potassium salt 2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one 0.5 calcium salt 2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one hydrochloride 2-methyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one hydrobromide

Example 236 methyl 5-[4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]-2,3-dihydro-1-benzofuran-7-carboxylate

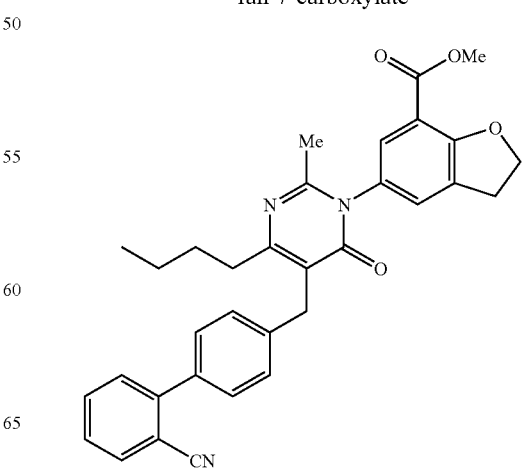

236a) methyl 5-[4-butyl-5-[(2'-cyanobiphenyl-4-yl)methyl]-2-methyl-6-oxopyrimidin-1(6H)-yl]-2,3-dihydro-1-benzofuran-7-carboxylate To a suspension of 4'-[(4-butyl-2-methyl-6-oxo-1,6-dihydropyrimidin-5-yl)methyl]biphenyl-2-carbonitrile (2.0 g), [7-(methoxycarbonyl)-2,3-dihydro-1-benzofuran-5-yl]boronic acid (1.64 g), triethylamine (4.0 mL), pyridine (2.0 mL) and molecular sieves 4 A (4.0 g) in methylene chloride (30 mL) was added copper(II) acetate (2.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (0.24 g, 8%).

$^1$H NMR (300 MHz, CDCl$_3$) δ 0.95 (t, J=7.4, 3 H), 1.30-1.71 (m, 4 H), 2.21 (s, 3 H), 2.54-2.77 (m, 2 H), 3.11-3.45 (m, 2 H), 3.89 (s, 3 H), 3.91-4.02 (m, 2 H), 4.81 (t, J=8.9, 2 H), 7.15-7.79 (m, 10 H)

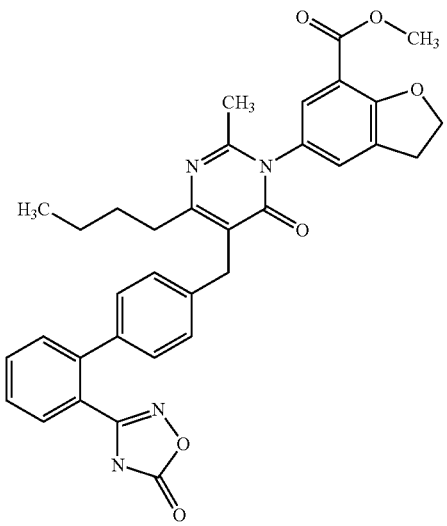

236b) methyl 5-[4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]-2,3-dihydro-1-benzofuran-7-carboxylate A mixture of hydroxylammonium chloride (0.31 g), sodium hydrogen carbonate (0.44 g) and dimethyl sulfoxide (3 mL) was stirred at 40° C. for 30 min, methyl 5-[4-butyl-5-[(2'-cyanobiphenyl-4-yl)methyl]-2-methyl-6-oxopyrimidin-1(6H)-yl]-2,3-dihydro-1-benzofuran-7-carboxylate (0.24 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (2.6 mL). N,N'-carbonyldiimidazole (0.055 g) and then 1,8-diazabicyclo[5.4.0]undec-7-ene (0.051 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.081 g, 31%).

$^1$H NMR (300 MHz, DMSO-d$_6$) δ 0.85 (t, J=7.2, 3 H), 1.22-1.58 (m, 4 H), 2.09 (s, 3 H), 2.48-2.57 (m, 2 H), 3.27 (t, J=8.9, 2 H), 3.80 (s, 3 H), 3.86 (s, 2 H), 4.73 (t, J=8.7, 2 H), 7.13-7.73 (m, 10 H), 12.41 (s, 1 H)

Example 237

6-butyl-3-(3-hydroxy-2,3-dihydro-1H-inden-5-yl)-2-methyl-5-{[2'-(5-oxo-4,5-dihydro-1,2,4-oxadiazol-3-yl)biphenyl-4-yl]methyl}pyrimidin-4(3H)-one

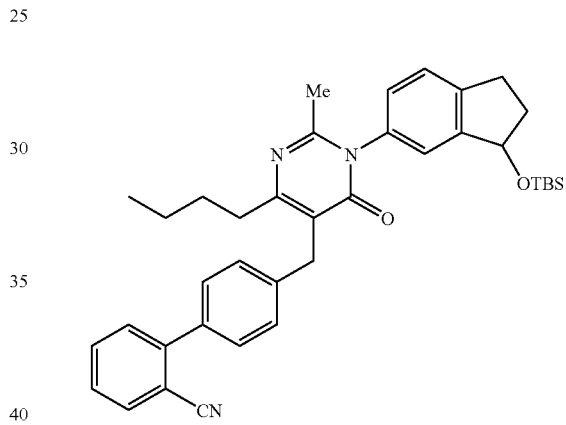

237a) 4'-{[4-butyl-1-(3-{[tert-butyl(dimethyl)silyl]oxy}-2,3-dihydro-1H-inden-5-yl)-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (3.0 g), (3-{[tert-butyl(dimethyl)silyl]oxy}-2,3-dihydro-1H-inden-5-yl)boronic acid (3.07 g), triethylamine (6.0 mL), pyridine (3.0 mL) and molecular sieves 4 A (6.0 g) in methylene chloride (50 mL) was added copper(II) acetate (3.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (3.7 g, 73%).

$^1$H NMR (300 MHz, CDCl$_3$) δ 0.14 (s, 6 H), 0.90-0.99 (m, 12 H), 1.38-1.71 (m, 4 H), 1.89-2.03 (m, 1 H), 2.18 (s, 3 H), 2.37-3.19 (m, 5 H), 3.98 (s, 2 H), 5.28 (t, J=6.8, 1 H), 6.95-8.24 (m, 11 H)

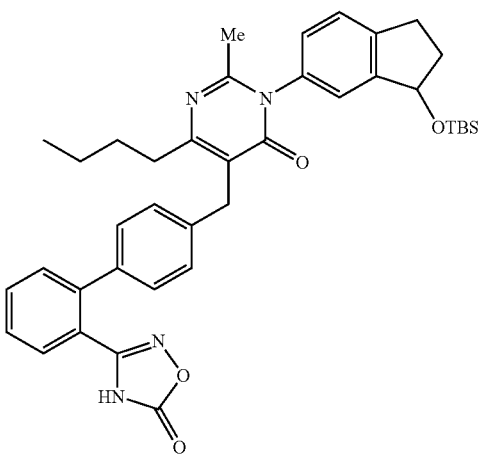

237b) 6-butyl-3-(3-{[tert-butyl(dimethyl)silyl]oxy}-2,3-dihydro-1H-inden-5-yl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (2.50 g), sodium hydrogen carbonate (3.70 g) and dimethyl sulfoxide (20 mL) was stirred at 40° C. for 30 min, 4'-{[4-butyl-1-(3-{[tert-butyl(dimethyl)silyl]oxy}-2,3-dihydro-1H-inden-5-yl)-2-methyl-6-oxo-1,6-dihydropyrimidin-5-yl]methyl}biphenyl-2-carbonitrile (2.20 g) was added, and the mixture was stirred at 90° C. for 18 hr. The mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10.0 mL). N,N'-carbonyldiimidazole (0.36 g) and then 1,8-diazabicyclo[5.4.0]undec-7-ene (0.33 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (1.02 g, 42%).

$^1$H NMR (300 MHz, CDCl$_3$) δ 0.14 (s, 6 H), 0.91 (s, 9 H), 0.97 (t, J=7.2, 3 H), 1.38-1.76 (m, 4 H), 1.89-2.03 (m, 1 H), 2.16 (s, 3 H), 2.31-3.17 (m, 5 H), 3.93 (s, 2 H), 5.25 (t, J=6.8, 1 H), 6.95-7.89 (m, 12 H)

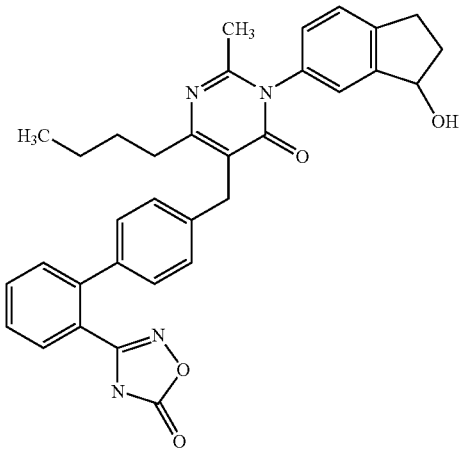

237c) 6-butyl-3-(3-hydroxy-2,3-dihydro-1H-inden-5-yl)-2-methyl-5-{[2'-(5-oxo-4,5-dihydro-1,2,4-oxadiazol-3-yl)biphenyl-4-yl]methyl}pyrimidin-4(3H)-one To a solution of 6-butyl-3-(3-{[tert-butyl(dimethyl)silyl]oxy}-2,3-dihydro-1H-inden-5-yl)-2-methyl-5-{[2'-(5-oxo-4,5-dihydro-1,2,4-oxadiazol-3-yl)biphenyl-4-yl]methyl}pyrimidin-4(3H)-one (1.02 g) in tetrahydrofuran (8 mL) was added tetrabutylammonium fluoride (0.60 g), and the mixture was stirred at 50° C. for 12 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a colorless solid (0.49 g, 59%).

$^1$H NMR (300 MHz, DMSO-d$_6$) δ 0.85 (t, J=7.2, 3 H), 1.22-1.57 (m, 4 H), 1.74-1.93 (m, 1 H), 2.06 (d, J=3.8, 3 H), 2.29-2.57 (m, 3 H), 2.67-3.08 (m, 2 H), 3.87 (s, 2 H), 5.09 (q, J=6.8, 1 H), 5.34 (dd, J=8.5, 5.9, 1 H), 7.04-7.80 (m, 11 H), 12.40 (s, 1 H)

Example 238

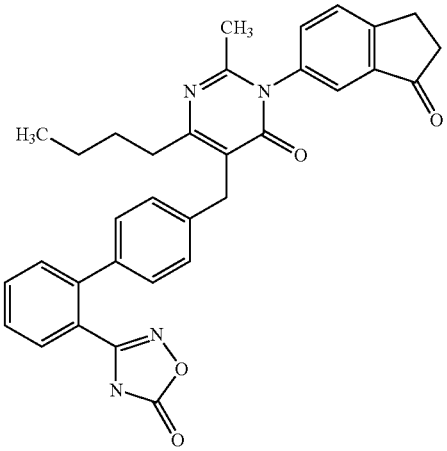

6-butyl-2-methyl-3-(3-oxo-2,3-dihydro-1H-inden-5-yl)-5-{[2'-(5-oxo-4,5-dihydro-1,2,4-oxadiazol-3-yl)biphenyl-4-yl]methyl}pyrimidin-4(3H)-one To a solution of 6-butyl-3-(3-hydroxy-2,3-dihydro-1H-inden-5-yl)-2-methyl-5-{[2'-(5-oxo-4,5-dihydro-1,2,4-oxadiazol-3-yl)biphenyl-4-yl]methyl}pyrimidin-4(3H)-one (0.30 g) in acetonitrile (3 mL) was added 1,1,1-tris(acetyloxy)-1,1-dihydro-1,2-benziodoxol-3(1H)-one (0.35 g), and the mixture was stirred at room temperature for 3 hr. Ethyl acetate, water and sodium thiosulfate were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a colorless solid (0.25 g, 82%).

¹H NMR (300 MHz, DMSO-d₆) δ 0.85 (t, J=7.4, 3 H), 1.22-1.58 (m, 4 H), 2.06 (s, 3 H), 2.47-2.57 (m, 2 H), 2.66-2.80 (m, 2 H), 3.11-3.25 (m, 2 H), 3.87 (s, 2 H), 7.07-7.80 (m, 11 H), 12.40 (s, 1 H)

Example 239

3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one

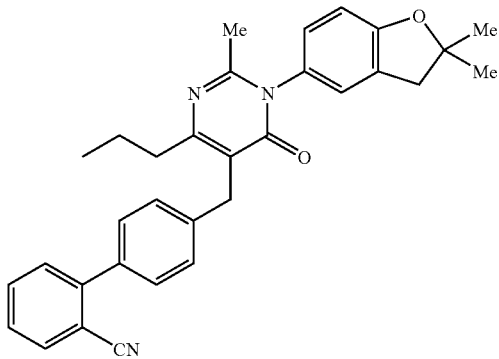

239a) 4'-{[1-(2,2-dimethyl-2,3-dihydro-1-benzofuran-5-yl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (4.0 g), (2,2-dimethyl-2,3-dihydro-1-benzofuran-5-yl)boronic acid (4.0 g), triethylamine (8.0 mL), pyridine (4.0 mL) and molecular sieves 4 A (8.0 g) in methylene chloride (60 mL) was added copper(II) acetate (4.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow solid (4.28 g, 75%).

¹H NMR (300 MHz, CDCl₃) δ 1.01 (t, J=7.4, 3 H), 1.48 (s, 3 H), 1.52 (s, 3 H), 1.61-1.77 (m, 2 H), 2.20 (s, 3 H), 2.60-2.70 (m, 2 H), 3.06 (s, 2 H), 3.97 (s, 2 H), 6.75-7.81 (m, 11 H)

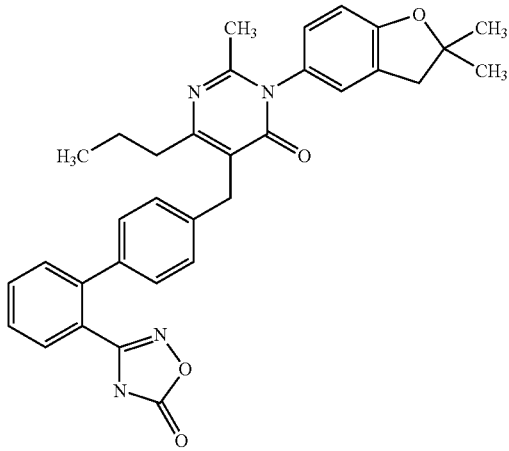

239b) 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (6.1 g), sodium hydrogen carbonate (8.80 g) and dimethyl sulfoxide (50 mL) was stirred at 40° C. for 30 min, 4'-{[1-(2,2-dimethyl-2,3-dihydro-1-benzofuran-5-yl)-2-methyl-6-oxo-4-propyl-1,6-dihydropyrimidin-5-yl]methyl}biphenyl-2-carbonitrile (4.28 g) was added, and the mixture was stirred at 90° C. for 23 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (50 mL). N,N'-carbonyldiimidazole (1.7 g) and then 1,8-diazabicyclo[5.4.0]undec-7-ene (1.57 mL) were added, and the mixture was stirred at room temperature for 1 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (3.64 g, 76%).

¹H NMR (300 MHz, DMSO-d₆) δ 0.88 (t, J=7.4, 3 H), 1.44 (s, 3 H), 1.45 (s, 3 H), 1.48-1.61 (m, 2 H), 2.08 (s, 3 H), 2.45-2.54 (m, 2 H), 3.05 (s, 2 H), 3.85 (s, 2 H), 6.74-7.74 (m, 11 H), 12.40 (s, 1 H)

239c) Crystalline 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one (1) A solution of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one (150 g) in acetone (400 ml) was stirred for 3 days. The precipitate was collected and washed with acetone. The solid was dried under reduced pressure at 120° C. for 8 hr to give the title compound (136 g, 91%) as colorless crystals.

Powder X-ray diffraction (Cu—Kα radiation, diffraction angle: 2θ(°)): 4.76, 6.10, 7.30, 7.86, 8.16, 9.18, 9.60, 10.66, 11.28, 11.94, 12.58, 13.34, 14.62, 15.10, 15.46, 16.34, 16.90, 17.76, 18.64, 19.34, 20.86, 21.58, 22.42, 24.36, 24.86. Anal calcd for C₃₃H₃₂N₄O₄: C, 72.24; H, 5.88; N, 10.21. Found C, 71.97; H, 5.86; N, 10.14.

(2) To a solution of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one (347 g) in methyl ethyl ketone (700 ml) was added heptane (1050 mL) dropwise at 60° C. and the mixture was allowed to cool to room temperature followed by stirring at this temperature for 12 hr. The obtained precipitate was collected, washed with methyl ethyl ketone, and dried under reduced pressure at 80° C. for 5 hr to give the title compound (293 g, 90%) as colorless crystals.

¹H NMR (300 MHz, DMSO-d₆) δ 0.88 (t, J=7.4, 3 H), 1.44 (s, 3 H), 1.45 (s, 3 H), 1.48-1.61 (m, 2 H), 2.08 (s, 3 H), 2.45-2.54 (m, 2 H), 3.05 (s, 2 H), 3.85 (s, 2 H), 6.74-7.74 (m, 11 H), 12.40 (s, 1 H)

Powder X-ray diffraction (Cu—Kα radiation, diffraction angle: 2θ(°)): 4.38, 7.42, 8.90, 9.68, 10.92, 11.24, 11.90, 12.56, 12.88, 13.34, 14.06, 14.92, 16.64, 17.30, 17.80, 18.70, 19.08, 19.40, 20.36, 20.90, 21.20, 21.50, 21.98, 22.40, 22.72, 22.98, 23.68. Anal calcd for $C_{33}H_{32}N_4O_4$: C, 72.24; H, 5.88; N, 10.21. Found C, 72.11; H, 5.85; N, 10.26.

3-(2,2-Dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 240

6-butyl-2-(methoxymethyl)-5-{[2'-(5-oxo-4,5-dihydro-1,2,4-oxadiazol-3-yl)biphenyl-4-yl]methyl}pyrimidin-4(3H)-one

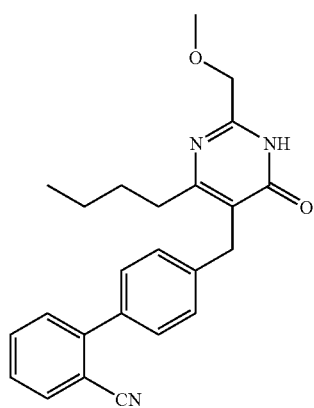

240a) 4'-{[4-butyl-2-(methoxymethyl)-6-oxo-1,6-dihydropyrimidin-5-yl]methyl}biphenyl-2-carbonitrile To a mixture of 2-methoxyethanimidamide hydrochloride (2.1 g) and methanol (15 mL) were added sodium methoxide (28% methanol solution, 4.8 g), and then a solution of ethyl 2-[(2'-cyanobiphenyl-4-yl)methyl]-3-oxoheptanoate (3.0 g) in methanol (25 mL) and 1,4-dioxane (10 mL) at 0° C., and the mixture was stirred at room temperature for 16 hr. The reaction mixture was concentrated, and the residue was adjusted to pH 5 with water (50 mL) and 50% aqueous acetic acid solution, and extracted with ethyl acetate. The obtained ethyl acetate layer was washed with saturated brine and dried over anhydrous magnesium sulfate. The solvent was evaporated under reduced pressure and the residue was purified by silica gel column chromatography to give the title compound as colorless crystals (2.4 g, 75%).

$^1$H NMR (300 MHz, DMSO-$d_6$) δ 0.82 (3H, t, J=7.3), 1.19-1.34 (2H, m), 1.37-1.50 (2H, m), 2.46-2.58 (5H, m), 3.33 (3H, s), 3.88 (2H, s), 4.23 (2H, s), 7.33 (2H, d, J=8.3), 7.48 (2H, d, J=8.3), 7.51-7.62 (2H, m), 7.72-7.82 (1H, m), 7.93 (1H, d, J=7.7), 12.37 (1H, br)

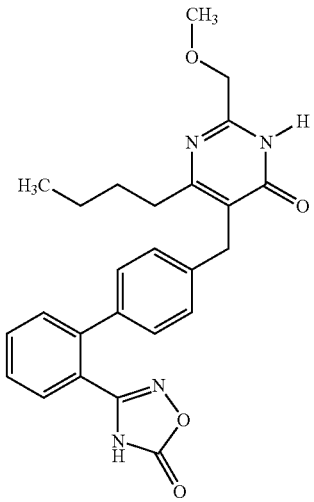

240b) 6-butyl-2-(methoxymethyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.89 g), sodium hydrogen carbonate (3.04 g) and dimethyl sulfoxide (15 mL) was stirred at 40° C. for 30 min, 4'-{[4-butyl-2-(methoxymethyl)-6-oxo-1,6-dihydropyrimidin-5-yl]methyl}biphenyl-2-carbonitrile (0.70 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL). N,N'-carbonyldiimidazole (0.35 g) and then 1,8-diazabicyclo[5.4.0]undec-7-ene (0.30 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.37 g, 47%).

$^1$H NMR (300 MHz, DMSO-$d_6$) δ 0.82 (3H, t, J=7.3), 1.19-1.37 (2H, m), 1.37-1.63 (2H, m), 2.46-2.55 (5H, m), 3.84 (2H, s), 4.23 (2H, s), 7.13-7.33 (4H, m), 7.46-7.61 (2H, m), 7.61-7.75 (2H, m), 12.36 (2H, s)

Example 241

3-(2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one

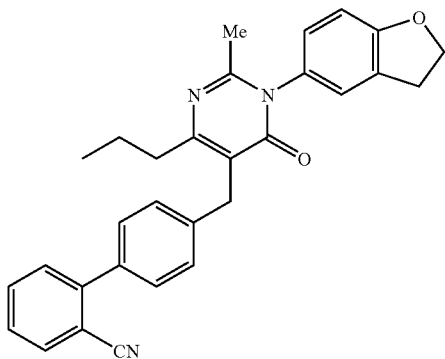

241a) 4'-{[1-(2,3-dihydro-1-benzofuran-5-yl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (2.0 g), 2,3-dihydro-1-benzofuran-5-ylboronic acid (2.0 g), triethylamine (4.0 mL), pyridine (2.0 mL) and molecular sieves 4 A (4.0 g) in methylene chloride (30 mL) was added copper(II) acetate (2.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (2.26 g, 84%).

$^1$H NMR (300 MHz, CDCl$_3$) δ 1.01 (t, J=7.4, 3 H), 1.55-1.79 (m, 2 H), 2.20 (d, J=2.3, 3 H), 2.55-2.75 (m, 2 H), 3.15-3.36 (m, 2 H), 3.96 (s, 2 H), 4.50-4.71 (m, 2 H), 6.54-7.80 (m, 11 H)

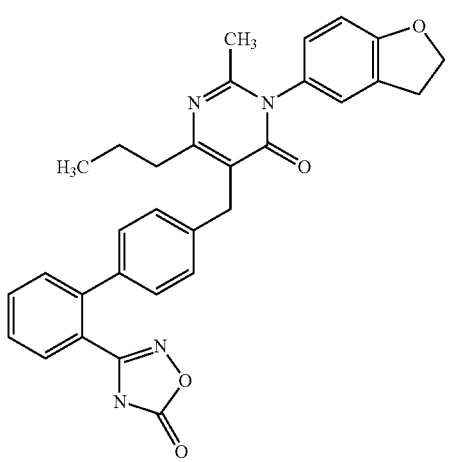

241b) 3-(2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (3.5 g), sodium hydrogen carbonate (5.0 g) and dimethyl sulfoxide (25 mL) was stirred at 40° C. for 30 min, 4'-{[1-(2,3-dihydro-1-benzofuran-5-yl)-2-methyl-6-oxo-4-propyl-1,6-dihydropyrimidin-5-yl]methyl}biphenyl-2-carbonitrile (2.26 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (25 mL). N,N'-carbonyldiimidazole (0.97 g) and then 1,8-diazabicyclo[5.4.0]undec-7-ene (0.90 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (1.61 g, 63%).

$^1$H NMR (300 MHz, DMSO-d$_6$) δ 0.88 (t, J=7.2, 3 H), 1.43-1.64 (m, 2 H), 2.09 (s, 3 H), 2.45-2.54 (m, 2 H), 3.15-3.29 (m, 2 H), 3.86 (s, 2 H), 4.61 (t, J=8.7, 2 H), 6.73-7.76 (m, 11 H), 12.39 (s, 1 H)

Example 242

3-(4-methoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

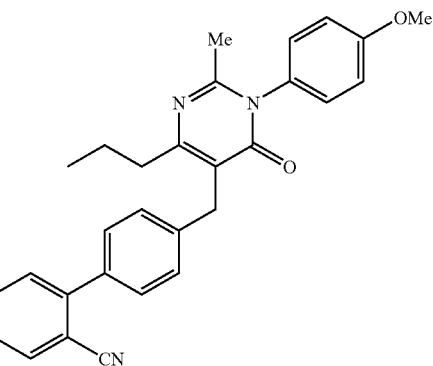

242a) 4'-{[1-(4-methoxyphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (2.0 g), (4-methoxyphenyl)boronic acid (2.0 g), triethylamine (4.0 mL), pyridine (2.0 mL) and molecular sieves 4 A (4.0 g) in methylene chloride (30 mL) was added copper(II) acetate (2.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (2.15 g, 82%).

¹H NMR (300 MHz, CDCl₃) δ 1.01 (t, J=7.4, 3 H), 1.54-1.84 (m, 2 H), 2.17 (s, 3 H), 2.54-2.78 (m, 2 H), 3.85 (s, 3 H), 3.97 (s, 2 H), 6.89-7.86 (m, 12 H)

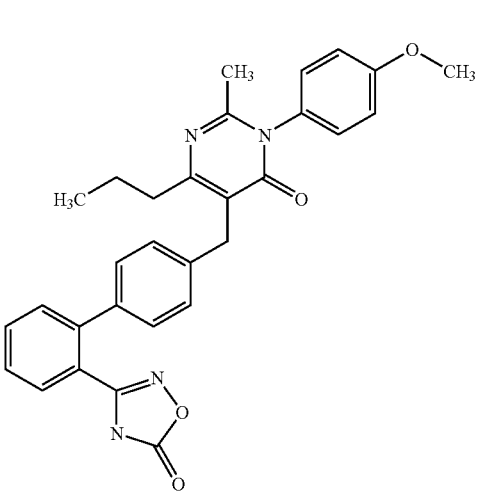

242b) 3-(4-methoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (3.5 g), sodium hydrogen carbonate (5.0 g) and dimethyl sulfoxide (25 mL) was stirred at 40° C. for 30 min, 4'-{[1-(4-methoxyphenyl)-2-methyl-6-oxo-4-propyl-1,6-dihydropyrimidin-5-yl]methyl}biphenyl-2-carbonitrile (2.15 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (25 mL). N,N'-carbonyldiimidazole (0.97 g) and then 1,8-diazabicyclo[5.4.0]undec-7-ene (0.90 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (1.46 g, 60%).

¹H NMR (300 MHz, DMSO-d₆) δ 0.89 (t, J=7.4, 3 H), 1.42-1.64 (m, 2 H), 2.06 (s, 3 H), 2.45-2.56 (m, 2 H), 3.81 (s, 3 H), 3.87 (s, 2 H), 7.00-7.75 (m, 12 H), 12.39 (s, 1 H)

Example 243

3-(4-ethoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

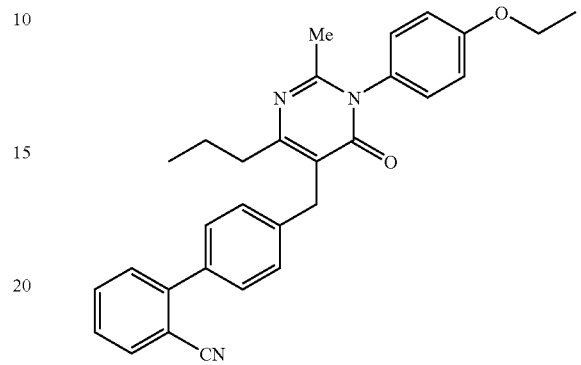

243a) 4'-{[1-(4-ethoxyphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (2.0 g), (4-ethoxyphenyl)boronic acid (2.0 g), triethylamine (4.0 mL), pyridine (2.0 mL) and molecular sieves 4 A (4.0 g) in methylene chloride (30 mL) was added copper(II) acetate (2.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (2.47 g, 91%).

¹H NMR (300 MHz, CDCl₃) δ 1.01 (t, J=7.4, 3 H), 1.43 (t, J=7.0, 3 H), 1.58-1.83 (m, 2 H), 2.17 (s, 3 H), 2.56-2.70 (m, 2 H), 3.97 (s, 2 H), 4.06 (q, J=6.8, 2 H), 6.93-7.79 (m, 12 H)

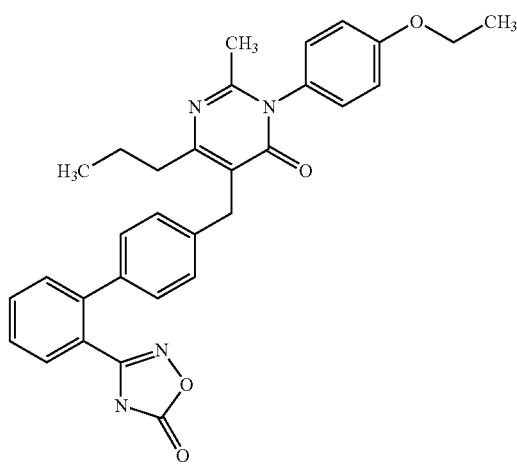

243b) 3-(4-ethoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (3.5 g), sodium hydrogen carbonate (5.0 g) and dimethyl sulfoxide (25 mL) was stirred at 40° C. for 30 min, 4'-{[1-(4-ethoxyphenyl)-2-methyl-6-oxo-4-propyl-1,6-dihydropyrimidin-5-yl]methyl}biphenyl-2-carbonitrile (2.47 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (25 mL). N,N'-carbonyldiimidazole (0.97 g) and then 1,8-diazabicyclo[5.4.0]undec-7-ene (0.90 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (2.18 g, 70%).

$^1$H NMR (300 MHz, DMSO-d$_6$) δ 0.89 (t, J=7.4, 3 H), 1.35 (t, J=7.0, 3 H), 1.44-1.63 (m, 2 H), 2.06 (s, 3 H), 2.45-2.55 (m, 2 H), 3.86 (s, 2 H), 4.08 (q, J=7.0, 2 H), 7.00-7.74 (m, 12 H), 12.39 (br s, 1 H)

Example 244

3-(3-fluoro-4-methoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

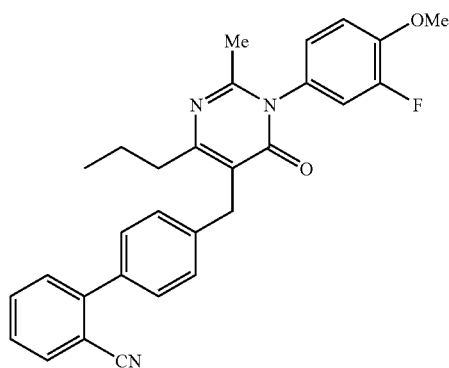

244a) 4'-{[1-(3-fluoro-4-methoxyphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (3-fluoro-4-methoxyphenyl)boronic acid (1.0 g), triethylamine (2.0 mL), pyridine (1.0 mL) and molecular sieves 4 A (3.0 g) in tetrahydrofuran (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.24 g, 91%).

$^1$H NMR (300 MHz, CDCl$_3$) δ 1.01 (t, J=7.4, 3 H), 1.58-1.77 (m, 2 H), 2.19 (s, 3 H), 2.57-2.72 (m, 2 H), 3.94 (s, 3 H), 3.96 (s, 2 H), 6.90-7.79 (m, 11 H)

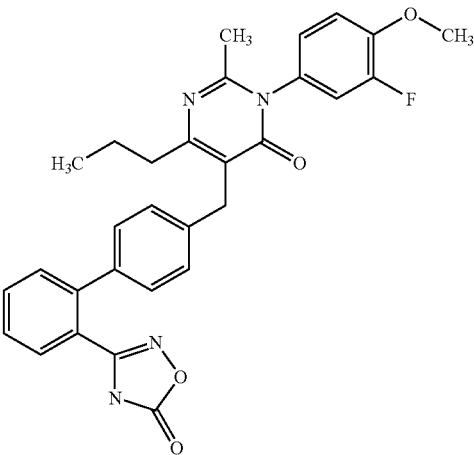

244b) 3-(3-fluoro-4-methoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.74 g), sodium hydrogen carbonate (2.5 g) and dimethyl sulfoxide (10 mL) was stirred at 40° C. for 30 min, 4'-{[1-(3-fluoro-4-methoxyphenyl)-2-methyl-6-oxo-4-propyl-1,6-dihydropyrimidin-5-yl]methyl}biphenyl-2-carbonitrile (1.24 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.45 g) and then 1,8-diazabicyclo[5.4.0]undec-7-ene (0.42 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (1.04 g, 74%).

$^1$H NMR (300 MHz, DMSO-d$_6$) δ 0.89 (t, J=7.4, 3 H), 1.45-1.62 (m, 2 H), 2.09 (s, 3 H), 2.45-2.53 (m, 2 H), 3.87 (s, 2 H), 3.90 (s, 3 H), 7.14-7.73 (m, 11 H), 12.39 (s, 1 H)

Example 245

3-(3-fluoro-4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

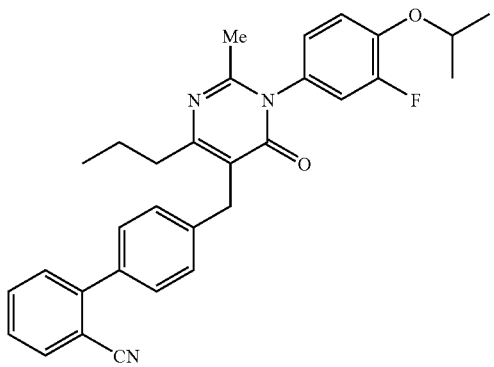

245a) 4'-{[1-(3-fluoro-4-isopropoxyphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (3-fluoro-4-isopropoxyphenyl)boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.15 g, 80%).

$^1$H NMR (300 MHz, CDCl$_3$) δ 1.01 (t, J=7.2, 3 H), 1.39 (t, J=6.6, 6 H), 1.60-1.79 (m, 2 H), 2.19 (s, 3 H), 2.59-2.70 (m, 2 H), 3.96 (s, 2 H), 4.51-4.68 (m, 1 H), 6.90-7.78 (m, 11 H)

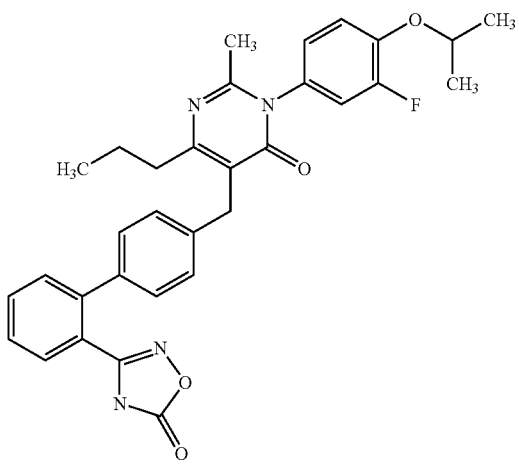

245b) 3-(3-fluoro-4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.7 g), sodium hydrogen carbonate (2.5 g) and dimethyl sulfoxide (10 mL) was stirred at 40° C. for 30 min, 4'-{[1-(3-fluoro-4-isopropoxyphenyl)-2-methyl-6-oxo-4-propyl-1,6-dihydropyrimidin-5-yl]methyl}biphenyl-2-carbonitrile (1.15 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.52 g) and then 1,8-diazabicyclo[5.4.0]undec-7-ene (0.47 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.83 g, 64%).

$^1$H NMR (300 MHz, DMSO-d$_6$) δ 0.89 (t, J=7.4, 3 H), 1.32 (dd, J=5.9, 2.5, 6 H), 1.45-1.62 (m, 2 H), 2.09 (s, 3 H), 2.46-2.54 (m, 2 H), 3.87 (s, 2 H), 4.63-4.81 (m, 1 H), 7.08-7.74 (m, 11 H), 12.39 (s, 1 H)

Example 246

3-[4-(cyclopropylmethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

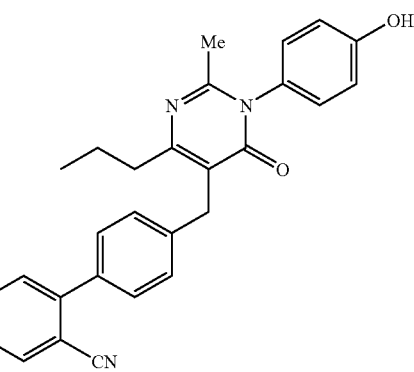

246a) 4'-{[1-(4-hydroxyphenyl)-2-methyl-6-oxo-4-propyl-1,6-dihydropyrimidin-5-yl]methyl}biphenyl-2-carbonitrile To a solution of 4'-{[1-(4-methoxyphenyl)-2-methyl-6-oxo-4-propyl-1,6-dihydropyrimidin-5-yl]methyl}biphenyl-2-carbonitrile (11.8 g) in methylene chloride (100 mL) was added boron tribromide (1.0 M methylene chloride solution, 50 mL), and the mixture was stirred at room temperature for 2 days. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow solid (12.22 g, 100%).

¹H NMR (300 MHz, DMSO-d₆) δ 0.97 (t, J=7.4, 3 H), 1.51-1.69 (m, 2 H), 2.27 (s, 3 H), 2.69 (t, J=7.8, 2 H), 3.96 (s, 2 H), 6.85-8.00 (m, 12 H), 9.97 (s, 1 H)

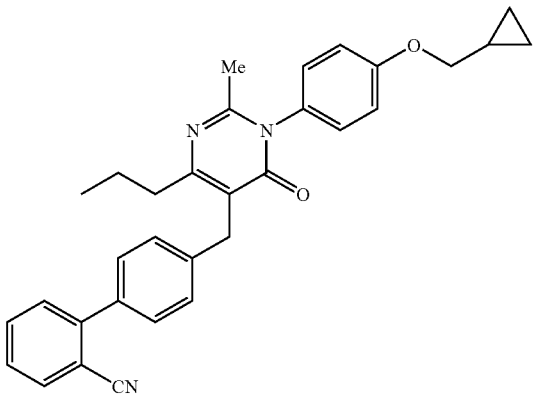

246b) 4'-({1-[4-(cyclopropylmethoxy)phenyl]-2-methyl-6-oxo-4-propyl-1,6-dihydropyrimidin-5-yl}methyl)biphenyl-2-carbonitrile To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and (bromomethyl)cyclopropane (0.70 mL) in N,N-dimethylformamide (10 mL) was added cesium carbonate (1.5 g), and the mixture was stirred at 70° C. for 12 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.93 g, 83%).

¹H NMR (300 MHz, CDCl₃) δ 0.31-0.40 (m, 2 H), 0.61-0.71 (m, 2 H), 1.01 (t, J=7.2, 3 H), 1.21-1.36 (m, 1 H), 1.63-1.76 (m, 2 H), 2.17 (s, 3 H), 2.60-2.70 (m, 2 H), 3.83 (d, J=7.2, 2 H), 3.96 (s, 2 H), 6.96-7.77 (m, 12 H)

246c) 3-[4-(cyclopropylmethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.3 g), sodium hydrogen carbonate (1.9 g) and dimethyl sulfoxide (10 mL) was stirred at 40° C. for 30 min, 4'-({1-[4-(cyclopropylmethoxy)phenyl]-2-methyl-6-oxo-4-propyl-1,6-dihydropyrimidin-5-yl}methyl)biphenyl-2-carbonitrile (0.93 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.37 g) and then 1,8-diazabicyclo[5.4.0]undec-7-ene (0.35 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.84 g, 81%).

¹H NMR (300 MHz, DMSO-d₆) δ 0.30-0.39 (m, 2 H), 0.53-0.63 (m, 2 H), 0.89 (t, J=7.4, 3 H), 1.19-1.32 (m, 1 H), 1.45-1.62 (m, 2 H), 2.06 (s, 3 H), 2.46-2.55 (m, 2 H), 3.86 (s, 2 H), 3.85-3.91 (m, 2 H), 6.98-7.74 (m, 12 H), 12.39 (s, 1 H)

Example 247

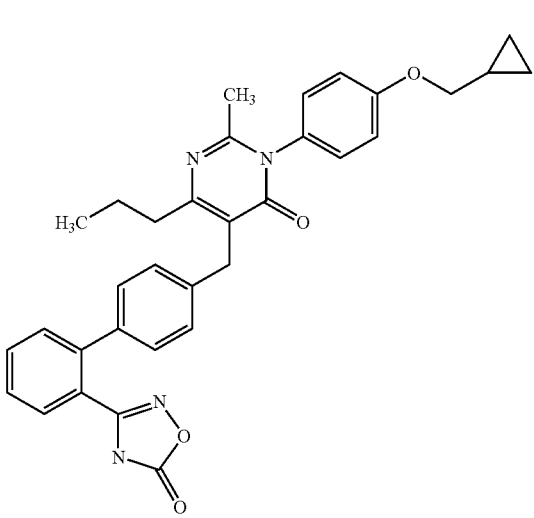

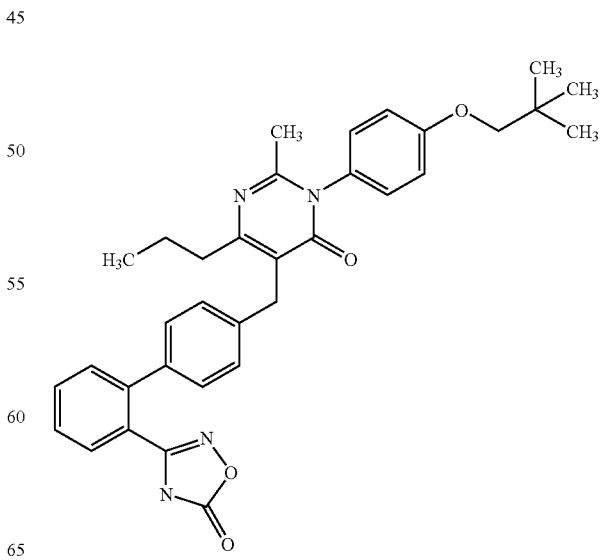

3-[4-(2,2-dimethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and 1-iodo-2,2-dimethylpropane (0.92 mL) in N,N-dimethylformamide (10 mL) was added cesium carbonate (1.5 g), and the mixture was stirred at 70° C. for 12 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was added to a mixture of hydroxylammonium chloride (1.3 g), sodium hydrogen carbonate (1.9 g) and dimethyl sulfoxide (10 mL), which had been stirred at 40° C. for 30 min, and the mixture was stirred at 90° C. for 18 hr. The mixture was allowed to cool to room temperature, ethyl acetate and water were added to the reaction mixture, and the aqueous layer was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.37 g) and then 1,8-diazabicyclo[5.4.0]undec-7-ene (0.35 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.78 g, 60%).

$^1$H NMR (300 MHz, DMSO-$d_6$) δ 0.89 (t, J=7.4, 3 H), 1.02 (s, 9 H), 1.45-1.63 (m, 2 H), 2.06 (s, 3 H), 2.46-2.54 (m, 2 H), 3.69 (s, 2 H), 3.87 (s, 2 H), 6.99-7.79 (m, 12 H), 12.38 (s, 1 H)

Example 248

3-[4-(2-hydroxy-2-methylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

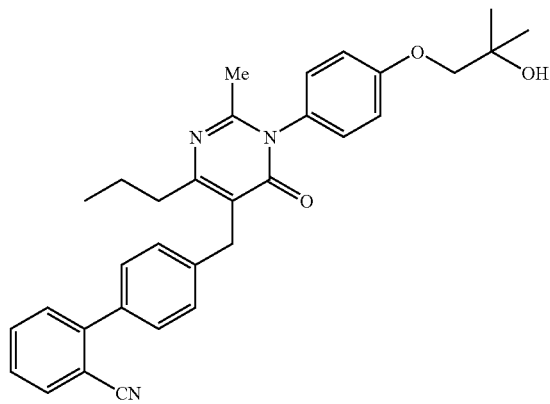

248a) 4'-({1-[4-(2-hydroxy-2-methylpropoxy)phenyl]-2-methyl-6-oxo-4-propyl-1,6-dihydropyrimidin-5-yl}methyl)biphenyl-2-carbonitrile To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and 2,2-dimethyloxirane (0.70 mL) in N,N-dimethylformamide (10 mL) was added cesium carbonate (1.5 g), and the mixture was stirred at 70° C. for 12 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.91 g, 78%).

$^1$H NMR (300 MHz, CDCl$_3$) δ 1.01 (t, J=7.2, 3 H), 1.36 (s, 6 H), 1.63-1.77 (m, 2 H), 2.18 (s, 3 H), 2.20 (s, 1 H), 2.62-2.68 (m, 2 H), 3.83 (s, 2 H), 3.97 (s, 2 H), 6.99-7.80 (m, 12 H)

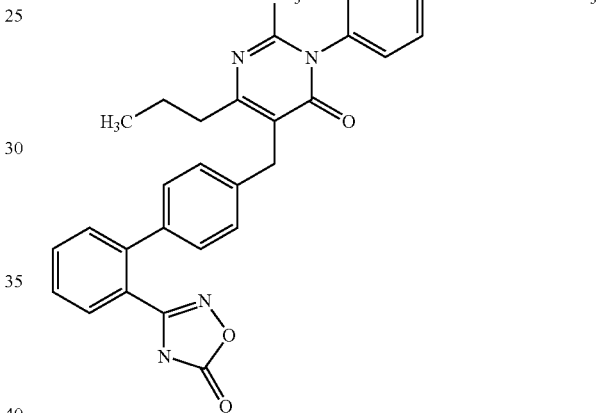

248b) 3-[4-(2-hydroxy-2-methylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.3 g), sodium hydrogen carbonate (1.9 g) and dimethyl sulfoxide (10 mL) was stirred at 40° C. for 30 min, 4'-({1-[4-(2-hydroxy-2-methylpropoxy)phenyl]-2-methyl-6-oxo-4-propyl-1,6-dihydropyrimidin-5-yl}methyl)biphenyl-2-carbonitrile (0.91 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.37 g) and then 1,8-diazabicyclo[5.4.0]undec-7-ene (0.35 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.69 g, 68%).

$^1$H NMR (300 MHz, DMSO-d$_6$) δ 0.89 (t, J=7.4, 3 H), 1.22 (s, 6 H), 1.46-1.61 (m, 2 H), 2.06 (s, 3 H), 2.46-2.54 (m, 2 H), 3.77 (s, 2 H), 3.86 (s, 2 H), 4.68 (s, 1 H), 6.99-7.75 (m, 12 H), 12.38 (s, 1 H)

Example 249

2-methyl-5-{[2'-(5-oxo-4,5-dihydro-1,2,4-oxadiazol-3-yl)biphenyl-4-yl]methyl}-3-(4-propoxyphenyl)-6-propylpyrimidin-4(3H)-one

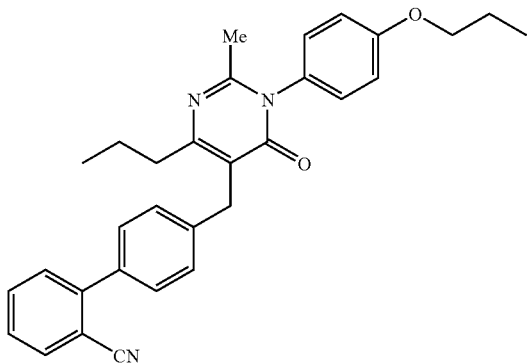

249a) 4'-{[2-methyl-6-oxo-1-(4-propoxyphenyl)-4-propyl-1,6-dihydropyrimidin-5-yl]methyl}biphenyl-2-carbonitrile To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and 1-iodopropane (1.1 mL) in N,N-dimethylformamide (10 mL) was added cesium carbonate (1.5 g), and the mixture was stirred at 80° C. for 5 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.91 g, 83%).

$^1$H NMR (300 MHz, CDCl$_3$) δ 1.01 (t, J=7.2, 3 H), 1.26 (t, J=7.0, 3 H), 1.63-1.90 (m, 4 H), 2.17 (s, 3 H), 2.59-2.69 (m, 2 H), 3.91-4.00 (m, 4 H), 6.94-7.77 (m, 12 H)

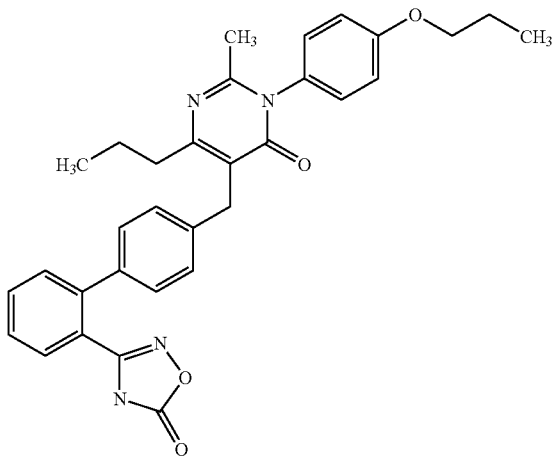

249b) 2-methyl-5-{[2'-(5-oxo-4,5-dihydro-1,2,4-oxadiazol-3-yl)biphenyl-4-yl]methyl}-3-(4-propoxyphenyl)-6-propylpyrimidin-4(3H)-one A mixture of hydroxylammonium chloride (1.32 g), sodium hydrogen carbonate (1.92 g) and dimethyl sulfoxide (10 mL) was stirred at 40° C. for 30 min, 4'-{[2-methyl-6-oxo-1-(4-propoxyphenyl)-4-propyl-1,6-dihydropyrimidin-5-yl]methyl}biphenyl-2-carbonitrile (0.91 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.37 g) and then 1,8-diazabicyclo[5.4.0]undec-7-ene (0.34 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.73 g, 71%).

$^1$H NMR (300 MHz, DMSO-d$_6$) δ 0.89 (t, J=7.4, 3 H), 1.00 (t, J=7.4, 3 H), 1.44-1.62 (m, 2 H), 1.68-1.83 (m, 2 H), 2.06 (s, 3 H), 2.46-2.54 (m, 2 H), 3.86 (s, 2 H), 3.98 (t, J=6.4, 2 H), 6.99-7.75 (m, 12 H), 12.38 (s, 1 H)

2-Methyl-5-{[2'-(5-oxo-4,5-dihydro-1,2,4-oxadiazol-3-yl)biphenyl-4-yl]methyl}-3-(4-propoxyphenyl)-6-propylpyrimidin-4(3H)-one obtained above is subjected to a conventional method of salt formation to give the following salts.

2-methyl-5-{[2'-(5-oxo-4,5-dihydro-1,2,4-oxadiazol-3-yl)biphenyl-4-yl]methyl}-3-(4-propoxyphenyl)-6-propylpyrimidin-4(3H)-one sodium salt 2-methyl-5-{[2'-(5-oxo-4,5-dihydro-1,2,4-oxadiazol-3-yl)biphenyl-4-yl]methyl}-3-(4-propoxyphenyl)-6-propylpyrimidin-4(3H)-one potassium salt 2-methyl-5-{[2'-(5-oxo-4,5-dihydro-1,2,4-oxadiazol-3-yl)biphenyl-4-yl]methyl}-3-(4-propoxyphenyl)-6-propylpyrimidin-4(3H)-one 0.5 calcium salt 2-methyl-5-{[2'-(5-oxo-4,5-dihydro-1,2,4-oxadiazol-3-yl)biphenyl-4-yl]methyl}-3-(4-propoxyphenyl)-6-propylpyrimidin-4(3H)-one hydrochloride 2-methyl-5-{[2'-(5-oxo-4,5-dihydro-1,2,4-oxadiazol-3-yl)biphenyl-4-yl]methyl}-3-(4-propoxyphenyl)-6-propylpyrimidin-4(3H)-one hydrobromide Example 250

3-(4-isopropoxy-3-methylphenyl)-2-methyl-5-{[2'-(5-oxo-4,5-dihydro-1,2,4-oxadiazol-3-yl)biphenyl-4-yl]methyl}-6-propylpyrimidin-4(3)-one

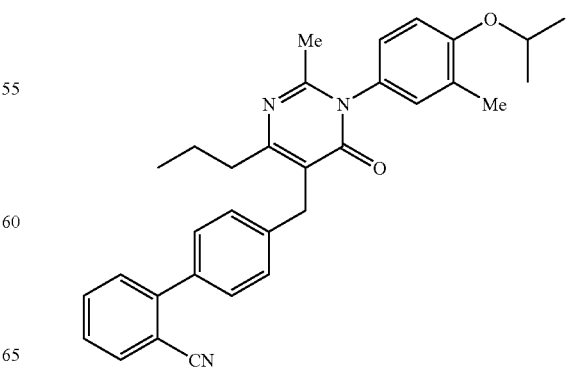

250a) 4'-{[1-(4-isopropoxy-3-methylphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (4-isopropoxy-3-methylphenyl)boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.34 g, 94%).

$^1$H NMR (300 MHz, CDCl$_3$) δ 0.97-1.03 (m, 3 H), 1.34 (d, J=6.1, 3 H), 1.38 (d, J=6.1, 3 H), 1.60-1.78 (m, 2 H), 2.18 (s, 3 H), 2.22 (s, 3 H), 2.58-2.72 (m, 2 H), 3.97 (s, 2 H), 4.45-4.65 (m, 1 H), 6.86-7.78 (m, 11 H)

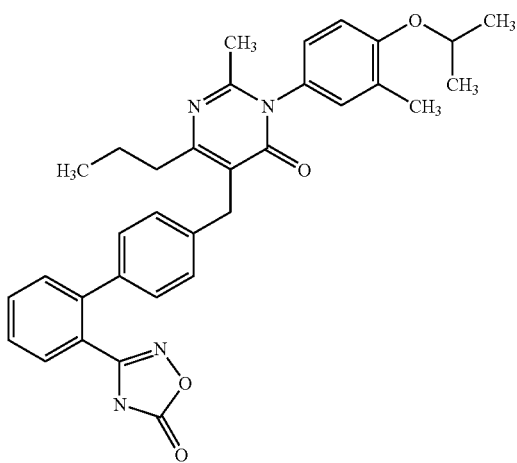

250b) 3-(4-isopropoxy-3-methylphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.9 g), sodium hydrogen carbonate (2.7 g) and dimethyl sulfoxide (10 mL) was stirred at 40° C. for 30 min, 4'-{[1-(4-isopropoxy-3-methylphenyl)-2-methyl-6-oxo-4-propyl-1,6-dihydropyrimidin-5-yl]methyl}biphenyl-2-carbonitrile (1.34 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.55 g) and then 1,8-diazabicyclo[5.4.0]undec-7-ene (0.51 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (1.09 g, 73%).

$^1$H NMR (300 MHz, DMSO-d$_6$) δ 0.88 (t, J=7.4, 3 H), 1.30 (d, J=3.4, 3 H), 1.32 (d, J=3.4, 3 H), 1.45-1.62 (m, 2 H), 2.07 (s, 3 H), 2.15 (s, 3 H), 2.47-2.55 (m, 2 H), 3.86 (s, 2 H), 4.56-4.75 (m, 1 H), 7.01-7.74 (m, 11 H), 12.38 (s, 1 H)

Example 251

3-(4-isobutylphenyl)-2-methyl-5-{[2'-(5-oxo-4,5-dihydro-1,2,4-oxadiazol-3-yl)biphenyl-4-yl]methyl}-6-propylpyrimidin-4(3H)-one

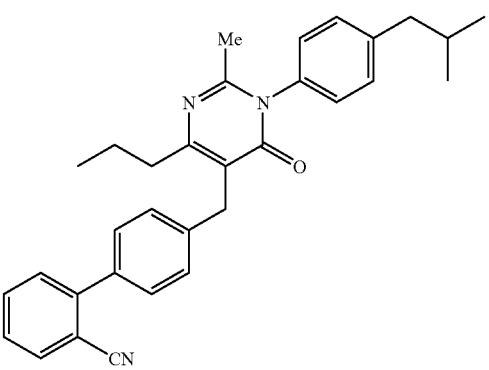

251a) 4'-{[1-(4-isobutylphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (4-isobutylphenyl)boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.34 g, 97%).

$^1$H NMR (300 MHz, CDCl$_3$) δ 0.92 (d, J=6.8, 6 H), 1.01 (t, J=7.4, 3 H), 1.61-1.77 (m, 2 H), 1.80-1.98 (m, 1 H), 2.16 (s, 3 H), 2.53 (d, J=7.2, 2 H), 2.60-2.70 (m, 2 H), 3.97 (s, 2 H), 7.06-7.78 (m, 12 H)

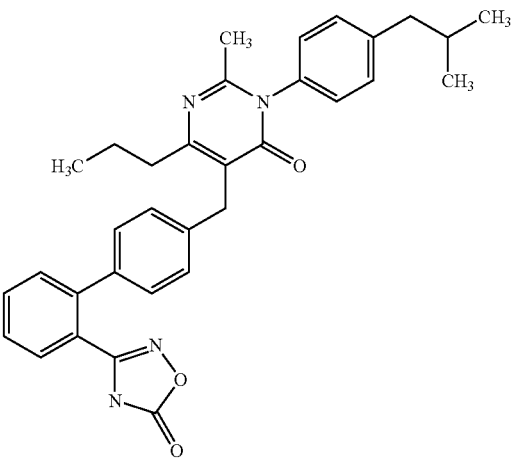

251b) 3-(4-isobutylphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.9 g), sodium hydrogen carbonate (2.7 g) and dimethyl sulfoxide (10 mL) was stirred at 40° C. for 30 min, 4'-{[1-(4-isobutylphenyl)-2-methyl-6-oxo-4-propyl-1,6-dihydropyrimidin-5-yl]methyl}biphenyl-2-carbonitrile (1.34 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.55 g) and then 1,8-diazabicyclo[5.4.0]undec-7-ene (0.51 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.60 g, 40%).

$^1$H NMR (300 MHz, DMSO-$d_6$) δ 0.80-0.94 (m, 9 H), 1.42-1.66 (m, 2 H), 1.80-1.97 (m, 1 H), 2.05 (s, 3 H), 2.47-2.59 (m, 4 H), 3.87 (s, 2 H), 7.16-7.75 (m, 12 H), 12.39 (s, 1 H)

Example 252

3-(4-isobutoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

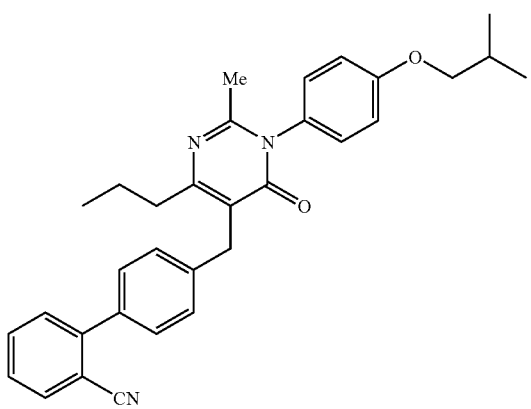

252a) 4'-{[1-(4-isobutoxyphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (4-isobutoxyphenyl)boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.30 g, 91%).

$^1$H NMR (300 MHz, CDCl$_3$) δ 1.01 (t, J=7.2, 3 H), 1.03 (d, J=6.4, 6 H), 1.59-1.77 (m, 2 H), 2.04-2.16 (m, 1 H), 2.18 (s, 3 H), 2.65 (dd, J=9.1, 6.8, 2 H), 3.75 (d, J=6.4, 2 H), 3.97 (s, 2 H), 6.94-7.79 (m, 12 H)

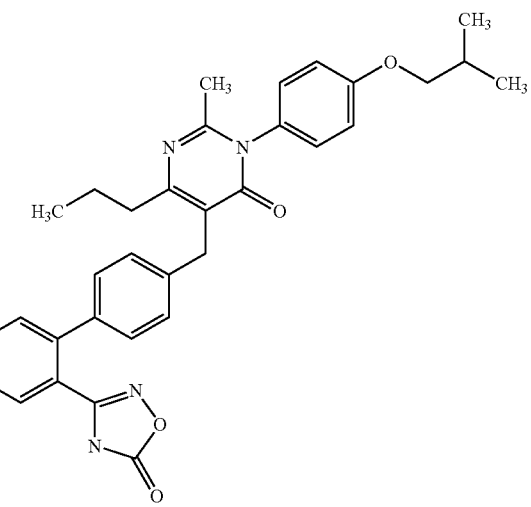

252b) 3-(4-isobutoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.9 g), sodium hydrogen carbonate (2.7 g) and dimethyl sulfoxide (10 mL) was stirred at 40° C. for 30 min, 4'-{[1-(4-isobutoxyphenyl)-2-methyl-6-oxo-4-propyl-1,6-dihydropyrimidin-5-yl]methyl}biphenyl-2-carbonitrile (1.30 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.55 g) and then 1,8-diazabicyclo[5.4.0]undec-7-ene (0.51 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (1.07 g, 40%).

$^1$H NMR (300 MHz, DMSO-$d_6$) δ 0.89 (t, J=7.4, 3 H), 1.00 (d, J=6.8, 6 H), 1.46-1.62 (m, 2 H), 1.96-2.12 (m, 1 H), 2.06 (s, 3 H), 2.46-2.54 (m, 2 H), 3.80 (d, J=6.4, 2 H), 3.86 (s, 2 H), 7.00-7.73 (m, 12 H), 12.38 (s, 1 H)

Example 253

3-(4-isopropylphenyl)-2-methyl-5-{[2'-(5-oxo-4,5-dihydro-1,2,4-oxadiazol-3-yl)biphenyl-4-yl]methyl}-6-propylpyrimidin-4(3H)-one

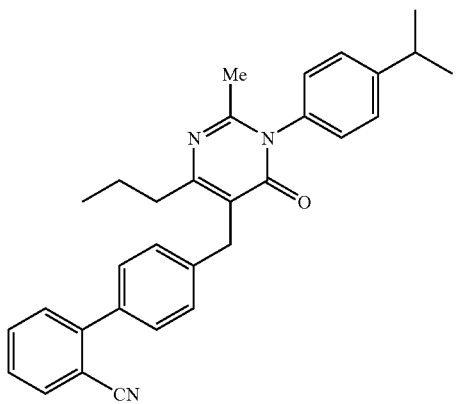

253a) 4'-{[1-(4-isopropylphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (4-isopropylphenyl)boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.21 g, 90%).

$^1$H NMR (300 MHz, CDCl$_3$) δ 1.01 (t, J=7.4, 3 H), 1.27 (d, J=7.2, 6 H), 1.60-1.79 (m, 2 H), 2.17 (s, 3 H), 2.55-2.78 (m, 2 H), 2.85-3.09 (m, 1 H), 3.97 (s, 2 H), 7.01-7.83 (m, 12 H)

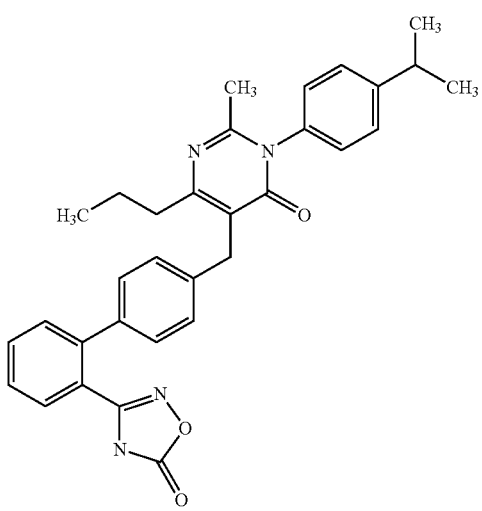

253b) 3-(4-isopropylphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.82 g), sodium hydrogen carbonate (2.64 g) and dimethyl sulfoxide (10 mL) was stirred at 40° C. for 30 min, 4'-{[1-(4-isopropylphenyl)-2-methyl-6-oxo-4-propyl-1,6-dihydropyrimidin-5-yl]methyl}biphenyl-2-carbonitrile (1.21 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.51 g) and then 1,8-diazabicyclo[5.4.0]undec-7-ene (0.47 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.90 g, 66%).

$^1$H NMR (300 MHz, DMSO-d$_6$) δ 0.89 (t, J=7.4, 3 H), 1.25 (d, J=6.8, 6 H), 1.46-1.62 (m, 2 H), 2.05 (s, 3 H), 2.50-2.55 (m, 2 H), 2.87-3.06 (m, 1 H), 3.86 (s, 2 H), 7.16-7.74 (m, 12 H), 12.38 (s, 1 H)

Example 254

3-(4-tert-butylphenyl)-2-methyl-5-{[2'-(5-oxo-4,5-dihydro-1,2,4-oxadiazol-3-yl)biphenyl-4-yl]methyl}-6-propylpyrimidin-4(3H)-one

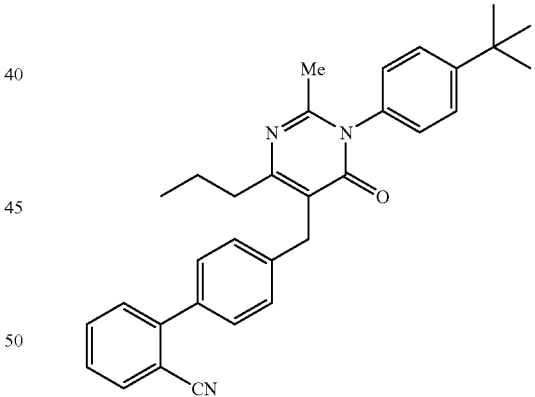

254a) 4'-{[1-(4-tert-butylphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (4-tert-butylphenyl)boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.12 g, 81%).

$^1$H NMR (300 MHz, CDCl$_3$) δ 1.02 (t, J=7.4, 3 H), 1.35 (s, 9 H), 1.59-1.80 (m, 2 H), 2.17 (s, 3 H), 2.56-2.73 (m, 2 H), 3.97 (s, 2 H), 7.03-7.79 (m, 12 H)

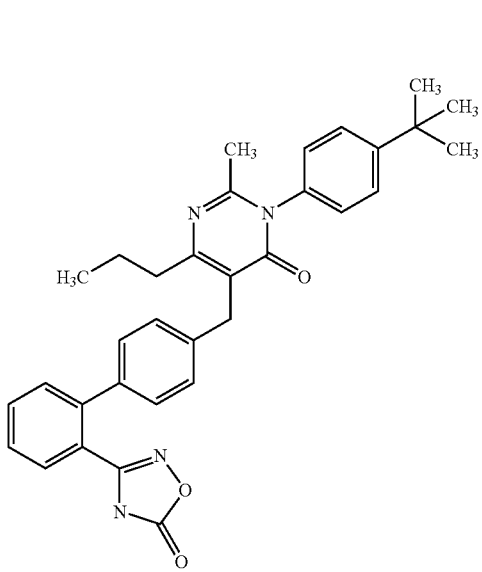

254b) 3-(4-tert-butylphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.8 g), sodium hydrogen carbonate (2.6 g) and dimethyl sulfoxide (12 mL) was stirred at 40° C. for 30 min, 4'-{[1-(4-tert-butylphenyl)-2-methyl-6-oxo-4-propyl-1,6-dihydropyrimidin-5-yl]methyl}biphenyl-2-carbonitrile (1.12 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.51 g) and then 1,8-diazabicyclo[5.4.0]undec-7-ene (0.47 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.91 g, 72%).

$^1$H NMR (300 MHz, DMSO-d$_6$) δ 0.89 (t, J=7.4, 3 H), 1.33 (s, 9 H), 1.42-1.64 (m, 2 H), 2.05 (s, 3 H), 2.49-2.57 (m, 2 H), 3.86 (s, 2 H), 7.18-7.73 (m, 12 H), 12.38 (s, 1 H)

Example 255

3-[4-(cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

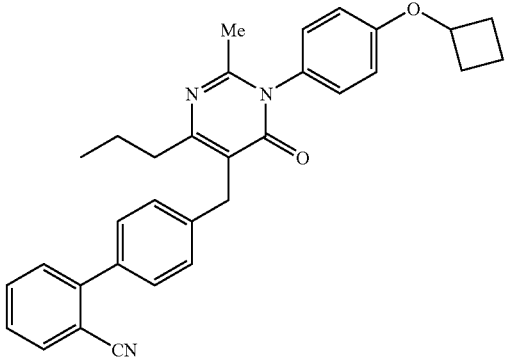

255a) 4'-({1-[4-(cyclobutyloxy)phenyl]-2-methyl-6-oxo-4-propyl-1,6-dihydropyrimidin-5-yl}methyl)biphenyl-2-carbonitrile To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and bromocyclobutane (1.1 mL) in N,N-dimethylformamide (10 mL) was added cesium carbonate (1.5 g), and the mixture was stirred at 80° C. for 5 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (1.02 g, 91%).

$^1$H NMR (300 MHz, CDCl$_3$) δ 1.01 (t, J=7.4, 3 H), 1.61-1.98 (m, 4 H), 2.14-2.27 (m, 2 H), 2.17 (s, 3 H), 2.39-2.53 (m, 2 H), 2.65 (dd, J=9.8, 5.7, 2 H), 3.96 (s, 2 H), 4.58-4.74 (m, 1 H), 6.87-7.78 (m, 12 H)

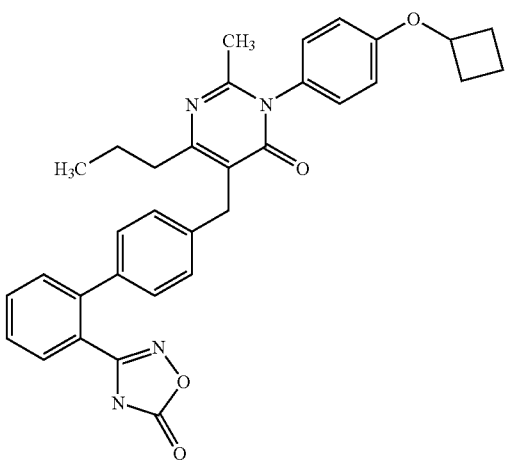

255b) 3-[4-(cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.45 g), sodium hydrogen carbonate (2.10 g) and dimethyl sulfoxide (10 mL) was stirred at 40° C. for 30 min, 4'-({1-[4-(cyclobutyloxy)phenyl]-2-methyl-6-oxo-4-propyl-1,6-dihydropyrimidin-5-yl}methyl)biphenyl-2-carbonitrile (1.02 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.41 g) and then 1,8-diazabicyclo[5.4.0]undec-7-ene (0.37 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.73 g, 64%).

$^1$H NMR (300 MHz, DMSO-$d_6$) δ 0.89 (t, J=7.4, 3 H), 1.46-1.90 (m, 4 H), 1.97-2.14 (m, 2 H), 2.06 (s, 3 H), 2.41-2.54 (m, 4 H), 3.86 (s, 2 H), 4.67-4.82 (m, 1 H), 6.92-7.75 (m, 12 H), 12.38 (s, 1 H)

3-[4-(Cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-[4-(cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-[4-(cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-[4-(cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-[4-(cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-[4-(cyclobutyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 256

3-[4-(1-ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

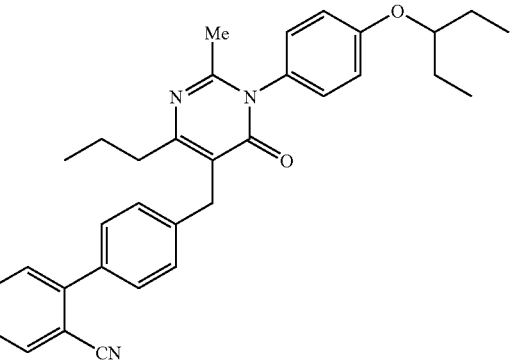

256a) 4'-({1-[4-(1-ethylpropoxy)phenyl]-2-methyl-6-oxo-4-propyl-1,6-dihydropyrimidin-5-yl}methyl)biphenyl-2-carbonitrile To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and 3-bromopentane (1.40 mL) in N,N-dimethylformamide (10 mL) was added cesium carbonate (1.5 g), and the mixture was stirred at 80° C. for 5 hr. The reaction mixture was allowed to cool to room temperature, ethyl acetate and water were added, and the aqueous layer was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.98 g, 84%).

$^1$H NMR (300 MHz, CDCl$_3$) δ 0.91-1.05 (m, 6 H), 1.62-1.76 (m, 6 H), 2.19 (s, 3 H), 2.59-2.71 (m, 2 H), 3.97 (s, 2 H), 4.10-4.18 (m, 1 H), 6.94-7.79 (m, 12 H)

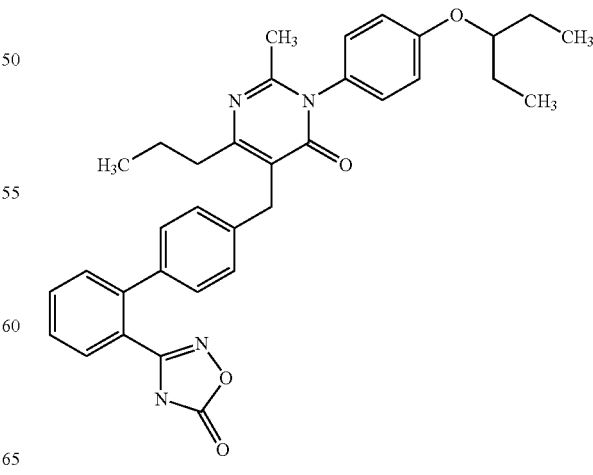

256b) 3-[4-(1-ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.45 g), sodium hydrogen carbonate (2.10 g) and dimethyl sulfoxide (10 mL) was stirred at 40° C. for 30 min, 4'-({1-[4-(1-ethylpropoxy)phenyl]-2-methyl-6-oxo-4-propyl-1,6-dihydropyrimidin-5-yl}methyl)biphenyl-2-carbonitrile (0.98 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.41 g) and then 1,8-diazabicyclo[5.4.0]undec-7-ene (0.37 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.77 g, 71%).

$^1$H NMR (300 MHz, DMSO-$d_6$) δ 0.78-0.99 (m, 9 H), 1.44-1.72 (m, 6 H), 2.07 (s, 3 H), 2.46-2.55 (m, 2 H), 3.86 (s, 2 H), 4.21-4.34 (m, 1 H), 6.93-7.75 (m, 12 H), 12.38 (s, 1 H)

3-[4-(1-Ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-[4-(1-ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-[4-(1-ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-[4-(1-ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-[4-(1-ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-[4-(1-ethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 257

2-methyl-3-[4-(methylthio)phenyl]-5-{[2'-(5-oxo-4,5-dihydro-1,2,4-oxadiazol-3-yl)biphenyl-4-yl]methyl}-6-propylpyrimidin-4(3H)-one

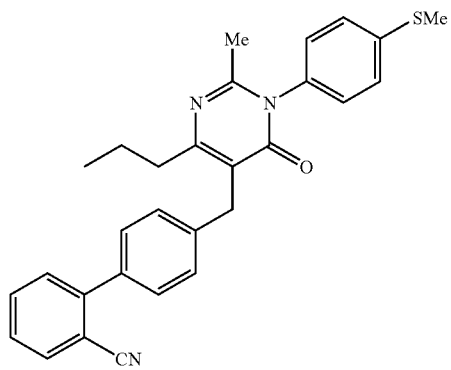

257a) 4'-({2-methyl-1-[4-(methylthio)phenyl]-6-oxo-4-propyl-1,6-dihydropyrimidin-5-yl}methyl)biphenyl-2-carbonitrile To a suspension of 4'-[(2-methyl-6-oxo-4-propyl-1,6-dihydropyrimidin-5-yl)methyl]biphenyl-2-carbonitrile (1.0 g), [4-(methylthio)phenyl]boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (0.24 g, 17%).

$^1$H NMR (300 MHz, CDCl$_3$) δ 1.01 (t, J=7.3, 3 H), 1.62-1.76 (m, 2 H), 2.18 (s, 3 H), 2.51 (s, 3 H), 2.60-2.71 (m, 2 H), 3.96 (s, 2 H), 7.05-7.80 (m, 12 H)

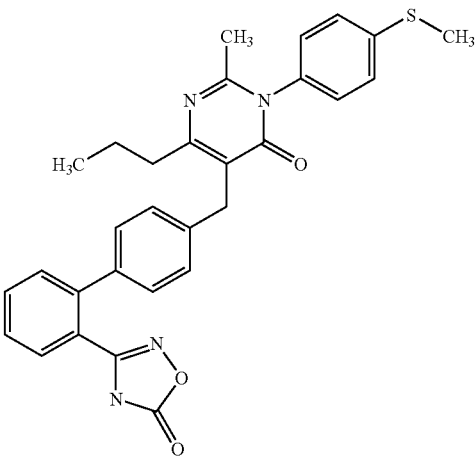

257b) 2-methyl-3-[4-(methylthio)phenyl]-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.35 g), sodium hydrogen carbonate (0.51 g) and dimethyl sulfoxide (3 mL) was stirred at 40° C. for 30 min, 4'-({2-methyl-1-[4-(methylthio)phenyl]-6-oxo-4-propyl-1,6-dihydropyrimidin-5-yl}methyl)biphenyl-2-carbonitrile (0.24 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (3 mL). N,N'-carbonyldiimidazole (0.10 g) and then 1,8-diazabicyclo[5.4.0]undec-7-ene (0.091 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.17 g, 64%).

$^1$H NMR (300 MHz, DMSO-d$_6$) δ 0.89 (t, J=7.4, 3 H), 1.46-1.62 (m, 2 H), 2.07 (s, 3 H), 2.48-2.52 (m, 2 H), 2.53 (s, 3 H), 3.86 (s, 2 H), 7.17-7.73 (m, 12 H), 12.38 (s, 1 H)

Example 258

2-methyl-5-{[2'-(5-oxo-4,5-dihydro-1,2,4-oxadiazol-3-yl)biphenyl-4-yl]methyl}-6-propyl-3-[4-(trifluoromethoxy)phenyl]pyrimidin-4(3H)-one

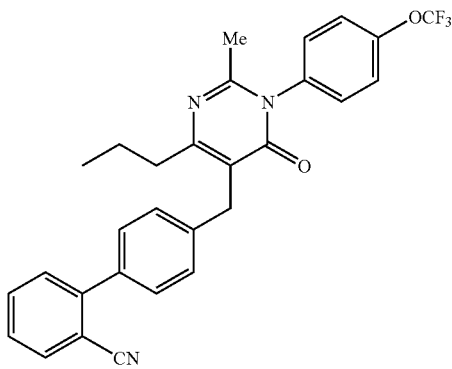

258a) 4'-({2-methyl-6-oxo-4-propyl-1-[4-(trifluoromethoxy)phenyl]-1,6-dihydropyrimidin-5-yl}methyl)biphenyl-2-carbonitrile To a suspension of 4'-[(2-methyl-6-oxo-4-propyl-1,6-dihydropyrimidin-5-yl)methyl]biphenyl-2-carbonitrile (1.0 g), [4-(trifluoromethoxy)phenyl]boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.12 g, 76%).
$^1$H NMR (300 MHz, CDCl$_3$) δ 1.02 (t, J=7.3, 3 H), 1.62-1.78 (m, 2 H), 2.17 (s, 3 H), 2.60-2.73 (m, 2 H), 3.96 (s, 2 H), 7.22-7.79 (m, 12 H)

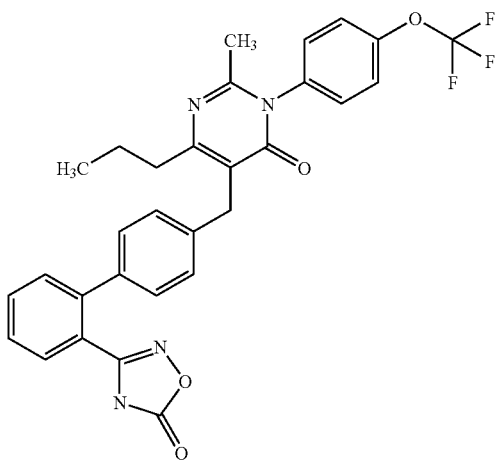

258b) 2-methyl-5-{[2'-(5-oxo-4,5-dihydro-1,2,4-oxadiazol-3-yl)biphenyl-4-yl]methyl}-6-propyl-3-[4-(trifluoromethoxy)phenyl]pyrimidin-4(3H)-one A mixture of hydroxylammonium chloride (1.54 g), sodium hydrogen carbonate (2.23 g) and dimethyl sulfoxide (11 mL) was stirred at 40° C. for 30 min, 4'-({2-methyl-6-oxo-4-propyl-1-[4-(trifluoromethoxy)phenyl]-1,6-dihydropyrimidin-5-yl}methyl)biphenyl-2-carbonitrile (1.12 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.43 g) and then 1,8-diazabicyclo[5.4.0]undec-7-ene (0.40 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (1.04 g, 83%).
$^1$H NMR (300 MHz, DMSO-d$_6$) δ 0.90 (t, J=7.4, 3 H), 1.45-1.64 (m, 2 H), 2.07 (s, 3 H), 2.49-2.57 (m, 2 H), 3.87 (s, 2 H), 7.15-7.76 (m, 12 H), 12.39 (s, 1 H)

Example 259

2-methyl-5-{[2'-(5-oxo-4,5-dihydro-1,2,4-oxadiazol-3-yl)biphenyl-4-yl]methyl}-3-(4-phenoxyphenyl)-6-propylpyrimidin-4(3H)-one

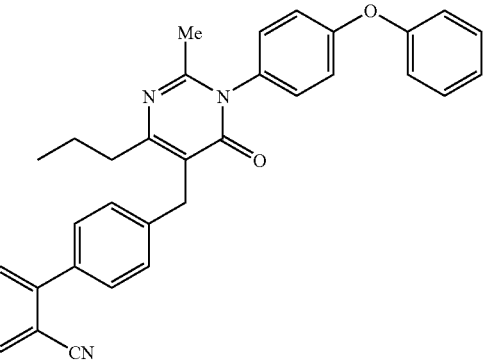

259a) 4'-{[2-methyl-6-oxo-1-(4-phenoxyphenyl)-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (4-phenoxyphenyl)boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.37 g, 92%).

525

$^1$H NMR (300 MHz, CDCl$_3$) δ 1.01 (t, J=7.3, 3 H), 1.62-1.82 (m, 2 H), 2.20 (s, 3 H), 2.52-2.78 (m, 2 H), 3.97 (s, 2 H), 6.89-7.83 (m 17 H)

259b) 2-methyl-5-{[2'-(5-oxo-4,5-dihydro-1,2,4-oxadiazol-3-yl)biphenyl-4-yl]methyl}-3-(4-phenoxyphenyl)-6-propylpyrimidin-4(3H)-one

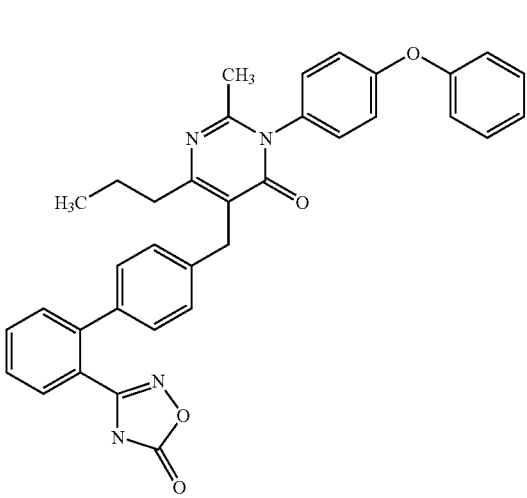

A mixture of hydroxylammonium chloride (1.86 g), sodium hydrogen carbonate (2.70 g) and dimethyl sulfoxide (13 mL) was stirred at 40° C. for 30 min, 4'-{[2-methyl-6-oxo-1-(4-phenoxyphenyl)-4-propyl-1,6-dihydropyrimidin-5-yl]methyl}biphenyl-2-carbonitrile (1.37 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.52 g) and then 1,8-diazabicyclo[5.4.0]undec-7-ene (0.48 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (1.15 g, 75%).

$^1$H NMR (300 MHz, DMSO-d$_6$) δ 0.89 (t, J=7.4, 3 H), 1.46-1.64 (m, 2 H), 2.10 (s, 3 H), 2.48-2.57 (m, 2 H), 3.87 (s, 2 H), 7.05-7.74 (m, 17 H), 12.38 (s, 1 H)

526

Example 260

3-(4-tert-butoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

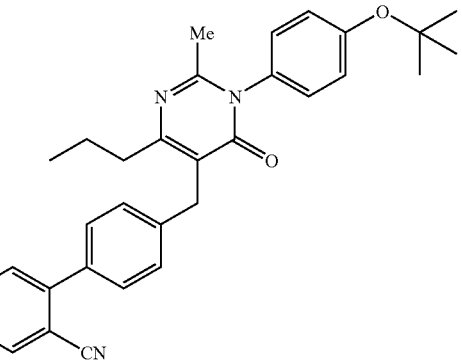

260a) 4'-{[1-(4-tert-butoxyphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (4-tert-butoxyphenyl)boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.39 g, 97%).

$^1$H NMR (300 MHz, CDCl$_3$) δ 1.01 (t, J=7.3, 3 H), 1.39 (s, 9 H), 1.61-1.77 (m, 2 H), 2.16 (s, 3 H), 2.59-2.69 (m, 2 H), 3.97 (s, 2 H), 7.08-7.78 (m, 12 H)

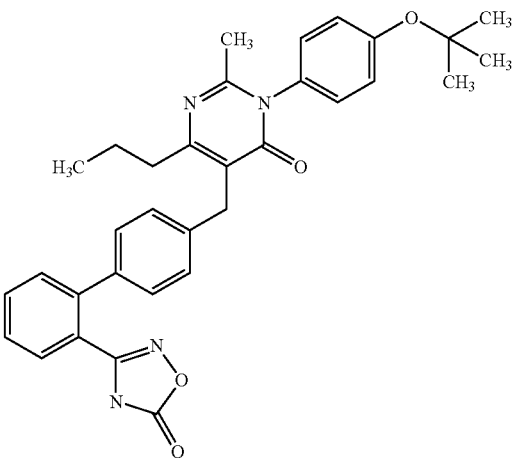

260b) 3-(4-tert-butoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.97 g), sodium hydrogen carbonate (2.86 g) and dimethyl sulfoxide (14 mL) was stirred at 40° C. for 30 min, 4'-{[1-(4-tert-butoxyphenyl)-2-methyl-6-oxo-4-propyl-1,6-dihydropyrimidin-5-yl]methyl}biphenyl-2-carbonitrile (1.39 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (14 mL). N,N'-carbonyldiimidazole (0.55 g) and then 1,8-diazabicyclo[5.4.0]undec-7-ene (0.51 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (1.21 g, 78%).

$^1$H NMR (300 MHz, DMSO-$d_6$) δ 0.89 (t, J=7.3, 3 H), 1.35 (s, 9 H), 1.44-1.63 (m, 2 H), 2.06 (s, 3 H), 2.51-2.55 (m, 2 H), 3.87 (s, 2 H), 7.04-7.73 (m, 12 H), 12.38 (s, 1 H)

Example 261

3-(3-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

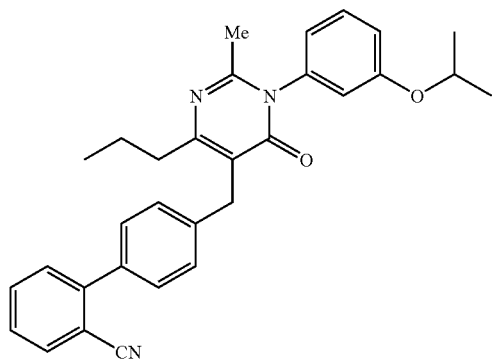

261a) 4'-{[1-(3-isopropoxyphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (3-isopropoxyphenyl)boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.24 g, 89%).

$^1$H NMR (300 MHz, CDCl$_3$) δ 1.01 (t, J=7.3, 3 H), 1.33 (d, J=6.0, 3 H), 1.35 (d, J=6.0, 3 H), 1.62-1.77 (m, 2 H), 2.20 (s, 3 H), 2.57-2.72 (m, 2 H), 3.97 (s, 2 H), 4.49-4.62 (m, 1 H), 6.70-7.78 (m, 12 H)

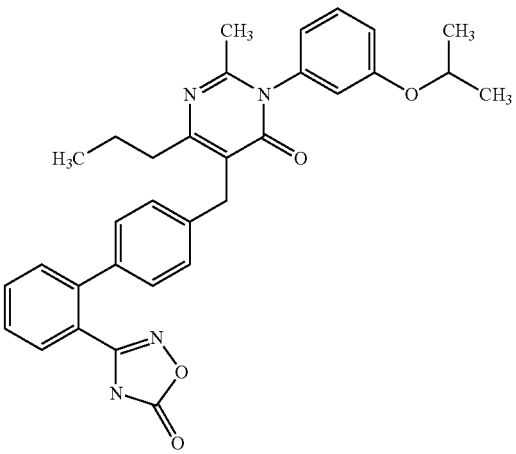

261b) 3-(3-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.81 g), sodium hydrogen carbonate (2.62 g) and dimethyl sulfoxide (13 mL) was stirred at 40° C. for 30 min, 4'-{[1-(3-isopropoxyphenyl)-2-methyl-6-oxo-4-propyl-1,6-dihydropyrimidin-5-yl]methyl}biphenyl-2-carbonitrile (1.24 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (13 mL). N,N'-carbonyldiimidazole (0.51 g) and then 1,8-diazabicyclo[5.4.0]undec-7-ene (0.47 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.96 g, 68%).

$^1$H NMR (300 MHz, DMSO-$d_6$) δ 0.89 (t, J=7.3, 3 H), 1.26 (d, J=4.0, 3 H), 1.28 (d, J=4.0, 3 H), 1.44-1.63 (m, 2 H), 2.09 (s, 3 H), 2.49-2.55 (m, 2 H), 3.87 (s, 2 H), 4.58-4.74 (m, 1 H), 6.83-7.74 (m, 12 H), 12.38 (s, 1 H)

Example 262

3-[4-(isopropylthio)phenyl]-2-methyl-5-{[2'-(5-oxo-4,5-dihydro-1,2,4-oxadiazol-3-yl)biphenyl-4-yl]methyl}-6-propylpyrimidin-4(3H)-one

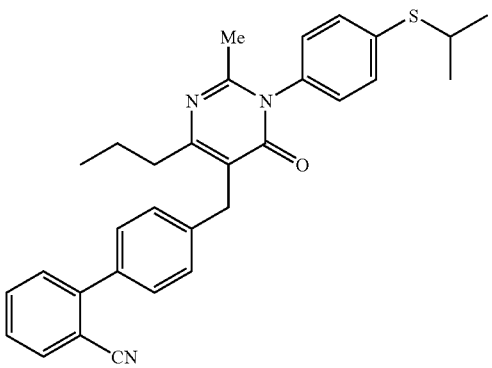

262a) 4'-({1-[4-(isopropylthio)phenyl]-2-methyl-6-oxo-4-propyl-1,6-dihydropyrimidin-5-yl}methyl)biphenyl-2-carbonitrile To a suspension of 4'-[(2-methyl-6-oxo-4-propyl-1,6-dihydropyrimidin-5-yl)methyl]biphenyl-2-carbonitrile (1.0 g), [4-(isopropylthio)phenyl]boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.20 g, 84%).

$^1$H NMR (300 MHz, CDCl$_3$) δ 1.01 (t, J=7.3, 3 H), 1.34 (d, J=6.8, 6 H), 1.62-1.77 (m, 2 H), 2.17 (s, 3 H), 2.59-2.71 (m, 2 H), 3.35-3.55 (m, 1 H), 3.97 (s, 2 H), 7.10-7.20 (m, 2 H), 7.36-7.78 (m, 10 H)

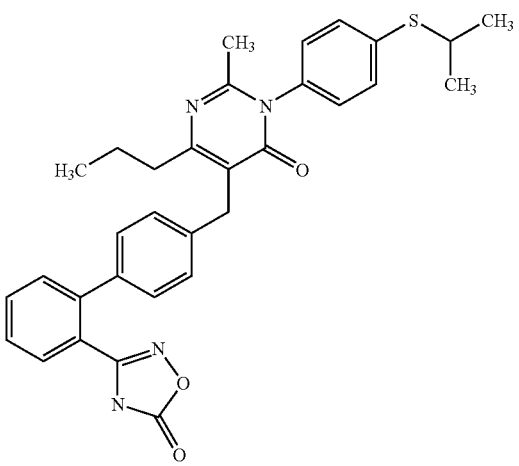

262b) 3-[4-(isopropylthio)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.70 g), sodium hydrogen carbonate (2.46 g) and dimethyl sulfoxide (12 mL) was stirred at 40° C. for 30 min, 4'-({1-[4-(isopropylthio)phenyl]-2-methyl-6-oxo-4-propyl-1,6-dihydropyrimidin-5-yl}methyl)biphenyl-2-carbonitrile (1.20 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (12 mL). N,N'-carbonyldiimidazole (0.48 g) and then 1,8-diazabicyclo[5.4.0]undec-7-ene (0.44 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.90 g, 67%).

$^1$H NMR (300 MHz, DMSO-d$_6$) δ 0.89 (t, J=7.3, 3 H), 1.29 (d, J=6.6, 6 H), 1.45-1.64 (m, 2 H), 2.07 (s, 3 H), 2.49-2.56 (m, 2 H), 3.51-3.70 (m, 1 H), 3.87 (s, 2 H), 7.17-7.73 (m, 12 H), 12.38 (s, 1 H)

Example 263

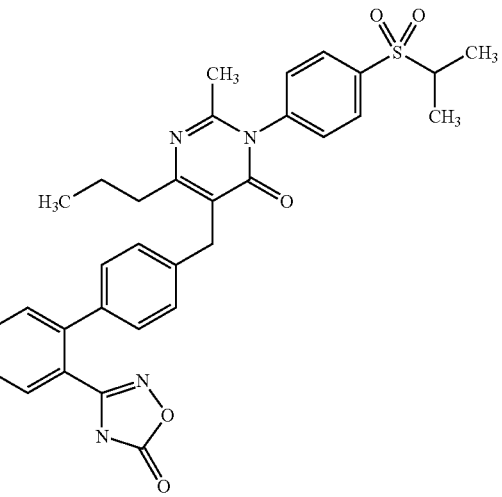

3-[4-(isopropylsulfonyl)phenyl]-2-methyl-5-{[2'-(5-oxo-4,5-dihydro-1,2,4-oxadiazol-3-yl)biphenyl-4-yl]methyl}-6-propylpyrimidin-4(3H)-one To a solution of 3-[4-(isopropylthio)phenyl]-2-methyl-5-{[2'-(5-oxo-4,5-dihydro-1,2,4-oxadiazol-3-yl)biphenyl-4-yl]methyl}-6-propylpyrimidin-4(3H)-one (0.28 g) in acetonitrile (3 mL) was added 3-chlorobenzenecarboperoxoic acid (0.26 g), and the mixture was stirred at 0° C. for 3 hr. Ethyl acetate, water and sodium thiosulfate were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a colorless solid (0.21 g, 71%).

$^1$H NMR (300 MHz, DMSO-$d_6$) δ 0.90 (t, J=7.3, 3 H), 1.20 (d, J=6.8, 6 H), 1.47-1.65 (m, 2 H), 2.07 (s, 3 H), 2.48-2.58 (m, 2 H), 3.32 (m, 1 H), 3.88 (s, 2 H), 7.16-8.08 (m, 12 H), 12.38 (s, 1 H)

Example 264

N,N-dimethyl-4-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]benzamide

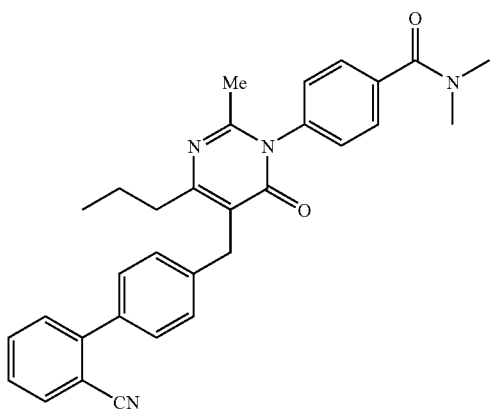

264a) 4-[5-[(2'-cyanobiphenyl-4-yl)methyl]-2-methyl-6-oxo-4-propylpyrimidin-1(6H)-yl]-N,N-dimethylbenzamide To a suspension of 4'-[(2-methyl-6-oxo-4-propyl-1,6-dihydropyrimidin-5-yl)methyl]biphenyl-2-carbonitrile (1.0 g), {4-[(dimethylamino)carbonyl]phenyl}boronic acid (1.0 g), triethylamine (2.0 mL), pyridine (1.0 mL) and molecular sieves 4 A (3.0 g) in methylene chloride (10 mL) was added copper(II) acetate (1.0 g), and the mixture was stirred at room temperature for 2 days. The reaction mixture was diluted with ethyl acetate, the insoluble material was filtered off through celite, and the filtrate was concentrated. The residue was purified by silica gel column chromatography to give the title compound as a pale-yellow viscous substance (0.92 g, 64%).

$^1$H NMR (300 MHz, CDCl$_3$) δ 1.01 (t, J=7.3, 3 H), 1.61-1.79 (m, 2 H), 2.16 (s, 3 H), 2.60-2.71 (m, 2 H), 3.01 (s, 3 H), 3.13 (s, 3 H), 3.97 (s, 2 H), 7.27-7.78 (m, 12 H)

264b) N,N-dimethyl-4-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]benzamide A mixture of hydroxylammonium chloride (1.30 g), sodium hydrogen carbonate (1.88 g) and dimethyl sulfoxide (10 mL) was stirred at 40° C. for 30 min, 4-[5-[(2'-cyanobiphenyl-4-yl)methyl]-2-methyl-6-oxo-4-propylpyrimidin-1(6H)-yl]-N,N-dimethylbenzamide (0.92 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (12 mL). N,N'-carbonyldiimidazole (0.48 g) and then 1,8-diazabicyclo[5.4.0]undec-7-ene (0.44 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.37 g, 36%).

$^1$H NMR (300 MHz, DMSO-$d_6$) δ 0.90 (t, J=7.3, 3 H), 1.45-1.65 (m, 2 H), 2.08 (s, 3 H), 2.50-2.59 (m, 2 H), 2.94 (s, 3 H), 3.01 (s, 3 H), 3.88 (s, 2 H), 7.16-7.73 (m, 12 H), 12.38 (s, 1 H)

Example 265

3-[4-(cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

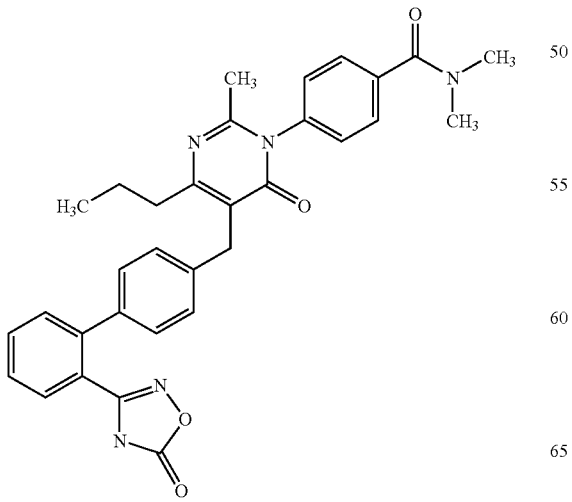

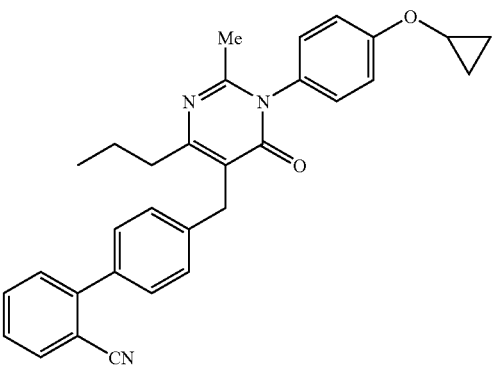

265a) 4'-({1-[4-(cyclopropyloxy)phenyl]-2-methyl-6-oxo-4-propyl-1,6-dihydropyrimidin-5-yl}methyl)biphenyl-2-carbonitrile To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and bromocyclopropane (1.8 mL) in N,N-dimethylformamide (10 mL) was added cesium carbonate (1.5 g), and the mixture was stirred at 80° C. for 5 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.097 g, 9%).

$^1$H NMR (300 MHz, CDCl$_3$) δ 0.76-0.84 (m, 4 H), 1.01 (t, J=7.3, 3 H), 1.61-1.77 (m, 2 H), 2.18 (s, 3 H), 2.59-2.70 (m, 2 H), 3.71-3.80 (m, 1 H), 3.97 (s, 2 H), 7.09-7.78 (m, 12H)

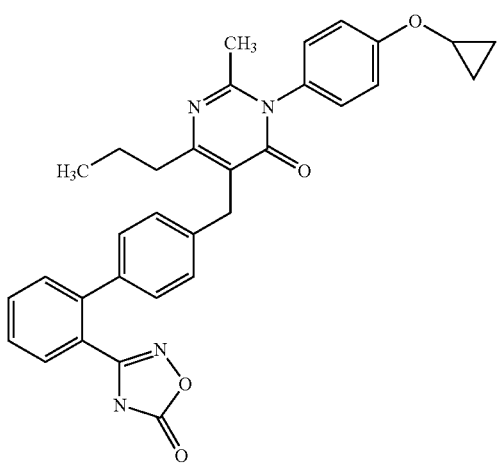

265b) 3-[4-(cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.014 g), sodium hydrogen carbonate (0.02 g) and dimethyl sulfoxide (1 mL) was stirred at 40° C. for 30 min, 4'-({1-[4-(cyclopropyloxy)phenyl]-2-methyl-6-oxo-4-propyl-1,6-dihydropyrimidin-5-yl}methyl)biphenyl-2-carbonitrile (0.097 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (1 mL). N,N'-carbonyldiimidazole (0.040 g) and then 1,8-diazabicyclo[5.4.0]undec-7-ene (0.040 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.046 g, 43%).

$^1$H NMR (300 MHz, DMSO-d$_6$) δ 0.59-0.84 (m, 4 H), 0.89 (t, J=7.3, 3 H), 1.45-1.62 (m, 2 H), 2.07 (s, 3 H), 2.49-2.56 (m, 2 H), 3.86 (s, 2 H), 3.87-3.95 (m, 1 H), 7.12-7.75 (m, 12H), 12.38 (br s, 1 H)

3-[4-(Cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-[4-(cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-[4-(cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-[4-(cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-[4-(cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-[4-(cyclopropyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 266

3-[4-(2-hydroxy-1,1-dimethylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

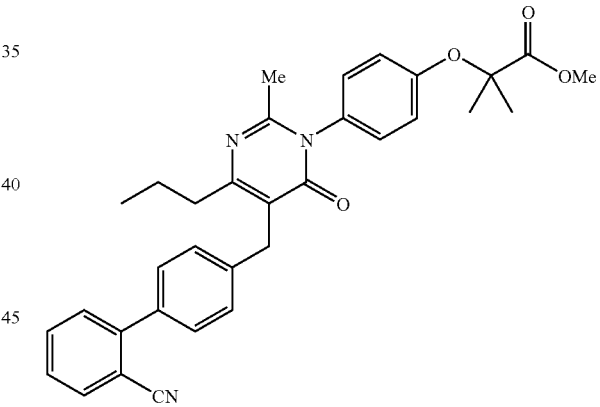

266a) methyl 2-(4-{5-[(2'-cyanobiphenyl-4-yl)methyl]-2-methyl-6-oxo-4-propylpyrimidin-1(6H)-yl}phenoxy)-2-methylpropanoate To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and methyl 2-bromo-2-methylpropanoate (1.25 g) in N,N-dimethylformamide (10 mL) was added cesium carbonate (1.5 g), and the mixture was stirred at 80° C. for 5 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.97 g, 79%).

$^1$H NMR (300 MHz, CDCl$_3$) δ 1.00 (t, J=7.4, 3 H), 1.63 (s, 6 H), 1.64-1.76 (m, 2 H), 2.15 (s, 3 H), 2.59-2.69 (m, 2 H), 3.78 (s, 3 H), 3.96 (s, 2 H), 6.89-7.79 (m, 12 H)

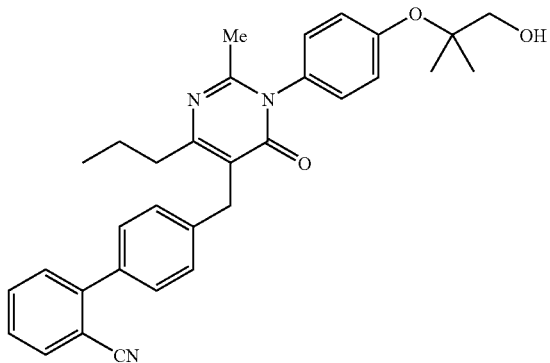

266b) 4'-({1-[4-(2-hydroxy-1,1-dimethylethoxy)phenyl]-2-methyl-6-oxo-4-propyl-1,6-dihydropyrimidin-5-yl}methyl)biphenyl-2-carbonitrile To a solution of methyl 2-(4-{5-[(2'-cyanobiphenyl-4-yl)methyl]-2-methyl-6-oxo-4-propylpyrimidin-1(6H)-yl}phenoxy)-2-methylpropanoate (0.97 g) in tetrahydrofuran (10 mL) was added lithium tetrahydroboron (0.048 g), and the mixture was stirred at room temperature for 24 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.49 g, 53%).

$^1$H NMR (300 MHz, CDCl$_3$) δ 1.01 (t, J=7.4, 3 H), 1.33 (s, 6 H), 1.61-1.77 (m, 2 H), 2.17 (s, 3 H), 2.61-2.70 (m, 2 H), 3.56-3.64 (m, 3 H), 3.97 (s, 2 H), 7.10-7.78 (m, 12 H)

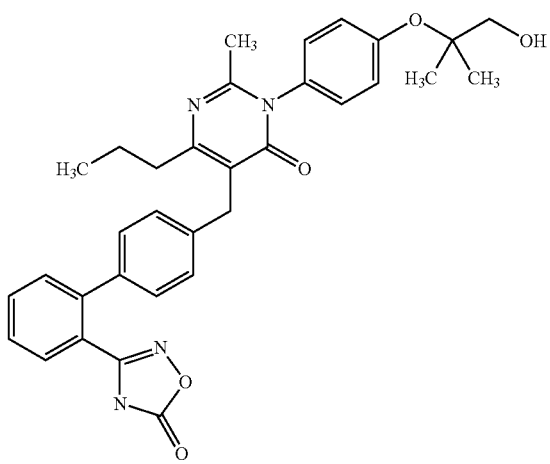

266c) 3-[4-(2-hydroxy-1,1-dimethylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.68 g), sodium hydrogen carbonate (0.98 g) and dimethyl sulfoxide (5 mL) was stirred at 40° C. for 30 min, 4'-({1-[4-(2-hydroxy-1,1-dimethylethoxy)phenyl]-2-methyl-6-oxo-4-propyl-1,6-dihydropyrimidin-5-yl}methyl)biphenyl-2-carbonitrile (0.49 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (5 mL). N,N'-carbonyldiimidazole (0.19 g) and then 1,8-diazabicyclo[5.4.0]undec-7-ene (0.17 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.14 g, 26%).

$^1$H NMR (300 MHz, DMSO-d$_6$) δ 0.89 (t, J=7.4, 3 H), 1.25 (s, 6 H), 1.45-1.63 (m, 2 H), 2.06 (s, 3 H), 2.50-2.56 (m, 2 H), 3.42 (d, J=5.5, 2 H), 3.87 (s, 2 H), 4.94 (t, J=5.5, 1 H), 7.09-7.73 (m, 12 H), 12.36 (br s, 1 H)

Example 267

3-[4-(1-hydroxyethyl)phenyl]-2-methyl-5-{[2'-(5-oxo-4,5-dihydro-1,2,4-oxadiazol-3-yl)biphenyl-4-yl]methyl}-6-propylpyrimidin-4(3H)-one

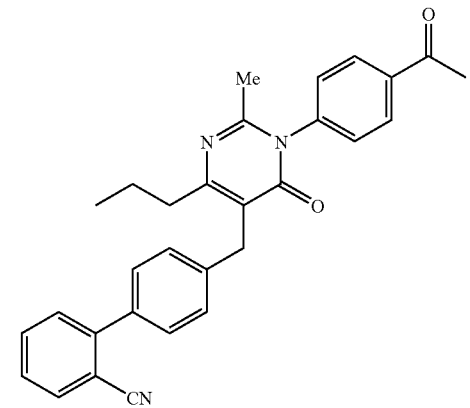

267a) 4'-{[1-(4-acetylphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (3.0 g), (4-acetylphenyl)boronic acid (3.0 g), triethylamine (6.0 mL), pyridine (3.0 mL) and molecular sieves 4 A (6.0 g) in methylene chloride (30 mL) was added copper(II) acetate (3.0 g), and the mixture was stirred at room temperature for 2 days.

The reaction mixture was diluted with ethyl acetate, the insoluble material was filtered off through celite, and the filtrate was concentrated. The residue was purified by silica gel column chromatography to give the title compound as a pale-yellow viscous substance (2.34 g, 58%).

$^1$H NMR (300 MHz, DMSO-d$_6$) δ 0.78-0.98 (m, 3 H), 1.46-1.70 (m, 2 H), 2.07 (s, 3 H), 2.52-2.60 (m, 2 H), 2.64 (s, 3 H), 3.93 (s, 2 H), 7.33-8.16 (m, 12 H)

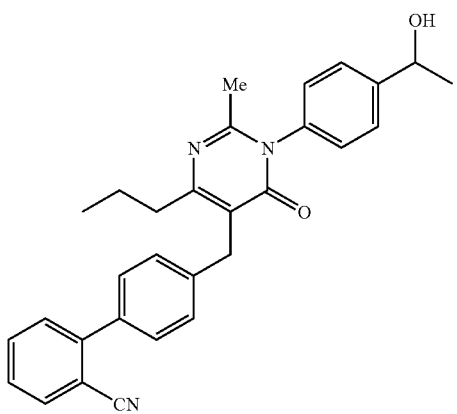

267b) 4'-({1-[4-(1-hydroxyethyl)phenyl]-2-methyl-6-oxo-4-propyl-1,6-dihydropyrimidin-5-yl}methyl)biphenyl-2-carbonitrile To a solution of 4'-{[1-(4-acetylphenyl)-2-methyl-6-oxo-4-propyl-1,6-dihydropyrimidin-5-yl]methyl}biphenyl-2-carbonitrile (1.0 g) in methanol (10 mL) was added sodium tetrahydroboron (0.11 g), and the mixture was stirred at 0° C. for 2 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (1.02 g, 100%).

$^1$H NMR (300 MHz, CDCl$_3$) δ 1.01 (t, J=7.4, 3 H), 1.51 (d, J=6.4, 3 H), 1.61-1.78 (m, 2 H), 2.16 (s, 3 H), 2.59-2.73 (m, 2 H), 3.97 (s, 2 H), 4.88-5.03 (m, 1 H), 7.15-7.80 (m, 12 H)

267c) 3-[4-(1-hydroxyethyl)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (3.30 g), sodium hydrogen carbonate (4.80 g) and dimethyl sulfoxide (20 mL) was stirred at 40° C. for 30 min, 4'-({1-[4-(1-hydroxyethyl)phenyl]-2-methyl-6-oxo-4-propyl-1,6-dihydropyrimidin-5-yl}methyl)biphenyl-2-carbonitrile (2.22 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (20 mL). N,N'-carbonyldiimidazole (0.77 g) and then 1,8-diazabicyclo[5.4.0]undec-7-ene (0.85 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.57 g, 23%).

$^1$H NMR (300 MHz, DMSO-d$_6$) δ 0.89 (t, J=7.4, 3 H), 1.37 (d, J=6.4, 3 H), 1.46-1.63 (m, 2 H), 2.05 (s, 3 H), 2.50-2.55 (m, 2 H), 3.87 (s, 2 H), 4.74-4.86 (m, 1 H), 5.28 (d, J=4.2, 1 H), 7.18-7.72 (m, 12 H), 12.36 (s, 1 H)

Example 268

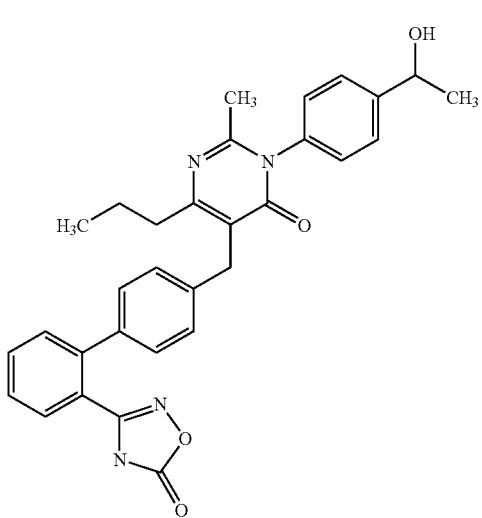

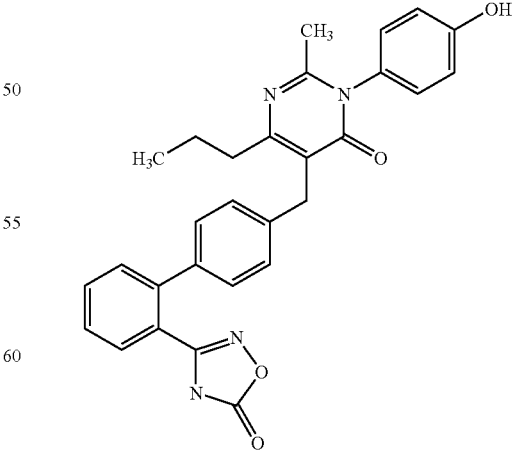

3-(4-hydroxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.40 g), sodium hydrogen carbonate (2.00 g) and dimethyl sulfoxide (10 mL) was stirred at 40° C. for 30 min, 4'-{[1-(4-hydroxyphenyl)-2-methyl-6-oxo-4-propyl-1,6-dihydropyrimidin-5-yl]methyl}biphenyl-2-carbonitrile (0.87 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.39 g) and then 1,8-diazabicyclo[5.4.0]undec-7-ene (0.36 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.48 g, 49%).

$^1$H NMR (300 MHz, DMSO-$d_6$) δ 0.88 (t, J=7.2, 3 H), 1.45-1.63 (m, 2 H), 2.06 (s, 3 H), 2.46-2.54 (m, 2 H), 3.86 (s, 2 H), 6.79-7.76 (m, 12 H), 9.78 (s, 1 H), 12.36 (s, 1 H)

Example 269

3-(3-fluoro-4-hydroxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

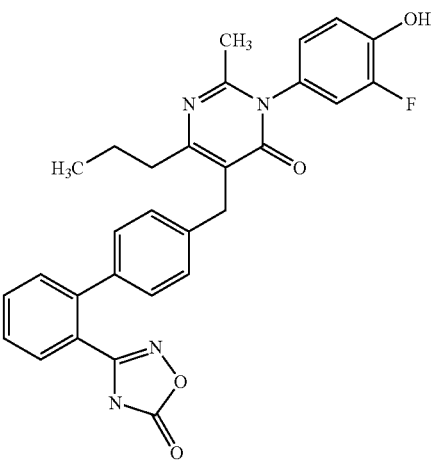

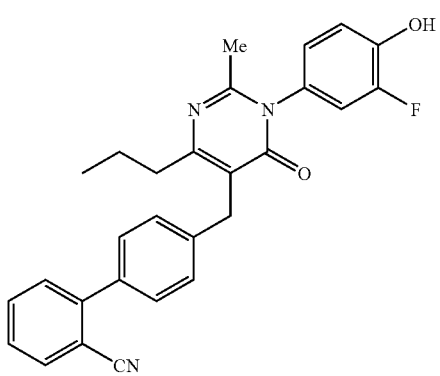

269a) 4'-{[1-(3-fluoro-4-hydroxyphenyl)-2-methyl-6-oxo-4-propyl-1,6-dihydropyrimidin-5-yl]methyl}biphenyl-2-carbonitrile To a solution of 4'-{[1-(3-fluoro-4-methoxyphenyl)-2-methyl-6-oxo-4-propyl-1,6-dihydropyrimidin-5-yl]methyl}biphenyl-2-carbonitrile (6.40 g) in methylene chloride (30 mL) was added boron tribromide (1.0 M methylene chloride solution, 27 mL), and the mixture was stirred at room temperature for 2 days. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow solid (6.27 g, 100%).

$^1$H NMR (300 MHz, CDCl$_3$) δ 1.00 (t, J=7.3, 3 H), 1.56-1.80 (m, 2 H), 2.19 (s, 3 H), 2.56-2.74 (m, 2 H), 4.01 (s, 2 H), 6.69-8.05 (m, 12 H)

269b) 3-(3-fluoro-4-hydroxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.40 g), sodium hydrogen carbonate (2.00 g) and dimethyl sulfoxide (10 mL) was stirred at 40° C. for 30 min, 4'-{[1-(3-fluoro-4-hydroxyphenyl)-2-methyl-6-oxo-4-propyl-1,6-dihydropyrimidin-5-yl]methyl}biphenyl-2-carbonitrile (0.91 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.39 g) and then 1,8-diazabicyclo[5.4.0]undec-7-ene (0.36 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.66 g, 64%).

¹H NMR (300 MHz, DMSO-d₆) δ 0.88 (t, J=7.2, 3 H), 1.41-1.64 (m, 2 H), 2.09 (s, 3 H), 2.42-2.55 (m, 2 H), 3.86 (s, 2 H), 6.95-7.72 (m, 11 H), 10.25 (s, 1 H), 12.36 (s, 1 H)

Example 270

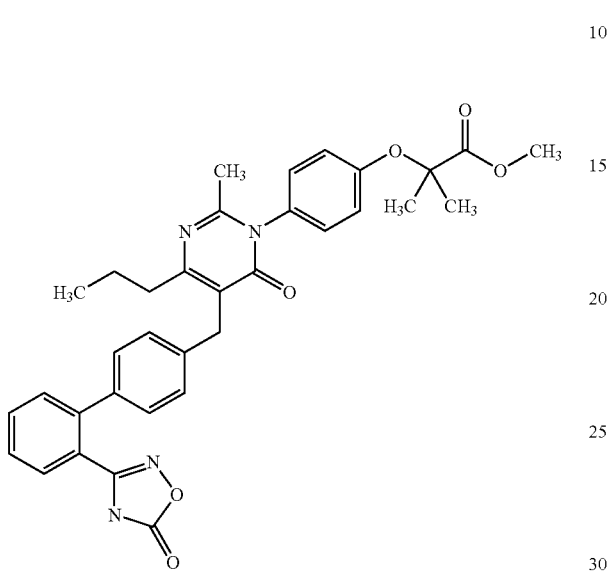

methyl 2-methyl-2-{4-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]phenoxy}propanoate A mixture of hydroxylammonium chloride (0.67 g), sodium hydrogen carbonate (1.00 g) and dimethyl sulfoxide (5 mL) was stirred at 40° C. for 30 min, methyl 2-{4-[5-[(2'-cyanobiphenyl-4-yl)methyl]-2-methyl-6-oxo-4-propylpyrimidin-1(6H)-yl]phenoxy}-2-methylpropanoate (0.87 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (5 mL). N,N'-carbonyldiimidazole (0.20 g) and then 1,8-diazabicyclo[5.4.0]undec-7-ene (0.20 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.24 g, 41%).

¹H NMR (300 MHz, DMSO-d₆) δ 0.89 (t, J=7.4, 3 H), 1.44-1.65 (m, 8 H), 2.05 (s, 3 H), 2.45-2.56 (m, 2 H), 3.72 (s, 3 H), 3.86 (s, 2 H), 6.83-7.76 (m, 12 H), 12.36 (s, 1 H)

Example 271

3-(4-sec-butoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

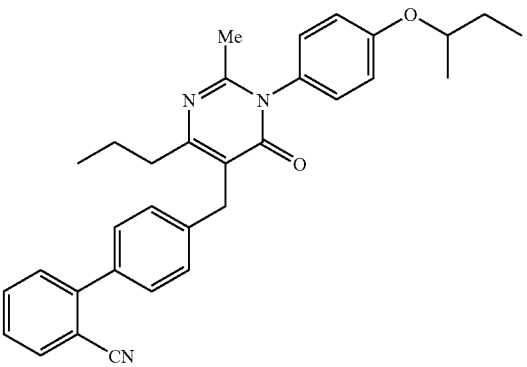

271a) 4'-{[1-(4-sec-butoxyphenyl)-2-methyl-6-oxo-4-propyl-1,6-dihydropyrimidin-5-yl]methyl}biphenyl-2-carbonitrile To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and 2-bromobutane (0.66 mL) in N,N-dimethylformamide (10 mL) was added cesium carbonate (1.5 g), and the mixture was stirred at 80° C. for 48 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.85 g, 76%).

¹H NMR (300 MHz, CDCl₃) δ 0.91-1.06 (m, 6 H), 1.32 (d, J=6.2, 3 H), 1.58-1.86 (m, 4 H), 2.18 (s, 3 H), 2.57-2.72 (m, 2 H), 3.97 (s, 2 H), 4.23-4.41 (m, 1 H), 6.89-7.81 (m, 12H)

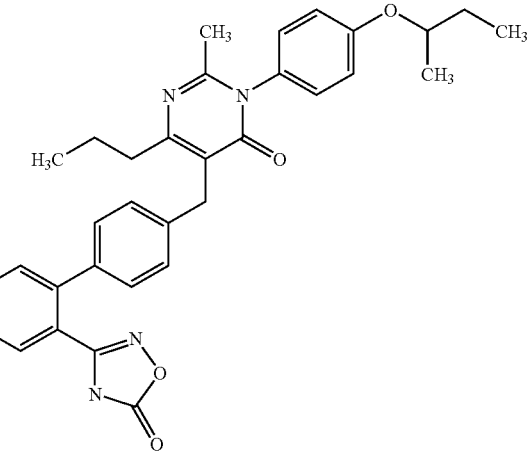

271b) 3-(4-sec-butoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.21 g), sodium hydrogen carbonate (1.76 g) and dimethyl sulfoxide (8 mL) was stirred at 40° C. for 30 min, 4'-{[1-(4-sec-butoxyphenyl)-2-methyl-6-oxo-4-propyl-1,6-dihydropyrimidin-5-yl]methyl}biphenyl-2-carbonitrile (0.34 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (8 mL). N,N'-carbonyldiimidazole (0.34 g) and then 1,8-diazabicyclo[5.4.0]undec-7-ene (0.31 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.47 g, 49%).

$^1$H NMR (300 MHz, DMSO-$d_6$) δ 0.83-0.99 (m, 6 H), 1.26 (d, J=6.1, 3 H), 1.45-1.78 (m, 4 H), 2.45-2.54 (m, 2 H), 3.86 (s, 2 H), 4.36-4.51 (m, 1 H), 6.94-7.75 (m, 12 H), 12.36 (s, 1 H)

3-(4-sec-Butoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-(4-sec-butoxyphenyl)-2-methyl-5-{[2'-(5-oxo-4,5-dihydro-1,2,4-oxadiazol-3-yl)biphenyl-4-yl]methyl}-6-propylpyrimidin-4(3H)(3H)-one sodium salt 3-(4-sec-butoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-(4-sec-butoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-(4-sec-butoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-(4-sec-butoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one hydrobromide

Example 272

3-[4-(cyclopropylmethoxy)-3-fluorophenyl]-2-methyl-5-{[2'-(5-oxo-4,5-dihydro-1,2,4-oxadiazol-3-yl)biphenyl-4-yl]methyl}-6-propylpyrimidin-4(3H)-one

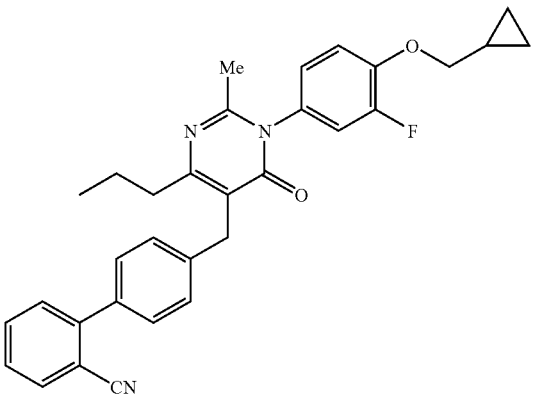

272a) 4'-({1-[4-(cyclopropylmethoxy)-3-fluorophenyl]-2-methyl-6-oxo-4-propyl-1,6-dihydropyrimidin-5-yl}methyl)biphenyl-2-carbonitrile To a solution of 4'-{[1-(3-fluoro-4-hydroxyphenyl)-2-methyl-6-oxo-4-propyl-1,6-dihydropyrimidin-5-yl]methyl}biphenyl-2-carbonitrile (1.0 g) and (bromomethyl)cyclopropane (0.64 mL) in N,N-dimethylformamide (10 mL) was added cesium carbonate (1.5 g), and the mixture was stirred at 80° C. for 48 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.95 g, 85%).

$^1$H NMR (300 MHz, CDCl$_3$) δ 0.33-0.42 (m, 2 H), 0.62-0.73 (m, 2 H), 1.01 (t, J=7.3, 3 H), 1.26-1.43 (m, 1 H), 1.62-1.77 (m, 2 H), 2.19 (s, 3 H), 2.59-2.70 (m, 2 H), 3.84-4.03 (m, 4 H), 6.88-7.83 (m, 11 H)

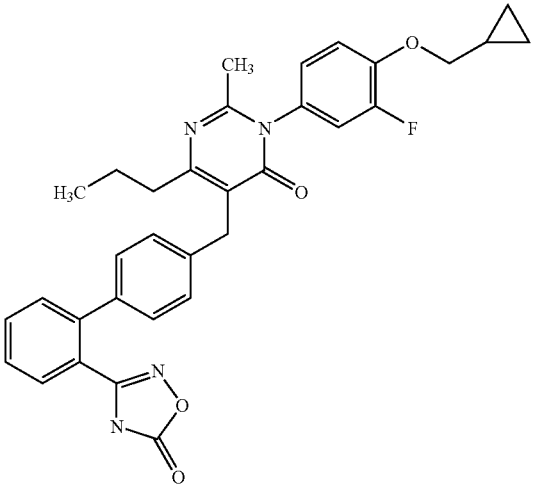

272b) 3-[4-(cyclopropylmethoxy)-3-fluorophenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.31 g), sodium hydrogen carbonate (1.90 g) and dimethyl sulfoxide (10 mL) was stirred at 40° C. for 30 min, 4'-({1-[4-(cyclopropylmethoxy)-3-fluorophenyl]-2-methyl-6-oxo-4-propyl-1,6-dihydropyrimidin-5-yl}methyl)biphenyl-2-carbonitrile (0.95 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.37 g) and then 1,8-diazabicyclo[5.4.0]undec-7-ene (0.34 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.74 g, 70%).

$^1$H NMR (300 MHz, DMSO-$d_6$) δ 0.31-0.41 (m, 2 H), 0.56-0.64 (m, 2 H), 0.88 (t, J=7.2, 3 H), 1.21-1.34 (m, 1 H), 1.45-1.61 (m, 2 H), 2.08 (s, 3 H), 2.45-2.53 (m, 2 H), 3.86 (s, 2H), 3.91-4.02 (m, 2 H), 7.10-7.74 (m, 11 H), 12.37 (s, 1H)

Example 273

3-[4-(2-hydroxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

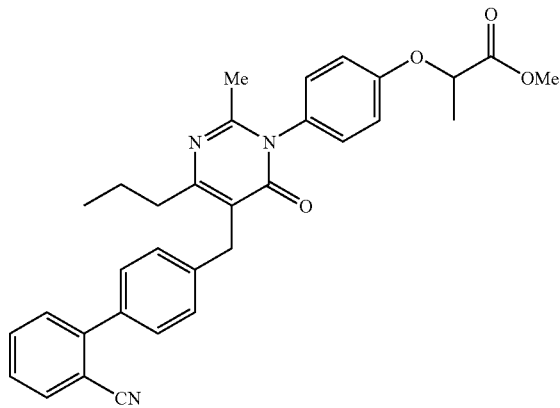

273a) methyl 2-(4-{5-[(2'-cyanobiphenyl-4-yl)methyl]-2-methyl-6-oxo-4-propylpyrimidin-1(6H)-yl}phenoxy)propanoate To a solution of 4'-{[1-(4-hydroxyphenyl)-2-methyl-6-oxo-4-propyl-1,6-dihydropyrimidin-2-yl]methyl}biphenyl-2-carbonitrile (2.0 g) and methyl 2-bromopropanoate (2.50 g) in N,N-dimethylformamide (20 mL) was added cesium carbonate (3.0 g), and the mixture was stirred at 80° C. for 15 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (2.12 g, 89%).

$^1$H NMR (300 MHz, CDCl$_3$) δ 1.01 (t, J=7.3, 3 H), 1.61-1.76 (m, 5 H), 2.16 (s, 3 H), 2.57-2.71 (m, 2 H), 3.78 (s, 3 H), 3.96 (s, 2 H), 4.78 (q, J=6.8, 1 H), 6.89-7.82 (m, 12 H)

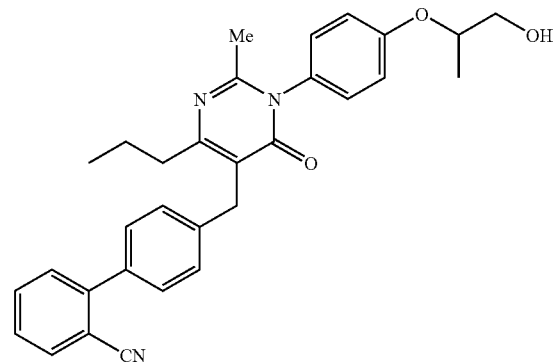

273b) 4'-({1-[4-(2-hydroxy-1-methylethoxy)phenyl]-2-methyl-6-oxo-4-propyl-1,6-dihydropyrimidin-5-yl}methyl)biphenyl-2-carbonitrile To a solution of methyl 2-(4-{5-[(2'-cyanobiphenyl-4-yl)methyl]-2-methyl-6-oxo-4-propylpyrimidin-1(6H)-yl}phenoxy]propanoate (1.60 g) in tetrahydrofuran (30 mL) was added lithium tetrahydroboron (80 mg), and the mixture was stirred at room temperature for 40 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (1.34 g, 88%).

$^1$H NMR (300 MHz, CDCl$_3$) δ 1.01 (t, J=7.3, 3 H), 1.30 (d, J=6.2, 3 H), 1.61-1.78 (m, 2 H), 2.05-2.15 (m, 1 H), 2.19 (s, 3 H), 2.60-2.71 (m, 2 H), 3.69-3.82 (m, 2 H), 3.97 (s, 2 H), 4.45-4.62 (m, 1 H), 6.99-7.79 (m, 12 H)

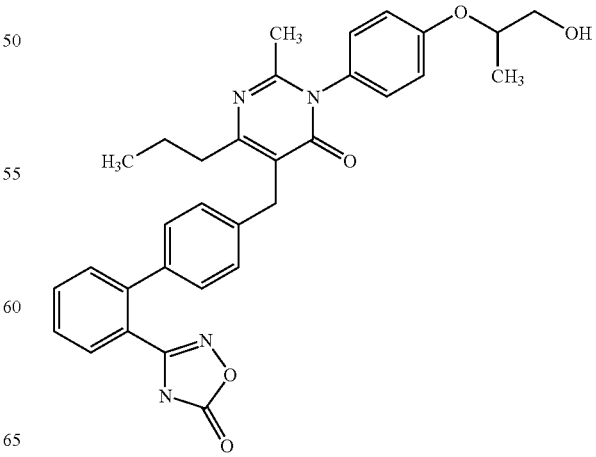

273c) 3-[4-(2-hydroxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.36 g), sodium hydrogen carbonate (2.18 g) and dimethyl sulfoxide (5 mL) was stirred at 40° C. for 30 min, 4'-({1-[4-(2-hydroxy-1-methylethoxy)phenyl]-2-methyl-6-oxo-4-propyl-1,6-dihydropyrimidin-5-yl}methyl)biphenyl-2-carbonitrile (0.64 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.20 g, 27%).

$^1$H NMR (300 MHz, DMSO-$d_6$) δ 0.89 (t, J=7.4, 3 H), 1.24 (d, J=6.1, 3 H), 1.47-1.61 (m, 2 H), 2.07 (s, 3 H), 2.47-2.54 (m, 2 H), 3.44-3.64 (m, 2 H), 3.86 (s, 2 H), 4.42-4.54 (m, 1 H), 4.88 (t, J=5.5, 1 H), 7.02-7.73 (m, 12 H), 12.32 (s, 1 H)

Example 274

3-[4-(2-methoxy-1,1-dimethylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

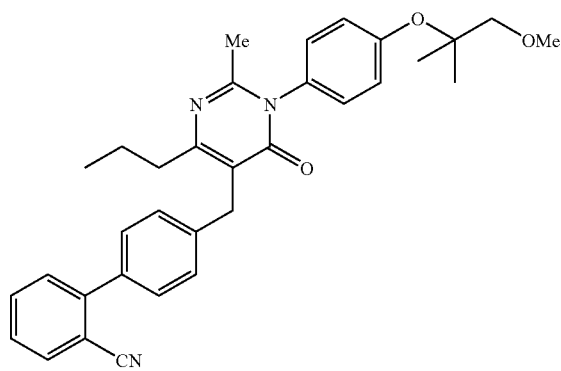

274a) 4'-({1-[4-(2-methoxy-1,1-dimethylethoxy)phenyl]-2-methyl-6-oxo-4-propyl-1,6-dihydropyrimidin-5-yl}methyl)biphenyl-2-carbonitrile To a solution of 4'-({1-[4-(2-hydroxy-1,1-dimethylethoxy)phenyl]-2-methyl-6-oxo-4-propyl-1,6-dihydropyrimidin-5-yl}methyl)biphenyl-2-carbonitrile (0.69 g) in N,N-dimethylformamide (7 mL) were added 60% sodium hydride (0.065 g) and then methyl iodide at 0° C., and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.52 g, 74%).

$^1$H NMR (300 MHz, CDCl$_3$) δ 1.01 (t, J=7.3, 3 H), 1.34 (s, 6 H), 1.62-1.77 (m, 2 H), 2.15 (s, 3 H), 2.60-2.69 (m, 2 H), 3.38 (s, 2 H), 3.43 (s, 3 H), 3.97 (s, 2 H), 7.06-7.78 (m, 12 H)

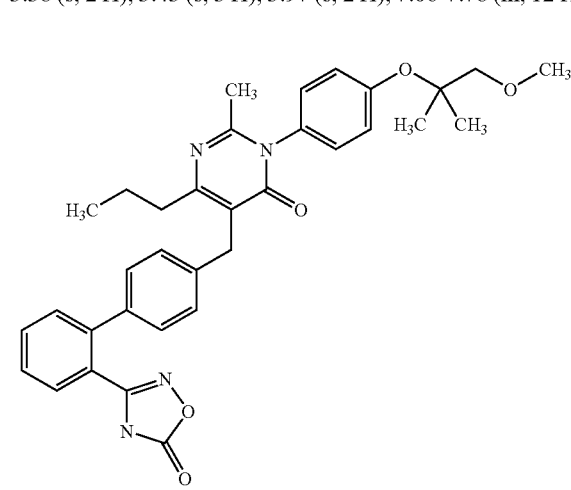

274b) 3-[4-(2-methoxy-1,1-dimethylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.83 g), sodium hydrogen carbonate (1.26 g) and dimethyl sulfoxide (5 mL) was stirred at 40° C. for 30 min, 4'-({1-[4-(2-methoxy-1,1-dimethylethoxy)phenyl]-2-methyl-6-oxo-4-propyl-1,6-dihydropyrimidin-5-yl}methyl)biphenyl-2-carbonitrile (0.52 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (5 mL). N,N'-carbonyldiimidazole (0.21 g) and then 1,8-diazabicyclo[5.4.0]undec-7-ene (0.19 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.27 g, 41%).

1H NMR (300 MHz, DMSO-$d_6$) δ 0.89 (t, J=7.3, 3 H), 1.28 (s, 6H), 1.47-1.62 (m, 2 H), 2.06 (s, 3 H), 2.47-2.55 (m, 2 H), 3.33 (s, 3 H), 3.36 (s, 2 H), 3.87 (s, 2 H), 7.07-7.74 (m, 12 H), 12.38 (s, 1 H)

Example 275

3-(7-fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one

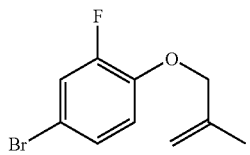

275a) 4-bromo-2-fluoro-1-[(2-methylprop-2-en-1-yl)oxy]benzene

To a solution of 4-bromo-2-fluorophenol (26.8 g) and 3-chloro-2-methylprop-1-ene (13.7 mL) in acetone (420 mL) was added potassium carbonate (29 g), and the mixture was stirred at 70° C. for 15 hr. The reaction mixture was allowed to cool to room temperature, water was added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (29.9 g, 87%).

$^1$H NMR (300 MHz, CDCl$_3$) δ 1.83 (s, 3 H), 4.48 (s, 2 H), 5.04 (d, J=23.5, 2 H), 6.84 (t, J=8.9, 1 H), 7.13-7.26 (m, 2 H)

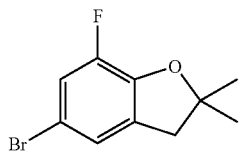

275b) 5-bromo-7-fluoro-2,2-dimethyl-2,3-dihydro-1-benzofuran

A solution of 4-bromo-2-fluoro-1-[(2-methylprop-2-en-1-yl)oxy]benzene (29.9 g) in N,N-diethylaniline (30 mL) was stirred at 190° C. for 5 hr. The mixture was allowed to cool to room temperature, and the reaction mixture was diluted with diisopropyl ether, washed with 1 M hydrochloric acid and then with saturated brine, and dried over anhydrous magnesium sulfate. The solvent was evaporated under reduced pressure. The residue was dissolved in toluene (240 mL), boron trifluoride diethyl ether complex was added, and the mixture was stirred at 60° C. for 15 hr. The mixture was allowed to cool to room temperature, water was added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (18.9 g, 63%).

$^1$H NMR (300 MHz, CDCl$_3$) δ 1.51 (s, 6 H), 3.04 (s, 2 H), 6.97-7.24 (m, 2 H)

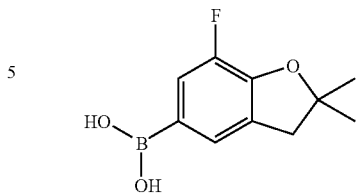

275c) (7-fluoro-2,2-dimethyl-2,3-dihydro-1-benzofuran-5-yl)boronic acid

To a solution of 5-bromo-7-fluoro-2,2-dimethyl-2,3-dihydro-1-benzofuran (18.9 g) in tetrahydrofuran (250 mL) was added butyllithium (53 mL, 1.60 M hexane solution) under an argon atmosphere at −78° C., and the mixture was stirred for 1 hr. Triisopropyl borate (21 mL) was added, and the mixture was stirred for 12 hr while allowing to warm to room temperature. 1 M hydrochloric acid (150 mL) was added, and the mixture was stirred for 1 hr, and extracted with ethyl acetate. The organic layer was washed with saturated brine and dried over anhydrous magnesium sulfate. The solvent was evaporated and the residue was purified by silica gel column chromatography to give the title compound as colorless crystals (6.54 g, 40%).

$^1$H NMR (300 MHz, DMSO-d$_6$) δ 1.45 (s, 6 H), 3.02-3.15 (m, 2 H), 7.26-8.00 (m, 4 H)

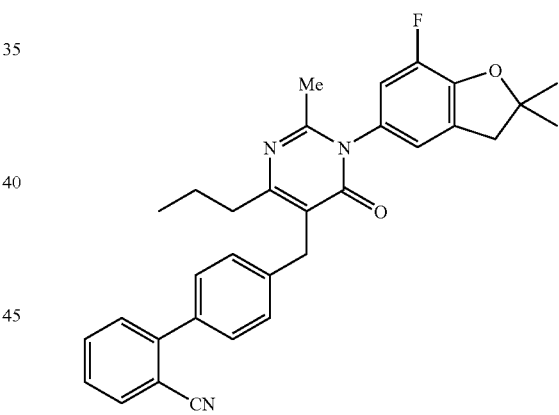

275d) 4'-{[1-(7-fluoro-2,2-dimethyl-2,3-dihydro-1-benzofuran-5-yl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (7-fluoro-2,2-dimethyl-2,3-dihydro-1-benzofuran-5-yl)boronic acid (1.22 g), triethylamine (2.0 mL), pyridine (1.0 mL) and molecular sieves 4 A (2.0 g) in methylene chloride (15 mL) was added copper(II) acetate (1.0 g), and the mixture was stirred at room temperature for 3 days. The reaction mixture was diluted with ethyl acetate, the insoluble material was filtered off through celite, and the filtrate was concentrated. The residue was purified by silica gel column chromatography to give the title compound as a pale-yellow viscous substance (1.20 g, 81%).

$^1$H NMR (300 MHz, CDCl$_3$) δ 1.01 (t, J=7.3, 3 H), 1.53 (s, 3 H), 1.57 (s, 3 H), 1.64-1.76 (m, 2 H), 2.22 (s, 3 H), 2.61-2.69 (m, 2 H), 3.04-3.18 (m, 2 H), 3.90-4.02 (m, 2 H), 6.77-6.85 (m, 2 H), 7.36-7.77 (m, 8 H)

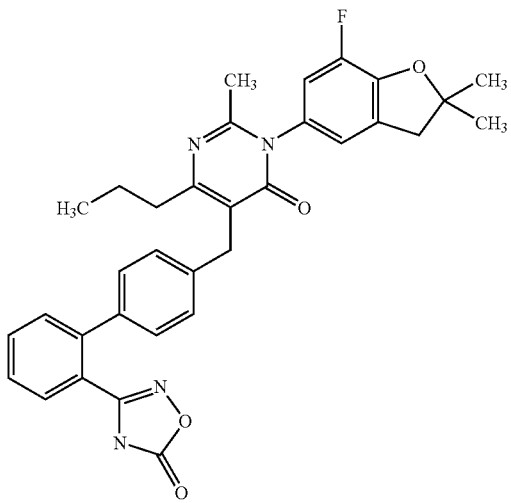

275e) 3-(7-fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.95 g), sodium hydrogen carbonate (2.95 g) and dimethyl sulfoxide (10 mL) was stirred at 40° C. for 30 min, 4'-{[1-(7-fluoro-2,2-dimethyl-2,3-dihydro-1-benzofuran-5-yl)-2-methyl-6-oxo-4-propyl-1,6-dihydropyrimidin-5-yl]methyl}biphenyl-2-carbonitrile (1.19 g) was added, and the mixture was stirred at 90° C. for 18 hr. The reaction mixture was allowed to cool to room temperature, ethyl acetate and water were added, and the aqueous layer was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.49 g) and then 1,8-diazabicyclo [5.4.0]undec-7-ene (0.45 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.95 g, 71%).

$^1$H NMR (300 MHz, DMSO-d$_6$) δ 0.88 (t, J=7.4, 3 H), 1.42-1.62 (m, 8 H), 2.11 (s, 3 H), 2.45-2.54 (m, 2 H), 3.13 (s, 2 H), 3.86 (s, 2 H), 6.98-7.73 (m, 10 H), 12.36 (s, 1 H)

3-(7-Fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.
3-(7-fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-(7-fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-(7-fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-(7-fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-(7-fluoro-2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 276

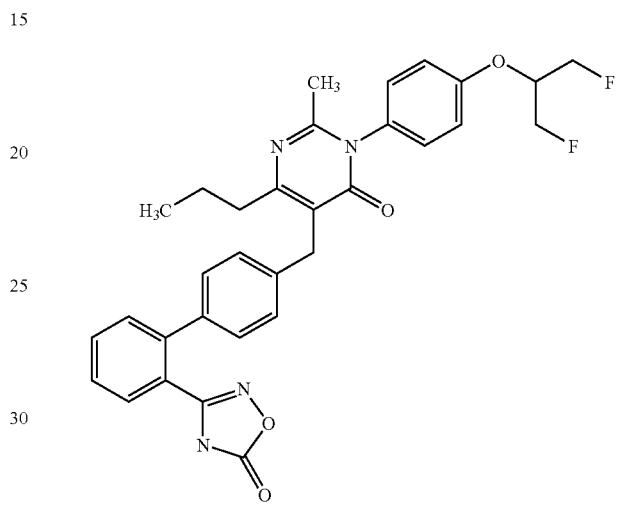

3-{4-[2-fluoro-1-(fluoromethyl)ethoxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (1.0 g), 1,3-difluoropropan-2-ol (0.66 mL), triphenylphosphine (1.2 g) in tetrahydrofuran (7 mL) was added diisopropyl azodicarboxylate (0.90 mL, 1.9 M toluene solution), and the mixture was stirred at room temperature for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (1.21 g), sodium hydrogen carbonate (1.38 g) and dimethyl sulfoxide (8 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.35 g) and then 1,8-diazabicyclo[5.4.0] undec-7-ene (0.32 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.68 g, 72%).

¹H NMR (300 MHz, DMSO-d₆) δ 0.89 (t, J=7.2, 3 H), 1.46-1.62 (m, 2 H), 2.07 (s, 3 H), 2.47-2.54 (m, 2 H), 3.87 (s, 2 H), 4.58-5.14 (m, 5 H), 7.14-7.73 (m, 12 H), 12.37 (s, 1 H)

Example 277

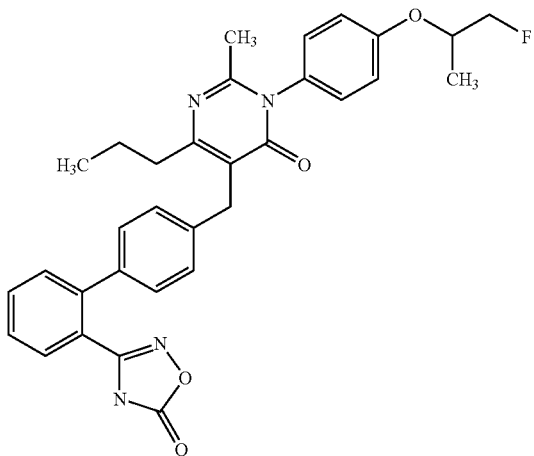

3-[4-(2-fluoro-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (0.65 g), 1-fluoropropan-2-ol (0.23 g), triphenylphosphine (0.78 g) in tetrahydrofuran (5 mL) was added diisopropyl azodicarboxylate (0.59 mL, 1.9 M toluene solution), and the mixture was stirred at room temperature for 2 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (1.24 g), sodium hydrogen carbonate (1.88 g) and dimethyl sulfoxide (8 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (8 mL). N,N'-carbonyldiimidazole (0.48 g) and then 1,8-diazabicyclo[5.4.0]undec-7-ene (0.45 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.47 g, 57%).

¹H NMR (300 MHz, DMSO-d₆) δ 0.89 (t, J=7.4, 3 H), 1.27 (dd, J=6.4, 1.5, 3 H), 1.47-1.61 (m, 2 H), 2.07 (s, 3 H), 2.46-2.55 (m, 2 H), 3.86 (s, 2 H), 4.39-4.92 (m, 3 H), 7.04-7.72 (m, 12 H), 12.36 (s, 1 H)

3-[4-(2-Fluoro-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-[4-(2-fluoro-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-[4-(2-fluoro-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-[4-(2-fluoro-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-[4-(2-fluoro-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-[4-(2-fluoro-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrobromide Example 278

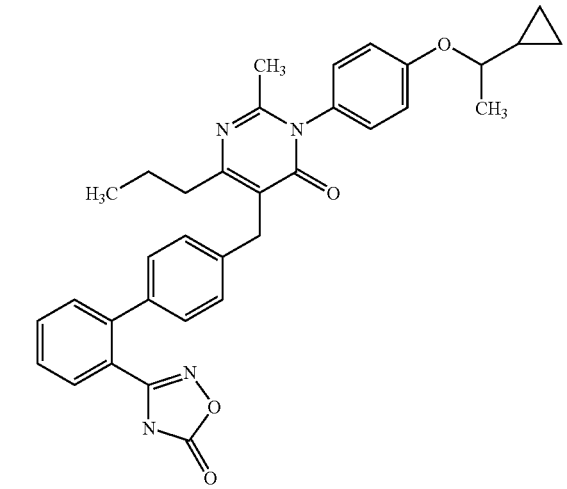

3-[4-(1-cyclopropylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (0.65 g), 1-cyclopropylethanol (0.26 g), triphenylphosphine (0.79 g) in tetrahydrofuran (5 mL) was added diisopropyl azodicarboxylate (0.59 mL, 1.9 M toluene solution), and the mixture was stirred at room temperature for 2 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (1.24 g), sodium hydrogen carbonate (1.88 g) and dimethyl sulfoxide (8 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (8 mL). N,N'-carbonyldiimidazole (0.48 g) and then 1,8-diazabicyclo[5.4.0]undec-7-ene (0.45 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.21 g, 25%).

$^1$H NMR (300 MHz, DMSO-d$_6$) δ 0.25-0.59 (m, 4 H), 0.89 (t, J=7.4, 3 H), 1.05-1.20 (m, 1 H), 1.31 (d, J=6.1, 3 H), 1.45-1.63 (m, 2 H), 2.07 (s, 3 H), 2.47-2.53 (m, 2 H), 3.86 (s, 2 H), 3.96-4.09 (m, 1 H), 6.97-7.73 (m, 12 H), 12.36 (s, 1H)

Example 279

3-(4-ethoxy-3-fluorophenyl)-2-methyl-5-{[2'-(5-oxo-4,5-dihydro-1,2,4-oxadiazol-3-yl)biphenyl-4-yl]methyl}-6-propylpyrimidin-4(3H)-one

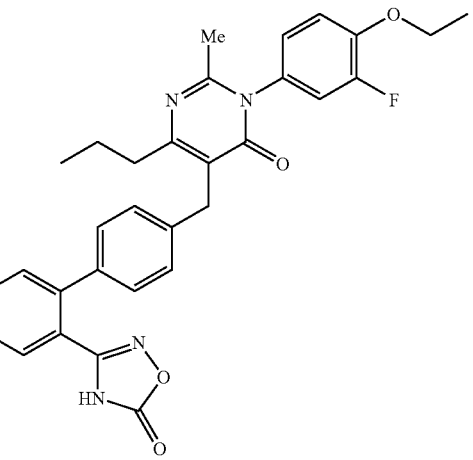

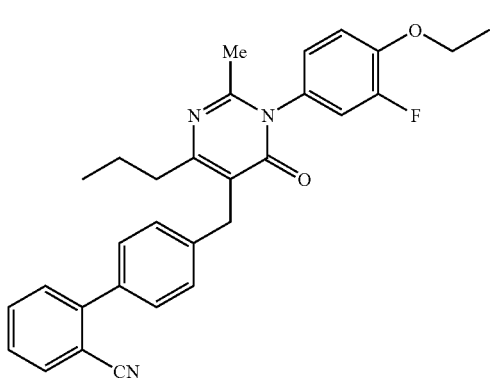

279a) 4'-{[1-(4-ethoxy-3-fluorophenyl)-2-methyl-6-oxo-4-propyl-1,6-dihydropyrimidin-5-yl]methyl}biphenyl-2-carbonitrile To a solution of 4'-{[1-(3-fluoro-4-hydroxyphenyl)-2-methyl-6-oxo-4-propyl-1,6-dihydropyrimidin-5-yl]methyl}biphenyl-2-carbonitrile (1.0 g) and ethyl iodide (0.53 mL) in N,N-dimethylformamide (10 mL) was added cesium carbonate (1.44 g), and the mixture was stirred at 80° C. for 2 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.96 g, 91%).

$^1$H NMR (300 MHz, CDCl$_3$) δ 1.01 (t, J=7.3, 3 H), 1.48 (t, J=7.1, 3 H), 1.60-1.77 (m, 2 H), 2.19 (s, 3 H), 2.59-2.71 (m, 2 H), 3.96 (s, 2 H), 4.15 (q, J=7.0, 2 H), 6.90-7.77 (m, 11 H)

279b) 3-(4-ethoxy-3-fluorophenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.40 g), sodium hydrogen carbonate (2.00 g) and dimethyl sulfoxide (10 mL) was stirred at 40° C. for 30 min, 4'-{[1-(4-ethoxy-3-fluorophenyl)-2-methyl-6-oxo-4-propyl-1,6-dihydropyrimidin-5-yl]methyl}biphenyl-2-carbonitrile (0.96 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.42 g) and then 1,8-diazabicyclo[5.4.0]undec-7-ene (0.39 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.76 g, 70%).

$^1$H NMR (300 MHz, DMSO-d$_6$) δ 0.89 (t, J=7.3, 3 H), 1.38 (t, J=7.0, 3 H), 1.47-1.61 (m, 2 H), 2.09 (s, 3 H), 2.46-2.53 (m, 2 H), 3.87 (s, 2 H), 4.17 (q, J=7.0, 2 H), 7.12-7.74 (m, 11 H), 12.38 (s, 1 H)

Example 280

3-[4-(cyclopropyloxy)-3-fluorophenyl]-2-methyl-5-{[2'-(5-oxo-4,5-dihydro-1,2,4-oxadiazol-3-yl)biphenyl-4-yl]methyl}-6-propylpyrimidin-4(3H)-one

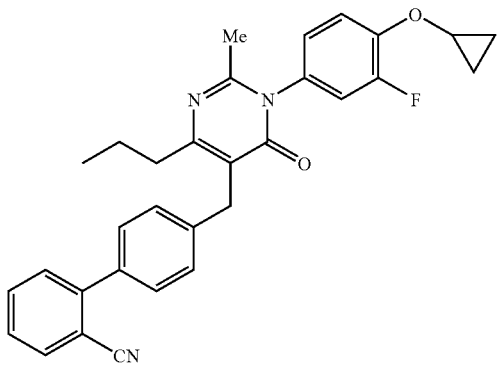

280a) 4'-({1-[4-(cyclopropyloxy)-3-fluorophenyl]-2-methyl-6-oxo-4-propyl-1,6-dihydropyrimidin-5-yl}methyl)biphenyl-2-carbonitrile To a solution of 4'-{[1-(3-fluoro-4-hydroxyphenyl)-2-methyl-6-oxo-4-propyl-1,6-dihydropyrimidin-5-yl]methyl}biphenyl-2-carbonitrile (1.0 g) and bromocyclopropane (1.8 mL) in N,N-dimethylformamide (10 mL) was added cesium carbonate (3.60 g), and the mixture was stirred at 150° C. for 2 days. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.15 g, 14%).

$^1$H NMR (300 MHz, CDCl$_3$) δ 0.78-0.90 (m, 4 H), 0.97-1.04 (m, 3 H), 1.62-1.76 (m, 2 H), 2.19 (d, J=3.4, 3 H), 2.61-2.69 (m, 2 H), 3.80-3.89 (m, 1 H), 3.92-4.02 (m, 2 H), 6.82-7.78 (m, 11 H)

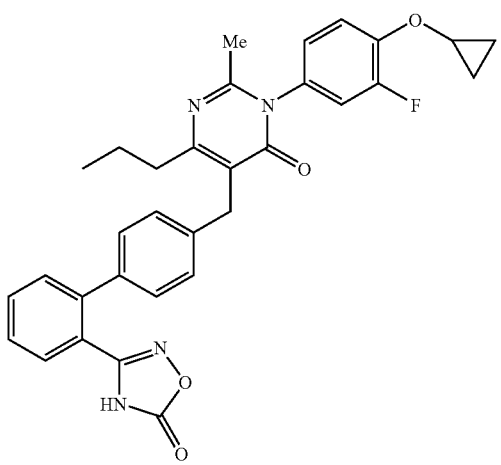

280b) 3-[4-(cyclopropyloxy)-3-fluorophenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.32 g), sodium hydrogen carbonate (0.52 g) and dimethyl sulfoxide (3 mL) was stirred at 40° C. for 30 min, 4'-({1-[4-(cyclopropyloxy)-3-fluorophenyl]-2-methyl-6-oxo-4-propyl-1,6-dihydropyrimidin-5-yl}methyl)biphenyl-2-carbonitrile (0.15 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (3 mL). N,N'-carbonyldiimidazole (0.075 g) and then 1,8-diazabicyclo[5.4.0]undec-7-ene (0.070 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.077 g, 45%).

$^1$H NMR (300 MHz, DMSO-d$_6$) δ 0.69-0.95 (m, 7 H), 1.43-1.61 (m, 2 H), 2.09 (s, 3 H), 2.46-2.54 (m, 2 H), 3.87 (s, 2 H), 3.98-4.11 (m, 1 H), 7.16-7.74 (m, 11 H), 12.38 (s, 1 H)

Example 281

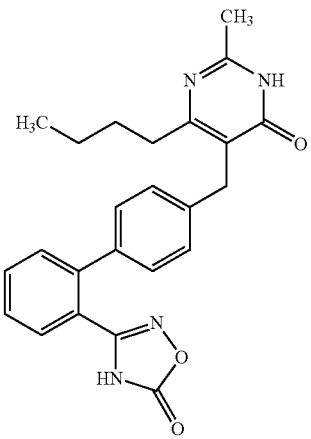

6-butyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.56 g), sodium hydrogen carbonate (2.35 g) and dimethyl sulfoxide (14 mL) was stirred at 40° C. for 30 min, 4'-[(4-butyl-2-methyl-6-oxo-1,6-dihydropyrimidin-5-yl)methyl]biphenyl-2-carbonitrile (1.20 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.48 g) and then 1,8-diazabicyclo[5.4.0]undec-7-ene (0.46 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.37 g, 31%).

$^1$H NMR (300 MHz, DMSO-$d_6$) δ 0.82 (t, J=7.2, 3 H), 1.21-1.49 (m, 4 H), 2.24 (s, 3 H), 2.38-2.49 (m, 2 H), 3.81 (s, 2 H), 7.17-7.72 (m, 9 H), 12.32 (s, 1 H)

Example 282

6-butyl-3-(cyclopropylmethyl)-2-methyl-5-{[2'-(5-oxo-4,5-dihydro-1,2,4-oxadiazol-3-yl)biphenyl-4-yl]methyl}pyrimidin-4(3H)-one

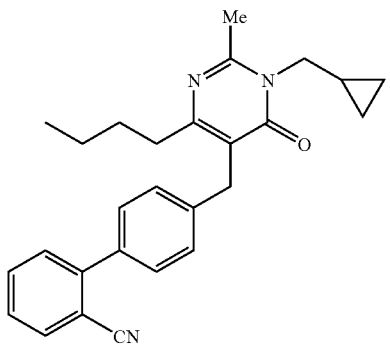

282a) 4'-{[4-butyl-1-(cyclopropylmethyl)-2-methyl-6-oxo-1,6-dihydropyrimidin-5-yl]methyl}biphenyl-2-carbonitrile To a solution of 4'-[(4-butyl-2-methyl-6-oxo-1,6-dihydropyrimidin-5-yl)methyl]biphenyl-2-carbonitrile (0.75 g) and (bromomethyl)cyclopropane (1.36 mL) in N,N-dimethylformamide (10 mL) was added 60% sodium hydride (0.17 g), and the mixture was stirred at room temperature for 15 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.55 g, 63%).

$^1$H NMR (300 MHz, CDCl$_3$) δ 0.37-0.68 (m, 4 H), 0.91 (t, J=7.3, 3 H), 1.08-1.64 (m, 5 H), 2.53-2.62 (m, 2 H), 2.58 (s, 3 H), 3.94-4.01 (m, 2 H), 3.96 (s, 2 H), 7.31-7.78 (m, 8H)

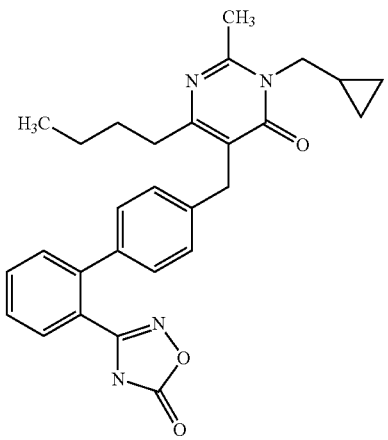

282b) 6-butyl-3-(cyclopropylmethyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.74 g), sodium hydrogen carbonate (1.1 g) and dimethyl sulfoxide (6 mL) was stirred at 40° C. for 30 min, 4'-{[4-butyl-1-(cyclopropylmethyl)-2-methyl-6-oxo-1,6-dihydropyrimidin-5-yl]methyl}biphenyl-2-carbonitrile (0.55 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (6 mL). N,N'-carbonyldiimidazole (0.29 g) and then 1,8-diazabicyclo[5.4.0]undec-7-ene (0.27 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.089 g, 14%).

$^1$H NMR (300 MHz, CDCl$_3$) δ 0.28-0.70 (m, 4 H), 0.93 (t, J=7.3, 3 H), 1.02-2.11 (m, 5 H), 2.51-2.69 (m, 2 H), 2.55 (s, 3 H), 3.86-3.96 (m, 4 H), 7.18-7.88 (m, 9 H)

Example 283

6-butyl-3-isopropyl-2-methyl-5-{[2'-(5-oxo-4,5-dihydro-1,2,4-oxadiazol-3-yl)biphenyl-4-yl]methyl}pyrimidin-4(3H)-one

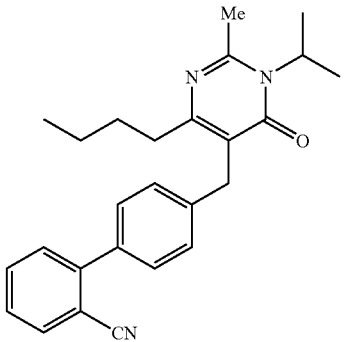

283a) 4'-[(4-butyl-1-isopropyl-2-methyl-6-oxo-1,6-dihydropyrimidin-5-yl)methyl]biphenyl-2-carbonitrile To a solution of 4'-[(4-butyl-2-methyl-6-oxo-1,6-dihydropyrimidin-5-yl)methyl]biphenyl-2-carbonitrile (2.00 g) and 2-iodopropane (2.8 mL) in N,N-dimethylformamide (20 mL) was added 60% sodium hydride (0.34 g), and the mixture was stirred at room temperature for 15 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.23 g, 10%).

$^1$H NMR (300 MHz, CDCl$_3$) δ 0.90 (t, J=7.3, 3 H), 1.27-1.68 (m, 4 H), 1.60 (d, J=1.9, 6 H), 2.47-2.60 (m, 2 H), 2.55 (s, 3 H), 3.93 (s, 2 H), 4.63 (s, 1 H), 7.29-7.78 (m, 8 H)

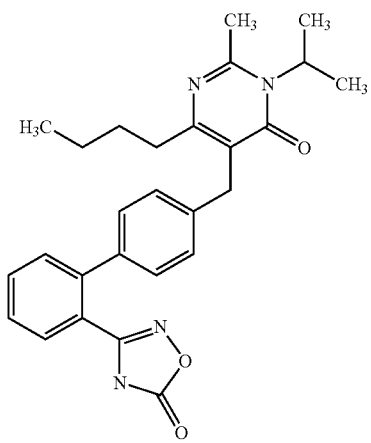

283b) 6-butyl-3-isopropyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.32 g), sodium hydrogen carbonate (0.48 g) and dimethyl sulfoxide (3 mL) was stirred at 40° C. for 30 min, 4'-[(4-butyl-1-isopropyl-2-methyl-6-oxo-1,6-dihydropyrimidin-5-yl)methyl]biphenyl-2-carbonitrile (0.23 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (4 mL). N,N'-carbonyldiimidazole (0.092 g) and then 1,8-diazabicyclo[5.4.0]undec-7-ene (0.085 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.14 g, 53%).

$^1$H NMR (300 MHz, CDCl$_3$) δ 0.91 (t, J=7.3, 3 H), 1.29-1.65 (m, 4 H), 1.53 (d, J=6.8, 6 H), 2.47-2.58 (m, 2 H), 2.52 (s, 3 H), 3.84 (s, 2 H), 4.42-4.68 (m, 1 H), 7.17-7.87 (m, 9 H)

Example 284

6-butyl-2,3-dimethyl-5-{[2'-(5-oxo-4,5-dihydro-1,2,4-oxadiazol-3-yl)biphenyl-4-yl]methyl}pyrimidin-4(3H)-one

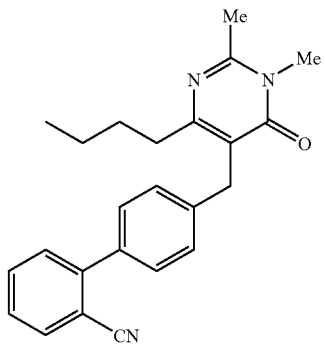

284a) 4'-[(4-butyl-1,2-dimethyl-6-oxo-1,6-dihydropyrimidin-5-yl)methyl]biphenyl-2-carbonitrile To a solution of 4'-[(4-butyl-2-methyl-6-oxo-1,6-dihydropyrimidin-5-yl)methyl]biphenyl-2-carbonitrile (1.00 g) and iodomethane (0.87 mL) in N,N-dimethylformamide (10 mL) was added 60% sodium hydride (0.17 g), and the mixture was stirred at room temperature for 15 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.95 g, 91%).

$^1$H NMR (300 MHz, CDCl$_3$) δ 0.91 (t, J=7.3, 3 H), 1.30-1.61 (m, 4 H), 2.51 (s, 3 H), 2.54-2.64 (m, 2 H), 3.53 (s, 3 H), 3.96 (s, 2 H), 7.32-7.78 (m, 8 H)

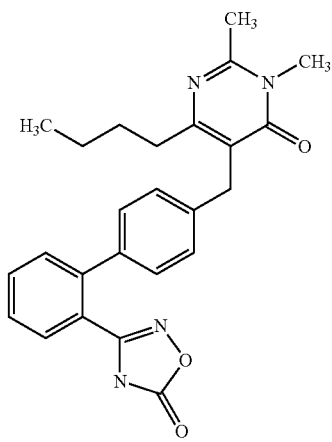

284b) 6-butyl-2,3-dimethyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.40 g), sodium hydrogen carbonate (2.10 g) and dimethyl sulfoxide (13 mL) was stirred at 40° C. for 30 min, 4'-[(4-butyl-1,2-dimethyl-6-oxo-1,6-dihydropyrimidin-5-yl)methyl]biphenyl-2-carbonitrile (0.95 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.32 g) and then 1,8-diazabicyclo[5.4.0]undec-7-ene (0.30 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.64 g, 59%).

$^1$H NMR (300 MHz, CDCl$_3$) δ 0.92 (t, J=7.3, 3 H), 1.27-1.67 (m, 4 H), 2.50 (s, 3 H), 2.52-2.65 (m, 2 H), 3.47 (s, 3 H), 3.87 (s, 2 H), 3.93-4.05 (m, 1 H), 7.15-7.84 (m, 8 H)

Example 285

6-butyl-2-(2-phenylethyl)-5-{[2'-(5-oxo-4,5-dihydro-1,2,4-oxadiazol-3-yl)biphenyl-4-yl]methyl}pyrimidin-4(3H)-one

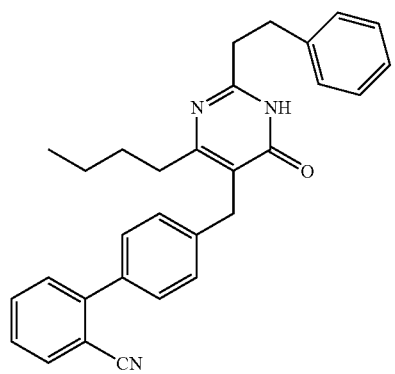

285a) 4'-{[4-butyl-6-oxo-2-(2-phenylethyl)-1,6-dihydropyrimidin-5-yl]methyl}biphenyl-2-carbonitrile To a solution of methyl 2-[(2'-cyanobiphenyl-4-yl)methyl]-3-oxoheptanoate (0.70 g) and 3-phenylpropanimidamide (0.63 g) in methanol (10 mL) was added 28% sodium methoxide-methanol solution (1.7 mL), and the mixture was stirred at room temperature for 24 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.71 g, 79%).

$^1$H NMR (300 MHz, CDCl$_3$) δ 0.91 (t, J=7.3, 3 H), 1.21-1.71 (m, 4 H), 2.53-2.70 (m, 2 H), 2.84-3.21 (m, 4 H), 3.98 (s, 2 H), 6.98-7.91 (m, 13 H), 12.73 (s, 1 H)

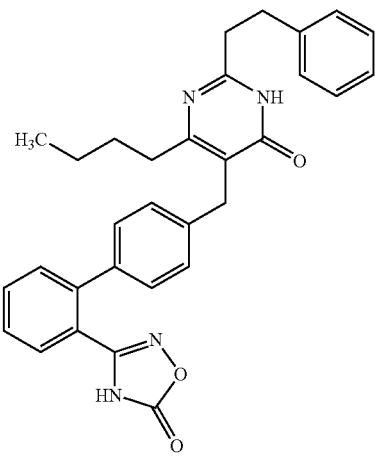

285b) 6-butyl-2-(2-phenylethyl)-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.88 g), sodium hydrogen carbonate (1.34 g) and dimethyl sulfoxide (8 mL) was stirred at 40° C. for 30 min, 4'-{[4-butyl-6-oxo-2-(2-phenylethyl)-1,6-dihydropyrimidin-5-yl]methyl}biphenyl-2-carbonitrile (0.71 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.30 g) and then 1,8-diazabicyclo[5.4.0]undec-7-ene (0.27 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.43 g, 53%).

$^1$H NMR (300 MHz, CDCl$_3$) δ 0.87 (t, J=7.2, 3 H), 1.21-1.54 (m, 4 H), 2.44-2.61 (m, 2 H), 2.77-2.90 (m, 2 H), 2.94-3.07 (m, 2 H), 3.77 (s, 2 H), 7.10-7.84 (m, 13 H), 11.08 (s, 1 H), 11.63 (s, 1 H)

Example 286

2-butyl-5-(2-hydroxy-3,3-dimethylbutyl)-6-methyl-3-{[2'-(5-oxo-4,5-dihydro-1,2,4-oxadiazol-3-yl)biphenyl-4-yl]methyl}pyrimidin-4(3H)-one

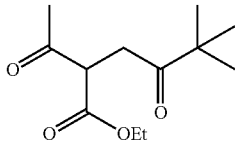

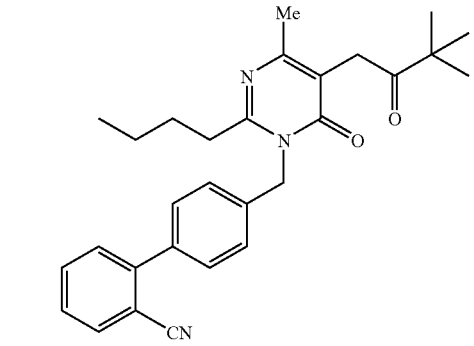

286a) ethyl 2-acetyl-5,5-dimethyl-4-oxohexanoate

To a solution of sodium 4-ethoxy-4-oxobut-2-en-2-olate (1.50 g) in N,N-dimethylformamide (50 mL) was added 1-bromo-3,3-dimethylbutan-2-one (2.0 mL), and the mixture was stirred at room temperature for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (1.51 g, 53%).

$^1$H NMR (300 MHz, CDCl$_3$) δ 1.17 (s, 9 H), 1.28 (t, J=7.2, 3 H), 2.37 (s, 3 H), 2.96-3.06 (m, 1 H), 3.17-3.29 (m, 1 H), 4.01 (dd, J=8.3, 5.7, 1 H), 4.19 (q, J=7.2, 2 H)

286c) 4'-{[2-butyl-5-(3,3-dimethyl-2-oxobutyl)-4-methyl-6-oxopyrimidin-1(6H)-yl]methyl}biphenyl-2-carbonitrile To a solution of 2-butyl-5-(3,3-dimethyl-2-oxobutyl)-6-methylpyrimidin-4(3H)-one (0.48 g) and 4'-(bromomethyl)biphenyl-2-carbonitrile (0.99 g) in N,N-dimethylformamide (9 mL) was added potassium carbonate (0.75 g), and the mixture was stirred at 80° C. for 24 hr. The reaction mixture was allowed to cool to room temperature, ethyl acetate and water were added, and the aqueous layer was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.33 g, 40%).

$^1$H NMR (300 MHz, CDCl$_3$) δ 0.90 (t, J=7.3, 3 H), 1.27 (s, 9 H), 1.30-1.78 (m, 4 H), 2.60-2.71 (m, 2 H), 3.82 (s, 2 H), 5.34 (s, 2 H), 7.20-7.83 (m, 8 H)

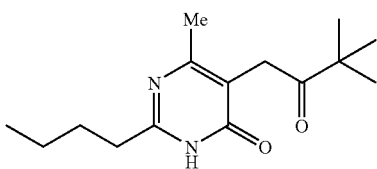

286b) 2-butyl-5-(3,3-dimethyl-2-oxobutyl)-6-methylpyrimidin-4(3H)-one

To a solution of ethyl 2-acetyl-5,5-dimethyl-4-oxohexanoate (1.04 g) and pentanimidamide (0.89 g) in methanol (10 mL) was added 28% sodium methoxide-methanol solution (3.7 mL), and the mixture was stirred at room temperature for 24 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.34 g, 36%).

$^1$H NMR (300 MHz, CDCl$_3$) δ 0.93 (t, J=7.3, 3 H), 1.26 (s, 9 H), 1.30-1.50 (m, 2 H), 1.62-1.79 (m, 2 H), 2.21 (s, 3 H), 2.49-2.66 (m, 2 H), 3.73 (s, 2 H), 12.59 (br s, 1 H)

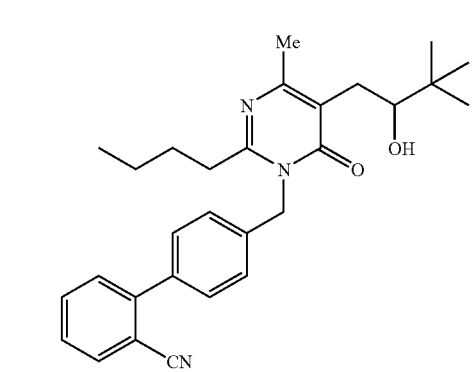

286d) 4'-{[2-butyl-5-(2-hydroxy-3,3-dimethylbutyl)-4-methyl-6-oxopyrimidin-1(6H)-yl]methyl}biphenyl-2-carbonitrile To a solution of 4'-{[2-butyl-5-(3,3-dimethyl-2-oxobutyl)-4-methyl-6-oxopyrimidin-1(6H)-yl]methyl}biphenyl-2-carbonitrile (0.33 g) in ethanol (4 mL) was added sodium tetrahydroboron (0.053 g), and the mixture was stirred at room temperature for 3 hr. Ethyl acetate and water were added to the reaction mixture, and the aqueous layer was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.20 g, 62%).

$^1$H NMR (300 MHz, CDCl$_3$) δ 0.90 (t, J=7.3, 3 H), 1.00 (s, 9 H), 1.31-1.74 (m, 4 H), 2.34 (s, 3 H), 2.62-2.85 (m, 4 H), 3.32-3.45 (m, 1 H), 3.59-3.67 (m, 1 H), 5.36 (s, 2 H), 7.24-7.80 (m, 8 H)

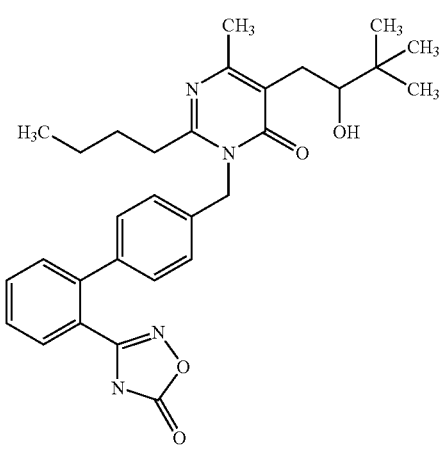

286e) 2-butyl-5-(2-hydroxy-3,3-dimethylbutyl)-6-methyl-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.24 g), sodium hydrogen carbonate (0.36 g) and dimethyl sulfoxide (4 mL) was stirred at 40° C. for 30 min, 4'-{[2-butyl-5-(2-hydroxy-3,3-dimethylbutyl)-4-methyl-6-oxopyrimidin-1 (6H)-yl]methyl}biphenyl-2-carbonitrile (0.20 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (3 mL). N,N'-carbonyldiimidazole (0.057 g) and then 1,8-diazabicyclo[5.4.0]undec-7-ene (0.052 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.082 g, 37%).

$^1$H NMR (300 MHz, CDCl$_3$) δ 0.83-0.97 (m, 12 H), 1.32-1.81 (m, 4 H), 2.30 (s, 3 H), 2.50-2.81 (m, 4 H), 3.21-3.39 (m, 1H), 3.67-3.82 (m, 1 H), 5.17-5.38 (m, 2 H), 7.18-7.83 (m, 8 H), 8.67 (s, 1 H)

Example 287

5-benzyl-6-methyl-3-{[2'-(5-oxo-4,5-dihydro-1,2,4-oxadiazol-3-yl)biphenyl-4-yl]methyl}-2-propylpyrimidin-4(3H)-one

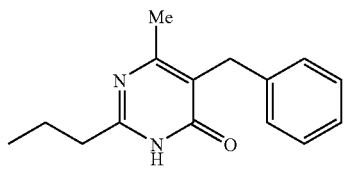

287a) 5-benzyl-6-methyl-2-propylpyrimidin-4(3H)-one

To a solution of ethyl 2-benzyl-3-oxobutanoate (2.13 mL) and butanimidamide hydrochloride (2.05 g) in methanol (50 mL) was added 28% sodium methoxide-methanol solution (5.8 g), and the mixture was stirred at room temperature for 24 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (1.61 g, 66%).

$^1$H NMR (300 MHz, CDCl$_3$) δ 0.97 (t, J=7.3, 3 H), 1.69-1.86 (m, 2 H), 2.34 (s, 3 H), 2.52-2.62 (m, 2 H), 3.89 (s, 2 H), 7.12-7.30 (m, 5 H), 12.99 (s, 1 H)

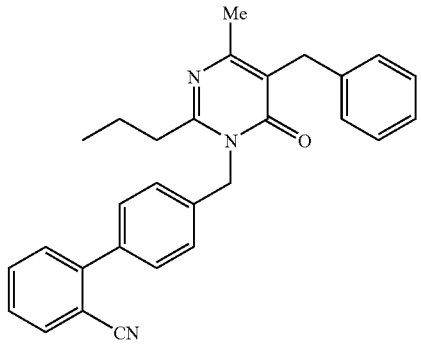

287b) 4'-[(5-benzyl-4-methyl-6-oxo-2-propylpyrimidin-1(6H)-yl)methyl]biphenyl-2-carbonitrile To a solution of 5-benzyl-6-methyl-2-propylpyrimidin-4 (3H)-one (0.80 g) and 4'-(bromomethyl)biphenyl-2-carbonitrile (1.08 g) in N,N-dimethylformamide (15 mL) was added 60% sodium hydride (0.17 g), and the mixture was stirred at room temperature for 3 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.61 g, 35%).

$^1$H NMR (300 MHz, CDCl$_3$) δ 0.98 (t, J=7.4, 3 H), 1.64-1.82 (m, 2 H), 2.34 (s, 3 H), 2.60-2.70 (m, 2 H), 3.95 (s, 2 H), 5.37 (s, 2 H), 7.08-7.83 (m, 13 H)

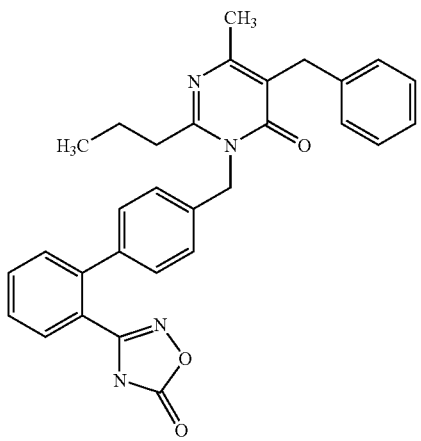

287c) 5-benzyl-6-methyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (1.20 g), sodium hydrogen carbonate (1.80 g) and dimethyl sulfoxide (10 mL) was stirred at 40° C. for 30 min, 4'-[(5-benzyl-4-methyl-6-oxo-2-propylpyrimidin-1(6H)-yl)methyl]biphenyl-2-carbonitrile (0.93 g) was added, and the mixture was stirred at 90° C. for 18 hr. The reaction mixture was allowed to cool to room temperature, ethyl acetate and water were added to the reaction mixture, and the aqueous layer was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.38 g) and then 1,8-diazabicyclo[5.4.0]undec-7-ene (0.36 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.59 g, 56%).

$^1$H NMR (300 MHz, CDCl$_3$) δ 0.95 (t, J=7.3, 3 H), 1.59-1.81 (m, 2 H), 2.27 (s, 3 H), 2.50-2.67 (m, 2 H), 3.79 (s, 2 H), 5.23 (s, 2 H), 7.08-7.75 (m, 13 H), 9.18 (s, 1 H)

5-Benzyl-6-methyl-3-{[2'-(5-oxo-4,5-dihydro-1,2,4-oxadiazol-3-yl)biphenyl-4-yl]methyl}-2-propylpyrimidin-4(3H)-one obtained above is subjected to a conventional method of salt formation to give the following salts.

5-benzyl-6-methyl-3-{[2'-(5-oxo-4,5-dihydro-1,2,4-oxadiazol-3-yl)biphenyl-4-yl]methyl}-2-propylpyrimidin-4(3H)-one sodium salt 5-benzyl-6-methyl-3-{[2'-(5-oxo-4,5-dihydro-1,2,4-oxadiazol-3-yl)biphenyl-4-yl]methyl}-2-propylpyrimidin-4(3H)-one potassium salt 5-benzyl-6-methyl-3-{[2'-(5-oxo-4,5-dihydro-1,2,4-oxadiazol-3-yl)biphenyl-4-yl]methyl}-2-propylpyrimidin-4(3H)-one 0.5 calcium salt 5-benzyl-6-methyl-3-{[2'-(5-oxo-4,5-dihydro-1,2,4-oxadiazol-3-yl)biphenyl-4-yl]methyl}-2-propylpyrimidin-4(3H)-one hydrochloride 5-benzyl-6-methyl-3-{[2'-(5-oxo-4,5-dihydro-1,2,4-oxadiazol-3-yl)biphenyl-4-yl]methyl}-2-propylpyrimidin-4(3H)-one hydrobromide Example 288

6-methyl-3-{[2'-(5-oxo-4,5-dihydro-1,2,4-oxadiazol-3-yl)biphenyl-4-yl]methyl}-5-phenyl-2-propylpyrimidin-4(3H)-one

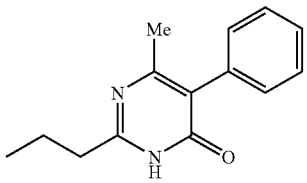

288a) 6-methyl-5-phenyl-2-propylpyrimidin-4(3H)-one

To a solution of ethyl 3-oxo-2-phenylbutanoate (2.28 g) and butanimidamide hydrochloride (2.04 g) in N,N-dimethylformamide (30 mL) was added 1,8-diazabicyclo[5.4.0]undec-7-ene (5.0 mL), and the mixture was stirred at 100° C. for 15 hr. Ethyl acetate and water were added to the reaction mixture, and the aqueous layer was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.26 g, 10%).

$^1$H NMR (300 MHz, CDCl$_3$) δ 0.72-1.20 (m, 3 H), 1.71-1.86 (m, 2 H), 2.22 (s, 3 H), 2.52-2.63 (m, 2 H), 7.27-7.48 (m, 5H), 12.06 (s, 1 H)

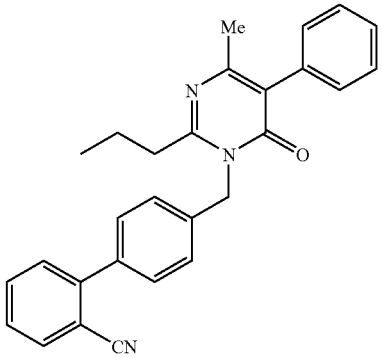

288b) 4'-[(4-methyl-6-oxo-5-phenyl-2-propylpyrimidin-1(6H)-yl)methyl]biphenyl-2-carbonitrile To a solution of 6-methyl-5-phenyl-2-propylpyrimidin-4(3H)-one (0.26 g) and 4'-(bromomethyl)biphenyl-2-carbonitrile (0.37 g) in N,N-dimethylformamide (6 mL) was added 60% sodium hydride (0.06 g), and the mixture was stirred at room temperature for 3 hr. Ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.30 g, 62%).

$^1$H NMR (300 MHz, CDCl$_3$) δ 1.02 (t, J=7.3, 3 H), 1.65-1.93 (m, 2 H), 2.23 (s, 3 H), 2.63-2.81 (m, 2 H), 5.39 (br s, 2H), 7.27-7.85 (m, 13 H)

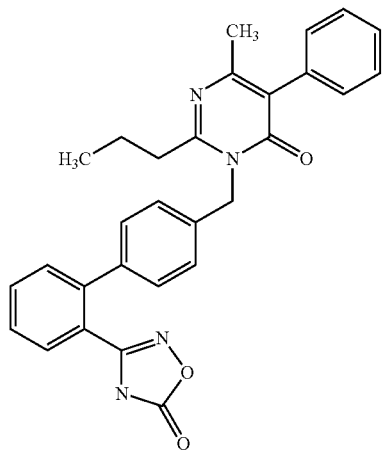

288c) 6-methyl-3-{[2'-(5-oxo-4,5-dihydro-1,2,4-oxadiazol-3-yl)biphenyl-4-yl]methyl}-5-phenyl-2-propylpyrimidin-4(3H)-one A mixture of hydroxylammonium chloride (0.39 g), sodium hydrogen carbonate (0.59 g) and dimethyl sulfoxide (4 mL) was stirred at 40° C. for 30 min, 4'-[(4-methyl-6-oxo-5-phenyl-2-propylpyrimidin-1(6H)-yl)methyl]biphenyl-2-carbonitrile (0.30 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (5 mL). N,N'-carbonyldiimidazole (0.14 g) and then 1,8-diazabicyclo[5.4.0]undec-7-ene (0.13 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.19 g, 55%).

$^1$H NMR (300 MHz, CDCl$_3$) δ 1.02 (t, J=7.3, 3 H), 1.71-1.86 (m, 2 H), 2.17 (s, 3 H), 2.66-2.77 (m, 2 H), 5.25 (s, 2 H), 7.17-7.74 (m, 13 H), 8.75 (s, 1 H)

Example 289

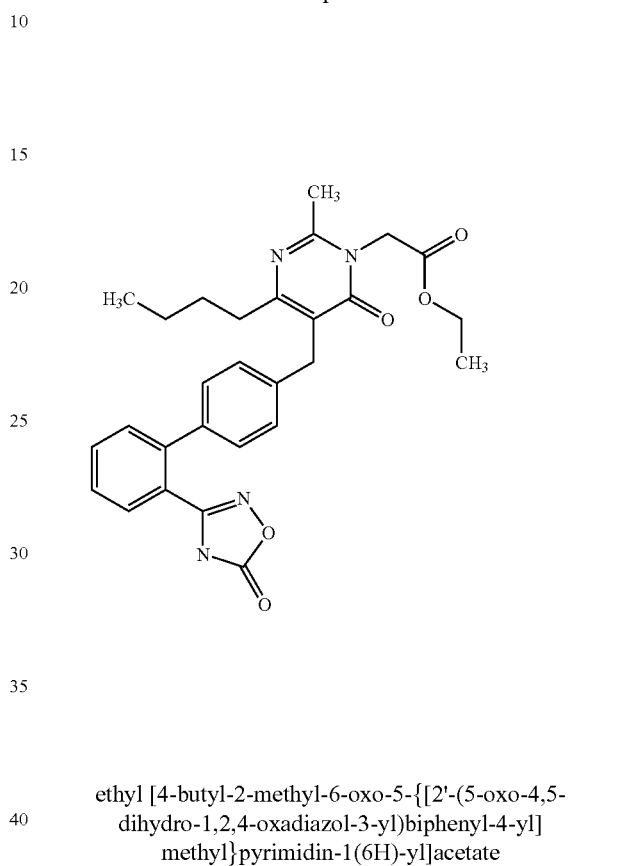

ethyl [4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]acetate A mixture of hydroxylammonium chloride (1.20 g), sodium hydrogen carbonate (1.90 g) and dimethyl sulfoxide (20 mL) was stirred at 40° C. for 30 min, ethyl [4-butyl-5-[(2'-cyanobiphenyl-4-yl)methyl]-2-methyl-6-oxopyrimidin-1(6H)-yl]acetate (0.50 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL). N,N'-carbonyldiimidazole (0.27 g) and then 1,8-diazabicyclo[5.4.0]undec-7-ene (0.25 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.29 g, 51%).

$^1$H NMR (300 MHz, CDCl$_3$) δ 0.94 (3H, t, J=7.5), 1.29 (3H, t, J=7.2), 1.34-1.48 (2H, m), 1.58-1.74 (2H, m), 2.45 (3H, s), 2.56-2.68 (2H, m), 3.92 (2H, s), 4.24 (2H, q, J=7.2), 4.74 (2H, s), 7.18-7.32 (4H, m), 7.36-7.42 (1H, m), 7.44-7.51 (1H, m), 7.55-7.62 (1H, m), 7.84-7.90 (1H, m)

Example 290

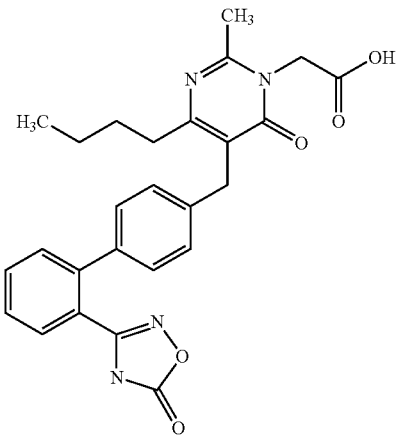

[4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]acetic acid A mixture of ethyl [4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]acetate (0.25 g), 1 M aqueous sodium hydroxide solution (1.2 mL), tetrahydrofuran (3 mL) and ethanol (3 mL) was stirred at room temperature for 3 hr. 1 M hydrochloric acid (1.2 mL) was added to the reaction solution, and the mixture was stirred for 10 min. The reaction mixture was diluted with ethyl acetate, washed with saturated brine, and dried over anhydrous magnesium sulfate. The solvent was evaporated under reduced pressure to give the title compound as colorless crystals (0.22 g, 92%).

$^1$H NMR (300 MHz, CDCl$_3$) δ 0.94 (3H, t, J=7.5), 1.34-1.48 (2H, m), 1.58-1.74 (2H, m), 2.50 (3H, s), 2.64-2.72 (2H, m), 3.83 (2H, s), 4.56 (2H, s), 7.15-7.28 (4H, m), 7.44-7.52 (2H, m), 7.58-7.66 (1H, m), 7.79-7.85 (1H, m)

Example 291

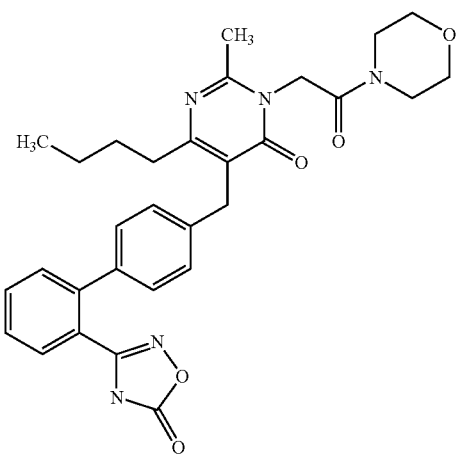

6-butyl-2-methyl-3-(2-morpholin-4-yl-2-oxoethyl)-5-{[2'-(5-oxo-4,5-dihydro-1,2,4-oxadiazol-3-yl)biphenyl-4-yl]methyl}pyrimidin-4(3H)-one A mixture of [4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]acetic acid (0.12 g), morpholine (0.033 g), 1-hydroxybenzotriazole (0.035 g), 1-ethyl-3-(3-dimethylaminopropyl)carbodiimide hydrochloride (0.05 g) and N,N-dimethylformamide (3 mL) was stirred at room temperature for 15 hr. The reaction mixture was diluted with ethyl acetate, washed with diluted hydrochloric acid and then with saturated brine, and dried over anhydrous magnesium sulfate. The solvent was evaporated under reduced pressure and the residue was purified by silica gel column chromatography to give the title compound as colorless crystals (0.080 g, 59%).

$^1$H NMR (300 MHz, CDCl$_3$) δ 0.94 (3H, t, J=7.5), 1.36-1.52 (2H, m), 1.56-1.70 (2H, m), 2.63 (3H, s), 2.66-2.76 (2H, m), 3.54-3.80 (8H, m), 3.89 (2H, s), 4.88 (2H, s), 7.17-7.28 (4H, m), 7.37-7.52 (2H, m), 7.55-7.63 (1H, m), 7.75-7.82 (1H, m)

Example 292

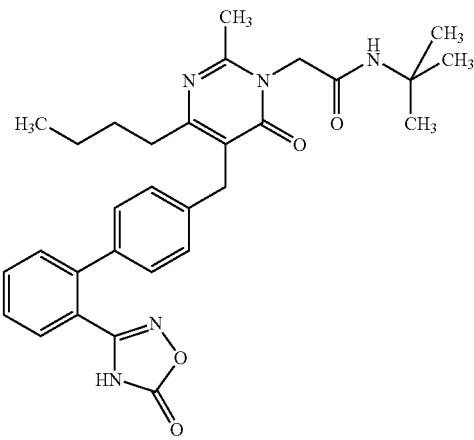

N-(tert-butyl)-2-[4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]acetamide A mixture of [4-butyl-2-methyl-6-oxo-5-{[2'-(5-oxo-4,5-dihydro-1,2,4-oxadiazol-3-yl)biphenyl-4-yl]methyl}pyrimidin-1(6H)-yl]acetic acid (0.10 g), tert-butylamine (0.02 g), 1-hydroxybenzotriazole (0.03 g), 1-ethyl-3-(3-dimethylaminopropyl)carbodiimide hydrochloride (0.044 g) and N,N-dimethylformamide (3 mL) was stirred at room temperature for 15 hr. The reaction mixture was diluted with ethyl acetate, washed with diluted hydrochloric acid and then with saturated brine, and dried over anhydrous magnesium sulfate. The solvent was evaporated under reduced pressure and the residue was purified by silica gel column chromatography to give the title compound as colorless crystals (0.074 g, 66%).

$^1$H NMR (300 MHz, CDCl$_3$) δ 0.93 (3H, t, J=7.5), 1.33 (9H, s), 1.36-1.48 (2H, m), 1.52-1.70 (2H, m), 2.66-2.76 (5H, m), 3.88 (2H, s), 4.58 (2H, s), 6.37 (1H, s), 7.14-7.26 (4H, m), 7.36-7.52 (2H, m), 7.55-7.63 (1H, m), 7.75-7.80 (1H, m)

Example 293

3-[4-(2-methoxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

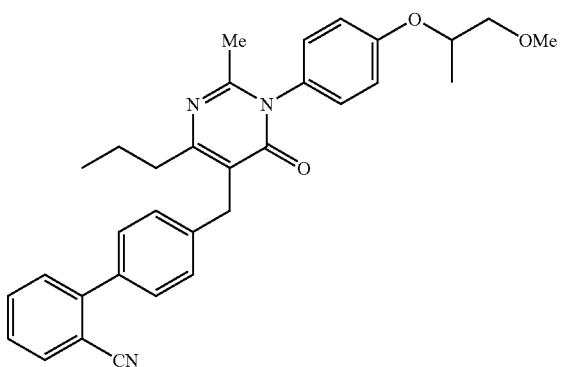

293a) 4'-({1-[4-(2-methoxy-1-methylethoxy)phenyl]-2-methyl-6-oxo-4-propyl-1,6-dihydropyrimidin-5-yl}methyl)biphenyl-2-carbonitrile To a solution of 4'-({1-[4-(2-hydroxy-1-methylethoxy)phenyl]-2-methyl-6-oxo-4-propyl-1,6-dihydropyrimidin-5-yl}methyl)biphenyl-2-carbonitrile (0.70 g) in N,N-dimethylformamide (7 mL) were added 60% sodium hydride (0.07 g) and then methyl iodide (0.18 mL) at 0° C., and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow viscous substance (0.53 g, 74%).

$^1$H NMR (300 MHz, CDCl$_3$) δ 1.01 (t, J=7.3, 3 H), 1.33 (d, J=6.4, 3 H), 1.61-1.78 (m, 2 H), 2.17 (s, 3 H), 2.59-2.71 (m, 2 H), 3.42 (s, 3 H), 3.46-3.65 (m, 2 H), 3.97 (s, 2 H), 4.50-4.63 (m, 1 H), 7.01-7.78 (m, 12 H)

293b) 3-[4-(2-methoxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.88 g), sodium hydrogen carbonate (1.32 g) and dimethyl sulfoxide (5 mL) was stirred at 40° C. for 30 min, 4'-({1-[4-(2-methoxy-1-methylethoxy)phenyl]-2-methyl-6-oxo-4-propyl-1,6-dihydropyrimidin-5-yl}methyl)biphenyl-2-carbonitrile (0.52 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (5 mL). N,N'-carbonyldiimidazole (0.22 g) and then 1,8-diazabicyclo[5.4.0]undec-7-ene (0.20 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.36 g, 41%).

$^1$H NMR (300 MHz, DMSO-d$_6$) δ 0.89 (t, J=7.3, 3 H), 1.25 (d, J=6.2, 3 H), 1.46-1.61 (m, 2 H), 2.07 (s, 3 H), 2.47-2.53 (m, 2 H), 3.30 (s, 3 H), 3.42-3.56 (m, 2 H), 3.86 (s, 2 H), 4.62-4.74 (m, 1 H), 7.02-7.73 (m, 12 H), 12.38 (s, 1 H)

3-[4-(2-Methoxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one obtained above is subjected to a conventional method of salt formation to give the following salts.

3-[4-(2-methoxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one sodium salt 3-[4-(2-methoxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-[4-(2-methoxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one 0.5 calcium salt 3-[4-(2-methoxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrochloride 3-[4-(2-methoxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one hydrobromide

Example 294

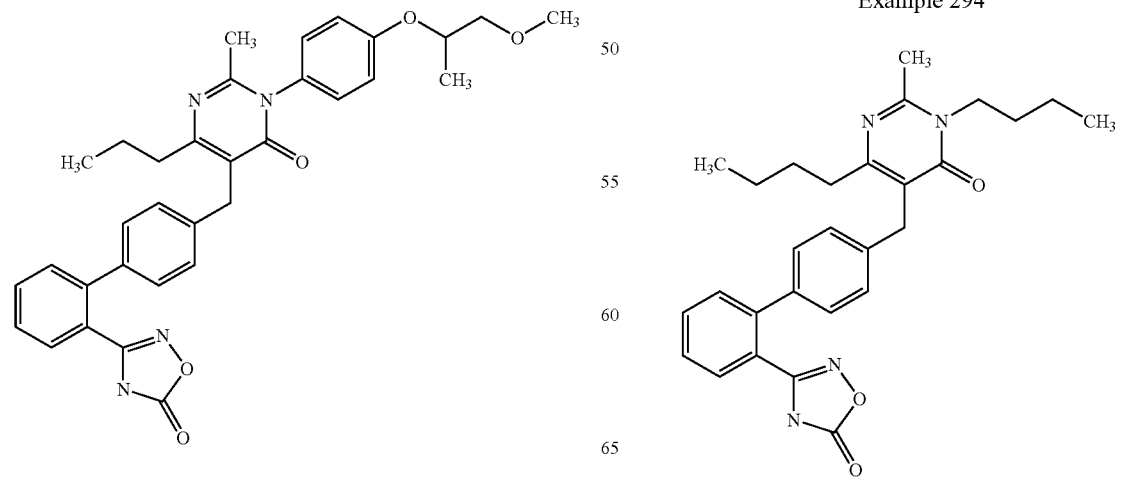

3,6-dibutyl-2-methyl-5-{[2'-(5-oxo-4,5-dihydro-1,2,
4-oxadiazol-3-yl)biphenyl-4-yl]methyl}pyrimidin-4
(3H)-one A mixture of 4'-[(4-butyl-2-methyl-6-oxo-1,6-dihydropyrimidin-5-yl)methyl]biphenyl-2-carbonitrile (1 g), sodium hydride (0.17 g) and N,N-dimethylformamide (10 mL) was stirred at room temperature for 10 min, 1-iodobutane (0.64 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL) and added to a mixture of hydroxylammonium chloride (1.27 g), sodium hydrogen carbonate (2.05 g) and dimethyl sulfoxide (10 mL), which had been mixed at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure and the residue was dissolved in tetrahydrofuran (20 mL). N,N'-carbonyldiimidazole (0.24 g) and then 1,8-diazabicyclo[5.4.0]undec-7-ene (0.20 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.24 g, 42%).

$^1$H NMR (300 MHz, DMSO-d$_6$) δ 0.82 (3H, t, J=7.3), 0.92 (3H, t, J=7.3), 1.18-1.48 (6H, m), 1.51-1.66 (2H, m), 2.41-2.50 (5H, m), 3.84 (2H, s), 3.88-4.00 (2H, m), 7.13-7.30 (4H, m), 7.44-7.59 (2H, m), 7.63-7.72 (2H, m), 12.38 (1H, s)

3,6-Dibutyl-2-methyl-5-{[2'-(5-oxo-4,5-dihydro-1,2,4-oxadiazol-3-yl)biphenyl-4-yl]methyl}pyrimidin-4(3H)-one obtained above is subjected to a conventional method of salt formation to give the following salts.

3,6-dibutyl-2-methyl-5-{[2'-(5-oxo-4,5-dihydro-1,2,4-oxadiazol-3-yl)biphenyl-4-yl]methyl}pyrimidin-4(3H)-one sodium salt 3,6-dibutyl-2-methyl-5-{[2'-(5-oxo-4,5-dihydro-1,2,4-oxadiazol-3-yl)biphenyl-4-yl]methyl}pyrimidin-4(3H)-one potassium salt 3,6-dibutyl-2-methyl-5-{[2'-(5-oxo-4,5-dihydro-1,2,4-oxadiazol-3-yl)biphenyl-4-yl]methyl}pyrimidin-4(3H)-one 0.5 calcium salt 3,6-dibutyl-2-methyl-5-{[2'-(5-oxo-4,5-dihydro-1,2,4-oxadiazol-3-yl)biphenyl-4-yl]methyl}pyrimidin-4(3H)-one hydrochloride 3,6-dibutyl-2-methyl-5-{[2'-(5-oxo-4,5-dihydro-1,2,4-oxadiazol-3-yl)biphenyl-4-yl]methyl}pyrimidin-4(3H)-one hydrobromide Example 295

6-butyl-3-(2-cyclohexyl-2-hydroxyethyl)-2-methyl-5-{[2'-(5-oxo-4,5-dihydro-1,2,4-oxadiazol-3-yl)biphenyl-4-yl]methyl}pyrimidin-4(3H)-one

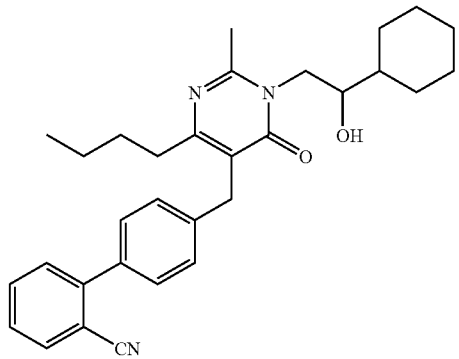

295a) 4'-{[4-butyl-1-(2-cyclohexyl-2-hydroxyethyl)-2-methyl-6-oxo-1,6-dihydropyrimidin-5-yl]methyl}biphenyl-2-carbonitrile To a mixture of cyclohexanecarbaldehyde (1.6 g), diiodomethane (1.39 mL) and tetrahydrofuran (40 mL) was added methyllithium (2.1 M diethyl ether solution, 13.9 mL) at 0° C. The reaction mixture was stirred at room temperature for 4 hr, and extracted with saturated aqueous ammonium chloride solution and diethyl ether. The diethyl ether layer was washed with saturated brine and dried over anhydrous magnesium sulfate. The solvent was evaporated under reduced pressure. The obtained oil was dissolved in N,N-dimethylformamide (15 mL), 4'-[(4-butyl-2-methyl-6-oxo-1,6-dihydropyrimidin-5-yl)methyl]biphenyl-2-carbonitrile (2.0 g) and potassium carbonate (1.5 g) were added, and the mixture was stirred at 90° C. for 24 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (1.75 g, 65%).

$^1$H NMR (300 MHz, CDCl$_3$) δ 0.90 (3H, t, J=7.3), 1.10-1.92 (14H, m), 2.52-2.63 (5H, m), 3.07 (1H, d, J=4.9), 3.71-3.83 (1H, m), 3.92-4.09 (3H, m), 4.13-4.27 (1H, m), 7.29-7.52 (6H, m), 7.58-7.66 (1H, m), 7.74 (1H, d, J=7.7)

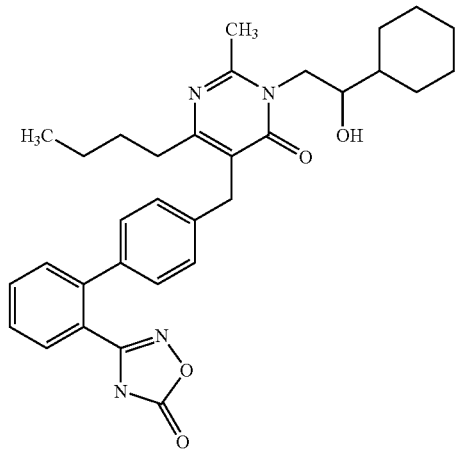

295b) 6-butyl-3-(2-cyclohexyl-2-hydroxyethyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (3.80 g), sodium hydrogen carbonate (6.08 g) and dimethyl sulfoxide (30 mL) was stirred at 40° C. for 30 min, 4'-{[4-butyl-1-(2-cyclohexyl-2-hydroxyethyl)-2-methyl-6-oxo-1,6-dihydropyrimidin-5-yl]methyl}biphenyl-2-carbonitrile (1.75 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (40 mL). N,N'-carbonyldiimidazole (0.7 g) and then 1,8-diazabicyclo[5.4.0]undec-7-ene (0.6 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.51 g, 26%).

$^1$H NMR (300 MHz, DMSO-$d_6$) δ 0.83 (3H, t, J=7.2), 1.09-1.52 (10H, m), 1.55-1.88 (5H, m), 2.41-2.47 (2H, m), 2.53 (3H, s), 3.50-3.70 (2H, m), 3.84 (2H, dd, J=23.6, 15.3), 4.18 (1H, d, J=11.9), 4.91 (1H, d, J=5.5), 7.17-7.30 (4H, m), 7.41-7.60 (2H, m), 7.60-7.76 (2H, m), 12.38 (1H, s)

Example 296

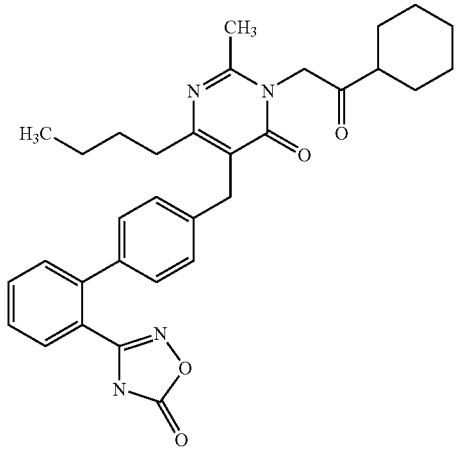

6-butyl-3-(2-cyclohexyl-2-oxoethyl)-2-methyl-5-{[2'-(5-oxo-4,5-dihydro-1,2,4-oxadiazol-3-yl)biphenyl-4-yl]methyl}pyrimidin-4(3H)-one A mixture of 6-butyl-3-(2-cyclohexyl-2-hydroxyethyl)-2-methyl-5-{[2'-(5-oxo-4,5-dihydro-1,2,4-oxadiazol-3-yl)biphenyl-4-yl]methyl}pyrimidin-4(3H)-one (0.3 g), 1,1,1-tris(acetyloxy)-1,1-dihydro-1,2-benziodoxol-3(1H)-one (0.35 g) and methylene chloride (15 mL) was stirred at room temperature for 2 hr. Saturated aqueous sodium hydrogen carbonate solution and sodium thiosulfate were added to the reaction mixture, and the mixture was stirred at room temperature for 2 hr and extracted with chloroform. The chloroform layer was washed with saturated brine, and dried over anhydrous magnesium sulfate. The solvent was evaporated under reduced pressure. The obtained residue was purified by silica gel column chromatography to give the title compound as colorless crystals (0.22 g, 74%).

$^1$H NMR (300 MHz, DMSO-$d_6$) δ 0.83 (3H, t, J=7.3), 1.13-1.37 (7H, m), 1.35-1.55 (2H, m), 1.58-1.78 (3H, m), 1.83-1.97 (2H, m), 2.27 (3H, s), 2.42-2.49 (2H, m), 2.57-2.71 (1H, m), 3.83 (2H, s), 5.07 (2H, s), 7.20 (4H, s), 7.42-7.60 (2H, m), 7.62-7.75 (2H, m), 12.38 (1H, s)

Example 297

6-butyl-3-(2-hydroxy-2-methylpropyl)-2-methyl-5-{[2'-(5-oxo-4,5-dihydro-1,2,4-oxadiazol-3-yl)biphenyl-4-yl]methyl}pyrimidin-4(3H)-one

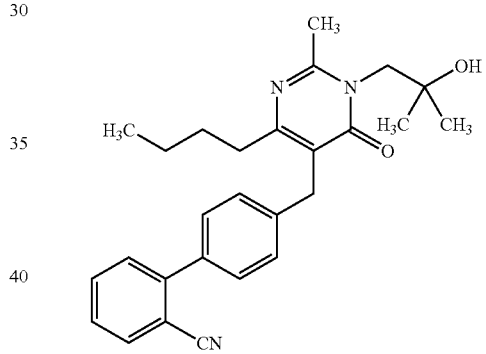

297a) 4'-{[4-butyl-1-(2-hydroxy-2-methylpropyl)-2-methyl-6-oxo-1,6-dihydropyrimidin-5-yl]methyl}biphenyl-2-carbonitrile A mixture of 4'-[(4-butyl-2-methyl-6-oxo-1,6-dihydropyrimidin-5-yl)methyl]biphenyl-2-carbonitrile (1 g), 2,2-dimethyloxirane (2.5 mL), cesium carbonate (1.83 g) and N,N-dimethylacetamide (10 mL) was stirred at 100° C. for 24 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.92 g, 76%).

$^1$H NMR (300 MHz, CDCl$_3$) δ 0.91 (3H, t, J=7.3), 1.29 (6H, s), 1.32-1.44 (2H, m), 1.50-1.60 (2H, m), 2.53-2.65 (5H, m), 3.97 (2H, s), 4.17 (2H, s), 4.35 (1H, s), 7.30-7.37 (2H, m), 7.37-7.51 (4H, m), 7.57-7.67 (1H, m), 7.74 (1H, dd, J=7.7, 0.9)

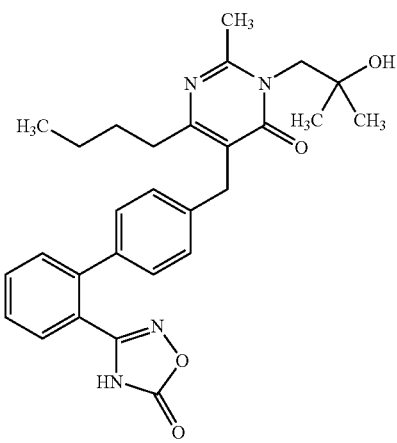

297b) 6-butyl-3-(2-hydroxy-2-methylpropyl)-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (2.23 g), sodium hydrogen carbonate (3.60 g) and dimethyl sulfoxide (15 mL) was stirred at 40° C. for 30 min, 4'-{[4-butyl-1-(2-hydroxy-2-methylpropyl)-2-methyl-6-oxo-1,6-dihydropyrimidin-5-yl]methyl}biphenyl-2-carbonitrile (0.92 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL). N,N'-carbonyldiimidazole (0.42 g) and then 1,8-diazabicyclo[5.4.0]undec-7-ene (0.35 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.25 g, 24%).

$^1$H NMR (300 MHz, DMSO-$d_6$) δ 0.83 (3H, t, J=7.4), 1.13 (6H, s), 1.20-1.35 (2H, m), 1.38-1.50 (2H, m), 2.40-2.48 (2H, m), 2.61 (3H, s), 3.85 (2H, s), 4.05 (2H, br), 4.83 (1H, s), 7.13-7.27 (4H, m), 7.44-7.58 (2H, m), 7.60-7.75 (2H, m), 12.37 (1H, s)

Example 298

3-{[5-(hydroxymethyl)pyridin-2-yl]methyl}-2-methyl-5-{[2'-(5-oxo-4,5-dihydro-1,2,4-oxadiazol-3-yl)biphenyl-4-yl]methyl}-6-propylpyrimidin-4(3H)-one

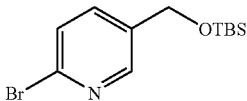

298a) 2-bromo-5-({[tert-butyl(dimethyl)silyl]oxy}methyl)pyridine

To a mixture of 6-bromonicotinaldehyde (10 g) and methanol (100 mL) was added sodium borohydride (2.44 g) at 0° C., and the reaction mixture was stirred at room temperature for 2 hr. The solvent was evaporated under reduced pressure, and the obtained residue was extracted with saturated aqueous ammonium chloride solution and ethyl acetate. The ethyl acetate layer was washed with saturated brine, and dried over anhydrous magnesium sulfate. The solvent was evaporated under reduced pressure. The obtained residue was dissolved in dichloromethane (50 mL), tert-butyldimethylsilylchloride (8.92 g), triethylamine (8.25 mL) and 4-dimethylaminopyridine (0.33 g) were added, and the mixture was stirred at room temperature for 2 hr. The reaction mixture was washed with water and then with saturated brine, and dried over anhydrous magnesium sulfate. The solvent was evaporated under reduced pressure and the residue was purified by silica gel column chromatography to give the title compound as a colorless oil (11 g, 64%).

$^1$H NMR (300 MHz, CDCl$_3$) δ 0.11 (6H, s), 0.93 (9H, s), 4.71 (2H, s), 7.42-7.58 (2H, m), 8.32 (1H, s)

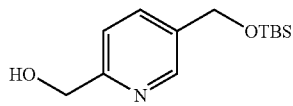

298b) [5-({[tert-butyl(dimethyl)silyl]oxy}methyl)pyridin-2-yl]methanol

To a mixture of 2-bromo-5-({[tert-butyl(dimethyl)silyl]oxy}methyl)pyridine (11 g) and tetrahydrofuran (450 mL) was added n-butyllithium (1.6 M hexane solution, 25.3 mL) at −78° C., and the reaction mixture was stirred for 1 hr. Then, N,N-dimethylformamide (3.17 mL) was added at −78° C., and the temperature of the mixture was raised to room temperature and stirred for 16 hr. The reaction mixture was diluted with diethyl ether, washed with saturated brine, and dried over anhydrous magnesium sulfate. The solvent was evaporated under reduced pressure. The obtained residue was dissolved in methanol (200 mL), sodium borohydride (1.95 g) was added at 0° C., and the reaction mixture was stirred at room temperature for 2 hr. The solvent was evaporated under reduced pressure, and the obtained residue was extracted with saturated aqueous ammonium chloride solution and ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (7.53 g, 64%).

$^1$H NMR (300 MHz, CDCl$_3$) δ 0.11 (6H, s), 0.92 (9H, s), 4.75 (4H, s), 7.15-7.37 (1H, m), 7.50-7.77 (1H, m), 8.50 (1H, s)

583

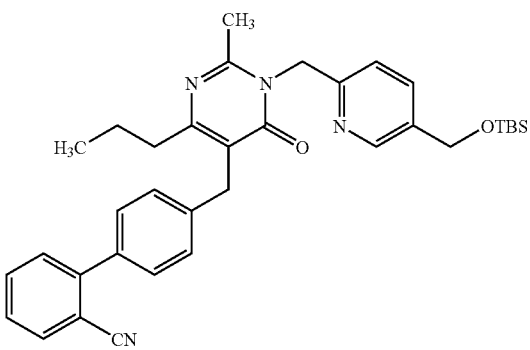

298c) 4'-[(1-{[5-({[tert-butyl(dimethyl)silyl]oxy}methyl)pyridin-2-yl]methyl}-2-methyl-6-oxo-4-propyl-1,6-dihydropyrimidin-5-yl)methyl]biphenyl-2-carbonitrile A mixture of 4'-[(2-methyl-6-oxo-4-propyl-1,6-dihydropyrimidin-5-yl)methyl]biphenyl-2-carbonitrile (0.6 g), 1,1'-(azodicarbonyl)dipiperidine (0.48 g), tributylphosphine (0.95 g), [5-({[tert-butyl(dimethyl)silyl]oxy}methyl)pyridin-2-yl]methanol (0.48 g) and tetrahydrofuran (50 mL) was stirred at room temperature for 4 hr. The reaction mixture was concentrated, and the residue was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.54 g, 49%).
$^1$H NMR (300 MHz, CDCl$_3$) δ 0.09 (6H, s), 0.89-1.01 (12H, m), 1.54-1.70 (2H, m), 2.52-2.63 (5H, m), 3.98 (2H, s), 4.73 (2H, s), 5.36 (2H, s), 7.21-7.28 (1H, m), 7.34-7.50 (6H, m), 7.59-7.66 (2H, m), 7.74 (1H, d, J=6.8), 8.48 (1H, s)

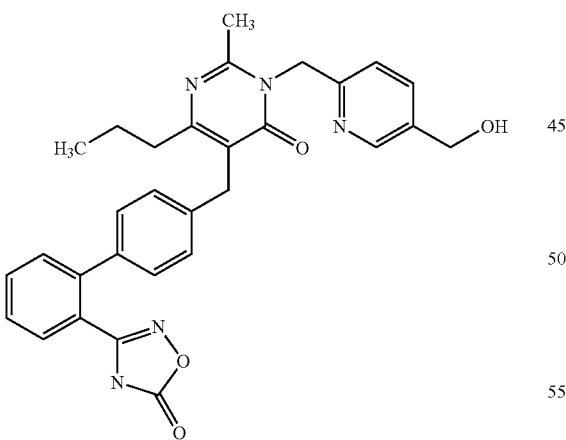

298d) 3-{[5-(hydroxymethyl)pyridin-2-yl]methyl}-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.97 g), sodium hydrogen carbonate (1.56 g) and dimethyl sulfoxide (15 mL) was stirred at 40° C. for 30 min, 4'-[(1-{[5-({[tert-butyl(dimethyl)silyl]oxy}methyl)pyridin-2-yl]methyl}-2-methyl-6-oxo-4-propyl-1,6-dihydropyrimidin-5-yl)methyl]biphenyl-2-carbonitrile (0.54 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL). N,N'-carbonyldiimidazole (0.18 g) and then 1,8-diazabicyclo[5.4.0]undec-7-ene (0.15 mL) were added, and the mixture was stirred at room temperature for 2 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure. The residue was dissolved in tetrahydrofuran (20 mL), tetrabutylammonium fluoride (1.0 M tetrahydrofuran solution, 2.7 mL) was added, and the mixture was stirred at room temperature for 3 hr. The reaction mixture was adjusted to pH 5 with water and 1 M hydrochloric acid, and extracted with ethyl acetate. The ethyl acetate layer was washed with saturated brine, and dried over anhydrous magnesium sulfate. The solvent was evaporated under reduced pressure and the residue was purified by silica gel column chromatography to give the title compound as colorless crystals (0.27 g, 56%).
$^1$H NMR (300 MHz, DMSO-d$_6$) δ 0.85 (3H, t, J=7.4), 1.43-1.62 (2H, m), 2.43-2.51 (5H, m), 3.85 (2H, s), 4.49 (2H, s), 5.24-5.36 (3H, m), 7.14-7.27 (4H, m), 7.30 (1H, d, J=8.0), 7.44-7.56 (2H, m), 7.60-7.77 (3H, m), 8.41 (1H, s), 12.37 (1H, s)

Example 299

3-(2,3-dihydro-1-benzofuran-5-yl)-6-ethoxy-2-methyl-5-{[2'-(5-oxo-4,5-dihydro-1,2,4-oxadiazol-3-yl)biphenyl-4-yl]methyl}pyrimidin-4(3H)-one

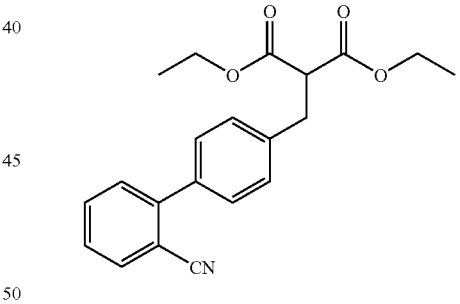

299a) diethyl [(2'-cyanobiphenyl-4-yl)methyl]malonate

To a mixture of sodium hydride (2.86 g) and tetrahydrofuran (250 mL) were added a solution of diethyl malonate (16.7 mL) in tetrahydrofuran (100 mL) and then 4'-(bromomethyl)biphenyl-2-carbonitrile (15 g), and the mixture was stirred at room temperature for 16 hr. The reaction mixture was concentrated under reduced pressure, and the obtained residue was extracted with 5% aqueous potassium hydrogen sulfate solution and ethyl acetate. The ethyl acetate layer was washed with saturated brine, and dried over anhydrous magnesium sulfate. The solvent was evaporated under reduced pressure and the residue was purified by silica gel column chromatography to give the title compound as a colorless oil (18.3 g, 95%).

¹H NMR (300 MHz, CDCl₃) δ 1.23 (6H, t, J=7.2), 3.28 (2H, d, J=7.6), 3.70 (1H, s), 4.18 (4H, q, J=7.2), 7.34 (2H, d, J=8.3), 7.41-7.54 (4H, m), 7.63 (1H, s), 7.75 (1H, d, J=7.6)

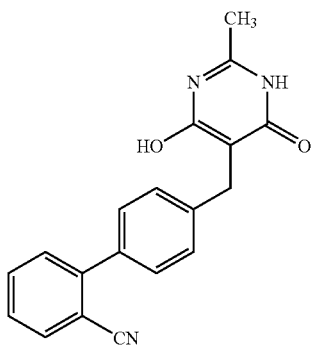

299b) 4'-[(4-hydroxy-2-methyl-6-oxo-1,6-dihydro-pyrimidin-5-yl)methyl]biphenyl-2-carbonitrile To a solution of acetamidine hydrochloride (2.68 g) in ethanol (30 mL) were added sodium ethoxide (20% ethanol solution, 14.5 g) and then a solution of diethyl [(2'-cyanobiphenyl-4-yl)methyl]malonate in ethanol (30 mL)-1,4-dioxane (15 mL) at 0° C., and the reaction mixture was stirred at room temperature for 16 hr. The reaction mixture was concentrated, and the residue was adjusted to pH 5 with water (50 mL) and 50% aqueous acetic acid solution. The obtained crystallized product was collected by filtration and washed with water to give the title compound as colorless crystals (1.8 g, 40%).

¹H NMR (300 MHz, DMSO-d₆) δ 2.23 (3H, s), 3.62 (2H, s), 7.27-7.49 (4H, m), 7.48-7.63 (2H, m), 7.77 (1H, t, J=7.6), 7.92 (1H, d, J=7.6), 11.56-12.08 (2H, m)

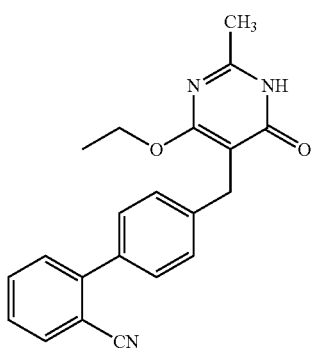

299c) 4'-[(4-ethoxy-2-methyl-6-oxo-1,6-dihydropyrimidin-5-yl)methyl]biphenyl-2-carbonitrile A mixture of 4'-[(4-hydroxy-2-methyl-6-oxo-1,6-dihydropyrimidin-5-yl)methyl]biphenyl-2-carbonitrile (1 g), cesium carbonate (3.01 g), diethyl sulfate (0.41 mL) and N,N-dimethylformamide (20 mL) was stirred at 0° C. for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.17 g, 16%).

¹H NMR (300 MHz, DMSO-d₆) δ 1.25 (3H, t, J=7.0), 2.27 (3H, s), 3.67 (2H, s), 4.31 (2H, q, J=7.2), 7.35 (2H, d, J=8.0), 7.39-7.49 (2H, m), 7.48-7.60 (2H, m), 7.72-7.81 (1H, m), 7.92 (1H, d, J=7.6), 12.35 (1H, s)

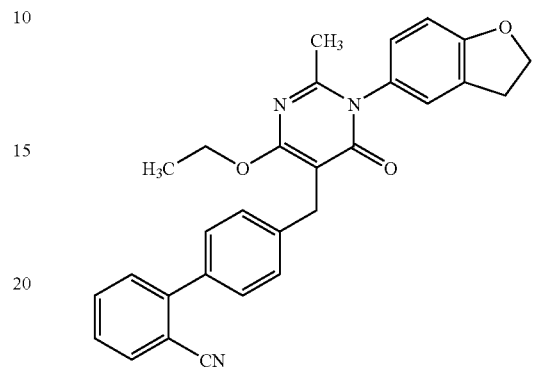

299d) 4'-{[1-(2,3-dihydro-1-benzofuran-5-yl)-4-ethoxy-2-methyl-6-oxo-1,6-dihydropyrimidin-5-yl]methyl}biphenyl-2-carbonitrile To a suspension of 4'-[(4-ethoxy-2-methyl-6-oxo-1,6-dihydropyrimidin-5-yl)methyl]biphenyl-2-carbonitrile (0.17 g), 2,3-dihydro-1-benzofuran-5-ylboronic acid (0.16 g), triethylamine (0.17 mL), pyridine (0.34 mL) and molecular sieves 4 A (0.34 g) in tetrahydrofuran (5 mL) was added copper(II) acetate (0.17 g), and the mixture was stirred for 1 day. The reaction mixture was diluted with ethyl acetate, the insoluble material was filtered off through celite, and the filtrate was concentrated. The residue was purified by silica gel column chromatography to give the title compound as a colorless solid (0.21 g, 92%).

¹H NMR (300 MHz, CDCl₃) δ 1.41 (3H, t, J=7.0), 2.17 (3H, s), 3.16-3.35 (2H, m), 3.84 (2H, s), 4.44 (2H, q, J=6.9), 4.63 (2H, t, J=8.9), 6.82-6.95 (2H, m), 7.01 (1H, s), 7.35-7.65 (7H, m), 7.74 (1H, d, J=8.0)

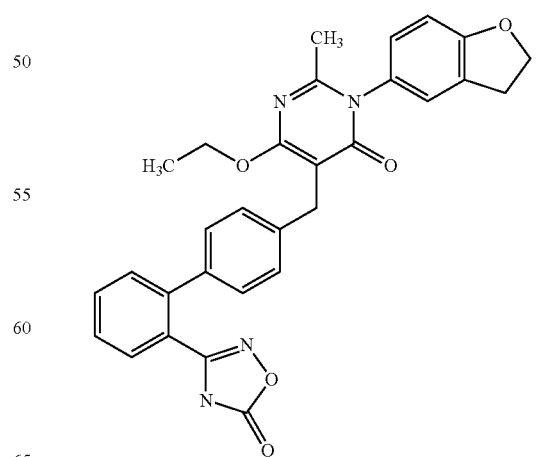

299e) 3-(2,3-dihydro-1-benzofuran-5-yl)-6-ethoxy-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (0.47 g), sodium hydrogen carbonate (0.76 g) and dimethyl sulfoxide (15 mL) was stirred at 40° C. for 30 min, 4'-{[1-(2,3-dihydro-1-benzofuran-5-yl)-4-ethoxy-2-methyl-6-oxo-1,6-dihydro-pyrimidin-5-yl]methyl}biphenyl-2-carbonitrile (0.21 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL). N,N'-carbonyldiimidazole (0.088 g) and then 1,8-diazabicyclo[5.4.0]undec-7-ene (0.074 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure, and the residue was purified by silica gel column chromatography to give the title compound as colorless crystals (0.083 g, 35%).

$^1$H NMR (300 MHz, DMSO-$d_6$) δ 1.29 (3H, t, J=7.1), 2.10 (3H, s), 3.22 (2H, t, J=8.7), 3.68 (2H, s), 4.37 (2H, q, J=7.0), 4.61 (2H, t, J=8.9), 6.86 (1H, d, J=8.5), 7.03 (1H, dd, J=8.5, 2.3), 7.17-7.24 (3H, m), 7.26-7.33 (2H, m), 7.47-7.58 (2H, m), 7.61-7.71 (2H, m), 12.39 (1H, s)

Example 300

5-(2,3-difluorobenzyl)-6-methyl-3-{[2'-(5-oxo-4,5-dihydro-1,2,4-oxadiazol-3-yl)biphenyl-4-yl]methyl}-2-propylpyrimidin-4(3H)-one

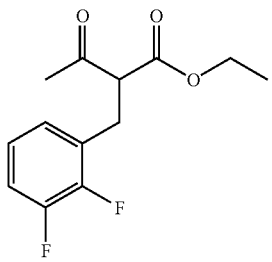

300a) ethyl 2-(2,3-difluorobenzyl)-3-oxobutyrate

A solution of 1-(bromomethyl)-2,3-difluorobenzene (1.6 g) and ethyl acetoacetate sodium salt (2.36 g) in tetrahydrofuran (20 mL) was stirred for 12 hr. The insoluble material was filtered off, and the filtrate was concentrated. The residue was purified by silica gel column chromatography to give the title compound (1.56 g, 79%) as a colorless viscous oil.

$^1$H NMR (300 MHz, CDCl$_3$) δ 1.29 (3H, t, J=7.2), 2.28 (3H, s), 3.21 (1H, t, J=7.2), 4.09-4.25 (4H, m), 6.90-7.13 (3H, m)

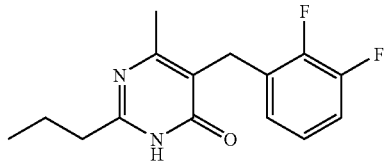

300b) 5-(2,3-difluorobenzyl)-6-methyl-2-propylpyrimidin-4(3H)-one

To a solution of ethyl 2-(2,3-difluorobenzyl)-3-oxobutyrate (1.56 g) and propylamidine hydrochloride (1.5 g) in methanol (10 mL) was added sodium methoxide (28% methanol solution, 3.53 mL), and the mixture was stirred for 12 hr. The reaction mixture was concentrated, and the residue was dissolved in water and diethyl ether. The aqueous layer was separated and weakly acidified with 1 M hydrochloric acid. The precipitate was collected by filtration and dried under reduced pressure to give the title compound (0.55 g, 22%) as colorless crystals.

$^1$H NMR (300 MHz, DMSO-$d_6$) δ 0.89 (3H, t, J=7.4), 1.59-1.73 (2H, m), 2.15 (3H, s), 2.40-2.48 (2H, m), 3.79 (2H, s), 6.89 (1H, t, J=7.2), 7.01-7.13 (1H, m), 7.17-7.33 (1H, m), 12.32 (1H, br)

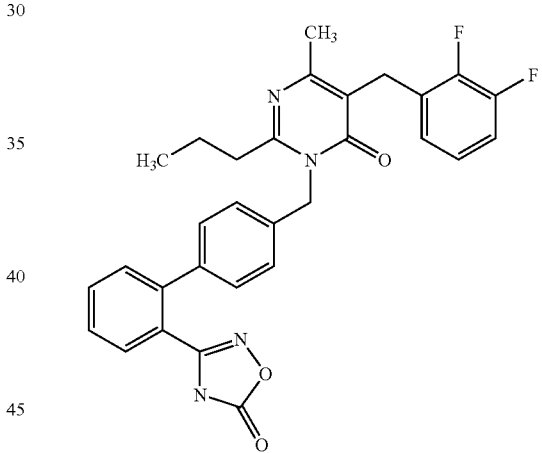

300c) 5-(2,3-difluorobenzyl)-6-methyl-3-{[2'-(5-oxo-4,5-dihydro-1,2,4-oxadiazol-3-yl)biphenyl-4-yl]methyl}-2-propylpyrimidin-4(3H)-one To a solution of 5-(2,3-difluorobenzyl)-6-methyl-2-propylpyrimidin-4(3H)-one (0.55 g) and 3-[4'-(bromomethyl)biphenyl-2-yl]-5-(trichloromethyl)-1,2,4-oxadiazole (1.03 g) in N,N-dimethylformamide (5 mL) was added cesium carbonate (0.44 g), and the mixture was stirred for 12 hr. The reaction mixture was diluted with ethyl acetate, washed with 1 M hydrochloric acid and saturated brine and dried over anhydrous sodium sulfate. The solvent was evaporated under reduced pressure. The residue was dissolved in acetone (10 mL), 1 M sodium hydroxide (2 mL) was added, and the mixture was stirred for 30 min. The reaction mixture was weakly acidified with 1 M hydrochloric acid, and extracted with ethyl acetate. The organic layer was washed with saturated brine and dried over anhydrous sodium sulfate. The solvent was evaporated under reduced pressure. The residue was purified by silica gel column chromatography to give the title compound (0.11 g, 20%) as a colorless solid.

$^1$H NMR (300 MHz, DMSO-$d_6$) δ 0.86 (3H, t, J=7.4), 1.47-1.70 (2H, m), 2.25 (3H, s), 2.62 (2H, t, J=7.4), 3.90 (2H, s), 5.33 (2H, s), 6.94 (1H, t, J=7.0), 7.02-7.40 (6H, m), 7.55 (2H, dd, J=17.4, 7.6), 7.63-7.77 (2H, m), 12.40 (1H, s)

Example 301

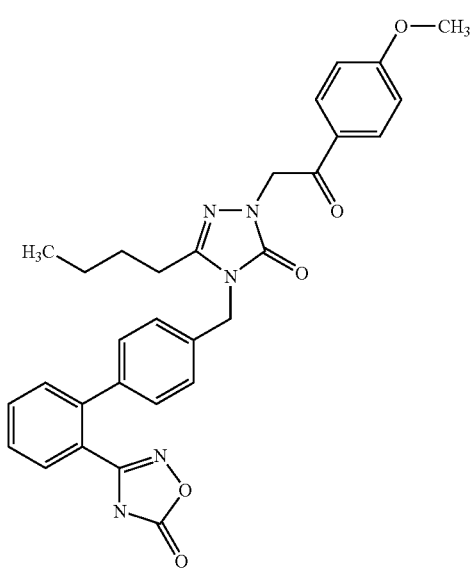

3-[4'-({3-butyl-1-[2-(4-methoxyphenyl)-2-oxoethyl]-5-oxo-1,5-dihydro-4H-1,2,4-triazol-4-yl}methyl)biphenyl-2-yl]-1,2,4-oxadiazol-5(4 H)-one A mixture of 4'-[(3-butyl-5-oxo-1,5-dihydro-4H-1,2,4-triazol-4-yl)methyl]biphenyl-2-carbonitrile (0.6 g), sodium hydride (0.11 g) and N,N-dimethylformamide (10 mL) was stirred at room temperature for 10 min, 2-bromo-1-(4-methoxyphenyl)ethanone (0.54 g) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. The residue obtained by silica gel column chromatography was dissolved in dimethyl sulfoxide (5 mL) and added to a mixture of hydroxylammonium chloride (0.83 g), sodium hydrogen carbonate (1.25 g) and dimethyl sulfoxide (20 mL), which had been mixed at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure and the residue was dissolved in tetrahydrofuran (20 mL). N,N'-carbonyldiimidazole (0.19 g) and then 1,8-diazabicyclo[5.4.0]undec-7-ene (0.16 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless solid (0.029 g, 3%).

$^1$H NMR (300 MHz, CDCl$_3$) δ 0.86 (3H, t, J=7.3), 1.27-1.41 (2H, m), 1.51-1.66 (2H, m), 2.37-2.48 (2H, m), 3.88 (3H, s), 4.84 (2H, s), 5.16 (2H, s), 6.95 (2H, d, J=9.0), 7.24-7.36 (4H, m), 7.36-7.49 (2H, m), 7.53-7.61 (1H, m), 7.71 (1H, d, J=7.7), 7.91 (2H, d, J=8.9)

Example 302

3-(4'-{[3-butyl-1-(3,3-dimethyl-2-oxobutyl)-5-oxo-1,5-dihydro-4H-1,2,4-triazol-4-yl]methyl}biphenyl-2-yl)-1,2,4-oxadiazol-5(4 H)-one

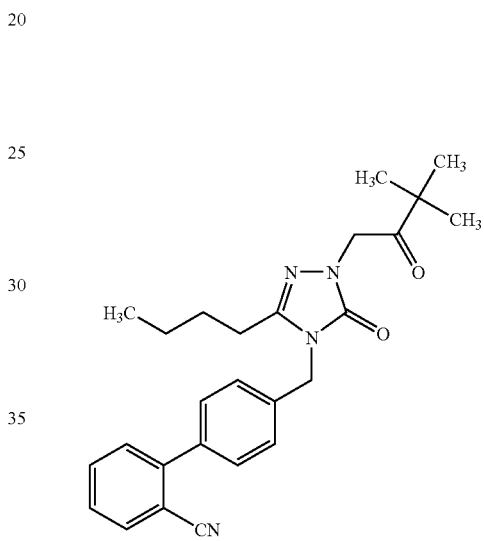

302a) 4'-{[3-butyl-1-(3,3-dimethyl-2-oxobutyl)-5-oxo-1,5-dihydro-4H-1,2,4-triazol-4-yl]methyl}biphenyl-2-carbonitrile A mixture of 4'-[(3-butyl-5-oxo-1,5-dihydro-4H-1,2,4-triazol-4-yl)methyl]biphenyl-2-carbonitrile (0.7 g), potassium tert-butoxide (1.0 M tetrahydrofuran solution, 1.75 mL) and N,N-dimethylformamide (10 mL) was stirred at room temperature for 10 min, 1-bromo-3,3-dimethylbutan-2-one (0.22 mL) was added, and the mixture was stirred at room temperature for 16 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound as a colorless powder (0.58 g, 92%).

$^1$H NMR (300 MHz, CDCl$_3$) δ 0.86 (3H, t, J=7.3), 1.26 (9H, s), 1.27-1.40 (2H, m), 1.50-1.60 (1H, m), 2.39-2.46 (2H, m), 4.81 (2H, s), 4.91 (2H, s), 7.34-7.51 (4H, m), 7.53-7.59 (2H, m), 7.61-7.69 (1H, m), 7.77 (1H, dd, J=7.7, 0.9)

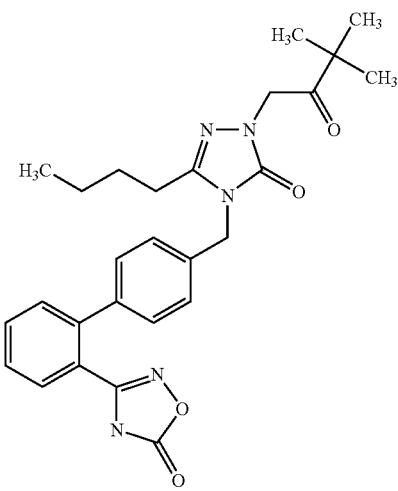

302b) 3-(4'-{[3-butyl-1-(3,3-dimethyl-2-oxobutyl)-5-oxo-1,5-dihydro-4H-1,2,4-triazol-4-yl]methyl}biphenyl-2-yl)-1,2,4-oxadiazol-5(4H)-one A mixture of hydroxylammonium chloride (1.12 g), sodium hydrogen carbonate (1.69 g) and dimethyl sulfoxide (15 mL) was stirred at 40° C. for 30 min, 4'-{[3-butyl-1-(3,3-dimethyl-2-oxobutyl)-5-oxo-1,5-dihydro-4H-1,2,4-triazol-4-yl]methyl}biphenyl-2-carbonitrile (0.58 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (20 mL). N,N'-carbonyldiimidazole (0.24 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.42 g, 63%).

$^1$H NMR (300 MHz, DMSO-$d_6$) δ 0.79 (3H, t, J=7.3), 1.16 (9H, s), 1.20-1.31 (2H, m), 1.37-1.51 (2H, m), 2.42 (2H, t, J=7.4), 4.85 (2H, s), 4.90 (2H, s), 7.24-7.35 (4H, m), 7.49-7.62 (2H, m), 7.64-7.76 (2H, m), 12.41 (1H, s)

Example 303

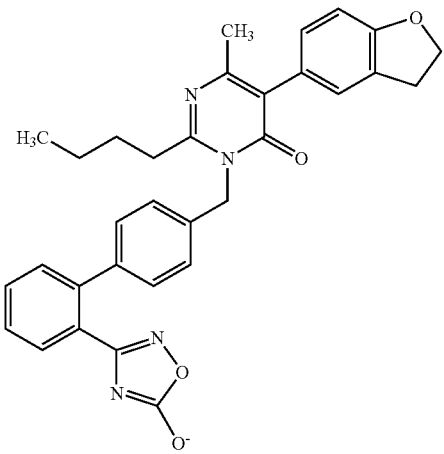

2-butyl-5-(2,3-dihydro-1-benzofuran-5-yl)-6-methyl-3-{[2'-(5-oxo-4,5-dihydro-1,2,4-oxadiazol-3-yl)biphenyl-4-yl]methyl}pyrimidin-4(3H)-one potassium salt To a solution of 2-butyl-5-(2,3-dihydro-1-benzofuran-5-yl)-6-methyl-3-{[2'-(5-oxo-4,5-dihydro-1,2,4-oxadiazol-3-yl)biphenyl-4-yl]methyl}pyrimidin-4(3H)-one (0.10 g) in ethanol (2 mL) was added 8 M potassium hydroxide solution (0.022 mL), and the solvent was evaporated under reduced pressure. The residue was triturated with diisopropyl ether to give the title compound as a colorless solid (0.09 g, 84%).

$^1$H NMR (300 MHz, DMSO-$d_6$) δ 0.84 (3H, t, J=7.2), 1.24-1.40 (2H, m), 1.53-1.68 (2H, m), 2.12 (3H, s), 2.70 (2H, t, J=7.2), 3.20 (2H, t, J=8.7), 4.55 (2H, t, J=8.7), 5.30 (2H, s), 6.78 (1H, d, J=8.1), 7.01 (1H, d, J=8.1), 7.12 (2H, d, J=8.4), 7.18 (1H, s), 7.30 (3H, d, J=8.1), 7.33-7.47 (2H, m), 7.51 (1H, d, J=5.7)

Example 304

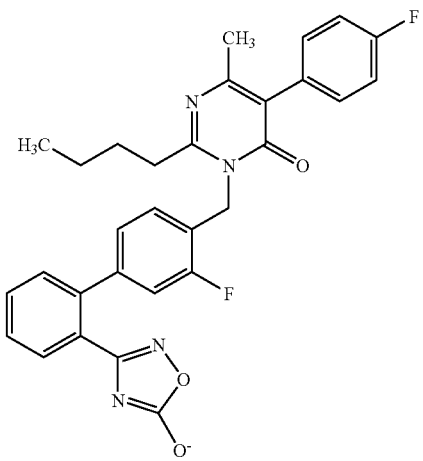

2-butyl-3-{[3-fluoro-2'-(5-oxo-4,5-dihydro-1,2,4-oxadiazol-3-yl)biphenyl-4-yl]methyl}-5-(4-fluorophenyl)-6-methylpyrimidin-4(3H)-one potassium salt To a solution of 2-butyl-3-{[3-fluoro-2'-(5-oxo-4,5-dihydro-1,2,4-oxadiazol-3-yl)biphenyl-4-yl]methyl}-5-(4-fluorophenyl)-6-methylpyrimidin-4(3H)-one (0.41 g) in ethanol (5 mL) was added 8 M potassium hydroxide solution (0.098 mL), and the solvent was evaporated under reduced pressure. The residue was triturated with diisopropyl ether to give the title compound as a colorless solid (0.42 g, 95%).

$^1$H NMR (300 MHz, DMSO-$d_6$) δ 0.86 (3H, t, J=7.5), 1.24-1.43 (2H, m), 1.55-1.72 (2H, m), 2.12 (3H, s), 2.73 (2H, t, J=7.5), 5.32 (2H, s), 6.89-7.00 (1H, m), 7.06-7.48 (9H, m), 7.49-7.58 (1H, m)

Example 305

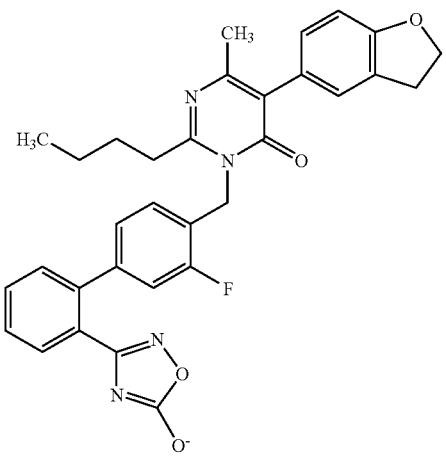

2-butyl-5-(2,3-dihydro-1-benzofuran-5-yl)-3-{[3-fluoro-2'-(5-oxo-4,5-dihydro-1,2,4-oxadiazol-3-yl)biphenyl-4-yl]methyl}-6-methylpyrimidin-4(3H)-one potassium salt To a solution of 2-butyl-5-(2,3-dihydro-1-benzofuran-5-yl)-3-{[3-fluoro-2'-(5-oxo-4,5-dihydro-1,2,4-oxadiazol-3-yl)biphenyl-4-yl]methyl}-6-methylpyrimidin-4(3H)-one (0.38 g) in ethanol (5 mL) was added 8 M potassium hydroxide solution (0.086 mL), and the solvent was evaporated under reduced pressure. The residue was triturated with diisopropyl ether to give the title compound as a colorless solid (0.25 g, 62%).

$^1$H NMR (300 MHz, DMSO-d$_6$) δ 0.86 (3H, t, J=7.5), 1.26-1.41 (2H, m), 1.55-1.71 (2H, m), 2.13 (3H, s), 2.71 (2H, t, J=7.5), 3.19 (2H, t, J=8.4), 4.54 (2H, t, J=8.4), 5.31 (2H, s), 6.77 (1H, d, J=8.4), 6.87-7.03 (2H, m), 7.07-7.19 (3H, m), 7.28-7.35 (1H, m), 7.35-7.48 (2H, m), 7.53 (1H, d, J=9.0)

Example 306

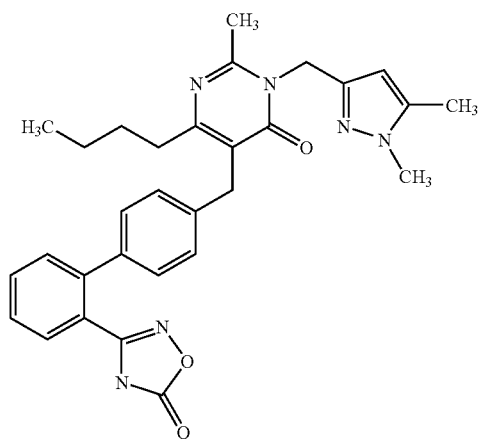

6-butyl-3-[(1,5-dimethyl-1H-pyrazol-3-yl)methyl]-2-methyl-5-{[2'-(5-oxo-4,5-dihydro-1,2,4-oxadiazol-3-yl)biphenyl-4-yl]methyl}pyrimidin-4(3H)-one hydrochloride To a mixture of 6-butyl-3-[(1,5-dimethyl-1H-pyrazol-3-yl)methyl]-2-methyl-5-{[2'-(5-oxo-4,5-dihydro-1,2,4-oxadiazol-3-yl)biphenyl-4-yl]methyl}pyrimidin-4(3H)-one (0.25 g) and ethyl acetate (10 mL) was added 4 M hydrochloric acid-ethyl acetate (0.14 mL) at room temperature. The obtained crystallized product was collected by filtration to give the title compound as colorless crystals (0.18 g, 68%).

$^1$H NMR (300 MHz, DMSO-d$_6$) δ 0.84 (3H, t, J=7.2), 1.27-1.39 (2H, m), 1.44-1.55 (2H, m), 2.07 (3H, s), 2.61-2.72 (2H, m), 2.75 (3H, s), 3.78 (3H, s), 3.91 (2H, s), 5.29 (2H, s), 5.91 (1H, s), 7.17-7.32 (4H, m), 7.45-7.61 (2H, m), 7.62-7.78 (2H, m), 12.48 (1H, s)

Example 307

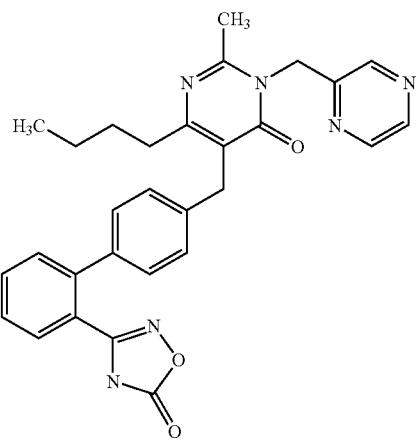

6-butyl-2-methyl-5-{[2'-(5-oxo-4,5-dihydro-1,2,4-oxadiazol-3-yl)biphenyl-4-yl]methyl}-3-(pyrazin-2-ylmethyl)pyrimidin-4(3H)-one hydrochloride To a mixture of 6-butyl-2-methyl-5-{[2'-(5-oxo-4,5-dihydro-1,2,4-oxadiazol-3-yl)biphenyl-4-yl]methyl}-3-(pyrazin-2-ylmethyl)pyrimidin-4(3H)-one (0.4 g) and ethyl acetate (10 mL) was added 4 M hydrochloric acid-ethyl acetate (0.22 mL) at room temperature. The obtained crystallized product was collected by filtration to give the title compound as colorless crystals (0.37 g, 86%).

$^1$H NMR (300 MHz, DMSO-d$_6$) δ 0.84 (3H, t, J=7.3), 1.25-1.41 (2H, m), 1.41-1.58 (2H, m), 2.62-2.90 (5H, m), 3.88 (2H, s), 5.49 (2H, s), 7.22 (4H, s), 7.45-7.60 (2H, m), 7.63-7.72 (2H, m), 8.53-8.62 (2H, m), 8.84 (1H, d, J=3.2), 12.48 (1H, s)

Example 308

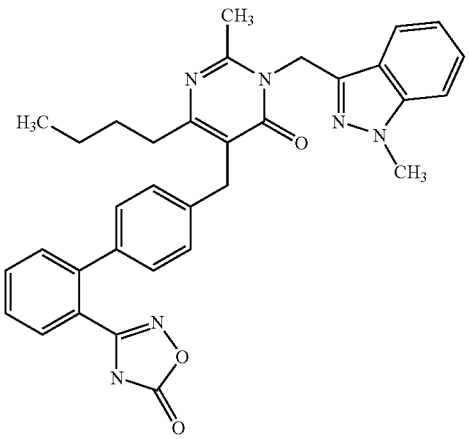

2-methyl-3-[(1-methyl-1H-indazol-3-yl)methyl]-5-{[2'-(5-oxo-4,5-dihydro-1,2,4-oxadiazol-3-yl)biphenyl-4-yl]methyl}-6-propylpyrimidin-4(3H)-one hydrochloride To a mixture of 2-methyl-3-[(1-methyl-1H-indazol-3-yl)methyl]-5-{[2'-(5-oxo-4,5-dihydro-1,2,4-oxadiazol-3-yl)biphenyl-4-yl]methyl}-6-propylpyrimidin-4(3H)-one (0.38 g) and ethyl acetate (10 mL) was added 4 M hydrochloric acid-ethyl acetate (0.19 mL) at room temperature. The obtained crystallized product was collected by filtration to give the title compound as colorless crystals (0.33 g, 83%).

$^1$H NMR (300 MHz, DMSO-d$_6$) δ 0.86 (3H, t, J=7.4), 1.37-1.60 (2H, m), 2.55-2.69 (2H, m), 2.84 (3H, s), 3.92 (2H, s), 3.95-4.05 (3H, m), 5.62 (2H, s), 7.06-7.17 (1H, m), 7.24 (4H, q, J=8.3), 7.36-7.46 (1H, m), 7.47-7.75 (5H, m), 7.84 (1H, d, J=8.3), 12.44 (1H, s)

Example 309

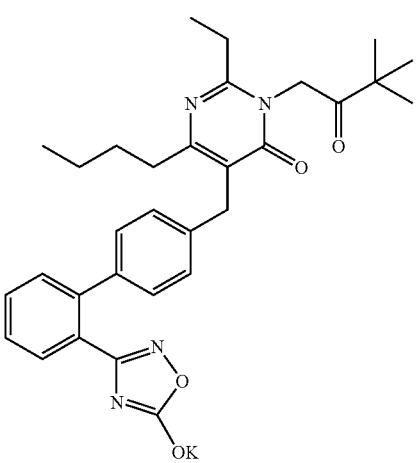

6-butyl-3-(3,3-dimethyl-2-oxobutyl)-2-ethyl-5-{[2'-(5-oxo-4,5-dihydro-1,2,4-oxadiazol-3-yl)biphenyl-4-yl]methyl}pyrimidin-4(3H)-one potassium salt 6-Butyl-3-(3,3-dimethyl-2-oxobutyl)-2-ethyl-5-{[2'-(5-oxo-4,5-dihydro-1,2,4-oxadiazol-3-yl)biphenyl-4-yl]methyl}pyrimidin-4(3H)-one (2.9 g) was dissolved in ethanol (30 mL), 8 M potassium hydroxide solution (0.68 mL) was added, and the mixture was stirred for 3 days. The solvent was removed under reduced pressure, diethyl ether and hexane were added, and the precipitated solid was collected by filtration to give the title compound (2.4 g, 76%) as an amorphous solid.

$^1$H NMR (300 MHz, DMSO-d$_6$) δ 0.86 (3H, t, J=7.1), 1.14 (3H, t, J=7.1), 1.21 (9H, s), 1.23-1.39 (2H, m), 1.47-1.60 (2H, m), 2.47-2.59 (4H, m), 3.79 (2H, s), 5.14 (2H, s), 7.05-7.09 (2H, m), 7.16-7.22 (2H, m), 7.25-7.48 (4H, m)

Example 310

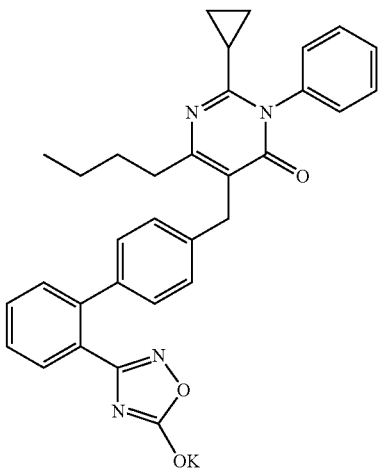

6-butyl-2-cyclopropyl-5-{[2'-(5-oxo-4,5-dihydro-1,2,4-oxadiazol-3-yl)biphenyl-4-yl]methyl}-3-phenylpyrimidin-4(3H)-one potassium salt 6-Butyl-2-cyclopropyl-5-{[2'-(5-oxo-4,5-dihydro-1,2,4-oxadiazol-3-yl)biphenyl-4-yl]methyl}-3-phenylpyrimidin-4(3H)-one (0.52 g) was dissolved in ethanol (5 mL), 8 M potassium hydroxide solution (0.13 mL) was added, and the mixture was stirred for 1 hr. Diethyl ether and diisopropyl ether were added to the reaction mixture, and the precipitated solid was collected by filtration to give the title compound (0.46 g, 83%) as an amorphous solid.

$^1$H NMR (300 MHz, DMSO-d$_6$) δ 0.75-0.82 (2H, m), 0.86 (3H, t, J=7.2), 0.96-1.13 (2H, m), 1.22-1.40 (3H, m), 1.45-1.53 (2H, m), 2.45-2.56 (2H, m), 3.80 (2H, s), 7.08-7.63 (13H, m)

Example 311

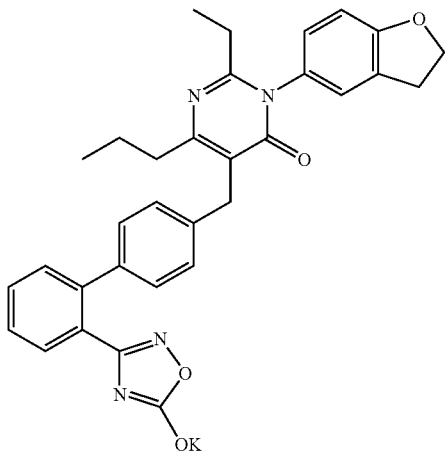

3-(2,3-dihydro-1-benzofuran-5-yl)-2-ethyl-5-{[2'-(5-oxo-4,5-dihydro-1,2,4-oxadiazol-3-yl)biphenyl-4-yl]methyl}-6-propylpyrimidin-4(3H)-one potassium salt 3-(2,3-Dihydro-1-benzofuran-5-yl)-2-ethyl-5-{[2'-(5-oxo-4,5-dihydro-1,2,4-oxadiazol-3-yl)biphenyl-4-yl]methyl}-6-propylpyrimidin-4(3H)-one (2.2 g) was dissolved in ethanol (21 mL), 8 M potassium hydroxide solution (0.50 mL) was added, and the mixture was stirred overnight. Diethyl ether and diisopropyl ether were added to the reaction mixture, and the precipitated solid was collected by filtration to give the title compound (2.1 g, 92%) as an amorphous solid.

$^1$H NMR (300 MHz, DMSO-$d_6$) δ 0.93 (3 H, t, J=7.3), 1.05 (3 H, t, J=7.0), 1.54-1.71 (2 H, m), 2.30 (2 H, q, J=7.1), 2.48-2.61 (2 H, m), 3.23 (2 H, t, J=8.6), 3.82 (2 H, s), 4.60 (2 H, t, J=8.6), 6.85 (1 H, d, J=8.2), 7.05 (1 H, dd, J=8.2, 2.0), 7.11-7.50 (9 H, m)

Example 312

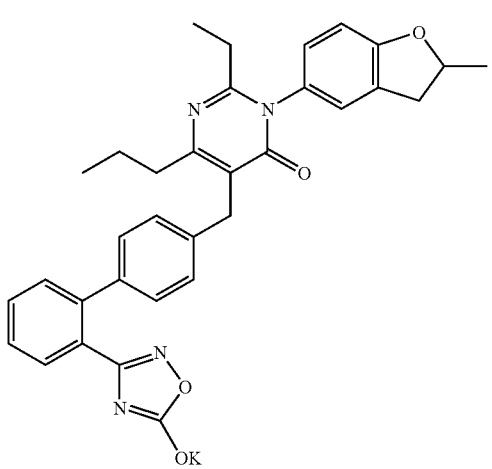

2-ethyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one potassium salt 2-Ethyl-3-(2-methyl-2,3-dihydro-1-benzofuran-5-yl)-5-{[2'-(5-oxo-4,5-dihydro-1,2,4-oxadiazol-3-yl)biphenyl-4-yl]methyl}-6-propylpyrimidin-4(3H)-one (2.3 g) was dissolved in ethanol (22 mL), 8 M potassium hydroxide solution (0.51 mL) was added, and the mixture was stirred overnight. Diethyl ether and diisopropyl ether were added to the reaction mixture, and the precipitated solid was collected by filtration to give the title compound (2.3 g, 94%) as an amorphous solid.

$^1$H NMR (300 MHz, DMSO-$d_6$) δ 0.93 (3 H, t, J=7.3), 1.02-1.12 (3 H, m), 1.38-1.46 (3 H, m), 1.55-1.70 (2 H, m), 2.24-2.36 (2 H, m), 2.47-2.60 (2 H, m), 2.76-2.89 (1 H, m), 3.30-3.50 (1 H, m), 3.81 (2 H, s), 4.92-5.06 (1 H, m), 6.82 (1 H, d, J=8.4), 7.04 (1 H, dd, J=8.4, 1.8), 7.11-7.51 (9 H, m)

Example 313

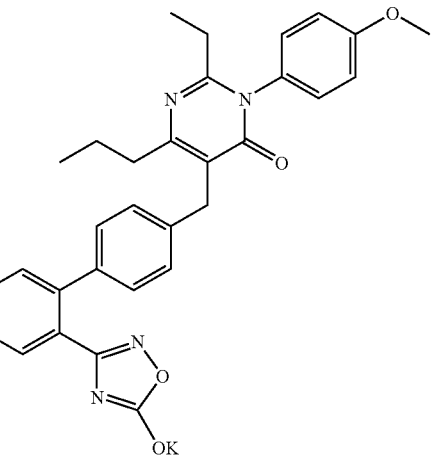

2-ethyl-3-(4-methoxyphenyl)-5-{[2'-(5-oxo-4,5-dihydro-1,2,4-oxadiazol-3-yl)biphenyl-4-yl]methyl}-6-propylpyrimidin-4(3H)-one potassium salt 2-Ethyl-3-(4-methoxyphenyl)-5-{[2'-(5-oxo-4,5-dihydro-1,2,4-oxadiazol-3-yl)biphenyl-4-yl]methyl}-6-propylpyrimidin-4(3H)-one (2.2 g) was dissolved in ethanol (22 mL), 8 M potassium hydroxide solution (0.53 mL) was added, and the mixture was stirred for 1 hr. The mixture was concentrated under reduced pressure, and acetone and hexane were added to the residue. The precipitated solid was collected by filtration to give the title compound (2.3 g, 95%) as an amorphous solid.

¹H NMR (300 MHz, DMSO-d₆) δ 0.94 (3 H, t, J=7.3), 1.00-1.13 (6 H, m), 1.55-1.70 (2 H, m), 2.27 (2 H, q, J=7.2), 2.48-2.63 (2 H, m), 3.38-3.52 (2 H, m), 6.99-7.53 (12 H, m)

Example 314

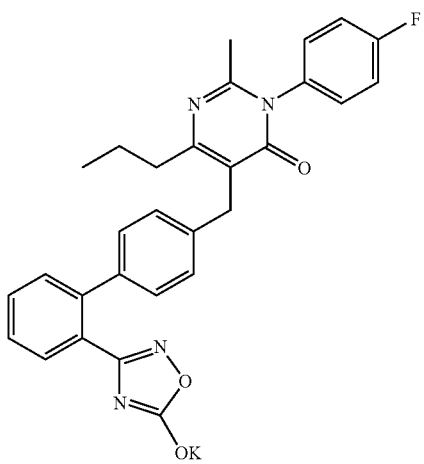

3-(4-fluorophenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt 3-(4-Fluorophenyl)-2-methyl-5-{[2'-(5-oxo-4,5-dihydro-1,2,4-oxadiazol-3-yl)biphenyl-4-yl]methyl}-6-propylpyrimidin-4(3H)-one (0.4 g) was dissolved in ethanol (10 mL), 8 M potassium hydroxide solution (0.51 mL) was added, and the mixture was stirred overnight. Ethyl acetate and diisopropyl ether were added to the reaction mixture. The precipitated solid was collected by filtration to give the title compound (0.35 g, 81%) as an amorphous solid.

¹H NMR (300 MHz, DMSO-d₆) δ 0.88-0.98 (3 H, m), 1.48-1.68 (2 H, m), 2.05 (3 H, s), 2.46-2.57 (2 H, m), 3.82 (2 H, s), 7.10-7.54 (12 H, m)

Example 315

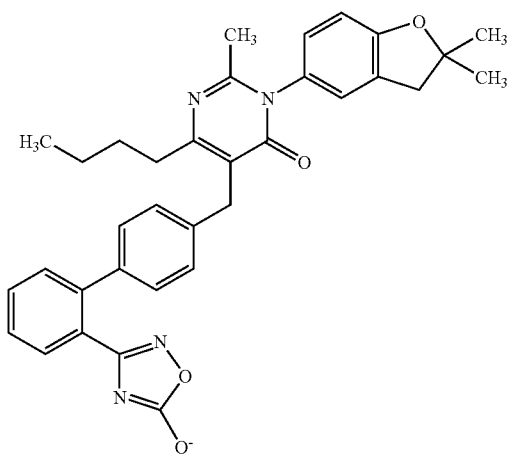

6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one potassium salt To a solution of 6-butyl-3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}pyrimidin-4(3H)-one (0.42 g) in ethanol (4 mL) was added 8 M potassium hydroxide solution (0.093 mL), and the solvent was evaporated under reduced pressure. The residue was triturated with diisopropyl ether to give the title compound as a colorless solid (0.42 g, 94%).

¹H NMR (300 MHz, DMSO-d₆) δ 0.87 (t, J=7.2, 3 H), 1.20-1.64 (m, 10 H), 2.07 (s, 3 H), 2.49-2.62 (m, 2 H), 3.05 (s, 2 H), 3.80 (s, 2 H), 6.60-7.62 (m, 11 H)

Example 316

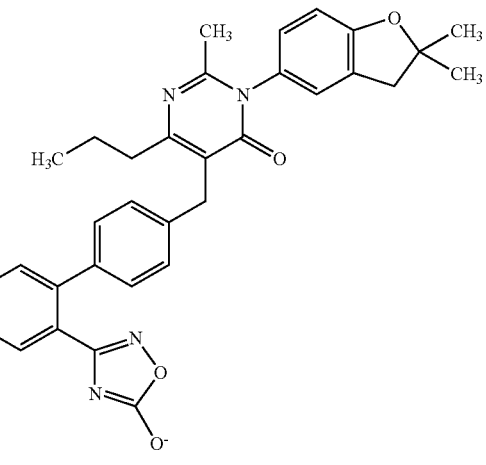

316a) 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt To a solution of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one (2.8 g) in ethanol (15 mL) was added 8 M potassium hydroxide solution (0.65 mL), and the solvent was evaporated under reduced pressure. The residue was triturated with diisopropyl ether to give the title compound as a colorless solid (2.9 g, 95%).

¹H NMR (300 MHz, DMSO-d₆) δ 0.92 (t, J=7.4, 3 H), 1.44 (s, 3 H), 1.45 (s, 3 H), 1.50-1.66 (m, 2 H), 2.07 (s, 3 H), 2.51-2.58 (m, 2 H), 3.05 (s, 2 H), 3.80 (s, 2 H), 6.73-7.53 (m, 11 H)

316b) Crystalline 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt hydrate.

To a suspension of 3-(2,2-dimethyl-2,3-dihydro-1-benzofuran-5-yl)-2-methyl-5-{[2'-(5-oxo-4,5-dihydro-1,2,4-oxadiazol-3-yl)biphenyl-4-yl]methyl}-6-propylpyrimidin-4(3H)-one (45 g) in acetone (135 ml) was added 8 M aqueous potassium hydroxide solution (10.3 mL) and the mixture was stirred at room temperature for 20 hr. The obtained precipitate was collected, washed with acetone and water successively, and dried under reduced pressure at 80° C. for 5 hr to give the title compound (32 g, 60%) as colorless crystals.

$^1$H NMR (300 MHz, DMSO-$d_6$) δ 0.92 (t, J=7.4, 3 H), 1.44 (s, 3H), 1.45 (s, 3 H), 1.51-1.66 (m, 2 H), 2.07 (s, 3 H), 2.48-2.57 (m, 2 H), 3.05 (s, 2 H), 3.81 (s, 2 H), 6.74-7.51 (m, 11 H)

Powder X-ray diffraction (Cu—Kα radiation, diffraction angle: 2θ(°)): 5.02, 5.36, 9.46, 10.66, 11.80, 13.42, 17.06, 17.78, 19.00, 19.18, 20.18, 20.88, 21.38, 23.26, 23.78, 25.06, 25.74, 26.06, 26.90, 27.34.

Anal calcd for $C_{33}H_{31}N_4O_4K+2.9H_2O$: C, 62.03; H, 5.81; N, 8.77.

Found C, 62.09; H, 5.75; N, 8.73.

Example 317

6-butyl-5-{[3-fluoro-2'-(5-oxo-4,5-dihydro-1,2,4-oxadiazol-3-yl)biphenyl-4-yl]methyl}-3-[(2Z)-2-(isopropoxyimino)-3,3-dimethylbutyl]-2-methylpyrimidin-4(3H)-one A mixture of 6-butyl-3-(3,3-dimethyl-2-oxobutyl)-5-{[3-fluoro-2'-(5-oxo-4,5-dihydro-1,2,4-oxadiazol-3-yl)biphenyl-4-yl]methyl}-2-methylpyrimidin-4(3H)-one (0.15 g),

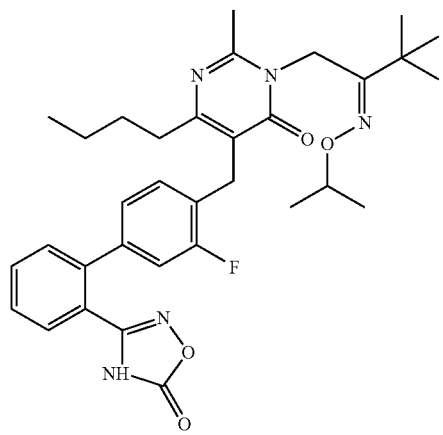

2-(aminooxy)propane hydrochloride (0.63 g) and pyridine (5 mL) was stirred at 100° C. for 16 hr. The mixture was allowed to cool to room temperature, and the reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless amorphous solid (0.036 g, 22%).

$^1$H NMR (300 MHz, DMSO-$d_6$) δ 0.82 (3H, t, J=7.4), 0.88 (6H, d, J=6.2), 1.15 (9H, s), 1.20-1.31 (2H, m), 1.36-1.51 (2H, m), 2.39-2.48 (5H, m), 3.81 (2H, s), 3.90-4.02 (1H, m), 4.81 (2H, s), 6.95 (1H, dd, J=7.9, 1.7), 7.06 (1H, t, J=8.0), 7.15 (1H, dd, J=11.1, 1.7), 7.48-7.61 (2H, m), 7.63-7.74 (2H, m), 12.45 (1H, br)

Example 318

3-[4-(cyclobutyloxy)-3-fluorophenyl]-2-methyl-5-{[2'-(5-oxo-4,5-dihydro-1,2,4-oxadiazol-3-yl)biphenyl-4-yl]methyl}-6-propylpyrimidin-4(3H)-one

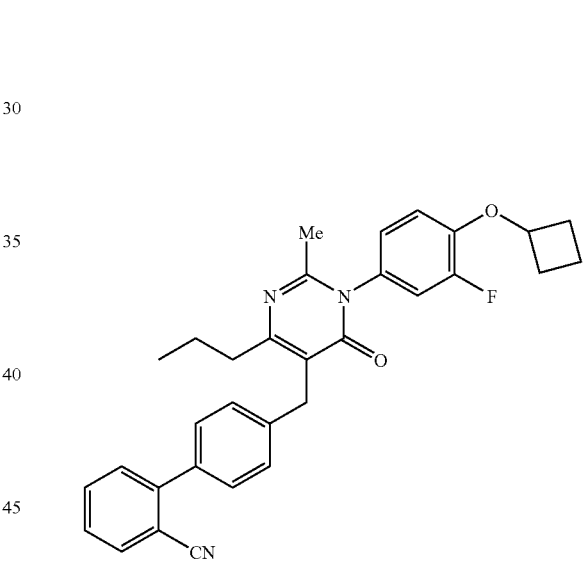

318a) 4'-({1-[4-(cyclobutyloxy)-3-fluorophenyl]-2-methyl-6-oxo-4-propyl-1,6-dihydropyrimidin-5-yl}methyl)biphenyl-2-carbonitrile To a solution of 4'-{[1-(3-fluoro-4-hydroxyphenyl)-2-methyl-6-oxo-4-propyl-1,6-dihydropyrimidin-5-yl]methyl}biphenyl-2-carbonitrile (1.0 g) and bromocyclobutane (0.90 g) in N,N-dimethylformamide (10 mL) was added cesium carbonate (1.44 g), and the mixture was stirred at 80° C. for 15 hr. After allowing to cool, ethyl acetate and water

Example 319

3-[4-(cyclopentyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

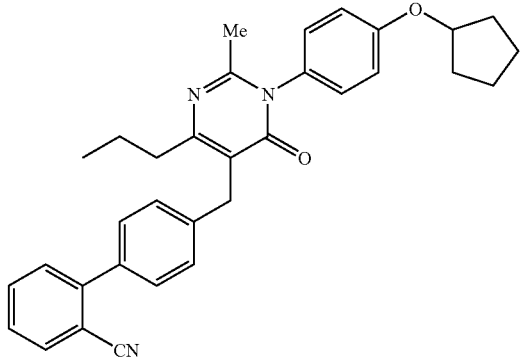

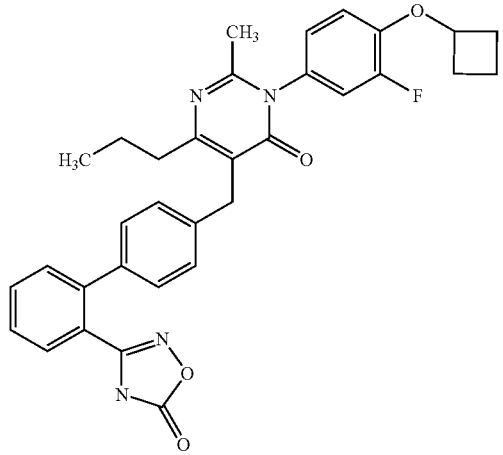

318b) 3-[4-(cyclobutyloxy)-3-fluorophenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.58 g), sodium hydrogen carbonate (2.39 g) and dimethyl sulfoxide (10 mL) was stirred at 40° C. for 30 min, 4'-({1-[4-(cyclobutyloxy)-3-fluorophenyl]-2-methyl-6-oxo-4-propyl-1,6-dihydropyrimidin-5-yl}methyl)biphenyl-2-carbonitrile (0.96 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.37 g) and then 1,8-diazabicyclo[5.4.0]undec-7-ene (0.34 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless amorphous solid (0.56 g, 52%).

$^1$H NMR (300 MHz, DMSO-$d_6$) δ 0.89 (t, J=7.3, 3 H), 1.43-2.24 (m, 9 H), 2.40-2.55 (m, 4 H), 3.86 (s, 2 H), 4.72-4.91 (m, 1 H), 7.08-7.74 (m, 11 H), 12.38 (s, 1 H)

319a) 4'-({1-[4-(cyclopentyloxy)phenyl]-2-methyl-6-oxo-4-propyl-1,6-dihydropyrimidin-5-yl}methyl)biphenyl-2-carbonitrile To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and bromocyclopentane (1.00 g) in N,N-dimethylformamide (10 mL) was added cesium carbonate (1.44 g), and the mixture was stirred at 80° C. for 15 hr. After allowing to cool, ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (1.05 g, 91%).

$^1$H NMR (300 MHz, CDCl$_3$) δ 1.01 (t, J=7.3, 3 H), 1.53-1.99 (m, 10 H), 2.18 (s, 3 H), 2.58-2.73 (m, 2 H), 3.97 (s, 2 H), 4.73-4.82 (m, 1 H), 6.90-7.78 (m, 12 H)

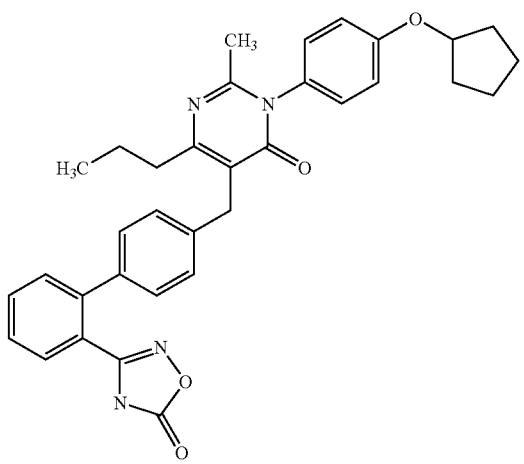

were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.96 g, 86%).

$^1$H NMR (300 MHz, CDCl$_3$) δ 1.01 (t, J=7.3, 3 H), 1.60-1.98 (m, 4 H), 2.14-2.56 (m, 7 H), 2.60-2.70 (m, 2 H), 3.96 (s, 2H), 4.61-4.79 (m, 1 H), 6.87-7.82 (m, 11 H)

319b) 3-[4-(cyclopentyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.70 g), sodium hydrogen carbonate (2.62 g) and dimethyl sulfoxide (10 mL) was stirred at 40° C. for 30 min, 4'-({1-[4-(cyclopentyloxy)phenyl]-2-methyl-6-oxo-4-propyl-1,6-dihydropyrimidin-5-yl}methyl)biphenyl-2-carbonitrile (0.96 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.41 g) and then 1,8-diazabicyclo[5.4.0]undec-7-ene (0.37 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless amorphous solid (0.78 g, 66%).

$^1$H NMR (300 MHz, DMSO-$d_6$) δ 0.89 (t, J=7.3, 3 H), 1.44-2.01 (m, 10 H), 2.06 (s, 3 H), 2.45-2.55 (m, 2 H), 3.86 (s, 2 H), 4.82-4.94 (m, 1 H), 6.98-7.73 (m, 12 H), 12.37 (s, 1 H)

Example 320

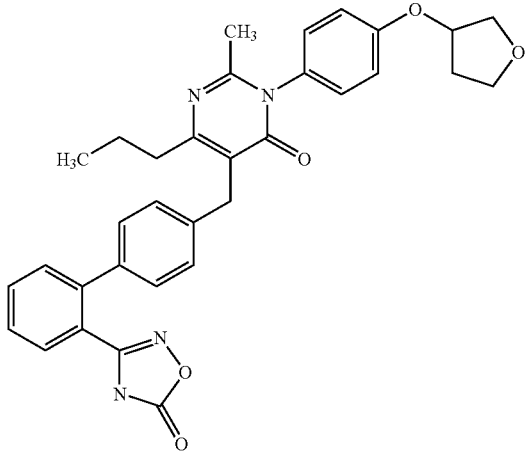

2-methyl-5-{[2'-(5-oxo-4,5-dihydro-1,2,4-oxadiazol-3-yl)biphenyl-4-yl]methyl}-6-propyl-3-[4-(tetrahydrofuran-3-yloxy)phenyl]pyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (1.00 g), tetrahydrofuran-3-ol (0.37 mL) and triphenylphosphine (1.21 g) in tetrahydrofuran (7 mL) was added diisopropyl azodicarboxylate (1.9 M toluene solution, 0.91 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (1.90 g), sodium hydrogen carbonate (2.90 g) and dimethyl sulfoxide (10 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (20 mL). N,N'-carbonyldiimidazole (0.45 g) and then 1,8-diazabicyclo[5.4.0]undec-7-ene (0.41 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.69 g, 53%).

$^1$H NMR (300 MHz, DMSO-$d_6$) δ 0.89 (t, J=7.3, 3 H), 1.43-1.65 (m, 2 H), 1.91-2.36 (m, 5 H), 2.45-2.56 (m, 2 H), 3.67-3.99 (m, 6 H), 5.03-5.14 (m, 1 H), 7.00-7.74 (m, 12 H), 12.38 (s, 1 H)

Example 321

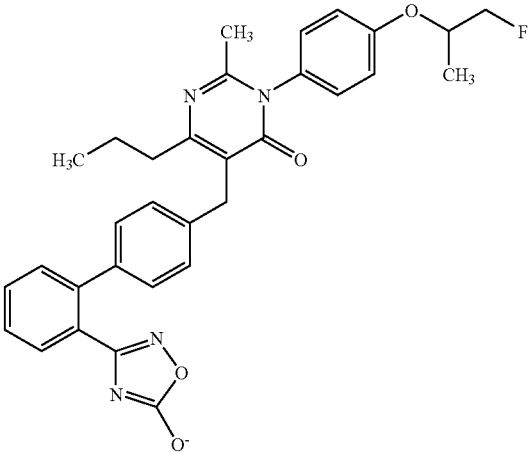

3-[4-(2-fluoro-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one potassium salt To a solution of 3-[4-(2-fluoro-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one (0.35 g) in ethanol (3 mL) was added 8 M potassium hydroxide solution (0.079 mL), and the mixture was stirred at room temperature for 1 hr. The reaction mixture was concentrated under reduced pressure, and the residue was triturated with diisopropyl ether to give the title compound as a pale-yellow amorphous solid (0.38 g, 100%).

$^1$H NMR (300 MHz, DMSO-$d_6$) δ 0.93 (t, J=7.4, 3 H), 1.27 (dd, J=6.4, 1.1, 3 H), 1.53-1.67 (m, 2 H), 2.06 (s, 3 H), 2.47-2.57 (m, 2 H), 3.81 (s, 2 H), 4.40-4.92 (m, 3 H), 7.04-7.51 (m, 12 H)

Example 322

3-(3-chloro-4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one

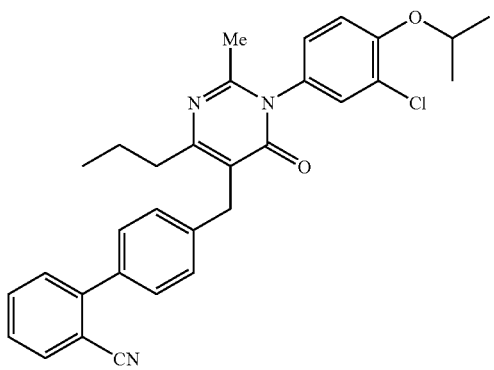

322a) 4'-{[1-(3-chloro-4-isopropoxyphenyl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (3-chloro-4-isopropoxyphenyl)boronic acid (1.00 g), triethylamine (2.00 mL), pyridine (1.00 mL) and molecular sieves 4 A (2.0 g) in methylene chloride (15 mL) was added copper(II) acetate (1.00 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow viscous substance (1.00 g, 67%).

$^1$H NMR (300 MHz, CDCl$_3$) δ 1.01 (t, J=7.4, 3 H), 1.41 (dd, J=10.6, 6.1, 6 H), 1.60-1.78 (m, 2 H), 2.19 (s, 3 H), 2.58-2.71 (m, 2 H), 3.96 (s, 2 H), 4.51-4.68 (m, 1 H), 6.98-7.79 (m, 11 H)

322b) 3-(3-chloro-4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.63 g), sodium hydrogen carbonate (2.46 g) and dimethyl sulfoxide (10 mL) was stirred at 40° C. for 30 min, 4'-{[1-(3-chloro-4-isopropoxyphenyl)-2-methyl-6-oxo-4-propyl-1,6-dihydropyrimidin-5-yl]methyl}biphenyl-2-carbonitrile (1.00 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.41 g) and then 1,8-diazabicyclo[5.4.0]undec-7-ene (0.39 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.63 g, 57%).

$^1$H NMR (300 MHz, DMSO-d$_6$) δ 0.88 (t, J=7.3, 3 H), 1.33 (dd, J=5.9, 3.3, 6 H), 1.44-1.61 (m, 2 H), 2.09 (s, 3 H), 2.45-2.53 (m, 2 H), 3.86 (s, 2 H), 4.66-4.84 (m, 1 H), 7.16-7.74 (m, 11 H), 12.38 (s, 1 H)

Example 323

2-methyl-3-(2-methylprop-1-en-1-yl)-5-{[2'-(5-oxo-4,5-dihydro-1,2,4-oxadiazol-3-yl)biphenyl-4-yl]methyl}-6-propylpyrimidin-4(3H)-one

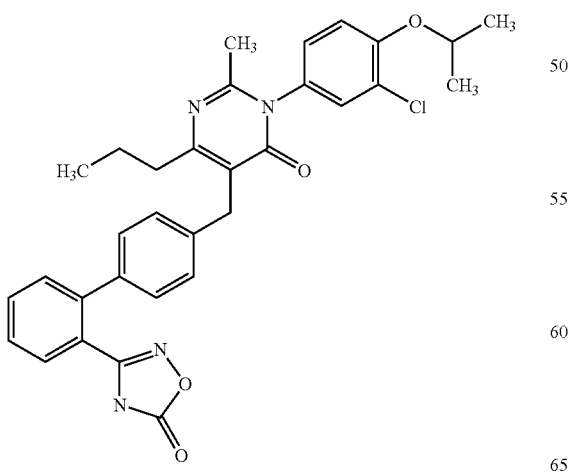

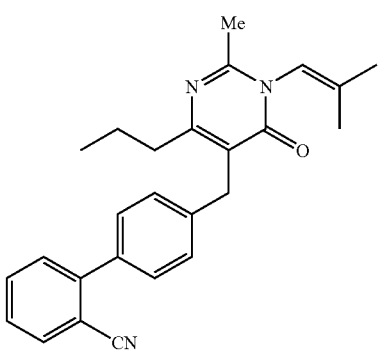

323a) 4'-{[2-methyl-1-(2-methylprop-1-en-1-yl)-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (2-methylprop-1-en-1-yl)boronic acid (1.00 g), triethylamine (2.00 mL), pyridine (1.00 mL) and molecular sieves 4 A (2.0 g) in methylene chloride (15 mL) was added copper(II) acetate (1.00 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow viscous substance (0.080 g, 7%).

$^1$H NMR (300 MHz, CDCl$_3$) δ 0.97 (t, J=7.4, 3 H), 1.49-1.73 (m, 8 H), 2.34 (s, 3 H), 2.51-2.65 (m, 2 H), 3.95 (s, 2 H), 6.05 (s, 1 H), 7.31-7.78 (m, 8 H)

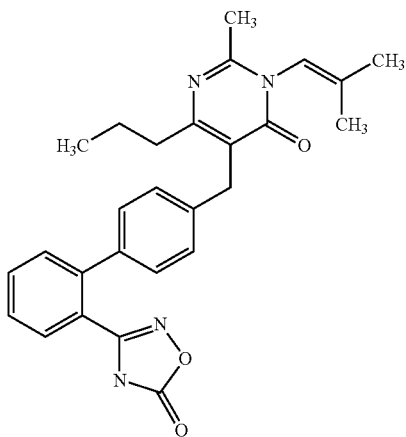

323b) 2-methyl-3-(2-methylprop-1-en-1-yl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.21 g), sodium hydrogen carbonate (0.34 g) and dimethyl sulfoxide (2 mL) was stirred at 40° C. for 30 min, 4'-{[2-methyl-1-(2-methylprop-1-en-1-yl)-6-oxo-4-propyl-1,6-dihydropyrimidin-5-yl]methyl}biphenyl-2-carbonitrile (0.080 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (2 mL). N,N'-carbonyldiimidazole (0.050 g) and then 1,8-diazabicyclo[5.4.0]undec-7-ene (0.050 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.029 g, 32%).

$^1$H NMR (300 MHz, DMSO-d$_6$) δ 0.84 (t, J=7.3, 3 H), 1.42 (d, J=0.9, 3 H), 1.45-1.58 (m, 2 H), 1.84 (d, J=1.3, 3 H), 2.27 (s, 3 H), 2.42-2.52 (m, 2 H), 3.84 (s, 2 H), 6.12 (s, 1 H), 7.16-7.74 (m, 8 H), 12.36 (s, 1 H)

Example 324

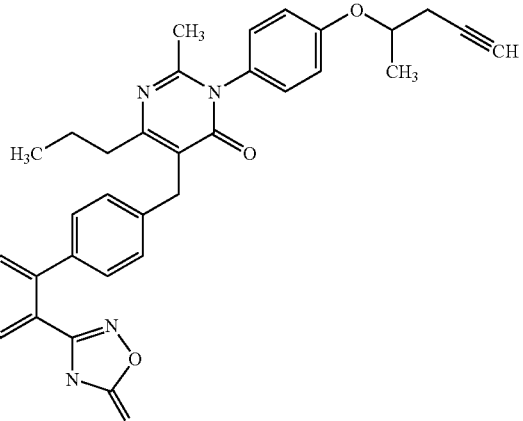

2-methyl-3-{4-[(1-methylbut-3-yn-1-yl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (1.00 g), pent-4-yn-2-ol (0.43 mL) and triphenylphosphine (1.21 g) in tetrahydrofuran (10 mL) was added diisopropyl azodicarboxylate (1.9 M toluene solution, 0.91 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (0.81 g), sodium hydrogen carbonate (1.31 g) and dimethyl sulfoxide (8 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (20 mL). N,N'-carbonyldiimidazole (0.15 g) and then 1,8-diazabicyclo[5.4.0]undec-7-ene (0.14 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.077 g, 6%).

$^1$H NMR (300 MHz, DMSO-d$_6$) δ 0.89 (t, J=7.3, 3 H), 1.36 (d, J=6.0, 2 H), 1.47-1.61 (m, 2 H), 2.07 (s, 3 H), 2.49-2.59 (m, 2 H), 2.91 (t, J=2.6, 1 H), 3.28-3.34 (m, 2 H), 3.86 (s, 2 H), 4.61-4.71 (m, 1 H), 7.00-7.72 (m, 12 H), 12.38 (s, 1H)

Example 325

3-(6-isopropoxypyridin-3-yl)-2-methyl-5-{[2'-(5-oxo-4,5-dihydro-1,2,4-oxadiazol-3-yl)biphenyl-4-yl]methyl}-6-propylpyrimidin-4(3H)-one

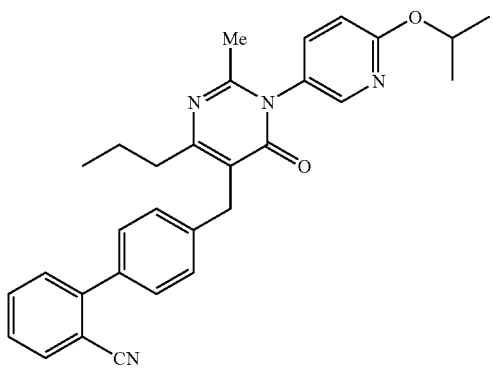

325a) 4'-{[1-(6-isopropoxypyridin-3-yl)-2-methyl-6-oxo-4-propyl-1,6-dihydropyrimidin-5-yl]methyl}biphenyl-2-carbonitrile To a suspension of 4'-[(2-methyl-6-oxo-4-propyl-1,6-dihydropyrimidin-5-yl)methyl]biphenyl-2-carbonitrile (1.0 g), (6-isopropoxypyridin-3-yl)boronic acid (1.00 g), triethylamine (2.00 mL), pyridine (1.00 mL) and molecular sieves 4 A (2.0 g) in methylene chloride (15 mL) was added copper(II) acetate (1.00 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow viscous substance (0.98 g, 70%).

$^1$H NMR (300 MHz, CDCl$_3$) δ 1.01 (t, J=7.4, 3 H), 1.35 (d, J=6.1, 3 H), 1.38 (d, J=6.4, 3 H), 1.64-1.78 (m, 1 H), 2.21 (s, 3H), 2.61-2.70 (m, 2 H), 3.97 (s, 2 H), 5.27-5.40 (m, 1 H), 6.76-8.03 (m, 11 H)

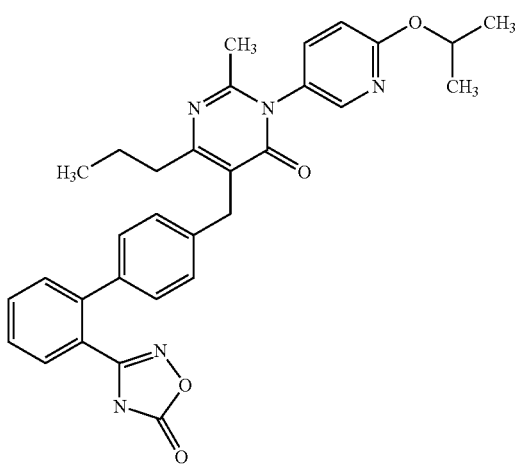

325b) 3-(6-isopropoxypyridin-3-yl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.70 g), sodium hydrogen carbonate (2.57 g) and dimethyl sulfoxide (10 mL) was stirred at 40° C. for 30 min, 4'-{[1-(6-isopropoxypyridin-3-yl)-2-methyl-6-oxo-4-propyl-1,6-dihydropyrimidin-5-yl]methyl}biphenyl-2-carbonitrile (0.98 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.40 g) and then 1,8-diazabicyclo[5.4.0]undec-7-ene (0.37 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.81 g, 73%).

$^1$H NMR (300 MHz, DMSO-d$_6$) δ 0.89 (t, J=7.4, 3 H), 1.32 (d, J=6.1, 6 H), 1.46-1.62 (m, 2 H), 2.10 (s, 3 H), 2.48-2.54 (m, 2 H), 3.87 (s, 2 H), 5.21-5.34 (m, 1 H), 6.84-8.22 (m, 11 H), 12.37 (s, 1 H)

Example 326

2-{4-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]phenoxy}propanamide

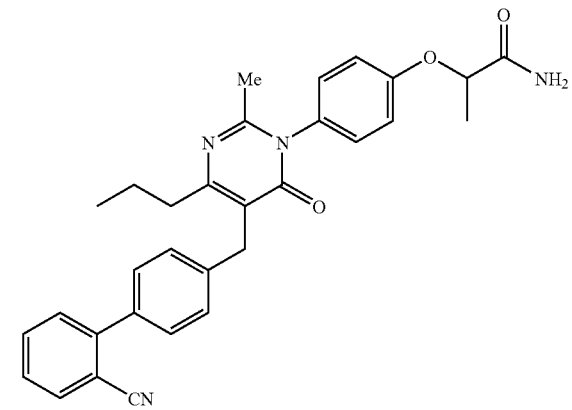

326a) 2-{4-[5-[(2'-cyanobiphenyl-4-yl)methyl]-2-methyl-6-oxo-4-propylpyrimidin-1(6H)-yl]phenoxy}propanamide To a solution of 4'-{[1-(4-hydroxyphenyl)-2-methyl-6-oxo-4-propyl-1,6-dihydropyrimidin-5-yl]methyl}biphenyl-2-carbonitrile (1.00 g) and 2-bromopropanamide (0.70 g) in N,N-dimethylformamide (10 mL) was added cesium carbonate (1.50 g), and the mixture was stirred at 80° C. for 15 hr. After allowing to cool, ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (1.03 g, 88%).

¹H NMR (300 MHz, CDCl₃) δ 1.01 (t, J=7.4, 3 H), 1.62 (d, J=6.8, 3 H), 1.65-1.76 (m, 2 H), 2.17 (s, 3 H), 2.61-2.68 (m, 2H), 3.96 (s, 2 H), 4.69 (q, J=6.7, 1 H), 5.65 (s, 1 H), 6.38 (s, 1 H), 6.94-7.79 (m, 12 H)

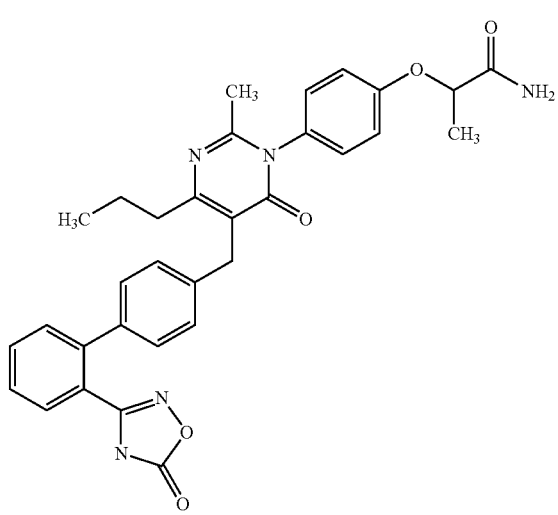

326b) 2-{4-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]phenoxy}propanamide A mixture of hydroxylammonium chloride (1.41 g), sodium hydrogen carbonate (2.05 g) and dimethyl sulfoxide (10 mL) was stirred at 40° C. for 30 min, 2-{4-[5-[(2'-cyanobiphenyl-4-yl)methyl]-2-methyl-6-oxo-4-propylpyrimidin-1(6H)-yl]phenoxy}propanamide (1.03 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.39 g) and then 1,8-diazabicyclo[5.4.0]undec-7-ene (0.36 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless amorphous solid (0.63 g, 55%).

¹H NMR (300 MHz, DMSO-d₆) δ 0.89 (t, J=7.2, 3 H), 1.47 (d, J=6.8, 3 H), 1.49-1.61 (m, 2 H), 2.06 (s, 3 H), 2.46-2.53 (m, 2 H), 3.86 (s, 2 H), 4.69 (q, J=6.7, 1 H), 6.98-7.74 (m, 14 H), 12.36 (s, 1 H)

Example 327

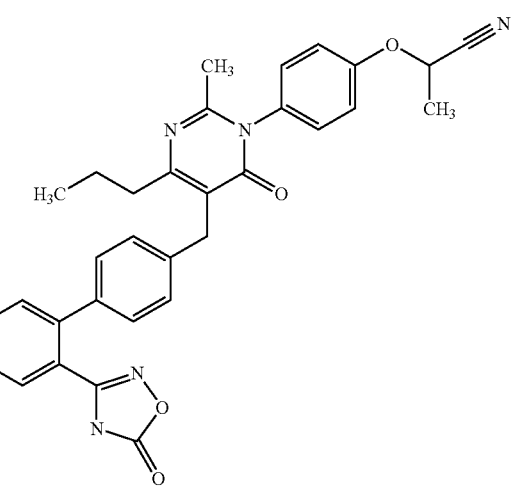

2-{4-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]phenoxy}propanenitrile To a solution of 2-{4-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]phenoxy}propanamide (0.57 g) and triethylamine (0.42 mL) in acetonitrile (5 mL) was added trifluoroacetic anhydride (0.28 mL), and the mixture was stirred for 12 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a colorless solid (0.35 g, 64%).

¹H NMR (300 MHz, DMSO-d₆) δ 0.89 (t, J=7.2, 3 H), 1.44-1.63 (m, 2 H), 1.73 (d, J=6.8, 3 H), 2.07 (s, 3 H), 2.46-2.56 (m, 2 H), 3.87 (s, 2 H), 5.54 (q, J=6.4, 1 H), 7.18-7.73 (m, 12 H), 12.37 (s, 1 H)

Example 328

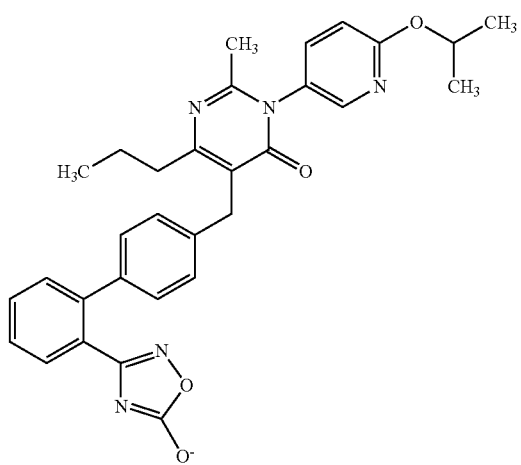

3-(6-isopropoxypyridin-3-yl)-2-methyl-5-{[2'-(5-oxo-4,5-dihydro-1,2,4-oxadiazol-3-yl)biphenyl-4-yl]methyl}-6-propylpyrimidin-4(3H)-one potassium salt To a solution of 3-(6-isopropoxypyridin-3-yl)-2-methyl-5-{[2'-(5-oxo-4,5-dihydro-1,2,4-oxadiazol-3-yl)biphenyl-4-yl]methyl}-6-propylpyrimidin-4(3H)-one (0.54 g) in ethanol (3 mL) was added 8 M potassium hydroxide solution (0.13 mL), and the mixture was stirred at room temperature for 1 hr. The reaction mixture was concentrated under reduced pressure, and the residue was triturated with diisopropyl ether to give the title compound as a colorless amorphous solid (0.54 g, 93%).

$^1$H NMR (300 MHz, DMSO-$d_6$) δ 0.93 (t, J=7.3, 3 H), 1.33 (d, J=6.2, 6 H), 1.50-1.69 (m, 2 H), 2.09 (s, 3 H), 2.48-2.58 (m, 2 H), 3.82 (s, 2 H), 5.21-5.35 (m, 1 H), 6.84-8.21 (m, 11 H)

Example 329

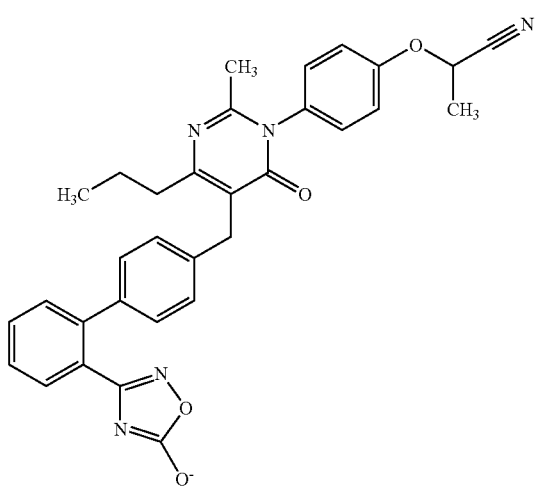

2-{4-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]phenoxy}propanenitrile potassium salt To a solution of 2-{4-[2-methyl-6-oxo-5-{[2'-(5-oxo-4,5-dihydro-1,2,4-oxadiazol-3-yl)biphenyl-4-yl]methyl}-4-propylpyrimidin-1(6H)-yl]phenoxy}propanenitrile (0.54 g) in ethanol (3 mL) was added 8 M potassium hydroxide solution (0.13 mL), and the mixture was stirred at room temperature for 1 hr. The reaction mixture was concentrated under reduced pressure, and the residue was triturated with diisopropyl ether to give the title compound as a colorless amorphous solid (0.54 g, 93%).

$^1$H NMR (300 MHz, DMSO-$d_6$) δ 0.24 (t, J=7.3, 3 H), 0.82-0.97 (m, 2 H), 1.03 (d, J=6.8, 3 H), 1.36 (s, 3 H), 1.78-1.89 (m, 2 H), 3.13 (s, 2 H), 4.84 (q, J=6.6, 1 H), 6.43-6.80 (m, 12 H)

Example 330

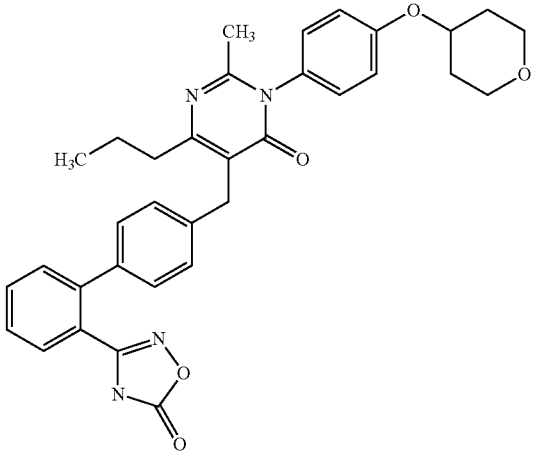

2-methyl-5-{[2'-(5-oxo-4,5-dihydro-1,2,4-oxadiazol-3-yl)biphenyl-4-yl]methyl}-6-propyl-3-[4-(tetrahydro-2H-pyran-4-yloxy)phenyl]pyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (1.00 g), tetrahydro-2H-pyran-4-ol (0.44 mL) and triphenylphosphine (1.21 g) in tetrahydrofuran (5 mL) was added diisopropyl azodicarboxylate (1.9 M toluene solution, 0.91 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (1.90 g), sodium hydrogen carbonate (2.90 g) and dimethyl sulfoxide (10 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.45 g) and then 1,8-diazabicyclo[5.4.0]undec-7-ene (0.41 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.81 g, 61%).

$^1$H NMR (300 MHz, DMSO-$d_6$) δ 0.89 (t, J=7.3, 3 H), 1.46-1.69 (m, 4 H), 1.95-2.11 (m, 5 H), 2.45-2.54 (m, 2 H), 3.44-3.55 (m, 2 H), 3.81-3.91 (m, 4 H), 4.57-4.70 (m, 1 H), 7.04-7.74 (m, 12 H), 12.38 (s, 1 H)

Example 331

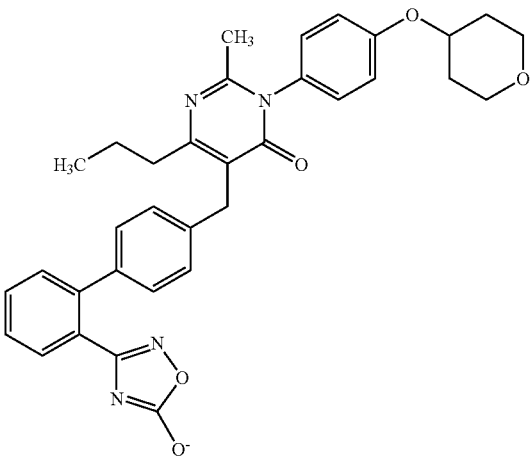

2-methyl-5-{[2'-(5-oxo-4,5-dihydro-1,2,4-oxadiazol-3-yl)biphenyl-4-yl]methyl}-6-propyl-3-[4-(tetrahydro-2H-pyran-4-yloxy)phenyl]pyrimidin-4(3H)-one potassium salt To a solution of 2-methyl-5-{[2'-(5-oxo-4,5-dihydro-1,2,4-oxadiazol-3-yl)biphenyl-4-yl]methyl}-6-propyl-3-[4-(tetrahydro-2H-pyran-4-yloxy)phenyl]pyrimidin-4(3H)-one (0.58 g) in ethanol (3 mL) was added 8 M potassium hydroxide solution (0.13 mL), and the mixture was stirred at room temperature for 1 hr. The reaction mixture was concentrated under reduced pressure, and the residue was triturated with diisopropyl ether to give the title compound as a colorless amorphous solid (0.61 g, 99%).

$^1$H NMR (300 MHz, DMSO-d$_6$) δ 0.89 (t, J=7.3, 3 H), 1.46-1.69 (m, 4 H), 1.95-2.11 (m, 5 H), 2.45-2.54 (m, 2 H), 3.44-3.55 (m, 2 H), 3.81-3.91 (m, 4 H), 4.57-4.70 (m, 1 H), 7.04-7.74 (m, 12 H), 12.38 (s, 1 H)

Example 332

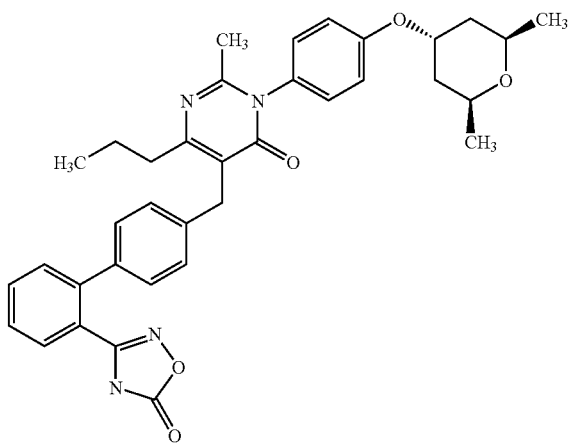

3-(4-{[(2R,4s,6S)-2,6-dimethyltetrahydro-2H-pyran-4-yl]oxy}phenyl)-2-methyl-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (0.50 g), (2R,4s,6S)-2,6-dimethyltetrahydro-2H-pyran-4-ol (0.30 g) and triphenylphosphine (0.60 g) in tetrahydrofuran (3 mL) was added diisopropyl azodicarboxylate (1.9 M toluene solution, 1.21 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (0.96 g), sodium hydrogen carbonate (1.45 g) and dimethyl sulfoxide (6 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (6 mL). N,N'-carbonyldiimidazole (0.22 g) and then 1,8-diazabicyclo[5.4.0]undec-7-ene (0.21 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.43 g, 62%).

$^1$H NMR (300 MHz, DMSO-d$_6$) δ 0.89 (t, J=7.3, 3 H), 1.08 (s, 3 H), 1.10 (s, 3 H), 1.36-1.63 (m, 4 H), 1.81-1.90 (m, 2 H), 2.07 (s, 3 H), 2.47-2.54 (m, 2 H), 3.77-3.90 (m, 4H), 4.81-4.87 (m, 1 H), 7.04-7.73 (m, 12 H), 12.38 (s, 1 H)

Example 333

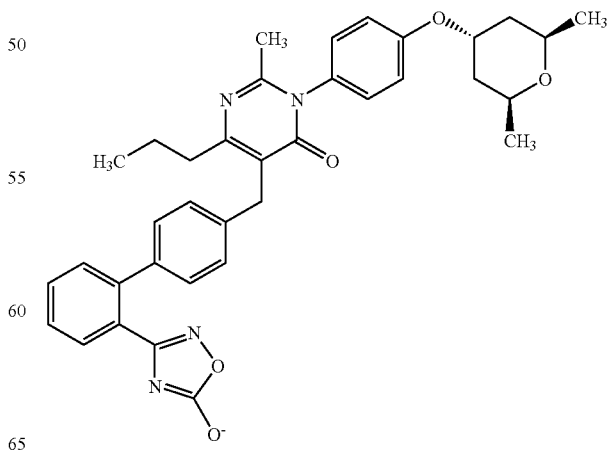

3-(4-{[(2R,4s,6S)-2,6-dimethyltetrahydro-2H-pyran-4-yl]oxy}phenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt To a solution of 3-(4-{[(2R,4s,6S)-2,6-dimethyltetrahydro-2H-pyran-4-yl]oxy}phenyl)-2-methyl-5-{[2'-(5-oxo-4,5-dihydro-1,2,4-oxadiazol-3-yl)biphenyl-4-yl]methyl}-6-propylpyrimidin-4(3H)-one (0.30 g) in ethanol (2 mL) was added 8 M potassium hydroxide solution (0.063 mL), and the mixture was stirred at room temperature for 1 hr. The reaction mixture was concentrated under reduced pressure, and the residue was triturated with diisopropyl ether to give the title compound as a colorless amorphous solid (0.28 g, 86%).

$^1$H NMR (300 MHz, DMSO-$d_6$) δ 0.89 (t, J=7.3, 3 H), 1.46-1.69 (m, 4 H), 1.95-2.11 (m, 5 H), 2.45-2.54 (m, 2 H), 3.44-3.55 (m, 2 H), 3.81-3.91 (m, 4 H), 4.57-4.70 (m, 1 H), 7.04-7.74 (m, 12 H), 12.38 (s, 1 H)

Example 334

3-{4-[(4-hydroxycyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one

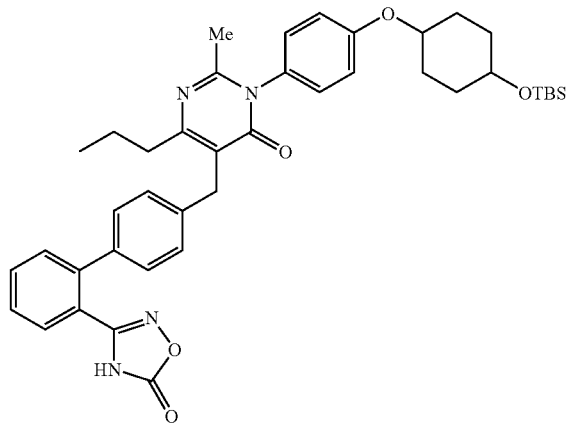

334a) 3-{4-[(4-{[tert-butyl(dimethyl)silyl]oxy}cyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (3.00 g), 4-{[tert-butyl(dimethyl)silyl]oxy}cyclohexanol (3.20 g) and triphenylphosphine (3.60 g) in tetrahydrofuran (20 mL) was added diisopropyl azodicarboxylate (1.9 M toluene solution, 7.3 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (3.00 g), sodium hydrogen carbonate (5.80 g) and dimethyl sulfoxide (16 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (20 mL). N,N'-carbonyldiimidazole (0.59 g) and then 1,8-diazabicyclo[5.4.0]undec-7-ene (0.54 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (1.74 g, 88%).

$^1$H NMR (300 MHz, CDCl$_3$) δ 0.06 (s, 6H), 0.89-0.92 (m, 9H), 1.03 (t, J=7.3, 3 H), 1.41-2.02 (m, 10 H), 2.11 (s, 3 H), 2.62-2.69 (m, 2 H), 3.74-3.88 (m, 3 H), 4.24-4.35 (m, 1 H), 6.88-7.74 (m, 12 H), 8.86 (s, 1 H)

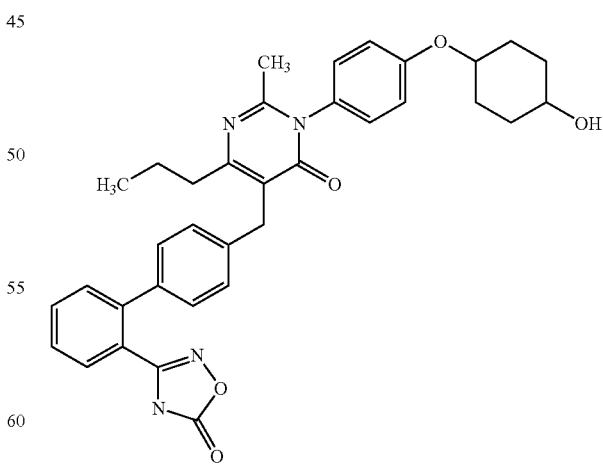

334b) 3-{4-[(4-hydroxycyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one To a solution of 3-{4-[(4-{[tert-butyl(dimethyl)silyl]oxy}cyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (1.74 g) in tetrahydrofuran (6 mL) was added tetrabutylammonium fluoride (1.0 M tetrahydrofuran solution, 3.7 mL), and the mixture was stirred at 60° C. for 12 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a colorless amorphous solid (0.99 g, 68%).

$^1$H NMR (300 MHz, DMSO-$d_6$) δ 0.89 (t, J=7.3, 3 H), 1.26-2.10 (m, 13 H), 2.45-2.55 (m, 2 H), 3.47-3.71 (m, 1 H), 3.86 (s, 2 H), 4.30-4.64 (m, 2 H), 7.01-7.72 (m, 12 H), 12.37 (s, 1 H)

Example 335

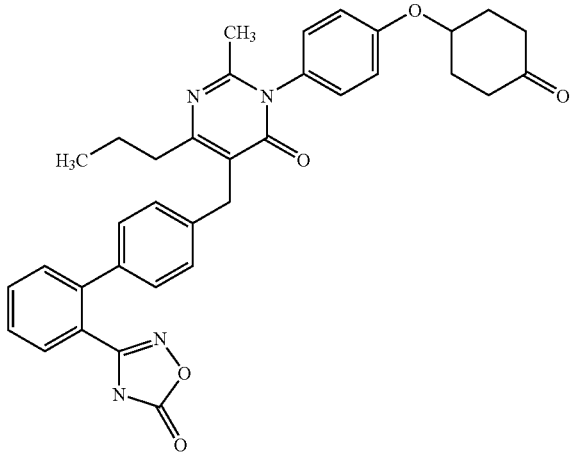

2-methyl-3-{4-[(4-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 3-{4-[(4-hydroxycyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (0.49 g) in methylene chloride (4 mL) was added 1,1,1-tris(acetyloxy)-1,1-dihydro-1,2-benziodoxol-3(1H)-one (0.52 g), and the mixture was stirred for 2 hr. Ethyl acetate, water and sodium thiosulfate were added to the reaction mixture, and the mixture was stirred for 30 min and extracted with ethyl acetate. The organic layer was washed with saturated brine and dried over anhydrous magnesium sulfate. The solvent was evaporated and the residue was purified by silica gel column chromatography to give the title compound as a colorless amorphous solid (0.38 g, 79%).

$^1$H NMR (300 MHz, DMSO-$d_6$) δ 0.89 (t, J=7.4, 3 H), 1.46-1.64 (m, 2 H), 1.97-2.55 (m, 13 H), 3.87 (s, 2 H), 4.81-4.94 (m, 1 H), 7.13-7.73 (m, 12 H), 12.39 (s, 1 H)

Example 336

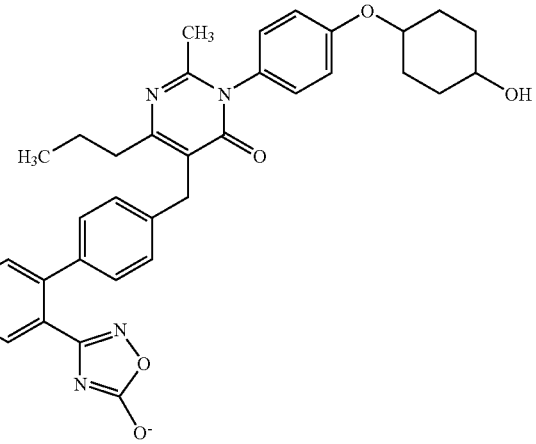

3-{4-[(4-hydroxycyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one potassium salt To a solution of 3-{4-[(4-hydroxycyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (0.30 g) in ethanol (2 mL) was added 8 M potassium hydroxide solution (0.063 mL), and the mixture was stirred at room temperature for 1 hr. The reaction mixture was concentrated under reduced pressure, and the residue was triturated with diisopropyl ether to give the title compound as a colorless amorphous solid (0.29 g, 93%).

$^1$H NMR (300 MHz, DMSO-$d_6$) δ 0.93 (t, J=7.3, 3 H), 1.21-2.10 (m, 13 H), 2.44-2.62 (m, 2 H), 3.47-3.68 (m, 1 H), 3.81 (s, 2 H), 4.31-4.80 (m, 2 H), 7.00-7.51 (m, 12 H)

Example 337

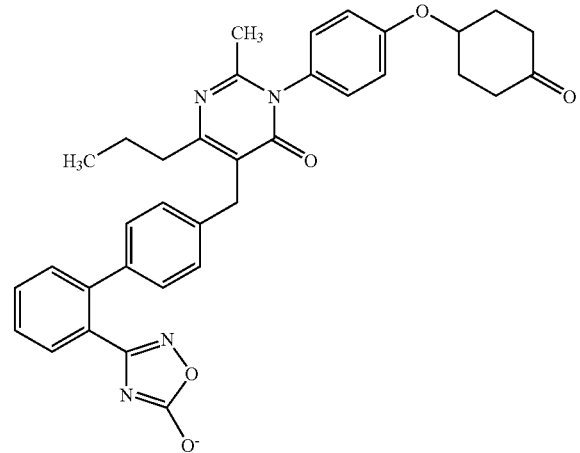

2-methyl-3-{4-[(4-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt To a solution of 2-methyl-3-{4-[(4-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (0.30 g) in ethanol (2 mL) was added 8 M potassium hydroxide solution (0.063 mL), and the mixture was stirred at room temperature for 1 hr. The reaction mixture was concentrated under reduced pressure, and the residue was triturated with diisopropyl ether to give the title compound as a colorless amorphous solid (0.31 g, 98%).

$^1$H NMR (300 MHz, DMSO-$d_6$) δ 0.93 (t, J=7.3, 3 H), 1.51-1.68 (m, 2 H), 1.99-2.23 (m, 7 H), 2.31-2.58 (m, 6 H), 3.82 (s, 2 H), 4.83-4.92 (m, 1 H), 7.11-7.51 (m, 12 H)

Example 338

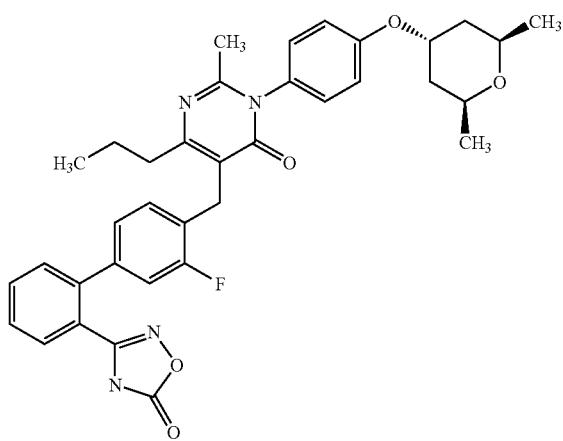

3-(4-{[(2R,4s,6S)-2,6-dimethyltetrahydro-2H-pyran-4-yl]oxy}phenyl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one To a solution of 3'-fluoro-4'-{[1-(4-hydroxyphenyl)-2-methyl-6-oxo-4-propyl-1,6-dihydropyrimidin-5-yl]methyl}biphenyl-2-carbonitrile (0.50 g), (2R,4s,6S)-2,6-dimethyltetrahydro-2H-pyran-4-ol (0.29 g) and triphenylphosphine (0.58 g) in tetrahydrofuran (2 mL) was added diisopropyl azodicarboxylate (1.9 M toluene solution, 1.16 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (1.15 g), sodium hydrogen carbonate (1.85 g) and dimethyl sulfoxide (6 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (6 mL). N,N'-carbonyldiimidazole (0.21 g) and then 1,8-diazabicyclo[5.4.0]undec-7-ene (0.20 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless solid (0.52 g, 76%).

$^1$H NMR (300 MHz, DMSO-$d_6$) δ 0.89 (t, J=7.3, 3 H), 1.08 (d, J=6.2, 6 H), 1.36-1.63 (m, 4 H), 1.79-1.90 (m, 2 H), 2.08 (s, 3 H), 3.75-3.89 (m, 4 H), 4.80-4.87 (m, 1 H), 6.97-7.74 (m, 11 H), 12.47 (s, 1 H)

Example 339

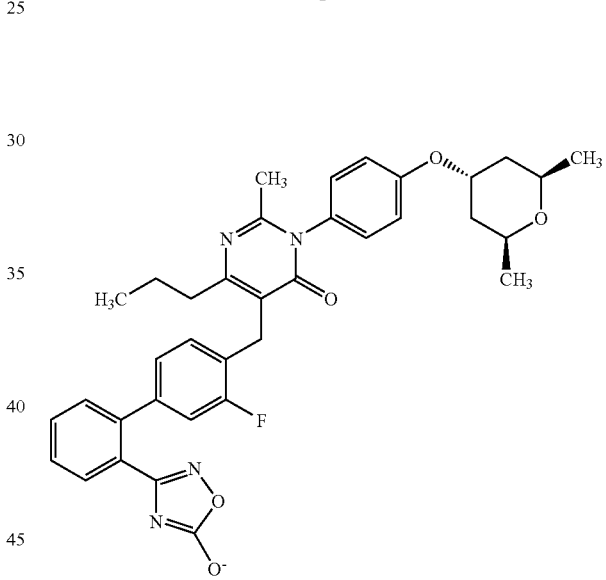

3-(4-{[(2R,4s,6S)-2,6-dimethyltetrahydro-2H-pyran-4-yl]oxy}phenyl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one potassium salt To a solution of 3-(4-{[(2R,4s,6S)-2,6-dimethyltetrahydro-2H-pyran-4-yl]oxy}phenyl)-5-{[3-fluoro-2'-(5-oxo-4,5-dihydro-1,2,4-oxadiazol-3-yl)biphenyl-4-yl]methyl}-2-methyl-6-propylpyrimidin-4(3H)-one (0.30 g) in ethanol (3 mL) was added 8 M potassium hydroxide solution (0.060 mL), and the mixture was stirred at room temperature for 1 hr. The reaction mixture was concentrated under reduced pressure, and the residue was triturated with diisopropyl ether to give the title compound as a colorless amorphous solid (0.27 g, 85%).

¹H NMR (300 MHz, DMSO-d₆) δ 0.92 (t, J=7.4, 3 H), 1.08 (d, J=6.4, 6 H), 1.35-1.67 (m, 4 H), 1.80-1.90 (m, 2 H), 2.07 (s, 3 H), 2.47-2.55 (m, 2 H), 3.76-3.90 (m, 4 H), 4.79-4.88 (m, 1 H), 6.98-7.52 (m, 11 H)

Example 340

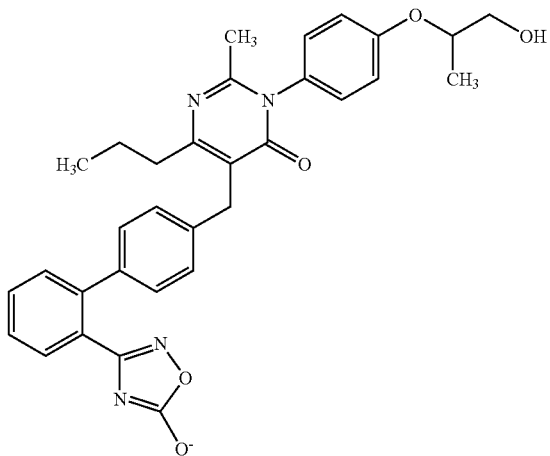

3-[4-(2-hydroxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one potassium salt To a solution of 3-[4-(2-hydroxy-1-methylethoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one (0.10 g) in ethanol (1 mL) was added 8 M potassium hydroxide solution (0.023 mL), and the mixture was stirred at room temperature for 1 hr. The reaction mixture was concentrated under reduced pressure, and the residue was triturated with diisopropyl ether to give the title compound a a colorless amorphous solid (0.11 g, 100%).

¹H NMR (300 MHz, DMSO-d₆) δ 0.93 (t, J=7.4, 3 H), 1.24 (d, J=6.1, 3 H), 1.46-1.70 (m, 2 H), 2.06 (s, 3 H), 2.42-2.62 (m, 2 H), 3.42-3.64 (m, 2 H), 3.81 (s, 2 H), 4.37-4.57 (m, 1 H), 4.68-5.13 (m, 1 H), 6.95-7.51 (m, 12 H)

Example 341

5-{[3-fluoro-2'-(5-oxo-4,5-dihydro-1,2,4-oxadiazol-3-yl)biphenyl-4-yl]methyl}-3-[4-(2-hydroxy-1,1-dimethylethoxy)phenyl]-2-methyl-6-propylpyrimidin-4(3H)-one

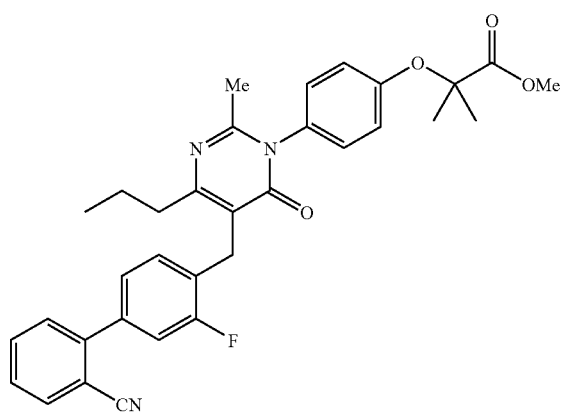

341a) methyl 2-{4-[5-[(2'-cyano-3-fluorobiphenyl-4-yl)methyl]-2-methyl-6-oxo-4-propylpyrimidin-1(6H)-yl]phenoxy}-2-methylpropanoate To a solution of 3'-fluoro-4'-{[1-(4-hydroxyphenyl)-2-methyl-6-oxo-4-propyl-1,6-dihydropyrimidin-5-yl]methyl}biphenyl-2-carbonitrile (0.50 g) and methyl 2-bromo-2-methylpropanoate (1.00 g) in N,N-dimethylformamide (5 mL) was added cesium carbonate (0.72 g), and the mixture was stirred at 80° C. for 12 hr. After allowing to cool, ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.58 g, 96%).

¹H NMR (300 MHz, CDCl₃) δ 1.00 (t, J=7.3, 3 H), 1.60-1.78 (m, 8 H), 2.16 (s, 3 H), 2.59-2.68 (m, 2 H), 3.78 (s, 3 H), 3.98 (s, 2 H), 6.89-7.78 (m, 11 H)

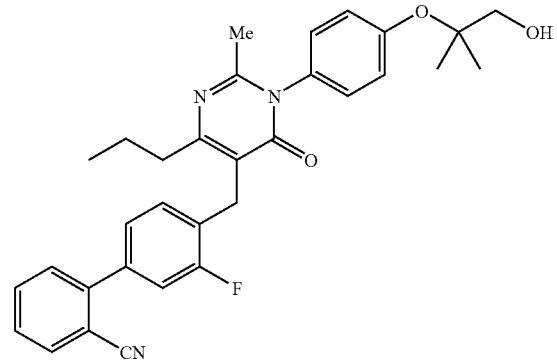

341b) 3'-fluoro-4'-({1-[4-(2-hydroxy-1,1-dimethylethoxy)phenyl]-2-methyl-6-oxo-4-propyl-1,6-dihydropyrimidin-5-yl}methyl)biphenyl-2-carbonitrile To a solution of methyl 2-{4-[5-[(2'-cyano-3-fluorobiphenyl-4-yl)methyl]-2-methyl-6-oxo-4-propylpyrimidin-1(6H)-yl]phenoxy}-2-methylpropanoate (1.00 g) in tetrahydrofuran (11 mL) was added lithium tetrahydroborate (0.056 g), and the mixture was stirred for 24 hr. Ethyl acetate and water were added, to the reaction mixture and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.41 g, 73%).

$^1$H NMR (300 MHz, CDCl$_3$) δ 1.01 (t, J=7.3, 3 H), 1.33 (s, 6 H), 1.59-1.77 (m, 2 H), 2.13 (t, J=6.6, 1 H), 2.17 (s, 3 H), 2.61-2.67 (m, 2 H), 3.62 (d, J=6.4, 2 H), 3.99 (s, 2 H), 7.09-7.78 (m, 11 H)

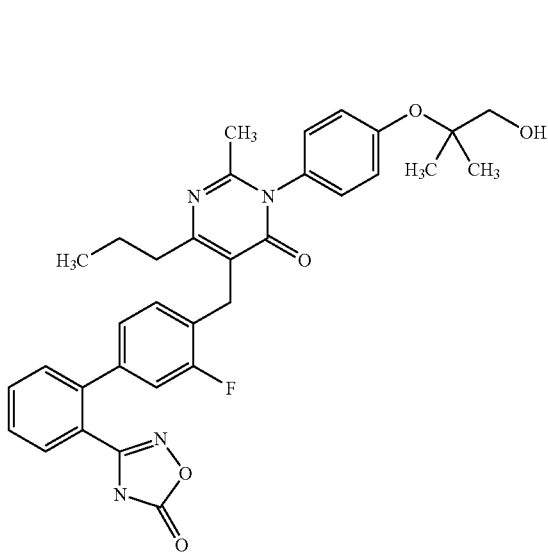

341c) 5-{[3-fluoro-2'-(5-oxo-4,5-dihydro-1,2,4-oxa-diazol-3-yl)biphenyl-4-yl]methyl}-3-[4-(2-hydroxy-1,1-dimethylethoxy)phenyl]-2-methyl-6-propylpyrimidin-4(3H)-one A mixture of hydroxylammonium chloride (0.81 g), sodium hydrogen carbonate (1.29 g) and dimethyl sulfoxide (4 mL) was stirred at 40° C. for 30 min, 3'-fluoro-4'-({1-[4-(2-hydroxy-1,1-dimethylethoxy)phenyl]-2-methyl-6-oxo-4-propyl-1,6-dihydropyrimidin-5-yl}methyl)biphenyl-2-carbonitrile (0.41 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (4 mL). N,N'-carbonyldiimidazole (0.15 g) and then 1,8-diazabicyclo[5.4.0]undec-7-ene (0.14 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless amorphous solid (0.28 g, 61%).

$^1$H NMR (300 MHz, DMSO-d$_6$) δ 0.89 (t, J=7.2, 3 H), 1.24 (s, 6 H), 1.47-1.64 (m, 2 H), 2.07 (s, 3 H), 2.46-2.53 (m, 2 H), 3.41 (d, J=5.3, 2 H), 3.86 (s, 2 H), 4.96 (t, J=5.7, 1 H), 6.99-7.74 (m, 11 H), 12.47 (s, 1 H)

Example 342

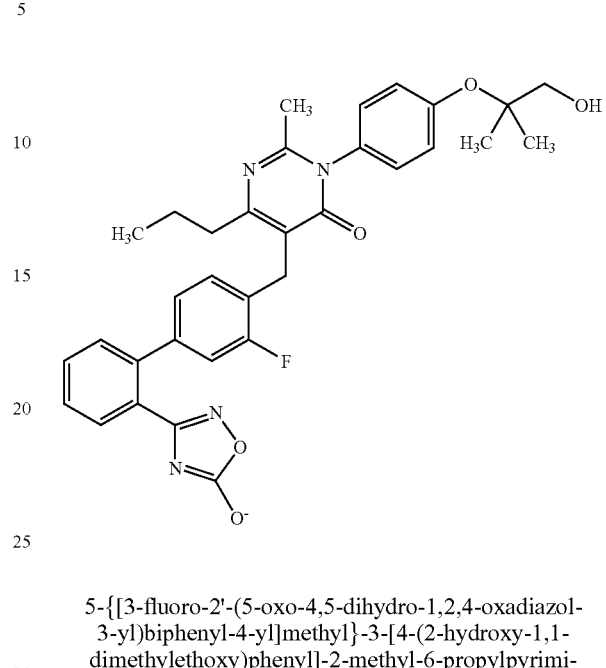

5-{[3-fluoro-2'-(5-oxo-4,5-dihydro-1,2,4-oxadiazol-3-yl)biphenyl-4-yl]methyl}-3-[4-(2-hydroxy-1,1-dimethylethoxy)phenyl]-2-methyl-6-propylpyrimidin-4(3H)-one potassium salt To a solution of 5-{[3-fluoro-2'-(5-oxo-4,5-dihydro-1,2,4-oxadiazol-3-yl)biphenyl-4-yl]methyl}-3-[4-(2-hydroxy-1,1-dimethylethoxy)phenyl]-2-methyl-6-propylpyrimidin-4(3H)-one (0.20 g) in ethanol (2 mL) was added 8 M potassium hydroxide solution (0.043 mL), and the mixture was stirred at room temperature for 1 hr. The reaction mixture was concentrated under reduced pressure, and the residue was triturated with diisopropyl ether to give the title compound as a colorless amorphous solid (0.21 g, 98%).

$^1$H NMR (300 MHz, DMSO-d$_6$) δ 0.92 (t, J=7.3, 3H), 1.24 (s, 6H), 1.50-1.68 (m, 2H), 2.06 (s, 3H), 2.48-2.57 (m, 2H), 3.41 (s, 2H), 3.82 (s, 2H), 6.99-7.55 (m, 11H)

Example 343

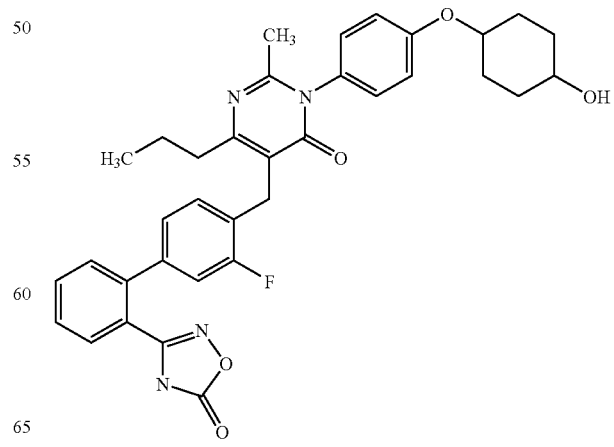

5-{[3-fluoro-2'-(5-oxo-4,5-dihydro-1,2,4-oxadiazol-3-yl)biphenyl-4-yl]methyl}-3-{4-[(4-hydroxycyclohexyl)oxy]phenyl}-2-methyl-6-propylpyrimidin-4(3H)-one To a solution of 3'-fluoro-4'-{[1-(4-hydroxyphenyl)-2-methyl-6-oxo-4-propyl-1,6-dihydropyrimidin-5-yl]methyl}biphenyl-2-carbonitrile (1.23 g), 4-{[tert-butyl(dimethyl)silyl]oxy}cyclohexanol (1.25 g) and triphenylphosphine (1.42 g) in tetrahydrofuran (5 mL) was added diisopropyl azodicarboxylate (1.9 M toluene solution, 2.9 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (2.26 g), sodium hydrogen carbonate (3.42 g) and dimethyl sulfoxide (14 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (14 mL). N,N'-carbonyldiimidazole (0.57 g) and then 1,8-diazabicyclo[5.4.0]undec-7-ene (0.54 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure. The residue was dissolved in tetrahydrofuran (6 mL), tetrabutylammonium fluoride (1.0 M tetrahydrofuran solution, 3.7 mL) was added, and the mixture was stirred at 60° C. for 12 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a colorless amorphous solid (0.71 g, 43%).

$^1$H NMR (300 MHz, DMSO-$d_6$) δ 0.89 (t, J=7.3, 3H), 1.28-1.94 (m, 10H), 2.06-2.10 (m, 3H), 2.45-2.53 (m, 2H), 3.47-3.69 (m, 1H), 3.85 (s, 2H), 4.29-4.63 (m, 2H), 6.95-7.75 (m, 11H), 12.44 (s, 1H)

Example 344

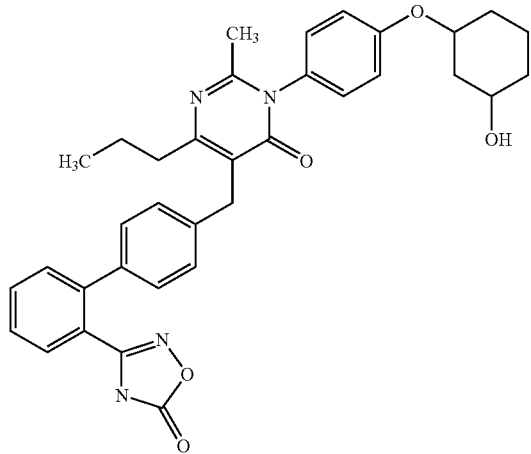

3-{4-[(3-hydroxycyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (1.00 g), 3-{[tert-butyl(dimethyl)silyl]oxy}cyclohexanol (1.06 g) and triphenylphosphine (1.21 g) in tetrahydrofuran (5 mL) was added diisopropyl azodicarboxylate (1.9 M toluene solution, 2.4 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (1.90 g), sodium hydrogen carbonate (2.90 g) and dimethyl sulfoxide (12 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (12 mL). N,N'-carbonyldiimidazole (0.49 g) and then 1,8-diazabicyclo[5.4.0]undec-7-ene (0.45 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure. The residue was dissolved in tetrahydrofuran (6 mL), tetrabutylammonium fluoride (1.0 M tetrahydrofuran solution, 3.5 mL) was added, and the mixture was stirred at 60° C. for 12 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a colorless amorphous solid (0.69 g, 50%).

$^1$H NMR (300 MHz, DMSO-$d_6$) δ 0.89 (t, J=7.3, 3H), 1.04-2.34 (m, 13H), 2.46-2.54 (m, 2H), 3.45-3.97 (m, 3H), 4.24-4.79 (m, 2H), 6.99-7.73 (m, 12H), 12.37 (s, 1H)

Example 345

3-(4-{[(1S,2S)-2-hydroxycyclohexyl]oxy}phenyl)-2-methyl-5-{[2'-(5-oxo-4,5-dihydro-1,2,4-oxadiazol-3-yl)biphenyl-4-yl]methyl}-6-propylpyrimidin-4(3H)-one

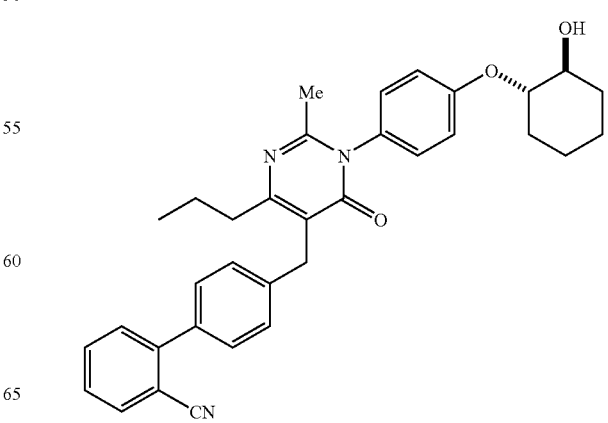

345a) 4'-{[1-(4-{[(1S,2S)-2-hydroxycyclohexyl]oxy}phenyl)-2-methyl-6-oxo-4-propyl-1,6-dihydropyrimidin-5-yl]methyl}biphenyl-2-carbonitrile To a solution of 4'-{[1-(4-hydroxyphenyl)-2-methyl-6-oxo-4-propyl-1,6-dihydropyrimidin-5-yl]methyl}biphenyl-2-carbonitrile (1.0 g) and cyclohexene oxide (1.20 mL) in N,N-dimethylformamide (10 mL) was added cesium carbonate (2.25 g), and the mixture was stirred at 100° C. for 20 hr. After allowing to cool, ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.93 g, 76%).

$^1$H NMR (300 MHz, CDCl$_3$) δ 1.01 (t, J=7.4, 3H), 1.23-1.51 (m, 4H), 1.61-1.84 (m, 4H), 2.06-2.23 (m, 5H), 2.56 (d, J=1.5, 1H), 2.59-2.71 (m, 2H), 3.68-3.80 (m, 1H), 3.96 (s, 2H), 3.98-4.09 (m, 1H), 7.01-7.77 (m, 12H)

345b) 3-(4-{[(1S,2S)-2-hydroxycyclohexyl]oxy}phenyl)-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.46 g), sodium hydrogen carbonate (2.21 g) and dimethyl sulfoxide (10 mL) was stirred at 40° C. for 30 min, 4'-{[1-(4-{[(1S,2S)-2-hydroxycyclohexyl]oxy}phenyl)-2-methyl-6-oxo-4-propyl-1,6-dihydropyrimidin-5-yl]methyl}biphenyl-2-carbonitrile (0.94 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.34 g) and then 1,8-diazabicyclo[5.4.0]undec-7-ene (0.31 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless amorphous solid (0.077 g, 45%).

$^1$H NMR (300 MHz, DMSO-d$_6$) δ 0.89 (t, J=7.3, 3H), 1.20-2.14 (m, 13H), 2.45-2.54 (m, 2H), 3.48-3.60 (m, 1H), 3.86 (s, 2H), 4.04-4.15 (m, 1H), 4.93 (d, J=4.3, 1H), 7.04-7.73 (m, 12H), 12.37 (s, 1H)

Example 346

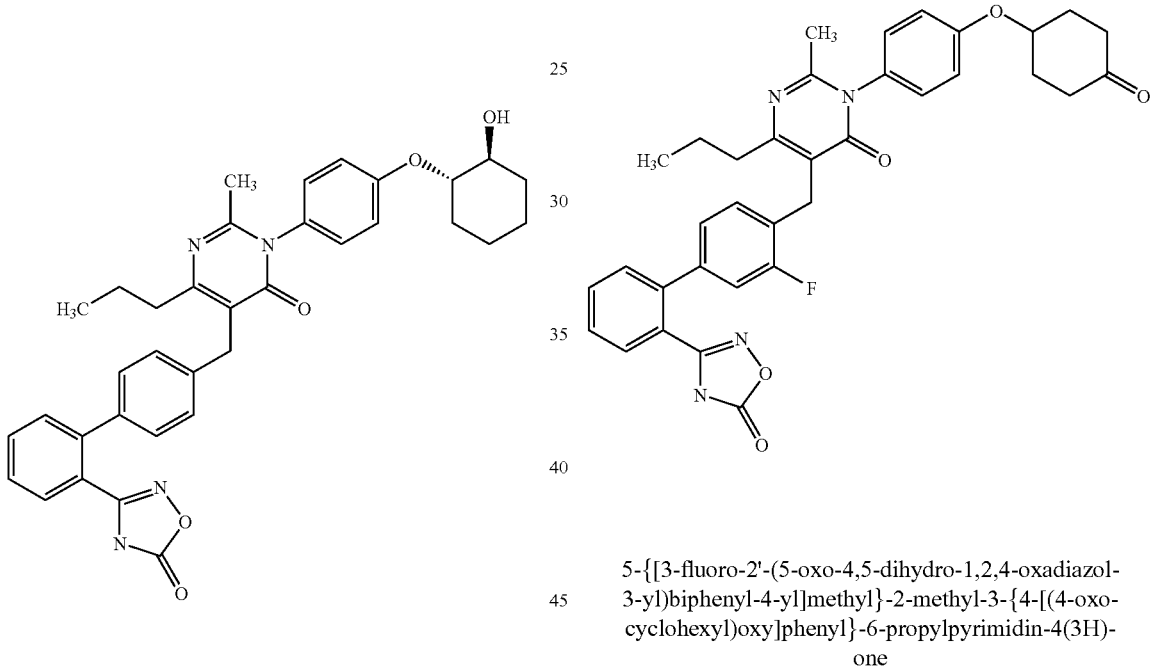

5-{[3-fluoro-2'-(5-oxo-4,5-dihydro-1,2,4-oxadiazol-3-yl)biphenyl-4-yl]methyl}-2-methyl-3-{4-[(4-oxocyclohexyl)oxy]phenyl}-6-propylpyrimidin-4(3H)-one To a solution of 5-{[3-fluoro-2'-(5-oxo-4,5-dihydro-1,2,4-oxadiazol-3-yl)biphenyl-4-yl]methyl}-3-{4-[(4-hydroxycyclohexyl)oxy]phenyl}-2-methyl-6-propylpyrimidin-4(3H)-one (0.40 g) in methylene chloride (4 mL) was added 1,1,1-tris(acetyloxy)-1,1-dihydro-1,2-benziodoxol-3(1H)-one (0.42 g), and the mixture was stirred for 15 hr. Ethyl acetate, water and sodium thiosulfate were added to the reaction mixture, and the mixture was stirred for 30 min and extracted with ethyl acetate. The organic layer was washed with saturated brine and dried over anhydrous magnesium sulfate. The solvent was evaporated and the residue was purified by silica gel column chromatography to give the title compound as a colorless amorphous solid (0.35 g, 88%).

$^1$H NMR (300 MHz, DMSO-d$_6$) δ 0.89 (t, J=7.2, 3 H), 1.48-1.64 (m, 2 H), 1.97-2.23 (m, 7 H), 2.29-2.49 (m, 6 H), 3.86 (s, 2 H), 4.81-4.93 (m, 1 H), 6.97-7.75 (m, 11 H), 12.46 (s, 1 H)

Example 347

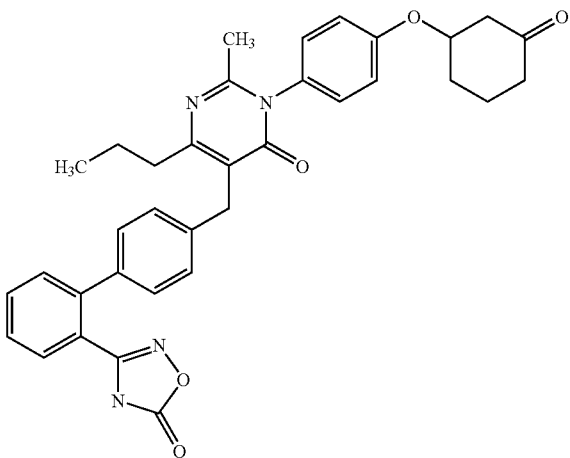

2-methyl-3-{4-[(3-oxocyclohexyl)oxy]phenyl}-5-
{[2'-(5-oxo-4,5-dihydro-1,2,4-oxadiazol-3-yl)biphe-
nyl-4-yl]methyl}-6-propylpyrimidin-4(3H)-one To a solution of 3-{4-[(3-hydroxycyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (0.40 g) in methylene chloride (4 mL) was added 1,1,1-tris(acetyloxy)-1,1-dihydro-1,2-benziodoxol-3(1H)-one (0.43 g), and the mixture was stirred for 15 hr. Ethyl acetate, water and sodium thiosulfate were added to the reaction mixture, and the mixture was stirred for 30 min and extracted with ethyl acetate. The organic layer was washed with saturated brine and dried over anhydrous magnesium sulfate. The solvent was evaporated and the residue was purified by silica gel column chromatography to give the title compound as a colorless amorphous solid (0.33 g, 84%).

$^1$H NMR (300 MHz, DMSO-d$_6$) δ 0.89 (t, J=7.3, 3 H), 1.47-1.62 (m, 2 H), 1.71-2.12 (m, 7 H), 2.22-2.86 (m, 6 H), 3.86 (s, 2 H), 4.95-5.03 (m, 1 H), 7.00-7.73 (m, 12 H), 12.38 (s, 1 H)

Example 348

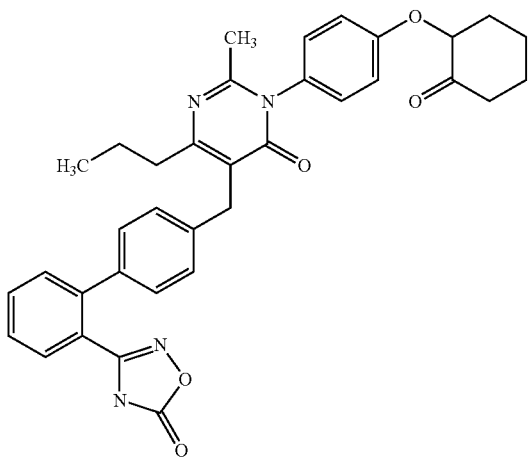

2-methyl-3-{4-[(2-oxocyclohexyl)oxy]phenyl}-5-
{[2'-(5-oxo-4,5-dihydro-1,2,4-oxadiazol-3-yl)biphe-
nyl-4-yl]methyl}-6-propylpyrimidin-4(3H)-one To a solution of 3-(4-{[(1S,2S)-2-hydroxycyclohexyl]oxy}phenyl)-2-methyl-5-{[2'-(5-oxo-4,5-dihydro-1,2,4-oxadiazol-3-yl)biphenyl-4-yl]methyl}-6-propylpyrimidin-4(3H)-one (0.30 g) in methylene chloride (3 mL) was added 1,1,1-tris(acetyloxy)-1,1-dihydro-1,2-benziodoxol-3(1H)-one (0.32 g), and the mixture was stirred for 15 hr. Ethyl acetate, water and sodium thiosulfate were added to the reaction mixture, and the mixture was stirred for 30 min and extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.27 g, 90%).

$^1$H NMR (300 MHz, DMSO-d$_6$) δ 0.89 (t, J=7.3, 3 H), 2.23-2.77 (m, 5 H), 3.86 (s, 2 H), 5.05-5.14 (m, 1 H), 6.92-7.73 (m, 12 H), 12.37 (s, 1 H)

Example 349

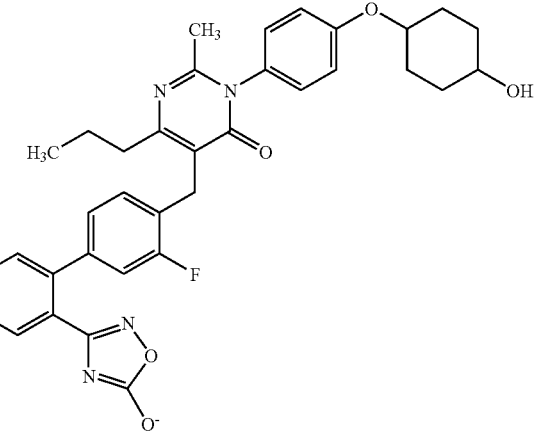

5-{[3-fluoro-2'-(5-oxo-4,5-dihydro-1,2,4-oxadiazol-
3-yl)biphenyl-4-yl]methyl}-3-{4-[(4-hydroxycyclo-
hexyl)oxy]phenyl}-2-methyl-6-propylpyrimidin-4
(3H)-one potassium salt To a solution of 5-{[3-fluoro-2'-(5-oxo-4,5-dihydro-1,2,4-oxadiazol-3-yl)biphenyl-4-yl]methyl}-3-{4-[(4-hydroxycyclohexyl)oxy]phenyl}-2-methyl-6-propylpyrimidin-4(3H)-one (0.20 g) in ethanol (2 mL) was added 8 M potassium hydroxide solution (0.041 mL), and the mixture was stirred at room temperature for 1 hr. The reaction mixture was concentrated under reduced pressure, and the residue was triturated with diisopropyl ether to give the title compound as a colorless amorphous solid (0.19 g, 86%).

$^1$H NMR (300 MHz, DMSO-d$_6$) δ 0.92 (t, J=7.3, 3 H), 1.25-2.11 (m, 10 H), 2.47-2.54 (m, 2 H), 3.46-3.68 (m, 1 H), 3.81 (s, 2 H), 4.31-4.65 (m, 2 H), 6.96-7.54 (m, 11 H)

Example 350

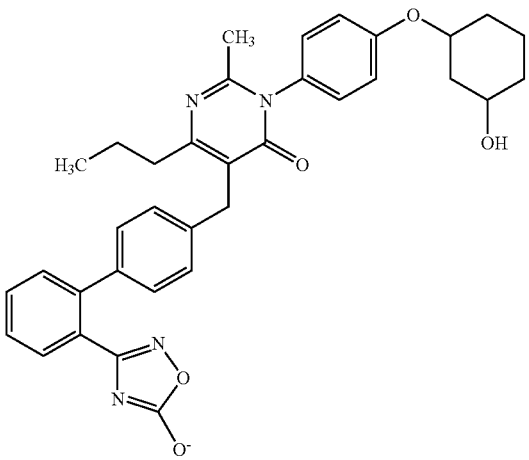

3-{4-[(3-hydroxycyclohexyl)oxy]phenyl}-2-methyl-
5-{[2'-(5-oxo-4,5-dihydro-1,2,4-oxadiazol-3-yl)bi-
phenyl-4-yl]methyl}-6-propylpyrimidin-4(3H)-one
potassium salt To a solution of 3-{4-[(3-hydroxycyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (0.20 g) in ethanol (2 mL) was added 8 M potassium hydroxide solution (0.041 mL), and the mixture was stirred at room temperature for 1 hr. The reaction mixture was concentrated under reduced pressure, and the residue was triturated with diisopropyl ether to give the title compound as a colorless amorphous solid (0.19 g, 86%).

$^1$H NMR (300 MHz, DMSO-$d_6$) δ 0.93 (t, J=7.3, 3 H), 1.07-2.34 (m, 10 H), 2.47-2.56 (m, 2 H), 3.44-3.97 (m, 3 H), 4.23-4.79 (m, 2 H), 6.97-7.50 (m, 12 H)

Example 351

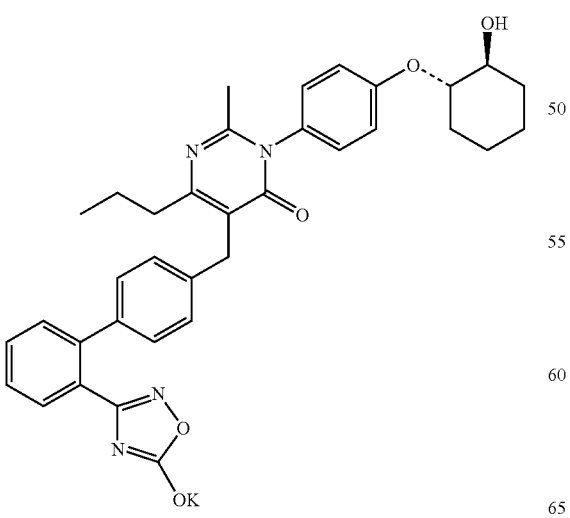

3-(4-{[(1S,2S)-2-hydroxycyclohexyl]oxy}phenyl)-2-
methyl-5-{[2'-(5-oxo-4,5-dihydro-1,2,4-oxadiazol-3-
yl)biphenyl-4-yl]methyl}-6-propylpyrimidin-4(3H)-
one potassium salt To a solution of 3-(4-{[(1S,2S)-2-hydroxycyclohexyl]oxy}phenyl)-2-methyl-5-{[2'-(5-oxo-4,5-dihydro-1,2,4-oxadiazol-3-yl)biphenyl-4-yl]methyl}-6-propylpyrimidin-4(3H)-one (0.20 g) in ethanol (2 mL) was added 8 M potassium hydroxide solution (0.042 mL), and the mixture was stirred at room temperature for 1 hr. The reaction mixture was concentrated under reduced pressure, and the residue was triturated with diisopropyl ether to give the title compound as a colorless amorphous solid (0.18 g, 83%).

$^1$H NMR (300 MHz, DMSO-$d_6$) δ 0.93 (t, J=7.3, 3 H), 1.21-2.12 (m, 13 H), 2.46-2.58 (m, 2 H), 3.46-3.64 (m, 1 H), 3.82 (s, 2 H), 4.02-4.16 (m, 1 H), 4.89-5.00 (m, 1 H), 7.00-7.51 (m, 12 H)

Example 352

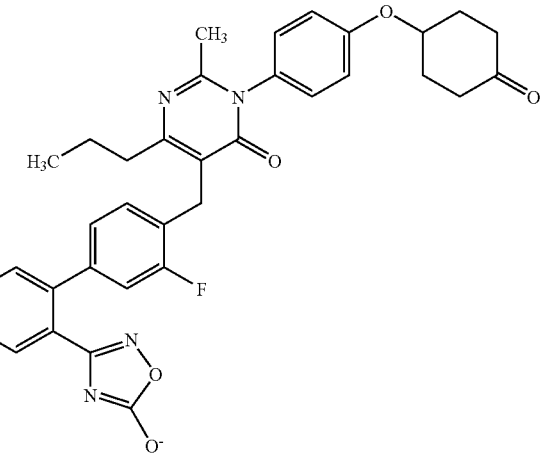

5-{[3-fluoro-2'-(5-oxo-4,5-dihydro-1,2,4-oxadiazol-
3-yl)biphenyl-4-yl]methyl}-2-methyl-3-{4-[(4-oxo-
cyclohexyl)oxy]phenyl}-6-propylpyrimidin-4(3H)-
one potassium salt To a solution of 5-{[3-fluoro-2'-(5-oxo-4,5-dihydro-1,2,4-oxadiazol-3-yl)biphenyl-4-yl]methyl}-2-methyl-3-{4-[(4-oxocyclohexyl)oxy]phenyl}-6-propylpyrimidin-4(3H)-one (0.20 g) in ethanol (2 mL) was added 8 M potassium hydroxide solution (0.041 mL), and the mixture was stirred at room temperature for 1 hr. The reaction mixture was concentrated under reduced pressure, and the residue was triturated with diisopropyl ether to give the title compound as a pale-yellow amorphous solid (0.18 g, 86%).

$^1$H NMR (300 MHz, DMSO-$d_6$) δ 0.92 (t, J=7.3, 3 H), 1.50-1.70 (m, 2 H), 1.94-2.58 (m, 13 H), 3.82 (s, 2 H), 4.81-4.94 (m, 1 H), 6.98-7.53 (m, 11 H)

Example 353

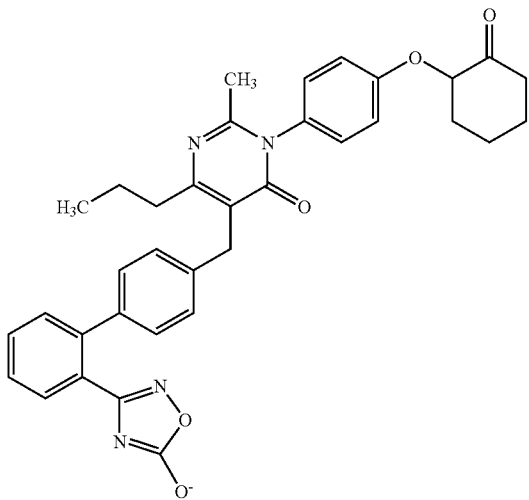

2-methyl-3-{4-[(2-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt To a solution of 2-methyl-3-{4-[(2-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (0.20 g) in ethanol (1.5 mL) was added 8 M potassium hydroxide solution (0.042 mL), and the mixture was stirred at room temperature for 1 hr. The reaction mixture was concentrated under reduced pressure, and the residue was triturated with diisopropyl ether to give the title compound as a pale-yellow amorphous solid (0.19 g, 88%).

$^1$H NMR (300 MHz, DMSO-$d_6$) δ 0.93 (t, J=7.3, 3 H), 1.49-2.74 (m, 15 H), 3.81 (s, 2 H), 5.03-5.15 (m, 1 H), 6.91-7.50 (m, 12 H)

Example 354

3-{4-[(4-hydroxy-4-methylcyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4 (3H)-one To a solution of 4'-{[1-(4-hydroxyphenyl)-2-methyl-6-oxo-4-propyl-1,6-dihydropyrimidin-5-yl]methyl}biphenyl-2-carbonitrile (1.00 g), 1-methylcyclohexane-1,4-diol (0.60 g) and triphenylphosphine (1.21 g) in tetrahydrofuran (5 mL) was added diisopropyl azodicarboxylate (1.9 M toluene solution, 2.42 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (0.73 g), sodium hydrogen carbonate (1.20 g) and dimethyl sulfoxide (4 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.11 g) and then 1,8-diazabicyclo[5.4.0]undec-7-ene (0.10 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless amorphous solid (0.25 g, 17%).

$^1$H NMR (300 MHz, DMSO-$d_6$) δ 0.89 (t, J=7.4, 3 H), 1.15 (s, 3 H), 1.35-1.71 (m, 8 H), 1.85-1.98 (m, 2 H), 2.06 (s, 3 H), 2.47-2.54 (m, 2 H), 3.86 (s, 2 H), 4.20 (s, 1 H), 4.51-4.59 (m, 1 H), 7.01-7.72 (m, 12 H), 12.38 (s, 1 H)

Example 355

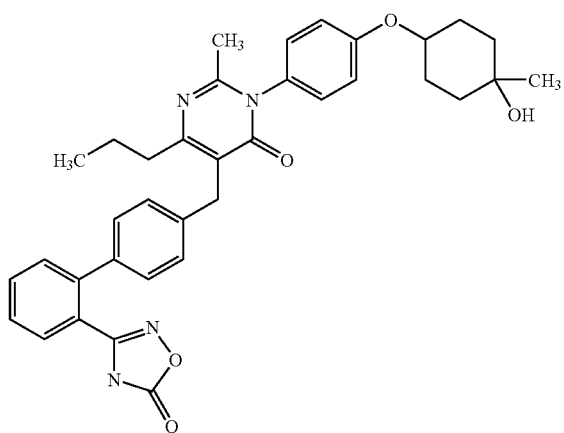

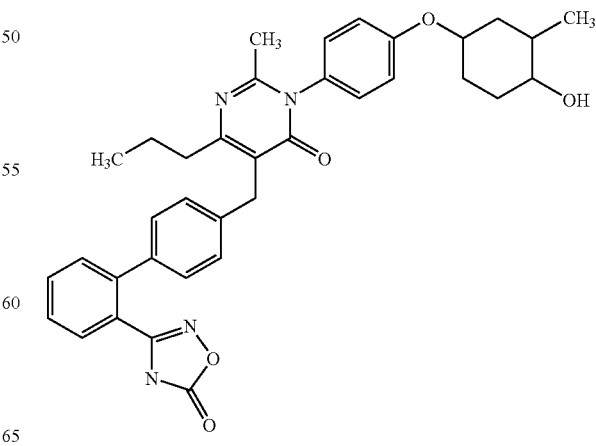

3-{4-[(4-hydroxy-3-methylcyclohexyl)oxy]phenyl}-
2-methyl-5-{[2'-(5-oxo-4,5-dihydro-1,2,4-oxadiazol-
3-yl)biphenyl-4-yl]methyl}-6-propylpyrimidin-4
(3H)-one To a solution of 4'-{[1-(4-hydroxyphenyl)-2-methyl-6-oxo-4-propyl-1,6-dihydropyrimidin-5-yl]methyl}biphenyl-2-carbonitrile (2.00 g), 4-hydroxy-2-methylcyclohexanone (1.18 g) and triphenylphosphine (2.42 g) in tetrahydrofuran (10 mL) was added diisopropyl azodicarboxylate (1.9 M toluene solution, 4.84 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was dissolved in ethanol (20 mL), sodium tetrahydroborate (0.17 g) was added, and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was added to a mixture of hydroxylammonium chloride (1.27 g), sodium hydrogen carbonate (1.85 g) and dimethyl sulfoxide (10 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (8 mL). N,N'-carbonyldiimidazole (0.36 g) and then 1,8-diazabicyclo[5.4.0]undec-7-ene (0.33 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless amorphous solid (0.91 g, 33%).

$^1$H NMR (300 MHz, DMSO-$d_6$) δ 0.82-1.00 (m, 6 H), 1.22-2.16 (m, 12 H), 2.46-2.54 (m, 2 H), 2.93-3.11 (m, 1 H), 3.86 (s, 2 H), 4.26-4.71 (m, 2 H), 6.98-7.73 (m, 12 H), 12.37 (s, 1 H)

Example 356

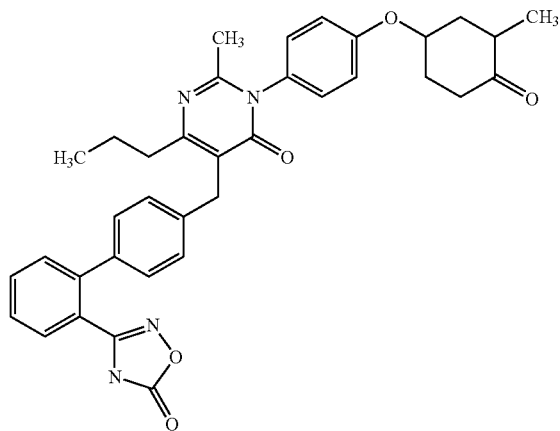

2-methyl-3-{4-[(3-methyl-4-oxocyclohexyl)oxy]
phenyl}-5-{[2'-(5-oxo-4,5-dihydro-1,2,4-oxadiazol-
3-yl)biphenyl-4-yl]methyl}-6-propylpyrimidin-4
(3H)-one To a solution of 3-{4-[(4-hydroxy-3-methylcyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (0.50 g) in methylene chloride (4 mL) was added 1,1,1-tris(acetyloxy)-1,1-dihydro-1,2-benziodoxol-3(1H)-one (0.52 g), and the mixture was stirred for 1 hr. Ethyl acetate, water and sodium thiosulfate were added to the reaction mixture, and the mixture was stirred for 30 min and extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.38 g, 77%).

$^1$H NMR (300 MHz, DMSO-$d_6$) δ 0.83-0.99 (m, 6 H), 1.43-1.63 (m, 2 H), 1.67-2.93 (m, 12 H), 3.87 (s, 2 H), 4.81-5.04 (m, 1 H), 7.10-7.73 (m, 12 H), 12.38 (s, 1 H)

Example 357

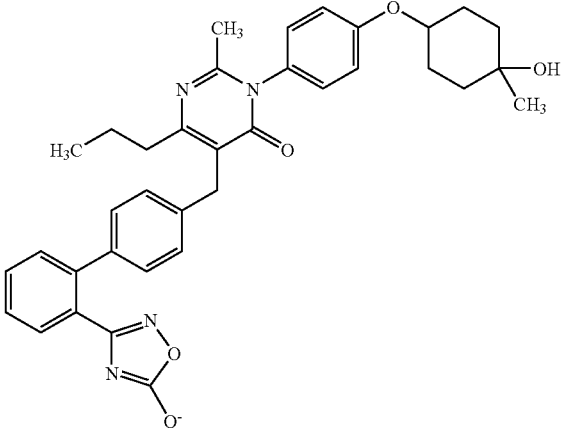

3-{4-[(4-hydroxy-4-methylcyclohexyl)oxy]phenyl}-
2-methyl-5-{[2'-(5-oxo-4,5-dihydro-1,2,4-oxadiazol-
3-yl)biphenyl-4-yl]methyl}-6-propylpyrimidin-4
(3H)-one potassium salt To a solution of 3-{4-[(4-hydroxy-4-methylcyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (0.20 g) in ethanol (2 mL) was added 8 M potassium hydroxide solution (0.041 mL), and the mixture was stirred at room temperature for 1 hr. The reaction mixture was concentrated under reduced pressure, and the residue was triturated with diisopropyl ether to give the title compound as a colorless amorphous solid (0.18 g, 83%).

$^1$H NMR (300 MHz, DMSO-$d_6$) δ 0.93 (t, J=7.3, 3 H), 1.15 (s, 3 H), 1.32-2.00 (m, 10 H), 2.05 (s, 3 H), 2.46-2.57 (m, 2 H), 3.81 (s, 2 H), 4.48-4.59 (m, 1 H), 6.99-7.50 (m, 12 H)

Example 358

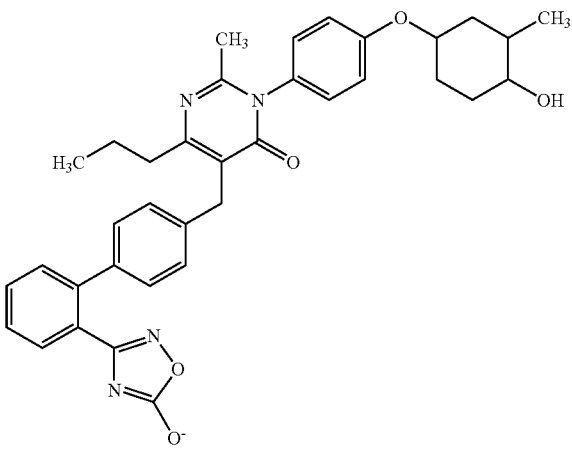

3-{4-[(4-hydroxy-3-methylcyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one potassium salt To a solution of 3-{4-[(4-hydroxy-3-methylcyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (0.30 g) in ethanol (2 mL) was added 8 M potassium hydroxide solution (0.061 mL), and the mixture was stirred at room temperature for 1 hr. The reaction mixture was concentrated under reduced pressure, and the residue was triturated with diisopropyl ether to give the title compound as a colorless amorphous solid (0.30 g, 96%).

$^1$H NMR (300 MHz, DMSO-$d_6$) δ 0.86-0.99 (m, 6 H), 1.23-2.11 (m, 12 H), 2.47-2.57 (m, 2 H), 2.93-3.13 (m, 1 H), 3.81 (s, 2 H), 4.27-4.69 (m, 2 H), 6.98-7.50 (m, 12 H)

Example 359

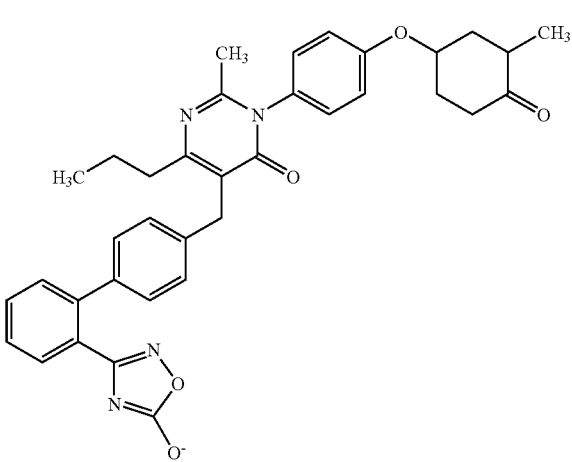

2-methyl-3-{4-[(3-methyl-4-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt To a solution of 2-methyl-3-{4-[(3-methyl-4-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (0.30 g) in ethanol (2.0 mL) was added 8 M potassium hydroxide solution (0.062 mL), and the mixture was stirred at room temperature for 1 hr. The reaction mixture was concentrated under reduced pressure, and the residue was triturated with diisopropyl ether to give the title compound as a pale-yellow amorphous solid (0.31 g, 96%).

$^1$H NMR (300 MHz, DMSO-$d_6$) δ 0.89-0.97 (m, 6 H), 1.44-2.90 (m, 14 H), 3.82 (s, 2 H), 4.84-5.02 (m, 1 H), 7.08-7.49 (m, 12 H)

Example 360

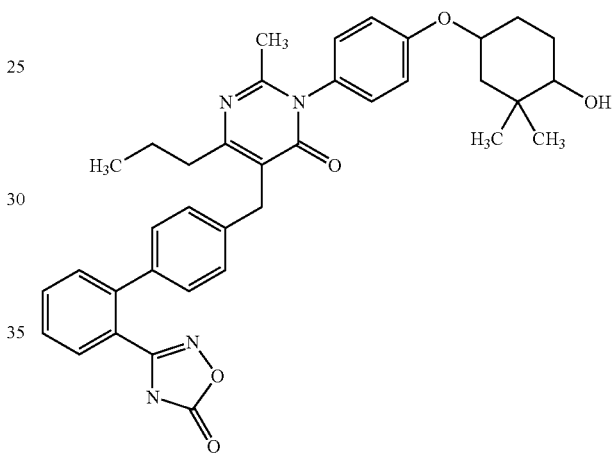

3-{4-[(4-hydroxy-3,3-dimethylcyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (1.00 g), 4-{[tert-butyl(dimethyl)silyl]oxy}-3,3-dimethylcyclohexanol (1.13 g) and triphenylphosphine (1.15 g) in tetrahydrofuran (5 mL) was added diisopropyl azodicarboxylate (1.9 M toluene solution, 2.30 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (1.60 g), sodium hydrogen carbonate (2.32 g) and dimethyl sulfoxide (10 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.41 g) and then 1,8-diazabicyclo[5.4.0]undec-7-ene (0.41 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure. The residue was dissolved in tetrahydrofuran (6 mL), tetrabutylammonium fluoride (1.0 M tetrahydrofuran solution, 5.8 mL) was added, and the mixture was stirred at 60° C. for 12 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a colorless amorphous solid (0.65 g, 46%).

$^1$H NMR (300 MHz, DMSO-$d_6$) δ 0.85-0.98 (m, 9 H), 1.45-1.84 (m, 8 H), 2.07 (s, 3 H), 2.46-2.54 (m, 2 H), 3.20-3.27 (m, 1 H), 3.86 (s, 2 H), 4.43-4.60 (m, 2 H), 6.98-7.73 (m, 12 H), 12.37 (s, 1 H)

Example 361

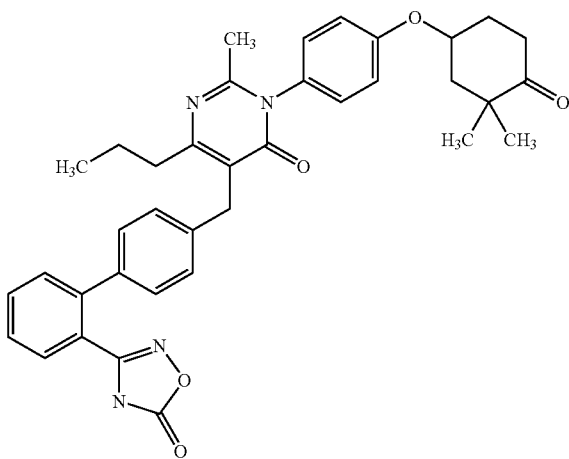

3-{4-[(3,3-dimethyl-4-oxocyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one To a solution of 3-{4-[(4-hydroxy-3,3-dimethylcyclohexyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (0.33 g) in methylene chloride (3 mL) was added 1,1,1-tris(acetyloxy)-1,1-dihydro-1,2-benziodoxol-3(1H)-one (0.34 g), and the mixture was stirred for 1 hr. Ethyl acetate, water and sodium thiosulfate were added to the reaction mixture, and the mixture was stirred for 30 min and extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.20 g, 61%).

$^1$H NMR (300 MHz, DMSO-$d_6$) δ 0.89 (t, J=7.4, 3H), 1.06 (s, 3H), 1.20 (s, 3H), 1.47-1.62 (m, 2H), 1.78-1.91 (m, 2H), 3.87 (s, 2H), 4.94-5.05 (m, 1H), 7.10-7.73 (m, 12H), 12.39 (s, 1H)

Example 362

2-ethyl-3-(4-isopropoxyphenyl)-5-{[2'-(5-oxo-4,5-dihydro-1,2,4-oxadiazol-3-yl)biphenyl-4-yl]methyl}-6-propylpyrimidin-4(3H)-one

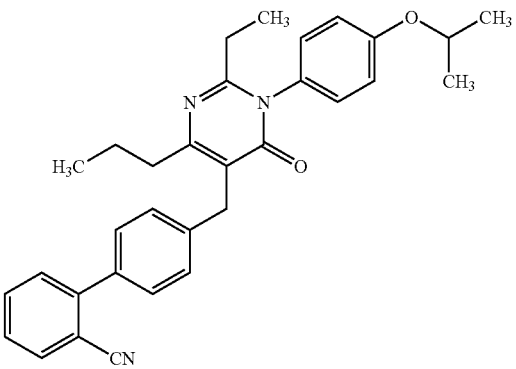

362a) 4'-{[2-ethyl-1-(4-isopropoxyphenyl)-6-oxo-4-propyl-1,6-dihydropyrimidin-5-yl]methyl}biphenyl-2-carbonitrile To a suspension of 4'-[(2-ethyl-6-oxo-4-propyl-1,6-dihydropyrimidin-5-yl)methyl]biphenyl-2-carbonitrile (0.5 g), 4-isopropoxyphenylboronic acid (0.5 g), triethylamine (0.97 mL), pyridine (0.57 mL) and molecular sieves 4 A (1 g) in dichloromethane (10 mL) was added copper(II) acetate (0.51 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow solid (0.51 g, 77%).

$^1$H NMR (300 MHz, CDCl$_3$) δ 1.01 (3H, t, J=7.5), 1.14 (3H, t, J=7.5), 1.36 (6H, d, J=6.0), 1.65-1.79 (2H, m), 2.39 (2H, q, J=7.5), 2.67 (2H, t, J=7.5), 3.97 (2H, s), 4.49-4.64 (1H, m), 6.98 (2H, d, J=8.7), 7.10 (2H, d, J=8.7), 7.36-7.51 (6H, m), 7.57-7.66 (1H, m), 7.74 (1H, d, J=7.8)

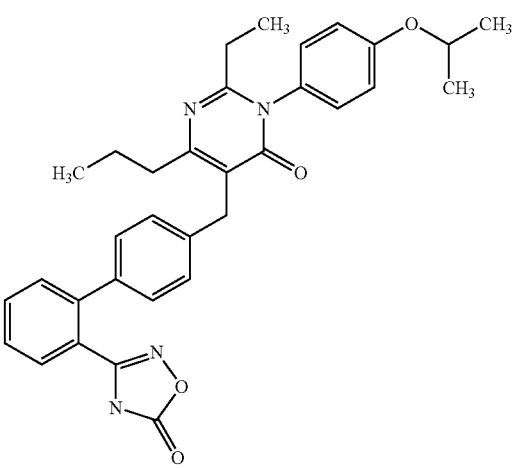

362b) 2-ethyl-3-(4-isopropoxyphenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.2 g), sodium hydrogen carbonate (1.7 g) and dimethyl sulfoxide (10 mL) was stirred at 40° C. for 30 min, 4'-{[2-ethyl-1-(4-isopropoxyphenyl)-6-oxo-4-propyl-1,6-dihydropyrimidin-5-yl]methyl}biphenyl-2-carbonitrile (0.51 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.36 g, 63%).

$^1$H NMR (300 MHz, DMSO-$d_6$) δ 0.90 (3H, t, J=7.5), 1.05 (3H, t, J=7.2), 1.30 (6H, d, J=6.0), 1.50-1.65 (2H, m), 2.28 (2H, q, J=7.2), 2.45-2.58 (2H, m), 3.86 (2H, s), 4.61-4.74 (1H, m), 7.02 (2H, d, J=9.0), 7.18-7.32 (6H, m), 7.46-7.58 (2H, m), 7.61-7.72 (2H, m), 12.39 (1H, br)

Example 363

2-ethyl-3-(3-fluoro-4-isopropoxyphenyl)-5-{[2'-(5-oxo-4,5-dihydro-1,2,4-oxadiazol-3-yl)biphenyl-4-yl]methyl}-6-propylpyrimidin-4(3H)-one

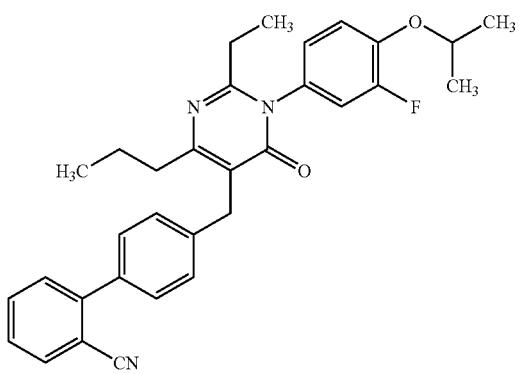

363a) 4'-{[2-ethyl-1-(3-fluoro-4-isopropoxyphenyl)-6-oxo-4-propyl-1,6-dihydropyrimidin-5-yl]methyl}biphenyl-2-carbonitrile To a suspension of 4'-[(2-ethyl-6-oxo-4-propyl-1,6-dihydropyrimidin-5-yl)methyl]biphenyl-2-carbonitrile (0.5 g), 3-fluoro-4-isopropoxyphenylboronic acid (0.55 g), triethylamine (0.97 mL), pyridine (0.57 mL) and molecular sieves 4 A (1 g) in dichloromethane (10 mL) was added copper(II) acetate (0.51 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow solid (0.43 g, 61%).

$^1$H NMR (300 MHz, CDCl$_3$) δ 1.10 (3H, t, J=7.5), 1.16 (3H, t, J=7.5), 1.35-1.45 (6H, m), 1.64-1.80 (2H, m), 2.39 (2H, q, J=7.5), 2.61-2.71 (2H, m), 3.96 (2H, s), 4.52-4.66 (1H, m), 6.89-7.11 (3H, m), 7.37-7.51 (6H, m), 7.57-7.66 (1H, m), 7.74 (1H, d, J=7.8)

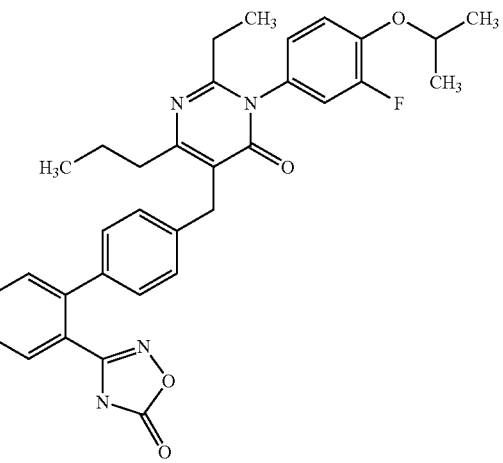

363b) 2-ethyl-3-(3-fluoro-4-isopropoxyphenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.2 g), sodium hydrogen carbonate (1.7 g) and dimethyl sulfoxide (10 mL) was stirred at 40° C. for 30 min, 4'-{[2-ethyl-1-(3-fluoro-4-isopropoxyphenyl)-6-oxo-4-propyl-1,6-dihydropyrimidin-5-yl]methyl}biphenyl-2-carbonitrile (0.43 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.23 g, 48%).

$^1$H NMR (300 MHz, DMSO-$d_6$) δ 0.90 (3H, t, J=7.2), 1.06 (3H, t, J=7.2), 1.20-1.35 (6H, m), 1.49-1.65 (2H, m), 2.31 (2H, q, J=7.2), 2.46-2.58 (2H, m), 3.87 (2H, s), 4.65-4.79 (1H, m), 7.09-7.44 (7H, m), 7.46-7.58 (2H, m), 7.61-7.72 (2H, m), 12.38 (1H, br)

Example 364

3-(4-tert-butoxyphenyl)-2-ethyl-5-{[2'-(5-oxo-4,5-dihydro-1,2,4-oxadiazol-3-yl)biphenyl-4-yl]methyl}-6-propylpyrimidin-4(3H)-one

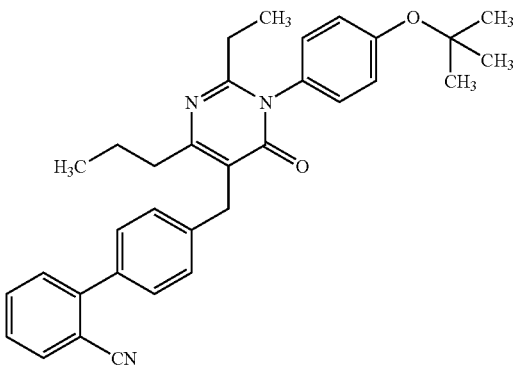

364a) 4'-{[1-(4-tert-butoxyphenyl)-2-ethyl-6-oxo-4-propyl-1,6-dihydropyrimidin-5-yl]methyl}biphenyl-2-carbonitrile To a suspension of 4'-[(2-ethyl-6-oxo-4-propyl-1,6-dihydropyrimidin-5-yl)methyl]biphenyl-2-carbonitrile (0.5 g), 4-tert-butoxyphenylboronic acid (0.54 g), triethylamine (0.97 mL), pyridine (0.57 mL) and molecular sieves 4 A (1 g) in dichloromethane (10 mL) was added copper(II) acetate (0.51 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow solid (0.47 g, 66%).

$^1$H NMR (300 MHz, CDCl$_3$) δ 1.01 (3H, t, J=7.5), 1.13 (3H, t, J=7.5), 1.39 (9H, s), 1.64-1.79 (2H, m), 2.36 (2H, q, J=7.5), 22.62-2.71 (2H, m), 3.97 (2H, s), 7.07-7.14 (4H, m), 7.35-7.51 (6H, m), 7.57-7.66 (1H, m), 7.74 (1H, d, J=7.8)

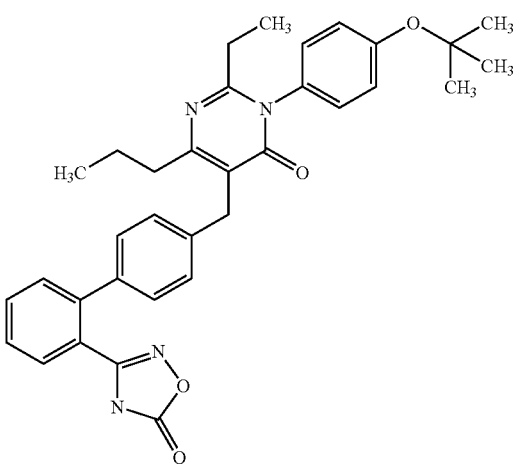

364b) 3-(4-tert-butoxyphenyl)-2-ethyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.2 g), sodium hydrogen carbonate (1.7 g) and dimethyl sulfoxide (10 mL) was stirred at 40° C. for 30 min, 4'-{[1-(4-tert-butoxyphenyl)-2-ethyl-6-oxo-4-propyl-1,6-dihydropyrimidin-5-yl]methyl}biphenyl-2-carbonitrile (0.47 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.28 g, 54%).

$^1$H NMR (300 MHz, DMSO-d$_6$) δ 0.91 (3H, t, J=7.2), 1.05 (3H, t, J=7.2), 1.35 (9H, s), 1.51-1.65 (2H, m), 2.28 (2H, q, J=7.2), 2.51-2.59 (2H, m), 3.87 (2H, s), 7.09 (2H, d, J=8.7), 7.17-7.31 (6H, m), 7.46-7.58 (2H, m), 7.61-7.71 (2H, m), 12.39 (1H, br)

Example 365

2-ethyl-3-[3-(1-hydroxy-1-methylethyl)phenyl]-5-{[2'-(5-oxo-4,5-dihydro-1,2,4-oxadiazol-3-yl)biphenyl-4-yl]methyl}-6-propylpyrimidin-4(3H)-one

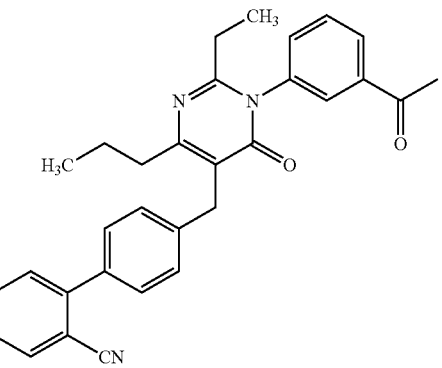

365a) 4'-{[1-(3-acetylphenyl)-2-ethyl-6-oxo-4-propyl-1,6-dihydropyrimidin-5-yl]methyl}biphenyl-2-carbonitrile To a suspension of 4'-[(2-ethyl-6-oxo-4-propyl-1,6-dihydropyrimidin-5-yl)methyl]biphenyl-2-carbonitrile (1.0 g), 3-acetylphenylboronic acid (1.0 g), triethylamine (2.0 mL), pyridine (1.1 mL) and molecular sieves 4 A (2 g) in dichloromethane (20 mL) was added copper(II) acetate (1.0 g), and the mixture was stirred for 2 days. The reaction mixture was diluted with ethyl acetate, the insoluble material was filtered off through celite, and the filtrate was concentrated. The residue was purified by silica gel column chromatography to give the title compound as a colorless solid (0.63 g, 47%).

¹H NMR (300 MHz, CDCl₃) δ 1.02 (3H, t, J=7.5), 1.15 (3H, t, J=7.5), 1.66-1.81 (2H, m), 2.27-2.39 (2H, m), 2.63 (3H, s), 2.65-2.74 (2H, m), 3.97 (2H, s), 7.37-7.52 (7H, m), 7.57-7.69 (2H, m), 7.71-7.77 (1H, m), 7.82 (1H, s), 8.05 (1H, d, J=6.3)

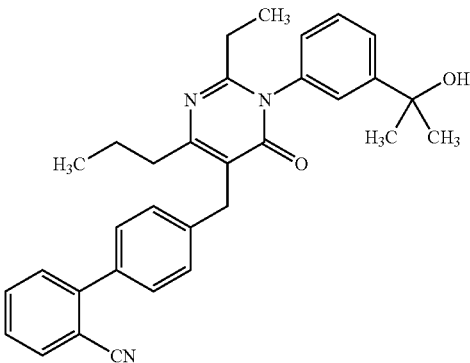

365b) 4'-({2-ethyl-1-[3-(1-hydroxy-1-methylethyl)phenyl]-6-oxo-4-propyl-1,6-dihydropyrimidin-5-yl}methyl)biphenyl-2-carbonitrile To a solution of 4'-{[1-(3-acetylphenyl)-2-ethyl-6-oxo-4-propyl-1,6-dihydropyrimidin-5-yl]methyl}biphenyl-2-carbonitrile (0.63 g) in tetrahydrofuran (10 mL) was added methyllithium (1.2 mL, 2.2 M diethyl ether solution) under ice-cooling, and the mixture was stirred for 1 hr. A saturated aqueous ammonium chloride solution was added to the reaction mixture, and the mixture was extracted with ethyl acetate, washed with saturated brine and dried over anhydrous sodium sulfate. The solvent was evaporated under reduced pressure. The residue was purified by silica gel column chromatography to give the title compound as a pale-yellow solid (0.54 g, 83%).

¹H NMR (300 MHz, CDCl₃) δ 1.01 (3H, t, J=7.5), 1.14 (3H, t, J=7.5), 1.59 (3H, s), 1.61 (3H, s), 1.65-1.81 (2H, m), 2.01 (1H, s), 2.34 (2H, q, J=7.5), 2.63-2.74 (2H, m), 3.89-4.05 (2H, m), 7.10 (1H, d, J=7.5), 7.35-7.66 (10H, m), 7.73 (1H, d, J=7.8)

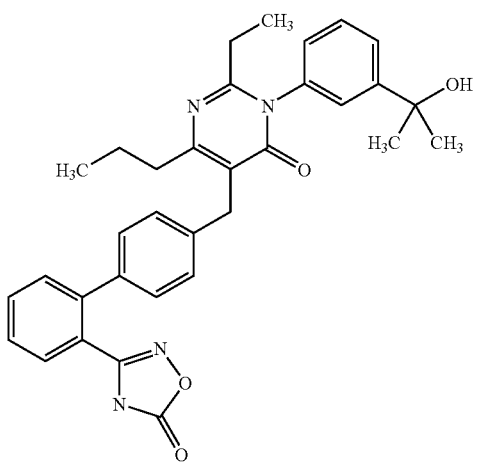

365c) 2-ethyl-3-[3-(1-hydroxy-1-methylethyl)phenyl]-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.3 g), sodium hydrogen carbonate (1.9 g) and dimethyl sulfoxide (10 mL) was stirred at 40° C. for 30 min, 4'-({2-ethyl-1-[3-(1-hydroxy-1-methylethyl)phenyl]-6-oxo-4-propyl-1,6-dihydropyrimidin-5-yl}methyl)biphenyl-2-carbonitrile (0.54 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.22 g) and then 1,8-diazabicyclo[5.4.0]undec-7-ene (0.20 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.39 g, 65%).

¹H NMR (300 MHz, DMSO-d₆) δ 0.91 (3H, t, J=7.5), 1.04 (3H, t, J=7.2), 1.44 (6H, s), 1.50-1.68 (2H, m), 2.25 (2H, q, J=7.2), 2.51-2.60 (2H, m), 3.88 (2H, s), 5.14 (1H, s), 7.13-7.33 (5H, m), 7.36-7.73 (7H, m), 12.39 (1H, br)

Example 366

3-(4-tert-butoxyphenyl)-6-butyl-2-methyl-5-{[2'-(5-oxo-4,5-dihydro-1,2,4-oxadiazol-3-yl)biphenyl-4-yl]methyl}pyrimidin-4(3H)-one

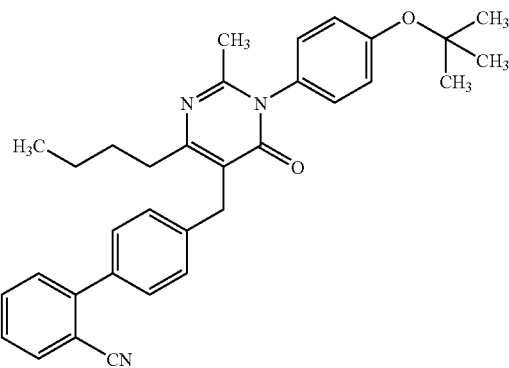

366a) 4'-{[1-(4-tert-butoxyphenyl)-4-butyl-2-methyl-6-oxo-1,6-dihydropyrimidin-5-yl]methyl}biphenyl-2-carbonitrile To a suspension of 4'-[(4-butyl-2-methyl-6-oxo-1,6-dihydropyrimidin-5-yl)methyl]biphenyl-2-carbonitrile (0.5 g), 4-tert-butoxyphenylboronic acid (0.54 g), triethylamine (0.97 mL), pyridine (0.57 mL) and molecular sieves 4 A (1 g) in dichloromethane (10 mL) was added copper(II) acetate (0.54 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow solid (0.51 g, 72%).

¹H NMR (300 MHz, CDCl₃) δ 0.94 (3H, t, J=7.2), 1.30-1.49 (11H, m), 1.55-1.68 (2H, m), 2.10 (3H, s), 2.61-2.71 (2H, m), 3.97 (2H, s), 7.07-7.15 (4H, m), 7.36-7.51 (6H, s), 7.51-7.65 (1H, m), 7.74 (1H, d, J=7.8)

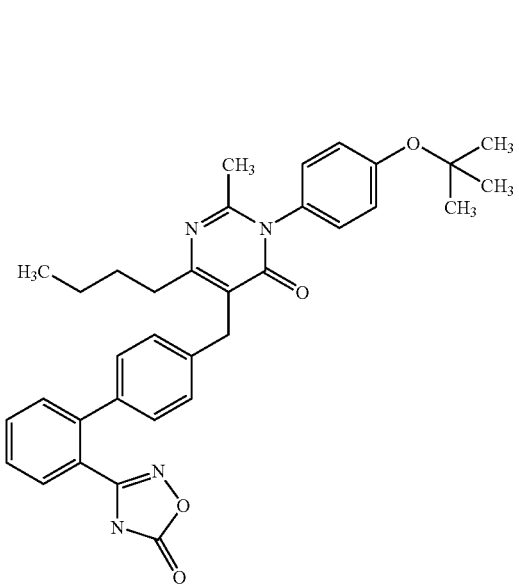

366b) 3-(4-tert-butoxyphenyl)-6-butyl-2-methyl-5-{[2'-(5-oxo-4,5-dihydro-1,2,4-oxadiazol-3-yl)biphenyl-4-yl]methyl}pyrimidin-4(3H)-one A mixture of hydroxylammonium chloride (1.2 g), sodium hydrogen carbonate (1.7 g) and dimethyl sulfoxide (10 mL) was stirred at 40° C. for 30 min, 4'-{[1-(4-tert-butoxyphenyl)-4-butyl-2-methyl-6-oxo-1,6-dihydropyrimidin-5-yl]methyl}biphenyl-2-carbonitrile (0.51 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.27 g, 48%).

¹H NMR (300 MHz, DMSO-d₆) δ 0.86 (3H, t, J=7.2), 1.26-1.39 (11H, m), 1.42-1.57 (2H, m), 2.06 (3H, s), 2.50-2.59 (2H, m), 3.86 (2H, s), 7.10 (2H, d, J=8.7), 7.18-7.31 (6H, m), 7.45-7.57 (2H, m), 7.61-7.71 (2H, m), 12.41 (1H, br)

Example 367

3-[4-(2,2-dimethylpropoxy)phenyl]-2-ethyl-5-{[2'-(5-oxo-4,5-dihydro-1,2,4-oxadiazol-3-yl)biphenyl-4-yl]methyl}-6-propylpyrimidin-43H)-one

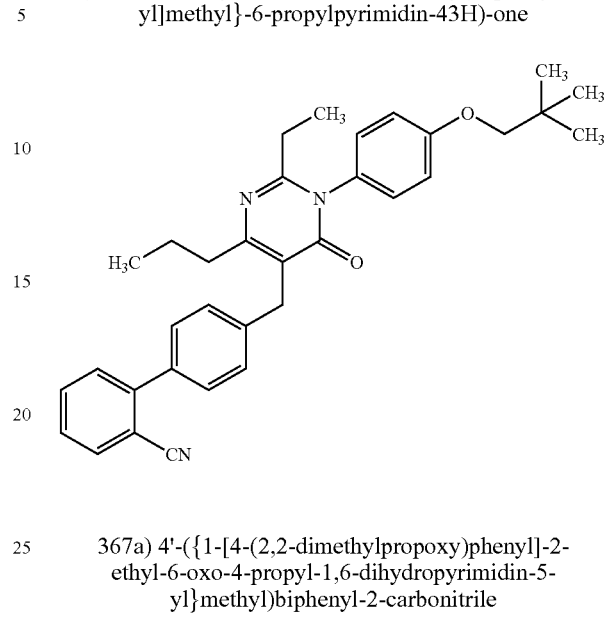

367a) 4'-({1-[4-(2,2-dimethylpropoxy)phenyl]-2-ethyl-6-oxo-4-propyl-1,6-dihydropyrimidin-5-yl}methyl)biphenyl-2-carbonitrile To a solution of 4'-{[2-ethyl-1-(4-hydroxyphenyl)-6-oxo-4-propyl-1,6-dihydropyrimidin-5-yl]methyl}biphenyl-2-carbonitrile (0.4 g) in N,N-dimethylacetamide (10 mL) were added 1-iodo-2,2-dimethylpropane (0.26 g) and cesium carbonate (0.44 g), and the mixture was stirred at 120° C. for 24 hr. The mixture was allowed to cool to room temperature and the insoluble material was filtered off. The filtrate was diluted with ethyl acetate, washed with 1 M hydrochloric acid, saturated sodium hydrogen carbonate and saturated brine, and dried over anhydrous sodium sulfate. The solvent was evaporated under reduced pressure. The residue was purified by silica gel chromatography to give the title compound as a pale-yellow solid (0.40 g, 87%).

¹H NMR (300 MHz, CDCl₃) δ 1.01 (3H, t, J=7.2), 1.04 (9H, s), 1.14 (3H, t, J=7.2), 1.63-1.79 (2H, m), 2.39 (2H, q, J=7.2), 2.61-2.72 (2H, m), 3.62 (2H, s), 3.97 (2H, s), 7.01 (2H, d, J=8.7), 7.11 (2H, d, J=8.7), 7.36-7.51 (6H, m), 7.57-7.65 (1H, m), 7.74 (1H, d, J=7.8)

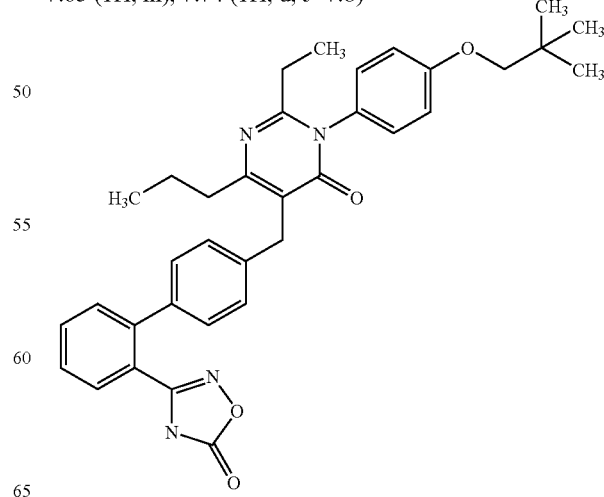

367b) 3-[4-(2,2-dimethylpropoxy)phenyl]-2-ethyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.91 g), sodium hydrogen carbonate (1.3 g) and dimethyl sulfoxide (10 mL) was stirred at 40° C. for 30 min, 4'-({1-[4-(2,2-dimethylpropoxy)phenyl]-2-ethyl-6-oxo-4-propyl-1,6-dihydropyrimidin-5-yl}methyl)biphenyl-2-carbonitrile (0.46 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.19 g) and then 1,8-diazabicyclo[5.4.0]undec-7-ene (0.17 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.33 g, 73%).

$^1$H NMR (300 MHz, DMSO-$d_6$) δ 0.90 (3H, t, J=7.2), 0.98-1.09 (12H, m), 1.50-1.66 (2H, m), 2.28 (2H, q, J=7.2), 2.50-2.58 (2H, m), 3.69 (2H, s), 3.87 (2H, s), 7.05 (2H, d, J=9.0), 7.18-7.32 (6H, m), 7.46-7.58 (2H, m), 7.61-7.71 (2H, m), 12.39 (1H, br)

Example 368

3-(4-isopropoxyphenyl)-2-methoxy-5-{[2'-(5-oxo-4,5-dihydro-1,2,4-oxadiazol-3-yl)biphenyl-4-yl]methyl}-6-propylpyrimidin-4(3H)-one

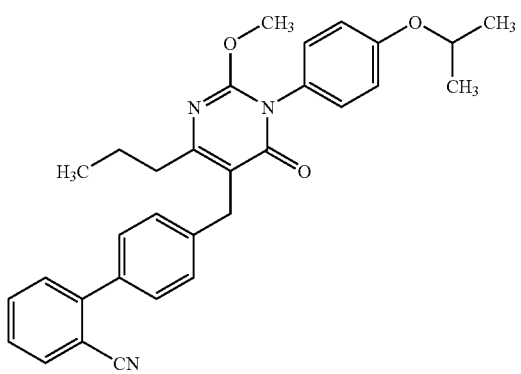

368a) 4'-{[1-(4-isopropoxyphenyl)-2-methoxy-6-oxo-4-propyl-1,6-dihydropyrimidin-5-yl]methyl}biphenyl-2-carbonitrile To a suspension of 4'-[(2-methoxy-6-oxo-4-propyl-1,6-dihydropyrimidin-5-yl)methyl]biphenyl-2-carbonitrile (0.5 g), 4-isopropoxyphenylboronic acid (0.56 g), triethylamine (0.97 mL), pyridine (0.57 mL) and molecular sieves 4 A (1 g) in dichloromethane (10 mL) was added copper(II) acetate (0.51 g), and the mixture was stirred for 2 days. The reaction mixture was diluted with ethyl acetate, the insoluble material was filtered off through celite, and the filtrate was concentrated. The residue was purified by silica gel column chromatography to give the title compound as a pale-yellow solid (0.56 g, 82%).

$^1$H NMR (300 MHz, CDCl$_3$) δ 1.10 (3H, t, J=7.5), 1.35 (6H, d, J=6.3), 1.64-1.79 (2H, m), 2.57-2.66 (2H, m), 3.88 (3H, s), 3.93 (2H, s), 4.49-4.62 (1H, m), 6.90 (2H, d, J=9.0), 7.10 (2H, d, J=9.0), 7.35-7.52 (6H, m), 7.57-7.75 (1H, m), 7.74 (1H, d, J=7.8)

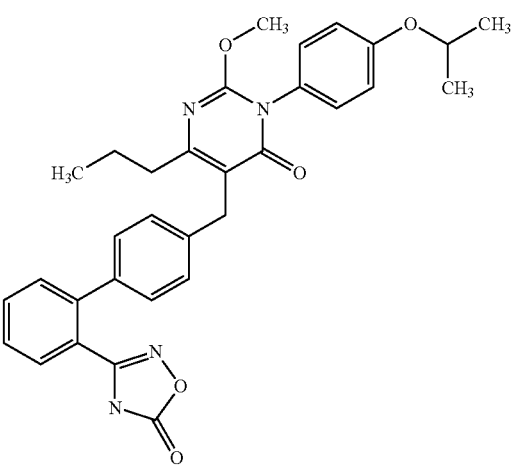

368b) 3-(4-isopropoxyphenyl)-2-methoxy-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.4 g), sodium hydrogen carbonate (1.9 g) and dimethyl sulfoxide (10 mL) was stirred at 40° C. for 30 min, 4'-{[1-(4-isopropoxyphenyl)-2-methoxy-6-oxo-4-propyl-1,6-dihydropyrimidin-5-yl]methyl}biphenyl-2-carbonitrile (0.56 g) was added, and the mixture was stirred at 90° C. for 5 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (5 mL). N,N'-carbonyldiimidazole (0.13 g) and then 1,8-diazabicyclo[5.4.0]undec-7-ene (0.12 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.21 g, 33%).

$^1$H NMR (300 MHz, DMSO-$d_6$) δ 0.90 (3H, t, J=7.2), 1.29 (6H, d, J=6.0), 1.49-1.66 (2H, m), 2.46-2.56 (2H, m), 3.81 (3H, s), 3.83 (2H, s), 4.57-4.71 (1H, m), 6.97 (2H, d, J=9.0), 7.14-7.30 (6H, m), 7.46-7.58 (2H, m), 7.60-7.71 (2H, m), 12.41 (1H, br)

Example 369

3-(4-tert-butoxyphenyl)-2-methoxy-5-{[2'-(5-oxo-4,5-dihydro-1,2,4-oxadiazol-3-yl)biphenyl-4-yl]methyl}-6-propylpyrimidin-4(3H)-one

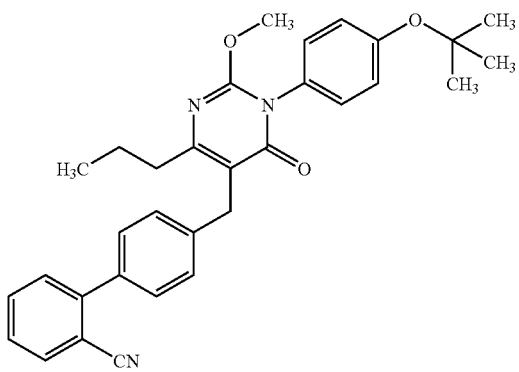

369a) 4'-{[1-(4-tert-butoxyphenyl)-2-methoxy-6-oxo-4-propyl-1,6-dihydropyrimidin-5-yl]methyl}biphenyl-2-carbonitrile To a suspension of 4'-[(2-methoxy-6-oxo-4-propyl-1,6-dihydropyrimidin-5-yl)methyl]biphenyl-2-carbonitrile (0.5 g), 4-tert-butoxyphenylboronic acid (0.54 g), triethylamine (0.97 mL), pyridine (0.57 mL) and molecular sieves 4 A (1 g) in dichloromethane (10 mL) was added copper(II) acetate (0.51 g), and the mixture was stirred for 2 days. The reaction mixture was diluted with ethyl acetate, the insoluble material was filtered off through celite, and the filtrate was concentrated. The residue was purified by silica gel column chromatography to give the title compound as a colorless solid (0.53 g, 75%).

$^1$H NMR (300 MHz, CDCl$_3$) δ 1.10 (3H, t, J=7.5), 1.38 (9H, s), 1.64-1.80 (2H, m), 2.56-2.66 (2H, m), 3.88 (3H, s), 3.94 (2H, s), 7.02-7.14 (4H, m), 7.34-7.52 (6H, m), 7.56-7.66 (1H, m), 7.73 (1H, d, J=7.8)

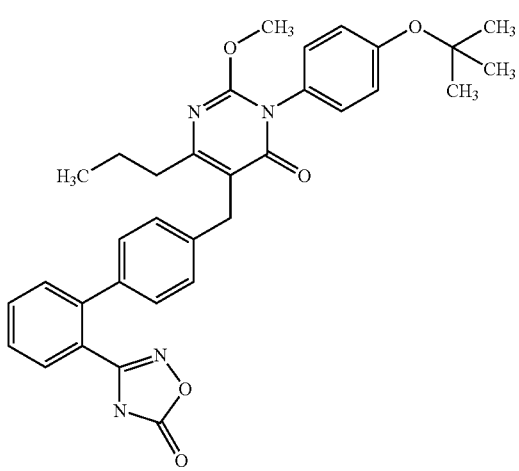

369b) 3-(4-tert-butoxyphenyl)-2-methoxy-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.2 g), sodium hydrogen carbonate (1.7 g) and dimethyl sulfoxide (10 mL) was stirred at 40° C. for 30 min, 4'-{[1-(4-tert-butoxyphenyl)-2-methoxy-6-oxo-4-propyl-1,6-dihydropyrimidin-5-yl]methyl}biphenyl-2-carbonitrile (0.53 g) was added, and the mixture was stirred at 90° C. for 5 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.10 g) and then 1,8-diazabicyclo[5.4.0]undec-7-ene (0.095 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.16 g, 26%).

$^1$H NMR (300 MHz, DMSO-d$_6$) δ 0.91 (3H, t, J=7.2), 1.35 (9H, s), 1.50-1.67 (2H, m), 2.44-2.58 (2H, m), 3.82 (5H, s), 7.05 (2H, d, J=9.0), 7.14-7.31 (6H, m), 7.45-7.58 (2H, m), 7.58-7.73 (2H, m), 12.39 (1H, br)

Example 370

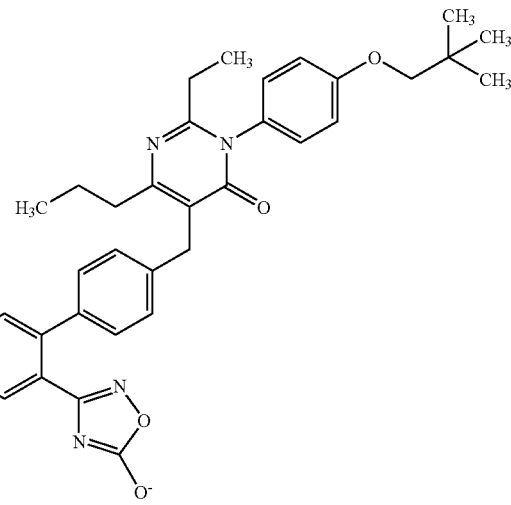

K-salt

3-[4-(2,2-dimethylpropoxy)phenyl]-2-ethyl-5-{[2'-(5-oxo-4,5-dihydro-1,2,4-oxadiazol-3-yl)biphenyl-4-yl]methyl}-6-propylpyrimidin-4(4H)-one potassium salt To a solution of 3-[4-(2,2-dimethylpropoxy)phenyl]-2-ethyl-5-{[2'-(5-oxo-4,5-dihydro-1,2,4-oxadiazol-3-yl)biphenyl-4-yl]methyl}-6-propylpyrimidin-4(3H)-one (0.15 g) in ethanol (2 mL) was added 8 M potassium hydroxide solution (0.032 mL), and the solvent was evaporated under reduced pressure. The residue was triturated with diisopropyl ether to give the title compound as a colorless solid (0.15 g, 91%).

¹H NMR (300 MHz, DMSO-d₆) δ 0.93 (3H, t, J=7.2), 0.98-1.08 (12H, m), 1.54-1.71 (2H, m), 2.27 (2H, q, J=7.2), 2.51-2.61 (2H, m), 3.68 (2H, s), 3.82 (2H, s), 7.04 (2H, d, J=9.0), 7.11-7.49 (10H, m)

Example 371

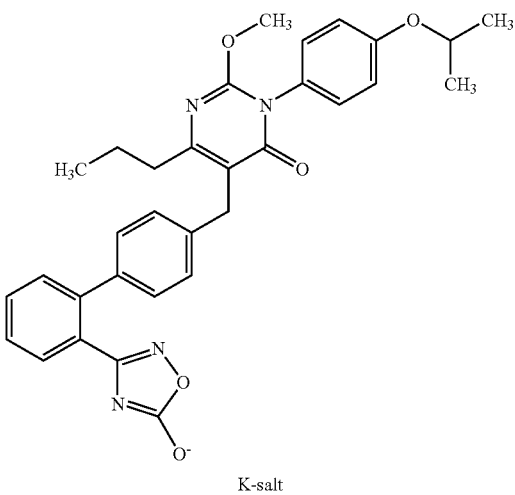

K-salt 3-(4-isopropoxyphenyl)-2-methoxy-5-{[2'-(5-oxo-4,5-dihydro-1,2,4-oxadiazol-3-yl)biphenyl-4-yl]methyl}-6-propylpyrimidin-4(4H)-one potassium salt To a solution of 3-(4-isopropoxyphenyl)-2-methoxy-5-{[2'-(5-oxo-4,5-dihydro-1,2,4-oxadiazol-3-yl)biphenyl-4-yl]methyl}-6-propylpyrimidin-4(3H)-one (0.15 g) in ethanol (2 mL) was added 8 M potassium hydroxide solution (0.035 mL), and the solvent was evaporated under reduced pressure. The residue was triturated with diisopropyl ether to give the title compound as a colorless solid (0.15 g, 90%).

¹H NMR (300 MHz, DMSO-d₆) δ 0.94 (3H, t, J=7.2), 1.29 (6H, d, J=6.0), 1.56-1.70 (2H, m), 2.48-2.57 (2H, m), 3.78 (2H, s), 3.80 (3H, s), 4.57-4.71 (1H, m), 6.96 (2H, d, J=9.0), 7.11-7.23 (6H, m), 7.25-7.49 (4H, m)

Example 372

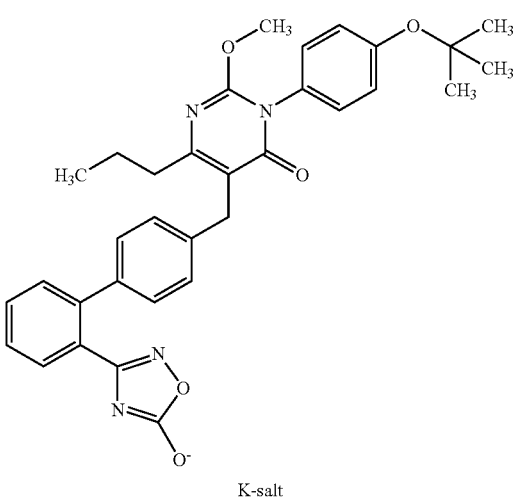

K-salt 3-(4-tert-butoxyphenyl)-2-methoxy-5-{[2'-(5-oxo-4,5-dihydro-1,2,4-oxadiazol-3-yl)biphenyl-4-yl]methyl}-6-propylpyrimidin-4(4H)-one potassium salt To a solution of 3-(4-tert-butoxyphenyl)-2-methoxy-5-{[2'-(5-oxo-4,5-dihydro-1,2,4-oxadiazol-3-yl)biphenyl-4-yl]methyl}-6-propylpyrimidin-4(3H)-one (0.12 g) in ethanol (2 mL) was added 8 M potassium hydroxide solution (0.026 mL), and the solvent was evaporated under reduced pressure. The residue was triturated with diisopropyl ether to give the title compound as a colorless solid (0.10 g, 81%).

¹H NMR (300 MHz, DMSO-d₆) δ 0.95 (3H, t, J=7.2), 1.35 (9H, s), 1.56-1.71 (2H, m), 2.50-2.57 (2H, m), 3.78 (2H, s), 3.81 (3H, s), 7.04 (2H, d, J=8.7), 7.11-7.24 (6H, m), 7.25-7.49 (4H, m)

Example 373

2-ethyl-3-(6-isopropoxypyridin-3-yl)-5-{[2'-(5-oxo-4,5-dihydro-1,2,4-oxadiazol-3-yl)biphenyl-4-yl]methyl}-6-propylpyrimidin-4(3H)-one

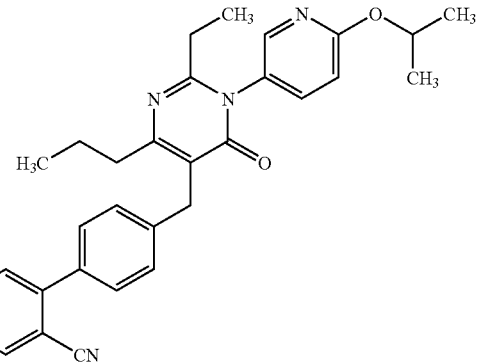

373a) 4'-{[2-ethyl-1-(6-isopropoxypyridin-3-yl)-6-oxo-4-propyl-1,6-dihydropyrimidin-5-yl]methyl}biphenyl-2-carbonitrile To a suspension of 4'-[(2-ethyl-6-oxo-4-propyl-1,6-dihydropyrimidin-5-yl)methyl]biphenyl-2-carbonitrile (0.5 g), 6-isopropoxy-3-pyridylboronic acid (0.51 g), triethylamine (0.97 mL), pyridine (0.57 mL) and molecular sieves 4 A (1 g) in dichloromethane (10 mL) was added copper(II) acetate (0.51 g), and the mixture was stirred for 2 days. The reaction mixture was diluted with ethyl acetate, the insoluble material was filtered off through celite, and the filtrate was concentrated. The residue was purified by silica gel column chromatography to give the title compound as a colorless solid (0.39 g, 56%).

¹H NMR (300 MHz, CDCl₃) δ 1.01 (3H, t, J=7.2), 1.17 (3H, t, J=7.2), 1.31-1.42 (6H, m), 1.64-1.80 (2H, m), 2.30-2.48 (2H, m), 2.62-2.73 (2H, m), 3.96 (2H, s), 5.25-5.38 (1H, m), 6.80 (1H, d, J=8.7), 7.36-7.51 (7H, m), 7.57-7.66 (1H, m), 7.70-7.78 (1H, m), 7.99 (1H, d, J=2.4)

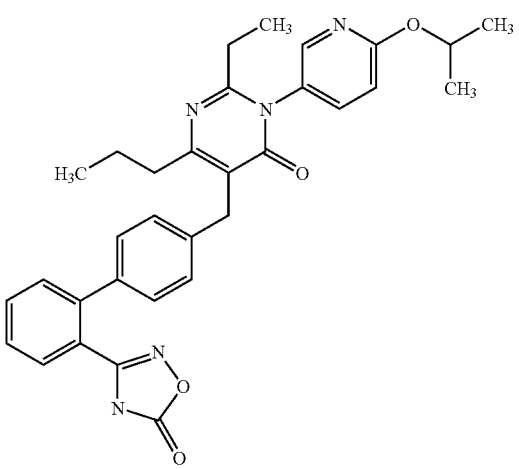

373b) 2-ethyl-3-(6-isopropoxypyridin-3-yl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.92 g), sodium hydrogen carbonate (1.3 g) and dimethyl sulfoxide (10 mL) was stirred at 40° C. for 30 min, 4'-{[2-ethyl-1-(6-isopropoxypyridin-3-yl)-6-oxo-4-propyl-1,6-dihydropyrimidin-5-yl]methyl}biphenyl-2-carbonitrile (0.39 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.19 g) and then 1,8-diazabicyclo[5.4.0]undec-7-ene (0.18 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.30 g, 68%).

$^1$H NMR (300 MHz, DMSO-$d_6$) δ 0.91 (3H, t, J=7.5), 1.07 (3H, t, J=7.5), 1.32 (6H, d, J=6.0), 1.50-1.66 (2H, m), 2.20-2.42 (2H, m), 2.52-2.59 (2H, m), 3.87 (2H, s), 5.20-5.34 (1H, m), 6.89 (1H, d, J=8.7), 7.21 (2H, d, J=8.1), 7.28 (2H, d, J=8.1), 7.46-7.59 (2H, m), 7.61-7.79 (3H, m), 8.16 (1H, s), 12.39 (1H, br)

Example 374

2-ethyl-3-[4-(1-methoxy-1-methylethyl)phenyl]-5-{[2'-(5-oxo-4,5-dihydro-1,2,4-oxadiazol-3-yl)biphenyl-4-yl]methyl}-6-propylpyrimidin-4(3H)-one

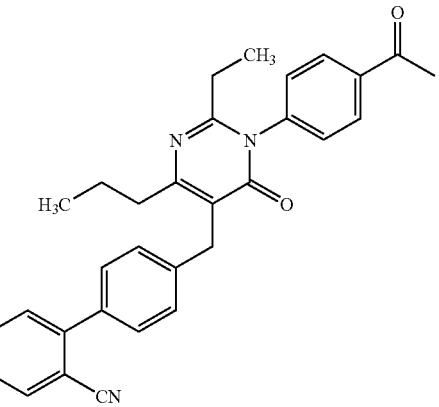

374a) 4'-{[1-(4-acetylphenyl)-2-ethyl-6-oxo-4-propyl-1,6-dihydropyrimidin-5-yl]methyl}biphenyl-2-carbonitrile To a suspension of 4'-[(2-ethyl-6-oxo-4-propyl-1,6-dihydropyrimidin-5-yl)methyl]biphenyl-2-carbonitrile (1.2 g), 4-acetylphenylboronic acid (1.1 g), triethylamine (2.2 mL), pyridine (1.3 mL) and molecular sieves 4 A (2.4 g) in dichloromethane (30 mL) was added copper(II) acetate (1.2 g), and the mixture was stirred for 2 days. The reaction mixture was diluted with ethyl acetate, the insoluble material was filtered off through celite, and the filtrate was concentrated. The residue was purified by silica gel column chromatography to give the title compound as a colorless solid (0.78 g, 51%).

$^1$H NMR (300 MHz, CDCl$_3$) δ 1.02 (3H, t, J=7.2), 1.15 (3H, t, J=7.2), 1.65-1.80 (2H, m), 2.34 (2H, q, J=7.2), 2.65 (3H, s), 2.66-2.73 (2H, m), 3.97 (2H, s), 7.32-7.51 (8H, m), 7.58-7.65 (1H, m), 7.74 (1H, d, J=7.8), 8.11 (2H, d, J=8.7)

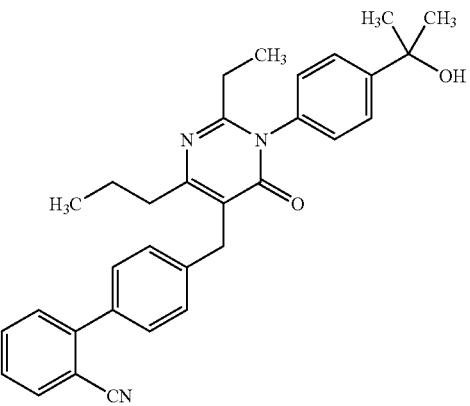

374b) 4'-({2-ethyl-1-[4-(1-hydroxy-1-methylethyl)phenyl]-6-oxo-4-propyl-1,6-dihydropyrimidin-5-yl}methyl)biphenyl-2-carbonitrile To a solution of 4'-{[1-(4-acetylphenyl)-2-ethyl-6-oxo-4-propyl-1,6-dihydropyrimidin-5-yl]methyl}biphenyl-2-carbonitrile (0.78 g) in tetrahydrofuran (20 mL) was added methyllithium (2.4 mL, 1.4 M diethyl ether solution) under ice-cooling, and the mixture was stirred for 1 hr. A saturated aqueous ammonium chloride solution was added to the reaction mixture, and the mixture was extracted with ethyl acetate, washed with saturated brine, and dried over anhydrous sodium sulfate. The solvent was evaporated under reduced pressure. The residue was purified by silica gel column chromatography to give the title compound as a colorless solid (0.30 g, 37%).

$^1$H NMR (300 MHz, CDCl$_3$) δ 1.01 (3H, t, J=7.2), 1.15 (3H, t, J=7.2), 1.61 (6H, s), 2.66-1.79 (2H, m), 1.82 (1H, s), 2.36 (2H, q, J=7.2), 2.62-2.72 (2H, m), 3.97 (2H, s), 7.19 (2H, d, J=8.7), 7.37-7.51 (6H, m), 7.57-7.68 (3H, m), 7.74 (1H, d, J=7.5)

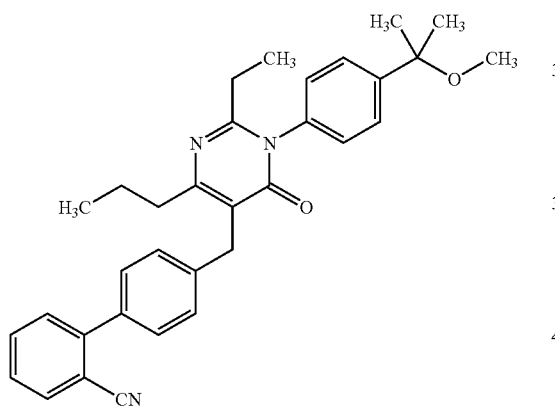

374c) 4'-({2-ethyl-1-[4-(1-methoxy-1-methylethyl)phenyl]-6-oxo-4-propyl-1,6-dihydropyrimidin-5-yl}methyl)biphenyl-2-carbonitrile To a solution of 4'-({2-ethyl-1-[4-(1-hydroxy-1-methylethyl)phenyl]-6-oxo-4-propyl-1,6-dihydropyrimidin-5-yl}methyl)biphenyl-2-carbonitrile (0.30 g) in N,N-dimethylformamide (5 mL) was added sodium hydride (0.049 g, 60%), and the mixture was stirred for 15 min. Then methyl iodide (0.076 mL) was added, and the mixture was further stirred for 2 hr. Small pieces of ice were added to the reaction mixture. The reaction mixture was diluted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a colorless solid (0.10 g, 32%).

$^1$H NMR (300 MHz, CDCl$_3$) δ 1.02 (3H, t, J=7.5), 1.15 (3H, t, J=7.5), 1.56 (6H, s), 1.66-1.80 (2H, m), 2.36 (2H, q, J=7.5), 2.64-2.70 (2H, m), 3.12 (3H, s), 3.97 (2H, s), 7.20 (2H, d, J=8.4), 7.36-7.51 (6H, m), 7.52-7.65 (3H, m), 7.40 (1H, d, J=7.5)

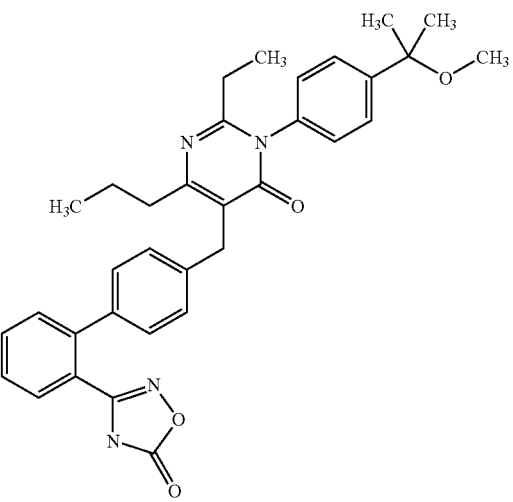

374d) 2-ethyl-3-[4-(1-methoxy-1-methylethyl)phenyl]-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.23 g), sodium hydrogen carbonate (0.33 g) and dimethyl sulfoxide (4 mL) was stirred at 40° C. for 30 min, 4'-({2-ethyl-1-[4-(1-methoxy-1-methylethyl)phenyl]-6-oxo-4-propyl-1,6-dihydropyrimidin-5-yl}methyl)biphenyl-2-carbonitrile (0.1 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (4 mL). N,N'-carbonyldiimidazole (0.05 g) and then 1,8-diazabicyclo[5.4.0]undec-7-ene (0.05 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.025 g, 22%).

$^1$H NMR (300 MHz, DMSO-d$_6$) δ 0.91 (3H, t, J=7.2), 1.05 (3H, t, J=7.2), 1.50 (6H, s), 1.54-1.65 (2H, m), 2.26 (2H, q, J=7.2), 2.52-2.62 (2H, m), 3.03 (3H, s), 3.86 (2H, s), 7.17-7.30 (4H, m), 7.30-7.37 (2H, m), 7.44-7.56 (4H, m), 7.58-7.68 (2H, m), 12.44 (1H, br)

Example 375

2-ethyl-3-[4-(2-methoxy-2-methylpropoxy)phenyl]-5-{[2'-(5-oxo-4,5-dihydro-1,2,4-oxadiazol-3-yl)biphenyl-4-yl]methyl}-6-propylpyrimidin-4(3H)-one

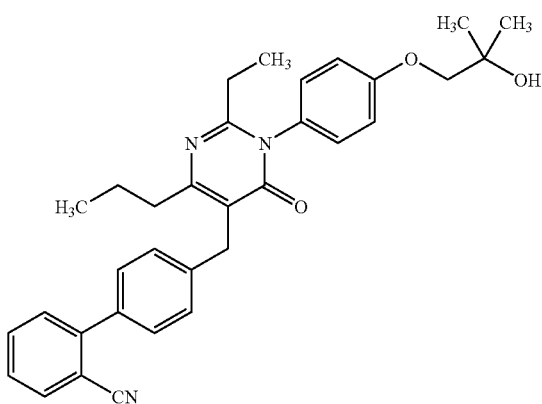

375a) 4'-({2-ethyl-1-[4-(2-hydroxy-2-methylpropoxy)phenyl]-6-oxo-4-propyl-1,6-dihydropyrimidin-5-yl}methyl)biphenyl-2-carbonitrile To a solution of 4'-{[2-ethyl-1-(4-hydroxyphenyl)-6-oxo-4-propyl-1,6-dihydropyrimidin-5-yl]methyl}biphenyl-2-carbonitrile (0.48 g) in N,N-dimethylacetamide (10 mL) were added 2,2-dimethyloxirane (0.77 g) and cesium carbonate (0.70 g), and the mixture was stirred at 120° C. for 24 hr. The mixture was allowed to cool to room temperature. The insoluble material was filtered off, and the filtrate was diluted with ethyl acetate, washed with 1 M hydrochloric acid, saturated sodium hydrogen carbonate and saturated brine, and dried over anhydrous sodium sulfate. The solvent was evaporated under reduced pressure. The residue was purified by silica gel chromatography to give the title compound as a pale-yellow solid (0.36 g, 64%).

$^1$H NMR (300 MHz, CDCl$_3$) δ 1.09 (3H, t, J=7.2), 1.15 (3H, t, J=7.2), 1.36 (6H, s), 1.65-1.79 (2H, m), 2.19 (1H, s), 2.37 (2H, q, J=7.2), 2.62-2.71 (2H, m), 3.83 (2H, s), 3.97 (2H, s), 7.04 (2H, d, J=9.0), 7.14 (2H, d, J=9.0), 7.37-7.51 (6H, m), 7.58-7.65 (1H, m), 7.74 (1H, d, J=9.0)

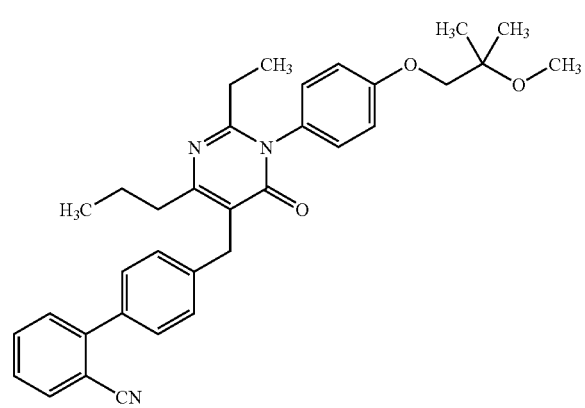

375b) 4'-({2-ethyl-1-[4-(2-methoxy-2-methylpropoxy)phenyl]-6-oxo-4-propyl-1,6-dihydropyrimidin-5-yl}methyl)biphenyl-2-carbonitrile To a solution of 4'-({2-ethyl-1-[4-(2-hydroxy-2-methylpropoxy)phenyl]-6-oxo-4-propyl-1,6-dihydropyrimidin-5-yl}methyl)biphenyl-2-carbonitrile (0.33 g) in N,N-dimethylformamide (5 mL) was added sodium hydride (0.05 g, 60%), and the mixture was stirred for 15 min. Then methyl iodide (0.08 mL) was added, and the mixture was further stirred for 2 hr. Small pieces of ice were added to the reaction mixture, and the mixture was stirred for 15 min. The reaction mixture was diluted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a colorless solid (0.10 g, 29%).

$^1$H NMR (300 MHz, CDCl$_3$) δ 1.01 (3H, t, J=7.2), 1.14 (3H, t, J=7.2), 1.31 (6H, s), 1.64-1.79 (2H, m), 2.38 (2H, q, J=7.2), 2.62-2.71 (2H, m), 3.31 (3H, s), 3.85 (2H, s), 3.96 (2H, s), 7.05 (2H, d, J=9.0), 7.13 (2H, d, J=9.0), 7.36-7.51 (6H, m), 7.57-7.65 (1H, m), 7.73 (1H, d, J=7.8)

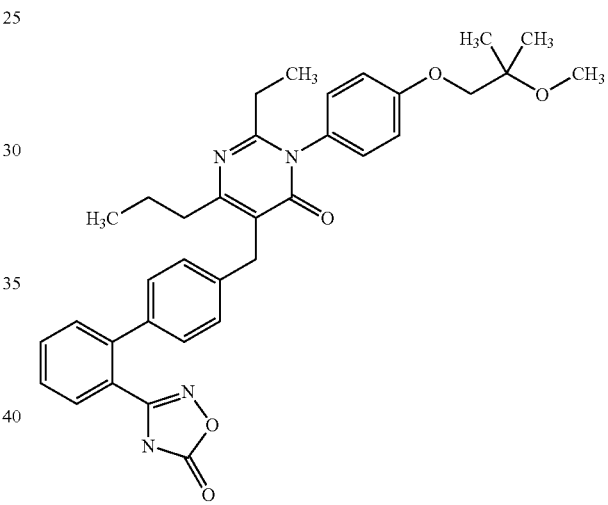

375c) 2-ethyl-3-[4-(2-methoxy-2-methylpropoxy)phenyl]-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.23 g), sodium hydrogen carbonate (0.33 g) and dimethyl sulfoxide (4 mL) was stirred at 40° C. for 30 min, 4'-({2-ethyl-1-[4-(2-methoxy-2-methylpropoxy)phenyl]-6-oxo-4-propyl-1,6-dihydropyrimidin-5-yl}methyl)biphenyl-2-carbonitrile (0.1 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (4 mL). N,N'-carbonyldiimidazole (0.05 g) and then 1,8-diazabicyclo[5.4.0]undec-7-ene (0.05 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.048 g, 43%).

$^1$H NMR (300 MHz, DMSO-d$_6$) δ 0.90 (3H, t, J=7.2), 1.05 (3H, t, J=7.2), 1.23 (6H, s), 1.50-1.66 (2H, m), 2.28 (2H, q, J=7.2), 2.50-2.57 (2H, m), 3.18 (3H, s), 3.87 (2H, s), 3.90 (2H, s), 7.08 (2H, q, J=9.0), 7.18-7.32 (6H, m), 7.46-7.57 (2H, m), 7.60-7.72 (2H, m), 12.39 (1H, br)

Example 376

2-ethyl-3-[4-(2-methoxy-1,1-dimethylethoxy)phenyl]-5-{[2'-(5-oxo-4,5-dihydro-1,2,4-oxadiazol-3-yl)biphenyl-4-yl]methyl}-6-propylpyrimidin-4(3H)-one

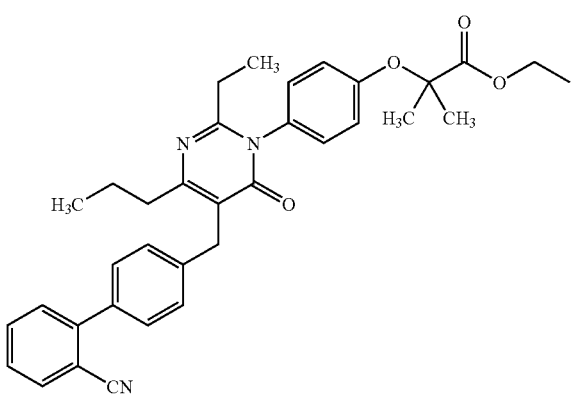

376a) ethyl 2-{4-[5-[(2'-cyanobiphenyl-4-yl)methyl]-2-ethyl-6-oxo-4-propylpyrimidin-1(6H)-yl]phenoxy}-2-methylpropanoate To a solution of 4'-{[2-ethyl-1-(4-hydroxyphenyl)-6-oxo-4-propyl-1,6-dihydropyrimidin-5-yl]methyl}biphenyl-2-carbonitrile (1.5 g) in N,N-dimethylacetamide (20 mL) were added ethyl 2-bromo-2-methylpropionate (0.98 g) and cesium carbonate (1.6 g), and the mixture was stirred at 120° C. for 24 hr. The mixture was allowed to cool to room temperature, and the insoluble material was filtered off. The filtrate was diluted with ethyl acetate, washed with 1 M hydrochloric acid, saturated sodium hydrogen carbonate and saturated brine, and dried over anhydrous sodium sulfate. The solvent was evaporated under reduced pressure. The residue was purified by silica gel chromatography to give the title compound as a colorless solid (1.6 g, 83%).

$^1$H NMR (300 MHz, CDCl$_3$) δ 1.00 (3H, t, J=7.2), 1.12 (3H, t, J=7.2), 1.25 (3H, t, J=7.2), 1.63 (6H, s), 1.66-1.77 (2H, m), 2.34 (2H, q, J=7.2), 2.61-2.70 (2H, m), 3.96 (2H, s), 4.25 (2H, q, J=7.2), 6.95 (2H, d, J=9.0), 7.08 (2H, d, J=9.0), 7.36-7.51 (6H, m), 7.57-7.66 (1H, m), 7.74 (1H, d, J=7.8)

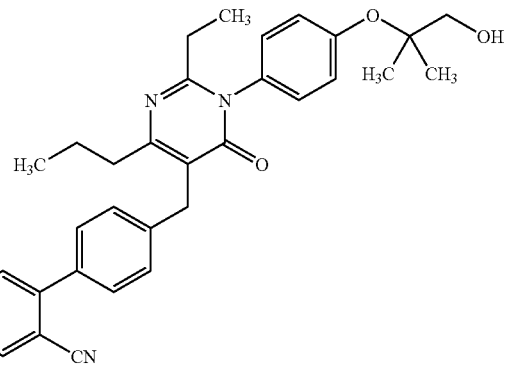

376b) 4'-({2-ethyl-1-[4-(2-hydroxy-1,1-dimethylethoxy)phenyl]-6-oxo-4-propyl-1,6-dihydropyrimidin-5-yl}methyl)biphenyl-2-carbonitrile To a solution of sodium borohydride (0.84 g) in ethanol (20 mL)-tetrahydrofuran (20 mL) was added calcium chloride (1.2 g) under ice-cooling, and the mixture was stirred for 15 min. A solution of ethyl 2-{4-[5-[(2'-cyanobiphenyl-4-yl)methyl]-2-ethyl-6-oxo-4-propylpyrimidin-1(6H)-yl]phenoxy}-2-methylpropanoate (1.6 g) in tetrahydrofuran (20 mL) was added, and the mixture was further stirred for 2 hr. Small pieces of ice were added in the reaction mixture, and the mixture was stirred for 15 min, and diluted with ethyl acetate and 1 M hydrochloric acid. The organic layer was separated, washed with saturated sodium hydrogen carbonate and saturated brine, and dried over anhydrous sodium sulfate. The solvent was evaporated under reduced pressure. The residue was purified by silica gel chromatography to give the title compound as a colorless solid (1.0 g, 71%).

$^1$H NMR (300 MHz, CDCl$_3$) δ 1.01 (3H, t, J=7.2), 1.14 (3H, t, J=7.2), 1.33 (6H, s), 1.64-1.80 (2H, m), 2.36 (2H, q, J=7.2), 2.62-2.71 (2H, m), 3.62 (2H, d, J=5.7), 3.97 (2H, s), 7.08-7.18 (4H, m), 7.37-7.51 (6H, m), 7.58-7.66 (1H, m), 7.74 (1H, d, J=7.8)

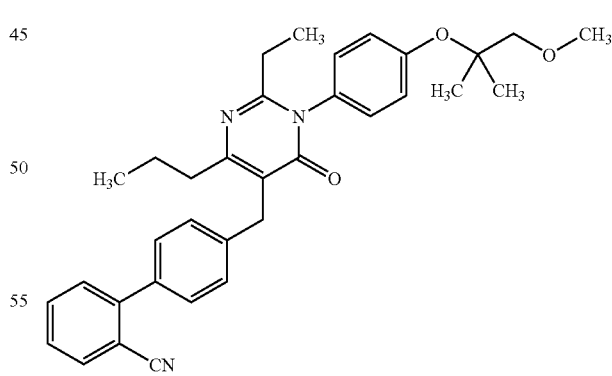

376c) 4'-({2-ethyl-1-[4-(2-methoxy-1,1-dimethylethoxy)phenyl]-6-oxo-4-propyl-1,6-dihydropyrimidin-5-yl}methyl)biphenyl-2-carbonitrile To a solution of 4'-({2-ethyl-1-[4-(2-hydroxy-1,1-dimethylethoxy)phenyl]-6-oxo-4-propyl-1,6-dihydropyrimidin-5-yl}methyl)biphenyl-2-carbonitrile (0.48 g) in N,N-dimethylformamide (10 mL) was added sodium hydride (0.07 g, 60%), and the mixture was stirred for 15 min. Then methyl iodide (0.11 mL) was added, and the mixture was further stirred for 2 hr. Small pieces of ice were added to the reaction mixture, and the mixture was stirred for 15 min, diluted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a colorless solid (0.24 g, 48%).

$^1$H NMR (300 MHz, CDCl$_3$) δ 1.00 (3H, t, J=7.2), 1.13 (3H, t, J=7.2), 1.34 (6H, s), 1.65-1.79 (2H, m), 2.34 (2H, q, J=7.2), 2.62-2.70 (2H, m), 3.39 (2H, s), 3.43 (3H, s), 3.97 (2H, s), 7.09-7.17 (4H, m), 7.37-7.50 (6H, m), 7.57-7.66 (1H, m), 7.74 (1H, d, J=7.5)

$^1$H NMR (300 MHz, CDCl$_3$) δ 1.03 (3H, t, J=7.2), 1.12 (3H, t, J=7.2), 1.33 (6H, s), 1.69-1.85 (2H, m), 2.32 (2H, q, J=7.2), 2.65-2.75 (2H, m), 3.38 (2H, s), 3.42 (3H, s), 3.89 (2H, s), 6.98-7.12 (4H, m), 7.20 (2H, d, J=8.1), 7.29 (2H, d, J=8.1), 7.37-7.49 (2H, m), 7.53-7.62 (1H, m), 7.75 (1H, d, J=7.5)

Example 377

2-ethyl-3-[4-(2-hydroxy-1,1-dimethylethoxy)phenyl]-5-{[2'-(5-oxo-4,5-dihydro-1,2,4-oxadiazol-3-yl)biphenyl-4-yl]methyl}-6-propylpyrimidin-4(3H)-one

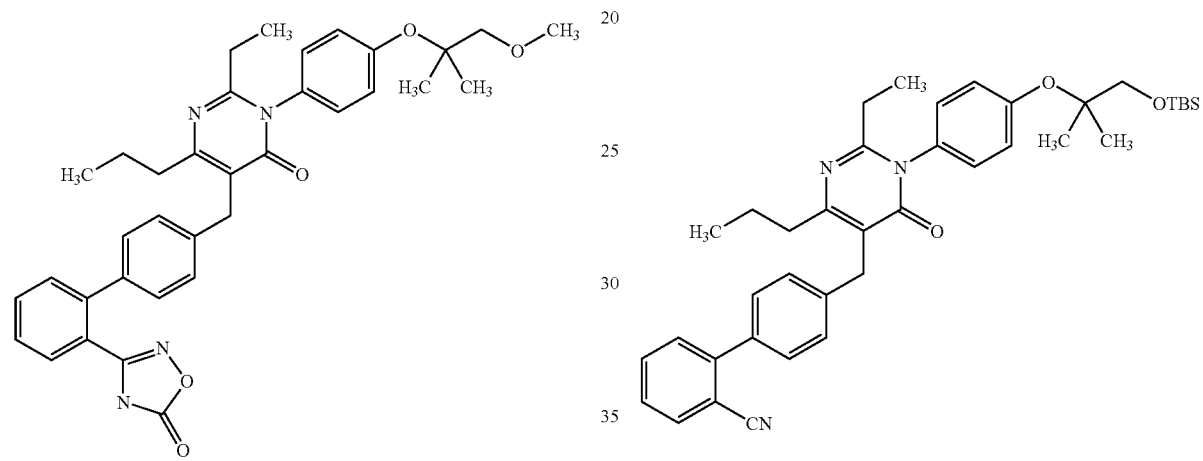

376d) 2-ethyl-3-[4-(2-methoxy-1,1-dimethylethoxy)phenyl]-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.52 g), sodium hydrogen carbonate (0.74 g) and dimethyl sulfoxide (10 mL) was stirred at 40° C. for 30 min, 4'-({2-ethyl-1-[4-(2-methoxy-1,1-dimethylethoxy)phenyl]-6-oxo-4-propyl-1,6-dihydropyrimidin-5-yl}methyl)biphenyl-2-carbonitrile (0.24 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.11 g) and then 1,8-diazabicyclo[5.4.0]undec-7-ene (0.1 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.16 g, 61%).

377a) 4'-({1-[4-(2-{[tert-butyl(dimethyl)silyl]oxy}-1,1-dimethylethoxy)phenyl]-2-ethyl-6-oxo-4-propyl-1,6-dihydropyrimidin-5-yl}methyl)biphenyl-2-carbonitrile To a solution of 4'-({2-ethyl-1-[4-(2-hydroxy-1,1-dimethylethoxy)phenyl]-6-oxo-4-propyl-1,6-dihydropyrimidin-5-yl}methyl)biphenyl-2-carbonitrile (0.49 g) and 2,6-lutidine (0.33 mL) in dichloromethane (10 mL) was added tert-butyl(dimethyl)silyl trifluoromethanesulfonate (0.32 mL) under ice-cooling, and the mixture was stirred for 1 hr. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.50 g, 85%).

$^1$H NMR (300 MHz, CDCl$_3$) δ 0.08 (6H, s), 0.93 (9H, s), 1.10 (3H, t, J=7.2), 1.13 (3H, t, J=7.2), 1.30 (6H, s), 1.64-1.80 (2H, m), 2.36 (2H, q, J=7.2), 2.62-2.71 (2H, m), 3.59 (2H, s), 3.97 (2H, s), 7.06-7.18 (4H, m), 7.36-7.51 (6H, m), 7.58-7.65 (1H, m), 7.74 (1H, d, J=7.8)

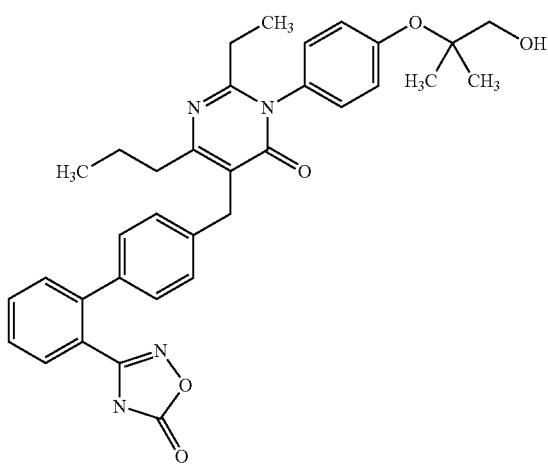

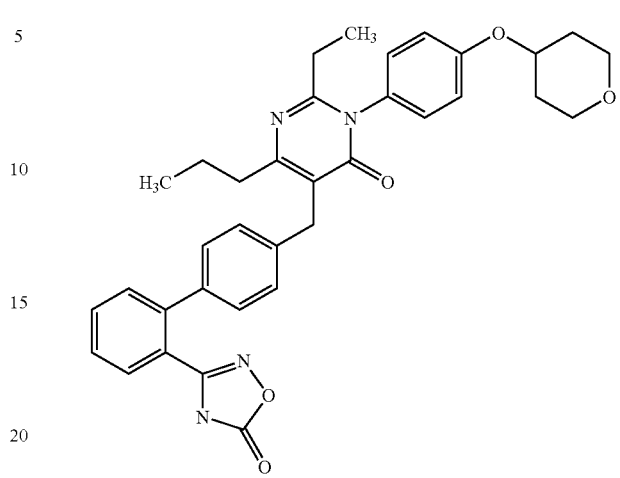

Example 378

377b) 2-ethyl-3-[4-(2-hydroxy-1,1-dimethylethoxy)phenyl]-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.93 g), sodium hydrogen carbonate (1.3 g) and dimethyl sulfoxide (10 mL) was stirred at 40° C. for 30 min, 4'-({1-[4-(2-{[tert-butyl(dimethyl)silyl]oxy}-1,1-dimethylethoxy)phenyl]-2-ethyl-6-oxo-4-propyl-1,6-dihydropyrimidin-5-yl}methyl)biphenyl-2-carbonitrile (0.5 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.19 g) and then 1,8-diazabicyclo[5.4.0]undec-7-ene (0.18 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was dissolved in tetrahydrofuran (10 mL), tetrabutylammonium fluoride (2.1 mL, 1.0 M tetrahydrofuran solution) was added, and the mixture was stirred for 2 hr. The reaction mixture was diluted with ethyl acetate, washed with 1 M hydrochloric acid and saturated brine, and dried over anhydrous sodium sulfate. The solvent was evaporated under reduced pressure and the residue was purified by silica gel column chromatography to give the title compound as a colorless solid (0.33 g, 72%).

$^1$H NMR (300 MHz, DMSO-$d_6$) δ 0.91 (3H, t, J=7.2), 1.05 (3H, t, J=7.2), 1.25 (6H, s), 1.49-1.66 (2H, m), 2.28 (2H, q, J=7.2), 2.51-2.58 (2H, m), 3.41 (2H, d, J=5.7), 3.87 (2H, s), 4.96 (1H, t, J=5.7), 7.13 (2H, t, J=8.7), 7.19-7.32 (6H, m), 7.46-7.58 (2H, m), 7.60-7.72 (2H, m), 12.40 (1H, br)

2-ethyl-5-{[2'-(5-oxo-4,5-dihydro-1,2,4-oxadiazol-3-yl)biphenyl-4-yl]methyl}-6-propyl-3-[4-(tetrahydro-2H-pyran-4-yloxy)phenyl]pyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (0.37 g), tetrahydro-4-pyranol (0.26 g) and triphenylphosphine (0.66 g) in tetrahydrofuran (1.5 mL) was added diisopropyl azodicarboxylate (1.3 mL, 1.9 M toluene solution), and the mixture was stirred at room temperature for 12 hr. The reaction mixture was diluted with ethyl acetate, washed with 1 M hydrochloric acid and then with saturated brine, and dried over anhydrous sodium sulfate. The solvent was evaporated under reduced pressure. The residue was crudely purified by silica gel column chromatography. The crudely purified product was dissolved in dimethyl sulfoxide (10 mL), hydroxylammonium chloride (0.98 g) and sodium hydrogen carbonate (1.4 g) were added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.20 g) and then 1,8-diazabicyclo[5.4.0]undec-7-ene (0.19 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.17 g, 35%).

$^1$H NMR (300 MHz, DMSO-$d_6$) δ 0.90 (3H, t, J=7.2), 1.05 (3H, t, J=7.2), 1.50-1.69 (4H, m), 1.95-2.07 (2H, m), 2.28 (2H, q, J=7.2), 2.51-2.57 (2H, m), 3.43-3.56 (4H, m), 3.81-3.92 (2H, m), 4.58-4.70 (1H, m), 7.10 (2H, d, J=8.7), 7.16-7.31 (6H, m), 7.46-7.58 (2H, m), 7.61-7.72 (2H, m), 12.40 (1H, br)

Example 379

2-methyl-5-{[2'-(5-oxo-4,5-dihydro-1,2,4-oxadiazol-3-yl)biphenyl-4-yl]methyl}-6-propyl-3-(tetrahydro-2H-pyran-4-yloxy)pyrimidin-4(3H)-one

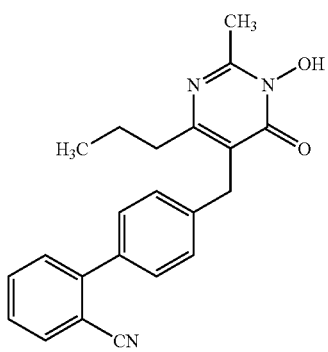

379a) 4'-[(1-hydroxy-2-methyl-6-oxo-4-propyl-1,6-dihydropyrimidin-5-yl)methyl]biphenyl-2-carbonitrile A mixture of 4'-[2-methyl-6-oxo-4-propyl-1,6-dihydropyrimidin-5-yl]methyl}biphenyl-2-carbonitrile (1.0 g), chlorotrimethylsilane (0.36 mL) and hexamethyldisilazane (20 mL) was heated under reflux for 12 hr. The reaction mixture was concentrated, and the residue was dissolved in dichloromethane (20 mL). Molybdenum pentoxide/hexamethylphosphoramide/pyridine complex (2.3 g) was added, and the mixture was stirred at room temperature for 12 hr. The reaction mixture was diluted with ethyl acetate, saturated tetrasodium ethylenediaminetetraacetate was added, and the mixture was stirred for 2 hr. The organic layer was separated, washed with saturated brine, and dried over anhydrous sodium sulfate. The solvent was evaporated under reduced pressure. The residue was purified by silica gel column chromatography to give the title compound as a colorless solid (0.53 g, 50%).

$^1$H NMR (300 MHz, DMSO-$d_6$) δ 0.86 (3H, t, J=7.2), 1.45-1.62 (2H, m), 2.41 (3H, s), 2.45-2.55 (2H, m), 3.91 (2H, s), 7.34 (2H, d, J=8.1), 7.47 (2H, d, J=8.1), 7.51-7.62 (2H, m), 7.72-7.82 (1H, m), 7.92 (1H, d, J=7.8), 11.75 (1H, br)

379b) 2-methyl-5-{[2'-(5-oxo-4,5-dihydro-1,2,4-oxadiazol-3-yl)biphenyl-4-yl]methyl}-6-propyl-3-(tetrahydro-2H-pyran-4-yloxy)pyrimidin-4(3H)-one To a solution of 4'-[(1-hydroxy-2-methyl-6-oxo-4-propyl-1,6-dihydropyrimidin-5-yl)methyl]biphenyl-2-carbonitrile (0.41 g), tetrahydro-4-pyranol (0.35 g) and triphenylphosphine (0.91 g) in tetrahydrofuran (4 mL) was added diisopropyl azodicarboxylate (1.8 mL, 1.9 M toluene solution), and the mixture was stirred at room temperature for 12 hr. The reaction mixture was diluted with ethyl acetate, washed with 1 M hydrochloric acid and then with saturated brine, and dried over anhydrous sodium sulfate. The solvent was evaporated under reduced pressure. The residue was crudely purified by silica gel column chromatography. The crudely purified product was dissolved in dimethyl sulfoxide (10 mL), hydroxylammonium chloride (1.4 g), sodium hydrogen carbonate (1.9 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.28 g) and then 1,8-diazabicyclo[5.4.0]undec-7-ene (0.26 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.29 g, 49%).

$^1$H NMR (300 MHz, DMSO-$d_6$) δ 0.84 (3H, t, J=7.2), 1.39-1.56 (2H, m), 1.58-1.75 (2H, m), 1.84-1.96 (2H, m), 2.40-2.53 (5H, m), 3.27-3.40 (2H, m), 3.83-3.95 (4H, m), 4.56-4.69 (1H, m), 7.18-7.27 (4H, m), 7.46-7.57 (2H, m), 7.61-7.71 (2H, m), 12.38 (1H, br)

Example 380

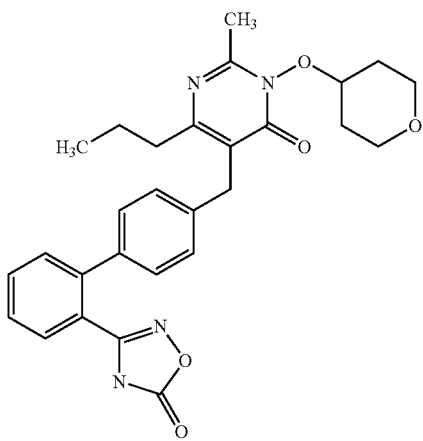

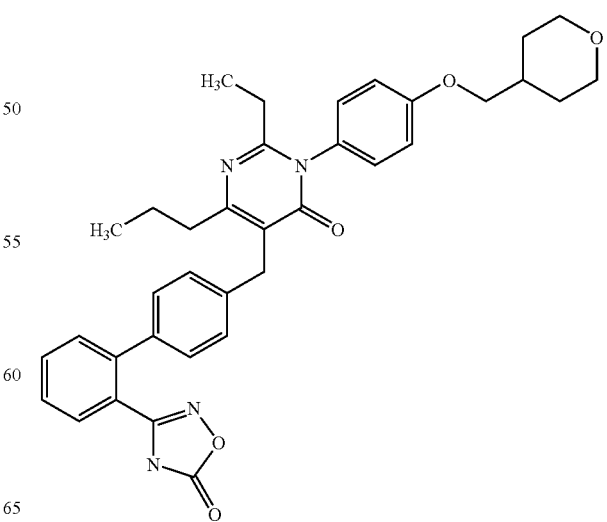

2-ethyl-5-{[2'-(5-oxo-4,5-dihydro-1,2,4-oxadiazol-3-yl)biphenyl-4-yl]methyl}-6-propyl-3-[4-(tetrahydro-2H-pyran-4-ylmethoxy)phenyl]pyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (0.5 g), tetrahydropyranyl-4-methanol (0.26 g) and triphenylphosphine (0.58 g) in tetrahydrofuran (5 mL) was added diisopropyl azodicarboxylate (1.2 mL, 1.9 M toluene solution), and the mixture was stirred at room temperature for 12 hr. The reaction mixture was diluted with ethyl acetate, washed with 1 M hydrochloric acid and then with saturated brine, and dried over anhydrous sodium sulfate. The solvent was evaporated under reduced pressure. The residue was crudely purified by silica gel column chromatography. The crudely purified product was dissolved in dimethyl sulfoxide (10 mL), hydroxylammonium chloride (1.0 g), sodium hydrogen carbonate (1.5 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.21 g) and then 1,8-diazabicyclo[5.4.0]undec-7-ene (0.19 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.49 g, 73%).

$^1$H NMR (300 MHz, DMSO-d$_6$) δ 0.90 (3H, t, J=7.2), 1.04 (3H, t, J=7.2), 1.25-1.45 (2H, m), 1.49-1.65 (2H, m), 1.65-1.76 (2H, m), 1.94-2.11 (1H, m), 2.27 (2H, q, J=7.2), 2.46-2.58 (2H, m), 3.26-3.41 (2H, m), 3.83-3.94 (6H, m), 7.05 (2H, d, J=8.7), 7.16-7.31 (6H, m), 7.44-7.58 (2H, m), 7.60-7.72 (2H, m), 12.39 (1H, br)

Example 381

2-ethyl-3-(4-{[(2R)-2-hydroxycyclopentyl]oxy}phenyl)-5-{[2'-(5-oxo-4,5-dihydro-1,2,4-oxadiazol-3-yl)biphenyl-4-yl]methyl}-6-propylpyrimidin-4(3H)-one

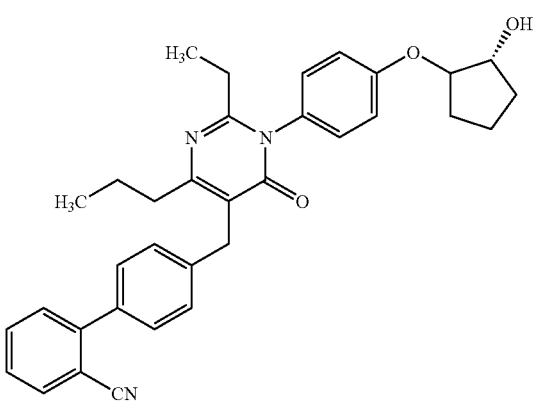

381a) 4'-{[2-ethyl-1-(4-{[(2R)-2-hydroxycyclopentyl]oxy}phenyl)-6-oxo-4-propyl-1,6-dihydropyrimidin-5-yl]methyl}biphenyl-2-carbonitrile To a solution of 4'-{[2-ethyl-1-(4-hydroxyphenyl)-6-oxo-4-propyl-1,6-dihydropyrimidin-5-yl]methyl}biphenyl-2-carbonitrile (0.99 g) in N,N-dimethylacetamide (10 mL) were added 6-oxabicyclo[3.1.0]hexane (0.56 g) and cesium carbonate (1.4 g), and the mixture was stirred at 120° C. for 24 hr. The mixture was allowed to cool to room temperature. The insoluble material was filtered off, diluted with ethyl acetate, washed with 1 M hydrochloric acid, saturated sodium hydrogen carbonate and saturated brine, and dried over anhydrous sodium sulfate. The solvent was evaporated under reduced pressure and the residue was purified by silica gel chromatography to give the title compound (0.59 g, 50%) as a solid.

$^1$H NMR (300 MHz, CDCl$_3$) δ 1.01 (3H, t, J=7.2), 1.14 (3H, t, J=7.2), 1.62-1.90 (6H, m), 2.00-2.25 (2H, m), 2.38 (2H, q, J=7.2), 2.61-2.72 (2H, m), 3.96 (2H, s), 4.26-4.36 (1H, br), 4.48-4.59 (1H, br), 6.96-7.16 (4H, m), 7.36-7.51 (6H, m), 7.57-7.66 (1H, m), 7.74 (1H, d, J=7.8)

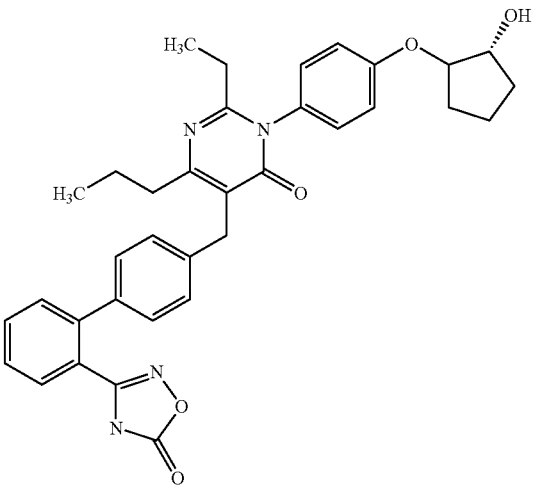

381b) 2-ethyl-3-(4-{[(2R)-2-hydroxycyclopentyl]oxy}phenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.3 g), sodium hydrogen carbonate (1.9 g) and dimethyl sulfoxide (10 mL) was stirred at 40° C. for 30 min, 4'-{[2-ethyl-1-(4-{[(2R)-2-hydroxycyclopentyl]oxy}phenyl)-6-oxo-4-propyl-1,6-dihydropyrimidin-5-yl]methyl}biphenyl-2-carbonitrile (0.59 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.18 g) and then 1,8-diazabicyclo[5.4.0]undec-7-ene (0.17 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.29 g, 44%).

$^1$H NMR (300 MHz, DMSO-d$_6$) δ 0.90 (3H, t, J=7.2), 1.05 (3H, t, J=7.2), 1.48-1.95 (7H, m), 2.05-2.20 (1H, m), 2.28 (2H, q, J=7.2), 2.46-2.59 (2H, m), 3.86 (2H, s), 4.08 (1H, br), 4.49 (1H, br), 5.02 (1H, d, J=3.9), 7.01-7.09 (2H, m), 7.17-7.30 (6H, m), 7.44-7.56 (2H, m), 7.60-7.69 (2H, m), 12.42 (1H, br)

Example 382

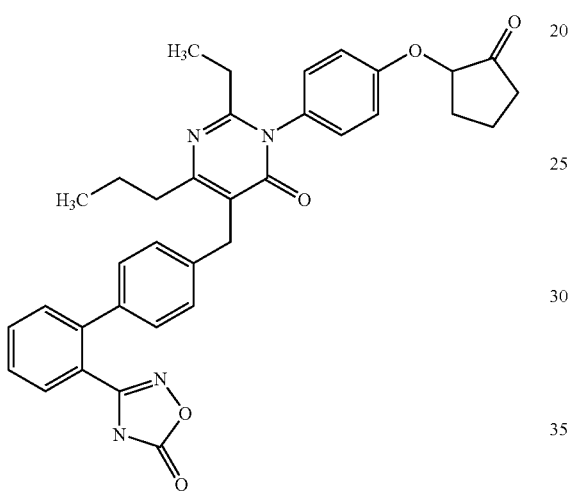

2-ethyl-3-{4-[(2-oxocyclopentyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 2-ethyl-3-(4-{[(2R)-2-hydroxycyclopentyl]oxy}phenyl)-5-{[2'-(5-oxo-4,5-dihydro-1,2,4-oxadiazol-3-yl)biphenyl-4-yl]methyl}-6-propylpyrimidin-4(3H)-one (0.2 g) in dichloromethane (4 mL) was added 1,1,1-tris(acetyloxy)-1,1-dihydro-1,2-benziodoxol-3(1H)-one (0.22 g), and the mixture was stirred for 2 hr. Ethyl acetate, water and sodium thiosulfate were added to the reaction mixture, and the mixture was stirred for 30 min and extracted with ethyl acetate. The organic layer was washed with saturated brine, and dried over anhydrous sodium sulfate. The solvent was evaporated and the residue was purified by silica gel column chromatography to give the title compound as a colorless solid (0.13 g, 65%).

$^1$H NMR (300 MHz, DMSO-d$_6$) δ 0.90 (3H, t, J=7.2), 1.05 (3H, t, J=7.2), 1.49-1.66 (2H, m), 1.75-2.04 (3H, m), 2.22-2.37 (4H, m), 2.44-2.59 (3H, m), 3.87 (2H, s), 5.00 (1H, d, J=9.6), 7.10 (2H, d, J=8.4), 7.17-7.32 (6H, m), 7.45-7.59 (2H, m), 7.60-7.73 (2H, m), 12.39 (1H, br)

Example 383

3-{[(2R,6S)-2,6-dimethyltetrahydro-2H-pyran-4-yl]oxy}-2-methyl-5-{[2'-(5-oxo-4,5-dihydro-1,2,4-oxadiazol-3-yl)biphenyl-4-yl]methyl}-6-propylpyrimidin-4(3H)-one

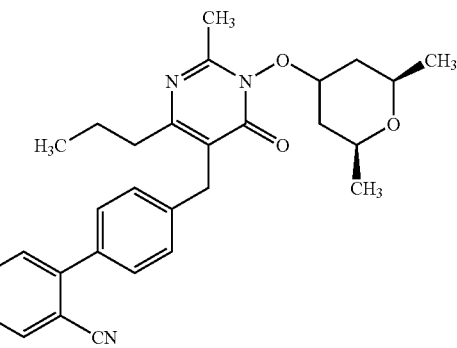

383a) 4'-[(1-{[(2R,6S)-2,6-dimethyltetrahydro-2H-pyran-4-yl]oxy}-2-methyl-6-oxo-4-propyl-1,6-dihydropyrimidin-5-yl)methyl]biphenyl-2-carbonitrile To a solution of 4'-[(1-hydroxy-2-methyl-6-oxo-4-propyl-1,6-dihydropyrimidin-5-yl)methyl]biphenyl-2-carbonitrile (0.50 g), (2R,4s,6S)-2,6-dimethyltetrahydro-2H-pyran-4-ol (0.54 g) and triphenylphosphine (1.1 g) in tetrahydrofuran (5 mL) was added diisopropyl azodicarboxylate (2.2 mL, 1.9 M toluene solution), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a colorless solid (0.62 g, 95%).

$^1$H NMR (300 MHz, CDCl$_3$) δ 0.95 (3H, t, J=7.2), 1.07-1.30 (6H, m), 1.39-1.53 (2H, m), 1.87-1.97 (2H, m), 1.99-2.10 (2H, m), 2.48-2.59 (5H, m), 3.38-3.53 (2H, m), 3.95 (2H, s), 3.98-4.14 (1H, m), 7.30-7.51 (6H, m), 7.56-7.66 (1H, m), 7.74 (1H, d, J=8.1)

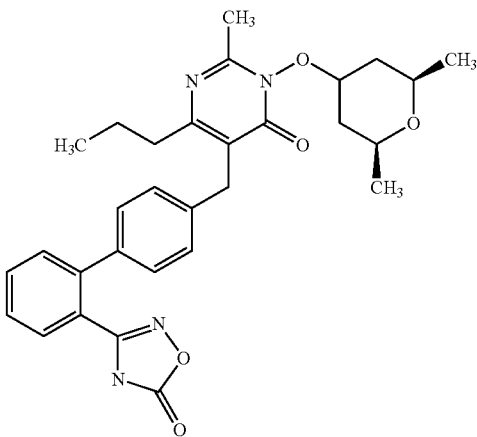

383b) 3-{[(2R,6S)-2,6-dimethyltetrahydro-2H-pyran-4-yl]oxy}-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.6 g), sodium hydrogen carbonate (2.2 g) and dimethyl sulfoxide (8 mL) was stirred at 40° C. for 30 min, 4'-[(1-{[(2R,6S)-2,6-dimethyltetrahydro-2H-pyran-4-yl]oxy}-2-methyl-6-oxo-4-propyl-1,6-dihydropyrimidin-5-yl)methyl]biphenyl-2-carbonitrile (0.62 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.32 g) and then 1,8-diazabicyclo[5.4.0]undec-7-ene (0.29 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.25 g, 35%).

$^1$H NMR (300 MHz, DMSO-$d_6$) δ 0.84 (3H, t, J=7.2), 1.09 (6H, d, J=6.6), 1.26-1.41 (2H, m), 1.41-1.56 (2H, m), 1.86-1.98 (2H, m), 2.40-2.53 (5H, m), 3.85 (2H, s), 3.87-4.01 (2H, m), 4.60 (1H, br), 7.15-7.29 (4H, m), 7.45-7.58 (2H, m), 7.61-7.72 (2H, m), 12.37 (1H, br)

Example 384

2-ethyl-3-(4-{[(1R,2R)-2-hydroxycyclohexyl]oxy}phenyl)-5-{[2'-(5-oxo-4,5-dihydro-1,2,4-oxadiazol-3-yl)biphenyl-4-yl]methyl}-6-propylpyrimidin-4(3H)-one

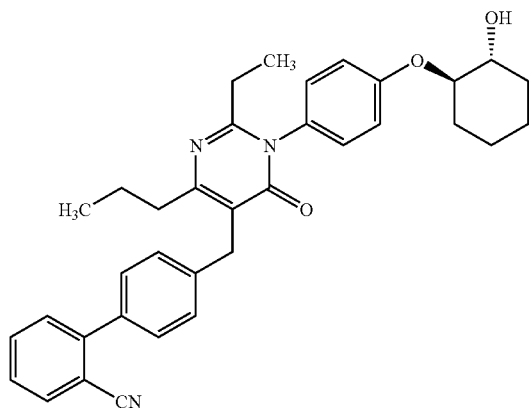

384a) 4'-{[2-ethyl-1-(4-{[(1R,2R)-2-hydroxycyclohexyl]oxy}phenyl)-6-oxo-4-propyl-1,6-dihydropyrimidin-5-yl]methyl}biphenyl-2-carbonitrile To a solution of 4'-{[2-ethyl-1-(4-hydroxyphenyl)-6-oxo-4-propyl-1,6-dihydropyrimidin-5-yl]methyl}biphenyl-2-carbonitrile (1.0 g) in N,N-dimethylacetamide (20 mL) were added 7-oxabicyclo[4.1.0]heptane (0.66 g) and cesium carbonate (1.5 g), and the mixture was stirred at 120° C. for 24 hr. The mixture was allowed to cool to room temperature. The insoluble material was filtered off, diluted with ethyl acetate, washed with 1 M hydrochloric acid, saturated sodium hydrogen carbonate and saturated brine, and dried over anhydrous sodium sulfate. The solvent was evaporated under reduced pressure. The residue was purified by silica gel chromatography to give the title compound (0.76 g, 62%) as a pale-yellow solid.

$^1$H NMR (300 MHz, CDCl$_3$) δ 1.01 (3H, t, J=7.2), 1.15 (3H, t, J=7.2), 1.24-1.48 (4H, m), 1.63-1.83 (4H, m), 2.07-2.23 (2H, m), 2.31-2.44 (2H, m), 2.38 (2H, q, J=7.2), 2.51 (1H, br), 2.61-2.72 (2H, m), 3.67-3.80 (1H, m), 3.96 (2H, s), 3.98-4.10 (1H, m), 7.00-7.17 (4H, m), 7.35-7.51 (6H, m), 7.56-7.66 (1H, m), 7.74 (1H, d, J=7.8)

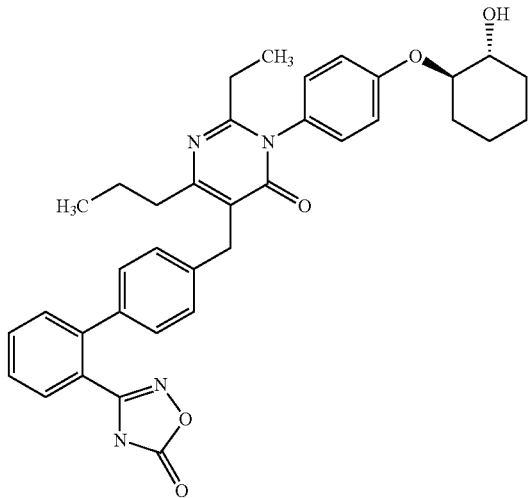

384b) 2-ethyl-3-(4-{[(1R,2R)-2-hydroxycyclohexyl]oxy}phenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.6 g), sodium hydrogen carbonate (2.3 g) and dimethyl sulfoxide (8 mL) was stirred at 40° C. for 30 min, 4'-{[2-ethyl-1-(4-{[(1R,2R)-2-hydroxycyclohexyl]oxy}phenyl)-6-oxo-4-propyl-1,6-dihydropyrimidin-5-yl]methyl}biphenyl-2-carbonitrile (0.76 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.22 g) and then 1,8-diazabicyclo[5.4.0]undec-7-ene (0.21 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.46 g, 55%).

$^1$H NMR (300 MHz, CDCl$_3$) δ 0.90 (3H, t, J=7.2), 1.05 (3H, t, J=7.2), 1.23-1.43 (4H, m), 1.47-1.68 (4H, m), 1.80-1.94 (1H, m), 2.00-2.09 (1H, m), 2.29 (2H, q, J=7.2), 2.49-

2.58 (2H, m), 3.46-3.61 (1H, m), 2.86 (2H, s), 4.04-4.15 (1H, m), 4.93 (1H, d, J=4.5), 7.02-7.13 (2H, m), 7.16-7.31 (6H, m), 7.46-7.59 (2H, m), 7.60-7.73 (2H, m), 12.38 (1H, br)

Example 385

6-butyl-2-ethyl-3-[4-(2-hydroxy-1,1-dimethylethoxy)phenyl]-5-{[2'-(5-oxo-4,5-dihydro-1,2,4-oxadiazol-3-yl)biphenyl-4-yl]methyl}pyrimidin-4(3H)-one

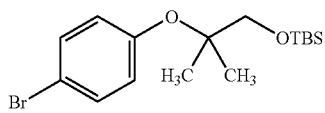

385a) [2-(4-bromophenoxy)-2-methylpropoxy](tert-butyl)dimethylsilane

To a solution of 2-(4-bromophenoxy)-2-methylpropan-1-ol (25.4 g) and 2,6-lutidine (30.2 mL) in dichloromethane (300 mL) was added tert-butyl(dimethyl)silyl trifluoromethanesulfonate (28.6 mL) under ice-cooling, and the mixture was stirred for 1 hr. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless oil (37.1 g, 100%).

$^1$H NMR (300 MHz, CDCl$_3$) δ 0.07 (6H, s), 0.92 (9H, s), 1.25 (6H, s), 5.53 (2H, s), 6.90 (2H, d, J=8.7), 7.35 (2H, d, J=8.7)

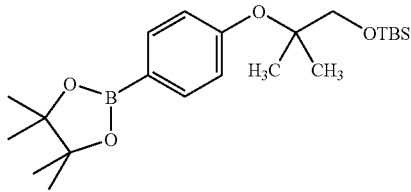

385b) tert-butyl(dimethyl){2-methyl-2-[4-(4,4,5,5-tetramethyl-1,3,2-dioxaborolan-2-yl)phenoxy]propoxy}silane To a solution of [2-(4-bromophenoxy)-2-methylpropoxy](tert-butyl)dimethylsilane (33.8 g), 4,4,4',4',5,5,5',5'-octamethyl-2,2'-bi-1,3,2-dioxaborolane (28.7 g), potassium acetate (27.7 g) in N,N-dimethylformamide (400 mL) was added [1,1'-bis(diphenylphosphino)ferrocene]dichloropalladium (2.3 g), and the mixture was stirred at 90° C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a pale-yellow oil (27.3 g, 71%).

$^1$H NMR (300 MHz, CDCl$_3$) δ 0.07 (6H, s), 0.92 (9H, s), 1.28 (6H, s), 1.34 (12H, s), 3.56 (2H, s), 7.01 (2H, d, J=8.7), 7.71 (2H, d, J=8.7)

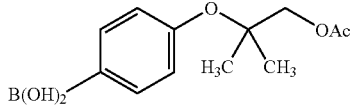

385c) {4-[2-(acetyloxy)-1,1-dimethylethoxy]phenyl}boronic acid

A solution of tert-butyl(dimethyl){2-methyl-2-[4-(4,4,5,5-tetramethyl-1,3,2-dioxaborolan-2-yl)phenoxy]propoxy}silane (5.0 g) in acetic acid (30 mL)-tetrahydrofuran (10 mL)-water (10 mL) was stirred for 2 days. The reaction mixture was diluted with toluene and the solvent was evaporated under reduced pressure. The residue was dissolved in ethyl acetate, washed with saturated aqueous sodium hydrogen carbonate solution and saturated brine, and dried over anhydrous sodium sulfate. The solvent was evaporated under reduced pressure. The residue was dissolved in dichloromethane (20 mL), pyridine (2.4 mL), acetic anhydride (1.5 g) and N,N-dimethyl-4-aminopyridine (0.1 g) were added and the mixture was stirred for 2 hr. Small pieces of ice were added to the reaction mixture, and the mixture was stirred for 30 min, extracted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was dissolved in 1 M hydrochloric acid (10 mL)-tetrahydrofuran (10 mL)-water (10 mL), sodium periodate (3.2 g) was added, and the mixture was stirred at room temperature for 3 hr. The reaction mixture was diluted with water, extracted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was triturated with diisopropyl ether to give the title compound as a pale-yellow solid (1.6 g, 52%).

$^1$H NMR (300 MHz, CDCl$_3$) δ 1.28 (6H, s), 2.09 (3H, s), 4.04 (2H, s), 6.97 (2H, d, J=7.8), 7.79 (2H, d, J=7.8)

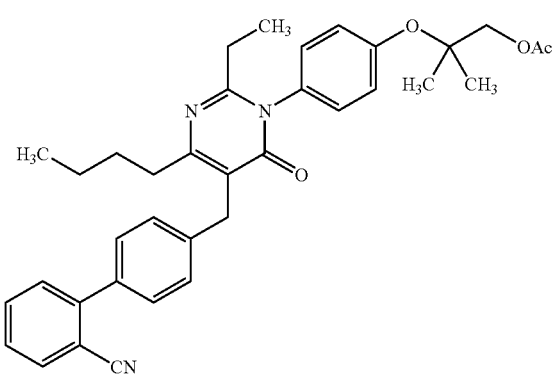

385d) 2-{4-[4-butyl-5-[(2'-cyanobiphenyl-4-yl)methyl]-2-ethyl-6-oxopyrimidin-1(6H)-yl]phenoxy}-2-methylpropyl acetate To a suspension of 4'-[(4-butyl-2-ethyl-6-oxo-1,6-dihydropyrimidin-5-yl)methyl]biphenyl-2-carbonitrile (0.5 g), {4-[2-(acetyloxy)-1,1-dimethylethoxy]phenyl}boronic acid (0.68 g), triethylamine (0.96 mL), pyridine (0.56 mL) and molecular sieves 4 A (1 g) in dichloromethane (10 mL) was added copper(II) acetate (0.68 g) and the mixture was stirred for 2 days. The reaction mixture was diluted with ethyl acetate, the insoluble material was filtered off through celite, and the filtrate was concentrated. The residue was purified by silica gel column chromatography to give the title compound as a colorless solid (0.6 g, 76%).

$^1$H NMR (300 MHz, CDCl$_3$) δ 0.95 (3H, t, J=7.2), 1.14 (3H, t, J=7.2), 1.36 (6H, s), 1.37-1.46 (2H, m), 1.59-1.71 (2H, m), 2.15 (3H, s), 2.35 (2H, q, J=7.2), 2.63-2.73 (2H, m), 3.97 (2H, s), 4.15 (2H, s), 7.14 (4H, s), 7.37-7.52 (6H, m), 7.58-7.66 (1H, m), 7.74 (1H, d, J=7.5)

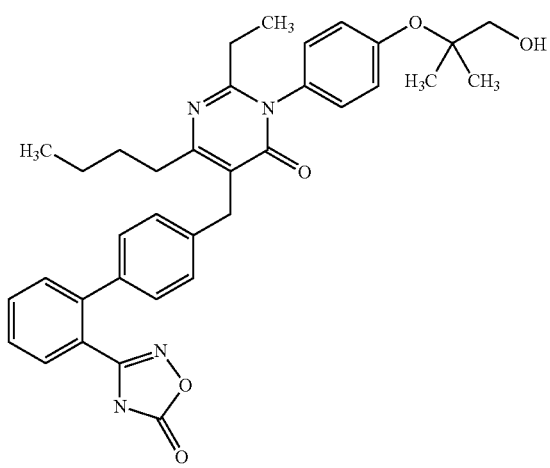

385e) 6-butyl-2-ethyl-3-[4-(2-hydroxy-1,1-dimethylethoxy)phenyl]-5-{[2'-(5-oxo-4,5-dihydro-1,2,4-oxadiazol-3-yl)biphenyl-4-yl]methyl}pyrimidin-4(3H)-one To a solution of 2-{4-[4-butyl-5-[(2'-cyanobiphenyl-4-yl)methyl]-2-ethyl-6-oxopyrimidin-1(6H)-yl]phenoxy}-2-methylpropyl acetate (0.6 g) in methanol (4 mL)-tetrahydrofuran (4 mL) was added potassium carbonate (0.29 g), and the mixture was stirred for 1 hr. 1 M hydrochloric acid was added to the reaction mixture, and the mixture was extracted with ethyl acetate, washed with saturated brine, and dried over anhydrous sodium sulfate. The solvent was evaporated under reduced pressure. The residue was dissolved in dichloromethane (10 mL), 2,6-lutidine (0.3 mL) and tert-butyl(dimethyl)silyl trifluoromethanesulfonate (0.36 mL) were added under ice-cooling, and the mixture was stirred for 1 hr. The reaction mixture was diluted with ethyl acetate, washed with 1 M hydrochloric acid and then with saturated brine, and dried over anhydrous sodium sulfate. The solvent was evaporated under reduced pressure. The residue was dissolved in dimethyl sulfoxide (8 mL), hydroxylammonium chloride (1.2 g) and sodium hydrogen carbonate (1.8 g) were added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was dissolved in tetrahydrofuran (6 mL), tetrabutylammonium fluoride (2.4 mL, 1.0 M tetrahydrofuran solution) was added, and the mixture was stirred for 2 hr. The reaction mixture was diluted with ethyl acetate, washed with 1 M hydrochloric acid and saturated brine, and dried over anhydrous sodium sulfate, and the solvent was evaporated under reduced pressure. The residue was purified by silica gel column chromatography to give the title compound as a colorless solid (0.28 g, 45%).

$^1$H NMR (300 MHz, DMSO-d$_6$) δ 0.86 (3H, t, J=7.2), 1.05 (3H, t, J=7.2), 1.25 (6H, s), 1.27-1.40 (2H, m), 1.45-1.59 (2H, m), 2.28 (2H, q, J=7.2), 2.52-2.60 (2H, m), 3.41 (2H, d, J=4.5), 3.86 (2H, s), 4.90-4.98 (1H, m), 7.13 (2H, d, J=8.7), 7.18-7.31 (6H, m), 7.47-7.58 (2H, m), 7.62-7.73 (2H, m), 12.39 (1H, br)

Example 386

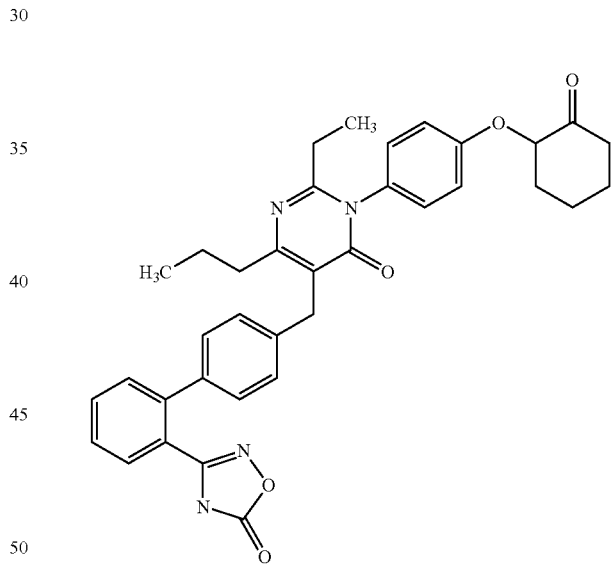

2-ethyl-3-{4-[(2-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 2-ethyl-3-(4-{[(1R,2R)-2-hydroxycyclohexyl]oxy}phenyl)-5-{[2'-(5-oxo-4,5-dihydro-1,2,4-oxadiazol-3-yl)biphenyl-4-yl]methyl}-6-propylpyrimidin-4(3H)-one (0.2 g) in dichloromethane (5 mL) was added 1,1,1-tris(acetyloxy)-1,1-dihydro-1,2-benziodoxol-3(1H)-one (0.21 g), and the mixture was stirred for 2 hr. Ethyl acetate, water and sodium thiosulfate were added to the reaction mixture, and the mixture was stirred for 30 min and extracted with ethyl acetate. The organic layer was washed with saturated brine, and dried over anhydrous sodium sulfate. The solvent was evaporated and the residue was purified by silica gel column chromatography to give the title compound as a colorless solid (0.13 g, 65%).

$^1$H NMR (300 MHz, DMSO-$d_6$) δ 0.90 (3H, t, J=7.2), 1.05 (3H, t, J=7.2), 1.48-1.67 (3H, m), 1.73-1.93 (3H, m), 2.21-2.43 (5H, m), 2.51-2.58 (2H, m), 2.58-2.75 (1H, m), 3.86 (2H, s), 5.04-5.15 (1H, m), 6.97 (2H, d, J=7.8), 7.16-7.32 (6H, m), 7.45-7.58 (2H, m), 7.60-7.72 (2H, m), 12.39 (1H, br)

Example 387

2-ethyl-3-(4-{[4-(hydroxymethyl)cyclohexyl]oxy}phenyl)-5-{[2'-(5-oxo-4,5-dihydro-1,2,4-oxadiazol-3-yl)biphenyl-4-yl]methyl}-6-propylpyrimiin-4(3H)-one

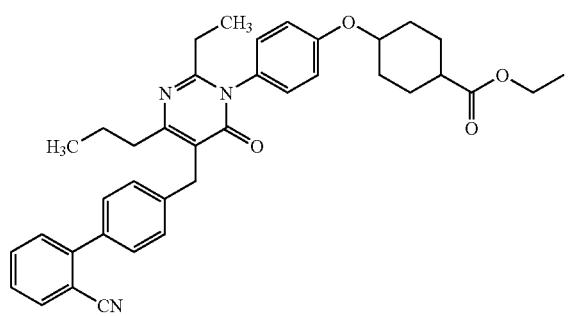

387a) ethyl 4-{4-[5-[(2'-cyanobiphenyl-4-yl)methyl]-2-ethyl-6-oxo-4-propylpyrimidin-1(6H)-yl]phenoxy}cyclohexanecarboxylate To a solution of 4'-{[2-ethyl-1-(4-hydroxyphenyl)-6-oxo-4-propyl-1,6-dihydropyrimidin-5-yl]methyl}biphenyl-2-carbonitrile (1.50 g), ethyl 4-hydroxycyclohexanecarboxylate (1.7 g) and triphenylphosphine (2.6 g) in tetrahydrofuran (15 mL) was added diisopropyl azodicarboxylate (5.3 mL, 1.9 M toluene solution), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a colorless solid (1.78 g, 88%).

$^1$H NMR (300 MHz, CDCl$_3$) δ 1.01 (3H, t, J=7.2), 1.14 (3H, t, J=7.2), 1.20-1.32 (5H, m), 1.43-1.82 (4H, m), 1.91-2.27 (4H, m), 2.32-2.45 (3H, m), 2.61-2.72 (2H, m), 3.96 (2H, s), 4.08-4.30 (3H, m), 6.95-7.04 (2H, m), 7.11 (2H, d, J=9.0), 7.36-7.51 (6H, m), 7.57-7.65 (1H, m), 7.74 (1H, d, J=7.8)

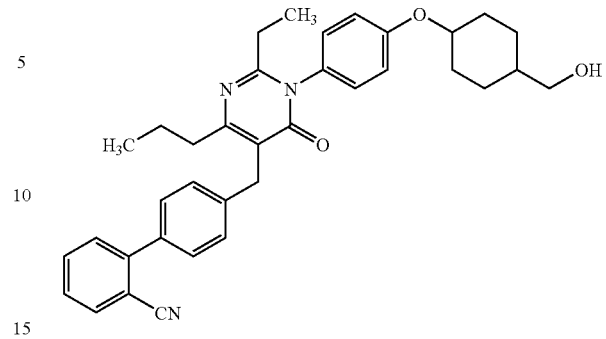

387b) 4'-{[2-ethyl-1-(4-{[4-(hydroxymethyl)cyclohexyl]oxy}phenyl)-6-oxo-4-propyl-1,6-dihydropyrimidin-5-yl]methyl}biphenyl-2-carbonitrile To a solution of sodium borohydride (0.85 g) in ethanol (10 mL)-tetrahydrofuran (10 mL) was added calcium chloride (1.3 g) under ice-cooling, and the mixture was stirred for 15 min. A solution of ethyl 4-{4-[5-[(2'-cyanobiphenyl-4-yl)methyl]-2-ethyl-6-oxo-4-propylpyrimidin-1(6H)-yl]phenoxy}cyclohexanecarboxylate (1.7 g) in tetrahydrofuran (10 mL) was added, and the mixture was further stirred for 2 hr. Small pieces of ice were added in the reaction mixture and the mixture was stirred for 15 min and diluted with ethyl acetate and 1 M hydrochloric acid. The organic layer was separated, washed with saturated sodium hydrogen carbonate and saturated brine, and dried over anhydrous sodium sulfate. The solvent was evaporated under reduced pressure. The residue was purified by silica gel chromatography to give the title compound (1.1 g, 71%) as a solid.

$^1$H NMR (300 MHz, CDCl$_3$) δ 1.01 (3H, t, J=7.2), 1.10-1.19 (4H, m), 1.30-1.64 (5H, m), 1.64-1.79 (2H, m), 1.85-1.98 (1H, m), 2.02-2.12 (1H, m), 2.14-2.27 (1H, m), 2.39 (2H, q, J=7.2), 2.62-2.72 (2H, m), 3.45-3.56 (2H, br), 3.96 (2H, s), 4.13-4.25 (1H, m), 4.58 (1H, br), 6.95-7.04 (2H, m), 7.06-7.15 (2H, m), 7.36-7.52 (6H, m), 7.57-7.65 (1H, m), 7.73 (1H, d, J=7.8)

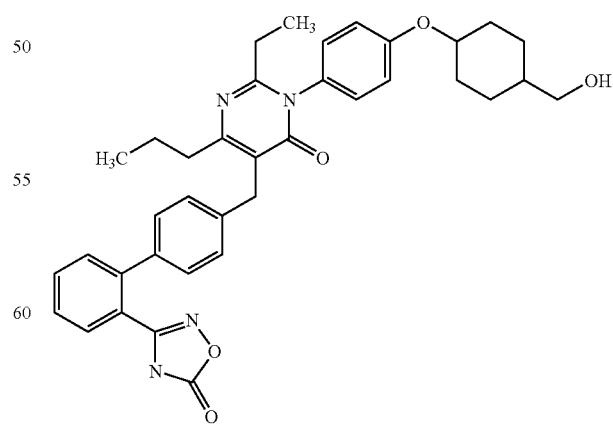

387c) 2-ethyl-3-(4-{[4-(hydroxymethyl)cyclohexyl]oxy}phenyl)-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-{[4-(hydroxymethyl)cyclohexyl]oxy}phenyl)-6-oxo-4-propyl-1,6-dihydropyrimidin-5-yl]methyl}biphenyl-2-carbonitrile (0.4 g) and 2,6-lutidine (0.25 mL) in dichloromethane (6 mL) was added tert-butyl(dimethyl)silyl trifluoromethanesulfonate (0.33 mL) under ice-cooling, and the mixture was stirred for 1 hr. The reaction mixture was diluted with ethyl acetate, washed with 1 M hydrochloric acid and then with saturated brine, and dried over anhydrous sodium sulfate. The solvent was evaporated under reduced pressure. The residue was dissolved in dimethyl sulfoxide (6 mL), hydroxylammonium chloride (0.85 g) and sodium hydrogen carbonate (1.2 g) were added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (8 mL). N,N'-carbonyldiimidazole (0.17 g) and then 1,8-diazabicyclo[5.4.0]undec-7-ene (0.16 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was dissolved in tetrahydrofuran (5 mL), tetrabutylammonium fluoride (1.6 mL, 1.0 M tetrahydrofuran solution) was added, and the mixture was stirred for 2 hr. The reaction mixture was diluted with ethyl acetate, washed with 1 M hydrochloric acid and saturated brine, and dried over anhydrous sodium sulfate. The solvent was evaporated under reduced pressure and the residue was purified by silica gel column chromatography to give the title compound as a colorless solid (0.26 g, 77%).

$^1$H NMR (300 MHz, DMSO-$d_6$) δ 0.90 (3H, t, J=7.2), 0.98-1.22 (6H, m), 1.26-1.67 (6H, m), 1.72-7.92 (2H, m), 2.04-2.18 (1H, m), 2.29 (2H, q, J=7.2), 2.50-2.60 (2H, m), 3.19-3.30 (2H, m), 3.87 (2H, s), 4.23-4.37 (1H, m), 7.04 (2H, d, J=9.0), 7.17-7.32 (6H, m), 7.46-7.58 (2H, m), 7.61-7.72 (1H, m), 12.38 (1H, br)

Example 388

3-(4-{[(2R,4s,6S)-2,6-dimethyltetrahydro-2H-pyran-4-yl]oxy}phenyl)-2-methoxy-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methoxy-6-oxo-4-propyl-1,6-dihydropyrimidin-5-yl]methyl}biphenyl-2-carbonitrile (0.50 g), (2R,4s,6S)-2,6-dimethyltetrahydro-2H-pyran-4-ol (0.43 g) and triphenylphosphine (0.87 g) in tetrahydrofuran (5 mL) was added diisopropyl azodicarboxylate (1.75 mL, 1.9 M toluene solution), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. The crudely purified product was dissolved in dimethyl sulfoxide (10 mL), hydroxylammonium chloride (1.3 g) and sodium hydrogen carbonate (1.9 g) were added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.21 g, 31%).

$^1$H NMR (300 MHz, DMSO-$d_6$) δ 0.90 (3H, t, J=7.2), 1.09 (6H, d, J=6.0), 1.34-1.48 (2H, m), 1.50-1.66 (2H, m), 1.78-1.91 (2H, m), 2.45-2.55 (2H, m), 3.75-3.91 (7H, m), 4.81 (1H, s), 7.01 (2H, d, J=9.0), 7.16-7.31 (6H, m), 7.45-7.58 (2H, m), 7.60-7.72 (2H, m), 12.33 (1H, br)

Example 389

2-ethyl-3-(4-{[1-(methoxymethyl)cyclopentyl]oxy}phenyl)-5-{[2'-(5-oxo-4,5-dihydro-1,2,4-oxadiazol-3-yl)biphenyl-4-yl]methyl}-6-propylpyrimidin-4(3H)-one

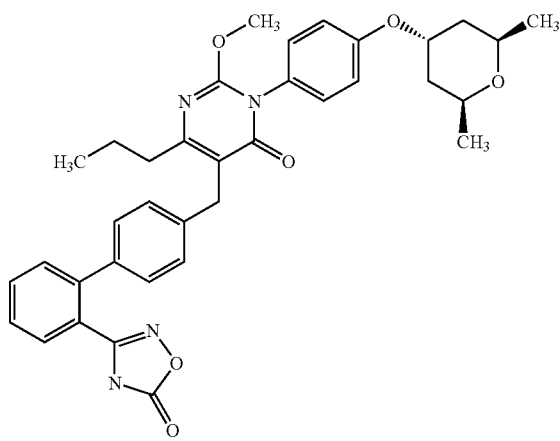

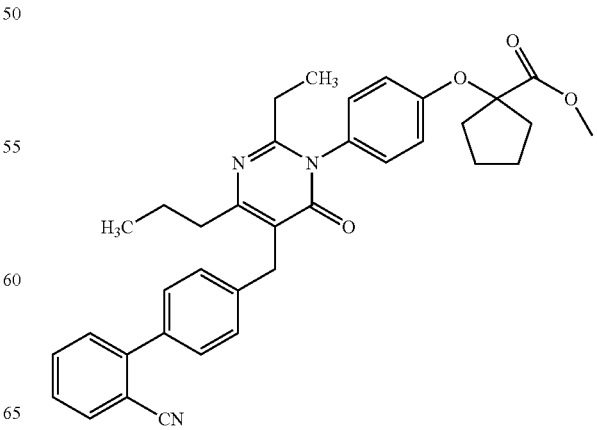

389a) methyl 1-{4-[5-[(2'-cyanobiphenyl-4-yl)methyl]-2-ethyl-6-oxo-4-propylpyrimidin-1(6H)-yl]phenoxy}cyclopentanecarboxylate To a solution of 4'-{[2-ethyl-1-(4-hydroxyphenyl)-6-oxo-4-propyl-1,6-dihydropyrimidin-5-yl]methyl}biphenyl-2-carbonitrile (1.0 g) in N,N-dimethylacetamide (10 mL) were added methyl 1-bromocyclopentanecarboxylate (1.4 g) and cesium carbonate (2.2 g), and the mixture was stirred at 120° C. for 24 hr. The mixture was allowed to cool to room temperature. The insoluble material was filtered off, diluted with ethyl acetate, washed with 1 M hydrochloric acid, saturated sodium hydrogen carbonate and saturated brine, and dried over anhydrous sodium sulfate. The solvent was evaporated under reduced pressure. The residue was purified by silica gel chromatography to give the title compound (0.94 g, 77%) as a pale-yellow solid.

$^1$H NMR (300 MHz, CDCl$_3$) δ 1.00 (3H, t, J=7.4), 1.13 (3H, t, J=7.4), 1.63-1.90 (6H, m), 2.15-2.41 (6H, m), 2.62-2.70 (2H, m), 3.75 (3H, s), 3.96 (2H, s), 6.80-6.88 (2H, m), 7.02-7.11 (2H, m), 7.35-7.51 (6H, m), 7.57-7.65 (1H, m), 7.74 (1H, d, J=7.6)

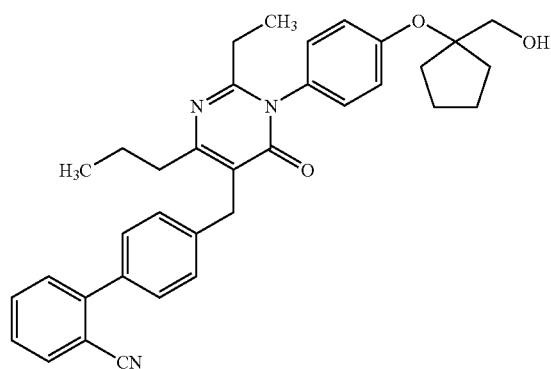

389b) 4'-{[2-ethyl-1-(4-{[1-(hydroxymethyl)cyclopentyl]oxy}phenyl)-6-oxo-4-propyl-1,6-dihydropyrimidin-5-yl]methyl}biphenyl-2-carbonitrile To a solution of sodium borohydride (0.39 g) in methanol (10 mL)-tetrahydrofuran (10 mL) was added calcium chloride (0.57 g) under ice-cooling, and the mixture was stirred for 15 min. A solution of methyl 1-{4-[5-[(2'-cyanobiphenyl-4-yl)methyl]-2-ethyl-6-oxo-4-propylpyrimidin-1(6H)-yl]phenoxy}cyclopentanecarboxylate (0.94 g) in tetrahydrofuran (10 mL) was added, and the mixture was further stirred for 2 hr. Small pieces of ice were added in the reaction mixture and the mixture was stirred for 15 min. The mixture was diluted with ethyl acetate and 1 M hydrochloric acid. The organic layer was separated, washed with saturated sodium hydrogen carbonate and saturated brine, and dried over anhydrous sodium sulfate. The solvent was evaporated under reduced pressure. The residue was purified by silica gel chromatography to give the title compound (0.83 g, 93%) as a colorless solid.

$^1$H NMR (300 MHz, CDCl$_3$) δ 1.01 (3H, t, J=7.2), 1.15 (3H, t, J=7.2), 1.61-1.88 (8H, m), 1.95-2.14 (3H, m), 2.37 (2H, q, J=7.2), 2.61-2.72 (2H, m), 3.77 (2H, d, J=5.4), 3.97 (2H, s), 7.06-7.15 (4H, m), 7.37-7.50 (6H, m), 7.58-7.65 (1H, m), 7.74 (1H, d, J=7.8)

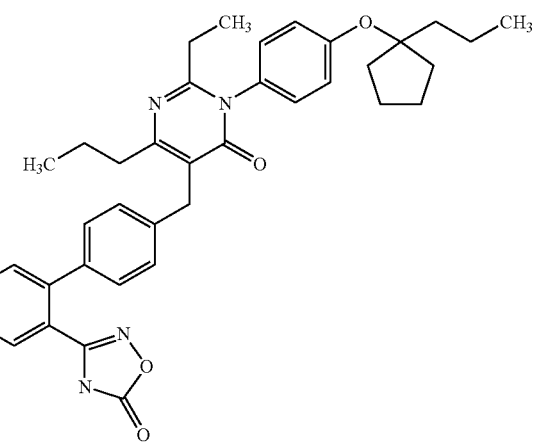

389c) 2-ethyl-3-(4-{[1-(methoxymethyl)cyclopentyl]oxy}phenyl)-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-{[1-(hydroxymethyl)cyclopentyl]oxy}phenyl)-6-oxo-4-propyl-1,6-dihydropyrimidin-5-yl]methyl}biphenyl-2-carbonitrile (0.41 g) in N,N-dimethylformamide (5 mL) was added sodium hydride (0.06 g, 60%), and the mixture was stirred for 15 min. Then methyl iodide (0.09 mL) was added, and the mixture was further stirred for 2 hr. Small pieces of ice were added to the reaction mixture and the mixture was stirred for 15 min. The reaction mixture was diluted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was dissolved in dimethyl sulfoxide (5 mL), hydroxylammonium chloride (0.91 g) and sodium hydrogen carbonate (1.3 g) were added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (6 mL). N,N'-carbonyldiimidazole (0.19 g) and then 1,8-diazabicyclo[5.4.0]undec-7-ene (0.17 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel chromatography to give the title compound (0.17 g, 36%) as a colorless solid.

$^1$H NMR (300 MHz, DMSO-d$_6$) δ 0.90 (3H, t, J=7.2), 1.05 (3H, t, J=7.5), 1.49-2.00 (10H, m), 2.28 (2H, q, J=7.2), 2.51-2.58 (2H, m), 3.28 (3H, s), 3.55 (2H, s), 3.87 (2H, s), 7.07 (2H, d, J=8.7), 7.18-7.31 (6H, m), 7.46-7.58 (2H, m), 7.61-7.72 (2H, m), 12.38 (1H, s)

Example 390

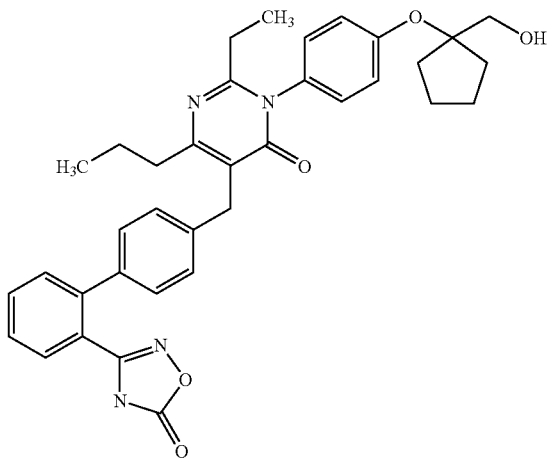

2-ethyl-3-(4-{[1-(hydroxymethyl)cyclopentyl]oxy}phenyl)-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-{[1-(hydroxymethyl)cyclopentyl]oxy}phenyl)-6-oxo-4-propyl-1,6-dihydropyrimidin-5-yl]methyl}biphenyl-2-carbonitrile (0.42 g) and 2,6-lutidine (0.27 mL) in dichloromethane (10 mL) was added tert-butyl(dimethyl)silyl trifluoromethanesulfonate (0.35 mL) under ice-cooling, and the mixture was stirred for 1 hr. The reaction mixture was diluted with ethyl acetate, washed with 1 M hydrochloric acid and then with saturated brine, and dried over anhydrous sodium sulfate. The solvent was evaporated under reduced pressure. The residue was dissolved in dimethyl sulfoxide (5 mL), hydroxylammonium chloride (0.91 g) and sodium hydrogen carbonate (1.3 g) were added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (6 mL). N,N'-carbonyldiimidazole (0.19 g) and then 1,8-diazabicyclo[5.4.0]undec-7-ene (0.17 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was dissolved in tetrahydrofuran (5 mL), tetrabutylammonium fluoride (4 mL, 1.0 M tetrahydrofuran solution) was added, and the mixture was stirred for 2 hr. The reaction mixture was diluted with ethyl acetate, washed with 1 M hydrochloric acid and saturated brine, and dried over anhydrous sodium sulfate. The solvent was evaporated under reduced pressure and the residue was purified by silica gel column chromatography to give the title compound as a colorless solid (0.27 g, 58%).

$^1$H NMR (300 MHz, DMSO-$d_6$) δ 0.90 (3H, t, J=7.2), 1.05 (3H, t, J=7.2), 1.49-1.96 (10H, m), 2.8 (2H, q, J=7.2), 2.50-2.59 (2H, m), 3.61 (2H, d, J=4.8), 3.86 (2H, s), 4.97 (1H, t, J=4.8), 7.08 (2H, d, J=8.7), 7.16-7.32 (6H, m), 7.45-7.58 (2H, m), 7.60-7.73 (2H, m), 12.38 (1H, br)

Example 391

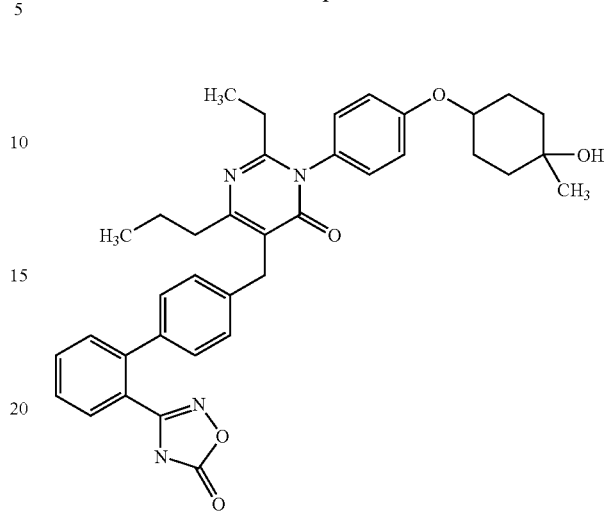

2-ethyl-3-{4-[(4-hydroxy-4-methylcyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (0.50 g), 1-methylcyclohexane-1,4-diol (0.43 g) and triphenylphosphine (0.88 g) in tetrahydrofuran (3 mL) was added diisopropyl azodicarboxylate (1.8 mL, 1.9 M toluene solution), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. The crudely purified product was dissolved in dimethyl sulfoxide (6 mL), hydroxylammonium chloride (0.76 g) and sodium hydrogen carbonate (1.1 g) were added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (6 mL). N,N'-carbonyldiimidazole (0.10 g) and then 1,8-diazabicyclo[5.4.0]undec-7-ene (0.10 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.13 g, 19%).

$^1$H NMR (300 MHz, DMSO-$d_6$) δ 0.90 (3H, t, J=7.2), 1.05 (3H, t, J=7.2), 1.16 (3H, s), 1.35-1.71 (8H, m), 1.84-2.03 (2H, m), 2.28 (2H, q, J=7.2), 2.44-2.59 (2H, m), 3.86 (2H, s), 4.20

(1H, s), 4.48-4.60 (1H, m), 7.05 (2H, d, J=9.3), 7.17-7.31 (6H, m), 7.46-7.59 (2H, m), 7.60-7.74 (2H, m), 12.39 (1H, br)

Example 392

2-ethyl-3-(4-{[trans-4-(1-hydroxy-1-methylethyl) cyclohexyl]oxy}phenyl)-5-{[2'-(5-oxo-4,5-dihydro-1,2,4-oxadiazol-3-yl)biphenyl-4-yl]methyl}-6-propylpyrimidin-4(3H)-one

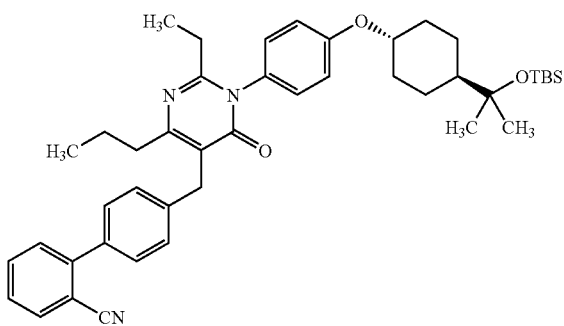

392a) 4'-{[1-(4-{[trans-4-(1-{[tert-butyl(dimethyl) silyl]oxy}-1-methylethyl)cyclohexyl]oxy}phenyl)-2-ethyl-6-oxo-4-propyl-1,6-dihydropyrimidin-5-yl] methyl}biphenyl-2-carbonitrile To a solution of 4'-{[2-ethyl-1-(4-hydroxyphenyl)-6-oxo-4-propyl-1,6-dihydropyrimidin-5-yl]methyl}biphenyl-2-carbonitrile (0.58 g), cis-4-(1-{[tert-butyl(dimethyl)silyl] oxy}-1-methylethyl)cyclohexanol (1.05 g) and triphenylphosphine (1.01 g) in tetrahydrofuran (10 mL) was added diisopropyl azodicarboxylate (2.0 mL, 1.9 M toluene solution), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a colorless solid (0.49 g, 54%).

$^1$H NMR (300 MHz, CDCl$_3$) δ 0.07 (6H, s), 0.86 (6H, s), 0.87 (9H, s), 1.01 (3H, t, J=7.2), 1.10-1.28 (6H, m), 1.30-1.50 (2H, m), 1.63-1.79 (2H, m), 1.79-1.97 (2H, m), 2.14-2.28 (2H, m), 2.38 (2H, q, J=7.2), 2.62-2.72 (2H, m), 3.97 (2H, s), 4.05-4.20 (1H, m), 6.99 (2H, d, J=9.0), 7.08 (2H, d, J=9.0), 7.36-7.52 (6H, m), 7.56-7.66 (1H, m), 7.74 (1H, d, J=6.9)

392b) 2-ethyl-3-(4-{[trans-4-(1-hydroxy-1-methylethyl)cyclohexyl]oxy}phenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.82 g), sodium hydrogen carbonate (1.2 g) and dimethyl sulfoxide (5 mL) was stirred at 40° C. for 30 min, 4'-{[1-(4-{[trans-4-(1-{[tert-butyl(dimethyl)silyl]oxy}-1-methylethyl)cyclohexyl]oxy}phenyl)-2-ethyl-6-oxo-4-propyl-1,6-dihydropyrimidin-5-yl]methyl}biphenyl-2-carbonitrile (0.48 g) was added, and the mixture was stirred at 90° C. for 8 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (5 mL). N,N'-carbonyldiimidazole (0.17 g) and then 1,8-diazabicyclo [5.4.0]undec-7-ene (0.16 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was dissolved in 1,4-dioxane (5 mL), tetrabutylammonium fluoride (2.1 mL, 1.0 M tetrahydrofuran solution) was added and the mixture was heated under reflux for 24 hr. The reaction mixture was diluted with ethyl acetate, washed with 1 M hydrochloric acid and saturated brine, and dried over anhydrous sodium sulfate, and the solvent was evaporated under reduced pressure. The residue was purified by silica gel column chromatography to give the title compound as a colorless solid (0.094 g, 21%).

$^1$H NMR (300 MHz, DMSO-d$_6$) δ 0.90 (3H, t, J=7.5), 0.99-1.09 (9H, m), 1.13-1.40 (4H, m), 1.42-1.65 (3H, m), 1.78-1.91 (2H, m), 2.08-2.20 (2H, m), 2.28 (2H, q, J=7.2), 2.49-2.58 (2H, m), 3.86 (2H, s), 4.09 (1H, s), 4.21-4.35 (1H, m), 7.04 (2H, d, J=9.0), 7.16-7.30 (6H, m), 7.43-7.56 (2H, m), 7.58-7.70 (2H, m)

Example 393

2-ethyl-3-(4-morpholin-4-ylphenyl)-5-{[2'-(5-oxo-4,5-dihydro-1,2,4-oxadiazol-3-yl)biphenyl-4-yl]methyl}-6-propylpyrimidin-4(3H)-one

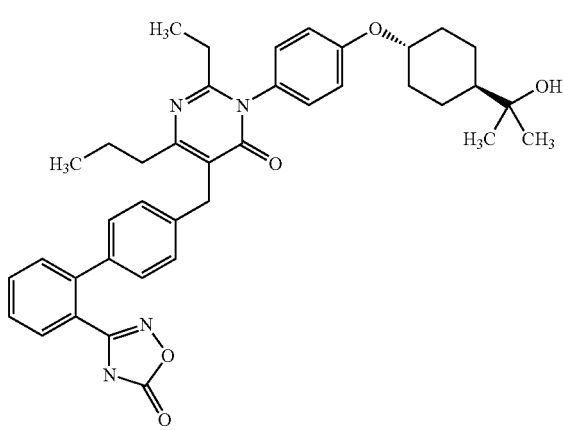

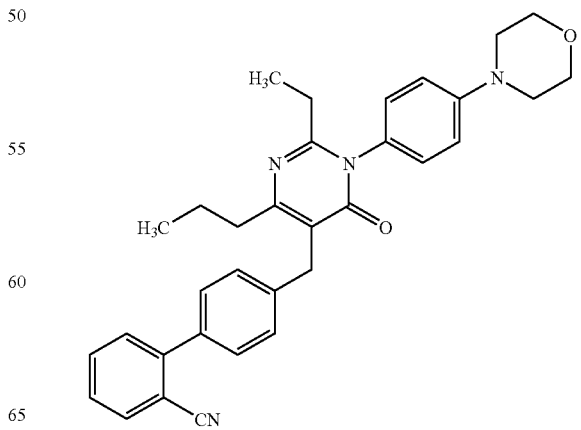

393a) 4'-{[2-ethyl-1-(4-morpholin-4-ylphenyl)-6-oxo-4-propyl-1,6-dihydropyrimidin-5-yl]methyl}biphenyl-2-carbonitrile To a suspension of 4'-[(2-ethyl-6-oxo-4-propyl-1,6-dihydropyrimidin-5-yl)methyl]biphenyl-2-carbonitrile (0.5 g), (4-morpholin-4-ylphenyl)boronic acid (0.58 g), triethylamine (0.97 mL), pyridine (0.57 mL) and molecular sieves 4 A (1 g) in dichloromethane (10 mL) was added copper(II) acetate (0.51 g) and the mixture was stirred for 2 days. The reaction mixture was diluted with ethyl acetate, the insoluble material was filtered off through celite, and the filtrate was concentrated. The residue was purified by silica gel column chromatography to give the title compound as a colorless solid (0.53 g, 73%).

$^1$H NMR (300 MHz, CDCl$_3$) δ 1.01 (3H, t, J=7.2), 1.14 (3H, t, J=7.2), 1.64-1.79 (2H, m), 2.19 (2H, q, J=7.2), 2.62-2.72 (2H, m), 3.21 (4H, t, J=4.8), 3.87 (4H, t, J=4.8), 3.96 (2H, s), 6.99 (2H, d, J=9.0), 7.10 (2H, d, J=9.0), 7.36-7.51 (6H, m), 7.57-7.65 (1H, m), 7.73 (1H, d, J=6.3)

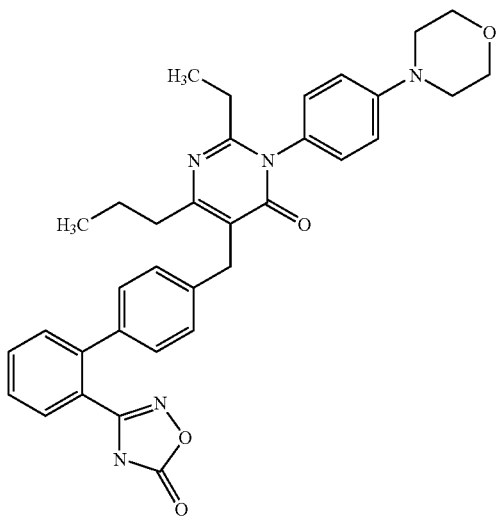

393b) 2-ethyl-3-(4-morpholin-4-ylphenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.2 g), sodium hydrogen carbonate (1.7 g) and dimethyl sulfoxide (8 mL) was stirred at 40° C. for 30 min, 4'-{[2-ethyl-1-(4-morpholin-4-ylphenyl)-6-oxo-4-propyl-1,6-dihydropyrimidin-5-yl]methyl}biphenyl-2-carbonitrile (0.53 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.32 g, 54%).

$^1$H NMR (300 MHz, DMSO-d$_6$) δ 0.90 (3H, t, J=7.2), 1.05 (3H, t, J=7.2), 1.48-1.67 (2H, m), 2.29 (2H, q, J=7.2), 2.45-2.58 (2H, m), 3.12-3.24 (4H, m), 3.69-3.81 (4H, m), 3.86 (2H, s), 7.04 (2H, d, J=9.0), 7.11-7.32 (6H, m), 7.45-7.60 (2H, m), 7.61-7.73 (2H, m), 12.38 (1H, br)

Example 394

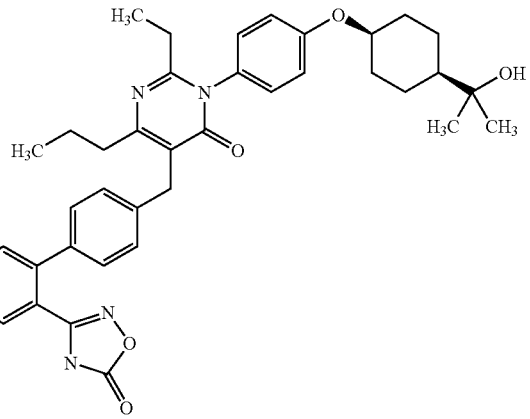

2-ethyl-3-(4-{[cis-4-(1-hydroxy-1-methylethyl)cyclohexyl]oxy}phenyl)-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (0.50 g), trans-4-(1-{[tert-butyl(dimethyl)silyl]oxy}-1-methylethyl)cyclohexanol (0.91 g) and triphenylphosphine (0.88 g) in tetrahydrofuran (5 mL) was added diisopropyl azodicarboxylate (1.8 mL, 1.9 M toluene solution), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. The crudely purified product was dissolved in dimethyl sulfoxide (10 mL), hydroxylammonium chloride (1.3 g) and sodium hydrogen carbonate (1.9 g) were added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was dissolved in 1,4-dioxane (5 mL), tetrabutylammonium fluoride (2.1 mL, 1.0 M tetrahydrofuran solution) was added, and the mixture was heated under reflux for 24 hr. The reaction mixture was diluted with ethyl acetate, washed with 1 M hydrochloric acid and saturated brine, and dried over anhydrous sodium sulfate. The solvent was evaporated under reduced pressure and the residue was purified by silica gel column chromatography to give the title compound as a colorless solid (0.16 g, 23%).

$^1$H NMR (300 MHz, DMSO-$d_6$) δ 0.90 (3H, t, J=7.2), 0.96-1.11 (9H, m), 1.22-1.69 (9H, m), 1.92-2.09 (2H, m), 2.29 (2H, q, J=7.2), 2.44-2.62 (2H, m), 3.86 (2H, s), 4.02-4.07 (1H, m), 4.65 (1H, s), 7.04 (2H, d, J=9.0), 7.16-7.31 (6H, m), 7.44-7.58 (2H, m), 7.60-7.72 (2H, m), 12.38 (1H, br)

Example 395

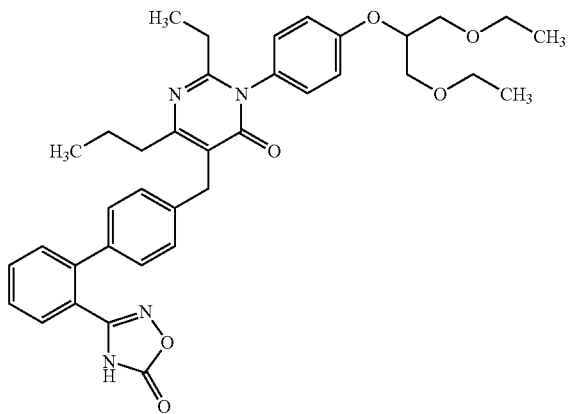

3-{4-[2-ethoxy-1-(ethoxymethyl)ethoxy]phenyl}-2-ethyl-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (0.50 g), 1,3-diethoxypropan-2-ol (0.49 g) and triphenylphosphine (0.88 g) in tetrahydrofuran (5 mL) was added diisopropyl azodicarboxylate (1.8 mL, 1.9 M toluene solution), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. The crudely purified product was dissolved in dimethyl sulfoxide (10 mL), hydroxylammonium chloride (1.3 g) and sodium hydrogen carbonate (1.9 g) were added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.42 g, 60%).

$^1$H NMR (300 MHz, DMSO-$d_6$) δ 0.90 (3H, t, J=7.2), 0.99-1.14 (9H, m), 1.49-1.66 (2H, m), 2.29 (2H, q, J=7.2), 2.50-2.58 (2H, m), 3.48 (4H, q, J=7.2), 3.54-3.67 (4H, m), 3.87 (2H, s), 4.58-4.68 (1H, m), 7.10 (2H, d, J=9.0), 7.17-7.38 (6H, m), 7.46-7.58 (2H, m), 7.60-7.72 (2H, m), 12.39 (1H, br)

Example 396

5-{[3-chloro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one

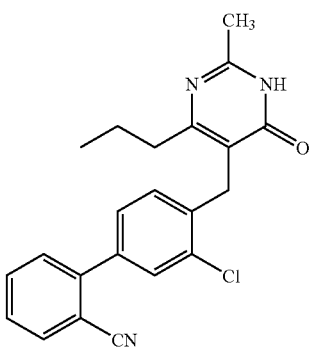

396a) 3'-chloro-4'-[(2-methyl-6-oxo-4-propyl-1,6-dihydropyrimidin-5-yl)methyl]biphenyl-2-carbonitrile To a suspension of 60% sodium hydride (0.40 g) in tetrahydrofuran (20 mL) was added dropwise a solution of ethyl butyrylacetate (2.13 g) in tetrahydrofuran (10 mL). After stirring for 30 min, 4'-(bromomethyl)-3'-chlorobiphenyl-2-carbonitrile (2.06 g) was added. The mixture was stirred at room temperature for 15 hr, and 1 M hydrochloric acid was added. The mixture was extracted with ethyl acetate, and the organic layer was washed with saturated brine, dried over anhydrous magnesium sulfate and concentrated. The residue was purified by silica gel column chromatography to give ethyl 2-[(3-chloro-2'-cyanobiphenyl-4-yl)methyl]-3-oxohexanoate. Then, a solution of the obtained ethyl 2-[(3-chloro-2'-cyanobiphenyl-4-yl)methyl]-3-oxohexanoate, ethanimidamide hydrochloride (2.55 g), 28% sodium methoxide (7.80 g) in methanol (50 mL) was stirred overnight. The solvent was evaporated under reduced pressure, and saturated aqueous ammonium chloride solution was added to the residue. The precipitated solid was collected by filtration, and washed with water and diethyl ether to give the title compound (0.64 g, 73%) as a white solid.

$^1$H NMR (300 MHz, CDCl$_3$) δ 0.93 (t, J=7.5, 3H), 1.48-1.66 (m, 2H), 2.42 (s, 3H), 2.45-2.54 (m, 2H), 4.06 (s, 2H), 7.13 (d, J=8.1, 1H), 7.30-7.36 (m, 1H), 7.40-7.50 (m, 2H), 7.56 (d, J=2.1, 1H), 7.59-7.66 (m, 1H), 7.71-7.77 (m, 1H)

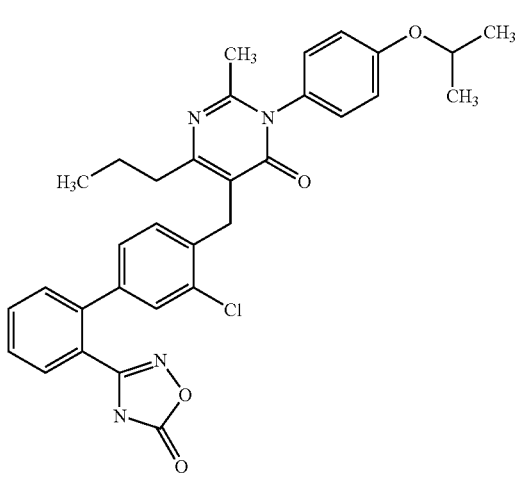
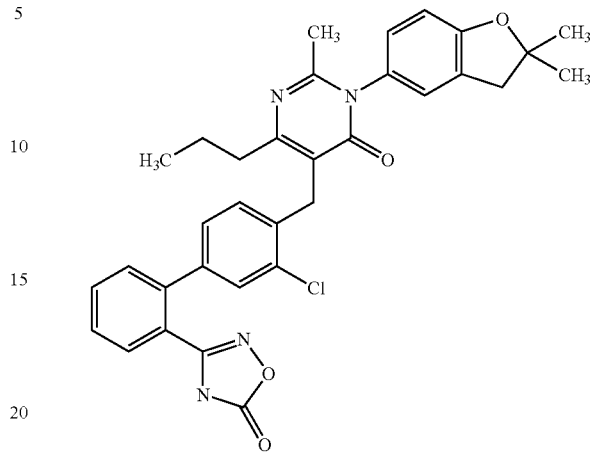

Example 397

396b) 5-{[3-chloro-2'-(5-oxo-4,5-dihydro-1,2,4-oxa-diazol-3-yl)biphenyl-4-yl]methyl}-3-(4-isopropoxyphenyl)-2-methyl-6-propylpyrimidin-4(3H)-one To a suspension of 3'-chloro-4'-[(2-methyl-6-oxo-4-propyl-1,6-dihydropyrimidin-5-yl)methyl]biphenyl-2-carbonitrile (0.65 g), (4-isopropoxyphenyl)boronic acid (0.62 g), triethylamine (0.8 mL), pyridine (1.6 mL) and molecular sieves 4 A (1.60 g) in dichloromethane (20 mL) was added copper(II) acetate (0.65 g) and the mixture was stirred at room temperature for 2 days. The reaction mixture was diluted with ethyl acetate, the insoluble material was filtered off through celite, and the filtrate was concentrated. The residue was purified by silica gel column chromatography. The crudely purified product was added to a mixture of hydroxylammonium chloride (1.30 g), sodium hydrogen carbonate (2.10 g) and dimethyl sulfoxide (25 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (20 mL). N,N'-carbonyldiimidazole (0.31 g) and then 1,8-diazabicyclo[5.4.0]undec-7-ene (0.30 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.57 g, 58%).

$^1$H NMR (300 MHz, CDCl$_3$) δ 1.01 (t, J=7.2, 3H), 1.35 (d, J=6.3, 6H), 1.53-1.80 (m, 2H), 2.17 (s, 3 H), 2.60-2.70 (m, 2 H), 3.99 (s, 2 H), 4.48-4.62 (m, 1 H), 6.87-7.10 (m, 6H), 7.34-7.50 (m, 3H), 7.54-7.62 (m, 1H), 7.68-7.75 (m, 1H)

5-{[3-chloro-2'-(5-oxo-4,5-dihydro-1,2,4-oxadiazol-3-yl)biphenyl-4-yl]methyl}-3-(2,2-dimethyl-2,3-dihydro-1-benzofuran-5-yl)-2-methyl-6-propylpyrimidin-4(3H)-one To a suspension of 3'-chloro-4'-[(2-methyl-6-oxo-4-propyl-1,6-dihydropyrimidin-5-yl)methyl]biphenyl-2-carbonitrile (0.65 g), (2,2-dimethyl-2,3-dihydro-1-benzofuran-5-yl) boronic acid (0.66 g), triethylamine (0.8 mL), pyridine (1.6 mL) and molecular sieves 4 A (1.60 g) in dichloromethane (20 mL) was added copper(II) acetate (0.65 g) and the mixture was stirred at room temperature for 2 days. The reaction mixture was diluted with ethyl acetate, the insoluble material was filtered off through celite, and the filtrate was concentrated. The residue was purified by silica gel column chromatography. The crudely purified product was added to a mixture of hydroxylammonium chloride (1.38 g), sodium hydrogen carbonate (2.22 g) and dimethyl sulfoxide (20 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (20 mL). N,N'-carbonyldiimidazole (0.33 g) and then 1,8-diazabicyclo[5.4.0]undec-7-ene (0.30 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.68 g, 62%).

$^1$H NMR (300 MHz, CDCl$_3$) δ 1.01 (t, J=7.2, 3H), 1.47 (s, 3H), 1.49 (s, 3H), 1.54-1.80 (m, 2H), 2.19 (s, 3 H), 2.54-2.72 (m, 2 H), 3.02 (s, 2H), 3.99 (s, 2 H), 6.68 (d, J=8.1, 1H), 6.77-7.10 (m, 4H), 7.32-7.50 (m, 3H), 7.54-7.62 (m, 1H), 7.66-7.75 (m, 1H)

Example 398

5-{[2-chloro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one

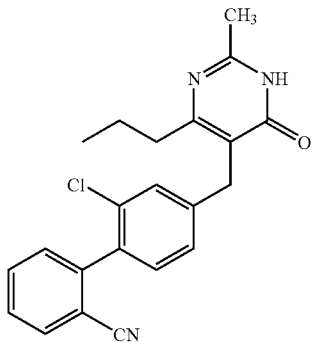

398a) 2'-chloro-4'-[(2-methyl-6-oxo-4-propyl-1,6-dihydropyrimidin-5-yl)methyl]biphenyl-2-carbonitrile To a suspension of 60% sodium hydride (0.50 g) in tetrahydrofuran (20 mL) was added dropwise a solution of ethyl butyrylacetate (2.40 g) in tetrahydrofuran (10 mL). After stirring for 30 min, 4'-(bromomethyl)-2'-chlorobiphenyl-2-carbonitrile (2.30 g) was added. The mixture was stirred at room temperature for 15 hr, and 1 M hydrochloric acid was added. The mixture was extracted with ethyl acetate, and the organic layer was washed with saturated brine, dried over anhydrous magnesium sulfate and concentrated. The residue was purified by silica gel column chromatography to give ethyl 2-[(2-chloro-2'-cyanobiphenyl-4-yl)methyl]-3-oxohexanoate. Then, a solution of the obtained ethyl 2-[(2-chloro-2'-cyanobiphenyl-4-yl)methyl]-3-oxohexanoate, ethanimidamide hydrochloride (1.35 g) and 28% sodium methoxide (4.09 g) in methanol (30 mL) was stirred overnight. The solvent was evaporated under reduced pressure, and saturated aqueous ammonium chloride solution was added to the residue. The precipitated solid was collected by filtration, and washed with water and diethyl ether to give the title compound (1.95 g, 73%) as a white solid.

$^1$H NMR (300 MHz, CDCl$_3$) δ 0.97 (t, J=7.5, 3H), 1.52-1.72 (m, 2H), 2.43 (s, 3H), 2.54-2.64 (m, 2H), 3.93 (s, 2H), 7.20-7.28 (m, 2H), 7.37-7.50 (m, 3H), 7.58-7.65 (m, 1H), 7.71-7.76 (m, 1H), 12.32 (s, 1H)

398b) 5-{[2-chloro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one To a suspension of 2'-chloro-4'-[(2-methyl-6-oxo-4-propyl-1,6-dihydropyrimidin-5-yl)methyl]biphenyl-2-carbonitrile (0.65 g), (4-isopropoxyphenyl)boronic acid (0.62 g), triethylamine (0.8 mL), pyridine (1.6 mL) and molecular sieves 4 A (1.60 g) in dichloromethane (20 mL) was added copper(II) acetate (0.65 g) and the mixture was stirred at room temperature for 2 days. The reaction mixture was diluted with ethyl acetate, the insoluble material was filtered off through celite, and the filtrate was concentrated. The residue was purified by silica gel column chromatography. The crudely purified product was added to a mixture of hydroxylammonium chloride (1.42 g), sodium hydrogen carbonate (2.30 g) and dimethyl sulfoxide (20 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (20 mL). N,N'-carbonyldiimidazole (0.33 g) and then 1,8-diazabicyclo[5.4.0]undec-7-ene (0.31 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.75 g, 78%).

$^1$H NMR (300 MHz, CDCl$_3$) δ 1.05 (t, J=7.2, 3H), 1.35 (d, J=6.0, 6H), 1.53-1.80 (m, 2H), 2.17 (s, 3H), 2.64-2.74 (m, 2H), 3.89 (s, 2H), 4.48-4.60 (m, 1H), 6.88-6.97 (m, 2H), 7.02-7.10 (m, 2H), 7.14 (d, J=7.8, 1H), 7.22-7.37 (m, 3H), 7.46-7.62 (m, 2H), 7.81 (d, J=7.8, 1H)

Example 399

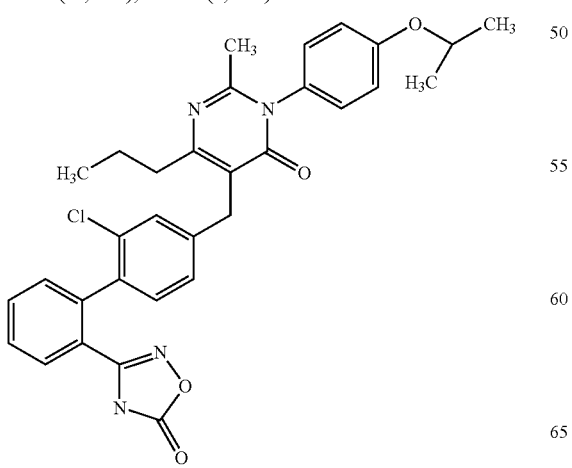

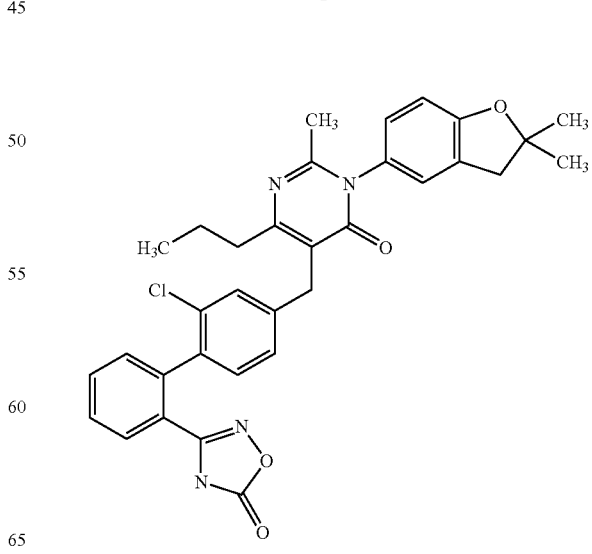

5-{[2-chloro-2'-(5-oxo-4,5-dihydro-1,2,4-oxadiazol-3-yl)biphenyl-4-yl]methyl}-3-(2,2-dimethyl-2,3-dihydro-1-benzofuran-5-yl)-2-methyl-6-propylpyrimidin-4(3H)-one To a suspension of 2'-chloro-4'-[(2-methyl-6-oxo-4-propyl-1,6-dihydropyrimidin-5-yl)methyl]biphenyl-2-carbonitrile (0.65 g), (2,2-dimethyl-2,3-dihydro-1-benzofuran-5-yl)boronic acid (0.66 g), triethylamine (0.8 mL), pyridine (1.6 mL) and molecular sieves 4 A (1.60 g) in dichloromethane (20 mL) was added copper(II) acetate (0.65 g) and the mixture was stirred at room temperature for 2 days. The reaction mixture was diluted with ethyl acetate, the insoluble material was filtered off through celite, and the filtrate was concentrated. The residue was purified by silica gel column chromatography. The crudely purified product was added to a mixture of hydroxylammonium chloride (1.57 g), sodium hydrogen carbonate (2.53 g) and dimethyl sulfoxide (25 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (20 mL). N,N'-carbonyldiimidazole (0.37 g) and then 1,8-diazabicyclo[5.4.0]undec-7-ene (0.34 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.75 g, 75%).

$^1$H NMR (300 MHz, CDCl$_3$) δ 1.05 (t, J=7.2, 3 H), 1.47 (s, 3H), 1.50 (s, 3H), 1.64-1.82 (m, 2H), 2.19 (s, 3 H), 2.64-2.74 (m, 2 H), 3.04 (s, 2H), 3.89 (s, 2 H), 6.73 (dd, J=8.1, 3.9, 1H), 6.82-6.96 (m, 2H), 7.10-7.38 (m, 4H), 7.45-7.62 (m, 2H), 7.78-7.86 (m, 1H)

Example 400

3-(4-isopropoxyphenyl)-5-{[2-methoxy-2'-(5-oxo-4,5-dihydro-1,2,4-oxadiazol-3-yl)biphenyl-4-yl]methyl}-2-methyl-6-propylpyrimidin-4(3H)-one

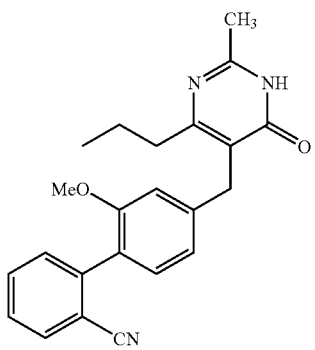

400a) 2'-methoxy-4'-[(2-methyl-6-oxo-4-propyl-1,6-dihydropyrimidin-5-yl)methyl]biphenyl-2-carbonitrile To a suspension of 60% sodium hydride (1.80 g) in tetrahydrofuran (50 mL) was added dropwise a solution of ethyl butyrylacetate (9.50 g) in tetrahydrofuran (30 mL). After stirring for 30 min, 4'-(bromomethyl)-2'-methoxybiphenyl-2-carbonitrile (8.79 g) was added. The mixture was stirred at room temperature for 15 hr, and 1 M hydrochloric acid was added. The mixture was extracted with ethyl acetate, and the organic layer was washed with saturated brine, dried over anhydrous magnesium sulfate and concentrated. The residue was purified by silica gel column chromatography to give ethyl 2-[(2'-cyano-2-methoxybiphenyl-4-yl)methyl]-3-oxohexanoate. Then, a solution of the obtained ethyl 2-[(2'-cyano-2-methoxybiphenyl-4-yl)methyl]-3-oxohexanoate, ethanimidamide hydrochloride (3.25 g) and 28% sodium methoxide (9.91 g) in methanol (70 mL) was stirred overnight. The solvent was evaporated under reduced pressure, and saturated aqueous ammonium chloride solution was added to the residue. The precipitated solid was collected by filtration, and washed with water and diethyl ether to give the title compound (5.63 g, 52%) as a white solid.

$^1$H NMR (300 MHz, CDCl$_3$) δ 0.96 (t, J=7.5, 3H), 1.54-1.72 (m, 2H), 2.41 (s, 3H), 2.56-2.66 (m, 2H), 3.80 (s, 3H), 3.95 (s, 2H), 6.86-6.97 (m, 2H), 7.09-7.15 (m, 1H), 7.34-7.44 (m, 2H), 7.54-7.62 (m, 1H), 7.66-7.72 (m, 1H)

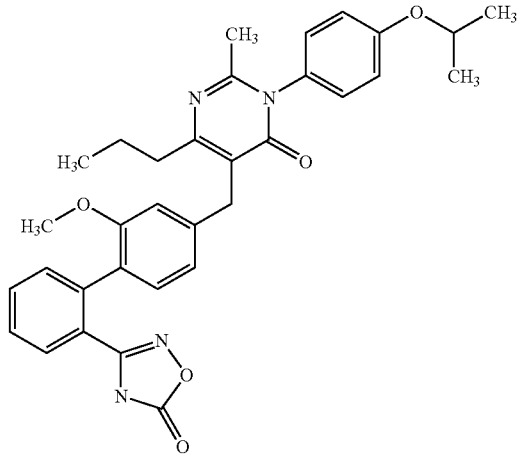

400b) 3-(4-isopropoxyphenyl)-5-{[2-methoxy-2'-(5-oxo-4,5-dihydro-1,2,4-oxadiazol-3-yl)biphenyl-4-yl]methyl}-2-methyl-6-propylpyrimidin-4(3H)-one To a suspension of 2'-methoxy-4'-[(2-methyl-6-oxo-4-propyl-1,6-dihydropyrimidin-5-yl)methyl]biphenyl-2-carbonitrile (1.00 g), (4-isopropoxyphenyl)boronic acid (1.00 g), triethylamine (1.3 mL), pyridine (2.5 mL) and molecular sieves 4 A (2.50 g) in dichloromethane (30 mL) was added copper(II) acetate (0.98 g) and the mixture was stirred at room temperature for 2 days. The reaction mixture was diluted with ethyl acetate, the insoluble material was filtered off through celite, and the filtrate was concentrated. The residue was purified by silica gel column chromatography. The crudely purified product was added to a mixture of hydroxylammonium chloride (2.05 g), sodium hydrogen carbonate (3.31 g) and dimethyl sulfoxide (10 mL), which had been stirred at 40°

C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.48 g) and then 1,8-diazabicyclo[5.4.0]undec-7-ene (0.45 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as colorless crystals (0.88 g, 58%).

$^1$H NMR (300 MHz, CDCl$_3$) δ 1.05 (t, J=7.5, 3H), 1.36 (d, J=6.0, 6H), 1.68-1.84 (m, 2H), 2.18 (s, 3H), 2.66-2.76 (m, 2H), 3.67 (s, 3H), 3.93 (s, 2H), 4.48-4.64 (m, 1H), 6.92-7.02 (m, 4H), 7.05-7.12 (m, 3H), 7.28-7.34 (m, 1H), 7.41-7.49 (m, 1H), 7.53-7.60 (m, 1H), 7.81-7.86 (m, 1H)

Example 401

5-{[2-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one

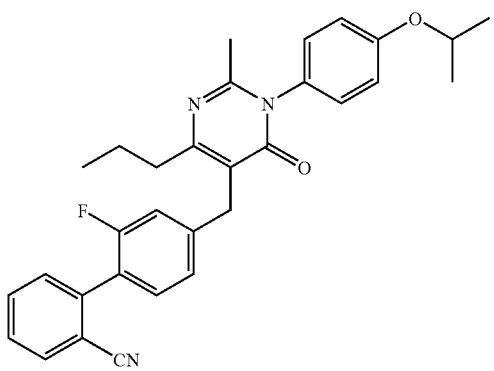

401a) 2'-fluoro-4'-{[1-(4-isopropoxyphenyl)-2-methyl-6-oxo-4-propyl-1,6-dihydropyrimidin-5-yl]methyl}biphenyl-2-carbonitrile A mixture of 2'-fluoro-4'-[(2-methyl-6-oxo-4-propyl-1,6-dihydropyrimidin-5-yl)methyl]biphenyl-2-carbonitrile (1.0 g), (4-isopropoxyphenyl)boronic acid (0.51 g), copper acetate (0.5 g), pyridine (1.1 mL), triethylamine (1.9 mL), molecular sieves 4 A (2.0 g) and methylene chloride (10 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless amorphous solid (0.94 g, 69%).

$^1$H NMR (300 MHz, CDCl$_3$) δ 1.02 (t, J=7.4, 3 H), 1.36 (d, J=6.0, 6 H), 1.63-1.79 (m, 2 H), 2.19 (s, 3 H), 2.59-2.69 (m, 2 H), 3.95 (s, 2 H), 4.51-4.64 (m, 1 H), 6.96-7.02 (m, 2 H), 7.08-7.23 (m, 4 H), 7.27-7.33 (m, 1 H), 7.41-7.50 (m, 2H), 7.59-7.66 (m, 1 H), 7.75 (dd, J=8.01, 1.04, 1 H)

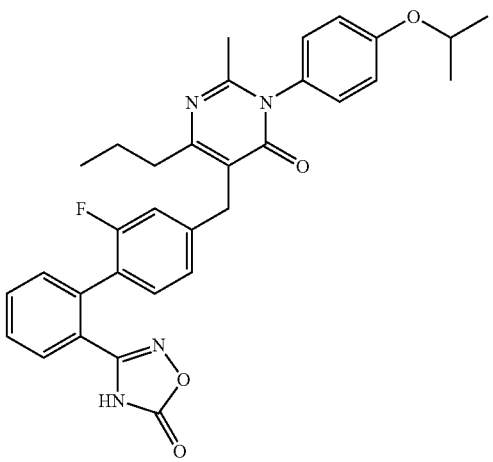

401b) 5-{[2-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one A mixture of hydroxylammonium chloride (1.12 g), sodium hydrogen carbonate (1.6 g) and dimethyl sulfoxide (10 mL) was stirred at 40° C. for 30 min, 2'-fluoro-4'-{[1-(4-isopropoxyphenyl)-2-methyl-6-oxo-4-propyl-1,6-dihydropyrimidin-5-yl]methyl}biphenyl-2-carbonitrile (0.94 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (15 mL). N,N'-carbonyldiimidazole (0.4 g) and then 1,8-diazabicyclo[5.4.0]undec-7-ene (0.4 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.53 g, 50%).

$^1$H NMR (300 MHz, DMSO-d$_6$) δ 0.90 (t, J=7.4, 3 H), 1.30 (d, J=6.1, 6 H), 1.47-1.63 (m, 2 H), 2.07 (s, 3 H), 2.47-2.54 (m, 2 H), 3.88 (s, 2 H), 4.59-4.74 (m, 1 H), 7.00-7.17 (m, 4 H), 7.20-7.31 (m, 3 H), 7.44-7.53 (m, 1 H), 7.57-7.65 (m, 1 H), 7.66-7.74 (m, 2 H), 12.59 (s, 1 H)

Example 402

3-(2,2-dimethyl-2,3-dihydro-1-benzofuran-5-yl)-5-{[2-fluoro-2'-(5-oxo-4,5-dihydro-1,2,4-oxadiazol-3-yl)biphenyl-4-yl]methyl}-2-methyl-6-propylpyrimidin-4(3H)-one

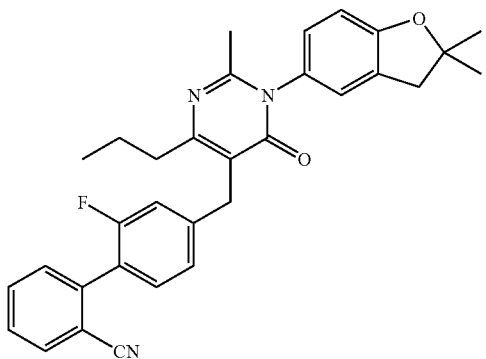

402a) 4'-{[1-(2,2-dimethyl-2,3-dihydro-1-benzofuran-5-yl)-2-methyl-6-oxo-4-propyl-1,6-dihydropyrimidin-5-yl]methyl}-2'-fluorobiphenyl-2-carbonitrile A mixture of 2'-fluoro-4'-[(2-methyl-6-oxo-4-propyl-1,6-dihydropyrimidin-5-yl)methyl]biphenyl-2-carbonitrile (1.0 g), (2,2-dimethyl-2,3-dihydro-1-benzofuran-5-yl)boronic acid (0.53 g), copper acetate (0.5 g), pyridine (1.1 mL), triethylamine (1.9 mL), molecular sieves 4 A (2.0 g) and methylene chloride (10 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless amorphous solid (0.98 g, 69%).

$^1$H NMR (300 MHz, CDCl$_3$) δ 1.02 (t, J=7.4, 3 H), 1.50 (d, J=11, 6 H), 1.63-1.77 (m, 2 H), 2.21 (s, 3 H), 2.60-2.68 (m, 2H), 3.06 (d, J=2.6, 2 H), 3.95 (d, J=1.9, 2 H), 6.79-6.84 (m, 1 H), 6.89-7.00 (m, 2 H), 7.10-7.22 (m, 2 H), 7.27-7.33 (m, 1 H), 7.41-7.49 (m, 2 H), 7.59-7.66 (m, 1 H), 7.73-7.78 (m, 1 H)

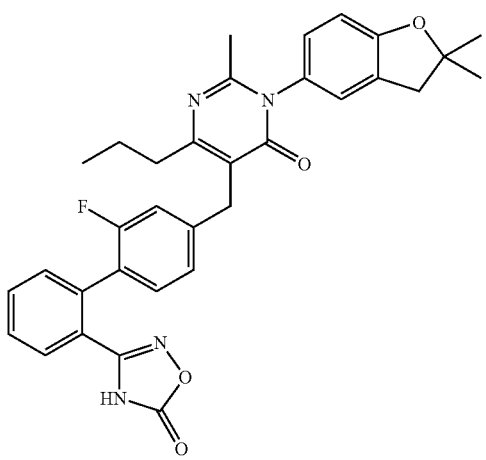

402b) 3-(2,2-dimethyl-2,3-dihydro-1-benzofuran-5-yl)-5-{[2-fluoro-2'-(5-oxo-4,5-dihydro-1,2,4-oxadiazol-3-yl)biphenyl-4-yl]methyl}-2-methyl-6-propylpyrimidin-4(3H)-one A mixture of hydroxylammonium chloride (1.14 g), sodium hydrogen carbonate (1.6 g) and dimethyl sulfoxide (10 mL) was stirred at 40° C. for 30 min, 4'-{[1-(2,2-dimethyl-2,3-dihydro-1-benzofuran-5-yl)-2-methyl-6-oxo-4-propyl-1,6-dihydropyrimidin-5-yl]methyl}-2'-fluorobiphenyl-2-carbonitrile (0.98 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (15 mL). N,N'-carbonyldiimidazole (0.4 g) and then 1,8-diazabicyclo[5.4.0]undec-7-ene (0.4 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as colorless crystals (0.6 g, 55%).

$^1$H NMR (300 MHz, DMSO-d$_6$) δ 0.90 (t, J=7.2, 3 H), 1.45 (d, J=3.8, 6 H), 1.49-1.61 (m, 2 H), 2.09 (s, 3 H), 2.45-2.58 (m, 2 H), 3.05 (s, 2 H), 3.88 (s, 2 H), 6.80 (d, J=8.3, 1 H), 7.02-7.19 (m, 4 H), 7.25 (t, J=8.0, 1 H), 7.48 (d, J=7.6, 1H), 7.57-7.64 (m, 1 H), 7.65-7.74 (m, 2 H), 12.59 (s, 1 H)

Example 403

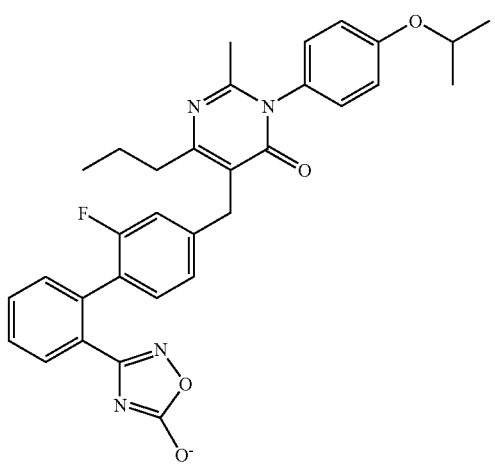

5-{[2-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one potassium salt To a mixture of 5-{[2-fluoro-2'-(5-oxo-4,5-dihydro-1,2,4-oxadiazol-3-yl)biphenyl-4-yl]methyl}-3-(4-isopropoxyphenyl)-2-methyl-6-propylpyrimidin-4(3H)-one (0.44 g) and ethanol (8 mL) was added dropwise 0.1 M potassium hydroxide-ethanol solution (8 mL), and the mixture was stirred at room temperature for 6 hr. The solvent was evaporated from the reaction mixture under reduced pressure to give crude

Example 404

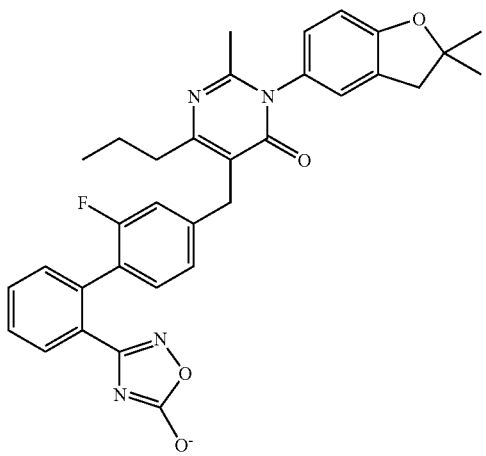

3-(2,2-dimethyl-2,3-dihydro-1-benzofuran-5-yl)-5-{[2-fluoro-2'-(5-oxo-4,5-dihydro-1,2,4-oxadiazol-3-yl)biphenyl-4-yl]methyl}-2-methyl-6-propylpyrimidin-4(3H)-one potassium salt To a mixture of 3-(2,2-dimethyl-2,3-dihydro-1-benzofuran-5-yl)-5-{[2-fluoro-2'-(5-oxo-4,5-dihydro-1,2,4-oxadiazol-3-yl)biphenyl-4-yl]methyl}-2-methyl-6-propylpyrimidin-4(3H)-one (0.47 g) and ethanol (8 mL) was added dropwise 0.1 M potassium hydroxide-ethanol solution (8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.47 g, 95%).

$^1$H NMR (300 MHz, DMSO-$d_6$) δ 0.93 (t, J=7.4, 3 H), 1.45 (d, J=3.8, 6 H), 1.52-1.66 (m, 2 H), 2.08 (s, 3 H), 2.51-2.56 (m, 2 H), 3.05 (s, 2 H), 3.84 (s, 2 H), 6.80 (d, J=8.5, 1 H), 6.93-7.26 (m, 6 H), 7.39-7.46 (m, 2 H), 7.69-7.73 (m, 1H)

Example 405

2-methyl-5-{[2'-(5-oxo-4,5-dihydro-1,2,4-oxadiazol-3-yl)biphenyl-4-yl]methyl}-6-propyl-3-[6-(tetrahydro-2H-pyran-4-yloxy)pyridin-3-yl]pyrimidin-4(3H)-one

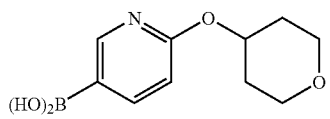

405a) [6-(tetrahydro-2H-pyran-4-yloxy)pyridin-3-yl]boronic acid

A mixture of 5-bromo-2-chloropyridine (8.6 g), tetrahydro-2H-pyran-4-ol (5.0 g), sodium hydride (3.6 g) and dimethylformamide (80 mL) were stirred at 60° C. for 12 hr. The reaction mixture was partitioned between ethyl acetate and water. The ethyl acetate layer was washed with water and saturated brine, and dried over anhydrous magnesium sulfate. The solvent was evaporated under reduced pressure. The residue was dissolved in dimethylformamide (100 mL), 4,4,4',4',5,5,5',5'-octamethyl-2,2'-bi-1,3,2-dioxaborolane (13.6 g), palladium acetate(II)(0.05 g) and potassium acetate (13.1 g) were added and the mixture was stirred at 90° C. for 12 hr. The reaction mixture was partitioned between ethyl acetate and water. The ethyl acetate layer was washed with water and saturated brine, and dried over anhydrous magnesium sulfate. The solvent was evaporated under reduced pressure. The residue was dissolved in tetrahydrofuran (260 mL), sodium periodate (19 g) and 0.5 M hydrochloric acid (130 mL) were added, and the mixture was stirred at 0° C. for 2 hr, and at room temperature for 12 hr. The solvent was evaporated from the reaction mixture under reduced pressure, and the residue was diluted with ethyl acetate, washed with saturated aqueous sodium hydrogen carbonate, water and saturated brine, and dried over anhydrous magnesium sulfate. The solvent was evaporated under reduced pressure and the residue was purified by silica gel column chromatography to give the title compound as a colorless solid (2.23 g, 22%).

$^1$H NMR (300 MHz, CDCl$_3$) δ 1.74-1.89 (m, 2 H), 2.02-2.15 (m, 2 H), 3.56-3.70 (m, 2 H), 3.92-4.07 (m, 2 H), 5.23-5.35 (m, 1 H), 6.71 (s, 1H), 6.74 (s, 1H), 6.81 (d, J=8.5, 1 H), 7.72 (dd, J=8.5 2.5, 1 H), 8.28 (d, J=2.5, 1 H)

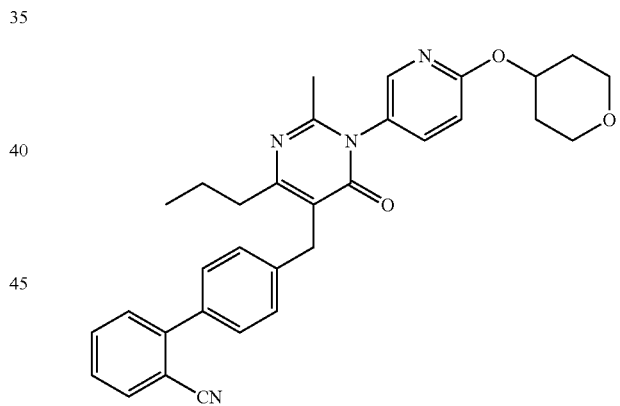

405b) 4'-({2-methyl-6-oxo-4-propyl-1-[6-(tetrahydro-2H-pyran-4-yloxy)pyridin-3-yl]-1,6-dihydropyrimidin-5-yl}methyl)biphenyl-2-carbonitrile A mixture of 4'-[(2-methyl-6-oxo-4-propyl-1,6-dihydropyrimidin-5-yl)methyl]biphenyl-2-carbonitrile (0.5 g), [6-(tetrahydro-2H-pyran-4-yloxy)pyridin-3-yl]boronic acid (0.49 g), copper acetate (0.53 g), pyridine (0.6 mL), triethylamine (1 mL), molecular sieves 4 A (1 g) and methylene chloride (10 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless amorphous solid (0.25 g, 33%).

$^1$H NMR (300 MHz, CDCl$_3$) δ 1.01 (t, J=7.4, 3 H), 1.62-1.91 (m, 4 H), 2.01-2.14 (m, 2 H), 2.21 (s, 3 H), 2.62-2.70 (m, 2H), 3.55-3.68 (m, 2 H), 3.92-4.05 (m, 4 H), 5.21-5.34 (m, 1 H), 6.87 (d, J=8.9, 1 H), 7.37-7.50 (m, 7 H), 7.58-7.65 (m, 1 H), 7.74 (dd, J=7.7, 1.1, 1 H), 8.00 (d, J=2.6, 1 H)

405c) 2-methyl-5-{[2'-(5-oxo-4,5-dihydro-1,2,4-oxadiazol-3-yl)biphenyl-4-yl]methyl}-6-propyl-3-[6-(tetrahydro-2H-pyran-4-yloxy)pyridin-3-yl]pyrimidin-4(3H)-one

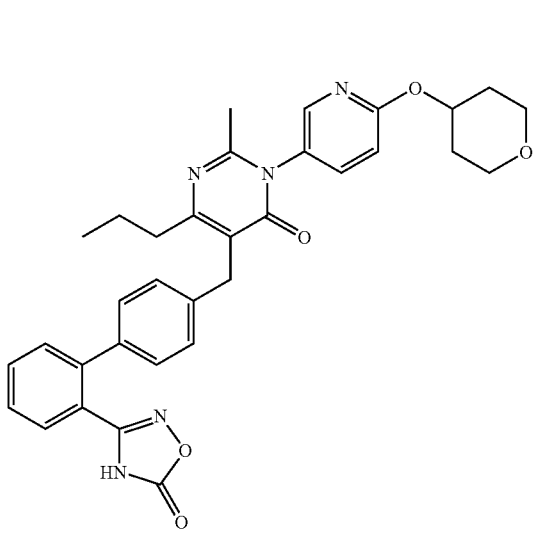

A mixture of hydroxylammonium chloride (0.28 g), sodium hydrogen carbonate (0.4 g) and dimethyl sulfoxide (8 mL) was stirred at 40° C. for 30 min, 4'-({2-methyl-6-oxo-4-propyl-1-[6-(tetrahydro-2H-pyran-4-yloxy)pyridin-3-yl]-1,6-dihydropyrimidin-5-yl}methyl)biphenyl-2-carbonitrile (0.25 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL) N,N'-carbonyldiimidazole (0.12 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless amorphous solid (0.18 g, 64%).

$^1$H NMR (300 MHz, DMSO-d$_6$) δ 0.84-0.94 (m, 3 H), 1.46-1.76 (m, 4 H), 2.00-2.13 (m, 5 H), 3.27-3.37 (m, 2 H), 3.44-3.56 (m, 2 H), 3.81-3.96 (m, 4 H), 5.17-5.28 (m, 1 H), 6.96 (d, J=8.7, 1 H), 7.18-7.32 (m, 4 H), 7.46-7.58 (m, 2H), 7.63-7.72 (m, 2 H), 7.79 (dd, J=8.9, 2.6, 1 H), 8.19 (d, J=2.3, 1 H), 12.38 (s, 1 H)

Example 406

2-ethyl-5-{[2'-(5-oxo-4,5-dihydro-1,2,4-oxadiazol-3-yl)biphenyl-4-yl]methyl}-6-propyl-3-[6-(tetrahydro-2H-pyran-4-yloxy)pyridin-3-yl]pyrimidin-4(3H)-one

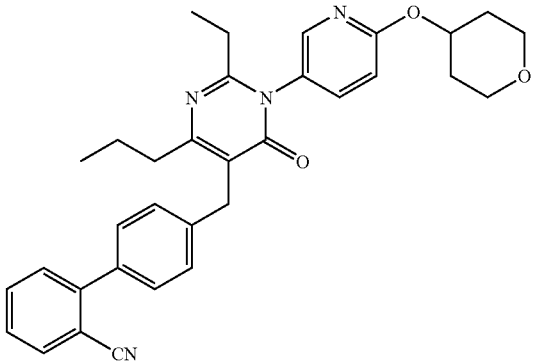

406a) 4'-({2-ethyl-6-oxo-4-propyl-1-[6-(tetrahydro-2H-pyran-4-yloxy)pyridin-3-yl]-1,6-dihydropyrimidin-5-yl}methyl)biphenyl-2-carbonitrile A mixture of 4'-[(2-ethyl-6-oxo-4-propyl-1,6-dihydropyrimidin-5-yl)methyl]biphenyl-2-carbonitrile (0.52 g), [6-(tetrahydro-2H-pyran-4-yloxy)pyridin-3-yl]boronic acid (0.49 g), copper acetate (0.53 g), pyridine (0.6 mL), triethylamine (1 mL), molecular sieves 4 A (1 g) and methylene chloride (10 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless amorphous solid (0.2 g, 26%).

$^1$H NMR (300 MHz, CDCl$_3$) δ 1.01 (t, J=7.4, 3 H), 1.17 (t, J=7.5, 3 H), 1.65-1.91 (m, 4 H), 2.06-2.13 (m, 2 H), 2.31-2.48 (m, 2 H), 2.65-2.73 (m, 2 H), 3.56-3.67 (m, 2 H), 3.94-4.07 (m, 4 H), 5.21-5.32 (m, 1 H), 6.77-6.90 (m, 1 H), 7.36-7.50 (m, 7 H), 7.57-7.65 (m, 1 H), 7.68-7.76 (m, 1H), 7.99 (d, J=2.6, 1 H)

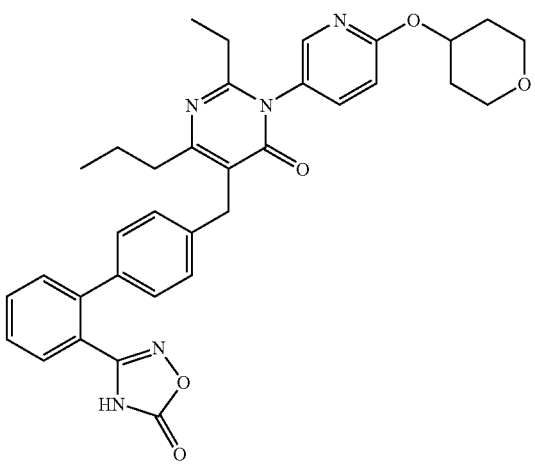

406b) 2-ethyl-5-{[2'-(5-oxo-4,5-dihydro-1,2,4-oxa-diazol-3-yl)biphenyl-4-yl]methyl}-6-propyl-3-[6-(tetrahydro-2H-pyran-4-yloxy)pyridin-3-yl]pyrimi-din-4(3H)-one A mixture of hydroxylammonium chloride (0.23 g), sodium hydrogen carbonate (0.32 g) and dimethyl sulfoxide (8 mL) was stirred at 40° C. for 30 min, 4'-({2-ethyl-6-oxo-4-propyl-1-[6-(tetrahydro-2H-pyran-4-yloxy)pyridin-3-yl]-1,6-dihydropyrimidin-5-yl}methyl)biphenyl-2-carbonitrile (0.2 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (4 mL) N,N'-carbonyldiimidazole (0.09 g) and then 1,8-diazabicyclo[5.4.0]undec-7-ene (0.09 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless amorphous solid (0.6 g, 27%).

$^1$H NMR (300 MHz, DMSO-$d_6$) δ 0.90 (t, J=7.4, 3 H), 1.06 (t, J=7.3, 3 H), 1.46-1.76 (m, 4 H), 1.96-2.09 (m, 2 H), 2.20-2.39 (m, 2 H), 2.52-2.59 (m, 2 H), 3.46-3.56 (m, 2 H), 3.80-3.94 (m, 4 H), 5.14-5.29 (m, 1 H), 6.96 (d, J=8.9, 1H), 7.18-7.31 (m, 4 H), 7.46-7.60 (m, 2 H), 7.61-7.74 (m, 2 H), 7.79 (dd, J=8.8, 2.7, 1 H), 8.17 (d, J=2.5, 1 H), 12.38 (s, 1 H)

Example 407

3-[6-(2,2-dimethylpropoxy)pyridin-3-yl]-2-ethyl-5-{[2'-(5-oxo-4,5-dihydro-1,2,4-oxadiazol-3-yl)biphe-nyl-4-yl]methyl}-6-propylpyrimidin-4(3H)-one

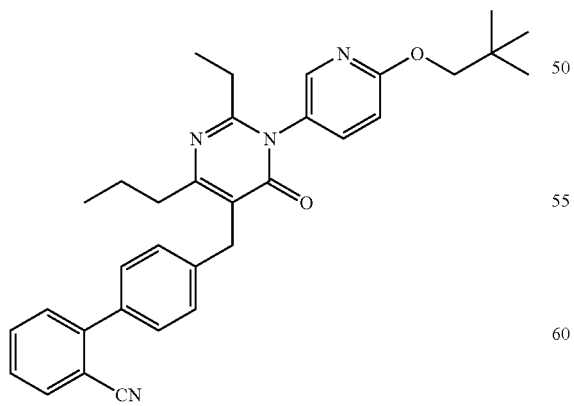

407a) 4'-({1-[6-(2,2-dimethylpropoxy)pyridin-3-yl]-2-ethyl-6-oxo-4-propyl-1,6-dihydropyrimidin-5-yl}methyl)biphenyl-2-carbonitrile A mixture of 4'-[(2-ethyl-6-oxo-4-propyl-1,6-dihydropy-rimidin-5-yl)methyl]biphenyl-2-carbonitrile (0.7 g), [6-(2,2-dimethylpropoxy)pyridin-3-yl]boronic acid (0.61 g), copper acetate (0.71 g), pyridine (0.8 mL), triethylamine (1.4 mL), molecular sieves 4 A (1.4 g) and methylene chloride (10 mL) was stirred at room temperature for 24 hr. Ethyl acetate was added to the reaction mixture, and the insoluble solid was filtered off. The solvent of the filtrate was evaporated under reduced pressure, and the residue was purified by silica gel column chromatography to give the title compound as a colorless amorphous solid (0.12 g, 12%).

$^1$H NMR (300 MHz, CDCl$_3$) δ 0.96-1.09 (m, 12 H), 1.17 (t, J=7.4, 3 H), 1.65-1.80 (m, 2 H), 2.29-2.51 (m, 2 H), 2.64-2.72 (m, 2 H), 3.92-4.06 (m, 4 H), 6.90 (d, J=8.7, 1 H), 7.36-7.50 (m, 7 H), 7.58-7.65 (m, 1 H), 7.74 (dd, J=7.8, 1.0, 1H), 8.00 (d, J=2.3, 1 H)

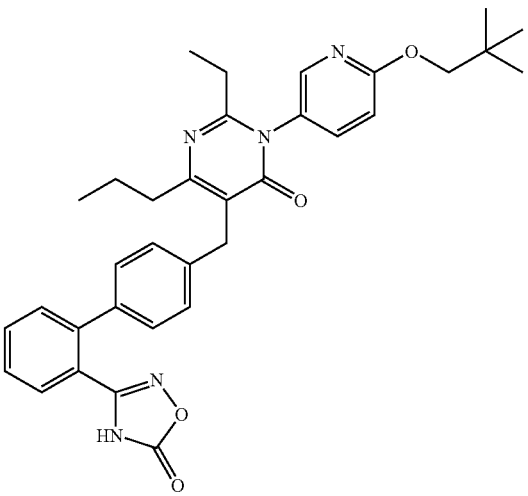

407b) 3-[6-(2,2-dimethylpropoxy)pyridin-3-yl]-2-ethyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.12 g), sodium hydrogen carbonate (0.19 g) and dimethyl sulfoxide (5 mL) was stirred at 40° C. for 30 min, 4'-({1-[6-(2,2-dimethylpropoxy)pyridin-3-yl]-2-ethyl-6-oxo-4-propyl-1,6-dihydropyrimidin-5-yl}methyl)biphenyl-2-carbonitrile (0.12 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (3 mL) N,N'-carbonyldiimidazole (0.06 g) and then 1,8-diazabicyclo[5.4.0]undec-7-ene (0.05 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless amorphous solid (0.08 g, 62%).

$^1$H NMR (300 MHz, DMSO-d$_6$) δ 0.90 (t, J=7.4, 3 H), 0.97-1.10 (m, 12 H), 1.51-1.65 (m, 2 H), 2.19-2.42 (m, 2 H), 2.52-2.58 (m, J=7.4, 2 H), 3.88 (s, 2 H), 3.94-4.06 (m, 2 H), 6.98 (d, J=8.9, 1 H), 7.18-7.31 (m, 4 H), 7.45-7.58 (m, 2H), 7.60-7.71 (m, 2 H), 7.78 (dd, J=8.8, 2.7, 1 H), 8.16 (d, J=2.6, 1 H), 12.38 (s, 1 H)

Example 408

5-{[3-fluoro-2'-(5-oxo-4,5-dihydro-1,2,4-oxadiazol-3-yl)biphenyl-4-yl]methyl}-2-methyl-6-propyl-3-[4-(vinyloxy)phenyl]pyrimidin-4(3H)-one

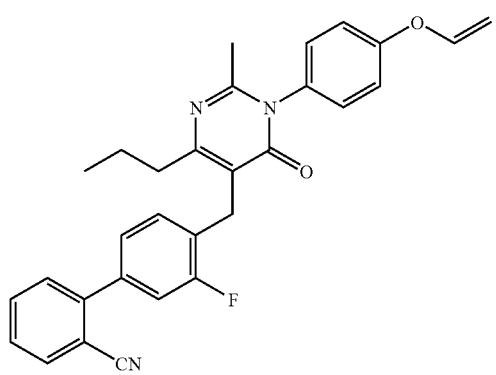

408a) 3'-fluoro-4'-({2-methyl-6-oxo-4-propyl-1-[4-(vinyloxy)phenyl]-1,6-dihydropyrimidin-5-yl}methyl)biphenyl-2-carbonitrile A mixture of 3'-fluoro-4'-{[1-(4-hydroxyphenyl)-2-methyl-6-oxo-4-propyl-1,6-dihydropyrimidin-5-yl]methyl}biphenyl-2-carbonitrile (2 g), vinyl acetate (0.82 mL), sodium carbonate (0.28 g), bis(1,5-cyclooctadiene)diiridium(I) dichloride (0.02 g) and toluene (10 mL) were stirred at 100° C. for 48 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (1.59 g, 75%).

$^1$H NMR (300 MHz, CDCl$_3$) δ 1.01 (t, J=7.4, 3 H), 1.60-1.75 (m, 3 H), 2.18 (s, 3 H), 2.60-2.70 (m, 2 H), 3.98 (s, 2 H), 4.54 (dd, J=6.0, 1.9, 1 H), 4.87 (dd, J=13, 1.9, 1 H), 6.65 (dd, J=13, 6.0, 1 H), 7.10-7.24 (m, 6 H), 7.39-7.49 (m, 3 H), 7.57-7.68 (m, 1 H), 7.72-7.78 (m, 1 H)

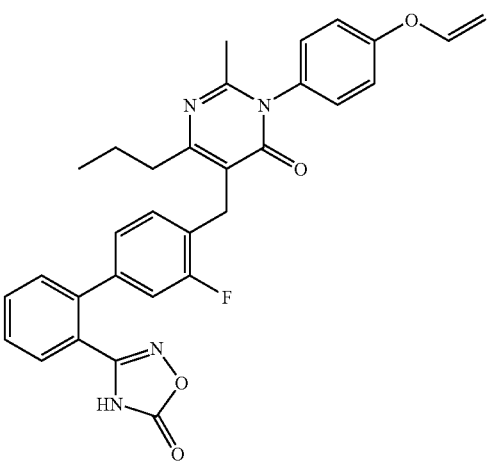

408b) 5-{[3-fluoro-2'-(5-oxo-4,5-dihydro-1,2,4-oxadiazol-3-yl)biphenyl-4-yl]methyl}-2-methyl-6-propyl-3-[4-(vinyloxy)phenyl]pyrimidin-4(3H)-one A mixture of hydroxylammonium chloride (0.72 g), sodium hydrogen carbonate (1.02 g) and dimethyl sulfoxide (15 mL) was stirred at 40° C. for 30 min, 3'-fluoro-4'-({2-methyl-6-oxo-4-propyl-1-[4-(vinyloxy)phenyl]-1,6-dihydropyrimidin-5-yl}methyl)biphenyl-2-carbonitrile (0.58 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (4 mL). N,N'-carbonyldiimidazole (0.3 g) and then 1,8-diazabicyclo[5.4.0]undec-7-ene (0.27 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless amorphous solid (0.44 g, 67%).

$^1$H NMR (300 MHz, DMSO-d$_6$) δ 0.89 (t, J=7.4, 3 H), 1.49-1.63 (m, 2 H), 2.08 (s, 3 H), 2.45-2.54 (m, 2 H), 3.86 (s, 2 H), 4.56 (dd, J=5.9, 1.6, 1 H), 4.79-4.85 (m, 1 H), 6.90-7.04 (m, 2 H), 7.11-7.23 (m, 4 H), 7.34-7.42 (m, 2 H), 7.51-7.61 (m, 2 H), 7.65-7.73 (m, 2 H), 12.46 (s, 1 H)

Example 409

2-methyl-5-{[2'-(5-oxo-4,5-dihydro-1,2,4-oxadiazol-3-yl)biphenyl-4-yl]methyl}-6-propyl-3-(tetrahydro-2H-pyran-4-yl)pyrimidin-4(3H)-one

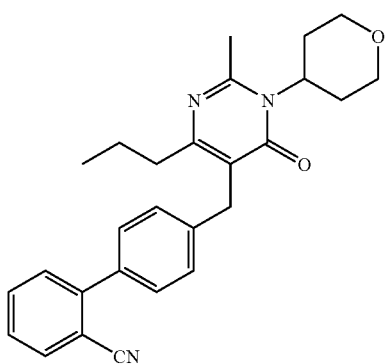

409a) 4'-{[2-methyl-6-oxo-4-propyl-1-(tetrahydro-2H-pyran-4-yl)-1,6-dihydropyrimidin-5-yl]methyl}biphenyl-2-carbonitrile A mixture of 5-(4-bromobenzyl)-2-methyl-6-propyl-3-(tetrahydro-2H-pyran-4-yl)pyrimidin-4(3H)-one (0.7 g), (2-cyanophenyl)boronic acid (0.36 g), [1,1'-bis(diphenylphosphino)ferrocene]dichloropalladium(II) dichloromethane adduct (0.07 g), 2 M aqueous sodium carbonate solution (1.5 mL) and 1,4-dioxane (15 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.61 g, 83%).

$^1$H NMR (300 MHz, CDCl$_3$) δ 0.95 (t, J=7.4, 3 H), 1.52-1.68 (m, 4 H), 2.04 (s, 1 H), 2.47-2.57 (m, 2 H), 2.59 (s, 3 H), 2.85-3.14 (m, J=8.9, 2 H), 3.37-3.51 (m, 2 H), 3.93 (s, 2 H), 4.05-4.15 (m, 2 H), 4.46 (s, 1 H), 7.31-7.52 (m, 6 H), 7.69-7.76 (m, 1 H)

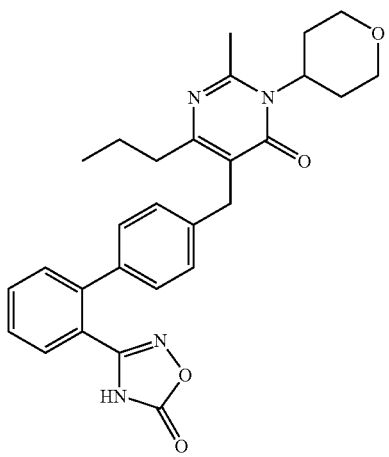

409b) 2-methyl-5-{[2'-(5-oxo-4,5-dihydro-1,2,4-oxadiazol-3-yl)biphenyl-4-yl]methyl}-6-propyl-3-(tetrahydro-2H-pyran-4-yl)pyrimidin-4(3H)-one A mixture of hydroxylammonium chloride (0.12 g), sodium hydrogen carbonate (0.19 g) and dimethyl sulfoxide (5 mL) was stirred at 40° C. for 30 min, 4'-{[2-methyl-6-oxo-4-propyl-1-(tetrahydro-2H-pyran-4-yl)-1,6-dihydropyrimidin-5-yl]methyl}biphenyl-2-carbonitrile (0.12 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (3 mL). N,N'-carbonyldiimidazole (0.06 g) and then 1,8-diazabicyclo[5.4.0]undec-7-ene (0.05 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless amorphous solid (0.08 g, 62%).

$^1$H NMR (300 MHz, DMSO-d$_6$) δ 0.83 (t, J=7.4, 3 H), 1.38-1.54 (m, 2 H), 1.61 (dd, J=11.5, 2.3, 2 H), 2.36-2.45 (m, J=8.7, 6.8, 2 H), 2.57 (s, 3 H), 2.71-2.90 (m, 2 H), 3.33-3.45 (m, 2 H), 3.81 (s, 2 H), 3.93 (dd, J=11.1, 4.0, 2 H), 4.24-4.39 (m, 1 H), 7.16-7.27 (m, 4 H), 7.45-7.58 (m, 2 H), 7.62-7.72 (m, 2 H), 12.35 (s, 1 H)

Example 410

2-(difluoromethyl)-3-(4-methoxyphenyl)-5-{[2'-(5-oxo-4,5-dihydro-1,2,4-oxadiazol-3-yl)biphenyl-4-yl]methyl}-6-propylpyrimidin-4(3H)-one

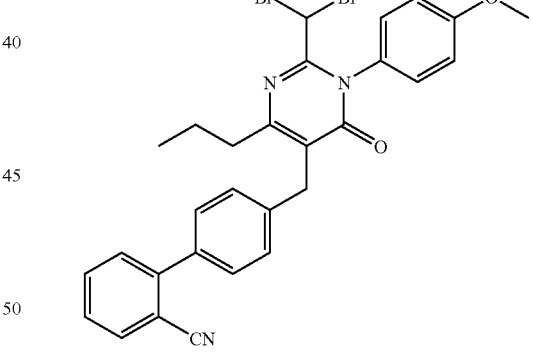

410a) 4'-{[2-(dibromomethyl)-1-(4-methoxyphenyl)-6-oxo-4-propyl-1,6-dihydropyrimidin-5-yl]methyl}biphenyl-2-carbonitrile Bromine (0.57 mL) was gradually added to a mixture of 4'-{[1-(4-methoxyphenyl)-2-methyl-6-oxo-4-propyl-1,6-dihydropyrimidin-5-yl]methyl}biphenyl-2-carbonitrile (1.5 g), sodium acetate (0.3 g) and acetic acid (15 mL), and the mixture was stirred at room temperature for 12 hr. The solvent was evaporated from the reaction mixture under reduced pressure, and the residue was diluted with ethyl acetate, washed with saturated aqueous sodium hydrogen carbonate, water and saturated brine, and dried over anhydrous magnesium sulfate. The solvent was evaporated under reduced pressure and the residue was purified by silica gel column chromatography to give the title compound as a colorless amorphous solid (1.63 g, 81%).

¹H NMR (300 MHz, CDCl₃) δ 1.03 (t, J=7.3, 3 H), 1.72-1.88 (m, 2 H), 2.70-2.84 (m, 2 H), 3.85 (s, 3 H), 4.00 (s, 2 H), 6.05 (s, 1 H), 7.05 (d, J=8.7, 2 H), 7.17-7.27 (m, 2 H), 7.34-7.65 (m, 7 H), 7.70-7.77 (m, 1 H)

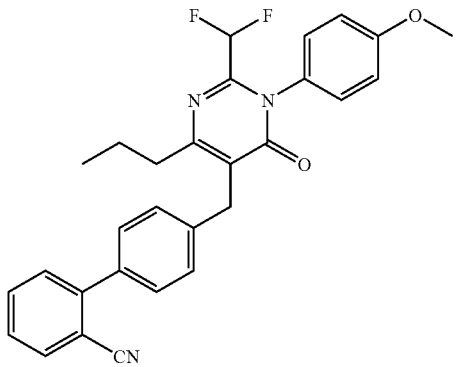

410b) 4'-{[2-(difluoromethyl)-1-(4-methoxyphenyl)-6-oxo-4-propyl-1,6-dihydropyrimidin-5-yl]methyl}biphenyl-2-carbonitrile A mixture of 4'-{[2-(dibromomethyl)-1-(4-methoxyphenyl)-6-oxo-4-propyl-1,6-dihydropyrimidin-5-yl]methyl}biphenyl-2-carbonitrile (1.0 g), tetrabutylammonium fluoride (1.0 M, 3.3 mL) and tetrahydrofuran (10 mL) were stirred at 80° C. for 12 hr. The solvent was evaporated from the reaction mixture under reduced pressure, and the residue was diluted with ethyl acetate, washed with water and saturated brine, and dried over anhydrous magnesium sulfate. The solvent was evaporated under reduced pressure and the residue was purified by silica gel column chromatography to give the title compound as a colorless amorphous solid (0.16 g, 20%).

¹H NMR (300 MHz, CDCl₃) δ 1.02 (t, J=7.4, 3 H), 1.67-1.80 (m, 2 H), 2.68-2.79 (m, 2 H), 3.84 (s, 3 H), 4.01 (s, 2 H), 5.97-6.40 (m, 1H), 6.97-7.07 (m, 2 H), 7.15-7.23 (m, 2 H), 7.36-7.50 (m, 6 H), 7.57-7.65 (m, 1 H), 7.71-7.77 (m, 1H)

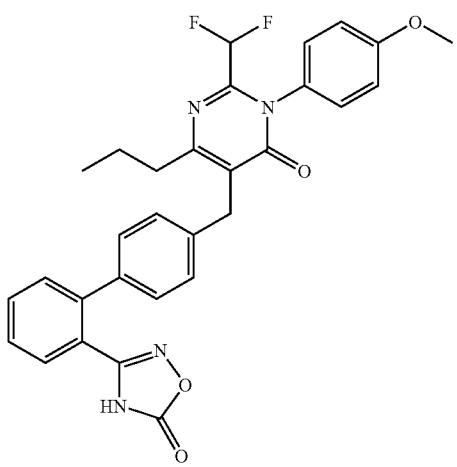

410c) 2-(difluoromethyl)-3-(4-methoxyphenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.19 g), sodium hydrogen carbonate (0.27 g) and dimethyl sulfoxide (5 mL) was stirred at 40° C. for 30 min, 4'-{[2-(difluoromethyl)-1-(4-methoxyphenyl)-6-oxo-4-propyl-1,6-dihydropyrimidin-5-yl]methyl}biphenyl-2-carbonitrile (0.16 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL). N,N'-carbonyldiimidazole (0.08 g) and then 1,8-diazabicyclo[5.4.0]undec-7-ene (0.07 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless amorphous solid (0.11 g, 60%).

¹H NMR (300 MHz, DMSO-d₆) δ 0.90 (t, J=7.3, 3 H), 1.50-1.65 (m, 2 H), 2.56-2.65 (m, 2 H), 3.82 (s, 3 H), 3.94 (s, 2 H), 6.22-6.62 (m, 1 H), 7.07 (d, J=8.9, 2 H), 7.19-7.38 (m, 6H), 7.48-7.59 (m, 2 H), 7.63-7.72 (m, 2 H), 12.39 (s, 1 H)

Example 411

2-(fluoromethyl)-3-(4-methoxyphenyl)-5-{[2'-(5-oxo-4,5-dihydro-1,2,4-oxadiazol-3-yl)biphenyl-4-yl]methyl}-6-propylpyrimidin-4(3H)-one

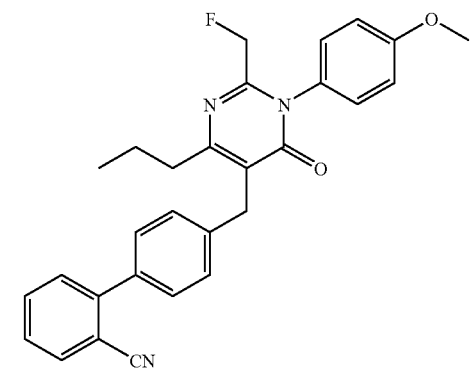

411a) 4'-{[2-(fluoromethyl)-1-(4-methoxyphenyl)-6-oxo-4-propyl-1,6-dihydropyrimidin-5-yl]methyl}biphenyl-2-carbonitrile A mixture of 4'-{[2-(dibromomethyl)-1-(4-methoxyphenyl)-6-oxo-4-propyl-1,6-dihydropyrimidin-5-yl]methyl}biphenyl-2-carbonitrile (1.0 g), tetrabutylammonium fluoride (1.0 M, 3.3 mL) and tetrahydrofuran (10 mL) were stirred at 80° C. for 12 hr. The solvent was evaporated from the reaction mixture under reduced pressure, and the residue was diluted with ethyl acetate, washed with water and saturated brine, and dried over anhydrous magnesium sulfate. The solvent was evaporated under reduced pressure and the residue was purified by silica gel column chromatography to give the title compound as a colorless amorphous solid (0.21 g, 27%).

$^1$H NMR (300 MHz, CDCl$_3$) δ 1.01 (t, J=7.4, 3 H), 1.65-1.80 (m, 2 H), 2.67-2.77 (m, 2 H), 3.84 (s, 3 H), 4.00 (s, 2 H), 4.86 (s, 1 H), 5.02 (s, 1 H), 6.99-7.08 (m, 2 H), 7.15-7.21 (m, 2 H), 7.36-7.51 (m, 6 H), 7.58-7.65 (m, 1 H), 7.71-7.76 (m, 1 H)

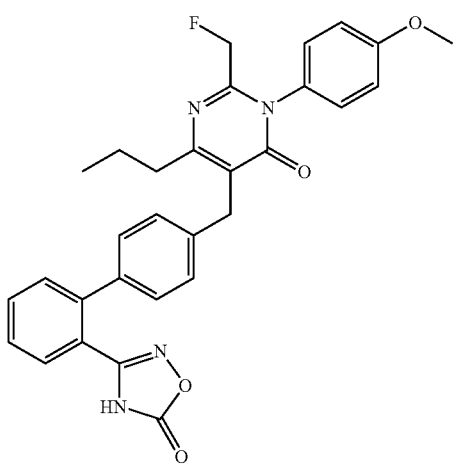

411b) 2-(fluoromethyl)-3-(4-methoxyphenyl)-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.26 g), sodium hydrogen carbonate (0.37 g) and dimethyl sulfoxide (8 mL) was stirred at 40° C. for 30 min, 4'-{[2-(fluoromethyl)-1-(4-methoxyphenyl)-6-oxo-4-propyl-1,6-dihydropyrimidin-5-yl]methyl}biphenyl-2-carbonitrile (0.21 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL). N,N'-carbonyldiimidazole (0.11 g) and then 1,8-diazabicyclo[5.4.0]undec-7-ene (0.1 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless amorphous solid (0.08 g, 36%).

$^1$H NMR (300 MHz, DMSO-d$_6$) δ 0.90 (t, J=7.3, 3 H), 1.50-1.63 (m, 2 H), 2.54-2.61 (m, 2 H), 3.32 (s, 3 H), 3.91 (s, 2 H), 4.87 (s, 1 H), 5.03 (s, 1 H), 7.04-7.11 (m, 2 H), 7.20-7.36 (m, 6 H), 7.48-7.59 (m, 2 H), 7.60-7.73 (m, 2 H), 12.39 (s, 1 H)

Example 412

3-{4-[(2,2-dimethyltetrahydro-2H-pyran-4-yl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one

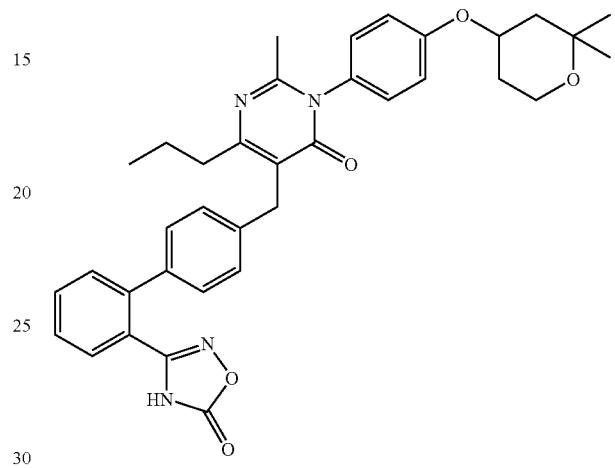

To a solution of 4'-{[1-(4-hydroxyphenyl)-2-methyl-6-oxo-4-propyl-1,6-dihydropyrimidin-5-yl]methyl}biphenyl-2-carbonitrile (0.87 g), 2,2-dimethyltetrahydro-2H-pyran-4-ol (0.78 g) and triphenylphosphine (1.6 g) in tetrahydrofuran (9 mL) was added dropwise diisopropyl azodicarboxylate (1.9 M toluene solution, 3.2 mL). After stirring for 2 hr, water was added, and the mixture was extracted with ethyl acetate. The organic layer was washed with saturated brine, and dried over anhydrous magnesium sulfate. The solvent was evaporated under reduced pressure, and a mixture of the residue, hydroxylammonium chloride (1.4 g), sodium hydrogen carbonate (2 g) and dimethyl sulfoxide (10 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.48 g) and then 1,8-diazabicyclo[5.4.0]undec-7-ene (0.45 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.42 g, 35%) as an amorphous solid.

$^1$H NMR (300 MHz, DMSO-d$_6$) δ 0.89 (3 H, t, J=7.4), 1.19 (3 H, s), 1.23 (3 H, s), 1.35-1.63 (4 H, m), 1.92-2.05 (2 H, m), 2.06 (3 H, s), 2.45-2.56 (2 H, m), 3.63-3.81 (2 H, m), 3.86 (2 H, s), 4.69-4.82 (1 H, m), 7.05-7.12 (2 H, m), 7.18-7.31 (6 H, m), 7.47-7.58 (2 H, m), 7.62-7.72 (2 H, m), 12.39 (1 H, s)

Example 413

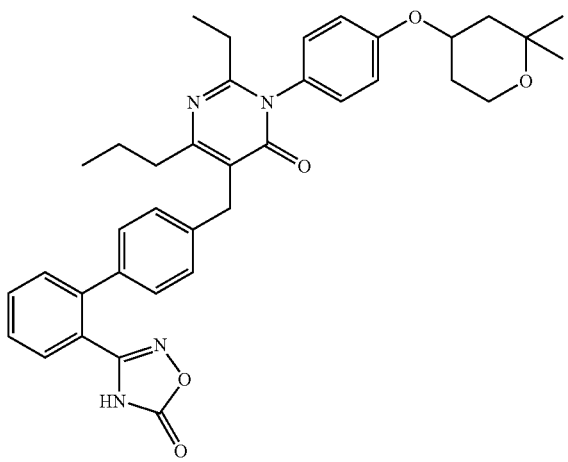

3-{4-[(2,2-dimethyltetrahydro-2H-pyran-4-yl)oxy]phenyl}-2-ethyl-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (0.9 g), 2,2-dimethyltetrahydro-2H-pyran-4-ol (0.78 g) and triphenylphosphine (1.6 g) in tetrahydrofuran (9 mL) was added dropwise diisopropyl azodicarboxylate (1.9 M toluene solution, 3.2 mL). After stirring for 2 hr, water was added, and the mixture was extracted with ethyl acetate. The organic layer was washed with saturated brine, and dried over anhydrous magnesium sulfate. The solvent was evaporated under reduced pressure, and a mixture of the residue, hydroxylammonium chloride (1.4 g), sodium hydrogen carbonate (2 g) and dimethyl sulfoxide (10 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.48 g) and then 1,8-diazabicyclo[5.4.0]undec-7-ene (0.45 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.51 g, 41%) as an amorphous solid.

$^1$H NMR (300 MHz, DMSO-$d_6$) δ 0.90 (3 H, t, J=7.4), 1.05 (3 H, t, J=7.4), 1.20 (3 H, s), 1.24 (3 H, s), 1.34-1.67 (4 H, m), 1.92-2.07 (2 H, m), 2.28 (2 H, q, J=7.6), 2.47-2.57 (2 H, m), 3.60-3.81 (2 H, m), 3.86 (2 H, s), 4.68-4.83 (1 H, m), 7.04-7.13 (2 H, m), 7.18-7.31 (6 H, m), 7.47-7.58 (2 H, m), 7.61-7.74 (2 H, m), 12.39 (1 H, s)

Example 414

2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one

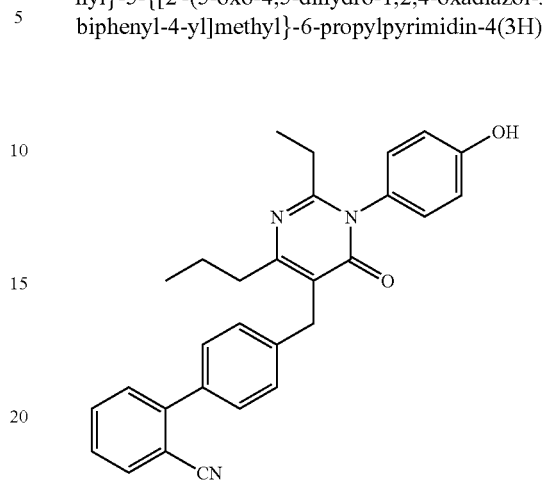

414a) 4'-{[2-ethyl-1-(4-hydroxyphenyl)-6-oxo-4-propyl-1,6-dihydropyrimidin-5-yl]methyl}biphenyl-2-carbonitrile To a solution of 4'-{[2-ethyl-1-(4-methoxyphenyl)-6-oxo-4-propyl-1,6-dihydropyrimidin-5-yl]methyl}biphenyl-2-carbonitrile (26.2 g) in dichloromethane (100 mL) was added dropwise boron tribromide (1.0 M dichloromethane solution, 170 mL) at 0° C. After stirring for 18 hr, ethyl acetate and water were added, and the mixture was extracted with ethyl acetate. The organic layer was washed with saturated sodium hydrogen carbonate and saturated brine, and dried over anhydrous magnesium sulfate. The solvent was evaporated under reduced pressure and the residue was purified by silica gel column chromatography to give the title compound (22.1 g, 87%) as a colorless solid.

$^1$H NMR (300 MHz, CDCl$_3$) δ 0.96-1.04 (m, 3 H), 1.12 (t, J=7.4, 3 H), 1.64-1.79 (m, 2 H), 2.38 (q, J=7.6, 2 H), 2.62-2.73 (m, 2 H), 4.02 (s, 2 H), 6.62-6.69 (m, 2 H), 6.86-6.93 (m, 2 H), 7.36-7.78 (m, 9 H)

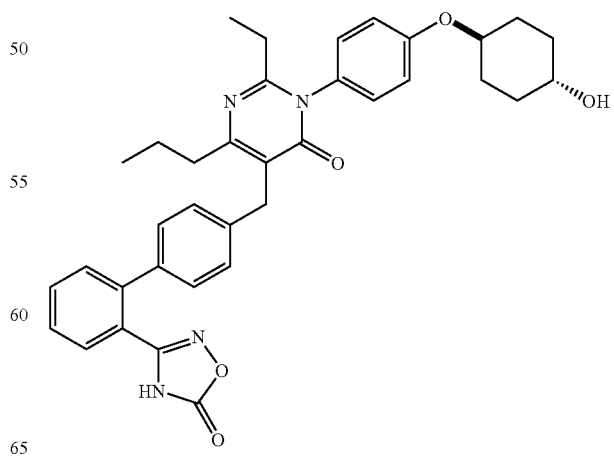

414b) 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (1.2 g), 4-{[tert-butyl(dimethyl)silyl]oxy}cyclohexanol (1.2 g) and triphenylphosphine (1.4 g) in tetrahydrofuran (12 mL) was added dropwise diisopropyl azodicarboxylate (1.9 M toluene solution, 2.8 mL). After stirring for 2 hr, water was added, and the mixture was extracted with ethyl acetate. The organic layer was washed with saturated brine, and dried over anhydrous magnesium sulfate. The solvent was evaporated under reduced pressure, the residue was crudely purified by silica gel column chromatography. This was added to a mixture of hydroxylammonium chloride (0.87 g), sodium hydrogen carbonate (1.3 g) and dimethyl sulfoxide (9 mL) and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (9 mL). N,N'-carbonyldiimidazole (0.3 g) and then 1,8-diazabicyclo[5.4.0]undec-7-ene (0.28 mL) were added, and the mixture was stirred at room temperature for 30 min. Tetrabutylammonium fluoride (1.0 M tetrahydrofuran solution, 2.5 mL) was added, and the mixture was stirred overnight at 50° C. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.56 g, 35%) as an amorphous solid.

$^1$H NMR (300 MHz, DMSO-$d_6$) δ 0.90 (3 H, t, J=7.3), 1.04 (3 H, t, J=7.3), 1.21-1.67 (6 H, m), 1.76-2.11 (4 H, m), 2.28 (2 H, q, J=7.3), 2.44-2.58 (2 H, m), 3.47-3.60 (1 H, m), 3.86 (2 H, s), 4.32-4.44 (1 H, m), 4.59 (1 H, d, J=4.0), 7.04 (2 H, d, J=8.9), 7.16-7.32 (6 H, m), 7.46-7.59 (2 H, m), 7.62-7.72 (2 H, m), 12.38 (1 H, s)

Rf=0.43 (ethyl acetate, silica gel 60 F 254 precoated TLC plates (E. Merck))

414c) Crystalline 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (1) 2-Ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (amorphous powder, 100 mg) was dissolved in ethyl acetate (1 mL) and stood overnight. The obtained colorless crystals were collected to give the title compound (87 mg).

Powder X-ray diffraction (Cu—Kα radiation, diffraction angle:
2θ(°)): 4.60, 8.38, 9.28, 9.66, 10.46, 12.26, 12.86, 13.98, 16.92, 17.32, 18.70, 18.94, 19.62, 20.18, 20.98.

(2) 2-Ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (amorphous powder, 100 mg) was dissolved in acetonitrile (1 mL) and stood overnight. The obtained colorless crystals were collected to give the title compound (81 mg).

Powder X-ray diffraction (Cu—Kα radiation, diffraction angle:
2θ(°)): 8.50, 11.86, 12.26, 13.98, 17.14, 18.46, 19.04, 19.28, 19.62, 20.16, 20.48, 22.58, 24.60.

(3) 2-Ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (amorphous powder, 100 mg) was dissolved in acetone (1 mL) and stood overnight. The obtained colorless crystals were collected to give the title compound (67 mg).

Powder X-ray diffraction (Cu—Kα radiation, diffraction angle:
2θ(°)): 7.36, 7.66, 11.58, 12.84, 13.28, 13.64, 14.50, 15.28, 15.50, 18.38, 18.66, 19.28, 20.20, 20.70, 21.72, 22.14, 22.82.

(4) 2-Ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (2.47 g) was dissolved in acetonitrile (18 ml) at 85° C. followed by being cooled to room temperature over 3 hr with stirring. The precipitate was collected, washed with acetonitrile, and dried under reduced pressure at 80° C. for 3 hr to give the title compound (1.71 g, 69%) as colorless crystals.

Powder X-ray diffraction (Cu—Kα radiation, diffraction angle:
2θ(°)): 8.34, 9.16, 10.64, 11.08, 11.42, 12.42, 13.18, 13.88, 14.78, 15.58, 16.28, 17.10, 17.80, 18.56, 18.94, 19.18, 20.14, 20.86, 21.56, 22.04, 22.44, 23.14, 23.66, 24.80, 26.18, 27.96, 29.16.

Anal calcd for $C_{36}H_3N_4O_5$: C, 71.27; H, 6.31; N, 9.23. Found C, 70.99; H, 6.20; N, 9.14.

Example 415

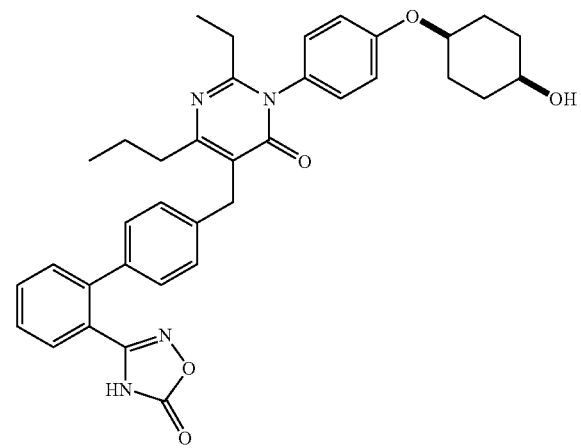

2-ethyl-3-{4-[(cis-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (1.2 g), 4-{[tert-butyl(dimethyl)silyl]oxy}cyclohexanol (1.2 g) and triphenylphosphine (1.4 g) in tetrahydrofuran (12 mL) was added dropwise diisopropyl azodicarboxylate (1.9 M toluene solution, 2.8 mL). After stirring for 2 hr, water was added and the mixture was extracted with ethyl acetate. The organic layer was washed with saturated brine, and dried over anhydrous magnesium sulfate. The solvent was evaporated under reduced pressure, and the residue was crudely purified by silica gel column chromatography. This was added to a mixture of hydroxylammonium chloride (0.87 g), sodium hydrogen carbonate (1.3 g) and dimethyl sulfoxide (9 mL) and the mixture was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (9 mL). N,N'-carbonyldiimidazole (0.3 g) and then 1,8-diazabicyclo[5.4.0]undec-7-ene (0.28 mL) were added, and the mixture was stirred at room temperature for 30 min. Tetrabutylammonium fluoride (1.0 M tetrahydrofuran solution, 2.5 mL) was added, and the mixture was stirred overnight at 50° C. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.47 g, 29%) as an amorphous solid.

$^1$H NMR (300 MHz, DMSO-d$_6$) δ 0.90 (3 H, t, J=7.3), 1.05 (3 H, t, J=7.3), 1.50-1.74 (8 H, m), 1.76-1.93 (2 H, m), 2.29 (2 H, q, J=7.3), 2.46-2.58 (2 H, m), 3.57-3.70 (1 H, m), 3.87 (2 H, s), 4.42-4.54 (2 H, m), 7.01-7.09 (2 H, m), 7.17-7.32 (6 H, m), 7.47-7.59 (2 H, m), 7.61-7.73 (2 H, m), 12.38 (1H, s)

Rf=0.46 (ethyl acetate, silica gel 60 F 254 precoated TLC plates (E. Merck))

Example 416

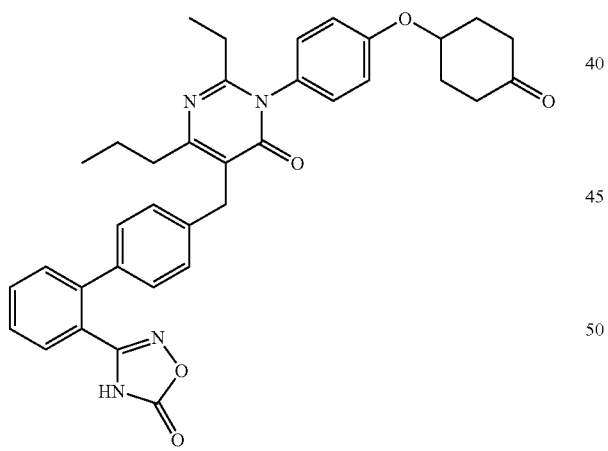

2-ethyl-3-{4-[(4-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one 2-Ethyl-3-{4-[(4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (0.4 g) and 1,1,1-tris(acetyloxy)-1,1-dihydro-1,2-benziodoxol-3(1H)-one (0.42 g) were dissolved in dichloromethane (4 mL) and the mixture was stirred for 1 hr. The reaction mixture was diluted with ethyl acetate, washed with saturated aqueous sodium hydrogen carbonate solution and then with saturated brine, and dried over anhydrous magnesium sulfate. The solvent was evaporated under reduced pressure and the residue was purified by silica gel column chromatography to give the title compound (0.32 g, 80%) as a colorless amorphous solid.

$^1$H NMR (300 MHz, DMSO-d$_6$) δ 0.90 (3 H, t, J=7.3), 1.05 (3 H, t, J=7.3), 1.49-1.67 (2 H, m), 1.96-2.61 (12 H, m), 3.87 (2 H, s), 4.82-4.93 (1 H, m), 7.12-7.32 (8 H, m), 7.46-7.59 (2 H, m), 7.62-7.73 (2 H, m), 12.38 (1 H, s)

Example 417

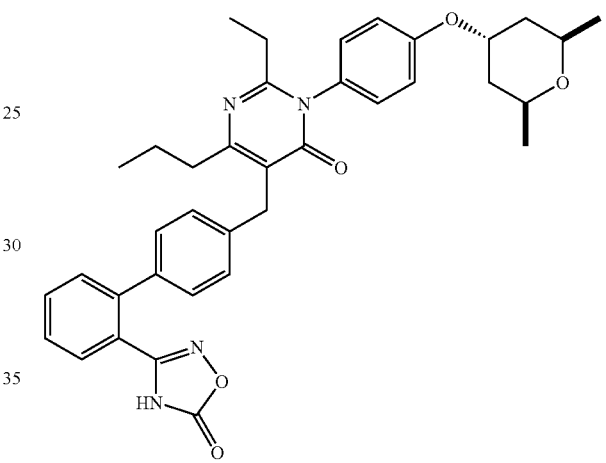

3-(4-{[(2R,4s,6S)-2,6-dimethyltetrahydro-2H-pyran-4-yl]oxy}phenyl)-2-ethyl-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (0.5 g), (2R,4s,6S)-2,6-dimethyltetrahydro-2H-pyran-4-ol (0.29 g) and triphenylphosphine (0.58 g) in tetrahydrofuran (5 mL) was added dropwise diisopropyl azodicarboxylate (1.9 M toluene solution, 1.2 mL). After stirring for 2 hr, water was added, and the mixture was extracted with ethyl acetate. The organic layer was washed with saturated brine, and dried over anhydrous magnesium sulfate. The solvent was evaporated under reduced pressure, a mixture of the residue, hydroxylammonium chloride (0.77 g), sodium hydrogen carbonate (1.1 g) and dimethyl sulfoxide (10 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.27 g) and then 1,8-diazabicyclo

[5.4.0]undec-7-ene (0.25 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.39 g, 57%) as an amorphous solid.

$^1$H NMR (300 MHz, DMSO-$d_6$) δ 0.90 (3 H, t, J=7.4), 1.00-1.19 (9 H, m), 1.35-1.49 (2 H, m), 1.50-1.65 (2 H, m), 1.85 (2 H, d, J=13.3), 2.29 (2 H, q, J=7.4), 2.46-2.58 (2 H, m), 3.77-3.92 (4 H, m), 4.84 (1 H, s), 7.06 (2 H, d, J=8.7), 7.17-7.33 (6 H, m), 7.46-7.59 (2 H, m), 7.62-7.73 (2 H, m), 12.38 (1 H, s)

Example 418

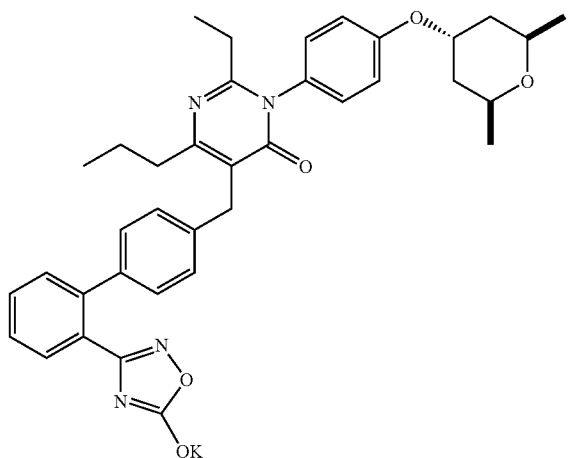

3-(4-{[(2R,4s,6S)-2,6-dimethyltetrahydro-2H-pyran-4-yl]oxy}phenyl)-2-ethyl-5-{[2'-(5-oxo-4,5-dihydro-1,2,4-oxadiazol-3-yl)biphenyl-4-yl]methyl}-6-propylpyrimidin-4(3H)-one potassium salt 3-(4-{[(2R,4s,6S)-2,6-Dimethyltetrahydro-2H-pyran-4-yl]oxy}phenyl)-2-ethyl-5-{[2'-(5-oxo-4,5-dihydro-1,2,4-oxadiazol-3-yl)biphenyl-4-yl]methyl}-6-propylpyrimidin-4(3H)-one (0.3 g) was dissolved in ethanol (10 mL), 8 M potassium hydroxide solution (0.06 mL) was added, and the mixture was stirred for 1 hr. The mixture was concentrated under reduced pressure, and diisopropyl ether was added to the residue. The precipitated solid was collected by filtration to give the title compound (0.22 g, 69%) as an amorphous solid.

$^1$H NMR (300 MHz, DMSO-$d_6$) δ 0.94 (3 H, t, J=7.4), 1.01-1.12 (9 H, m), 1.34-1.49 (2 H, m), 1.54-1.71 (2 H, m), 1.86 (2 H, d, J=12.9), 2.28 (2 H, q, J=7.2), 2.52-2.62 (2 H, m), 3.76-3.92 (4 H, m), 4.83 (1 H, s), 7.00-7.53 (12 H, m)

Example 419

2-ethyl-3-(4-{[1-(hydroxymethyl)cyclobutyl]oxy}phenyl)-5-{[2'-(5-oxo-4,5-dihydro-1,2,4-oxadiazol-3-yl)biphenyl-4-yl]methyl}-6-propylpyrimidin-4(3H)-one

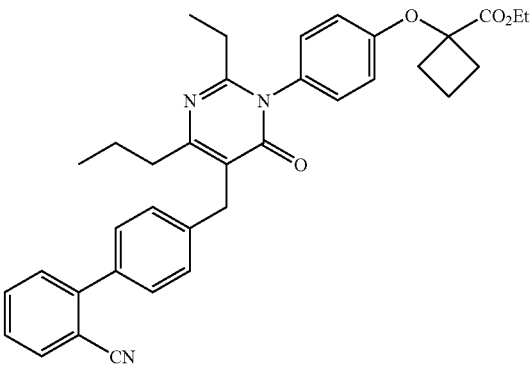

419a) ethyl 1-{4-[5-[(2'-cyanobiphenyl-4-yl)methyl]-2-ethyl-6-oxo-4-propylpyrimidin-1(6H)-yl]phenoxy}cyclobutanecarboxylate A solution of 4'-{[2-ethyl-1-(4-hydroxyphenyl)-6-oxo-4-propyl-1,6-dihydropyrimidin-5-yl]methyl}biphenyl-2-carbonitrile (1.4 g), ethyl 1-bromocyclobutanecarboxylate (1.5 mL) and cesium carbonate (3 g) in dimethylacetamide (14 mL) was stirred at 100° C. for 2 days. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.76 g, 42%) as a pale-yellow liquid.

$^1$H NMR (300 MHz, CDCl$_3$) δ 1.00 (3 H, t, J=7.4), 1.12 (3 H, t, J=7.4), 1.19 (3 H, t, J=7.2), 1.64-1.78 (2 H, m), 1.94-2.10 (2 H, m), 2.34 (2 H, q, J=7.6), 2.41-2.55 (2 H, m), 2.62-2.82 (4 H, m), 3.96 (2 H, s), 4.22 (2 H, q, J=7.2), 6.75-6.82 (2 H, m), 7.04-7.12 (2 H, m), 7.37-7.50 (6 H, m), 7.57-7.66 (1 H, m), 7.74 (1 H, d, J=8.0)

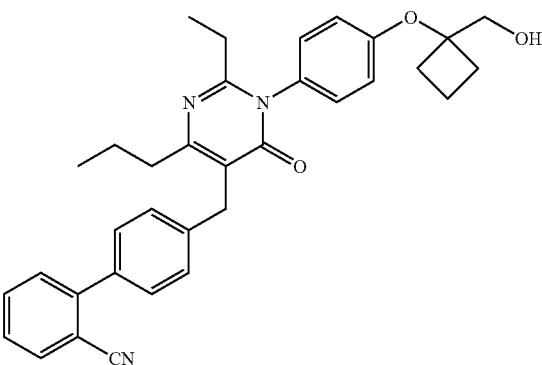

419b) 4'-{[2-ethyl-1-(4-{[1-(hydroxymethyl)cy-clobutyl]oxy}phenyl)-6-oxo-4-propyl-1,6-dihydro-pyrimidin-5-yl]methyl}biphenyl-2-carbonitrile Sodium borohydride (0.3 g) was dissolved in tetrahydrofuran (10 mL) and ethanol (10 mL), and calcium chloride (0.44 g) was added at 0° C. The reaction solution was stirred at 0° C. for 1 hr, ethyl 1-{4-[5-[(2'-cyanobiphenyl-4-yl)methyl]-2-ethyl-6-oxo-4-propylpyrimidin-1(6H)-yl]phenoxy}cyclobutanecarboxylate (0.76 g) was added, and the mixture was stirred overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.5 g, 73%) as a pale-yellow liquid.

$^1$H NMR (300 MHz, CDCl$_3$) δ 1.01 (3 H, t, J=7.3), 1.15 (3 H, t, J=7.3), 1.60-1.94 (4 H, m), 2.22-2.48 (6 H, m), 2.61-2.72 (2 H, m), 3.88-3.99 (4 H, m), 6.91-7.15 (4 H, m), 7.35-7.52 (6 H, m), 7.56-7.67 (1 H, m), 7.70-7.77 (1 H, m)

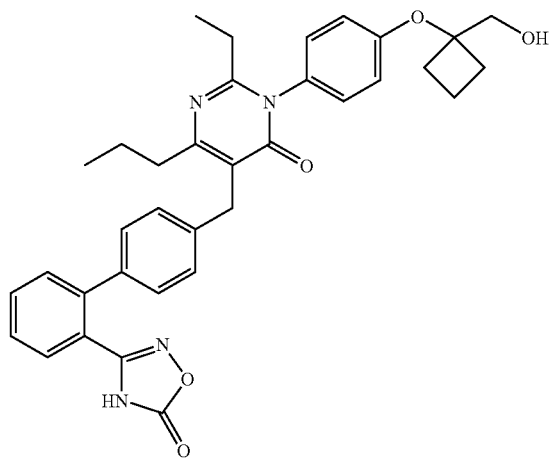

419c) 2-ethyl-3-(4-{[1-(hydroxymethyl)cyclobutyl]oxy}phenyl)-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-{[1-(hydroxymethyl)cyclobutyl]oxy}phenyl)-6-oxo-4-propyl-1,6-dihydropyrimidin-5-yl]methyl}biphenyl-2-carbonitrile (0.5 g) and 2,6-lutidine (0.17 mL) in dichloromethane (5 mL) was added tert-butyl(dimethyl)silyl trifluoromethanesulfonate (0.34 mL) at 0° C., and the mixture was stirred overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure. A mixture of the residue, hydroxylammonium chloride (0.67 g), sodium hydrogen carbonate (0.97 g) and dimethyl sulfoxide (5 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL). N,N'-carbonyldiimidazole (0.23 g) and then 1,8-diazabicyclo[5.4.0]undec-7-ene (0.23 mL) were added, and the mixture was stirred at room temperature for 30 min. Tetrabutylammonium fluoride (1.0 M tetrahydrofuran solution, 1.9 mL) was added, and the mixture was stirred overnight at 50° C. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.43 g, 76%) as an amorphous solid.

$^1$H NMR (300 MHz, DMSO-d$_6$) δ 0.90 (3 H, t, J=7.4), 1.05 (3 H, t, J=7.4), 1.50-1.92 (4 H, m), 2.12-2.76 (6 H, m), 2.70-2.75 (2 H, m), 3.72 (2 H, d, J=5.7), 3.86 (2 H, s), 6.92 (2 H, d, J=9.1), 7.17-7.30 (6 H, m), 7.48-7.58 (2 H, m), 7.62-7.73 (2 H, m), 12.38 (1 H, s)

Example 420

6-butyl-3-[4-(2-hydroxy-1,1-dimethylethoxy)phenyl]-2-methyl-5-{[2'-(5-oxo-4,5-dihydro-1,2,4-oxadiazol-3-yl)biphenyl-4-yl]methyl}pyrimidin-4(3H)-one

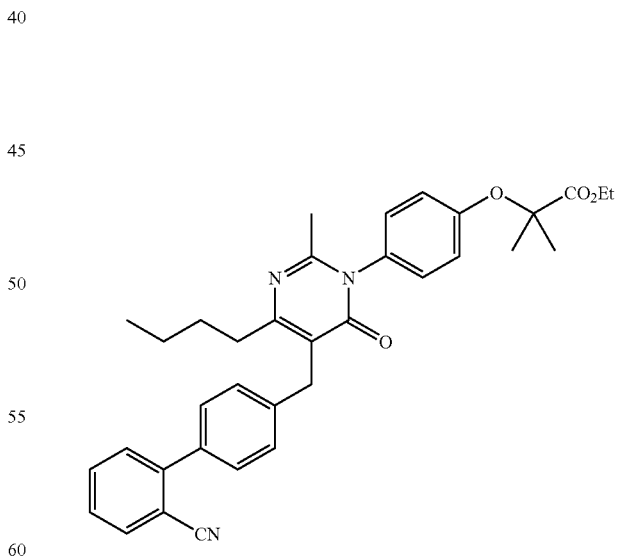

420a) ethyl 2-{4-[4-butyl-5-[(2'-cyanobiphenyl-4-yl)methyl]-2-methyl-6-oxopyrimidin-1(6H)-yl]phenoxy}-2-methylpropanoate A solution of 4'-{[4-butyl-1-(4-hydroxyphenyl)-2-methyl-6-oxo-1,6-dihydropyrimidin-5-yl]methyl}biphenyl-2-carbonitrile (2.3 g), ethyl 2-bromo-2-methylpropanoate (2.2 mL) and cesium carbonate (4.9 g) in dimethylacetamide (23 mL) was stirred at 100° C. for 2 days. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (2.1 g, 74%) as a pale-yellow liquid.

$^1$H NMR (300 MHz, CDCl$_3$) δ 0.90-0.99 (3 H, m), 1.22-1.30 (3 H, m), 1.34-1.50 (2 H, m), 1.59 (3 H, s), 1.55-1.70 (8 H, m), 2.61-2.71 (2 H, m), 3.96 (2 H, s), 4.25 (2 H, q, J=7.2), 6.92-6.99 (2 H, m), 7.06-7.14 (2 H, m), 7.36-7.53 (6 H, m), 7.62 (1 H, t, J=7.8), 7.74 (1 H, d, J=7.6)

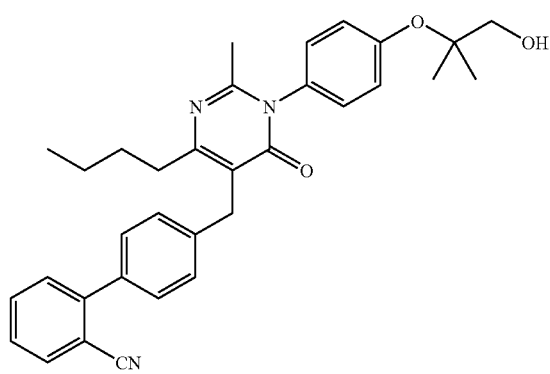

420b) 4'-({4-butyl-1-[4-(2-hydroxy-1,1-dimethylethoxy)phenyl]-2-methyl-6-oxo-1,6-dihydropyrimidin-5-yl}methyl)biphenyl-2-carbonitrile Sodium borohydride (0.85 g) was dissolved in tetrahydrofuran (20 mL) and ethanol (20 mL), and calcium chloride (1.2 g) was added at 0° C. The reaction solution was stirred at 0° C. for 1 hr, ethyl 2-{4-[4-butyl-5-[(2'-cyanobiphenyl-4-yl)methyl]-2-methyl-6-oxopyrimidin-1(6H)-yl]phenoxy}-2-methylpropanoate (2.1 g) was added, and the mixture was stirred overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (1.2 g, 60%) as a pale-yellow liquid.

$^1$H NMR (300 MHz, CDCl$_3$) δ 0.94 (3 H, t, J=7.3), 1.33 (6 H, s), 1.35-1.51 (2 H, m), 1.56-1.69 (2 H, m), 2.17 (3 H, s), 2.61-2.71 (2 H, m), 3.62 (2 H, d, J=6.4), 3.97 (2 H, s), 7.09-7.19 (4 H, m), 7.37-7.50 (6 H, m), 7.57-7.66 (1 H, m), 7.74 (1 H, dd, J=7.7, 0.9)

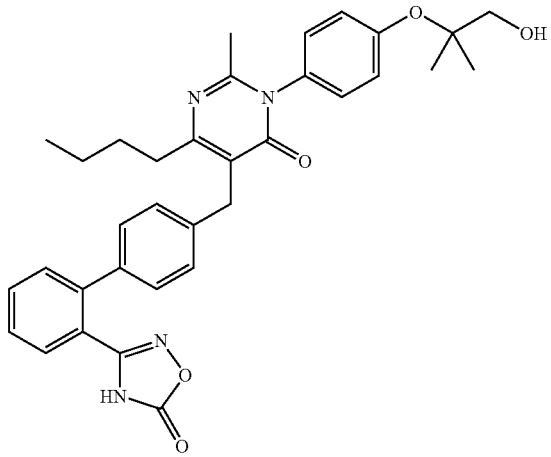

420c) 6-butyl-3-[4-(2-hydroxy-1,1-dimethylethoxy)phenyl]-2-methyl-5-{[2'-(5-oxo-4,5-dihydro-1,2,4-oxadiazol-3-yl)biphenyl-4-yl]methyl}pyrimidin-4(3H)-one To a solution of 4'-({4-butyl-1-[4-(2-hydroxy-1,1-dimethylethoxy)phenyl]-2-methyl-6-oxo-1,6-dihydropyrimidin-5-yl}methyl)biphenyl-2-carbonitrile (1.2 g) and 2,6-lutidine (0.34 mL) in dichloromethane (12 mL) was added tert-butyl(dimethyl)silyl trifluoromethanesulfonate (0.79 mL) at 0° C., and the mixture was stirred overnight. The reaction mixture was diluted with ethyl acetate, washed with 5% aqueous potassium hydrogen sulfate solution and then with saturated brine, and dried over anhydrous magnesium sulfate. The solvent was evaporated under reduced pressure. A mixture of the residue, hydroxylammonium chloride (1.5 g), sodium hydrogen carbonate (2.2 g) and dimethyl sulfoxide (10 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.54 g) and then 1,8-diazabicyclo[5.4.0]undec-7-ene (0.5 mL) were added, and the mixture was stirred at room temperature for 30 min. Tetrabutylammonium fluoride (1.0 M tetrahydrofuran solution, 4.4 mL) was added, and the mixture was stirred overnight at 50° C. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.67 g, 52%) as an amorphous solid.

$^1$H NMR (300 MHz, DMSO-d$_6$) δ 0.86 (3 H, t, J=7.4), 1.24 (6 H, s), 1.32 (2 H, dd, J=14.8, 7.6), 1.43-1.56 (2 H, m), 2.06 (3 H, s), 2.46-2.58 (2 H, m), 3.34-3.45 (2 H, m), 3.86 (2 H, s), 4.95 (1 H, t, J=5.9), 7.10-7.31 (8 H, m), 7.53 (2 H, dd, J=16.8, 7.8), 7.62-7.73 (2 H, m), 12.39 (1 H, s)

Example 421

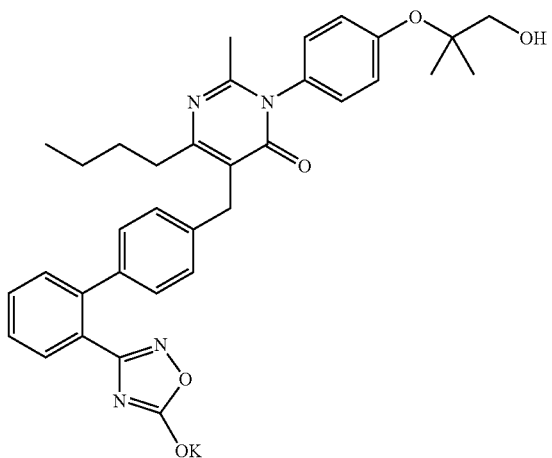

6-butyl-3-[4-(2-hydroxy-1,1-dimethylethoxy)phenyl]-2-methyl-5-{[2'-(5-oxo-4,5-dihydro-1,2,4-oxadiazol-3-yl)biphenyl-4-yl]methyl}pyrimidin-4(3H)-one potassium salt 6-Butyl-3-[4-(2-hydroxy-1,1-dimethylethoxy)phenyl]-2-methyl-5-{[2'-(5-oxo-4,5-dihydro-1,2,4-oxadiazol-3-yl)biphenyl-4-yl]methyl}pyrimidin-4(3H)-one (0.5 g) was dissolved in ethanol (10 mL), 8 M potassium hydroxide solution (0.11 mL) was added, and the mixture was stirred for 1 hr. The mixture was concentrated under reduced pressure, and diisopropyl ether was added to the residue. The precipitated solid was collected by filtration to give the title compound (0.5 g, 94%) as an amorphous solid.

$^1$H NMR (300 MHz, DMSO-$d_6$) δ 0.81-0.94 (3 H, m), 1.24 (6 H, s), 1.27-1.43 (2 H, m), 1.46-1.60 (2 H, m), 2.04 (3 H, s), 2.47-2.60 (2 H, m), 3.28-3.46 (2 H, m), 3.81 (2 H, s), 4.09 (1 H, s), 7.08-7.51 (12 H, m)

Example 422

2-ethyl-3-{4-[(3-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (1.2 g), 3-{[tert-butyl(dimethyl)silyl]oxy}cyclohexanol (1.2 g) and triphenylphosphine (1.4 g) in tetrahydrofuran (12 mL) was added dropwise diisopropyl azodicarboxylate (1.9 M toluene solution, 2.8 mL). After stirring for 2 hr, water was added, and the mixture was extracted with ethyl acetate. The organic layer was washed with saturated brine, and dried over anhydrous magnesium sulfate. The solvent was evaporated under reduced pressure, and a mixture of the residue, hydroxylammonium chloride (0.87 g), sodium hydrogen carbonate (1.3 g) and dimethyl sulfoxide (9 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (9 mL). N,N'-carbonyldiimidazole (0.3 g) and then 1,8-diazabicyclo[5.4.0]undec-7-ene (0.28 mL) were added, and the mixture was stirred at room temperature for 30 min. Tetrabutylammonium fluoride (1.0 M tetrahydrofuran solution, 2.5 mL) was added, and the mixture was stirred overnight at 50° C. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (1.3 g, 71%) as an amorphous solid.

$^1$H NMR (300 MHz, DMSO-$d_6$) δ 0.90 (3 H, t, J=7.3), 1.05 (3 H, t, J=7.3), 1.12-1.88 (10 H, m), 2.29 (2 H, q, J=7.2), 2.46-2.57 (2 H, m), 3.87 (2 H, s), 4.27-4.78 (2 H, m), 6.99-7.09 (2 H, m), 7.18-7.31 (6 H, m), 7.48-7.58 (2 H, m), 7.61-7.73 (2 H, m), 12.38 (1 H, s)

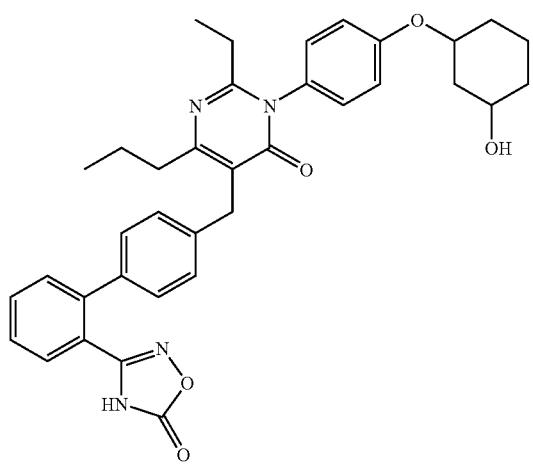

Example 423

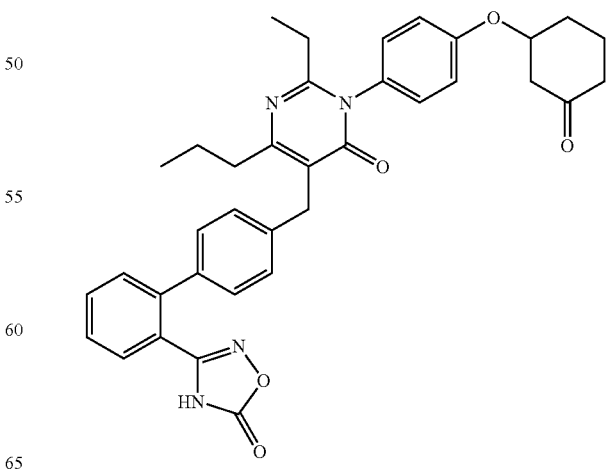

2-ethyl-3-{4-[(3-oxocyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one 2-Ethyl-3-{4-[(3-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (0.5 g) and 1,1,1-tris(acetyloxy)-1,1-dihydro-1,2-benziodoxol-3(1H)-one (0.52 g) were dissolved in dichloromethane (5 mL) and the mixture was stirred for 1 hr. The reaction mixture was diluted with ethyl acetate, washed with saturated aqueous sodium hydrogen carbonate solution and then with saturated brine, and dried over anhydrous magnesium sulfate. The solvent was evaporated under reduced pressure and the residue was purified by silica gel column chromatography to give the title compound (0.38 g, 76%) as a colorless amorphous solid.

$^1$H NMR (300 MHz, DMSO-$d_6$) δ 0.90 (3 H, t, J=7.3), 1.05 (3 H, t, J=7.3), 1.50-2.14 (6 H, m), 2.22-2.59 (6 H, m), 2.74-2.84 (1 H, m), 3.86 (2 H, s), 4.94-5.04 (1 H, m), 7.01-7.11 (2 H, m), 7.17-7.32 (6 H, m), 7.47-7.58 (2 H, m), 7.62-7.73 (2 H, m), 12.38 (1 H, s)

Example 424

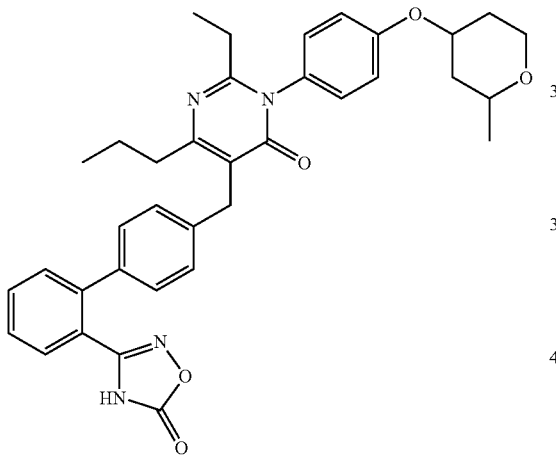

2-ethyl-3-{4-[(2-methyltetrahydro-2H-pyran-4-yl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (0.5 g), 2-methyltetrahydro-2H-pyran-4-ol (0.26 g) and triphenylphosphine (0.58 g) in tetrahydrofuran (5 mL) was added dropwise diisopropyl azodicarboxylate (1.9 M toluene solution, 1.2 mL). After stirring for 2 hr, water was added, and the mixture was extracted with ethyl acetate. The organic layer was washed with saturated brine, and dried over anhydrous magnesium sulfate. The solvent was evaporated under reduced pressure, and a mixture of the residue, hydroxylammonium chloride (0.77 g), sodium hydrogen carbonate (1.1 g) and dimethyl sulfoxide (10 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.37 g, 60%) as an amorphous solid.

$^1$H NMR (300 MHz, DMSO-$d_6$) δ 0.90 (3 H, t, J=7.2), 1.00-1.12 (6 H, m), 1.45-1.93 (6 H, m), 2.29 (2 H, q, J=7.4), 2.47-2.58 (2 H, m), 3.67-3.90 (5 H, m), 4.80-4.87 (1 H, m), 7.08 (2 H, d, J=9.1), 7.17-7.32 (6 H, m), 7.47-7.58 (2 H, m), 7.62-7.73 (2 H, m), 12.38 (1 H, s)

Example 425

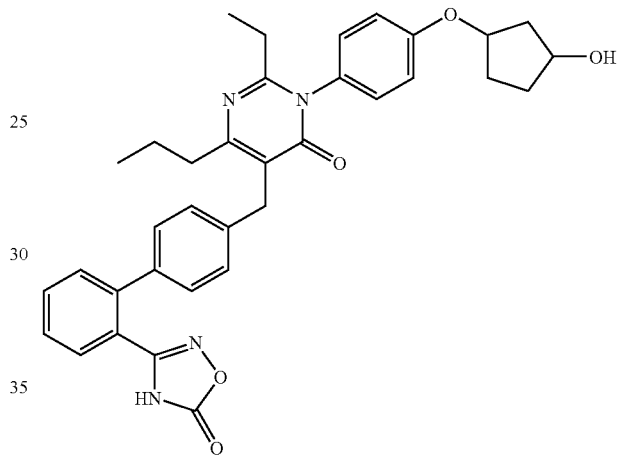

2-ethyl-3-{4-[(3-hydroxycyclopentyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (1 g), 3-{[tert-butyl(dimethyl)silyl]oxy}cyclopentanol (0.72 g) and triphenylphosphine (0.87 g) in tetrahydrofuran (10 mL) was added dropwise diisopropyl azodicarboxylate (1.9 M toluene solution, 1.8 mL). After stirring for 2 hr, water was added, and the mixture was extracted with ethyl acetate. The organic layer was washed with saturated brine, and dried over anhydrous magnesium sulfate. The solvent was evaporated under reduced pressure, and a mixture of the residue, hydroxylammonium chloride (1.5 g), sodium hydrogen carbonate (2.2 g) and dimethyl sulfoxide (10 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.54 g) and then 1,8-diazabicyclo[5.4.0]undec-7-ene (0.5 mL) were added, and the mixture was stirred at room temperature for 30 min. Tetrabutylammonium fluoride (1.0 M tetrahydrofuran solution, 4.4 mL) was added, and the mixture was stirred overnight at 50° C. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.98 g, 74%) as an amorphous solid.

$^1$H NMR (300 MHz, DMSO-d$_6$) δ 0.90 (3 H, t, J=7.4), 1.05 (3 H, t, J=7.4), 1.20-1.32 (2 H, m), 1.50-2.06 (3 H, m), 2.23-2.44 (4 H, m), 2.44-2.58 (4 H, m), 3.86 (2 H, s), 4.66 (1 H, d, J=4.2), 4.76 (1 H, s), 6.99 (2 H, d, J=9.1), 7.18-7.32 (6H, m), 7.47-7.58 (2 H, m), 7.62-7.73 (2 H, m), 12.38 (1 H, s)

Example 426

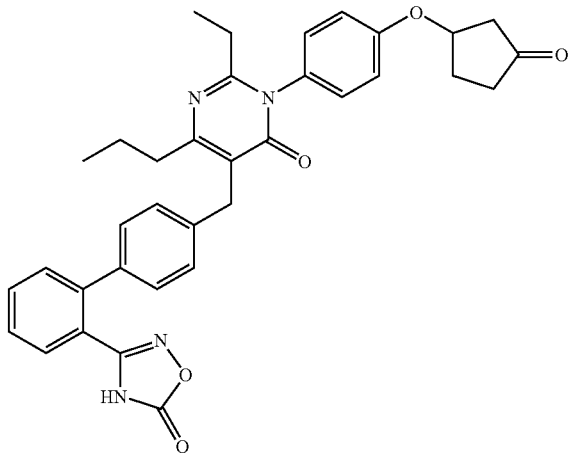

2-ethyl-3-{4-[(3-oxocyclopentyl)oxy]phenyl}-5-{[2'-(5-oxo-4,5-dihydro-1,2,4-oxadiazol-3-yl)biphenyl-4-yl]methyl}-6-propylpyrimidin-4(3H)-one 2-Ethyl-3-{4-[(3-hydroxycyclopentyl)oxy]phenyl}-5-{[2'-(5-oxo-4,5-dihydro-1,2,4-oxadiazol-3-yl)biphenyl-4-yl]methyl}-6-propylpyrimidin-4(3H)-one (0.5 g) and 1,1,1-tris(acetyloxy)-1,1-dihydro-1,2-benziodoxol-3(1H)-one (0.54 g) were dissolved in dichloromethane (10 mL) and the mixture was stirred for 1 hr. The reaction mixture was diluted with ethyl acetate, washed with saturated aqueous sodium hydrogen carbonate solution and then with saturated brine, and dried over anhydrous magnesium sulfate. The solvent was evaporated under reduced pressure and the residue was purified by silica gel column chromatography to give the title compound (0.32 g, 64%) as a colorless amorphous solid.

$^1$H NMR (300 MHz, DMSO-d$_6$) δ 0.90 (3 H, t, J=7.2), 1.05 (3 H, t, J=7.4), 1.50-1.66 (2 H, m), 2.12-2.42 (7 H, m), 2.46-2.59 (2 H, m), 2.74 (1 H, dd, J=18.2, 5.7), 3.87 (2 H, s), 5.19 (1 H, s), 7.03-7.12 (2 H, m), 7.17-7.34 (6 H, m), 7.47-7.58 (2 H, m), 7.61-7.73 (2 H, m), 12.38 (1 H, s)

Example 427

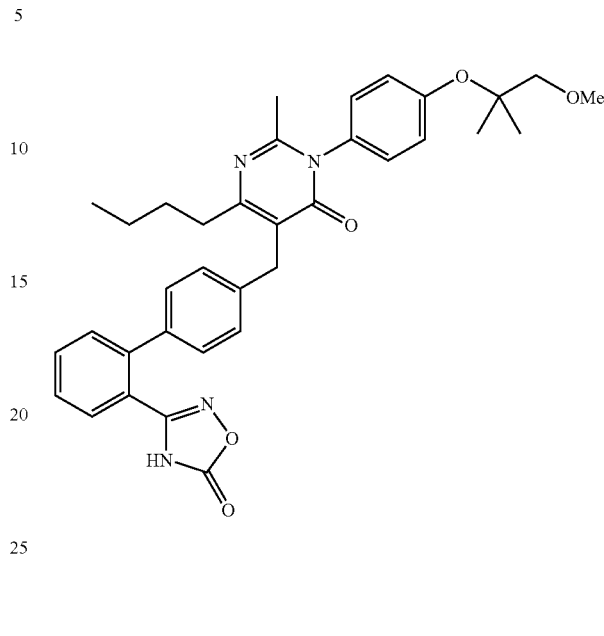

6-butyl-3-[4-(2-methoxy-1,1-dimethylethoxy)phenyl]-2-methyl-5-{[2'-(5-oxo-4,5-dihydro-1,2,4-oxadiazol-3-yl)biphenyl-4-yl]methyl}pyrimidin-4(3H)-one A solution of 4'-({4-butyl-1-[4-(2-hydroxy-1,1-dimethylethoxy)phenyl]-2-methyl-6-oxo-1,6-dihydropyrimidin-5-yl}methyl)biphenyl-2-carbonitrile (0.52 g), 60% sodium hydride (0.08 g) and iodomethane (0.28 g) in DMF (5 mL) solution was stirred at room temperature for 1 hr. The reaction mixture was diluted with ethyl acetate, washed with 5% aqueous potassium hydrogen sulfate solution and then with saturated brine, and dried over anhydrous magnesium sulfate. The solvent was evaporated under reduced pressure. A mixture of the residue, hydroxylammonium chloride (0.69 g), sodium hydrogen carbonate (1.1 g) and dimethyl sulfoxide (5 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL). N,N'-carbonyldiimidazole (0.24 g) and then 1,8-diazabicyclo[5.4.0]undec-7-ene (0.22 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.14 g, 24%) as an amorphous solid.

$^1$H NMR (300 MHz, DMSO-d$_6$) δ 0.86 (3 H, t, J=7.2), 1.25-1.40 (8 H, m), 1.41-1.57 (2 H, m), 2.06 (3 H, s), 2.47-2.57 (2H, m), 3.33 (3 H, s), 3.36 (2 H, s), 3.86 (2 H, s), 7.06-7.14 (2 H, m), 7.18-7.31 (6 H, m), 7.52 (2 H, dd, J=16.7, 7.6), 7.61-7.72 (2 H, m), 12.39 (1 H, s)

Example 428

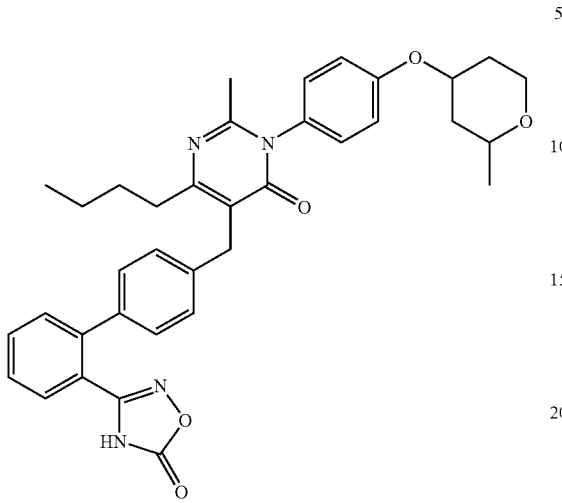

6-butyl-2-methyl-3-{4-[(2-methyltetrahydro-2H-pyran-4-yl)oxy]phenyl}-5-{[2'-(5-oxo-4,5-dihydro-1,2,4-oxadiazol-3-yl)biphenyl-4-yl]methyl}pyrimidin-4(3H)-one To a solution of 6-butyl-3-(4-hydroxyphenyl)-2-methyl-5-{[2'-(5-oxo-4,5-dihydro-1,2,4-oxadiazol-3-yl)biphenyl-4-yl]methyl}pyrimidin-4(3H)-one (0.5 g), 2-methyltetrahydro-2H-pyran-4-ol (0.26 g) and triphenylphosphine (0.58 g) in tetrahydrofuran (5 mL) was added dropwise diisopropyl azodicarboxylate (1.9 M toluene solution, 1.2 mL). After stirring for 2 hr, water was added, and the mixture was extracted with ethyl acetate. The organic layer was washed with saturated brine, and dried over anhydrous magnesium sulfate. The solvent was evaporated under reduced pressure, and a mixture of the residue, hydroxylammonium chloride (0.77 g), sodium hydrogen carbonate (1.1 g) and dimethyl sulfoxide (10 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.36 g, 53%) as an amorphous solid.

$^1$H NMR (300 MHz, DMSO-$d_6$) δ 0.85 (3 H, t, J=7.4), 1.08 (3 H, d, J=6.4), 1.24-1.60 (5 H, m), 1.69-1.94 (3 H, m), 2.07 (3 H, s), 2.47-2.57 (2 H, m), 3.67-3.90 (5 H, m), 4.84 (1 H, s), 7.08 (2 H, d, J=8.7), 7.19-7.31 (6 H, m), 7.46-7.59 (2 H, m), 7.61-7.73 (2 H, m), 12.39 (1 H, s)

Example 429

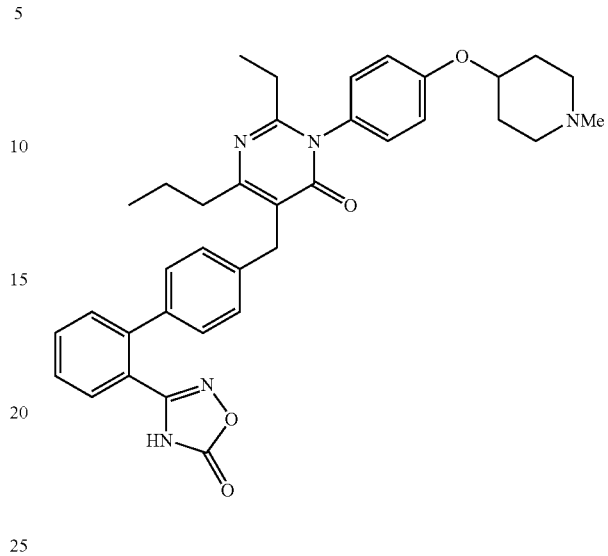

2-ethyl-3-{4-[(1-methylpiperidin-4-yl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 4'-{[2-ethyl-1-(4-hydroxyphenyl)-6-oxo-4-propyl-1,6-dihydropyrimidin-5-yl]methyl}biphenyl-2-carbonitrile (0.5 g), 1-methylpiperidin-4-ol (0.26 g) and triphenylphosphine (0.58 g) in tetrahydrofuran (5 mL) was added dropwise diisopropyl azodicarboxylate (1.9 M toluene solution, 1.2 mL). After stirring for 2 hr, water was added, and the mixture was extracted with ethyl acetate. The organic layer was washed with saturated brine, and dried over anhydrous magnesium sulfate. The solvent was evaporated under reduced pressure, and a mixture of the residue, hydroxylammonium chloride (0.77 g), sodium hydrogen carbonate (1.1 g) and dimethyl sulfoxide (10 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 30 min. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.16 g, 25%) as an amorphous solid.

$^1$H NMR (300 MHz, DMSO-$d_6$) δ 0.91 (3 H, t, J=7.4), 1.01-1.08 (3 H, m), 1.50-1.84 (4 H, m), 1.96-2.09 (2 H, m), 2.28 (2H, q, J=7.2), 2.42 (3 H, s), 2.48-2.65 (4 H, m), 2.84-2.97 (2 H, m), 3.85 (2 H, s), 4.48-4.59 (1 H, m), 7.09 (2 H, d, J=9.1), 7.18-7.30 (6 H, m), 7.42-7.53 (2 H, m), 7.57-7.65 (2 H, m)

Example 430

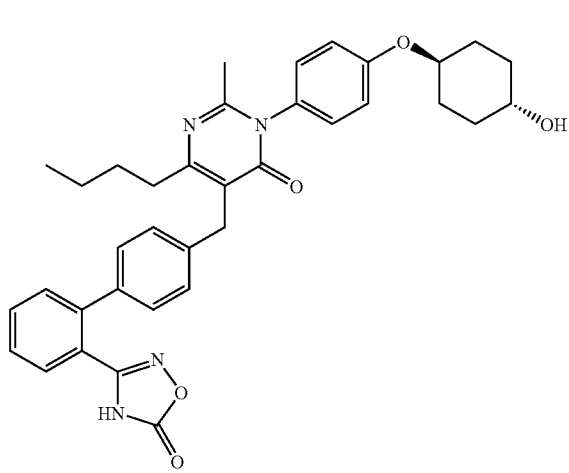

6-butyl-3-{4-[(trans-4-hydroxycyclohexyl)oxy]phenyl}-2-methyl-5-{[2'-(5-oxo-4,5-dihydro-1,2,4-oxadiazol-3-yl)biphenyl-4-yl]methyl}pyrimidin-4(3H)-one To a solution of 6-butyl-3-(4-hydroxyphenyl)-2-methyl-5-{[2'-(5-oxo-4,5-dihydro-1,2,4-oxadiazol-3-yl)biphenyl-4-yl]methyl}pyrimidin-4(3H)-one (1.2 g), 4-{[tert-butyl(dimethyl)silyl]oxy}cyclohexanol (1.2 g) and triphenylphosphine (1.4 g) in tetrahydrofuran (12 mL) was added dropwise diisopropyl azodicarboxylate (1.9 M toluene solution, 2.8 mL). After stirring for 2 hr, water was added, and the mixture was extracted with ethyl acetate. The organic layer was washed with saturated brine, and dried over anhydrous magnesium sulfate. The solvent was evaporated under reduced pressure, and a mixture of the residue, hydroxylammonium chloride (0.87 g), sodium hydrogen carbonate (1.3 g) and dimethyl sulfoxide (9 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (9 mL). N,N'-carbonyldiimidazole (0.3 g) and then 1,8-diazabicyclo[5.4.0]undec-7-ene (0.28 mL) were added, and the mixture was stirred at room temperature for 30 min. Tetrabutylammonium fluoride (1.0 M tetrahydrofuran solution, 2.5 mL) was added, and the mixture was stirred overnight at 50° C. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.45 g, 33%) as an amorphous solid.

$^1$H NMR (300 MHz, DMSO-$d_6$) δ 0.82-0.90 (3 H, m), 1.20-1.73 (10 H, m), 1.78-1.93 (2 H, m), 2.07 (3 H, s), 2.46-2.57 (2H, m), 3.57-3.69 (1 H, m), 3.86 (2 H, s), 4.43-4.56 (2 H, m), 7.05 (2 H, d, J=9.1), 7.17-7.33 (6 H, m), 7.46-7.58 (2 H, m), 7.62-7.74 (2 H, m), 12.39 (1 H, s)

Example 431

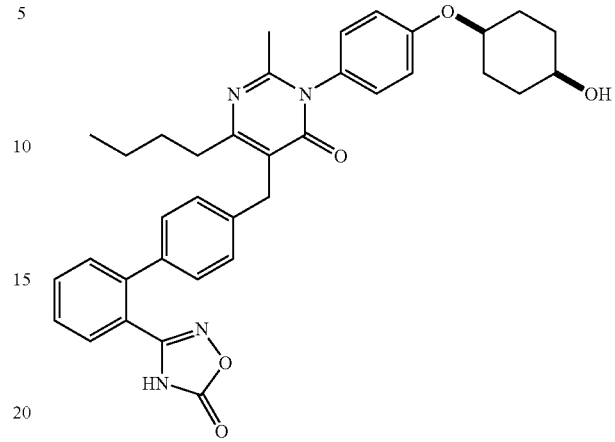

6-butyl-3-{4-[(cis-4-hydroxycyclohexyl)oxy]phenyl}-2-methyl-5-{[2'-(5-oxo-4,5-dihydro-1,2,4-oxadiazol-3-yl)biphenyl-4-yl]methyl}pyrimidin-4(3H)-one To a solution of 6-butyl-3-(4-hydroxyphenyl)-2-methyl-5-{[2'-(5-oxo-4,5-dihydro-1,2,4-oxadiazol-3-yl)biphenyl-4-yl]methyl}pyrimidin-4(3H)-one (1.2 g), 4-{[tert-butyl(dimethyl)silyl]oxy}cyclohexanol (1.2 g) and triphenylphosphine (1.4 g) in tetrahydrofuran (12 mL) was added dropwise diisopropyl azodicarboxylate (1.9 M toluene solution, 2.8 mL). After stirring for 2 hr, water was added, and the mixture was extracted with ethyl acetate. The organic layer was washed with saturated brine, and dried over anhydrous magnesium sulfate. The solvent was evaporated under reduced pressure, and a mixture of the residue, hydroxylammonium chloride (0.87 g), sodium hydrogen carbonate (1.3 g) and dimethyl sulfoxide (9 mL) was stirred overnight at 90° C. The reaction mixture was diluted with ethyl acetate, washed with water and then with saturated brine, and dried over anhydrous magnesium sulfate. The solvent was evaporated under reduced pressure. The residue was dissolved in tetrahydrofuran (9 mL). N,N'-carbonyldiimidazole (0.3 g) and then 1,8-diazabicyclo[5.4.0]undec-7-ene (0.28 mL) were added, and the mixture was stirred at room temperature for 30 min. Tetrabutylammonium fluoride (1.0 M tetrahydrofuran solution, 2.5 mL) was added, and the mixture was stirred overnight at 50° C. The reaction mixture was diluted with ethyl acetate, washed with 5% aqueous potassium hydrogen sulfate solution and then with saturated brine, and dried over anhydrous magnesium sulfate. The solvent was evaporated under reduced pressure and the residue was purified by silica gel column chromatography to give the title compound (0.37 g, 28%) as an amorphous solid.

$^1$H NMR (300 MHz, DMSO-$d_6$) δ 0.81-0.89 (3 H, m), 1.22-1.56 (8 H, m), 1.78-1.89 (2 H, m), 1.98-2.09 (5 H, m), 2.47-2.56 (2 H, m), 3.47-3.61 (1 H, m), 3.86 (2 H, s), 4.31-4.45 (1 H, m), 4.59 (1 H, d, J=4.2), 7.05 (2 H, d, J=9.1), 7.18-7.31 (6 H, m), 7.47-7.58 (2 H, m), 7.62-7.73 (2 H, m), 12.39 (1 H, s)

Example 432

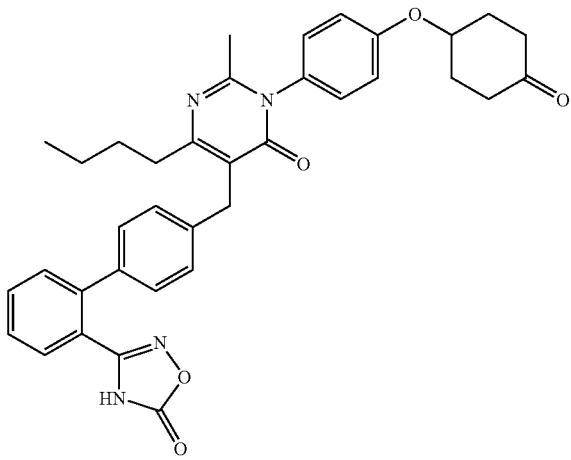

6-butyl-2-methyl-3-{4-[(4-oxocyclohexyl)oxy]phenyl}-5-{[2'-(5-oxo-4,5-dihydro-1,2,4-oxadiazol-3-yl)biphenyl-4-yl]methyl}pyrimidin-4(3H)-one 6-Butyl-3-{4-[(4-hydroxycyclohexyl)oxy]phenyl}-2-methyl-5-{[2'-(5-oxo-4,5-dihydro-1,2,4-oxadiazol-3-yl)biphenyl-4-yl]methyl}pyrimidin-4(3H)-one (0.4 g) and 1,1,1-tris(acetyloxy)-1,1-dihydro-1,2-benziodoxol-3(1H)-one (0.42 g) were dissolved in dichloromethane (4 mL) and the mixture was stirred for 1 hr. The reaction mixture was diluted with ethyl acetate, washed with saturated aqueous sodium hydrogen carbonate solution and then with saturated brine, and dried over anhydrous magnesium sulfate. The solvent was evaporated under reduced pressure and the residue was purified by silica gel column chromatography to give the title compound (0.37 g, 93%) as a colorless amorphous solid.

$^1$H NMR (300 MHz, DMSO-$d_6$) δ 0.81-0.90 (3 H, m), 1.21-1.57 (4 H, m), 1.96-2.24 (7 H, m), 2.30-2.56 (6 H, m), 3.86 (2H, s), 4.82-4.93 (1 H, m), 7.11-7.35 (8 H, m), 7.47-7.59 (2 H, m), 7.62-7.74 (2 H, m), 12.39 (1 H, s)

Example 433

2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt

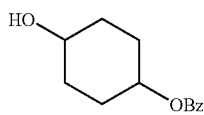

433a) 4-hydroxycyclohexyl benzoate

A mixture of benzoyl chloride (50 mL), cyclohexanediol (150 g), pyridine (105 mL) and tetrahydrofuran (1300 mL) was stirred at room temperature overnight. The reaction mixture was concentrated under reduced pressure, the residue was diluted with ethyl acetate, successively washed with saturated aqueous sodium hydrogen carbonate, water, and brine, dried over anhydrous magnesium sulfate, and concentrated under reduced pressure. The residue was purified by silica gel column chromatography to give the title compound as a colorless oil (81.5 g, 86%).

$^1$H NMR (300 MHz, CHLOROFORM-d) δ ppm 1.42-2.19 (m, 9 H), 3.75-3.91 (m, 1 H), 4.96-5.20 (m, 1 H), 7.38-7.60 (m, 3 H), 8.01-8.10 (m, 2 H)

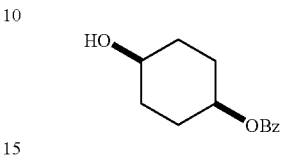

433b) cis-4-hydroxycyclohexyl benzoate

To a solution of 4-hydroxycyclohexyl benzoate (81.5 g) and Lipase QLG (40 g) in diisopropyl ether (800 mL) was added vinyl acetate (120 mL) at room temperature. After being stirred at room temperature for 2 hr, Lipase QLG was filtered off. The filtrate was concentrated under reduced pressure. The residue was purified by silica gel column chromatography to give the title compound as a colorless solid (37.5 g, 46%).

$^1$H NMR (300 MHz, CHLOROFORM-d) δ ppm 1.63-1.89 (m, 7H), 1.94-2.13 (m, 2H), 3.77-3.90 (m, 1H), 5.07-5.21 (m, 1H), 7.37-7.61 (m, 3H), 8.00-8.11 (m, 2H)

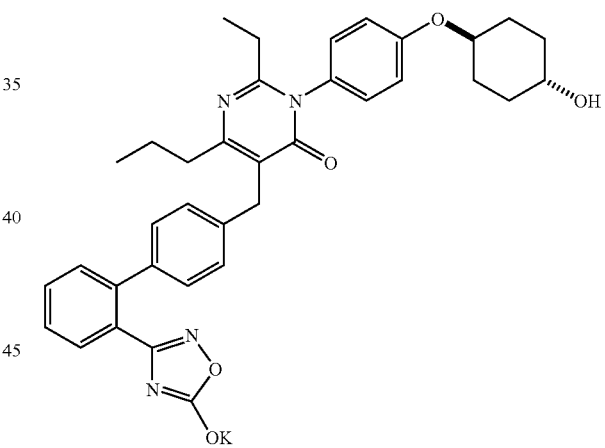

433c) 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt 2-Ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (0.1 g) was dissolved in ethanol (1 mL), 8 M potassium hydroxide solution (0.021 mL) was added, and the mixture was stirred for 1 hr. The mixture was concentrated under reduced pressure, and diisopropyl ether was added to the residue. The precipitated solid was collected by filtration to give the title compound (0.05 g, 47%) as an amorphous solid.

$^1$H NMR (300 MHz, DMSO-$d_6$) δ 0.94 (3 H, t, J=7.3), 1.04 (3 H, t, J=7.3), 1.21-1.52 (4 H, m), 1.54-1.70 (2 H, m), 1.78-1.89 (2 H, m), 1.98-2.08 (2 H, m), 2.27 (2 H, q, J=7.3), 2.56 (2 H, dd, J=8.4, 6.7), 3.47-3.60 (1 H, m), 3.81 (2 H, s), 4.31-4.45 (1 H, m), 4.59 (1 H, d, J=4.1), 6.99-7.07 (2 H, m), 7.11-7.50 (10 H, m)

433d) Crystalline 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt (1a) To a solution of 4'-{[2-ethyl-1-(4-hydroxyphenyl)-6-oxo-4-propyl-1,6-dihydropyrimidin-5-yl]methyl}biphenyl-2-carbonitrile (45.0 g), cis-4-hydroxycyclohexyl benzoate (44.1 g) and triphenylphosphine (52.5 g) in tetrahydrofuran (600 mL) was added dropwise diisopropyl azodicarboxylate (1.9 M toluene solution, 105 mL) over a period of 30 min. After stirring for 20 min, water was added thereto, and the mixture was extracted with ethyl acetate. The organic layer was washed with saturated brine, and dried over anhydrous magnesium sulfate. The solvent was evaporated under reduced pressure, hexane and ethyl acetate was added to the residue. The obtained white solid was removed by filtration. The filtrate was evaporated under reduced pressure. The residue was crudely purified by silica gel column chromatography. This was added to a mixture of hydroxylammonium chloride (102.8 g), sodium hydrogen carbonate (149.2 g) and dimethyl sulfoxide (680 mL) and the resulting mixture was stirred overnight at 90° C. The reaction mixture was diluted with ethyl acetate, washed with water and saturated brine successively, and dried over anhydrous magnesium sulfate. The solvent was evaporated under reduced pressure. To a mixture of the residue in tetrahydrofuran (800 mL) were added N,N'-carbonyldiimidazole (48.6 g) and 1,8-diazabicyclo[5.4.0]undec-7-ene (44.8 mL) in turn, and the mixture was stirred at room temperature for 30 min. The reaction mixture was diluted with ethyl acetate, washed with 1M hydrochloric acid and then with saturated brine, and dried over anhydrous magnesium sulfate. The solvent was evaporated under reduced pressure. To a mixture of the residue in methanol (1500 mL) was added sodium methoxide (28 wt % in methanol, 85.3 g) at room temperature, and the mixture was stirred at this temperature overnight. The mixture was evaporated under reduced pressure, the residue was dissolved in tetrahydrofuran (1500 mL). To the resulting tetrahydrofuran solution were added N,N'-carbonyldiimidazole (18.0 g) and 1,8-diazabicyclo[5.4.0]undec-7-ene (16.6 mL) in turn, and the mixture was stirred at room temperature for 2 hr. The reaction mixture was diluted with ethyl acetate, washed with 1M hydrochloric acid and then with saturated brine, and dried over anhydrous magnesium sulfate. The solvent was evaporated under reduced pressure to give a crude solid. The crude solid was recrystallized from hexane/ethyl acetate (1:1) to give colorless crystals. The crystals were dissolved in acetone (1000 mL). To the acetone solution was added 8M potassium hydroxide solution (27.6 mL), and the mixture was stirred overnight to give a colorless solid (130 g, 91%).

$^1$H NMR (300 MHz, DMSO-d$_6$) δ 0.94 (3 H, t, J=7.4) 1.04 (3 H, t, J=7.4) 1.27-1.48 (4H, m) 1.57-1.70 (2H, m) 1.77-1.92 (2H, m) 1.98-2.07 (2H, m) 2.27 (2H, d, J=7.4) 2.52-2.60 (2H, m) 3.44-3.61 (1H, m) 3.81 (2H, s) 4.29-4.45 (1H, m) 4.64 (1H, s) 7.03 (2H, d, J=8.9) 7.11-7.51 (10H, m)

(1b) A solution of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt (226.9 g) in ethanol (900 mL) was stirred at 60° C. for 2 hr. The mixture was allowed to cool to room temperature, an insoluble material was filtered off. The filtrate was stirred at 60° C., and heptane (600 mL) was added thereto over a period of 1 hr. The mixture was allowed to cool to room temperature, and heptane (600 mL) was added thereto. The resulting solution was stirred at this temperature overnight. The obtained colorless crystals were collected, washed with heptane/ethanol (2:1) and dried under reduced pressure at 50° C. for 6 hr to give the title compound (191.2 g, 84%).

$^1$H NMR (300 MHz, DMSO-d$_6$) δ 0.94 (3 H, t, J=7.3), 1.04 (3 H, t, J=7.3), 1.21-1.52 (4 H, m), 1.54-1.70 (2 H, m), 1.78-1.89 (2 H, m), 1.98-2.08 (2 H, m), 2.27 (2 H, q, J=7.3), 2.56 (2 H, dd, J=8.4, 6.7), 3.47-3.60 (1 H, m), 3.81 (2 H, s), 4.31-4.45 (1 H, m), 4.59 (1H, d, J=4.1), 6.99-7.07 (2 H, m), 7.11-7.50 (10 H, m)

Powder X-ray diffraction (Cu—Kα radiation, diffraction angle:

2θ(°)): 4.32, 8.70, 9.86, 12.76, 13.10, 15.48, 18.36, 19.68, 20.62, 21.36, 21.76, 22.04, 22.44, 23.10, 24.22, 24.62, 27.94, 28.24.

(2) A mixture of 2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt (5.0 g) and isopropyl alcohol (50 mL) was stirred at 90° C. for 30 min. The mixture was cooled to room temperature and an insoluble material was filtered off. To the filtrate was added 1-methylethyl acetate (60 mL) dropwise, and the obtained colorless crystals were collected. The crystals were washed with isopropyl alcohol to give the title compound (4.5 g).

Anal. Calcd for $C_{36}H_{37}N_4O_5K$: C, 67.06; H, 5.78; N, 8.69%. Found: C, 64.69; H, 5.91; N, 8.47%

Powder X-ray diffraction (Cu—Kα radiation, diffraction angle:

2θ(°)): 6.32, 6.84, 8.90, 14.36, 16.64, 17.96, 19.18, 19.94, 21.82, 22.04, 22.90, 23.62, 24.92.

Example 434

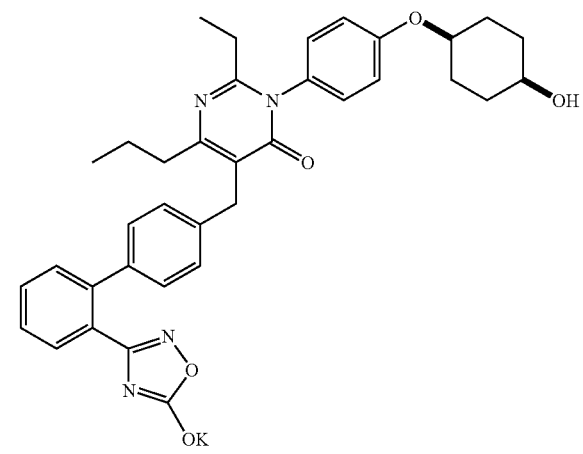

2-ethyl-3-{4-[(cis-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one potassium salt 2-Ethyl-3-{4-[(cis-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (0.3 g) was dissolved in ethanol (10 mL), 8 M potassium hydroxide solution (0.63 mL) was added, and the mixture was stirred for 1 hr. The mixture was concentrated under reduced pressure, and acetone and hexane were added to the residue. The precipitated solid was collected by filtration to give the title compound (0.32 g, 100%) as an amorphous solid.

$^1$H NMR (300 MHz, DMSO-$d_6$) δ 0.94 (3 H, t, J=7.3), 1.04 (3 H, t, J=7.3), 1.52-1.72 (8 H, m), 1.77-1.93 (2 H, m), 2.28 (2 H, q, J=7.3), 2.56 (2 H, dd, J=8.3, 6.8), 3.55-3.70 (1 H, m), 3.82 (2 H, s), 4.42-4.52 (2 H, m), 7.00-7.08 (2 H, m), 7.11-7.49 (10 H, m)

Example 435

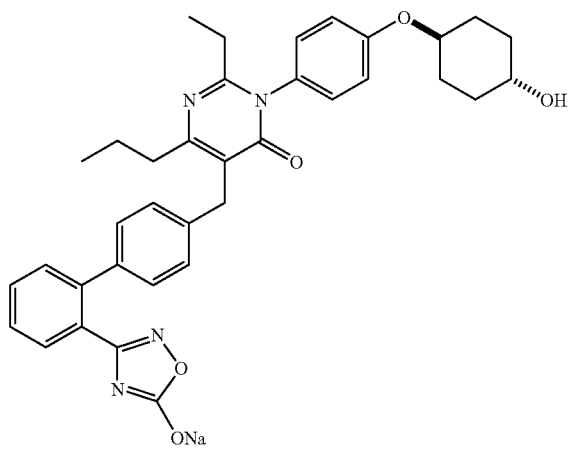

2-ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one sodium salt 2-Ethyl-3-{4-[(trans-4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one (0.3 g) was dissolved in ethanol (10 mL), 8 M sodium hydroxide solution (0.63 mL) was added, and the mixture was stirred for 1 hr. The mixture was concentrated under reduced pressure, and acetone and hexane were added to the residue. The precipitated solid was collected by filtration to give the title compound (0.3 g, 96%) as an amorphous solid.

$^1$H NMR (300 MHz, DMSO-$d_6$) δ 0.94 (3 H, t, J=7.3), 1.04 (3 H, t, J=7.3), 1.21-1.52 (4 H, m), 1.54-1.70 (2 H, m), 1.78-1.89 (2 H, m), 1.98-2.08 (2 H, m), 2.27 (2 H, q, J=7.3), 2.56 (2 H, dd, J=8.4, 6.7), 3.47-3.60 (1 H, m), 3.81 (2 H, s), 4.31-4.45 (1 H, m), 4.59 (1 H, d, J=4.1), 6.99-7.07 (2 H, m), 7.11-7.50 (10 H, m)

Example 436

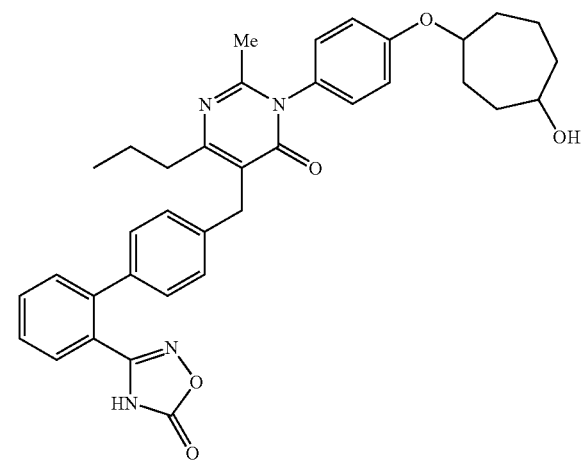

3-{4-[(4-hydroxycycloheptyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one To a solution of 4'-{[1-(4-hydroxyphenyl)-2-methyl-6-oxo-4-propyl-1,6-dihydropyrimidin-5-yl]methyl}biphenyl-2-carbonitrile (0.11 g), 4-{[tert-butyl(dimethyl)silyl]oxy}cycloheptanol (0.29 g) and triphenylphosphine (0.18 g) in tetrahydrofuran (2 mL) was added diisopropyl azodicarboxylate (1.9 M toluene solution, 0.36 mL), and the mixture was stirred for 1 hr. Ethyl acetate and water were added to the reaction mixture, and the mixture was extracted with ethyl acetate. The organic layer was washed with saturated brine and dried over anhydrous magnesium sulfate. The solvent was evaporated and the residue was crudely purified by silica gel column chromatography. This was added to a mixture of hydroxylammonium chloride (0.47 g), sodium hydrogen carbonate (0.76 g) and dimethyl sulfoxide (3 mL), which had been stirred at 40° C. for 30 min, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (3 mL). N,N'-carbonyldiimidazole (0.088 g) and then 1,8-diazabicyclo[5.4.0]undec-7-ene (0.081 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure. The residue was dissolved in tetrahydrofuran (2 mL), tetrabutylammonium fluoride (1.0 M tetrahydrofuran solution, 0.9 mL) was added, and the mixture was stirred at 70° C. for 5 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a colorless amorphous solid (0.15 g, 53%).

$^1$H NMR (300 MHz, DMSO-d$_6$) δ 0.89 (t, J=7.3, 3H), 1.21-2.09 (m, 15H), 2.47-2.54 (m, 2H), 3.64-3.76 (m, 1H), 3.86 (s, 2H), 4.41-4.61 (m, 2H), 6.95-7.73 (m, 12H), 12.33 (s, 1H)

Example 437

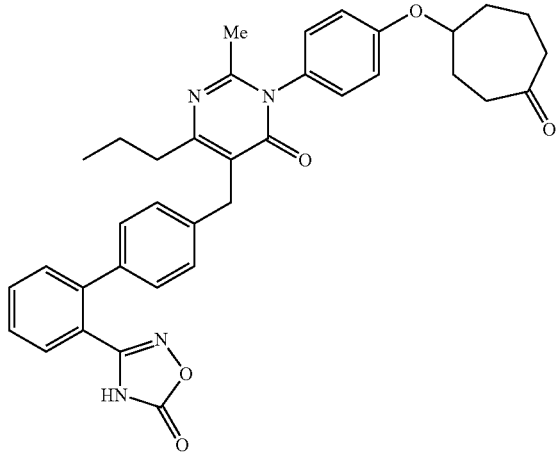

2-methyl-3-{4-[(4-oxocycloheptyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a solution of 3-{4-[(4-hydroxycycloheptyl)oxy]phenyl}-2-methyl-5-{[2'-(5-oxo-4,5-dihydro-1,2,4-oxadiazol-3-yl)biphenyl-4-yl]methyl}-6-propylpyrimidin-4(3H)-one (0.10 g) in methylene chloride (2 mL) was added 1,1,1-tris(acetyloxy)-1,1-dihydro-1,2-benziodoxol-3(1H)-one (0.11 g), and the mixture was stirred for 1 hr. Ethyl acetate, water and sodium thiosulfate were added to the reaction mixture, and the mixture was stirred for 30 min and extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.051 g, 53%).

$^1$H NMR (300 MHz, DMSO-d$_6$) δ 0.89 (t, J=7.3, 3H), 1.46-2.12 (m, 11H), 2.41-2.57 (m, 6H), 3.86 (s, 2H), 4.60-4.71 (m, 1H), 7.04-7.72 (m, 12H), 12.38 (s, 1H)

Example 438

3-[4-(2-hydroxy-1,1,2-trimethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

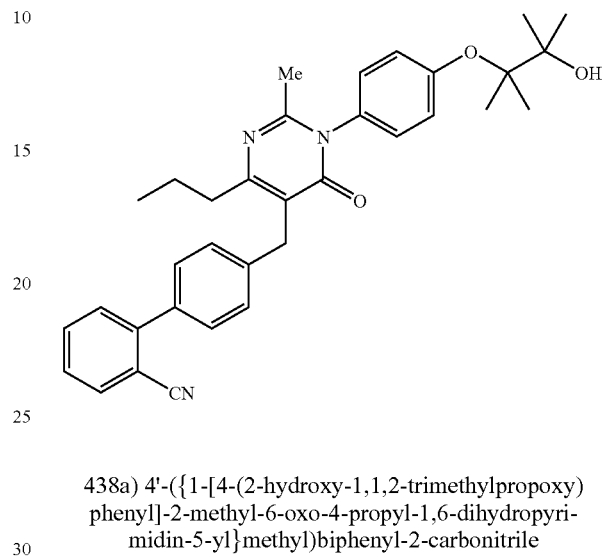

438a) 4'-({1-[4-(2-hydroxy-1,1,2-trimethylpropoxy)phenyl]-2-methyl-6-oxo-4-propyl-1,6-dihydropyrimidin-5-yl}methyl)biphenyl-2-carbonitrile To a solution of methyl 2-{4-[5-[(2'-cyanobiphenyl-4-yl)methyl]-2-methyl-6-oxo-4-propylpyrimidin-1(6H)-yl]phenoxy}-2-methylpropanoate (1.15 g) in tetrahydrofuran (10 mL) was added methylmagnesium bromide (1.0 M diethyl ether solution, 2.15 mL) at −78° C., and the mixture was stirred for 6 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.75 g, 65%).

$^1$H NMR (300 MHz, CHLOROFORM-d) δ 1.01 (t, J=7.2, 3H), 1.30 (s, 6H), 1.34 (s, 6H), 1.64-1.76 (m, 2H), 2.18 (s, 3H), 2.62-2.70 (m, 3H), 3.97 (s, 2H), 7.09-7.77 (m, 12H)

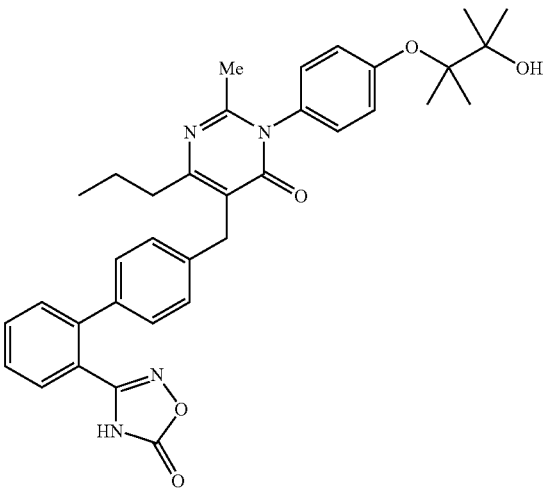

438b) 3-[4-(2-hydroxy-1,1,2-trimethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.70 g), sodium hydrogen carbonate (2.62 g) and dimethyl sulfoxide (10 mL) was stirred at 40° C. for 30 min, 4'-({1-[4-(2-hydroxy-1,1,2-trimethylpropoxy)phenyl]-2-methyl-6-oxo-4-propyl-1,6-dihydropyrimidin-5-yl}methyl)biphenyl-2-carbonitrile (0.96 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.41 g) and then 1,8-diazabicyclo[5.4.0]undec-7-ene (0.37 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless amorphous solid (0.78 g, 66%).

$^1$H NMR (300 MHz, DMSO-d$_6$) δ 0.89 (t, J=7.4, 3H), 1.25 (s, 6H), 1.26 (s, 6H), 1.47-1.62 (m, 2H), 2.06 (s, 3H), 2.48-2.55 (m, 2H), 3.87 (s, 2H), 4.45 (s, 1H), 7.09-7.74 (m, 12H), 12.38 (s, 1H)

Example 439

3-[4-(2-hydroxy-1,1-dimethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one

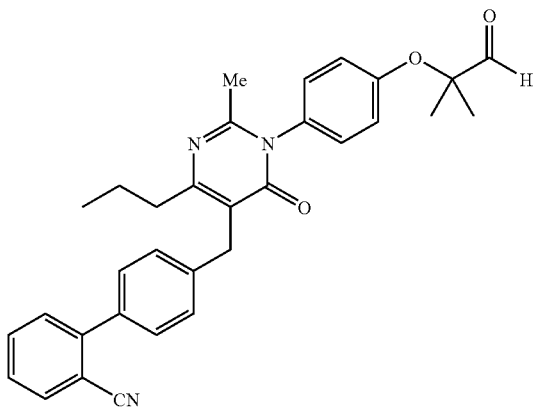

439a) 4'-({1-[4-(1,1-dimethyl-2-oxoethoxy)phenyl]-2-methyl-6-oxo-4-propyl-1,6-dihydropyrimidin-5-yl}methyl)biphenyl-2-carbonitrile To a solution of 4'-({1-[4-(2-hydroxy-1,1-dimethylethoxy)phenyl]-2-methyl-6-oxo-4-propyl-1,6-dihydropyrimidin-5-yl}methyl)biphenyl-2-carbonitrile (1.01 g) in methylene chloride (10 mL) was added 1,1,1-tris(acetyloxy)-1,1-dihydro-1,2-benziodoxol-3(1H)-one (1.26 g), and the mixture was stirred for 1 hr. Ethyl acetate, water and sodium thiosulfate were added to the reaction mixture, and the mixture was stirred for 30 min and extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.79 g, 79%).

$^1$H NMR (300 MHz, CDCl$_3$) δ 1.01 (t, J=7.3, 3H), 1.48 (s, 6H), 1.59-1.78 (m, 2H), 2.16 (s, 3H), 2.61-2.71 (m, 2H), 3.96 (s, 2H), 6.93-7.78 (m, 12H), 9.83 (s, 1H)

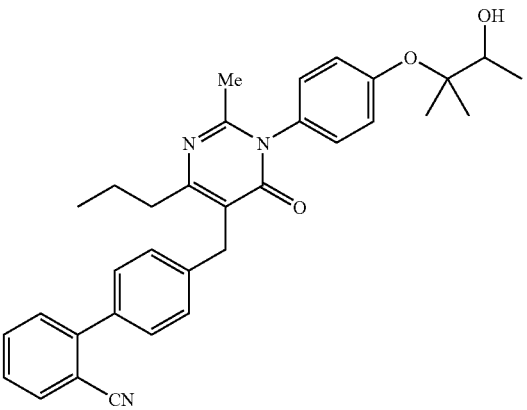

439b) 4'-({1-[4-(2-hydroxy-1,1-dimethylpropoxy)phenyl]-2-methyl-6-oxo-4-propyl-1,6-dihydropyrimidin-5-yl}methyl)biphenyl-2-carbonitrile To a solution of 4'-({1-[4-(1,1-dimethyl-2-oxoethoxy)phenyl]-2-methyl-6-oxo-4-propyl-1,6-dihydropyrimidin-5-yl}methyl)biphenyl-2-carbonitrile (1.15 g) in tetrahydrofuran (10 mL) was added methylmagnesium bromide (3.0 M diethyl ether solution, 0.78 mL) at −78° C., and the mixture was stirred for 3 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.60 g, 74%).

$^1$H NMR (300 MHz, CDCl$_3$) δ 1.01 (t, J=7.4, 3H), 1.20-1.30 (m, 9H), 1.61-1.78 (m, 2H), 2.17 (s, 3H), 2.59 (d, J=3.8, 1H), 2.61-2.69 (m, 2H), 3.82-3.93 (m, 1H), 3.97 (s, 2H), 7.09-7.77 (m, 12H)

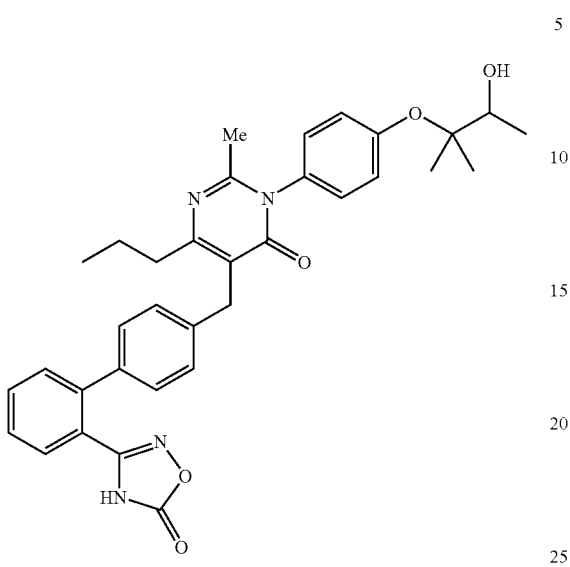

439c) 3-[4-(2-hydroxy-1,1-dimethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.70 g), sodium hydrogen carbonate (2.62 g) and dimethyl sulfoxide (10 mL) was stirred at 40° C. for 30 min, 4'-({1-[4-(2-hydroxy-1,1-dimethylpropoxy)phenyl]-2-methyl-6-oxo-4-propyl-1,6-dihydropyrimidin-5-yl}methyl)biphenyl-2-carbonitrile (0.60 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (6 mL). N,N'-carbonyldiimidazole (0.22 g) and then 1,8-diazabicyclo[5.4.0]undec-7-ene (0.21 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a pale-yellow amorphous solid (0.46 g, 68%).

$^1$H NMR (300 MHz, DMSO-$d_6$) δ 0.89 (t, J=7.4, 3H), 1.16 (d, J=6.4, 3H), 1.19 (s, 6H), 1.25 (s, 6H), 1.47-1.62 (m, 2H), 2.06 (s, 3H), 2.48-2.55 (m, 2H), 3.62-3.74 (m, 1H), 3.87 (s, 2H), 4.78 (d, J=5.3, 1H), 7.06-7.73 (m, 12H), 12.38 (s, 1H)

Example 440

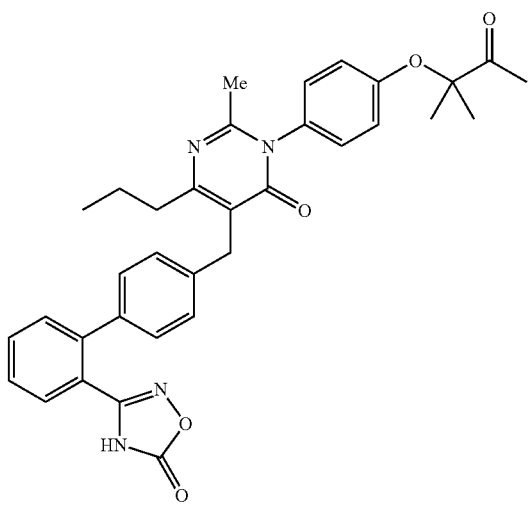

3-[4-(1,1-dimethyl-2-oxopropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one To a solution of 3-[4-(2-hydroxy-1,1-dimethylpropoxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one (0.26 g) in methylene chloride (3 mL) was added 1,1,1-tris(acetyloxy)-1,1-dihydro-1,2-benziodoxol-3(1H)-one (0.28 g), and the mixture was stirred for 1 hr. Ethyl acetate, water and sodium thiosulfate were added to the reaction mixture, and the mixture was stirred for 30 min and extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.19 g, 74%).

$^1$H NMR (300 MHz, DMSO-$d_6$) δ 0.89 (t, J=7.4, 3H), 1.48 (s, 6H), 1.49-1.62 (m, 2H), 2.05 (s, 3H), 2.27 (s, 3H), 2.47-2.55 (m, 2H), 3.86 (s, 2H), 6.85-7.75 (m, 12H), 12.38 (s, 1H)

Example 441

5-{[3-fluoro-2'-(5-oxo-4,5-dihydro-1,2,4-oxadiazol-3-yl)biphenyl-4-yl]methyl}-3-[4-(2-hydroxy-1,1,2-trimethylpropoxy)phenyl]-2-methyl-6-propylpyrimidin-4(3H)-one

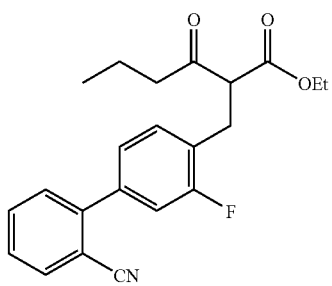

441a) ethyl 2-[(2'-cyano-3-fluorobiphenyl-4-yl)methyl]-3-oxohexanoate

To a suspension of sodium hydride (60% in oil, 0.89 g) in tetrahydrofuran (70 ml) was added a solution of ethyl 3-oxohexanoate (5.45 g) in tetrahydrofuran (20 ml) dropwise at room temperature. After being stirred at room temperature for 1 hr, 4'-(bromomethyl)-3'-fluorobiphenyl-2-carbonitrile (5.0 g) was added to the mixture and the mixture was stirred at room temperature for 15 hr. Ethyl acetate and saturated aqueous ammonium chloride solution were added to the mixture. The layers were separated and the aqueous layer was extracted with ethyl acetate. The combined organic layer was successively washed with water and saturated brine, dried over anhydrous magnesium sulfate and concentrated under reduced pressure. The residue was purified by silica gel column chromatography to give the title compound as a pale yellow oil (5.18 g, 82%).

$^1$H NMR (300 MHz, CDCl$_3$) δ 0.87 (t, J=7.4 Hz, 3 H), 1.22 (t, J=7.2 Hz, 3 H), 1.51-1.67 (m, 2 H), 2.36-2.68 (m, 2 H), 3.14-3.33 (m, 2 H), 3.91 (t, J=7.6 Hz, 1 H), 4.16 (qd, J=7.1, 0.7 Hz, 2 H), 7.18-7.80 (m, 7 H)

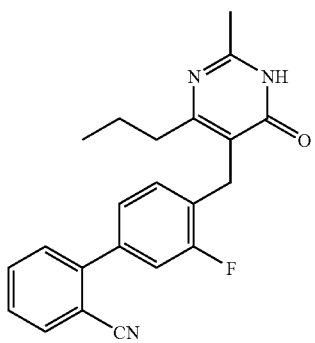

441b) 3'-fluoro-4'-[(2-methyl-6-oxo-4-propyl-1,6-dihydropyrimidin-5-yl)methyl]biphenyl-2-carbonitrile To a suspension of acetamidine hydrochloride (2.67 g) in methanol (50 ml) was added sodium methoxide (28% in methanol, 8.2 mL) dropwise, followed by addition of a solution of ethyl 2-[(2'-cyano-3-fluorobiphenyl-4-yl)methyl]-3-oxohexanoate (5.18 g) in methanol (20 ml) at room temperature. After being stirred at room temperature for 15 hr, ethyl acetate and saturated aqueous ammonium chloride solution were added. The layers were separated and the aqueous layer was extracted with ethyl acetate. The combined organic layer was successively washed with water and saturated brine, dried over anhydrous magnesium sulfate and concentrated under reduced pressure. The resulting solid was collected and washed with diisopropyl ether to give the title compound as a white solid (3.97 g, 78%).

$^1$H NMR (300 MHz, DMSO-d$_6$) δ 0.84 (t, J=7.4 Hz, 3 H), 1.44-1.59 (m, J=7.5, 7.5, 7.5, 7.5, 7.3 Hz, 2 H), 2.26 (s, 3 H), 2.40-2.49 (m, 2 H), 3.84 (s, 2 H), 7.00-8.18 (m, 7 H), 12.35 (s, 1 H)

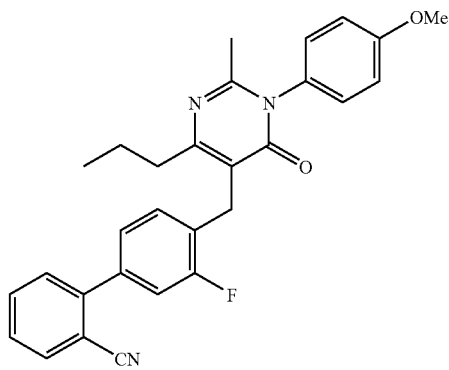

441c) 3'-fluoro-4'-{[1-(4-methoxyphenyl)-2-methyl-6-oxo-4-propyl-1,6-dihydropyrimidin-5-yl]methyl}biphenyl-2-carbonitrile To a suspension of 3'-fluoro-4'-[(2-methyl-6-oxo-4-propyl-1,6-dihydropyrimidin-5-yl)methyl]biphenyl-2-carbonitrile (2.0 g), (4-methoxyphenyl)boronic acid (2.0 g), triethylamine (4.0 mL), pyridine (2.0 mL) and molecular sieves 4 A (4.0 g) in methylene chloride (30 mL) was added copper(II) acetate (1.0 g), and the mixture was stirred at room temperature for 4 days. The reaction mixture was diluted with ethyl acetate, the insoluble material was filtered off through celite, and the filtrate was concentrated. The residue was purified by silica gel column chromatography to give the title compound as a pale-yellow amorphous solid (2.35 g, 91%).

$^1$H NMR (300 MHz, CDCl$_3$) δ 1.01 (t, J=7.3 Hz, 3 H), 1.63-1.76 (m, 2 H), 2.18 (s, 3 H), 2.60-2.69 (m, 2 H), 3.85 (s, 3 H), 3.98 (s, 2 H), 6.97-7.79 (m, 11 H)

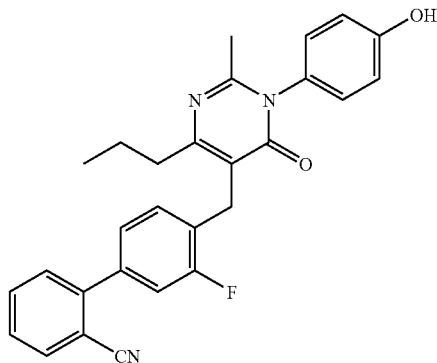

441d) 3'-fluoro-4'-{[1-(4-hydroxyphenyl)-2-methyl-6-oxo-4-propyl-1,6-dihydropyrimidin-5-yl]methyl}biphenyl-2-carbonitrile To a solution of 3'-fluoro-4'-{[1-(4-methoxyphenyl)-2-methyl-6-oxo-4-propyl-1,6-dihydropyrimidin-5-yl]methyl}biphenyl-2-carbonitrile (2.35 g) in methylene chloride (10 mL) was added tribromoborane (1.0 M methylene chloride solution, 20 mL) at room temperature. After being stirred at room temperature for 12 hr, ethyl acetate and water were added, and the mixture was extracted with ethyl acetate. The organic layer was washed with saturated brine and dried over anhydrous magnesium sulfate. The solvent was evaporated and the residue was purified by silica gel column chromatography to give the title compound as a white solid (2.25 g, 99%).

$^1$H NMR (300 MHz, CDCl$_3$) δ 1.00 (t, J=7.3 Hz, 3 H), 1.57-1.76 (m, 3 H), 2.18 (s, 3 H), 2.61-2.70 (m, 2 H), 4.03 (s, 2 H), 6.62-7.79 (m, 11 H)

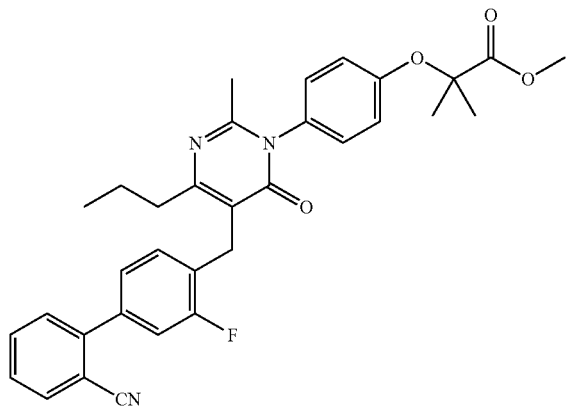

441e) methyl 2-{4-[5-[(2'-cyano-3-fluorobiphenyl-4-yl)methyl]-2-methyl-6-oxo-4-propylpyrimidin-1(6H)-yl]phenoxy}-2-methylpropanoate To a solution of 3'-fluoro-4'-{[1-(4-hydroxyphenyl)-2-methyl-6-oxo-4-propyl-1,6-dihydropyrimidin-5-yl]methyl}biphenyl-2-carbonitrile (0.50 g) and methyl 2-bromo-2-methylpropanoate (1.0 g) in N,N-dimethylformamide (10 mL) was added cesium carbonate (0.72 g), and the mixture was stirred at 80° C. for 12 hr. After allowing to cool to room temperature, ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.58 g, 96%).

$^1$H NMR (300 MHz, CDCl$_3$) δ 1.00 (t, J=7.3 Hz, 3 H), 1.60-1.78 (m, 8 H), 2.16 (s, 3 H), 2.59-2.68 (m, 2 H), 3.78 (s, 3 H), 3.98 (s, 2 H), 6.89-7.78 (m, 11 H)

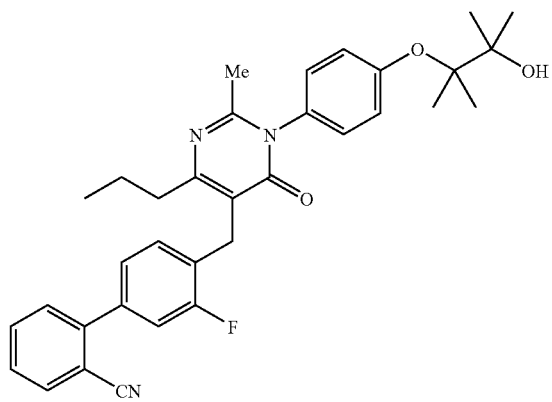

441f) 3'-fluoro-4'-({1-[4-(2-hydroxy-1,1,2-trimethylpropoxy)phenyl]-2-methyl-6-oxo-4-propyl-1,6-dihydropyrimidin-5-yl}methyl)biphenyl-2-carbonitrile To a solution of methyl 2-{4-[5-[(2'-cyano-3-fluorobiphenyl-4-yl)methyl]-2-methyl-6-oxo-4-propylpyrimidin-1(6H)-yl]phenoxy}-2-methylpropanoate (1.00 g) in tetrahydrofuran (8 mL) was added methylmagnesium bromide (3.0 M diethyl ether solution, 1.84 mL) at −78° C., and the mixture was stirred for 3 hr. Ethyl acetate and water were added to the reaction mixture, and the mixture was extracted with ethyl acetate. The organic layer was washed with saturated brine and dried over anhydrous magnesium sulfate. The solvent was evaporated and the residue was purified by silica gel column chromatography to give the title compound as a pale-yellow amorphous solid (0.77 g, 77%).

$^1$H NMR (300 MHz, CDCl$_3$) δ 1.01 (t, J=7.4, 3H), 1.30 (s, 6H), 1.34 (s, 6H), 1.63-1.75 (m, 2H), 2.18 (s, 3H), 2.60-2.68 (m, 3H), 3.99 (s, 2H), 7.09-7.78 (m, 11H)

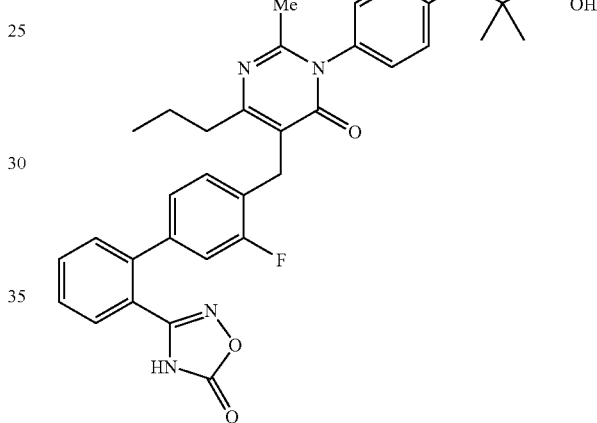

441 g) 5-{[3-fluoro-2'-(5-oxo-4,5-dihydro-1,2,4-oxadiazol-3-yl)biphenyl-4-yl]methyl}-3-[4-(2-hydroxy-1,1,2-trimethylpropoxy)phenyl]-2-methyl-6-propylpyrimidin-4(3H)-one A mixture of hydroxylammonium chloride (0.97 g), sodium hydrogen carbonate (1.40 g) and dimethyl sulfoxide (7 mL) was stirred at 40° C. for 30 min, 3'-fluoro-4'-({1-[4-(2-hydroxy-1,1,2-trimethylpropoxy)phenyl]-2-methyl-6-oxo-4-propyl-1,6-dihydropyrimidin-5-yl}methyl)biphenyl-2-carbonitrile (0.77 g) was added, and the mixture was stirred at 90° C. for 18 hr. The reaction mixture was allowed to cool to room temperature, ethyl acetate and water were added, and the mixture was extracted with ethyl acetate. The organic layer was washed with saturated brine and dried over anhydrous magnesium sulfate. The solvent was evaporated and the residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 3 hr. The reaction mixture was diluted with ethyl acetate, washed with 1 M hydrochloric acid and then with saturated brine, and dried over anhydrous magnesium sulfate. The solvent was evaporated under reduced pressure and the residue was purified by silica gel column chromatography to give the title compound as a colorless amorphous solid (0.71 g, 84%).

¹H NMR (300 MHz, DMSO-d₆) δ 0.89 (t, J=7.3, 3H), 1.24 (s, 6H), 1.25 (s, 6H), 1.50-1.63 (m, 2H), 2.07 (s, 3H), 2.46-2.54 (m, 2H), 3.86 (s, 2H), 4.44 (s, 1H), 6.98-7.74 (m, 11H), 12.46 (s, 1H)

Example 442

2-ethyl-3-{[(2RS,4s,6SR)-4-hydroxy-2,6-dimethyltetrahydro-2H-pyran-4-yl]methyl}-5-{[2'-(5-oxo-4,5-dihydro-1,2,4-oxadiazol-3-yl)biphenyl-4-yl]methyl}-6-propylpyrimidin-4(3H)-one

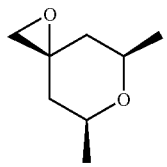

442a)(3s,5RS,7SR)-5,7-dimethyl-1,6-dioxaspiro[2.5]octane

To a solution of trimethylsulfoxonium iodide (6.2 g) in dimethyl sulfoxide (50 mL) was added sodium hydride (1.1 g, 60%) and the mixture was stirred for 30 min. To the reaction mixture was added a solution of (2R,6S)-2,6-dimethyltetrahydro-4H-pyran-4-one (3 g) in dimethyl sulfoxide (10 mL), and the mixture was stirred at room temperature for 30 min. The reaction mixture was poured into ice water, and the mixture was extracted with ethyl acetate, washed with saturated brine, and dried over anhydrous sodium sulfate. The solvent was evaporated under reduced pressure to give the title compound as a colorless oil (2.5 g, 74%).

¹H NMR (300 MHz, CDCl₃) δ 1.10-1.32 (8H, m), 1.71-1.87 (2H, m), 2.67 (2H, s), 3.73-3.90 (2H, m)

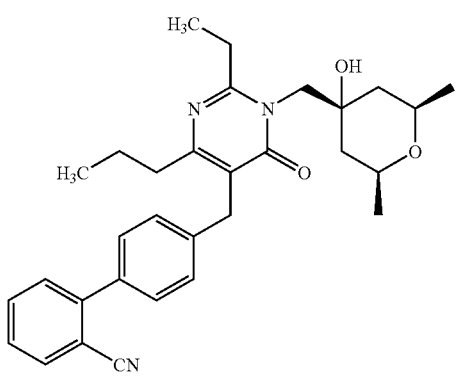

442b) 4'-[(2-ethyl-1-{[(2RS,4s,6SR)-4-hydroxy-2,6-dimethyltetrahydro-2H-pyran-4-yl]methyl}-6-oxo-4-propyl-1,6-dihydropyrimidin-5-yl)methyl]biphenyl-2-carbonitrile To a solution of 4'-{[2-ethyl-1-(4-hydroxyphenyl)-6-oxo-4-propyl-1,6-dihydropyrimidin-5-yl]methyl}biphenyl-2-carbonitrile (1.0 g) in N,N-dimethylacetamide (20 mL) were added (3s,5RS,7SR)-5,7-dimethyl-1,6-dioxaspiro[2.5]octane (0.6 g) and cesium carbonate (1.4 g), and the mixture was stirred at 120° C. for 24 hr. The mixture was allowed to cool to room temperature. The insoluble material was filtered off, diluted with ethyl acetate, washed with 1 M hydrochloric acid, saturated sodium hydrogen carbonate and saturated brine, and dried over anhydrous sodium sulfate. The solvent was evaporated under reduced pressure. The residue was purified by silica gel chromatography to give the title compound as a pale-yellow solid (0.38 g, 27%).

¹H NMR (300 MHz, CDCl₃) δ 0.96 (3H, t, J=7.2), 1.18 (6H, d, J=6.3), 1.20-1.39 (5H, m), 1.47-1.78 (4H, m), 2.55-2.66 (2H, m), 2.79 (2H, q, J=7.2), 3.82-3.97 (2H, m), 3.97 (2H, s), 4.14 (2H, s), 4.99 (1H, s), 7.29-7.51 (6H, m), 7.57-7.66 (1H, m), 7.74 (1H, d, J=7.8)

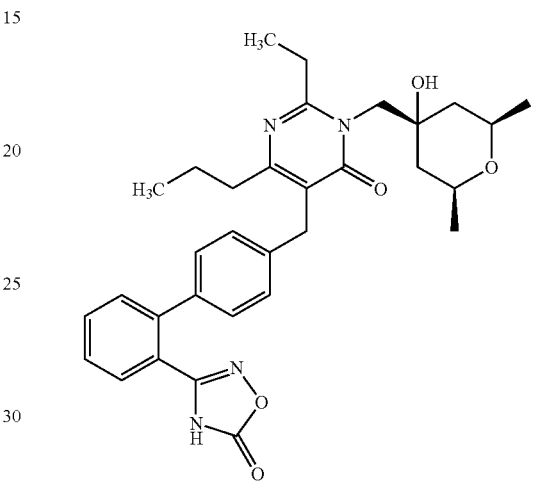

442c) 2-ethyl-3-{[(2RS,4s,6SR)-4-hydroxy-2,6-dimethyltetrahydro-2H-pyran-4-yl]methyl}-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.9 g), sodium hydrogen carbonate (1.3 g) and dimethyl sulfoxide (5 mL) was stirred at 40° C. for 30 min, 4'-[(2-ethyl-1-{[(2RS,4s,6SR)-4-hydroxy-2,6-dimethyltetrahydro-2H-pyran-4-yl]methyl}-6-oxo-4-propyl-1,6-dihydropyrimidin-5-yl)methyl]biphenyl-2-carbonitrile (0.38 g) was added, and the mixture was stirred at 90° C. for 8 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (5 mL). N,N'-carbonyldiimidazole (0.12 g) and then 1,8-diazabicyclo[5.4.0]undec-7-ene (0.11 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.2 g, 47%).

¹H NMR (300 MHz, DMSO-d₆) δ 0.86 (3H, t, J=7.2), 0.94-1.08 (6H, m), 1.09-1.29 (5H, m), 1.33-1.46 (2H, m), 1.46-1.63 (2H, m), 2.41-2.50 (2H, m), 2.98 (2H, q, J=7.2), 3.56-3.74 (2H, m), 3.86 (2H, s), 4.04 (2H, s), 4.92 (1H, s), 7.13-7.29 (4H, m), 7.42-7.58 (2H, m), 7.59-7.72 (2H, m), 12.38 (1H, br)

Example 443

2-ethyl-5-{[2'-(5-oxo-4,5-dihydro-1,2,4-oxadiazol-3-yl)biphenyl-4-yl]methyl}-3-[4-(4-oxopiperidin-1-yl)phenyl]-6-propylpyrimidin-4(3H)-one

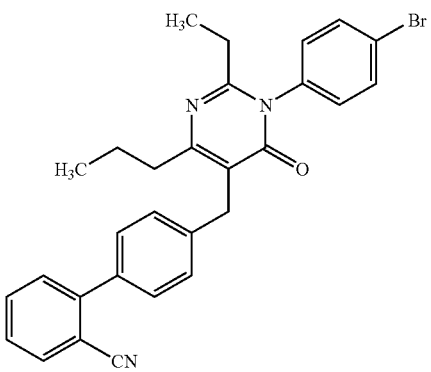

443a) 4'-{[1-(4-bromophenyl)-2-ethyl-6-oxo-4-propyl-1,6-dihydropyrimidin-5-yl]methyl}biphenyl-2-carbonitrile To a suspension of 4'-[(2-ethyl-6-oxo-4-propyl-1,6-dihydropyrimidin-5-yl)methyl]biphenyl-2-carbonitrile (2 g), 4-bromophenylboronic acid (2.3 g), triethylamine (3.9 mL), pyridine (2.3 mL) and molecular sieves 4 A (4 g) in dichloromethane (20 mL) was added copper(II) acetate (2.0 g) and the mixture was stirred for 2 days. The reaction mixture was diluted with ethyl acetate, the insoluble material was filtered off through celite, and the filtrate was concentrated. The residue was purified by silica gel column chromatography to give the title compound as a colorless solid (1.6 g, 56%).

$^1$H NMR (300 MHz, CDCl$_3$) δ 1.01 (3H, t, J=7.2), 1.15 (3H, t, J=7.2), 1.63-1.80 (2H, m), 2.35 (2H, q, J=7.2), 2.62-2.72 (2H, m), 3.96 (2H, s), 7.12 (2H, d, J=8.4), 7.36-7.51 (6H, m), 7.57-7.69 (3H, m), 7.74 (1H, d, J=8.1)

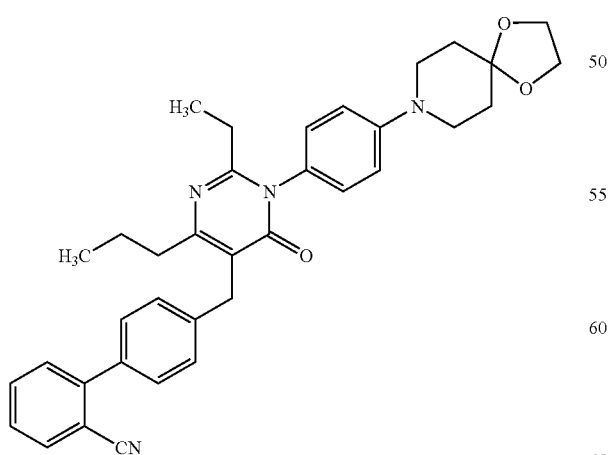

443b) 4'-({1-[4-(1,4-dioxa-8-azaspiro[4.5]dec-8-yl)phenyl]-2-ethyl-6-oxo-4-propyl-1,6-dihydropyrimidin-5-yl}methyl)biphenyl-2-carbonitrile To a solution of 4'-{[1-(4-bromophenyl)-2-ethyl-6-oxo-4-propyl-1,6-dihydropyrimidin-5-yl]methyl}biphenyl-2-carbonitrile (1.6 g), 1,1'-binaphthalene-2,2'-diylbis(diphenylphosphine)(0.29 g), 1,4-dioxa-8-azaspiro[4.5]decane (0.9 g) and sodium tert-butoxide (0.45 g) in toluene (40 mL) was added tris(dibenzylideneacetone)dipalladium (0.14 g), and the mixture was stirred at 100° C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a colorless solid (1.1 g, 60%).

$^1$H NMR (300 MHz, CDCl$_3$) δ 1.00 (3H, t, J=7.2), 1.14 (3H, t, J=7.2), 1.63-1.77 (2H, m), 1.79-1.88 (4H, m), 2.39 (2H, q, J=7.2), 2.61-2.71 (2H, m), 3.34-3.43 (4H, m), 3.96 (2H, s), 4.00 (4H, s), 6.96-7.10 (4H, m), 7.36-7.51 (6H, m), 7.56-7.66 (1H, m), 7.73 (1H, d, J=7.8)

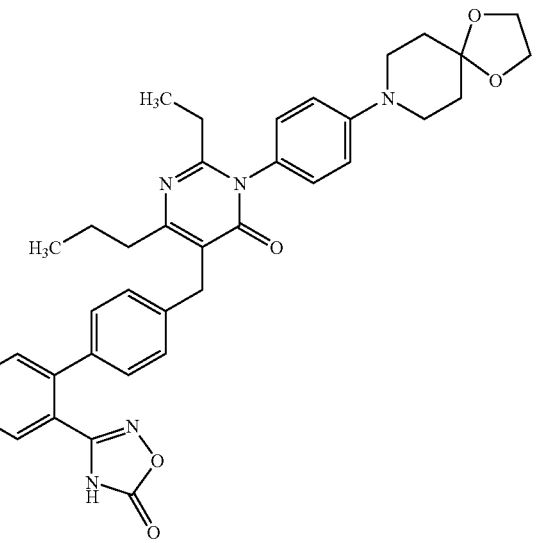

443c) 3-[4-(1,4-dioxa-8-azaspiro[4.5]dec-8-yl)phenyl]-2-ethyl-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (2.6 g), sodium hydrogen carbonate (3.2 g) and dimethyl sulfoxide (20 mL) was stirred at 40° C. for 30 min, 4'-({1-[4-(1,4-dioxa-8-azaspiro[4.5]dec-8-yl)phenyl]-2-ethyl-6-oxo-4-propyl-1,6-dihydropyrimidin-5-yl}methyl)biphenyl-2-carbonitrile (1.1 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (20 mL). N,N'-carbonyldiimidazole (0.46 g) and then 1,8- diazabicyclo[5.4.0]undec-7-ene (0.42 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.45 g, 38%).

$^1$H NMR (300 MHz, CDCl$_3$) δ 1.04 (3H, t, J=7.2), 1.13 (3H, t, J=7.2), 1.71-1.87 (6H, m), 2.37 (2H, q, J=7.2), 2.66-2.75 (2H, m), 3.33-3.43 (4H, m), 3.90 (2H, s), 4.00 (4H, s), 6.92-7.02 (4H, m), 7.20 (2H, d, J=8.4), 7.31 (2H, d, J=8.4), 7.38-7.49 (2H, m), 7.54-7.62 (1H, m), 7.79 (1H, d, J=7.2)

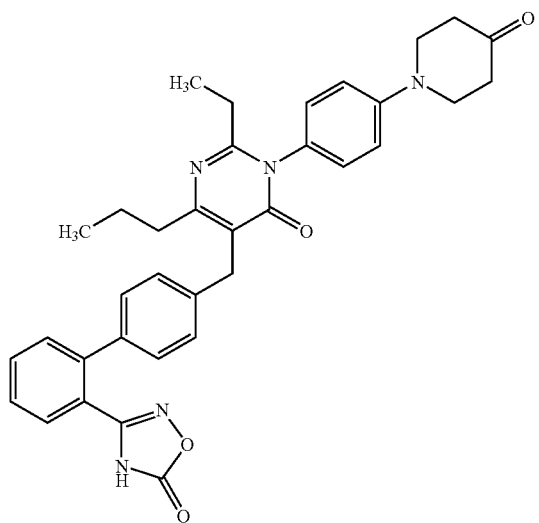

443d) 2-ethyl-5-{[2'-(5-oxo-4,5-dihydro-1,2,4-oxadiazol-3-yl)biphenyl-4-yl]methyl}-3-[4-(4-oxopiperidin-1-yl)phenyl]-6-propylpyrimidin-4(3H)-one A solution of 3-[4-(1,4-dioxa-8-azaspiro[4.5]dec-8-yl)phenyl]-2-ethyl-5-{[2'-(5-oxo-4,5-dihydro-1,2,4-oxadiazol-3-yl)biphenyl-4-yl]methyl}-6-propylpyrimidin-4(3H)-one (0.45 g) in tetrahydrofuran (10 mL)-1 M hydrochloric acid (10 mL) was stirred at 60° C. for 2 days. The reaction mixture was diluted with ethyl acetate, washed with saturated aqueous sodium hydrogen carbonate solution and saturated brine, and dried over anhydrous sodium sulfate. The solvent was evaporated under reduced pressure. The residue was purified by silica gel column chromatography to give the title compound as a colorless solid (0.45 g, 38%).

$^1$H NMR (300 MHz, DMSO-d$_6$) δ 0.90 (3H, t, J=7.2), 1.05 (3H, t, J=7.2), 1.49-1.65 (2H, m), 2.31 (2H, q, J=7.2), 2.42-2.58 (6H, m), 3.67 (4H, t, J=6.0), 3.87 (2H, s), 7.07-7.31 (8H, m), 7.47-7.59 (2H, m), 7.62-7.73 (2H, m), 12.38 (1H, br)

Example 444

2-ethyl-3-[4-(2-hydroxy-1,1-dimethylpropoxy)phenyl]-5-{[2'-(5-oxo-4,5-dihydro-1,2,4-oxadiazol-3-yl)biphenyl-4-yl]methyl}-6-propylpyrimidin-4(3H)-one

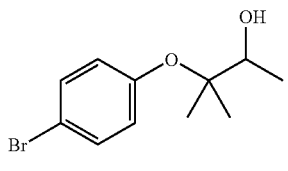

444a) 3-(4-bromophenoxy)-3-methylbutan-2-ol

To a solution of 2-(4-bromophenoxy)-2-methylpropanal (5.3 g) in tetrahydrofuran (100 mL) was added methylmagnesium bromide (9.5 mL, 3 M diethyl ether solution) at −20° C., and the mixture was stirred for 1 hr. A saturated ammonium chloride solution was added to the reaction mixture, and the mixture was extracted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a colorless solid (4.0 g, 70%).

$^1$H NMR (300 MHz, CDCl$_3$) δ 1.15-1.25 (9H, m), 2.59 (1H, d, J=3.3), 3.77-3.90 (1H, m), 6.86 (2H, d, J=8.7), 7.79 (2H, d, J=8.7)

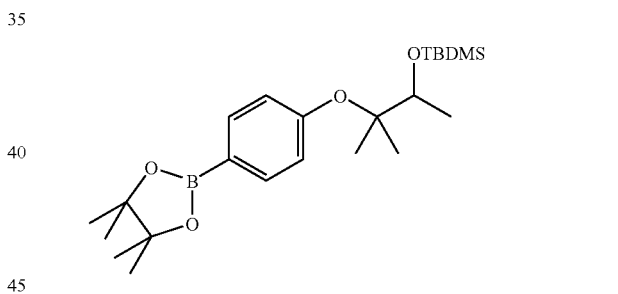

444b) tert-butyl{1,2-dimethyl-2-[4-(4,4,5,5-tetramethyl-1,3,2-dioxaborolan-2-yl)phenoxy]propoxy}dimethylsilane To a solution of 3-(4-bromophenoxy)-3-methylbutan-2-ol (4.0 g) and 2,6-lutidine (4.6 mL) in dichloromethane (40 mL) was added tert-butyl(dimethyl)silyl trifluoromethanesulfonate (4.2 mL) under ice-cooling, and the mixture was stirred for 1 hr. The reaction mixture was diluted with ethyl acetate, washed with 1 M hydrochloric acid and then with saturated brine, and dried over anhydrous sodium sulfate. The solvent was evaporated under reduced pressure. The residue was dissolved in N,N-dimethylformamide (50 mL), 4,4,4',4',5,5,5',5'-octamethyl-2,2'-bi-1,3,2-dioxaborolane (4.7 g), potassium acetate (4.5 g) and [1,1'-bis(diphenylphosphino)ferrocene]dichloropalladium (0.37 g) were added, and the mixture was stirred at 90° C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a pale-yellow oil (5.8 g, 91%).

$^1$H NMR (300 MHz, CDCl$_3$) δ 0.06 (3H, s), 0.09 (3H, s), 0.90 (9H, s), 1.15-1.37 (21H, m), 3.81-3.91 (1H, m), 6.97 (2H, d, J=8.4), 7.71 (2H, d, J=8.4)

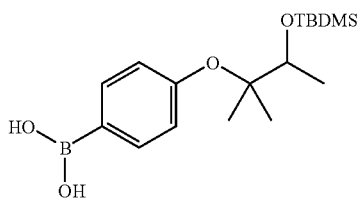

444c) [4-(2-{[tert-butyl(dimethyl)silyl]oxy}-1,1-dimethylpropoxy)phenyl]boronic acid tert-Butyl{1,2-dimethyl-2-[4-(4,4,5,5-tetramethyl-1,3,2-dioxaborolan-2-yl)phenoxy]propoxy}dimethylsilane (5.8 g) was dissolved in 1 M hydrochloric acid (20 mL)-tetrahydrofuran (20 mL)-water (20 mL), sodium periodate (5.9 g) was added, and the mixture was stirred at room temperature for 3 hr. The reaction mixture was diluted with water, extracted with ethyl acetate, washed with 1 M hydrochloric acid, saturated aqueous sodium hydrogen carbonate solution and saturated brine, and dried over anhydrous sodium sulfate. The solvent was evaporated under reduced pressure and the title compound as a pale-yellow solid (1.1 g, 23%).

$^1$H NMR (300 MHz, CDCl$_3$) δ 0.09 (3H, s), 0.17 (3H, s), 0.92 (9H, s), 1.17-1.31 (9H, m), 3.82-3.97 (1H, m), 7.09 (2H, d, J=8.4), 8.12 (2H, d, J=8.4)

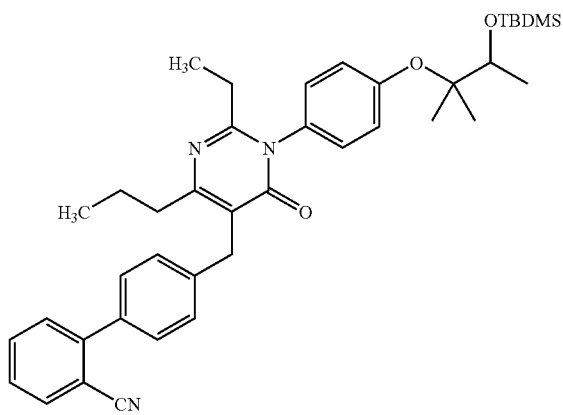

444d) 4'-({1-[4-(2-{[tert-butyl(dimethyl)silyl]oxy}-1,1-dimethylpropoxy)phenyl]-2-ethyl-6-oxo-4-propyl-1,6-dihydropyrimidin-5-yl}methyl)biphenyl-2-carbonitrile To a suspension of 4'-[(2-ethyl-6-oxo-4-propyl-1,6-dihydropyrimidin-5-yl)methyl]biphenyl-2-carbonitrile (0.56 g), [4-(2-{[tert-butyl(dimethyl)silyl]oxy}-1,1-dimethylpropoxy)phenyl]boronic acid (1.1 g), triethylamine (1.1 mL), pyridine (0.63 mL) and molecular sieves 4 A (1.1 g) in dichloromethane (10 mL) was added copper(II) acetate (0.56 g) and the mixture was stirred for 2 days. The reaction mixture was diluted with ethyl acetate, the insoluble material was filtered off through celite, and the filtrate was concentrated. The residue was purified by silica gel column chromatography to give the title compound as a colorless solid (0.87 g, 87%).

$^1$H NMR (300 MHz, CDCl$_3$) δ 0.08 (3H, s), 0.10 (3H, s), 0.91 (9H, s), 1.01 (3H, t, J=7.2), 1.14 (3H, t, J=7.2), 1.18-1.32 (9H, m), 1.63-1.81 (2H, m), 2.36 (2H, q, J=7.2), 2.30-2.43 (2H, m), 3.86 (1H, q, J=6.3), 3.97 (2H, s), 7.10 (4H, s), 7.36-7.75 (6H, m), 7.57-7.66 (1H, m), 7.74 (1H, d, J=7.8)

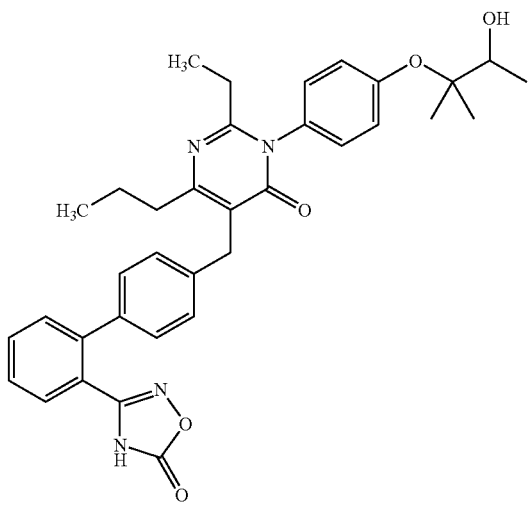

444e) 2-ethyl-3-[4-(2-hydroxy-1,1-dimethylpropoxy)phenyl]-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (1.6 g), sodium hydrogen carbonate (2.3 g) and dimethyl sulfoxide (10 mL) was stirred at 40° C. for 30 min, 4'-({1-[4-(2-{[tert-butyl(dimethyl)silyl]oxy}-1,1-dimethylpropoxy)phenyl]-2-ethyl-6-oxo-4-propyl-1,6-dihydropyrimidin-5-yl}methyl)biphenyl-2-carbonitrile (0.87 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (12 mL). N,N'-carbonyldiimidazole (0.33 g) and then 1,8-diazabicyclo[5.4.0]undec-7-ene (0.30 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was dissolved in tetrahydrofuran (5 mL), tetrabutylammonium fluoride (2.5 mL and 1.0 M tetrahydrofuran solution) were added, and the mixture was stirred for 24 hr. The reaction mixture was diluted with ethyl acetate, washed with 1 M hydrochloric acid and saturated brine, and dried over anhydrous sodium sulfate. The solvent was evaporated under reduced pressure and the residue was purified by silica gel column chromatography to give the title compound as a colorless solid (0.54 g, 68%).

$^1$H NMR (300 MHz, DMSO-d$_6$) δ 0.93 (3H, t, J=7.2), 1.05 (3H, t, J=7.2), 1.11-1.28 (9H, m), 1.49-1.66 (2H, m), 2.28 (2H, q, J=7.2), 2.51-2.59 (2H, m), 3.62-3.74 (1H, m), 3.87 (2H, s), 4.78 (1H, d, J=5.4), 7.12 (2H, d, J=9.0), 7.17-7.33 (6H, m), 7.46-7.59 (2H, m), 7.61-7.74 (2H, m), 12.38 (1H, br)

Example 445

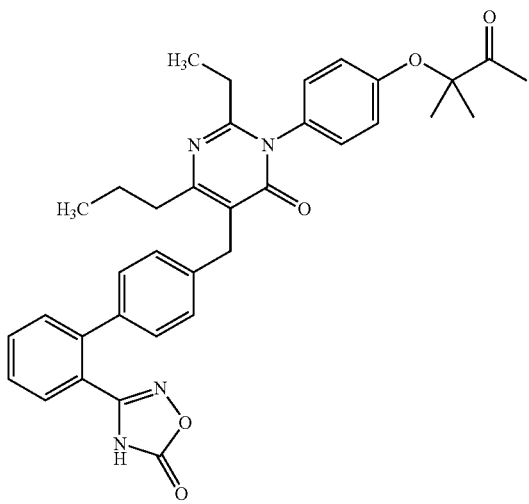

3-[4-(1,1-dimethyl-2-oxopropoxy)phenyl]-2-ethyl-5-{[2'-(5-oxo-4,5-dihydro-1,2,4-oxadiazol-3-yl)biphenyl-4-yl]methyl}-6-propylpyrimidin-4(3H)-one To a solution of 2-ethyl-3-[4-(2-hydroxy-1,1-dimethylpropoxy)phenyl]-5-{[2'-(5-oxo-4,5-dihydro-1,2,4-oxadiazol-3-yl)biphenyl-4-yl]methyl}-6-propylpyrimidin-4(3H)-one (0.2 g) in dichloromethane (6 mL) was added 1,1,1-tris(acetyloxy)-1,1-dihydro-1,2-benziodoxol-3(1H)-one (0.21 g), and the mixture was stirred for 2 hr. Ethyl acetate, water and sodium thiosulfate were added to the reaction mixture, and the mixture was stirred for 30 min and extracted with ethyl acetate. The organic layer was washed with saturated brine, and dried over anhydrous sodium sulfate. The solvent was evaporated and the residue was purified by silica gel column chromatography to give the title compound as a colorless solid (0.18 g, 89%).

$^1$H NMR (300 MHz, DMSO-d$_6$) δ 0.90 (3H, t, J=7.2), 1.05 (3H, t, J=7.2), 1.48 (6H, s), 1.51-1.65 (2H, m), 2.21-2.32 (5H, m), 2.51-2.58 (2H, m), 3.86 (2H, s), 6.89 (2H, d, J=9.0), 7.16-7.31 (6H, m), 7.46-7.59 (2H, m), 7.61-7.72 (2H, m), 12.38 (1H, br)

Example 446

2-(fluoromethyl)-3-{4-[(4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one

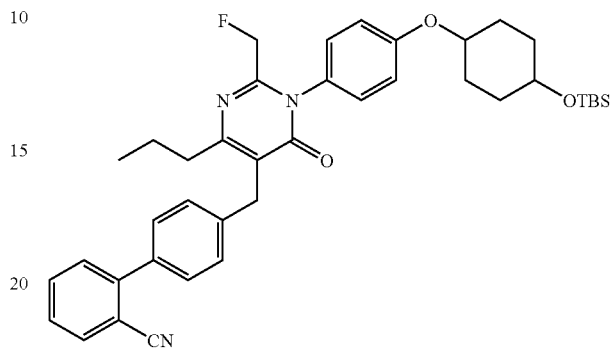

446a) 4'-{[1-{4-[(4-{[tert-butyl(dimethyl)silyl]oxy}cyclohexyl)oxy]phenyl}-2-(fluoromethyl)-6-oxo-4-propyl-1,6-dihydropyrimidin-5-yl]methyl}biphenyl-2-carbonitrile To a mixture of 4'-[(1-{4-[(4-{[tert-butyl(diphenyl)silyl]oxy}cyclohexyl)oxy]phenyl}-2-methyl-6-oxo-4-propyl-1,6-dihydropyrimidin-5-yl)methyl]biphenyl-2-carbonitrile (2.33 g), sodium acetate (0.5 g) and acetic acid (20 mL) was added bromine (0.31 mL), and the mixture was stirred at room temperature for 3 hr. The solvent was evaporated from the reaction mixture under reduced pressure, and the residue was diluted with ethyl acetate. dilution solution was washed with water, saturated aqueous sodium hydrogen carbonate solution and saturated brine, dried over anhydrous magnesium sulfate, and the solvent was evaporated under reduced pressure. The residue was dissolved in tetrahydrofuran (20 mL), tetrabutylammonium fluoride (1.0 M, 6 mL) was added, and the mixture was stirred at 80° C. for 12 hr. The solvent was evaporated from the reaction mixture under reduced pressure. The residue was diluted with ethyl acetate, washed with water and then with saturated brine, and dried over anhydrous magnesium sulfate. The solvent was evaporated under reduced pressure. The residue was dissolved in methylene chloride (10 mL), tert-butyl(dimethyl)silyl trifluoromethanesulfonate (0.43 mL) and 2,6-lutidine (0.32 mL) were added, and the mixture was stirred at 0° C. for 1 hr and at room temperature for 12 hr. The solvent was evaporated from the reaction mixture under reduced pressure, and the residue was diluted with ethyl acetate. The diluted solution was washed with water, saturated aqueous sodium hydrogen carbonate solution and saturated brine, dried over anhydrous magnesium sulfate, and the solvent was evaporated under reduced pressure. The residue was purified by silica gel column chromatography to give the title compound as a colorless amorphous solid (0.18 g, 9%).

$^1$H NMR (300 MHz, CDCl$_3$) δ ppm 0.00 (s, 6 H), 0.84 (s, 9 H), 0.95 (t, J=7.2 3 H), 1.42-1.75 (m, 8 H), 1.87-1.98 (m, 2 H), 2.57-2.71 (m, 2 H), 3.68-3.82 (m, 1 H), 3.93 (s, 2 H), 4.19-4.31 (m, 1 H), 4.75-5.00 (m, 2 H), 6.89-6.98 (m, 2 H), 7.05-7.12 (m, 2 H), 7.30-7.43 (m, 6 H), 7.51-7.58 (m, 1 H), 7.63-7.70 (m, 1 H)

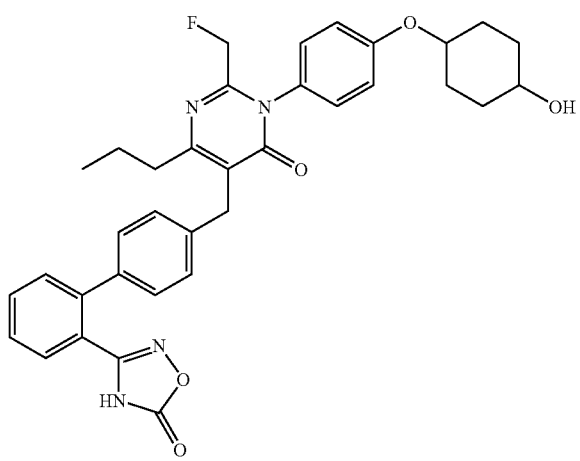

446b) 2-(fluoromethyl)-3-{4-[(4-hydroxycyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.16 g), sodium hydrogen carbonate (0.23 g) and dimethyl sulfoxide (3 mL) was stirred at 40° C. for 30 min, 4'-{[1-{4-[(4-{[tert-butyl(dimethyl)silyl]oxy}cyclohexyl)oxy]phenyl}-2-(fluoromethyl)-6-oxo-4-propyl-1,6-dihydropyrimidin-5-yl]methyl}biphenyl-2-carbonitrile (0.18 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (2 mL). N,N'-carbonyldiimidazole (0.07 g) and then 1,8-diazabicyclo[5.4.0]undec-7-ene (0.06 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure. The residue was dissolved in tetrahydrofuran (1 mL), tetrabutylammonium fluoride tetrahydrofuran solution (1 mol/L, 0.1 mL) was added, and the mixture was stirred at room temperature for 3 hr. The solvent was evaporated from the reaction mixture under reduced pressure. The residue was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.01 g, 6%).

$^1$H NMR (300 MHz, CDCl$_3$) δ ppm 1.06 (t, J=7.3, 3 H), 1.33-1.65 (m, 5 H), 1.72-2.06 (m, 6 H), 2.61-2.83 (m, 2 H), 3.49-3.73 (m, 1 H), 3.80-3.97 (m, 3 H), 4.25-4.37 (m, 1 H), 4.83 (s, 1 H), 4.99 (s, 1 H), 6.85-6.98 (m, 2 H), 6.99-7.13 (m, 2 H), 7.16-7.30 (m, 4 H), 7.40-7.50 (m, 2 H), 7.55-7.64 (m, 1 H), 7.71-7.80 (m, 1 H), 8.04 (s, 1H)

Example 447

2-ethyl-3-[4-(2-hydroxy-1,1,2-trimethylpropoxy)phenyl]-5-{[2'-(5-oxo-4,5-dihydro-1,2,4-oxadiazol-3-yl)biphenyl-4-yl]methyl}-6-propylpyrimidin-4(3H)-one

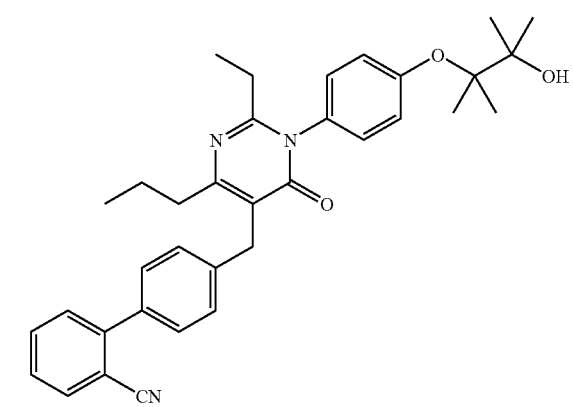

447a) 4'-({2-ethyl-1-[4-(2-hydroxy-1,1,2-trimethylpropoxy)phenyl]-6-oxo-4-propyl-1,6-dihydropyrimidin-5-yl}methyl)biphenyl-2-carbonitrile A mixture of 4'-{[2-ethyl-1-(4-hydroxyphenyl)-6-oxo-4-propyl-1,6-dihydropyrimidin-5-yl]methyl}biphenyl-2-carbonitrile (1 g), ethyl 2-bromo-2-methylpropanoate (0.66 g), cesium carbonate (1.09 g) and dimethylformamide (15 mL) were stirred at 100° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), methylmagnesium bromide (3.0 M, 0.6 mL) was added, and the mixture was stirred at −78° C. for 2 hr and room temperature for 12 hr. The solvent was evaporated from the reaction mixture under reduced pressure. The residue was diluted with ethyl acetate, washed with water and then with saturated brine, and dried over anhydrous magnesium sulfate. The solvent was evaporated under reduced pressure, obtained the residue was purified by silica gel column chromatography to give the title compound as a colorless amorphous solid (0.36 g, 30%).

$^1$H NMR (300 MHz, CDCl$_3$) δ ppm 1.01 (t, J=7.4, 3 H), 1.15 (t, J=7.5, 3 H), 1.31 (s, 6 H), 1.34 (s, 6 H), 1.64-1.80 (m, 2H), 2.37 (q, J=7.5, 2 H), 2.64-2.71 (m, 3 H), 3.98 (s, 2 H), 7.09-7.19 (m, 4 H), 7.35-7.50 (m, 6 H), 7.57-7.64 (m, 1H), 7.73 (dd, J=7.7, 0.9, 1 H)

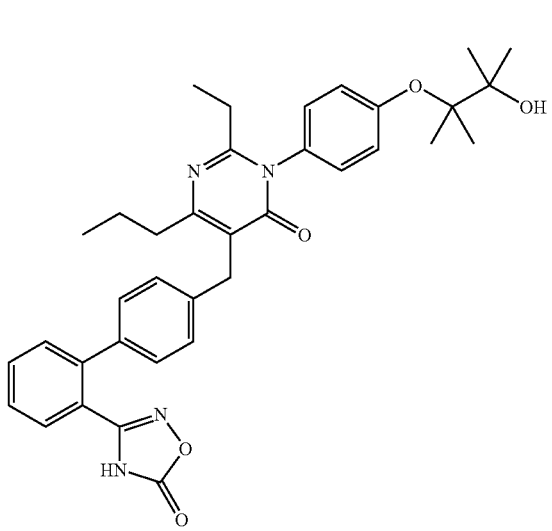

447b) 2-ethyl-3-[4-(2-hydroxy-1,1,2-trimethylpropoxy)phenyl]-5-{[2'-(5-oxo-4,5-dihydro-1,2,4-oxadiazol-3-yl)biphenyl-4-yl]methyl}-6-propylpyrimidin-4(3H)-one A mixture of hydroxylammonium chloride (0.38 g), sodium hydrogen carbonate (0.55 g) and dimethyl sulfoxide (10 mL) was stirred at 40° C. for 30 min, 4'-({2-ethyl-1-[4-(2-hydroxy-1,1,2-trimethylpropoxy)phenyl]-6-oxo-4-propyl-1,6-dihydropyrimidin-5-yl}methyl)biphenyl-2-carbonitrile (0.36 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL). N,N'-carbonyldiimidazole (0.16 g) and then 1,8-diazabicyclo[5.4.0]undec-7-ene (0.15 mL) were added, and the mixture was stirred at room temperature for 2 hr. The reaction mixture was diluted with ethyl acetate, washed with saturated aqueous potassium hydrogen sulfate solution and then with saturated brine, and dried over anhydrous magnesium sulfate. The solvent was evaporated under reduced pressure and the residue was purified by silica gel column chromatography to give the title compound as a colorless amorphous solid (0.14 g, 35%).

$^1$H NMR (300 MHz, DMSO-d$_6$) δ ppm 0.90 (t, J=7.4, 3H), 1.01-1.08 (m, 4H), 1.26 (d, J=1.3, 20H), 1.51-1.66 (m, 2H), 2.28 (q, J=7.5, 2H), 3.53-3.67 (m, 1H), 3.87 (s, 2H), 4.45 (s, 1H), 7.09-7.15 (m, 2H), 7.19-7.31 (m, 6H), 7.47-7.58 (m, 2H), 7.63-7.72 (m, 2H)

Example 448

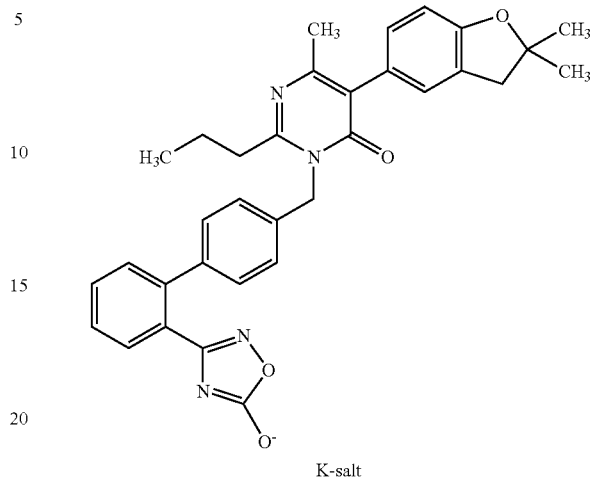

5-(2,2-dimethyl-2,3-dihydro-1-benzofuran-5-yl)-6-methyl-3-{[2'-(5-oxo-4,5-dihydro-1,2,4-oxadiazol-3-yl)biphenyl-4-yl]methyl}-2-propylpyrimidin-4(3H)-one potassium salt To a solution of 5-(2,2-dimethyl-2,3-dihydro-1-benzofuran-5-yl)-6-methyl-3-{[2'-(5-oxo-4,5-dihydro-1,2,4-oxadiazol-3-yl)biphenyl-4-yl]methyl}-2-propylpyrimidin-4(3H)-one (0.10 g) in ethanol (2 mL) was added 8 M potassium hydroxide solution (0.022 mL), and the solvent was evaporated under reduced pressure. The residue was triturated with diisopropyl ether to give the title compound as a colorless solid (0.09 g, 84%).

$^1$H NMR (300 MHz, DMSO-d$_6$) δ 0.90 (3H, t, J=7.5), 1.42 (6H, s), 1.58-1.72 (2H, m), 2.11 (3H, s), 2.67 (2H, t, J=7.5), 3.01 (2H, s), 5.28 (2H, s), 6.69 (1H, d, J=8.1), 6.97 (1H, d, J=8.1), 7.06-7.13 (3H, m), 7.23-7.30 (3H, m), 7.31-7.44 (2H, m), 7.46-7.50 (1H, m)

Example 449

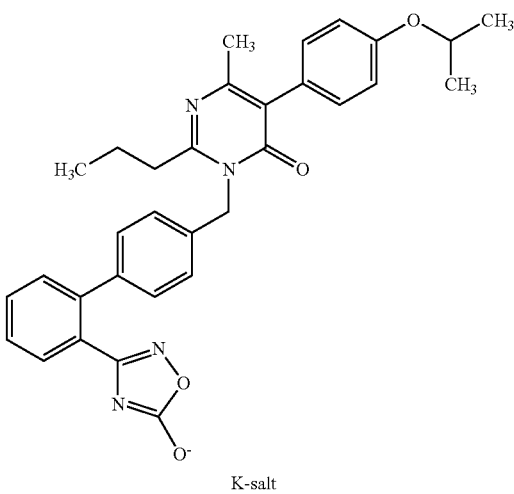

5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one potassium salt To a solution of 5-(4-isopropoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one (0.10 g) in ethanol (2 mL) was added 8 M potassium hydroxide solution (0.023 mL), and the solvent was evaporated under reduced pressure. The residue was triturated with diisopropyl ether to give the title compound as a colorless solid (0.05 g, 46%).

$^1$H NMR (300 MHz, DMSO-d$_6$) δ 0.91 (3H, t, J=7.5), 1.29 (6H, d, J=6.0), 1.57-1.73 (2H, m), 2.12 (3H, s), 2.68 (2H, t, J=7.5), 4.56-4.70 (1H, m), 5.30 (2H, s), 6.93 (2H, d, J=8.7), 7.12 (2H, d, J=8.1), 7.21 (2H, d, J=8.7), 7.25-7.46 (5H, m), 7.50 (1H, d, J=7.5)

Example 450

3-{[3-fluoro-2'-(5-oxo-4,5-dihydro-1,2,4-oxadiazol-3-yl)biphenyl-4-yl]methyl}-5-(4-isopropoxyphenyl)-6-methyl-2-propylpyrimidin-4(3H)-one

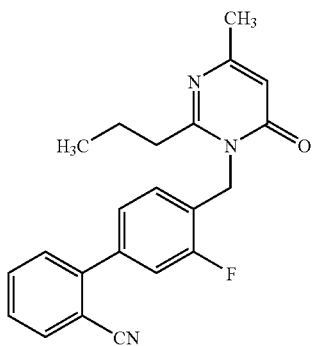

450a) 3'-fluoro-4'-[(4-methyl-6-oxo-2-propylpyrimidin-1(6H)-yl)methyl]biphenyl-2-carbonitrile To a solution of 6-methyl-2-propylpyrimidin-4(3H)-one (2.0 g) and 4'-(bromomethyl)-3'-fluorobiphenyl-2-carbonitrile (4.4 g) in acetonitrile (50 mL) was added potassium carbonate (3.6 g), and the mixture was stirred at 50° C. for 12 hr. The insoluble material was filtered off, the filtrate was concentrated, and the residue was purified by silica gel column chromatography to give the title compound (1.4 g, 29%) as a colorless viscous substance.

$^1$H NMR (300 MHz, CDCl$_3$) δ 1.00 (3H, t, J=7.5), 1.68-1.83 (2H, m), 2.29 (3H, s), 2.66 (2H, t, J=7.5), 5.39 (2H, s), 6.29 (1H, s), 7.08-7.17 (1H, m), 7.24-7.36 (2H, m), 7.43-7.52 (2H, m), 7.61-7.70 (1H, m), 7.77 (1H, d, J=7.8)

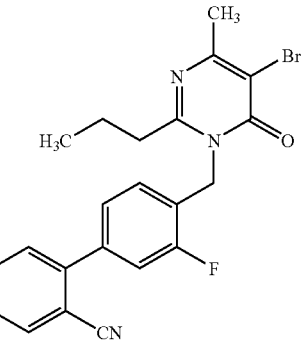

450b) 4'-[(5-bromo-4-methyl-6-oxo-2-propylpyrimidin-1(6H)-yl)methyl]-3'-fluorobiphenyl-2-carbonitrile To a solution of 3'-fluoro-4'-[(4-methyl-6-oxo-2-propylpyrimidin-1(6H)-yl)methyl]biphenyl-2-carbonitrile (1.4 g) and sodium acetate (0.32 g) in acetic acid (20 mL) was added bromine (0.2 mL), and the mixture was stirred at 70° C. for 2 hr. The reaction mixture was diluted with toluene and concentrated under reduced pressure. The residue was dissolved in ethyl acetate, 1 M aqueous sodium thiosulfate solution, washed with saturated aqueous sodium hydrogen carbonate solution and saturated brine, and dried over anhydrous sodium sulfate. The solvent was evaporated under reduced pressure. The residue was purified by silica gel column chromatography to give the title compound (0.65 g, 38%) as a colorless solid.

$^1$H NMR (300 MHz, DMSO-d$_6$) δ 0.91 (3H, t, J=7.2), 1.60-1.74 (2H, m), 2.42 (3H, s), 2.72 (2H, t, J=7.2), 5.39 (2H, s), 7.12 (1H, t, J=8.1), 7.38 (1H, d, J=7.8), 7.50-7.61 (3H, m), 7.75-7.85 (1H, m), 7.97 (1H, d, J=7.8)

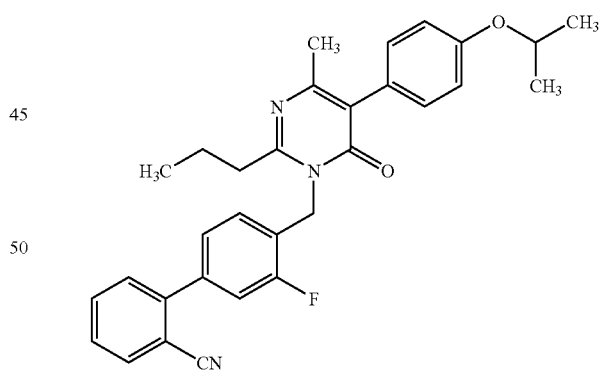

450c) 3'-fluoro-4'-{[5-(4-isopropoxyphenyl)-4-methyl-6-oxo-2-propylpyrimidin-1(6H)-yl]methyl}biphenyl-2-carbonitrile To a solution of 4'-[(5-bromo-4-methyl-6-oxo-2-propylpyrimidin-1(6H)-yl)methyl]-3'-fluorobiphenyl-2-carbonitrile (0.65 g) and 4-isopropoxyphenylboronic acid (0.40 g) in 1,4-dioxane (16 mL) were added 2 M aqueous cesium carbonate solution (4 mL) and [1,1'-bis(diphenylphosphino)ferrocene]dichloropalladium (0.06 g), and the mixture was stirred at 90°

C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine in this order, and dried over anhydrous sodium sulfate. The solvent was evaporated under reduced pressure and the residue was purified by silica gel column chromatography to give the title compound (0.49 g, 67%) as a colorless amorphous solid.

$^1$H NMR (300 MHz, CDCl$_3$) δ 1.04 (3H, t, J=7.2), 1.35 (6H, d, J=6.0), 1.72-1.87 (2H, m), 2.25 (3H, s), 2.71 (2H, t, J=7.2), 4.50-4.64 (1H, m), 5.41 (2H, s), 6.93 (2H, d, J=8.7), 7.21-7.34 (5H, m), 7.43-7.52 (2H, m), 7.61-7.70 (1H, m), 7.77 (1H, d, J=6.9)

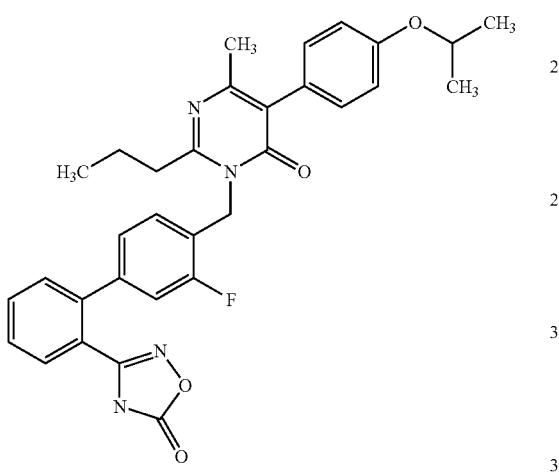

450d) 3-{[3-fluoro-2'-(5-oxo-4,5-dihydro-1,2,4-oxadiazol-3-yl)biphenyl-4-yl]methyl}-5-(4-isopropoxyphenyl)-6-methyl-2-propylpyrimidin-4(3H)-one A mixture of hydroxylammonium chloride (1.2 g), sodium hydrogen carbonate (1.7 g) and dimethyl sulfoxide (10 mL) was stirred at 40° C. for 30 min, 3'-fluoro-4'-{[5-(4-isopropoxyphenyl)-4-methyl-6-oxo-2-propylpyrimidin-1(6H)-yl]methyl}biphenyl-2-carbonitrile (0.49 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.24 g) and then 1,8-diazabicyclo[5.4.0]undec-7-ene (0.22 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.39 g, 72%).

$^1$H NMR (300 MHz, DMSO-d$_6$) δ 0.91 (3H, t, J=7.2), 1.28 (6H, d, J=6.0), 1.58-1.74 (2H, m), 2.14 (3H, s), 2.68 (2H, t, J=7.2), 4.57-4.69 (1H, m), 5.34 (2H, s), 6.92 (2H, d, J=8.4), 7.00-7.14 (2H, m), 7.16-7.29 (3H, m), 7.50-7.64 (2H, m), 7.65-7.75 (2H, m), 12.48 (1H, s)

Example 451

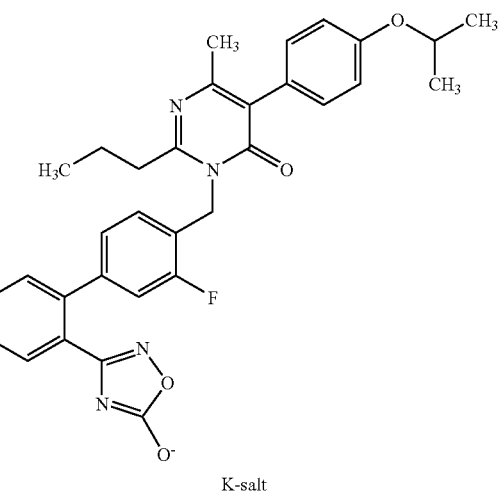

K-salt

3-{[3-fluoro-2'-(5-oxo-4,5-dihydro-1,2,4-oxadiazol-3-yl)biphenyl-4-yl]methyl}-5-(4-isopropoxyphenyl)-6-methyl-2-propylpyrimidin-4(3H)-one potassium salt To a solution of 3-{[3-fluoro-2'-(5-oxo-4,5-dihydro-1,2,4-oxadiazol-3-yl)biphenyl-4-yl]methyl}-5-(4-isopropoxyphenyl)-6-methyl-2-propylpyrimidin-4(3H)-one (0.36 g) in ethanol (10 mL) was added 8 M potassium hydroxide solution (0.081 mL), and the solvent was evaporated under reduced pressure. The residue was triturated with diisopropyl ether to give the title compound as a colorless solid (0.33 g, 87%).

$^1$H NMR (300 MHz, DMSO-d$_6$) δ 0.93 (3H, t, J=7.2), 1.28 (6H, d, J=6.0), 1.60-1.78 (2H, m), 2.13 (3H, s), 2.70 (2H, t, J=7.2), 4.57-4.69 (1H, m), 5.31 (2H, s), 6.88-6.95 (3H, m), 7.07-7.23 (4H, m), 7.30-7.47 (3H, m), 7.50-7.56 (1H, m)

Example 452

2-butyl-5-[hydroxy(phenyl)methyl]-6-methyl-3-{[2'-(5-oxo-4,5-dihydro-1,2,4-oxadiazol-3-yl)biphenyl-4-yl]methyl}pyrimidin-4(3H)-one

452a) 4'-[(2-butyl-4-methyl-6-oxo-5-vinylpyrimidin-1(6H)-yl)methyl]biphenyl-2-carbonitrile To a solution of 4'-[(5-bromo-2-butyl-4-methyl-6-oxopyrimidin-1(6H)-yl)methyl]biphenyl-2-carbonitrile (1.9 g), tributyl(vinyl)tin (2.1 g) and lithium chloride (0.55 g) in N,N-dimethylformamide (30 mL) was added dichlorobis(triphenylphosphine)palladium (0.15 g), and the mixture was stirred at 90° C. for 12 hr under an argon atmosphere. The reaction mixture was diluted with ethyl acetate, 15% aqueous potassium fluoride solution was added, and the mixture was stirred for 2 hr. The insoluble material was filtered off through celite, and the organic layer of the filtrate was separated, washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a colorless solid (1.1 g, 63%).

$^1$H NMR (300 MHz, CDCl$_3$) δ 0.91 (3H, t, J=7.2), 1.31-1.46 (2H, m), 1.61-1.75 (2H, m), 2.43 (3H, s), 2.64 (2H, t, J=7.2), 5.38 (2H, s), 5.53 (1H, dd, J=2.4, 12.0), 6.29 (1H, dd, J=2.4, 17.4), 6.68 (1H, dd, J=12.0, 17.4), 7.26-7.31 (2H, m), 7.40-7.56 (4H, m), 7.60-7.68 (1H, m), 7.76 (1H, d, J=8.4)

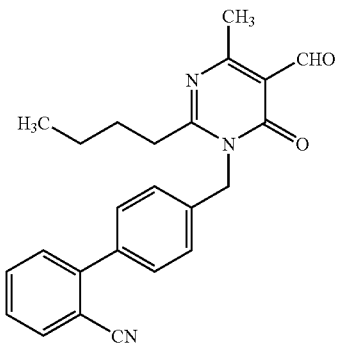

452b) 4'-[(2-butyl-5-formyl-4-methyl-6-oxopyrimidin-1(6H)-yl)methyl]biphenyl-2-carbonitrile To a solution of 4'-[(2-butyl-4-methyl-6-oxo-5-vinylpyrimidin-1(6H)-yl)methyl]biphenyl-2-carbonitrile (0.91 g) and sodium periodate (2.56 g) in acetone (10 mL)-acetonitrile (10 mL)-water (10 mL) was added osmium tetroxide (0.9 g, 7% polymer-bound catalyst), and the mixture was stirred for 4 hr. The insoluble material was filtered off through celite, and the filtrate was diluted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a pale-yellow oil (0.66 g, 71%).

$^1$H NMR (300 MHz, CDCl$_3$) δ 0.91 (3H, t, J=7.2), 1.29-1.46 (2H, m), 1.58-1.79 (2H, m), 2.67 (3H, s), 2.75 (2H, t, J=7.2), 5.39 (2H, s), 7.29-7.36 (2H, m), 7.42-7.52 (2H, m), 7.56 (2H, d, J=8.4), 7.61-7.69 (1H, m), 7.77 (1H, d, J=7.8), 10.50 (1H, s)

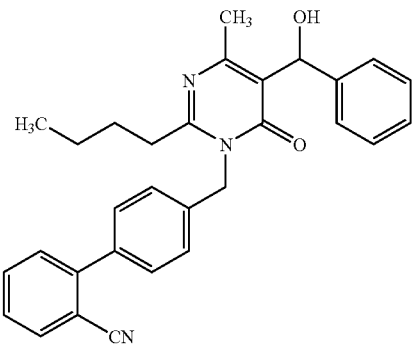

452c) 4'-{[2-butyl-5-[hydroxy(phenyl)methyl]-4-methyl-6-oxopyrimidin-1(6H)-yl]methyl}biphenyl-2-carbonitrile To a solution of 4'-[(2-butyl-5-formyl-4-methyl-6-oxopyrimidin-1(6H)-yl)methyl]biphenyl-2-carbonitrile (0.66 g) in tetrahydrofuran (10 mL) was added phenylmagnesium bromide (1.0 mL, 1 M tetrahydrofuran solution) at −78° C., and the mixture was allowed to warm to 0° C. over 3 hr. A saturated aqueous ammonium chloride solution was added to the reaction mixture, and the mixture was diluted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a pale-yellow oil (0.36 g, 46%).

$^1$H NMR (300 MHz, CDCl$_3$) δ 0.90 (3H, t, J=7.2), 1.30-1.46 (2H, m), 1.62-1.77 (2H, m), 2.42 (3H, s), 2.68 (2H, t, J=7.2), 5.20-5.45 (2H, m), 5.09 (1H, d, J=10.8), 5.82 (1H, d, J=10.8), 7.18-7.29 (3H, m), 7.30-7.39 (2H, m), 7.40-7.55 (6H, m), 7.60-7.69 (1H, m), 7.76 (1H, d, J=7.2)

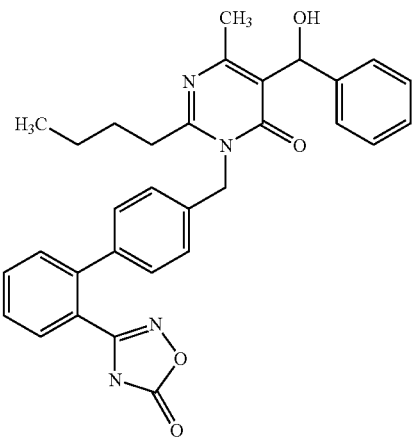

452d) 2-butyl-5-[hydroxy(phenyl)methyl]-6-methyl-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.92 g), sodium hydrogen carbonate (1.3 g) and dimethyl sulfoxide (5 mL) was stirred at 40° C. for 30 min, 4'-{[2-butyl-5-[hydroxy (phenyl)methyl]-4-methyl-6-oxopyrimidin-1(6H)-yl]methyl}biphenyl-2-carbonitrile (0.36 g) was added, and the mixture was stirred at 90° C. for 24 hr. The mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.13 g) and then 1,8-diazabicyclo[5.4.0]undec-7-ene (0.12 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.19 g, 46%).

$^1$H NMR (300 MHz, DMSO-$d_6$) δ 0.80 (3H, t, J=7.2), 1.18-1.33 (2H, m), 1.46-1.60 (2H, m), 2.13 (3H, s), 2.59-2.69 (2H, m), 5.26-5.50 (2H, m), 5.82 (1H, d, J=5.1), 6.23 (1H, d, J=5.1), 7.15-7.40 (9H, m), 7.48-7.61 (2H, m), 7.63-7.74 (2H, m)

Example 453

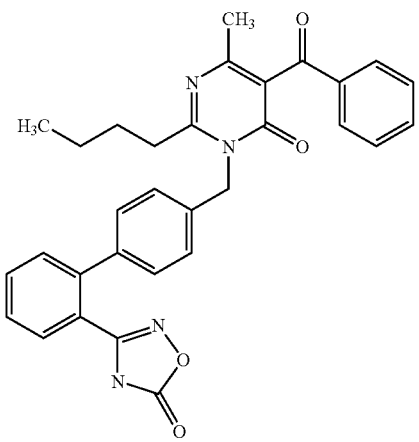

5-benzoyl-2-butyl-6-methyl-3-{[2'-(5-oxo-4,5-dihydro-1,2,4-oxadiazol-3-yl)biphenyl-4-yl]methyl}pyrimidin-4(3H)-one To a solution of 2-butyl-5-[hydroxy(phenyl)methyl]-6-methyl-3-{[2'-(5-oxo-4,5-dihydro-1,2,4-oxadiazol-3-yl)biphenyl-4-yl]methyl}pyrimidin-4(3H)-one (0.1 g) in dichloromethane (4 mL) was added 1,1,1-tris(acetyloxy)-1,1-dihydro-1,2-benziodoxol-3(1H)-one (0.12 g), and the mixture was stirred for 2 hr. Ethyl acetate, water and sodium thiosulfate were added to the reaction mixture, and the mixture was stirred for 30 min and extracted with ethyl acetate. The organic layer was washed with saturated brine, and dried over anhydrous sodium sulfate. The solvent was evaporated and the residue was purified by silica gel column chromatography to give the title compound as a colorless solid (0.07 g, 70%).

$^1$H NMR (300 MHz, DMSO-$d_6$) δ 0.84 (3H, t, J=7.2), 1.25-1.39 (2H, m), 1.54-1.69 (2H, m), 2.11 (3H, s), 2.75 (2H, t, J=7.2), 5.34 (2H, s), 7.25 (2H, d, J=8.1), 7.33 (2H, d, J=8.1), 7.48-7.61 (4H, m), 7.64-7.74 (3H, m), 7.85 (2H, d, J=7.2)

Example 454

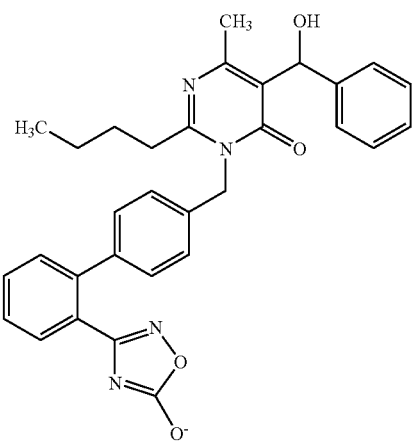

2-butyl-5-[hydroxy(phenyl)methyl]-6-methyl-3-{[2'-(5-oxo-4,5-dihydro-1,2,4-oxadiazol-3-yl)biphenyl-4-yl]methyl}pyrimidin-4(3H)-one potassium salt To a solution of 2-butyl-5-[hydroxy(phenyl)methyl]-6-methyl-3-{[2'-(5-oxo-4,5-dihydro-1,2,4-oxadiazol-3-yl)biphenyl-4-yl]methyl}pyrimidin-4(3H)-one (0.1 g) in ethanol (2 mL) was added 8 M potassium hydroxide solution (0.024 mL), and the solvent was evaporated under reduced pressure. The residue was triturated with diisopropyl ether to give the title compound as a colorless solid (0.046 g, 43%).

$^1$H NMR (300 MHz, DMSO-$d_6$) δ 0.81 (3H, t, J=7.2), 1.21-1.35 (2H, m), 1.47-1.63 (2H, m), 2.12 (3H, s), 2.59-2.74 (2H, m), 5.23 (1H, d, J=15.9), 5.42 (1H, d, J=15.9), 5.84 (1H, s), 6.24 (1H, s), 7.10 (2H, d, J=7.8), 7.16-7.23 (1H, m), 7.26-7.46 (9H, m), 7.50 (1H, d, J=7.5)

Example 455

6-ethyl-5-(morpholin-4-ylmethyl)-3-{[2'-(5-oxo-4,5-dihydro-1,2,4-oxadiazol-3-yl)biphenyl-4-yl]methyl}-2-propylpyrimidin-4(3H)-one

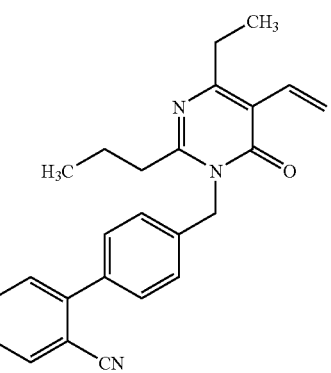

455a) 4'-[(4-ethyl-6-oxo-2-propyl-5-vinylpyrimidin-1(6H)-yl)methyl]biphenyl-2-carbonitrile To a solution of 4'-[(5-bromo-4-ethyl-6-oxo-2-propylpyrimidin-1(6H)-yl)methyl]biphenyl-2-carbonitrile (10 g), tributyl(vinyl)tin (10 g) and lithium chloride (2.9 g) in N,N-dimethylformamide (200 mL) was added dichlorobis(triphenylphosphine)palladium (0.80 g), and the mixture was stirred at 90° C. for 12 hr under an argon atmosphere. The reaction mixture was diluted with ethyl acetate, 15% aqueous potassium fluoride solution was added, and the mixture was stirred for 2 hr. The insoluble material was filtered off through celite, and the organic layer of the filtrate was separated, washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a colorless solid (5.9 g, 68%).

$^1$H NMR (300 MHz, DMSO-$d_6$) δ 0.89 (3H, t, J=7.2), 1.18 (3H, t, J=7.5), 1.60-1.74 (2H, m), 2.65-2.74 (4H, m), 5.38 (2H, s), 5.43 (1H, dd, J=3.8, 12.6), 6.32 (1H, dd, J=3.0, 17.4), 6.69 (1H, dd, J=12.6, 17.4), 7.30 (2H, d, J=8.4), 7.53-7.65 (4H, m), 7.75-7.83 (1H, m), 7.94 (1H, d, J=8.1)

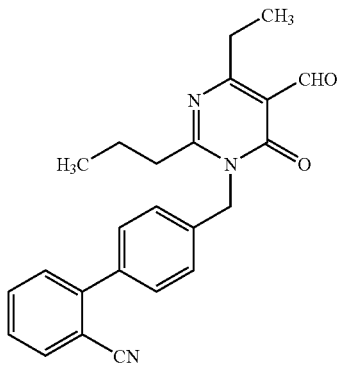

455b) 4'-[(4-ethyl-5-formyl-6-oxo-2-propylpyrimidin-1(6H)-yl)methyl]biphenyl-2-carbonitrile To a solution of 4'-[(4-ethyl-6-oxo-2-propyl-5-vinylpyrimidin-1(6H)-yl)methyl]biphenyl-2-carbonitrile (5.9 g) and sodium periodate (16 g) in acetone (100 mL)-acetonitrile (100 mL)-water (100 mL) was added osmium tetroxide (5 g, 7% polymer-bound catalyst), and the mixture was stirred for 4 hr. The insoluble material was filtered off through celite, and the filtrate was diluted with ethyl acetate, washed with 1 M hydrochloric acid, saturated aqueous sodium hydrogen carbonate solution and saturated brine, and dried over anhydrous sodium sulfate. The solvent was evaporated under reduced pressure. The residue was purified by silica gel column chromatography to give the title compound as a colorless solid (3.8 g, 64%).

$^1$H NMR (300 MHz, CDCl$_3$) δ 1.00 (3H, t, J=7.2), 1.25 (3H, t, J=7.5), 1.71-1.90 (2H, m), 2.74 (2H, t, J=7.2), 3.05 (2H, q, J=7.5), 5.38 (2H, s), 7.30-7.37 (2H, m), 7.42-7.52 (2H, m), 7.53-7.60 (2H, m), 7.61-7.70 (1H, m), 7.77 (1H, d, J=7.2), 10.49 (1H, s)

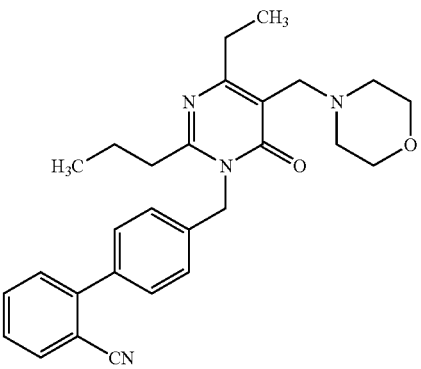

455c) 4'-{[4-ethyl-5-(morpholin-4-ylmethyl)-6-oxo-2-propylpyrimidin-1(6H)-yl]methyl}biphenyl-2-carbonitrile To a solution of 4'-[(4-ethyl-5-formyl-6-oxo-2-propylpyrimidin-1(6H)-yl)methyl]biphenyl-2-carbonitrile (0.5 g) and morpholine (0.17 mL) in acetic acid (10 mL) was added sodium triacetoxyborohydride (0.41 g), and the mixture was stirred for 12 hr. The reaction mixture was diluted with ethyl acetate, washed with saturated aqueous sodium hydrogen carbonate solution and saturated brine, and dried over anhydrous sodium sulfate. The solvent was evaporated under reduced pressure. The residue was purified by silica gel column chromatography to give the title compound as a pale-yellow oil (0.21 g, 35%).

$^1$H NMR (300 MHz, CDCl$_3$) δ 0.88-1.07 (3H, m), 1.16-1.38 (3H, m), 1.70-1.87 (2H, m), 2.44-2.60 (4H, m), 2.60-2.81 (4H, m), 3.50 (2H, s), 3.58-3.81 (4H, m), 5.35 (2H, s), 7.22-7.36 (2H, m), 7.37-7.59 (4H, m), 7.59-7.71 (1H, m), 7.71-7.82 (1H, m)

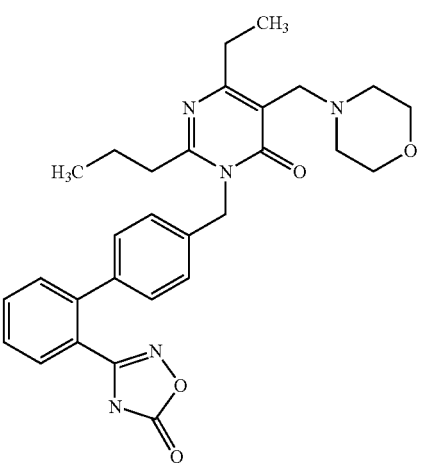

455d) 6-ethyl-5-(morpholin-4-ylmethyl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.54 g), sodium hydrogen carbonate (0.77 g) and dimethyl sulfoxide (5 mL) was stirred at 40° C. for 30 min, 4'-{[4-ethyl-5-(morpholin-4-ylmethyl)-6-oxo-2-propylpyrimidin-1(6H)-yl]methyl}biphenyl-2-carbonitrile (0.21 g) was added, and the mixture was stirred at 90° C. for 24 hr. The reaction mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (5 mL). N,N'-carbonyldiimidazole (0.11 g) and then 1,8-diazabicyclo[5.4.0]undec-7-ene (0.10 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.14 g, 61%).

<sup>1</sup>H NMR (300 MHz, DMSO-d<sub>6</sub>) δ 0.86 (3H, t, J=7.2), 1.19 (3H, t, J=7.2), 1.54-1.70 (2H, m), 2.38 (4H, br), 2.56-2.68 (4H, m), 3.41 (2H, s), 3.53 (4H, br), 5.31 (2H, s), 7.17 (2H, d, J=8.4), 7.29 (2H, d, J=8.4), 7.47-7.60 (2H, m), 7.61-7.73 (2H, m)

Example 456

6-ethyl-5-(4-methoxyphenyl)-3-{[2'-(5-oxo-4,5-dihydro-1,2,4-oxadiazol-3-yl)biphenyl-4-yl]methyl}-2-propylpyrimidin-4(3H)-one

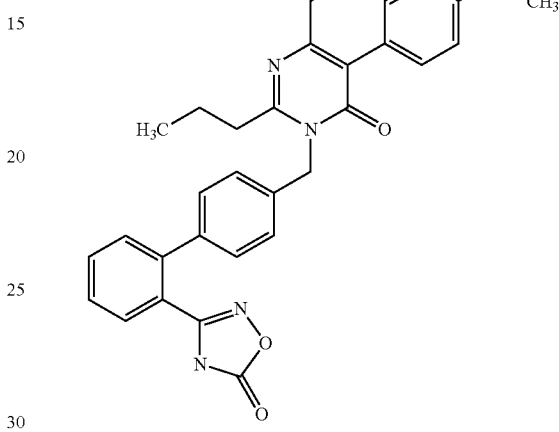

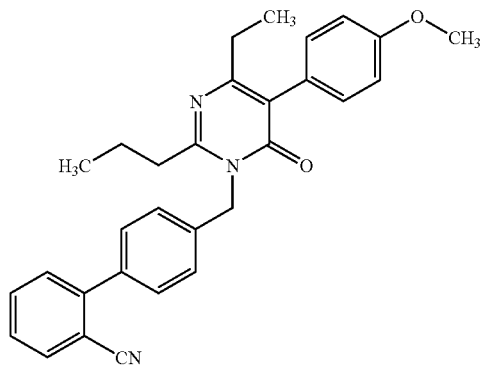

456a) 4'-{[4-ethyl-5-(4-methoxyphenyl)-6-oxo-2-propylpyrimidin-1(6H)-yl]methyl}biphenyl-2-carbonitrile To a solution of 4'-[(5-bromo-4-ethyl-6-oxo-2-propylpyrimidin-1(6H)-yl)methyl]biphenyl-2-carbonitrile (0.5 g), 4-methoxyphenylboronic acid (0.26 g) in 1,4-dioxane (15 mL) were added 2 M aqueous cesium carbonate solution (3 mL) and [1,1'-bis(diphenylphosphino)ferrocene]dichloropalladium (0.05 g), and the mixture was stirred at 90° C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine in this order, and dried over anhydrous sodium sulfate. The solvent was evaporated under reduced pressure and the residue was purified by silica gel column chromatography to give the title compound (0.48 g, 91%) as a colorless solid.

<sup>1</sup>H NMR (300 MHz, CDCl<sub>3</sub>) δ 1.02 (3H, t, J=7.5), 1.18 (3H, t, J=7.2), 1.74-1.89 (2H, m), 2.48 (2H, q, J=7.2), 2.73 (2H, t, J=7.5), 3.83 (3H, s), 5.37 (2H, s), 6.98 (2H, d, J=9.0), 7.22-7.28 (2H, m), 7.33-7.39 (2H, m), 7.40-7.56 (4H, m), 7.60-7.68 (1H, m), 7.76 (1H, d, J=7.5)

456b) 6-ethyl-5-(4-methoxyphenyl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (1.2 g), sodium hydrogen carbonate (1.7 g) and dimethyl sulfoxide (10 mL) was stirred at 40° C. for 30 min, 4'-{[4-ethyl-5-(4-methoxyphenyl)-6-oxo-2-propylpyrimidin-1(6H)-yl]methyl}biphenyl-2-carbonitrile (0.48 g) was added, and the mixture was stirred at 90° C. for 24 hr. The reaction mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.44 g, 81%).

<sup>1</sup>H NMR (300 MHz, DMSO-d<sub>6</sub>) δ 0.89 (3H, t, J=7.2), 1.10 (3H, t, J=7.2), 1.57-1.73 (2H, m), 2.36 (2H, q, J=7.2), 2.68 (2H, t, J=7.2), 3.79 (3H, s), 5.34 (2H, s), 6.97 (2H, d, J=9.0), 7.16-7.35 (6H, m), 7.48-7.61 (2H, m), 7.63-7.74 (2H, m), 12.40 (1H, br)

Example 457

6-ethyl-3-{[2'-(5-oxo-4,5-dihydro-1,2,4-oxadiazol-3-yl)biphenyl-4-yl]methyl}-2-propyl-5-[4-(trifluoromethoxy)phenyl]pyrimidin-4(3H)-one

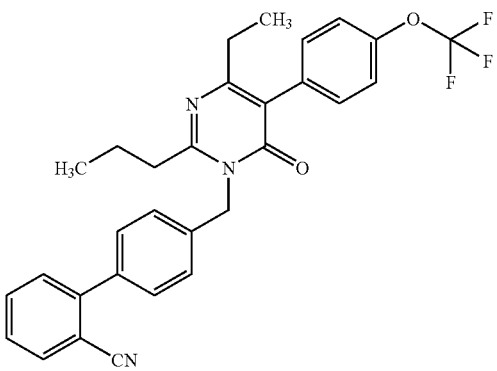

457a) 4'-{[4-ethyl-6-oxo-2-propyl-5-[4-(trifluoromethoxy)phenyl]pyrimidin-1(6H)-yl]methyl}biphenyl-2-carbonitrile To a solution of 4'-[(5-bromo-4-ethyl-6-oxo-2-propylpyrimidin-1(6H)-yl)methyl]biphenyl-2-carbonitrile (0.5 g) and 4-trifluoromethoxyphenylboronic acid (0.35 g) in 1,4-dioxane (15 mL) were added 2 M aqueous cesium carbonate solution (3 mL) and [1,1'-bis(diphenylphosphino)ferrocene] dichloropalladium (0.05 g), and the mixture was stirred at 90° C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine in this order, and dried over anhydrous sodium sulfate. The solvent was evaporated under reduced pressure and the residue was purified by silica gel column chromatography to give the title compound (0.56 g, 95%) as a colorless amorphous solid.

$^1$H NMR (300 MHz, CDCl$_3$) δ 1.03 (3H, t, J=7.5), 1.19 (3H, t, J=7.5), 1.74-1.92 (2H, m), 2.46 (2H, q, J=7.5), 2.75 (2H, t, J=7.5), 5.37 (2H, s), 7.22-7.30 (2H, m), 7.36 (4H, m), 7.42-7.58 (4H, m), 7.59-7.69 (1H, m), 7.76 (1H, d, J=7.8)

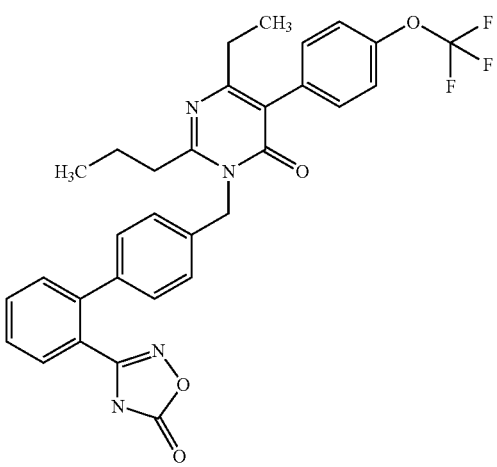

457b) 6-ethyl-3-{[2'-(5-oxo-4,5-dihydro-1,2,4-oxadiazol-3-yl)biphenyl-4-yl]methyl}-2-propyl-5-[4-(trifluoromethoxy)phenyl]pyrimidin-4(3H)-one A mixture of hydroxylammonium chloride (1.3 g), sodium hydrogen carbonate (1.8 g) and dimethyl sulfoxide (10 mL) was stirred at 40° C. for 30 min, 4'-{[4-ethyl-6-oxo-2-propyl-5-[4-(trifluoromethoxy)phenyl]pyrimidin-1(6H)-yl]methyl}biphenyl-2-carbonitrile (0.56 g) was added, and the mixture was stirred at 90° C. for 24 hr. The reaction mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.39 g, 62%).

$^1$H NMR (300 MHz, DMSO-d$_6$) δ 0.90 (3H, t, J=7.2), 1.11 (3H, t, J=7.2), 1.58-1.74 (2H, m), 2.35 (2H, q, J=7.5), 2.70 (2H, t, J=7.2), 5.35 (2H, s), 7.23-7.35 (4H, m), 7.36-7.47 (4H, m), 7.47-7.61 (2H, m), 7.63-7.73 (2H, m), 12.41 (1H, br)

Example 458

6-ethyl-5-(2-fluoro-4-isopropoxyphenyl)-3-{[2'-(5-oxo-4,5-dihydro-1,2,4-oxadiazol-3-yl)biphenyl-4-yl]methyl}-2-propylpyrimidin-4(3H)-one

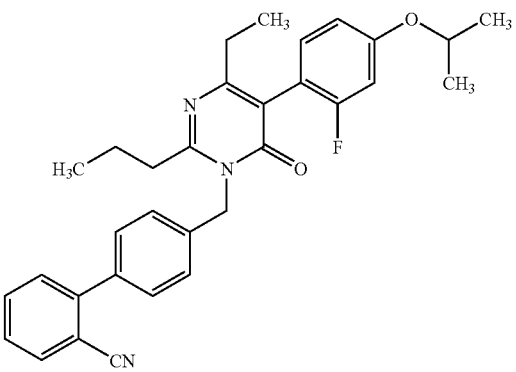

458a) 4'-{[4-ethyl-5-(2-fluoro-4-isopropoxyphenyl)-6-oxo-2-propylpyrimidin-1(6H)-yl]methyl}biphenyl-2-carbonitrile To a solution of 4'-[(5-bromo-4-ethyl-6-oxo-2-propylpyrimidin-1(6H)-yl)methyl]biphenyl-2-carbonitrile (0.5 g) and 2-fluoro-4-isopropoxyphenylboronic acid (0.34 g) in 1,4-dioxane (15 mL) were added 2 M aqueous cesium carbonate solution (3 mL) and [1,1'-bis(diphenylphosphino)ferrocene]dichloropalladium (0.05 g), and the mixture was stirred at 90° C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine in this order, and dried over anhydrous sodium sulfate. The solvent was evaporated under reduced pressure and the residue was purified by silica gel column chromatography to give the title compound (0.35 g, 59%) as a colorless amorphous solid.

$^1$H NMR (300 MHz, CDCl$_3$) δ 1.02 (3H, t, J=7.2), 1.17 (3H, t, J=7.2), 1.35 (6H, d, J=6.3), 1.73-1.59 (2H, m), 2.36-2.51 (2H, m), 2.73 (2H, t, J=7.2), 4.47-4.60 (1H, m), 5.38 (2H, s), 6.62-6.76 (2H, m), 7.12-7.26 (1H, m), 7.31-7.39 (2H, m), 7.40-7.57 (4H, m), 7.60-7.68 (1H, m), 7.76 (1H, d, J=7.8)

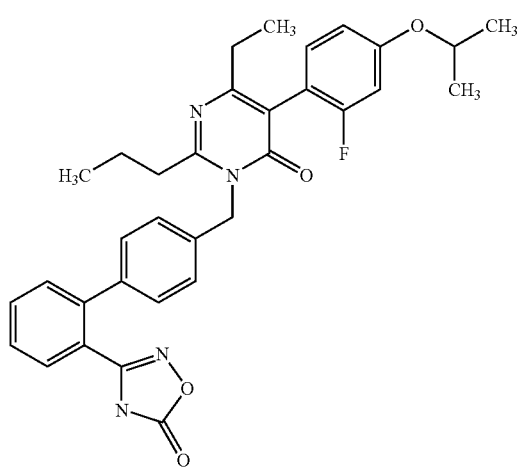

458b) 6-ethyl-5-(2-fluoro-4-isopropoxyphenyl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.80 g), sodium hydrogen carbonate (1.1 g) and dimethyl sulfoxide (10 mL) was stirred at 40° C. for 30 min, 4'-{[4-ethyl-5-(2-fluoro-4-isopropoxyphenyl)-6-oxo-2-propylpyrimidin-1(6H)-yl]methyl}biphenyl-2-carbonitrile (0.35 g) was added, and the mixture was stirred at 90° C. for 24 hr. The reaction mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.17 g) and then 1,8-diazabicyclo[5.4.0]undec-7-ene (0.15 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.25 g, 66%).

$^1$H NMR (300 MHz, DMSO-d$_6$) δ 0.89 (3H, t, J=7.2), 1.09 (3H, t, J=7.2), 1.29 (6H, d, J=6.0), 1.56-1.74 (2H, m), 2.31 (2H, q, J=7.2), 2.64-2.76 (2H, m), 4.59-4.74 (1H, m), 5.24-5.43 (2H, m), 6.77-6.90 (2H, m), 7.15-7.36 (5H, m), 7.47-7.61 (2H, m), 7.63-7.74 (2H, m), 12.39 (1H, br)

Example 459

6-ethyl-3-{[2'-(5-oxo-4,5-dihydro-1,2,4-oxadiazol-3-yl)biphenyl-4-yl]methyl}-5-(4-propoxyphenyl)-2-propylpyrimidin-4(3H)-one

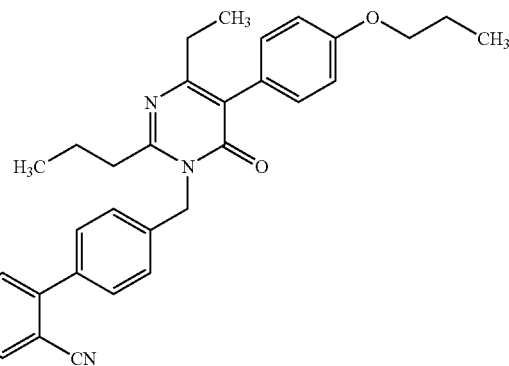

459a) 4'-{[4-ethyl-6-oxo-5-(4-propoxyphenyl)-2-propylpyrimidin-1(6H)-yl]methyl}biphenyl-2-carbonitrile To a solution of 4'-[(5-bromo-4-ethyl-6-oxo-2-propylpyrimidin-1(6H)-yl)methyl]biphenyl-2-carbonitrile (0.5 g) and 4-propoxyphenylboronic acid (0.31 g) in 1,4-dioxane (15 mL) were added 2 M aqueous cesium carbonate solution (3 mL) and [1,1'-bis(diphenylphosphino)ferrocene]dichloropalladium (0.05 g), and the mixture was stirred at 90° C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine in this order, and dried over anhydrous sodium sulfate. The solvent was evaporated under reduced pressure and the residue was purified by silica gel column chromatography to give the title compound (0.52 g, 93%) as a colorless amorphous solid.

$^1$H NMR (300 MHz, CDCl$_3$) δ 0.96-1.08 (6H, m), 1.18 (3H, t, J=7.2), 1.72-1.90 (4H, m), 2.48 (2H, q, J=7.2), 2.73 (2H, t, J=7.2), 3.95 (2H, t, J=6.6), 5.37 (2H, s), 6.95 (2H, d, J=8.7), 7.23 (2H, d, J=8.7), 7.32-7.40 (2H, m), 7.40-7.57 (4H, m), 7.60-7.68 (1H, m), 7.76 (1H, d, J=6.9)

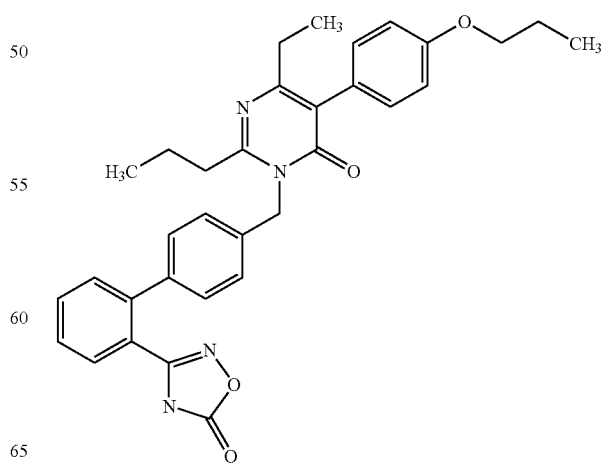

459b) 6-ethyl-3-{[2'-(5-oxo-4,5-dihydro-1,2,4-oxadiazol-3-yl)biphenyl-4-yl]methyl}-5-(4-propoxyphenyl)-2-propylpyrimidin-4(3H)-one A mixture of hydroxylammonium chloride (1.3 g), sodium hydrogen carbonate (1.8 g) and dimethyl sulfoxide (10 mL) was stirred at 40° C. for 30 min, 4'-{[4-ethyl-6-oxo-5-(4-propoxyphenyl)-2-propylpyrimidin-1(6H)-yl]methyl}biphenyl-2-carbonitrile (0.52 g) was added, and the mixture was stirred at 90° C. for 24 hr. The reaction mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.26 g) and then 1,8-diazabicyclo[5.4.0]undec-7-ene (0.24 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.39 g, 66%).

$^1$H NMR (300 MHz, DMSO-$d_6$) δ 0.89 (3H, t, J=7.2), 0.99 (3H, t, J=7.2), 1.10 (3H, t, J=7.2), 1.57-1.82 (4H, m), 2.36 (2H, q, J=7.2), 2.68 (2H, t, J=7.2), 3.96 (2H, t, J=7.2), 5.34 (2H, s), 6.96 (2H, d, J=8.7), 7.13-7.35 (6H, m), 7.49-7.61 (2H, m), 7.63-7.74 (2H, m), 12.40 (1H, br)

Example 460

6-ethyl-5-(3-fluoro-4-isopropoxyphenyl)-3-{[2'-(5-oxo-4,5-dihydro-1,2,4-oxadiazol-3-yl)biphenyl-4-yl]methyl}-2-propylpyrimidin-4(3H)-one

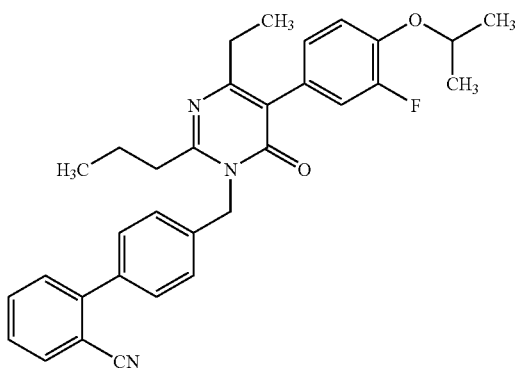

460a) 4'-{[4-ethyl-5-(3-fluoro-4-isopropoxyphenyl)-6-oxo-2-propylpyrimidin-1(6H)-yl]methyl}biphenyl-2-carbonitrile To a solution of 4'-[(5-bromo-4-ethyl-6-oxo-2-propylpyrimidin-1(6H)-yl)methyl]biphenyl-2-carbonitrile (0.5 g) and 3-fluoro-4-isopropoxyphenylboronic acid (0.34 g) in 1,4-dioxane (15 mL) were added 2 M aqueous cesium carbonate solution (3 mL) and [1,1'-bis(diphenylphosphino)ferrocene]dichloropalladium (0.05 g), and the mixture was stirred at 90° C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine in this order, and dried over anhydrous sodium sulfate. The solvent was evaporated under reduced pressure and the residue was purified by silica gel column chromatography to give the title compound (0.53 g, 91%) as a colorless amorphous solid.

$^1$H NMR (300 MHz, CDCl$_3$) δ 1.02 (3H, t, J=7.2), 1.19 (3H, t, J=7.2), 1.38 (6H, d, J=6.0), 1.74-1.89 (2H, m), 2.48 (2H, q, J=7.2), 2.73 (2H, t, J=7.2), 4.49-4.63 (1H, m), 5.36 (2H, s), 6.97-7.10 (3H, m), 7.31-7.39 (2H, m), 7.41-7.57 (4H, m), 7.60-7.68 (1H, m), 7.76 (1H, d, J=7.8)

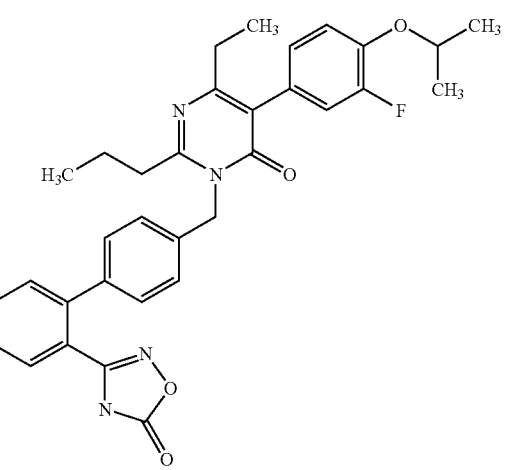

460b) 6-ethyl-5-(3-fluoro-4-isopropoxyphenyl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (1.3 g), sodium hydrogen carbonate (1.8 g) and dimethyl sulfoxide (10 mL) was stirred at 40° C. for 30 min, 4'-{[4-ethyl-5-(3-fluoro-4-isopropoxyphenyl)-6-oxo-2-propylpyrimidin-1(6H)-yl]methyl}biphenyl-2-carbonitrile (0.53 g) was added, and the mixture was stirred at 90° C. for 24 hr. The reaction mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.47 g, 79%).

$^1$H NMR (300 MHz, DMSO-$d_6$) δ 0.89 (3H, t, J=7.2), 1.11 (3H, t, J=7.2), 1.31 (6H, d, J=6.0), 1.57-1.74 (2H, m), 2.37 (2H, q, J=7.2), 2.68 (2H, t, J=7.2), 4.60-4.73 (1H, m), 5.34 (2H, s), 6.97-7.06 (1H, m), 7.11-7.36 (6H, m), 7.49-7.61 (2H, m), 7.63-7.74 (2H, m), 12.40 (1H, br)

Example 461

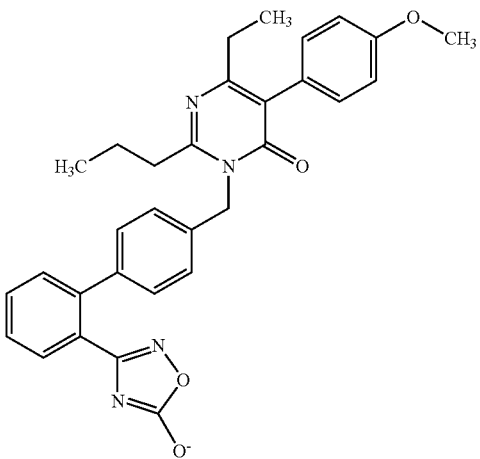

6-ethyl-5-(4-methoxyphenyl)-3-{[2'-(5-oxo-4,5-dihydro-1,2,4-oxadiazol-3-yl)biphenyl-4-yl]methyl}-2-propylpyrimidin-4(3H)-one potassium salt To a solution of 6-ethyl-5-(4-methoxyphenyl)-3-{[2'-(5-oxo-4,5-dihydro-1,2,4-oxadiazol-3-yl)biphenyl-4-yl]methyl}-2-propylpyrimidin-4(3H)-one (0.31 g) in ethanol (10 mL) was added 8 M potassium hydroxide solution (0.073 mL), and the solvent was evaporated under reduced pressure. The residue was triturated with diisopropyl ether to give the title compound as a colorless solid (0.33 g, 99%).

$^1$H NMR (300 MHz, DMSO-d$_6$) δ 0.92 (3H, t, J=7.2), 1.10 (3H, t, J=7.2), 1.61-1.77 (2H, m), 2.35 (2H, q, J=7.2), 2.71 (2H, t, J=7.2), 3.79 (3H, s), 5.30 (2H, s), 6.97 (2H, d, J=8.7), 7.13 (2H, d, J=8.4), 7.20 (2H, d, J=8.7), 7.26-7.47 (5H, m), 7.51 (1H, d, J=7.5)

Example 462

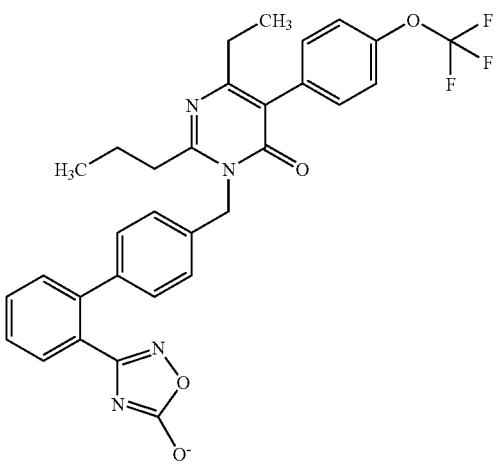

6-ethyl-3-{[2'-(5-oxo-4,5-dihydro-1,2,4-oxadiazol-3-yl)biphenyl-4-yl]methyl}-2-propyl-5-[4-(trifluoromethoxy)phenyl]pyrimidin-4(3H)-one potassium salt To a solution of 6-ethyl-3-{[2'-(5-oxo-4,5-dihydro-1,2,4-oxadiazol-3-yl)biphenyl-4-yl]methyl}-2-propyl-5-[4-(trifluoromethoxy)phenyl]pyrimidin-4(3H)-one (0.30 g) in ethanol (10 mL) was added 8 M potassium hydroxide solution (0.065 mL), and the solvent was evaporated under reduced pressure. The residue was triturated with diisopropyl ether to give the title compound as a colorless solid (0.31 g, 96%).

$^1$H NMR (300 MHz, DMSO-d$_6$) δ 0.93 (3H, t, J=7.2), 1.11 (3H, t, J=7.5), 1.61-1.78 (2H, m), 2.34 (2H, q, J=7.5), 2.74 (2H, t, J=7.2), 5.31 (2H, s), 7.15 (2H, d, J=8.1), 7.25-7.54 (10H, m)

Example 463

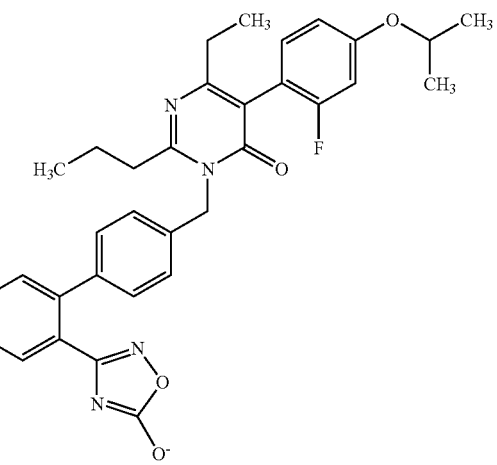

6-ethyl-5-(2-fluoro-4-isopropoxyphenyl)-3-{[2'-(5-oxo-4,5-dihydro-1,2,4-oxadiazol-3-yl)biphenyl-4-yl]methyl}-2-propylpyrimidin-4(3H)-one potassium salt To a solution of 6-ethyl-5-(2-fluoro-4-isopropoxyphenyl)-3-{[2'-(5-oxo-4,5-dihydro-1,2,4-oxadiazol-3-yl)biphenyl-4-yl]methyl}-2-propylpyrimidin-4(3H)-one (0.19 g) in ethanol (10 mL) was added 8 M potassium hydroxide solution (0.047 mL), and the solvent was evaporated under reduced pressure. The residue was triturated with diisopropyl ether to give the title compound as a colorless solid (0.15 g, 68%).

$^1$H NMR (300 MHz, DMSO-d$_6$) δ 0.92 (3H, t, J=7.2), 1.08 (3H, t, J=7.5), 1.29 (6H, d, J=6.0), 1.59-1.78 (2H, m), 2.30 (2H, q, J=7.5), 2.62-2.82 (2H, m), 4.57-4.75 (1H, m), 5.19-5.40 (2H, m), 6.73-6.90 (2H, m), 7.12 (2H, d, J=8.1), 7.16-7.25 (1H, m), 7.25-7.46 (5H, m), 7.50 (1H, d, J=7.5)

Example 464

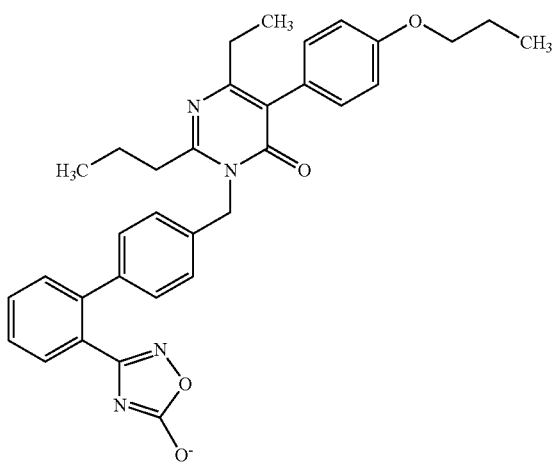

6-ethyl-3-{[2'-(5-oxo-4,5-dihydro-1,2,4-oxadiazol-3-yl)biphenyl-4-yl]methyl}-5-(4-propoxyphenyl)-2-propylpyrimidin-4(3H)-one potassium salt To a solution of 6-ethyl-3-{[2'-(5-oxo-4,5-dihydro-1,2,4-oxadiazol-3-yl)biphenyl-4-yl]methyl}-5-(4-propoxyphenyl)-2-propylpyrimidin-4(3H)-one (0.31 g) in ethanol (2 mL) was added 8 M potassium hydroxide solution (0.069 mL), and the solvent was evaporated under reduced pressure. The residue was triturated with diisopropyl ether to give the title compound as a colorless solid (0.32 g, 97%).

$^1$H NMR (300 MHz, DMSO-$d_6$) δ 0.87-1.04 (6H, m), 1.10 (3H, t, J=7.2), 1.60-1.83 (4H, m), 2.36 (2H, q, J=7.2), 2.71 (2H, t, J=7.5), 3.96 (2H, t, J=6.6), 5.29 (2H, s), 6.95 (2H, d, J=8.7), 7.13 (2H, d, J=8.7), 7.19 (2H, d, J=8.7), 7.25-7.47 (5H, m), 7.50 (1H, d, J=7.5)

Example 465

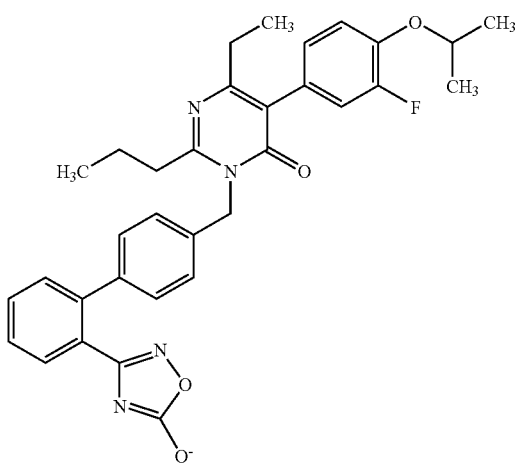

6-ethyl-5-(3-fluoro-4-isopropoxyphenyl)-3-{[2'-(5-oxo-4,5-dihydro-1,2,4-oxadiazol-3-yl)biphenyl-4-yl]methyl}-2-propylpyrimidin-4(3H)-one potassium salt To a solution of 6-ethyl-5-(3-fluoro-4-isopropoxyphenyl)-3-{[2'-(5-oxo-4,5-dihydro-1,2,4-oxadiazol-3-yl)biphenyl-4-yl]methyl}-2-propylpyrimidin-4(3H)-one (0.32 g) in ethanol (10 mL) was added 8 M potassium hydroxide solution (0.078 mL), and the solvent was evaporated under reduced pressure. The residue was triturated with diisopropyl ether to give the title compound as a colorless solid (0.32 g, 85%).

$^1$H NMR (300 MHz, DMSO-$d_6$) δ 0.92 (3H, t, J=7.2), 1.11 (3H, t, J=7.2), 1.31 (6H, d, J=6.0), 1.61-1.76 (2H, m), 2.37 (2H, q, J=7.2), 2.72 (2H, t, J=7.2), 4.59-4.73 (1H, m), 5.30 (2H, s), 6.99-7.06 (1H, m), 7.10-7.23 (4H, m), 7.26-7.46 (5H, m), 7.48-7.54 (1H, m)

Example 466

6-ethyl-5-(morpholin-4-ylcarbonyl)-3-{[2'-(5-oxo-4,5-dihydro-1,2,4-oxadiazol-3-yl)biphenyl-4-yl]methyl}-2-propylpyrimidin-4(3H-one

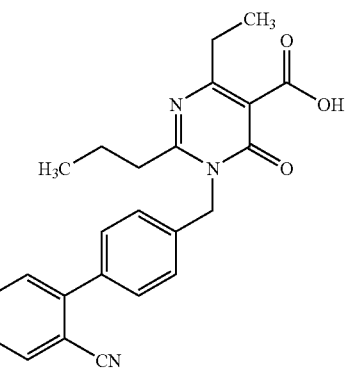

466a) 1-[(2'-cyanobiphenyl-4-yl)methyl]-4-ethyl-6-oxo-2-propyl-1,6-dihydropyrimidine-5-carboxylic acid To a solution of 4'-[(4-ethyl-5-formyl-6-oxo-2-propylpyrimidin-1(6H)-yl)methyl]biphenyl-2-carbonitrile (0.5 g), sodium dihydrogen phosphate (0.93 g) and 2-methyl-2-butene (4 mL) in tert-butyl alcohol (10 mL)—water (8 mL) was added sodium chlorite (0.7 g), and the mixture was stirred at room temperature for 1 hr. The reaction mixture was diluted with ethyl acetate, washed with 1 M hydrochloric acid and then with saturated brine, and dried over anhydrous sodium sulfate. The solvent was evaporated under reduced pressure to give the title compound as a colorless solid (0.53 g, 100%).

$^1$H NMR (300 MHz, DMSO-$d_6$) δ 0.89 (3H, t, J=7.2), 1.17 (3H, t, J=7.2), 1.63-1.73 (2H, m), 2.60-2.82 (4H, m), 5.40 (2H, s), 7.35 (2H, d, J=8.4), 7.53-7.66 (4H, m), 7.74-7.56 (1H, m), 7.95 (1H, d, J=7.8), 13.52 (1H, br)

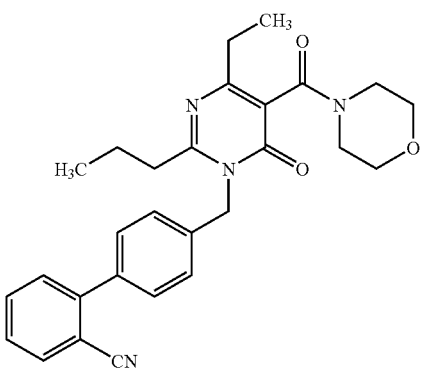

466b) 4'-{[4-ethyl-5-(morpholin-4-ylcarbonyl)-6-oxo-2-propylpyrimidin-1(6H)-yl]methyl}biphenyl-2-carbonitrile To a solution of 1-[(2'-cyanobiphenyl-4-yl)methyl]-4-ethyl-6-oxo-2-propyl-1,6-dihydropyrimidine-5-carboxylic acid (0.21 g), morpholine (0.07 g) and triethylamine (0.22 mL) in N,N-dimethylformamide were added N-(3-dimethylaminopropyl)-N'-ethylcarbodiimide hydrochloride (0.15 g) and 1-hydroxybenzotriazole monohydrate (0.12 g), and the mixture was stirred for 12 hr. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.22 g, 89%).

$^1$H NMR (300 MHz, DMSO-$d_6$) δ 0.99 (3H, t, J=7.5), 1.27 (3H, t, J=7.5), 1.68-1.83 (2H, m), 2.57 (2H, q, J=7.5), 2.65-2.74 (2H, m), 3.25-3.47 (2H, m), 3.54-3.65 (1H, m), 3.68-3.93 (5H, m), 5.33 (2H, s), 7.30 (2H, d, J=8.1), 7.41-7.56 (4H, m), 7.60-7.69 (1H, m), 7.76 (1H, d, J=7.5)

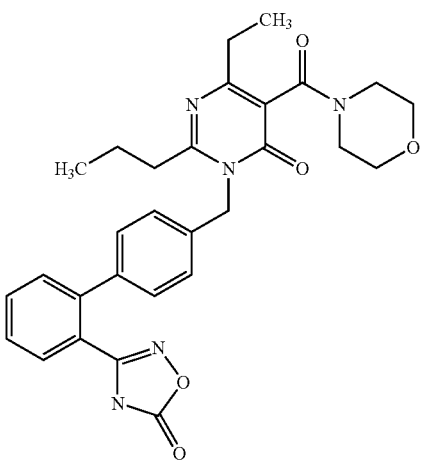

466c) 6-ethyl-5-(morpholin-4-ylcarbonyl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.56 g), sodium hydrogen carbonate (0.79 g) and dimethyl sulfoxide (4 mL) was stirred at 40° C. for 30 min, 4'-{[4-ethyl-5-(morpholin-4-ylcarbonyl)-6-oxo-2-propylpyrimidin-1(6H)-yl]methyl}biphenyl-2-carbonitrile (0.22 g) was added, and the mixture was stirred at 90° C. for 24 hr. The reaction mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.12 g) and then 1,8-diazabicyclo[5.4.0]undec-7-ene (0.11 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.10 g, 39%).

$^1$H NMR (300 MHz, DMSO-$d_6$) δ 0.88 (3H, t, J=7.5), 1.16 (3H, t, J=7.2), 1.55-1.72 (2H, m), 2.42 (2H, q, J=7.5), 2.69 (2H, t, J=7.5), 3.15-3.40 (3H, m), 3.40-3.71 (5H, m), 5.32 (2H, s), 7.22 (2H, d, J=8.1), 7.31 (2H, d, J=8.1), 7.48-7.61 (2H, m), 7.48-7.61 (2H, m), 7.62-7.74 (2H, m), 12.41 (1H, br)

Example 467

6-ethyl-3-{[3-fluoro-2'-(5-oxo-4,5-dihydro-1,2,4-oxadiazol-3-yl)biphenyl-4-yl]methyl}-5-(6-isopropoxypyridin-3-yl)-2-propylpyrimidin-4(3H)-one

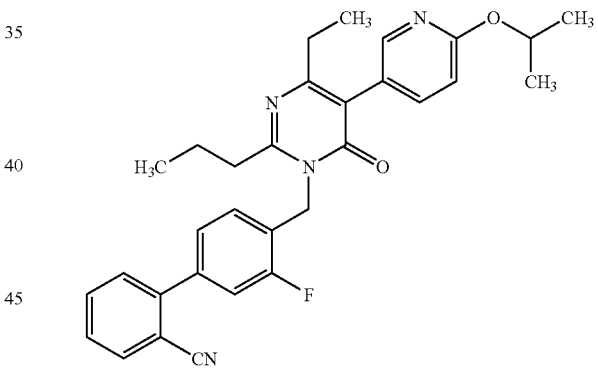

467a) 4'-{[4-ethyl-5-(6-isopropoxypyridin-3-yl)-6-oxo-2-propylpyrimidin-1(6H)-yl]methyl}-3'-fluorobiphenyl-2-carbonitrile To a solution of 4'-[(S-bromo-4-ethyl-6-oxo-2-propylpyrimidin-1(6H)-yl)methyl]-3'-fluorobiphenyl -2carbonitrile (0.49 g) and 6-isopropoxy-3-pyridylboronic acid (0.43 g) in 1,4-dioxane (20 mL) were added 2 M aqueous cesium carbonate solution (4 mL) and [1,1'bis(diphenylphosphino)ferrocene]dichloropalladium (0.04 g), and the mixture was stirred at 90° C. for 12 hr under an argon atmosphere. The reaction mixture was diluted with ethyl acetate, and the insoluble material was filtered off through celite. The filtrate was washed with 1 M hydrochloric acid, saturated aqueous sodium hydrogen carbonate solution and saturated brine in this order, and dried over anhydrous sodium sulfate. The solvent was evaporated under reduced pressure and the residue was purified by silica gel column chromatography to give the title compound (0.39 g, 70%) as a colorless amorphous solid.

¹H NMR (300 MHz, CDCl₃) δ 1.04 (3H, t, J=7.2), 1.21 (3H, t, J=7.5), 1.36 (6H, d, J=6.0), 1.75-1.90 (2H, m), 2.51 (2H, q, J=7.5), 2.68-2.78 (2H, m), 5.26-5.37 (1H, m), 5.40 (2H, s), 6.74 (1H, d, J=9.0), 7.20-7.35 (3H, m), 7.44-7.52 (2H, m), 7.55-7.70 (2H, m), 7.78 (1H, d, J=8.4), 8.07 (1H, d, J=2.1)

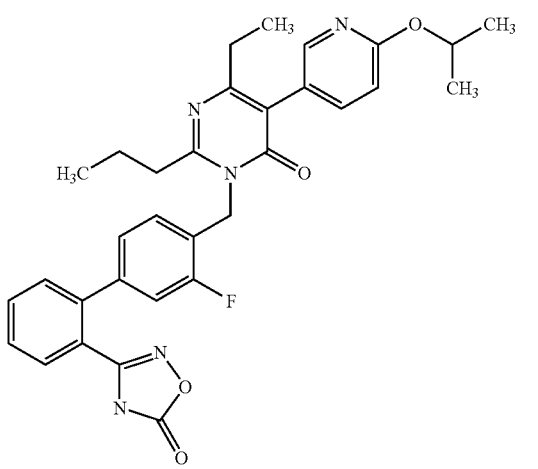

467b) 6-ethyl-3-{[3-fluoro-2'-(5-oxo-4,5-dihydro-1, 2,4-oxadiazol-3-yl)biphenyl-4-yl]methyl}-5-(6-isopropoxypyridin-3-yl)-2-propylpyrimidin-4(3H)-one A mixture of hydroxylammonium chloride (0.89 g), sodium hydrogen carbonate (1.3 g) and dimethyl sulfoxide (10 mL) was stirred at 40° C. for 30 min, 4'-{[4-ethyl-5-(6-isopropoxypyridin-3-yl)-6-oxo-2-propylpyrimidin-1(6H)-yl]methyl}-3'-fluorobiphenyl-2-carbonitrile (0.39 g) was added, and the mixture was stirred at 90° C. for 24 hr. The reaction mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.18 g) and then 1,8-diazabicyclo[5.4.0]undec-7-ene (0.17 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.23 g, 54%).

¹H NMR (300 MHz, DMSO-d₆) δ 0.92 (3H, t, J=7.5), 1.13 (3H, t, J=7.5), 1.30 (6H, d, J=6.3), 1.61-1.78 (2H, m), 2.39 (2H, q, J=7.5), 2.71 (2H, t, J=7.5), 5.20-5.32 (1H, m), 5.35 (2H, s), 6.78 (1H, d, J=8.4), 7.01-7.14 (2H, m), 7.22-7.28 (1H, m), 7.49-7.76 (5H, m), 8.03 (1H, s), 12.49 (1H, br)

Example 468

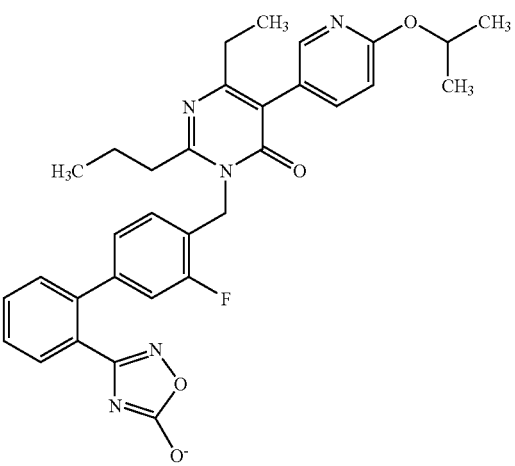

6-ethyl-3-{[3-fluoro-2'-(5-oxo-4,5-dihydro-1,2,4-oxadiazol-3-yl)biphenyl-4-yl]methyl}-5-(6-isopropoxypyridin-3-yl)-2-propylpyrimidin-4(4H)-one potassium salt To a solution of 6-ethyl-3-{[3-fluoro-2'-(5-oxo-4,5-dihydro-1,2,4-oxadiazol-3-yl)biphenyl-4-yl]methyl}-5-(6-isopropoxypyridin-3-yl)-2-propylpyrimidin-4(4H)-one (0.16 g) in ethanol (5 mL) was added 8 M potassium hydroxide solution (0.036 mL), and the solvent was evaporated under reduced pressure. The residue was triturated with diisopropyl ether to give the title compound as a colorless solid (0.14 g, 82%).

¹H NMR (300 MHz, DMSO-d₆) δ 0.94 (3H, t, J=7.2), 1.13 (3H, t, J=7.2), 1.31 (6H, d, J=6.3), 1.64-1.80 (2H, m), 2.39 (2H, q, J=7.2), 2.73 (2H, t, J=7.2), 5.21-5.35 (3H, m), 6.78 (1H, d, J=8.7), 6.91-7.00 (1H, m), 7.07-7.20 (2H, m), 7.29-7.48 (3H, m), 7.51-7.57 (1H, m), 7.58-7.64 (1H, m), 8.04 (1H, s)

Example 469

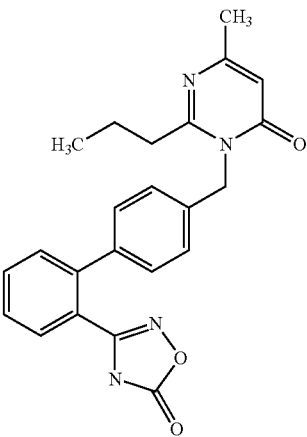

6-methyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (1.7 g), sodium hydrogen carbonate (2.5 g) and dimethyl sulfoxide (10 mL) was stirred at 40° C. for 30 min, 4'-[(4-methyl-6-oxo-2-propylpyrimidin-1(6H)-yl)methyl]biphenyl-2-carbonitrile (0.5 g) was added, and the mixture was stirred at 90° C. for 24 hr. The reaction mixture was allowed to cool to room temperature, water was added to the reaction mixture, and the precipitated solid was collected by filtration. The obtained solid was dissolved in ethyl acetate. The solution was washed with saturated brine and dried over anhydrous sodium sulfate. The solvent was evaporated and the residue was dissolved in tetrahydrofuran (10 mL). N,N'-carbonyldiimidazole (0.35 g) and then 1,8-diazabicyclo[5.4.0]undec-7-ene (0.33 mL) were added, and the mixture was stirred at room temperature for 30 min. The reaction mixture was diluted with ethyl acetate, washed with 1 M hydrochloric acid and then with saturated brine, and dried over anhydrous sodium sulfate. The solvent was evaporated under reduced pressure. The residue was purified by silica gel column chromatography to give the title compound as a colorless solid (0.26 g, 44%).

$^1$H NMR (300 MHz, DMSO-$d_6$) δ 0.85 (3H, t, J=7.5), 1.50-1.67 (2H, m), 2.20 (3H, s), 2.62 (2H, t, J=7.5), 5.31 (2H, s), 6.26 (1H, s), 7.19 (2H, d, J=8.4), 7.30 (2H, d, J=8.4), 7.48-7.61 (2H, m), 7.63-7.73 (2H, m), 12.40 (1H, br)

Example 470

3-{[2-fluoro-2'-(5-oxo-4,5-dihydro-1,2,4-oxadiazol-3-yl)biphenyl-4-yl]methyl}-5-(4-isopropoxyphenyl)-6-methyl-2-propylpyrimidin-4(3H)-one

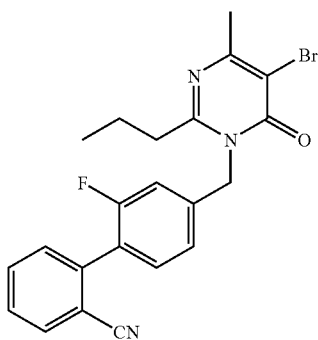

470a) 4'-[(5-bromo-4-methyl-6-oxo-2-propylpyrimidin-1(6H)-yl)methyl]-2'-fluorobiphenyl-2-carbonitrile To a mixture of 2'-fluoro-4'-[(4-methyl-6-oxo-2-propylpyrimidin-1(6H)-yl)methyl]biphenyl-2-carbonitrile (0.78 g), sodium acetate (0.19 g) and acetic acid (10 mL) was added bromine (0.12 mL), and the mixture was stirred at room temperature for 3 hr. The solvent was evaporated from the reaction mixture under reduced pressure, and the residue was diluted with ethyl acetate. The diluted solution was washed with water, saturated aqueous sodium hydrogen carbonate solution and saturated brine, and dried over anhydrous magnesium sulfate, and the solvent was evaporated under reduced pressure. The residue was purified by silica gel column chromatography to give the title compound as a colorless amorphous solid (0.54 g, 57%).

$^1$H NMR (300 MHz, CDCl$_3$) δ 1.00 (t, J=7.4, 3 H), 1.68-1.85 (m, 2 H), 2.50 (s, 3 H), 2.61-2.71 (m, 2 H), 5.36 (s, 2 H), 7.01-7.13 (m, 2 H), 7.35-7.53 (m, 3 H), 7.62-7.70 (m, 1H), 7.77 (d, J=8.3, 1 H)

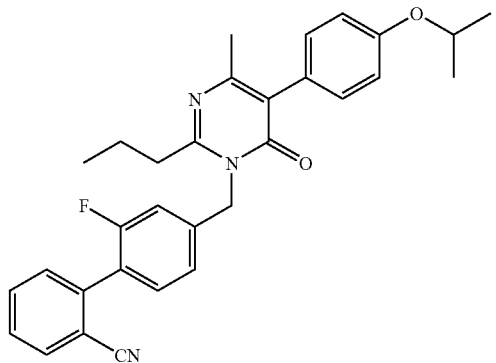

470b) 2'-fluoro-4'-{[5-(4-isopropoxyphenyl)-4-methyl-6-oxo-2-propylpyrimidin-1(6H)-yl]methyl}biphenyl-2-carbonitrile A mixture of 4'-[(5-bromo-4-methyl-6-oxo-2-propylpyrimidin-1(6H)-yl)methyl]-2'-fluorobiphenyl-2-carbonitrile (0.54 g), (4-isopropoxyphenyl)boronic acid (0.33 g), [1,1'-bis(diphenylphosphino)ferrocene]dichloropalladium(II) dichloromethane adduct (0.05 g), 2 M aqueous cesium carbonate solution (5 mL) and 1,4-dioxane (5 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.6 g, 99%).

$^1$H NMR (300 MHz, CDCl$_3$) δ 1.03 (t, J=7.4, 3 H), 1.35 (d, J=6.1, 6 H), 1.72-1.87 (m, 2 H), 2.25 (s, 2 H), 2.50 (s, 1 H), 2.68-2.75 (m, 2 H), 4.50-4.64 (m, 1 H), 5.35 (s, 2 H), 6.89-7.02 (m, 2 H), 7.05-7.16 (m, 2 H), 7.24 (d, J=9.8, 2 H), 7.36-7.44 (m, 1 H), 7.44-7.53 (m, 2 H), 7.61-7.69 (m, 1 H), 7.74-7.80 (m, 1 H)

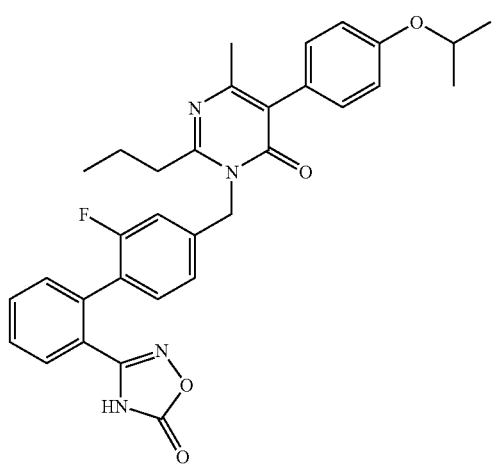

470c) 3-{[2-fluoro-2'-(5-oxo-4,5-dihydro-1,2,4-oxa-diazol-3-yl)biphenyl-4-yl]methyl}-5-(4-isopropoxyphenyl)-6-methyl-2-propylpyrimidin-4(3H)-one A mixture of hydroxylammonium chloride (0.72 g), sodium hydrogen carbonate (1.02 g) and dimethyl sulfoxide (8 mL) was stirred at 40° C. for 30 min, 2'-fluoro-4'-{[5-(4-isopropoxyphenyl)-4-methyl-6-oxo-2-propylpyrimidin-1(6H)-yl]methyl}biphenyl-2-carbonitrile (0.6 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (8 mL). N,N'-carbonyldiimidazole (0.17 g) and then 1,8-diazabicyclo[5.4.0]undec-7-ene (0.2 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as colorless crystals (0.3 g, 45%).

$^1$H NMR (300 MHz, DMSO-$d_6$) δ 0.90 (t, J=7.6, 3 H), 1.29 (d, J=6.1, 6 H), 1.57-1.72 (m, 2 H), 2.13 (s, 3 H), 2.63-2.71 (m, 2 H), 4.57-4.70 (m, 1 H), 5.35 (s, 2 H), 6.90-6.97 (m, 2 H), 7.01-7.16 (m, 2 H), 7.19-7.25 (m, 2 H), 7.29-7.40 (m, 1 H), 7.47-7.56 (m, 1 H), 7.62-7.66 (m, 1 H), 7.68-7.75 (m, 2 H), 12.62 (s, 1 H)

Example 471

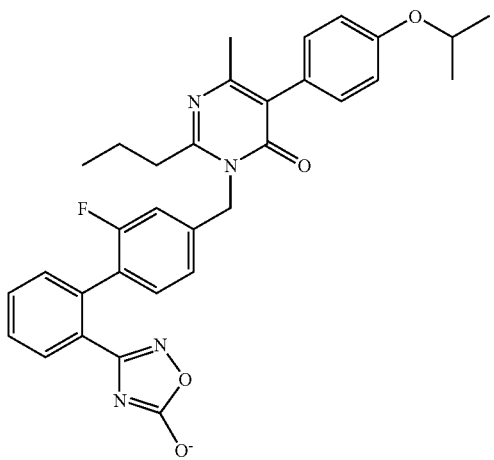

3-{[2-fluoro-2'-(5-oxo-4,5-dihydro-1,2,4-oxadiazol-3-yl)biphenyl-4-yl]methyl}-5-(4-isopropoxyphenyl)-6-methyl-2-propylpyrimidin-4(3H)-one potassium salt To a mixture of 3-{[2-fluoro-2'-(5-oxo-4,5-dihydro-1,2,4-oxadiazol-3-yl)biphenyl-4-yl]methyl}-5-(4-isopropoxyphenyl)-6-methyl-2-propylpyrimidin-4(3H)-one (0.24 g) and ethanol (4 mL) was added dropwise 0.1 M potassium hydroxide-ethanol solution (4.4 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.25 g, 95%).

$^1$H NMR (300 MHz, DMSO-$d_6$) δ 0.93 (t, J=7.8, 3 H), 1.29 (d, J=6.1, 6 H), 1.61-1.75 (m, 2 H), 2.13 (s, 3 H), 2.63-2.76 (m, 2 H), 4.56-4.72 (m, 1 H), 5.33 (s, 2 H), 6.89-7.01 (m, 4 H), 7.16-7.26 (m, 4 H), 7.37-7.45 (m, 2 H), 7.73-7.78 (m, 1 H)

Example 472

5-(1H-indol-5-yl)-6-methyl-3-{[2'-(5-oxo-4,5-dihydro-1,2,4-oxadiazol-3-yl)biphenyl-4-yl]methyl}-2-propylpyrimidin-4(3H)-one potassium salt

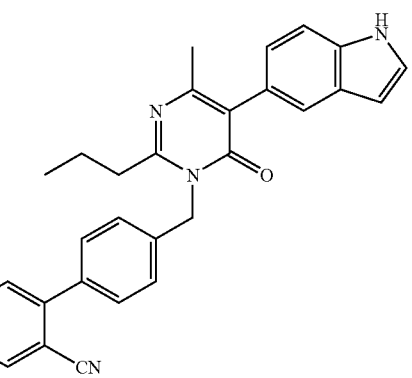

472a) 4'-{[5-(1H-indol-5-yl)-4-methyl-6-oxo-2-propylpyrimidin-1(6H)-yl]methyl}biphenyl-2-carbonitrile A mixture of 4'-[(5-bromo-4-methyl-6-oxo-2-propylpyrimidin-1(6H)-yl)methyl]biphenyl-2-carbonitrile (0.61 g), 1H-indol-5-ylboronic acid (0.33 g), [1,1'-bis(diphenylphosphino)ferrocene]dichloropalladium(II) dichloromethane adduct (0.06 g), 2 M aqueous cesium carbonate solution (5 mL) and 1,4-dioxane (5 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.41 g, 62%).

$^1$H NMR (300 MHz, CDCl$_3$) δ 1.02 (t, J=7.4, 3 H), 1.72-1.87 (m, 2 H), 2.25 (s, 3 H), 2.69-2.78 (m, 2 H), 5.41 (s, 2 H), 6.47-6.55 (m, 1 H), 7.04-7.14 (m, 2 H), 7.24-7.68 (m, 9 H), 7.75 (d, J=7.4, 1 H), 8.51 (s, 1 H)

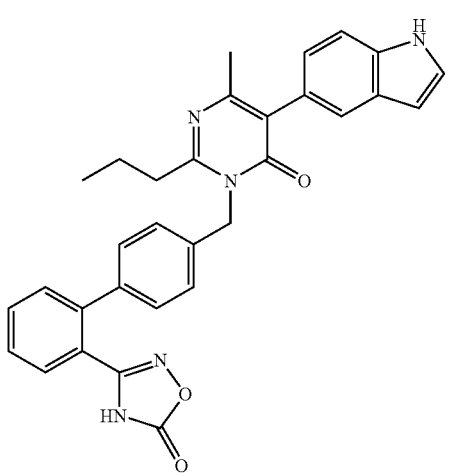

472b) 5-(1H-indol-5-yl)-6-methyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.52 g), sodium hydrogen carbonate (0.75 g) and dimethyl sulfoxide (5 mL) was stirred at 40° C. for 30 min, 4'-{[5-(1H-indol-5-yl)-4-methyl-6-oxo-2-propylpyrimidin-1(6H)-yl]methyl}biphenyl-2-carbonitrile (0.41 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (40 mL). N,N'-carbonyldiimidazole (0.22 g) and then 1,8-diazabicyclo[5.4.0]undec-7-ene (0.2 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as colorless crystals (0.09 g, 20%).

$^1$H NMR (300 MHz, DMSO-$d_6$) δ 0.93 (t, J=7.4, 3 H), 1.61-1.76 (m, 2 H), 2.13 (s, 3 H), 2.66-2.73 (m, 2 H), 5.32 (s, 2 H), 6.43 (s, 1 H), 6.97-7.04 (m, 1 H), 7.14 (d, J=8.3, 2 H), 7.27-7.47 (m, 8 H), 7.49-7.54 (m, 1 H), 8.32 (s, 1 H), 11.19 (s, 1 H)

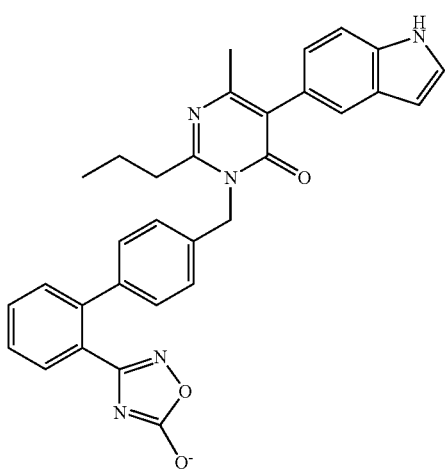

472c) 5-(1H-indol-5-yl)-6-methyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-(1H-indol-5-yl)-6-methyl-3-{[2'-(5-oxo-4,5-dihydro-1,2,4-oxadiazol-3-yl)biphenyl-4-yl]methyl}-2-propylpyrimidin-4(3H)-one (0.09 g) and ethanol (2 mL) was added dropwise 0.1 M potassium hydroxide-ethanol solution (2 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.07 g, 79%).

$^1$H NMR (300 MHz, CDCl$_3$) δ 0.95 (t, J=7.4, 3 H), 1.64-1.80 (m, 2 H), 2.13 (s, 3 H), 2.60-2.68 (m, 2 H), 5.21 (s, 2 H), 6.42 (s, 1 H), 6.93 (d, J=8.3, 1 H), 7.04-7.07 (m, 1 H), 7.09-7.21 (m, 5 H), 7.24-7.35 (m, 3 H), 7.39 (s, 1 H), 7.44-7.51 (m, 1 H), 8.59 (s, 1 H)

Example 473

6-ethyl-5-(1-hydroxy-2-methylpropyl)-3-{[2'-(5-oxo-4,5-dihydro-1,2,4-oxadiazol-3-yl)biphenyl-4-yl]methyl}-2-propylpyrimidin-4(3H)-one potassium salt

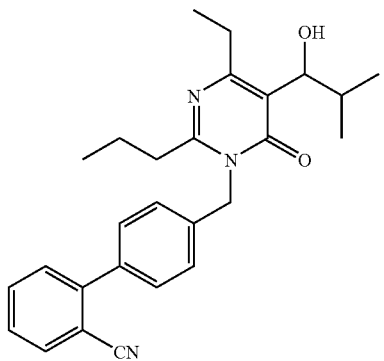

473a) 4'-{[4-ethyl-5-(1-hydroxy-2-methylpropyl)-6-oxo-2-propylpyrimidin-1(6H)-yl]methyl}biphenyl-2-carbonitrile A mixture of 4'-[(4-ethyl-5-formyl-6-oxo-2-propylpyrimidin-1(6H)-yl)methyl]biphenyl-2-carbonitrile (0.6 g) and tetrahydrofuran (10 mL) was cooled to −78° C., isopropyl Grignard reagent tetrahydrofuran solution (1.0 M, 1.9 mL) was added dropwise, and the mixture was stirred for 1 hr. Then, the mixture was gradually warmed to room temperature, and the mixture was stirred for 12 hr. The solvent was evaporated from the reaction mixture under reduced pressure, and the residue was diluted with ethyl acetate. The diluted solution was washed with water and saturated brine, dried over anhydrous magnesium sulfate, and the solvent was evaporated under reduced pressure. The residue was purified by silica gel column chromatography to give the title compound as a colorless amorphous solid (0.38 g, 57%).

¹H NMR (300 MHz, CDCl₃) δ 0.76-1.15 (m, 8 H), 1.27 (t, J=7.3, 3 H), 1.48-1.89 (m, 3 H), 2.15-2.41 (m, 1 H), 2.48-2.79 (m, 3 H), 2.99-3.11 (m, 1 H), 4.27-4.44 (m, 1 H), 4.80-5.10 (m, 1 H), 5.35 (s, 2 H), 7.23-7.38 (m, 2 H), 7.39-7.59 (m, 4 H), 7.60-7.68 (m, 1 H), 7.75 (d, J=7.7, 1 H)

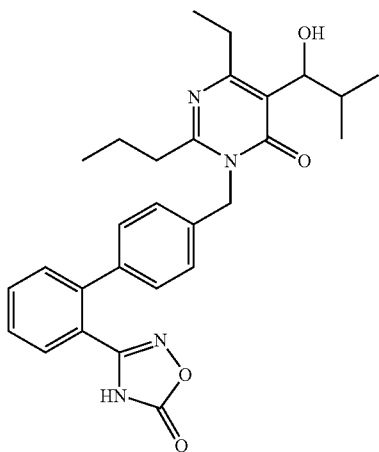

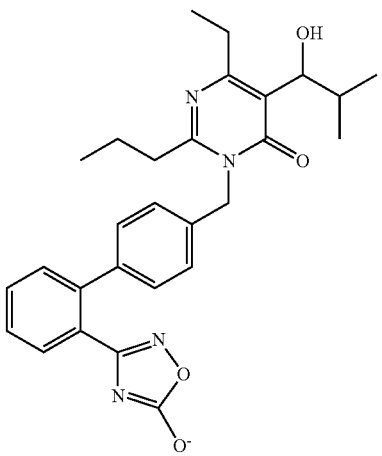

473b) 6-ethyl-5-(1-hydroxy-2-methylpropyl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.53 g), sodium hydrogen carbonate (0.75 g) and dimethyl sulfoxide (5 mL) was stirred at 40° C. for 30 min, 4'-{[4-ethyl-5-(1-hydroxy-2-methylpropyl)-6-oxo-2-propylpyrimidin-1(6H)-yl]methyl}biphenyl-2-carbonitrile (0.38 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.12 g) and then 1,8-diazabicyclo[5.4.0]undec-7-ene (0.1 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as colorless crystals (0.13 g, 29%).

¹H NMR (300 MHz, DMSO-d₆) δ 0.73 (d, J=6.8, 3 H), 0.86 (t, J=7.4, 3 H), 1.01 (d, J=6.8, 3 H), 1.15 (t, J=7.4, 3 H), 1.54-1.68 (m, 2 H), 2.57-2.75 (m, 4 H), 3.55-3.66 (m, 1 H), 4.51 (dd, J=8.8, 6.3, 1 H), 5.02 (d, J=6.3, 1 H), 5.31 (s, 2 H), 7.14-7.22 (m, 2 H), 7.27-7.34 (m, 2 H), 7.50-7.61 (m, 2 H), 7.63-7.73 (m, 2 H), 12.39 (s, 1 H)

473c) 6-ethyl-5-(1-hydroxy-2-methylpropyl)-3-{[2'-(5-oxo-4,5-dihydro-1,2,4-oxadiazol-3-yl)biphenyl-4-yl]methyl}-2-propylpyrimidin-4(3H)-one potassium salt To a mixture of 6-ethyl-5-(1-hydroxy-2-methylpropyl)-3-{[2'-(5-oxo-4,5-dihydro-1,2,4-oxadiazol-3-yl)biphenyl-4-yl]methyl}-2-propylpyrimidin-4(3H)-one (0.13 g) and ethanol (3 mL) was added dropwise 0.1 M potassium hydroxide-ethanol solution (2.6 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.09 g, 68%).

¹H NMR (300 MHz, DMSO-d₆) δ 0.73 (d, J=6.8, 3 H), 0.88 (t, J=7.4, 3 H), 0.99-1.07 (m, 3 H), 1.15 (t, J=7.4, 3 H), 1.58-1.73 (m, 2 H), 2.58-2.74 (m, 5 H), 4.52 (dd, J=8.5, 6.0, 1H), 5.05 (d, J=6.0, 1 H), 5.18-5.36 (m, 2 H), 7.03-7.09 (m, 2 H), 7.25-7.32 (m, 3 H), 7.32-7.45 (m, 2 H), 7.47-7.52 (m, 1 H)

Example 474

6-methyl-3-{[2'-(5-oxo-4,5-dihydro-1,2,4-oxadiazol-3-yl)biphenyl-4-yl]methyl}-5-phenoxy-2-propylpyrimidin-4(3H)-one

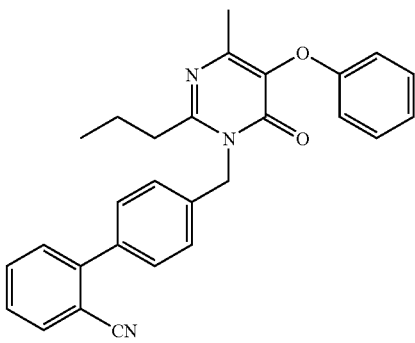

474a) 4'-[(4-methyl-6-oxo-5-phenoxy-2-propylpyrimidin-1(6H)-yl)methyl]biphenyl-2-carbonitrile A mixture of 4'-[(5-bromo-4-methyl-6-oxo-2-propylpyrimidin-1(6H)-yl)methyl]biphenyl-2-carbonitrile (0.5 g), phenol (0.16 g), 8 M potassium hydroxide solution (0.2 mL) and dimethyl sulfoxide (5 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.07 g, 13%).

$^1$H NMR (300 MHz, CDCl$_3$) δ 1.00 (t, J=7.4, 3 H), 1.71-1.84 (m, 2 H), 2.29 (s, 3 H), 2.65-2.74 (m, 2 H), 5.35 (s, 2 H), 6.90-7.05 (m, 3 H), 7.24-7.33 (m, 3 H), 7.40-7.56 (m, 5 H), 7.60-7.67 (m, 1 H), 7.75 (dd, J=7.6, 0.9, 1 H)

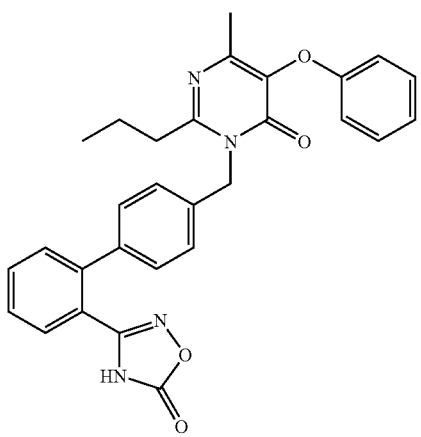

474b) 6-methyl-3-{[2'-(5-oxo-4,5-dihydro-1,2,4-oxadiazol-3-yl)biphenyl-4-yl]methyl}-5-phenoxy-2-propylpyrimidin-4(3H)-one A mixture of hydroxylammonium chloride (0.09 g), sodium hydrogen carbonate (0.13 g) and dimethyl sulfoxide (2 mL) was stirred at 40° C. for 30 min, 4'-[(4-methyl-6-oxo-5-phenoxy-2-propylpyrimidin-1(6H)-yl)methyl]biphenyl-2-carbonitrile (0.07 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (15 mL). N,N'-carbonyldiimidazole (0.04 g) and then 1,8-diazabicyclo[5.4.0]undec-7-ene (0.03 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as colorless crystals (0.01 g, 19%).

$^1$H NMR (300 MHz, CDCl$_3$) δ 1.01 (t, J=7.4, 3 H), 1.72-1.86 (m, 2 H), 2.26 (s, 3 H), 2.66-2.74 (m, 2 H), 5.26 (s, 2 H), 6.84 (d, J=8.0, 2 H), 7.00 (t, J=7.4, 1 H), 7.18-7.31 (m, 6 H), 7.38 (d, J=7.2, 1 H), 7.47 (t, J=7.2, 1 H), 7.60 (t, J=7.0, 1H), 7.73-7.79 (m, 1 H)

Example 475

5-(4-tert-butoxyphenyl)-3-{[3-fluoro-2'-(5-oxo-4,5-dihydro-1,2,4-oxadiazol-3-yl)biphenyl-4-yl]methyl}-6-methyl-2-propylpyrimidin-4(3H)-one

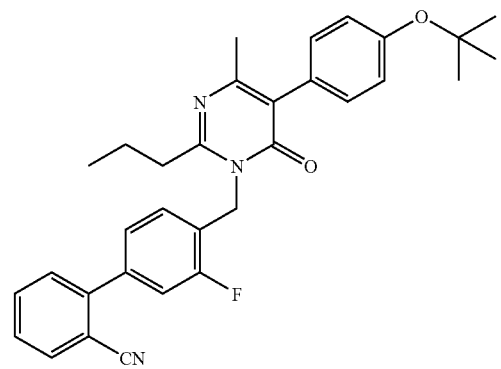

475a) 4'-{[5-(4-tert-butoxyphenyl)-4-methyl-6-oxo-2-propylpyrimidin-1(6H)-yl]methyl}-3'-fluorobiphenyl-2-carbonitrile A mixture of 4'-[(5-bromo-4-methyl-6-oxo-2-propylpyrimidin-1(6H)-yl)methyl]-2'-fluorobiphenyl-2-carbonitrile (0.5 g), (4-tert-butoxyphenyl)boronic acid (0.26 g), [1,1'-bis(diphenylphosphino)ferrocene]dichloropalladium(II) dichloromethane adduct (0.05 g), 2 M aqueous cesium carbonate solution (5 mL) and 1,4-dioxane (5 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.51 g, 89%).

$^1$H NMR (300 MHz, CDCl$_3$) δ 1.04 (t, J=7.4, 3 H), 1.37 (s, 9 H), 1.73-1.88 (m, 2 H), 2.23 (s, 3 H), 2.66-2.77 (m, 2 H), 5.42 (s, 2 H), 7.00-7.07 (m, 2 H), 7.20-7.35 (m, 5 H), 7.43-7.51 (m, 2 H), 7.61-7.69 (m, 1 H), 7.74-7.80 (m, 1H)

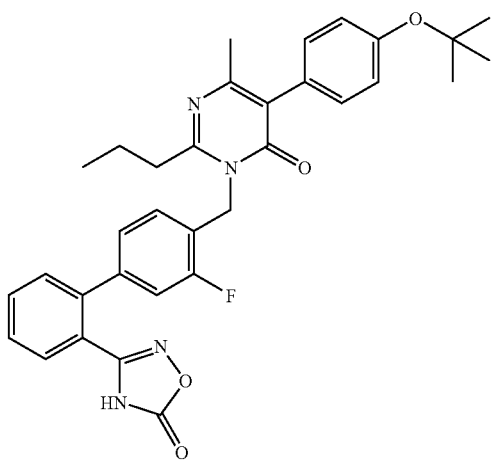

475b) 5-(4-tert-butoxyphenyl)-3-{[3-fluoro-2'-(5-oxo-4,5-dihydro-1,2,4-oxadiazol-3-yl)biphenyl-4-yl]methyl}-6-methyl-2-propylpyrimidin-4(3H)-one A mixture of hydroxylammonium chloride (0.6 g), sodium hydrogen carbonate (0.85 g) and dimethyl sulfoxide (15 mL) was stirred at 40° C. for 30 min, 4'-{[5-(4-tert-butoxyphenyl)-4-methyl-6-oxo-2-propylpyrimidin-1(6H)-yl]methyl}-3'-fluorobiphenyl-2-carbonitrile (0.51 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure and the residue was dissolved in tetrahydrofuran (15 mL). N,N'-carbonyldiimidazole (0.25 g) and then 1,8-diazabicyclo[5.4.0]undec-7-ene (0.23 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as colorless crystals (0.44 g, 77%).

$^1$H NMR (300 MHz, DMSO-$d_6$) δ 0.91 (t, J=7.4, 3 H), 1.33 (s, 9 H), 1.60-1.75 (m, 2 H), 2.14 (s, 3 H), 2.70 (t, J=7.4, 2 H), 5.35 (s, 2 H), 6.96-7.14 (m, 4 H), 7.17-7.29 (m, 3 H), 7.53-7.64 (m, 2 H), 7.67-7.75 (m, 2 H), 12.48 (s, 1 H)

Example 476

5-(4-methoxyphenoxy)-6-methyl-3-{[2'-(5-oxo-4,5-dihydro-1,2,4-oxadiazol-3-yl)biphenyl-4-yl]methyl}-2-propylpyrimidin-4(3H)-one potassium salt

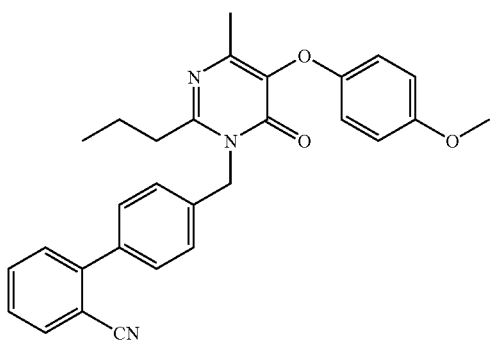

476a) 4'-{[5-(4-methoxyphenoxy)-4-methyl-6-oxo-2-propylpyrimidin-1(6H)-yl]methyl}biphenyl-2-carbonitrile A mixture of 4'-[(5-bromo-4-methyl-6-oxo-2-propylpyrimidin-1(6H)-yl)methyl]biphenyl-2-carbonitrile (0.41 g), 4-methoxyphenol (0.13 g), 8 M potassium hydroxide solution (0.13 mL) and dimethyl sulfoxide (5 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.12 g, 28%).

$^1$H NMR (300 MHz, CDCl$_3$) δ 1.00 (t, J=7.4, 3 H), 1.70-1.83 (m, 2 H), 2.30 (s, 3 H), 2.65-2.73 (m, 2 H), 3.76 (s, 3 H), 5.34 (s, 2 H), 6.80-6.91 (m, 4 H), 7.27-7.33 (m, 2 H), 7.41-7.50 (m, 2 H), 7.50-7.55 (m, 2 H), 7.60-7.68 (m, 1 H), 7.76 (dd, J=7.7, 0.9, 1 H)

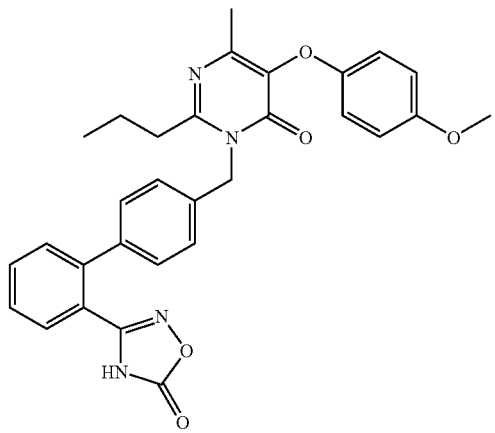

476b) 5-(4-methoxyphenoxy)-6-methyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.16 g), sodium hydrogen carbonate (0.22 g) and dimethyl sulfoxide (3 mL) was stirred at 40° C. for 30 min, 4'-{[5-(4-methoxyphenoxy)-4-methyl-6-oxo-2-propylpyrimidin-1(6H)-yl]methyl}biphenyl-2-carbonitrile (0.12 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL). N,N'-carbonyldiimidazole (0.06 g) and then 1,8-diazabicyclo[5.4.0]undec-7-ene (0.06 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as colorless crystals (0.08 g, 56%).

$^1$H NMR (300 MHz, CDCl$_3$) δ 0.96 (t, J=7.4, 3 H), 1.65-1.81 (m, 2 H), 2.22 (s, 3 H), 2.60-2.69 (m, 2 H), 3.74 (s, 3 H), 5.16 (s, 2 H), 6.63-6.78 (m, 4 H), 7.09-7.15 (m, 2 H), 7.20-7.26 (m, 2 H), 7.34-7.48 (m, 2 H), 7.53-7.66 (m, 2 H)

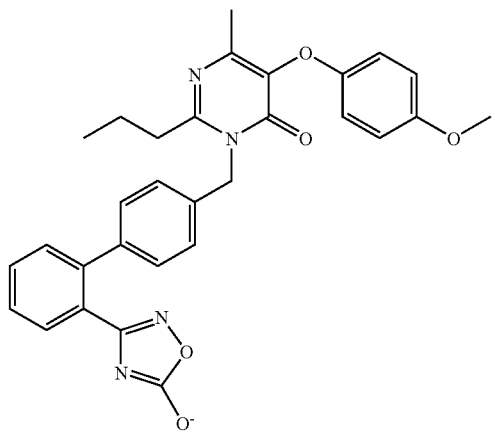

476c) 5-(4-methoxyphenoxy)-6-methyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-(4-methoxyphenoxy)-6-methyl-3-{[2'-(5-oxo-4,5-dihydro-1,2,4-oxadiazol-3-yl)biphenyl-4-yl]methyl}-2-propylpyrimidin-4(3H)-one (0.08 g) and ethanol (2 mL) was added dropwise 0.1 M potassium hydroxide-ethanol solution (1.4 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.08 g, 99%).

$^1$H NMR (300 MHz, DMSO-$d_6$) δ 0.91 (t, J=7.4, 3 H), 1.59-1.75 (m, 2 H), 2.17 (s, 3 H), 2.68 (t, J=7.4, 2 H), 3.70 (s, 3 H), 5.28 (s, 2 H), 6.79-6.91 (m, 4 H), 7.08 (d, J=8.3, 2 H), 7.30 (d, J=8.0, 3 H), 7.33-7.47 (m, 2 H), 7.51 (dd, J=7.2, 1.5, 1 H)

Example 477

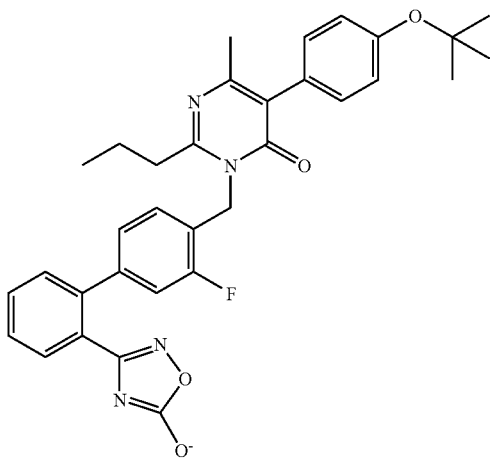

5-(4-tert-butoxyphenyl)-3-{[3-fluoro-2'-(5-oxo-4,5-dihydro-1,2,4-oxadiazol-3-yl)biphenyl-4-yl]methyl}-6-methyl-2-propylpyrimidin-4(3H)-one potassium salt To a mixture of 5-(4-tert-butoxyphenyl)-3-{[3-fluoro-2'-(5-oxo-4,5-dihydro-1,2,4-oxadiazol-3-yl)biphenyl-4-yl]methyl}-6-methyl-2-propylpyrimidin-4(3H)-one (0.39 g) and ethanol (7 mL) was added dropwise 0.1 M potassium hydroxide-ethanol solution (7 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.41 g, 99%).

$^1$H NMR (300 MHz, DMSO-$d_6$) δ 0.94 (t, J=7.2, 3 H), 1.33 (s, 9 H), 1.63-1.79 (m, 2 H), 2.14 (s, 3 H), 2.67-2.76 (m, 2 H), 5.33 (s, 2 H), 6.92-7.04 (m, 3 H), 7.09-7.26 (m, 4 H), 7.33-7.52 (m, 3 H), 7.58 (dd, J=7.4, 1.7, 1 H)

Example 478

5-(3,4-dimethoxyphenoxy)-6-ethyl-3-{[2'-(5-oxo-4,5-dihydro-1,2,4-oxadiazol-3-yl)biphenyl-4-yl]methyl}-2-propylpyrimidin-4(3H)-one

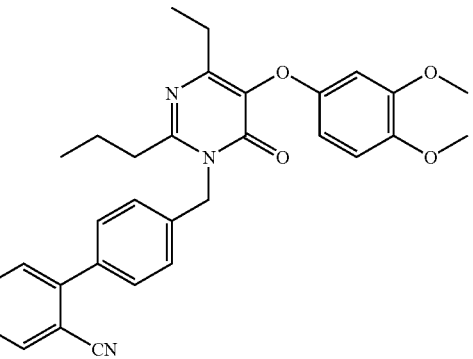

478a) 4'-{[5-(3,4-dimethoxyphenoxy)-4-ethyl-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.8 g), 3,4-dimethoxyphenol (0.42 g), 8 M potassium hydroxide solution (0.34 mL) and dimethyl sulfoxide (10 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.57 g, 61%).

$^1$H NMR (300 MHz, CDCl$_3$) δ 0.99 (t, J=7.4, 3 H), 1.23 (t, J=7.4, 3 H), 1.73-1.87 (m, 2 H), 2.60-2.75 (m, 4 H), 3.80 (s, 3H), 3.84 (s, 3 H), 5.36 (s, 2 H), 6.35 (dd, J=8.7, 2.8, 1 H), 6.70 (d, J=2.8, 1 H), 6.76 (d, J=8.9, 1 H), 7.29-7.36 (m, 2H), 7.36-7.48 (m, 2 H), 7.50-7.55 (m, 2 H), 7.56-7.65 (m, 1 H), 7.69-7.75 (m, 1 H)

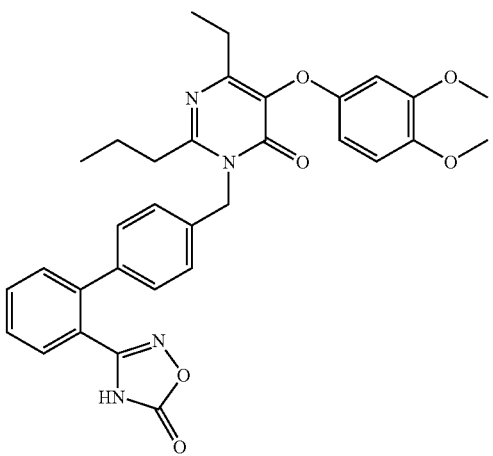

478b) 5-(3,4-dimethoxyphenoxy)-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.66 g), sodium hydrogen carbonate (0.93 g) and dimethyl sulfoxide (15 mL) was stirred at 40° C. for 30 min, 4'-{[5-(3,4-dimethoxyphenoxy)-4-ethyl-6-oxo-2-propylpyrimidin-1(6H)-yl]methyl}biphenyl-2-carbonitrile (0.57 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.44 g, 77%).

$^1$H NMR (300 MHz, DMSO-$d_6$) δ 0.89 (t, J=7.4, 3 H), 1.13 (t, J=7.5, 3 H), 1.59-1.74 (m, 2 H), 2.44-2.57 (m, 2 H), 2.68 (t, J=7.3, 2 H), 3.69 (s, 3 H), 3.72 (s, 3 H), 5.33 (s, 2 H), 6.26 (dd, J=8.9, 2.83, 1 H), 6.65 (d, J=2.8, 1 H), 6.82 (d, J=8.9, 1 H), 7.19-7.25 (m, 2 H), 7.27-7.35 (m, 2 H), 7.49-7.61 (m, 2 H), 7.64-7.74 (m, 2 H), 12.40 (s, 1H)

Example 479

6-ethyl-5-(3-methoxyphenoxy)-3-{[2'-(5-oxo-4,5-dihydro-1,2,4-oxadiazol-3-yl)biphenyl-4-yl]methyl}-2-propylpyrimidin-4(3H)-one

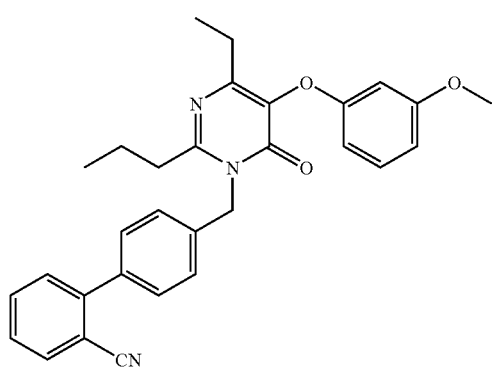

479a) 4'-{[4-ethyl-5-(3-methoxyphenoxy)-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.8 g), 3-methoxyphenol (0.34 g), 8 M potassium hydroxide solution (0.34 mL) and dimethyl sulfoxide (10 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.45 g, 51%).

$^1$H NMR (300 MHz, CDCl$_3$) δ 0.99 (t, J=7.4, 3 H), 1.22 (t, J=7.5, 3 H), 1.72-1.86 (m, 2 H), 2.57-2.73 (m, 4 H), 3.74 (s, 3H), 5.34 (s, 2 H), 6.48-6.60 (m, 3 H), 7.13-7.21 (m, 1 H), 7.32 (d, J=8.3, 2 H), 7.36-7.47 (m, 2 H), 7.49-7.54 (m, 2H), 7.56-7.63 (m, 1 H), 7.72 (dd, J=7.7, 0.9, 1 H)

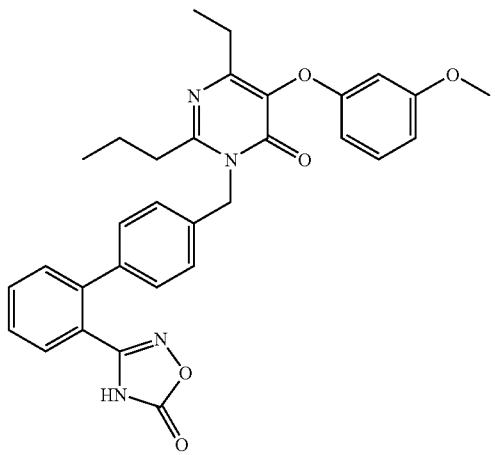

479b) 6-ethyl-5-(3-methoxyphenoxy)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.56 g), sodium hydrogen carbonate (0.79 g) and dimethyl sulfoxide (12 mL) was stirred at 40° C. for 30 min, 4'-{[4-ethyl-5-(3-methoxyphenoxy)-6-oxo-2-propylpyrimidin-1(6H)-yl]methyl}biphenyl-2-carbonitrile (0.45 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.23 g) and then 1,8-diazabicyclo[5.4.0]undec-7-ene (0.21 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.27 g, 53%).

$^1$H NMR (300 MHz, DMSO-$d_6$) δ 0.89 (t, J=7.4, 3 H), 1.12 (t, J=7.6, 3 H), 1.59-1.74 (m, 2 H), 2.44-2.55 (m, 2 H), 2.68 (t, J=7.4, 2 H), 3.72 (s, 3 H), 5.33 (s, 2 H), 6.39-6.52 (m, 2 H), 6.60 (dd, J=8.2, 2.0, 1 H), 7.14-7.27 (m, 3 H), 7.28-7.35 (m, 2 H), 7.50-7.61 (m, 2 H), 7.64-7.74 (m, 2 H), 12.41 (s, 1H)

Example 480

6-ethyl-5-(4-ethylphenoxy)-3-{[2'-(5-oxo-4,5-dihydro-1,2,4-oxadiazol-3-yl)biphenyl-4-yl]methyl}-2-propylpyrimidin-4(3H)-one

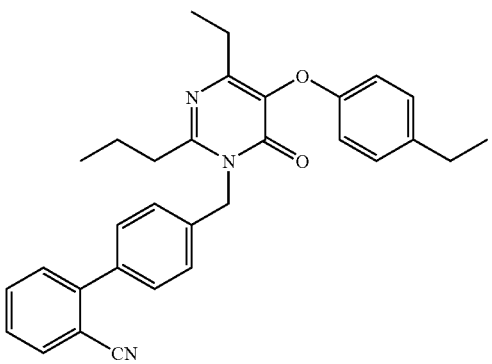

480a) 4'-{[4-ethyl-5-(4-ethylphenoxy)-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.8 g), 4-ethylphenol (0.34 g), 8 M potassium hydroxide solution (0.34 mL) and dimethyl sulfoxide (10 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.59 g, 67%).

$^1$H NMR (300 MHz, CDCl$_3$) δ 0.97 (t, J=7.4, 3 H), 1.14-1.26 (m, 6 H), 1.71-1.85 (m, 2 H), 2.52-2.72 (m, 6 H), 5.34 (s, 2H), 6.87 (d, J=8.7, 2 H), 7.10 (d, J=8.5, 2 H), 7.28-7.46 (m, 4 H), 7.48-7.61 (m, 3 H), 7.69 (dd, J=7.7, 0.9, 1 H)

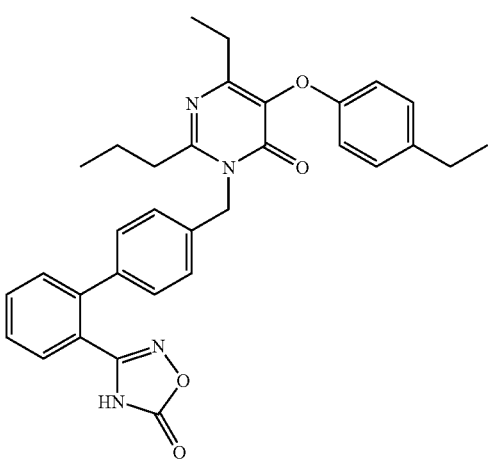

480b) 6-ethyl-5-(4-ethylphenoxy)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.72 g), sodium hydrogen carbonate (1.03 g) and dimethyl sulfoxide (12 mL) was stirred at 40° C. for 30 min, 4'-{[4-ethyl-5-(4-ethylphenoxy)-6-oxo-2-propylpyrimidin-1(6H)-yl]methyl}biphenyl-2-carbonitrile (0.59 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.3 g) and then 1,8-diazabicyclo[5.4.0]undec-7-ene (0.28 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.47 g, 71%).

$^1$H NMR (300 MHz, DMSO-d$_6$) δ 0.89 (t, J=7.4, 3 H), 1.07-1.20 (m, 6 H), 1.60-1.74 (m, 2 H), 2.44-2.60 (m, 2 H), 2.63-2.72 (m, 4 H), 5.32 (s, 2 H), 6.76-6.83 (m, 2 H), 7.13 (d, J=8.7, 2 H), 7.20-7.26 (m, 2 H), 7.30-7.36 (m, 2 H), 7.50-7.62 (m, 2 H), 7.64-7.74 (m, 2 H), 12.40 (s, 1 H)

Example 481

6-ethyl-5-(3-ethylphenoxy)-3-{[2'-(5-oxo-4,5-dihydro-1,2,4-oxadiazol-3-yl)biphenyl-4-yl]methyl}-2-propylpyrimidin-4(3H)-one

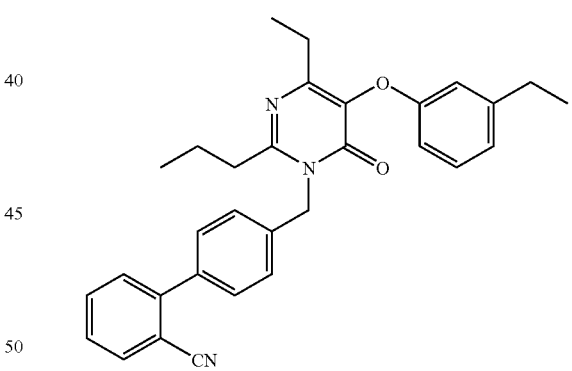

481a) 4'-{[4-ethyl-5-(3-ethylphenoxy)-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.8 g), 3-ethylphenol (0.34 g), 8 M potassium hydroxide solution (0.34 mL) and dimethyl sulfoxide (10 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.54 g, 62%).

¹H NMR (300 MHz, CDCl₃) δ 0.99 (t, J=7.4, 3 H), 1.16-1.27 (m, 6 H), 1.73-1.86 (m, 2 H), 2.56-2.73 (m, 6 H), 5.34 (s, 2 H), 6.73 (dd, J=7.9, 2.1, 1 H), 6.79-6.88 (m, 2 H), 7.13-7.22 (m, 1 H), 7.29-7.47 (m, 4 H), 7.49-7.54 (m, 2 H), 7.55-7.63 (m, 1 H), 7.68-7.74 (m, 1 H)

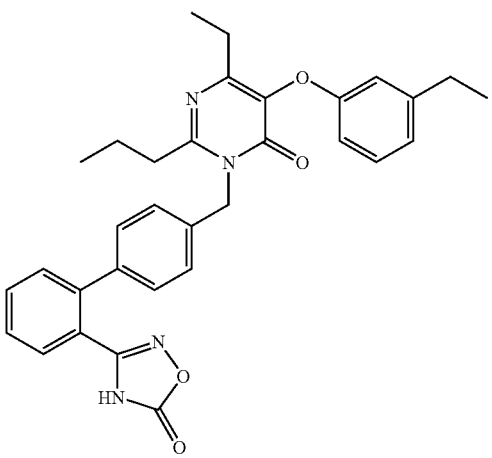

481b) 6-ethyl-5-(3-ethylphenoxy)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.67 g), sodium hydrogen carbonate (0.95 g) and dimethyl sulfoxide (10 mL) was stirred at 40° C. for 30 min, 4'-{[4-ethyl-5-(3-ethylphenoxy)-6-oxo-2-propylpyrimidin-1(6H)-yl]methyl}biphenyl-2-carbonitrile (0.54 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.47 g, 78%).

¹H NMR (300 MHz, DMSO-d₆) δ 0.90 (t, J=7.4, 3 H), 1.07-1.19 (m, 6 H), 1.59-1.76 (m, 2 H), 2.44-2.62 (m, 4 H), 2.65-2.72 (m, 2 H), 5.33 (s, 2 H), 6.68 (dd, J=8.0, 2.2, 1 H), 6.72-6.76 (m, 1 H), 6.86 (d, J=7.5, 1 H), 7.16-7.26 (m, 3 H), 7.28-7.34 (m, 2 H), 7.49-7.60 (m, 2 H), 7.64-7.75 (m, 2H), 12.40 (s, 1 H)

Example 482

3-{[3-fluoro-2'-(5-oxo-4,5-dihydro-1,2,4-oxadiazol-3-yl)biphenyl-4-yl]methyl}-5-(6-isopropoxypyridin-3-yl)-6-methyl-2-propylpyrimidin-4(3H)-one

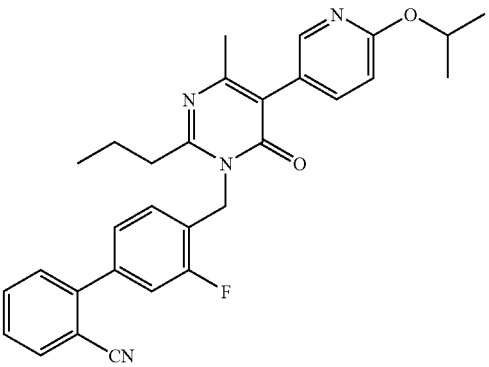

482a) 3'-fluoro-4'-{[5-(6-isopropoxypyridin-3-yl)-4-methyl-6-oxo-2-propylpyrimidin-1(6H)-yl]methyl}biphenyl-2-carbonitrile A mixture of 4'-[(5-bromo-4-methyl-6-oxo-2-propylpyrimidin-1(6H)-yl)methyl]-3'-fluorobiphenyl-2-carbonitrile (0.58 g), (6-isopropoxypyridin-3-yl)boronic acid (0.42 g), [1,1'-bis(diphenylphosphino)ferrocene]dichloropalladium(II) dichloromethane adduct (0.05 g), 2 M aqueous cesium carbonate solution (5 mL) and 1,4-dioxane (5 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.6 g, 91%).

¹H NMR (300 MHz, CDCl₃) δ 1.04 (t, J=7.4, 3 H), 1.36 (d, J=6.2, 6 H), 1.74-1.89 (m, 2 H), 2.29 (s, 3 H), 2.68-2.79 (m, 2 H), 5.26-5.38 (m, 1 H), 5.42 (s, 2 H), 6.72-6.77 (m, 1 H), 7.22-7.35 (m, 3 H), 7.42-7.50 (m, 2 H), 7.58-7.68 (m, 2H), 7.76 (dd, J=8.1, 1.3, 1 H), 8.10-8.13 (m, 1 H)

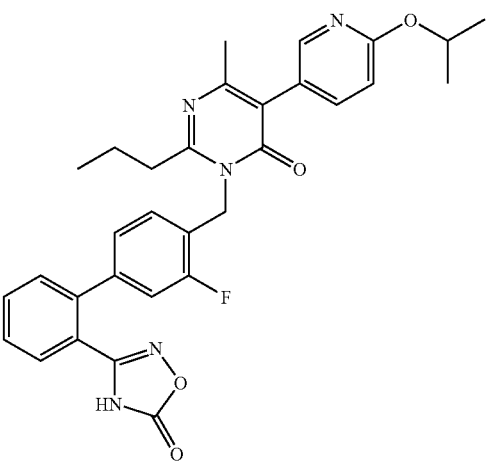

482b) 3-{[3-fluoro-2'-(5-oxo-4,5-dihydro-1,2,4-oxadiazol-3-yl)biphenyl-4-yl]methyl}-5-(6-isopropoxypyridin-3-yl)-6-methyl-2-propylpyrimidin-4(3H)-one A mixture of hydroxylammonium chloride (0.71 g), sodium hydrogen carbonate (1.01 g) and dimethyl sulfoxide (10 mL) was stirred at 40° C. for 30 min, 3'-fluoro-4'-{[5-(6-isopropoxypyridin-3-yl)-4-methyl-6-oxo-2-propylpyrimidin-1(6H)-yl]methyl}biphenyl-2-carbonitrile (0.6 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.29 g) and then 1,8-diazabicyclo[5.4.0]undec-7-ene (0.27 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.49 g, 74%).

$^1$H NMR (300 MHz, DMSO-$d_6$) δ 0.91 (t, J=7.4, 3 H), 1.31 (d, J=6.2 6 H), 1.60-1.75 (m, 2 H), 2.18 (s, 3 H), 2.70 (t, J=7.4, 2 H), 5.20-5.34 (m, 1 H), 5.36 (s, 2 H), 6.76-6.81 (m, 1 H), 7.03-7.13 (m, 2 H), 7.22-7.30 (m, 1 H), 7.53-7.59 (m, 1 H), 7.59-7.66 (m, 2 H), 7.67-7.75 (m, 2 H), 8.06-8.11 (m, 1 H), 12.49 (s, 1 H)

Example 483

6-ethyl-5-(6-isopropoxypyridin-3-yl)-3-{[2'-(5-oxo-4,5-dihydro-1,2,4-oxadiazol-3-yl)biphenyl-4-yl]methyl}-2-propylpyrimidin-4(3H)-one

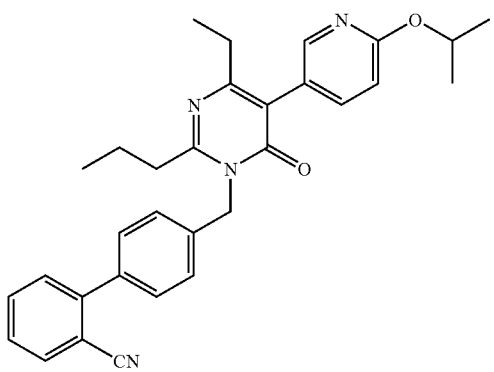

483a) 4'-{[4-ethyl-5-(6-isopropoxypyridin-3-yl)-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.6 g), (6-isopropoxypyridin-3-yl)boronic acid (0.43 g), [1,1'-bis(diphenylphosphino)ferrocene]dichloropalladium(II) dichloromethane adduct (0.05 g), 2 M aqueous cesium carbonate solution (5 mL) and 1,4-dioxane (5 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.57 g, 84%).

$^1$H NMR (300 MHz, CDCl$_3$) δ 1.01 (t, J=7.4, 3 H), 1.22 (t, J=7.5, 3 H), 1.36 (d, J=6.0, 6 H), 1.74-1.89 (m, 2 H), 2.52 (q, J=7.5, 2 H), 2.68-2.79 (m, 2 H), 5.28-5.43 (m, 3 H), 6.75 (d, J=8.5, 1 H), 7.33-7.50 (m, 4 H), 7.52-7.66 (m, 4 H), 7.73 (dd, J=7.7, 1.1, 1 H), 8.10 (d, J=2.1, 1 H)

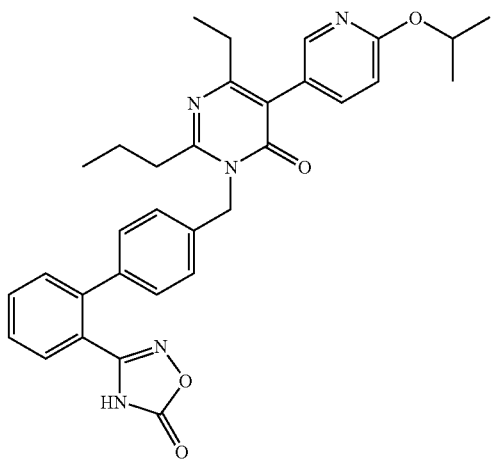

483b) 6-ethyl-5-(6-isopropoxypyridin-3-yl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.68 g), sodium hydrogen carbonate (0.97 g) and dimethyl sulfoxide (10 mL) was stirred at 40° C. for 30 min, 4'-{[4-ethyl-5-(6-isopropoxypyridin-3-yl)-6-oxo-2-propylpyrimidin-1(6H)-yl]methyl}biphenyl-2-carbonitrile (0.57 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.28 g) and then 1,8-diazabicyclo[5.4.0]undec-7-ene (0.26 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.48 g, 76%).

$^1$H NMR (300 MHz, DMSO-$d_6$) δ 0.90 (t, J=7.4, 3 H), 1.12 (t, J=7.5, 3 H), 1.31 (d, J=6.2, 6 H), 1.59-1.74 (m, 2 H), 2.39 (q, J=7.5, 2 H), 2.64-2.76 (m, 2 H), 5.20-5.39 (m, 3 H), 6.79 (d, J=8.7, 1 H), 7.24-7.36 (m, 4 H), 7.50-7.75 (m, 5H), 8.06 (d, J=2.1, 1 H), 12.40 (s, 1 H)

Example 484

5-(2,5-difluorophenoxy)-6-ethyl-3-{[2'-(5-oxo-4,5-dihydro-1,2,4-oxadiazol-3-yl)biphenyl-4-yl]methyl}-2-propylpyrimidin-4(3H)-one

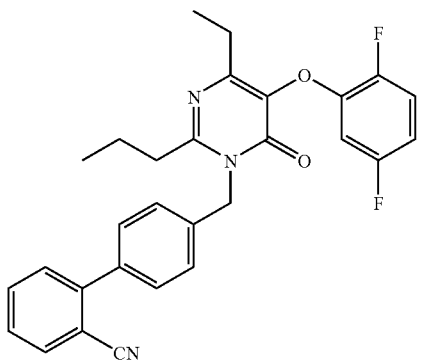

484a) 4'-{[5-(2,5-difluorophenoxy)-4-ethyl-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.5 g), 2,5-difluorophenol (0.23 g), 8 M potassium hydroxide solution (0.22 mL) and dimethyl sulfoxide (8 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.29 g, 52%).

$^1$H NMR (300 MHz, CDCl$_3$) δ 1.00 (t, J=7.4, 3 H), 1.24 (t, J=7.6, 3 H), 1.73-1.89 (m, 2 H), 2.59-2.77 (m, 4 H), 5.35 (s, 2H), 6.50-6.60 (m, 1 H), 6.61-6.70 (m, 1 H), 7.01-7.14 (m, 1 H), 7.26-7.34 (m, 2 H), 7.39-7.50 (m, 2 H), 7.53 (d, J=8.3, 2 H), 7.59-7.67 (m, 1 H), 7.71-7.78 (m, 1 H)

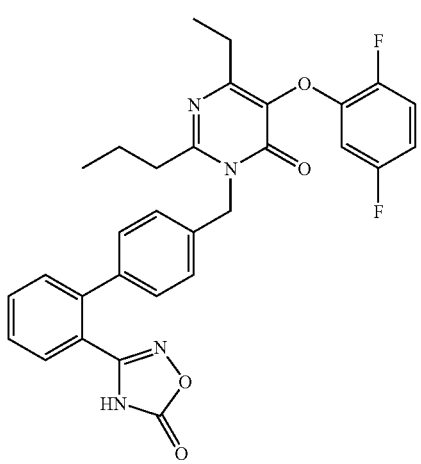

484b) 5-(2,5-difluorophenoxy)-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.35 g), sodium hydrogen carbonate (0.5 g) and dimethyl sulfoxide (5 mL) was stirred at 40° C. for 30 min, 4'-{[5-(2,5-difluorophenoxy)-4-ethyl-6-oxo-2-propylpyrimidin-1(6H)-yl]methyl}biphenyl-2-carbonitrile (0.29 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL). N,N'-carbonyldiimidazole (0.15 g) and then 1,8-diazabicyclo[5.4.0]undec-7-ene (0.13 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.19 g, 57%).

$^1$H NMR (300 MHz, DMSO-d$_6$) δ 0.90 (t, J=7.4, 3 H), 1.16 (t, J=7.5, 3 H), 1.60-1.77 (m, 2 H), 2.47-2.59 (m, 2 H), 2.68 (t, J=7.5, 2 H), 5.33 (s, 2 H), 6.81-6.93 (m, 2 H), 7.19-7.43 (m, 5 H), 7.46-7.61 (m, 2 H), 7.64-7.74 (m, 2 H), 12.40 (s, 1 H)

Example 485

5-(1,3-benzodioxol-5-yloxy)-6-ethyl-3-{[2'-(5-oxo-4,5-dihydro-1,2,4-oxadiazol-3-yl)biphenyl-4-yl]methyl}-2-propylpyrimidin-4(3H)-one

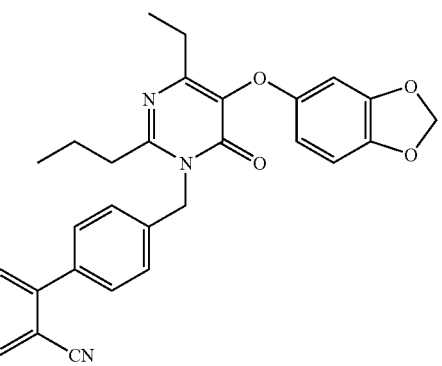

485a) 4'-{[5-(1,3-benzodioxol-5-yloxy)-4-ethyl-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.45 g), 1,3-benzodioxol-5-ol (0.21 g), 8 M potassium hydroxide solution (0.19 mL) and dimethyl sulfoxide (8 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.44 g, 86%).

$^1$H NMR (300 MHz, CDCl$_3$) δ 0.97 (t, J=7.4, 3 H), 1.22 (t, J=7.5, 3 H), 1.70-1.86 (m, 2 H), 2.59-2.76 (m, 4 H), 5.34 (s, 2

H), 5.80 (s, 2 H), 6.18 (dd, J=8.3, 2.7, 1 H), 6.34 (d, J=2.3, 1 H), 6.52-6.57 (m, 1 H), 6.62-6.68 (m, 1 H), 7.30 (s, 1H), 7.35-7.46 (m, 2 H), 7.49-7.54 (m, 2 H), 7.56-7.63 (m, 1 H), 7.71 (dd, J=7.7, 1.0, 1 H)

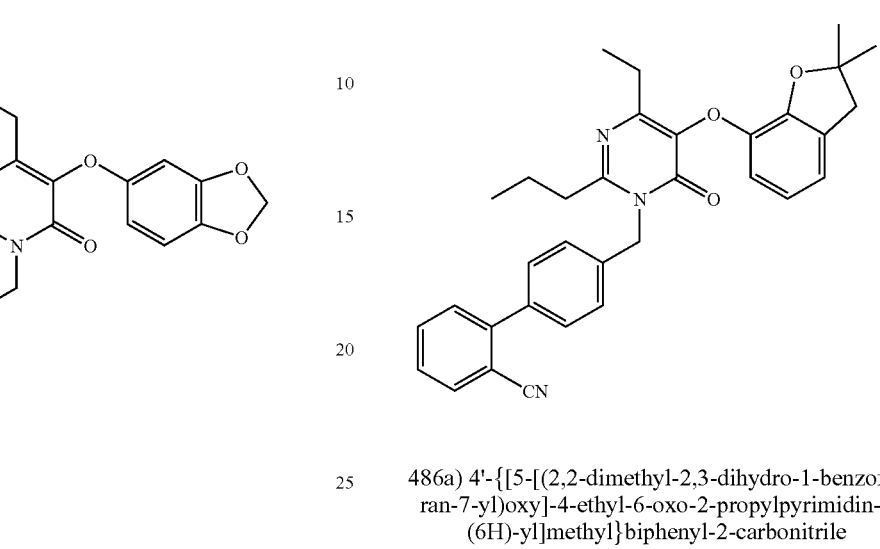

485b) 5-(1,3-benzodioxol-5-yloxy)-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.52 g), sodium hydrogen carbonate (0.74 g) and dimethyl sulfoxide (8 mL) was stirred at 40° C. for 30 min, 4'-{[5-(1,3-benzodioxol-5-yloxy)-4-ethyl-6-oxo-2-propylpyrimidin-1(6H)-yl]methyl}biphenyl-2-carbonitrile (0.44 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.21 g) and then 1,8-diazabicyclo[5.4.0]undec-7-ene (0.2 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.26 g, 53%).

$^1$H NMR (300 MHz, DMSO-d$_6$) δ 0.89 (t, J=7.4, 3 H), 1.12 (t, J=7.5, 3 H), 1.57-1.76 (m, 2 H), 2.45-2.55 (m, 2 H), 2.62-2.70 (m, 2 H), 5.31 (s, 2 H), 5.98 (s, 2 H), 6.29 (dd, J=8.5, 2.6, 1 H), 6.64 (d, J=2.6, 1 H), 6.76-6.81 (m, 1 H), 7.16-7.25 (m, 2 H), 7.29-7.34 (m, 2 H), 7.48-7.60 (m, 2 H), 7.63-7.74 (m, 2 H), 12.40 (s, 1 H)

Example 486

5-[(2,2-dimethyl-2,3-dihydro-1-benzofuran-7-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one

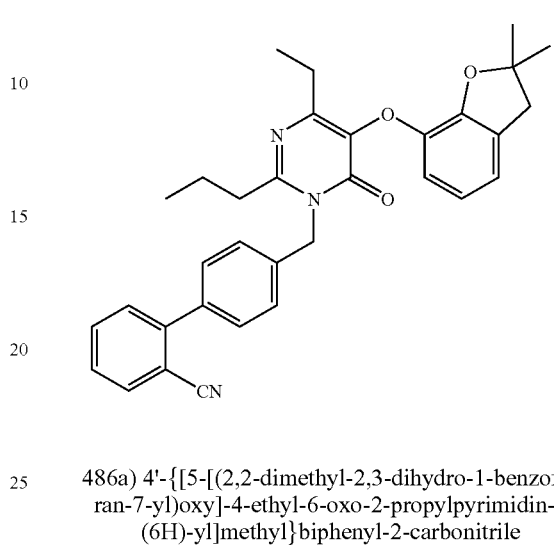

486a) 4'-{[5-[(2,2-dimethyl-2,3-dihydro-1-benzofuran-7-yl)oxy]-4-ethyl-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.45 g), 2,2-dimethyl-2,3-dihydro-1-benzofuran-7-ol (0.25 g), 8 M potassium hydroxide solution (0.19 mL) and dimethyl sulfoxide (8 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.21 g, 39%).

$^1$H NMR (300 MHz, CDCl$_3$) δ 0.98 (t, J=7.4, 3 H), 1.22 (t, J=7.6, 3 H), 1.51 (s, 6 H), 1.71-1.86 (m, 2 H), 2.61-2.72 (m, 4H), 3.03 (s, 2 H), 5.34 (s, 2 H), 6.55-6.61 (m, 1 H), 6.65-6.73 (m, 1 H), 6.81 (dd, J=7.3, 0.9, 1 H), 7.27-7.31 (m, 2H), 7.39-7.54 (m, 4 H), 7.58-7.66 (m, 1 H), 7.73 (dd, J=7.7, 0.9, 1 H)

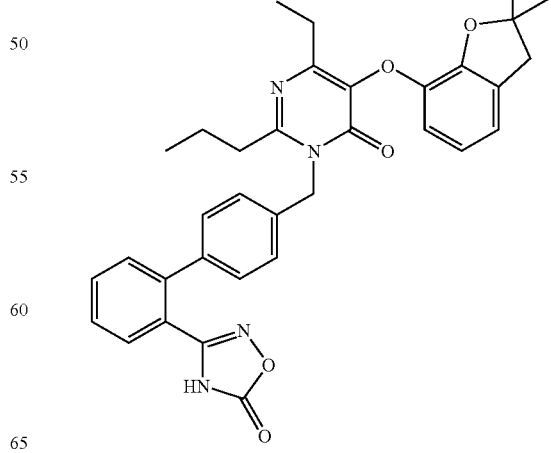

486b) 5-[(2,2-dimethyl-2,3-dihydro-1-benzofuran-7-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.24 g), sodium hydrogen carbonate (0.34 g) and dimethyl sulfoxide (5 mL) was stirred at 40° C. for 30 min, 4'-{[5-[(2,2-dimethyl-2,3-dihydro-1-benzofuran-7-yl)oxy]-4-ethyl-6-oxo-2-propylpyrimidin-1(6H)-yl]methyl}biphenyl-2-carbonitrile (0.21 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL). N,N'-carbonyldiimidazole (0.09 g) and then 1,8-diazabicyclo[5.4.0]undec-7-ene (0.1 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.11 g, 49%).

$^1$H NMR (300 MHz, DMSO-$d_6$) δ 0.88 (t, J=7.4, 3 H), 1.11 (t, J=7.5, 3 H), 1.41 (s, 6 H), 1.59-1.73 (m, 2 H), 2.42-2.57 (m, 4 H), 2.61-2.73 (m, 2 H), 5.32 (s, 2 H), 6.50-6.56 (m, 1 H), 6.63-6.70 (m, 1 H), 6.81-6.87 (m, 1 H), 7.18-7.25 (m, 2 H), 7.28-7.34 (m, 2 H), 7.50-7.61 (m, 2 H), 7.64-7.73 (m, 2 H), 12.40 (s, 1 H)

Example 487

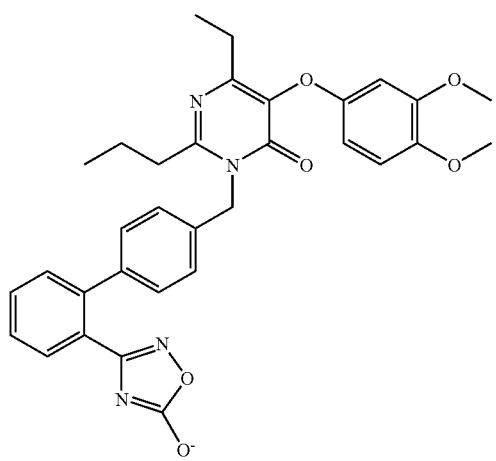

5-(3,4-dimethoxyphenoxy)-6-ethyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-(3,4-dimethoxyphenoxy)-6-ethyl-3-{[2'-(5-oxo-4,5-dihydro-1,2,4-oxadiazol-3-yl)biphenyl-4-yl]methyl}-2-propylpyrimidin-4(3H)-one (0.21 g) and ethanol (4 mL) was added dropwise 0.1 M potassium hydroxide-ethanol solution (3.6 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.2 g, 90%).

$^1$H NMR (300 MHz, DMSO-$d_6$) δ 0.92 (t, J=7.4, 3 H), 1.13 (t, J=7.5, 3 H), 1.62-1.76 (m, 2 H), 2.45-2.56 (m, 2 H), 2.70 (t, J=7.4, 2 H), 3.69 (s, 3 H), 3.72 (s, 3 H), 5.29 (s, 2 H), 6.25 (dd, J=8.8, 2.9, 1 H), 6.64 (d, J=2.8, 1 H), 6.84 (d, J=8.9, 1 H), 7.12 (d, J=8.1, 2 H), 7.27-7.36 (m, 3 H), 7.37-7.44 (m, 1 H), 7.47 (dd, J=7.5, 1.7, 1 H), 7.49-7.56 (m, 1H)

Example 488

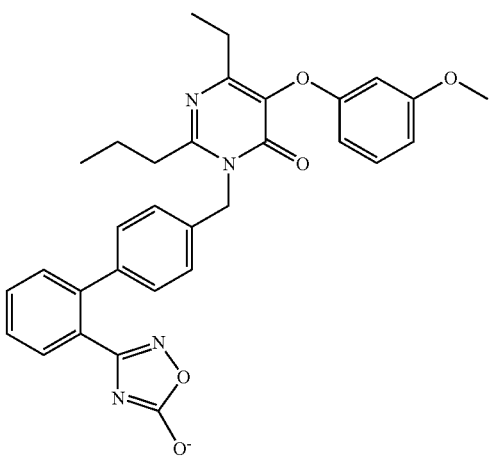

6-ethyl-5-(3-methoxyphenoxy)-3-{[2'-(5-oxo-4,5-dihydro-1,2,4-oxadiazol-3-yl)biphenyl-4-yl]methyl}-2-propylpyrimidin-4(3H)-one potassium salt To a mixture of 6-ethyl-5-(3-methoxyphenoxy)-3-{[2'-(5-oxo-4,5-dihydro-1,2,4-oxadiazol-3-yl)biphenyl-4-yl]methyl}-2-propylpyrimidin-4(3H)-one (0.2 g) and ethanol (4 mL) was added dropwise 0.1 M potassium hydroxide-ethanol solution (3.7 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.2 g, 92%).

$^1$H NMR (300 MHz, DMSO-$d_6$) δ 0.92 (t, J=7.4, 3 H), 1.12 (t, J=7.5, 3 H), 1.63-1.78 (m, 2 H), 2.43-2.56 (m, 2 H), 2.66-2.77 (m, 2 H), 3.72 (s, 3 H), 5.30 (s, 2 H), 6.38-6.50 (m, 2 H), 6.60 (dd, J=8.2, 2.0, 1 H), 7.07-7.16 (m, 2 H), 7.16-7.24 (m, 1 H), 7.27-7.34 (m, 3 H), 7.34-7.48 (m, 2 H), 7.53 (dd, J=7.3, 1.4, 1 H)

Example 489

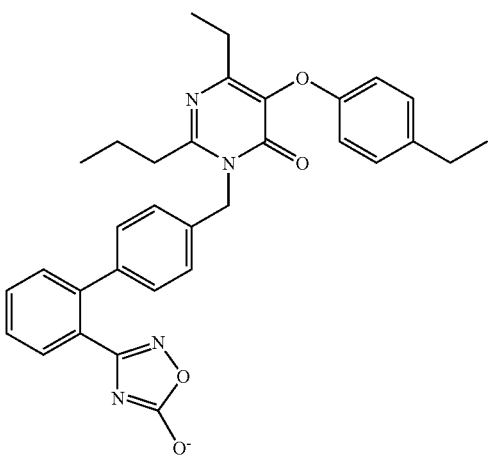

6-ethyl-5-(4-ethylphenoxy)-3-{[2'-(5-oxo-4,5-dihydro-1,2,4-oxadiazol-3-yl)biphenyl-4-yl]methyl}-2-propylpyrimidin-4(3H)-one potassium salt To a mixture of 6-ethyl-5-(4-ethylphenoxy)-3-{[2'-(5-oxo-4,5-dihydro-1,2,4-oxadiazol-3-yl)biphenyl-4-yl]methyl}-2-propylpyrimidin-4(3H)-one (0.2 g) and ethanol (4 mL) was added dropwise 0.1 M potassium hydroxide-ethanol solution (3.7 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.17 g, 79%).

$^1$H NMR (300 MHz, DMSO-$d_6$) δ 0.92 (t, J=7.4, 3 H), 1.08-1.20 (m, 6 H), 1.62-1.77 (m, 2 H), 2.44-2.60 (m, 4 H), 2.65-2.75 (m, 2 H), 5.29 (s, 2 H), 6.80 (d, J=8.7, 2 H), 7.13 (dd, J=8.4, 2.9, 4 H), 7.27-7.36 (m, 3 H), 7.37-7.44 (m, 1 H), 7.44-7.51 (m, 1 H), 7.55 (dd, J=7.4, 1.4, 1 H)

Example 490

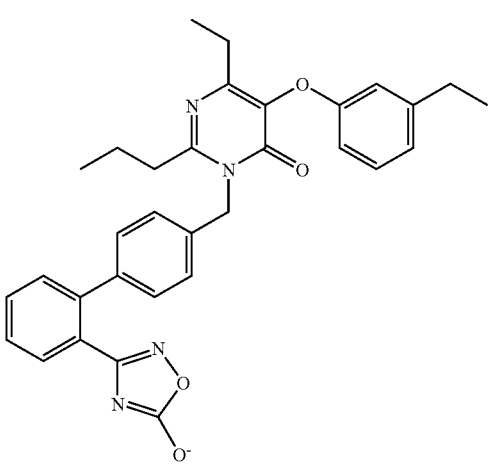

6-ethyl-5-(3-ethylphenoxy)-3-{[2'-(5-oxo-4,5-dihydro-1,2,4-oxadiazol-3-yl)biphenyl-4-yl]methyl}-2-propylpyrimidin-4(3H)-one potassium salt To a mixture of 6-ethyl-5-(3-ethylphenoxy)-3-{[2'-(5-oxo-4,5-dihydro-1,2,4-oxadiazol-3-yl)biphenyl-4-yl]methyl}-2-propylpyrimidin-4(3H)-one (0.21 g) and ethanol (4 mL) was added dropwise 0.1 M potassium hydroxide-ethanol solution (3.8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.18 g, 81%).

$^1$H NMR (300 MHz, DMSO-$d_6$) δ 0.93 (t, J=7.4, 3 H), 1.08-1.19 (m, 6 H), 1.63-1.78 (m, 2 H), 2.44-2.62 (m, 4 H), 2.68-2.76 (m, 2 H), 5.29 (s, 2 H), 6.67 (dd, J=7.9, 2.1, 1 H), 6.71-6.76 (m, 1 H), 6.83-6.89 (m, 1 H), 7.09-7.14 (m, 2 H), 7.17-7.24 (m, 1 H), 7.27-7.33 (m, 3 H), 7.34-7.48 (m, 2H), 7.53 (dd, J=7.4, 1.4, 1 H)

Example 491

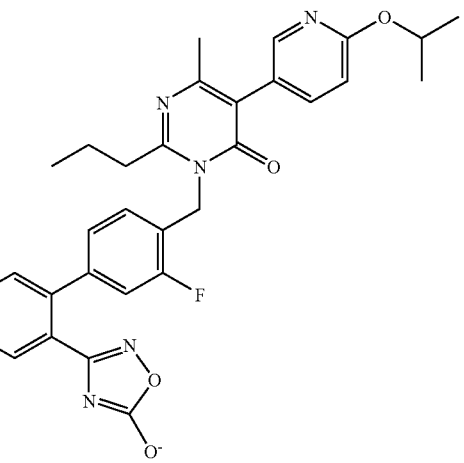

3-{[3-fluoro-2'-(5-oxo-4,5-dihydro-1,2,4-oxadiazol-3-yl)biphenyl-4-yl]methyl}-5-(6-isopropoxypyridin-3-yl)-6-methyl-2-propylpyrimidin-4(3H)-one potassium salt To a mixture of 3-{[3-fluoro-2'-(5-oxo-4,5-dihydro-1,2,4-oxadiazol-3-yl)biphenyl-4-yl]methyl}-5-(6-isopropoxypyridin-3-yl)-6-methyl-2-propylpyrimidin-4(3H)-one (0.21 g) and ethanol (4 mL) was added dropwise 0.1 M potassium hydroxide-ethanol solution (3.8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.2 g, 94%).

¹H NMR (300 MHz, DMSO-d₆) δ 0.93 (t, J=7.4, 3 H), 1.31 (d, J=6.2, 6 H), 1.61-1.76 (m, 2 H), 2.17 (s, 3 H), 2.67-2.76 (m, 2 H), 5.21-5.37 (m, 3 H), 6.75-6.80 (m, 1 H), 6.94-7.01 (m, 1 H), 7.08-7.13 (m, 1 H), 7.15-7.21 (m, 1 H), 7.37 (dd, J=7.5, 1.3, 1 H), 7.40-7.53 (m, 2 H), 7.55-7.60 (m, 1 H), 7.64 (dd, J=8.7, 2.5, 1 H), 8.07-8.11 (m, 1 H)

Example 492

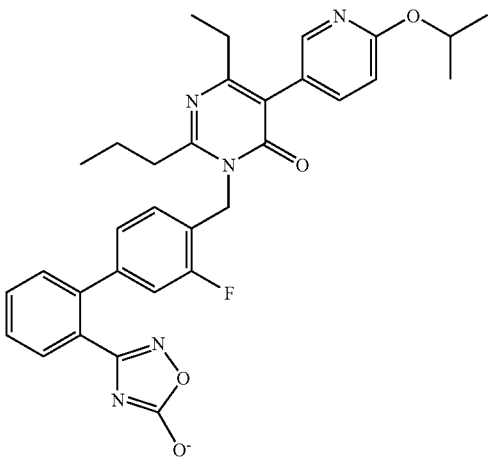

6-ethyl-5-(6-isopropoxypyridin-3-yl)-3-{[2'-(5-oxo-4,5-dihydro-1,2,4-oxadiazol-3-yl)biphenyl-4-yl]methyl}-2-propylpyrimidin-4(3H)-one potassium salt To a mixture of 6-ethyl-5-(6-isopropoxypyridin-3-yl)-3-{[2'-(5-oxo-4,5-dihydro-1,2,4-oxadiazol-3-yl)biphenyl-4-yl]methyl}-2-propylpyrimidin-4(3H)-one (0.2 g) and ethanol (4 mL) was added dropwise 0.1 M potassium hydroxide-ethanol solution (3.8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.19 g, 87%).

¹H NMR (300 MHz, DMSO-d₆) δ 0.92 (t, J=7.4, 3 H), 1.12 (t, J=7.5, 3 H), 1.31 (d, J=6.2, 6 H), 1.61-1.76 (m, 2 H), 2.38 (q, J=7.5, 2 H), 2.65-2.77 (m, 2 H), 5.19-5.38 (m, 3 H), 6.78 (dd, J=8.6, 0.7, 1 H), 7.15-7.21 (m, 2 H), 7.26-7.32 (m, 2 H), 7.33-7.39 (m, 1 H), 7.42 (dd, J=7.4, 1.5, 1 H), 7.47 (dd, J=7.5, 1.7, 1 H), 7.51-7.57 (m, 1 H), 7.63 (dd, J=8.7, 2.5, 1 H), 8.03-8.08 (m, 1 H)

Example 493

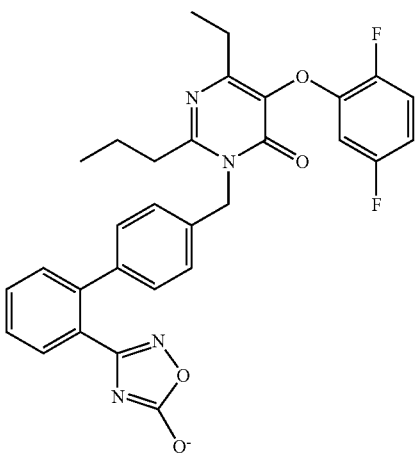

5-(2,5-difluorophenoxy)-6-ethyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-(2,5-difluorophenoxy)-6-ethyl-3-{[2'-(5-oxo-4,5-dihydro-1,2,4-oxadiazol-3-yl)biphenyl-4-yl]methyl}-2-propylpyrimidin-4(3H)-one (0.14 g) and ethanol (4 mL) was added dropwise 0.1 M potassium hydroxide-ethanol solution (3.8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.19 g, 85%).

¹H NMR (300 MHz, DMSO-d₆) δ 0.93 (t, J=7.4, 3 H), 1.15 (t, J=7.4, 3 H), 1.62-1.80 (m, 2 H), 2.49-2.58 (m, 2 H), 2.71 (t, J=7.4, 2 H), 5.28 (s, 2 H), 6.83-6.92 (m, 2 H), 7.12 (d, J=8.1, 2 H), 7.26-7.33 (m, 3 H), 7.32-7.47 (m, 3 H), 7.51 (dd, J=7.4, 1.4, 1 H)

Example 494

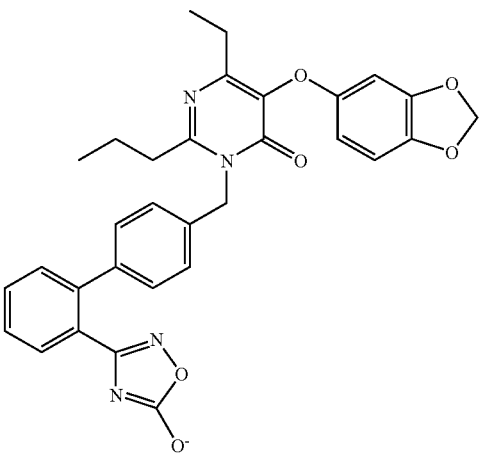

5-(1,3-benzodioxol-5-yloxy)-6-ethyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-(1,3-benzodioxol-5-yloxy)-6-ethyl-3-{[2'-(5-oxo-4,5-dihydro-1,2,4-oxadiazol-3-yl)biphenyl-4-yl]methyl}-2-propylpyrimidin-4(3H)-one (0.2 g) and ethanol (4 mL) was added dropwise 0.1 M potassium hydroxide-ethanol solution (3.8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.2 g, 95%).

¹H NMR (300 MHz, DMSO-d₆) δ 0.92 (t, J=7.4, 3 H), 1.12 (t, J=7.5, 3 H), 1.62-1.77 (m, 2 H), 2.43-2.54 (m, 2 H), 2.64-2.74 (m, 2 H), 5.27 (s, 2 H), 5.98 (s, 2 H), 6.28 (dd, J=8.5, 2.6, 1 H), 6.63 (d, J=2.6, 1 H), 6.80 (d, J=8.5, 1 H), 7.09 (d, J=8.3, 2 H), 7.24-7.32 (m, 3 H), 7.33-7.47 (m, 2 H), 7.51 (dd, J=7.4, 1.4, 1 H)

Example 495

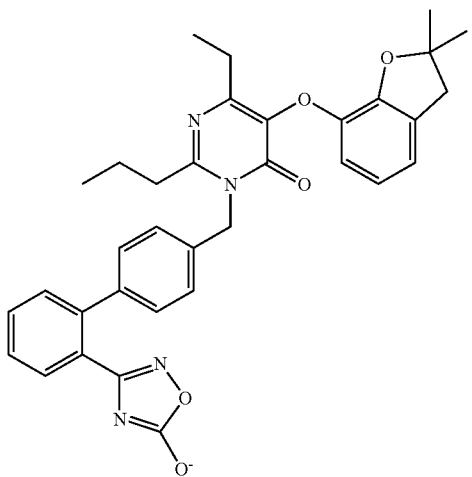

5-[(2,2-dimethyl-2,3-dihydro-1-benzofuran-7-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-[(2,2-dimethyl-2,3-dihydro-1-benzofuran-7-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one (0.07 g) and ethanol (2 mL) was added dropwise 0.1 M potassium hydroxide-ethanol solution (2 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.08 g, 96%).

¹H NMR (300 MHz, DMSO-d₆) δ 0.91 (t, J=7.4, 3 H), 1.11 (t, J=7.5, 3 H), 1.41 (s, 6 H), 1.60-1.79 (m, 2 H), 2.43-2.57 (m, 2 H), 2.65-2.75 (m, 2 H), 3.02 (s, 2 H), 5.27 (s, 2 H), 6.49-6.53 (m, 1 H), 6.64-6.71 (m, 1 H), 6.79-6.85 (m, 1 H), 7.06-7.14 (m, 2 H), 7.26-7.32 (m, 3 H), 7.33-7.47 (m, 2 H), 7.51 (dd, J=7.4, 1.5, 1 H)

Example 496

5-[(4,6-dimethylpyridin-3-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one

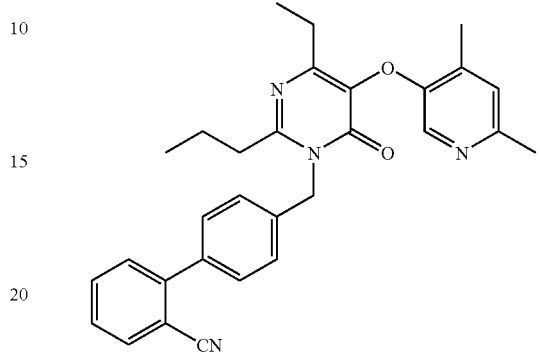

496a) 4'-{[5-[(4,6-dimethylpyridin-3-yl)oxy]-4-ethyl-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.45 g), 4,6-dimethylpyridin-3-ol (0.19 g), 8 M potassium hydroxide solution (0.19 mL) and dimethyl sulfoxide (8 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.4 g, 80%).

¹H NMR (300 MHz, CDCl₃) δ 1.00 (t, J=7.4, 3 H), 1.18-1.28 (m, 5 H), 1.72-1.88 (m, 2 H), 2.45 (s, 3 H), 2.65 (s, 3 H), 2.68-2.75 (m, 2 H), 5.36 (s, 2 H), 6.74-6.81 (m, 1 H), 6.86-6.92 (m, 1 H), 7.31 (d, J=8.0, 2 H), 7.39-7.50 (m, 2 H), 7.52-7.57 (m, 2 H), 7.59-7.66 (m, 1 H), 7.72-7.76 (m, 1 H)

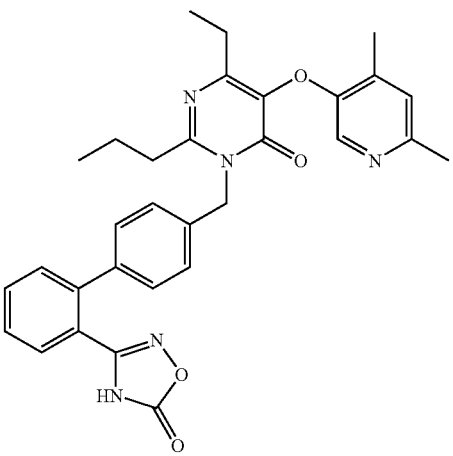

496b) 5-[(4,6-dimethylpyridin-3-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.49 g), sodium hydrogen carbonate (0.69 g) and dimethyl sulfoxide (6 mL) was stirred at 40° C. for 30 min, 4'-{[5-[(4,6-dimethylpyridin-3-yl)oxy]-4-ethyl-6-oxo-2-propylpyrimidin-1(6H)-yl]methyl}biphenyl-2-carbonitrile (0.4 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.2 g) and then 1,8-diazabicyclo[5.4.0]undec-7-ene (0.19 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.27 g, 60%).

$^1$H NMR (300 MHz, DMSO-$d_6$) δ 0.89 (t, J=7.4, 3 H), 1.13 (t, J=7.5, 3 H), 1.57-1.76 (m, 2 H), 2.36 (s, 3 H), 2.44-2.56 (m, 5 H), 2.62-2.74 (m, 2 H), 5.32 (s, 2 H), 6.84-6.90 (m, 1 H), 6.92-6.98 (m, 1 H), 7.19-7.26 (m, 2 H), 7.29-7.36 (m, 2 H), 7.49-7.56, (m, 1 H), 7.58 (dd, J=7.4, 1.1, 1 H), 7.64-7.74 (m, 2 H), 12.42 (s, 1 H)

Example 497

5-[(4,6-dimethylpyridin-2-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one

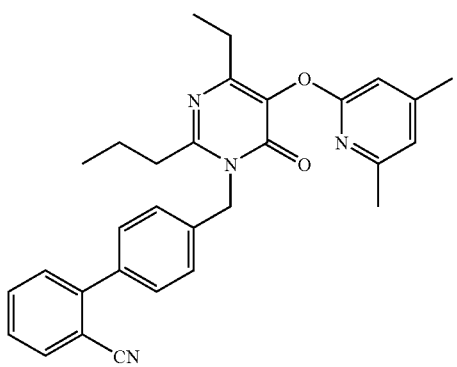

497a) 4'-{[5-[(4,6-dimethylpyridin-2-yl)oxy]-4-ethyl-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.45 g), 4,6-dimethylpyridin-2-ol (0.19 g), 8 M potassium hydroxide solution (0.19 mL) and dimethyl sulfoxide (8 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.24 g, 48%).

$^1$H NMR (300 MHz, CDCl$_3$) δ 0.99 (t, J=7.4, 3 H), 1.21 (t, J=7.6, 3 H), 1.63-1.89 (m, 2 H), 2.27 (s, 3 H), 2.33 (s, 3 H), 2.52-2.73 (m, 4 H), 5.36 (s, 2 H), 6.61 (s, 1 H), 6.63 (s, 1 H), 7.26-7.55 (m, 6 H), 7.58-7.66 (m, 1 H), 7.74 (dd, J=7.8, 1.0, 1 H)

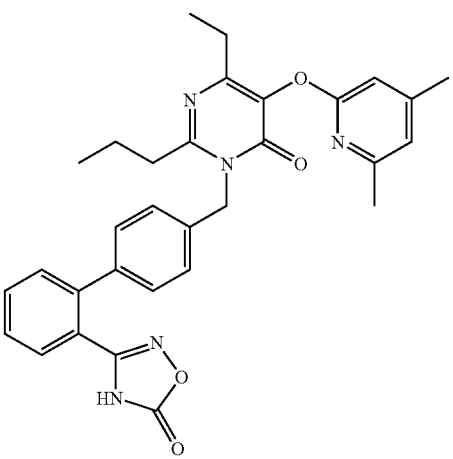

497b) 5-[(4,6-dimethylpyridin-2-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.29 g), sodium hydrogen carbonate (0.42 g) and dimethyl sulfoxide (6 mL) was stirred at 40° C. for 30 min, 4'-{[5-[(4,6-dimethylpyridin-2-yl)oxy]-4-ethyl-6-oxo-2-propylpyrimidin-1(6H)-yl]methyl}biphenyl-2-carbonitrile (0.24 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (8 mL). N,N'-carbonyldiimidazole (0.12 g) and then 1,8-diazabicyclo[5.4.0]undec-7-ene (0.11 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.16 g, 60%).

$^1$H NMR (300 MHz, DMSO-$d_6$) δ 0.89 (t, J=7.4, 3 H), 1.11 (t, J=7.5, 3 H), 1.57-1.73 (m, 2 H), 2.24 (s, 3 H), 2.28 (s, 3 H), 2.41-2.53 (m, 2 H), 2.61-2.70 (m, 2 H), 5.33 (s, 2 H), 6.69 (s, 1 H), 6.77 (s, 1 H), 7.21-7.27 (m, 2 H), 7.27-7.33 (m, 2 H), 7.51-7.61 (m, 2 H), 7.64-7.74 (m, 2 H), 12.39 (s, 1 H)

Example 498

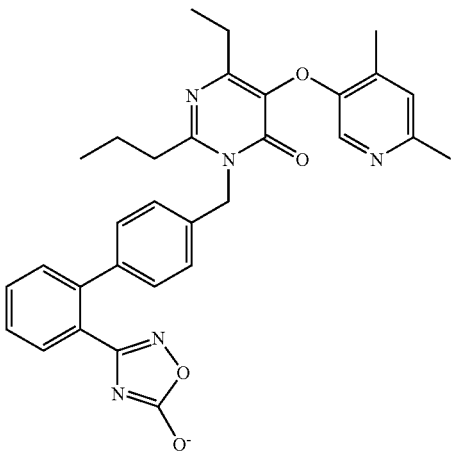

5-[(4,6-dimethylpyridin-3-yl)oxy]-6-ethyl-3-{[2'-(5-oxo-4,5-dihydro-1,2,4-oxadiazol-3-yl)biphenyl-4-yl]methyl}-2-propylpyrimidine-4(3H) potassium salt To a mixture of 5-[(4,6-dimethylpyridin-3-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one (0.2 g) and ethanol (4 mL) was added dropwise 0.1 M potassium hydroxide-ethanol solution (3.8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.21 g, 99%).

$^1$H NMR (300 MHz, CDCl$_3$) δ 0.99 (t, J=7.4, 3 H), 1.21 (t, J=7.6, 3 H), 1.63-1.89 (m, 2 H), 2.27 (s, 3 H), 2.33 (s, 3 H), 2.52-2.73 (m, 4 H), 5.36 (s, 2 H), 6.61 (s, 1 H), 6.63 (s, 1 H), 7.26-7.55 (m, 6 H), 7.58-7.66 (m, 1 H), 7.74 (dd, J=7.8, 1.0, 1 H)

Example 499

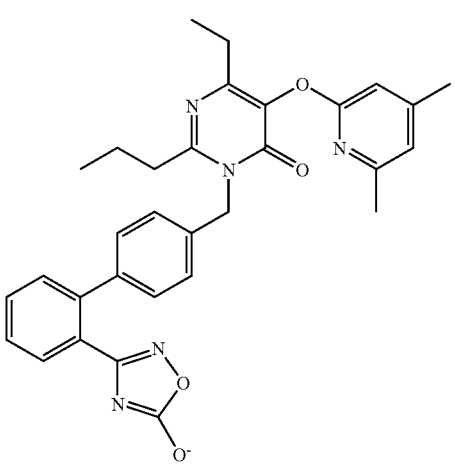

5-[(4,6-dimethylpyridin-2-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-[(4,6-dimethylpyridin-2-yl)oxy]-6-ethyl-3-{[2'-(5-oxo-4,5-dihydro-1,2,4-oxadiazol-3-yl)biphenyl-4-yl]methyl}-2-propylpyrimidin-4(3H)-one (0.13 g) and ethanol (3 mL) was added dropwise 0.1 M potassium hydroxide-ethanol solution (3 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.13 g, 95%).

$^1$H NMR (300 MHz, DMSO-d$_6$) δ 0.92 (t, J=7.4, 3 H), 1.11 (t, J=7.5, 3 H), 1.61-1.76 (m, 2 H), 2.24 (s, 3 H), 2.28 (s, 3 H), 2.41-2.53 (m, 2 H), 2.62-2.74 (m, 2 H), 5.29 (s, 2 H), 6.68 (s, 1 H), 6.77 (s, 1 H), 7.09-7.15 (m, 2 H), 7.25-7.32 (m, 3 H), 7.32-7.47 (m, 2 H), 7.51 (dd, J=7.4, 1.5, 1 H)

Example 500

5-[6-(cyclopropylmethoxy)pyridin-3-yl]-6-ethyl-3-{[2'-(5-oxo-4,5-dihydro-1,2,4-oxadiazol-3-yl)biphenyl-4-yl]methyl}-2-propylpyrimidin-4(3H)-one

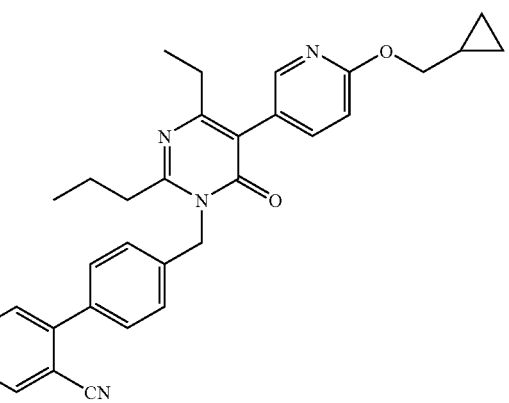

500a) 4'-{[5-[6-(cyclopropylmethoxy)pyridin-3-yl]-4-ethyl-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.5 g), [6-(cyclopropylmethoxy)pyridin-3-yl]boronic acid (0.38 g), [1,1'-bis(diphenylphosphino)ferrocene]dichloropalladium(II) dichloromethane adduct (0.05 g), 2 M aqueous cesium carbonate solution (5 mL) and 1,4-dioxane (5 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.5 g, 86%).

$^1$H NMR (300 MHz, CDCl$_3$) δ 0.31-0.40 (m, 2 H), 0.55-0.66 (m, 2 H), 1.01 (t, J=7.4, 3 H), 1.17-1.38 (m, 4 H), 1.73-1.90 (m, 2 H), 2.51 (q, J=7.4, 2 H), 2.69-2.79 (m, 2 H), 4.16 (d, J=7.2, 2 H), 5.38 (s, 2 H), 6.84 (d, J=7.9, 1 H), 7.33-7.51 (m, 4 H), 7.52-7.57 (m, 2 H), 7.58-7.66 (m, 2 H), 7.74 (dd, J=7.7, 0.9, 1 H), 8.08 (d, J=1.7, 1 H)

Example 501

5-[6-(cyclopropylmethoxy)pyridin-3-yl]-3-{[3-fluoro-2'-(5-oxo-4,5-dihydro-1,2,4-oxadiazol-3-yl)biphenyl-4-yl]methyl}-6-methyl-2-propylpyrimidin-4(3H)-one

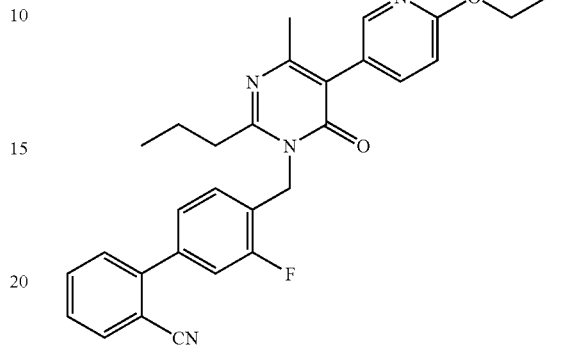

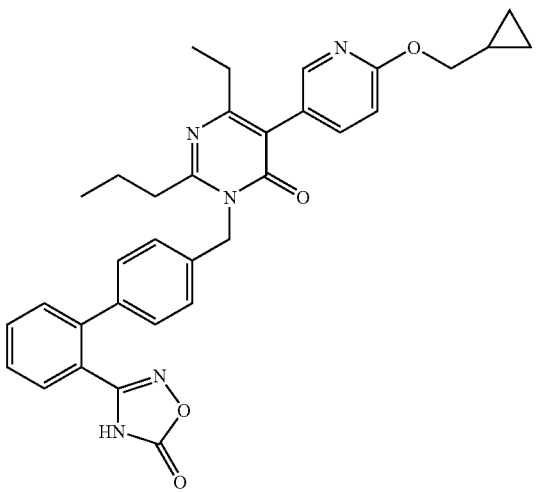

500b) 5-[6-(cyclopropylmethoxy)pyridin-3-yl]-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.58 g), sodium hydrogen carbonate (0.83 g) and dimethyl sulfoxide (10 mL) was stirred at 40° C. for 30 min, 4'-{[5-[6-(cyclopropylmethoxy)pyridin-3-yl]-4-ethyl-6-oxo-2-propylpyrimidin-1(6H)-yl]methyl}biphenyl-2-carbonitrile (0.5 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.24 g) and then 1,8-diazabicyclo[5.4.0]undec-7-ene (0.22 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.32 g, 57%).

$^1$H NMR (300 MHz, DMSO-$d_6$) δ 0.29-0.37 (m, 2 H), 0.52-0.60 (m, 2 H), 0.90 (t, J=7.4, 3 H), 1.08-1.35 (m, 4 H), 1.59-1.74 (m, 2 H), 2.38 (q, J=7.5, 2 H), 2.66-2.74 (m, 2 H), 4.12 (d, J=7.2, 2 H), 5.35 (s, 2 H), 6.88 (d, J=8.5, 1 H), 7.24-7.36 (m, 4 H), 7.49-7.75 (m, 5 H), 8.05 (d, J=1.9, 1H), 12.41 (s, 1 H)

501a) 4'-{[5-[6-(cyclopropylmethoxy)pyridin-3-yl]-4-methyl-6-oxo-2-propylpyrimidin-1(6H)-yl]methyl}-3'-fluorobiphenyl-2-carbonitrile A mixture of 4'-[(5-bromo-4-methyl-6-oxo-2-propylpyrimidin-1(6H)-yl)methyl]-3'-fluorobiphenyl-2-carbonitrile (0.5 g), [6-(cyclopropylmethoxy)pyridin-3-yl]boronic acid (0.47 g), [1,1'-bis(diphenylphosphino)ferrocene]dichloropalladium(II) dichloromethane adduct (0.05 g), 2 M aqueous cesium carbonate solution (5 mL) and 1,4-dioxane (5 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.53 g, 91%).

$^1$H NMR (300 MHz, CDCl$_3$) δ 0.32-0.39 (m, 2 H), 0.57-0.65 (m, 2 H), 1.04 (t, J=7.4, 3 H), 1.29-1.38 (m, 1 H), 1.73-1.89 (m, 2 H), 2.28 (s, 3 H), 2.68-2.78 (m, 2 H), 4.16 (d, J=7.0, 2 H), 5.42 (s, 2 H), 6.81-6.87 (m, 1 H), 7.21-7.36 (m, 3 H), 7.43-7.51 (m, 2 H), 7.60-7.70 (m, 2 H), 7.76 (dd, J=8.0, 1.2, 1 H), 8.10 (d, J=1.7, 1 H)

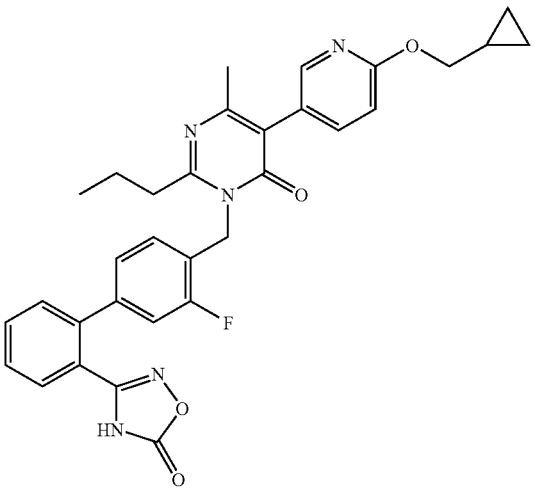

501b) 5-[6-(cyclopropylmethoxy)pyridin-3-yl]-3-{[3-fluoro-2'-(5-oxo-4,5-dihydro-1,2,4-oxadiazol-3-yl)biphenyl-4-yl]methyl}-6-methyl-2-propylpyrimidin-4(3H)-one A mixture of hydroxylammonium chloride (0.71 g), sodium hydrogen carbonate (1.01 g) and dimethyl sulfoxide (10 mL) was stirred at 40° C. for 30 min, 4'-{[5-[6-(cyclopropylmethoxy)pyridin-3-yl]-4-methyl-6-oxo-2-propylpyrimidin-1(6H)-yl]methyl}-3'-fluorobiphenyl-2-carbonitrile (0.53 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.29 g) and then 1,8-diazabicyclo[5.4.0]undec-7-ene (0.27 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.41 g, 60%).

$^1$H NMR (300 MHz, CDCl$_3$) δ 0.29-0.44 (m, 2 H), 0.59-0.68 (m, 2 H), 1.01 (t, J=7.4, 3 H), 1.24-1.31 (m, 1 H), 1.68-1.87 (m, 2 H), 2.20 (s, 3 H), 2.63-2.78 (m, 2 H), 4.09 (d, J=7.0, 2 H), 5.26 (s, 2 H), 6.63 (d, J=8.5, 1 H), 6.94-7.10 (m, 3 H), 7.34-7.52 (m, 3 H), 7.54-7.67 (m, 2 H), 7.92 (d, J=2.1, 1 H), 9.68 (s, 1 H)

Example 502

6-(1-morpholin-4-ylethyl)-3-{[2'-(5-oxo-4,5-dihydro-1,2,4-oxadiazol-3-yl)biphenyl-4-yl]methyl}-2-propylpyrimidin-4(3H)-one

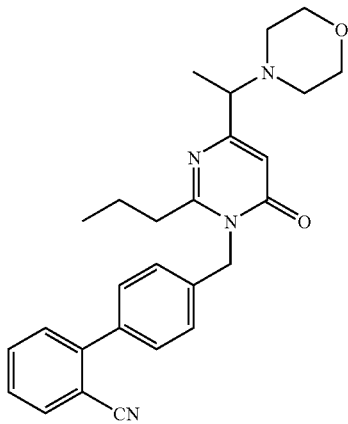

502a) 4'-{[4-(1-morpholin-4-ylethyl)-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.5 g) and morpholine (8 mL) was stirred at 90° C. for 12 hr. The solvent was evaporated from the reaction mixture under reduced pressure. The residue was diluted with ethyl acetate, washed with water and saturated brine, and dried over anhydrous magnesium sulfate. The solvent was evaporated under reduced pressure and the residue was purified by silica gel column chromatography to give the title compound as a colorless amorphous solid (0.43 g, 83%).

$^1$H NMR (300 MHz, CDCl$_3$) δ 0.97 (t, J=7.4, 3 H), 1.35 (d, J=6.8, 3 H), 1.67-1.84 (m, 2 H), 2.51-2.64 (m, 4 H), 2.65-2.73 (m, 2 H), 3.31 (q, J=6.8, 1 H), 3.69-3.78 (m, 4 H), 5.29-5.48 (m, 2 H), 6.53 (s, 1 H), 7.32 (d, J=8.3, 2 H), 7.41-7.51 (m, 2 H), 7.52-7.58 (m, 2 H), 7.60-7.68 (m, 1 H), 7.75 (dd, J=7.7, 0.9, 1 H)

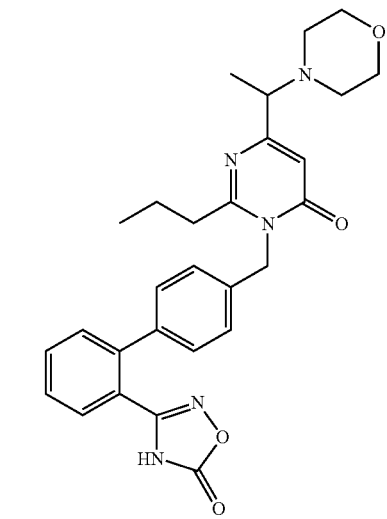

502b) 6-(1-morpholin-4-ylethyl)-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.71 g), sodium hydrogen carbonate (1.01 g) and dimethyl sulfoxide (10 mL) was stirred at 40° C. for 30 min, 4'-{[4-(1-morpholin-4-ylethyl)-6-oxo-2-propylpyrimidin-1(6H)-yl]methyl}biphenyl-2-carbonitrile (0.43 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.24 g) and then 1,8-diazabicyclo[5.4.0]undec-7-ene (0.22 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.12 g, 26%).

$^1$H NMR (300 MHz, DMSO-d$_6$) δ 0.85 (t, J=7.4, 3 H), 1.27 (d, J=6.8, 3 H), 1.55-1.69 (m, 2 H), 2.45-2.54 (m, 4 H), 2.61-2.70 (m, 2 H), 3.34 (q, J=6.8, 1 H), 3.55-3.62 (m, 4 H), 5.25-5.40 (m, 2 H), 6.36 (s, 1 H), 7.19-7.26 (m, 2 H), 7.29-7.35 (m, 2 H), 7.49-7.61 (m, 2 H), 7.64-7.74 (m, 2H), 12.36 (s, 1 H)

Example 503

6-ethyl-5-[(4-methylpyridin-2-yl)oxy]-3-{[2'-(5-oxo-4,5-dihydro-1,2,4-oxadiazol-3-yl)biphenyl-4-yl]methyl}-2-propylpyrimidin-4(3H)-one potassium salt

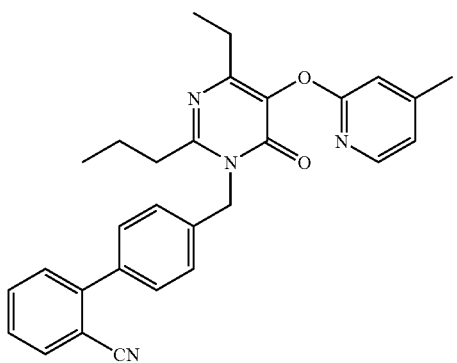

503a) 4'-{[4-ethyl-5-[(4-methylpyridin-2-yl)oxy]-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.45 g), 4-methylpyridin-2-ol (0.19 g), 8 M potassium hydroxide solution (0.22 mL) and dimethyl sulfoxide (8 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.13 g, 25%).

$^1$H NMR (300 MHz, CDCl$_3$) δ 0.99 (t, J=7.4, 3 H), 1.22 (t, J=8.3, 3 H), 1.72-1.86 (m, 2 H), 2.34 (s, 3 H), 2.57-2.72 (m, 4 H), 5.33 (s, 2 H), 6.79 (d, J=5.3, 1 H), 6.88 (s, 1 H), 7.34 (d, J=8.3, 2 H), 7.39-7.56 (m, 4 H), 7.59-7.66 (m, 1 H), 7.74 (dd, J=7.7, 0.9, 1 H), 7.97 (d, J=5.3, 1 H)

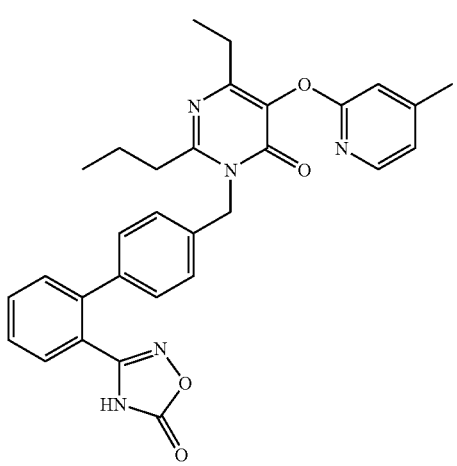

503b) 6-ethyl-5-[(4-methylpyridin-2-yl)oxy]-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.17 g), sodium hydrogen carbonate (0.24 g) and dimethyl sulfoxide (5 mL) was stirred at 40° C. for 30 min, 4'-{[4-ethyl-5-[(4-methylpyridin-2-yl)oxy]-6-oxo-2-propylpyrimidin-1(6H)-yl]methyl}biphenyl-2-carbonitrile (0.13 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL). N,N'-carbonyldiimidazole (0.07 g) and then 1,8-diazabicyclo[5.4.0]undec-7-ene (0.07 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.1 g, 64%).

$^1$H NMR (300 MHz, DMSO-d$_6$) δ 0.89 (t, J=7.4, 3 H), 1.10 (t, J=7.6, 3 H), 1.58-1.73 (m, 2 H), 2.33 (s, 3 H), 2.46 (q, J=7.6, 2 H), 2.62-2.72 (m, 2 H), 5.32 (s, 2 H), 6.90-6.94 (m, 2 H), 7.21-7.27 (m, 2 H), 7.29-7.34 (m, 2 H), 7.51-7.61 (m, 2 H), 7.64-7.74 (m, 2 H), 7.92-7.97 (m, 1 H), 12.39 (s, 1 H)

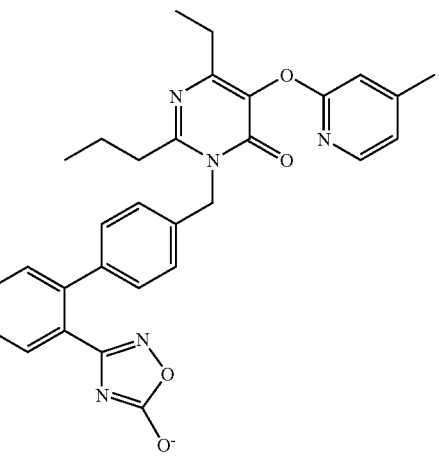

503c) 6-ethyl-5-[(4-methylpyridin-2-yl)oxy]-3-{[2'-(5-oxo-4,5-dihydro-1,2,4-oxadiazol-3-yl)biphenyl-4-yl]methyl}-2-propylpyrimidin-4(3H)-one potassium salt To a mixture of 6-ethyl-5-[(4-methylpyridin-2-yl)oxy]-3-{[2'-(5-oxo-4,5-dihydro-1,2,4-oxadiazol-3-yl)biphenyl-4-yl]methyl}-2-propylpyrimidin-4(3H)-one (0.09 g) and ethanol (2 mL) was added dropwise 0.1 M potassium hydroxide-ethanol solution (2 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.09 g, 97%).

$^1$H NMR (300 MHz, DMSO-$d_6$) δ 0.92 (t, J=7.4, 3 H), 1.10 (t, J=7.5, 3 H), 1.61-1.76 (m, 2 H), 2.33 (s, 3 H), 2.41-2.53 (m, 2 H), 2.66-2.74 (m, 2 H), 5.28 (s, 2 H), 6.88-6.96 (m, 2 H), 7.11 (d, J=8.1, 2 H), 7.25-7.48 (m, 5 H), 7.53 (dd, J=7.4, 1.3, 1 H), 7.92-7.98 (m, 1 H)

Example 504

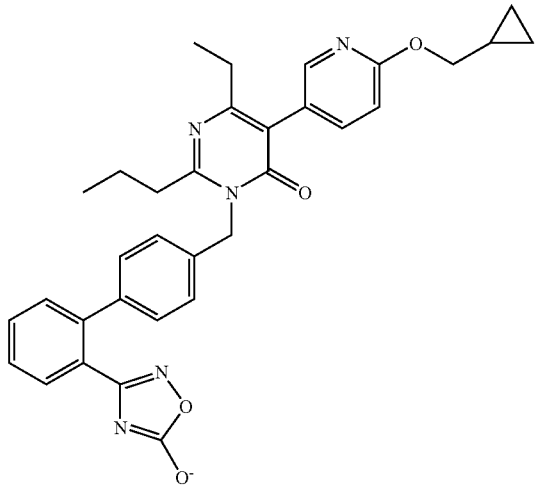

5-[6-(cyclopropylmethoxy)pyridin-3-yl]-6-ethyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-[6-(cyclopropylmethoxy)pyridin-3-yl]-6-ethyl-3-{[2'-(5-oxo-4,5-dihydro-1,2,4-oxadiazol-3-yl)biphenyl-4-yl]methyl}-2-propylpyrimidin-4(3H)-one (0.21 g) and ethanol (4 mL) was added dropwise 0.1 M potassium hydroxide-ethanol solution (3.8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.22 g, 99%).

$^1$H NMR (300 MHz, DMSO-$d_6$) δ 0.29-0.37 (m, 2 H), 0.52-0.59 (m, 2 H), 0.93 (t, J=7.4, 3 H), 1.12 (t, J=7.5, 3 H), 1.19-1.34 (m, 1 H), 1.63-1.76 (m, 2 H), 2.37 (q, J=7.5, 2 H), 2.67-2.77 (m, 2 H), 4.12 (d, J=7.16, 2 H), 5.30 (s, 2 H), 6.86 (d, J=8.5, 1 H), 7.12-7.17 (m, J=8.1, 2 H), 7.25-7.32 (m, 3 H), 7.33-7.46 (m, 2 H), 7.48-7.52 (m, 1 H), 7.65 (dd, J=8.5, 2.5, 1 H), 8.04 (d, J=1.9, 1 H)

Example 505

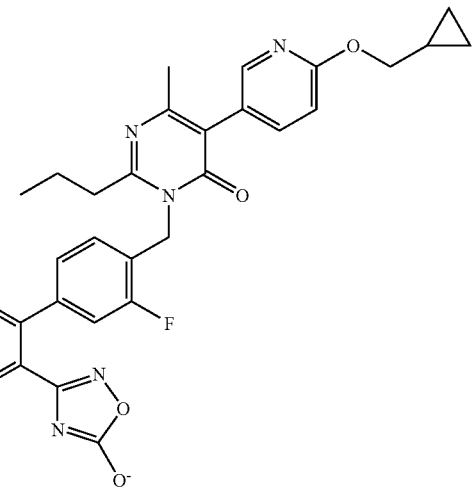

5-[6-(cyclopropylmethoxy)pyridin-3-yl]-3-{[3-fluoro-2'-(5-oxo-4,5-dihydro-1,2,4-oxadiazol-3-yl)biphenyl-4-yl]methyl}-6-methyl-2-propylpyrimidin-4(3H)-one potassium salt To a mixture of 5-[6-(cyclopropylmethoxy)pyridin-3-yl]-3-{[3-fluoro-2'-(5-oxo-4,5-dihydro-1,2,4-oxadiazol-3-yl)biphenyl-4-yl]methyl}-6-methyl-2-propylpyrimidin-4(3H)-one (0.21 g) and ethanol (4 mL) was added dropwise 0.1 M potassium hydroxide-ethanol solution (3.8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.21 g, 96%).

$^1$H NMR (300 MHz, DMSO-$d_6$) δ 0.30-0.36 (m, 2 H), 0.51-0.60 (m, 2 H), 0.93 (t, J=7.4, 3 H), 1.18-1.32 (m, 1 H), 1.61-1.77 (m, 2 H), 2.16 (s, 3 H), 2.68-2.76 (m, 2 H), 4.11 (d, J=7.2, 2 H), 5.32 (s, 2 H), 6.85 (d, J=8.5, 1 H), 6.91-6.99 (m, 1 H), 7.06-7.20 (m, 2 H), 7.33 (dd, J=7.4, 1.5, 1 H), 7.37-7.49 (m, 2 H), 7.52-7.57 (m, 1 H), 7.67 (dd, J=8.5, 2.5, 1 H), 8.07 (d, J=1.9, 1 H)

Example 506

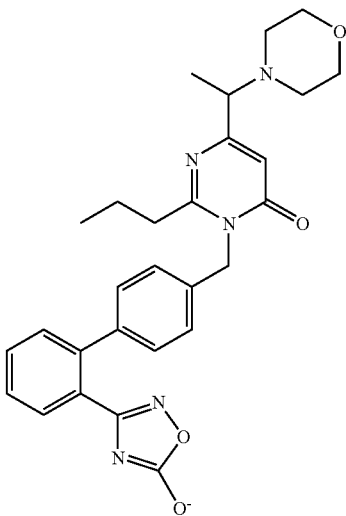

6-(1-morpholin-4-ylethyl)-3-{[2'-(5-oxo-4,5-dihydro-1,2,4-oxadiazol-3-yl)biphenyl-4-yl]methyl}-2-propylpyrimidin-4(3H)-one potassium salt To a mixture of 6-(1-morpholin-4-ylethyl)-3-{[2'-(5-oxo-4,5-dihydro-1,2,4-oxadiazol-3-yl)biphenyl-4-yl]methyl}-2-propylpyrimidin-4(3H)-one (0.08 g) and ethanol (2 mL) was added dropwise 0.1 M potassium hydroxide-ethanol solution (2 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.08 g, 97%).

$^1$H NMR (300 MHz, DMSO-$d_6$) δ 0.88 (t, J=7.4, 3 H), 1.26 (d, J=6.8, 3 H), 1.58-1.72 (m, 2 H), 2.45-2.58 (m, 5 H), 2.63-2.74 (m, 2 H), 3.53-3.63 (m, 4 H), 5.20-5.32 (m, 2 H), 6.34 (s, 1 H), 7.04-7.14 (m, 2 H), 7.26-7.32 (m, 3 H), 7.33-7.45 (m, 2 H), 7.50 (dd, J=7.4, 1.5, 1 H)

Example 507

5-(6-ethoxypyridin-3-yl)-6-ethyl-3-{[2'-(5-oxo-4,5-dihydro-1,2,4-oxadiazol-3-yl)biphenyl-4-yl]methyl}-2-propylpyrimidin-4(3H)-one

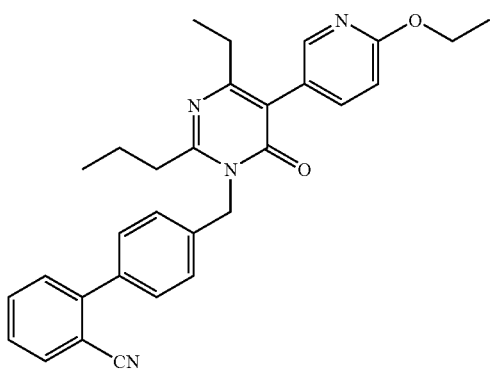

507a) 4'-{[5-(6-ethoxypyridin-3-yl)-4-ethyl-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.5 g), (6-ethoxypyridin-3-yl)boronic acid (0.23 g), [1,1'-bis(diphenylphosphino)ferrocene]dichloropalladium(II) dichloromethane adduct (0.05 g), 2 M aqueous cesium carbonate solution (5 mL) and 1,4-dioxane (5 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.54 g, 98%).

$^1$H NMR (300 MHz, CDCl$_3$) δ 1.02 (t, J=7.4, 3 H), 1.21 (t, J=7.4, 3 H), 1.40 (t, J=7.2, 3 H), 1.74-1.90 (m, 2 H), 2.51 (q, J=7.4, 2 H), 2.69-2.79 (m, 2 H), 4.39 (q, J=7.2, 2 H), 5.37 (s, 2 H), 6.79 (d, J=8.7, 1 H), 7.36 (d, J=8.3, 2 H), 7.39-7.51 (m, 2 H), 7.51-7.58 (m, 2 H), 7.58-7.68 (m, 2 H), 7.70-7.79 (m, 1 H), 8.10 (d, J=1.9, 1 H)

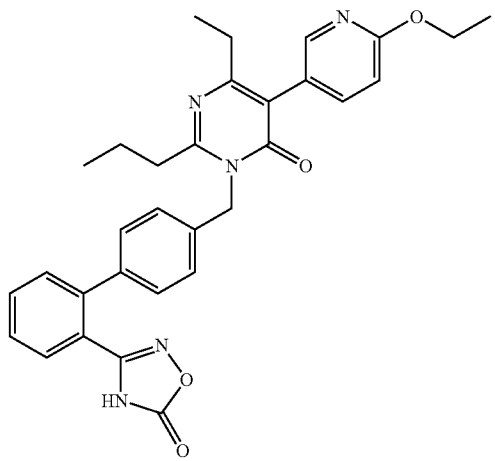

507b) 5-(6-ethoxypyridin-3-yl)-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.67 g), sodium hydrogen carbonate (0.95 g) and dimethyl sulfoxide (10 mL) was stirred at 40° C. for 30 min, 4'-{[5-(6-ethoxypyridin-3-yl)-4-ethyl-6-oxo-2-propylpyrimidin-1(6H)-yl]methyl}biphenyl-2-carbonitrile (0.54 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.28 g) and then 1,8-diazabicyclo[5.4.0]undec-7-ene (0.25 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.32 g, 60%).

$^1$H NMR (300 MHz, DMSO-$d_6$) δ 0.89 (t, J=7.4, 3 H), 1.12 (t, J=7.4, 3 H), 1.34 (t, J=7.1, 3 H), 1.59-1.73 (m, 2 H), 2.38 (q, J=7.4, 2 H), 2.69 (t, J=7.3, 2 H), 4.33 (q, J=7.1, 2 H), 5.35 (s, 2 H), 6.85 (d, J=8.5, 1 H), 7.23-7.34 (m, 4 H), 7.50-7.75 (m, 5 H), 8.06 (d, J=1.9, 1 H)

Exampl 508

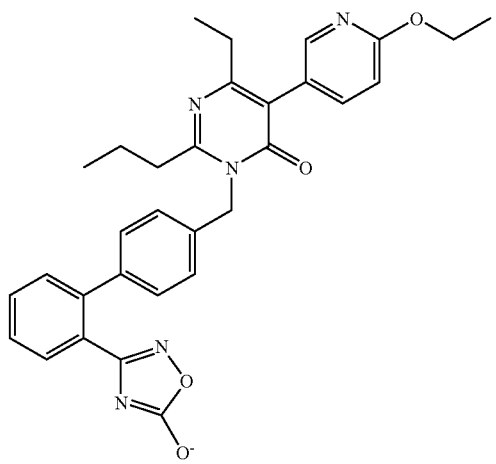

5-(6-ethoxypyridin-3-yl)-6-ethyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-(6-ethoxypyridin-3-yl)-6-ethyl-3-{[2'-(5-oxo-4,5-dihydro-1,2,4-oxadiazol-3-yl)biphenyl-4-yl]methyl}-2-propylpyrimidin-4(3H)-one (0.2 g) and ethanol (4 mL) was added dropwise 0.1 M potassium hydroxide-ethanol solution (3.8 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.18 g, 85%).

$^1$H NMR (300 MHz, DMSO-d$_6$) δ 0.92 (t, J=7.4, 3 H), 1.12 (t, J=7.4, 3 H), 1.34 (t, J=7.1, 3 H), 1.61-1.75 (m, 2 H), 2.38 (q, J=7.4, 2 H), 2.71 (t, J=7.4, 2 H), 4.33 (q, J=7.1, 2 H), 5.31 (s, 2 H), 6.84 (d, J=8.5, 1 H), 7.16-7.20 (m, 2 H), 7.27-7.32 (m, 2 H), 7.34-7.40 (m, 1 H), 7.43 (dd, J=7.4, 1.5, 1 H), 7.49 (dd, J=7.5, 1.7, 1 H), 7.52-7.58 (m, 1 H), 7.65 (dd, J=8.5, 2.5, 1 H), 8.06 (d, J=1.9, 1 H)

Example 509

3-{[3-fluoro-2'-(5-oxo-4,5-dihydro-1,2,4-oxadiazol-3-yl)biphenyl-4-yl]methyl}-5-[4-(2-hydroxy-1,1-dimethylethoxy)phenyl]-6-methyl-2-propylpyrimidin-4(3H)-one

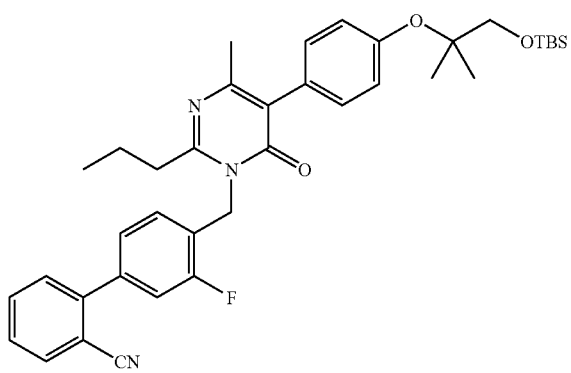

509a) 4'-{[5-[4-(2-{[tert-butyl(dimethyl)silyl]oxy}-1,1-dimethylethoxy)phenyl]-4-methyl-6-oxo-2-propylpyrimidin-1(6H)-yl]methyl}-3'-fluorobiphenyl-2-carbonitrile A mixture of 4'-[(5-bromo-4-methyl-6-oxo-2-propylpyrimidin-1(6H)-yl)methyl]-3'-fluorobiphenyl-2-carbonitrile (0.6 g), [4-(2-{[tert-butyl(dimethyl)silyl]oxy}-1,1-dimethylethoxy)phenyl]boronic acid (0.83 g), [1,1'-bis(diphenylphosphino)ferrocene]dichloropalladium(II) dichloromethane adduct (0.06 g), 2 M aqueous cesium carbonate solution (6 mL) and 1,4-dioxane (6 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.76 g, 89%).

$^1$H NMR (300 MHz, CDCl$_3$) δ 0.00 (s, 6 H), 0.84 (s, 9 H), 0.95 (t, J=7.4, 3 H), 1.22 (s, 6 H), 1.65-1.81 (m, 2 H), 2.15 (s, 3 H), 2.59-2.68 (m, 2 H), 3.51 (s, 2 H), 5.34 (s, 2 H), 6.94-7.02 (m, 2 H), 7.11-7.26 (m, 5 H), 7.33-7.42 (m, 2 H), 7.52-7.60 (m, 1 H), 7.68 (dd, J=8.0, 1.2, 1 H)

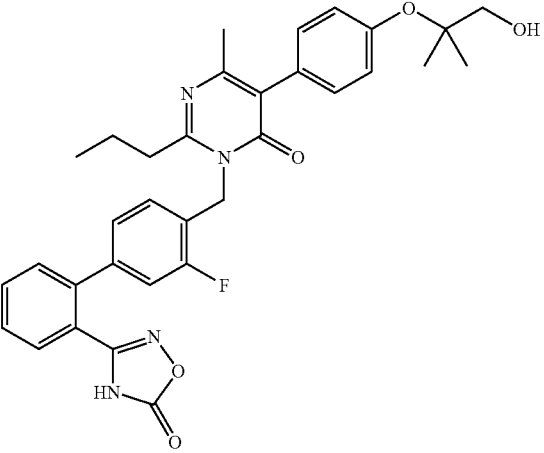

509b) 3-{[3-fluoro-2'-(5-oxo-4,5-dihydro-1,2,4-oxadiazol-3-yl)biphenyl-4-yl]methyl}-5-[4-(2-hydroxy-1,1-dimethylethoxy)phenyl]-6-methyl-2-propylpyrimidin-4(3H)-one A mixture of hydroxylammonium chloride (0.69 g), sodium hydrogen carbonate (0.99 g) and dimethyl sulfoxide (10 mL) was stirred at 40° C. for 30 min, 4'-{[5-[4-(2-{[tert-butyl(dimethyl)silyl]oxy}-1,1-dimethylethoxy)phenyl]-4-methyl-6-oxo-2-propylpyrimidin-1(6H)-yl]methyl}-3'-fluorobiphenyl-2-carbonitrile (0.76 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.29 g) and then 1,8-diazabicyclo[5.4.0]undec-7-ene (0.26 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), tetrabutylammonium fluoride tetrahydrofuran solution (1 mol/L, 2.3 mL) was added, and the mixture was stirred at room temperature for 3 hr. The solvent was evaporated from the reaction mixture under reduced pressure. The residue was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.3 g, 68%).

$^1$H NMR (300 MHz, DMSO-d$_6$) δ 0.91 (t, J=7.4, 3 H), 1.04 (d, J=6.0, 3 H), 1.22 (s, 6 H), 1.60-1.75 (m, 2 H), 2.69 (t, J=7.5, 2 H), 3.40 (d, J=5.6, 2 H), 4.85-4.99 (m, 1 H), 5.35 (s, 2 H), 6.99-7.14 (m, 4 H), 7.16-7.28 (m, 3 H), 7.52-7.64 (m, 2 H), 7.67-7.75 (m, 2 H), 12.48 (s, 1 H)

Example 510

2-butyl-6-cyclopropyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}pyrimidin-4(3H)-one

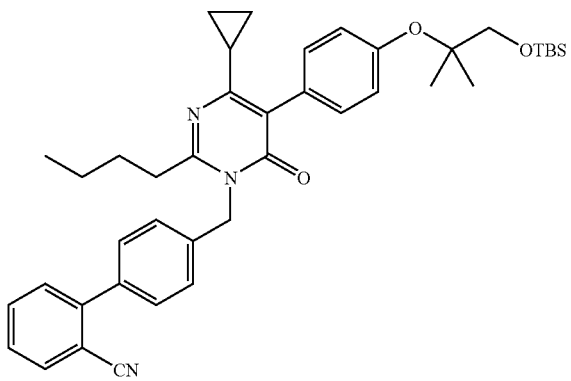

510a) 4'-{[2-butyl-5-[4-(2-{[tert-butyl(dimethyl)silyl]oxy}-1,1-dimethylethoxy)phenyl]-4-cyclopropyl-6-oxopyrimidin-1(6H)-yl]methyl}biphenyl-2-carbonitrile A mixture of 4'-[(5-bromo-2-butyl-4-cyclopropyl-6-oxopyrimidin-1(6H)-yl)methyl]biphenyl-2-carbonitrile (0.6 g), [4-(2-{[tert-butyl(dimethyl)silyl]oxy}-1,1-dimethylethoxy)phenyl]boronic acid (0.79 g), [1,1'-bis(diphenylphosphino)ferrocene]dichloropalladium(II) dichloromethane adduct (0.06 g), 2 M aqueous cesium carbonate solution (6 mL) and 1,4-dioxane (6 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.69 g, 80%).

$^1$H NMR (300 MHz, CDCl$_3$) δ 0.00 (s, 6 H), 0.70-0.78 (m, 2 H), 0.79-0.87 (m, 12 H), 1.04-1.11 (m, 2 H), 1.20-1.35 (m, 8 H), 1.54-1.67 (m, 2 H), 1.72-1.85 (m, 1 H), 2.59 (t, J=7.4, 2 H), 3.51 (s, 2 H), 5.27 (s, 2 H), 6.95-7.04 (m, 2 H), 7.23-7.47 (m, 8 H), 7.50-7.57 (m, 1 H), 7.65 (dd, J=7.7, 0.9, 1H)

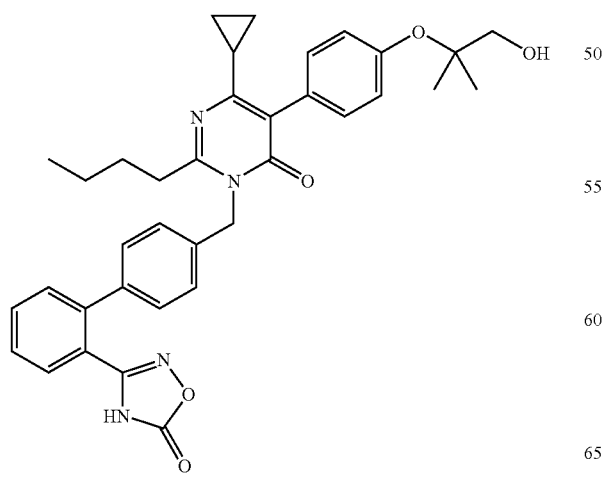

510b) 2-butyl-6-cyclopropyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}pyrimidin-4(3H)-one A mixture of hydroxylammonium chloride (0.62 g), sodium hydrogen carbonate (0.87 g) and dimethyl sulfoxide (10 mL) was stirred at 40° C. for 30 min, 4'-{[2-butyl-5-[4-(2-{[tert-butyl(dimethyl)silyl]oxy}-1,1-dimethylethoxy)phenyl]-4-cyclopropyl-6-oxopyrimidin-1(6H)-yl]methyl}biphenyl-2-carbonitrile (0.69 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.25 g) and then 1,8-diazabicyclo[5.4.0]undec-7-ene (0.23 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), tetrabutylammonium fluoride tetrahydrofuran solution (1 mol/L, 1.5 mL) was added, and the mixture was stirred at room temperature for 3 hr. The solvent was evaporated from the reaction mixture under reduced pressure. The residue was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.29 g, 65%).

$^1$H NMR (300 MHz, DMSO-d$_6$) δ 0.81-0.91 (m, 6 H), 0.93-1.01 (m, 2 H), 1.24-1.41 (m, 8 H), 1.52-1.66 (m, 2 H), 1.73-1.85 (m, 1 H), 2.63-2.75 (m, 1 H), 3.13-3.28 (m, 1 H), 3.45 (s, 2 H), 5.35 (s, 2 H), 7.07-7.14 (m, 2 H), 7.23-7.40 (m, 6 H), 7.49-7.62 (m, 2 H), 7.66-7.74 (m, 2 H), 12.04 (s, 1 H)

Example 511

6-ethyl-3-{[3-fluoro-2'-(5-oxo-4,5-dihydro-1,2,4-oxadiazol-3-yl)biphenyl-4-yl]methyl}-5-[4-(2-hydroxy-1,1-dimethylethoxy)phenyl]-2-propylpyrimidin-4(3H)-one

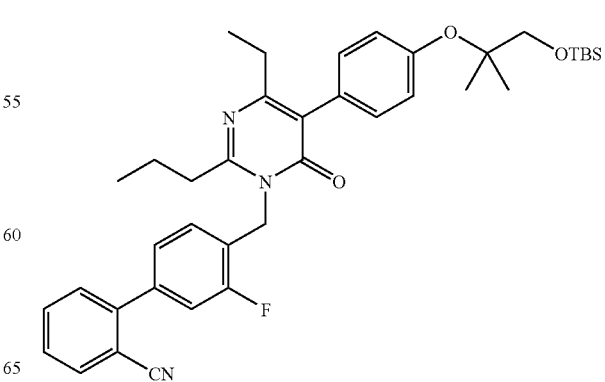

511a) 4'-{[5-[4-(2-{[tert-butyl(dimethyl)silyl]oxy}-1,1-dimethylethoxy)phenyl]-4-ethyl-6-oxo-2-propylpyrimidin-1(6H)-yl]methyl}-3'-fluorobiphenyl-2-carbonitrile A mixture of 4'-[(5-bromo-4-ethyl-6-oxo-2-propylpyrimidin-1(6H)-yl)methyl]-3'-fluorobiphenyl-2-carbonitrile (0.6 g), [4-(2-{[tert-butyl(dimethyl)silyl]oxy}-1,1-dimethylethoxy)phenyl]boronic acid (0.84 g), [1,1'-bis(diphenylphosphino)ferrocene]dichloropalladium(II) dichloromethane adduct (0.06 g), 2 M aqueous cesium carbonate solution (6 mL) and 1,4-dioxane (6 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.78 g, 90%).

$^1$H NMR (300 MHz, CDCl$_3$) δ 0.00 (s, 6H), 0.84 (s, 9H), 0.95 (t, J=7.4, 3 H), 1.10 (t, J=7.5, 3 H), 1.22 (s, 6 H), 1.67-1.82 (m, 2 H), 2.39 (q, J=7.5, 2 H), 2.60-2.69 (m, 2 H), 3.51 (s, 2 H), 5.33 (s, 2 H), 6.94-7.01 (m, 2 H), 7.10-7.24 (m, 5H), 7.33-7.41 (m, 2 H), 7.52-7.60 (m, 1 H), 7.65-7.70 (m, 1 H)

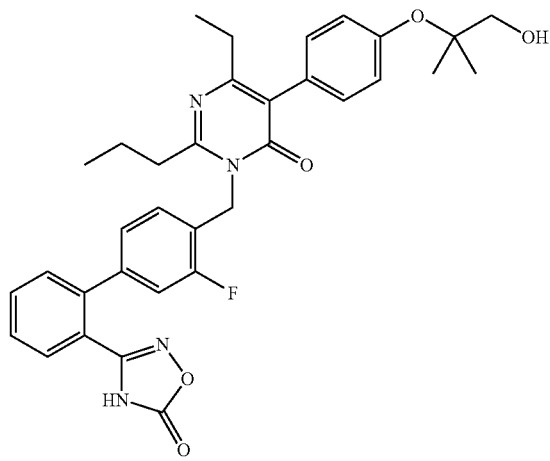

511b) 6-ethyl-3-{[3-fluoro-2'-(5-oxo-4,5-dihydro-1,2,4-oxadiazol-3-yl)biphenyl-4-yl]methyl}-5-[4-(2-hydroxy-1,1-dimethylethoxy)phenyl]-2-propylpyrimidin-4(3H)-one A mixture of hydroxylammonium chloride (0.66 g), sodium hydrogen carbonate (0.95 g) and dimethyl sulfoxide (10 mL) was stirred at 40° C. for 30 min, 4'-{[5-[4-(2-{[tert-butyl(dimethyl)silyl]oxy}-1,1-dimethylethoxy)phenyl]-4-ethyl-6-oxo-2-propylpyrimidin-1(6H)-yl]methyl}-3'-fluorobiphenyl-2-carbonitrile (0.74 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.27 g) and then 1,8-diazabicyclo[5.4.0]undec-7-ene (0.25 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), tetrabutylammonium fluoride tetrahydrofuran solution (1 mol/L, 2.4 mL) was added, and the mixture was stirred at room temperature for 3 hr. The solvent was evaporated from the reaction mixture under reduced pressure. The residue was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.39 g, 82%).

$^1$H NMR (300 MHz, DMSO-d$_6$) δ 0.92 (t, J=7.4, 3 H), 1.11 (t, J=7.5, 3 H), 1.23 (s, 6 H), 1.61-1.78 (m, 2 H), 2.37 (q, J=7.5, 2 H), 2.71 (t, J=7.4, 2 H), 3.22-3.46 (m, 4 H), 5.34 (s, 2 H), 6.99-7.20 (m, 6 H), 7.22-7.30 (m, 1 H), 7.53-7.63 (m, 2 H), 7.67-7.75 (m, 2 H), 12.48 (s, 1 H)

Example 512

6-ethyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}-2-propylpyrimidin-4(3H)-one

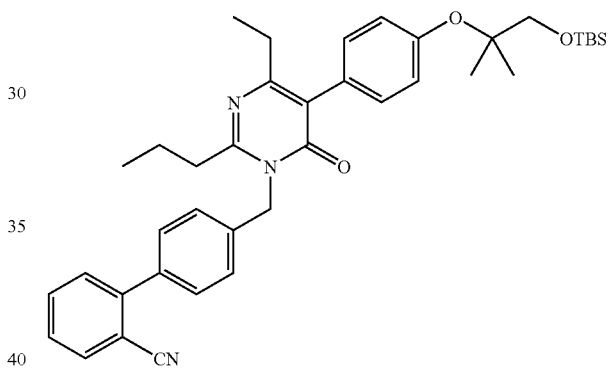

512a) 4'-{[5-[4-(2-{[tert-butyl(dimethyl)silyl]oxy}-1,1-dimethylethoxy)phenyl]-4-ethyl-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.6 g), [4-(2-{[tert-butyl(dimethyl)silyl]oxy}-1,1-dimethylethoxy)phenyl]boronic acid (0.84 g), [1,1'-bis(diphenylphosphino)ferrocene]dichloropalladium(II) dichloromethane adduct (0.06 g), 2 M aqueous cesium carbonate solution (6 mL) and 1,4-dioxane (6 mL) was stirred at 100° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.99 g, 85%).

$^1$H NMR (300 MHz, CDCl$_3$) δ 0.00 (s, 6 H), 0.84 (s, 9 H), 0.92 (t, J=7.4, 3 H), 1.09 (t, J=7.5, 3 H), 1.22 (s, 6 H), 1.66-1.80 (m, 2 H), 2.39 (q, J=7.5, 2 H), 2.61-2.67 (m, 2 H), 3.51 (s, 2 H), 5.29 (s, 2 H), 6.94-7.02 (m, 2 H), 7.11-7.17 (m, 2 H), 7.22-7.41 (m, 4 H), 7.42-7.47 (m, 2 H), 7.50-7.56 (m, 1 H), 7.65 (dd, J=7.8, 0.9, 1 H)

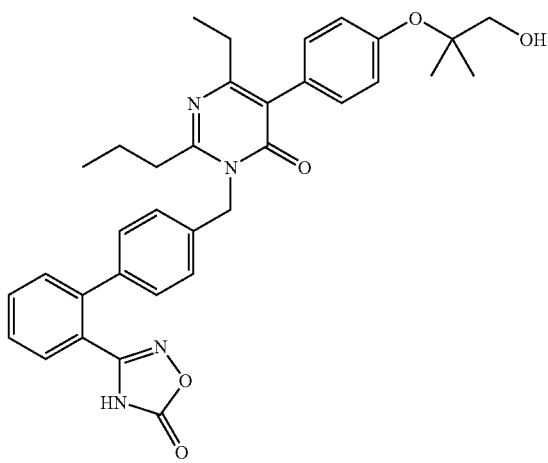

512b) 6-ethyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.92 g), sodium hydrogen carbonate (1.31 g) and dimethyl sulfoxide (12 mL) was stirred at 40° C. for 30 min, 4'-{[5-[4-(2-{[tert-butyl(dimethyl)silyl]oxy}-1,1-dimethylethoxy)phenyl]-4-ethyl-6-oxo-2-propylpyrimidin-1(6H)-yl]methyl}biphenyl-2-carbonitrile (0.99 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (12 mL). N,N'-carbonyldiimidazole (0.38 g) and then 1,8-diazabicyclo[5.4.0]undec-7-ene (0.35 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL), tetrabutylammonium fluoride tetrahydrofuran solution (1 mol/L, 2.6 mL) was added, and the mixture was stirred at room temperature for 3 hr. The solvent was evaporated from the reaction mixture under reduced pressure. The residue was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.38 g, 75%).

$^1$H NMR (300 MHz, DMSO-$d_6$) δ 0.90 (t, J=7.4, 3 H), 1.11 (t, J=7.5, 3 H), 1.24 (s, 6 H), 1.59-1.74 (m, 2 H), 2.37 (q, J=7.4, 2 H), 2.65-2.74 (m, 2 H), 3.42 (s, 2 H), 5.35 (s, 2 H), 7.05 (d, J=8.5, 2 H), 7.19 (d, J=8.5, 2 H), 7.24-7.36 (m, 4 H), 7.50-7.62 (m, 2 H), 7.65-7.74 (m, 2 H), 12.40 (s, 1 H)

Example 513

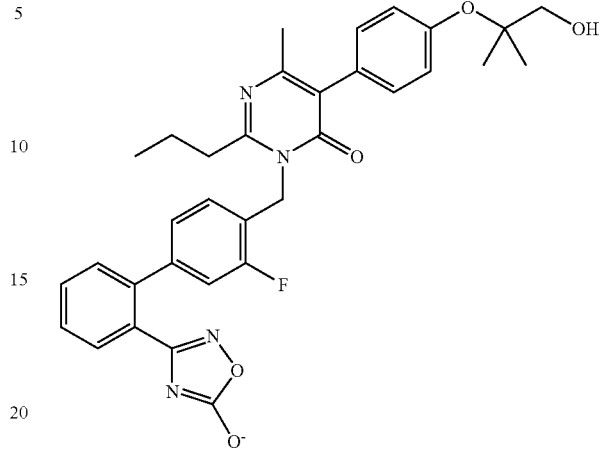

3-{[3-fluoro-2'-(5-oxo-4,5-dihydro-1,2,4-oxadiazol-3-yl)biphenyl-4-yl]methyl}-5-[4-(2-hydroxy-1,1-dimethylethoxy)phenyl]-6-methyl-2-propylpyrimidin-4(3H)-one potassium salt To a mixture of 3-{[3-fluoro-2'-(5-oxo-4,5-dihydro-1,2,4-oxadiazol-3-yl)biphenyl-4-yl]methyl}-5-[4-(2-hydroxy-1,1-dimethylethoxy)phenyl]-6-methyl-2-propylpyrimidin-4(3H)-one (0.2 g) and ethanol (4 mL) was added dropwise 0.1 M potassium hydroxide-ethanol solution (3.5 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.19 g, 87%).

$^1$H NMR (300 MHz, DMSO-$d_6$) δ 0.93 (t, J=7.4, 3 H), 1.22 (s, 6 H), 1.62-1.77 (m, 2 H), 2.13 (s, 3 H), 2.71 (t, J=7.5, 2 H), 3.37-3.49 (m, 3 H), 5.32 (s, 2 H), 6.91-7.07 (m, 3 H), 7.08-7.25 (m, 4 H), 7.34-7.52 (m, 3 H), 7.53-7.59 (m, 1H)

Example 514

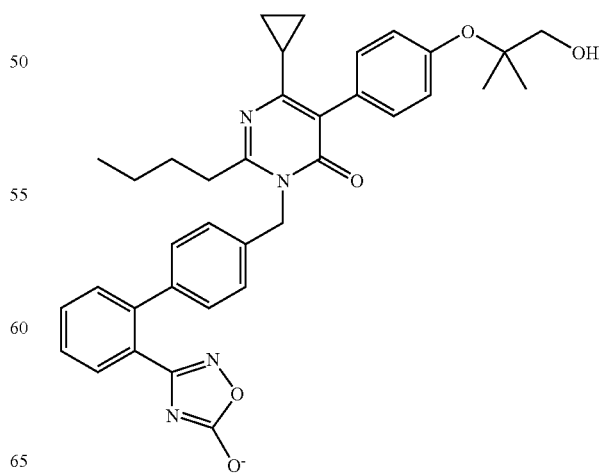

2-butyl-6-cyclopropyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}pyrimidin-4(3H)-one potassium salt To a mixture of 2-butyl-6-cyclopropyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}pyrimidin-4(3H)-one (0.2 g) and ethanol (4 mL) was added dropwise 0.1 M potassium hydroxide-ethanol solution (3.5 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.2 g, 95%).

$^1$H NMR (300 MHz, DMSO-$d_6$) δ 0.84-0.91 (m, 6 H), 0.93-0.99 (m, 2 H), 1.25-1.42 (m, 8 H), 1.56-1.68 (m, 2 H), 1.72-1.85 (m, 1 H), 2.67-2.79 (m, 2 H), 3.15-3.25 (m, 1 H), 3.37-3.47 (m, 1 H), 5.32 (s, 2 H), 7.10 (d, J=8.48, 2 H), 7.17 (d, J=8.29, 2 H), 7.30-7.50 (m, 7 H), 7.56 (dd, J=7.35, 1.51, 1 H)

Example 515

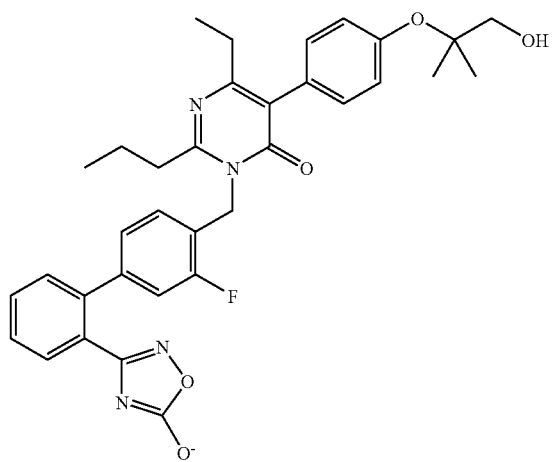

6-ethyl-3-{[3-fluoro-2'-(5-oxo-4,5-dihydro-1,2,4-oxadiazol-3-yl)biphenyl-4-yl]methyl}-5-[4-(2-hydroxy-1,1-dimethylethoxy)phenyl]-2-propylpyrimidin-4(3H)-one potassium salt To a mixture of 6-ethyl-3-{[3-fluoro-2'-(5-oxo-4,5-dihydro-1,2,4-oxadiazol-3-yl)biphenyl-4-yl]methyl}-5-[4-(2-hydroxy-1,1-dimethylethoxy)phenyl]-2-propylpyrimidin-4(3H)-one (0.2 g) and ethanol (4 mL) was added dropwise 0.1 M potassium hydroxide-ethanol solution (3.5 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.18 g, 96%).

$^1$H NMR (300 MHz, DMSO-$d_6$) δ 0.94 (t, J=7.4, 3 H), 1.12 (t, J=7.5, 3 H), 1.23 (s, 6 H), 1.66-1.80 (m, 2 H), 2.37 (q, J=7.5, 2 H), 2.70-2.77 (m, 2 H), 3.38-3.49 (m, 3 H), 5.32 (s, 2 H), 6.93-7.07 (m, 3 H), 7.09-7.21 (m, 4 H), 7.35-7.54 (m, 3 H), 7.56-7.61 (m, 1 H)

Example 516

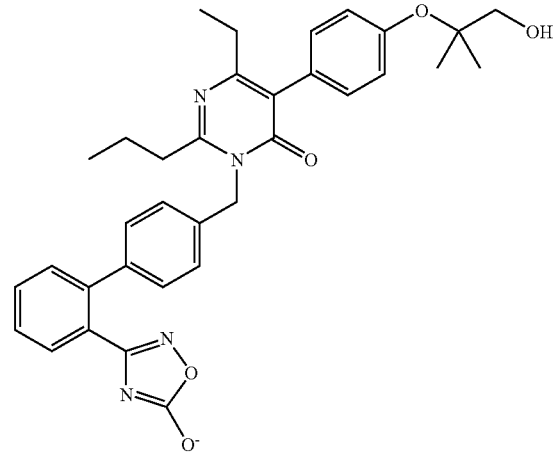

6-ethyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}-2-propylpyrimidin-4(3H)-one potassium salt To a mixture of 6-ethyl-5-[4-(2-hydroxy-1,1-dimethylethoxy)phenyl]-3-{[2'-(5-oxo-4,5-dihydro-1,2,4-oxadiazol-3-yl)biphenyl-4-yl]methyl}-2-propylpyrimidin-4(3H)-one (0.2 g) and ethanol (4 mL) was added dropwise 0.1 M potassium hydroxide-ethanol solution (3.5 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.21 g, 93%).

$^1$H NMR (300 MHz, DMSO-$d_6$) δ 0.92 (t, J=7.4, 3 H), 1.11 (t, J=7.5, 3 H), 1.23 (s, 6 H), 1.62-1.76 (m, 2 H), 2.36 (q, J=7.5, 2 H), 2.67-2.75 (m, 2 H), 3.41 (s, 2 H), 5.31 (s, 2 H), 7.02-7.08 (m, 2 H), 7.14-7.23 (m, 4 H), 7.28-7.32 (m, 2 H), 7.34-7.40 (m, 1 H), 7.43 (dd, J=7.44, 1.41, 1 H), 7.46-7.59 (m, 2 H)

Example 517

6-ethyl-5-[4-(2-hydroxy-1,1-dimethylethoxy)phenoxy]-3-{[2'-(5-oxo-4,5-dihydro-1,2,4-oxadiazol-3-yl)biphenyl-4-yl]methyl}-2-propylpyrimidin-4(3H)-one

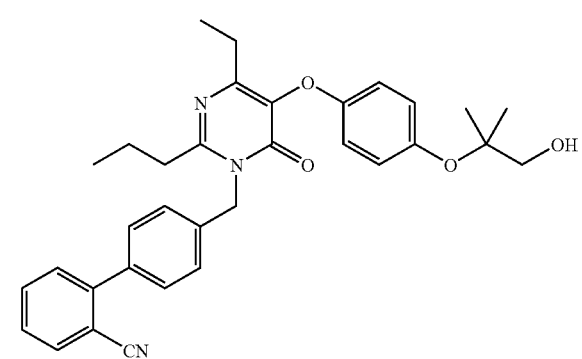

517a) 4'-{[4-ethyl-5-[4-(2-hydroxy-1,1-dimethyl-ethoxy)phenoxy]-6-oxo-2-propylpyrimidin-1(6H)-yl]methyl}biphenyl-2-carbonitrile A mixture of 4'-[(5-bromo-4-ethyl-6-oxo-2-propylpyrimidin-1(6H)-yl)methyl]biphenyl-2-carbonitrile (0.52 g), 4-(2-hydroxy-1,1-dimethylethoxy)phenol (0.32 g), 8 M potassium hydroxide solution (0.22 mL) and dimethyl sulfoxide (8 mL) was stirred at 150° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.36 g, 58%).

$^1$H NMR (300 MHz, CDCl$_3$) δ 1.00 (t, J=7.4, 3 H), 1.16-1.29 (m, 10 H), 1.73-1.86 (m, 2 H), 2.39-2.50 (m, 1 H), 2.62 (q, J=7.5, 2 H), 2.67-2.74 (m, 2 H), 3.52-3.58 (m, 1 H), 5.35 (s, 2 H), 6.81-6.93 (m, 4 H), 7.28-7.34 (m, 2 H), 7.40-7.50 (m, 2 H), 7.52-7.56 (m, 2 H), 7.60-7.67 (m, 1 H), 7.73-7.78 (m, 1 )

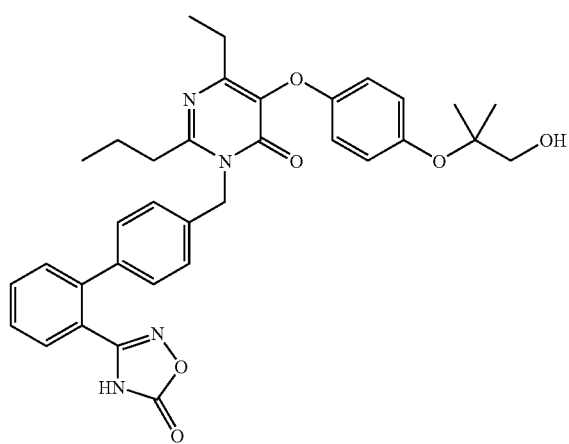

517b) 6-ethyl-5-[4-(2-hydroxy-1,1-dimethylethoxy)phenoxy]-3-{[2'-(5-oxo-4,5-dihydro-1,2,4-oxadiazol-3-yl)biphenyl-4-yl]methyl}-2-propylpyrimidin-4(3H)-one A mixture of 4'-{[4-ethyl-5-[4-(2-hydroxy-1,1-dimethylethoxy)phenoxy]-6-oxo-2-propylpyrimidin-1(6H)-yl]methyl}biphenyl-2-carbonitrile (0.36 g), tert-butyl(chloro)dimethylsilane (0.12 g), imidazole (0.14 g) and N,N'-dimethylformamide (10 mL) were stirred at room temperature for 12 hr. The reaction mixture was diluted with ethyl acetate, washed with water and then with saturated brine, and dried over anhydrous magnesium sulfate. The solvent was evaporated under reduced pressure.

A mixture of hydroxylammonium chloride (0.34 g), sodium hydrogen carbonate (0.48 g) and dimethyl sulfoxide (10 mL) was stirred at 40° C. for 30 min, the concentrate obtained above was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL) N,N'-carbonyldiimidazole (0.14 g) and then 1,8-diazabicyclo[5.4.0]undec-7-ene (0.13 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (5 mL), tetrabutylammonium fluoride tetrahydrofuran solution (1 mol/L, 1.3 mL) was added, and the mixture was stirred at room temperature for 3 hr. The solvent was evaporated from the reaction mixture under reduced pressure. The residue was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.15 g, 39%).

$^1$H NMR (300 MHz, DMSO-d$_6$) δ 0.87-1.02 (m, 6 H), 1.11-1.25 (m, 8 H), 1.62-1.78 (m, 2 H), 2.46-2.62 (m, 2 H), 2.67-2.76 (m, 2 H), 3.57-3.71 (m, 1 H), 5.37 (s, 2 H), 6.80-6.87 (m, 2 H), 6.94-7.00 (m, 2 H), 7.23-7.30 (m, 2 H), 7.34-7.38 (m, 2 H), 7.52-7.64 (m, 2 H), 7.67-7.76 (m, 2 H), 12.39 (s, 1 H)

Example 518

5-[4-(2,2-dimethylpropoxy)phenyl]-6-ethyl-3-{[2'-(5-oxo-4,5-dihydro-1,2,4-oxadiazol-3-yl)biphenyl-4-yl]methyl}-2-propylpyrimidin-4(3H)-one

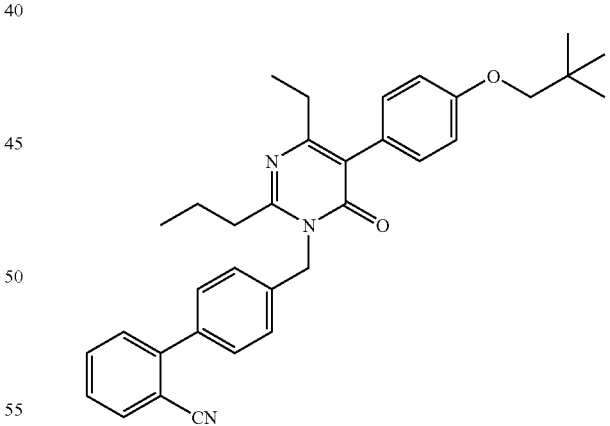

518a) 4'-{[5-[4-(2,2-dimethylpropoxy)phenyl]-4-ethyl-6-oxo-2-propylpyrimidin-1(6H)-yl]methyl}biphenyl-2-carbonitrile A mixture of 4'-{[4-ethyl-5-(4-hydroxyphenyl)-6-oxo-2-propylpyrimidin-1(6H)-yl]methyl}biphenyl-2-carbonitrile (0.52 g), 1-iodo-2,2-dimethylpropane (0.29 g), cesium carbonate (0.45 g) and dimethylformamide (10 mL) were stirred at 80° C. for 12 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.37 g, 62%).

$^1$H NMR (300 MHz, CDCl$_3$) δ 0.98-1.07 (m, 12 H), 1.18 (t, J=7.6, 3 H), 1.74-1.89 (m, 2 H), 2.49 (q, J=7.6, 2 H), 2.68-2.75 (m, 2 H), 3.61 (s, 2 H), 5.37 (s, 2 H), 6.93-7.00 (m, 2 H), 7.20-7.27 (m, 2 H), 7.34-7.56 (m, 6 H), 7.58-7.65 (m, 1 H), 7.72-7.76 (m, 1 H)

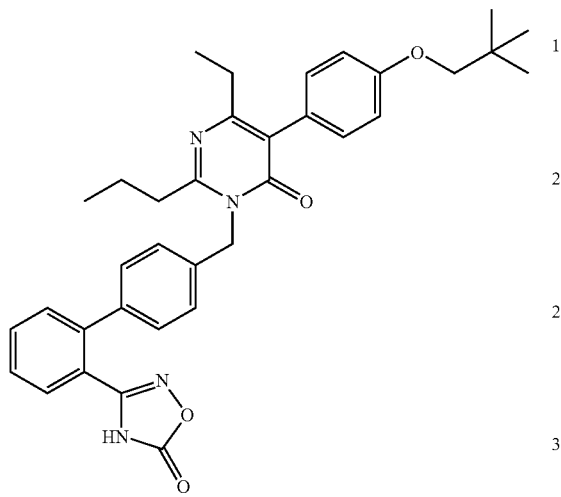

518b) 5-[4-(2,2-dimethylpropoxy)phenyl]-6-ethyl-3-{[2'-(5-oxo-4,5-dihydro-1,2,4-oxadiazol-3-yl)biphenyl-4-yl]methyl}-2-propylpyrimidin-4(3H)-one A mixture of hydroxylammonium chloride (0.42 g), sodium hydrogen carbonate (0.6 g) and dimethyl sulfoxide (10 mL) was stirred at 40° C. for 30 min, 4'-{[5-[4-(2,2-dimethylpropoxy)phenyl]-4-ethyl-6-oxo-2-propylpyrimidin-1(6H)-yl]methyl}biphenyl-2-carbonitrile (0.37 g) was added, and the mixture was stirred at 90° C. for 12 hr. The reaction mixture was diluted with ethyl acetate, washed with water and then with saturated brine, and dried over anhydrous magnesium sulfate. The solvent was evaporated under reduced pressure. The residue was dissolved in tetrahydrofuran (10 mL). N,N'-carbonyldiimidazole (0.17 g) and then 1,8-diazabicyclo[5.4.0]undec-7-ene (0.16 mL) were added, and the mixture was stirred at room temperature for 2 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless amorphous solid (0.2 g, 65%).

$^1$H NMR (300 MHz, DMSO-d$_6$) δ 0.89 (t, J=7.4, 3 H), 1.02 (s, 9 H), 1.10 (t, J=7.4, 3 H), 1.52-1.73 (m, 2 H), 2.36 (q, J=7.5, 2 H), 2.64-2.72 (m, 2 H), 3.66 (s, 2 H), 5.34 (s, 2 H), 6.92-7.02 (m, 2 H), 7.14-7.22 (m, 2 H), 7.22-7.28 (m, 2 H), 7.30-7.35 (m, 2 H), 7.50-7.60 (m, 2 H), 7.64-7.73 (m, 2 H), 12.40 (s, 1 H)

Example 519

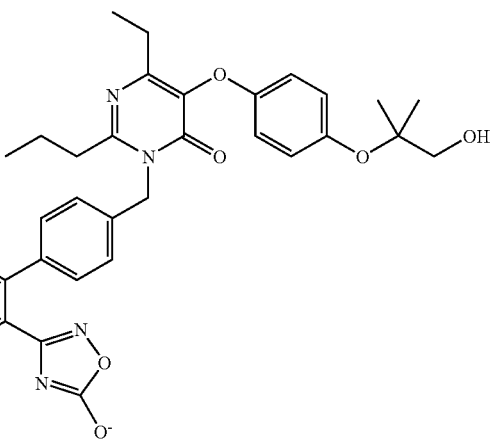

6-ethyl-5-[4-(2-hydroxy-1,1-dimethylethoxy)phenoxy]-3-{[2'-(5-oxo-4,5-dihydro-1,2,4-oxadiazol-3-yl)biphenyl-4-yl]methyl}-2-propylpyrimidin-4(3H)-one potassium salt To a mixture of 6-ethyl-5-[4-(2-hydroxy-1,1-dimethylethoxy)phenoxy]-3-{[2'-(5-oxo-4,5-dihydro-1,2,4-oxadiazol-3-yl)biphenyl-4-yl]methyl}-2-propylpyrimidin-4(3H)-one (0.13 g) and ethanol (3 mL) was added dropwise 0.1 M potassium hydroxide-ethanol solution (2.2 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.13 g, 90%).

$^1$H NMR (300 MHz, DMSO-d$_6$) δ 0.92 (t, J=7.4, 3 H), 1.07-1.17 (m, 9 H), 1.59-1.78 (m, 2 H), 2.65-2.75 (m, 2 H), 3.27-3.39 (m, 4 H), 4.83-4.95 (m, 1 H), 5.28 (s, 2 H), 6.75-6.82 (m, 2 H), 6.89-6.98 (m, 2 H), 7.09 (d, J=8.3, 2 H), 7.25-7.33 (m, 3 H), 7.33-7.46 (m, 2 H), 7.51 (dd, J=7.4, 1.5, 1 H)

Example 520

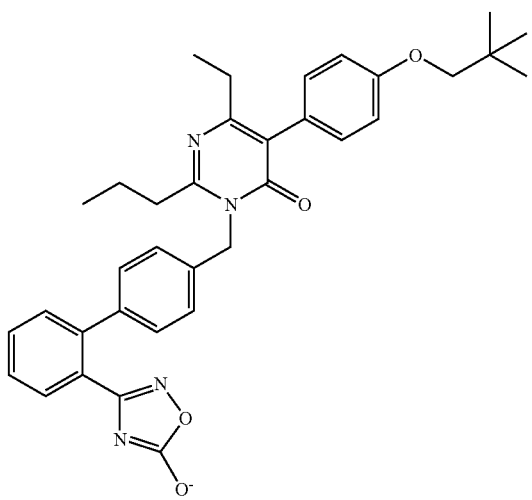

5-[4-(2,2-dimethylpropoxy)phenyl]-6-ethyl-3-{[2'-(5-oxo-4,5-dihydro-1,2,4-oxadiazol-3-yl)biphenyl-4-yl]methyl}-2-propylpyrimidin-4(3H)-one potassium salt To a mixture of 5-[4-(2,2-dimethylpropoxy)phenyl]-6-ethyl-3-{[2'-(5-oxo-4,5-dihydro-1,2,4-oxadiazol-3-yl)biphenyl-4-yl]methyl}-2-propylpyrimidin-4(3H)-one (0.19 g) and ethanol (4 mL) was added dropwise 0.1 M potassium hydroxide-ethanol solution (3.3 mL), and the mixture was stirred at room temperature for 6 hr. The solvent was evaporated from the reaction mixture under reduced pressure to give crude crystals. The crude crystals were recrystallized from hexane-diisopropyl ether (5:1) to give the title compound as colorless crystals (0.2 g, 97%).

$^1$H NMR (300 MHz, DMSO-$d_6$) δ 0.92 (t, J=7.4, 3 H), 1.02 (s, 9 H), 1.10 (t, J=7.4, 3 H), 1.62-1.78 (m, 2 H), 2.36 (q, J=7.4, 2 H), 2.66-2.75 (m, 2 H), 3.66 (s, 2 H), 5.29 (s, 2 H), 6.96 (d, J=8.7, 2 H), 7.09-7.25 (m, 4 H), 7.27-7.33 (m, 3 H), 7.33-7.47 (m, 2 H), 7.49-7.53 (m, 1 H)

Example 521

6-ethyl-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one potassium salt

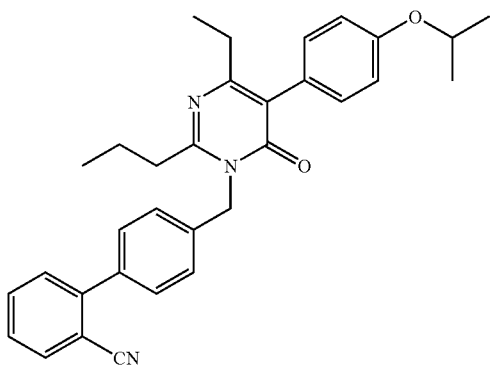

521a) 4'-{[4-ethyl-5-(4-isopropoxyphenyl)-6-oxo-2-propylpyrimidin-1(6H)-yl]methyl}biphenyl-2-carbonitrile A mixture of (4-isopropoxyphenyl)boronic acid (0.31 g), [1,1'-bis(diphenylphosphino)ferrocene]dichloropalladium (0.05 g) and 4'-[(5-bromo-4-ethyl-6-oxo-2-propylpyrimidin-1(6H)-yl)methyl]biphenyl-2-carbonitrile (0.5 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate and concentrated. The residue was purified by silica gel column chromatography to give the title compound as a colorless solid (0.50 g, 89%).

$^1$H NMR (300 MHz, CDCl$_3$-d) δ 1.02 (3 H, t, J=7.4 Hz), 1.18 (3 H, t, J=7.4 Hz), 1.35 (3 H, d, J=6.0 Hz), 1.36 (3 H, s), 1.74-1.89 (2 H, m), 2.49 (2 H, q, J=7.4 Hz), 2.68-2.77 (2 H, m), 4.50-4.64 (1 H, m), 5.37 (2 H, s), 6.93 (2 H, d, J=8.67 Hz), 7.22 (2 H, d, J=8.8 Hz), 7.36 (2 H, d, J=8.4 Hz), 7.41-7.56 (4 H, m), 7.60-7.68 (1 H, m), 7.76 (1 H, dd, J=7.7, 0.94 Hz)

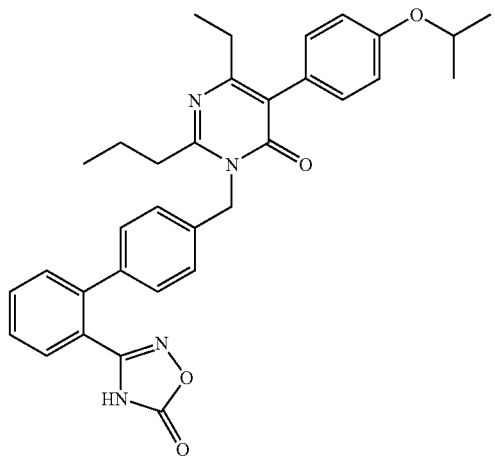

521b) 6-ethyl-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one 4'-{[4-Ethyl-5-(4-isopropoxyphenyl)-6-oxo-2-propylpyrimidin-1(6H)-yl]methyl}biphenyl-2-carbonitrile (0.5 g) was dissolved in dimethyl sulfoxide (5 mL), and hydroxylamine hydrochloride (0.71 g) and sodium hydrogen carbonate (1 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.25 g) and 1,8-diazabicyclo[5.4.0]undec-7-ene (0.23 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.44 g, 79%).

$^1$H NMR (300 MHz, DMSO-$d_6$) δ 0.89 (3 H, t, J=7.3 Hz), 1.10 (3 H, t, J=7.4 Hz), 1.29 (6 H, d, J=6.0 Hz), 1.58-1.73 (2 H, m), 2.37 (2 H, q, J=7.4 Hz), 2.68 (2 H, t, J=7.4 Hz), 4.57-4.70 (1 H, m), 5.34 (2 H, s), 6.90-6.97 (2 H, m), 7.14-7.21 (2 H, m), 7.23-7.35 (4 H, m), 7.49-7.61 (2 H, m), 7.63-7.74 (2 H, m), 12.39 (1 H, s)

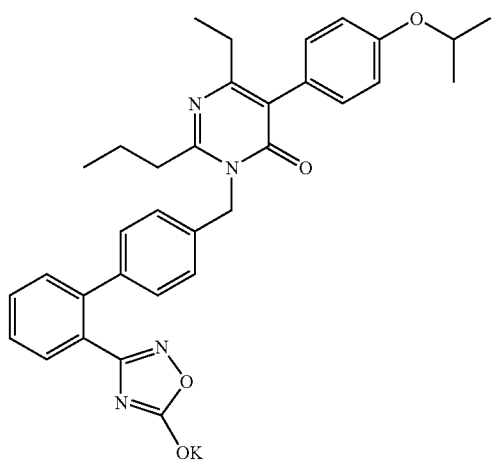

521c) 6-ethyl-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one potassium salt 6-Ethyl-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one (0.3 g) was dissolved in ethanol (3 mL), and 8 M potassium hydroxide solution (0.07 mL) was added. The mixture was stirred for 1 hr. Ethanol was removed in vacuo, diethyl ether was added, and the resulting solid was collected by filtration to give the title compound as a colorless solid (0.32 g, 99%).

$^1$H NMR (300 MHz, DMSO-$d_6$) δ 0.92 (3 H, t, J=7.38 Hz), 1.10 (3 H, t, J=7.57 Hz), 1.28 (3 H, s), 1.30 (3 H, s), 1.61-1.77 (2 H, m), 2.36 (2 H, q, J=7.45 Hz), 2.71 (2 H, t, J=7.38 Hz), 4.57-4.71 (1 H, m), 5.29 (2 H, s), 6.93 (2 H, d, J=8.71 Hz), 7.09-7.22 (4 H, m), 7.26-7.46 (5 H, m), 7.50 (1 H, dd, J=7.57, 1.51 Hz)

Example 522

2-butyl-5-(4-isopropoxyphenyl)-6-methyl-3-{[2'-(5-oxo-4,5-dihydro-1,2,4-oxadiazol-3-yl)biphenyl-4-yl]methyl}pyrimidin-4(3H)-one potassium salt

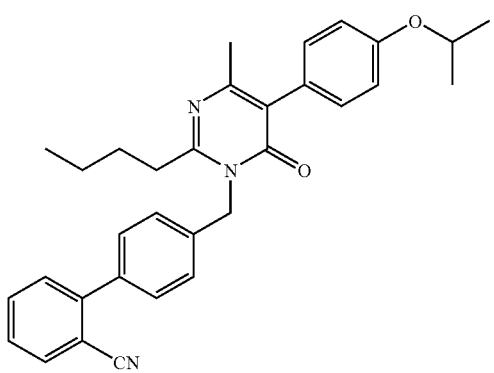

522a) 4'-{[2-butyl-5-(4-isopropoxyphenyl)-4-methyl-6-oxopyrimidin-1(6H)-yl]methyl}biphenyl-2-carbonitrile A mixture of (4-isopropoxyphenyl)boronic acid (0.31 g), [1,1'-bis(diphenylphosphino)ferrocene]dichloropalladium (0.05 g) and 4'-[(5-bromo-2-butyl-4-methyl-6-oxopyrimidin-1(6H)-yl)methyl]biphenyl-2-carbonitrile (0.5 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate and concentrated. The residue was purified by silica gel column chromatography to give the title compound as a colorless solid (0.56 g, 99%).

$^1$H NMR (300 MHz, CDCl$_3$) δ 0.93 (3 H, t, J=7.3 Hz), 1.32-1.49 (2 H, m), 1.35 (6 H, d, J=6.0 Hz), 1.66-1.79 (2 H, m), 2.24 (3 H, s), 2.69-2.78 (2 H, m), 4.50-4.65 (1 H, m), 5.38 (2 H, s), 6.89-6.97 (2 H, m), 7.21-7.29 (2 H, m), 7.35 (2 H, d, J=8.4 Hz), 7.40-7.56 (4 H, m), 7.60-7.68 (1 H, m), 7.76 (1 H, dd, J=7.8, 0.85 Hz)

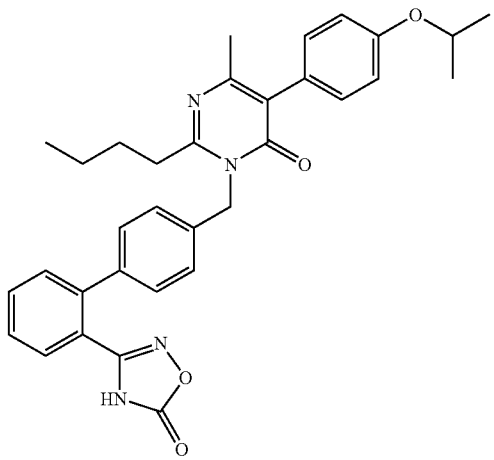

522b) 2-butyl-5-(4-isopropoxyphenyl)-6-methyl-3-{[2'-(5-oxo-4,5-dihydro-1,2,4-oxadiazol-3-yl)biphenyl-4-yl]methyl}pyrimidin-4(3H)-one 4'-{[2-Butyl-5-(4-isopropoxyphenyl)-4-methyl-6-oxopyrimidin-1(6H)-yl]methyl}biphenyl-2-carbonitrile (0.56 g) was dissolved in dimethyl sulfoxide (5 mL), and hydroxylamine hydrochloride (0.79 g) and sodium hydrogen carbonate (1.2 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.28 g) and 1,8-diazabicyclo[5.4.0]undec-7-ene (0.26 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.49 g, 78%).

$^1$H NMR (300 MHz, DMSO-$d_6$) δ 0.82 (3 H, t, J=7.5 Hz), 1.21-1.38 (8 H, m), 1.51-1.65 (2 H, m), 2.13 (3 H, s), 2.63-2.73 (2 H, m), 4.56-4.72 (1 H, m), 5.35 (2 H, s), 6.89-6.97 (2 H, m), 7.16-7.36 (6 H, m), 7.48-7.61 (2 H, m), 7.63-7.74 (2 H, m), 12.40 (1 H, s)

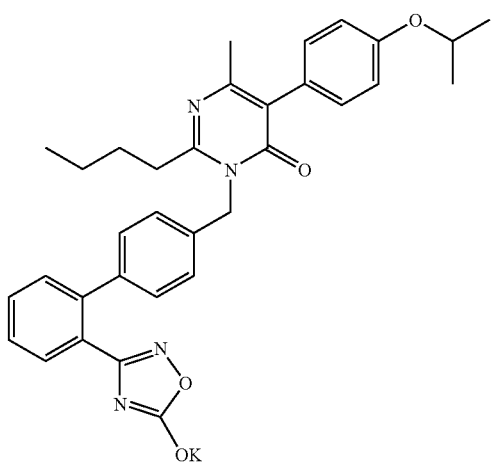

522c) 2-butyl-5-(4-isopropoxyphenyl)-6-methyl-3-{[2'-(5-oxo-4,5-dihydro-1,2,4-oxadiazol-3-yl)biphenyl-4-yl]methyl}pyrimidin-4(3H)-one potassium salt 2-Butyl-5-(4-isopropoxyphenyl)-6-methyl-3-{[2'-(5-oxo-4,5-dihydro-1,2,4-oxadiazol-3-yl)biphenyl-4-yl]methyl}pyrimidin-4(3H)-one (0.3 g) was dissolved in ethanol (3 mL), and 8 M potassium hydroxide solution (0.07 mL) was added. The mixture was stirred for 1 hr. Ethanol was removed in vacuo, diethyl ether was added, and the resulting solid was collected by filtration to give the title compound as a colorless solid (0.29 g, 89%).

$^1$H NMR (300 MHz, DMSO-$d_6$) δ 0.84 (3 H, t, J=7.38 Hz), 1.21-1.42 (8 H, m), 1.54-1.69 (2 H, m), 2.12 (3 H, s), 2.70 (2 H, t, J=7.57 Hz), 4.56-4.70 (1 H, m), 5.30 (2 H, s), 6.93 (2 H, d, J=8.71 Hz), 7.12 (2 H, d, J=7.95 Hz), 7.18-7.46 (7 H, m), 7.50 (1 H, d, J=7.19 Hz)

Example 523

5-[4-(cyclopropylmethoxy)phenyl]-6-methyl-3-{[2'-(5-oxo-4,5-dihydro-1,2,4-oxadiazol-3-yl)biphenyl-4-yl]methyl}-2-propylpyrimidin-4(3H)-one

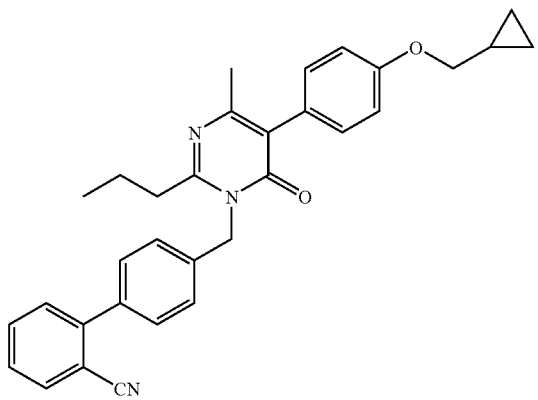

523a) 4'-{[5-[4-(cyclopropylmethoxy)phenyl]-4-methyl-6-oxo-2-propylpyrimidin-1(6H)-yl]methyl}biphenyl-2-carbonitrile A mixture of (bromomethyl)cyclopropane (0.17 mL), cesium carbonate (1.7 g) and 4'-{[5-(4-hydroxyphenyl)-4-methyl-6-oxo-2-propylpyrimidin-1(6H)-yl]methyl}biphenyl-2-carbonitrile (0.5 g) in N,N-dimethylformamide (5 mL) was stirred for 2 hr at 80° C. The reaction mixture was diluted with ethyl acetate, washed with 1 M hydrochloric acid, dried over sodium sulfate and concentrated. The residue was purified by silica gel column chromatography to give the title compound as a pale yellow oil (0.56 g, 100%).

$^1$H NMR (300 MHz, CDCl$_3$) δ 0.31-0.40 (2 H, m), 0.58-0.70 (2 H, m), 1.02 (3 H, t, J=7.35 Hz), 1.21-1.38 (1 H, m), 1.79 (2H, dd, J=15.45, 7.54 Hz), 2.24 (3 H, s), 2.67-2.75 (2 H, m), 3.82 (2 H, d, J=6.78 Hz), 5.37 (2 H, s), 6.91-6.99 (2 H, m), 7.21-7.30 (2 H, m), 7.35 (2 H, d, J=8.48 Hz), 7.40-7.57 (4 H, m), 7.60-7.69 (1 H, m), 7.76 (1 H, dd, J=7.72, 0.75 Hz)

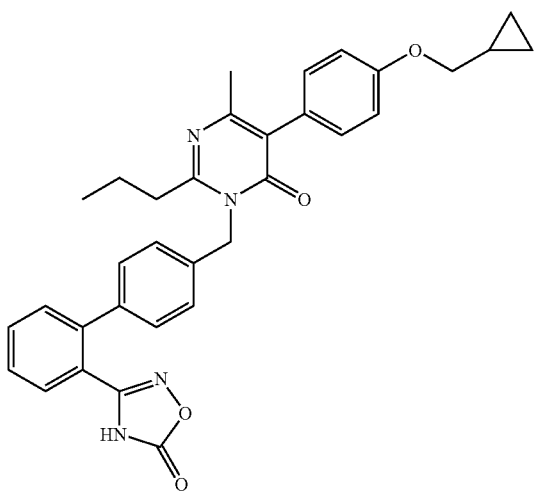

523b) 5-[4-(cyclopropylmethoxy)phenyl]-6-methyl-3-{[2'-(5-oxo-4,5-dihydro-1,2,4-oxadiazol-3-yl)biphenyl-4-yl]methyl}-2-propylpyrimidin-4(3H)-one 4'-{[5-[4-(Cyclopropylmethoxy)phenyl]-4-methyl-6-oxo-2-propylpyrimidin-1(6H)-yl]methyl}biphenyl-2-carbonitrile (0.56 g) was dissolved in dimethyl sulfoxide (5 mL), and hydroxylamine hydrochloride (0.79 g) and sodium hydrogen carbonate (1.2 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.28 g) and 1,8-diazabicyclo[5.4.0]undec-7-ene (0.26 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.49 g, 78%).

$^1$H NMR (300 MHz, DMSO-$d_6$) δ 0.29-0.37 (2 H, m), 0.53-0.63 (2 H, m), 0.88 (3 H, t, J=7.44 Hz), 1.16-1.32 (1 H, m), 1.54-1.71 (2 H, m), 2.12 (3 H, s), 2.66 (2 H, t, J=7.54 Hz), 3.84 (2 H, d, J=6.97 Hz), 5.35 (2 H, s), 6.91-6.99 (2 H, m), 7.18-7.35 (6 H, m), 7.49-7.61 (2 H, m), 7.64-7.74 (2 H, m), 12.39 (1 H, s)

Example 524

5-(4-sec-butoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one

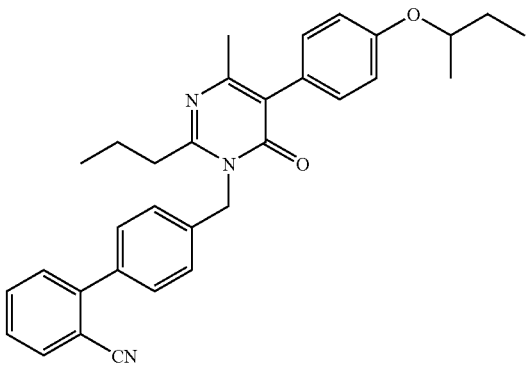

524a) 4'-{[5-(4-sec-butoxyphenyl)-4-methyl-6-oxo-2-propylpyrimidin-1(6H)-yl]methyl}biphenyl-2-carbonitrile A mixture of 2-bromobutane (0.19 mL), cesium carbonate (1.7 g) and 4'-{[5-(4-hydroxyphenyl)-4-methyl-6-oxo-2-propylpyrimidin-1(6H)-yl]methyl}biphenyl-2-carbonitrile (0.5 g) in N,N-dimethylformamide (5 mL) was stirred for 2 hr at 80° C. The mixture was diluted with ethyl acetate, washed with 1 M hydrochloric acid, dried over sodium sulfate and concentrated. The residue was purified by silica gel column chromatography to give the title compound as a pale yellow oil (0.5 g, 89%).

$^1$H NMR (300 MHz, CDCl$_3$) δ 0.94-1.06 (6 H, m), 1.31 (3 H, d, J=6.22 Hz), 1.55-1.87 (4 H, m), 2.25 (3 H, s), 2.66-2.77 (2 H, m), 4.24-4.39 (1 H, m), 5.38 (2 H, s), 6.88-6.97 (2 H, m), 7.21-7.28 (2 H, m), 7.35 (2 H, d, J=8.48 Hz), 7.39-7.57 (4 H, m), 7.59-7.68 (1 H, m), 7.76 (1 H, dd, J=7.82, 0.85 Hz)

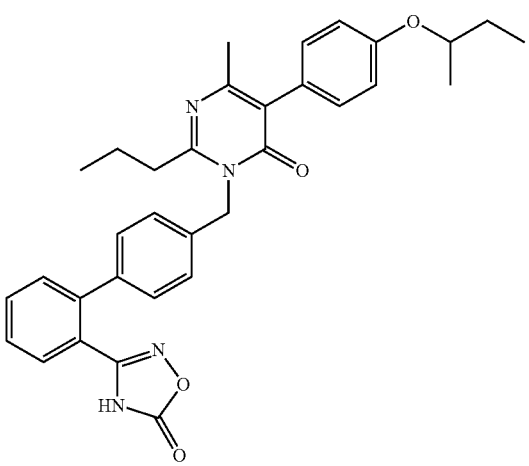

524b) 5-(4-sec-butoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one 4'-{[5-(4-sec-Butoxyphenyl)-4-methyl-6-oxo-2-propylpyrimidin-1(6H)-yl]methyl}biphenyl-2-carbonitrile (0.5 g) was dissolved in dimethyl sulfoxide (5 mL), and hydroxylamine hydrochloride (0.79 g) and sodium hydrogen carbonate (1.2 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.28 g) and 1,8-diazabicyclo[5.4.0]undec-7-ene (0.26 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.45 g, 81%).

$^1$H NMR (300 MHz, DMSO-d$_6$) δ 0.83-0.99 (6 H, m), 1.25 (3 H, d, J=6.03 Hz), 1.52-1.77 (4 H, m), 2.13 (3 H, s), 2.66 (2 H, t, J=7.44 Hz), 4.34-4.49 (1 H, m), 5.35 (2 H, s), 6.89-6.98 (2 H, m), 7.17-7.35 (6 H, m), 7.49-7.61 (2 H, m), 7.64-7.74 (2 H, m), 12.39 (1 H, s)

Example 525

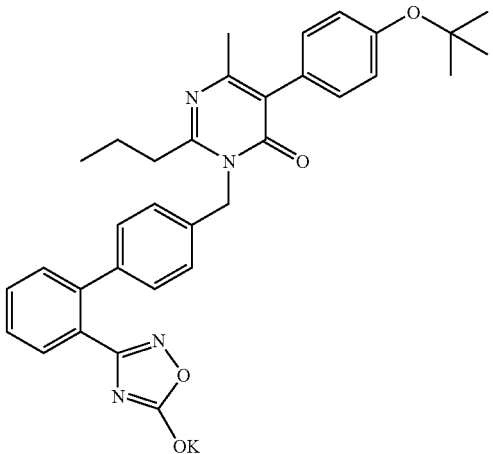

5-(4-tert-Butoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one potassium salt 5-(4-tert-Butoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one (0.3 g) was dissolved in ethanol (3 mL), and 8 M potassium hydroxide solution (0.07 mL) was added. The mixture was stirred for 1 hr. Ethanol was removed in vacuo, diethyl ether was added, and the resulting solid was collected by filtration to give the title compound as a colorless solid (0.32 g, 100%).

$^1$H NMR (300 MHz, DMSO-d$_6$) δ 0.92 (3 H, t, J=7.35 Hz), 1.33 (9 H, s), 1.58-1.75 (2 H, m), 2.12 (3 H, s), 2.69 (2 H, t, J=7.54 Hz), 5.30 (2 H, s), 6.95-7.03 (2 H, m), 7.13 (2 H, d, J=8.29 Hz), 7.20-7.46 (7 H, m), 7.50 (1 H, dd, J=7.35, 1.51 Hz)

Example 526

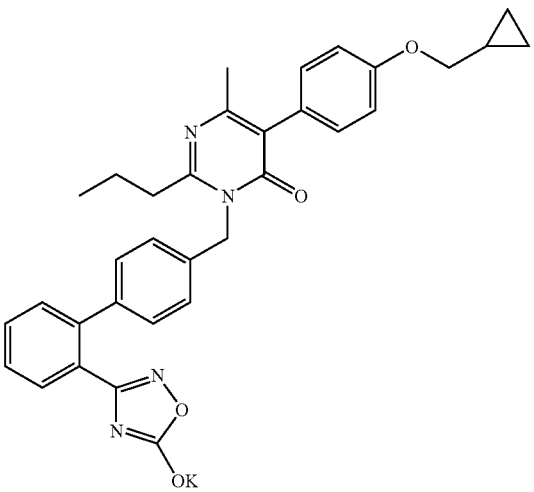

5-[4-(cyclopropylmethoxy)phenyl]-6-methyl-3-{[2'-(5-oxo-4,5-dihydro-1,2,4-oxadiazol-3-yl)biphenyl-4-yl]methyl}-2-propylpyrimidin-4(3H)-one potassium salt 5-[4-(Cyclopropylmethoxy)phenyl]-6-methyl-3-{[2'-(5-oxo-4,5-dihydro-1,2,4-oxadiazol-3-yl)biphenyl-4-yl]methyl}-2-propylpyrimidin-4(3H)-one (0.3 g) was dissolved in ethanol (3 mL), and 8 M potassium hydroxide solution (0.07 mL) was added. The mixture was stirred for 1 hr. Ethanol was removed in vacuo, diethyl ether was added, and the resulting solid was collected by filtration to give the title compound as a colorless solid (0.28 g, 89%).

$^1$H NMR (300 MHz, DMSO-d$_6$) δ 0.30-0.37 (2 H, m), 0.53-0.62 (2 H, m), 0.91 (3 H, t, J=7.35 Hz), 1.15-1.32 (1 H, m), 1.58-1.74 (2 H, m), 2.12 (3 H, s), 2.68 (2 H, t, J=7.54 Hz), 3.84 (2 H, d, J=6.97 Hz), 5.30 (2 H, s), 6.94 (2 H, d, J=8.67 Hz), 7.12 (2 H, d, J=8.29 Hz), 7.19-7.26 (2 H, m), 7.26-7.46 (5H, m), 7.50 (1 H, dd, J=7.44, 1.41 Hz)

Example 527

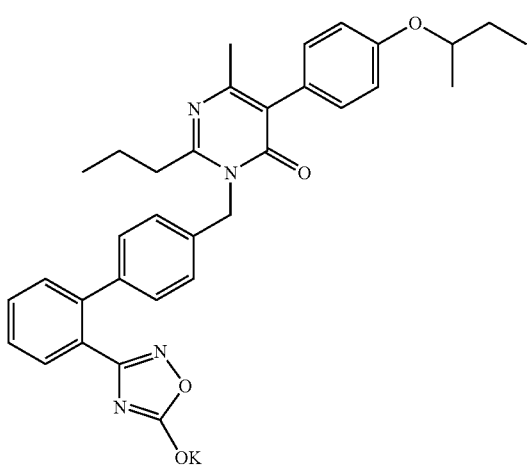

5-(4-sec-butoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one potassium salt 5-(4-sec-Butoxyphenyl)-6-methyl-3-{[2'-(5-oxo-4,5-dihydro-1,2,4-oxadiazol-3-yl)biphenyl-4-yl]methyl}-2-propylpyrimidin-4(3H)-one (0.3 g) was dissolved in ethanol (3 mL), and 8 M potassium hydroxide solution (0.07 mL) was added. The mixture was stirred for 1 hr. Ethanol was removed in vacuo, diethyl ether was added, and the resulting solid was collected by filtration to give the title compound as a colorless solid (0.29 g, 90%).

$^1$H NMR (300 MHz, DMSO-d$_6$) δ 0.87-0.99 (6 H, m), 1.25 (3 H, d, J=6.06 Hz), 1.52-1.75 (4 H, m), 2.13 (3 H, s), 2.68 (2 H, t, J=7.57 Hz), 4.34-4.47 (1 H, m), 5.30 (2 H, s), 6.93 (2 H, d, J=8.71 Hz), 7.12 (2 H, d, J=7.95 Hz), 7.22 (2 H, d, J=8.71 Hz), 7.29 (2 H, d, J=8.33 Hz), 7.31-7.47 (3 H, m), 7.47-7.53 (1H, m)

Example 528

5-(2,2-dimethyl-2,3-dihydro-1-benzofuran-5-yl)-6-ethyl-3-{[2'-(5-oxo-4,5-dihydro-1,2,4-oxadiazol-3-yl)biphenyl-4-yl]methyl}-2-propylpyrimidin-4(3H)-one potassium salt

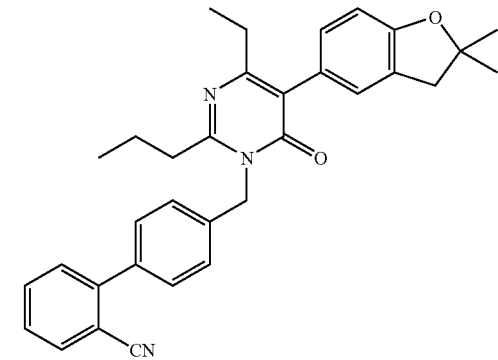

528a) 4'-{[5-(2,2-dimethyl-2,3-dihydro-1-benzofuran-5-yl)-4-ethyl-6-oxo-2-propylpyrimidin-1(6H)-yl]methyl}biphenyl-2-carbonitrile A mixture of (2,2-dimethyl-2,3-dihydro-1-benzofuran-5-yl)boronic acid (0.33 g), [1,1'-bis(diphenylphosphino)ferrocene]dichloropalladium (0.05 g) and 4'-[(5-bromo-4-ethyl-6-oxo-2-propylpyrimidin-1(6H)-yl)methyl]biphenyl-2-carbonitrile (0.5 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate and concentrated. The residue was purified by silica gel column chromatography to give the title compound as a colorless solid (0.58 g, 100%).

$^1$H NMR (300 MHz, CDCl$_3$) δ 1.02 (3 H, t, J=7.35 Hz), 1.19 (3 H, t, J=7.44 Hz), 1.49 (6 H, s), 1.74-1.90 (2 H, m), 2.50 (2 H, q, J=7.54 Hz), 2.68-2.77 (2 H, m), 3.04 (2 H, s), 5.36 (2 H, s), 6.76 (1 H, d, J=8.29 Hz), 7.01 (1 H, dd, J=8.10, 1.88 Hz), 7.10 (1 H, d, J=1.32 Hz), 7.36 (2 H, d, J=8.48 Hz), 7.40-7.56 (4 H, m), 7.60-7.68 (1 H, m), 7.76 (1 H, dd, J=7.63, 0.85 Hz)

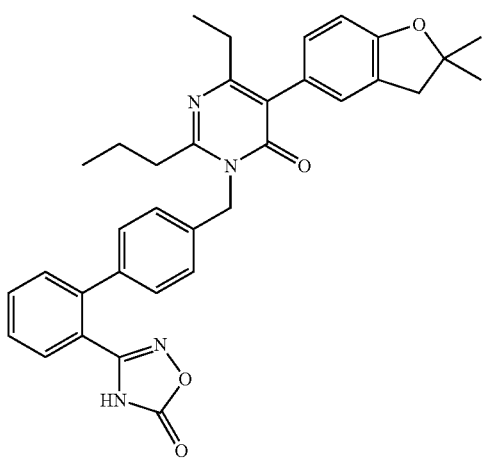

528b) 5-(2,2-dimethyl-2,3-dihydro-1-benzofuran-5-yl)-6-ethyl-3-{[2'-(5-oxo-4,5-dihydro-1,2,4-oxadiazol-3-yl)biphenyl-4-yl]methyl}-2-propylpyrimidin-4(3H)-one 4'-{[5-(2,2-Dimethyl-2,3-dihydro-1-benzofuran-5-yl)-4-ethyl-6-oxo-2-propylpyrimidin-1(6H)-yl]methyl}biphenyl-2-carbonitrile (0.58 g) was dissolved in dimethyl sulfoxide (5 mL), and hydroxylamine hydrochloride (0.71 g) and sodium hydrogen carbonate (1 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.25 g) and 1,8-diazabicyclo[5.4.0]undec-7-ene (0.23 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.48 g, 74%).

$^1$H NMR (300 MHz, DMSO-$d_6$) δ 0.89 (3 H, t, J=7.38 Hz), 1.10 (3 H, t, J=7.38 Hz), 1.43 (6 H, s), 1.59-1.73 (2 H, m), 2.37 (2 H, q, J=7.57 Hz), 2.68 (2 H, t, J=7.19 Hz), 3.03 (2 H, s), 5.33 (2 H, s), 6.72 (1 H, d, J=7.95 Hz), 6.95 (1 H, dd, J=8.14, 1.70 Hz), 7.07 (1 H, s), 7.21-7.35 (4 H, m), 7.50-7.60 (2H, m), 7.64-7.73 (2 H, m), 12.38 (1 H, br. s.)

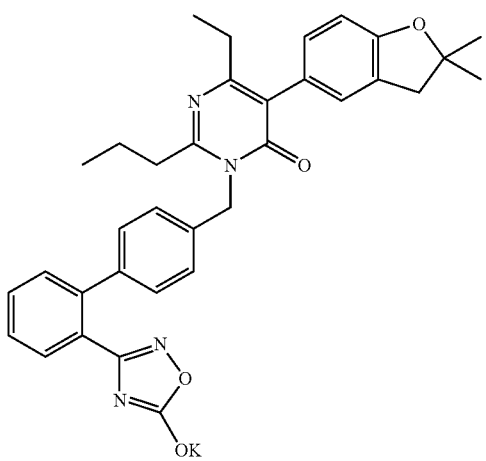

528c) 5-(2,2-dimethyl-2,3-dihydro-1-benzofuran-5-yl)-6-ethyl-3-{[2'-(5-oxo-4,5-dihydro-1,2,4-oxadiazol-3-yl)biphenyl-4-yl]methyl}-2-propylpyrimidin-4(3H)-one potassium salt 5-(2,2-Dimethyl-2,3-dihydro-1-benzofuran-5-yl)-6-ethyl-3-{[2'-(5-oxo-4,5-dihydro-1,2,4-oxadiazol-3-yl)biphenyl-4-yl]methyl}-2-propylpyrimidin-4(3H)-one (0.3 g) was dissolved in ethanol (3 mL), and 8 M potassium hydroxide solution (0.07 mL) was added. The mixture was stirred for 1 hr. Ethanol was removed in vacuo, diethyl ether was added, and the resulting solid was collected by filtration to give the title compound as a colorless solid (0.21 g, 65%).

$^1$H NMR (300 MHz, DMSO-$d_6$) δ 0.92 (3 H, t, J=7.19 Hz), 1.10 (3 H, t, J=7.38 Hz), 1.43 (6 H, s), 1.61-1.78 (2 H, m), 2.37 (2 H, q, J=7.45 Hz), 2.70 (2 H, t, J=7.19 Hz), 3.03 (2 H, s), 5.29 (2 H, s), 6.71 (1 H, d, J=8.33 Hz), 6.96 (1 H, d, J=8.33 Hz), 7.06-7.17 (3 H, m), 7.25-7.46 (5 H, m), 7.50 (1 H, d, J=7.19 Hz)

Example 529

5-(4-methoxy-2,2-dimethyl-3,4-dihydro-2H-chromen-6-yl)-6-methyl-3-{[2'-(5-oxo-4,5-dihydro-1,2,4-oxadiazol-3-yl)biphenyl-4-yl]methyl}-2-propylpyrimidin-4(3H)-one potassium salt

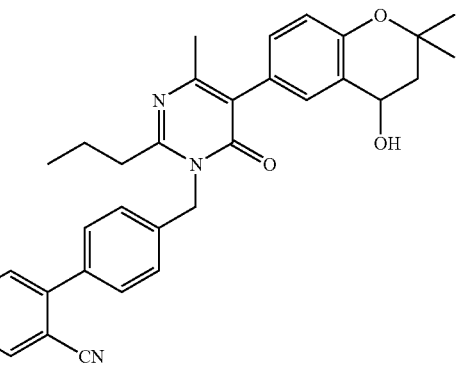

529a) 4'-{[5-(4-hydroxy-2,2-dimethyl-3,4-dihydro2H-chromen-6-yl)-4-methyl-6-oxo-2-propylpyrimidin-1(6H)-yl]methyl}biphenyl-2-carbonitrile A mixture of (4-hydroxy-2,2-dimethyl-3,4-dihydro-2H-chromen-6-yl)boronic acid (0.79 g), [1,1'-bis(diphenylphosphino)ferrocene]dichloropalladium (0.1 g) and 4'-[(5-bromo-4-methyl-6-oxo-2-propylpyrimidin-1(6H)-yl)methyl]biphenyl-2-carbonitrile (1 g) in 1,4-dioxane (10 mL) and 2 M cesium carbonate (4 mL) was stirred overnight at 100° C. under an argon atmosphere. After cooling, the reaction mixture was diluted with ethyl acetate, washed with water, dried over sodium sulfate and concentrated. The residue was purified by silica gel column chromatography to give the title compound as a colorless solid (0.94 g, 76%).

$^1$H NMR (300 MHz, CDCl$_3$) δ 1.01 (3 H, t, J=7.44 Hz), 1.33 (3 H, s), 1.45 (3 H, s), 1.64-1.94 (3 H, m), 2.12-2.22 (1 H, m), 2.25 (3 H, s), 2.67-2.75 (2 H, m), 4.79-4.93 (1 H, m), 5.36 (2 H, s), 6.83 (1 H, d, J=8.48 Hz), 7.13 (1 H, dd, J=8.29, 1.70 Hz), 7.33 (2 H, d, J=8.10 Hz), 7.40-7.56 (5 H, m), 7.60-7.68 (1 H, m), 7.72-7.79 (1 H, m) -

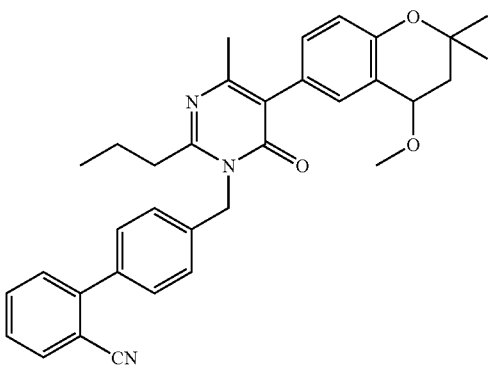

529b) 4'-{[5-(4-methoxy-2,2-dimethyl-3,4-dihydro-2H-chromen-6-yl)-4-methyl-6-oxo-2-propylpyrimidin-1(6H)-yl]methyl}biphenyl-2-carbonitrile A mixture of iodomethane (0.76 g), 60% sodium hydride (0.22 g) and 4'-{[5-(4-hydroxy-2,2-dimethyl-3,4-dihydro-2H-chromen-6-yl)-4-methyl-6-oxo-2-propylpyrimidin-1(6H)-yl]methyl}biphenyl-2-carbonitrile (0.56 g) in N,N-dimethylformamide (5 mL) was stirred for 1 hr. The reaction mixture was diluted with ethyl acetate, washed with water, dried over sodium sulfate and concentrated. The residue was purified by silica gel column chromatography to give the title compound as a colorless solid (0.38 g, 66%).

$^1$H NMR (300 MHz, CDCl$_3$) δ 1.01 (3 H, t, J=7.35 Hz), 1.34 (3 H, s), 1.46 (3 H, s), 1.69-1.86 (2 H, m), 1.91-2.02 (1 H, m), 2.12 (1 H, dd), 2.25 (3 H, s), 2.65-2.77 (2 H, m), 3.45 (3 H, s), 4.49 (1 H, dd, J=7.54, 6.03 Hz), 5.38 (2 H, s), 6.83 (1 H, d, J=8.48 Hz), 7.14 (1 H, dd, J=8.48, 2.07 Hz), 7.34 (2 H, d, J=8.10 Hz), 7.39-7.56 (5 H, m), 7.59-7.69 (1 H, m), 7.73-7.79 (1 H, m)

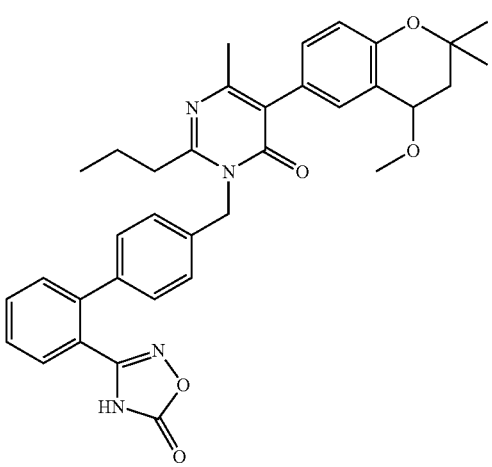

529c) 5-(4-methoxy-2,2-dimethyl-3,4-dihydro-2H-chromen-6-yl)-6-methyl-3-{[2'-(5-oxo-4,5-dihydro-1,2,4-oxadiazol-3-yl)biphenyl-4-yl]methyl}-2-propylpyrimidin-4(3H)-one 4'-{[5-(4-Methoxy-2,2-dimethyl-3,4-dihydro-2H-chromen-6-yl)-4-methyl-6-oxo-2-propylpyrimidin-1(6H)-yl]methyl}biphenyl-2-carbonitrile (0.38 g) was dissolved in dimethyl sulfoxide (5 mL), and hydroxylamine hydrochloride (0.49 g) and sodium hydrogen carbonate (0.72 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.17 g) and 1,8-diazabicyclo[5.4.0]undec-7-ene (0.16 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.27 g, 64%).

$^1$H NMR (300 MHz, DMSO-d$_6$) δ 0.88 (3 H, t, J=7.38 Hz), 1.31 (3 H, s), 1.39 (3 H, s), 1.55-1.71 (2 H, m), 1.88 (1 H, dd, J=13.63, 7.19 Hz), 2.11-2.20 (1 H, m), 2.13 (3 H, s), 2.66 (2 H, t, J=7.38 Hz), 3.38 (3 H, s), 4.43 (1 H, t, J=6.25 Hz), 5.34 (2 H, s), 6.76 (1 H, d, J=8.33 Hz), 7.09 (1 H, dd, J=8.33, 2.27 Hz), 7.22-7.35 (5 H, m), 7.50-7.61 (2 H, m), 7.64-7.73 (2 H, m), 12.38 (1 H, s)

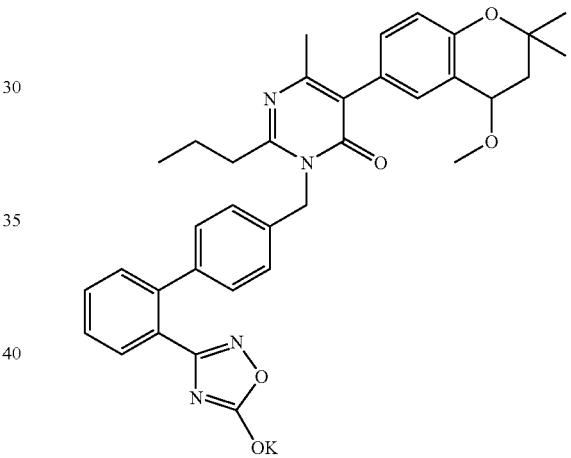

529d) 5-(4-methoxy-2,2-dimethyl-3,4-dihydro-2H-chromen-6-yl)-6-methyl-3-{[2'-(5-oxo-4,5-dihydro-1,2,4-oxadiazol-3-yl)biphenyl-4-yl]methyl}-2-propylpyrimidin-4(3H)-one potassium salt 5-(4-Methoxy-2,2-dimethyl-3,4-dihydro-2H-chromen-6-yl)-6-methyl-3-{[2'-(5-oxo-4,5-dihydro-1,2,4-oxadiazol-3-yl)biphenyl-4-yl]methyl}-2-propylpyrimidin-4(3H)-one (0.26 g) was dissolved in ethanol (3 mL), and 8 M potassium hydroxide solution (0.06 mL) was added. The mixture was stirred for 1 hr. Ethanol was removed in vacuo, diethyl ether was added, and the resulting solid was collected by filtration to give the title compound as a colorless solid (0.27 g, 97%).

$^1$H NMR (300 MHz, DMSO-d$_6$) δ 0.91 (3 H, t, J=7.38 Hz), 1.31 (3 H, s), 1.39 (3 H, s), 1.57-1.75 (2 H, m), 1.89 (1 H, dd, J=13.63, 7.19 Hz), 2.09-2.20 (4 H, m), 2.68 (2 H, t, J=7.57 Hz), 3.31 (3 H, s), 4.43 (1 H, t, J=6.25 Hz), 5.30 (2 H, s), 6.75 (1 H, d, J=8.71 Hz), 7.05-7.15 (3 H, m), 7.24-7.46 (6H, m), 7.47-7.54 (1 H, m)

Example 530

6-ethyl-5-(4-hydroxy-2,2-dimethyl-3,4-dihydro-2H-chromen-6-yl)-3-{[2'-(5-oxo-4,5-dihydro-1,2,4-oxadiazol-3-yl)biphenyl-4-yl]methyl}-2-propylpyrimidin-4(3H)-one

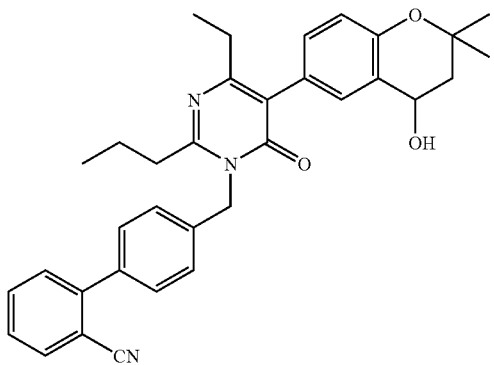

530a) 4'-{[4-ethyl-5-(4-hydroxy-2,2-dimethyl-3,4-dihydro-2H-chromen-6-yl)-6-oxo-2-propylpyrimidin-1(6H)-yl]methyl}biphenyl-2-carbonitrile A mixture of (4-hydroxy-2,2-dimethyl-3,4-dihydro-2H-chromen-6-yl)boronic acid (1.1 g), [1,1'-bis(diphenylphosphino)ferrocene]dichloropalladium (0.14 g) and 4'-[(5-bromo-4-ethyl-6-oxo-2-propylpyrimidin-1(6H)-yl)methyl]biphenyl-2-carbonitrile (1.5 g) in 1,4-dioxane (10 mL) and 2 M cesium carbonate (4 mL) was stirred overnight at 100° C. under an argon atmosphere. After cooling, the mixture was diluted with ethyl acetate, washed with water, dried over sodium sulfate and concentrated. The residue was purified by silica gel column chromatography to give the title compound as a colorless solid (1.5 g, 82%).

$^1$H NMR (300 MHz, CDCl$_3$) δ 1.01 (3 H, t, J=7.38 Hz), 1.19 (3 H, t, J=7.57 Hz), 1.33 (3 H, s), 1.45 (3 H, s), 1.73-1.94 (3 H, m), 2.09-2.22 (1 H, m), 2.50 (2 H, q, J=7.32 Hz), 2.67-2.77 (2 H, m), 4.86 (1 H, q, J=7.19 Hz), 5.35 (2 H, s), 6.83 (1 H, d, J=8.33 Hz), 7.11 (1 H, dd, J=8.52, 2.08 Hz), 7.34 (2H, d, J=7.95 Hz), 7.39-7.56 (5 H, m), 7.59-7.68 (1 H, m), 7.76 (1 H, d, J=7.57 Hz)

530b) 6-ethyl-5-(4-hydroxy-2,2-dimethyl-3,4-dihydro-2H-chromen-6-yl)-3-{[2'-(5-oxo-4,5-dihydro-1,2,4-oxadiazol-3-yl)biphenyl-4-yl]methyl}-2-propylpyrimidin-4(3H)-one To a mixture of 4'-{[4-ethyl-5-(4-hydroxy-2,2-dimethyl-3,4-dihydro-2H-chromen-6-yl)-6-oxo-2-propylpyrimidin-1(6H)-yl]methyl}biphenyl-2-carbonitrile (1.5 g) and 2,6-lutidine (0.98 mL) in dichloromethane (10 mL) was added triisopropylsilyl trifluoromethanesulfonate (1.5 mL) at 0° C. After stirring for 2 hr, the reaction mixture was diluted with ethyl acetate, washed with water, dried over sodium sulfate and concentrated. The residue was dissolved in dimethyl sulfoxide (5 mL), and then hydroxylamine hydrochloride (1.7 g) and sodium hydrogen carbonate (2.5 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.6 g) and 1,8-diazabicyclo[5.4.0]undec-7-ene (0.6 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (1.3 g, 77%).

$^1$H NMR (300 MHz, DMSO-d$_6$) δ 0.89 (3 H, t, J=7.19 Hz), 1.11 (3 H, t, J=7.38 Hz), 1.27 (3 H, s), 1.39 (3 H, s), 1.58-1.81 (3 H, m), 2.09 (1 H, dd, J=13.25, 6.06 Hz), 2.38 (2 H, q, J=7.57 Hz), 2.68 (2 H, t, J=7.38 Hz), 4.63-4.76 (1 H, m), 5.30-5.38 (2H, m), 6.72 (1 H, d, J=8.71 Hz), 7.01 (1 H, dd, J=8.33, 2.27 Hz), 7.21-7.37 (5 H, m), 7.49-7.61 (2 H, m), 7.63-7.74 (2 H, m), 12.38 (1 H, s)

Example 531

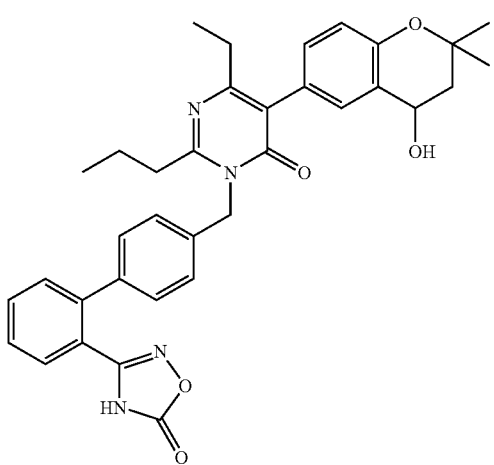

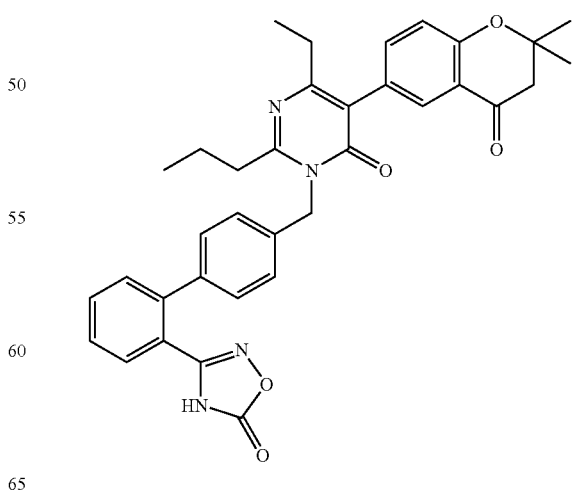

5-(2,2-dimethyl-4-oxo-3,4-dihydro-2H-chromen-6-yl)-6-ethyl-3-{[2'-(5-oxo-4,5-dihydro-1,2,4-oxadiazol-3-yl)biphenyl-4-yl]methyl}-2-propylpyrimidin-4(3H)-one A mixture of 6-ethyl-5-(4-hydroxy-2,2-dimethyl-3,4-dihydro-2H-chromen-6-yl)-3-{[2'-(5-oxo-4,5-dihydro-1,2,4-oxadiazol-3-yl)biphenyl-4-yl]methyl}-2-propylpyrimidin-4(3H)-one (0.78 g) and 1,1,1-tris(acetyloxy)-1,1-dihydro-1,2-benziodoxol-3(1H)-one (0.84 g) in dichloromethane (8 mL) was stirred for 1 hr. The reaction mixture was diluted with ethyl acetate, washed with water, dried over sodium sulfate and concentrated. The residue was purified by silica gel column chromatography to give the title compound as a colorless solid (0.63 g, 81%).

$^1$H NMR (300 MHz, DMSO-$d_6$) δ 0.89 (3 H, t, J=7.19 Hz), 1.11 (3 H, t, J=7.57 Hz), 1.43 (6 H, s), 1.59-1.74 (2 H, m), 2.37 (2 H, q, J=7.32 Hz), 2.69 (2 H, t, J=7.19 Hz), 2.83 (2 H, s), 5.34 (2 H, s), 7.03 (1 H, d, J=8.33 Hz), 7.22-7.35 (4 H, m), 7.44-7.74 (6 H, m), 12.38 (1 H, s)

Example 532

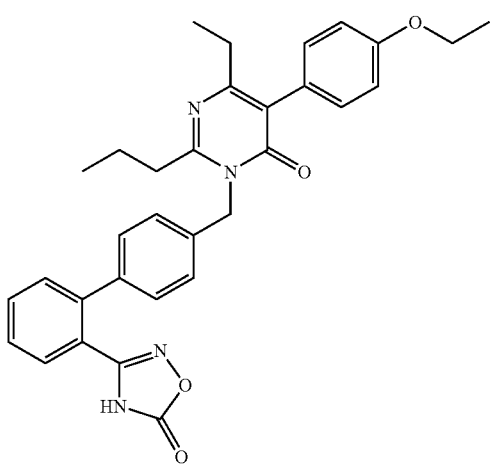

5-(4-ethoxyphenyl)-6-ethyl-3-{[2'-(5-oxo-4,5-dihydro-1,2,4-oxadiazol-3-yl)biphenyl-4-yl]methyl}-2-propylpyrimidin-4(3H)-one A mixture of (4-ethoxyphenyl)boronic acid (0.29 g), [1,1'-bis(diphenylphosphino) ferrocene]dichloropalladium (0.05 g) and 4'-[(5-bromo-4-ethyl-6-oxo-2-propylpyrimidin-1(6H)-yl)methyl]biphenyl-2-carbonitrile (0.5 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate and concentrated. The residue was dissolved in dimethyl sulfoxide (5 mL), and then hydroxylamine hydrochloride (0.8 g) and sodium hydrogen carbonate (1.2 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.28 g) and 1,8-diazabicyclo[5.4.0]undec-7-ene (0.26 mL) were added. After stirring for 30 min, the mixture was diluted with ethyl acetate, washed with 1 M hydrochloric acid, dried over sodium sulfate and concentrated. The residue was purified by silica gel column chromatography to give the title compound as a colorless solid (0.41 g, 66%).

$^1$H NMR (300 MHz, DMSO-$d_6$) δ 0.89 (3 H, t, J=7.3 Hz), 1.10 (3 H, t, J=7.5 Hz), 1.35 (3 H, t, J=7.0 Hz), 1.59-1.73 (2 H, m), 2.36 (2 H, q, J=7.5 Hz), 2.68 (2 H, t, J=7.3 Hz), 4.05 (2 H, q, J=7.0 Hz), 5.34 (2 H, s), 6.91-6.99 (2 H, m), 7.15-7.35 (6 H, m), 7.49-7.74 (4 H, m), 12.39 (1 H, br. s.)

Example 533

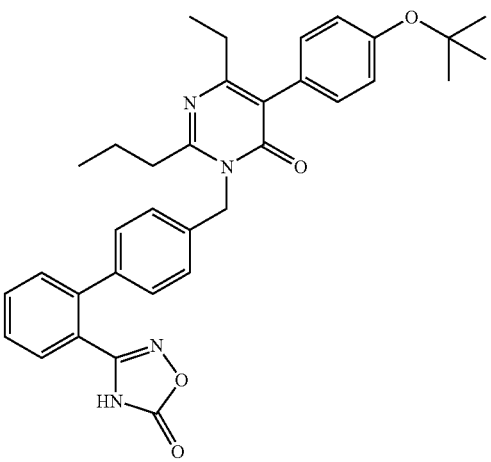

5-(4-tert-butoxyphenyl)-6-ethyl-3-{[2'-(5-oxo-4,5-dihydro-1,2,4-oxadiazol-3-yl)biphenyl-4-yl]methyl}-2-propylpyrimidin-4(3H)-one A mixture of (4-tert-butoxyphenyl)boronic acid (0.33 g), [1,1'-bis(diphenylphosphino)ferrocene]dichloropalladium (0.05 g) and 4'-[(5-bromo-4-ethyl-6-oxo-2-propylpyrimidin-1(6H)-yl)methyl]biphenyl-2-carbonitrile (0.5 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate and concentrated. The residue was dissolved in dimethyl sulfoxide (5 mL), and then hydroxylamine hydrochloride (0.8 g) and sodium hydrogen carbonate (1.2 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.28 g) and 1,8-diazabicyclo[5.4.0]undec-7-ene (0.26 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.46 g, 72%).

$^1$H NMR (300 MHz, DMSO-$d_6$) δ 0.90 (3 H, t, J=7.3 Hz), 1.10 (3 H, t, J=7.4 Hz), 1.33 (9 H, s), 1.59-1.73 (2 H, m), 2.36 (2 H, q, J=7.5 Hz), 2.69 (2 H, t, J=7.3 Hz), 5.34 (2 H, s), 7.00 (2H, d, J=8.7 Hz), 7.19 (2 H, d, J=8.5 Hz), 7.24-7.35 (4 H, m), 7.55 (2 H, dd, J=15.7, 7.6 Hz), 7.64-7.74 (2 H, m), 12.39 (1H, br. s.)

Example 534

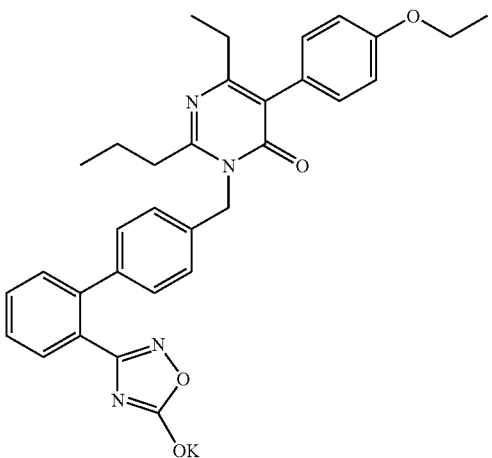

5-(4-ethoxyphenyl)-6-ethyl-3-{[2'-(5-oxo-4,5-dihydro-1,2,4-oxadiazol-3-yl)biphenyl-4-yl]methyl}-2-propylpyrimidin-4(3H)-one potassium salt 5-(4-Ethoxyphenyl)-6-ethyl-3-{[2'-(5-oxo-4,5-dihydro-1,2,4-oxadiazol-3-yl)biphenyl-4-yl]methyl}-2-propylpyrimidin-4(3H)-one (0.3 g) was dissolved in ethanol (3 mL), and 8 M potassium hydroxide solution (0.07 mL) was added. The mixture was stirred for 1 hr. Ethanol was removed in vacuo, diethyl ether was added, and the resulting solid was collected by filtration to give the title compound as a colorless solid (0.31 g, 95%).

$^1$H NMR (300 MHz, DMSO-$d_6$) δ 0.92 (3 H, t, J=7.3 Hz), 1.10 (3 H, t, J=7.5 Hz), 1.35 (3 H, t, J=7.0 Hz), 1.62-1.78 (2 H, m), 2.36 (2 H, q, J=7.5 Hz), 2.71 (2 H, t, J=7.3 Hz), 4.05 (2 H, q, J=7.0 Hz), 5.29 (2 H, s), 6.91-6.99 (2 H, m), 7.09-7.23 (4H, m), 7.25-7.53 (6 H, m)

Example 535

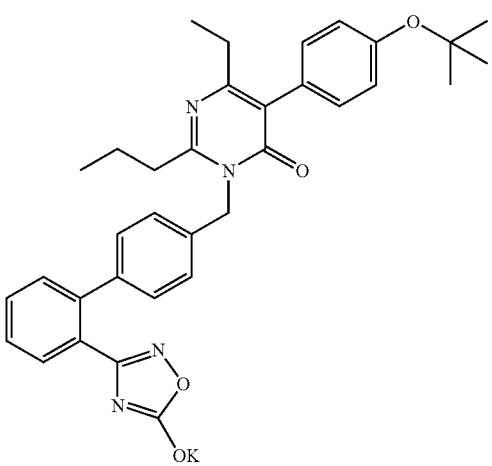

5-(4-tert-butoxyphenyl)-6-ethyl-3-{[2'-(5-oxo-4,5-dihydro-1,2,4-oxadiazol-3-yl)biphenyl-4-yl]methyl}-2-propylpyrimidin-4(3H)-one potassium salt 5-(4-tert-Butoxyphenyl)-6-ethyl-3-{[2'-(5-oxo-4,5-dihydro-1,2,4-oxadiazol-3-yl)biphenyl-4-yl]methyl}-2-propylpyrimidin-4(3H)-one (0.31 g) was dissolved in ethanol (3 mL), and 8 M potassium hydroxide solution (0.07 mL) was added. The mixture was stirred for 1 hr. Ethanol was removed in vacuo, diethyl ether was added, and the resulting solid was collected by filtration to give the title compound as a colorless solid (0.31 g, 91%).

$^1$H NMR (300 MHz, DMSO-$d_6$) δ 0.93 (3 H, t, J=7.3 Hz), 1.10 (3 H, t, J=7.4 Hz), 1.33 (9 H, s), 1.62-1.77 (2 H, m), 2.36 (2 H, q, J=7.4 Hz), 2.72 (2 H, t, J=7.3 Hz), 5.29 (2 H, s), 6.97-7.03 (2 H, m), 7.10-7.23 (4 H, m), 7.26-7.52 (6 H, m)

Example 536

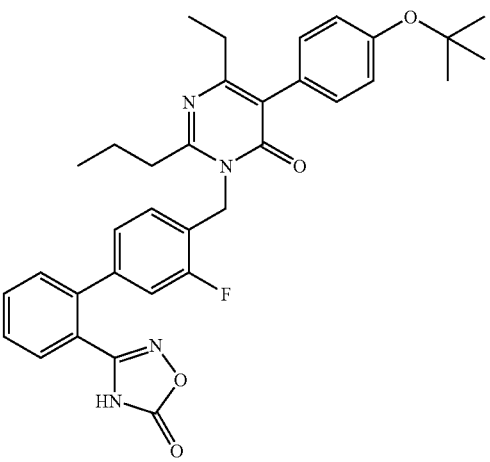

5-(4-tert-butoxyphenyl)-6-ethyl-3-{[3-fluoro-2'-(5-oxo-4,5-dihydro-1,2,4-oxadiazol-3-yl)biphenyl-4-yl]methyl}-2-propylpyrimidin-4(3H)-one A mixture of (4-tert-butoxyphenyl)boronic acid (0.33 g), [1,1'-bis (diphenylphosphino)ferrocene]dichloropalladium (0.05 g) and 3'-fluoro-4'-[(5-bromo-4-ethyl-6-oxo-2-propylpyrimidin-1(6H)-yl) methyl]biphenyl-2-carbonitrile (0.5 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate and concentrated. The residue was dissolved in dimethyl sulfoxide (5 mL), and then hydroxylamine hydrochloride (0.8 g) and sodium hydrogen carbonate (1.2 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'carbonyldiimidazole (0.28 g) and 1,8-diazabicyclo[5.4.0]undec7-ene (0.26 mL) were added. After stirring for 30 min, the reaction mixture was diluted with ethyl acetate, washed with 1M hydrochloric acid, dried over sodium sulfate and concentrated. The residue was purified by silica gel column chromatography to give the title compound as a colorless solid (0.5 g, 64%).

881

¹H NMR (300 MHz, DMSO-d₆) δ 0.92 (3 H, t, J=7.2 Hz), 1.11 (3 H, t, J=7.4 Hz), 1.33 (9 H, s), 1.63-1.77 (2 H, m), 2.37 (2 H, q, J=7.6 Hz), 2.71 (2 H, t, J=7.2 Hz), 5.34 (2 H, s), 6.96-7.28 (7 H, m), 7.52-7.75 (4 H, m), 12.47 (1 H, s)

Examle 537

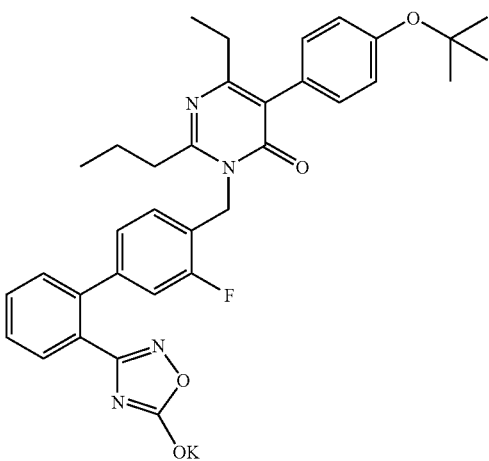

5-(4-tert-butoxyphenyl)-6-ethyl-3-{[3-fluoro-2'-(5-oxo-4,5-dihydro-1,2,4-oxadiazol-3-yl)biphenyl-4-yl]methyl}-2-propylpyrimidin-4(3H)-one potassium salt 5-(4-tert-Butoxyphenyl)-6-ethyl-3-{[3-fluoro-2'-(5-oxo-4,5-dihydro-1,2,4-oxadiazol-3-yl)biphenyl-4-yl]methyl}-2-propylpyrimidin-4(3H)-one (0.31 g) was dissolved in ethanol (3 mL), and 8 M potassium hydroxide solution (0.07 mL) was added. The mixture was stirred for 1 hr. Ethanol was removed in vacuo, diethyl ether was added, and the resulting solid was collected by filtration to give the title compound as a colorless solid (0.31 g, 91%).

¹H NMR (300 MHz, DMSO-d₆) δ 0.94 (3 H, t, J=7.4 Hz), 1.11 (3 H, t, J=7.6 Hz), 1.33 (9 H, s), 1.65-1.80 (2 H, m), 2.37 (2 H, q, J=7.6 Hz), 2.73 (2 H, t, J=7.4 Hz), 5.30 (2 H, s), 6.88-7.03 (3 H, m), 7.08-7.21 (4 H, m), 7.29-7.48 (3 H, m), 7.50-7.57 (1 H, m)

Example 538

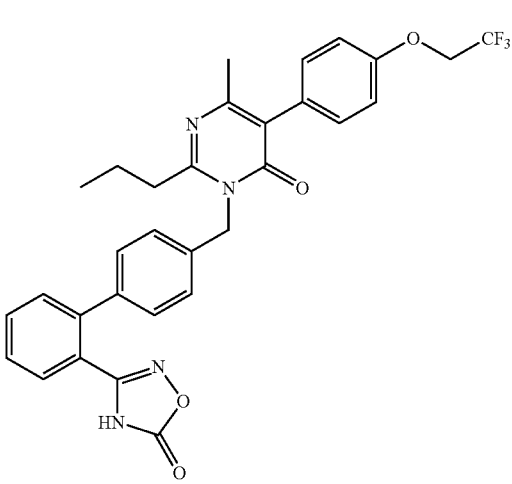

882

6-methyl-3-{[2'-(5-oxo-4,5-dihydro-1,2,4-oxadiazol-3-yl)biphenyl-4-yl]methyl}-2-propyl-5-[4-(2,2,2-trifluoroethoxy)phenyl]pyrimidin-4(3H)-one A mixture of 1,1,1-trifluoro-2-iodoethane (0.91 mL), cesium carbonate (1.5 g) and 4'-{[5-(4-hydroxyphenyl)-4-methyl-6-oxo-2-propylpyrimidin-1(6H)-yl]methyl}biphenyl-2-carbonitrile (1 g) in N,N-dimethylformamide (10 mL) was stirred overnight at 100° C. The reaction mixture was diluted with ethyl acetate, washed with water, dried over sodium sulfate and concentrated. The residue was dissolved in dimethyl sulfoxide (6 mL), and hydroxylamine hydrochloride (0.79 g) and sodium hydrogen carbonate (1.2 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.28 g) and 1,8-diazabicyclo[5.4.0]undec-7-ene (0.26 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a pale yellow solid (0.41 g, 62%).

¹H NMR (300 MHz, DMSO-d₆) 6.0.88 (3 H, t, J=7.3 Hz), 1.55-1.72 (2 H, m), 2.12 (3 H, s), 2.66 (2 H, t, J=7.5 Hz), 4.80 (2H, q, J=8.9 Hz), 5.35 (2 H, s), 7.05-7.14 (2 H, m), 7.23-7.36 (6 H, m), 7.48-7.75 (4 H, m), 12.40 (1 H, br. s.)

Example 539

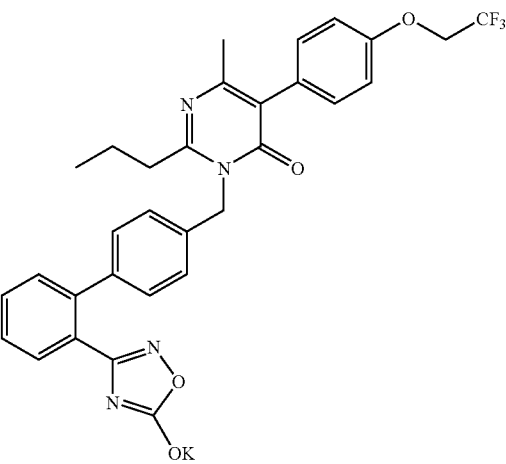

6-methyl-3-{[2'-(5-oxo-4,5-dihydro-1,2,4-oxadiazol-3-yl)biphenyl-4-yl]methyl}-2-propyl-5-[4-(2,2,2-trifluoroethoxy)phenyl]pyrimidin-4(3H)-one potassium salt 6-Methyl-3-{[2'-(5-oxo-4,5-dihydro-1,2,4-oxadiazol-3-yl)biphenyl-4-yl]methyl}-2-propyl-5-[4-(2,2,2-trifluoroethoxy)phenyl]pyrimidin-4(3H)-one (0.3 g) was dissolved in ethanol (10 mL), and 8 M potassium hydroxide solution (0.065 mL) was added. The mixture was stirred for 1 hr. Ethanol was removed in vacuo, diethyl ether was added, and the resulting solid was collected by filtration to give the title compound as a colorless solid (0.32 g, 97%).

¹H NMR (300 MHz, DMSO-d₆) δ 0.91 (3 H, t, J=7.3 Hz), 1.58-1.76 (2 H, m), 2.12 (3 H, s), 2.69 (2 H, t, J=7.4 Hz), 4.80 (2H, q, J=9.0 Hz), 5.31 (2 H, s), 7.05-7.16 (4 H, m), 7.24-7.54 (8 H, m)

Example 540

6-(1-fluoroethyl)-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one

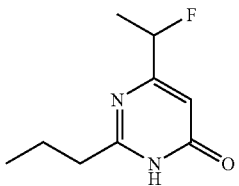

540a) 6-(1-fluoroethyl)-2-propylpyrimidin-4(3H)-one

A mixture of ethyl 4-fluoro-3-oxopentanoate (5.0 g), butanimidamide hydrochloride (4.6 g) and sodium methoxide (28% methanol solution, 16 mL) in methanol (50 mL) was stirred overnight. The reaction mixture was diluted with ethyl acetate, washed with 1 M hydrochloric acid, dried over sodium sulfate and concentrated. The residue was purified by silica gel column chromatography to give the title compound as a pale yellow oil (5.7 g, 100%).
¹H NMR (300 MHz, CDCl₃) δ 1.00 (3 H, t, J=7.3 Hz), 1.55-1.68 (3 H, m), 1.74-1.90 (2 H, m), 2.63-2.70 (2 H, m), 5.23-5.49 (1 H, m), 6.48 (1 H, s), 13.17 (1 H, br. s.)

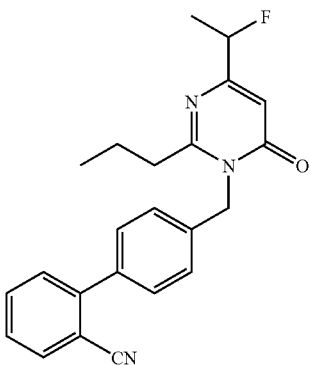

540b) 4'-{[4-(1-fluoroethyl)-6-oxo-2-propylpyrimidin-1(6H)-yl]methyl}biphenyl-2-carbonitrile A mixture of 6-(1-fluoroethyl)-2-propylpyrimidin-4(3H)-one (5.7 g), 4'-(bromomethyl)biphenyl-2-carbonitrile (9.3 g) and potassium carbonate (8.5 g) in acetonitrile (50 mL) was stirred overnight at 50° C. The reaction mixture was diluted with ethyl acetate, washed with 1 M hydrochloric acid, dried over sodium sulfate and concentrated. The residue was purified by silica gel column chromatography to give the title compound as a pale yellow solid (5 g, 43%).
¹H NMR (300 MHz, CDCl₃) δ 0.96 (3 H, t, J=7.3 Hz), 1.56-1.83 (5 H, m), 2.63-2.71 (2 H, m), 5.21-5.51 (3 H, m), 6.57 (1H, s), 7.30 (2 H, d, J=8.3 Hz), 7.41-7.81 (6 H, m)

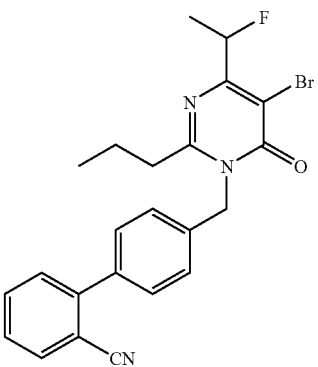

540c) 4'-{[5-bromo-4-(1-fluoroethyl)-6-oxo-2-propylpyrimidin-1(6H)-yl]methyl}biphenyl-2-carbonitrile To a solution of sodium acetate (1.2 g) and 4'-{[4-(1-fluoroethyl)-6-oxo-2-propylpyrimidin-1(6H)-yl]methyl}biphenyl-2-carbonitrile (5 g) in acetic acid (50 mL) was added bromine (0.72 mL), and the mixture was stirred for 4 hr. Acetic acid was removed in vacuo, and the mixture was diluted with ethyl acetate, washed with saturated aqueous sodium hydrogen carbonate, dried over sodium sulfate and concentrated. The residue was purified by silica gel column chromatography to give the title compound as a pale yellow solid (5 g, 83%).
¹H NMR (300 MHz, DMSO-d₆) δ 0.90 (3 H, t, J=7.3 Hz), 1.51-1.78 (5 H, m), 2.71-2.79 (2 H, m), 5.42 (2 H, s), 5.75-6.02 (1 H, m), 7.34 (2 H, d, J=8.3 Hz), 7.55-7.65 (4 H, m), 7.76-7.83 (1 H, m), 7.95 (1 H, dd, J=7.8, 0.8 Hz)

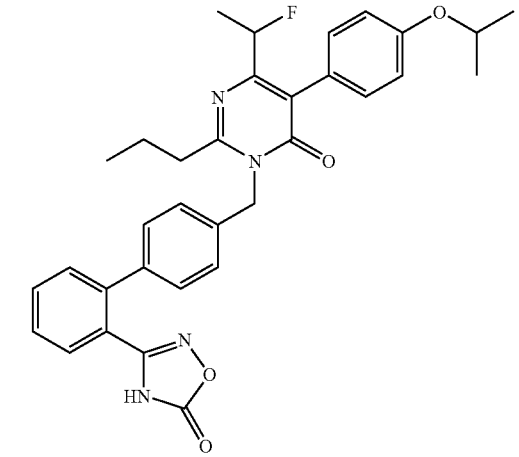

540d) 6-(1-fluoroethyl)-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one A mixture of (4-isopropoxyphenyl)boronic acid (0.27 g), [1,1'-bis(diphenylphosphino)ferrocene]dichloropalladium (0.041 g) and 4'-{[5-bromo-4-(1-fluoroethyl)-6-oxo-2-propylpyrimidin-1(6H)-yl]methyl}biphenyl-2-carbonitrile (0.45 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate, passed through silica gel pad and concentrated. The residue was dissolved in dimethyl sulfoxide (5 mL), and hydroxylamine hydrochloride (0.7 g) and sodium hydrogen carbonate (1 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.24 g) and 1,8-diazabicyclo[5.4.0]undec-7-ene (0.22 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.22 g, 39%).

$^1$H NMR (300 MHz, DMSO-$d_6$) δ 0.91 (3 H, t, J=7.4 Hz), 1.29 (6 H, d, J=6.1 Hz), 1.47-1.78 (5 H, m), 2.73 (2 H, t, J=7.2 Hz), 4.60-4.71 (1 H, m), 5.21-5.44 (3 H, m), 6.97 (2 H, d, J=8.7 Hz), 7.18-7.36 (6 H, m), 7.50-7.61 (2 H, m), 7.64-7.73 (2 H, m), 12.39 (1 H, s)

Example 541

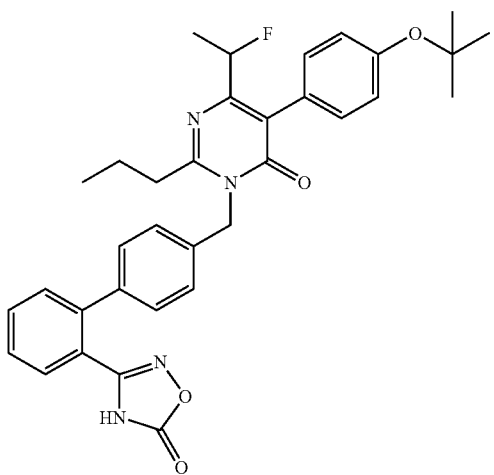

5-(4-tert-butoxyphenyl)-6-(1-fluoroethyl)-3-{[2'-(5-oxo-4,5-dihydro-1,2,4-oxadiazol-3-yl)biphenyl-4-yl]methyl}-2-propylpyrimidin-4(3H)-one A mixture of (4-tert-butoxyphenyl)boronic acid (0.29 g), [1,1'-bis(diphenylphosphino)ferrocene]dichloropalladium (0.041 g) and 4'-{[5-bromo-4-(1-fluoroethyl)-6-oxo-2-propylpyrimidin-1(6H)-yl]methyl}biphenyl-2-carbonitrile (0.45 g) in 1,4-dioxane (10 mL) and 2 M cesium carbonate (2 mL) was stirred overnight at 100° C. under an argon atmosphere. After cooling, the mixture was diluted with ethyl acetate, washed with water, dried over sodium sulfate, passed through silica gel pad and concentrated. The residue was dissolved in dimethyl sulfoxide (5 mL), and hydroxylamine hydrochloride (0.7 g) and sodium hydrogen carbonate (1 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.24 g) and 1,8-diazabicyclo[5.4.0]undec-7-ene (0.22 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.30 g, 52%).

$^1$H NMR (300 MHz, DMSO-$d_6$) δ 0.91 (3 H, t, J=7.4 Hz), 1.34 (9 H, s), 1.49-1.76 (5 H, m), 2.74 (2 H, t, J=7.2 Hz), 5.19-5.45 (3 H, m), 7.04 (2 H, d, J=8.3 Hz), 7.22 (2 H, d, J=8.3 Hz), 7.26-7.36 (4 H, m), 7.50-7.61 (2 H, m), 7.64-7.74 (2 H, m), 12.39 (1 H, s)

Example 542

6-(difluoromethyl)-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one

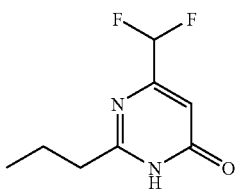

542a) 6-(difluoromethyl)-2-propylpyrimidin-4(3H)-one

A mixture of ethyl 4,4-difluoro-3-oxobutanoate (5.0 g), butanimidamide hydrochloride (4.1 g) and sodium methoxide (28% methanol solution, 15 mL) in methanol (50 mL) was stirred overnight. The reaction mixture was diluted with ethyl acetate, washed with 1 M hydrochloric acid, dried over sodium sulfate and concentrated. The residue was purified by silica gel column chromatography to give the title compound as a pale yellow oil (5.6 g, 100%).

$^1$H NMR (300 MHz, CDCl$_3$) δ 0.98 (3 H, t, J=7.3 Hz), 1.71-1.86 (2 H, m), 2.61-2.68 (2 H, m), 6.13-6.57 (2 H, m)

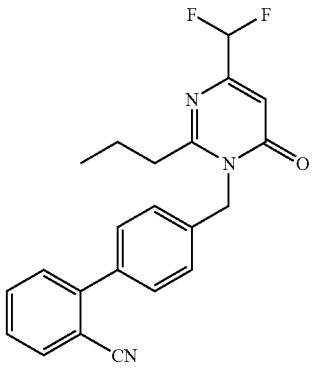

542b) 4'-{[4-(difluoromethyl)-6-oxo-2-propylpyrimidin-1(6H)-yl]methyl}biphenyl-2-carbonitrile A mixture of 6-(difluoromethyl)-2-propylpyrimidin-4(3H)-one (5.6 g), 4'-(bromomethyl)biphenyl-2-carbonitrile (9 g) and potassium carbonate (8.3 g) in acetonitrile (60 mL) was stirred overnight at 50° C. The reaction mixture was diluted with ethyl acetate, washed with 1 M hydrochloric acid, dried over sodium sulfate and concentrated. The residue was purified by silica gel column chromatography to give the title compound as a pale yellow solid (4.4 g, 38%).

$^1$H NMR (300 MHz, CDCl$_3$) δ 0.98 (3 H, t, J=7.4 Hz), 1.71-1.85 (2 H, m), 2.67-2.77 (2 H, m), 5.38 (2 H, s), 6.14-6.77 (2 H, m), 7.23-7.33 (2 H, m), 7.40-7.81 (6 H, m)

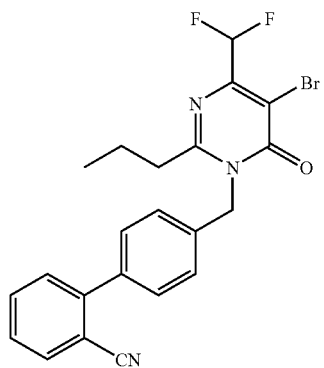

542c) 4'-{[5-bromo-4-(difluoromethyl)-6-oxo-2-propylpyrimidin-1(6H)-yl]methyl}biphenyl-2-carbonitrile To a solution of sodium acetate (1 g) and 4'-{[4-(difluoromethyl)-6-oxo-2-propylpyrimidin-1(6H)-yl] methyl}biphenyl-2-carbonitrile (4.4 g) in acetic acid (44 mL) was added bromine (0.62 mL), and the mixture was stirred for 4 hr. Acetic acid was removed in vacuo, and the mixture was diluted with ethyl acetate, washed with saturated aqueous sodium hydrogen carbonate, dried over sodium sulfate and concentrated. The residue was purified by silica gel column chromatography to give the title compound as a pale yellow solid (2.7 g, 61%).

$^1$H NMR (300 MHz, CDCl$_3$) δ 1.00 (3 H, t, J=7.4 Hz), 1.74-1.89 (2 H, m), 2.69-2.81 (2 H, m), 5.42 (2 H, s), 6.81 (1 H, t, J=53.8 Hz), 7.32 (2 H, d, J=8.3 Hz), 7.40-7.81 (6 H, m)

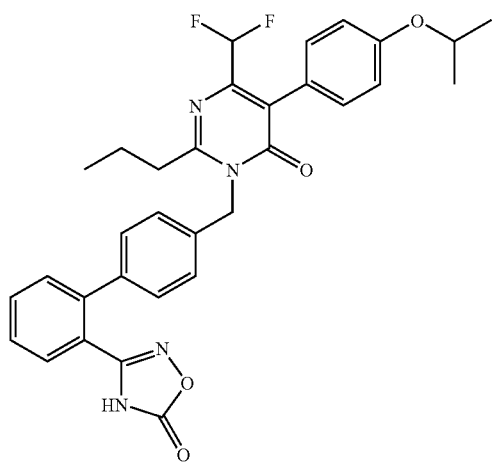

542d) 6-(difluoromethyl)-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one A mixture of (4-isopropoxyphenyl)boronic acid (0.27 g), [1,1'-bis(diphenylphosphino)ferrocene]dichloropalladium (0.041 g) and 4'-{[5-bromo-4-(difluoromethyl)-6-oxo-2-propylpyrimidin-1(6H)-yl]methyl}biphenyl-2-carbonitrile (0.46 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate, passed through silica gel pad and concentrated. The residue was dissolved in dimethyl sulfoxide (5 mL), and hydroxylamine hydrochloride (0.7 g) and sodium hydrogen carbonate (1 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.24 g) and 1,8-diazabicyclo[5.4.0]undec-7-ene (0.22 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.41 g, 72%).

$^1$H NMR (300 MHz, DMSO-d$_6$) δ 0.90 (3 H, t, J=7.4 Hz), 1.30 (6 H, d, J=6.0 Hz), 1.58-1.74 (2 H, m), 2.75 (2 H, t, J=7.3 Hz), 4.59-4.75 (1 H, m), 5.39 (2 H, s), 6.47 (1 H, t, J=53.4 Hz), 6.96-7.03 (2 H, m), 7.20-7.37 (6 H, m), 7.50-7.74 (4 H, m), 12.40 (1 H, br. s.)

Example 543

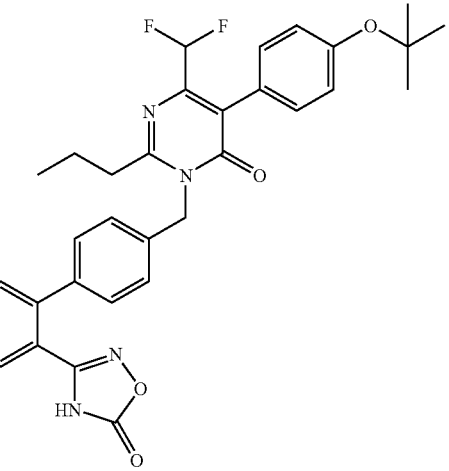

5-(4-tert-butoxyphenyl)-6-(difluoromethyl)-3-{[2'-(5-oxo-4,5-dihydro-1,2,4-oxadiazol-3-yl)biphenyl-4-yl]methyl}-2-propylpyrimidin-4(3H)-one A mixture of (4-tert-butoxyphenyl)boronic acid (0.29 g), [1,1'-bis(diphenylphosphino) ferrocene]dichloropalladium (0.041 g) and 4'-{[5-bromo-4-(difluoromethyl)-6-oxo-2-propylpyrimidin-1(6H)-yl]methyl}biphenyl-2-carbonitrile (0.45 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate, passed through silica gel pad and concentrated. The residue was dissolved in dimethyl sulfoxide (5 mL), and hydroxylamine hydrochloride (0.7 g) and sodium hydrogen carbonate (1 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.24 g) and 1,8-diazabicyclo[5.4.0]undec-7-ene (0.22 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.4 g, 68%).

$^1$H NMR (300 MHz, DMSO-$d_6$) δ 0.90 (3 H, t, J=7.4 Hz), 1.35 (9 H, s), 1.59-1.74 (2 H, m), 2.76 (2 H, t, J=7.4 Hz), 5.39 (2 H, s), 6.46 (1 H, t, J=53.4 Hz), 7.06 (2 H, d, J=8.7 Hz), 7.21-7.36 (6 H, m), 7.48-7.75 (4 H, m), 12.40 (1 H, s)

Example 544

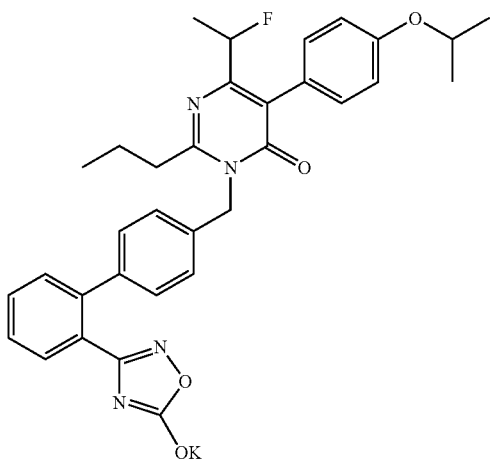

6-(1-fluoroethyl)-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one potassium salt 6-(1-Fluoroethyl)-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one (0.2 g) was dissolved in ethanol (5 mL), and 8 M potassium hydroxide solution (0.044 mL) was added. The mixture was stirred for 1 hr. Ethanol was removed in vacuo, diethyl ether was added, and the resulting solid was collected by filtration to give the title compound as a colorless solid (0.18 g, 84%).

$^1$H NMR (300 MHz, DMSO-$d_6$) δ 0.94 (3 H, t, J=7.4 Hz), 1.29 (6 H, d, J=6.1 Hz), 1.47-1.81 (5 H, m), 2.65-2.88 (2 H, m), 4.58-4.74 (1 H, m), 5.18-5.47 (3 H, m), 6.96 (2 H, d, J=8.7 Hz), 7.12-7.26 (4 H, m), 7.26-7.54 (6 H, m)

Example 545

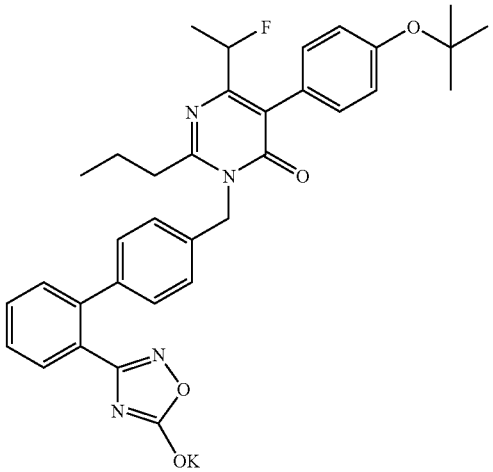

5-(4-tert-butoxyphenyl)-6-(1-fluoroethyl)-3-{[2'-(5-oxo-4,5-dihydro-1,2,4-oxadiazol-3-yl)biphenyl-4-yl]methyl}-2-propylpyrimidin-4(3H)-one potassium salt 5-(4-tert-Butoxyphenyl)-6-(1-fluoroethyl)-3-{[2'-(5-oxo-4,5-dihydro-1,2,4-oxadiazol-3-yl)biphenyl-4-yl]methyl}-2-propylpyrimidin-4(3H)-one (0.21 g) was dissolved in ethanol (5 mL), and 8 M potassium hydroxide solution (0.044 mL) was added. The mixture was stirred for 1 hr. Ethanol was removed in vacuo, diethyl ether was added, and the resulting solid was collected by filtration to give the title compound as a colorless solid (0.18 g, 82%).

$^1$H NMR (300 MHz, DMSO-$d_6$) δ 0.94 (3 H, t, J=7.2 Hz), 1.34 (9 H, s), 1.47-1.80 (5 H, m), 2.68-2.87 (2 H, m), 5.17-5.44 (3H, m), 7.03 (2 H, d, J=8.7 Hz), 7.12-7.55 (10 H, m)

Example 546

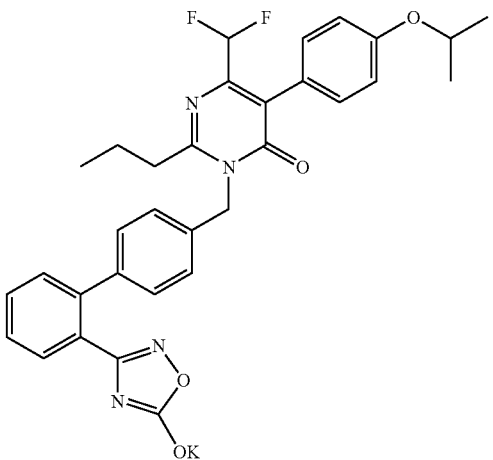

6-(difluoromethyl)-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one potassium salt 6-(Difluoromethyl)-5-(4-isopropoxyphenyl)-3-{[2'-(5-oxo-4,5-dihydro-1,2,4-oxadiazol-3-yl)biphenyl-4-yl]methyl}-2-propylpyrimidin-4(3H)-one (0.3 g) was dissolved in ethanol (5 mL), and 8 M potassium hydroxide solution (0.066 mL) was added. The mixture was stirred for 1 hr. Ethanol was removed in vacuo, diethyl ether was added, and the resulting solid was collected by filtration to give the title compound as a colorless solid (0.29 g, 89%).

$^1$H NMR (300 MHz, DMSO-$d_6$) δ 0.93 (3 H, t, J=7.4 Hz), 1.30 (6 H, d, J=6.1 Hz), 1.61-1.77 (2 H, m), 2.78 (2 H, t, J=7.4 Hz), 4.59-4.74 (1 H, m), 5.34 (2 H, s), 6.45 (1 H, t, J=53.6 Hz), 6.99 (2 H, d, J=8.7 Hz), 7.12-7.55 (10 H, m)

Example 547

5-(4-tert-butoxyphenyl)-6-(difluoromethyl)-3-{[2'-(5-oxo-4,5-dihydro-1,2,4-oxadiazol-3-yl)biphenyl-4-yl]methyl}-2-propylpyrimidin-4(3H)-one potassium salt 5-(4-tert-Butoxyphenyl)-6-(difluoromethyl)-3-{[2'-(5-oxo-4,5-dihydro-1,2,4-oxadiazol-3-yl)biphenyl-4-yl]methyl}-2-propylpyrimidin-4(3H)-one (0.31 g) was dissolved in ethanol (5 mL), and 8 M potassium hydroxide solution (0.066 mL) was added. The mixture was stirred for 1 hr. Ethanol was removed in vacuo, diethyl ether was added, and the resulting solid was collected by filtration to give the title compound as a colorless solid (0.28 g, 85%).

$^1$H NMR (300 MHz, DMSO-$d_6$) δ 0.93 (3 H, t, J=7.4 Hz), 1.35 (9 H, s), 1.62-1.77 (2 H, m), 2.79 (2 H, t, J=7.4 Hz), 5.34 (2 H, s), 6.45 (1 H, t, J=53.4 Hz), 7.01-7.54 (12 H, m)

Example 548

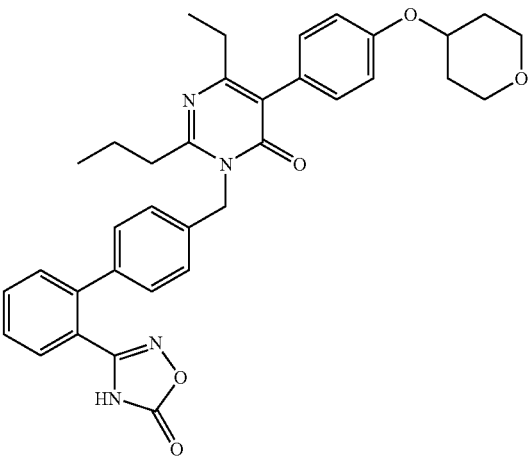

6-ethyl-3-{[2'-(5-oxo-4,5-dihydro-1,2,4-oxadiazol-3-yl)biphenyl-4-yl]methyl}-2-propyl-5-[4-(tetrahydro-2H-pyran-4-yloxy)phenyl]pyrimidin-4(3H)-one To a solution of tetrahydro-2H-pyran-4-ol (0.23 mL), triphenylphosphine (1.2 g) and 4'-{[4-ethyl-5-(4-hydroxyphenyl)-6-oxo-2-propylpyrimidin-1(6H)-yl]methyl}biphenyl-2-carbonitrile (1 g) in tetrahydrofuran (5 mL) was added diisopropyl azodicarboxylate (2.3 mL, 1.9 M toluene solution), and the mixture was stirred for 2 hr at 50° C. After cooling, the reaction mixture was diluted with ethyl acetate, washed with water, dried over sodium sulfate and concentrated. The residue was dissolved in dimethyl sulfoxide (5 mL), and hydroxylamine hydrochloride (0.72 g) and sodium hydrogen carbonate (1 g) were added. The mixture was stirred overnight at 90° C. After cooling, the mixture was diluted with ethyl acetate, washed with water, dried over sodium sulfate and concentrated. The residue was dissolved in tetrahydrofuran (5 mL), and N,N'-carbonyldiimidazole (0.25 g) and 1,8-diazabicyclo[5.4.0]undec-7-ene (0.23 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.47 g, 36%).

$^1$H NMR (300 MHz, DMSO-$d_6$) δ 0.89 (3 H, t, J=7.3 Hz), 1.06-1.14 (3 H, m), 1.53-1.73 (4 H, m), 1.94-2.06 (2 H, m), 2.36 (2 H, q, J=7.5 Hz), 2.68 (2 H, t, J=7.3 Hz), 3.44-3.55 (2 H, m), 3.81-3.91 (2 H, m), 4.53-4.67 (1 H, m), 5.34 (2H, s), 6.97-7.05 (2 H, m), 7.15-7.35 (6 H, m), 7.49-7.75 (4 H, m), 12.40 (1 H, s)

Example 549

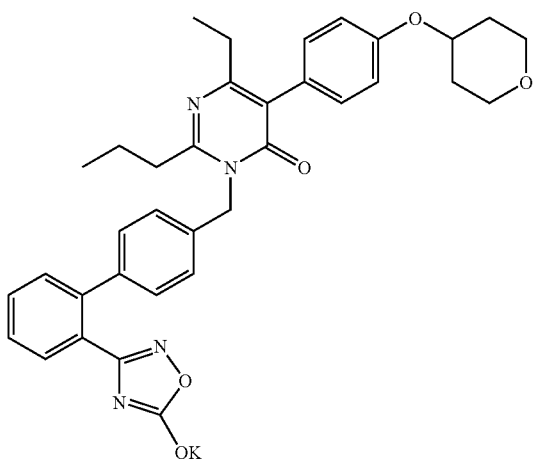

6-ethyl-3-{[2'-(5-oxo-4,5-dihydro-1,2,4-oxadiazol-3-yl)biphenyl-4-yl]methyl}-2-propyl-5-[4-(tetrahydro-2H-pyran-4-yloxy)phenyl]pyrimidin-4(3H)-one potassium salt 6-Ethyl-3-{[2'-(5-oxo-4,5-dihydro-1,2,4-oxadiazol-3-yl)biphenyl-4-yl]methyl}-2-propyl-5-[4-(tetrahydro-2H-pyran-4-yloxy)phenyl]pyrimidin-4(3H)-one (0.3 g) was dissolved in ethanol (5 mL), and 8 M potassium hydroxide solution (0.063 mL) was added. The mixture was stirred for 1 hr. Ethanol was removed in vacuo, diethyl ether was added, and the resulting solid was collected by filtration to give the title compound as a colorless solid (0.29 g, 90%).

$^1$H NMR (300 MHz, DMSO-d$_6$) δ 0.92 (3 H, t, J=7.3 Hz), 1.10 (3 H, t, J=7.4 Hz), 1.53-1.77 (4 H, m), 1.93-2.06 (2 H, m), 2.36 (2 H, q, J=7.3 Hz), 2.71 (2 H, t, J=7.3 Hz), 3.44-3.55 (2 H, m), 3.81-3.92 (2 H, m), 4.54-4.67 (1 H, m), 5.29 (2 H, s), 7.00 (2 H, d, J=8.7 Hz), 7.10-7.23 (4 H, m), 7.25-7.55 (6H, m)

Example 550

5-(4-isopropoxyphenyl)-6-(methoxymethyl)-3-{[2'-(5-oxo-4,5-dihydro-1,2,4-oxadiazol-3-yl)biphenyl-4-yl]methyl}-2-propylpyrimidin-4(3H)-one

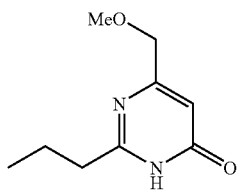

550a)
6-(methoxymethyl)-2-propylpyrimidin-4(3H)-one

A mixture of methyl 4-methoxy-3-oxobutanoate (15.0 g), butanimidamide hydrochloride (15 g) and sodium methoxide (28% in methanol, 51 mL) in methanol (150 mL) was stirred overnight. The reaction mixture was diluted with ethyl acetate, washed with 1M hydrochloric acid, dried over sodium sulfate and concentrated. The residue was purified by silica gel column chromatography to give the title compound as a pale yellow oil (17 g, 91%).

$^1$H NMR (300 MHz, CDCl$_3$) δ 1.00 (3 H, t, J=7.4 Hz), 1.72-1.89 (2 H, m), 2.65 (2 H, t, J=7.8 Hz), 3.48 (3 H, s), 4.32 (2 H, s), 6.45 (1 H, s), 12.80 (1 H, br. s.)

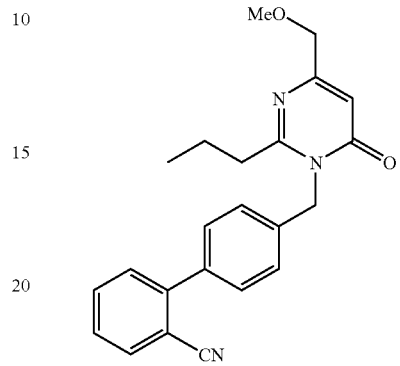

550b) 4'-{[4-(methoxymethyl)-6-oxo-2-propylpyrimidin-1(6H)-yl]methyl}biphenyl-2-carbonitrile A mixture of 6-(methoxymethyl)-2-propylpyrimidin-4(3H)-one (17 g), 4'-(bromomethyl)biphenyl-2-carbonitrile (27 g) and potassium carbonate (25 g) in acetonitrile (300 mL) was stirred overnight at 50° C. The reaction mixture was diluted with ethyl acetate, washed with 1 M hydrochloric acid, dried over sodium sulfate and concentrated. The residue was purified by silica gel column chromatography to give the title compound as a pale yellow solid (15 g, 43%).

$^1$H NMR (300 MHz, CDCl$_3$) δ 0.97 (3 H, t, J=7.4 Hz), 1.66-1.81 (2 H, m), 2.62-2.71 (2 H, m), 3.50 (3 H, s), 4.31 (2 H, s), 5.37 (2 H, s), 6.55 (1 H, s), 7.29 (2 H, d, J=8.3 Hz), 7.41-7.57 (4 H, m), 7.60-7.79 (2 H, m)

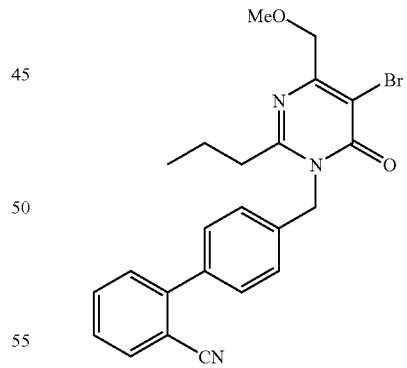

550c) 4'-{[5-bromo-4-(methoxymethyl)-6-oxo-2-propylpyrimidin-1(6H)-yl]methyl}biphenyl-2-carbonitrile To a solution of sodium acetate (3.4 g) and 4'-{[4-(methoxymethyl)-6-oxo-2-propylpyrimidin-1(6H)-yl]methyl}biphenyl-2-carbonitrile (15 g) in acetic acid (150 mL) was added bromine (2.1 mL), and the mixture was stirred for 4 hr. Acetic acid was removed in vacuo, and the reaction mixture was diluted with ethyl acetate, washed with saturated aqueous sodium hydrogen carbonate, dried over sodium sulfate and concentrated. The residue was purified by silica gel column chromatography to give the title compound as a pale yellow solid (7 g, 39%).

$^1$H NMR (300 MHz, CDCl$_3$) δ 0.99 (3 H, t, J=7.4 Hz), 1.70-1.87 (2 H, m), 2.70-2.78 (2 H, m), 3.52 (3 H, s), 4.54 (2 H, s), 5.41 (2 H, s), 7.31 (2 H, d, J=8.0 Hz), 7.41-7.57 (4 H, m), 7.61-7.78 (2 H, m)

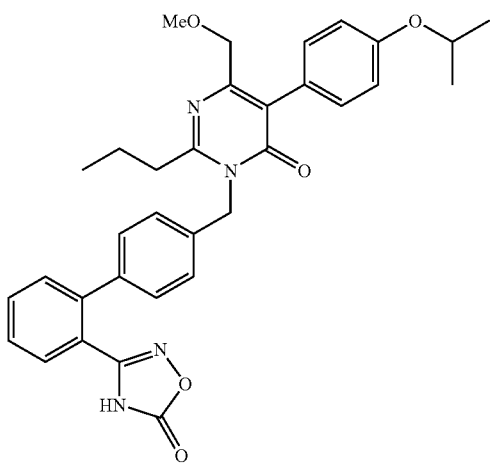

550d) 5-(4-isopropoxyphenyl)-6-(methoxymethyl)-3-{[2'-(5-oxo-4,5-dihydro-1,2,4-oxadiazol-3-yl)biphenyl-4-yl]methyl}-2-propylpyrimidin-4(3H)-one A mixture of (4-isopropoxyphenyl)boronic acid (0.27 g), [1,1'-bis(diphenylphosphino)ferrocene]dichloropalladium (0.041 g) and 4'-{[5-bromo-4-(methoxymethyl)-6-oxo-2-propylpyrimidin-1(6H)-yl]methyl}biphenyl-2-carbonitrile (0.5 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate, passed through silica gel pad and concentrated. The residue was dissolved in dimethyl sulfoxide (5 mL), and hydroxylamine hydrochloride (0.7 g) and sodium hydrogen carbonate (1 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.24 g) and 1,8-diazabicyclo[5.4.0]undec-7-ene (0.22 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.35 g, 56%).

$^1$H NMR (300 MHz, DMSO-d$_6$) δ 0.89 (3 H, t, J=7.4 Hz), 1.29 (6 H, d, J=6.0 Hz), 1.59-1.70 (2 H, m), 2.65-2.75 (2 H, m), 3.25 (3 H, s), 4.07 (2 H, s), 4.59-4.72 (1 H, m), 5.36 (2 H, s), 6.91-6.98 (2 H, m), 7.20-7.34 (6 H, m), 7.50-7.73 (4 H, m) 12.39 (1 H, s)

Example 551

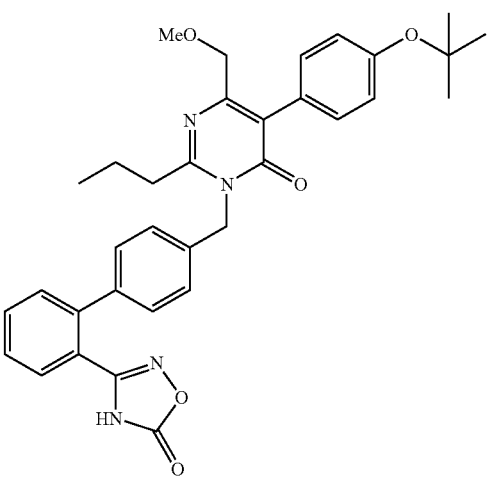

5-(4-tert-butoxyphenyl)-6-(methoxymethyl)-3-{[2'-(5-oxo-4,5-dihydro-1,2,4-oxadiazol-3-yl)biphenyl-4-yl]methyl}-2-propylpyrimidin-4(3H)-one A mixture of (4-tert-butoxyphenyl)boronic acid (0.29 g), [1,1'-bis(diphenylphosphino)ferrocene]dichloropalladium (0.041 g) and 4'-{[5-bromo-4-(methoxymethyl)-6-oxo-2-propylpyrimidin-1(6H)-yl]methyl}biphenyl-2-carbonitrile (0.45 g) in 1,4-dioxane (10 mL) and 2 M cesium carbonate (2 mL) was stirred overnight at 100° C. under an argon atmosphere. After cooling, the reaction mixture was diluted with ethyl acetate, washed with water, dried over sodium sulfate, passed through silica gel pad and concentrated. The residue was dissolved in dimethyl sulfoxide (5 mL), and hydroxylamine hydrochloride (0.7 g) and sodium hydrogen carbonate (1 g) were added. The mixture was stirred overnight at 90° C. After cooling, the reaction mixture was diluted with ethyl acetate, washed with water, dried over sodium sulfate and concentrated. The residue was dissolved in tetrahydrofuran (5 mL), and N,N'-carbonyldiimidazole (0.24 g) and 1,8-diazabicyclo[5.4.0]undec-7-ene (0.22 mL) were added. After stirring for 30 min, the reaction mixture was diluted with ethyl acetate, washed with 1 M hydrochloric acid, dried over sodium sulfate and concentrated. The residue was purified by silica gel column chromatography to give the title compound as a colorless solid (0.52 g, 81%).

$^1$H NMR (300 MHz, DMSO-d$_6$) δ 0.89 (3 H, t, J=7.3 Hz), 1.34 (9 H, s), 1.57-1.73 (2 H, m), 2.71 (2 H, t, J=7.4 Hz), 3.23 (3 H, s), 4.07 (2 H, s), 5.37 (2 H, s), 6.98-7.04 (2 H, m), 7.22-7.35 (6 H, m), 7.50-7.74 (4 H, m), 12.39 (1 H, s)

Example 552

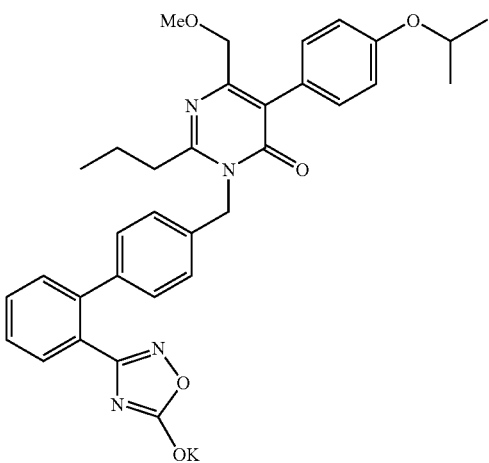

5-(4-isopropoxyphenyl)-6-(methoxymethyl)-3-{[2'-(5-oxo-4,5-dihydro-1,2,4-oxadiazol-3-yl)biphenyl-4-yl]methyl}-2-propylpyrimidin-4(3H)-one potassium salt 5-(4-Isopropoxyphenyl)-6-(methoxymethyl)-3-{[2'-(5-oxo-4,5-dihydro-1,2,4-oxadiazol-3-yl)biphenyl-4-yl]methyl}-2-propylpyrimidin-4(3H)-one (0.3 g) was dissolved in ethanol (10 mL), and 8 M potassium hydroxide solution (0.066 mL) was added. The mixture was stirred for 1 hr. Ethanol was removed in vacuo, diethyl ether was added, and the resulting solid was collected by filtration to give the title compound as a colorless solid (0.29 g, 91%).

$^1$H NMR (300 MHz, DMSO-$d_6$) δ 0.92 (3 H, t, J=7.4 Hz), 1.29 (6 H, d, J=6.0 Hz), 1.63-1.73 (2 H, m), 2.72 (2 H, t, J=7.3 Hz), 3.25 (3 H, s), 4.07 (2 H, s), 4.59-4.71 (1 H, m), 5.32 (2 H, s), 6.90-6.97 (2 H, m), 7.13 (2 H, d, J=8.3 Hz), 7.20-7.54 (8 H, m)

Example 553

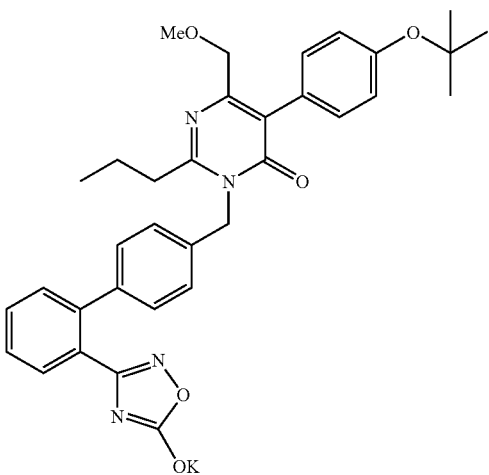

5-(4-tert-butoxyphenyl)-6-(methoxymethyl)-3-{[2'-(5-oxo-4,5-dihydro-1,2,4-oxadiazol-3-yl)biphenyl-4-yl]methyl}-2-propylpyrimidin-4(3H)-one potassium salt 5-(4-tert-Butoxyphenyl)-6-(methoxymethyl)-3-{[2'-(5-oxo-4,5-dihydro-1,2,4-oxadiazol-3-yl)biphenyl-4-yl]methyl}-2-propylpyrimidin-4(3H)-one (0.31 g) was dissolved in ethanol (10 mL), and 8 M potassium hydroxide solution (0.066 mL) was added. The mixture was stirred for 1 hr. Ethanol was removed in vacuo, diethyl ether was added, and the resulting solid was collected by filtration to give the title compound as a colorless solid (0.31 g, 93%).

$^1$H NMR (300 MHz, DMSO-$d_6$) δ 0.92 (3 H, t, J=7.3 Hz), 1.33 (9 H, s), 1.61-1.76 (2 H, m), 2.73 (2 H, t, J=7.4 Hz), 3.23 (3 H, s), 4.06 (2 H, s), 5.32 (2 H, s), 6.97-7.03 (2 H, m), 7.13 (2 H, d, J=8.3 Hz), 7.22-7.53 (8 H, m)

Example 554

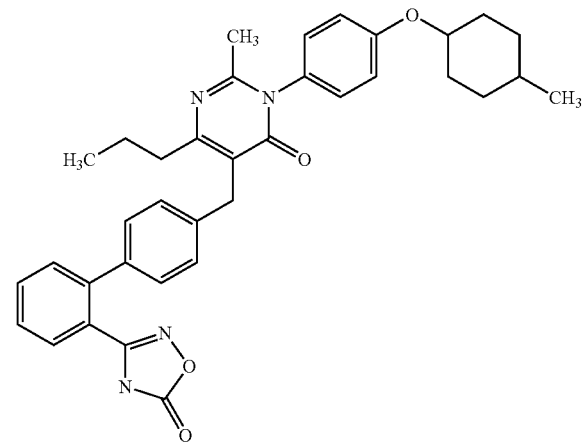

2-methyl-3-{4-[(4-methylcyclohexyl)oxy]phenyl}-5-{[2'-(5-oxo-4,5-dihydro-1,2,4-oxadiazol-3-yl)biphenyl-4-yl]methyl}-6-propylpyrimidin-4(3H)-one To a mixture of 4'-{[1-(4-hydroxyphenyl)-2-methyl-6-oxo-4-propyl-1,6-dihydropyrimidin-5-yl]methyl}biphenyl-2-carbonitrile (0.50 g), 4-methylcyclohexanol (0.29 mL), triphenylphosphine (0.60 g) and tetrahydrofuran (3.5 mL) was dropwise added diisopropyl azodicarboxylate (1.9 M in toluene, 1.21 mL) at 60° C. The mixture was stirred at 60° C. for 15 hr, and ethyl acetate and water were added to the mixture. The layers were separated, and the aqueous layer was extracted with ethyl acetate. The combined organic layer was successively washed with water and saturated brine, dried over anhydrous magnesium sulfate and concentrated under reduced pressure. The residue was purified by silica gel column chromatography to give the crude compound. To a suspension of hydroxylamine hydrochloride (0.96 g) in dimethyl sulfoxide (6 mL) was added sodium hydrogen carbonate (1.45 g) at 50° C. The mixture was stirred at 50° C. for 30 min, and the crude compound obtained above was added. The mixture was stirred at 90° C. for 20 hr and cooled to room temperature, and then ethyl acetate and water were added. The layers were separated, and the aqueous layer was extracted with ethyl acetate. The combined organic layer was successively washed with water and saturated brine, dried over anhydrous magnesium sulfate and concentrated under reduced pressure. A mixture of the resulting residue, 1,1'-carbonyldiimidazole (0.22 g) and 1,8-diazabicyclo[5.4.0]undec-7-ene (0.21 ml) in tetrahydrofuran (6.0 ml) was stirred at room temperature for 3 hr. Ethyl acetate and 1 M hydrochloric acid were added to the reaction mixture, and the layers were separated. The aqueous layer was extracted with ethyl acetate. The combined organic layer was successively washed with water and saturated brine, dried over anhydrous magnesium sulfate and concentrated under reduced pressure. The residue was purified by silica gel column chromatography to give the title compound as a white amorphous solid (0.31 g, 46%).

$^1$H NMR (300 MHz, DMSO-d$_6$) δ 0.85-0.94 (m, 6 H), 1.01-2.14 (m, 14 H), 2.47-2.54 (m, 2 H), 3.86 (s, 2 H), 4.58-4.66 (m, 1 H), 6.99-7.73 (m, 12 H), 12.37 (s, 1 H)

Example 555

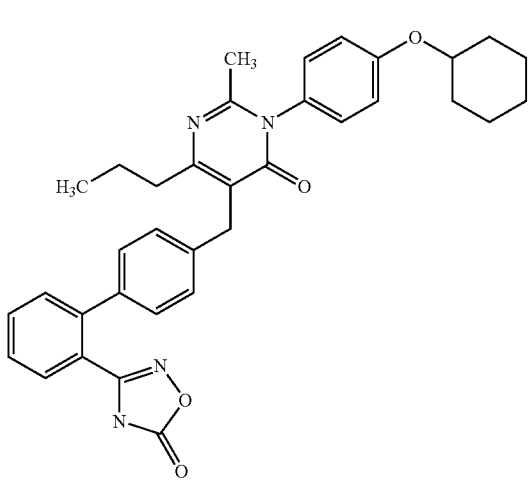

3-[4-(cyclohexyloxy)phenyl]-2-methyl-5-{[2'-(5-oxo-4,5-dihydro-1,2,4-oxadiazol-3-yl)biphenyl-4-yl]methyl}-6-propylpyrimidin-4(3H)-one To a mixture of 4'-{[1-(4-hydroxyphenyl)-2-methyl-6-oxo-4-propyl-1,6-dihydropyrimidin-5-yl]methyl}biphenyl-2-carbonitrile (0.50 g), cyclohexanol (0.24 mL), triphenylphosphine (0.60 g) and tetrahydrofuran (3.5 mL) was dropwise added diisopropyl azodicarboxylate (1.9 M in toluene, 1.2 mL) at 60° C. The mixture was stirred at 60° C. for 15 hr, and ethyl acetate and water were added to the mixture. The layers were separated, and the aqueous layer was extracted with ethyl acetate. The combined organic layer was successively washed with water and saturated brine, dried over anhydrous magnesium sulfate and concentrated under reduced pressure. The residue was purified by silica gel column chromatography to give the crude compound. To a suspension of hydroxylamine hydrochloride (0.96 g) in dimethyl sulfoxide (6 mL) was added sodium hydrogen carbonate (1.45 g) at 50° C. The mixture was stirred at 50° C. for 30 min, and the crude compound obtained above was added. The mixture was stirred at 90° C. for 20 hr and cooled to room temperature, and then ethyl acetate and water were added. The layers were separated, and the aqueous layer was extracted with ethyl acetate. The combined organic layer was successively washed with water and saturated brine, dried over anhydrous magnesium sulfate and concentrated under reduced pressure. A mixture of the resulting residue, 1,1'-carbonylidimidazole (0.22 g) and 1,8-diazabicyclo[5.4.0]undec-7-ene (0.21 ml) in tetrahydrofuran (6.0 ml) was stirred at room temperature for 3 hr. Ethyl acetate and 1 M hydrochloric acid were added to the reaction mixture and the layers were separated. The aqueous layer was extracted with ethyl acetate. The combined organic layer was successively washed with water and saturated brine, dried over anhydrous magnesium sulfate and concentrated under reduced pressure. The residue was purified by silica gel column chromatography to give the title compound as a white amorphous solid (0.29 g, 44%).

$^1$H NMR (300 MHz, DMSO-d$_6$) δ 0.89 (t, J=7.4 Hz, 3H), 1.22-2.01 (m, 12H), 2.06 (s, 3H), 2.46-2.53 (m, 2H), 3.86 (s, 2H), 4.33-4.48 (m, 1H), 7.00-7.74 (m, 12H), 12.37 (s, 1H)

Example 556

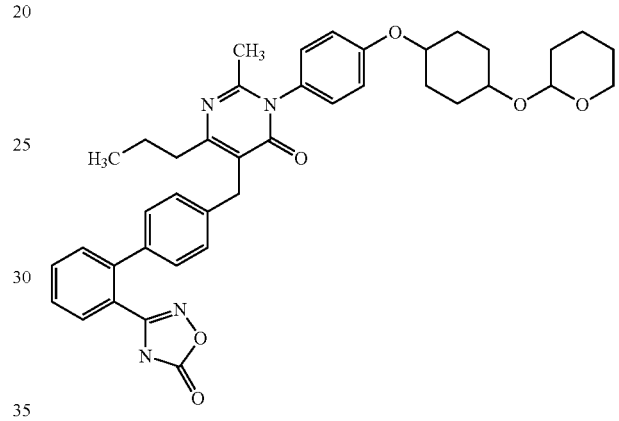

2-methyl-5-{[2'-(5-oxo-4,5-dihydro-1,2,4-oxadiazol-3-yl)biphenyl-4-yl]methyl}-6-propyl-3-(4-{[4-(tetrahydro-2H-pyran-2-yloxy)cyclohexyl]oxy}phenyl)pyrimidin-4(3H)-one To a mixture of 4'-{[1-(4-hydroxyphenyl)-2-methyl-6-oxo-4-propyl-1,6-dihydropyrimidin-5-yl]methyl}biphenyl-2-carbonitrile (1.0 g), 4-(tetrahydro-2H-pyran-2-yloxy)cyclohexanol (0.69 g), triphenylphosphine (0.90 g) and tetrahydrofuran (4.6 mL) was dropwise added diisopropyl azodicarboxylate (1.9 M in toluene, 1.8 mL) at 60° C. The mixture was stirred at 50° C. for 3 hr, and ethyl acetate and water were added to the mixture. The layers were separated, and the aqueous layer was extracted with ethyl acetate. The combined organic layer was successively washed with water and saturated brine, dried over anhydrous magnesium sulfate and concentrated under reduced pressure. The residue was purified by silica gel column chromatography to give the crude compound. To a suspension of hydroxylamine hydrochloride (1.60 g) in dimethyl sulfoxide (12 mL) was added sodium hydrogen carbonate (2.3 g) at 50° C. The mixture was stirred at 50° C. for 30 min, and the crude compound obtained above was added. The mixture was stirred at 90° C. for 15 hr and cooled to room temperature, and then ethyl acetate and water were added. The layers were separated, and the aqueous layer was extracted with ethyl acetate. The combined organic layer was successively washed with water and saturated brine, dried over anhydrous magnesium sulfate and concentrated under reduced pressure. A mixture of the resulting residue, 1,1'-carbonyldiimidazole (0.45 g) and 1,8-diazabicyclo[5.4.0]undec-7-ene (0.42 ml) in tetrahydrofuran (10 ml) was stirred at room temperature for 2 hr. Ethyl acetate and 1M hydrochloric acid were added to the reaction mixture, and the layers were separated. The aqueous layer was extracted with ethyl acetate. The combined organic layer was successively washed with water and saturated brine, dried over anhydrous magnesium sulfate and concentrated under reduced pressure. The residue was purified by silica gel column chromatography to give the title compound as a white amorphous solid (0.29 g, 50%).

$^1$H NMR (300 MHz, DMSO-$d_6$) δ 0.89 (t, J=7.3 Hz, 3 H), 1.35-2.11 (m, 18 H), 2.46-2.56 (m, 2 H), 3.37-3.92 (m, 5 H), 4.37-4.55 (m, 1 H), 4.66-4.73 (m, 1 H), 7.01-7.72 (m, 12H), 12.38 (s, 1 H)

Example 557

3-{4-[(4,4-difluorocyclohexyl)oxy]phenyl}-2-ethyl-5-{[2'-(5-oxo-4,5-dihydro-1,2,4-oxadiazol-3-yl)biphenyl-4-yl]methyl}-6-propylpyrimidin-4(3H)-one

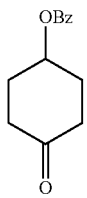

557a) 4-oxocyclohexyl benzoate

A mixture of 1,4-dioxaspiro[4.5]decan-8-ol (4.44 g), benzoyl chloride (3.9 mL), pyridine (2.7 mL) and tetrahydrofuran (50 mL) was stirred at room temperature for 12 hr. The reaction mixture was diluted with ethyl acetate, and washed with saturated aqueous sodium hydrogen carbonate and saturated brine, dried over anhydrous magnesium sulfate and concentrated in vacuo. The residue was dissolved in tetrahydrofuran (50 mL), and 6 M hydrochloric acid (4.7 mL) was added thereto, and then the mixture was stirred at 60° C. for 12 hr. The reaction mixture was diluted with ethyl acetate, and the organic layer was separated. The aqueous layer was extracted with ethyl acetate, and the combined organic layer was successively washed with water and saturated brine, dried over anhydrous magnesium sulfate and concentrated in vacuo. The residue was purified by column chromatography on silica gel to give the title compound as a pale yellow oil (2.64 g, 43%).

$^1$H NMR (300 MHz, CDCl$_3$) δ 2.10-2.34 (m, 4H) 2.38-2.51 (m, 2H), 2.59-2.73 (m, 2H), 5.40-5.48 (m, 1H), 7.41-7.51 (m, 2H), 7.54-7.63 (m, 1H), 8.02-8.12 (m, 2H)

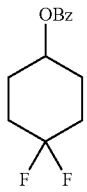

557b) 4,4-difluorocyclohexyl benzoate

To a solution of 4-oxocyclohexyl benzoate (2.64 g) in toluene (40 ml) was added dropwise diethylaminosulfur trifluoride (2.4 mL) at 0° C. over a period of 5 min, and the mixture was stirred at room temperature for 12 hr. The reaction mixture was concentrated in vacuo, and the residue was diluted with ethyl acetate. The mixture was washed with water and saturated brine, dried over anhydrous magnesium sulfate and concentrated in vacuo. The residue was purified by column chromatography on silica gel to give the title compound as a pale yellow oil (2.0 g, 69%).

$^1$H NMR (300 MHz, CDCl$_3$) δ 1.69-2.41 (m, 8 H) 4.97-5.36 (m, 1 H) 7.40-7.50 (m, 2 H) 7.52-7.62 (m, 1 H) 8.00-8.07 (m, 2 H)

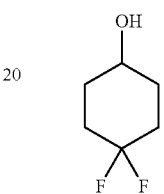

557c) 4,4-difluorocyclohexanol

A mixture of 4,4-difluorocyclohexyl benzoate (2.0 g), 1M sodium hydroxide solution (10 mL) and ethanol (20 mL) was stirred at 70° C. for 3 hr. The reaction mixture was added to a mixture of ethyl acetate and water, and the organic layer was separated. The aqueous layer was extracted with ethyl acetate, and the combined organic layer was successively washed with water and saturated brine, dried over anhydrous magnesium sulfate and concentrated in vacuo. The residue was purified by column chromatography on silica gel to give the title compound (1.0 g, 90%).

$^1$H NMR (300 MHz, CDCl$_3$) δ 1.56-2.22 (m, 8 H) 3.85-4.05 (m, 2 H)

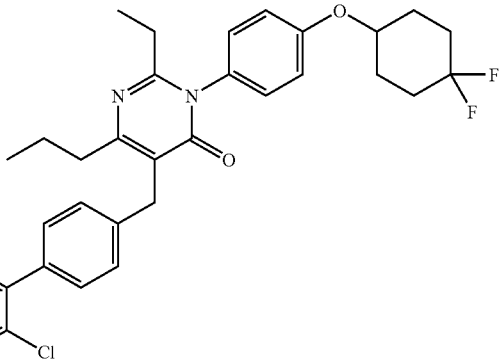

557d) 4'-[(1-{4-[(4,4-difluorocyclohexyl)oxy]phenyl}-2-ethyl-6-oxo-4-propyl-1,6-dihydropyrimidin-5-yl)methyl]biphenyl-2-carbonitrile A mixture of 4'-{[2-ethyl-1-(4-hydroxyphenyl)-6-oxo-4-propyl-1,6-dihydropyrimidin-5-yl]methyl}biphenyl-2-carbonitrile (600 mg), 4,4-difluorocyclohexanol (362 mg,), diisopropyl azodicarboxylate (1.9 M in toluene, 1.4 mL), triphenylphosphine (698 mg) and tetrahydrofuran (10 ml) was stirred at 60° C. for 3 hr. The reaction mixture was diluted with ethyl acetate, and successively washed with water and saturated brine, dried over anhydrous magnesium sulfate and concentrated in vacuo. The residue was purified by column chromatography on silica gel to give the title compound as a pale yellow oil (635 mg, 86%).

$^1$H NMR (300 MHz, CDCl$_3$) δ 1.01 (t, J=7. Hz, 3 H) 1.15 (t, J=7.44 Hz, 3 H) 1.62-2.26 (m, 12 H) 2.63-2.73 (m, 2 H) 3.96 (s, 2 H) 4.49-4.60 (m, 1 H) 6.98-7.06 (m, 2 H) 7.11-7.17 (m, 2 H) 7.37-7.51 (m, 6 H) 7.58-7.66 (m, 1 H) 7.74 (dd, J=7.72, 0.94 Hz, 1 H)

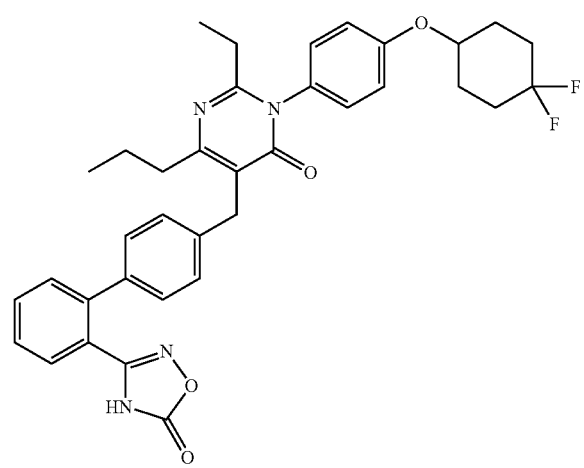

557e) 3-{4-[(4,4-difluorocyclohexyl)oxy]phenyl}-2-ethyl-5-{[2'-(5-oxo-4,5-dihydro-1,2,4-oxadiazol-3-yl)biphenyl-4-yl]methyl}-6-propylpyrimidin-4(3H)-one A suspension of hydroxylamine hydrochloride (661 mg) and sodium hydrogen carbonate (941 mg) in dimethyl sulfoxide (5 mL) was stirred at 40° C. for 30 min, and then 4'-[(1-{4-[(4,4-difluorocyclohexyl)oxy]phenyl}-2-ethyl-6-oxo-4-propyl-1,6-dihydropyrimidin-5-yl)methyl]biphenyl-2-carbonitrile (635 mg) was added to the mixture, and the mixture was stirred at 90° C. for 12 hr. Water was added to the reaction mixture, and the precipitated solid was collected by filtration. The obtained solid was dissolved in ethyl acetate. The solution was washed with saturated brine and dried over anhydrous sodium sulfate, and the solvent was evaporated. The residue was dissolved in tetrahydrofuran (20 mL), and then 1,1'-carbonyldiimidazole (272 mg) and 1,8-diazabicyclo[5,4,0]undec-7-ene (0.25 mL) were added thereto. The mixture was stirred at room temperature for 2 hr. The reaction mixture was diluted with ethyl acetate, and the mixture was successively washed with water and saturated brine (20 mL), dried over anhydrous magnesium sulfate and concentrated in vacuo. The residue was purified by column chromatography on silica gel to give the title compound as a pale yellow amorphous solid (12.1 mg, 2%).

$^1$H NMR (300 MHz, DMSO-d$_6$) δ 0.90 (t, J=7.25 Hz, 3 H) 1.17 (t, J=7.16 Hz, 3 H) 1.51-1.67 (m, 2 H) 1.73-2.15 (m, 6 H) 2.22-2.36 (m, 2 H) 2.49-2.59 (m, 2 H) 3.87 (s, 2 H) 4.03 (q, J=7.16 Hz, 2 H) 4.61-4.73 (m, 1 H) 7.08-7.15 (m, 2 H) 7.19-7.33 (m, 6 H) 7.46-7.59 (m, 2 H) 7.62-7.73 (m, 2 H) 12.17-12.51 (m, 1 H)

Example 558

3-[4-(1,4-dioxaspiro[4.5]dec-8-yloxy)phenyl]-2-ethyl-5-{[2'-(5-oxo-4,5-dihydro-1,2,4-oxadiazol-3-yl)biphenyl-4-yl]methyl}-6-propylpyrimidin-4(3H)-one

558a) 1,4-dioxaspiro[4.5]decan-8-ol

To a solution of 1,4-dioxaspiro[4.5]decan-8-one (10.0 g) in methanol (120 ml) was added sodium borohydride (4.84 g) at 0° C. over a period of 15 min, and the mixture was stirred at room temperature for 3 hr. The reaction mixture was concentrated in vacuo, and the residue was diluted with ethyl acetate. The mixture was washed with water and saturated brine, dried over anhydrous magnesium sulfate and concentrated in vacuo. The residue was purified by column chromatography on silica gel to give the title compound as a pale yellow oil (6.24 g, 62%).

$^1$H NMR (300 MHz, CDCl$_3$) δ 1.30 (d, J=4.52 Hz, 1 H) 1.53-1.72 (m, 4 H) 1.77-1.94 (m, 4 H) 3.75-3.86 (m, 1 H) 3.93-3.97 (m, 4 H)

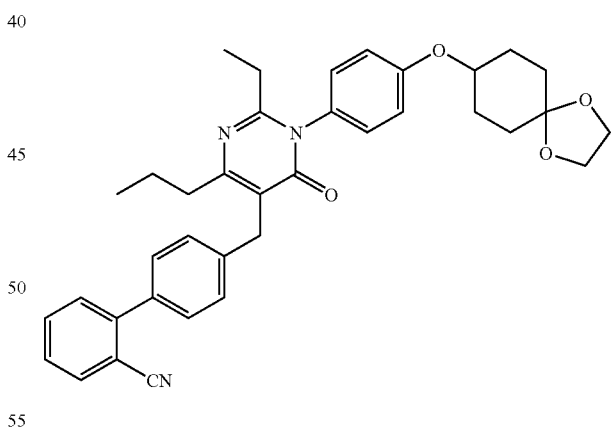

558b) 4'-({1-[4-(1,4-dioxaspiro[4.5]dec-8-yloxy)phenyl]-2-ethyl-6-oxo-4-propyl-1,6-dihydropyrimidin-5-yl}methyl)biphenyl-2-carbonitrile A mixture of 4'-{[2-ethyl-1-(4-hydroxyphenyl)-6-oxo-4-propyl-1,6-dihydropyrimidin-5-yl]methyl}biphenyl-2-carbonitrile (4.0 g), 1,4-dioxaspiro[4.5]decan-8-ol (2.82 g), diisopropyl azodicarboxylate (1.9 M in toluene, 3.2 mL), triphenylphosphine (4.67 g) and tetrahydrofuran (20 ml) was stirred at room temperature for 2 hr. The reaction mixture was diluted with ethyl acetate, successively washed with water and saturated brine, dried over anhydrous magnesium sulfate and concentrated in vacuo. The residue was purified by column chromatography on silica gel to give the title compound as a pale yellow amorphous solid (5.13 g, 98%).

$^1$H NMR (300 MHz, CDCl$_3$) δ 1.01 (t, J=7.35 Hz, 3 H) 1.14 (t, J=7.44 Hz, 3 H) 1.56-1.79 (m, 4 H) 1.84-2.04 (m, 6 H) 2.38 (q, J=7.41 Hz, 2 H) 2.62-2.72 (m, 2 H) 3.89-4.05 (m, 6 H) 4.38-4.49 (m, 1 H) 6.98-7.05 (m, 2 H) 7.07-7.14 (m, 2 H) 7.35-7.52 (m, 6 H) 7.55-7.66 (m, 1 H) 7.74 (dd, J=7.72, 0.94 Hz, 1 H)

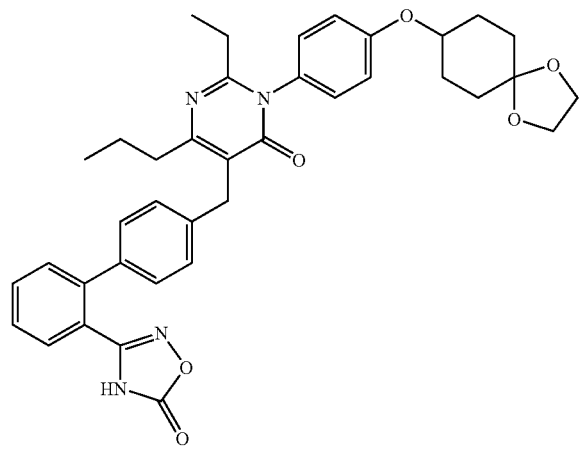

558c) 3-[4-(1,4-dioxaspiro[4.5]dec-8-yloxy)phenyl]-2-ethyl-5-{[2'-(5-oxo-4,5-dihydro-1,2,4-oxadiazol-3-yl)biphenyl-4-yl]methyl}-6-propylpyrimidin-4(3H)-one A suspension of hydroxylamine hydrochloride (5.14 g) and sodium hydrogen carbonate (7.31 g) in dimethyl sulfoxide (30 mL) was stirred at 40° C. for 30 min, and then 4'-({1-[4-(1,4-dioxaspiro[4.5]dec-8-yloxy)phenyl]-2-ethyl-6-oxo-4-propyl-1,6-dihydropyrimidin-5-yl}methyl)biphenyl-2-carbonitrile (5.13 g) was added to the mixture, and the mixture was stirred at 90° C. for 12 hr. Water was added to the reaction mixture, and the precipitated solid was collected by filtration. The obtained solid was dissolved in ethyl acetate. The solution was washed with saturated brine and dried over anhydrous sodium sulfate, and the solvent was evaporated. The residue was dissolved in tetrahydrofuran (40 mL), and then 1,1'-carbonyldiimidazole (2.12 g, 13.1 mmol) and 1,8-diazabicyclo[5,4,0]undec-7-ene (2.0 mL, 13.1 mmol) were added thereto. The mixture was stirred at room temperature for 2 hr. The reaction mixture was diluted with ethyl acetate, and the mixture was successively washed with water and saturated brine, dried over anhydrous magnesium sulfate and concentrated in vacuo. The residue was purified by column chromatography on silica gel to give the title compound as a pale yellow amorphous solid (3.63 g, 64%).

$^1$H NMR (300 MHz, DMSO-d$_6$) δ 0.92 (t, J=7.35 Hz, 3 H) 1.05 (t, J=6.88 Hz, 3 H) 1.48-2.00 (m, 12 H) 2.28 (q, J=7.41 Hz, 2 H) 2.52-2.58 (m, 2 H) 3.80-3.86 (m, 2 H) 3.88 (s, 2 H) 4.49-4.60 (m, 1 H) 6.98-7.12 (m, 4 H) 7.18-7.29 (m, 3 H) 7.37-7.49 (m, 2 H) 7.52-7.68 (m, 3 H) 12.47 (s, 1 H)

Experimental Example 1

Binding Assay Using Human AT1 Receptor-Expressing CHO-K1 Cell Membrane Fraction

The membrane fraction for human AT1 receptor binding assay was prepared as follows. CHO-K1 cell capable of stable expression of human AT1 receptor was cultured, recovered, suspended in homogenize buffer (10 mM NaHCO$_3$ (pH 7.4), 5 mM EDTA, 1×Complete EDTA free) [manufactured by Roche, Switzerland], and homogenized. The homogenate was centrifuged at low-speed (900×g, 10 min, 4° C.), and the supernatant was recovered and ultracentrifuged (90,000×g, 1 hr, 4° C.). The supernatant was discarded, and the pellets were resuspended in resuspension buffer (50 mM Tris (pH 7.4), 1 mM EDTA, 1×Complete EDTA free).

The binding assay was performed in the presence of 22.5 pM [$^{125}$I]-angiotensin II [manufactured by PerkinElmer, USA], 9 μg of AT1 membrane and test compound in 100 μL (total reaction volume) of reaction buffer (50 mM Tris (pH 7.4), 10 mM MgCl$_2$ supplemented or not supplemented with 0.3 mg/mL fatty acid-free bovine serum albumin [manufactured by Wako Pure Chemical Industries, Ltd., Japan]). The reaction mixture was incubated in 96 well polypropylene plate for 1 hr at room temperature, and the reaction was quenched by rapid filtration (96 well cell harvester) through a GF/C filter treated with wash buffer (50 mM Tris (pH 7.4)). Subsequently, the filter was washed 5 times with 0.3 mL of ice-cooled wash buffer. The filter was air-dried, and [$^{125}$I]-angiotensin II binding radioactivity was assayed with Top Count scintillation counter. Total binding was measured in the presence of 1% DMSO and nonspecific binding was measured in the presence of 1 μM CV-11974. The binding data was analyzed by GraphPad Prism program and the IC$_{50}$ value (compound concentration showing 50% of the maximum value of inhibition percent) of the test compound was calculated. The results are shown in Tables 1 to 5.

Experimental Example 2

Evaluation of PPARγ Activating Action

PPARγ:RXRα:4ERPP/CHO-K1 cells obtained in the following Reference Example 5 were cultured in F12 medium [manufactured by INVITROGEN, USA] containing 10% fetal bovine serum [manufactured by MOREGATE, Australia], seeded in a 96-well half area white plate [manufactured by Corning Coster Corporation, USA] at the density of 5×10$^3$ cells/well and cultured in a CO$_2$ gas incubator at 37° C. overnight.

Then the medium was removed from the 96-well half area white plate, 45 μl of Ham's F12 medium containing 0.1% fatty acid-free bovine serum albumin (BSA) and 5 μl of test compound were added, and the cells were cultured in a CO$_2$ gas incubator at 37° C. for 1 day. The medium was removed and 20 μl of PicaGene 7.5 [manufactured by TOYO INK MFG. CO., LTD., Japan] diluted 2-fold with HBSS (HANKS' BALANCED SALT SOLUTION) [manufactured by BIO WHITTAKER, USA] was added. After stirring, the luciferase activity was determined using 1420 ARVO Multilabel Counter [manufactured by PerkinElmer, USA].

The percent (%) was calculated from the luciferase activity of each test compound when the luciferase activity of the control compound (compound X: 5-[3-(4-{[2-(2-furyl)-5-methyl-1,3-oxazol-4-yl]methoxy}-3-methoxyphenyl)propyl]-1,3-oxazolidine-2,4-dione) (1 μM) was 100% and that of the test compound non-administration group was 0%. The results are shown in Tables 1 to 5.

TABLE 1

| Example No. | AT$_1$ receptor binding inhibitory action (IC$_{50}$ (nM)) | PPARγ activating action (activation % ($10^{-6 M}$)) |
|---|---|---|
| 3 | 2.5 | 57.1 |
| 4 | 1.9 | 35.8 |
| 7 | 1.4 | 42.6 |
| 28 | 1.6 | 16.2 |
| 32 | 1.3 | 55.6 |
| 37 | 1.3 | 29.8 |
| 42 | 1.5 | 61.2 |
| 47 | 1.4 | 61.2 |
| 48 | 1.8 | 68.8 |
| 50 | 1.7 | 34.3 |
| 51 | 1.5 | 19.6 |
| 58 | 1.5 | 55.1 |
| 64 | 2.0 | 59.9 |
| 67 | 2.0 | 49.4 |
| 71 | 1.8 | 46.3 |
| 81 | 1.6 | 62.9 |
| 88 | 1.7 | 31.2 |
| 94 | 1.8 | 41.5 |
| 103 | 1.5 | 50.2 |
| 105 | 1.9 | 64.1 |
| 107 | 2.0 | 60.0 |
| 108 | 2.2 | 31.7 |
| 112 | 1.7 | 52.1 |
| 118 | 1.8 | 50.2 |
| 128 | 1.9 | 24.3 |
| 131 | 2.2 | 34.2 |
| 136 | 2.9 | 32.9 |
| 141 | 1.8 | 38.3 |
| 142 | 1.7 | 32.8 |
| 144 | 1.5 | 22.7 |
| 145 | 1.8 | 36.5 |

TABLE 2

| Example No. | AT$_1$ receptor binding inhibitory action (IC$_{50}$ (nM)) | PPARγ activating action (activation % ($10^{-6 M}$)) |
|---|---|---|
| 152 | 2.1 | 64.8 |
| 160 | 1.8 | 61.6 |
| 165 | 1.7 | 59.0 |
| 178 | 2.6 | 37.5 |
| 202 | 1.5 | 25.3 |
| 204 | 1.6 | 27.4 |
| 206 | 2.0 | 21.8 |
| 217 | 1.1 | 26.8 |
| 222 | 1.3 | 29.3 |
| 234 | 1.2 | 33.9 |
| 235 | 1.5 | 27.6 |
| 239 | 1.8 | 31.6 |
| 249 | 1.6 | 30.5 |
| 255 | 1.7 | 30.5 |
| 256 | 2.0 | 45.7 |
| 265 | 1.7 | 27.8 |
| 271 | 1.9 | 37.1 |
| 275 | 1.8 | 17.0 |
| 277 | 1.8 | 33.5 |
| 287 | 1.8 | 40.9 |
| 293 | 1.8 | 28.2 |
| 294 | 1.8 | 47.1 |
| 309 | 1.6 | 31.5 |
| 310 | 1.9 | 27.1 |
| 311 | 1.6 | 38.1 |
| 312 | 1.6 | 50.3 |
| 313 | 1.5 | 31.0 |
| 318 | 1.8 | 19.2 |
| 319 | 1.8 | 17.2 |

TABLE 2-continued

| Example No. | AT$_1$ receptor binding inhibitory action (IC$_{50}$ (nM)) | PPARγ activating action (activation % ($10^{-6 M}$)) |
|---|---|---|
| 323 | 2.1 | 20.0 |
| 324 | 1.7 | 45.2 |

TABLE 3

| Example No. | AT$_1$ receptor binding inhibitory action (IC$_{50}$ (nM)) | PPARγ activating action (activation % ($10^{-6 M}$)) |
|---|---|---|
| 325 | 3.4 | 30.2 |
| 327 | 2.2 | 22.6 |
| 338 | 1.8 | 32.5 |
| 343 | 0.7 | 15.2 |
| 346 | 1.0 | 21.8 |
| 356 | 1.1 | 16.6 |
| 362 | 2.4 | 58.7 |
| 363 | 2.1 | 53.7 |
| 364 | 1.9 | 32.6 |
| 365 | 1.8 | 25.3 |
| 368 | 2.0 | 50.2 |
| 369 | 1.9 | 36.3 |
| 373 | 2.4 | 48.4 |
| 376 | 1.7 | 22.0 |
| 377 | 1.5 | 30.3 |
| 378 | 1.5 | 46.9 |
| 379 | 3.4 | 31.0 |
| 381 | 1.2 | 28.2 |
| 382 | 1.2 | 27.2 |
| 388 | 1.6 | 34.4 |
| 389 | 1.8 | 18.1 |
| 390 | 1.2 | 19.9 |
| 395 | 1.7 | 16.0 |
| 396 | 2.2 | 50.6 |
| 397 | 2.1 | 48.6 |
| 400 | 2.8 | 21.3 |
| 401 | 1.5 | 25.3 |
| 402 | 1.8 | 24.1 |
| 406 | 1.5 | 41.9 |
| 408 | 1.4 | 48.7 |
| 410 | 2.1 | 19.5 |

TABLE 4

| Example No. | AT$_1$ receptor binding inhibitory action (IC$_{50}$ (nM)) | PPARγ activating action (activation % ($10^{-6 M}$)) |
|---|---|---|
| 413 | 1.7 | 18.9 |
| 414 | 1.1 | 45.0 |
| 415 | 1.0 | 49.7 |
| 416 | 1.2 | 53.5 |
| 417 | 1.6 | 33.7 |
| 419 | 1.3 | 27.2 |
| 422 | 0.9 | 22.2 |
| 424 | 1.3 | 33.5 |
| 425 | 1.2 | 37.5 |
| 427 | 1.4 | 17.7 |
| 437 | 1.0 | 18.1 |
| 439 | 1.4 | 20.1 |
| 440 | 1.6 | 29.9 |
| 444 | 1.3 | 55.4 |
| 445 | 1.2 | 62.9 |
| 450 | 1.8 | 23.7 |
| 452 | 2.1 | 52.9 |
| 453 | 2.9 | 22.5 |
| 455 | 2.0 | 16.0 |
| 456 | 1.8 | 30.0 |
| 457 | 3.5 | 36.0 |
| 458 | 2.2 | 36.0 |
| 459 | 2.1 | 40.0 |
| 460 | 2.2 | 30.0 |
| 467 | 2.5 | 35.7 |
| 473 | 3.6 | 15.7 |
| 475 | 2.0 | 28.7 |

TABLE 4-continued

| Example No. | AT$_1$ receptor binding inhibitory action (IC$_{50}$ (nM)) | PPARγ activating action (activation % (10$^{-6}$ M)) |
| --- | --- | --- |
| 476 | 2.1 | 18.5 |
| 480 | 3.2 | 30.8 |
| 482 | 1.9 | 30.4 |
| 483 | 2.4 | 31.5 |

TABLE 5

| Example No. | AT$_1$ receptor binding inhibitory action (IC$_{50}$ (nM)) | PPARγ activating action (activation % (10$^{-6}$ M)) |
| --- | --- | --- |
| 484 | 2.3 | 19.4 |
| 485 | 2.0 | 23.5 |
| 488 | 1.9 | 16.7 |
| 500 | 2.7 | 35.9 |
| 501 | 2.6 | 31.8 |
| 507 | 2.2 | 32.4 |
| 509 | 1.2 | 16.2 |
| 510 | 2.3 | 24.4 |
| 511 | 1.3 | 31.0 |
| 512 | 1.3 | 20.3 |

In the above-mentioned Tables, the compounds of Examples 309, 310, 311, 312, 313, 473, 476 and 488 are potassium salts and other Example compounds are free forms.

Reference Example 1

Cloning of Human PPARγ Gene

Human PPARγ gene was cloned by a PCR method using heart cDNA [manufactured by Toyobo Co., Ltd., QUICK-Clone cDNA] as a template, and a primer set shown below which was prepared by reference to the base sequence of PPARγ gene reported by Greene et al. [Gene Expr., 1995, vol. 4(4-5), pp. 281-299].

PAG-U:
(SEQ ID NO: 1)
5'-GTG GGT ACC GAA ATG ACC ATG GTT GAC ACA GAG-3'

PAG-L:
(SEQ ID NO: 2)
5'-GGG GTC GAC CAG GAC TCT CTG CTA GTA CAA GTC-3'

The PCR reaction was performed by Hot Start method using AmpliWax PCR Gem 100 [manufactured by Takara Shuzo Co., Ltd., Japan]. First, 2 μl of 10×LA PCR Buffer, 3 μl of 2.5 mM dNTP solution, 2.5 μl each of 12.5 μM primer solutions and 10 μl of sterile distilled water were mixed to obtain a bottom layer solution mixture. One μl of human heart cDNA (1 ng/ml) as a template, 3 μl of 10×LA PCR Buffer, 1 μl of 2.5 mM dNTP solution, 0.5 μl of TaKaRa LA Taq DNA polymerase [manufactured by Takara Shuzo Co., Ltd., Japan] and 24.5 μl of sterile distilled water were mixed to obtain a top layer solution mixture.

To the bottom layer solution mixture described above was added one unit of AmpliWax PCR Gem 100 [manufactured by Takara Shuzo Co., Ltd., Japan], which was treated at 70° C. for 5 minutes and then in ice for 5 minutes. Then, the top layer solution mixture was added to the mixture to prepare the reaction mixture for PCR. A tube containing the reaction mixture was set on a thermal cycler [manufactured by Perkinelmer, USA] and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 1.4 kb DNA fragment containing PPARγ gene was recovered from the gel, and then inserted into pT7 Blue-T vector [manufactured by Takara Shuzo Co., Ltd., Japan] to obtain plasmid pTBT-hPPARγ.

Reference Example 2

Cloning of Human RXRα Gene

A human RXRα gene was cloned by a PCR method using kidney cDNA [manufactured by Toyobo Co., Ltd., QUICK-Clone cDNA] as a template, and a primer set shown below which was prepared with reference to the base sequence of RXRα gene reported by Mangelsdorf, D. J. et al. (Nature, 1990, vol. 345 (6272), pp. 224-229).

XRA-U:
(SEQ ID NO: 3)
5'-TTA GAA TTC GAC ATG GAC ACC AAA CAT TTC CTG-3'

XRA-L:
(SEQ ID NO: 4)
5'-CCC CTC GAG CTA AGT CAT TTG GTG CGG CGC CTC-3'

The PCR reaction was performed by Hot Start method using AmpliWax PCR Gem 100 [manufactured by Takara Shuzo Co., Ltd., Japan]. First, 2 μl of 10×LA PCR Buffer, 3 μl of 2.5 mM dNTP solution, 2.5 μl each of 12.5 μM primer solutions and 10 μl of sterile distilled water were mixed to obtain a bottom layer solution mixture. One μl of human kidney cDNA (1 ng/ml) as a template, 3 μl of 10×LA PCR Buffer, 1 μl of 2.5 mM dNTP solution, 0.5 μl of TaKaRa LA Taq DNA polymerase [manufactured by Takara Shuzo Co., Ltd., Japan] and 24.5 μl of sterile distilled water were mixed to obtain a top layer solution mixture.

To the bottom layer solution mixture described above was added one unit of AmpliWax PCR Gem 100 [manufactured by Takara Shuzo Co., Ltd., Japan], which was treated at 70° C. for 5 minutes and then in ice for 5 minutes. Then, the top layer solution mixture was added to the mixture to prepare the reaction mixture for PCR. A tube containing the reaction mixture was set on a thermal cycler [manufactured by Perkinelmer, USA] and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 1.4 kb DNA fragment containing RXRα gene was recovered from the gel, and then inserted into pT7 Blue-T vector [manufactured by Takara Shuzo Co., Ltd., Japan] to obtain plasmid pTBT-hRXRα.

Reference Example 3

Construction of Reporter Plasmid

A DNA fragment containing PPAR-response element (PPRE) of an acyl CoA oxidase was prepared using the following 5'-terminal phosphorylated synthetic DNA.

```
PPRE-U:
                                           (SEQ ID NO: 5)
5'-pTCGACAGGGGACCAGGACAAAGGTCACGTTCGGGAG-3'

PPRE-L:
                                           (SEQ ID NO: 6)
5'-pTCGACTCCCGAACGTGACCTTTGTCCTGGTCCCCTG-3'
```

First, PPRE-U and PPRE-L were annealed and inserted to SalI site of plasmid pBlueScript SK+. By determining the base sequence of the inserted fragment, plasmid pBSS-PPRE4, in which 4 PPREs were ligated in tandem, was selected.

An HSV thymidine kinase minimum promoter (TK promoter) region was cloned by a PCR method using pRL-TK vector [manufactured by Promega, USA] as a template, and a primer set shown below which was prepared with reference to the base sequence of the promoter region of thymidine kinase gene reported by Luckow, B et al. (Nucleic Acids Res., 1987, vol. 15(13), p. 5490)

```
                                           (SEQ ID NO: 7)
TK-U: 5'-CCCAGATCTCCCCAGCGTCTTGTCATTG-3'

(SEQ ID NO: 8)
TK-L: 5'-TCACCATGGTCAAGCTTTTAAGCGGGTC-3'
```

The PCR reaction was performed by Hot Start method using AmpliWax PCR Gem 100 [manufactured by Takara Shuzo Co., Ltd., Japan]. First, 2 µl of 10×LA PCR Buffer, 3 µl of 2.5 mM dNTP solution, 2.5 µl each of 12.5 µM primer solutions and 10 µl of sterile distilled water were mixed to obtain a bottom layer solution mixture. One µl of pRL-TK vector [manufactured by Promega, USA] as a template, 3 µl of 10×LA PCR Buffer, 1 µl of 2.5 mM dNTP solution, 0.5 µl of TaKaRa LA Taq DNA polymerase [manufactured by Takara Shuzo Co., Ltd., Japan] and 24.5 µl of sterile distilled water were mixed to obtain a top layer solution mixture.

To the bottom layer solution mixture described above was added one unit of AmpliWax PCR Gem 100 [manufactured by Takara Shuzo Co., Ltd., Japan], which was treated at 70° C. for 5 minutes and then in ice for 5 minutes. Then, the top layer solution mixture was added to the mixture to prepare the reaction mixture for PCR. A tube containing the reaction mixture was set on a thermal cycler [manufactured by PerkinElmer, USA] and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 140 bp DNA fragment containing TK promoter was recovered from the gel, and then inserted into pT7 Blue-T vector [manufactured by Takara Shuzo Co., Ltd., Japan]. By digesting the plasmid thus obtained with the restriction enzymes BglII and NcoI, a fragment containing TK promoter was obtained, which was ligated to the BglII-NcoI fragment of plasmid pGL3-Basic vector [manufactured by Promega, USA] to obtain plasmid pGL3-TK.

A 4.9 kb NheI-XhoI fragment of plasmid pGL3-TK thus obtained was ligated to a 200 bp NheI-XhoI fragment of plasmid pBSS-PPRE4 to obtain plasmid pGL3-4ERPP-TK.

This plasmid pGL3-4ERPP-TK was digested with BamHI [manufactured by Takara Shuzo Co., Ltd., Japan], and then treated with T4DNA polymerase [manufactured by Takara Shuzo Co., Ltd., Japan] to form a blunt-end, whereby obtaining a DNA fragment.

On the other hand, pGFP-C1 [manufactured by Toyobo Co., Ltd., Japan] was digested with Bsu36I [manufactured by NEB, UK], and then treated with T4DNA polymerase [manufactured by Takara Shuzo Co., Ltd., Japan] to form a blunt-end whereby obtaining a 1.6 kb DNA fragment.

The both DNA fragments were ligated to construct a reporter plasmid pGL3-4ERPP-TK neo.

Reference Example 4

Construction of Expression Plasmid for Human PPARγ and RXRα)

A 7.8 kb FspI-NotI fragment of plasmid pVgRXR [manufactured by Invitrogen, USA] was ligated to a 0.9 kb FspI-NotI fragment containing RXRα gene of plasmid pTBT-hRXRα obtained in Reference Example 2 to prepare plasmid pVgRXR2. Then, pVgRXR2 was digested with BstXI, and then treated with T4DNA polymerase [manufactured by Takara Shuzo Co., Ltd., Japan] to give a blunt-ended product. Then digestion with KpnI gave a 6.5 kb DNA fragment.

On the other hand, plasmid pTBT-hPPARγ obtained in Reference Example 1 was digested with SalI, and then treated with T4DNA polymerase [manufactured by Takara Shuzo Co., Ltd., Japan] to give a blunt-ended product. Then digestion with KpnI gave a 1.4 kb DNA fragment containing human PPARγ gene.

The both DNA fragments were ligated to construct plasmid pVgRXR2-hPPARγ.

Reference Example 5

Introduction of Human PPARγ- and RXRα-Expression Plasmid and Reporter Plasmid into CHO-K1 Cell as Well as Establishment of Expressed Cell A CHO-K1 cell cultured in a 150 $cm^2$ cell culture flask [manufactured by Corning Costar Corporation, USA] containing Ham's F12 medium [manufactured by INVITROGEN, USA] supplemented with 10% fetal bovine serum [manufactured by INVITROGEN, USA] was scraped by treating with 0.5 g/L trypsin-0.2 g/L EDTA (ethylenediaminetetraacetic acid) [manufactured by Life Technologies, Inc., USA], and then the cell was washed with PBS (Phosphate-buffered saline) [manufactured by INVITROGEN, USA], centrifuged (1000 rpm, 5 minutes) and suspended in PBS. Subsequently, DNA was introduced into the cell under the conditions shown below using GENE PULSER [manufactured by Bio-Rad Laboratories, USA].

Namely, to a cuvette having a 0.4 cm gap were added $8 \times 10^6$ cells and 10 µg of plasmid pVgRXR2-hPPARγ obtained in Reference Example 4 and 10 µg of reporter plasmid pGL3-4ERPP-TK neo obtained in Reference Example 3, which was subjected to electroporation at the voltage of 0.25 kV under the capacitance of 960 µF. Subsequently, the cell was transferred into a F12 medium containing 10% fetal bovine serum and cultured for 24 hours, and then the cell was scraped again and centrifuged, and then suspended in Ham's F12 medium containing 10% fetal bovine serum supplemented with 500 µg/ml of Geneticin [manufactured by INVITROGEN, USA] and 250 µg/ml of Zeocin [manufactured by INVITROGEN, USA]. The obtained suspension was diluted to the density of 1 cells/ml and inoculated in a 96-well plate [manufactured by Corning Costar Corporation, USA], which was cultured in a $CO_2$ gas incubator at 37° C., whereby obtaining a Geneticin- and Zeocin-resistant transformant.

Subsequently, after the transformant cell line thus obtained was cultured in a 24-well plate [manufactured by Corning Costar Corporation, USA], a cell line in which the luciferase was expressed and induced, i.e., PPARγ:RXRα:4ERPP/CHO-K1 cell was selected by the addition of 10 μM pioglitazone hydrochloride.

Formulation Examples

When compound (I) of the present invention is to be used, for example, as an agent for the prophylaxis or treatment of cardiovascular diseases, metabolic diseases, and/or central nervous system diseases, it can be used, for example, according to the following formulations. For example, using a compound of Example 7, 47, 88, 165 or 239 as compound (I), preparations having the following formulations can be produced.

| Formulation Example 1 (capsule) | |
| --- | --- |
| (1) compound (I) | 10 mg |
| (2) lactose | 90 mg |
| (3) microcrystalline cellulose | 70 mg |
| (4) magnesium stearate | 10 mg |
| 1 capsule | 180 mg |

(1), (2), (3) and ½ of (4) are blended and granulated. The rest of (4) is added and the whole is encapsulated in a gelatin capsule.

| Formulation Example 2 (tablet) | |
| --- | --- |
| (1) compound (I) | 10 mg |
| (2) lactose | 35 mg |
| (3) cornstarch | 150 mg |
| (4) microcrystalline cellulose | 30 mg |
| (5) magnesium stearate | 5 mg |
| 1 tablet | 230 mg |

(1), (2), (3), ⅔ of (4) and ½ of (5) are blended and granulated. The rest of (4) and (5) are added to the granules and the mixture is compression molded to give tablet.

| Formulation Example 3 (injection) | |
| --- | --- |
| (1) compound (I) | 10 mg |
| (2) inositol | 100 mg |
| (3) benzyl alcohol | 20 mg |
| 1 ampoule | 130 mg |

(1), (2) and (3) are dissolved in distilled water for injection to the total amount of 2 mL and filled in an ampoule. All steps are performed under aseptic conditions.

INDUSTRIAL APPLICABILITY

The compound of the present invention has an angiotensin II receptor antagonistic action and a peroxisome proliferator-activated receptor (PPAR) agonistic action, and is useful as a pharmaceutical agent such as an agent for the prophylaxis or treatment of cardiovascular diseases such as hypertension, cardiac diseases (cardiac hypertrophy, cardiac failure, myocardial infarction and the like), arteriosclerosis, kidney diseases (diabetic nephropathy, chronic glomerulonephritis and the like), stroke and the like; metabolic diseases such as hyperlipidemia, obesity, diabetes and the like; and/or central nervous system diseases such as depression, dementia, Alzheimer's disease and the like, and the like.

The invention claimed is:

1. 3-(4-Isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof.

2. A crystalline compound of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof.

3. A crystalline compound of a hydrate of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof.

4. A crystalline compound of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one, which has an X-ray powder diffraction analysis pattern with peaks at diffraction angle:)2θ(°) of 4.64, 5.46, 8.40, 11.10, 12.60, 13.10, 14.14, 14.36, 14.60, 15.58, 15.86, 16.24, 16.86, 17.52, 19.26, 19.72, 20.00, 20.40, 20.80, 21.12, 21.70.

5. A crystalline compound of a hydrate of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt, which has an X-ray powder diffraction analysis pattern with peaks at diffraction angle: 2θ(°) of 4.46, 6.32, 12.66, 12.84, 13.46, 13.74, 16.82, 17.08, 17.82, 17.98, 18.38, 19.70, 20.34, 21.80, 22.18, 22.80, 24.08, 25.40, 26.70.

6. A crystalline compound of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt.

7. A crystalline compound of a hydrate of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one potassium salt.

8. A compound according to claim 1, which is a hydrate of 3-(4-isopropoxyphenyl)-2-methyl-5-{[2'-(5-oxo-4,5-dihydro-1,2,4-oxadiazol-3-yl)biphenyl-4-yl]methyl}-6-propylpyrimidin-4(3H)-one or a salt thereof.

* * * * *